(12) United States Patent
Osterroth et al.

(10) Patent No.: US 9,995,733 B2
(45) Date of Patent: Jun. 12, 2018

(54) AGENTS FOR TREATING DISEASE

(75) Inventors: Frank Osterroth, Dietzenbach (DE); Christoph Uherek, Seligenstadt (DE); Christoph Bruecher, Eschborn (DE); Benjamin Daelken, Frankfurt am Main (DE); André Engling, Frankfurt am Main (DE); Chantal Zuber, Frankfurt am Main (DE); Niklas Czeloth, Dreieich (DE); Holger Wallmeier, Sulzbach (DE); Kirsten Völp, Karben (DE); Gregor Schulz, Umkirch (DE)

(73) Assignee: BIOTEST AG, Dreieich (DE)

( * ) Notice: Subject to any disclaimer, the term of this patent is extended or adjusted under 35 U.S.C. 154(b) by 1301 days.

(21) Appl. No.: 13/483,280

(22) Filed: May 30, 2012

(65) Prior Publication Data
US 2013/0004513 A1    Jan. 3, 2013

Related U.S. Application Data

(63) Continuation of application No. PCT/EP2010/068579, filed on Nov. 30, 2010.

(30) Foreign Application Priority Data

Nov. 30, 2009 (GB) .................................. 0920944.6

(51) Int. Cl.
G01N 33/48 (2006.01)
G01N 33/50 (2006.01)
C07K 16/28 (2006.01)
G06G 7/58 (2006.01)

(52) U.S. Cl.
CPC ....... *G01N 33/505* (2013.01); *C07K 16/2812* (2013.01); *C07K 2299/00* (2013.01); *C07K 2317/34* (2013.01); *C07K 2317/55* (2013.01); *C07K 2317/565* (2013.01); *C07K 2317/75* (2013.01); *G01N 2333/70514* (2013.01)

(58) Field of Classification Search
CPC .......................... G01N 33/505; C07K 16/2812
See application file for complete search history.

(56) References Cited

U.S. PATENT DOCUMENTS

| | | | |
|---|---|---|---|
| 5,530,101 A | 6/1996 | Queen et al. |
| 5,604,209 A | 2/1997 | Ubasawa et al. |
| 5,654,407 A | 8/1997 | Boyle et al. |
| 5,690,933 A | 11/1997 | Cobbold et al. |
| 5,777,085 A | 7/1998 | Co et al. |
| 5,859,205 A | 1/1999 | Adair et al. |
| 5,871,732 A | 2/1999 | Burkly et al. |
| 5,886,152 A | 3/1999 | Nakatani et al. |
| 6,037,454 A | 3/2000 | Jardieu et al. |
| 6,056,956 A | 5/2000 | Cobbold et al. |
| 6,270,766 B1 | 8/2001 | Feldman et al. |
| 6,987,171 B1 | 1/2006 | Hunig et al. |
| 7,074,403 B1 | 7/2006 | Goldenburg et al. |
| 7,125,679 B2 | 10/2006 | Askhar |
| 7,138,118 B2 | 11/2006 | Le et al. |
| 7,304,127 B2 | 12/2007 | Saxinger |
| 7,338,658 B2 | 3/2008 | Hanna et al. |
| 7,452,981 B2 | 11/2008 | Wijdenes |
| 7,722,873 B2 | 5/2010 | Lonberg |
| 7,838,489 B2 | 11/2010 | Feldmann et al. |
| 7,846,442 B2 | 12/2010 | Feldmann et al. |
| 2001/0056066 A1 | 12/2001 | Bugelski et al. |
| 2002/0058029 A1 | 5/2002 | Hanna |
| 2002/0068057 A1 | 6/2002 | Feldmann et al. |
| 2002/0099179 A1 | 7/2002 | Jolliffe et al. |
| 2002/0187526 A1 | 12/2002 | Ruben et al. |
| 2003/0166860 A1 | 9/2003 | Hunig et al. |
| 2003/0170239 A1 | 9/2003 | Hering et al. |
| 2003/0219403 A1 | 11/2003 | Frewin et al. |
| 2004/0092718 A1 | 5/2004 | Hunig |
| 2004/0137000 A1 | 7/2004 | Lynn et al. |
| 2004/0247594 A1 | 12/2004 | Hunig et al. |
| 2006/0008457 A1 | 1/2006 | Hanke |
| 2006/0009382 A1 | 1/2006 | Hanke et al. |
| 2006/0051346 A1 | 3/2006 | Wijdenes |
| 2006/0121021 A1 | 6/2006 | Hunig |
| 2006/0188493 A1 | 8/2006 | Hunig |
| 2006/0246063 A1 | 11/2006 | Sakaguchi et al. |
| 2007/0071745 A1 | 3/2007 | Umana et al. |
| 2007/0077246 A1 | 4/2007 | Koenig et al. |
| 2007/0166307 A1 | 7/2007 | Bushell et al. |
| 2007/0218062 A1 | 9/2007 | Irving |
| 2007/0270431 A1 | 11/2007 | Tabunoki et al. |

(Continued)

FOREIGN PATENT DOCUMENTS

| | | |
|---|---|---|
| EP | 0344006 | 11/1989 |
| EP | 0449769 | 10/1991 |

(Continued)

OTHER PUBLICATIONS

Rumbach, L., et al., Biological assessment and MRI monitoring of the therapeutic efficacy of a monoclonal anti-T CD4 antibody in multiple sclerosis patients, Multiple Sclerosis 1996;1:207-212.

Rizova et al., The effect of anti-CD4 monoclonal antibody treatment on immunopathological changes in psoriatic skin. J Dermatolog. Sci. 1994; 7: 1-13.

Roberts and Szostak, RNA-peptide fusions for the in vitro selection of peptides and proteins. PNAS (1997) 94(23):12297-302.

Robertson and Ritz (1990), Biology and clinical relevance of human natural killer cells. Blood. 76: 2421-38.

Rudd et al., The CD4 receptor is complexed in detergent lysates to a protein-tyrosine kinase (pp58) from human T-lymphocytes, PNAS USA 85, 5190-5194 (1988).

(Continued)

*Primary Examiner* — Eric S Dejong
(74) *Attorney, Agent, or Firm* — Cermak Nakajima & McGowan LLP; Shelly Guest Cermak

(57) ABSTRACT

Provided are methods of screening to identify molecules capable of binding to CD4 and capable of activating CD4+CD25+ regulatory T cells. Further provided are antibodies and antibody fragments capable of activating CD4+CD25+ regulatory T cells and methods and uses involving the antibodies and fragments thereof.

28 Claims, 13 Drawing Sheets

(56) References Cited

U.S. PATENT DOCUMENTS

Figure 3:
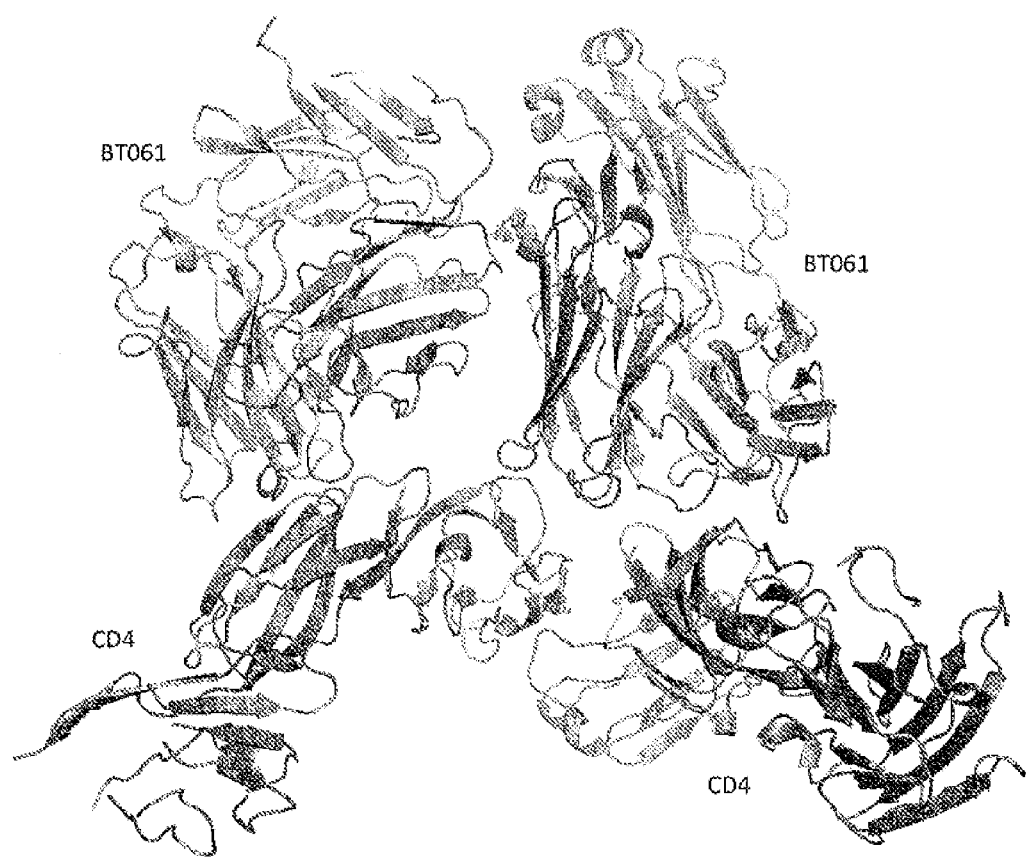

| | | |
|---|---|---|
| 2008/0213280 A1 | 9/2008 | Benyunes |
| 2009/0123477 A1 | 5/2009 | Hanke et al. |
| 2011/0059082 A1 | 3/2011 | Germer et al. |
| 2011/0059083 A1 | 3/2011 | Aigner et al. |
| 2011/0059084 A1 | 3/2011 | Osterroth et al. |
| 2011/0229465 A1 | 9/2011 | Osterroth et al. |
| 2012/0225790 A1 | 9/2012 | Julia Cano et al. |
| 2012/0231460 A1 | 9/2012 | Tsuzaka |

FOREIGN PATENT DOCUMENTS

| | | |
|---|---|---|
| EP | 0568925 | 11/1993 |
| EP | 1161955 | 12/2001 |
| EP | 1241249 | 9/2002 |
| EP | 1460088 | 9/2004 |
| EP | 2333110 A1 | 6/2011 |
| GB | 2376467 | 12/2002 |
| JP | H02-152989 | 6/1990 |
| JP | 2006-511516 A | 4/2006 |
| JP | 2009-521956 A | 6/2009 |
| JP | 2009-529915 A | 8/2009 |
| WO | WO90/07861 | 7/1990 |
| WO | WO90/13562 | 11/1990 |
| WO | WO90/15152 | 12/1990 |
| WO | WO91/09966 | 7/1991 |
| WO | WO1994/008619 | 4/1994 |
| WO | WO1995/009652 | 4/1995 |
| WO | WO97/09351 | 3/1997 |
| WO | WO97/29131 | 8/1997 |
| WO | WO1998/014211 | 4/1998 |
| WO | WO01/16182 | 3/2001 |
| WO | WO2001/093908 | 12/2001 |
| WO | WO02/22212 | 3/2002 |
| WO | WO02/062335 | 8/2002 |
| WO | WO02/085405 | 10/2002 |
| WO | WO2002/102853 | 12/2002 |
| WO | WO2004/024097 | 3/2004 |
| WO | WO2004/050016 A2 | 6/2004 |
| WO | WO2004/067554 A2 | 8/2004 |
| WO | WO2004/083247 | 9/2004 |
| WO | WO2004/112835 | 12/2004 |
| WO | WO2005/019254 | 3/2005 |
| WO | WO2006/002377 | 1/2006 |
| WO | WO2006/050949 | 5/2006 |
| WO | WO2006/0055077 | 5/2006 |
| WO | WO2007/019865 | 2/2007 |
| WO | WO2008/092905 A2 | 8/2007 |
| WO | WO2007/111661 A2 | 10/2007 |
| WO | WO2007/117602 | 10/2007 |
| WO | WO2007/124299 A2 | 11/2007 |
| WO | WO2007/130697 A2 | 11/2007 |
| WO | WO2007/135684 | 11/2007 |
| WO | WO2008/0982895 | 8/2008 |
| WO | WO2008/134046 | 11/2008 |
| WO | WO2009/112502 | 9/2009 |
| WO | WO2009/112592 | 9/2009 |
| WO | WO2009/121690 | 10/2009 |
| WO | WO2009/124815 | 10/2009 |
| WO | WO2010/022341 | 2/2010 |
| WO | 2010/034590 | 4/2010 |
| WO | 2011/158798 | 12/2011 |

OTHER PUBLICATIONS

Takai, T. Fc receptors and their role in immune regulation and autoimmunity. J Clin Immunol 25, 1-18 (2005).

Rumbach et al., Essai thérapeutique ouvert d'un anticorps monoclonal anti-T CD4 dans la sclérose en plaques. Rev. Neurol. (Paris) 1994; 150 (6-7): 418-424.

Rump et al., A double blind, placebo-controlled, crossover therapy study with natural human IL-2 (nhuIL-2) in combination with regular intravenous gammaglobulin (IVIG) infusions in 10 patients with common variable immunodeficiency (CVID). Clin. Exp. Immunol. 1997; 110:167-173.

Salfeld. Isotype selection in antibody engineering. Nat Biotechnol 2007. 25: 1369.

Sakaguchi et al., Immunologic tolerance maintained by CD25+ CD4+ regulatory T cells: their common role in controlling autoimmunity, tumor immunity, and transplantation tolerance. Immunol. Rev. 182: 18-32 (2001).

Salmond, R.J., et al. T-cell receptor proximal signaling via the Src-family kinases, Lck and Fyn, influences T-cell activation, differentiation, and tolerance. Immunol Rev 228, 9-22 (2009). Published online Mar. 6, 2009.

Salomon et al., B7/CD28 costimulation is essential for the homeostasis of the CD4+CD25+ immunoregulatory T cells that control autoimmune diabetes. Immunity 12: 431-440 (2000).

Sany J. Immunological treatment of rheumatoid arthritis. Clin Exp. Rheumatol; 8 (Suppl 5): 81-88, 1990.

Sattentau et al., Epitopes of CD4 antigen and HIV infection. Science 1986. 234: 1120.

Sattentau et al., Structural Analysis of the Human Immunodeficiency Virus-Binding Domain of CD4, J. Exp. Med. 170, 1319-1334 (1989).

Setoguchi et al., Repression of the Transcription Factor Th-POK by Runx Complexes in Cytotoxic T Cell Development, Science 319, 822-825 (2008).

Schulze-Koops et al., "Reduction of Th1 Cell Activity in the Peripheral Circulation of Patients with Rheumatoid Arthritis After Treatment with a Non-Depleting Humanized Monoclonal Antibody to CD4," J. Rheumatol. 1998;25(11):2065-2076.

Seddon and Mason, Peripheral Autoantigen induces regulatory T cells that prevent autoimmunity. J. Exp. Med. 189(5): 877-881, 1999.

Sharma et al., Protein Minimization of the gp120 Binding Region of Human CD4, Biochemistry 44, 16192-16202 (2005).

Shevach, Regulatory T cells in autoimmunity. Annu. Rev. Immunol. 18: 423-449 (2000).

Shevach, CD4+CD25+ suppressor T cells: more questions than answers. Nature Rev. Immunol 2 : 389 (2002).

Stumpp et al., DARPins: a new generation of protein therapeutics. Drug Discov. Today (2008) 13, Nr. 15-16, S. 695-701.

Skerra, Alternative binding proteins: Anticalins—harnessing the structural plasticity of the lipocalin ligand pocket to engineer novel binding activities, FEBS J. 275, 2677-2683 (2008).

Skerra et al. "Engineered protein scaffolds for molecular recognition," J. Mol. Recognit. 2000;13:167-187.

Simon et al., A Rat CD4 Mutant Containing the gp120-binding Site Mediates Human Immunodeficiency Virus Type 1 Infection, J. Exp. Med. 177, 949-954 (1993).

Smeets et al., Poor expression of T cell derived cytokines and activation and proliferation markers in early rheumatoid synovial tissue. Clin. Immunol. Immunopathol. 88: 84-90, 1998.

Smolen et al., Efficacy and safety of certolizumab pegol plus methotrexate in active rheumatoid arthritis: the RAPID 2 study. A randomised controlled trial. Ann Rheum Dis. Jun. 2009;68(6):797-804. Epub Nov. 17, 2008.

Smolen, J.S., et al. Validity and reliability of the twenty-eight-joint count for the assessment of rheumatoid arthritis activity. Arthritis Rheum 38, 38-43 (1995).

Soundararajan et al., Clinical and immunological effects of a primatized anti CD4 antibody used concomitantly with methotrexate in rheumatoid arthritis. J. Allergy & Clin. Immunol. 1997; 99 No. 1 Pt. 2: S193 No. 777.

Stassen et al., Differential regulatory capacity of CD25+ T regulatory cells and preactivated CD25+ T regulatory cells on development, functional activation, and proliferation of Th2 cells. J. Immunol. (2004); 173(1): 267-74.

Stein et al., Immunohistological analysis of human lymphoma: correlation of histological and immunological categories. Adv Cancer Res. 1984;42:67-147.

Straub et al., Circadian rhythms in rheumatoid arthritis. Athr. & Rheumat. 2007; 56(2): 399-408.

(56) References Cited

OTHER PUBLICATIONS

Suri-Payer et al., Pathogenesis of post-thymectomy autoimmune gastritis. Identification of anti-H/K adenosine triphosphatase-reactive T cells. J Immunol. 157: 1799-1805 (1996).
Suri-Payer et al., CD4+CD25+ T cells inhibit both the induction and effector function of autoreactive T cells and represent a unique lineage of immunoregulatory cells. J. Immunol. 160: 1212-1218 (1998).
Suto et al., Role of CD4+CD25+ regulatory T cells in T helper 2 cell-mediated allergic inflammation in the airways. Am. J. Respir. Crit. Care Med. 2001; 164: 680-687.
Suntharalingam et al, Cytokine storm in a phase I trial of the anti-CD28 monoclonal antibody TGN1412. N Engl. J Med. Sep. 7, 2006;355(10):1018-28.
Saitovich, D,, et al., "Kinetics of Induction of Transplantation Tolerance With a Nondepleting Anti-CD4 Monoclonal Antibody and Donor-Specific Transfusion Before Transplantation: A Critical Period of Time Is Required for Development of Immunological Unresponsiveness," Transplant. 1996;61(11):1642-1647.
Sakaguchi, S., et al., "Immunologic Self-Tolerance Maintained by Activated T Cells Expressing IL-2 Receptor a-Chains (CD25)," J. Immunol. 1995;155:1151-1164.
Sastry, L., et al., "Cloning of the immunological repertoire in *Escherichia coli* for generation of monoclonal catalytic antibodies: Construction of a heavy chain variable region-specific cDNA library," Proc. Natl. Acad. Sci. USA 1989;86:5728-5732.
Schimke, R. T., "Gene Amplification in Cultured Animal Cells," Cell 1984;37:705-713.
Schulz, Biotest Autumn Conference Presentation for Journalists and Analysts, Frankfurt/Main, Nov. 22, 2004.
Shevach, E. M., "Certified Professionals: CD4+CD25+ Suppressor T Cells," J. Exp. Med. 2001;193(11):F41-F45.
Skov, L., et al., "HuMax-CD4 A Fully Human Monoclonal Anti-CD4 Antibody for the Treatment of Psoriasis Vulgaris," Arch. Dermatol. 2003;139:1433-1439.
Southern, P. J., et al., "Transformation of Mammalian Cells to Antibiotic Resistance with a Bacterial Gene Under Control of the SV40 Early Region Promoter," J. Mol. Appl. Genetics 1982;1:327-341.
Strand et al., Biologic Therapies in rheumatology: lessons learned, future directions. Nat. Rev. Drug Dis. 2007; 6:75-92.
Subramani, S,, et al., "Expression of the Mouse Dihydrofolate Reductase Complementary Deoxyribonucleic Acid in Simian Virus 40 Vectors," Mol. Cell. Biol. 1981;1(9):854-864.
Sugiyama et al., Dysfunctional blood and target tissue CD4+CD25high regulatory T cells in psoriasis: Mechanism underlying unrestrained pathogenic effector T cell proliferation. J Immunol, 174: 164-173, 2005.
Swierkot et al., Methotrexate in rheumatoid arthritis. Pharmacological Reports 2006; 58: 473-492.
Spalding et al., Cost Effectiveness of Tumor Necrosis Factor-α Inhibition on First Line Agents in Rheumatoid Arthritis. Pharmacoeconomics (2006); 24(12): 1221-1232.
Frey et al., The role of regulatory T cells in antigen-induced arthritis: aggravation of arthritis after depletion and amelioration after transfer of CD4+CD25+ T cells. Arthritis Res Ther, 7: R291-R301, 2005.
Gimeno et al., Monitoring the effect of gene silencing by RNA interference in human CD34+ cells injected into newborn RAG2-/-gammac-/- mice: functional inactivation of p53 in developing T cells. Blood 104, 3886-93, 2004.
Goronzy and Weyand, T cell regulation in rheumatoid arthritis. Curr Opin Rheumatol, 16: 212-7, 2004.
Godfrey et al., NKT cells: facts, functions and fallacies, Immunology Today (2000): 21(11): 573-583.
Glamann et al., Characterization of a Macaque Recombinant Monoclonal Antibody That Binds to a CD4-Induced Epitope and Neutralizes Simian Immunodeficiency Virus. J. Virol. Aug. 2000; 74(15): 7158-63.

Gehan EA, George SL, Estimation of human body surface area from height and weight. Cancer Chemother Rep 1970 54:225-35.
Gellman, Foldamers: A Manifesto. Acc. Chem. Res (1998) 31 (4): 173-180.
Gessner et al., The IgG Fc receptor family. Ann Hematol 1998. 76: 231.
Gorelik and Flavell, Abrogation of TGFß signaling in T cells leads to spontaneous T cell differentiation and autoimmune disease. Immunity 12: 171-181, 2000.
Gottlieb et al., Anti-CD4 monoclonal antibody treatment of moderate to severe psoriasis vulgaris: Results of a pilot, multicenter, multiple-dose, placebo-controlled study. Acad Dermatol 2000; 43: 595-604.
Gottlieb et al., Infliximab induction therapy for patients with severe plaque-type psoriasis: a randomised double-blind, placebo-controlled trial. J. Am Acad. Dermatol. 2004; 51(4):534-542.
Göttlinger et al., Vpu protein of human immunodeficiency virus type 1 enhances the release of capsids produced by gag gene constructs of widely divergent retroviruses, Proc. Natl. Acad. Sci. USA 90, 7381-7385 (1993).
Gillies, S. D,, et al., "A Tissue-specific Transcription Enhancer Element Is Located in the Major Intron of a Rearranged Immmunoglobulin Heavy Chain Gene," Cell 1983;33:717-728.
Goetzl, E. J., et al., "Affinity Labeling of a Mouse Myeloina Protein Which Binds Nitrophenyl Ligands, Kinetics of Labeling and Isolation of a Labeled Peptide," Biochemistry 1970;9(5):1267-1278.
Goldberg, D., et al., "Immunological Effects of High Dose Administration of Anti-CD4 Antibody in Rheumatoid Arthritis Patients," J. Autoimmun. 1991;4:617-630.
Gorman, C. M., et al., "The Rous sarcoma virus long terminal repeat is a strong promoter when introduced into a variety of eukaryotic cells by DNA-mediated transfection," Proc. Natl. Acad. Sci, USA 1982;79:6777-6781.
Gorman, S. D., et al., "Reshaping a therapeutic CD4 antibody," Proc. Natl. Acad. Sci. USA 1991;88:4181-4185.
Graham, F. L., et al., "A New Technique for the Assay of Infectivity of Human Adenovirus 5 DNA," Virology 1973; 52:456-467.
Gray et al., (1994), The role of transforming growth factor beta in the generation of suppression: an interaction between CD8+ T and NK cells. J Exp Med. 180:1937-42.
Grynkiewicz, G., Poenie, M. & Tsien, R.Y. A new generation of Ca2+ indicators with greatly improved fluorescence properties. J Biol Chem 260, 3440-3450 (1985).
Hori, S., Nomura, T. & Sakaguchi, S. Control of regulatory T cell development by the transcription factor Foxp3. Science 299, 1057-1061 (2003).
Hammond et al., Antigenic Variation within the CD4 Binding Site of Human Immunodeficiency Virus Type 1 gp120: Effects on Chemokine Receptor Utilization, J. Virology 75, 5593-5603 (2001).
Hara et al., (2001), IL-10 is required for regulatory T cells to mediate tolerance to alloantigens in vivo. J Immunol. 166:3789-96.
Haas et al., Prevalence of newly generated naive regulatory T cells (Treg) is critical for Treg suppressive function and determines Treg dysfunction in multiple sclerosis. J Immunol. Jul. 15, 2007;179(2):1322-30.
Haas et al., Reduced suppressive effect of CD4+CD25high regulatory T cells on the T cell immune response again myelin oligodendrocyte glycoprotein in patients with multiple sclerosis. Eur. J. Immunol. 2005: 35:3343-3352.
Herman et al., Low dose methotrexate induces apoptosis with reactive oxygen species involvement in T lymphocytic cell lines to a greater extent than in monocytic lines. Inflamm Res. Jul. 2005;54(7):273-80.
Haycock G.B., Schwartz G.J.,Wisotsky D.H. Geometric method for measuring body surface area: A height weight formula validated in infants, children and adults. The Journal of Pediatrics 1978 93:1:62-66.
Hepburn et al., Antibody-mediated stripping of CD4 from lymphocyte cell surface in patients with rheumatoid arthritis. Rheumatology Jan. 2003;42(1): 54-61.
Herold et al., Anti-CD3 monoclonal antibody in new-onset Type 1 Disease Mellitus. N. Engl. J. Med. 2002; 346(22):1692-1698.

(56) References Cited

OTHER PUBLICATIONS

Herzyk et al., Immunomodulatory Effects of Anti-CD4 Antibody in Host Resistance against Infections and Tumors in Human CD4 Transgenic Mice. Infect Immun. 69(2): 1032-43 (2001).
Hill et al., A Field Guide to Foldamers. Chem. Rev. (2001) 101 (12): 3893-4012.
Hornell, G., et al., "Treatment of Rheumatoid Arthritis With an Anti-CD4 Monoclonal Antibody," Arthritis & Rheumatism 1991;34(2):129-140.
Horwitz et al., (1999), Role of NK cells and TGF-beta in the regulation of T-cell-dependent antibody production in health and autoimmune disease. Microbes Infect. 1:1305-11.
Howie et al., Synthetic peptides representing discontinuous CD4 binding epitopes of HIV-1 gp120 that induce T cell apoptosis and block cell death induced by gp120, FASEB J. 12, 991-998 (1998).
Hoffmann, P., et al., "Donor-type CD4+CD25+ Regulatory T Cells Suppress Lethal Acute Graft-Versus-Host Disease after Allogenic Bone Marrow Transplantation," J. Exp. Med. 2002;196(3):389-399.
Humphreys et al., "F(ab')2 molecules made from *Escherichia coli* produced Fab' with hinge sequences conferring increased serum survival in animal model," J. Immunol. Methods 1998;217:1-10.
Huang et al., Structures of the CCR5 N Terminus and of a Tyrosine-Sulfated Antibody with HIV-1 gp120 and CD4, Science 317, 1930-1934 (2007).
Ivan and Colovai, Human Fc receptors: critical targets in the treatment of autoimmune diseases and transplant rejections. Hum Immunol 2006. 67: 479.
Isaacs et al., A therapeutic human IgG4 monoclonal antibody that depletes target cells in humans, Clin. Exp. Immunol. 1996; 106: 427-433.
Isaacs, J. D., et al., "Humanized Anti-CD4 Monoclonal Antibody Therapy of Autoimmune and Inflammatory Disease," Clin. Exp. Innnunol. 1997;110:158-166.
Jabado et al., CD4 ligands inhibit the formation of multifunctional transduction complexes involved in T cell activation. J Immunol. 158(1): 94-103 (1997).
Jameson et al., Location and Chemical Synthesis of a Binding Site for HIV-1 on the CD4 Protein, Science 240, 1335-1339 (1988).
Jefferis and Lund, Interaction sites on human IgG-Fc for Fcγ: current models. Immunol. Lett. 2002;82: 57.
Jonuleit, H., et al., "Identification and Functional Characterization of Human CD4+CD25+ T Cells with Regulatory Properties Isolated from Peripheral Blood," J. Exp. Med. 2001;193(11):1285-1294.
Jonuleit and Schmitt, The regulatory T cell family: distinct subsets and their interrelations, J. Immunol. 2003; 171: 6323-6327.
Jiang and Chess, An integrated view of suppressor T cell subsets in immunoregulation. J Clin Invest, 114(9):1198-1208, 2004.
Jiang and Chess, Regulation of Immune responses by T cells. NEJM, 354: 1166-1176, 2006.
Kelchtermans et al., Defective CD4+CD25+ regulatory T cell function in collagen-induced arthritis: an important factor in pathogenesis, counter-regulated by endogenous IFN-•. Arthritis Res Ther, 7: R 402-R415, 2005.
Kabat E. A., "Structure and Heterogeneity of Antibodies," Proc, 10th Congr. Eur. Soc. Haematl., Strasbourg Acta haemat. 1966;36;198-238.
Karim et al. CD25+ CD4+ regulatory T cells generated by exposure to a model protein antigen prevent allograft rejection: antigen-specific reactivation in vivo is critical for bystander regulation. Blood. 2005; 105:4871-4877.
Kettleborough, C. A., et al., "Humanization of a mouse monoclonal antibody by CDR-grafting: the importance of framework residues on loop conformation," Protein Eng. 1991;4(7):773-783.
Keymeulen et al., Insulin Needs after CD3-Antibody Therapy in New-Onset Type 1 Diabetes. New Engl. J. Med, 2005; 352(25): 2598-2608.
Keystone et al., Radiographic, clinical, and functional outcomes of treatment with adalimumab (a human anti-tumor necrosis factor monoclonal antibody) in patients with active rheumatoid arthritis receiving concomitant methotrexate therapy: a randomized, placebo-controlled, 52-week trial. Arthritis Rheum. May 2004;50(5):1400-11.
Keystone et al., Golimumab, a human antibody to tumour necrosis factor {alpha} given by monthly subcutaneous injections, in active rheumatoid arthritis despite methotrexate therapy: the Go-Forward Study. Ann Rheum Dis. Jun. 2009;68(6):789-96. Epub Dec. 9, 2008.
Kim et al., When Does Rheumatoid Arthritis Begin and Why Do We Need to Know? Arthritis & Rheumatism 2000;43(3):473-484.
Kingsley et al., CD4+CD25+ regulatory T cells prevent graft rejection: CTLA-4- and IL-10 dependent immunoregulation of alloresponses. J Immunol. 168: 1080 (2002).
Kraan et al., "Asymptomatic Synovitis Precedes Clinically Manifest Arthritis," Arthritis & Rheumatism 1998;41(8):1481-1488.
Kingsley et al., Immunogenetic and cellular immune mechanism in rheumatoid arthritis: relevance to new therapeutic strategies. Br J Rheumatol, 29, 58-64, 1990.
Kipps et al., Importance of immunoglobulin isotype in human antibody-dependent, cell-mediated cytotoxicity directed by murine monoclonal antibodies, J. Exp. Med. 1985; 161: 1-17.
Kon et al., Randomised, dose-ranging , placebo-controlled study of chimeric antibody to CD4 (keliximab) in chronic severe asthma, Lancet Oct. 3, 1998; 352 (9134):1109-13.
Kon et al., The effects of an anti-CD4 monoclonal antibody, keliximab, on peripheral blood CD4zT-cells in asthma. Eur Respir J. 18(1): 45-52 (2001).
König et al., Glycosylation of CD4. J. Biol. Chem. 263, 9502-9507 (1988).
Korndörfer et al., Structural Mechanism of Specific Ligand Recognition by Lipocalin Tailored for the Complexation of Digoxigenin, J. Mol. Biol. Jul. 4, 2003; 330, 385-396.
Kwong et al., Structure of an HIV gp120 envelope glycoprotein in complex with the CD4 receptor and a neztralizing human antibody, Nature 393, 648-659 (1998).
Kriegel et al., Defective suppressor function of human CD4+CD25+ regulatory T cells in autoimmune polyglandular syndrome type II. J Exp Med, 199: 1285-1291, 2004.
Kuritzkes et al., Antiretroviral activity of the anti-CD4 monoclonal antibody TNX-355 in patients infected with HIV type 1. J. Infect. Dis. 2004 ;189 :286-91.
Liu et al., The presence of cytokine-suppressive CD4+CD25+ T cells in the peripheral blood and synovial fluid of patients with rheumatoid arthritis. Scand J Immunol, 62 (3): 312-317, 2005.
Wang et al., Expression of GARP selectively identifies activated human FOXP3+ regulatory T cells. PNAS (2009) 106, 32. 13439-13444. Published online Jul. 28, 2009.
Lam TK, Leung DT: More on simplified calculation of body-surface area. N Engl J Med Apr. 28, 1988;318(17):1130.
Lamarre et al., The MHC-Binding and gp120-Binding Functions of CD4 Are Separable, Science 245, 743-746 (1989).
Lanza et al., Active immunity against the CD4 receptor by using an antibody antigenized with residues 41-55 of the first extracellular domain, PNAS USA 90, 11683-11687 (1993).
Lawendowski et al., Solid phase epitope recovery. J Immunol., (2002) 169: 2414-2421).
Levings, M. K., et al., Human CD4+CD25+T Regulatory Cells Suppress Naïve and Memory T Cell Proliferation and Can Be Expanded In Vitro without Loss of Function, J. Exp. Med. 2001;193(11):1295-1301.
Lindley, S., et al. Defective suppressor function in CD4(+)CD25(+) T-cells from patients with type 1 diabetes. Diabetes 54, 92-99 (2005).
Ling et al., Relation of CD4+CD25+ regulatory T-cell suppression of allergen-driven T-cell activation to atopic status and expression of allergic disease. Lancet (2004) 363(9409): 608-15.
Lipsky et al., Infliximab and Methotrexate in the treatment of rheumatoid arthritis. The New England Journal of Medicine, vol. 343; pp. 1594-1602; Nov. 30, 2000.
Lin, C.H. & Hunig, T. Efficient expansion of regulatory T cells in vitro and in vivo with a CD28 superagonist. Eur J Immunol 33, 626-638 (2003).

(56) References Cited

OTHER PUBLICATIONS

Livesay et al., Conserved sequence and structure association motifs in antibody-protein and antibody hapten complexes, Prot. Eng. Des. & Select. 17, 463-472 (2004).

Lusky, M., et al., "Inhibition of SV40 replication in simian cells by specific pBR322 DNA sequences," Nature 1981;293:79-81.

Luggen et al., Results of a phase II double-blind, randomized study of a nondepleting anti-CD4 monoclonal antibody (Clenoliximab) given in combination with methotrexate (MTX) in patients with moderate to severe rheumatoid arthritis. Annals of Rheum. Dis. 2003; 62(1): 99.

Lusso et al., CD4 is a critical component of the receptor for human herpes virus 7: Interference with human immunodeficiency virus, Proc. Natl. Acad. Sci. USA 91, 3872-3876 (1994).

Maddon et al., The isolation and nucleotide sequence of a cDNA encoding the T cell surface protein T4. Cell. 1985; 42(1):93-104.

Maloy et al., CD4+ CD25+ TR cells suppress innate immune pathology through cytokine-dependent mechanisms. J. Exp. Med. (2003); 197(1): 111-119.

Mason et al., CD4 coating, but not CD4 depletion, is a predictor of efficacy with primatized monoclonal anti-CD4 treatment of active rheumatoid arthritis. J Rheumatol. 29(2): 220-9 (2002).

Mattheakis et al., An in vitro polysome display system for identifying ligands from large peptide libraries. PNAS 1994; 91(19):9022-6.

Mazerolles et al., A synthetic peptide mimicking the HLA-DR β2-binding site for CD4+ T cell adhesion to B cells and CD4+ T cell activation, Int. Immunology 8, 267-274 (1996).

Marie et al., TGF-beta1 maintains suppressor function and Foxp3 expression in CD4+CD25+ regulatory T cells. J Exp Med. Apr. 4, 2005;201(7):1061-7.

McKeithan, Kinetic proofreading in T-cell receptor signal transduction, PNAS 1995, 92; 5042-5046.

Mima et al., Transfer of rheumatoid arthritis into severe combined immunodeficient mice. The pathogenic implications of T cell populations oligoclonally expanding in the rheumatoid joints. J Clin Invest; 96:1746-1758, 1995.

Mizkami et al., Binding region for human immunodeficiency virus (HIV) and epitopes for HIV-blocking monoclonal antibodies of the CD4 molecule defined by site-directed mutagenesis. Proc. Natl. Acad. Sci. USA 1988;85:9273-9277.

Moebius et al., Human immunodeficiency virus gp120 binding C'C" ridge of CD4 domain 1 is also involved in interaction with class II major histocompatibility comlex molecules, PNAS USA 89, 12008-120012 (1992).

Moebius et al., Delination of an extended surface contact area on human CD4 involved in class II major histocompatibility complex binding, Proc. Natl. Acad. Sci. USA 90, 8259-8263 (1993).

Moore and Stevenson, New Targets for Inhibitors of HIV-1 Replication, Nature Rev. Mol. Cell Biol. 1, 40-49 (2000).

Moreau et al., Bioinformatics. Discontinuous epitope prediction based on mimotope analysis May 1, 2006;22(9):1088-95. Epub Jan. 24, 2006.

Morgan et al., CD25+ cell depletion hastens the onset of severe disease in collagen-induced arthritis. Arthritis and Rheumatism, 48 (5): 1452-1460, (2003).

Mottet et al., Cutting Edge: Cure of Colitis by CD4+CD25+ Regulatory T Cells. J. Immunol. (2003); 170: 3939-3943.

Mottonen et al., CD4+CD25+ T cells with the phenotypic and functional characteristics of regulatory T cells are enriched in the synovial fluid of patients with rheumatoid arthritis. Clin Exp Immunol,140 (2): 360-367, 2005.

Morel et al., Down-regulation of lymphocyte CD4 antigen expression by administration of anti-CD4 monoclonal antibody. Clin. Immunol. Immunopath. 1992; 64(3): 248-253.

Morel et al., "Internalization and Degradation of Anti-CD4 Monoclonal Antibodies Bound to Human Peripheral Blood Lymphocytes," Mol. Immunol. 1993;30(7):649-657.

Morel, P., et al., "Anti-CD4 Monoclonal Antibody Administration in Renal Transplanted Patients," Clin. Immunol. Immunopath. 1990;56:311-322.

Morel, P., et al., "Anti-CD4 Monoclonal Antibody Therapy in Severe Psoriasis," J. Autoimmun. 1992;5:465-477.

Mount, D. W., et al., "Microcomputer programs for back translation of protein to DNA sequences and analysis of ambiguous DNA sequences," Nucl. Acids Res. 1984;12(1):819-823.

Mosteller RD: Simplified Calculation of Body Surface Area. N Engl J Med Oct. 22, 1987;317(17):1098.

Mourad et al., Humanized IgG1 and IgG4 anti-CD4 monoclonal antibodies: Effects on Lymphocytes in the Blood, Lymph Nodes, and Renal Allografts in Cynomolgus Monkeys1. Transplantation 65(5): 632-41 (1998).

Muyldermans et al., Camelid immunoglobulin and nanobody technology. Veterinary Immunology and Immunopathology, 128; 1-3; pp. 178-183 (2009) Epub. Oct. 17, 2008.

Myszka et al., Energetics of the HIV gp120-CD4 binding reaction, Proc. Natl. Acad. Sci. USA 97, 9026-9031 (2000).

Nakamura et al., Cell contact-dependent immunosuppression by CD4(+)CD25(+) regulatory T cells is mediated by cell surface-bound transforming growth factor beta. J Exp. Med. 194: 629-644 (2001).

Nakanishi et al., Structural and thermodynamic analyses of interaction between a humanized antibody and its antigen: The case of anti-lysozyme antibody, HyHEL-10, Photon Factory Activity Report 2006 #24 Part p. 248.

Nakatani et al., "Functional Expression of Human Monoclonal Antibody Genes Directed Against Pseudomonal Exotoxin A in Mouse Myeloma Cells" Biotechnology 1989; 7: 805-810.

Ng et al., Pharmacokinetics/pharmacodynamics of nondepleting anti-CD4 monoclonal antibody (TRX1) in healthy human volunteers. Pharm Res. Jan. 2006;23(1):95-103. Epub Nov. 30, 2006.

Nimmerjahn and Ravetch, Fc gamma receptors as regulators of immune responses. Nature Reviews Immunology 2008. 8: 34.

Newsome, G. Guidelines for the management of rheumatoid arthritis: 2002 update. J Am Acad Nurse Pract 14, 432-437 (2002).

Orlandi, R., et al., "Cloning immunoglobulin variable domains for expression by the polymerase chain reaction," Proc, Natl. Acad. Sci. USA 1989;86:3833-3837.

Osterburg, G., et al "Computer programs for the analysis and the management of DNA sequences," Nuc. Acids Res. 1982;10(1):207-216.

Oosterhout et al., Regulatory T-lymphocytes in asthma. Eur. Resp. Journal (2005); 26: 918-932.

Panaccione, R., Ferraz, J.G. & Beck, P. Advances in medical therapy of inflammatory bowel disease. Curr Opin Pharmacol 5, 566-572 (2005).

Panka, et al., "Variable region framework differences result in decreased or increased affinity of variant anti-digoxin antibodies," Proc. Natl. Acad. Sci. 1988;85:3080-3084.

Pandiyan et al., CD4+CD25+Foxp3+ regulatory T cells induce cytokine deprivation—mediated apoptosis of effector CD4+ T cells. Nature Immunol. (2007) 8 1353-1362.

Peters et al., Clinical grade Treg: GMP isolation, improvement of purity by CD127 Depletion, Treg expansion, and Treg cryopreservation. PLoS One. Sep. 8, 2008;3(9):e3161.

Piatier-Tonneau et al., Characterization of 18 workshop anti-CD4 mAb: epitope mapping to CD4 mutants and effects on CD4-HLA class II interaction. Leucocyte Typing V: White Cell Differentiation Antigens. Proceedings of the 5th Int. Workshop and Conference. Boston, USA Nov. 1993. vol. 1: T39.6: 476-478. Ed. Schlossman et al., OUP 1995.

Piccirillo et al., Cutting edge: control of CD8+ T cell activation by CD4+CD25+ immunoregulatory cells. J. Immunol. 2001; 167: 1137-1140.

Pohlers et al., Differential clinical efficacy of anti-CD4 monoclonal antibodies in rat adjuvant arthritis is paralleled by differential influence on NF-κB binding activity and TNF-α secretion of T cells. Arthritis Res 2002, 4:184-189.

Pollock et al., Identification of mutant monoclonal antibodies with increase antigen binding, PNAS 1988; 85: 2298-2302.

(56) References Cited

OTHER PUBLICATIONS

Pontoux et al., Natural CD4 CD25+ regulatory T cells control the burst of superantigen-induced cytokine production: the role of IL-10, Int. Immunol. 2002; 14(2):233-239.
Porter et al., Suppressor function of umbilical cord blood-derived CD4+ CD25+ T regulatory cells exposed to Graft-versus-host disease drugs. Cell Therapy and Islet Transplantation. 2006. 83(1); 23-29.
Potter, H., et al., "Enhancer-dependent expression of human K immunoglobulin genes introduced into mouse pre-B lymphocytes by electroporation," Proc. Natl. Acad. Sci. USA 1984;81:7161-7165.
Prevoo, M.L., et al. Modified disease activity scores that include twenty-eight-joint counts. Development and validation in a prospective longitudinal study of patients with rheumatoid arthritis. Arthritis Rheum 38, 44-48 (1995).
Puls, R. L, et al., "Gene transfer and expression of a non-viral polycation-based vector in CD4+ cells," Gene Ther. 1999;6:1774-1778.
Racadot, E., et al., "Treatment of Multiple Sclerosis with Anti-CD4 Monoclonal Antibody," J. Autoimmun. 1993;6:771-786.
Racadot, E., et al, "Immunological follow-up of 17 patients with rheumatoid arthritis treated in vivo with an anti-T CD4+ monoclonal antibody (B-F5)," Clin. Exp, Rheumatol. 1992;10:365-374.
Raganath VK, Khanna D, Paulus HE. ACR remission criteria and response criteria. Clin Exp Rheumatol 24 (Suppl 43), S14-S21, 2006.
Raja et al., CD4 Binding Site Antibodies Inhibit Human Immunodeficiency Virus gp120 Envelope Glycoprotein Interaction with CCR5, J. Virology Jan. 2003; 77, 713-718.
Rau et al., Adalimumab (a fully human anti-tumour necrosis factor α monoclonal antibody) in the treatment of active rheumatoid arthritis: the initial results of five trials. Ann Rheum Dis 2002; 61(Suppl II): ii70-ii73.
Ravetch and Kinet Fc receptors. Annu Rev Immunol 1991. 9: 457.
Raziuddin et al., (1990), Increased circulating HLA-DR+ CD4+ T cells in systemic lupus erythematosus: alterations associated with prednisolone therapy. Scand J Immunol.31, 139-45.
Read et al., Cytotoxic T Lymphocyte—Associated Antigen 4 Plays an Essential Role in the Function of Cd25+Cd4+ Regulatory Cells That Control Intestinal Inflammation. J Exp. Med. 192: 295-302 (2000).
Reich et al., Infliximab induction and maintenance therapy for moderate-to-severe psoriasis: a phase III, multicentre, double-blind trial. The Lancet, vol. 366, Issue 9494, pp. 1367-1374, Oct. 15, 2005.
Riechmann et al., "Re-shaping human antibodies for therapy", Nature (1988); 332: 323-327.
Reinerz and Schlossman, The differentiation and function of human T lymphocytes. Cell 19, 821-827 (1980).
Reinerz et al., Discrete stages of human intrathymic differentiation: Analysis of normal thymocytes and leukemic lymphoblasts of T-cell lineage, PNAS USA 77, 1588-1592 (1980).
Reiter, C., et al., "Treatment of Rheumatoid Arthritis With Monoclonal CD4 Antibody M-T151," Arthritis & Rheumatism 1991;34(5):525-536.
Robinet, E., et al., "Clinical Improvement of a Patient With Severe Psoriasis Following CD4 Antibody Administration Despite a Blocking Antibody-host Response," Eur. J. Dermatol. 1996;6:141-146.
Robinet, E et al., "CD4 Monoclonal Antibody Administration in Atopic Dermatitis," J. Amer. Acad. Dermatol. 1997; 36:582-8.
Roitt, A. et al., Extract from Chapter 6, Immunology (2000), Moscow "Mir", pp. 110-111, and English translation of section bridging pp. 110-111.
Reczko, M., et al., "Prediction of hypervariable CDR-H3 loop structures in antibodies," Protein Eng. 1995;8(4):389-395.
Reddy, M.P., et al. Elimination of Fc receptor-dependent effector functions of a modified IgG4 monoclonal antibody to human CD4. J Immunol 164, 1925-1933 (2000).
Rep, M. H. G., et al., "Treatment with Depleting CD4 Monoclonal Antibody Results in a Preferential Loss of Circulating Naïve T Cells but Does Not Affect IFN-y Secreting TH1 Cells in Humans," J. Clin. Invest. 1997;99(9):2225-223.
Abufarag, A., et al., Selective activation of naturally occurring regulatory T cells (Tregs) by the monoclonal antibody BT-061 as a novel therapeutic opportunity is psoriasis: Early clinical results after single doses, J. Invest. Dermatol., 2010, vol. 130, Issue S2, Abstract No. 379.
Abufarag, A., et al., Selective activation of naturally occurring regulatory T cells (Tregs) by the monoclonal antibody BT-061 as a novel therapeutic opportunity in psoriasis: early clinical results after single doses, Poster No. 379, presented at 40th Annual Meeting of the European Society for Dermatological Research, Sep. 8-11, 2010, Helsinki, Finland.
Czeloth, N., et al., Selective activation of naturally occurring regulatory T cells (Tregs) by the monoclonal antibody BT-061 as a novel therapeutic opportunity: pre-clinical and early clinical results, Ann. Rheu. Dis. 2010; 69 (Suppl 3): 99, No. OP0138.
Fleischmann, R. M., Progressive multifocal leukoencephalopathy following rituximab treatment in a patient with rheumatoid arthritis, Arthritis Rheum., 2009; 60(11): 3225-8.
Jacobs, J. F. M., et al., Dendritic cell vaccination in combination with anti-CD25 monoclonal antibody treatment: a phase I/II study in metastatic melanoma patients, Clin. Cancer Res. 2010; 16: 5067-5078.
Moebius, U., et al., "The Human Immunodeficiency Virus gp120 Binding Site on CD4: Delineation by Quantitative Equilibrium and Kinetic Binding Studies of Mutants in Conjunction with a High-Resolution CD4 Atomic Structure", J. Exp. Med. 176, 507-517, 1992.
Pakula, A. A., et al., "Genetic analysis of protein stability and function", Annu. Rev. Genet., 1989; 23, 289-310, p. 289 & 306, 1989.
Tamura, M., et al., "Structural correlates of an anticarcinoma antibody: Identification of specificity-determining residues (SDRs) and development of a minimally immunogenic antibody variant by retention of SDRs only", The Journal of Immunology, 2000, 164: 1432-1441, 2000.
Wang, W., "Oral protein drug delivery", Journal of Drug Targeting, 1996, vol. 4, No. 4, pp. 195-232, 1996.
Biotest AG Press release—Biotest Phase IIb study of Tregalizumab (BT-061) in moderate to severe rheumatoide Arthritis did not meet the primary endpoint—potential one time effect of up to—EUR 30 million, Apr. 24, 2015, pp. 1-3, 2015.
Biotest half-year report of Aug. 11, 2015—Biotest increase revenues in first half year 2015 by 8.9%, pp. 1-3, 2015.
Severin, E. S., et al., "Biochemistry", textbook M.: Meditsina, 2000, 168 p.; p. 7 in Russian with English translation, 2009.
Final Office Action for co-pending U.S. Appl. No. 12/880,837 (dated Jun. 10, 2015).
Non-Final Office Action for co-pending U.S. Appl. No. 12/880,768 (dated Jun. 8, 2015).
Final Office Action for co-pending U.S. Appl. No. 13/074,357 (dated Sep. 17, 2015).
Abramowicz et al., Release of tumor necrosis factor, interleukin-2, and gamma-interferon in serum after injection of OKT3 monoclonal antibody in kidney transplant recipients. Transplantation. Apr. 1989;47(4):606-8.
Abramowicz et al, Anaphylactic shock after retreatment with OKT3 monoclonal antibody. N Engl. J Med. Sep. 3, 1992;327(10):736
Allez and Mayer, Regulatory T cells: peace keepers in the gut, Inflamm. Bowel Dis. Sep. 2004;10(5):666-76.
American College of Rheumatology Subcommittee on Rheumatoid Arthritis. Guidelines for the management of rheumatoid arthritis: 2002 update. Arthritis Rheum. (2002) 46(2):328-46.
Andersson, J., et al. CD4+ FoxP3+ regulatory T cells confer infectious tolerance in a TGF-beta-dependent manner. J Exp Med 205, 1975-1981 (2008).
Azuma et al., Human CD4+ CD25+ regulatory T cells suppress NKT cell functions. Cancer Research (2003); 63: 4516-4520.
Anderson et al., (1983) Antigens on human plasma cells identified by monoclonal antibodies. J Immunol. 130:1132-8.

(56) References Cited

OTHER PUBLICATIONS

Andersson et al., Neutralizing IL-21 and IL-15 inhibits pro-inflammatory cytokine production in rheumatoid arthritis. Scand J Immunol. Jul. 2008:68(1):103-11. Epub May 9, 2008.
Anderson, D., et al. A primatized MAb to human CD4 causes receptor modulation, without marked reduction in CD4+ T cells in chimpanzees: in vitro and in vivo characterization of a MAb (IDEC-CE9.1) to human CD4. Clin Immunol Immunopathol 84, 73-84 (1997).
Anonymous: T regalizumab (BT-061) shows efficacy in Chronic Plaque Psoriasis. Nov. 24, 2011, pp. 1-2.
Ansel et al., Pharmaceutical Dosage Forms and Drug Delivery Systems, Lippincott Williams & Wilkens, Philadelphia (1999), pp. 126-127.
Apostolou, I., Sarukhan, A., Klein, L. & von Boehmer, H. Origin of regulatory T cells with known specificity for antigen. Nat Immunol 3, 756-763 (2002).
Asano et al., Autoimmune disease as a consequence of developmental abnormality of a T cell subpopulation. J Exp. Med. 184:387-396 (1996).
Ashkenazi et al., Mapping the CD4 binding site for human immunodefincinecy virus by alanine-scanning mutagenesis, PNAS USA 87, 7150-7154 (1990).
Bach, Regulatory T cells under Scrutiny, Nat Rev Immunol. Mar. 2003;3(3):189-98.
Baecher-Allan et al. Functional analysis of highly defined, FACS-isolated populations of human regulatory CD4+CD25+ T cells, Clinical Immunology 115 (2005) 10-18.
Baecher-Allan et al. Inhibition of Human CD4+CD25+high Regulatory T Cell Function, Journal of Immunology (2002), 169:6210-6217.
Baecher-Allan et al., Human Regulatory T cells and their role in autoimmune disease. Immunol. Review 212: 203-216 (2006).
Bachelez et al., Treatment of recalcitrant plaque psoriasis with a humanized non-depleting antibody to CD4. J. Autoimmunity 1998; 11: 53-62.
Bartholomew, M.; et al., "Functional analysis of the effects of a fully humanized anti-CD4 antibody on resting and activated human T cells" Immunology 1995;85(1):41-48.
Baca et al., Antibody Humanization Using Monovalent Phage Display, J. Biol. Chem. 1997;272(16):10678¬10684.
Bayry et al., Rescuing CD4+CD25+ regulatory T-cell functions in rheumatoid arthritis by cytokine-targeted monoclonal antibody therapy. Drug Discov. Today. 2007; 12 (13-14): 548-552.
Balandina, A., Saoudi, A., Dartevelle, P. & Berrih-Aknin, S. Analysis of CD4+CD25+ cell population in the thymus from myasthenia gravis patients. Ann N Y Acad Sci 998, 275-277 (2003).
Becker et al., Functional activation of human CD4+CD25+ regulatory T cells by an anti-CD4 antibody, 9th Basic Science Symposium of the Transplantation Society, Nantes, Abstract No. 24, Jun. 22, 2005.
Becker et al., Induction of suppressive activity in human CD4+CD25+ regulatory T cells by an anti-CD4 antibody, Abstract Marburg 2005.
Becker et al., Funktionelle Aktivierung humaner CD4+CD25+ regulatorischer T-Zellen durch einer anti-CD4 Antikörper (Functional activation of human CD4+CD25+ regulatory T cells by an anti-CD4 antibody), Allergieworkshop 2005, Abstract and Presentation, Johannes Gutenberg Universität Mainz.
Bennett, C.L., et al. The immune dysregulation, polyendocrinopathy, enteropathy, X-linked syndrome (IPEX) is caused by mutations of FOXP3. Nat Genet 27, 20-21 (2001).
Brooks, P. & Hochberg, M. Outcome measures and classification criteria for the rheumatic diseases. A compilation of data from OMERACT (Outcome Measures for Arthritis Clinical Trials), ILAR (International League of Associations for Rheumatology), regional leagues and other groups. Rheumatology (Oxford) 40, 896-906 (2001).

Kaufman, A. & Herold, K.C. Anti-CD3 mAbs for treatment of type 1 diabetes. Diabetes Metab Res Rev 25, 302-306 (2009). Published online: Mar. 24, 2009.
Becker et al., Protection from graft-versus-host disease by HIV-1 envelope protein gp120-mediated activation of human CD4+CD25+ regulatory T cells, Blood 114, 1263-1269 (2009).
Beyersdorf et al., Selective targeting of regulatory T cells with CD28 superagonists allows effective therapy of experimental autoimmune encephalomyelitis. J. Exp. Med. (2005) 202(3): 445-455.
Beste et al., Small antibody-like proteins with prescribed ligand specificities derived from the lipocalin fold, Proc. Natl. Acad. Sci. USA 96, 1898-1903 (1999).
Biaze et al., T cell activation, from atopy to asthma: more a paradox than a paradigm. Allergy Sep. 2003; 58(9): 844.
Biotest AG/Research Update, DGAP publisher, Sep. 8, 2008, pp. 1-2.
Biotest AG, Analystenkonferenz Slides, Sep. 29, 2008.
Beissert et al., Regulatory T cells. J Investigative Dermatology, 126:15-24, 2006.
Becker et al., CD4-mediated activation of human CD4+CD25+ regulatory T cells, Experimental Dermatology 2006, 15, Abstract, p. 204 (33rd Meeting of the Arbeitsgemeinschaft Dermatologische Forschung (ADF), Aachen, Germany, Mar. 23-25, 2006.
Brass et al., Identification of Host Protein Required for HIV Infection Through a Functional Genomics Screen, Science 319, 921-926 (2008).
Bruhns et al., Specificity and affinity of human Fcgamma receptors and their polymorphic variants for human IgG subclasses. Blood 2009. 113: 3716. Epub. Nov. 18, 2008.
Burgdorf et al., Distinct Pathways of Antigen Uptake and Intracellular Routing in CD4 and CD8 T Cell Activation, Science 316, 612-616 (2007).
Bone and Handy, Ab initio studies of internal rotation barriers and vibrational frequencies of $(C2H2)2$, $(CO2)2$, and $C2H2$—$CO2$, Theor. Chim. Acta 78, 133-163 (1990).
Bonomo et al., Pathogenesis of post-thymectomy autoimmunity. Role of syngeneic MLR-reactive T cells. J. Immunol. 154: 6602-6611 (1995).
Bopp et al., Cyclic adenosine monophosphate is key component of regulatory T cell-mediated suppression. J. Exp. Med. 2007; 204: 1303-1310.
Borselino et al., Expression of ectonucleotidase CD39 by Foxp3+ Treg cells: hydrolysis of extracellular ATP and immune suppression. Blood (2007) 110, 1225-1232.
Boshart, M., et al. "A Very Strong Enhancer Is Located Upstream of an Immediate Early Gene of Human Cytomegalovirus," Cell 1985;41:521-530.
Briand et al., Application and limitations of the multi antigen peptide (MAP) system in the production and evaluation of anti-peptide and anti-protein antibodies. J Immunol Methods (1992). 156; 2: pp. 255-265.
Camara et al., Human CD4+CD25+ regulatory cells have marked and sustained effects on CD8+ T cell activation. Eur. J. Immunol. 2003; 33: 3473-3483.
Cammarota et al., Identification of a CD4 binding site on the beta2 domain of HLA-DR molecules, Nature 356, 799-801 (1992).
Cao and Leroux-Roels Antigen-specific T cell responses in human peripheral blood leucocyte (hu-PBL-)-mouse chimera conditioned with radiation and an antibody directed against the mouse IL-2 receptor beta-chain.Clin. Exp. Immunol. Oct. 2000;122(1): 117-123.
Cao et al., Isolation and functional characterisation of regulatory CD25brightCD4+ T cells from the target organ of patients with rheumatoid arthritis. Eur J Immunol, 33: 215-223, 2003.
Hoffmann, P., et al., Large-scale in vitro expansion of polyclonal human CD4+ CD25 high regulatory T cells. Blood. 2004; 104(3): 895-903.
Khapalyuk, A.V., "The Genera Questions of Clinical Pharmacology and Demonstrative Medicine", Minsk, Oformlenie, 2003, 90 p., p. 49, pp. 9-11, 25-31.
Klareskog, L., et al., "Therapeutic effect of the combination of etanercept and methotrexate compared with each treatment alone in

(56) References Cited

OTHER PUBLICATIONS patients with rheumatoid arthritis: double-blind randomised controlled trial", The Lancet (2004) 363: 675-681.
Ramalingam, T. R., et al., "Ramalingam et al., Exploiting worm and allergy models to understand Th2 cytokine biology," Curr. Opin. Allergy Clin. Immunol. 2005; 5(5): 392-8.
Reich, G., "Pharmaceutical Formulations and Clinical Application", Chapter 10, pp. 239-265, Handbook of Therapeutic Antibodies, Ed. S. Dübel, Wiley-VCH Verlag GmbH & Co. KGaA, Weinheim, 2007.
Wijdenes, J., Slides presented during oral presentation in Heidelberg in Aug. 2003.
Nandakuma, S., et al., "T regulatory cells: an overview and intervention techniques to modulate allergy outcome," Clin. Mol. Allergy. 2009;7:5 (published online Mar. 12, 2009).
Robinson, D.S., "Regulatory T cells and asthma," Clin. Exp. Allergy. 2009; 39(9): 1314-23 (published online Jun. 17, 2009).
Cao et al., CD25brightCD4+ regulatory T cells are enriched in inflamed joints of patients with chronic rheumatic disease. Arthritis Res Ther, 6(4): R335-46, 2004.
Carr et al., Protein and carbohydrate structural analysis of a recombinant soluble CD4 receptor by mass spectrometry, J. Biol. Chem. 264, 21286-21295 (1989).
Carriere et al., "CD4 Masking during Human Immunodeficiency Virus Type 1 Infection, Quantified on Peripheral Blood Lymphocytes, Is a Potential Marker of Disease Progression" J. Inf. Dis. 1996;173: 565-73.
Carter et al., Humanization of an anti-p185HER2 antibody for human cancer therapy, Proc. Natl. Acad. Sci. USA 89, 4285-4289 (1992).
Canva-Delcambre, V., et al., "Treatment of severe Crohn's disease with anti-CD4 monoclonal antibody," Aliment. Pharmacol. Ther. 1996;10:721-727.
Chapman et al, "Therapeutic antibody fragments with prolonged in vivo half-lives," Nature Biotechnol. 1999;17:780-783.
Chen et al., Induction of autoantigen-specific Th2 and Tr1 regulatory T cells and modulation of autoimmune diabetes. J. Immunol. Jul. 15, 2003; 171: 733-744.
Chothia, C., et. al, "Conformation of immunoglobulin hypervariable regions," Nature 1989;342:877-883.
Chothia, C., et al "Canonical Structures for the Hypervariable Regions of Immunoglobulins," J. Mol. Biol. 1987;196:901-917.
Cohen, J. L., et al, "CD4+CD25+ Immunoregulatory T Cells: New Therapeutics for Graft-Versus-Host Disease," J. Exp, Med. 2002;196(3):401-406.
Coloma, M. J., et al., "Primer Design for the Cloning of Immunoglobulin Heavy-Chain Leader-Variable Regions from Mouse Hybridoma Cells Using the PCR," BioTechniques 1991;11(2):152-156.
Common Terminology Criteria for Adverse Events, Aug. 9, 2006, web page: http://ctep.cancer.gov/protocolDevelopment/electonic_applications/docs/ctcaev3.pdf.
Chen et al., Regulatory T cell clones induced by oral tolerance: suppression of autoimmune encephalomyelitis. Science 265:1237-1240 (1994).
Choy et al., Monoclonal antibody therapy in rheumatoid arthritis, B. J. Rheumatol. 1998;37: 484-490.
Choy et al., Pharmacokinetic, pharmacodynamic and clinical effects of a humanized IgG1 anti-CD4 monoclonal antibody in the peripheral blood and synovial fluid of rheumatoid arthritis. Rheumatology 39(10): 1139-46 (2000).
Choy et al., Repeat-cycle study of high-dose intravenous 4162W94 anti-CD4 humanized monoclonal antibody in rheumatoid arthritis. A randomized placebo-controlled trial. Rheumatology 41 (10):1142-8 (2002).
Choy et al., "Anti-CD4 monoclonal antibodies in rheumatoid arthritis," Springer Semin. Immunopathol. 1998;20:261-273.
Casset et al., "A peptide mimetic of an anti-CD4 monoclonal antibody by rational design," Biochem Biophys. Res. Comm. 2003;307:198-205.

Choy et al., "Chimaeric anti-CD4 monoclonal antibody cross-linked by monocyte Fcγ receptor mediates apoptosis of human CD4 lymphocytes," Eur. J. Immunol. 1993;23:2676-2681.
Choy, E. H. S., et al., "Percentage of Anti-CD4 Monoclonal Antibody-Coated Lymphocytes in the Rheumatoid Joint is Associated With Clinical Improvement," Arthritis & Rheumatism 1996;39(1):52-56.
Choy et al., Efficacy of a novel PEGylated humanized anti-TNF fragment (CDP870) in patients with rheumatoid arthritis: a phase II double-blinded, randomized, dose-escalating trial. Rheumatology 2002; 41: 1133-1137.
Mandapathil et al., Isolation of functional human regulatory T cells (Treg) from the peripheral blood based on the CD39 expression. J Immunol. Methods (2009). 346 (1-2), 55-63). Published Jul. 31, 2009.
Committee for Medicinal Products for Human Use (CHMP). Guideline on clinical investigation of medicinal products for the treatment of psoriasis. Nov. 18, 2004.
Shevach et al., Mechanism of Foxp3+ T regulatory cell-mediated suppression. Immunity (2009) 30; 636-645). Published May 22, 2009.
Dantal, J., et al., "Anti-CD4 MAb Therapy in Kidney Transplantation—A Pilot Study in Early Prophylaxis of Rejection," Transplantation 1996;62(10):1502-1506.
Darby, C. R., et al., "Nondepleting Anti-CD4 Antibodies in Transplantation," Transplant, 1994;57(10):1419-1426.
Dieckmann, D., et al, "Ex Vivo Isolation and Characterization of CD4+CD25+ T Cells with Regulatory Properties from Human Blood," J. Exp. Med. 2001;193(11):1303-1310.
Dieckman et al., Activated CD4+CD25+ T cells suppress antigen-specific CD4+ and CD8+ T cells but induce a suppressive phenotype only in CD4+ T cells. Immunology 2005; 115(3): 305-14.
Dowd et al., β-Turn Phe in HIV-1 Env Binding Site of CD4 and CD4 Mimetic Miniprotein Enhances Env Binding Affinity but is Not Required for Activation of Co-Receptor/17b Site, Biochemistry 41, 7038-7046 (2002).
DuBois D; DuBois EF: A formula to estimate the approximate surface area if height and weight be known. Arch Int Med 1916 17:863-71.
Dynabeads Reg CD4+CD25+ T Cell Kit Leaflet (Invitrogen) Copyright 2008.
Dynal Pure and Functional Treg cells: Isolate human and mouse regulatory T cells with Dynabeads (Invitrogen) Copyright 2008.
Earle et al., In vitro expanded human CD4+CD25+ regulatory T cells suppress effector T cell proliferation. Clin. Immunol. (2005) 115: 3-9.
Edmundson A. B., et al., "A Search for Site-Filling Ligands in the Mcg Bence-Jones Diener: Crystal Binding Studies of Fluorescent Compounds," Mol, Immunol, 1984;21(7):561-576.
Ehrenstein et al., Compromised function of regulatory T cells in rheumatoid arthritis and reversal by anti-TNFalpha therapy. J. Exp. Med. 2004; 200(3): 277-285.
Ellis and Mohanakumar, Dissociation of autologous and allogeneic mixed lymphocyte reactivity by using a monoclonal antibody specific for human T helper cells, J. Immunol. 1983, 131(5): 2323-7.
Fehérvari and Sakaguchi, CD4+ Tregs and immune control. J Clin Invest, 114 (9):1209-1217, 2004.
Felgner, P. L. et al., "Lipofection: A highly efficient, lipid-mediated DNA-transfection procedure," Proc. Natl. Acad. Sci. USA 1987;84:7413-7417.
Felson, D.T., et al. The American College of Rheumatology preliminary core set of disease activity measures for rheumatoid arthritis clinical trials. The Committee on Outcome Measures in Rheumatoid Arthritis Clinical Trials. Arthritis Rheum 36, 729-740 (1993).
Fontenot, J.D., Gavin, M.A. & Rudensky, A.Y. Foxp3 programs the development and function of CD4+CD25+ regulatory T cells. Nat Immunol 4, 330-336 (2003).
Fellouse et al., "Synthetic antibodies from a four-amino-acid code: A dominant role for tyrosine in antigen recognition" PNAS Aug. 2004; 101:12467-12472.

(56) References Cited

OTHER PUBLICATIONS

Foote, J., et al., "Antibody Framework Residues Affecting the Conformation of the Hypervariable Loops," J. Mol. Biol. 1992;224:487-499.
Fournel et al., "Clonal deletion and clonal anergy mediated by antibodies to the human CD4 protein," pp. 255-264 from Rejection and tolerance: proceedings of the 25th Conference on Transplantation and Clinical Immunology, published by Springer, 1994.
Fleischmann et al., Efficacy and safety of certolizumab pegol monotherapy every 4 weeks in patients with rheumatoid arthritis failing previous disease-modifying antirheumatic therapy: the FAST4WARD study. Ann Rheum Dis. Jun. 2009;68(6):805-11. Epub Nov. 17, 2008.
Fleischmann RM., Safety of biologic therapy in rheumatoid arthritis and other autoimmune diseases: focus on rituximab. Semin Arthritis Rheum. Feb. 2009;38(4):265-80. Epub Mar. 12, 2008.
Furst et al., Adalimumab, a fully human anti tumor necrosis factor-alpha monoclonal antibody, and concomitant standard antirheumatic therapy for the treatment of rheumatoid arthritis: results of STAR (Safety Trial of Adalimumab in Rheumatoid Arthritis). J. Rheumatol. Dec. 2003;30(12):2563-71.
Felson et al., Preliminary definition of improvement in rheumatoid arthritis. Arthritis & Rheumatism, 1995, 38(6), 727-735.
Fitch, T-cell clones and T-cell receptors, Microbiol. Rev. 50, 50-69 (1986).
Froebel et al., 1999. Standardization and quality assurance of lymphocyte proliferation assays for use in the assessment of immune function. J. Immunol. Methods 227: 85-97.
Fuss et al., Nonclassical CD1d-restricted Nk T cells that produce IL-13 characterize an atypical Th2 response in ulcerative colitis. J. Clin. Invest. (2004): 113(10): 1490-1497.
Tracey et al., Tumor necrosis factor antagonist mechanisms of action: a comprehensive review. Pharmacol Ther. Feb. 2008;117(2):244-79. Epub Oct. 26, 2007.
Tamm et al., IgG binding sites on human Fcgamma receptors. Intern. Rev. Immunol. 1997; 16: 57-85.
Tak, P. P., et al., "Reduction of Synovial inflammation After Anti-CD4 Monoclonal Antibody Treatment in Early Rheumatoid Arthritis," Arth. Rheum. 1995;38(1):1457-1465.
Takahashi, T., et al., "Immunologic self-tolerance maintained by CD4+CD25+naturally anergic and suppressive T cells: Induction of autoimmune disease by breaking their anergic/suppressive state," Internatl. Immunol. 1998;10(12):1969-1980.
Takahashi, N., et al., "Structure of Human Immunoglobulin Gamma Genes: Implication for Evolution of a Gene Family," Cell 1982;29(2):671-679.
Taylor, P. A., et al., "The infusion of ex vivo activated and expanded CD4+CD25+ immune regulatory cells inhibits graft-versus-host disease lethality," Blood 2002;99(10):3493-3499.
Thornton, A. M., et al., "Suppressor Effector Function of CD4+CD25+ Immunoregulatory T Cells Is Antigen Nonspecific," J. Immunol. 2000;164:183-190.
Thornton and Shevach, CD4+CD25+ immunoregulatory T cell suppress polyclonal T cell activation in vitro by inhibiting interleukin-2 production, J. Exp. Med. 1998; 188(2): 287-96.
Tifft et al., The Folding and Cell Surface Expression of CD4 Requires Glycosylation, J. Biol. Chem. 267, 3268-3273 (1992).
Traggiai et al., Development of a human adaptive immune system in cord blood cell-transplanted mice. Science 304, 104-7, 2004.
Tribbick et al., Multipin peptide libraries for antibody and receptor epitope screening and characterization. J Immunl. Methods (2002) 267: 27-35).
Trickett et al, T cell stimulation and expansion using anti-CD3/CD28 beads, J. Immunol. Methods, 2003; 275: 251-255.
Tuosto et al., Differential susceptibility of monomeric HIV gp120-mediateds apoptosis in antigen-activated CD4+ T cell populations, Eur. J. Immunol. 25, 2907-2916 (1995).
The Merck Manual of Diagnosis and Therapy, Merck Research Laboratories, 1999, pp. 940-941, 949-951 and 968-969.

Valencia, X., et al., TNF downmodulates the function of human CD4(+) CD25 hi T regulatory cells. Blood (2006); 108(1): 253-261.
van Der Lubbe, P. A., et al., "Chimeric CD4 Monoclonal Antibody cM-T412 as a Therapeutic Approach to Rheumatoid Arthritis," Arthritis & Rheumatism 1993;36(10):1375-1379.
Verbraecken J, Van de Heyning P, De Backer W, Van Gaal L. Body surface area in normal-weight, overweight, and obese adults. A comparison study. Metabolism. Apr. 2006;55(4):515-24.
van Amelsfort et al., CD4(+)CD25(+) regulatory T cells in rheumatoid arthritis: differences in the presence, phenotype, and function between peripheral blood and synovial fluid. Arthritis Rheum, 50 (9): 2775-2785, 2004.
van de Putte et al., Efficacy and safety of the fully human anti-tumour necrosis factor α monoclonal antibody adalimumab (D2E7) in DMARD refractory patients with rheumatoid arthritis: a 12 week, phase II study. Ann Rheum Dis. 2003; 62: 1168-1177.
van de Putte et al., Efficacy and safety of adalimumab as monotherapy in patients with rheumatoid arthritis for whom previous disease modifying antirheumatic drug treatment has failed. Ann. Rheum. Dis. (2004); 63: 508-516.
Viglietta et al., Loss of functional suppression by CD4+CD25+ regulatory T cell in patients with multiple sclerosis. J Exp Med 199: 971-979, 2004.
Veillette et al., The CD4 and CD8 T cell surface antigens are associated with the internal membrane tyrosine-protein kinase p56lck, Cell 55, 301 (1988).
Vieira, J., et al., "Production of Single-Stranded Plasmid DNA," Methods Enzymol. 1987;153:3-11.
Vogt et al., Construction of an Artificial Receptor Protein ("Anticalin") Based on the Human Apolipoprotein D, ChemBioChem 5, 191-199 (2004).
Voo et al., Identification of IL-17-producing FOXP3+ regulatory T cells in humans, Proc. Natl. Acad. Sci. USA 106, 4793-4798 (2009) Epub Mar 9, 2009.
Ward, S., et al., "Binding activities of a repertoire of single immunoglobulin variable domains secreted from *Escherichia coli*," Nature 1989;341;544-546.
Wendling, D., et al., "Treatment of Rheumatoid Arthritis with Anti CD4 Monoclonal Antibody. Open Study of 25 Patients with the B-F5 Clone," Clin. Rheumatol. 1992;11(4):542-547.
Wendling, D., et al., "A Randomized, Double Blind, Placebo Controlled Multicenter Trial of Murine Anti-CD4 Monoclonal Antibody Therapy in Rheumatoid Arthritis," J. Rheumatol. 1998;25(8):1457-1461.
Wendling et al., Combination therapy of anti-CD4 and anti-IL6 monoclonal antibodies in a case of severe spondylarthropathy. British J. Of Rheumatol. 1996. 35(12): 1330.
Wessels et al., Recent insights in the pharmacological actions of methotrexate in the treatment of rheumatoid arthritis. Rheumatology (Oxford). Mar. 2008;47(3):249-55. Epub Nov. 28, 2007.
Walsh et al., Tregs and transplantation tolerance, J. Clin. Invest. 2004; 114(10): 1398-1403.
Wang et al., Crystal structure of the human CD4 N-terminal two-domain fragment complexed to a class II MHC molecule, Proc. Natl. Acad. Sci. USA 98, 10799-10804 (2001).
Wascher et al., Cell-type specific response of peripheral blood lymphocytes to methotrexate in the treatment of rheumatoid arthritis. Clin Investig. Jul. 1994;72(7):535-40.
Webster's New World Dictionary, Third College Edition, 1988, pp. 1067-1068.
Wendling et al., Therapeutic use of monoclonal anti-CD4 antibody in rheumatoid arthritis. J Rheumatol 18, 325-327, 1991.
Wijdenes et al., Monoclonal antibodies in human organ transplantation and auto-immune disease. Therapie 1992; 47: 283-7.
Wijdenes et al., A new type of monoclonal antibody to CD4 for the therapy of rheumatoid arthritis (RA). Poster, EULAR 2005.
Wijngaarden et al., A shift in the balance of inhibitory and activating Fcgamma receptors on monocytes toward the inhibitory Fcgamma receptor IIb is associated with prevention of monocyte activation in rheumatoid arthritis.Arthritis Rheum. Dec. 2004;50(12):3878-87.
Wijngaarden et al., Down-regulation of activating Fcgamma receptors on monocytes of patients with rheumatoid arthritis upon

(56) References Cited

OTHER PUBLICATIONS methotrexate treatment. Rheumatology (Oxford). Jun. 2005;44(6):729-34. Epub Mar. 9, 2005.
Wijngaarden et al., Treatment of rheumatoid arthritis patients with anti-TNF-alpha monoclonal antibody is accompanied by down-regulation of the activating Fcgamma receptor I on monocytes. Clin Exp Rheumatol. Jan.-Feb. 2008;26(1):89-95.
Willerford et al., Interleukin-2 receptor alpha chain regulates the size and content of the peripheral lymphoid compartment. Immunity 3: 521-530 (1995).
Willkommen and Löwer. Theoretical considerations on viral inactivation or elimination. Brown F (ed): Virological Safety Aspects of Plasma Derivatives Dev Biol Stand. Basel, Karger 1993, vol. 81: 109-116.
Yamaguchi et al., Control of immune responses by antigen-specific regulatory T cells expressing the folate receptor. Immunity. Jul. 2007;27(1):145-59. Epub Jul. 5, 2007.
Yi et al., The effects of antibody treatment on regulatory CD4+CD25+ T cells. Transplant Immunol. 2007; 19(1): 37-44.
Zhou et al., Structural definition of a conserved neutralization epitope on HIV-1 gp120, Nature 445, 732-737 (2007).
Zhu, Z., et al., "Inhibition of human leukemia in an animal model with human antibodies directed against vascular endothelial growth factor 2. Correlation between antibody affinity and biological activity," Leukemia 2003;17:604¬611.
Anonymous, Further interim analyses confirm good clinical efficacy of the BT-061 monoclonal antibody. Biotest Press Release. Evaluate Pharma. Jul. 7, 2009.
Biotest Analyst Conference. Mar. 11, 2009, pp. 28-37.
Abramowicz et al., Release of tumor necrosis factor, interleukin-2, and gamma-interferon in serum after injection of OKT3 monoclonal antibody in kidney transplant recipients. Transplantation. Apr. 1989;47(4):606-8 .
American College of Rheumatology Subcommittee on Rheumatoid Arthritis. Guidelines for the management of arthritis: 2002 update. Arthritis Rheum. (2002) 46(2):328-46 rheumatoid.
Andersson et al., Neutralizing IL-21 and IL-15 inhibits pro-inflammatory cytokine production in rheumatoid arthritis. Scand J Immunol. Jul. 2008;68(1):103-11. Epub May 9, 2008.
Camara et al., Human CD4+CD25° regulatory cells have marked and sustained effects on CD8+ T cell activation. Eur. J. Immunol. 2003; 33: 3473-3483.
Anderson, A. E., et al., "Tregs and Rheumatoid Arthritis," Acta Rheumatol. Port. 2008;33:17-33.
Cools, N., et al., "Regulatory T Cells and Human Disease," Clinical and Developmental Immunology, vol. 2007, pp. 1-11.
Korn, T., et al., "Dynamics of antigen-specific regulatory T-cells in the context of autoimmunity," Seminars in Immunol. 2007;19:272-278.
Lobo, E. D., et al., "Antibody Pharmacokinetics and Pharmacodynamics," J. Pharm. Sci. 2004;93(11):2645-2668.
Mäkinen, H., et al., "Definition of remission for rheumatoid arthritis and review of selected clinical cohorts and randomised clinical trials for the rate of remission," Clin. Exp. Rheumatol. 2006;24(Suppl. 43):S22-S28.
MedLinePlus dictionary sponsored by the National Institutes of Health and the National Library of medicine, pp. 1-3, downloaded Nov. 14, 2014, see http://www.meriam-webster.com/medlineplus/dose.
Merriam Webster online dictionary definition of "dose," pp. 1-4, downloaded Nov. 14, 2014, http://www.meriam-webster.com/dictionary/dose.
Non-Final Office Action for co-pending U.S. Appl. No. 12/880,837 (dated Dec. 2, 2014).
Non-Final Office Action for co-pending U.S. Appl. No. 12/880,623 (dated Nov. 28, 2014).
Non-Final Office Action for co-pending U.S. Appl. No. 12/880,768 (dated Nov. 26, 2014).

Pincus, T., "Quantitative measure for assessing rheumatoid arthritis in clinical trials and clinical care," Best Practice & Research Clinical Rheumatology 2003;17(5):753-781.
Vajdos, F. F., et al., "Comprehensive Functional Maps of the Antigen-binding Site of an Anti-ErbB2 Antibody Obtained with Shotgun Scanning Mutagenesis," J. Mol. Biol. 2002;320:415-428.
Pincus, T., et al., "Methotrexate as the "anchor drug" for the treatment of early rheumatoid arthritis," Clin. Exp. Rheumatol. 2003;21(Suppl. 31):S179-S185.
Lorenz, H.-M., et al., "Biological Agents in Rheumatoid Arthritis," BioDrugs 1998;4:303-324.
Becker, C., et al., "CD4-mediates functional activation of human CD4+CD25+ regulatory T cells," Eur. J. Immunol. 2007;37:1217-1223.
Strom T. B., et al., "Therapeutic Approach to Organ Transplantation," Therapeutic Immunology edited by Austen et al., Blackwell Science, Cambridge, MA, 1996; pp. 451-456.
The Biotest AG Company Presentation dated Jan. 2008, pp. 1-33.
Colman, P. M., "Effects of amino acid sequence changes on antibody-antigen interactions," Res. Immunol. 1994;145:33-36.
Cronstein, B. N., "Low-Dose Methotrexate: A Mainstay in the Treatment of Rheumatoid Arthritis," Pharmacol. Rev. 2005;57:163-172.
Rudikoff, S., et al., "Single amino acid substitution altering antigen-binding specificity," Proc. Natl. Acad. Sci. USA 1982:79:1979-1983.
Wijdenes, J., et al., "A New Type of Monoclonal Antibody to CD4 for the Therapy of Rheumatoid Arthritis (RA)," Ann. Rheum. Dis. 2005;64(Suppl. III):444.
Lack, J.A., et al., "Calculation of drug dosage and body surface area of children," Br. J. Anaesth. 1997;78(5):601-605.
Dimasi J. A., et al., "The price of innovation: new estimates of drug development costs," J. Health Economics 2003;22:151-185.
Biotest half-year report of Jun. 30, 2008, pp. 1-6.
Biotest Analyst Conference, Mar. 20, 2008, pp. 0-38.
Feldmann, M., et al., "Role of cytokines in rheumatoid arthritis: an education in pathophysiology and therapeutics," Immunol. Rev. 2008;223:7-19.
Bingham et al., "Immunization responses in rheumatoid arthritis patients treated with rituximab: results from a controlled clinical trial", Arthritis & Rheum, 2010; 62(1): 64-74.
Duarte et al., "Natural Treg cells spontaneously differentiate into pathogenic helper cells in lymphopenic conditions", Eur. J. Immunol., (2009) 39:948-55.
Lloyd and Hawrylowicz, "Regulatory T cells in Asthma", Immunity (2009), 31(3): 438-449.
Love & Hayes, "ITAM-mediated signalling by the T-cell antigen receptor" , Cold Srping Harb. Perspect. Biol. 2, a002485 (2010) Epub Apr. 28, 2010.
Ohlson et al., "Detection and characterization of weak affinity antibody antigen recognition with biomolecular interaction analysis", J. Mol Recognit. May-Jun. 1997; 10(3): 135-8.
Salemi, S. et al., "HIVgp120 Activates Autoreactive CD4-specific T Cell Responses by Unveiling of Hidden CD4 Peptides During Processing", Journal of Experimental Medicine. 1995 vol. 181 pp. 2253-2257.
Song et al., "Epitope matting of ibalizumab, a humanized anti-CD4 monoclonal antibody with anti-HIV activity in infected patients", J. Virol. 2010; 84(14): 6935-42 Epub. May 12, 2010.
Tarantul V.Z. Explanatory dictionary of biotechnology. Russian-English, M. Yaziki slavyanskih kultur, 2009, p. 510 + English translation of cited paragraph.
Zhou et al., "Foxp3 instability leads to the generation of pathogenic memory T cells in vivo", Nat Immunol. Sep. 2009; 10(9):1000-1007, Published online Jul. 26, 2009.
Makrides, S. C., "Components of Vectors for Gene Transfer and Expression in Mammalian Cells," Protein Expression and Purification 1999;17:183-202.
Non-Final Office Action from co-pending U.S. Appl. No. 14/176,485 (dated Dec. 9, 2016).
Helling, B., et al., "A specific CD4 epitope bound by tregalizumab mediates activation of regulatory T cells by a unique signaling pathway", Immunology and Cell Biology (2015) 93, 396-405.

(56) References Cited

OTHER PUBLICATIONS

Freidlin, I. S., "Regulatory T Cells: Origin and Function," Med. Immunol. 2005;7(4):347-354, with English language translation thereof.

Moore, J. P., et al., "A Monoclonal Antibody to CD4 Domain 2 Blocks Soluble CD4-Induced Conformational Change in the Envelope Glycoproteins of Human Immunodeficiency Virus Type 1 (HIV-1) and HIV-1 Infection of CD4+ Cells," J. Virol. 1992;66(8):4784-4793.

Krueger, G. G., et al., "A randomized, double-blind, placebo-controlled phase III study evaluating efficacy and tolerability of 2 courses of alefacept in patients with chronic plaque psoriasis," J. Am. Acad. Dermatol. 2002;47 (6):821-833.

Rudnev, A., et al., "[1125]—Selective Activation of Naturally Occurring Regulatory T Cells (Tregs) by the Monoclonal Antibody (mAb) BT-061. Markers of Clinical Activity and Early Phase II Results in Patients with Rheumatoid Arthritis," American College of Rheumatology 2010 Annual Scientific Meeting, Abstract 1125, Presented Tuesday, Nov. 9, 2010.

Dore, J.-M., et al., "Identification and location on syndecan-1 core protein of the epitopes of B-B2 and B-B4 monoclonal antibodies," FEBS Lett. 1998;426:67-70.

Hartl, D., et al., "Quantitative and functional impairment of pulmonary CD4+CD25hi regulatory T cells in pediatric asthma," J. Allergy Clin. Immunol. 2007;119:1258-1266.

Van Amelsfort, J. M. R., et al., "Proinflammatory Mediator-Induced Reversal of CD4+, CD25+ Regulatory T Cell-Mediated Suppression in Rheumatoid Arthritis," Arthritis & Rheumatism, Mar. 2007, vol. 56, No. 3, pp. 732-742.

Williams, R. O., et al., "Synergy between anti-CD4 and anti-tumor necrosis factor in the amelioration of established collagen-induced arthritis," Proc. Natl. Acad. Sci. USA 1994;91:2762-2766.

Wailoo, A., et al., Agency for Healthcare Research and Quality, 540 Gaither Road, Rockville, MD 20850, Oct. 12, 2006, pp. 1-74.

Office Action from U.S. Appl. No. 13/074,357 (dated Mar. 30, 2016).

Notices of Allowance/Allowability from U.S. Appl. No. 14/176,485 dated May 18, 2017.

Van Maurik, A., et al., "Cutting Edge: CD4+CD25+ Alloantigen-Specific Immunoregulatory Cells That Can Prevent CD8+ T Cell-Mediated Graft Rejection: Implications for Anti-CD154 Immunotherapy," J. Immunol. 2002;169:5401-5404.

Kingsley, C. I., et al., "CD25+CD4+ Regulatory T Cells Prevent Graft Rejection: CTLA-4- and IL-10-Dependent Immunoregulation of Alloresponses," J. Immunol. 2002;168:1080-1086.

Wood, K. J., et al., "Regulatory T Cells in Transplantation Tolerance," Nat. Rev. Immunol. 2003;3:199-210.

"Life After Your Transplant: Signs of Rejection," WebMD, Organt Transplant Rejection Signs, downloaded May 10, 2017, http://www.webmd.com/a-to-z-guides/life-after-transplant-signs-rejection, pp. 1-4.

"Managing Your Health After an Organ Transplant," WebMD, After an Organ Transplant: Medication, Preventing Rejection, Diet and More, downloaded May 10, 2017, http://www.webmd.com/a-to-z-guides/organ-transplant-after-the-transplant, pp. 1-7.

Rajpal, A., et al., "A general method for greatly improving the affinity of antibodies by using combinatorial libraries," PNAS 2005;102(24):8466-8471.

```
              10          20          30          40          50          60
        MNRGVPPRHL  LLVLQLALLP  AATQGKKVVL  GKKGDTVELT  CTASQKKSIQ  FHWKNSNQIK 70          80          90         100         110         120
        ILGNQGSFLT  KGPSKLNDRA  DSRRSLWDQG  NFPLIIKNLK  IEDSDTYICE  VEDQKEEVQL 130         140         150         160         170         180
        LVFGLTANSD  THLLQGQSLT  LTLESPPGSS  PSVQCRSPRG  KNIQGGKTLS  VSQLELQDSG 190         200         210         220         230         240
        TWTCTVLQNQ  RKVEFKIDIV  VLAFQKASSI  VYKKEGEQVE  FSFPLAFTVE  KLTGSGELWW 250         260         270         280         290         300
        QAERASSSKS  WITFDLKNKE  VSVKRVTQDP  KLQMGKKLPL  HLTLPQALPQ  YAGSGNLTLA 310         320         330         340         350         360
        LEAKTGKLHQ  EVNLVVMRAT  QLQKNLTCEV  WGPTSPKLML  SLKLENKEAK  VSKREKAVWV 370         380         390         400         410         420
        LNPEAGMWQC  LLSDSGQVLL  ESNIKVLPTW  STPVQPMALI  VLGGVAGLLL  FIGLGIFFCV 430         440         450
        RCRHRRRQAE  RMSQIKRLLS  RKKTCQCPHR  FQKTCSPI
``` not represented by
the crystal structure

Figure 1

A. Light chain.

```
         10          20          30          40          50          60
                                    ..........CDR1..........              .....CDR2.....
DIVMTQSPDS  LAVSLGERAT  INCRASKSVS  TSGYSYIYWY  QQKPGQPPKL  LIYLASILES 70          80          90         100         110         120
                                                ......CDR3......
GVPDRFSGSG  SGTDFTLTIS  SLQAEDVAVY  YCQHSRELPW  TFGQGTKVEI  KRTVAAPSVF 130         140         150         160         170         180
IFPPSDEQLK  SGTASVVCLL  NNFYPREAKV  QWKVDNALQS  GNSQESVTEQ  DSKDSTYSLS 190         200         210
STLTLSKADY  EKHKVYACEV  THQGLSSPVT  KSFNRGEC
```

Figure 2A

B. Heavy chain.

```
         10         20         30         40         50         60
                                          ┌─ CDR1 ─┐              ┌───── CDR2 ──────
    EEQLVESGGG LVKPGGSLRL SCAASGFSFS DCRMYWLRQA PGKGLEWIGV ISVKSENYGA 70         80         90        100        110        120
    ── CDR2 ──┐                                      ┌──────── CDR3 ──────────┐
    NYAESVRGRF TISRDDSKNT VYLQMNSLKT EDTAVYYCSA SYYRYDVGAW FAYWGQGTLV 130        140        150        160        170        180
    TVSSASTKGP SVFPLAPSSK STSGGTAALG CLVKDYFPEP VTVSWNSGAL TSGVHTFPAV 190        200        210        220        230        240
    LQSSGLYSLS SVVTVPSSSL GTQTYICNVN HKPSNTKVDK KVEPKSCDKT HTCPPCPAPE 250        260        270        280        290        300
    LLGGPSVFLF PPKPKDTLMI SRTPEVTCVV VDVSHEDPEV KFNWYVDGVE VHNAKTKPRE 310        320        330        340        350        360
    EQYNSTYRVV SVLTVLHQDW LNGKEYKCKV SNKALPAPIE KTISKAKGQP REPQVYTLPP 370        380        390        400        410        420
    SRDELTKNQV SLTCLVKGFY PSDIAVEWES NGQPENNYKT TPPVLDSDGS FFLYSKLTVD 430        440        450
    KSRWQQGNVF SCSVMHEALH NHYTQKSLSL SPGK
```

[ ] not represented by
     the crystal structure

Figure 2B

```
              10          20          30          40          50          60
        DIVMTQSPDS  LAVSLGERAT  INCRASKSVS  TSGYSYIYWY  QQKPGQPPKL  LIYLASILES 70          80          90         100         110         120
        GVPDRFSGSG  SGTDFTLTIS  SLQAEDVAVY  YCQHSRELPW  TFGQGTKVEI  KRTVAAPSVF 130         140         150         160         170         180
        IFPPSDEQLK  SGTASVVCLL  NNFYPREAKV  QWKVDNALQS  GNSQESVTEQ  DSKDSTYSLS 190         200         210
        STLTLSKADY  EKHKVYACEV  THQGLSSPVT  KSFNRGEC
```

[ CDR1 ]   [ CDR2 ]   [ CDR3 ]

( CD4 binding sites )

Figure 8

```
        10         20         30         40         50         60
EEQLVESGGG LVKPGGSLRL SCAASGFSFS DCRMYNLRQA PGKGLEWIGV ISVKSENYGA 70         80         90        100        110        120
NYAESVRGRF TISRDDSKNT VYLQMNSLKT EDTAVYYCSA SYRMDVGAW FAYWGQGTLV 130        140        150        160        170        180
TVSSASTKGP SVFPLAPSSK STSGGTAALG CLVKDYFPEP VTVSWNSGAL TSGVHTFPAV 190        200        210        220        230        240
LQSSGLYSLS SVVTVPSSSL GTQTYICNVN HKPSNTKVDK KVEPKSCDKT HTCPPCPAPE 250        260        270        280        290        300
LLGGPSVFLF PPKPKDTLMI SRTPEVTCVV VDVSHEDPEV KFNWYVDGVE VHNAKTKPRE 310        320        330        340        350        360
EQYNSTYRVV SVLTVLHQDW LNGKEYKCKV SNKALPAPIE KTISKAKGQP REPQVYTLPP 370        380        390        400        410        420
SRDELTKNQV SLTCLVKGFY PSDIAVEWES NGQPENNYKT TPPVLDSDGS FFLYSKLTVD 430        440        450
KSRWQQGNVF SCSVMHEALH NHYTQKSLSL SPGK
```

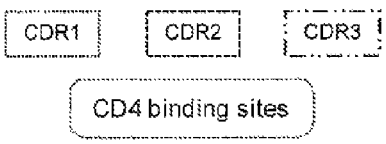

Figure 9

SEQUENCE LISTING

<160> NUMBER OF SEQ ID NOS: 15

<210> SEQ ID NO 1
<211> LENGTH: 458
<212> TYPE: PRT
<213> ORGANISM: Human

<400> SEQUENCE: 1

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

-continued

```
Lys Gly Asp Thr Val Glu Leu Thr Cys Thr Ala Ser Gln Lys Lys Ser
            35                  40                  45
Ile Gln Phe His Trp Lys Asn Ser Asn Gln Ile Lys Ile Leu Gly Asn
 50                  55                  60
Gln Gly Ser Phe Leu Thr Lys Gly Pro Ser Lys Leu Asn Asp Arg Ala
 65                  70                  75                  80
Asp Ser Arg Arg Ser Leu Trp Asp Gln Gly Asn Phe Pro Leu Ile Ile
                 85                  90                  95
Lys Asn Leu Lys Ile Glu Asp Ser Asp Thr Tyr Ile Cys Glu Val Glu
            100                 105                 110
Asp Gln Lys Glu Glu Val Gln Leu Leu Val Phe Gly Leu Thr Ala Asn
            115                 120                 125
Ser Asp Thr His Leu Leu Gln Gly Gln Ser Leu Thr Leu Thr Leu Glu
 130                 135                 140
Ser Pro Pro Gly Ser Ser Pro Ser Val Gln Cys Arg Ser Pro Arg Gly
 145                 150                 155                 160
Lys Asn Ile Gln Gly Gly Lys Thr Leu Ser Val Ser Gln Leu Glu Leu
                 165                 170                 175
Gln Asp Ser Gly Thr Trp Thr Cys Thr Val Leu Gln Asn Gln Lys Lys
            180                 185                 190
Val Glu Phe Lys Ile Asp Ile Val Val Leu Ala Phe Gln Lys Ala Ser
            195                 200                 205
Ser Ile Val Tyr Lys Lys Glu Gly Glu Gln Val Glu Phe Ser Phe Pro
 210                 215                 220
Leu Ala Phe Thr Val Glu Lys Leu Thr Gly Ser Gly Glu Leu Trp Trp
 225                 230                 235                 240
Gln Ala Glu Arg Ala Ser Ser Ser Lys Ser Trp Ile Thr Phe Asp Leu
                 245                 250                 255
Lys Asn Lys Glu Val Ser Val Lys Arg Val Thr Gln Asp Pro Lys Leu
            260                 265                 270
Gln Met Gly Lys Lys Leu Pro Leu His Leu Thr Leu Pro Gln Ala Leu
            275                 280                 285
Pro Gln Tyr Ala Gly Ser Gly Asn Leu Thr Leu Ala Leu Glu Ala Lys
 290                 295                 300
Thr Gly Lys Leu His Gln Glu Val Asn Leu Val Val Met Arg Ala Thr
 305                 310                 315                 320
Gln Leu Gln Lys Asn Leu Thr Cys Glu Val Trp Gly Pro Thr Ser Pro
                 325                 330                 335
Lys Leu Met Leu Ser Leu Lys Leu Glu Asn Lys Glu Ala Lys Val Ser
            340                 345                 350
Lys Arg Glu Lys Ala Val Trp Val Leu Asn Pro Glu Ala Gly Met Trp
            355                 360                 365
Gln Cys Leu Leu Ser Asp Ser Gly Gln Val Leu Leu Glu Ser Asn Ile
 370                 375                 380
Lys Val Leu Pro Thr Trp Ser Thr Pro Val Gln Pro Met Ala Leu Ile
 385                 390                 395                 400
Val Leu Gly Gly Val Ala Gly Leu Leu Leu Phe Ile Gly Leu Gly Ile
                 405                 410                 415
Phe Phe Cys Val Arg Cys Arg His Arg Arg Gln Ala Glu Arg Met
            420                 425                 430
Ser Gln Ile Lys Arg Leu Leu Ser Glu Lys Lys Thr Cys Gln Cys Pro
            435                 440                 445
His Arg Phe Gln Lys Thr Cys Ser Pro Ile
```

```
            450             455

<210> SEQ ID NO 2
<211> LENGTH: 218
<212> TYPE: PRT
<213> ORGANISM: Artificial Sequence
<220> FEATURE:
<223> OTHER INFORMATION: Light chain BT-061

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Tyr Ile Tyr Trp Tyr Gln Gln Lys Pro Gly Gln Pro Pro
        35                  40                  45

Lys Leu Leu Ile Tyr Leu Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Leu Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 3
<211> LENGTH: 454
<212> TYPE: PRT
<213> ORGANISM: Artificial sequence
<220> FEATURE:
<223> OTHER INFORMATION: Heavy chain BT-061

<400> SEQUENCE: 3

Glu Glu Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asp Cys
            20                  25                  30

Arg Met Tyr Trp Leu Arg Gln Ala Pro Gly Lys Gly Leu Glu Trp Ile
        35                  40                  45

Gly Val Ile Ser Val Lys Ser Glu Asn Tyr Gly Ala Asn Tyr Ala Glu
    50                  55                  60

Ser Val Arg Gly Arg Phe Thr Ile Ser Arg Asp Asp Ser Lys Asn Thr
65                  70                  75                  80
```

```
Val Tyr Leu Gln Met Asn Ser Leu Lys Thr Glu Asp Thr Ala Val Tyr
                85                  90                  95

Tyr Cys Ser Ala Ser Tyr Arg Tyr Asp Val Gly Ala Trp Phe Ala
        100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 4
<211> LENGTH: 15
<212> TYPE: PRT
<213> ORGANISM: Artificial Sequence
<220> FEATURE:
<223> OTHER INFORMATION: BT-061 light chain CDR1
```

<400> SEQUENCE: 4

Arg Ala Ser Lys Ser Val Ser Thr Ser Gly Tyr Ser Tyr Ile Tyr
1               5                   10                  15

<210> SEQ ID NO 5
<211> LENGTH: 7
<212> TYPE: PRT
<213> ORGANISM: Artificial sequence
<220> FEATURE:
<223> OTHER INFORMATION: BT-061 light chain CDR2

<400> SEQUENCE: 5

Leu Ala Ser Ile Leu Glu Ser
1               5

<210> SEQ ID NO 6
<211> LENGTH: 9
<212> TYPE: PRT
<213> ORGANISM: Artificial sequence
<220> FEATURE:
<223> OTHER INFORMATION: BT-061 light chain CDR3

<400> SEQUENCE: 6

Gln His Ser Arg Glu Leu Pro Trp Thr
1               5

<210> SEQ ID NO 7
<211> LENGTH: 5
<212> TYPE: PRT
<213> ORGANISM: Artificial sequence
<220> FEATURE:
<223> OTHER INFORMATION: BT-061 heavy chain CDR1

<400> SEQUENCE: 7

Asp Cys Arg Met Tyr
1               5

<210> SEQ ID NO 8
<211> LENGTH: 18
<212> TYPE: PRT
<213> ORGANISM: Artificial sequence
<220> FEATURE:
<223> OTHER INFORMATION: BT-061 heavy chain CDR2

<400> SEQUENCE: 8

Ile Ser Val Lys Ser Glu Asn Tyr Gly Ala Asn Tyr Ala Glu Ser Val
1               5                   10                  15

Arg Gly

<210> SEQ ID NO 9
<211> LENGTH: 13
<212> TYPE: PRT
<213> ORGANISM: Artificial sequence
<220> FEATURE:
<223> OTHER INFORMATION: BT-061 heavy chain CDR3

<400> SEQUENCE: 9

Ser Tyr Tyr Arg Tyr Asp Val Gly Ala Trp Phe Ala Tyr
1               5                   10

<210> SEQ ID NO 10
<211> LENGTH: 5
<212> TYPE: PRT
<213> ORGANISM: Artificial sequence
<220> FEATURE:

```
<223> OTHER INFORMATION: Light chain V domain sequence motif

<400> SEQUENCE: 10

Ser Gly Tyr Ser Tyr
1               5

<210> SEQ ID NO 11
<211> LENGTH: 6
<212> TYPE: PRT
<213> ORGANISM: Artificial sequence
<220> FEATURE:
<223> OTHER INFORMATION: Light chain V domain sequence motif

<400> SEQUENCE: 11

Leu Ala Ser Ile Leu Glu
1               5

<210> SEQ ID NO 12
<211> LENGTH: 5
<212> TYPE: PRT
<213> ORGANISM: Artificial sequence
<220> FEATURE:
<223> OTHER INFORMATION: Heavy chain V domain sequence motif

<400> SEQUENCE: 12

Tyr Tyr Arg Tyr Asp
1               5

<210> SEQ ID NO 13
<211> LENGTH: 6
<212> TYPE: PRT
<213> ORGANISM: Artificial sequence
<220> FEATURE:
<223> OTHER INFORMATION: Heavy chain V domain sequence motif
<220> FEATURE:
<221> NAME/KEY: Xaa
<222> LOCATION: (3)..(3)
<223> OTHER INFORMATION: Xaa is Tyr, Phe or His

<400> SEQUENCE: 13

Ser Tyr Xaa Arg Tyr Asp
1               5

<210> SEQ ID NO 14
<211> LENGTH: 218
<212> TYPE: PRT
<213> ORGANISM: Artificial sequence
<220> FEATURE:
<223> OTHER INFORMATION: Light chain V domain sequence
<220> FEATURE:
<221> NAME/KEY: MISC_FEATURE
<222> LOCATION: (24)..(24)
<223> OTHER INFORMATION: Xaa is Arg, Lys, Gln or Asn
<220> FEATURE:
<221> NAME/KEY: MISC_FEATURE
<222> LOCATION: (25)..(25)
<223> OTHER INFORMATION: Xaa is Ala or Gly
<220> FEATURE:
<221> NAME/KEY: MISC_FEATURE
<222> LOCATION: (26)..(26)
<223> OTHER INFORMATION: Xaa is Ser or Thr
<220> FEATURE:
<221> NAME/KEY: MISC_FEATURE
<222> LOCATION: (27)..(27)
<223> OTHER INFORMATION: Xaa is Lys, Arg or Glu
<220> FEATURE:
<221> NAME/KEY: MISC_FEATURE
<222> LOCATION: (28)..(28)
<223> OTHER INFORMATION: Xaa is Ser, Gly or Pro
<220> FEATURE:
<221> NAME/KEY: MISC_FEATURE
```

<222> LOCATION: (29)..(29)
<223> OTHER INFORMATION: Xaa is Val, Ala or Ile
<220> FEATURE:
<221> NAME/KEY: MISC_FEATURE
<222> LOCATION: (31)..(31)
<223> OTHER INFORMATION: Xaa is Thr, Ser, Asn, Gln or Asp
<220> FEATURE:
<221> NAME/KEY: MISC_FEATURE
<222> LOCATION: (37)..(37)
<223> OTHER INFORMATION: Xaa is Ile, Val or Leu
<220> FEATURE:
<221> NAME/KEY: MISC_FEATURE
<222> LOCATION: (60)..(60)
<223> OTHER INFORMATION: Xaa is Ser, Asn, Gln, Thr, Glu or Asp
<220> FEATURE:
<221> NAME/KEY: MISC_FEATURE
<222> LOCATION: (96)..(96)
<223> OTHER INFORMATION: Xaa is Arg or Lys
<220> FEATURE:
<221> NAME/KEY: MISC_FEATURE
<222> LOCATION: (97)..(97)
<223> OTHER INFORMATION: Xaa is Glu, Asp or Arg
<220> FEATURE:
<221> NAME/KEY: MISC_FEATURE
<222> LOCATION: (98)..(98)
<223> OTHER INFORMATION: Xaa is Leu, Gly or Ile
<220> FEATURE:
<221> NAME/KEY: MISC_FEATURE
<222> LOCATION: (101)..(101)
<223> OTHER INFORMATION: Xaa is Thr or Ser

<400> SEQUENCE: 14

Asp Ile Val Met Thr Gln Ser Pro Asp Ser Leu Ala Val Ser Leu Gly
1               5                   10                  15

Glu Arg Ala Thr Ile Asn Cys Xaa Xaa Xaa Xaa Xaa Ser Xaa Ser
            20                  25                  30

Gly Tyr Ser Tyr Xaa Tyr Trp Tyr Gln Gln Lys Pro Gly Gln Pro Pro
        35                  40                  45

Lys Leu Leu Ile Tyr Leu Ala Ser Ile Leu Glu Xaa Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Xaa
                85                  90                  95

Xaa Xaa Pro Trp Xaa Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 15
<211> LENGTH: 454
<212> TYPE: PRT

```
<213> ORGANISM: Artificial sequence
<220> FEATURE:
<223> OTHER INFORMATION: Heavy chain V domain sequence
<220> FEATURE:
<221> NAME/KEY: MISC_FEATURE
<222> LOCATION: (31)..(31)
<223> OTHER INFORMATION: Xaa is Asp, Glu, Thr, Cys, Pro, Met or Tyr
<220> FEATURE:
<221> NAME/KEY: MISC_FEATURE
<222> LOCATION: (32)..(32)
<223> OTHER INFORMATION: Xaa is Cys, Ser, Ala, Gly or Val
<220> FEATURE:
<221> NAME/KEY: MISC_FEATURE
<222> LOCATION: (33)..(33)
<223> OTHER INFORMATION: Xaa is Arg, Lys, Ser, Thr or Glu
<220> FEATURE:
<221> NAME/KEY: MISC_FEATURE
<222> LOCATION: (34)..(34)
<223> OTHER INFORMATION: Xaa is Met, Ile, Leu, Ala or Val
<220> FEATURE:
<221> NAME/KEY: MISC_FEATURE
<222> LOCATION: (51)..(51)
<223> OTHER INFORMATION: Xaa is Ile, Ala, Val or Gly
<220> FEATURE:
<221> NAME/KEY: MISC_FEATURE
<222> LOCATION: (52)..(52)
<223> OTHER INFORMATION: Xaa is Ser, Asp, Gly, Ala or Thr
<220> FEATURE:
<221> NAME/KEY: MISC_FEATURE
<222> LOCATION: (53)..(53)
<223> OTHER INFORMATION: Xaa is Val, Ser, Gly, Thr or Ile
<220> FEATURE:
<221> NAME/KEY: MISC_FEATURE
<222> LOCATION: (54)..(54)
<223> OTHER INFORMATION: Xaa is Lys, Arg or Tyr
<220> FEATURE:
<221> NAME/KEY: MISC_FEATURE
<222> LOCATION: (55)..(55)
<223> OTHER INFORMATION: Xaa is Ser, Asn, Gln, Thr or Glu
<220> FEATURE:
<221> NAME/KEY: MISC_FEATURE
<222> LOCATION: (56)..(56)
<223> OTHER INFORMATION: Xaa is Glu, Asp or Arg
<220> FEATURE:
<221> NAME/KEY: MISC_FEATURE
<222> LOCATION: (57)..(57)
<223> OTHER INFORMATION: Xaa is Asn, Asp, Tyr, Gln or Glu
<220> FEATURE:
<221> NAME/KEY: MISC_FEATURE
<222> LOCATION: (58)..(58)
<223> OTHER INFORMATION: Xaa is Tyr, His or Lys
<220> FEATURE:
<221> NAME/KEY: MISC_FEATURE
<222> LOCATION: (59)..(59)
<223> OTHER INFORMATION: Xaa is Gly or Ser
<220> FEATURE:
<221> NAME/KEY: MISC_FEATURE
<222> LOCATION: (60)..(60)
<223> OTHER INFORMATION: Xaa is Ala, Ser or Thr
<220> FEATURE:
<221> NAME/KEY: MISC_FEATURE
<222> LOCATION: (61)..(61)
<223> OTHER INFORMATION: Xaa is Asn, Gln or Asp
<220> FEATURE:
<221> NAME/KEY: MISC_FEATURE
<222> LOCATION: (62)..(62)
<223> OTHER INFORMATION: Xaa is Tyr, Phe or His
<220> FEATURE:
<221> NAME/KEY: MISC_FEATURE
<222> LOCATION: (63)..(63)
<223> OTHER INFORMATION: Xaa is Ala, Gly or Ser
<220> FEATURE:
<221> NAME/KEY: MISC_FEATURE
<222> LOCATION: (64)..(64)
<223> OTHER INFORMATION: Xaa is Glu, Asp, Gln, Asn or Arg
<220> FEATURE:
<221> NAME/KEY: MISC_FEATURE
<222> LOCATION: (65)..(65)
<223> OTHER INFORMATION: Xaa is Ser, Gly, Ala or Asn
```

```
<220> FEATURE:
<221> NAME/KEY: MISC_FEATURE
<222> LOCATION: (66)..(66)
<223> OTHER INFORMATION: Xaa is Val, Ile, Ala, Ser or Gly
<220> FEATURE:
<221> NAME/KEY: MISC_FEATURE
<222> LOCATION: (67)..(67)
<223> OTHER INFORMATION: Xaa is Arg, Lys, Gln, Tyr, His or Glu
<220> FEATURE:
<221> NAME/KEY: MISC_FEATURE
<222> LOCATION: (103)..(103)
<223> OTHER INFORMATION: Xaa is Tyr, Phe or His
<220> FEATURE:
<221> NAME/KEY: MISC_FEATURE
<222> LOCATION: (107)..(107)
<223> OTHER INFORMATION: Xaa is Val, Ile, Pro, Asp, Thr or Glu
<220> FEATURE:
<221> NAME/KEY: MISC_FEATURE
<222> LOCATION: (108)..(108)
<223> OTHER INFORMATION: Xaa is Gly or Ala
<220> FEATURE:
<221> NAME/KEY: MISC_FEATURE
<222> LOCATION: (109)..(109)
<223> OTHER INFORMATION: Xaa is Ala or Ser
<220> FEATURE:
<221> NAME/KEY: MISC_FEATURE
<222> LOCATION: (110)..(110)
<223> OTHER INFORMATION: Xaa is Trp, Phe, His or Tyr
<220> FEATURE:
<221> NAME/KEY: MISC_FEATURE
<222> LOCATION: (112)..(112)
<223> OTHER INFORMATION: Xaa is Ala or Ser
<220> FEATURE:
<221> NAME/KEY: MISC_FEATURE
<222> LOCATION: (113)..(113)
<223> OTHER INFORMATION: Xaa is Tyr, Phe, His or Asn

<400> SEQUENCE: 15

Glu Glu Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Xaa Xaa
            20                  25                  30

Xaa Xaa Tyr Trp Leu Arg Gln Ala Pro Gly Lys Gly Leu Glu Trp Ile
        35                  40                  45

Gly Val Xaa Xaa Xaa Xaa Xaa Xaa Xaa Xaa Xaa Xaa Xaa Xaa Xaa Xaa
    50                  55                  60

Xaa Xaa Xaa Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Ser Ala Ser Tyr Xaa Arg Tyr Asp Xaa Xaa Xaa Phe Xaa
            100                 105                 110

Xaa Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
```

-continued

```
            210                 215                 220
Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

AGENTS FOR TREATING DISEASE

This application is a Continuation of, and claims priority under 35 U.S.C. § 120 to, International Application No. PCT/EP2010/068579, filed Nov. 30, 2010, and claims priority therethrough under 35 U.S.C. § 119 to Great Britain Patent Application No. 0920944.6, filed Nov. 30, 2009, the entireties of which are incorporated by reference herein. Also, the Sequence Listing filed electronically herewith is hereby incorporated by reference (File name: 2012-05-30T_060-013_Seq_List; File size: 22 KB; Date recorded: May 30, 2012).

FIELD OF THE INVENTION

The present invention is concerned with agents for the treatment of disease, and specifically treatment via the activation of CD4+CD25+ regulatory T cells through the T-cell surface receptor CD4. The invention involves screening methods for identifying such agents, agents capable of the activation of CD4+CD25+ regulatory T cells and their use in the treatment of disease, in particular autoimmune diseases, as well as in methods performed in vitro.

BACKGROUND ART

T-cells belong to the lymphocytes and are responsible for a number of key functions in the immune system. In mammals, T-cells (thymocytes) differentiate in the thymus gland from hematopoietic progenitor cells formed in bone marrow. Part of the differentiation process is the expression of characteristic surface receptors, mainly the glycoproteins CD4 and CD8. T-cells expressing CD4, so-called CD4+ T-cells, bind MHC class II complexes (Reinerz and Schlossman, Cell 19, 821-827 (1980); Reinerz et al., PNAS USA 77, 1588-1592 (1980)), while CD8+ T-cells bind MHC class I complexes (Fitch, Microbiol. Rev. 50, 50-69 (1986)). T-cells are released into blood and lymph.

CD4 positive cells can differentiate into T helper subpopulations (Th1 and Th2), but also into regulatory T-cells. Regulatory T-cells can be further divided into subclasses, the thymus derived (nTreg) inducible ones (iTregs) being the most evaluated.

Although there are other Treg subpopulations, such as for example Tr1 or Th3, the present invention refers to CD4 positive thymus derived Tregs (nTregs) and inducible Tregs, both expressing the transcription factor Foxp3. As a major difference Foxp3 is stably and permanently expressed in nTregs confirming the irreversible Treg phenotype, whereas inducible Tregs display inducible or transient Foxp3 expression, which is reversible.

Tregs secrete immunomodulatory cytokines such as IL-10, TGF beta or IL-35 and exert suppressive activity on effector T-cells via several mechanisms, for example via suppression of the production of proinflammatory cytokines, direct cell-cell contact and modulating the activation state or function on antigen presenting cells (APC) (Shevach et al., Immunity (2009) 30; 636-645). A main characteristic of CD4 positive CD25 Treg cells is their anergic phenotype, meaning that they do not proliferate upon TCR stimulation, which can be restored by the addition of exogenous IL-2.

A prominent role for Tregs comprises maintaining homeostasis concerning immune responses and self tolerance. Treg dysfunction is correlated with autoimmune diseases.

Commonly, regulatory T-cells can be isolated via the surface receptor glycoproteins CD4, CD25, and characterized by intracellular staining of FOXP3. A further surface protein represents CD127 (IL-7 R), which is downregulated in Treg cells, and can be used for further purification of Tregs. Additionally, expression of CD39 (endonucleotidase) (Borselino et al., Blood (2007) 110, 1225-1232) or GARP (glycoprotein A repetitions predominant (GARP, or LRRC32) (Wang et al., PNAS (2009) 106, 32. 13439-13444).

Human CD4 is encoded on chromosome 12 and belongs to the immunoglobulin (Ig) superfamily. Its natural function as a T-cell surface receptor is related to T-cell activation by binding of MHC class II complexes. In addition, CD4 can bind the HIV-1 gp120 protein, the P4HB/CDI protein, and human herpes virus HHV-7 capsid proteins. Interactions with the HIV-1 gp120 and Vpu proteins also have been reported. CD4 has 458 amino acids. The peptide sequence is shown in FIG. 1.

The UniProt entry P01730 provides the domain structure of CD4 as shown below in Table 1, and in FIG. 6. The first 25 amino acids are a signal peptide, which is cleaved off in the biologically active form. Positions 26 through 396 constitute the extracellular domain, which is followed by the transmembrane region, positions 397 through 418. $Asn_{296}$ and $Asn_{325}$ are known glycosylation sites (König et al., J. Biol. Chem. 263, 9502-9507 (1988); Carr et al., J. Biol. Chem. 264, 21286-21295 (1989)).

The last part, positions 419 through 458, is the cytoplasmic domain. Here is the binding site for the Tyrosine protein kinase LCK (p56$^{lck}$) (Rudd et al., PNAS USA 85, 5190-5194 (1988); Veillette et al., Cell 55, 301 (1988)), which is part of the signaling pathway activated by ligands binding to CD4.

TABLE 1

Table showing the domain structure of CD4 (according to UniProt P01730)

| Feature | Positions | Length | Description |
|---|---|---|---|
| Signal peptide | 1-25 | 25 | |
| Chain | 26-458 | 433 | T-cell surface glycoprotein CD4 |
| Topological domain | 26-396 | 371 | Extracellular |
| Transmembrane region | 397-418 | 22 | Potential |
| Topological domain | 419-458 | 40 | Cytoplasmic (potential) |
| Domain | 26-125 | 100 | Ig-like V-type |
| Domain | 126-203 | 78 | Ig-like C2-type 1 |
| Domain | 204-317 | 78 | Ig-like C2-type 2 |
| Domain | 318-374 | 78 | Ig-like C2-type 3 |
| Region | 427-455 | 29 | HIV-1 Vpu-susceptibility domain |
| Glycosylation site | 296 | 1 | NeuAc(a2-3)Gal(b1-4)GlcNAc(b1-2)Man(a1-3)[Gal(b1-4)GlcNAc(b1-2)Man(a1-6)]Man(b1-4)GlcNAc(b1-4)GlcNAc |

TABLE 1-continued

Table showing the domain structure of CD4 (according to UniProt P01730)

| Feature | Positions | Length | Description |
|---|---|---|---|
| Glycosylation site | 325 | 1 | NeuAc(a2-3)Gal(b1-4)GlcNAc(b1-2)Man(a1-3)[Gal(b1-4)GlcNAc(b1-2)Man(a1-6)]Man(b1-4)GlcNAc(b1-4)GlcNAc |
| Disulfide bond | 41 ←→ 109 | | |
| Disulfide bond | 155 ←→ 184 | | |
| Disulfide bond | 328 ←→ 370 | | |
| Lipidation site | 419 | 1 | S-palmitoyl cysteine |
| Lipidation site | 422 | 1 | S-palmitoyl cysteine |

The extracellular part comprises 4 immunoglobulin-like domains. The first one, the N-terminal domain, comprising positions 26 through 125 is an Ig-like V-type domain. Based on the homology to antibodies, it has three homologues of antigen-complementary-determining regions, CDR1, CDR2, and CDR3 (Ashkenazi et al., PNAS USA 87, 7150-7154 (1990)) (see FIG. 6). The CDR1 and CDR2 spans are involved in the binding of class II MHC molecules (Moebius et al., PNAS USA 89, 12008-120012 (1992)), the gp120 HIV-1 envelope protein (Moebius et al., J. Exp. Med. 176, 507-517 (1992)) and anti-CD4 antibodies (Lanza et al., PNAS USA 90, 11683-11687 (1993)). $Phe_{68}$ of CDR2 plays a key role for recognition and binding of class II MHC molecules and the gp120 HIV-1 envelope protein (Sharma et al., Biochemistry 44, 16192-16202 (2005)). All known ligands of CD4 bind to the N-terminal Ig-like V-type domain.

The mechanism of how regulatory T cells work is not fully clear. $CD4^+CD25^+$ Tregs inhibit polyclonal and antigen-specific T cell activation. The suppression can be mediated e.g. by a cell contact-dependent mechanism that requires activation of $CD4^+CD25^+$ Tregs via the TCR but Tregs do not show a proliferative response upon TCR activation or stimulation with mitogenic antibodies (anergic) (Shevach, Nature Rev. Immunol 2: 389 (2002). Once stimulated, they are competent to suppress in an antigen-independent manner the response of CD4+ T cells and CD8+ T cells as well as inhibit B-cell activation and clonal expansion.

The ability of CD4+CD25+ regulatory T cells to have a controlling influence on immune system activity has meant that they have been recognized as a potential target for treating diseases, such as autoimmune diseases, where it is desirable to exert a control on the immune system.

Autoimmunity is the failure of an organism to recognise its own constituent parts (down to sub-molecular levels) as "self", which results in an immune response against its own cells and tissues. Any disease that results from such an aberrant immune response is termed an autoimmune disease. Autoimmune diseases include multiple sclerosis (MS), rheumatoid arthritis (RA), psoriasis, psoriatic arthritis, colitis ulcerosa, Crohn's disease, Type I Diabetes Mellitus (T1D), myasthenia gravis (MG), autoimmune polyglandular syndrome type II (APS-II), Hashimoto's thyroiditis (HT), systemic lupus erythematosus (SLE), Sjörgens Syndrome and autoimmune lymphoproliferative syndrome (ALS).

Autoimmune disease occurs when T cells recognise and react to 'self' molecules, that is, molecules produced by the cells of the host. Activation of 'autoreactive' T cells by presentation of autoantigens processed by antigen presenting cells (APC) leads to their clonal expansion and migration to the specific tissues, where they induce inflammation and tissue destruction.

Suppression of these T effector cell function by using immunosuppressive drugs is a principal therapeutic strategy that has been used successfully to treat autoimmune diseases. However these drugs induce general immune suppression due to their poor selectivity, resulting in inhibition of not only the harmful functions of the immune system, but also useful ones. As a consequence, several risks like infection, cancer and drug toxicity may occur.

It is generally agreed that $CD4^+$ T cells play a major part in initiating and maintaining autoimmunity. Accordingly, it has been proposed to use mAbs against $CD4^+$ T cells surface molecules, and in particular anti-CD4 mAbs, as immunosuppressive agents. Although numerous clinical studies confirmed the potential interest of this approach, they also raised several issues to be addressed in order to make anti-CD4 mAbs more suitable for use in routine clinical practice.

Several different mechanisms of action for CD4 mAbs have been proposed including: (1) antagonism of CD4-MHC II interactions resulting in inhibition of T cell activation, (2) CD4 receptor modulation as determined by a decrease in cell surface expression of CD4, (3) partial signaling through the CD4 receptor in the absence of T cell receptor cross-linking which can suppress subsequent T cell activation and trigger CD4 T cell apoptotic death, (4) Fc-mediated complement-dependent cytotoxicity (CDC) or antibody-dependent cellular cytotoxicity (ADCC) leading to CD4 T cell depletion, and (5) stimulation of regulatory T cells.

Several anti-CD4 antibodies targeting T cells have been in clinical development (Schulze-Koops et al., J. Rheumatol. 25(11): 2065-76 (1998); Mason et al., J. Rheumatol. 29(2): 220-9 (2002); Choy et al., Rheumatology 39(10): 1139-46 (2000); Herzyk et al., Infect Immun. 69(2): 1032-43 (2001); Kon et al., Eur Respir J. 18(1): 45-52 (2001); Mourad et al., Transplantation 65(5): 632-41 (1998); Skov et al., Arch Dermatol. 139(11): 1433-9 (2003); Jabado et al., J. Immunol. 158(1): 94-103 (1997)) mainly aiming at CD4 cell depletion with only a few CD4 antibodies having been attributed to the other mechanisms like TRX-1, TNX-355, IDEC-151, OKTcdr4A.

The approach of using agents aimed at the activation of regulatory T cells for the therapy of autoimmune diseases has proven to be extremely difficult. Activation of Tregs via the TCR using the agonistic anti-CD3 antibody OKT-3 (Abramowicz et al, N Engl. J. Med. 1992 Sep. 3; 327(10): 736) or via the co-stimulatory molecule CD28 using the superagonistic anti-CD28 antibody TGN 1412 lead to complete depletion of regulatory T cell population as well as other conventional T cells and the systemic induction and release of excessive amounts of pro-inflammatory cytokines including IFN-γ, TNF-α, IL-1 and IL-2, resulting in a clinically apparent cytokine release syndrome (CRS) in humans (Suntharalingam et al, N Engl. J. Med. 2006 Sep. 7; 355(10):1018-28).

However, recently humanized anti-CD4 antibodies have been described in WO2004/083247 which are capable of activating CD4+CD25+ regulatory T cells. The antibodies described in WO2004/083247 are humanized versions of the mouse antibody, mB-F5, a murine IgG1 anti-human CD4 described by Racadot et al. (Clin. Exp. Rheum., 10, 365-374 (1992)). The epitope of mB-F5 was reported by Racadot et al., as spanning the Ig-like C2 type 1 and type 2 domains of human CD4 from amino acid 162 to amino acid 232 as shown in FIG. 6.

Subsequent clinical trials reported in WO2009/112502, WO2009/121690, WO2009/124815 and in WO2010/034590, using one of these antibodies, designated BT061 (a humanized monoclonal IgG1), has resulted in the successful treatment of patients suffering from psoriasis and rheumatoid arthritis, providing proof that these antibodies are capable of treating autoimmune diseases safely and with good efficacy.

The promising clinical results achieved has increased the interest in providing further therapeutic agents having similar properties. It is therefore the aim of the present invention to provide screening methods for identifying such agents, and to provide further therapeutic agents.

Accordingly the present invention provides a method for screening for a molecule capable of binding to CD4 comprising:
(a) providing one or more candidate molecules;
(b) determining whether the one or more candidate molecules is capable of binding to one or more of the following regions of human CD4: amino acids 148 to 154, amino acids 164 to 168 and amino acids 185 to 192; and
(c) selecting a molecule determined in step (b) to be capable of binding to CD4.

The present inventors have unexpectedly found that the humanized antibody BT061 binds to a domain of CD4 which was previously unrecognized as a ligand binding site. This finding is particularly surprising given what was known in the art as the epitope for the murine antibody, mB-F5, from which BT061 was derived. The present inventors have also established the residues of BT061 that are involved in binding the CD4 molecule and have surprisingly found that not all of the CDRs of BT061 are involved in CD4 binding.

The identification of the binding region, and details of the mechanism of binding, has enabled the development of further screening methods, and of antibodies and antibody fragments capable of activating CD4+CD25+ regulatory T cells.

Accordingly, the present invention also provides a method for screening for an antibody or antibody fragment capable of binding with CD4 comprising:
(a) providing an antibody or antibody fragment comprising CDR1 and CDR2 of BT061 light chain and CDR1 and CDR3 of BT061 heavy chain optionally with amino acid substitutions in the sequences of the CDRs provided:
(i) the light chain CDR1 comprises: Ser32; Gly33; and Tyr 34;
(ii) the light chain CDR2 comprises: Leu54; and Ile57;
(iii) the heavy chain CDR1 comprises Asp31, Glu31, Thr31, Cys31, Pro31, Met31 or Tyr31; and
(iv) the heavy chain CDR3 comprises Tyr103, Phe103 or His103; Arg104; Tyr105; Asp106; and Trp110, Phe110, His 110 or Tyr110,
(b) determining whether the antibody or antibody fragment is capable of binding to CD4, and
(c) selecting the antibody or antibody fragment determined in step (b) to be capable of binding to CD4,
wherein the antibody or antibody fragment does not comprise CDR1, CDR2 and CDR3 of BT061 heavy chain and CDR1, CDR2 and CDR3 of BT061 light chain.

Still further the present invention provides an antibody or antibody fragment capable of activating CD4+CD25+ regulatory T cells comprising an antibody or antibody fragment capable of activating CD4+CD25+ regulatory T cells comprising CDR1 and CDR2 of BT061 light chain and CDR1 and CDR3 of BT061 heavy chain optionally with amino acid substitutions in the sequences of the CDRs provided:
(i) the light chain CDR1 comprises: Ser32; Gly33; and Tyr 34;
(ii) the light chain CDR2 comprises: Leu54; and Ile57;
(iii) the heavy chain CDR1 comprises Asp31, Glu31, Thr31, Cys31, Pro31, Met31 or Tyr31; and
(iv) the heavy chain CDR3 comprises Tyr103, Phe103 or His103; Arg104; Tyr105; Asp106; and Trp110, Phe110, His 110 or Tyr110,
and wherein the antibody or antibody fragment does not comprise CDR1, CDR2 and CDR3 of BT061 heavy chain and CDR1, CDR2 and CDR3 of BT061 light chain.

The invention will be illustrated by way of example only, with reference to the following Figures, in which:

FIG. 1 shows the peptide sequence (SEQ ID No: 1) and disulphide bridges of human CD4 (UniProt ID P01730).

FIG. 2A shows the peptide sequence (SEQ ID No: 2) of the light chain of the humanized antibody BT-061. The residues of the CDRs are shown with boxes (CDR1: SEQ ID No: 4, CDR2: SEQ ID No: 5 and CDR3: SEQ ID No: 6). Residues surrounded by dashed frames are not represented by the crystal structure.

FIG. 2B shows the peptide sequence (SEQ ID No: 3) of the heavy chain of the humanized antibody BT-061. The residues of the CDRs are shown with boxes (CDR 1: SEQ ID No: 7, CDR2: SEQ ID No: 8 and CDR 3: SEQ ID No: 9). Residues surrounded by dashed frames are not represented by the crystal structure.

FIG. 3 provides a representation of the asymmetric unit of CD4-BT061 crystal structure.

Figure 4:
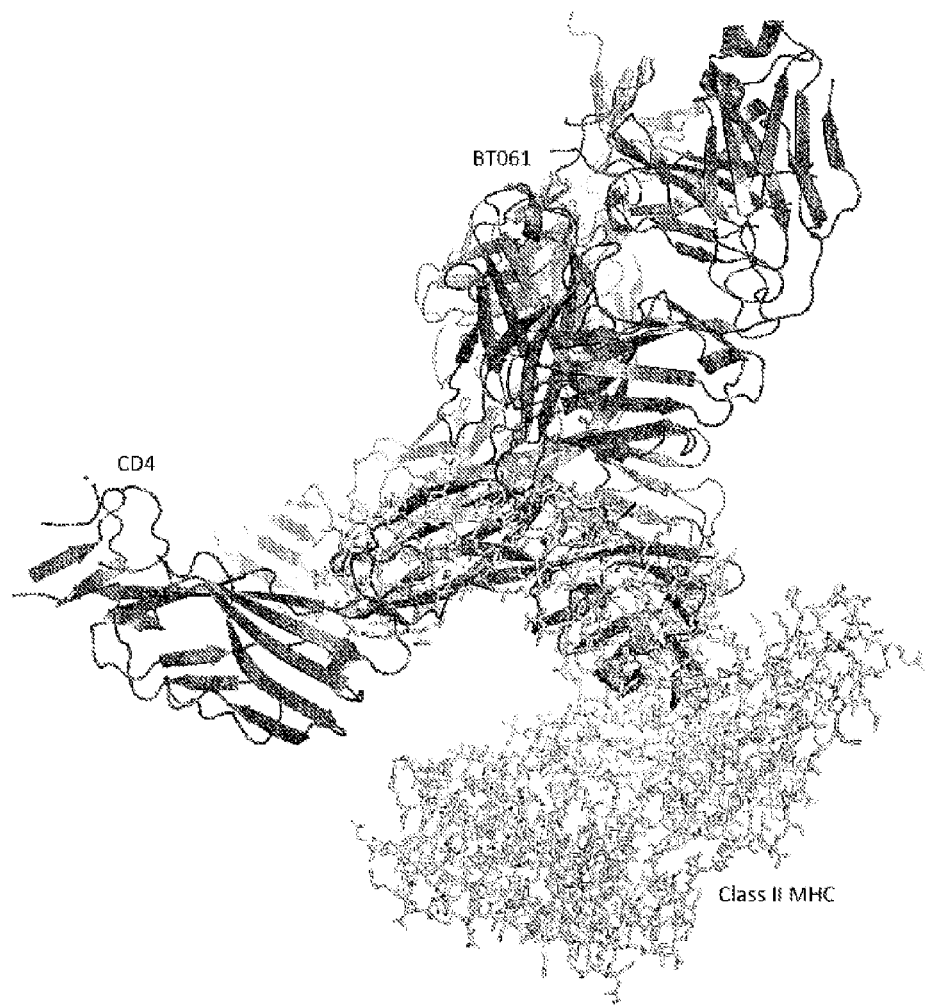

FIG. 4 provides a representation of the CD4-BT061 crystal structure superimposed with a crystal structure of a CD4 complex with a class II MHC molecule (PDB code 1JL4).

Figure 5:
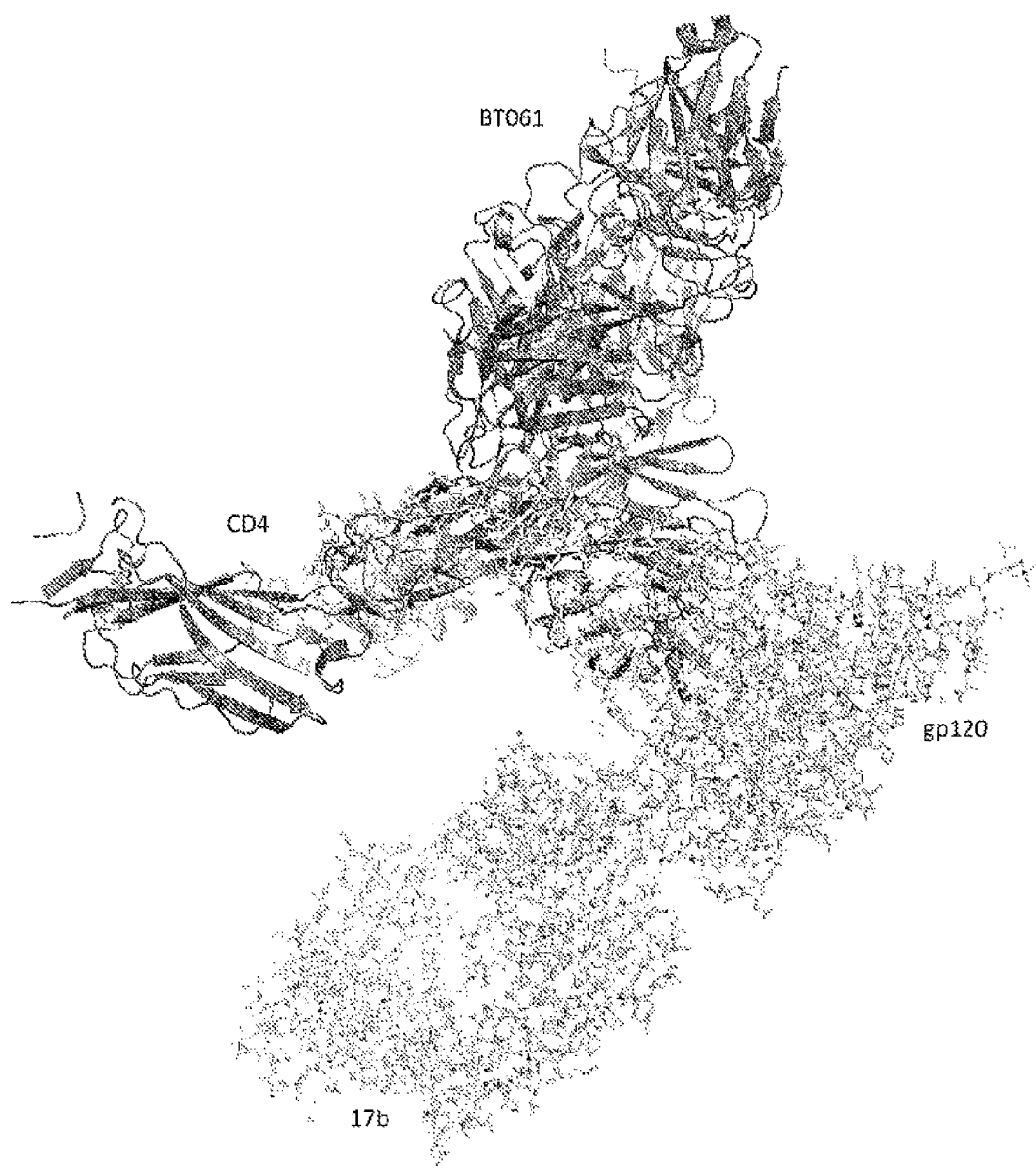

FIG. 5 provides a representation of the CD4-BT061 crystal structure superimposed with a crystal structure of a complex of CD4 with the gp120 HIV-1 protein (PDB code 2NY1). The latter, in addition, is bound to the antibody 17b.

Figure 6:
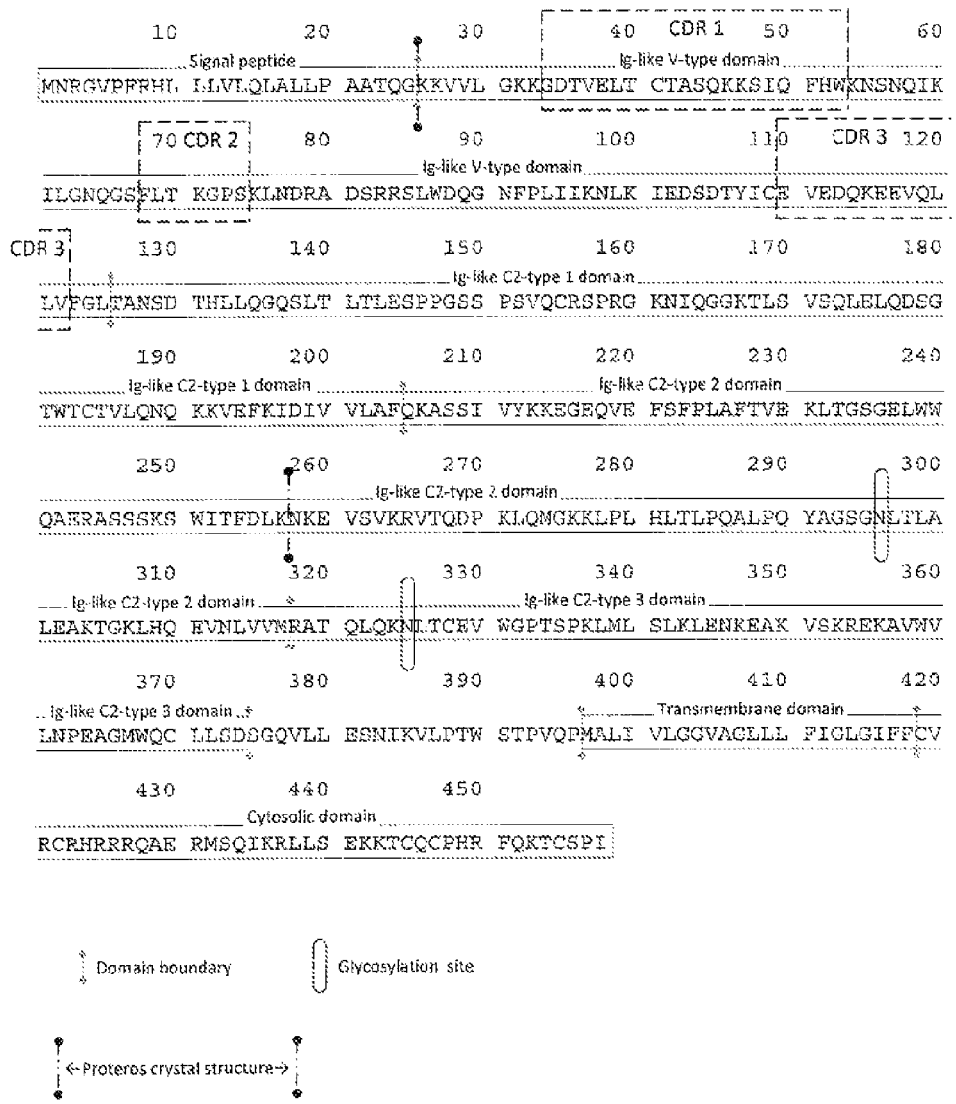

FIG. 6 shows the peptide sequence (SEQ ID No: 1) and domain structure of human CD4 (Uniprot ID P01730).

Figure 7:
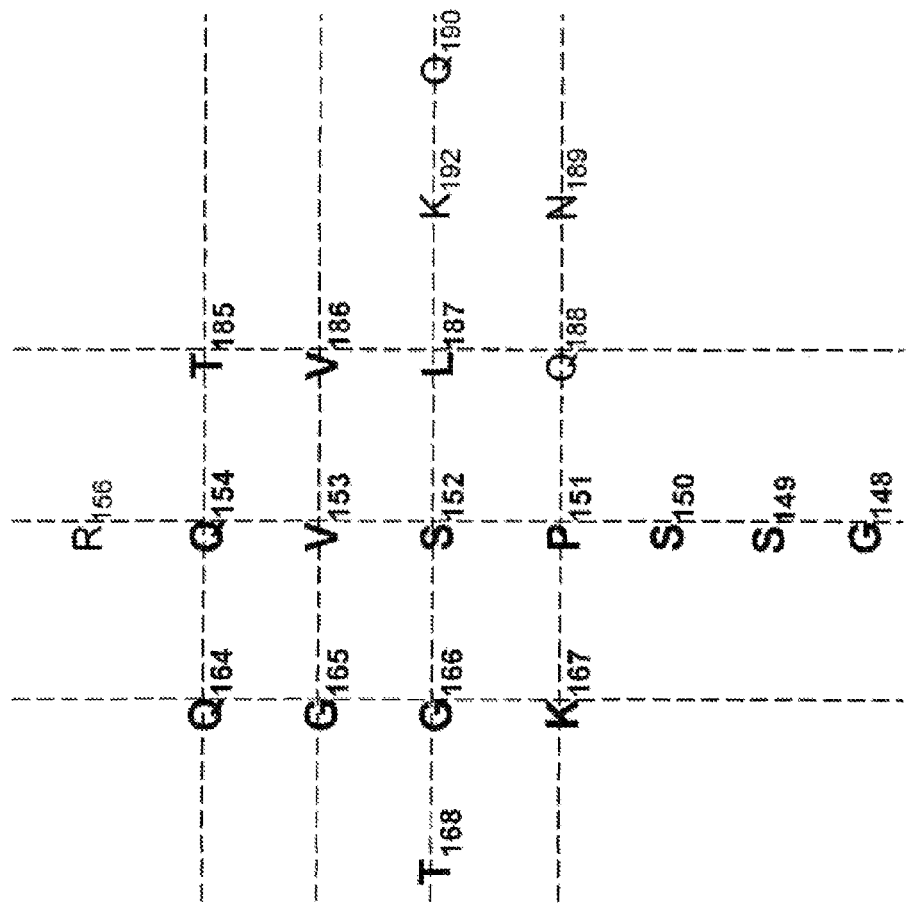

FIG. 7 provides a representation of the BT061 binding site on the surface of CD4. All amino acids shown are part of the Ig-like C2-type 1 domain, which follows the N-terminal Ig-like V-type domain.

FIG. 8 provides the BT061 amino acid light chain sequence (SEQ ID No: 2). Amino acids involved in binding to CD4 are marked by rounded frames.

FIG. 9 provides the BT061 amino acid heavy chain sequence (SEQ ID No: 3). Amino acids involved in binding to CD4 are marked by rounded frames.

Figure 10:
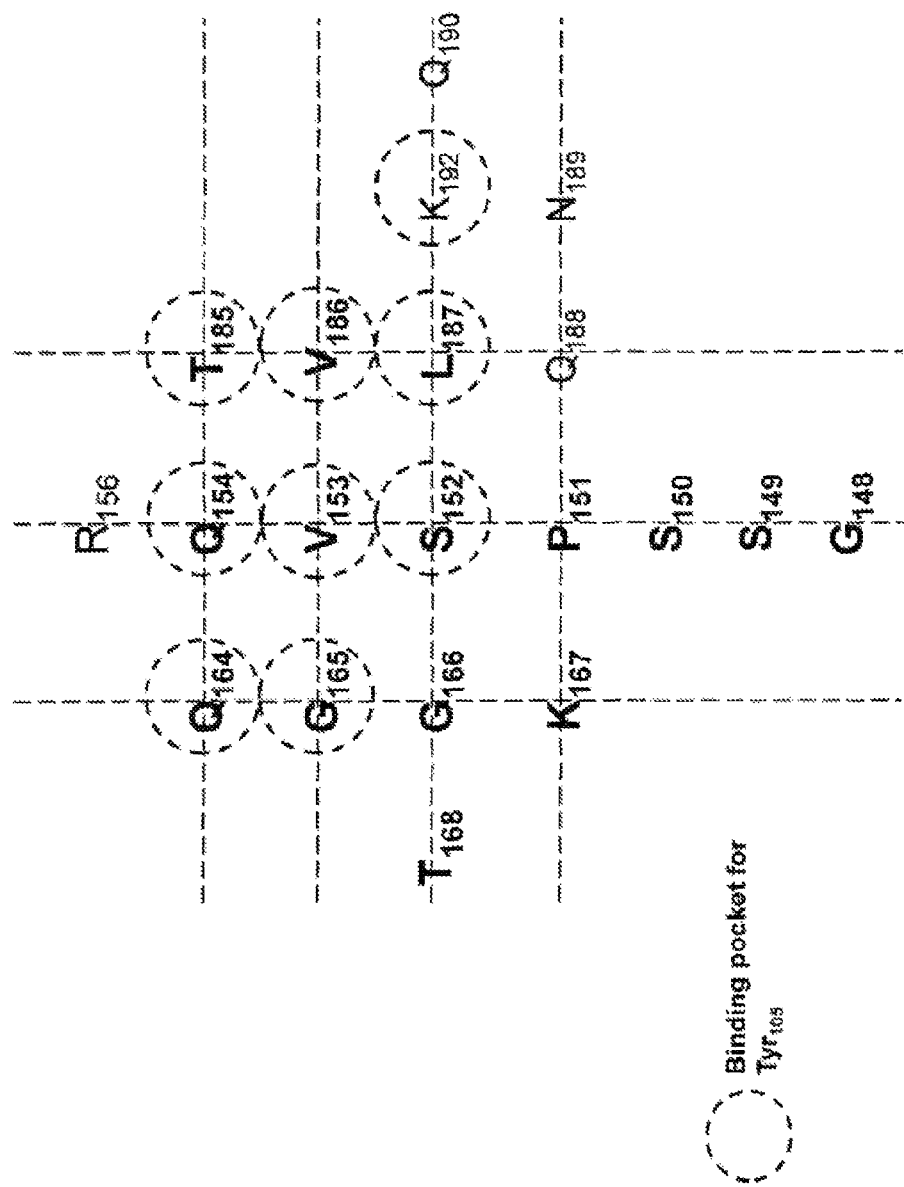

FIG. 10 provides a representation of the BT061 binding site on surface of CD4. Amino acids forming the binding pocket for $Tyr_{105}$ of the BT061 heavy chain are circled.

Figure 11:
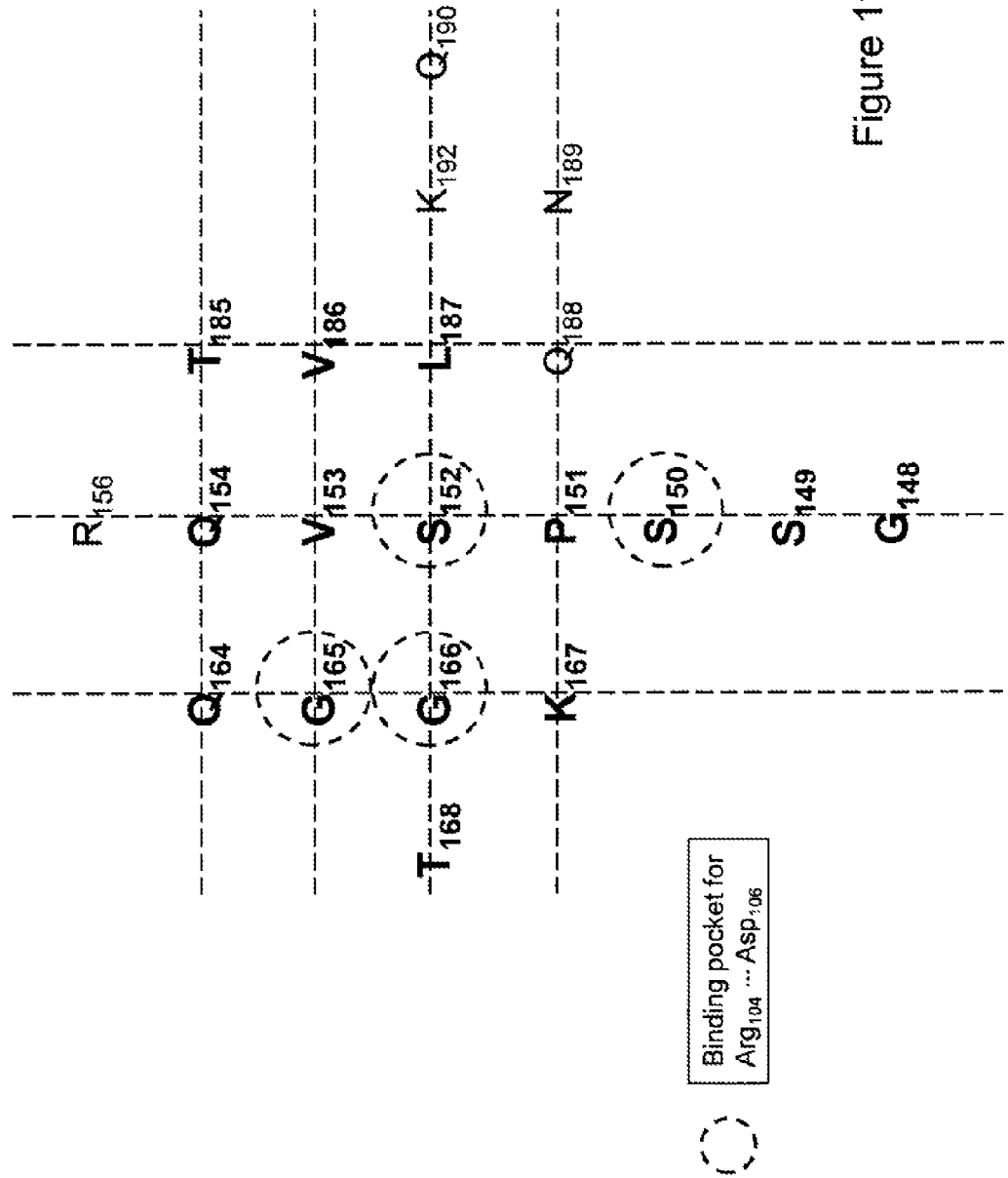

FIG. 11 provides a representation of the BT061 binding site on surface of CD4. Amino acids forming the binding pocket for $Arg_{104}$ to $Asp_{106}$ of the BT061 heavy chain are circled.

Figure 12:
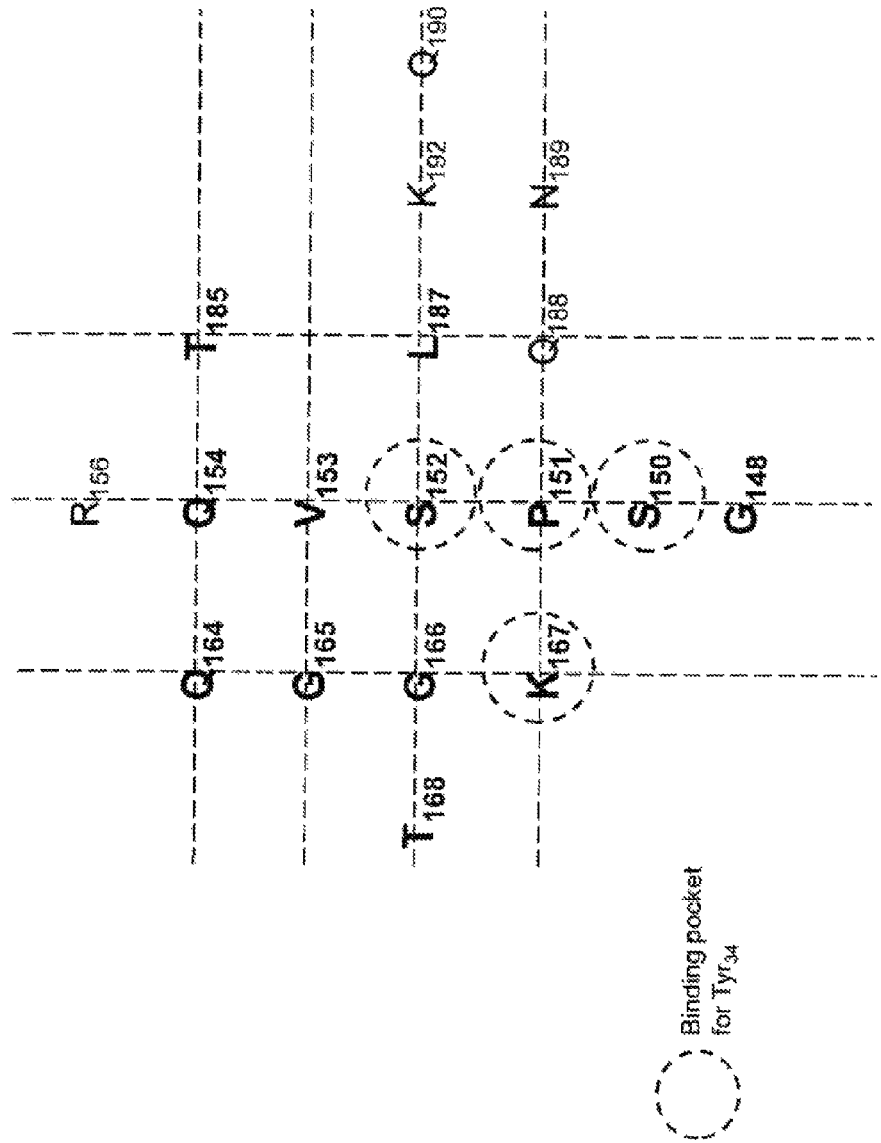

FIG. 12 provides a representation of the BT061 binding site on surface of CD4. Amino acids forming the binding pocket for $Tyr_{34}$ of the BT061 light chain are circled.

DETAILED DESCRIPTION OF THE INVENTION

Screening Methods

The present invention provides methods for screening for one or more molecules capable of binding to CD4, and preferably human CD4. As indicated above, the information provided herein describes the interaction between CD4 and antibody BT061, which is capable of activating CD4+ CD25+ regulatory T cells. In particular, BT-061 binds to both T helper and regulatory Tcells and selectively activates regulatory T cells without activation of T helper cells. The knowledge of the structures of BT061 and how these interact with the extracellular region of CD4 provides a means to design and produce agents with similar properties to BT061 in terms of CD4 binding and selective activation of regulatory T cells.

In a first aspect the present invention provides a method for screening for a molecule capable of binding to CD4 comprising: (a) providing one or more candidate molecules; and (b) determining whether the one or more candidate molecules is capable of binding to one or more of the following regions or amino acids of human CD4: amino acids 148 to 154, amino acids 164 to 168 and amino acids amino acids 185, 187, 189, 190 and 192; (c) selecting a molecule determined in step (b) to be capable of binding to CD4. More particularly, the regions of human CD4 are amino acids 148 to 154, amino acids 164 to 168 and amino acids 185 to 192.

In one embodiment steps (a) to (c) can be completed on a computer system and the interaction between CD4 and one or more candidate molecules modeled, based on the information provided herein regarding the interaction between BT061 and human CD4, i.e. the screening is conducted via computer assisted molecule design. In particular, a three dimensional structural model of CD4, and in particular, the extracellular region thereof, is generated in the computer system by interaction of the amino acids sequence for at least part of CD4 and software known to the person skilled in the art, for example Discovery Studio (Accelrys®) or Benchware 3D Explorer (Tripos). These programs further allow the inputting of, or de novo generation of, sequence and/or structural information on one or more candidate molecules. The ability of a candidate molecule to bind to the regions of CD4 identified as being important for BT061 binding (which are discussed further below) can then be examined.

In particular, the method for screening for a molecule capable of binding to CD4 can comprise as steps (a) and (b): (i) entering into a computer system or program an amino acid sequence from CD4 comprising at least amino acids 148 to 154, 164 to 168 and acids 185, 187, 189, 190 and 192; (ii) generating a three-dimensional model of the polypeptide or peptide encoded by the amino acid sequence; (iii) generating or entering the three dimensional structure of one or more candidate molecules; and (iv) simulating the interaction between the amino acid sequences of CD4 and a candidate molecule to determine whether the candidate molecule is capable of binding to CD4 via amino acids 148 to 154, 164 to 168 and acids 185, 187, 189, 190 and 192.

The selection of candidate molecules can further be restricted by considering the features of the CD4-BT061 interaction described below in Example 1. In particular, candidate molecules can be restricted to those that bind to the regions of CD4 without salt bridges and/or those that include one or more components which are accommodated in one or more of the binding pockets on the surface of CD4 involving:

(i) amino acids residues S152, V153, Q154, Q164, G165, T185, V186, L187 and K192 of CD4 (as shown in FIG. 10);

(ii) amino acid residues S150, S152, G165 and G166 of CD4 (as shown in FIG. 11); and/or (iii) amino acid residue S150, P151, S152 and K167 (as shown in FIG. 12).

The method of this computer implemented embodiment can further comprise a step (d) in which the molecule selected in step (c) is produced. For example, where the selected molecule is a peptide the amino acid sequence of the peptide is taken from the computer and the peptide is manufactured in vitro. Thereafter, the activity of the selected molecule can be assessed in vitro, by contacting the selected molecule with a peptide or polypeptide comprising the relevant regions/amino acids of CD4, or by contacting the selected molecule with a cell expressing CD4. These in vitro steps are described further below in relation to the embodiment of the first aspect in which steps (a) to (c) are conducted in vitro.

In particular, as an alternative to the computer assisted embodiment described above, steps (a) to (c) of the method of screening may be conducted in vitro, and step (b) can comprise contacting one or more candidate molecules with the relevant regions/amino acids of CD4 and determining whether the candidate molecule is able to bind to one or more of these regions. An example of this embodiment comprises a method for screening for one or more molecules capable of binding to CD4 comprising: (a) contacting the one or more molecules with a peptide comprising one or more of the following regions of human CD4: amino acids 148 to 154, amino acids 164 to 168, and amino acids 185 to 192; and (b) detecting whether the one or more molecules binds to the one or more regions of the peptide, wherein the molecule does not comprise CDR1, CDR2 and CDR3 of BT061 heavy chain and CDR1, CDR2 and CDR3 of BT061 light chain.

The method of the present invention preferably comprises screening a library of molecules. In particular, the library can be a phage display library prepared according to methods known in the art. The library may be a peptide library reflecting a systematic combination of different amino acids/peptides in large number. Usually, a peptide library is synthesized on solid phase, mostly on resin, which can be made as flat surface or beads (solid phase peptide synthesis). This library can be used for protein-protein interactions, drug discovery, purification of proteins and variation in the antibody recognition sequence to generate antibody variants with different affinities.

Further libraries besides the phage display include yeast display, bacterial display, mRNA display, ribosomal and polysomal display. Ribosome display comprises a process which results in translated proteins that are associated with their mRNA progenitor which is used, as a complex, to bind to an immobilized ligand in a selection step. mRNA display results in translated peptides or proteins that are associated with their mRNA progenitor via a puromycin linkage.

Bacterial display represent a library technology of polypeptides displayed on the surface of bacteria can be screened using flow cytometry or iterative selection procedures (biopanning).

In the yeast display (Abbott) technique, a protein of interest is displayed as a fusion to the Aga2p protein on the surface of yeast. The Aga2p protein is naturally used by yeast to mediate cell-cell contacts during yeast cell mating. As such, display of a protein via Aga2p projects the protein away from the cell surface, minimizing potential interactions with other molecules on the yeast cell wall. The use of magnetic separation and flow cytometry in conjunction with a yeast display library is a highly effective method to isolate high affinity protein ligands against nearly any receptor through directed evolution.

Polysome display comprises very large library of peptides displayed on bacterial polysomes (Mattheakis et al., 1994). MULTIPIN® peptide technology can also be used to generate the libraries (Tribbick et al., J. Immunl. Methods (2002) 267: 27-35).

In the in vitro contacting step the selected molecule or a candidate molecule can be contacted with a peptide or polypeptide comprising one or more of the following regions or amino acids (the "relevant regions/amino acids of CD4") of human CD4: amino acids 148 to 154, amino acids 164 to 168 and amino acids 185, 187, 189, 190 and 192, wherein the amino acids are numbered as shown in FIG. 6. Preferably the regions of human CD4 are: amino acids 148 to 154, amino acids 164 to 168 and amino acids 185 to 192. More preferably, the peptide or polypeptide comprises all of these regions. Still more preferably the peptide or polypeptide further comprises at least one of the following amino acids of human CD4: Lys26, Arg156, Arg159, Lys161 and Lys192. Most preferably the peptide or polypeptide comprises the Ig-like C2-type 1 domain of human CD4 (i.e. amino acids 126 to 205) and optionally also the Ig-like V-type domain. In particular, D1 of CD4 is utilized to stabilize the epitope. Accordingly, where the peptide or polypeptide is to be used in a competitive binding assay, the use of D1 is preferred. However, it is noted that one or two amino acids from these regions may be removed. It is preferred that the peptide is less than 50 amino acids in length and more preferably less than 20 amino acids in length.

The peptides may be natural peptides, for example those made by enzymatic cleavage of CD4 or directly by host cell expression, or they may be synthetic peptides. The peptides may also be modified, for example via PEGylation, phosphorylation, amydation, acetylation, labeling with Biotin, or fluorescent dyes such as FITC, or labeling with isotopes. Further modifications might use techniques like the "Multiple antigen peptide application". With such a technology one can produce high-titer anti-peptide antibodies and synthetic peptide vaccines. This system utilizes the α- and ε-amino groups of lysine to form a backbone to which multiple peptide chains can be attached. Depending on the number of lysine tiers, different numbers of peptide branches can be synthesized. This eliminates the need to conjugate the antigen to a protein carrier (Briand et al., J Immunol Methods (1992). 156; 2: pp 255-265).

As indicated above, the methods of the present invention are preferably performed with peptides sequences from human CD4. However, they can equally be performed with homologous regions of CD4 proteins of other mammals, or other molecules containing the Ig-like C2-type 1 domain.

The step of contacting the one or more molecules, selected molecule or candidate molecule with a peptide and the step of detecting whether the one or more molecules binds to the one or more regions of the peptide, can be conducted according to methods known in the art. In particular, in one embodiment of the invention the peptide is a linear peptide which is spotted or fixed onto a membrane. During the contacting step, the molecules which are able to bind to the CD4 peptide sequence become trapped.

In an alternative embodiment peptides are created which can mimic the conformation of the wild-type human CD4 epitope. This can be done by structure-based molecular design methods known in the art.

The following display methods are mentioned which can be used for screening:

To screen for linear epitopes an epitope mapping technique can be used. Amino acid sequence representing parts of the target epitope (e.g. 10-15 amino acids), which overlap by one amino acid, are spotted onto a membrane (e.g. cellulose). Subsequently it is possible to screen for proteins, or peptides recognizing the spotted amino acid sequence. Several rounds of selection can be done with different stringency conditions to select high affinity binders.

To screen for discontinuous epitopes techniques such as phage display have been developed. Contemporary standard libraries of linear or cyclic peptides have a diversity of approximately $10^9$ independent clones, meaning libraries with up to seven randomized positions can theoretically guarantee comprehensive coverage of the potential sequence repertoire. In vitro translation systems result in peptide libraries with a higher diversity since coupling of the peptide with its mRNA is achieved in a cell-free system involving small particles of RNA/peptide/ribosome or only mRNA/peptide complexes. Further libraries include polysomal or ribosomal display (Mattheakis et al., PNAS 1994; 91(19): 9022-6) or the PROfusion technology Roberts and Szostak, PNAS (1997) 94(23):12297-302). The latter technology comprises a covalent fusion between an mRNA and the peptide or protein that it encodes can be generated by in vitro translation of synthetic mRNAs that carry puromycin, a peptidyl acceptor antibiotic, at their 3' end.

Minicell display (U.S. Pat. No. 7,125,679) is also possible, which includes the preparation of peptides for screening that are expressed on the outer surface containing oligonucleotide library. Similarly. Flitrix (Invitrogen Corp.) random peptide library which uses the bacterial flagellar protein FliC and thioredoxin can also be used.

Further, as well as the above mentioned display methods, mass spectrometry or Solid Phase Epitope Recovery (SPHERE) (Genzyme) can also be utilized (Lawendowski et al., J. Immunol., (2002) 169: 2414-2421).

In one embodiment detection of binding comprises performing X-ray crystallography or NMR. In particular, molecules can be selected which bind to the peptide without a salt bridge, using methods of X-ray crystallography which are known in the art.

Alternatively, or in addition, the method of the first aspect can comprise contacting the selected molecule or candidate molecule with a cell expressing CD4, and in particular a CD4+CD25+ regulatory T cell. This can be done in particular to determine the ability of the selected molecule or candidate molecule to modulate the activity of, and in particular activate CD4+ CD25+ regulatory T cells (preferably selectively activate T regs cells without activation of T helper cells), or to determine the ability of the selected molecule or candidate molecule to reduce, or down modulate, CD4 receptor expression, in particular on specific lymphocyte populations in an in vitro culture of PBMC (peripheral blood mononuclear cells). In these embodiments it is preferred that the selected molecule or the candidate molecule are antibodies or antibody fragments, and in particular those of the IgG1 type, as discussed further below.

For the modulation assay, Treg can, in general, be isolated using commercially available isolation kits (magnetic beads isolation) sorting for CD25, CD27, CD62L and/or CD127 and additional intracellular staining for FoxP3. Tregs are negative for CD127, positive for CD25 and Foxp3. CD39, a cell surface associated ectonucleotidase, can be also used to purify Treg with strong suppressor functions (Mandapathil et al., J. Immunol. Methods (2009). 346 (1-2), 55-63). Commercially available kits may use a combination of negative selection of CD4+ followed by positive isolation of CD25 positive resulting in a CD4 CD25 positive cell population. These cells can be further processed. CD25 and the transcription factor Foxp3 are expression markers associated with suppressive function of Tregs. Although intracellular staining with Foxp3 confirms the regulatory phenotype, due to the intracellular staining the cells are not viable for further therapeutic use. Foxp3 is commonly used as an intracellular marker of activated Tregs/functionally active Tregs.

Further, due to the fact that BT061, and the molecule being screened for, binds to an epitope which is distinct from that bound by other commercially available antibodies, one can purify Tregs with commercially available isolation kits (magnetic bead isolation) and additionally another CD4 antibody (e.g. SK-3 OKT4), which are non-competing for the BT061 binding site on CD4 and subsequently assay for activation of Tregs with the candidate molecule or selected molecule.

The ability of the candidate molecule to activate Tregs can be assayed by examining the Treg suppressive activity, after contact with the candidate molecule, by co-culturing Tregs with CD4 positive CD25 negative effector T-cells. Activated Tregs are able to inhibit proliferation of CD4+ CD25− effector T-cells, which can be labeled with CFSE (assessment of cell expansion via CFSE dilution assay). Alternatively the proliferation of effector cells can be determined by [3H] Thymidine incorporation.

More particularly, suppressive capacity can be assayed by for example a mixed lymphocyte reaction (MLR). Cell division of effector T-cell can be inhibited by the suppressive action of Tregs. For this naive autologous CD4+ CD25− T responder cells are stimulated with irradiated allogenic stimulator PBMCs. Tregs or conventional T cells are titrated into the culture and proliferation can be assessed by Thymidine incorporation.

Activation of Treg can also be assayed through determination of cyclic AMP production (as described in WO 2008/092905).

Cytokines affected by activated Tregs in a co-culture can also be measured to determine the activity of these cells towards effector cells. For example, Tregs exert their suppressive activity also via IL-2 consumption which results in proliferation inhibition of T effector cells. IL-4 or IFN gamma can be also determined in the co-culture assay and are reduced in case of activated Tregs. Furthermore surface activation markers on T effector cells, such as CD25, are reduced when Treg cells are activated and exert suppressive activity.

Additionally, determination of cell death (via factors such as Bim) in effector cells (which can be also CD4 positive) induced by activated Tregs in co-culture represents a further method to examine whether Tregs are activated (Pandiyan et al., Nature Immunol. (2007) 8 1353-1362).

Since Tregs represent only a small proportion in the blood (2-10%), several expansion strategies are known. For example following TCR stimulation with an anti-CD3 and costimulation with anti-CD28 and rapamycin can be used to increase the number of T-cells. Rapamycin promotes the selective survival of Tregs, but not Teffector cells.

Several polyclonal expansion protocols are available e.g. Following positive selection for CD4/CD25 Treg cells can be expanded polyclonally in vitro by using anti-CD3 and anti-CD28 antibody (for stimulation) in combination with IL-2 and/or IL-15 able to increase Treg numbers while preserving suppressive capacity (Earle et al., Clin. Immunol. (2005) 115: 3-9).

In relation to modulation of CD4 expression, it is noted that by adding anti-CD4 antibodies, the expression of CD4 receptors on cell surfaces can be reduced. This feature can be used as basis for a potency assay to determine the degree of CD4 binding. In particular, in this assay the step of contacting can comprise (i) incubating the candidate or selected molecule with peripheral blood mononuclear cells (PBMC) from human donor blood at 37° C.; (ii) staining the incubated cells with an anti-CD4 labeled antibody which does not compete with BT061 for CD4 binding; and (iii) detecting the quantity of staining, to determine the occupation of CD4 receptors, and therefore the quantity of CD4 molecules present on the cell surfaces.

More specifically, this assay involves isolating PBMC (i.e. lymphocytes and monocytes) from human donor blood, which are then incubated with various concentrations of the candidate or selected molecule (preferably an antibody or antibody fragment) at 37° C. After incubation for 3 hours, the cells are stained by adding fluorochrome-labelled antibodies, such as phycoerythrin anti-CD4, which bind to a different epitope on CD4 to that bound by BT061. These staining antibodies label CD4 receptors on specific lymphocyte populations. As the BT061 epitope and the fluorochrome-labelled CD4 antibody used recognise different epitopes on the CD4 molecule and do not compete, this technique enables the quantity of CD4 receptors on the cell surface to be determined, independently of binding of CD4 by the candidate or selected molecule. The measurement is performed in a flow cytometer in which the antibody-labelled cells pass through a laser beam and are stimulated. When stimulated by the laser beam, the stained cells fluoresce in proportion to the bound antibody, and the light emitted is captured by the flow cytometer and then evaluated using the software known in the art, e.g. FlowJo software (Tree Star, Inc). Using the software (such as Parallel Line Assay software, Stegmann Systems) it is then possible to calculate a relative activity (potency) for the sample in relation to the standard run in parallel.

In a further embodiment of this aspect of the invention the contacting step can comprise contacting the CD4 peptide or polypeptide (preferably comprising D1 and D2 of CD4) or cell expressing CD4, and the candidate/selected molecule with a competitor antibody or antibody fragment having the heavy and light chain variable domains of BT061 to determine if the candidate/selected molecule is able to block binding of the competitor antibody or antibody fragment to CD4.

The one or more candidate molecules in the first aspect may be a peptide or a non-peptide. In particular, the one or more molecules may be a mimotope, a peptidomimetic, a small molecule, a recognition protein based on a natural or engineered lipocalin, an oligonucleotide, an siRNA, a DARPin, a fibronectin, an affibody, a Kunitz-type inhibitor, a peptide aptamer, a ribozyme, a toxin, a camelid, an antibody, an antibody fragment or an antibody-derived molecule.

Mimotopes are peptides mimicking protein, carbohydrates or lipid epitopes and can be generated by phage display technology. When selected by antibodies, they represent exclusively B-cell epitopes and are devoid of antigen/allergen-specific T-cell epitopes. Coupled to carriers or presented in a multiple antigenic peptide form mimotopes achieve immunogenicity and induce epitope-specific antibody responses upon vaccination.

A peptidomimetic is a small protein-like chain designed to mimic a peptide. They typically arise from modification of an existing peptide in order to alter the molecule's properties. For example, they may arise from modifications to change the molecule's stability or biological activity. These modifications involve changes to the peptide that will not occur naturally (such as altered backbones and the incorporation of non-natural amino acids).

An example of peptidomimetics were those designed and synthesized with the purpose of binding to target proteins in order to induce cancer cells into a form of programmed cell death called apoptosis. Essentially these work by mimicking key interactions that activate apoptotic pathway in the cell.

A foldamer is a discrete chain molecule or oligomer that adopts a secondary structure stabilized by non-covalent interactions (Gellman, Acc. Chem. Res (1998) 31 (4): 173-180; Hill et al., Chem. Rev. (2001) 101 (12): 3893-4012). They are artificial molecules that mimic the ability of proteins, nucleic acids, and polysaccharides to fold into well-defined conformations, such as helices and β-sheets. Foldamers have been demonstrated to display a number of interesting supramolecular properties including molecular self-assembly, molecular recognition, and host-guest chemistry. They are studied as models of biological molecules and have been shown to display antimicrobial activity. They also have great potential application to the development of new functional materials.

A small molecule is a low molecular weight organic compound which is by definition not a polymer. The upper molecular weight limit for a small molecule is approximately 800 Daltons which allows for the possibility to rapidly diffuse across cell membranes so that they can reach intracellular sites of action. A small molecule exerts high affinity to a biopolymer such as protein, nucleic acid, or polysaccharide and in addition alters the activity or function of the biopolymer.

DARPins (Designed Ankyrin Repeat Proteins) are artificial proteins which are also able to recognize an antigen or antigenic structures. They are structurally derived from Ankyrin Proteins, are about 14 kDa (166 amino acid) and consist of three repeat motifs. They display a comparable affinity to antigens as antibodies. (Stumpp et al., Drug Discov. Today (2008) 13, Nr. 15-16, S. 695-701).

The Affibody® molecules are small and robust high affinity protein molecules that can be engineered to bind specifically to a large number of target proteins.

The term "camelid" refers to antibodies produced by camelids and comprising a heavy chain homodimer, and derivatives of these molecules (Muyldermans et al., Veterinary Immunology and Immunopathology, 128; 1-3; pp. 178-183 (2009)).

It is preferred that the candidate molecule is an antibody or an antibody fragment. The phrase "an antibody, an antibody fragment or an antibody-derived molecule" covers monoclonal antibodies, polyclonal antibodies, multi-specific antibodies and antibody fragments. The term "antibody fragment" includes, in particular, fragments comprising Fab, Fab', F(ab)'$_2$, Fv and scFv fragments and dia- or tribodies. Preferably these are based on humanized or human antibodies. More preferably the antibody comprises a constant region/domain, i.e. an Fc portion. Where the antibody comprises a human constant region, this constant region can be selected among constant domains from any class of immunoglobulins, including IgM, IgG, IgD, IgA and IgE, and any isotype including IgG1, IgG2, IgG3 and IgG4. Preferred constant regions are selected among constant domains of IgG, in particular IgG1.

The Fc portions of different Ig subclasses are bound by cellular FcR that are specific for individual subclasses. Three different FcR classes are known that bind IgG isotypes with discrete affinities, CD16, CD32 and CD64. Diverse patterns of FcγR are expressed by various different immune cells such as monocytes, B cells, natural killer (NK) cells and others. The present inventors have found in vitro that the ability of the constant region of the antibody BT061 to bind Fc receptors (FcR) is critical for the ability of the antibody to cause CD4 down modulation in T cells. In particular, in vitro studies indicate that of the Fcγ receptors, Fcγ1 receptor, which is mainly expressed on monocytes, is primarily involved; the presence of monocytes in a culture of PBMC is necessary and sufficient to confer CD4 down modulation in BT061-treated T cells.

Accordingly, in an embodiment of the invention the candidate molecule is capable of binding to an Fc receptor, preferably FcγRI (i.e. CD64) and most preferably comprises the Fc portion of an IgG1 antibody. In addition, or alternatively, the candidate molecule is capable of binding to monocytes via an Fc receptor.

In this aspect of the present invention the molecule being screened is not an antibody or antibody fragment which comprises CDR1, CDR2 and CDR3 of BT061 heavy chain and CDR1, CDR2 and CDR3 of BT061 light chain. These CDR sequences are shown in FIGS. 2A and 2B. In a preferred embodiment the molecule being screened is not the murine B-F5 molecule described by Racadot et al. (Clin. Exp. Rheum., 10, 365-374 (1992)).

In a preferred embodiment of the first aspect of the invention where the one or more candidate molecules are antibodies or antibody fragments, the antibodies or antibody fragments comprise CDR1 and CDR2 of BT061 light chain and CDR1 and CDR3 of BT061 heavy chain optionally with amino acid substitutions in the sequences of the CDRs provided:

a. the light chain CDR1 comprises: Ser32; Gly33; and Tyr 34;
b. the light chain CDR2 comprises: Leu54; and Ile57;
c. the heavy chain CDR1 comprises Asp31, Glu31, Thr31, Cys31, Pro31, Met31 or Tyr31; and
d. the heavy chain CDR3 comprises Tyr103, Phe103 or His103; Arg104; Tyr105; Asp106; and Trp110, Phe110, His 110 or Tyr110.

Alternatively, the candidate molecule is an antibody or antibody fragment comprising V domains having at least 70%, at least 80%, at least 85%, more preferably at least 90% sequence identity with the V domains of BT061 (i.e. SEQ ID No: 2 and SEQ ID No: 3) and comprising the sequence motif SGYSY (SEQ ID No: 10) in CDR1 of the light chain V domain, the sequence motif LASILE (SEQ ID No: 11) in CDR2 of the light chain V domain and the sequence motif SYY/F/HRYD (SEQ ID No: 13) in CDR3 of the heavy chain V domain.

In this method the one or more molecules screened are a set of candidate molecules defined by their similarity to the antibody BT061 and those residues within BT061 which the present inventors have identified as being important in the interaction between the BT061 antibody and the CD4. In particular, this method is preferably one which identifies molecules having approximately equivalent or better binding affinity/specificity and Treg activation activity compared to BT061.

The peptide sequences of the light chain and heavy chain of the humanized antibody BT061 are shown in FIGS. 2A and 2B, respectively. The CDRs of the light and heavy chain are marked on these Figures. Herein the amino acid residues within these CDRs are identified by residue type and number, in which the number represents the position of the amino acid within the variable region of the light or heavy chain BT061 antibody as represented in FIGS. 2A and 2B. The use of residue type and number has been done for the purpose of clearly identifying the amino acid residue of the BT061 CDR which is being referred to. However, it will be appreciated that the number of the residue is not intended to limit the residue to being in that position in the candidate antibody or fragment being screened in the method. For example, in an antibody of this embodiment Ser32 may be at position 31 within a light chain CDR1 if a non-essential amino acid residue has been deleted from the section 1 to 30 of the light chain.

In a preferred embodiment the amino acid substitutions in the sequence of CDR1 and CDR2 of BT061 light chain and CDR1 and CDR3 of the BT061 heavy chain are selected from those set out in Table 4 and Table 5 below. More preferably the antibody or antibody fragment comprises a light chain comprising Tyr53 or Phe53 and a heavy chain comprising Ser28 (as shown in Table 7 in Example 1). Alternatively, or in addition, the antibody or antibody fragment comprises a light chain containing Asp64, and/or the antibody or antibody fragment comprises a heavy chain having at least one of Asp31 and Glu56 (as shown in Table 8, in Example 1). The antibody or antibody fragment may further comprise the CDR3 of BT061 light chain and/or the CDR2 of BT061 heavy chain optionally with amino acid substitutions in the sequences of these CDRs wherein the substitutions are selected from those set out in Table 4 and Table 5.

Candidate antibody or antibody fragments for use in the screening methods can be generated by mutating the known sequence of BT061. In particular, where these mutations are within the CDRs they can be targeted mutations to ensure that the amino acids recited above are retained, or the desired substitutions are made.

Where step (a) of the screening method is performed in vitro, targeted mutagenesis can be used to cause amino acid exchange in the defined positions within the CDRs. Through knowing the corresponding DNA sequence of the amino acids one can create a library of specific mutants containing a range of desired amino acid substitutions. Where steps (a) to (c) of the screening method are to be performed in a computer system, the three dimensional structure of the candidate antibodies or antibody fragments can be generated by inputting the amino acid sequence in a manner similar to that indicated above in relation to CD4.

TABLE 4

Table showing sequence variations of the BT061 light chain CDRs

| | | BT061 Position sequence | | Isosteric Variations | | |
|---|---|---|---|---|---|---|
| CDR1 | 24 | Arg 24 | Lys | Gln | Asn | |
| | 25 | Ala 25 | Gly | | | |
| | 26 | Ser 26 | Thr | | | |
| | 27 | Lys 27 | Arg | Glu | | |
| | 28 | Ser 28 | Gly | Pro | | |
| | 29 | Val 29 | Ala | Ile | | |
| | 30 | Ser 30 | | | | |
| | 31 | Thr 31 | Ser | Asn | Gln | Asp |
| | 32 | Ser 32 | | | | |
| | 33 | Gly 33 | | | | |
| | 34 | Tyr 34 | | | | |
| | 35 | Ser 35 | | | | |
| | 36 | Tyr 36 | | | | |

TABLE 4-continued

Table showing sequence variations of the BT061 light chain CDRs

| | | BT061 Position sequence | | Isosteric Variations | | |
|---|---|---|---|---|---|---|
| | 37 | Ile 37 | Val | Leu | | |
| | 38 | Tyr 38 | | | | |
| CDR2 | 54 | Leu 54 | | | | |
| | 55 | Ala 55 | | | | |
| | 56 | Ser 56 | | | | |
| | 57 | Ile 57 | | | | |
| | 58 | Leu 58 | | | | |
| | 59 | Glu 59 | | | | |
| | 60 | Ser 60 | Asn | Gln | Thr | Glu | Asp |
| CDR3 | 93 | Gln 93 | | | | |
| | 94 | His 94 | | | | |
| | 95 | Ser 95 | | | | |
| | 96 | Arg 96 | Lys | | | |
| | 97 | Glu 97 | Asp | Arg | | |
| | 98 | Leu 98 | Gly | Ile | | |
| | 99 | Pro 99 | | | | |
| | 100 | Trp 100 | | | | |
| | 101 | Thr 101 | Ser | | | |

TABLE 5

Table showing sequence variations of the BT061 heavy chain CDRs.

| | | BT061 Position sequence | | Isosteric Variations | | | |
|---|---|---|---|---|---|---|---|
| CDR1 | 31 | Asp 31 | Glu | Thr | Cys | Pro | Met | Tyr |
| | 32 | Cys 32 | Ser | Ala | Gly | Val | | |
| | 33 | Arg 33 | Lys | Ser | Thr | Glu | | |
| | 34 | Met 34 | Ile | Leu | Ala | Val | | |
| | 35 | Tyr 35 | | | | | | |
| CDR2 | 51 | Ile 51 | Ala | Val | Gly | | | |
| | 52 | Ser 52 | Asp | Gly | Ala | Thr | | |
| | 53 | Val 53 | Ser | Gly | Thr | Ile | | |
| | 54 | Lys 54 | Arg | Tyr | | | | |
| | 55 | Ser 55 | Asn | Gln | Thr | Glu | | |
| | 56 | Glu 56 | Asp | Arg | | | | |
| | 57 | Asn 57 | Asp | Tyr | Gln | Glu | | |
| | 58 | Tyr 58 | His | Lys | | | | |
| | 59 | Gly 59 | Ser | | | | | |
| | 60 | Ala 60 | Ser | Thr | | | | |
| | 61 | Asn 61 | Gln | Asp | | | | |
| | 62 | Tyr 62 | Phe | His | | | | |
| | 63 | Ala 63 | Gly | Ser | | | | |
| | 64 | Glu 64 | Asp | Gln | Asn | Arg | | |
| | 65 | Ser 65 | Gly | Ala | Asn | | | |
| | 66 | Val 66 | Ile | Ala | Ser | Gly | | |
| | 67 | Arg 67 | Lys | Gln | Tyr | His | Glu | |
| | 68 | Gly 68 | | | | | | |
| CDR3 | 101 | Ser 101 | | | | | | |
| | 102 | Tyr 102 | | | | | | |
| | 103 | Tyr 103 | Phe | His | | | | |
| | 104 | Arg 104 | | | | | | |
| | 105 | Tyr 105 | | | | | | |
| | 106 | Asp 106 | | | | | | |
| | 107 | Val 107 | Ile | Pro | Asp | Thr | Glu | |
| | 108 | Gly 108 | Ala | | | | | |
| | 109 | Ala 109 | Ser | | | | | |
| | 110 | Trp 110 | Phe | His | Tyr | | | |
| | 111 | Phe 111 | | | | | | |
| | 112 | Ala 112 | Ser | | | | | |
| | 113 | Tyr 113 | Phe | His | Asn | | | |

Isosteric variations are those which do not cause steric effects, i.e. they do not change the conformation of the antibody in any way.

In a second aspect the present invention provides a method for screening for a candidate molecule, which is an antibody or antibody fragment, that is capable of binding with CD4 comprising: (a) providing an antibody or antibody fragment comprising CDR1 and CDR2 of BT061 light chain and CDR1 and CDR3 of BT061 heavy chain optionally with amino acid substitutions in the sequences of the CDRs provided:
(i) the light chain CDR1 comprises: Ser32; Gly33; and Tyr 34;
(ii) the light chain CDR2 comprises: Leu54; and Ile57;
(iii) the heavy chain CDR1 comprises Asp31, Glu31, Thr31, Cys31, Pro31, Met31 or Tyr31; and
(iv) the heavy chain CDR3 comprises Tyr103, Phe103 or His103; Arg104; Tyr105; Asp106; and Trp110, Phe110, His 110 or Tyr110,
(b) determining whether the antibody or antibody fragment is capable of binding to CD4, and (c) selecting the antibody or antibody fragment determined in step (b) to be capable of binding to CD4, wherein the antibody or antibody fragment does not comprise CDR1, CDR2 and CDR3 of BT061 heavy chain and CDR1, CDR2 and CDR3 of BT061 light chain.

In one embodiment, steps (a) to (c) of the screening method according to the second aspect of the present invention can be performed in a computer system in a manner similar to that described above in relation to the first aspect of the invention. In particular, a number of BT061 variants can be generated in silico based on information provided herein on the residues important for the interaction of BT061 with its CD4 epitope, and the interaction of these variants with CD4 simulated.

In this embodiment the method can further comprise a step in which the candidate antibody or antibody fragment is contacted with a cell expressing CD4.

In an alternative embodiment to that performed in a computer system, steps (a) to (c) of the screening method according to the second aspect of the invention can be performed in vitro and step (b) can comprise contacting the candidate antibody or antibody fragment with a cell expressing CD4. Preferably the ability to bind CD4 is determined based on the ability of the candidate to activate CD4+CD25+ regulatory T cells.

In particular, this aspect of the present invention can be a method for screening for an antibody or antibody fragment capable of activating CD4+CD25+regulatory T cells which comprises:

(a) contacting one or more antibody or antibody fragments with CD4+CD25+ regulatory T cells;

(b) assessing the ability of the antibody or antibody fragment to activate said CD4+CD25+ regulatory T cells; and (c) identifying an antibody or antibody fragment which activates the CD4+CD25+ regulatory T cells, wherein the antibody or antibody fragment comprise CDR1 and CDR2 of BT061 light chain and CDR1 and CDR3 of BT061 heavy chain optionally with amino acid substitutions in the sequences of the CDRs provided:

(i) the light chain CDR1 comprises: Ser32; Gly33; and Tyr 34;

(ii) the light chain CDR2 comprises: Leu54; and Ile57;

(iii) the heavy chain CDR1 comprises Asp31, Glu31, Thr31, Cys31, Pro31, Met31 or Tyr31; and (iv) the heavy chain CDR3 comprises Tyr103, Phe103 or His103; Arg104; Tyr105; Asp106; and Trp110, Phe110, His 110 or Tyr110, and wherein the antibody or antibody fragment does not comprise CDR1, CDR2 and CDR3 of BT061 heavy chain and CDR1, CDR2 and CDR3 of BT061 light chain.

It is noted that the description of the embodiments and preferred features provided above in relation to the screening method according to the first aspect of the present invention also apply to the screening method according to the second aspect of the present invention.

These aspects of the invention may both further comprise production of the selected molecule, and in particular the selected antibody or antibody fragment, in order for their further use or downstream analysis.

Accordingly, the invention further provides a method for producing a therapeutic composition and therapeutic compositions obtainable by the method. In particular, the method comprises:

(a) selecting a molecule determined as being capable of activating CD4+CD25+ regulatory T cells using the method according the screening methods described above: and (b) producing a therapeutic composition comprising the molecule.

In particular, the therapeutic composition can be manufactured by combining the molecule with one or more pharmaceutically acceptable carriers or diluents.

Antibodies and Antibody Fragments

The work of the present inventors has allowed the identification of the features of BT061 which are important for their interaction with, and activation of, CD4+ CD25+ regulatory T cells. This has led to the identification of specific mutants/variants of the BT061 antibody which will be capable of activating CD4+CD25+ regulatory T cells.

Accordingly, in a third aspect the present invention provides an antibody or antibody fragment capable of activating CD4+CD25+ regulatory T cells comprising CDR1 and CDR2 of BT061 light chain and CDR1 and CDR3 of BT061 heavy chain optionally with amino acid substitutions in the sequences of the CDRs provided:

(i) the light chain CDR1 comprises: Ser32; Gly33; and Tyr 34;

(ii) the light chain CDR2 comprises: Leu54; and Ile57;

(iii) the heavy chain CDR1 comprises Asp31, Glu31, Thr31, Cys31, Pro31, Met31 or Tyr31; and (iv) the heavy chain CDR3 comprises Tyr103, Phe103 or His103; Arg104; Tyr105; Asp106; and Trp110, Phe110, His 110 or Tyr110, and wherein the antibody or antibody fragment does not comprise CDR1, CDR2 and CDR3 of BT061 heavy chain and CDR1, CDR2 and CDR3 of BT061 light chain.

Alternatively, the third aspect provides an antibody or antibody fragment capable of activating CD4+CD25+ regulatory T cells comprising CDR1 and CDR2 of BT061 light chain and CDR1 and CDR3 of BT061 heavy chain optionally with amino acid substitutions in the sequences of the CDRs provided:

(i) the light chain CDR1 comprises: Ser32 or Pro32; Gly33 or Ala33; and Tyr 34;

(ii) the light chain CDR2 comprises: Leu54, Ile54 or Thr54; and Ile57, Leu57; Val57 or Thr57;

(iii) the heavy chain CDR1 comprises Asp31, Glu31, Thr31, Cys31, Pro31, Met31 or Tyr31; and (iv) the heavy chain CDR3 comprises Tyr103, Phe103 or His103; Arg104; Tyr105; Asp106; and Trp110, Phe110, His 110 or Tyr110, and wherein the antibody or antibody fragment does not comprise CDR1, CDR2 and CDR3 of BT061 heavy chain and CDR1, CDR2 and CDR3 of BT061 light chain.

As discussed above, the peptide sequences of the light chain and heavy chain of the humanized antibody BT061 are shown in FIGS. 2A and 2B, respectively. The CDRs of the light and heavy chain are marked on these Figures. As discussed above, the amino acid residues within these CDRs are identified by residue type and number, in which the number represents the position of the amino acid within the variable region of the light or heavy chain BT061 antibody as represented in FIGS. 2A and 2B. The use of residue type and number has been done for the purpose of clearly identifying the amino acid residue of the BT061 CDR which is being referred to. However, it will be appreciated that the number of the residue is not intended to limit the residue to being in that position in the antibody, or fragment, of the invention. For example, in an antibody of the invention Ser32 may be at position 31 within a light chain CDR1 if a non-essential amino acid residue has been deleted from the section 1 to 30 of the light chain.

In a preferred embodiment the amino acid substitutions in the sequence of CDR1 and CDR2 of BT061 light chain and CDR1 and CDR3 of the BT061 heavy chain are selected from those set out in Table 4 and Table 5 above. More preferably the antibody or antibody fragment comprises a light chain comprising Tyr53 or Phe53 and a heavy chain comprising Ser28. Alternatively, or in addition, the antibody or antibody fragment comprises a light chain containing Asp64, and/or the antibody or antibody fragment comprises a heavy chain having at least one of amino acids indicated in Table 8 of Example 1 to be important for interaction. In particular, the heavy chain comprises Asp31 and/or Glu56. The antibody or antibody fragment may further comprise the CDR3 of BT061 light chain and/or the CDR2 of BT061 heavy chain optionally with amino acid substitutions in the sequences of these CDRs wherein the substitutions are selected from those set out in Table 4 and Table 5.

In particular, recognition and binding of the CD4 epitope by the BT061 antibody is based on a particular constitution and conformation of the three complementarity determining areas CDR1, CDR2, and CDR3. Even though only CDR1 and CDR2 of the light chain and CDR1 and CDR3 of the heavy chain are in direct contact with CD4, all six CDRs are very densely packed and mutually support each other's conformation. As a consequence, many positions in the CDRs do not tolerate any amino acid substitution without significant loss of affinity and potency of BT061. In some positions, however, substitutions do not destabilize the structure.

Examples of such conservative substitutions are given in Tables 4 and 5. In these tables the sequence variations have been selected such that the overall interaction network is preserved. The syntax of attractive as well as repulsive interactions is maintained. Directed polar interactions can be inverted, e.g. donor-acceptor pair of hydrogen bridges, the ionic partners of salt bridges, or loci of the partners of dipole-quadrupole interactions can be switched.

In further embodiments the antibody or antibody fragment comprises the sequence (SEQ ID No: 14):

```
        10         20         30         40         50         60
DIVMTQSPDS LAVSLGERAT INCXXXXXXS XSGYSYXYWY QQKPGQPPKL LIYLASILEX 70         80         90        100        110        120
GVPDRFSGSG SGTDFTLTIS SLQAEDVAVY YCQHSXXXPW XFGQGTKVEI KRTVAAPSVF 130        140        150        160        170        180
IFPPSDEQLK SGTASVVCLL NNFYPREAKV QWKVDNALQS GNSQESVTEQ DSKDSTYSLS 190        200        210        218
STLTLSKADY EKHKVYACEV THQGLSSPVT KSFNRGEC
``` wherein the amino acids at positions 24 to 29, 31, 37, 60, 96 to 98 and 101 marked as "X" are selected from those shown at the corresponding positions in Table 4, and further comprising the sequence (SEQ ID No: 15):

```
        10         20         30         40         50         60
EEQLVESGGG LVKPGGSLRL SCAASGFSFS XXXXYWLRQA PGKGLEWIGV XXXXXXXXXX 70         80         90        100        110        120
XXXXXXXGRF TISRDDSKNT VYLQMNSLKT EDTAVYYCSA SYXRYDXXXX FXXWGQGTLV 130        140        150        160        170        180
TVSSASTKGP SVFPLAPSSK STSGGTAALG CLVKDYFPEP VTVSWNSGAL TSGVHTFPAV 190        200        210        220        230        240
LQSSGLYSLS SVVTVPSSSL GTQTYICNVN HKPSNTKVDK KVEPKSCDKT HTCPPCPAPE 250        260        270        280        290        300
LLGGPSVFLF PPKPKDTLMI SRTPEVTCVV VDVSHEDPEV KFNWYVDGVE VHNAKTKPRE 310        320        330        340        350        360
EQYNSTYRVV SVLTVLHQDW LNGKEYKCKV SNKALPAPIE KTISKAKGQP REPQVYTLPP 370        380        390        400        410        420
SRDELTKNQV SLTCLVKGFY PSDIAVEWES NGQPENNYKT TPPVLDSDGS FFLYSKLTVD 430        440        450        454
KSRWQQGNVF SCSVMHEALH NHYTQKSLSL SPGK
``` wherein the amino acids at positions 31 to 34, 51 to 67, 103, 107 to 110, 111 and 112 marked as "X" are selected from those shown at the corresponding positions in Table 5.

In particular, specific amino acid motifs within CDR1 and CDR2 of the light chain and within CDR3 of the heavy chain of BT061 are important for CD4 binding. Accordingly, the antibody or antibody fragment may comprise SGYSY (SEQ ID No: 10) from CDR1 of BT061 light chain and/or the sequence LASILE (SEQ ID No: 11) from CDR2 of BT061 light chain and/or the sequence YYRYD (SEQ ID No: 12) from CDR3 of BT061 heavy chain.

Further, the antibody or antibody fragment capable of activating CD4+CD25+ regulatory T cells may have V domains that are at least 80% identical, more preferably at least 90% identical to the V domains of the antibody BT061, the V domains comprising:

(i) the sequence motif SGYSY (SEQ ID No: 10) in CDR1 of the light chain V domain;
(ii) the sequence motif LASILE (SEQ ID No: 11) in CDR2 of the light chain V domain; and
(iii) the sequence motif SYXRYD where X is Y, F or H (SEQ ID No: 13) in CDR3 of the heavy chain V domain, with the proviso that the antibody or antibody fragment does not comprise V domains that are 100% identical to the V domains of the antibody BT061.

In specific embodiments of the third aspect of the present invention the antibody or antibody fragment comprises the CDR sequence of BT061 light chain and the CDR sequences of BT061 heavy chain with a single amino acid substitution wherein the substitution is:

(i) A63G in the heavy chain;
(ii) R33K in the heavy chain; or
(iii) L98I in the light chain.

or the antibody or antibody fragment comprising the CDR sequences of BT061 light chain and the CDR sequences of BT061 heavy chain and a double amino acid substitution wherein the substitutions are:

(i) R33K and A63G in the heavy chain; or
(ii) L98I in the light chain and R33K in the heavy chain.

In these specific embodiments of the invention the antibody or antibody fragment may further comprising the remaining variable domain sequences of BT061 heavy and light chains.

The antibodies or fragments thereof of the present invention can, in particular, be manufactured by mutagenesis of the polynucleotide sequence known to encode the variable domains of the murine B-F5 antibody and the BT061 antibody (as described in WO2004/083247).

It is noted that the definitions and preferred embodiments for antibody and antibody fragments described above in relation to the first and second aspects of the present invention also apply to the third aspect of the invention. In particular, the antibodies and fragments are preferably IgG1 antibodies, and/or preferably comprise an Fc portion such that the antibody or antibody fragment is capable of binding to an Fc receptor, preferably FcγRI (i.e. CD64). Most preferably the antibody or antibody fragment comprises the Fc portion of an IgG1 antibody. In addition, or alternatively, the antibody or antibody fragment is capable of binding to monocytes via an Fc receptor.

Further, the present invention provides an isolated peptide comprising less than 50 amino acids of human CD4 protein and including one or more of the following regions of human CD4: amino acids 148 to 154, amino acids 164 to 168, and amino acids 185 to 192. Preferably, the isolated peptide comprises two of these regions, more preferably three. In addition or alternatively the isolated peptide comprises less than 30 amino acids, and most preferably the isolated peptide comprises less than 20 amino acids.

Further, the present invention provides a mimotope peptide of the isolated peptide described above.

The present invention also includes nucleic acids encoding the antibody or antibody fragment described herein. The nucleic acid can be RNA or DNA but is preferably DNA, and most preferably encodes the V domain of the H chain or of the L chain of the antibodies or fragments. The polynucleotide may be fused with a polynucleotide coding for the constant region of a human H or L chain, for the purpose of expressing the complete H and L chains.

The invention also makes use of expression cassettes, wherein a polynucleotide as described above is linked to appropriate control sequences to allow the regulation of its transcription and translation in a chosen host cell. Further embodiments are recombinant vectors comprising a polynucleotide or an expression cassette as described above.

The polynucleotide as described above can be linked within an expression vector to appropriate control sequences allowing the regulation of its transcription and translation in a chosen host cell. These recombinant DNA constructs can be obtained and introduced into host cells by the well known techniques of recombinant DNA and genetic engineering.

Useful host cells can be prokaryotic or eukaryotic cells. Among suitable eukaryotic cells are plant cells, cells of yeast such as Saccharomyces, cells of insects such as *Drosophila*, or *Spodoptera*, and mammalian cells such as HeLa, CHO, 3T3, C127, BHK, COS, etc. The antibodies or fragments described herein can be obtained by culturing a host cell containing an expression vector comprising a nucleic acid sequence encoding said antibody under conditions suitable for the expression thereof and recovering said antibody from the host cell culture.

According to the present invention the host cell can also be a hybridoma obtained by fusing a cell producing an antibody of the present invention with a myeloma cell.

The antibody or antibody fragment has medical and non-medical uses as described further below.

In view of the medical use, the antibody or antibody fragment described herein can be formulated in a pharmaceutical composition. In particular, a pharmaceutical composition of the present invention comprises the antibody or antibody fragment and a pharmaceutically-acceptable carrier or diluent.

Still further, the antibody or antibody fragment can further comprise a label. Techniques of antibody labeling are well known in the art. Accordingly, by way of example only, the antibody can be labeled with a fluorescent label, such as GFP or a fluorescent dye (e.g. FITC, high performance dyLight), a radioactive isotope, biotin, HRP, etc Uses of Antibodies and Epitopes The present invention further provides methods of treatment using the antibody or antibody fragment of the present invention. Since the antibody or antibody fragment is capable of selectively activating CD4+CD25+ regulatory T cells it has particular use in therapy. The present invention provides a method of treating a subject suffering from or preventing a subject suffering from an autoimmune disease or transplant rejection comprising administering to said subject an antibody or antibody fragment according to the present invention. Similarly, the present invention also provides an antibody or antibody fragment as described herein for use in medicine, and specifically for use in the treatment of autoimmune disease or transplant rejection. Accordingly, the present invention provides the use of an antibody or antibody fragment as described herein for the manufacture of a medicament for use in treating an autoimmune disease or transplant rejection. Suitable medical uses and methods of treatment are those as described for BT061 in WO2009/112502, WO2009/121690, WO2009/124815 and WO2010/034590, whose disclosures are incorporated herein by reference.

In a preferred embodiment the autoimmune disease is selected from psoriasis, rheumatoid arthritis, multiple sclerosis, type-1 diabetes, inflammatory bowel disease, Crohn's disease, autoimmune thyreoditis, autoimmune myasthenia gravis, systemic lupus erythematosus, ulcerative colitis, atopic dermatitis, myocarditis and transplant-related diseases such as graft-versus host or host-versus graft reactions, or general organ tolerance issues. The treatment of psoriasis and rheumatoid arthritis is particularly preferred.

The present invention further provides a method of treating a subject suffering from or preventing a subject suffering from an autoimmune disease or transplant rejection comprising removing a sample comprising CD4+ CD25+ regulatory T cells from the subject, contacting the sample with an antibody or antibody fragment as described herein to activate CD4+ CD25+ regulatory T cells and administering the activated cells to the subject. Such a method may additionally include an in vitro step of increasing the number of Treg cells. This can be done using the expansion strategies described herein (Peters et al., 2008).

Similarly, the present invention provides activated CD4+ CD25+ regulatory T cells, which have been activated in vitro using the antibody or antibody fragment of the present invention. These activated T regulatory cells can be for use in medicine, and in particular for use in the treatment of autoimmune disease or transplant rejection. Similarly, the present invention provides use of CD4+CD25+ regulatory T cells activated using the antibody or antibody fragment of the present invention for the manufacture of a medicament for use in the treatment of autoimmune disease or transplant rejection.

Patients with an autoimmune disease such as rheumatoid arthritis display Tregs which have a lower suppressive capacity, which might be due to pro-inflammatory cytokines, such as TNF alpha. The present invention includes a method for screening, isolating or/and activating Tregs from patients suffering from an autoimmune disease and may display (but not necessarily) a disabled population of Tregs. The specific binding mode of the antibody and fragments thereof of the present invention enables the antibody not only to bind to CD4 but more importantly to activate Tregs. Isolation of Tregs may occur using BT061 or the antibody or antibody fragment of the present invention. In case that an activation step will follow, CD4 selection has to occur by a CD4 antibody which does not compete with BT061 for binding to CD4. Alternatively an expansion strategy can be included before the activation step.

In the present invention Tregs might be isolated using BT061 and/or the antibody or antibody fragment of the present invention and transferred back to the patient in "Treg cell based immmunotherapy". Alternatively, Tregs might be stimulated directly by administering into a patient either intravenously or subcutaneously.

Treg based immunotherapy is of great public interest to induce tolerance in autoimmune diseases or transplants. Several approaches exist to generate inducible Tregs (Tregs) in vitro such as the use of retinoic acid inducing FoxP3 expression or co-culturing with bone marrow derived DCs in addition to stimulation with anti-CD3 and anti-CD28 antibodies. For example, PCT Application No. PCT/US2009/054631 refers to a method of purification of FoxP3 Tregs for the treatment of autoimmune diseases ("Treg based immunotherapy") using LAP and CD121b.

Therapeutic applications require large amounts of Tregs and these cells should retain their regulatory phenotype. This is at present only achieved by selecting natural Tregs. Inducible Tregs generated by vitro methods have the disadvantage that they might revert their phenotype into effector cells, causing an unpredictable risk for the patients.

However, BT061 has been demonstrated to activate Tregs in a mixed lymphocyte reaction (WO 2009112502 A1). This is due to the specific unexpected binding mode to CD4 described herein.

In Vitro Uses

The antibody and antibody fragments and isolated peptides of the present invention also have a number of in vitro uses. In particular, the antibody or antibody fragment described herein can be used for activating CD4+ CD25+ regulatory T cells in vitro, or for identifying CD4+ CD25+ regulatory T cells in vitro.

More specifically, the antibody or antibody fragment of the present invention can be used in a method for screening for the presence of CD4+ CD25+ T regulatory cells in a sample. Such a method can comprise the step of contacting a labeled antibody or antibody fragment with the sample, washing the sample to remove unbound antibody and detecting the presence of the label in the sample.

In particular, in such a method of screening the CD4+ CD25+ T regulatory cells are activated CD4+ CD25+ T regulatory cells. The sample is preferably a blood sample taken from a subject suffering from an autoimmune disease.

The present invention also describes a kit for isolating CD4+ CD25+ regulatory T cells comprising magnetic beads coated with the antibody or antibody fragment described herein. The kit may further comprise a second anti-CD25 antibody and/or anti-CD4+ antibody. Additional antibodies to carry out further selection steps, e.g. positive selection for CD39, a negative selection step for CD127, depletion of CD19 positive cells, can also be included. LAP (latency associated peptide), GARP or CD121b (Il-1 receptor type 2) can be used further for characterization of Treg phenotype.

Following Treg isolation, cells isolated with the antibody or antibody fragment of the present invention can be also cryopreserved (Peters et al., PLoS One (2008) 3; 9: e3161).

Still further, the present invention provides an in vitro method for the activation of CD4+ CD25+ regulatory T cells comprising contacting the cells with the antibody or antibody fragments described herein. Methods for assessing the suppressive capacity of activated Tregs comprise (beside the above mentioned MLR), MLR assays determining the activation state of effector T-cells via cytokine release or expressing of activation markers on T effector cells (such as the proliferation and cytokine assay described in WO 2009112592 A1, which is incorporated herein by reference). Such methods may additionally comprise a first step of isolating the CD4+CD25+ regulatory T cells. If such a step is completed with an antibody this antibody should be a non-competing CD4 antibody (e.g. OKT4 or SK3). This allows the cells to be activated in the main step with the antibody or fragment thereof of the present invention, which binds to a distinct epitope on CD4. In another scenario cells might be isolated using other surface expression markers of Tregs, which are distinct from CD4 such as CD25 or CD39, or by negative selection via CD127.

The antibody of the present invention has been described earlier as being capable of stimulating Tregs, which can be confirmed by co-culture with T effector cells. Tregs are able to suppress the proliferation of CD8 positive T cells by inhibiting the production of 11-2 and IFN gamma by alloreactive CD8 positive T-cells. In addition it has been demonstrated (WO 2009112592) that pre activated CD4+ CD25+ Tregs render suppressed CD8+ cells unable to express CD25 upon re-stimulation.

The invention will now be described further in relation to the following specific embodiments.

EXAMPLES

Example 1

Crystal Structure of CD4 Complexed with BT061

A crystal structure of human CD4 complexed with the BT061 Fab fragment was obtained by x-ray diffraction.

Crystallization Procedure of BT061 (Fab):CD4

Recombinant human CD4 has been produced using conventional methods: Different constructs of CD4 were cloned by standard procedures into vectors for heterologous expression in insect cells followed by purification via NiNTA. The Fab fragment of BT061 was cleaved from the intact antibody using the protease papain and purified by protein A. Subsequently the Fab fragment was further purified by size exclusion chromatography.

The CD4-Fab complex was formed by mixing the purified proteins, with a molar excess of CD4 and further purification by size exclusion chromatography.

Crystals of the CD4:BT061 complex were prepared by the method of co-crystallisation, meaning that the purified complex was used in crystallisation trials employing both, a standard screen with approximately 1200 different conditions, as well as crystallisation conditions identified using literature data. Conditions initially obtained have been optimised using standard strategies, systematically varying parameters critically influencing crystallisation, such as temperature, protein concentration, drop ratio, and others. These conditions were also refined by systematically varying pH or precipitant concentrations.

Crystals were flash-frozen and measured at a temperature of 100 K.

The X-ray Diffraction data of the CD4:BT061 complex were collected at the SWISS LIGHT SOURCE (SLS, Villigen, Switzerland) using cryogenic conditions. The structure was solved and refined to a final resolution of 2.9 A.

The crystals belong to space group P21 with two complexes in the asymmetric unit. Data were processed using the programmes XDS and XSCALE. Data collection statistics are summarised in Table 6 below.

TABLE 6

Statistics of data collection and processing

| Complex | CD4:BT061 |
|---|---|
| X-ray source | PX (SLS[1]) |
| Wavelength [Å] | 1.0000 |
| Detector | PILATUS 6M |
| Temperature [K] | 100 |
| Space group | P 2$_1$ |
| Cell: | |
| a; b; c [Å] | 110.18; 78.94; 132.85 |
| α; β; γ [°] | 90.0; 94.8; 90.0 |
| Resolution [Å][2] | 2.88 (3.15-2.99) |
| Unique reflections[2] | 50962 (6585) |
| Multiplicity[2] | 2.9 (2.8) |
| Completeness [%][2] | 98.2 (98.3) |

TABLE 6-continued

Statistics of data collection and processing

| Complex | CD4:BT061 |
|---|---|
| R$_{sym}$[%][2,3] | 8.4 (44.3) |
| R$_{meas}$[%][2,4] | 10.3 (54.7) |
| I/σI[2] | — (—) |
| mean(I)/sigma[2,5] | 11.60 (2.72) |

[1]SWISS LIGHT SOURCE (SLS, Villigen, Switzerland)
[2]Numbers in brackets correspond to the resolution bin with R$_{sym}$ = 44.3%.

The phase information necessary to determine and analyse the structure was obtained by molecular replacement. Published models of CD4 and a Fab fragment were used as a search model.

Subsequent model building and refinement was performed according to standard protocols with the software packages CCP4 and COOT. The asymmetric unit (as shown FIG. 3) consists of two such complexes with an overall RMS resolution of 2.9 Å.

In the crystal structure the signal peptides are absent from the CD4 molecule and the peptide chains only comprise the Ig-like V-type domain, the Ig-like C2-type 1 domain, and part of the Ig-like C2-type 2 domain. The exact chains in the crystal structure reach from amino acid residue 26 through to residue 258, as shown in FIG. 1 in which the amino acids not represented by the crystal structure are marked inside a dashed frame. Accordingly, the CD4 molecules only have the first two disulphide brides, one between Cys$_{41}$ and Cys$_{109}$, and another one between Cys$_{155}$ and Cys$_{184}$.

The light chains of the two BT061 units in the crystal structure reach from position 1 through to position 215 in one unit, and from 1 through only 182 in the other unit, as shown in FIG. 2A. There are two disulphide bridges in the BT061 light chains, Cys$_{23}$-Cys$_{92}$ and Cys$_{138}$-Cys$_{198}$.

The heavy chains of the two BT061 units in the crystal structure reach from position 2 through 219 in one unit, as shown in FIG. 2B, and from position 2 through 220 in the other unit. Also in the heavy chains there are two disulphide bridges, one between Cys$_{22}$ and Cys$_{98}$, and another one between Cys$_{151}$ and Cys$_{207}$.

Analysis of the crystal structure shows that in contrast to other known ligands of CD4, binding of BT061 involves the Ig-like C2-type 1 domain, only. This constitutes an entirely new binding mode, documented by the crystal structure given in the Appendix.

As shown in FIG. 3 BT061 does not bind to the N-terminal domain of CD4, there is the possibility of concurrent binding of BT061 and a class II MHC molecule, or a gp120 HIV-1 envelope protein (as shown in FIGS. 4 and 5).

Detailed analysis of the crystal structure reveals the interacting amino acids of both, CD4 and BT061. Selection was based on a distance criterion. Taking into account the resolution of the crystal structure, all CD4 amino acids having non-hydrogen atoms within a sphere of radius d=4.5 Å around any non-hydrogen atom of an BT061 amino acid have been selected as interacting partners. Radius d has been selected as the typical distance of a non-bonded interaction, 3 Å, extended by half the crystal structure resolution of 2.9 Å (d=3 Å+½×2.9 Å=4.45 Å).

Hence, the crystal structure shows that the binding site on the surface of CD4 consists of a cluster of 7 consecutive amino acids (Gly$_{148}$ through Gln$_{154}$), a cluster of 6 consecutive amino acids (Gln$_{164}$ through Thr$_{168}$), plus Thr$_{185}$, Leu$_{187}$, Asn$_{189}$, Gln$_{190}$, and Lys$_{192}$, as shown in FIG. 7.

Table 7 below shows the matrix of interacting partners of CD4 and BT061. There are only few pure 1:1 interactions; most of the listed amino acids of both, CD4 and BT061 interact with more than one partner. The interactions are mainly hydrogen bonds, complemented by van-der-Waals contacts and polar interactions.

In the top row of Table 7 the amino acids of CD4 that interact with amino acids of BT061 are shown. On the left margin the amino acids of BT061 interacting with CD4 are given. Each "x" corresponds to at least one interaction. Since there are only few 1:1 interaction pairings, pattern extended in rows or columns are found. $Ser_{150}$ and $Pro_{151}$ of CD4 interact with both, the light and the heavy chain of BT061. $Val_{186}$, which is an important part of the binding pocket for $Tyr_{105}$ of the BT061 heavy chain is not listed here, because there are no direct interactions with amino acids of BT061. All the interactions identified are either hydrogen bonds, polar interactions, van-der-Waals contacts, or combinations of these types of interaction. Identification of the interacting amino acids is based on the crystal structure given in the appendix. A distance criterion was applied, taking into account all amino acids which have at least one non-hydrogen atom closer than d=4.5 Å to a non-hydrogen atom of the other molecular partner. Roughly speaking, d corresponds to the typical distance for a non-covalent interaction of 3 Å augmented by half the overall resolution of the crystal structure (2.9 Å).

BT061 exist in the crystal structure. Interestingly, BT061 shows a number of intramolecular salt bridges. One of them, formed between $Arg_{104}$ and $Asp_{106}$, confers polar interactions with a pocket on the surface of CD4 (FIG. 11). The formation of the intramolecular salt bridges can be influenced by substances with buffer activity, which in turn can induce conformational changes of BT061 and the complex with CD4, thus contributing to signal transduction of CD4.

The other very important residue for the interaction with CD4 is $Tyr_{34}$ of the BT061 light chain. Much like $Tyr_{105}$ of the heavy chain, $Tyr_{34}$ accommodates in a pocket on the surface of CD4 (FIG. 12).

Comparing the crystal structure of the complex of CD4 with BT061 with crystal structures of the CD4 complexes with a class II MHC molecule, and with the gp120 HIV-1 envelope protein it can immediately be seen that BT061 is bound to an entirely different part of the CD4 surface. With respect to the other ligands of CD4, BT061 binds on the opposite side of the extracellular part of CD4 (FIGS. 4 and 5) and does not interfere with the binding sites of other ligands.

The CD4 amino acids $Lys_{26}$, $Arg_{156}$, $Lys_{161}$, and $Lys_{192}$ are available for additional interactions with charge complementary amino acids of BT061 as indicated in Table 8 shown below.

TABLE 7

Table showing the interacting amino acids of CD4 and BT061.

| | | | | CD4 | | | | | | | | | | | | | | |
|---|---|---|---|---|---|---|---|---|---|---|---|---|---|---|---|---|---|---|
| | | | Gly 148 | Ser 149 | Ser 150 | Pro 151 | Ser 152 | Val 153 | Gln 154 | Gln 164 | Gly 165 | Gly 166 | Lys 167 | Thr 168 | Thr 185 | Leu 187 | Asn 189 | Gln 190 | Lys 192 |
| BT061 | Light chain | Ser 32 | | | | | | | | | | | x | x | x | | | | |
| | | Gly 33 | | | | | | | | | | | x | | | | | | |
| | | Tyr 34 | | | x | x | | | | | | | | | | | | | |
| | | Tyr 53 | | | x | | | | | | | | | | | | | | |
| | | Leu 54 | | | x | | | | | | | | | | | | | | |
| | | Ile 57 | x | x | | | | | | | | | | | | | | | |
| | Heavy chain | Ser 28 | | | | | | | | | | | | | | | x | | |
| | | Asp 31 | | | | | | | | | | | | | | | x | | |
| | | Tyr 102 | | | | | | | | | | | | | | | x | x | |
| | | Tyr 103 | | | | | | | | | x | | | | x | | | | |
| | | Arg 104 | | | x | x | x | | | | | | | | x | | | | |
| | | Tyr 105 | | | | | x | x | x | x | | | | | x | x | | | x |
| | | Asp 106 | | | | | x | | | | | x | | | | | | | |
| | | Trp 110 | | | x | | | | | | | | | | | | | | |

FIG. 7 shows the CD4 amino acids of the BT061 binding site as a schematic representation of their relative orientation. Besides the amino acids fulfilling directly the above mentioned distance criterion, a number of amino acids are available for additional interactions with BT061 upon moderate changes of conformation of both, BT061 and CD4. Those amino acids, $Arg_{156}$, $Gln_{188}$, $Asn_{189}$, $Gln_{190}$, and $Lys_{192}$ are likely to be involved in the mechanism of signal transduction of CD4.

BT061 binds with both, the light and the heavy chain to CD4. The respective amino acids of the light chain are shown in FIG. 8. The amino acids of heavy chain involved in binding to CD4 are shown in FIG. 9.

$Tyr_{105}$ of the BT061 heavy chain plays a very important role for the interaction with CD4. Its side chain perfectly fits into a pocket on the surface of CD4 (FIG. 10).

Even though salt bridges are typical elements of interaction between antibodies no salt bridges between CD4 and

TABLE 8

Additional Interactions between CD4 and BT061

| | | | CD4 | | | | |
|---|---|---|---|---|---|---|---|
| | | | Lys 26 | Arg 156 | Arg 159 | Lys 161 | Lys 192 |
| BT061 | Light chain | Asp 64 | x | | | | |
| | Heavy chain | Asp 31 | | x | | | x |
| | | Glu 56 | | | x | x | |

In the top row of Table 8 the amino acids of CD4 that can form salt bridges with amino acids of BT061 are shown. On the left margin the possible salt bridge partner amino acids of BT061 are given. Each "x" corresponds to a possible salt bridge. The pairs indicated do not match the distance criterion of d=4.5 Å mentioned above. However, a series of moderate conformational changes in both, CD4 and BT061 can result in the formation of the indicated salt bridges. For BT061, a shift of the sequence stretches $Ser_{56}$ to $Gly_{68}$ of light chain, and $Ser_{25}$ to $Cys_{32}$, as well as $Ser_{52}$ to $Gly_{59}$ of the heavy chain allows forming the salt bridges with $Asp_{31}$ and $Glu_{56}$ of CD4.

Example 2

Creating and Testing Mutants of BT061

BT061 variable domain mutants were manufactured by introduction of specific mutations into the nucleotide sequences encoding the variable domains of BT061 and expression of the mutated amino acid sequence and therefore antibody or antibody fragments, using standard techniques for DNA manipulation and antibody production.

The following BT061 variants were made:

(1) six variants having one mutation each in all 6 CDRs: the mutations in CDR1, CDR2 and CDR3 of the light chain are G33A, A55G and L98I, respectively; the mutations in CDR1, CDR2 and CDR3 of the heavy chain are R33K, A63G, and S101T, respectively;

(2) one variant having two mutations in one variable domain: R33K and A63G in the heavy chain variable domain; and (3) three variants having parallel mutation of both heavy and light chain (e.g. combinations of heavy and light chain variants from part (1): light chain L98I with heavy chain R33K; light chain A55G with heavy chain R33K; and light chain G33A with heavy chain R33K.

The ability of the BT061 variants to activate CD4+CD25+ regulatory T cells was determined by in vitro assay. A negative control of an antibody which does not bind to CD4 was used. The BT061 variant having a mutation in the heavy chain CDR3 (Y105W) was also created as a negative control; based on the results obtained in example 1, it was predicted that this amino acid was critical to BT061 binding. As positive controls, an antibody produced from the master light and heavy chain sequence was used, as well as a sample from BT061 produced for clinical trials.

In Vitro Assay:

The induction of suppressive capacity of CD4+ CD25+ regulatory T cells (Tregs) from healthy donors by variants of the antibody BT061 was assessed in allogeneic mixed lymphocytes reactions (indirect co-culture).

CD4+ CD25+ regulatory T cells were freshly isolated from a first donor (donor A). PBMCs were obtained from EDTA-blood by density gradient centrifugation. Tregs, responder T cells (Tresp) and APCs were immunomagnetically separated from PBMCs as previously described (Haas et al., J. Immunol. 2007 Jul. 15; 179(2):1322-30). Tregs were pre-incubated with or without plate-bound antibody for 2 days. The number and phenotype of Tregs was determined by six colour flow cytometry as previously described (Haas et al., 2007). Pre-incubated Tregs were transferred to responder T cells (second donor B) in the presence of T-cell depleted and irradiated PBMCs (first donor A). After stimulation, [$^3$H] thymidine was added and proliferation of responder T cells was measured after five days.

Results:

The results of the in vitro assay are shown below in Table 9. The percentage inhibition of responder T cell inhibition was measured three times for each variant and an average was taken.

TABLE 9

Results from in vitro assay with BT061 variants

| Variant | % Inh1 | % Inh2 | % Inh3 | Avg. | Std. dev. |
|---|---|---|---|---|---|
| LC master HC master | 27.7% | 25.4% | 25.9% | 26.3% | 1.0% |
| BT61 Lot 52690 | 26.7% | 24.1% | 27.8% | 26.2% | 1.6% |
| LC master HC A63G | 33.1% | 25.5% | 19.5% | 26.0% | 5.6% |
| LC master HC R33K-A63G | 15.7% | 21.5% | 21.9% | 19.7% | 2.8% |
| LC L98I HC R33K | 9.2% | 24.3% | 24.6% | 19.4% | 7.2% |
| LC master HC R33K | 19.8% | 18.8% | 15.0% | 17.9% | 2.1% |
| HC master LC L98I | 12.2% | 8.4% | 18.2% | 12.9% | 4.0% |
| LC A55G HC R33K | 12.1% | 6.4% | 19.3% | 12.6% | 5.3% |
| LC G33A HC R33K | 6.5% | 7.9% | 9.0% | 7.8% | 1.0% |
| Negative control | 3.0% | 7.0% | 5.2% | 5.1% | 1.6% |
| LC master HC Y105W | 5.3% | 2.0% | 7.0% | 4.8% | 2.0% |
| LC master HC S101T | 3.1% | −3.6% | 0.0% | −0.2% | 2.7% |

As predicted the knockout mutant of LC master HC Y105W did not bind CD4 and was unable to activate regulatory T cells. Further the results indicate that single positions within the heavy chain can be mutated at least according to the substitutions set out in Table 5 (single variants HC R33K, A63G and double variants HC R33K and A63G retained activity). Further, as predicted by the crystal structure work, the residues surrounding Tyr34 in the light chain which make up a loop also appear to be crucial for binding.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

APPENDIX

| | | | |
|---|---|---|---|
| HEADER | | BIOTEST AG | 09 APR 2009 |
| TITLE | | FAB FRAGMENT OF BT061 IN COMPLEX WITH CD4 | |
| COMPND | | MOL_ID: 1; | |
| COMPND | 2 | MOLECULE: FAB FRAGMENT; | |
| COMPND | 3 | CHAIN: A; | |
| COMPND | 4 | FRAGMENT: CD4 | |
| SOURCE | | MOL_ID: 1; | |
| SOURCE | 2 | SYNTHETIC: YES; | |
| SOURCE | 3 | ORGANISM_SCIENTIFIC: *HOMO SAPIENS* | |
| SOURCE | 4 | ORGANISM_COMMON: HUMAN | |
| KEYWDS | | FAB FRAGMENT, CD4 | |
| EXPDTA | | X-RAY DIFFRACTION | |
| REMARK | 2 | | |
| REMARK | 2 | RESOLUTION: 2.9 ANGSTROMS. | |
| REMARK | 3 | | |
| REMARK | 3 | REFINEMENT. | |
| REMARK | 3 | PROGRAM : REFMAC 5.2.0005 | |

```
REMARK   3     AUTHORS     : MURSHUDOV, VAGIN, DODSON
REMARK   3
REMARK   3      REFINEMENT TARGET : MAXIMUM LIKELIHOOD
REMARK   3
REMARK   3     DATA USED IN REFINEMENT.
REMARK   3      RESOLUTION RANGE HIGH    (ANGSTROMS) :   2.88
REMARK   3      RESOLUTION RANGE LOW     (ANGSTROMS) :  49.27
REMARK   3      DATA CUTOFF              (SIGMA(F))  : NONE
REMARK   3      COMPLETENESS FOR RANGE        (%) : 100.00
REMARK   3      NUMBER OF REFLECTIONS            :  49941
REMARK   3
REMARK   3     FIT TO DATA USED IN REFINEMENT.
REMARK   3      CROSS-VALIDATION METHOD          : THROUGHOUT
REMARK   3      FREE R VALUE TEST SET SELECTION  : RANDOM
REMARK   3      R VALUE        (WORKING + TEST SET) : 0.23152
REMARK   3      R VALUE             (WORKING SET) : 0.23041
REMARK   3      FREE R VALUE                      : 0.28740
REMARK   3      FREE R VALUE TEST SET SIZE    (%) : 2.0
REMARK   3      FREE R VALUE TEST SET COUNT      : 1020
REMARK   3
REMARK   3     FIT IN THE HIGHEST RESOLUTION BIN.
REMARK   3      TOTAL NUMBER OF BINS USED           :    20
REMARK   3      BIN RESOLUTION RANGE HIGH           :  2.880
REMARK   3      BIN RESOLUTION RANGE LOW            :  2.955
REMARK   3      REFLECTION IN BIN      (WORKING SET) :  3636
REMARK   3      BIN COMPLETENESS   (WORKING + TEST) (%) : 100.00
REMARK   3      BIN R VALUE            (WORKING SET) : 0.376
REMARK   3      BIN FREE R VALUE SET COUNT          :    75
REMARK   3      BIN FREE R VALUE                    : 0.371
REMARK   3
REMARK   3     NUMBER OF NON-HYDROGEN ATOMS USED IN REFINEMENT.
REMARK   3      ALL ATOMS                   :   10284
REMARK   3
REMARK   3     B VALUES.
REMARK   3      FROM WILSON PLOT           (A**2) : NULL
REMARK   3      MEAN B VALUE          (OVERALL, A**2) : 52.022
REMARK   3      OVERALL ANISOTROPIC B VALUE.
REMARK   3      B11 (A**2) :    −1.61
REMARK   3      B22 (A**2) :     3.33
REMARK   3      B33 (A**2) :    −1.44
REMARK   3      B12 (A**2) :     0.00
REMARK   3      B13 (A**2) :     1.69
REMARK   3      B23 (A**2) :     0.00
REMARK   3
REMARK   3     ESTIMATED OVERALL COORDINATE ERROR.
REMARK   3      ESU BASED ON R VALUE                       (A):  0.722
REMARK   3      ESU BASED ON FREE R VALUE                  (A):  0.378
REMARK   3      ESU BASED ON MAXIMUM LIKELIHOOD            (A):  0.295
REMARK   3      ESU FOR B VALUES BASED ON MAXIMUM LIKELIHOOD (A**2): 33.905
REMARK   3
REMARK   3     CORRELATION COEFFICIENTS.
REMARK   3      CORRELATION COEFFICIENT FO-FC      :   0.912
REMARK   3      CORRELATION COEFFICIENT FO-FC FREE :   0.876
REMARK   3
REMARK   3     RMS DEVIATIONS FROM IDEAL VALUES            COUNT    RMS    WEIGHT
REMARK   3      BOND LENGTHS REFINED ATOMS       (A):    10456 ;  0.009 ;  0.022
REMARK   3      BOND LENGTHS OTHERS              (A):     9324 ;  0.001 ;  0.020
REMARK   3      BOND ANGLES REFINED ATOMS   (DEGREES):   14158 ;  1.228 ;  1.961
REMARK   3      BOND ANGLES OTHERS          (DEGREES):   21862 ;  0.727 ;  3.000
REMARK   3      TORSION ANGLES, PERIOD 1    (DEGREES):    1306 ;  7.017 ;  5.000
REMARK   3      TORSION ANGLES, PERIOD 2    (DEGREES):     424 ; 35.372 ; 24.858
REMARK   3      TORSION ANGLES, PERIOD 3    (DEGREES):    1818 ; 18.316 ; 15.000
REMARK   3      TORSION ANGLES, PERIOD 4    (DEGREES):      41 ; 16.414 ; 15.000
REMARK   3      CHIRAL-CENTER RESTRAINTS        (A**3):   1602 ;  0.069 ;  0.200
REMARK   3      GENERAL PLANES REFINED ATOMS     (A):    11455 ;  0.003 ;  0.020
REMARK   3      GENERAL PLANES OTHERS            (A):     1996 ;  0.001 ;  0.020
REMARK   3      NON-BONDED CONTACTS REFINED ATOMS (A):    1858 ;  0.192 ;  0.200
REMARK   3      NON-BONDED CONTACTS OTHERS       (A):     9611 ;  0.173 ;  0.200
REMARK   3      NON-BONDED TORSION REFINED ATOMS (A):     4911 ;  0.180 ;  0.200
REMARK   3      NON-BONDED TORSION OTHERS        (A):     6795 ;  0.083 ;  0.200
REMARK   3      H-BOND (X . . . Y) REFINED ATOMS (A):      238 ;  0.216 ;  0.200
REMARK   3      H-BOND (X . . . Y) OTHERS        (A):        2 ;  0.093 ;  0.200
REMARK   3      SYMMETRY VDW REFINED ATOMS       (A):       14 ;  0.169 ;  0.200
REMARK   3      SYMMETRY VDW OTHERS              (A):       58 ;  0.166 ;  0.200
REMARK   3      SYMMETRY H-BOND REFINED ATOMS    (A):        4 ;  0.117 ;  0.200
REMARK   3
REMARK   3     ISOTROPIC THERMAL FACTOR RESTRAINTS.        COUNT    RMS    WEIGHT
REMARK   3      MAIN-CHAIN BOND REFINED ATOMS   (A**2):    8442 ;  1.414 ;  2.000
REMARK   3      MAIN-CHAIN BOND OTHER ATOMS     (A**2):    2703 ;  0.279 ;  2.000
```

```
REMARK   3     MAIN-CHAIN ANGLE REFINED ATOMS     (A**2):   10593 ;  1.907 ;   3.000
REMARK   3     SIDE-CHAIN BOND REFINED ATOMS      (A**2):    4611 ;  2.821 ;   4.000
REMARK   3     SIDE-CHAIN ANGLE REFINED ATOMS     (A**2):    3565 ;  4.196 ;   6.000
REMARK   3
REMARK   3   NCS RESTRAINTS STATISTICS
REMARK   3    NUMBER OF DIFFERENT NCS GROUPS :     4
REMARK   3
REMARK   3    NCS GROUP NUMBER              :    1
REMARK   3       CHAIN NAMES                      : L A
REMARK   3       NUMBER OF COMPONENTS NCS GROUP :    1
REMARK   3        COMPONENT C    SSSEQI TO C    SSSEQI   CODE
REMARK   3             1    L      1    L     118        4
REMARK   3             1    A      1    A     118        4
REMARK   3                       GROUP CHAIN          COUNT   RMS    WEIGHT
REMARK   3     MEDIUM POSITIONAL     1      L       (A):   1730 ; 0.35 ;   0.50
REMARK   3     MEDIUM THERMAL        1      L    (A**2):   1730 ; 0.41 ;   2.00
REMARK   3
REMARK   3    NCS GROUP NUMBER              :    2
REMARK   3       CHAIN NAMES                      : L A
REMARK   3       NUMBER OF COMPONENTS NCS GROUP :    1
REMARK   3        COMPONENT C    SSSEQI TO C    SSSEQI   CODE
REMARK   3             1    L    119    L     222        4
REMARK   3             1    A    119    A     222        4
REMARK   3                       GROUP CHAIN          COUNT   RMS    WEIGHT
REMARK   3     MEDIUM POSITIONAL     2      L       (A):    478 ;  0.40 ;   0.50
REMARK   3     MEDIUM THERMAL        2      L    (A**2):    478 ;  0.30 ;   2.00
REMARK   3
REMARK   3    NCS GROUP NUMBER              :    3
REMARK   3       CHAIN NAMES                      : H B
REMARK   3       NUMBER OF COMPONENTS NCS GROUP :    1
REMARK   3        COMPONENT C    SSSEQI TO C    SSSEQI   CODE
REMARK   3             1    H      1    H     114        4
REMARK   3             1    B      1    B     114        4
REMARK   3                       GROUP CHAIN          COUNT   RMS    WEIGHT
REMARK   3     MEDIUM POSITIONAL     3      H       (A):   1679 ;  0.41 ;   0.50
REMARK   3     MEDIUM THERMAL        3      H    (A**2):   1679 ;  0.46 ;   2.00
REMARK   3
REMARK   3    NCS GROUP NUMBER              :    4
REMARK   3       CHAIN NAMES                      : H B
REMARK   3       NUMBER OF COMPONENTS NCS GROUP :    1
REMARK   3        COMPONENT C    SSSEQI TO C    SSSEQI   CODE
REMARK   3             1    H    115    H     222        4
REMARK   3             1    B    115    B     222        4
REMARK   3                       GROUP CHAIN          COUNT   RMS    WEIGHT
REMARK   3     MEDIUM POSITIONAL     4      H       (A):   1062 ;  0.33 ;   0.50
REMARK   3     MEDIUM THERMAL        4      H    (A**2):   1062 ;  0.33 ;   2.00
REMARK   3
REMARK   3
REMARK   3   TLS DETAILS
REMARK   3    NUMBER OF TLS GROUPS  :     6
REMARK   3    ATOM RECORD CONTAINS RESIDUAL B FACTORS ONLY
REMARK   3
REMARK   3    TLS GROUP :     1
REMARK   3     NUMBER OF COMPONENTS GROUP :     1
REMARK   3     COMPONENTS          C    SSSEQI    TO C    SSSEQI
REMARK   3     RESIDUE RANGE :       L     1        L     118
REMARK   3     ORIGIN FOR THE GROUP (A) :
REMARK   3      T TENSOR
REMARK   3        T11:     2.0000    T22:       0.0000
REMARK   3        T33:     0.0000    T12:       0.0000
REMARK   3        T13:     0.0000    T23:       0.0000
REMARK   3      L TENSOR
REMARK   3        L11:     0.0000    L22:     119.0000
REMARK   3        L33:     0.0000    L12:     222.0000
REMARK   3        L13:     0.0000    L23:       0.0000
REMARK   3      S TENSOR
REMARK   3        S11:     0.0000    S12:       0.0000 S13:     0.0000
REMARK   3        S21:     0.0000    S22:       0.0000 S23:     0.0000
REMARK   3        S31:     0.0000    S32:       0.0000 S33:     0.0000
REMARK   3
REMARK   3    TLS GROUP :     2
REMARK   3     NUMBER OF COMPONENTS GROUP :     1
REMARK   3     COMPONENTS          C    SSSEQI    TO C    SSSEQI
REMARK   3     RESIDUE RANGE :       H     1        H     118
REMARK   3     ORIGIN FOR THE GROUP (A) :
REMARK   3      T TENSOR
REMARK   3        T11:     4.0000    T22:       0.0000
REMARK   3        T33:     0.0000    T12:       0.0000
REMARK   3        T13:     0.0000    T23:       0.0000
```

-continued

```
REMARK   3         L   TENSOR
REMARK   3             L11:    0.0000 L22:   119.0000
REMARK   3             L33:    0.0000 L12:   222.0000
REMARK   3             L13:    0.0000 L23:     0.0000
REMARK   3         S   TENSOR
REMARK   3             S11:    0.0000 S12:     0.0000 S13:    0.0000
REMARK   3             S21:    0.0000 S22:     0.0000 S23:    0.0000
REMARK   3             S31:    0.0000 S32:     0.0000 S33:    0.0000
REMARK   3
REMARK   3      TLS GROUP :    3
REMARK   3         NUMBER OF COMPONENTS GROUP :     1
REMARK   3         COMPONENTS          C   SSSEQI      TO   C   SSSEQI
REMARK   3         RESIDUE RANGE :     A      1             A     114
REMARK   3         ORIGIN FOR THE GROUP (A) :
REMARK   3         T   TENSOR
REMARK   3             T11:    6.0000 T22:     0.0000
REMARK   3             T33:    0.0000 T12:     0.0000
REMARK   3             T13:    0.0000 T23:     0.0000
REMARK   3         L   TENSOR
REMARK   3             L11:    0.0000 L22:   115.0000
REMARK   3             L33:    0.0000 L12:   222.0000
REMARK   3             L13:    0.0000 L23:     0.0000
REMARK   3         S   TENSOR
REMARK   3             S11:    0.0000 S12:     0.0000 S13:    0.0000
REMARK   3             S21:    0.0000 S22:     0.0000 S23:    0.0000
REMARK   3             S31:    0.0000 S32:     0.0000 S33:    0.0000
REMARK   3
REMARK   3      TLS GROUP :    4
REMARK   3         NUMBER OF COMPONENTS GROUP :     1
REMARK   3         COMPONENTS          C   SSSEQI      TO   C   SSSEQI
REMARK   3         RESIDUE RANGE :     B      1             B     114
REMARK   3         ORIGIN FOR THE GROUP (A) :
REMARK   3         T   TENSOR
REMARK   3             T11:    8.0000 T22:     0.0000
REMARK   3             T33:    0.0000 T12:     0.0000
REMARK   3             T13:    0.0000 T23:     0.0000
REMARK   3         L   TENSOR
REMARK   3             L11:    0.0000 L22:   115.0000
REMARK   3             L33:    0.0000 L12:   222.0000
REMARK   3             L13:    0.0000 L23:     0.0000
REMARK   3         S   TENSOR
REMARK   3             S11:    0.0000 S12:     0.0000 S13:    0.0000
REMARK   3             S21:    0.0000 S22:     0.0000 S23:    0.0000
REMARK   3             S31:    0.0000 S32:     0.0000 S33:    0.0000
REMARK   3
REMARK   3      TLS GROUP :    5
REMARK   3         NUMBER OF COMPONENTS GROUP :     1
REMARK   3         COMPONENTS          C   SSSEQI      TO   C   SSSEQI
REMARK   3         RESIDUE RANGE :     C      1             C     180
REMARK   3         ORIGIN FOR THE GROUP (A):
REMARK   3         T   TENSOR
REMARK   3             T11:   10.0000 T22:     0.0000
REMARK   3             T33:    0.0000 T12:     0.0000
REMARK   3             T13:    0.0000 T23:     0.0000
REMARK   3         L   TENSOR
REMARK   3             L11:    0.0000 L22:     1.0000
REMARK   3             L33:    0.0000 L12:   180.0000
REMARK   3             L13:    0.0000 L23:     0.0000
REMARK   3         S   TENSOR
REMARK   3             S11:    0.0000 S12:     0.0000 S13:    0.0000
REMARK   3             S21:    0.0000 S22:     0.0000 S23:    0.0000
REMARK   3             S31:    0.0000 S32:     0.0000 S33:    0.0000
REMARK   3
REMARK   3      TLS GROUP :    6
REMARK   3         NUMBER OF COMPONENTS GROUP :     1
REMARK   3         COMPONENTS          C   SSSEQI      TO   C   SSSEQI
REMARK   3         RESIDUE RANGE :     C    181             C     380
REMARK   3         ORIGIN FOR THE GROUP (A):
REMARK   3         T   TENSOR
REMARK   3             T11:   12.0000 T22:     0.0000
REMARK   3             T33:    0.0000 T12:     0.0000
REMARK   3             T13:    0.0000 T23:     0.0000
REMARK   3         L   TENSOR
REMARK   3             L11:    0.0000 L22:   181.0000
REMARK   3             L33:    0.0000 L12:   380.0000
REMARK   3             L13:    0.0000 L23:     0.0000
REMARK   3         S   TENSOR
REMARK   3             S11:    0.0000 S12:     0.0000 S13:    0.0000
REMARK   3             S21:    0.0000 S22:     0.0000 S23:    0.0000
```

```
REMARK   3         S31:       0.0000 S32:       0.0000 S33:      0.0000
REMARK   3
REMARK   3    ATOM RECORD CONTAINS RESIDUAL B FACTORS ONLY
REMARK   3
REMARK   3    TLS GROUP :      1
REMARK   3     NUMBER OF COMPONENTS GROUP :     1
REMARK   3     COMPONENTS        C   SSSEQI    TO  C   SSSEQI
REMARK   3     RESIDUE RANGE :       L      1         L    118
REMARK   3     ORIGIN FOR THE GROUP (A):     34.0774      4.1630    34.7010
REMARK   3     T   TENSOR
REMARK   3         T11:      -0.0925 T22:      -0.0085
REMARK   3         T33:      -0.0772 T12:       0.0721
REMARK   3         T13:       0.1030 T23:       0.1518
REMARK   3     L   TENSOR
REMARK   3         L11:       2.1122 L22:       0.7711
REMARK   3         L33:       4.9967 L12:      -0.5661
REMARK   3         L13:       0.1050 L23:      -0.3455
REMARK   3     S   TENSOR
REMARK   3         S11:      -0.0080 S12:       0.5079 S13:      0.2345
REMARK   3         S21:      -0.4260 S22:      -0.2376 S23:     -0.3549
REMARK   3         S31:       0.3135 S32:       0.8283 S33:      0.2455
REMARK   3
REMARK   3    TLS GROUP :      2
REMARK   3     NUMBER OF COMPONENTS GROUP :     1
REMARK   3     COMPONENTS        C   SSSEQI    TO  C   SSSEQI
REMARK   3     RESIDUE RANGE :       L    119         L    222
REMARK   3     ORIGIN FOR THE GROUP (A):     21.6146     -3.8126     1.1893
REMARK   3     T   TENSOR
REMARK   3         T11:       0.4726 T22:       0.2750
REMARK   3         T33:      -0.0808 T12:      -0.0116
REMARK   3         T13:       0.1752 T23:      -0.0339
REMARK   3     L   TENSOR
REMARK   3         L11:       6.9206 L22:       1.9549
REMARK   3         L33:       9.3382 L12:      -1.0476
REMARK   3         L13:       4.6283 L23:       0.1643
REMARK   3     S   TENSOR
REMARK   3         S11:      -0.3330 S12:       1.0733 S13:     -0.2008
REMARK   3         S21:      -0.5473 S22:      -0.0661 S23:      0.0016
REMARK   3         S31:       0.3697 S32:       0.4209 S33:      0.3991
REMARK   3
REMARK   3    TLS GROUP :      3
REMARK   3     NUMBER OF COMPONENTS GROUP :     1
REMARK   3     COMPONENTS        C   SSSEQI    TO  C   SSSEQI
REMARK   3     RESIDUE RANGE :       H      1         H    118
REMARK   3     ORIGIN FOR THE GROUP (A):     12.9034      6.8440    41.4571
REMARK   3     T   TENSOR
REMARK   3         T11:      -0.1425 T22:      -0.2315
REMARK   3         T33:      -0.1588 T12:       0.0165
REMARK   3         T13:       0.0200 T23:      -0.0215
REMARK   3     L   TENSOR
REMARK   3         L11:       2.6891 L22:       1.4103
REMARK   3         L33:       2.8991 L12:      -0.9097
REMARK   3         L13:       0.3158 L23:       0.1940
REMARK   3     S   TENSOR
REMARK   3         S11:      -0.0860 S12:       0.1826 S13:     -0.0201
REMARK   3         S21:      -0.0986 S22:      -0.1525 S23:      0.3016
REMARK   3         S31:       0.2526 S32:      -0.1665 S33:      0.2385
REMARK   3
REMARK   3    TLS GROUP :      4
REMARK   3     NUMBER OF COMPONENTS GROUP :     1
REMARK   3     COMPONENTS        C   SSSEQI    TO  C   SSSEQI
REMARK   3     RESIDUE RANGE :       H    119         H    222
REMARK   3     ORIGIN FOR THE GROUP (A):     10.0696     -4.9768    15.4814
REMARK   3     T   TENSOR
REMARK   3         T11:       0.3487 T22:       0.1930
REMARK   3         T33:      -0.0301 T12:      -0.0884
REMARK   3         T13:       0.0902 T23:       0.0141
REMARK   3     L   TENSOR
REMARK   3         L11:       4.9078 L22:       0.9490
REMARK   3         L33:       2.3693 L12:       0.1356
REMARK   3         L13:      -1.4071 L23:       0.9275
REMARK   3     S   TENSOR
REMARK   3         S11:      -0.5914 S12:      -0.3320 S13:     -0.7844
REMARK   3         S21:      -0.5500 S22:       0.2083 S23:      0.0456
REMARK   3         S31:       0.8546 S32:      -0.5341 S33:      0.3830
REMARK   3
REMARK   3    TLS GROUP:       5
REMARK   3     NUMBER OF COMPONENTS GROUP :     1
REMARK   3     COMPONENTS        C   SSSEQI    TO  C   SSSEQI
```

```
REMARK   3        RESIDUE RANGE :      A      1        A    114
REMARK   3        ORIGIN FOR THE GROUP (A):   -15.4841   -4.3916    40.7560
REMARK   3        T   TENSOR
REMARK   3            T11:    0.0309 T22:   -0.0078
REMARK   3            T33:   -0.0631 T12:   -0.1474
REMARK   3            T13:   -0.0713 T23:    0.0966
REMARK   3        L   TENSOR
REMARK   3            L11:    2.9713 L22:    2.0240
REMARK   3            L33:    4.0886 L12:    1.7325
REMARK   3            L13:    0.6998 L23:   -0.4779
REMARK   3        S   TENSOR
REMARK   3            S11:   -0.5589 S12:    0.9646 S13:    0.4929
REMARK   3            S21:   -0.3574 S22:    0.2963 S23:    0.1246
REMARK   3            S31:   -0.6789 S32:    0.3641 S33:    0.2626
REMARK   3
REMARK   3     TLS GROUP:      6
REMARK   3        NUMBER OF COMPONENTS GROUP :     1
REMARK   3        COMPONENTS          C   SSSEQI    TO  C    SSSEQI
REMARK   3        RESIDUE RANGE :      A    115       A    222
REMARK   3        ORIGIN FOR THE GROUP (A):   -18.4640   -5.6643    13.2181
REMARK   3        T   TENSOR
REMARK   3            T11:    0.3721 T22:    0.5165
REMARK   3            T33:    0.1442 T12:   -0.1750
REMARK   3            T13:   -0.1099 T23:    0.3085
REMARK   3        L   TENSOR
REMARK   3            L11:    7.9687 L22:    9.9652
REMARK   3            L33:    6.7758 L12:    8.8789
REMARK   3            L13:    3.4153 L23:    4.4245
REMARK   3        S   TENSOR
REMARK   3            S11:   -0.5121 S12:   -0.1151 S13:    0.2897
REMARK   3            S21:   -0.6527 S22:    0.0754 S23:    0.2830
REMARK   3            S31:   -0.1875 S32:    0.5151 S33:    0.4367
REMARK   3
REMARK   3     TLS GROUP:      7
REMARK   3        NUMBER OF COMPONENTS GROUP :     1
REMARK   3        COMPONENTS          C   SSSEQI    TO  C    SSSEQI
REMARK   3        RESIDUE RANGE :      B      1        B    114
REMARK   3        ORIGIN FOR THE GROUP (A):   -26.6676  -23.2278    44.1916
REMARK   3        T   TENSOR
REMARK   3            T11:   -0.1839 T22:   -0.0790
REMARK   3            T33:   -0.0886 T12:   -0.0213
REMARK   3            T13:    0.0625 T23:   -0.1009
REMARK   3        L   TENSOR
REMARK   3            L11:    3.0455 L22:    1.4373
REMARK   3            L33:    2.6154 L12:    0.5832
REMARK   3            L13:    1.1863 L23:    0.0809
REMARK   3        S   TENSOR
REMARK   3            S11:   -0.1089 S12:    0.5431 S13:   -0.7596
REMARK   3            S21:   -0.1800 S22:    0.1339 S23:   -0.1796
REMARK   3            S31:    0.1077 S32:    0.0582 S33:   -0.0250
REMARK   3
REMARK   3     TLS GROUP:      8
REMARK   3        NUMBER OF COMPONENTS GROUP :     1
REMARK   3        COMPONENTS          C   SSSEQI    TO  C    SSSEQI
REMARK   3        RESIDUE RANGE :      B    115       B    222
REMARK   3        ORIGIN FOR THE GROUP (A):   -25.1927  -22.6544    15.6984
REMARK   3        T   TENSOR
REMARK   3            T11:    0.1708 T22:    0.8383
REMARK   3            T33:   -0.1174 T12:   -0.1954
REMARK   3            T13:    0.0466 T23:   -0.1825
REMARK   3        L   TENSOR
REMARK   3            L11:    0.6073 L22:    3.3530
REMARK   3            L33:    3.8016 L12:    1.4235
REMARK   3            L13:    0.2857 L23:    0.4225
REMARK   3        S   TENSOR
REMARK   3            S11:   -0.4259 S12:    0.6847 S13:    0.0804
REMARK   3            S21:   -0.7985 S22:    0.3366 S23:   -0.0886
REMARK   3            S31:    0.2684 S32:    0.4004 S33:    0.0893
REMARK   3
REMARK   3     TLS GROUP:      9
REMARK   3        NUMBER OF COMPONENTS GROUP :     1
REMARK   3        COMPONENTS          C   SSSEQI    TO  C    SSSEQI
REMARK   3        RESIDUE RANGE :      C      1        C    180
REMARK   3        ORIGIN FOR THE GROUP (A):    35.7158   -7.3606    65.7332
REMARK   3        T   TENSOR
REMARK   3            T11:   -0.1452 T22:   -0.0687
REMARK   3            T33:   -0.0721 T12:    0.0065
REMARK   3            T13:   -0.0658 T23:    0.0456
REMARK   3        L   TENSOR
```

-continued

| | | | | | | | |
|---|---|---|---|---|---|---|---|
| REMARK | 3 | | L11: | 1.1034 | L22: | 4.2466 | |
| REMARK | 3 | | L33: | 1.1325 | L12: | −0.2671 | |
| REMARK | 3 | | L13: | −0.3798 | L23: | 1.1165 | |
| REMARK | 3 | S | TENSOR | | | | |
| REMARK | 3 | | S11: | 0.0853 | S12: | −0.1113 | S13: −0.1585 |
| REMARK | 3 | | S21: | 0.0004 | S22: | −0.0963 | S23: −0.2630 |
| REMARK | 3 | | S31: | 0.0304 | S32: | 0.1813 | S33: 0.0109 |
| REMARK | 3 | | | | | | |
| REMARK | 3 | TLS GROUP: | 10 | | | | |
| REMARK | 3 | NUMBER OF COMPONENTS GROUP : | 1 | | | | |
| REMARK | 3 | COMPONENTS | C | SSSEQI | TO C | SSSEQI | |
| REMARK | 3 | RESIDUE RANGE : | D | 1 | D | 180 | |
| REMARK | 3 | ORIGIN FOR THE GROUP (A): | 1.4791 | −18.6629 | 63.8831 | | |
| REMARK | 3 | T | TENSOR | | | | |
| REMARK | 3 | | T11: | −0.0882 | T22: | −0.2158 | |
| REMARK | 3 | | T33: | −0.0033 | T12: | −0.0591 | |
| REMARK | 3 | | T13: | −0.0712 | T23: | 0.0506 | |
| REMARK | 3 | L | TENSOR | | | | |
| REMARK | 3 | | L11: | 4.1627 | L22: | 0.6887 | |
| REMARK | 3 | | L33: | 1.6928 | L12: | −0.5821 | |
| REMARK | 3 | | L13: | −1.3565 | L23: | −0.0674 | |
| REMARK | 3 | S | TENSOR | | | | |
| REMARK | 3 | | S11: | 0.0942 | S12: | 0.0481 | S13: −0.1530 |
| REMARK | 3 | | S21: | 0.0632 | S22: | −0.0674 | S23: −0.1425 |
| REMARK | 3 | | S31: | −0.0044 | S32: | 0.1570 | S33: −0.0268 |
| REMARK | 3 | | | | | | |
| REMARK | 3 | TLS GROUP: | 11 | | | | |
| REMARK | 3 | NUMBER OF COMPONENTS GROUP : | 1 | | | | |
| REMARK | 3 | COMPONENTS | C | SSSEQI | TO C | SSSEQI | |
| REMARK | 3 | RESIDUE RANGE : | C | 181 | C | 380 | |
| REMARK | 3 | ORIGIN FOR THE GROUP (A): | 36.5001 | 36.1209 | 86.2248 | | |
| REMARK | 3 | T | TENSOR | | | | |
| REMARK | 3 | | T11: | 0.0149 | T22: | 0.0474 | |
| REMARK | 3 | | T33: | 0.0512 | T12: | −0.0859 | |
| REMARK | 3 | | T13: | −0.0012 | T23: | 0.0006 | |
| REMARK | 3 | L | TENSOR | | | | |
| REMARK | 3 | | L11: | 0.4991 | L22: | 4.2729 | |
| REMARK | 3 | | L33: | 2.2884 | L12: | 0.0613 | |
| REMARK | 3 | | L13: | −0.0422 | L23: | 1.6006 | |
| REMARK | 3 | S | TENSOR | | | | |
| REMARK | 3 | | S11: | 0.0700 | S12: | −0.1894 | S13: 0.3339 |
| REMARK | 3 | | S21: | 0.3199 | S22: | −0.1636 | S23: 0.0538 |
| REMARK | 3 | | S31: | −0.4706 | S32: | −0.0348 | S33: 0.0936 |
| REMARK | 3 | | | | | | |
| REMARK | 3 | TLS GROUP: | 12 | | | | |
| REMARK | 3 | NUMBER OF COMPONENTS GROUP: | 1 | | | | |
| REMARK | 3 | COMPONENTS | C | SSSEQI | TO C | SSSEQI | |
| REMARK | 3 | RESIDUE RANGE: | D | 181 | D | 380 | |
| REMARK | 3 | ORIGIN FOR THE GROUP (A): | −22.0680 | −7.2511 | 94.0538 | | |
| REMARK | 3 | T | TENSOR | | | | |
| REMARK | 3 | | T11: | 0.3324 | T22: | −0.0300 | |
| REMARK | 3 | | T33: | 0.1241 | T12: | −0.0639 | |
| REMARK | 3 | | T13: | −0.0093 | T23: | −0.1280 | |
| REMARK | 3 | L | TENSOR | | | | |
| REMARK | 3 | | L11: | 3.2904 | L22: | 1.2480 | |
| REMARK | 3 | | L33: | 5.3741 | L12: | −0.6499 | |
| REMARK | 3 | | L13: | −3.1202 | L23: | 1.5523 | |
| REMARK | 3 | S | TENSOR | | | | |
| REMARK | 3 | | S11: | 0.2251 | S12: | −0.5588 | S13: 0.4970 |
| REMARK | 3 | | S21: | 0.6434 | S22: | −0.2477 | S23: −0.0135 |
| REMARK | 3 | | S31: | −0.3232 | S32: | 0.0394 | S33: 0.0226 |
| REMARK | 3 | | | | | | |
| REMARK | 3 | | | | | | |
| REMARK | 3 | BULK SOLVENT MODELLING. | | | | | |
| REMARK | 3 | METHOD USED : BABINET MODEL WITH MASK | | | | | |
| REMARK | 3 | PARAMETERS FOR MASK CALCULATION | | | | | |
| REMARK | 3 | VDW PROBE RADIUS : 1.20 | | | | | |
| REMARK | 3 | ION PROBE RADIUS : 0.80 | | | | | |
| REMARK | 3 | SHRINKAGE RADIUS : 0.80 | | | | | |
| REMARK | 3 | | | | | | |
| REMARK | 3 | OTHER REFINEMENT REMARKS: | | | | | |
| REMARK | 3 | HYDROGENS HAVE BEEN ADDED IN THE RIDING POSITIONS | | | | | |
| REMARK | 3 | | | | | | |
| REMARK | 200 | | | | | | |
| REMARK | 200 | EXPERIMENTAL DETAILS | | | | | |
| REMARK | 200 | EXPERIMENT TYPE | : X-RAY DIFFRACTION | | | | |
| REMARK | 200 | DATE OF DATA COLLECTION | : NULL | | | | |
| REMARK | 200 | TEMPERATURE | (KELVIN) : 100 | | | | |
| REMARK | 200 | PH | : NULL | | | | |

```
REMARK  200  NUMBER OF CRYSTALS USED              : 1
REMARK  200
REMARK  200  SYNCHROTRON              (Y/N) : Y
REMARK  200  RADIATION SOURCE               : SLS
REMARK  200  BEAMLINE                       : PX
REMARK  200  X-RAY GENERATOR MODEL          : NULL
REMARK  200  MONOCHROMATIC OR LAUE    (M/L) : M
REMARK  200  WAVELENGTH OR RANGE       (A) : 1.0000
REMARK  200  MONOCHROMATOR                  : NULL
REMARK  200  OPTICS                         : NULL
REMARK  200
REMARK  200  DETECTOR TYPE                  : PILATUS 6M
REMARK  200  DETECTOR MANUFACTURER          : DECTRIS
REMARK  200  INTENSITY-INTEGRATION SOFTWARE : XDS
REMARK  200  DATA SCALING SOFTWARE          : XSCALE
REMARK  200
REMARK  200  NUMBER OF UNIQUE REFLECTIONS   : 50962
REMARK  200  RESOLUTION RANGE HIGH      (A) : 2.88
REMARK  200  RESOLUTION RANGE LOW       (A) : 49.27
REMARK  200  REJECTION CRITERIA  (SIGMA(I)) : 0.0
REMARK  200
REMARK  200  OVERALL.
REMARK  200   COMPLETENESS FOR RANGE    (%) : 98.2
REMARK  200   DATA REDUNDANCY               : 2.9
REMARK  200   R MERGE                   (I) : 8.40
REMARK  200   R SYM                     (I) : NULL
REMARK  200   <I/SIGMA(I)> FOR THE DATA SET : NULL
REMARK  200
REMARK  200  IN THE HIGHEST RESOLUTION SHELL.
REMARK  200   HIGHEST RESOLUTION SHELL, RANGE HIGH (A) : 2.88
REMARK  200   HIGHEST RESOLUTION SHELL, RANGE LOW  (A) : 2.99
REMARK  200   COMPLETENESS FOR SHELL    (%) : 97.2
REMARK  200   DATA REDUNDANCY IN SHELL      : 2.9
REMARK  200   R MERGE FOR SHELL         (I) : 71.00
REMARK  200   R SYM FOR SHELL           (I) : NULL
REMARK  200   <I/SIGMA(I)> FOR SHELL        : NULL
REMARK  200
REMARK  200  DIFFRACTION PROTOCOL: SINGLE WAVELENGTH
REMARK  200  METHOD USED TO DETERMINE THE STRUCTURE: OTHER
REMARK  200  SOFTWARE USED: NULL
REMARK  200  STARTING MODEL: NONE
REMARK  200
REMARK  200  REMARK: NONE
REMARK  280
REMARK  280  CRYSTAL
REMARK  280  SOLVENT CONTENT, VS    (%): 80.54
REMARK  280  MATTHEWS COEFFICIENT, VM (ANGSTROMS**3/DA) : 6.32
REMARK  280
REMARK  280  CRYSTALLIZATION CONDITIONS: NULL
REMARK  290
REMARK  290  CRYSTALLOGRAPHIC SYMMETRY
REMARK  290  SYMMETRY OPERATORS FOR SPACE GROUP: P 1 21 1
REMARK  290
REMARK  290        SYMOP  SYMMETRY
REMARK  290       NNNMMM  OPERATOR
REMARK  290         1555  X, Y, Z
REMARK  290         2555  -X, Y + 1/2, -Z
REMARK  290
REMARK  290     WHERE  NNN   -> OPERATOR NUMBER
REMARK  290            MMM   -> TRANSLATION VECTOR
REMARK  290
REMARK  290  CRYSTALLOGRAPHIC SYMMETRY TRANSFORMATIONS
REMARK  290  THE FOLLOWING TRANSFORMATIONS OPERATE ON THE ATOM/HETATM
REMARK  290  RECORDS IN THIS ENTRY TO PRODUCE CRYSTALLOGRAPHICALLY
REMARK  290  RELATED MOLECULES.
REMARK  290  REMARK: NULL
REMARK  500
REMARK  500  GEOMETRY AND STEREOCHEMISTRY
REMARK  500  SUBTOPIC: COVALENT BOND ANGLES
REMARK  500
REMARK  500  THE STEREOCHEMICAL PARAMETERS OF THE FOLLOWING RESIDUES
REMARK  500  HAVE VALUES WHICH DEVIATE FROM EXPECTED VALUES BY MORE
REMARK  500  THAN 6*RMSD (M = MODEL NUMBER; RES = RESIDUE NAME; C = CHAIN
REMARK  500  IDENTIFIER; SSEQ = SEQUENCE NUMBER; I = INSERTION CODE).
REMARK  500
REMARK  500  STANDARD TABLE:
REMARK  500  FORMAT: (10X, I3, 1X, A3, 1X, A1, I4, A1, 3(1X, A4, 2X), 12X, F5.1)
REMARK  500
REMARK  500  EXPECTED VALUES: ENGH AND HUBER, 1991
```

-continued

| | | | | | | | | | | | |
|---|---|---|---|---|---|---|---|---|---|---|---|
| REMARK | 500 | | | | | | | | | | |
| REMARK | 500 | REMARK: NULL | | | | | | | | | |
| SSBOND | 1 CYS | L | 23 | | CYS | L | 92 | | | | |
| SSBOND | 2 CYS | L | 138 | | CYS | L | 198 | | | | |
| SSBOND | 3 CYS | H | 22 | | CYS | H | 98 | | | | |
| SSBOND | 4 CYS | H | 151 | | CYS | H | 207 | | | | |
| SSBOND | 5 CYS | A | 23 | | CYS | A | 92 | | | | |
| SSBOND | 6 CYS | B | 22 | | CYS | B | 98 | | | | |
| SSBOND | 7 CYS | B | 151 | | CYS | B | 207 | | | | |
| SSBOND | 8 CYS | C | 41 | | CYS | C | 109 | | | | |
| SSBOND | 9 CYS | C | 155 | | CYS | C | 184 | | | | |
| SSBOND | 10 CYS | D | 41 | | CYS | D | 109 | | | | |
| SSBOND | 11 CYS | D | 155 | | CYS | D | 184 | | | | |
| CISPEP | 1 SER | L | 7 | | PRO | L | 8 | | 0.00 | | |
| CISPEP | 2 LEU | L | 98 | | PRO | L | 99 | | 0.00 | | |
| CISPEP | 3 TYR | L | 144 | | PRO | L | 145 | | 0.00 | | |
| LINK | | PRO | H | 137 | | | LEU | H | 149 | | gap |
| CISPEP | 4 PHE | H | 157 | | PRO | H | 158 | | 0.00 | | |
| CISPEP | 5 GLU | H | 159 | | PRO | H | 160 | | 0.00 | | |
| LINK | | VAL | H | 192 | | | CYS | H | 207 | | gap |
| CISPEP | 6 SER | A | 7 | | PRO | A | 8 | | 0.00 | | |
| CISPEP | 7 LEU | A | 98 | | PRO | A | 99 | | 0.00 | | |
| LINK | | VAL | A | 119 | | | VAL | A | 137 | | gap |
| CISPEP | 8 TYR | A | 144 | | PRO | A | 145 | | 0.00 | | |
| LINK | | ARG | A | 146 | | | SER | A | 160 | | gap |
| LINK | | LEU | B | 135 | | | GLY | B | 150 | | gap |
| CISPEP | 9 PHE | B | 157 | | PRO | B | 158 | | 0.00 | | |
| CISPEP | 10 GLU | B | 159 | | PRO | B | 160 | | 0.00 | | |
| LINK | | VAL | B | 192 | | | CYS | B | 207 | | gap |
| CISPEP | 11 ASP | C | 269 | | PRO | C | 270 | | 0.00 | | |
| CISPEP | 12 LEU | C | 278 | | PRO | C | 279 | | 0.00 | | |
| LINK | | THR | C | 320 | | | VAL | C | 330 | | gap |
| LINK | | LYS | C | 337 | | | ARG | C | 354 | | gap |
| LINK | | VAL | C | 358 | | | GLN | C | 369 | | gap |
| LINK | | TYR | D | 212 | | | GLU | D | 220 | | gap |
| LINK | | LEU | D | 238 | | | TRP | D | 251 | | gap |
| LINK | | LYS | D | 264 | | | PRO | D | 270 | | gap |
| CISPEP | 13 LEU | D | 278 | | PRO | D | 279 | | 0.00 | | |
| LINK | | LEU | D | 282 | | | ASN | D | 296 | | gap |
| CRYST1 | 110.180 | 78.940 | 132.850 | 90.00 | | 94.83 | 90.00 | P 1 21 1 | | | |
| SCALE1 | 0.009076 | 0.000000 | 0.000767 | | 0.00000 | | | | | | |
| SCALE2 | 0.000000 | 0.012668 | 0.000000 | | 0.00000 | | | | | | |
| SCALE3 | 0.000000 | 0.000000 | 0.007554 | | 0.00000 | | | | | | |
| ATOM | 1 | N | ASP | L | 1 | 25.380 | 23.459 | 40.132 | 1.00 | 63.38 | N |
| ATOM | 2 | CA | ASP | L | 1 | 25.701 | 22.022 | 39.898 | 1.00 | 63.63 | C |
| ATOM | 4 | CB | ASP | L | 1 | 25.152 | 21.571 | 38.537 | 1.00 | 65.02 | C |
| ATOM | 7 | CG | ASP | L | 1 | 23.658 | 21.304 | 38.570 | 1.00 | 68.49 | C |
| ATOM | 8 | OD1 | ASP | L | 1 | 23.196 | 20.423 | 37.797 | 1.00 | 66.99 | O |
| ATOM | 9 | OD2 | ASP | L | 1 | 22.958 | 21.976 | 39.373 | 1.00 | 66.85 | O |
| ATOM | 10 | C | ASP | L | 1 | 27.193 | 21.736 | 39.943 | 1.00 | 61.99 | C |
| ATOM | 11 | O | ASP | L | 1 | 28.013 | 22.646 | 39.993 | 1.00 | 62.03 | O |
| ATOM | 15 | N | ILE | L | 2 | 27.518 | 20.449 | 39.938 | 1.00 | 60.78 | N |
| ATOM | 16 | CA | ILE | L | 2 | 28.867 | 19.976 | 39.683 | 1.00 | 60.23 | C |
| ATOM | 18 | CB | ILE | L | 2 | 29.363 | 19.040 | 40.806 | 1.00 | 59.25 | C |
| ATOM | 20 | CG1 | ILE | L | 2 | 29.357 | 19.783 | 42.139 | 1.00 | 60.29 | C |
| ATOM | 23 | CD1 | ILE | L | 2 | 30.101 | 19.074 | 43.258 | 1.00 | 61.36 | C |
| ATOM | 27 | CG2 | ILE | L | 2 | 30.776 | 18.548 | 40.510 | 1.00 | 60.46 | C |
| ATOM | 31 | C | ILE | L | 2 | 28.856 | 19.221 | 38.356 | 1.00 | 59.29 | C |
| ATOM | 32 | O | ILE | L | 2 | 28.034 | 18.319 | 38.159 | 1.00 | 59.02 | O |
| ATOM | 34 | N | VAL | L | 3 | 29.774 | 19.582 | 37.458 | 1.00 | 57.94 | N |
| ATOM | 35 | CA | VAL | L | 3 | 29.889 | 18.928 | 36.151 | 1.00 | 57.13 | C |
| ATOM | 37 | CB | VAL | L | 3 | 30.134 | 19.933 | 35.026 | 1.00 | 56.55 | C |
| ATOM | 39 | CG1 | VAL | L | 3 | 30.245 | 19.203 | 33.680 | 1.00 | 57.32 | C |
| ATOM | 43 | CG2 | VAL | L | 3 | 29.025 | 20.976 | 34.993 | 1.00 | 56.20 | C |
| ATOM | 47 | C | VAL | L | 3 | 31.017 | 17.899 | 36.101 | 1.00 | 56.43 | C |
| ATOM | 48 | O | VAL | L | 3 | 32.192 | 18.234 | 36.238 | 1.00 | 55.47 | O |
| ATOM | 50 | N | MET | L | 4 | 30.627 | 16.648 | 35.876 | 1.00 | 56.71 | N |
| ATOM | 51 | CA | MET | L | 4 | 31.553 | 15.549 | 35.670 | 1.00 | 55.20 | C |
| ATOM | 53 | CB | MET | L | 4 | 30.915 | 14.247 | 36.126 | 1.00 | 55.10 | C |
| ATOM | 56 | CG | MET | L | 4 | 30.512 | 14.258 | 37.561 | 1.00 | 55.51 | C |
| ATOM | 59 | SD | MET | L | 4 | 31.956 | 14.143 | 38.626 | 1.00 | 59.57 | S |
| ATOM | 60 | CE | MET | L | 4 | 31.566 | 15.426 | 39.802 | 1.00 | 62.32 | C |
| ATOM | 64 | C | MET | L | 4 | 31.900 | 15.446 | 34.187 | 1.00 | 54.82 | C |
| ATOM | 65 | O | MET | L | 4 | 31.045 | 15.149 | 33.351 | 1.00 | 54.44 | O |
| ATOM | 67 | N | THR | L | 5 | 33.162 | 15.694 | 33.871 | 1.00 | 53.54 | N |
| ATOM | 68 | CA | THR | L | 5 | 33.659 | 15.576 | 32.520 | 1.00 | 53.71 | C |
| ATOM | 70 | CB | THR | L | 5 | 34.503 | 16.793 | 32.181 | 1.00 | 53.53 | C |
| ATOM | 72 | OG1 | THR | L | 5 | 33.683 | 17.966 | 32.261 | 1.00 | 54.63 | O |
| ATOM | 74 | CG2 | THR | L | 5 | 35.102 | 16.677 | 30.796 | 1.00 | 53.09 | C |

-continued

| ATOM | 78 | C | THR | L | 5 | 34.518 | 14.330 | 32.433 | 1.00 | 54.11 | C |
| ATOM | 79 | O | THR | L | 5 | 35.487 | 14.195 | 33.166 | 1.00 | 54.88 | O |
| ATOM | 81 | N | GLN | L | 6 | 34.150 | 13.413 | 31.547 | 1.00 | 55.17 | N |
| ATOM | 82 | CA | GLN | L | 6 | 34.957 | 12.215 | 31.300 | 1.00 | 54.24 | C |
| ATOM | 84 | CB | GLN | L | 6 | 34.063 | 11.008 | 31.063 | 1.00 | 54.16 | C |
| ATOM | 87 | CG | GLN | L | 6 | 33.285 | 10.641 | 32.287 | 1.00 | 55.97 | C |
| ATOM | 90 | CD | GLN | L | 6 | 32.500 | 9.387 | 32.109 | 1.00 | 53.56 | C |
| ATOM | 91 | OE1 | GLN | L | 6 | 31.370 | 9.289 | 32.581 | 1.00 | 51.02 | O |
| ATOM | 92 | NE2 | GLN | L | 6 | 33.087 | 8.409 | 31.423 | 1.00 | 52.33 | N |
| ATOM | 95 | C | GLN | L | 6 | 35.902 | 12.380 | 30.114 | 1.00 | 53.83 | C |
| ATOM | 96 | O | GLN | L | 6 | 35.716 | 13.242 | 29.266 | 1.00 | 53.74 | O |
| ATOM | 98 | N | SER | L | 7 | 36.907 | 11.522 | 30.052 | 1.00 | 53.31 | N |
| ATOM | 99 | CA | SER | L | 7 | 37.941 | 11.649 | 29.050 | 1.00 | 52.92 | C |
| ATOM | 101 | CB | SER | L | 7 | 38.860 | 12.803 | 29.451 | 1.00 | 51.79 | C |
| ATOM | 104 | OG | SER | L | 7 | 40.157 | 12.650 | 28.914 | 1.00 | 55.05 | O |
| ATOM | 106 | C | SER | L | 7 | 38.716 | 10.326 | 28.934 | 1.00 | 52.77 | C |
| ATOM | 107 | O | SER | L | 7 | 39.139 | 9.776 | 29.949 | 1.00 | 52.30 | O |
| ATOM | 109 | N | PRO | L | 8 | 38.872 | 9.788 | 27.705 | 1.00 | 52.09 | N |
| ATOM | 110 | CA | PRO | L | 8 | 38.334 | 10.230 | 26.423 | 1.00 | 50.67 | C |
| ATOM | 112 | CB | PRO | L | 8 | 39.185 | 9.461 | 25.419 | 1.00 | 50.52 | C |
| ATOM | 115 | CG | PRO | L | 8 | 39.483 | 8.200 | 26.096 | 1.00 | 51.62 | C |
| ATOM | 118 | CD | PRO | L | 8 | 39.694 | 8.575 | 27.542 | 1.00 | 52.48 | C |
| ATOM | 121 | C | PRO | L | 8 | 36.879 | 9.840 | 26.255 | 1.00 | 50.37 | C |
| ATOM | 122 | O | PRO | L | 8 | 36.318 | 9.191 | 27.130 | 1.00 | 49.80 | O |
| ATOM | 123 | N | ASP | L | 9 | 36.289 | 10.232 | 25.127 | 1.00 | 51.41 | N |
| ATOM | 124 | CA | ASP | L | 9 | 34.908 | 9.893 | 24.800 | 1.00 | 51.96 | C |
| ATOM | 126 | CB | ASP | L | 9 | 34.356 | 10.828 | 23.724 | 1.00 | 51.80 | C |
| ATOM | 129 | CG | ASP | L | 9 | 34.053 | 12.218 | 24.259 | 1.00 | 54.57 | C |
| ATOM | 130 | OD1 | ASP | L | 9 | 33.314 | 12.333 | 25.258 | 1.00 | 58.63 | O |
| ATOM | 131 | OD2 | ASP | L | 9 | 34.538 | 13.206 | 23.676 | 1.00 | 58.36 | O |
| ATOM | 132 | C | ASP | L | 9 | 34.792 | 8.450 | 24.339 | 1.00 | 52.42 | C |
| ATOM | 133 | O | ASP | L | 9 | 33.896 | 7.734 | 24.768 | 1.00 | 53.87 | O |
| ATOM | 135 | N | SER | L | 10 | 35.692 | 8.024 | 23.464 | 1.00 | 52.69 | N |
| ATOM | 136 | CA | SER | L | 10 | 35.696 | 6.648 | 22.988 | 1.00 | 54.38 | C |
| ATOM | 138 | CB | SER | L | 10 | 35.133 | 6.564 | 21.577 | 1.00 | 55.07 | C |
| ATOM | 141 | OG | SER | L | 10 | 35.899 | 7.345 | 20.677 | 1.00 | 59.21 | O |
| ATOM | 143 | C | SER | L | 10 | 37.101 | 6.078 | 23.023 | 1.00 | 55.27 | C |
| ATOM | 144 | O | SER | L | 10 | 38.079 | 6.816 | 23.066 | 1.00 | 55.84 | O |
| ATOM | 146 | N | LEU | L | 11 | 37.193 | 4.757 | 22.991 | 1.00 | 56.01 | N |
| ATOM | 147 | CA | LEU | L | 11 | 38.438 | 4.086 | 23.304 | 1.00 | 55.98 | C |
| ATOM | 149 | CB | LEU | L | 11 | 38.651 | 4.118 | 24.819 | 1.00 | 56.96 | C |
| ATOM | 152 | CG | LEU | L | 11 | 39.813 | 3.304 | 25.387 | 1.00 | 57.49 | C |
| ATOM | 154 | CD1 | LEU | L | 11 | 41.134 | 3.780 | 24.769 | 1.00 | 59.64 | C |
| ATOM | 158 | CD2 | LEU | L | 11 | 39.828 | 3.382 | 26.917 | 1.00 | 56.04 | C |
| ATOM | 162 | C | LEU | L | 11 | 38.412 | 2.646 | 22.831 | 1.00 | 56.18 | C |
| ATOM | 163 | O | LEU | L | 11 | 37.454 | 1.920 | 23.085 | 1.00 | 57.30 | O |
| ATOM | 165 | N | ALA | L | 12 | 39.477 | 2.241 | 22.151 | 1.00 | 55.92 | N |
| ATOM | 166 | CA | ALA | L | 12 | 39.660 | 0.860 | 21.753 | 1.00 | 56.55 | C |
| ATOM | 168 | CB | ALA | L | 12 | 39.599 | 0.732 | 20.243 | 1.00 | 57.50 | C |
| ATOM | 172 | C | ALA | L | 12 | 41.011 | 0.397 | 22.252 | 1.00 | 57.38 | C |
| ATOM | 173 | O | ALA | L | 12 | 41.979 | 1.152 | 22.203 | 1.00 | 59.18 | O |
| ATOM | 175 | N | VAL | L | 13 | 41.079 | −0.840 | 22.731 | 1.00 | 56.85 | N |
| ATOM | 176 | CA | VAL | L | 13 | 42.357 | −1.448 | 23.090 | 1.00 | 56.67 | C |
| ATOM | 178 | CB | VAL | L | 13 | 42.770 | −1.087 | 24.551 | 1.00 | 57.06 | C |
| ATOM | 180 | CG1 | VAL | L | 13 | 42.256 | −2.121 | 25.547 | 1.00 | 57.39 | C |
| ATOM | 184 | CG2 | VAL | L | 13 | 44.293 | −0.921 | 24.674 | 1.00 | 58.38 | C |
| ATOM | 188 | C | VAL | L | 13 | 42.254 | −2.960 | 22.872 | 1.00 | 56.89 | C |
| ATOM | 189 | O | VAL | L | 13 | 41.146 | −3.501 | 22.845 | 1.00 | 57.82 | O |
| ATOM | 191 | N | SER | L | 14 | 43.395 | −3.631 | 22.703 | 1.00 | 55.08 | N |
| ATOM | 192 | CA | SER | L | 14 | 43.404 | −5.051 | 22.348 | 1.00 | 53.83 | C |
| ATOM | 194 | CB | SER | L | 14 | 44.764 | −5.459 | 21.799 | 1.00 | 54.07 | C |
| ATOM | 197 | OG | SER | L | 14 | 45.058 | −4.758 | 20.602 | 1.00 | 56.13 | O |
| ATOM | 199 | C | SER | L | 14 | 43.054 | −5.914 | 23.544 | 1.00 | 53.30 | C |
| ATOM | 200 | O | SER | L | 14 | 43.113 | −5.448 | 24.689 | 1.00 | 53.10 | O |
| ATOM | 202 | N | LEU | L | 15 | 42.683 | −7.168 | 23.273 | 1.00 | 52.90 | N |
| ATOM | 203 | CA | LEU | L | 15 | 42.353 | −8.125 | 24.343 | 1.00 | 52.23 | C |
| ATOM | 205 | CB | LEU | L | 15 | 42.037 | −9.531 | 23.800 | 1.00 | 51.58 | C |
| ATOM | 208 | CG | LEU | L | 15 | 40.609 | −10.098 | 23.763 | 1.00 | 49.56 | C |
| ATOM | 210 | CD1 | LEU | L | 15 | 40.642 | −11.575 | 24.161 | 1.00 | 45.14 | C |
| ATOM | 214 | CD2 | LEU | L | 15 | 39.621 | −9.369 | 24.663 | 1.00 | 52.95 | C |
| ATOM | 218 | C | LEU | L | 15 | 43.503 | −8.242 | 25.325 | 1.00 | 51.62 | C |
| ATOM | 219 | O | LEU | L | 15 | 44.663 | −8.288 | 24.928 | 1.00 | 53.26 | O |
| ATOM | 221 | N | GLY | L | 16 | 43.177 | −8.294 | 26.606 | 1.00 | 51.58 | N |
| ATOM | 222 | CA | GLY | L | 16 | 44.181 | −8.502 | 27.636 | 1.00 | 51.94 | C |
| ATOM | 225 | C | GLY | L | 16 | 45.024 | −7.285 | 27.951 | 1.00 | 51.47 | C |
| ATOM | 226 | O | GLY | L | 16 | 45.996 | −7.399 | 28.686 | 1.00 | 51.96 | O |
| ATOM | 228 | N | GLU | L | 17 | 44.640 | −6.120 | 27.430 | 1.00 | 51.42 | N |
| ATOM | 229 | CA | GLU | L | 17 | 45.424 | −4.895 | 27.593 | 1.00 | 52.11 | C |
| ATOM | 231 | CB | GLU | L | 17 | 45.699 | −4.290 | 26.219 | 1.00 | 51.96 | C |

-continued

| | | | | | | | | | | |
|---|---|---|---|---|---|---|---|---|---|---|
| ATOM | 234 | CG | GLU | L | 17 | 47.012 | −3.531 | 26.116 | 1.00 | 52.88 C |
| ATOM | 237 | CD | GLU | L | 17 | 47.389 | −3.222 | 24.675 | 1.00 | 54.10 C |
| ATOM | 238 | OE1 | GLU | L | 17 | 46.480 | −2.925 | 23.865 | 1.00 | 54.55 O |
| ATOM | 239 | OE2 | GLU | L | 17 | 48.596 | −3.278 | 24.350 | 1.00 | 55.90 O |
| ATOM | 240 | C | GLU | L | 17 | 44.716 | −3.874 | 28.497 | 1.00 | 52.53 C |
| ATOM | 241 | O | GLU | L | 17 | 43.513 | −3.986 | 28.759 | 1.00 | 52.88 O |
| ATOM | 243 | N | ARG | L | 18 | 45.464 | −2.877 | 28.969 | 1.00 | 52.79 N |
| ATOM | 244 | CA | ARG | L | 18 | 44.907 | −1.838 | 29.845 | 1.00 | 52.48 C |
| ATOM | 246 | CB | ARG | L | 18 | 46.022 | −1.030 | 30.522 | 1.00 | 52.23 C |
| ATOM | 249 | CG | ARG | L | 18 | 45.527 | −0.108 | 31.648 | 1.00 | 55.11 C |
| ATOM | 252 | CD | ARG | L | 18 | 46.640 | 0.740 | 32.240 | 1.00 | 56.70 C |
| ATOM | 255 | NE | ARG | L | 18 | 47.354 | 0.049 | 33.311 | 1.00 | 62.41 N |
| ATOM | 257 | CZ | ARG | L | 18 | 48.601 | 0.324 | 33.698 | 1.00 | 65.36 C |
| ATOM | 258 | NH1 | ARG | L | 18 | 49.306 | 1.287 | 33.102 | 1.00 | 64.22 N |
| ATOM | 261 | NH2 | ARG | L | 18 | 49.155 | −0.377 | 34.686 | 1.00 | 63.92 N |
| ATOM | 264 | C | ARG | L | 18 | 43.960 | −0.877 | 29.114 | 1.00 | 51.24 C |
| ATOM | 265 | O | ARG | L | 18 | 44.192 | −0.498 | 27.970 | 1.00 | 49.77 O |
| ATOM | 267 | N | ALA | L | 19 | 42.884 | −0.504 | 29.802 | 1.00 | 51.67 N |
| ATOM | 268 | CA | ALA | L | 19 | 41.957 | 0.526 | 29.348 | 1.00 | 52.18 C |
| ATOM | 270 | CB | ALA | L | 19 | 40.611 | −0.078 | 28.990 | 1.00 | 52.39 C |
| ATOM | 274 | C | ALA | L | 19 | 41.800 | 1.496 | 30.492 | 1.00 | 51.75 C |
| ATOM | 275 | O | ALA | L | 19 | 41.690 | 1.084 | 31.640 | 1.00 | 53.75 O |
| ATOM | 277 | N | THR | L | 20 | 41.793 | 2.782 | 30.187 | 1.00 | 51.92 N |
| ATOM | 278 | CA | THR | L | 20 | 41.799 | 3.792 | 31.232 | 1.00 | 52.69 C |
| ATOM | 280 | CB | THR | L | 20 | 43.236 | 4.258 | 31.501 | 1.00 | 51.99 C |
| ATOM | 282 | OG1 | THR | L | 20 | 43.952 | 3.180 | 32.108 | 1.00 | 52.75 O |
| ATOM | 284 | CG2 | THR | L | 20 | 43.280 | 5.469 | 32.422 | 1.00 | 51.10 C |
| ATOM | 288 | C | THR | L | 20 | 40.882 | 4.957 | 30.869 | 1.00 | 53.68 C |
| ATOM | 289 | O | THR | L | 20 | 40.926 | 5.469 | 29.748 | 1.00 | 53.88 O |
| ATOM | 291 | N | ILE | L | 21 | 40.040 | 5.349 | 31.826 | 1.00 | 54.16 N |
| ATOM | 292 | CA | ILE | L | 21 | 39.089 | 6.430 | 31.632 | 1.00 | 54.15 C |
| ATOM | 294 | CB | ILE | L | 21 | 37.652 | 5.930 | 31.697 | 1.00 | 54.03 C |
| ATOM | 296 | CG1 | ILE | L | 21 | 37.488 | 4.668 | 30.849 | 1.00 | 52.98 C |
| ATOM | 299 | CD1 | ILE | L | 21 | 36.156 | 4.011 | 30.996 | 1.00 | 53.32 C |
| ATOM | 303 | CG2 | ILE | L | 21 | 36.700 | 7.048 | 31.256 | 1.00 | 53.86 C |
| ATOM | 307 | C | ILE | L | 21 | 39.247 | 7.452 | 32.727 | 1.00 | 54.75 C |
| ATOM | 308 | O | ILE | L | 21 | 39.315 | 7.100 | 33.897 | 1.00 | 57.16 O |
| ATOM | 310 | N | ASN | L | 22 | 39.286 | 8.719 | 32.350 | 1.00 | 55.21 N |
| ATOM | 311 | CA | ASN | L | 22 | 39.362 | 9.788 | 33.321 | 1.00 | 55.96 C |
| ATOM | 313 | CB | ASN | L | 22 | 40.346 | 10.856 | 32.882 | 1.00 | 56.21 C |
| ATOM | 316 | CG | ASN | L | 22 | 41.769 | 10.434 | 33.093 | 1.00 | 58.98 C |
| ATOM | 317 | OD1 | ASN | L | 22 | 42.676 | 11.260 | 33.078 | 1.00 | 62.63 O |
| ATOM | 318 | ND2 | ASN | L | 22 | 41.982 | 9.136 | 33.295 | 1.00 | 60.66 N |
| ATOM | 321 | C | ASN | L | 22 | 38.021 | 10.422 | 33.538 | 1.00 | 57.66 C |
| ATOM | 322 | O | ASN | L | 22 | 37.162 | 10.415 | 32.658 | 1.00 | 59.39 O |
| ATOM | 324 | N | CYS | L | 23 | 37.859 | 10.968 | 34.735 | 1.00 | 58.38 N |
| ATOM | 325 | CA | CYS | L | 23 | 36.694 | 11.737 | 35.085 | 1.00 | 56.40 C |
| ATOM | 327 | CB | CYS | L | 23 | 35.699 | 10.860 | 35.814 | 1.00 | 57.46 C |
| ATOM | 330 | SG | CYS | L | 23 | 34.170 | 11.702 | 36.051 | 1.00 | 64.01 S |
| ATOM | 332 | C | CYS | L | 23 | 37.131 | 12.882 | 35.976 | 1.00 | 54.72 C |
| ATOM | 333 | O | CYS | L | 23 | 37.849 | 12.667 | 36.942 | 1.00 | 53.36 O |
| ATOM | 335 | N | ARG | L | 24 | 36.725 | 14.098 | 35.632 | 1.00 | 55.34 N |
| ATOM | 336 | CA | ARG | L | 24 | 37.128 | 15.280 | 36.382 | 1.00 | 55.30 C |
| ATOM | 338 | CB | ARG | L | 24 | 38.003 | 16.193 | 35.535 | 1.00 | 54.44 C |
| ATOM | 341 | CG | ARG | L | 24 | 38.513 | 17.408 | 36.314 | 1.00 | 58.14 C |
| ATOM | 344 | CD | ARG | L | 24 | 39.648 | 18.128 | 35.612 | 1.00 | 62.00 C |
| ATOM | 347 | NE | ARG | L | 24 | 40.875 | 17.326 | 35.557 | 1.00 | 67.28 N |
| ATOM | 349 | CZ | ARG | L | 24 | 42.021 | 17.732 | 35.007 | 1.00 | 70.82 C |
| ATOM | 350 | NH1 | ARG | L | 24 | 42.126 | 18.934 | 34.446 | 1.00 | 73.39 N |
| ATOM | 353 | NH2 | ARG | L | 24 | 43.075 | 16.926 | 35.013 | 1.00 | 72.54 N |
| ATOM | 356 | C | ARG | L | 24 | 35.893 | 16.020 | 36.801 | 1.00 | 54.29 C |
| ATOM | 357 | O | ARG | L | 24 | 34.916 | 16.024 | 36.062 | 1.00 | 57.57 O |
| ATOM | 359 | N | ALA | L | 25 | 35.939 | 16.662 | 37.965 | 1.00 | 52.05 N |
| ATOM | 360 | CA | ALA | L | 25 | 34.769 | 17.329 | 38.539 | 1.00 | 50.95 C |
| ATOM | 362 | CB | ALA | L | 25 | 34.510 | 16.759 | 39.909 | 1.00 | 51.27 C |
| ATOM | 366 | C | ALA | L | 25 | 34.982 | 18.837 | 38.636 | 1.00 | 49.44 C |
| ATOM | 367 | O | ALA | L | 25 | 36.085 | 19.255 | 38.948 | 1.00 | 49.36 O |
| ATOM | 369 | N | SER | L | 26 | 33.929 | 19.633 | 38.398 | 1.00 | 48.83 N |
| ATOM | 370 | CA | SER | L | 26 | 33.973 | 21.115 | 38.500 | 1.00 | 48.35 C |
| ATOM | 372 | CB | SER | L | 26 | 32.568 | 21.730 | 38.505 | 1.00 | 47.36 C |
| ATOM | 375 | OG | SER | L | 26 | 31.646 | 20.947 | 37.787 | 1.00 | 51.82 O |
| ATOM | 377 | C | SER | L | 26 | 34.664 | 21.621 | 39.759 | 1.00 | 48.75 C |
| ATOM | 378 | O | SER | L | 26 | 35.474 | 22.555 | 39.699 | 1.00 | 50.06 O |
| ATOM | 380 | N | LYS | L | 27 | 34.304 | 21.040 | 40.902 | 1.00 | 48.88 N |
| ATOM | 381 | CA | LYS | L | 27 | 34.964 | 21.353 | 42.163 | 1.00 | 50.43 C |
| ATOM | 383 | CB | LYS | L | 27 | 34.161 | 22.366 | 42.978 | 1.00 | 52.16 C |
| ATOM | 386 | CG | LYS | L | 27 | 32.749 | 21.981 | 43.368 | 1.00 | 54.56 C |
| ATOM | 389 | CD | LYS | L | 27 | 31.967 | 23.255 | 43.735 | 1.00 | 54.52 C |
| ATOM | 392 | CE | LYS | L | 27 | 30.692 | 22.965 | 44.503 | 1.00 | 57.35 C |

-continued

| | | | | | | | | | | |
|---|---|---|---|---|---|---|---|---|---|---|
| ATOM | 395 | NZ | LYS | L | 27 | 29.707 | 24.077 | 44.335 | 1.00 | 58.07 N |
| ATOM | 399 | C | LYS | L | 27 | 35.230 | 20.087 | 42.940 | 1.00 | 49.45 C |
| ATOM | 400 | O | LYS | L | 27 | 34.836 | 19.017 | 42.508 | 1.00 | 47.81 O |
| ATOM | 402 | N | SER | L | 28 | 35.939 | 20.202 | 44.059 | 1.00 | 51.44 N |
| ATOM | 403 | CA | SER | L | 28 | 36.385 | 19.020 | 44.799 | 1.00 | 51.83 C |
| ATOM | 405 | CB | SER | L | 28 | 37.304 | 19.379 | 45.964 | 1.00 | 52.23 C |
| ATOM | 408 | OG | SER | L | 28 | 37.520 | 18.241 | 46.785 | 1.00 | 52.48 O |
| ATOM | 410 | C | SER | L | 28 | 35.202 | 18.272 | 45.347 | 1.00 | 53.06 C |
| ATOM | 411 | O | SER | L | 28 | 34.250 | 18.877 | 45.839 | 1.00 | 54.62 O |
| ATOM | 413 | N | VAL | L | 29 | 35.293 | 16.951 | 45.292 | 1.00 | 52.94 N |
| ATOM | 414 | CA | VAL | L | 29 | 34.186 | 16.089 | 45.637 | 1.00 | 53.18 C |
| ATOM | 416 | CB | VAL | L | 29 | 33.727 | 15.308 | 44.367 | 1.00 | 53.28 C |
| ATOM | 418 | CG1 | VAL | L | 29 | 32.363 | 14.688 | 44.550 | 1.00 | 56.43 C |
| ATOM | 422 | CG2 | VAL | L | 29 | 34.735 | 14.247 | 43.974 | 1.00 | 54.81 C |
| ATOM | 426 | C | VAL | L | 29 | 34.616 | 15.181 | 46.799 | 1.00 | 53.03 C |
| ATOM | 427 | O | VAL | L | 29 | 34.156 | 14.046 | 46.916 | 1.00 | 53.62 O |
| ATOM | 429 | N | SER | L | 30 | 35.471 | 15.719 | 47.674 | 1.00 | 54.25 N |
| ATOM | 430 | CA | SER | L | 30 | 36.098 | 14.962 | 48.770 | 1.00 | 54.15 C |
| ATOM | 432 | CB | SER | L | 30 | 37.602 | 14.803 | 48.511 | 1.00 | 54.60 C |
| ATOM | 435 | OG | SER | L | 30 | 37.880 | 14.092 | 47.317 | 1.00 | 55.08 O |
| ATOM | 437 | C | SER | L | 30 | 35.940 | 15.634 | 50.142 | 1.00 | 54.40 C |
| ATOM | 438 | O | SER | L | 30 | 36.454 | 16.730 | 50.360 | 1.00 | 54.45 O |
| ATOM | 440 | N | THR | L | 31 | 35.253 | 14.962 | 51.063 | 1.00 | 54.06 N |
| ATOM | 441 | CA | THR | L | 31 | 35.161 | 15.389 | 52.467 | 1.00 | 53.25 C |
| ATOM | 443 | CB | THR | L | 31 | 33.993 | 16.393 | 52.726 | 1.00 | 53.03 C |
| ATOM | 445 | OG1 | THR | L | 31 | 33.060 | 16.367 | 51.636 | 1.00 | 54.02 O |
| ATOM | 447 | CG2 | THR | L | 31 | 34.517 | 17.807 | 52.899 | 1.00 | 54.14 C |
| ATOM | 451 | C | THR | L | 31 | 34.986 | 14.190 | 53.406 | 1.00 | 52.65 C |
| ATOM | 452 | O | THR | L | 31 | 34.466 | 13.141 | 53.019 | 1.00 | 50.65 O |
| ATOM | 454 | N | SER | L | 32 | 35.418 | 14.381 | 54.648 | 1.00 | 53.64 N |
| ATOM | 455 | CA | SER | L | 32 | 35.372 | 13.357 | 55.704 | 1.00 | 54.12 C |
| ATOM | 457 | CB | SER | L | 32 | 33.956 | 13.228 | 56.262 | 1.00 | 52.79 C |
| ATOM | 460 | OG | SER | L | 32 | 33.037 | 13.102 | 55.212 | 1.00 | 55.88 O |
| ATOM | 462 | C | SER | L | 32 | 35.954 | 11.993 | 55.288 | 1.00 | 53.54 C |
| ATOM | 463 | O | SER | L | 32 | 35.331 | 10.943 | 55.451 | 1.00 | 52.41 O |
| ATOM | 465 | N | GLY | L | 33 | 37.169 | 12.032 | 54.757 | 1.00 | 53.81 N |
| ATOM | 466 | CA | GLY | L | 33 | 37.924 | 10.822 | 54.469 | 1.00 | 54.19 C |
| ATOM | 469 | C | GLY | L | 33 | 37.477 | 10.089 | 53.231 | 1.00 | 53.03 C |
| ATOM | 470 | O | GLY | L | 33 | 37.937 | 8.978 | 52.970 | 1.00 | 55.58 O |
| ATOM | 472 | N | TYR | L | 34 | 36.597 | 10.715 | 52.462 | 1.00 | 52.53 N |
| ATOM | 473 | CA | TYR | L | 34 | 36.006 | 10.089 | 51.286 | 1.00 | 53.45 C |
| ATOM | 475 | CB | TYR | L | 34 | 34.537 | 9.740 | 51.539 | 1.00 | 53.20 C |
| ATOM | 478 | CG | TYR | L | 34 | 34.264 | 8.550 | 52.431 | 1.00 | 52.50 C |
| ATOM | 479 | CD1 | TYR | L | 34 | 34.930 | 7.355 | 52.253 | 1.00 | 49.83 C |
| ATOM | 481 | CE1 | TYR | L | 34 | 34.638 | 6.248 | 53.039 | 1.00 | 53.40 C |
| ATOM | 483 | CZ | TYR | L | 34 | 33.669 | 6.329 | 54.011 | 1.00 | 52.05 C |
| ATOM | 484 | OH | TYR | L | 34 | 33.407 | 5.234 | 54.783 | 1.00 | 52.72 O |
| ATOM | 486 | CE2 | TYR | L | 34 | 32.968 | 7.499 | 54.205 | 1.00 | 53.91 C |
| ATOM | 488 | CD2 | TYR | L | 34 | 33.258 | 8.601 | 53.405 | 1.00 | 58.63 C |
| ATOM | 490 | C | TYR | L | 34 | 36.051 | 11.021 | 50.081 | 1.00 | 53.06 C |
| ATOM | 491 | O | TYR | L | 34 | 36.016 | 12.249 | 50.224 | 1.00 | 51.85 O |
| ATOM | 493 | N | SER | L | 35 | 36.142 | 10.412 | 48.902 | 1.00 | 52.09 N |
| ATOM | 494 | CA | SER | L | 35 | 35.819 | 11.066 | 47.653 | 1.00 | 51.97 C |
| ATOM | 496 | CB | SER | L | 35 | 36.920 | 10.862 | 46.622 | 1.00 | 50.03 C |
| ATOM | 499 | OG | SER | L | 35 | 38.115 | 11.519 | 47.001 | 1.00 | 49.98 O |
| ATOM | 501 | C | SER | L | 35 | 34.529 | 10.410 | 47.181 | 1.00 | 53.64 C |
| ATOM | 502 | O | SER | L | 35 | 34.509 | 9.202 | 46.887 | 1.00 | 53.53 O |
| ATOM | 504 | N | TYR | L | 36 | 33.453 | 11.196 | 47.114 | 1.00 | 54.08 N |
| ATOM | 505 | CA | TYR | L | 36 | 32.147 | 10.663 | 46.743 | 1.00 | 55.43 C |
| ATOM | 507 | CB | TYR | L | 36 | 31.035 | 11.506 | 47.366 | 1.00 | 56.93 C |
| ATOM | 510 | CG | TYR | L | 36 | 31.100 | 11.479 | 48.876 | 1.00 | 57.15 C |
| ATOM | 511 | CD1 | TYR | L | 36 | 30.536 | 10.427 | 49.583 | 1.00 | 55.21 C |
| ATOM | 513 | CE1 | TYR | L | 36 | 30.599 | 10.375 | 50.960 | 1.00 | 57.63 C |
| ATOM | 515 | CZ | TYR | L | 36 | 31.254 | 11.369 | 51.661 | 1.00 | 57.30 C |
| ATOM | 516 | OH | TYR | L | 36 | 31.303 | 11.278 | 53.034 | 1.00 | 55.65 O |
| ATOM | 518 | CE2 | TYR | L | 36 | 31.845 | 12.429 | 50.983 | 1.00 | 55.89 C |
| ATOM | 520 | CD2 | TYR | L | 36 | 31.767 | 12.476 | 49.593 | 1.00 | 55.45 C |
| ATOM | 522 | C | TYR | L | 36 | 32.015 | 10.539 | 45.227 | 1.00 | 56.47 C |
| ATOM | 523 | O | TYR | L | 36 | 31.304 | 11.304 | 44.580 | 1.00 | 58.30 O |
| ATOM | 525 | N | ILE | L | 37 | 32.729 | 9.547 | 44.692 | 1.00 | 56.72 N |
| ATOM | 526 | CA | ILE | L | 37 | 32.740 | 9.187 | 43.276 | 1.00 | 55.37 C |
| ATOM | 528 | CB | ILE | L | 37 | 34.157 | 9.351 | 42.692 | 1.00 | 55.42 C |
| ATOM | 530 | CG1 | ILE | L | 37 | 34.521 | 10.838 | 42.602 | 1.00 | 59.90 C |
| ATOM | 533 | CD1 | ILE | L | 37 | 33.833 | 11.599 | 41.482 | 1.00 | 61.86 C |
| ATOM | 537 | CG2 | ILE | L | 37 | 34.297 | 8.689 | 41.324 | 1.00 | 54.24 C |
| ATOM | 541 | C | ILE | L | 37 | 32.309 | 7.727 | 43.128 | 1.00 | 54.15 C |
| ATOM | 542 | O | ILE | L | 37 | 32.612 | 6.887 | 43.982 | 1.00 | 51.17 O |
| ATOM | 544 | N | TYR | L | 38 | 31.598 | 7.437 | 42.042 | 1.00 | 54.32 N |
| ATOM | 545 | CA | TYR | L | 38 | 31.138 | 6.080 | 41.746 | 1.00 | 55.44 C |

|      |     |     |     |   |    |        |        |        |      |       |   |
|------|-----|-----|-----|---|----|--------|--------|--------|------|-------|---|
| ATOM | 547 | CB  | TYR | L | 38 | 29.694 | 5.907  | 42.252 | 1.00 | 55.24 | C |
| ATOM | 550 | CG  | TYR | L | 38 | 29.481 | 6.629  | 43.574 | 1.00 | 54.93 | C |
| ATOM | 551 | CD1 | TYR | L | 38 | 29.636 | 5.971  | 44.778 | 1.00 | 55.24 | C |
| ATOM | 553 | CE1 | TYR | L | 38 | 29.487 | 6.632  | 45.990 | 1.00 | 54.82 | C |
| ATOM | 555 | CZ  | TYR | L | 38 | 29.182 | 7.979  | 46.006 | 1.00 | 57.34 | C |
| ATOM | 556 | OH  | TYR | L | 38 | 29.022 | 8.642  | 47.205 | 1.00 | 55.61 | O |
| ATOM | 558 | CE2 | TYR | L | 38 | 29.039 | 8.665  | 44.815 | 1.00 | 56.07 | C |
| ATOM | 560 | CD2 | TYR | L | 38 | 29.197 | 7.993  | 43.611 | 1.00 | 54.45 | C |
| ATOM | 562 | C   | TYR | L | 38 | 31.272 | 5.838  | 40.236 | 1.00 | 56.25 | C |
| ATOM | 563 | O   | TYR | L | 38 | 31.170 | 6.790  | 39.454 | 1.00 | 57.66 | O |
| ATOM | 565 | N   | TRP | L | 39 | 31.551 | 4.590  | 39.837 | 1.00 | 55.93 | N |
| ATOM | 566 | CA  | TRP | L | 39 | 31.650 | 4.209  | 38.416 | 1.00 | 54.81 | C |
| ATOM | 568 | CB  | TRP | L | 39 | 33.042 | 3.682  | 38.053 | 1.00 | 54.09 | C |
| ATOM | 571 | CG  | TRP | L | 39 | 34.154 | 4.656  | 38.199 | 1.00 | 54.18 | C |
| ATOM | 572 | CD1 | TRP | L | 39 | 34.902 | 4.880  | 39.319 | 1.00 | 55.84 | C |
| ATOM | 574 | NE1 | TRP | L | 39 | 35.843 | 5.846  | 39.073 | 1.00 | 54.26 | N |
| ATOM | 576 | CE2 | TRP | L | 39 | 35.723 | 6.262  | 37.775 | 1.00 | 50.74 | C |
| ATOM | 577 | CD2 | TRP | L | 39 | 34.671 | 5.528  | 37.192 | 1.00 | 52.46 | C |
| ATOM | 578 | CE3 | TRP | L | 39 | 34.341 | 5.769  | 35.854 | 1.00 | 55.28 | C |
| ATOM | 580 | CZ3 | TRP | L | 39 | 35.066 | 6.718  | 35.147 | 1.00 | 55.11 | C |
| ATOM | 582 | CH2 | TRP | L | 39 | 36.110 | 7.429  | 35.753 | 1.00 | 55.77 | C |
| ATOM | 584 | CZ2 | TRP | L | 39 | 36.451 | 7.218  | 37.066 | 1.00 | 54.51 | C |
| ATOM | 586 | C   | TRP | L | 39 | 30.644 | 3.114  | 38.059 | 1.00 | 56.62 | C |
| ATOM | 587 | O   | TRP | L | 39 | 30.502 | 2.111  | 38.782 | 1.00 | 55.41 | O |
| ATOM | 589 | N   | TYR | L | 40 | 29.987 | 3.303  | 36.913 | 1.00 | 56.41 | N |
| ATOM | 590 | CA  | TYR | L | 40 | 29.020 | 2.352  | 36.396 | 1.00 | 54.40 | C |
| ATOM | 592 | CB  | TYR | L | 40 | 27.649 | 3.006  | 36.294 | 1.00 | 53.71 | C |
| ATOM | 595 | CG  | TYR | L | 40 | 27.197 | 3.584  | 37.609 | 1.00 | 54.69 | C |
| ATOM | 596 | CD1 | TYR | L | 40 | 26.392 | 2.846  | 38.469 | 1.00 | 54.76 | C |
| ATOM | 598 | CE1 | TYR | L | 40 | 25.988 | 3.371  | 39.694 | 1.00 | 54.40 | C |
| ATOM | 600 | CZ  | TYR | L | 40 | 26.393 | 4.646  | 40.068 | 1.00 | 51.99 | C |
| ATOM | 601 | OH  | TYR | L | 40 | 25.991 | 5.148  | 41.287 | 1.00 | 51.85 | O |
| ATOM | 603 | CE2 | TYR | L | 40 | 27.196 | 5.394  | 39.233 | 1.00 | 51.58 | C |
| ATOM | 605 | CD2 | TYR | L | 40 | 27.597 | 4.865  | 38.010 | 1.00 | 53.46 | C |
| ATOM | 607 | C   | TYR | L | 40 | 29.442 | 1.827  | 35.032 | 1.00 | 54.01 | C |
| ATOM | 608 | O   | TYR | L | 40 | 30.164 | 2.482  | 34.284 | 1.00 | 52.13 | O |
| ATOM | 610 | N   | GLN | L | 41 | 28.990 | 0.618  | 34.737 | 1.00 | 54.63 | N |
| ATOM | 611 | CA  | GLN | L | 41 | 29.155 | 0.025  | 33.434 | 1.00 | 54.67 | C |
| ATOM | 613 | CB  | GLN | L | 41 | 29.875 | -1.308 | 33.557 | 1.00 | 55.57 | C |
| ATOM | 616 | CG  | GLN | L | 41 | 30.049 | -2.048 | 32.229 | 1.00 | 53.36 | C |
| ATOM | 619 | CD  | GLN | L | 41 | 30.362 | -3.499 | 32.453 | 1.00 | 53.70 | C |
| ATOM | 620 | OE1 | GLN | L | 41 | 29.614 | -4.195 | 33.147 | 1.00 | 52.72 | O |
| ATOM | 621 | NE2 | GLN | L | 41 | 31.475 | -3.970 | 31.888 | 1.00 | 51.10 | N |
| ATOM | 624 | C   | GLN | L | 41 | 27.777 | -0.209 | 32.858 | 1.00 | 54.05 | C |
| ATOM | 625 | O   | GLN | L | 41 | 26.922 | -0.806 | 33.517 | 1.00 | 51.69 | O |
| ATOM | 627 | N   | GLN | L | 42 | 27.572 | 0.264  | 31.631 | 1.00 | 53.51 | N |
| ATOM | 628 | CA  | GLN | L | 42 | 26.314 | 0.057  | 30.930 | 1.00 | 54.34 | C |
| ATOM | 630 | CB  | GLN | L | 42 | 25.576 | 1.373  | 30.724 | 1.00 | 53.62 | C |
| ATOM | 633 | CG  | GLN | L | 42 | 24.115 | 1.187  | 30.355 | 1.00 | 53.29 | C |
| ATOM | 636 | CD  | GLN | L | 42 | 23.380 | 2.504  | 30.159 | 1.00 | 53.05 | C |
| ATOM | 637 | OE1 | GLN | L | 42 | 23.968 | 3.514  | 29.770 | 1.00 | 50.26 | O |
| ATOM | 638 | NE2 | GLN | L | 42 | 22.085 | 2.494  | 30.428 | 1.00 | 52.99 | N |
| ATOM | 641 | C   | GLN | L | 42 | 26.557 | -0.621 | 29.587 | 1.00 | 55.48 | C |
| ATOM | 642 | O   | GLN | L | 42 | 27.129 | -0.025 | 28.665 | 1.00 | 53.27 | O |
| ATOM | 644 | N   | LYS | L | 43 | 26.130 | -1.883 | 29.516 | 1.00 | 56.31 | N |
| ATOM | 645 | CA  | LYS | L | 43 | 26.078 | -2.649 | 28.276 | 1.00 | 56.15 | C |
| ATOM | 647 | CB  | LYS | L | 43 | 26.250 | -4.164 | 28.556 | 1.00 | 55.36 | C |
| ATOM | 650 | CG  | LYS | L | 43 | 27.711 | -4.598 | 28.760 | 1.00 | 53.71 | C |
| ATOM | 653 | CD  | LYS | L | 43 | 27.913 | -5.546 | 29.935 | 1.00 | 55.52 | C |
| ATOM | 656 | CE  | LYS | L | 43 | 27.712 | -7.011 | 29.574 | 1.00 | 59.61 | C |
| ATOM | 659 | NZ  | LYS | L | 43 | 28.948 | -7.681 | 29.059 | 1.00 | 57.53 | N |
| ATOM | 663 | C   | LYS | L | 43 | 24.734 | -2.357 | 27.589 | 1.00 | 56.42 | C |
| ATOM | 664 | O   | LYS | L | 43 | 23.745 | -2.067 | 28.268 | 1.00 | 53.62 | O |
| ATOM | 666 | N   | PRO | L | 44 | 24.692 | -2.452 | 26.243 | 1.00 | 57.78 | N |
| ATOM | 667 | CA  | PRO | L | 44 | 23.492 | -2.110 | 25.457 | 1.00 | 58.18 | C |
| ATOM | 669 | CB  | PRO | L | 44 | 23.914 | -2.391 | 24.006 | 1.00 | 58.48 | C |
| ATOM | 672 | CG  | PRO | L | 44 | 25.394 | -2.517 | 24.022 | 1.00 | 59.46 | C |
| ATOM | 675 | CD  | PRO | L | 44 | 25.793 | -2.941 | 25.392 | 1.00 | 57.45 | C |
| ATOM | 678 | C   | PRO | L | 44 | 22.281 | -2.969 | 25.816 | 1.00 | 58.75 | C |
| ATOM | 679 | O   | PRO | L | 44 | 22.401 | -4.195 | 25.904 | 1.00 | 59.48 | O |
| ATOM | 680 | N   | GLY | L | 45 | 21.136 | -2.323 | 26.025 | 1.00 | 59.04 | N |
| ATOM | 681 | CA  | GLY | L | 45 | 19.893 | -3.011 | 26.401 | 1.00 | 58.61 | C |
| ATOM | 684 | C   | GLY | L | 45 | 19.766 | -3.393 | 27.873 | 1.00 | 59.15 | C |
| ATOM | 685 | O   | GLY | L | 45 | 18.936 | -4.240 | 28.227 | 1.00 | 58.77 | O |
| ATOM | 687 | N   | GLN | L | 46 | 20.570 | -2.764 | 28.734 | 1.00 | 59.18 | N |
| ATOM | 688 | CA  | GLN | L | 46 | 20.612 | -3.111 | 30.159 | 1.00 | 57.60 | C |
| ATOM | 690 | CB  | GLN | L | 46 | 21.792 | -4.048 | 30.456 | 1.00 | 59.08 | C |
| ATOM | 693 | CG  | GLN | L | 46 | 21.709 | -5.463 | 29.846 | 1.00 | 59.83 | C |
| ATOM | 696 | CD  | GLN | L | 46 | 22.903 | -6.341 | 30.225 | 1.00 | 58.60 | C |

-continued

| ATOM | 697 | OE1 | GLN | L | 46 | 23.706 | −5.988 | 31.088 | 1.00 | 60.97 | O |
| ATOM | 698 | NE2 | GLN | L | 46 | 23.021 | −7.485 | 29.574 | 1.00 | 60.99 | N |
| ATOM | 701 | C | GLN | L | 46 | 20.764 | −1.878 | 31.037 | 1.00 | 56.58 | C |
| ATOM | 702 | O | GLN | L | 46 | 21.336 | −0.865 | 30.616 | 1.00 | 56.23 | O |
| ATOM | 704 | N | PRO | L | 47 | 20.274 | −1.964 | 32.278 | 1.00 | 55.72 | N |
| ATOM | 705 | CA | PRO | L | 47 | 20.547 | −0.897 | 33.233 | 1.00 | 55.56 | C |
| ATOM | 707 | CB | PRO | L | 47 | 19.786 | −1.332 | 34.485 | 1.00 | 54.62 | C |
| ATOM | 710 | CG | PRO | L | 47 | 19.575 | −2.795 | 34.316 | 1.00 | 56.19 | C |
| ATOM | 713 | CD | PRO | L | 47 | 19.454 | −3.036 | 32.860 | 1.00 | 55.23 | C |
| ATOM | 716 | C | PRO | L | 47 | 22.037 | −0.821 | 33.542 | 1.00 | 55.18 | C |
| ATOM | 717 | O | PRO | L | 47 | 22.740 | −1.821 | 33.402 | 1.00 | 53.89 | O |
| ATOM | 718 | N | PRO | L | 48 | 22.523 | 0.361 | 33.952 | 1.00 | 55.70 | N |
| ATOM | 719 | CA | PRO | L | 48 | 23.916 | 0.464 | 34.380 | 1.00 | 54.77 | C |
| ATOM | 721 | CB | PRO | L | 48 | 24.098 | 1.966 | 34.653 | 1.00 | 55.21 | C |
| ATOM | 724 | CG | PRO | L | 48 | 22.909 | 2.646 | 34.076 | 1.00 | 54.15 | C |
| ATOM | 727 | CD | PRO | L | 48 | 21.816 | 1.653 | 34.027 | 1.00 | 54.85 | C |
| ATOM | 730 | C | PRO | L | 48 | 24.207 | −0.363 | 35.645 | 1.00 | 54.20 | C |
| ATOM | 731 | O | PRO | L | 48 | 23.395 | −0.392 | 36.571 | 1.00 | 54.36 | O |
| ATOM | 732 | N | LYS | L | 49 | 25.365 | −1.014 | 35.668 | 1.00 | 53.47 | N |
| ATOM | 733 | CA | LYS | L | 49 | 25.785 | −1.850 | 36.787 | 1.00 | 52.96 | C |
| ATOM | 735 | CB | LYS | L | 49 | 26.279 | −3.192 | 36.251 | 1.00 | 51.47 | C |
| ATOM | 738 | CG | LYS | L | 49 | 27.192 | −3.954 | 37.162 | 1.00 | 53.42 | C |
| ATOM | 741 | CD | LYS | L | 49 | 27.500 | −5.331 | 36.599 | 1.00 | 55.24 | C |
| ATOM | 744 | CE | LYS | L | 49 | 28.178 | −6.217 | 37.636 | 1.00 | 58.11 | C |
| ATOM | 747 | NZ | LYS | L | 49 | 28.617 | −7.519 | 37.073 | 1.00 | 60.19 | N |
| ATOM | 751 | C | LYS | L | 49 | 26.876 | −1.114 | 37.555 | 1.00 | 52.05 | C |
| ATOM | 752 | O | LYS | L | 49 | 27.752 | −0.520 | 36.956 | 1.00 | 53.68 | O |
| ATOM | 754 | N | LEU | L | 50 | 26.820 | −1.140 | 38.880 | 1.00 | 52.75 | N |
| ATOM | 755 | CA | LEU | L | 50 | 27.820 | −0.452 | 39.697 | 1.00 | 52.69 | C |
| ATOM | 757 | CB | LEU | L | 50 | 27.339 | −0.263 | 41.136 | 1.00 | 50.73 | C |
| ATOM | 760 | CG | LEU | L | 50 | 28.370 | 0.307 | 42.123 | 1.00 | 52.58 | C |
| ATOM | 762 | CD1 | LEU | L | 50 | 28.665 | 1.778 | 41.846 | 1.00 | 53.41 | C |
| ATOM | 766 | CD2 | LEU | L | 50 | 27.902 | 0.138 | 43.556 | 1.00 | 53.16 | C |
| ATOM | 770 | C | LEU | L | 50 | 29.090 | −1.258 | 39.725 | 1.00 | 54.47 | C |
| ATOM | 771 | O | LEU | L | 50 | 29.051 | −2.478 | 39.870 | 1.00 | 58.94 | O |
| ATOM | 773 | N | LEU | L | 51 | 30.219 | −0.573 | 39.618 | 1.00 | 54.92 | N |
| ATOM | 774 | CA | LEU | L | 51 | 31.510 | −1.224 | 39.711 | 1.00 | 54.54 | C |
| ATOM | 776 | CB | LEU | L | 51 | 32.375 | −0.838 | 38.516 | 1.00 | 55.15 | C |
| ATOM | 779 | CG | LEU | L | 51 | 31.728 | −1.006 | 37.149 | 1.00 | 55.63 | C |
| ATOM | 781 | CD1 | LEU | L | 51 | 32.640 | −0.455 | 36.054 | 1.00 | 55.55 | C |
| ATOM | 785 | CD2 | LEU | L | 51 | 31.406 | −2.475 | 36.924 | 1.00 | 56.89 | C |
| ATOM | 789 | C | LEU | L | 51 | 32.213 | −0.812 | 40.985 | 1.00 | 54.28 | C |
| ATOM | 790 | O | LEU | L | 51 | 32.670 | −1.653 | 41.759 | 1.00 | 54.65 | O |
| ATOM | 792 | N | ILE | L | 52 | 32.316 | 0.496 | 41.185 | 1.00 | 54.53 | N |
| ATOM | 793 | CA | ILE | L | 52 | 33.220 | 1.047 | 42.178 | 1.00 | 54.82 | C |
| ATOM | 795 | CB | ILE | L | 52 | 34.519 | 1.569 | 41.507 | 1.00 | 54.75 | C |
| ATOM | 797 | CG1 | ILE | L | 52 | 35.289 | 0.370 | 40.943 | 1.00 | 57.46 | C |
| ATOM | 800 | CD1 | ILE | L | 52 | 36.673 | 0.673 | 40.438 | 1.00 | 58.45 | C |
| ATOM | 804 | CG2 | ILE | L | 52 | 35.380 | 2.374 | 42.503 | 1.00 | 54.63 | C |
| ATOM | 808 | C | ILE | L | 52 | 32.516 | 2.165 | 42.896 | 1.00 | 54.44 | C |
| ATOM | 809 | O | ILE | L | 52 | 31.845 | 2.987 | 42.258 | 1.00 | 55.52 | O |
| ATOM | 811 | N | TYR | L | 53 | 32.665 | 2.198 | 44.217 | 1.00 | 52.02 | N |
| ATOM | 812 | CA | TYR | L | 53 | 32.032 | 3.238 | 45.010 | 1.00 | 51.95 | C |
| ATOM | 814 | CB | TYR | L | 53 | 30.764 | 2.719 | 45.712 | 1.00 | 50.42 | C |
| ATOM | 817 | CG | TYR | L | 53 | 30.967 | 1.600 | 46.698 | 1.00 | 50.94 | C |
| ATOM | 818 | CD1 | TYR | L | 53 | 31.235 | 0.307 | 46.276 | 1.00 | 55.87 | C |
| ATOM | 820 | CE1 | TYR | L | 53 | 31.407 | −0.733 | 47.193 | 1.00 | 52.11 | C |
| ATOM | 822 | CZ | TYR | L | 53 | 31.304 | −0.477 | 48.536 | 1.00 | 49.69 | C |
| ATOM | 823 | OH | TYR | L | 53 | 31.480 | −1.495 | 49.450 | 1.00 | 51.98 | O |
| ATOM | 825 | CE2 | TYR | L | 53 | 31.030 | 0.796 | 48.975 | 1.00 | 52.89 | C |
| ATOM | 827 | CD2 | TYR | L | 53 | 30.861 | 1.824 | 48.060 | 1.00 | 55.48 | C |
| ATOM | 829 | C | TYR | L | 53 | 33.005 | 3.879 | 45.993 | 1.00 | 52.42 | C |
| ATOM | 830 | O | TYR | L | 53 | 33.951 | 3.247 | 46.467 | 1.00 | 51.02 | O |
| ATOM | 832 | N | LEU | L | 54 | 32.750 | 5.156 | 46.271 | 1.00 | 53.74 | N |
| ATOM | 833 | CA | LEU | L | 54 | 33.614 | 5.992 | 47.098 | 1.00 | 52.49 | C |
| ATOM | 835 | CB | LEU | L | 54 | 33.585 | 5.540 | 48.567 | 1.00 | 53.60 | C |
| ATOM | 838 | CG | LEU | L | 54 | 32.180 | 5.580 | 49.210 | 1.00 | 55.04 | C |
| ATOM | 840 | CD1 | LEU | L | 54 | 32.172 | 4.913 | 50.550 | 1.00 | 57.98 | C |
| ATOM | 844 | CD2 | LEU | L | 54 | 31.673 | 7.004 | 49.372 | 1.00 | 59.12 | C |
| ATOM | 848 | C | LEU | L | 54 | 34.999 | 5.963 | 46.482 | 1.00 | 52.10 | C |
| ATOM | 849 | O | LEU | L | 54 | 36.005 | 5.752 | 47.154 | 1.00 | 53.39 | O |
| ATOM | 851 | N | ALA | L | 55 | 35.011 | 6.134 | 45.164 | 1.00 | 51.42 | N |
| ATOM | 852 | CA | ALA | L | 55 | 36.227 | 6.322 | 44.385 | 1.00 | 51.30 | C |
| ATOM | 854 | CB | ALA | L | 55 | 37.083 | 7.447 | 44.977 | 1.00 | 50.70 | C |
| ATOM | 858 | C | ALA | L | 55 | 37.070 | 5.065 | 44.175 | 1.00 | 51.24 | C |
| ATOM | 859 | O | ALA | L | 55 | 37.636 | 4.884 | 43.082 | 1.00 | 51.52 | O |
| ATOM | 861 | N | SER | L | 56 | 37.182 | 4.209 | 45.192 | 1.00 | 49.46 | N |
| ATOM | 862 | CA | SER | L | 56 | 38.076 | 3.058 | 45.070 | 1.00 | 48.46 | C |
| ATOM | 864 | CB | SER | L | 56 | 39.380 | 3.391 | 45.750 | 1.00 | 45.78 | C |

| | | | | | | | | | | | |
|---|---|---|---|---|---|---|---|---|---|---|---|
| ATOM | 867 | OG | SER | L | 56 | 39.173 | 3.416 | 47.136 | 1.00 | 54.02 | O |
| ATOM | 869 | C | SER | L | 56 | 37.590 | 1.701 | 45.585 | 1.00 | 45.99 | C |
| ATOM | 870 | O | SER | L | 56 | 38.285 | 0.731 | 45.387 | 1.00 | 43.02 | O |
| ATOM | 872 | N | ILE | L | 57 | 36.424 | 1.613 | 46.219 | 1.00 | 46.73 | N |
| ATOM | 873 | CA | ILE | L | 57 | 35.975 | 0.337 | 46.785 | 1.00 | 48.73 | C |
| ATOM | 875 | CB | ILE | L | 57 | 35.035 | 0.517 | 48.001 | 1.00 | 48.71 | C |
| ATOM | 877 | CG1 | ILE | L | 57 | 35.658 | 1.431 | 49.061 | 1.00 | 46.23 | C |
| ATOM | 880 | CD1 | ILE | L | 57 | 34.633 | 2.004 | 50.033 | 1.00 | 47.63 | C |
| ATOM | 884 | CG2 | ILE | L | 57 | 34.711 | -0.831 | 48.638 | 1.00 | 46.23 | C |
| ATOM | 888 | C | ILE | L | 57 | 35.263 | -0.492 | 45.719 | 1.00 | 50.97 | C |
| ATOM | 889 | O | ILE | L | 57 | 34.290 | -0.038 | 45.117 | 1.00 | 54.06 | O |
| ATOM | 891 | N | LEU | L | 58 | 35.757 | -1.711 | 45.504 | 1.00 | 52.60 | N |
| ATOM | 892 | CA | LEU | L | 58 | 35.239 | -2.614 | 44.471 | 1.00 | 52.11 | C |
| ATOM | 894 | CB | LEU | L | 58 | 36.251 | -3.749 | 44.215 | 1.00 | 51.36 | C |
| ATOM | 897 | CG | LEU | L | 58 | 35.855 | -4.852 | 43.215 | 1.00 | 53.01 | C |
| ATOM | 899 | CD1 | LEU | L | 58 | 35.603 | -4.276 | 41.810 | 1.00 | 52.83 | C |
| ATOM | 903 | CD2 | LEU | L | 58 | 36.895 | -5.968 | 43.155 | 1.00 | 51.72 | C |
| ATOM | 907 | C | LEU | L | 58 | 33.910 | -3.224 | 44.910 | 1.00 | 52.58 | C |
| ATOM | 908 | O | LEU | L | 58 | 33.845 | -3.879 | 45.946 | 1.00 | 51.89 | O |
| ATOM | 910 | N | GLU | L | 59 | 32.859 | -3.019 | 44.123 | 1.00 | 52.83 | N |
| ATOM | 911 | CA | GLU | L | 59 | 31.572 | -3.654 | 44.406 | 1.00 | 54.04 | C |
| ATOM | 913 | CB | GLU | L | 59 | 30.503 | -3.169 | 43.416 | 1.00 | 53.52 | C |
| ATOM | 916 | CG | GLU | L | 59 | 29.182 | -3.929 | 43.421 | 1.00 | 55.28 | C |
| ATOM | 919 | CD | GLU | L | 59 | 28.447 | -3.865 | 44.737 | 1.00 | 56.48 | C |
| ATOM | 920 | OE1 | GLU | L | 59 | 29.054 | -4.202 | 45.765 | 1.00 | 62.78 | O |
| ATOM | 921 | OE2 | GLU | L | 59 | 27.251 | -3.508 | 44.747 | 1.00 | 51.37 | O |
| ATOM | 922 | C | GLU | L | 59 | 31.731 | -5.182 | 44.357 | 1.00 | 54.60 | C |
| ATOM | 923 | O | GLU | L | 59 | 32.406 | -5.706 | 43.476 | 1.00 | 54.40 | O |
| ATOM | 925 | N | SER | L | 60 | 31.126 | -5.897 | 45.302 | 1.00 | 54.98 | N |
| ATOM | 926 | CA | SER | L | 60 | 31.310 | -7.346 | 45.343 | 1.00 | 56.20 | C |
| ATOM | 928 | CB | SER | L | 60 | 30.816 | -7.948 | 46.654 | 1.00 | 55.93 | C |
| ATOM | 931 | OG | SER | L | 60 | 29.428 | -7.786 | 46.784 | 1.00 | 61.09 | O |
| ATOM | 933 | C | SER | L | 60 | 30.612 | -7.982 | 44.148 | 1.00 | 56.93 | C |
| ATOM | 934 | O | SER | L | 60 | 29.554 | -7.514 | 43.718 | 1.00 | 58.44 | O |
| ATOM | 936 | N | GLY | L | 61 | 31.242 | -9.019 | 43.599 | 1.00 | 55.93 | N |
| ATOM | 937 | CA | GLY | L | 61 | 30.791 | -9.643 | 42.362 | 1.00 | 56.18 | C |
| ATOM | 940 | C | GLY | L | 61 | 31.531 | -9.138 | 41.137 | 1.00 | 57.25 | C |
| ATOM | 941 | O | GLY | L | 61 | 31.611 | -9.831 | 40.119 | 1.00 | 58.16 | O |
| ATOM | 943 | N | VAL | L | 62 | 32.078 | -7.931 | 41.231 | 1.00 | 56.14 | N |
| ATOM | 944 | CA | VAL | L | 62 | 32.753 | -7.324 | 40.108 | 1.00 | 54.63 | C |
| ATOM | 946 | CB | VAL | L | 62 | 32.793 | -5.810 | 40.256 | 1.00 | 55.58 | C |
| ATOM | 948 | CG1 | VAL | L | 62 | 33.562 | -5.168 | 39.093 | 1.00 | 55.66 | C |
| ATOM | 952 | CG2 | VAL | L | 62 | 31.363 | -5.271 | 40.332 | 1.00 | 55.35 | C |
| ATOM | 956 | C | VAL | L | 62 | 34.164 | -7.854 | 40.031 | 1.00 | 53.37 | C |
| ATOM | 957 | O | VAL | L | 62 | 34.857 | -7.854 | 41.034 | 1.00 | 51.85 | O |
| ATOM | 959 | N | PRO | L | 63 | 34.592 | -8.315 | 38.838 | 1.00 | 55.14 | N |
| ATOM | 960 | CA | PRO | L | 63 | 35.972 | -8.764 | 38.607 | 1.00 | 54.76 | C |
| ATOM | 962 | CB | PRO | L | 63 | 36.043 | -8.909 | 37.080 | 1.00 | 54.50 | C |
| ATOM | 965 | CG | PRO | L | 63 | 34.656 | -9.189 | 36.661 | 1.00 | 53.15 | C |
| ATOM | 968 | CD | PRO | L | 63 | 33.763 | -8.463 | 37.622 | 1.00 | 55.43 | C |
| ATOM | 971 | C | PRO | L | 63 | 37.023 | -7.760 | 39.082 | 1.00 | 54.42 | C |
| ATOM | 972 | O | PRO | L | 63 | 36.939 | -6.572 | 38.758 | 1.00 | 52.19 | O |
| ATOM | 973 | N | ASP | L | 64 | 38.022 | -8.245 | 39.815 | 1.00 | 55.17 | N |
| ATOM | 974 | CA | ASP | L | 64 | 39.014 | -7.358 | 40.429 | 1.00 | 56.09 | C |
| ATOM | 976 | CB | ASP | L | 64 | 39.777 | -8.076 | 41.563 | 1.00 | 56.48 | C |
| ATOM | 979 | CG | ASP | L | 64 | 40.622 | -9.238 | 41.070 | 1.00 | 60.55 | C |
| ATOM | 980 | OD1 | ASP | L | 64 | 40.635 | -9.506 | 39.846 | 1.00 | 63.87 | O |
| ATOM | 981 | OD2 | ASP | L | 64 | 41.281 | -9.885 | 41.918 | 1.00 | 63.35 | O |
| ATOM | 982 | C | ASP | L | 64 | 39.989 | -6.707 | 39.429 | 1.00 | 55.97 | C |
| ATOM | 983 | O | ASP | L | 64 | 40.889 | -5.976 | 39.844 | 1.00 | 56.53 | O |
| ATOM | 985 | N | ARG | L | 65 | 39.820 | -6.959 | 38.130 | 1.00 | 55.08 | N |
| ATOM | 986 | CA | ARG | L | 65 | 40.575 | -6.212 | 37.119 | 1.00 | 54.31 | C |
| ATOM | 988 | CB | ARG | L | 65 | 40.439 | -6.834 | 35.728 | 1.00 | 52.42 | C |
| ATOM | 991 | CG | ARG | L | 65 | 39.017 | -7.000 | 35.212 | 1.00 | 54.44 | C |
| ATOM | 994 | CD | ARG | L | 65 | 39.026 | -7.328 | 33.713 | 1.00 | 54.08 | C |
| ATOM | 997 | NE | ARG | L | 65 | 37.712 | -7.686 | 33.170 | 1.00 | 54.88 | N |
| ATOM | 999 | CZ | ARG | L | 65 | 37.099 | -8.857 | 33.364 | 1.00 | 54.31 | C |
| ATOM | 1000 | NH1 | ARG | L | 65 | 37.643 | -9.801 | 34.128 | 1.00 | 55.55 | N |
| ATOM | 1003 | NH2 | ARG | L | 65 | 35.912 | -9.083 | 32.812 | 1.00 | 51.57 | N |
| ATOM | 1006 | C | ARG | L | 65 | 40.142 | -4.742 | 37.114 | 1.00 | 54.34 | C |
| ATOM | 1007 | O | ARG | L | 65 | 40.948 | -3.841 | 36.830 | 1.00 | 54.86 | O |
| ATOM | 1009 | N | PHE | L | 66 | 38.872 | -4.514 | 37.437 | 1.00 | 53.05 | N |
| ATOM | 1010 | CA | PHE | L | 66 | 38.350 | -3.163 | 37.606 | 1.00 | 53.28 | C |
| ATOM | 1012 | CB | PHE | L | 66 | 36.818 | -3.168 | 37.667 | 1.00 | 52.13 | C |
| ATOM | 1015 | CG | PHE | L | 66 | 36.171 | -3.510 | 36.361 | 1.00 | 51.63 | C |
| ATOM | 1016 | CD1 | PHE | L | 66 | 36.048 | -2.557 | 35.367 | 1.00 | 54.90 | C |
| ATOM | 1018 | CE1 | PHE | L | 66 | 35.467 | -2.873 | 34.132 | 1.00 | 54.83 | C |
| ATOM | 1020 | CZ | PHE | L | 66 | 35.001 | -4.155 | 33.895 | 1.00 | 54.18 | C |
| ATOM | 1022 | CE2 | PHE | L | 66 | 35.125 | -5.120 | 34.879 | 1.00 | 53.41 | C |

-continued

| | | | | | | | | | | |
|---|---|---|---|---|---|---|---|---|---|---|
| ATOM | 1024 | CD2 | PHE | L | 66 | 35.713 | −4.795 | 36.107 | 1.00 | 55.89 C |
| ATOM | 1026 | C | PHE | L | 66 | 38.924 | −2.543 | 38.870 | 1.00 | 53.24 C |
| ATOM | 1027 | O | PHE | L | 66 | 38.996 | −3.196 | 39.904 | 1.00 | 56.75 O |
| ATOM | 1029 | N | SER | L | 67 | 39.353 | −1.290 | 38.775 | 1.00 | 52.30 N |
| ATOM | 1030 | CA | SER | L | 67 | 39.835 | −0.552 | 39.934 | 1.00 | 51.60 C |
| ATOM | 1032 | CB | SER | L | 67 | 41.269 | −0.950 | 40.274 | 1.00 | 50.46 C |
| ATOM | 1035 | OG | SER | L | 67 | 42.206 | −0.173 | 39.561 | 1.00 | 50.17 O |
| ATOM | 1037 | C | SER | L | 67 | 39.770 | 0.949 | 39.672 | 1.00 | 52.16 C |
| ATOM | 1038 | O | SER | L | 67 | 39.894 | 1.387 | 38.524 | 1.00 | 53.02 O |
| ATOM | 1040 | N | GLY | L | 68 | 39.593 | 1.720 | 40.747 | 1.00 | 50.97 N |
| ATOM | 1041 | CA | GLY | L | 68 | 39.509 | 3.164 | 40.666 | 1.00 | 50.80 C |
| ATOM | 1044 | C | GLY | L | 68 | 40.435 | 3.896 | 41.620 | 1.00 | 50.07 C |
| ATOM | 1045 | O | GLY | L | 68 | 40.438 | 3.624 | 42.797 | 1.00 | 49.95 O |
| ATOM | 1047 | N | SER | L | 69 | 41.211 | 4.840 | 41.096 | 1.00 | 50.99 N |
| ATOM | 1048 | CA | SER | L | 69 | 42.014 | 5.742 | 41.908 | 1.00 | 51.86 C |
| ATOM | 1050 | CB | SER | L | 69 | 43.482 | 5.696 | 41.460 | 1.00 | 53.01 C |
| ATOM | 1053 | OG | SER | L | 69 | 43.613 | 5.878 | 40.055 | 1.00 | 58.20 O |
| ATOM | 1055 | C | SER | L | 69 | 41.504 | 7.178 | 41.796 | 1.00 | 52.61 C |
| ATOM | 1056 | O | SER | L | 69 | 40.693 | 7.507 | 40.922 | 1.00 | 51.85 O |
| ATOM | 1058 | N | GLY | L | 70 | 41.990 | 8.029 | 42.693 | 1.00 | 53.58 N |
| ATOM | 1059 | CA | GLY | L | 70 | 41.774 | 9.462 | 42.591 | 1.00 | 54.01 C |
| ATOM | 1062 | C | GLY | L | 70 | 41.381 | 10.140 | 43.883 | 1.00 | 55.34 C |
| ATOM | 1063 | O | GLY | L | 70 | 40.934 | 9.500 | 44.832 | 1.00 | 56.33 O |
| ATOM | 1065 | N | SER | L | 71 | 41.550 | 11.456 | 43.910 | 1.00 | 55.88 N |
| ATOM | 1066 | CA | SER | L | 71 | 41.042 | 12.264 | 44.998 | 1.00 | 54.92 C |
| ATOM | 1068 | CB | SER | L | 71 | 42.030 | 12.304 | 46.154 | 1.00 | 53.23 C |
| ATOM | 1071 | OG | SER | L | 71 | 42.895 | 13.411 | 46.004 | 1.00 | 55.47 O |
| ATOM | 1073 | C | SER | L | 71 | 40.809 | 13.678 | 44.516 | 1.00 | 55.33 C |
| ATOM | 1074 | O | SER | L | 71 | 41.396 | 14.127 | 43.526 | 1.00 | 51.70 O |
| ATOM | 1076 | N | GLY | L | 72 | 39.958 | 14.376 | 45.259 | 1.00 | 57.11 N |
| ATOM | 1077 | CA | GLY | L | 72 | 39.703 | 15.780 | 45.026 | 1.00 | 56.11 C |
| ATOM | 1080 | C | GLY | L | 72 | 38.845 | 15.924 | 43.805 | 1.00 | 56.31 C |
| ATOM | 1081 | O | GLY | L | 72 | 37.622 | 15.848 | 43.887 | 1.00 | 55.82 O |
| ATOM | 1083 | N | THR | L | 73 | 39.506 | 16.101 | 42.666 | 1.00 | 56.80 N |
| ATOM | 1084 | CA | THR | L | 73 | 38.834 | 16.488 | 41.434 | 1.00 | 55.61 C |
| ATOM | 1086 | CB | THR | L | 73 | 39.063 | 17.975 | 41.191 | 1.00 | 53.26 C |
| ATOM | 1088 | OG1 | THR | L | 73 | 38.041 | 18.470 | 40.323 | 1.00 | 56.96 O |
| ATOM | 1090 | CG2 | THR | L | 73 | 40.459 | 18.239 | 40.604 | 1.00 | 54.07 C |
| ATOM | 1094 | C | THR | L | 73 | 39.220 | 15.665 | 40.184 | 1.00 | 56.76 C |
| ATOM | 1095 | O | THR | L | 73 | 38.537 | 15.751 | 39.160 | 1.00 | 57.24 O |
| ATOM | 1097 | N | ASP | L | 74 | 40.301 | 14.883 | 40.268 | 1.00 | 57.91 N |
| ATOM | 1098 | CA | ASP | L | 74 | 40.699 | 13.944 | 39.206 | 1.00 | 56.78 C |
| ATOM | 1100 | CB | ASP | L | 74 | 42.155 | 14.184 | 38.788 | 1.00 | 56.63 C |
| ATOM | 1103 | CG | ASP | L | 74 | 42.380 | 15.589 | 38.276 | 1.00 | 62.56 C |
| ATOM | 1104 | OD1 | ASP | L | 74 | 41.382 | 16.236 | 37.885 | 1.00 | 67.01 O |
| ATOM | 1105 | OD2 | ASP | L | 74 | 43.543 | 16.058 | 38.276 | 1.00 | 69.21 O |
| ATOM | 1106 | C | ASP | L | 74 | 40.524 | 12.506 | 39.679 | 1.00 | 54.43 C |
| ATOM | 1107 | O | ASP | L | 74 | 41.003 | 12.145 | 40.752 | 1.00 | 52.01 O |
| ATOM | 1109 | N | PHE | L | 75 | 39.830 | 11.705 | 38.871 | 1.00 | 53.34 N |
| ATOM | 1110 | CA | PHE | L | 75 | 39.566 | 10.303 | 39.179 | 1.00 | 54.81 C |
| ATOM | 1112 | CB | PHE | L | 75 | 38.153 | 10.143 | 39.747 | 1.00 | 54.75 C |
| ATOM | 1115 | CG | PHE | L | 75 | 37.943 | 10.945 | 40.993 | 1.00 | 55.33 C |
| ATOM | 1116 | CD1 | PHE | L | 75 | 38.329 | 10.436 | 42.229 | 1.00 | 53.87 C |
| ATOM | 1118 | CE1 | PHE | L | 75 | 38.190 | 11.192 | 43.379 | 1.00 | 55.62 C |
| ATOM | 1120 | CZ | PHE | L | 75 | 37.674 | 12.474 | 43.299 | 1.00 | 58.22 C |
| ATOM | 1122 | CE2 | PHE | L | 75 | 37.306 | 13.002 | 42.061 | 1.00 | 56.85 C |
| ATOM | 1124 | CD2 | PHE | L | 75 | 37.447 | 12.242 | 40.923 | 1.00 | 54.25 C |
| ATOM | 1126 | C | PHE | L | 75 | 39.778 | 9.442 | 37.952 | 1.00 | 55.41 C |
| ATOM | 1127 | O | PHE | L | 75 | 39.706 | 9.936 | 36.827 | 1.00 | 57.09 O |
| ATOM | 1129 | N | THR | L | 76 | 40.075 | 8.160 | 38.171 | 1.00 | 56.45 N |
| ATOM | 1130 | CA | THR | L | 76 | 40.349 | 7.236 | 37.071 | 1.00 | 56.24 C |
| ATOM | 1132 | CB | THR | L | 76 | 41.850 | 7.129 | 36.813 | 1.00 | 55.71 C |
| ATOM | 1134 | OG1 | THR | L | 76 | 42.326 | 8.371 | 36.292 | 1.00 | 58.96 O |
| ATOM | 1136 | CG2 | THR | L | 76 | 42.149 | 6.039 | 35.803 | 1.00 | 56.70 C |
| ATOM | 1140 | C | THR | L | 76 | 39.811 | 5.834 | 37.314 | 1.00 | 55.99 C |
| ATOM | 1141 | O | THR | L | 76 | 40.001 | 5.282 | 38.392 | 1.00 | 54.19 O |
| ATOM | 1143 | N | LEU | L | 77 | 39.144 | 5.282 | 36.296 | 1.00 | 56.24 N |
| ATOM | 1144 | CA | LEU | L | 77 | 38.793 | 3.861 | 36.240 | 1.00 | 56.68 C |
| ATOM | 1146 | CB | LEU | L | 77 | 37.398 | 3.643 | 35.652 | 1.00 | 57.76 C |
| ATOM | 1149 | CG | LEU | L | 77 | 36.938 | 2.191 | 35.464 | 1.00 | 56.37 C |
| ATOM | 1151 | CD1 | LEU | L | 77 | 36.778 | 1.512 | 36.825 | 1.00 | 57.33 C |
| ATOM | 1155 | CD2 | LEU | L | 77 | 35.629 | 2.131 | 34.679 | 1.00 | 55.93 C |
| ATOM | 1159 | C | LEU | L | 77 | 39.798 | 3.151 | 35.354 | 1.00 | 57.54 C |
| ATOM | 1160 | O | LEU | L | 77 | 39.987 | 3.527 | 34.190 | 1.00 | 57.34 O |
| ATOM | 1162 | N | THR | L | 78 | 40.421 | 2.115 | 35.913 | 1.00 | 57.49 N |
| ATOM | 1163 | CA | THR | L | 78 | 41.395 | 1.305 | 35.207 | 1.00 | 56.32 C |
| ATOM | 1165 | CB | THR | L | 78 | 42.728 | 1.237 | 35.996 | 1.00 | 56.02 C |
| ATOM | 1167 | OG1 | THR | L | 78 | 42.882 | 2.421 | 36.795 | 1.00 | 56.83 O |
| ATOM | 1169 | CG2 | THR | L | 78 | 43.919 | 1.090 | 35.050 | 1.00 | 54.58 C |

-continued

| | | | | | | | | | | |
|---|---|---|---|---|---|---|---|---|---|---|
| ATOM | 1173 | C | THR | L | 78 | 40.822 | −0.099 | 35.047 | 1.00 | 55.35 C |
| ATOM | 1174 | O | THR | L | 78 | 40.325 | −0.686 | 36.009 | 1.00 | 52.97 O |
| ATOM | 1176 | N | ILE | L | 79 | 40.862 | −0.614 | 33.824 | 1.00 | 56.31 N |
| ATOM | 1177 | CA | ILE | L | 79 | 40.559 | −2.019 | 33.563 | 1.00 | 57.74 C |
| ATOM | 1179 | CB | ILE | L | 79 | 39.515 | −2.182 | 32.437 | 1.00 | 57.50 C |
| ATOM | 1181 | CG1 | ILE | L | 79 | 38.312 | −1.279 | 32.681 | 1.00 | 58.13 C |
| ATOM | 1184 | CD1 | ILE | L | 79 | 37.322 | −1.310 | 31.537 | 1.00 | 59.88 C |
| ATOM | 1188 | CG2 | ILE | L | 79 | 39.043 | −3.629 | 32.344 | 1.00 | 58.10 C |
| ATOM | 1192 | C | ILE | L | 79 | 41.862 | −2.732 | 33.174 | 1.00 | 57.37 C |
| ATOM | 1193 | O | ILE | L | 79 | 42.293 | −2.666 | 32.025 | 1.00 | 57.31 O |
| ATOM | 1195 | N | SER | L | 80 | 42.492 | −3.394 | 34.142 | 1.00 | 57.69 N |
| ATOM | 1196 | CA | SER | L | 80 | 43.743 | −4.124 | 33.900 | 1.00 | 58.45 C |
| ATOM | 1198 | CB | SER | L | 80 | 44.406 | −4.469 | 35.236 | 1.00 | 60.09 C |
| ATOM | 1201 | OG | SER | L | 80 | 43.535 | −5.250 | 36.052 | 1.00 | 61.16 O |
| ATOM | 1203 | C | SER | L | 80 | 43.466 | −5.414 | 33.129 | 1.00 | 57.69 C |
| ATOM | 1204 | O | SER | L | 80 | 42.903 | −6.347 | 33.683 | 1.00 | 60.35 O |
| ATOM | 1206 | N | SER | L | 81 | 43.863 | −5.480 | 31.866 | 1.00 | 55.77 N |
| ATOM | 1207 | CA | SER | L | 81 | 43.448 | −6.579 | 30.983 | 1.00 | 56.09 C |
| ATOM | 1209 | CB | SER | L | 81 | 43.730 | −7.954 | 31.600 | 1.00 | 55.99 C |
| ATOM | 1212 | OG | SER | L | 81 | 43.447 | −8.988 | 30.672 | 1.00 | 57.68 O |
| ATOM | 1214 | C | SER | L | 81 | 41.965 | −6.478 | 30.593 | 1.00 | 56.33 C |
| ATOM | 1215 | O | SER | L | 81 | 41.072 | −6.848 | 31.365 | 1.00 | 55.73 O |
| ATOM | 1217 | N | LEU | L | 82 | 41.717 | −5.984 | 29.381 | 1.00 | 55.01 N |
| ATOM | 1218 | CA | LEU | L | 82 | 40.366 | −5.842 | 28.868 | 1.00 | 54.17 C |
| ATOM | 1220 | CB | LEU | L | 82 | 40.338 | −4.758 | 27.789 | 1.00 | 53.78 C |
| ATOM | 1223 | CG | LEU | L | 82 | 38.957 | −4.295 | 27.329 | 1.00 | 53.78 C |
| ATOM | 1225 | CD1 | LEU | L | 82 | 38.201 | −3.652 | 28.482 | 1.00 | 56.84 C |
| ATOM | 1229 | CD2 | LEU | L | 82 | 39.076 | −3.328 | 26.174 | 1.00 | 52.87 C |
| ATOM | 1233 | C | LEU | L | 82 | 39.868 | −7.170 | 28.297 | 1.00 | 53.85 C |
| ATOM | 1234 | O | LEU | L | 82 | 40.520 | −7.756 | 27.437 | 1.00 | 52.59 O |
| ATOM | 1236 | N | GLN | L | 83 | 38.725 | −7.644 | 28.790 | 1.00 | 53.69 N |
| ATOM | 1237 | CA | GLN | L | 83 | 38.078 | −8.838 | 28.248 | 1.00 | 53.93 C |
| ATOM | 1239 | CB | GLN | L | 83 | 37.446 | −9.687 | 29.357 | 1.00 | 54.98 C |
| ATOM | 1242 | CG | GLN | L | 83 | 38.363 | −10.000 | 30.530 | 1.00 | 53.38 C |
| ATOM | 1245 | CD | GLN | L | 83 | 39.648 | −10.627 | 30.088 | 1.00 | 52.37 C |
| ATOM | 1246 | OE1 | GLN | L | 83 | 39.654 | −11.708 | 29.496 | 1.00 | 51.82 O |
| ATOM | 1247 | NE2 | GLN | L | 83 | 40.754 | −9.944 | 30.354 | 1.00 | 51.44 N |
| ATOM | 1250 | C | GLN | L | 83 | 37.002 | −8.431 | 27.261 | 1.00 | 53.94 C |
| ATOM | 1251 | O | GLN | L | 83 | 36.553 | −7.283 | 27.255 | 1.00 | 53.65 O |
| ATOM | 1253 | N | ALA | L | 84 | 36.579 | −9.389 | 26.443 | 1.00 | 54.11 N |
| ATOM | 1254 | CA | ALA | L | 84 | 35.666 | −9.110 | 25.338 | 1.00 | 54.22 C |
| ATOM | 1256 | CB | ALA | L | 84 | 35.546 | −10.315 | 24.420 | 1.00 | 53.53 C |
| ATOM | 1260 | C | ALA | L | 84 | 34.285 | −8.669 | 25.803 | 1.00 | 54.33 C |
| ATOM | 1261 | O | ALA | L | 84 | 33.653 | −7.865 | 25.129 | 1.00 | 54.33 O |
| ATOM | 1263 | N | GLU | L | 85 | 33.811 | −9.193 | 26.934 | 1.00 | 55.23 N |
| ATOM | 1264 | CA | GLU | L | 85 | 32.492 | −8.790 | 27.459 | 1.00 | 55.73 C |
| ATOM | 1266 | CB | GLU | L | 85 | 31.920 | −9.806 | 28.463 | 1.00 | 56.15 C |
| ATOM | 1269 | CG | GLU | L | 85 | 32.596 | −9.858 | 29.826 | 1.00 | 57.31 C |
| ATOM | 1272 | CD | GLU | L | 85 | 33.534 | −11.041 | 29.972 | 1.00 | 62.41 C |
| ATOM | 1273 | OE1 | GLU | L | 85 | 34.372 | −11.272 | 29.069 | 1.00 | 68.87 O |
| ATOM | 1274 | OE2 | GLU | L | 85 | 33.433 | −11.741 | 30.999 | 1.00 | 60.61 O |
| ATOM | 1275 | C | GLU | L | 85 | 32.502 | −7.397 | 28.085 | 1.00 | 55.79 C |
| ATOM | 1276 | O | GLU | L | 85 | 31.454 | −6.760 | 28.161 | 1.00 | 57.71 O |
| ATOM | 1278 | N | ASP | L | 86 | 33.677 | −6.929 | 28.508 | 1.00 | 54.50 N |
| ATOM | 1279 | CA | ASP | L | 86 | 33.827 | −5.597 | 29.099 | 1.00 | 54.34 C |
| ATOM | 1281 | CB | ASP | L | 86 | 35.249 | −5.401 | 29.609 | 1.00 | 53.96 C |
| ATOM | 1284 | CG | ASP | L | 86 | 35.595 | −6.355 | 30.708 | 1.00 | 56.40 C |
| ATOM | 1285 | OD1 | ASP | L | 86 | 34.724 | −6.610 | 31.562 | 1.00 | 64.93 O |
| ATOM | 1286 | OD2 | ASP | L | 86 | 36.733 | −6.857 | 30.728 | 1.00 | 58.96 O |
| ATOM | 1287 | C | ASP | L | 86 | 33.476 | −4.445 | 28.153 | 1.00 | 54.52 C |
| ATOM | 1288 | O | ASP | L | 86 | 33.398 | −3.285 | 28.576 | 1.00 | 54.01 O |
| ATOM | 1290 | N | VAL | L | 87 | 33.273 | −4.760 | 26.877 | 1.00 | 54.56 N |
| ATOM | 1291 | CA | VAL | L | 87 | 32.835 | −3.771 | 25.904 | 1.00 | 53.80 C |
| ATOM | 1293 | CB | VAL | L | 87 | 32.765 | −4.375 | 24.477 | 1.00 | 53.26 C |
| ATOM | 1295 | CG1 | VAL | L | 87 | 31.578 | −5.327 | 24.328 | 1.00 | 54.94 C |
| ATOM | 1299 | CG2 | VAL | L | 87 | 32.715 | −3.280 | 23.444 | 1.00 | 55.38 C |
| ATOM | 1303 | C | VAL | L | 87 | 31.496 | −3.157 | 26.354 | 1.00 | 52.87 C |
| ATOM | 1304 | O | VAL | L | 87 | 30.475 | −3.841 | 26.512 | 1.00 | 50.81 O |
| ATOM | 1306 | N | ALA | L | 88 | 31.539 | −1.853 | 26.591 | 1.00 | 52.72 N |
| ATOM | 1307 | CA | ALA | L | 88 | 30.429 | −1.151 | 27.203 | 1.00 | 52.43 C |
| ATOM | 1309 | CB | ALA | L | 88 | 30.253 | −1.623 | 28.628 | 1.00 | 51.93 C |
| ATOM | 1313 | C | ALA | L | 88 | 30.665 | 0.360 | 27.174 | 1.00 | 53.06 C |
| ATOM | 1314 | O | ALA | L | 88 | 31.712 | 0.835 | 26.701 | 1.00 | 53.38 O |
| ATOM | 1316 | N | VAL | L | 89 | 29.670 | 1.103 | 27.656 | 1.00 | 52.34 N |
| ATOM | 1317 | CA | VAL | L | 89 | 29.796 | 2.526 | 27.901 | 1.00 | 51.67 C |
| ATOM | 1319 | CB | VAL | L | 89 | 28.554 | 3.296 | 27.406 | 1.00 | 50.95 C |
| ATOM | 1321 | CG1 | VAL | L | 89 | 28.652 | 4.761 | 27.771 | 1.00 | 52.81 C |
| ATOM | 1325 | CG2 | VAL | L | 89 | 28.397 | 3.147 | 25.910 | 1.00 | 49.54 C |
| ATOM | 1329 | C | VAL | L | 89 | 29.939 | 2.671 | 29.406 | 1.00 | 51.58 C |

-continued

| ATOM | 1330 | O | VAL | L | 89 | 29.047 | 2.274 | 30.150 | 1.00 | 54.46 | O |
|---|---|---|---|---|---|---|---|---|---|---|---|
| ATOM | 1332 | N | TYR | L | 90 | 31.062 | 3.221 | 29.854 | 1.00 | 51.52 | N |
| ATOM | 1333 | CA | TYR | L | 90 | 31.337 | 3.371 | 31.287 | 1.00 | 52.57 | C |
| ATOM | 1335 | CB | TYR | L | 90 | 32.797 | 2.993 | 31.593 | 1.00 | 51.47 | C |
| ATOM | 1338 | CG | TYR | L | 90 | 33.051 | 1.510 | 31.450 | 1.00 | 50.52 | C |
| ATOM | 1339 | CD1 | TYR | L | 90 | 33.177 | 0.923 | 30.199 | 1.00 | 49.13 | C |
| ATOM | 1341 | CE1 | TYR | L | 90 | 33.379 | −0.434 | 30.060 | 1.00 | 47.35 | C |
| ATOM | 1343 | CZ | TYR | L | 90 | 33.454 | −1.223 | 31.179 | 1.00 | 50.51 | C |
| ATOM | 1344 | OH | TYR | L | 90 | 33.656 | −2.579 | 31.067 | 1.00 | 51.12 | O |
| ATOM | 1346 | CE2 | TYR | L | 90 | 33.326 | −0.664 | 32.436 | 1.00 | 51.36 | C |
| ATOM | 1348 | CD2 | TYR | L | 90 | 33.123 | 0.691 | 32.563 | 1.00 | 52.08 | C |
| ATOM | 1350 | C | TYR | L | 90 | 31.017 | 4.800 | 31.735 | 1.00 | 52.63 | C |
| ATOM | 1351 | O | TYR | L | 90 | 31.328 | 5.757 | 31.026 | 1.00 | 51.70 | O |
| ATOM | 1353 | N | TYR | L | 91 | 30.395 | 4.931 | 32.908 | 1.00 | 53.91 | N |
| ATOM | 1354 | CA | TYR | L | 91 | 29.901 | 6.223 | 33.403 | 1.00 | 55.09 | C |
| ATOM | 1356 | CB | TYR | L | 91 | 28.380 | 6.213 | 33.507 | 1.00 | 54.71 | C |
| ATOM | 1359 | CG | TYR | L | 91 | 27.641 | 6.358 | 32.204 | 1.00 | 54.89 | C |
| ATOM | 1360 | CD1 | TYR | L | 91 | 27.461 | 7.605 | 31.624 | 1.00 | 48.90 | C |
| ATOM | 1362 | CE1 | TYR | L | 91 | 26.765 | 7.739 | 30.446 | 1.00 | 49.97 | C |
| ATOM | 1364 | CZ | TYR | L | 91 | 26.234 | 6.620 | 29.841 | 1.00 | 53.05 | C |
| ATOM | 1365 | OH | TYR | L | 91 | 25.543 | 6.738 | 28.664 | 1.00 | 53.94 | O |
| ATOM | 1367 | CE2 | TYR | L | 91 | 26.399 | 5.369 | 30.402 | 1.00 | 54.39 | C |
| ATOM | 1369 | CD2 | TYR | L | 91 | 27.091 | 5.245 | 31.572 | 1.00 | 53.31 | C |
| ATOM | 1371 | C | TYR | L | 91 | 30.426 | 6.628 | 34.777 | 1.00 | 56.54 | C |
| ATOM | 1372 | O | TYR | L | 91 | 30.550 | 5.811 | 35.689 | 1.00 | 58.18 | O |
| ATOM | 1374 | N | CYS | L | 92 | 30.617 | 7.932 | 34.919 | 1.00 | 58.34 | N |
| ATOM | 1375 | CA | CYS | L | 92 | 31.134 | 8.568 | 36.109 | 1.00 | 57.04 | C |
| ATOM | 1377 | CB | CYS | L | 92 | 32.105 | 9.636 | 35.634 | 1.00 | 59.10 | C |
| ATOM | 1380 | SG | CYS | L | 92 | 33.016 | 10.328 | 36.933 | 1.00 | 67.16 | S |
| ATOM | 1382 | C | CYS | L | 92 | 30.003 | 9.246 | 36.883 | 1.00 | 56.04 | C |
| ATOM | 1383 | O | CYS | L | 92 | 29.027 | 9.666 | 36.277 | 1.00 | 55.74 | O |
| ATOM | 1385 | N | GLN | L | 93 | 30.132 | 9.382 | 38.203 | 1.00 | 56.50 | N |
| ATOM | 1386 | CA | GLN | L | 93 | 29.059 | 9.990 | 39.034 | 1.00 | 55.53 | C |
| ATOM | 1388 | CB | GLN | L | 93 | 27.924 | 8.993 | 39.245 | 1.00 | 55.82 | C |
| ATOM | 1391 | CG | GLN | L | 93 | 26.676 | 9.548 | 39.958 | 1.00 | 57.20 | C |
| ATOM | 1394 | CD | GLN | L | 93 | 26.391 | 8.920 | 41.317 | 1.00 | 54.95 | C |
| ATOM | 1395 | OE1 | GLN | L | 93 | 26.866 | 7.832 | 41.633 | 1.00 | 56.37 | O |
| ATOM | 1396 | NE2 | GLN | L | 93 | 25.590 | 9.602 | 42.118 | 1.00 | 51.50 | N |
| ATOM | 1399 | C | GLN | L | 93 | 29.556 | 10.425 | 40.392 | 1.00 | 54.46 | C |
| ATOM | 1400 | O | GLN | L | 93 | 30.358 | 9.728 | 41.004 | 1.00 | 57.26 | O |
| ATOM | 1402 | N | HIS | L | 94 | 29.057 | 11.557 | 40.873 | 1.00 | 52.91 | N |
| ATOM | 1403 | CA | HIS | L | 94 | 29.462 | 12.089 | 42.177 | 1.00 | 53.90 | C |
| ATOM | 1405 | CB | HIS | L | 94 | 30.100 | 13.471 | 42.020 | 1.00 | 54.57 | C |
| ATOM | 1408 | CG | HIS | L | 94 | 29.098 | 14.584 | 42.006 | 1.00 | 54.75 | C |
| ATOM | 1409 | ND1 | HIS | L | 94 | 28.735 | 15.275 | 43.141 | 1.00 | 54.59 | N |
| ATOM | 1411 | CE1 | HIS | L | 94 | 27.801 | 16.157 | 42.835 | 1.00 | 59.25 | C |
| ATOM | 1413 | NE2 | HIS | L | 94 | 27.536 | 16.057 | 41.545 | 1.00 | 57.68 | N |
| ATOM | 1415 | CD2 | HIS | L | 94 | 28.326 | 15.072 | 41.006 | 1.00 | 57.78 | C |
| ATOM | 1417 | C | HIS | L | 94 | 28.270 | 12.245 | 43.108 | 1.00 | 53.25 | C |
| ATOM | 1418 | O | HIS | L | 94 | 27.114 | 12.181 | 42.681 | 1.00 | 53.22 | O |
| ATOM | 1420 | N | SER | L | 95 | 28.553 | 12.512 | 44.377 | 1.00 | 53.15 | N |
| ATOM | 1421 | CA | SER | L | 95 | 27.498 | 12.890 | 45.310 | 1.00 | 53.23 | C |
| ATOM | 1423 | CB | SER | L | 95 | 26.858 | 11.636 | 45.923 | 1.00 | 52.60 | C |
| ATOM | 1426 | OG | SER | L | 95 | 27.766 | 10.992 | 46.812 | 1.00 | 49.79 | O |
| ATOM | 1428 | C | SER | L | 95 | 27.990 | 13.815 | 46.420 | 1.00 | 52.80 | C |
| ATOM | 1429 | O | SER | L | 95 | 27.553 | 13.695 | 47.551 | 1.00 | 56.31 | O |
| ATOM | 1431 | N | ARG | L | 96 | 28.895 | 14.734 | 46.125 | 1.00 | 52.61 | N |
| ATOM | 1432 | CA | ARG | L | 96 | 29.294 | 15.716 | 47.141 | 1.00 | 53.47 | C |
| ATOM | 1434 | CB | ARG | L | 96 | 30.408 | 16.624 | 46.612 | 1.00 | 53.66 | C |
| ATOM | 1437 | CG | ARG | L | 96 | 30.862 | 17.705 | 47.579 | 1.00 | 52.95 | C |
| ATOM | 1440 | CD | ARG | L | 96 | 31.613 | 17.142 | 48.764 | 1.00 | 52.49 | C |
| ATOM | 1443 | NE | ARG | L | 96 | 31.892 | 18.199 | 49.731 | 1.00 | 53.39 | N |
| ATOM | 1445 | CZ | ARG | L | 96 | 31.053 | 18.604 | 50.685 | 1.00 | 53.34 | C |
| ATOM | 1446 | NH1 | ARG | L | 96 | 29.860 | 18.041 | 50.847 | 1.00 | 58.89 | N |
| ATOM | 1449 | NH2 | ARG | L | 96 | 31.417 | 19.579 | 51.502 | 1.00 | 52.87 | N |
| ATOM | 1452 | C | ARG | L | 96 | 28.091 | 16.562 | 47.590 | 1.00 | 52.41 | C |
| ATOM | 1453 | O | ARG | L | 96 | 27.918 | 16.836 | 48.768 | 1.00 | 51.51 | O |
| ATOM | 1455 | N | GLU | L | 97 | 27.269 | 16.966 | 46.638 | 1.00 | 52.07 | N |
| ATOM | 1456 | CA | GLU | L | 97 | 26.111 | 17.784 | 46.920 | 1.00 | 53.05 | C |
| ATOM | 1458 | CB | GLU | L | 97 | 26.489 | 19.267 | 46.838 | 1.00 | 54.44 | C |
| ATOM | 1461 | CG | GLU | L | 97 | 27.058 | 19.715 | 45.483 | 1.00 | 56.59 | C |
| ATOM | 1464 | CD | GLU | L | 97 | 27.644 | 21.116 | 45.533 | 1.00 | 58.43 | C |
| ATOM | 1465 | OE1 | GLU | L | 97 | 28.282 | 21.450 | 46.554 | 1.00 | 66.43 | O |
| ATOM | 1466 | OE2 | GLU | L | 97 | 27.479 | 21.886 | 44.553 | 1.00 | 65.22 | O |
| ATOM | 1467 | C | GLU | L | 97 | 25.064 | 17.454 | 45.883 | 1.00 | 51.91 | C |
| ATOM | 1468 | O | GLU | L | 97 | 25.316 | 16.638 | 44.997 | 1.00 | 51.93 | O |
| ATOM | 1470 | N | LEU | L | 98 | 23.898 | 18.083 | 45.986 | 1.00 | 50.34 | N |
| ATOM | 1471 | CA | LEU | L | 98 | 22.882 | 17.940 | 44.954 | 1.00 | 50.49 | C |
| ATOM | 1473 | CB | LEU | L | 98 | 21.472 | 17.987 | 45.536 | 1.00 | 49.48 | C |

| | | | | | | | | | | |
|---|---|---|---|---|---|---|---|---|---|---|
| ATOM | 1476 | CG | LEU | L | 98 | 20.804 | 16.641 | 45.764 | 1.00 | 51.33 C |
| ATOM | 1478 | CD1 | LEU | L | 98 | 21.548 | 15.886 | 46.827 | 1.00 | 56.91 C |
| ATOM | 1482 | CD2 | LEU | L | 98 | 19.358 | 16.837 | 46.171 | 1.00 | 52.44 C |
| ATOM | 1486 | C | LEU | L | 98 | 23.050 | 19.041 | 43.928 | 1.00 | 49.66 C |
| ATOM | 1487 | O | LEU | L | 98 | 23.513 | 20.137 | 44.274 | 1.00 | 51.20 O |
| ATOM | 1489 | N | PRO | L | 99 | 22.670 | 18.760 | 42.661 | 1.00 | 48.26 N |
| ATOM | 1490 | CA | PRO | L | 99 | 22.170 | 17.476 | 42.177 | 1.00 | 49.09 C |
| ATOM | 1492 | CB | PRO | L | 99 | 21.466 | 17.835 | 40.865 | 1.00 | 49.32 C |
| ATOM | 1495 | CG | PRO | L | 99 | 21.617 | 19.295 | 40.678 | 1.00 | 46.87 C |
| ATOM | 1498 | CD | PRO | L | 99 | 22.699 | 19.752 | 41.579 | 1.00 | 47.57 C |
| ATOM | 1501 | C | PRO | L | 99 | 23.263 | 16.452 | 41.889 | 1.00 | 49.51 C |
| ATOM | 1502 | O | PRO | L | 99 | 24.367 | 16.799 | 41.485 | 1.00 | 50.96 O |
| ATOM | 1503 | N | TRP | L | 100 | 22.925 | 15.188 | 42.088 | 1.00 | 50.14 N |
| ATOM | 1504 | CA | TRP | L | 100 | 23.827 | 14.090 | 41.797 | 1.00 | 49.90 C |
| ATOM | 1506 | CB | TRP | L | 100 | 23.315 | 12.817 | 42.465 | 1.00 | 49.58 C |
| ATOM | 1509 | CG | TRP | L | 100 | 23.201 | 12.960 | 43.949 | 1.00 | 52.10 C |
| ATOM | 1510 | CD1 | TRP | L | 100 | 24.033 | 13.666 | 44.770 | 1.00 | 56.37 C |
| ATOM | 1512 | NE1 | TRP | L | 100 | 23.630 | 13.554 | 46.074 | 1.00 | 55.05 N |
| ATOM | 1514 | CE2 | TRP | L | 100 | 22.519 | 12.758 | 46.117 | 1.00 | 52.25 C |
| ATOM | 1515 | CD2 | TRP | L | 100 | 22.223 | 12.365 | 44.797 | 1.00 | 53.05 C |
| ATOM | 1516 | CE3 | TRP | L | 100 | 21.127 | 11.533 | 44.570 | 1.00 | 54.95 C |
| ATOM | 1518 | CZ3 | TRP | L | 100 | 20.376 | 11.137 | 45.641 | 1.00 | 55.55 C |
| ATOM | 1520 | CH2 | TRP | L | 100 | 20.692 | 11.550 | 46.944 | 1.00 | 54.45 C |
| ATOM | 1522 | CZ2 | TRP | L | 100 | 21.756 | 12.362 | 47.197 | 1.00 | 49.52 C |
| ATOM | 1524 | C | TRP | L | 100 | 23.961 | 13.919 | 40.279 | 1.00 | 49.78 C |
| ATOM | 1525 | O | TRP | L | 100 | 23.036 | 13.459 | 39.607 | 1.00 | 48.93 O |
| ATOM | 1527 | N | THR | L | 101 | 25.113 | 14.320 | 39.748 | 1.00 | 49.38 N |
| ATOM | 1528 | CA | THR | L | 101 | 25.311 | 14.404 | 38.303 | 1.00 | 48.66 C |
| ATOM | 1530 | CB | THR | L | 101 | 25.717 | 15.819 | 37.855 | 1.00 | 46.87 C |
| ATOM | 1532 | OG1 | THR | L | 101 | 26.804 | 16.309 | 38.655 | 1.00 | 46.30 O |
| ATOM | 1534 | CG2 | THR | L | 101 | 24.540 | 16.739 | 38.016 | 1.00 | 44.92 C |
| ATOM | 1538 | C | THR | L | 101 | 26.329 | 13.400 | 37.827 | 1.00 | 47.78 C |
| ATOM | 1539 | O | THR | L | 101 | 27.192 | 12.968 | 38.579 | 1.00 | 47.20 O |
| ATOM | 1541 | N | PHE | L | 102 | 26.197 | 13.037 | 36.561 | 1.00 | 47.97 N |
| ATOM | 1542 | CA | PHE | L | 102 | 26.962 | 11.966 | 35.960 | 1.00 | 48.82 C |
| ATOM | 1544 | CB | PHE | L | 102 | 26.021 | 11.021 | 35.207 | 1.00 | 49.42 C |
| ATOM | 1547 | CG | PHE | L | 102 | 25.300 | 10.039 | 36.076 | 1.00 | 46.67 C |
| ATOM | 1548 | CD1 | PHE | L | 102 | 25.742 | 8.720 | 36.164 | 1.00 | 47.15 C |
| ATOM | 1550 | CE1 | PHE | L | 102 | 25.085 | 7.800 | 36.936 | 1.00 | 46.15 C |
| ATOM | 1552 | CZ | PHE | L | 102 | 23.965 | 8.174 | 37.638 | 1.00 | 50.19 C |
| ATOM | 1554 | CE2 | PHE | L | 102 | 23.498 | 9.488 | 37.551 | 1.00 | 53.10 C |
| ATOM | 1556 | CD2 | PHE | L | 102 | 24.168 | 10.407 | 36.761 | 1.00 | 47.98 C |
| ATOM | 1558 | C | PHE | L | 102 | 27.926 | 12.571 | 34.956 | 1.00 | 49.48 C |
| ATOM | 1559 | O | PHE | L | 102 | 27.792 | 13.739 | 34.592 | 1.00 | 51.35 O |
| ATOM | 1561 | N | GLY | L | 103 | 28.882 | 11.774 | 34.495 | 1.00 | 49.86 N |
| ATOM | 1562 | CA | GLY | L | 103 | 29.714 | 12.143 | 33.351 | 1.00 | 50.55 C |
| ATOM | 1565 | C | GLY | L | 103 | 28.962 | 11.813 | 32.080 | 1.00 | 51.42 C |
| ATOM | 1566 | O | GLY | L | 103 | 27.832 | 11.324 | 32.142 | 1.00 | 54.44 O |
| ATOM | 1568 | N | GLN | L | 104 | 29.570 | 12.071 | 30.925 | 1.00 | 51.70 N |
| ATOM | 1569 | CA | GLN | L | 104 | 28.886 | 11.861 | 29.639 | 1.00 | 51.67 C |
| ATOM | 1571 | CB | GLN | L | 104 | 29.305 | 12.921 | 28.598 | 1.00 | 52.35 C |
| ATOM | 1574 | CG | GLN | L | 104 | 30.581 | 12.630 | 27.784 | 1.00 | 52.79 C |
| ATOM | 1577 | CD | GLN | L | 104 | 31.854 | 12.921 | 28.543 | 1.00 | 53.59 C |
| ATOM | 1578 | OE1 | GLN | L | 104 | 31.841 | 13.166 | 29.753 | 1.00 | 53.39 O |
| ATOM | 1579 | NE2 | GLN | L | 104 | 32.968 | 12.903 | 27.831 | 1.00 | 51.28 N |
| ATOM | 1582 | C | GLN | L | 104 | 29.098 | 10.449 | 29.096 | 1.00 | 51.16 C |
| ATOM | 1583 | O | GLN | L | 104 | 28.619 | 10.111 | 28.015 | 1.00 | 50.46 O |
| ATOM | 1585 | N | GLY | L | 105 | 29.818 | 9.629 | 29.852 | 1.00 | 52.46 N |
| ATOM | 1586 | CA | GLY | L | 105 | 30.071 | 8.249 | 29.470 | 1.00 | 52.57 C |
| ATOM | 1589 | C | GLY | L | 105 | 31.240 | 8.128 | 28.517 | 1.00 | 52.29 C |
| ATOM | 1590 | O | GLY | L | 105 | 31.511 | 9.045 | 27.734 | 1.00 | 52.99 O |
| ATOM | 1592 | N | THR | L | 106 | 31.928 | 6.990 | 28.590 | 1.00 | 52.25 N |
| ATOM | 1593 | CA | THR | L | 106 | 33.051 | 6.688 | 27.709 | 1.00 | 52.43 C |
| ATOM | 1595 | CB | THR | L | 106 | 34.391 | 6.741 | 28.477 | 1.00 | 52.12 C |
| ATOM | 1597 | OG1 | THR | L | 106 | 34.638 | 8.078 | 28.934 | 1.00 | 49.34 O |
| ATOM | 1599 | CG2 | THR | L | 106 | 35.551 | 6.290 | 27.595 | 1.00 | 52.62 C |
| ATOM | 1603 | C | THR | L | 106 | 32.855 | 5.300 | 27.102 | 1.00 | 52.40 C |
| ATOM | 1604 | O | THR | L | 106 | 32.718 | 4.323 | 27.828 | 1.00 | 53.01 O |
| ATOM | 1606 | N | LYS | L | 107 | 32.851 | 5.226 | 25.775 | 1.00 | 53.39 N |
| ATOM | 1607 | CA | LYS | L | 107 | 32.646 | 3.972 | 25.057 | 1.00 | 54.31 C |
| ATOM | 1609 | CB | LYS | L | 107 | 32.114 | 4.244 | 23.647 | 1.00 | 55.17 C |
| ATOM | 1612 | CG | LYS | L | 107 | 31.300 | 3.111 | 23.024 | 1.00 | 55.52 C |
| ATOM | 1615 | CD | LYS | L | 107 | 30.815 | 3.508 | 21.617 | 1.00 | 57.87 C |
| ATOM | 1618 | CE | LYS | L | 107 | 29.491 | 2.835 | 21.229 | 1.00 | 60.84 C |
| ATOM | 1621 | NZ | LYS | L | 107 | 28.967 | 3.298 | 19.891 | 1.00 | 58.55 N |
| ATOM | 1625 | C | LYS | L | 107 | 33.965 | 3.240 | 24.963 | 1.00 | 54.57 C |
| ATOM | 1626 | O | LYS | L | 107 | 34.946 | 3.775 | 24.450 | 1.00 | 53.85 O |
| ATOM | 1628 | N | VAL | L | 108 | 33.992 | 2.015 | 25.466 | 1.00 | 55.85 N |
| ATOM | 1629 | CA | VAL | L | 108 | 35.201 | 1.204 | 25.429 | 1.00 | 55.48 C |

-continued

| | | | | | | | | | | |
|---|---|---|---|---|---|---|---|---|---|---|
| ATOM | 1631 | CB | VAL | L | 108 | 35.516 | 0.622 | 26.821 | 1.00 | 54.97 C |
| ATOM | 1633 | CG1 | VAL | L | 108 | 36.545 | −0.498 | 26.735 | 1.00 | 54.29 C |
| ATOM | 1637 | CG2 | VAL | L | 108 | 36.006 | 1.738 | 27.744 | 1.00 | 54.20 C |
| ATOM | 1641 | C | VAL | L | 108 | 34.976 | 0.101 | 24.428 | 1.00 | 54.93 C |
| ATOM | 1642 | O | VAL | L | 108 | 33.910 | −0.506 | 24.417 | 1.00 | 55.37 O |
| ATOM | 1644 | N | GLU | L | 109 | 35.980 | −0.151 | 23.593 | 1.00 | 55.63 N |
| ATOM | 1645 | CA | GLU | L | 109 | 35.896 | −1.185 | 22.553 | 1.00 | 56.24 C |
| ATOM | 1647 | CB | GLU | L | 109 | 35.520 | −0.553 | 21.213 | 1.00 | 55.87 C |
| ATOM | 1650 | CG | GLU | L | 109 | 34.026 | −0.230 | 21.125 | 1.00 | 59.28 C |
| ATOM | 1653 | CD | GLU | L | 109 | 33.636 | 0.546 | 19.880 | 1.00 | 59.04 C |
| ATOM | 1654 | OE1 | GLU | L | 109 | 34.493 | 1.271 | 19.333 | 1.00 | 65.40 O |
| ATOM | 1655 | OE2 | GLU | L | 109 | 32.463 | 0.435 | 19.458 | 1.00 | 63.24 O |
| ATOM | 1656 | C | GLU | L | 109 | 37.172 | −2.022 | 22.421 | 1.00 | 55.96 C |
| ATOM | 1657 | O | GLU | L | 109 | 38.209 | −1.708 | 23.011 | 1.00 | 56.62 O |
| ATOM | 1659 | N | ILE | L | 110 | 37.070 | −3.103 | 21.655 | 1.00 | 55.26 N |
| ATOM | 1660 | CA | ILE | L | 110 | 38.171 | −4.044 | 21.471 | 1.00 | 54.84 C |
| ATOM | 1662 | CB | ILE | L | 110 | 37.676 | −5.520 | 21.615 | 1.00 | 53.97 C |
| ATOM | 1664 | CG1 | ILE | L | 110 | 37.964 | −6.046 | 23.018 | 1.00 | 53.00 C |
| ATOM | 1667 | CD1 | ILE | L | 110 | 37.208 | −5.335 | 24.077 | 1.00 | 57.14 C |
| ATOM | 1671 | CG2 | ILE | L | 110 | 38.358 | −6.449 | 20.626 | 1.00 | 57.07 C |
| ATOM | 1675 | C | ILE | L | 110 | 38.851 | −3.823 | 20.118 | 1.00 | 55.03 C |
| ATOM | 1676 | O | ILE | L | 110 | 38.176 | −3.633 | 19.100 | 1.00 | 55.16 O |
| ATOM | 1678 | N | LYS | L | 111 | 40.184 | −3.840 | 20.117 | 1.00 | 54.09 N |
| ATOM | 1679 | CA | LYS | L | 111 | 40.950 | −3.865 | 18.873 | 1.00 | 53.75 C |
| ATOM | 1681 | CB | LYS | L | 111 | 42.302 | −3.150 | 19.010 | 1.00 | 54.21 C |
| ATOM | 1684 | CG | LYS | L | 111 | 42.196 | −1.626 | 18.941 | 1.00 | 55.69 C |
| ATOM | 1687 | CD | LYS | L | 111 | 43.542 | −0.952 | 18.674 | 1.00 | 55.59 C |
| ATOM | 1690 | CE | LYS | L | 111 | 43.376 | 0.573 | 18.529 | 1.00 | 57.45 C |
| ATOM | 1693 | NZ | LYS | L | 111 | 44.562 | 1.256 | 17.911 | 1.00 | 56.32 N |
| ATOM | 1697 | C | LYS | L | 111 | 41.126 | −5.322 | 18.458 | 1.00 | 52.96 C |
| ATOM | 1698 | O | LYS | L | 111 | 41.512 | −6.174 | 19.257 | 1.00 | 53.46 O |
| ATOM | 1700 | N | ARG | L | 112 | 40.838 | −5.589 | 17.193 | 1.00 | 52.44 N |
| ATOM | 1701 | CA | ARG | L | 112 | 40.702 | −6.940 | 16.682 | 1.00 | 51.40 C |
| ATOM | 1703 | CB | ARG | L | 112 | 39.212 | −7.243 | 16.523 | 1.00 | 51.98 C |
| ATOM | 1706 | CG | ARG | L | 112 | 38.787 | −8.647 | 16.869 | 1.00 | 50.47 C |
| ATOM | 1709 | CD | ARG | L | 112 | 37.574 | −9.048 | 16.036 | 1.00 | 49.48 C |
| ATOM | 1712 | NE | ARG | L | 112 | 37.957 | −9.432 | 14.678 | 1.00 | 43.18 N |
| ATOM | 1714 | CZ | ARG | L | 112 | 38.354 | −10.652 | 14.317 | 1.00 | 42.39 C |
| ATOM | 1715 | NH1 | ARG | L | 112 | 38.422 | −11.634 | 15.200 | 1.00 | 43.28 N |
| ATOM | 1718 | NH2 | ARG | L | 112 | 38.683 | −10.900 | 13.057 | 1.00 | 45.12 N |
| ATOM | 1721 | C | ARG | L | 112 | 41.396 | −7.011 | 15.325 | 1.00 | 50.66 C |
| ATOM | 1722 | O | ARG | L | 112 | 41.635 | −5.982 | 14.692 | 1.00 | 49.67 O |
| ATOM | 1724 | N | THR | L | 113 | 41.721 | −8.220 | 14.878 | 1.00 | 50.47 N |
| ATOM | 1725 | CA | THR | L | 113 | 42.254 | −8.408 | 13.525 | 1.00 | 50.41 C |
| ATOM | 1727 | CB | THR | L | 113 | 42.738 | −9.851 | 13.293 | 1.00 | 50.23 C |
| ATOM | 1729 | OG1 | THR | L | 113 | 41.649 | −10.765 | 13.472 | 1.00 | 51.99 O |
| ATOM | 1731 | CG2 | THR | L | 113 | 43.850 | −10.209 | 14.262 | 1.00 | 50.47 C |
| ATOM | 1735 | C | THR | L | 113 | 41.162 | −8.082 | 12.511 | 1.00 | 50.13 C |
| ATOM | 1736 | O | THR | L | 113 | 39.978 | −8.076 | 12.852 | 1.00 | 50.91 O |
| ATOM | 1738 | N | VAL | L | 114 | 41.544 | −7.796 | 11.272 | 1.00 | 49.57 N |
| ATOM | 1739 | CA | VAL | L | 114 | 40.553 | −7.403 | 10.271 | 1.00 | 49.63 C |
| ATOM | 1741 | CB | VAL | L | 114 | 41.199 | −6.691 | 9.050 | 1.00 | 48.73 C |
| ATOM | 1743 | CG1 | VAL | L | 114 | 40.183 | −6.488 | 7.936 | 1.00 | 47.74 C |
| ATOM | 1747 | CG2 | VAL | L | 114 | 41.777 | −5.345 | 9.476 | 1.00 | 47.63 C |
| ATOM | 1751 | C | VAL | L | 114 | 39.722 | −8.622 | 9.848 | 1.00 | 49.92 C |
| ATOM | 1752 | O | VAL | L | 114 | 40.269 | −9.675 | 9.507 | 1.00 | 49.67 O |
| ATOM | 1754 | N | ALA | L | 115 | 38.399 | −8.462 | 9.906 | 1.00 | 49.86 N |
| ATOM | 1755 | CA | ALA | L | 115 | 37.451 | −9.497 | 9.507 | 1.00 | 49.19 C |
| ATOM | 1757 | CB | ALA | L | 115 | 36.633 | −9.947 | 10.698 | 1.00 | 49.31 C |
| ATOM | 1761 | C | ALA | L | 115 | 36.535 | −8.963 | 8.419 | 1.00 | 48.76 C |
| ATOM | 1762 | O | ALA | L | 115 | 35.754 | −8.039 | 8.654 | 1.00 | 47.41 O |
| ATOM | 1764 | N | ALA | L | 116 | 36.638 | −9.550 | 7.228 | 1.00 | 49.59 N |
| ATOM | 1765 | CA | ALA | L | 116 | 35.802 | −9.165 | 6.097 | 1.00 | 49.37 C |
| ATOM | 1767 | CB | ALA | L | 116 | 36.165 | −9.975 | 4.873 | 1.00 | 48.28 C |
| ATOM | 1771 | C | ALA | L | 116 | 34.340 | −9.383 | 6.461 | 1.00 | 50.11 C |
| ATOM | 1772 | O | ALA | L | 116 | 34.035 | −10.246 | 7.282 | 1.00 | 50.77 O |
| ATOM | 1774 | N | PRO | L | 117 | 33.428 | −8.588 | 5.879 | 1.00 | 50.29 N |
| ATOM | 1775 | CA | PRO | L | 117 | 32.023 | −8.851 | 6.133 | 1.00 | 50.04 C |
| ATOM | 1777 | CB | PRO | L | 117 | 31.356 | −7.489 | 5.893 | 1.00 | 49.53 C |
| ATOM | 1780 | CG | PRO | L | 117 | 32.410 | −6.599 | 5.286 | 1.00 | 49.57 C |
| ATOM | 1783 | CD | PRO | L | 117 | 33.601 | −7.442 | 4.976 | 1.00 | 50.58 C |
| ATOM | 1786 | C | PRO | L | 117 | 31.499 | −9.885 | 5.152 | 1.00 | 50.47 C |
| ATOM | 1787 | O | PRO | L | 117 | 31.836 | −9.837 | 3.972 | 1.00 | 50.01 O |
| ATOM | 1788 | N | SER | L | 118 | 30.703 | −10.825 | 5.648 | 1.00 | 51.10 N |
| ATOM | 1789 | CA | SER | L | 118 | 29.962 | −11.740 | 4.792 | 1.00 | 50.63 C |
| ATOM | 1791 | CB | SER | L | 118 | 29.693 | −13.059 | 5.513 | 1.00 | 51.05 C |
| ATOM | 1794 | OG | SER | L | 118 | 29.183 | −12.832 | 6.820 | 1.00 | 49.77 O |
| ATOM | 1796 | C | SER | L | 118 | 28.648 | −11.060 | 4.431 | 1.00 | 51.04 C |
| ATOM | 1797 | O | SER | L | 118 | 27.859 | −10.717 | 5.317 | 1.00 | 50.74 O |

-continued

| | | | | | | | | | | |
|---|---|---|---|---|---|---|---|---|---|---|
| ATOM | 1799 | N | VAL | L | 119 | 28.427 | −10.865 | 3.131 | 1.00 | 51.04 N |
| ATOM | 1800 | CA | VAL | L | 119 | 27.300 | −10.084 | 2.624 | 1.00 | 50.67 C |
| ATOM | 1802 | CB | VAL | L | 119 | 27.745 | −9.151 | 1.460 | 1.00 | 50.02 C |
| ATOM | 1804 | CG1 | VAL | L | 119 | 26.568 | −8.317 | 0.946 | 1.00 | 47.92 C |
| ATOM | 1808 | CG2 | VAL | L | 119 | 28.897 | −8.251 | 1.903 | 1.00 | 48.89 C |
| ATOM | 1812 | C | VAL | L | 119 | 26.179 | −10.983 | 2.113 | 1.00 | 50.98 C |
| ATOM | 1813 | O | VAL | L | 119 | 26.434 | −11.980 | 1.434 | 1.00 | 51.69 O |
| ATOM | 1815 | N | PHE | L | 120 | 24.942 | −10.612 | 2.429 | 1.00 | 51.17 N |
| ATOM | 1816 | CA | PHE | L | 120 | 23.757 | −11.283 | 1.903 | 1.00 | 53.08 C |
| ATOM | 1818 | CB | PHE | L | 120 | 23.068 | −12.106 | 3.002 | 1.00 | 53.27 C |
| ATOM | 1821 | CG | PHE | L | 120 | 23.970 | −13.113 | 3.687 | 1.00 | 54.14 C |
| ATOM | 1822 | CD1 | PHE | L | 120 | 24.866 | −12.714 | 4.675 | 1.00 | 54.71 C |
| ATOM | 1824 | CE1 | PHE | L | 120 | 25.690 | −13.636 | 5.313 | 1.00 | 51.45 C |
| ATOM | 1826 | CZ | PHE | L | 120 | 25.613 | −14.973 | 4.982 | 1.00 | 51.35 C |
| ATOM | 1828 | CE2 | PHE | L | 120 | 24.718 | −15.390 | 4.007 | 1.00 | 53.76 C |
| ATOM | 1830 | CD2 | PHE | L | 120 | 23.900 | −14.462 | 3.366 | 1.00 | 54.90 C |
| ATOM | 1832 | C | PHE | L | 120 | 22.795 | −10.215 | 1.383 | 1.00 | 53.98 C |
| ATOM | 1833 | O | PHE | L | 120 | 22.800 | −9.093 | 1.884 | 1.00 | 54.86 O |
| ATOM | 1835 | N | ILE | L | 121 | 21.982 | −10.550 | 0.381 | 1.00 | 55.74 N |
| ATOM | 1836 | CA | ILE | L | 121 | 20.916 | −9.645 | −0.083 | 1.00 | 56.42 C |
| ATOM | 1838 | CB | ILE | L | 121 | 21.187 | −9.069 | −1.491 | 1.00 | 56.16 C |
| ATOM | 1840 | CG1 | ILE | L | 121 | 20.244 | −7.894 | −1.776 | 1.00 | 55.98 C |
| ATOM | 1843 | CD1 | ILE | L | 121 | 20.615 | −7.095 | −3.018 | 1.00 | 56.25 C |
| ATOM | 1847 | CG2 | ILE | L | 121 | 21.056 | −10.145 | −2.569 | 1.00 | 56.85 C |
| ATOM | 1851 | C | ILE | L | 121 | 19.565 | −10.348 | −0.068 | 1.00 | 57.75 C |
| ATOM | 1852 | O | ILE | L | 121 | 19.470 | −11.535 | −0.373 | 1.00 | 58.73 O |
| ATOM | 1854 | N | PHE | L | 122 | 18.529 | −9.597 | 0.295 | 1.00 | 59.21 N |
| ATOM | 1855 | CA | PHE | L | 122 | 17.187 | −10.135 | 0.468 | 1.00 | 59.29 C |
| ATOM | 1857 | CB | PHE | L | 122 | 16.779 | −10.070 | 1.939 | 1.00 | 61.07 C |
| ATOM | 1860 | CG | PHE | L | 122 | 17.673 | −10.862 | 2.847 | 1.00 | 62.37 C |
| ATOM | 1861 | CD1 | PHE | L | 122 | 17.561 | −12.242 | 2.912 | 1.00 | 63.05 C |
| ATOM | 1863 | CE1 | PHE | L | 122 | 18.381 | −12.983 | 3.744 | 1.00 | 63.87 C |
| ATOM | 1865 | CZ | PHE | L | 122 | 19.331 | −12.341 | 4.526 | 1.00 | 63.53 C |
| ATOM | 1867 | CE2 | PHE | L | 122 | 19.456 | −10.960 | 4.468 | 1.00 | 62.76 C |
| ATOM | 1869 | CD2 | PHE | L | 122 | 18.630 | −10.228 | 3.630 | 1.00 | 62.86 C |
| ATOM | 1871 | C | PHE | L | 122 | 16.202 | −9.325 | −0.354 | 1.00 | 59.29 C |
| ATOM | 1872 | O | PHE | L | 122 | 16.111 | −8.107 | −0.187 | 1.00 | 59.29 O |
| ATOM | 1874 | N | PRO | L | 123 | 15.455 | −9.995 | −1.242 | 1.00 | 58.87 N |
| ATOM | 1875 | CA | PRO | L | 123 | 14.453 | −9.272 | −2.013 | 1.00 | 58.89 C |
| ATOM | 1877 | CB | PRO | L | 123 | 14.165 | −10.219 | −3.182 | 1.00 | 59.19 C |
| ATOM | 1880 | CG | PRO | L | 123 | 14.450 | −11.582 | −2.653 | 1.00 | 59.45 C |
| ATOM | 1883 | CD | PRO | L | 123 | 15.483 | −11.434 | −1.567 | 1.00 | 59.04 C |
| ATOM | 1886 | C | PRO | L | 123 | 13.201 | −9.027 | −1.168 | 1.00 | 58.28 C |
| ATOM | 1887 | O | PRO | L | 123 | 12.977 | −9.745 | −0.196 | 1.00 | 58.56 O |
| ATOM | 1888 | N | PRO | L | 124 | 12.394 | −8.013 | −1.522 | 1.00 | 57.89 N |
| ATOM | 1889 | CA | PRO | L | 124 | 11.140 | −7.784 | −0.798 | 1.00 | 58.13 C |
| ATOM | 1891 | CB | PRO | L | 124 | 10.569 | −6.532 | −1.471 | 1.00 | 58.19 C |
| ATOM | 1894 | CG | PRO | L | 124 | 11.211 | −6.493 | −2.808 | 1.00 | 57.53 C |
| ATOM | 1897 | CD | PRO | L | 124 | 12.586 | −7.031 | −2.600 | 1.00 | 57.38 C |
| ATOM | 1900 | C | PRO | L | 124 | 10.160 | −8.947 | −0.950 | 1.00 | 58.10 C |
| ATOM | 1901 | O | PRO | L | 124 | 10.000 | −9.475 | −2.051 | 1.00 | 58.38 O |
| ATOM | 1902 | N | SER | L | 125 | 9.509 | −9.331 | 0.145 | 1.00 | 57.47 N |
| ATOM | 1903 | CA | SER | L | 125 | 8.545 | −10.428 | 0.119 | 1.00 | 57.48 C |
| ATOM | 1905 | CB | SER | L | 125 | 8.179 | −10.849 | 1.541 | 1.00 | 57.88 C |
| ATOM | 1908 | OG | SER | L | 125 | 7.590 | −9.772 | 2.243 | 1.00 | 60.56 O |
| ATOM | 1910 | C | SER | L | 125 | 7.282 | −10.035 | −0.643 | 1.00 | 56.61 C |
| ATOM | 1911 | O | SER | L | 125 | 6.920 | −8.859 | −0.700 | 1.00 | 55.29 O |
| ATOM | 1913 | N | ASP | L | 126 | 6.619 | −11.031 | −1.228 | 1.00 | 56.62 N |
| ATOM | 1914 | CA | ASP | L | 126 | 5.383 | −10.800 | −1.974 | 1.00 | 56.49 C |
| ATOM | 1916 | CB | ASP | L | 126 | 4.930 | −12.075 | −2.697 | 1.00 | 55.78 C |
| ATOM | 1919 | CG | ASP | L | 126 | 5.773 | −12.383 | −3.921 | 1.00 | 54.08 C |
| ATOM | 1920 | OD1 | ASP | L | 126 | 5.370 | −13.253 | −4.720 | 1.00 | 53.82 O |
| ATOM | 1921 | OD2 | ASP | L | 126 | 6.837 | −11.753 | −4.093 | 1.00 | 51.90 O |
| ATOM | 1922 | C | ASP | L | 126 | 4.283 | −10.292 | −1.055 | 1.00 | 56.62 C |
| ATOM | 1923 | O | ASP | L | 126 | 3.468 | −9.462 | −1.457 | 1.00 | 57.02 O |
| ATOM | 1925 | N | GLU | L | 127 | 4.272 | −10.786 | 0.179 | 1.00 | 56.79 N |
| ATOM | 1926 | CA | GLU | L | 127 | 3.324 | −10.323 | 1.190 | 1.00 | 56.91 C |
| ATOM | 1928 | CB | GLU | L | 127 | 3.597 | −11.020 | 2.531 | 1.00 | 56.92 C |
| ATOM | 1931 | CG | GLU | L | 127 | 3.247 | −12.521 | 2.526 | 1.00 | 57.47 C |
| ATOM | 1934 | CD | GLU | L | 127 | 4.302 | −13.404 | 3.187 | 1.00 | 56.55 C |
| ATOM | 1935 | OE1 | GLU | L | 127 | 3.923 | −14.371 | 3.883 | 1.00 | 51.13 O |
| ATOM | 1936 | OE2 | GLU | L | 127 | 5.510 | −13.142 | 3.000 | 1.00 | 55.50 O |
| ATOM | 1937 | C | GLU | L | 127 | 3.365 | −8.796 | 1.346 | 1.00 | 57.23 C |
| ATOM | 1938 | O | GLU | L | 127 | 2.312 | −8.153 | 1.413 | 1.00 | 57.81 O |
| ATOM | 1940 | N | GLN | L | 128 | 4.574 | −8.225 | 1.376 | 1.00 | 56.33 N |
| ATOM | 1941 | CA | GLN | L | 128 | 4.756 | −6.777 | 1.559 | 1.00 | 55.91 C |
| ATOM | 1943 | CB | GLN | L | 128 | 6.225 | −6.431 | 1.833 | 1.00 | 55.96 C |
| ATOM | 1946 | CG | GLN | L | 128 | 6.441 | −4.959 | 2.208 | 1.00 | 55.23 C |
| ATOM | 1949 | CD | GLN | L | 128 | 7.893 | −4.555 | 2.254 | 1.00 | 53.28 C |

-continued

| | | | | | | | | | | |
|---|---|---|---|---|---|---|---|---|---|---|
| ATOM | 1950 | OE1 | GLN | L | 128 | 8.782 | −5.361 | 2.000 | 1.00 | 50.86 | O |
| ATOM | 1951 | NE2 | GLN | L | 128 | 8.142 | −3.293 | 2.576 | 1.00 | 48.52 | N |
| ATOM | 1954 | C | GLN | L | 128 | 4.291 | −5.974 | 0.355 | 1.00 | 55.73 | C |
| ATOM | 1955 | O | GLN | L | 128 | 3.665 | −4.925 | 0.502 | 1.00 | 55.43 | O |
| ATOM | 1957 | N | LEU | L | 129 | 4.627 | −6.457 | −0.833 | 1.00 | 56.19 | N |
| ATOM | 1958 | CA | LEU | L | 129 | 4.290 | −5.754 | −2.064 | 1.00 | 56.62 | C |
| ATOM | 1960 | CB | LEU | L | 129 | 4.842 | −6.515 | −3.273 | 1.00 | 56.91 | C |
| ATOM | 1963 | CG | LEU | L | 129 | 6.373 | −6.569 | −3.353 | 1.00 | 57.38 | C |
| ATOM | 1965 | CD1 | LEU | L | 129 | 6.849 | −7.667 | −4.293 | 1.00 | 57.69 | C |
| ATOM | 1969 | CD2 | LEU | L | 129 | 6.932 | −5.219 | −3.780 | 1.00 | 58.52 | C |
| ATOM | 1973 | C | LEU | L | 129 | 2.778 | −5.581 | −2.168 | 1.00 | 56.69 | C |
| ATOM | 1974 | O | LEU | L | 129 | 2.284 | −4.496 | −2.483 | 1.00 | 56.09 | O |
| ATOM | 1976 | N | LYS | L | 130 | 2.051 | −6.651 | −1.860 | 1.00 | 56.77 | N |
| ATOM | 1977 | CA | LYS | L | 130 | 0.594 | −6.615 | −1.833 | 1.00 | 56.47 | C |
| ATOM | 1979 | CB | LYS | L | 130 | 0.030 | −7.960 | −1.355 | 1.00 | 56.00 | C |
| ATOM | 1982 | CG | LYS | L | 130 | 0.195 | −9.078 | −2.389 | 1.00 | 55.88 | C |
| ATOM | 1985 | CD | LYS | L | 130 | −0.185 | −10.451 | −1.853 | 1.00 | 55.79 | C |
| ATOM | 1988 | CE | LYS | L | 130 | −0.033 | −11.517 | −2.930 | 1.00 | 53.50 | C |
| ATOM | 1991 | NZ | LYS | L | 130 | −0.372 | −12.874 | −2.429 | 1.00 | 52.48 | N |
| ATOM | 1995 | C | LYS | L | 130 | 0.073 | −5.458 | −0.979 | 1.00 | 56.78 | C |
| ATOM | 1996 | O | LYS | L | 130 | −0.971 | −4.892 | −1.290 | 1.00 | 56.99 | O |
| ATOM | 1998 | N | SER | L | 131 | 0.805 | −5.096 | 0.077 | 1.00 | 57.09 | N |
| ATOM | 1999 | CA | SER | L | 131 | 0.450 | −3.927 | 0.895 | 1.00 | 57.34 | C |
| ATOM | 2001 | CB | SER | L | 131 | 1.197 | −3.927 | 2.235 | 1.00 | 57.08 | C |
| ATOM | 2004 | OG | SER | L | 131 | 2.458 | −3.296 | 2.125 | 1.00 | 56.21 | O |
| ATOM | 2006 | C | SER | L | 131 | 0.690 | −2.605 | 0.151 | 1.00 | 57.77 | C |
| ATOM | 2007 | O | SER | L | 131 | 0.009 | −1.620 | 0.419 | 1.00 | 58.13 | O |
| ATOM | 2009 | N | GLY | L | 132 | 1.658 | −2.581 | −0.766 | 1.00 | 58.05 | N |
| ATOM | 2010 | CA | GLY | L | 132 | 1.823 | −1.449 | −1.686 | 1.00 | 58.27 | C |
| ATOM | 2013 | C | GLY | L | 132 | 3.159 | −0.715 | −1.674 | 1.00 | 58.75 | C |
| ATOM | 2014 | O | GLY | L | 132 | 3.303 | 0.305 | −2.352 | 1.00 | 58.07 | O |
| ATOM | 2016 | N | THR | L | 133 | 4.131 | −1.204 | −0.902 | 1.00 | 59.16 | N |
| ATOM | 2017 | CA | THR | L | 133 | 5.503 | −0.665 | −0.943 | 1.00 | 59.08 | C |
| ATOM | 2019 | CB | THR | L | 133 | 5.770 | 0.352 | 0.177 | 1.00 | 58.61 | C |
| ATOM | 2021 | OG1 | THR | L | 133 | 5.641 | −0.299 | 1.448 | 1.00 | 59.73 | O |
| ATOM | 2023 | CG2 | THR | L | 133 | 4.815 | 1.543 | 0.086 | 1.00 | 58.69 | C |
| ATOM | 2027 | C | THR | L | 133 | 6.543 | −1.770 | −0.802 | 1.00 | 58.73 | C |
| ATOM | 2028 | O | THR | L | 133 | 6.257 | −2.824 | −0.235 | 1.00 | 59.65 | O |
| ATOM | 2030 | N | ALA | L | 134 | 7.751 | −1.505 | −1.296 | 1.00 | 57.63 | N |
| ATOM | 2031 | CA | ALA | L | 134 | 8.834 | −2.483 | −1.270 | 1.00 | 58.37 | C |
| ATOM | 2033 | CB | ALA | L | 134 | 9.291 | −2.793 | −2.685 | 1.00 | 58.84 | C |
| ATOM | 2037 | C | ALA | L | 134 | 10.021 | −2.011 | −0.425 | 1.00 | 58.96 | C |
| ATOM | 2038 | O | ALA | L | 134 | 10.439 | −0.851 | −0.512 | 1.00 | 59.55 | O |
| ATOM | 2040 | N | SER | L | 135 | 10.547 | −2.927 | 0.391 | 1.00 | 58.21 | N |
| ATOM | 2041 | CA | SER | L | 135 | 11.784 | −2.717 | 1.133 | 1.00 | 57.20 | C |
| ATOM | 2043 | CB | SER | L | 135 | 11.523 | −2.746 | 2.644 | 1.00 | 57.71 | C |
| ATOM | 2046 | OG | SER | L | 135 | 11.108 | −1.476 | 3.121 | 1.00 | 58.76 | O |
| ATOM | 2048 | C | SER | L | 135 | 12.768 | −3.816 | 0.761 | 1.00 | 55.71 | C |
| ATOM | 2049 | O | SER | L | 135 | 12.458 | −4.992 | 0.929 | 1.00 | 55.68 | O |
| ATOM | 2051 | N | VAL | L | 136 | 13.938 | −3.434 | 0.248 | 1.00 | 54.44 | N |
| ATOM | 2052 | CA | VAL | L | 136 | 15.007 | −4.393 | −0.057 | 1.00 | 54.20 | C |
| ATOM | 2054 | CB | VAL | L | 136 | 15.438 | −4.351 | −1.568 | 1.00 | 54.24 | C |
| ATOM | 2056 | CG1 | VAL | L | 136 | 16.023 | −3.009 | −1.974 | 1.00 | 52.66 | C |
| ATOM | 2060 | CG2 | VAL | L | 136 | 16.421 | −5.471 | −1.884 | 1.00 | 55.76 | C |
| ATOM | 2064 | C | VAL | L | 136 | 16.183 | −4.182 | 0.912 | 1.00 | 53.60 | C |
| ATOM | 2065 | O | VAL | L | 136 | 16.612 | −3.050 | 1.158 | 1.00 | 53.72 | O |
| ATOM | 2067 | N | VAL | L | 137 | 16.687 | −5.284 | 1.465 | 1.00 | 53.30 | N |
| ATOM | 2068 | CA | VAL | L | 137 | 17.637 | −5.243 | 2.581 | 1.00 | 53.45 | C |
| ATOM | 2070 | CB | VAL | L | 137 | 17.087 | −6.015 | 3.804 | 1.00 | 52.01 | C |
| ATOM | 2072 | CG1 | VAL | L | 137 | 18.072 | −5.978 | 4.961 | 1.00 | 50.63 | C |
| ATOM | 2076 | CG2 | VAL | L | 137 | 15.749 | −5.450 | 4.228 | 1.00 | 51.67 | C |
| ATOM | 2080 | C | VAL | L | 137 | 18.981 | −5.854 | 2.200 | 1.00 | 54.41 | C |
| ATOM | 2081 | O | VAL | L | 137 | 19.038 | −6.880 | 1.521 | 1.00 | 55.20 | O |
| ATOM | 2083 | N | CYS | L | 138 | 20.056 | −5.212 | 2.647 | 1.00 | 55.76 | N |
| ATOM | 2084 | CA | CYS | L | 138 | 21.406 | −5.736 | 2.491 | 1.00 | 54.89 | C |
| ATOM | 2086 | CB | CYS | L | 138 | 22.298 | −4.729 | 1.779 | 1.00 | 55.45 | C |
| ATOM | 2089 | SG | CYS | L | 138 | 23.884 | −5.436 | 1.297 | 1.00 | 59.37 | S |
| ATOM | 2091 | C | CYS | L | 138 | 21.963 | −5.996 | 3.868 | 1.00 | 54.85 | C |
| ATOM | 2092 | O | CYS | L | 138 | 21.772 | −5.184 | 4.768 | 1.00 | 55.84 | O |
| ATOM | 2094 | N | LEU | L | 139 | 22.654 | −7.120 | 4.032 | 1.00 | 54.78 | N |
| ATOM | 2095 | CA | LEU | L | 139 | 23.214 | −7.519 | 5.331 | 1.00 | 54.82 | C |
| ATOM | 2097 | CB | LEU | L | 139 | 22.598 | −8.853 | 5.771 | 1.00 | 54.03 | C |
| ATOM | 2100 | CG | LEU | L | 139 | 23.274 | −9.583 | 6.933 | 1.00 | 53.90 | C |
| ATOM | 2102 | CD1 | LEU | L | 139 | 23.385 | −8.660 | 8.139 | 1.00 | 51.76 | C |
| ATOM | 2106 | CD2 | LEU | L | 139 | 22.516 | −10.861 | 7.269 | 1.00 | 52.76 | C |
| ATOM | 2110 | C | LEU | L | 139 | 24.737 | −7.651 | 5.245 | 1.00 | 55.59 | C |
| ATOM | 2111 | O | LEU | L | 139 | 25.232 | −8.375 | 4.384 | 1.00 | 57.06 | O |
| ATOM | 2113 | N | LEU | L | 140 | 25.472 | −6.955 | 6.117 | 1.00 | 55.07 | N |
| ATOM | 2114 | CA | LEU | L | 140 | 26.923 | −7.155 | 6.247 | 1.00 | 54.32 | C |

-continued

| | | | | | | | | | | |
|---|---|---|---|---|---|---|---|---|---|---|
| ATOM | 2116 | CB | LEU | L | 140 | 27.699 | −5.849 | 6.110 | 1.00 | 53.60 C |
| ATOM | 2119 | CG | LEU | L | 140 | 27.248 | −4.885 | 5.018 | 1.00 | 52.60 C |
| ATOM | 2121 | CD1 | LEU | L | 140 | 28.239 | −3.728 | 4.865 | 1.00 | 51.63 C |
| ATOM | 2125 | CD2 | LEU | L | 140 | 27.074 | −5.584 | 3.713 | 1.00 | 52.71 C |
| ATOM | 2129 | C | LEU | L | 140 | 27.196 | −7.772 | 7.604 | 1.00 | 54.65 C |
| ATOM | 2130 | O | LEU | L | 140 | 27.284 | −7.070 | 8.606 | 1.00 | 55.51 O |
| ATOM | 2132 | N | ASN | L | 141 | 27.337 | −9.091 | 7.625 | 1.00 | 54.62 N |
| ATOM | 2133 | CA | ASN | L | 141 | 27.370 | −9.837 | 8.872 | 1.00 | 54.74 C |
| ATOM | 2135 | CB | ASN | L | 141 | 26.737 | −11.214 | 8.658 | 1.00 | 54.71 C |
| ATOM | 2138 | CG | ASN | L | 141 | 26.514 | −11.960 | 9.945 | 1.00 | 52.97 C |
| ATOM | 2139 | OD1 | ASN | L | 141 | 26.712 | −13.163 | 10.008 | 1.00 | 51.47 O |
| ATOM | 2140 | ND2 | ASN | L | 141 | 26.097 | −11.250 | 10.981 | 1.00 | 56.80 N |
| ATOM | 2143 | C | ASN | L | 141 | 28.787 | −9.985 | 9.428 | 1.00 | 55.57 C |
| ATOM | 2144 | O | ASN | L | 141 | 29.748 | −10.164 | 8.663 | 1.00 | 55.86 O |
| ATOM | 2146 | N | ASN | L | 142 | 28.886 | −9.877 | 10.758 | 1.00 | 55.10 N |
| ATOM | 2147 | CA | ASN | L | 142 | 30.111 | −10.118 | 11.538 | 1.00 | 54.03 C |
| ATOM | 2149 | CB | ASN | L | 142 | 30.220 | −11.612 | 11.876 | 1.00 | 52.77 C |
| ATOM | 2152 | CG | ASN | L | 142 | 29.186 | −12.063 | 12.904 | 1.00 | 52.49 C |
| ATOM | 2153 | OD1 | ASN | L | 142 | 28.338 | −11.286 | 13.337 | 1.00 | 52.77 O |
| ATOM | 2154 | ND2 | ASN | L | 142 | 29.263 | −13.326 | 13.305 | 1.00 | 53.29 N |
| ATOM | 2157 | C | ASN | L | 142 | 31.413 | −9.619 | 10.902 | 1.00 | 54.05 C |
| ATOM | 2158 | O | ASN | L | 142 | 32.076 | −10.367 | 10.187 | 1.00 | 55.04 O |
| ATOM | 2160 | N | PHE | L | 143 | 31.777 | −8.363 | 11.171 | 1.00 | 54.33 N |
| ATOM | 2161 | CA | PHE | L | 143 | 32.999 | −7.774 | 10.601 | 1.00 | 54.32 C |
| ATOM | 2163 | CB | PHE | L | 143 | 32.690 | −7.096 | 9.265 | 1.00 | 55.46 C |
| ATOM | 2166 | CG | PHE | L | 143 | 31.807 | −5.882 | 9.378 | 1.00 | 55.14 C |
| ATOM | 2167 | CD1 | PHE | L | 143 | 32.360 | −4.627 | 9.589 | 1.00 | 56.14 C |
| ATOM | 2169 | CE1 | PHE | L | 143 | 31.555 | −3.499 | 9.684 | 1.00 | 56.42 C |
| ATOM | 2171 | CZ | PHE | L | 143 | 30.176 | −3.616 | 9.554 | 1.00 | 56.54 C |
| ATOM | 2173 | CE2 | PHE | L | 143 | 29.610 | −4.863 | 9.331 | 1.00 | 56.80 C |
| ATOM | 2175 | CD2 | PHE | L | 143 | 30.425 | −5.990 | 9.243 | 1.00 | 56.14 C |
| ATOM | 2177 | C | PHE | L | 143 | 33.692 | −6.778 | 11.525 | 1.00 | 54.20 C |
| ATOM | 2178 | O | PHE | L | 143 | 33.065 | −6.204 | 12.418 | 1.00 | 55.01 O |
| ATOM | 2180 | N | TYR | L | 144 | 34.989 | −6.585 | 11.295 | 1.00 | 53.47 N |
| ATOM | 2181 | CA | TYR | L | 144 | 35.779 | −5.605 | 12.028 | 1.00 | 53.67 C |
| ATOM | 2183 | CB | TYR | L | 144 | 36.611 | −6.275 | 13.125 | 1.00 | 53.71 C |
| ATOM | 2186 | CG | TYR | L | 144 | 37.268 | −5.270 | 14.034 | 1.00 | 53.86 C |
| ATOM | 2187 | CD1 | TYR | L | 144 | 38.530 | −4.755 | 13.749 | 1.00 | 54.17 C |
| ATOM | 2189 | CE1 | TYR | L | 144 | 39.121 | −3.807 | 14.577 | 1.00 | 52.92 C |
| ATOM | 2191 | CZ | TYR | L | 144 | 38.438 | −3.360 | 15.694 | 1.00 | 53.53 C |
| ATOM | 2192 | OH | TYR | L | 144 | 38.990 | −2.425 | 16.533 | 1.00 | 54.86 O |
| ATOM | 2194 | CE2 | TYR | L | 144 | 37.181 | −3.848 | 15.983 | 1.00 | 54.32 C |
| ATOM | 2196 | CD2 | TYR | L | 144 | 36.604 | −4.793 | 15.154 | 1.00 | 54.65 C |
| ATOM | 2198 | C | TYR | L | 144 | 36.708 | −4.890 | 11.060 | 1.00 | 54.69 C |
| ATOM | 2199 | O | TYR | L | 144 | 37.288 | −5.540 | 10.188 | 1.00 | 54.08 O |
| ATOM | 2201 | N | PRO | L | 145 | 36.865 | −3.555 | 11.203 | 1.00 | 56.43 N |
| ATOM | 2202 | CA | PRO | L | 145 | 36.252 | −2.625 | 12.167 | 1.00 | 57.34 C |
| ATOM | 2204 | CB | PRO | L | 145 | 37.319 | −1.532 | 12.325 | 1.00 | 57.48 C |
| ATOM | 2207 | CG | PRO | L | 145 | 38.198 | −1.630 | 11.084 | 1.00 | 57.29 C |
| ATOM | 2210 | CD | PRO | L | 145 | 37.772 | −2.838 | 10.288 | 1.00 | 56.61 C |
| ATOM | 2213 | C | PRO | L | 145 | 34.927 | −2.047 | 11.657 | 1.00 | 57.75 C |
| ATOM | 2214 | O | PRO | L | 145 | 34.408 | −2.526 | 10.647 | 1.00 | 57.75 O |
| ATOM | 2215 | N | ARG | L | 146 | 34.384 | −1.038 | 12.342 | 1.00 | 57.84 N |
| ATOM | 2216 | CA | ARG | L | 146 | 33.047 | −0.538 | 12.004 | 1.00 | 58.28 C |
| ATOM | 2218 | CB | ARG | L | 146 | 32.482 | 0.417 | 13.079 | 1.00 | 58.97 C |
| ATOM | 2221 | CG | ARG | L | 146 | 30.938 | 0.508 | 13.054 | 1.00 | 59.22 C |
| ATOM | 2224 | CD | ARG | L | 146 | 30.342 | 1.588 | 13.972 | 1.00 | 60.35 C |
| ATOM | 2227 | NE | ARG | L | 146 | 30.340 | 1.200 | 15.392 | 1.00 | 65.96 N |
| ATOM | 2229 | CZ | ARG | L | 146 | 29.422 | 1.566 | 16.303 | 1.00 | 66.50 C |
| ATOM | 2230 | NH1 | ARG | L | 146 | 28.378 | 2.333 | 15.975 | 1.00 | 66.24 N |
| ATOM | 2233 | NH2 | ARG | L | 146 | 29.540 | 1.151 | 17.566 | 1.00 | 62.60 N |
| ATOM | 2236 | C | ARG | L | 146 | 33.001 | 0.115 | 10.622 | 1.00 | 57.81 C |
| ATOM | 2237 | O | ARG | L | 146 | 32.230 | −0.321 | 9.778 | 1.00 | 57.22 O |
| ATOM | 2239 | N | GLU | L | 147 | 33.828 | 1.132 | 10.377 | 1.00 | 58.64 N |
| ATOM | 2240 | CA | GLU | L | 147 | 33.737 | 1.912 | 9.124 | 1.00 | 58.71 C |
| ATOM | 2242 | CB | GLU | L | 147 | 34.991 | 2.771 | 8.901 | 1.00 | 59.53 C |
| ATOM | 2245 | CG | GLU | L | 147 | 34.971 | 4.126 | 9.628 | 1.00 | 62.23 C |
| ATOM | 2248 | CD | GLU | L | 147 | 35.156 | 5.322 | 8.686 | 1.00 | 66.41 C |
| ATOM | 2249 | OE1 | GLU | L | 147 | 35.624 | 5.143 | 7.537 | 1.00 | 63.81 O |
| ATOM | 2250 | OE2 | GLU | L | 147 | 34.822 | 6.453 | 9.101 | 1.00 | 71.32 O |
| ATOM | 2251 | C | GLU | L | 147 | 33.495 | 1.024 | 7.902 | 1.00 | 57.91 C |
| ATOM | 2252 | O | GLU | L | 147 | 34.181 | 0.018 | 7.724 | 1.00 | 57.97 O |
| ATOM | 2254 | N | ALA | L | 148 | 32.513 | 1.388 | 7.074 | 1.00 | 57.47 N |
| ATOM | 2255 | CA | ALA | L | 148 | 32.159 | 0.575 | 5.895 | 1.00 | 57.40 C |
| ATOM | 2257 | CB | ALA | L | 148 | 31.487 | −0.723 | 6.326 | 1.00 | 57.19 C |
| ATOM | 2261 | C | ALA | L | 148 | 31.259 | 1.308 | 4.910 | 1.00 | 56.76 C |
| ATOM | 2262 | O | ALA | L | 148 | 30.408 | 2.104 | 5.304 | 1.00 | 56.64 O |
| ATOM | 2264 | N | LYS | L | 149 | 31.443 | 1.003 | 3.628 | 1.00 | 56.80 N |
| ATOM | 2265 | CA | LYS | L | 149 | 30.663 | 1.602 | 2.554 | 1.00 | 57.51 C |

-continued

| | | | | | | | | | | |
|---|---|---|---|---|---|---|---|---|---|---|
| ATOM | 2267 | CB | LYS | L | 149 | 31.605 | 2.128 | 1.460 | 1.00 | 57.49 C |
| ATOM | 2270 | CG | LYS | L | 149 | 30.924 | 2.854 | 0.280 | 1.00 | 56.81 C |
| ATOM | 2273 | CD | LYS | L | 149 | 31.212 | 4.358 | 0.274 | 1.00 | 56.29 C |
| ATOM | 2276 | CE | LYS | L | 149 | 30.764 | 5.022 | −1.034 | 1.00 | 57.19 C |
| ATOM | 2279 | NZ | LYS | L | 149 | 31.501 | 6.292 | −1.339 | 1.00 | 53.54 N |
| ATOM | 2283 | C | LYS | L | 149 | 29.697 | 0.563 | 1.972 | 1.00 | 58.12 C |
| ATOM | 2284 | O | LYS | L | 149 | 30.122 | −0.479 | 1.466 | 1.00 | 58.40 O |
| ATOM | 2286 | N | VAL | L | 150 | 28.401 | 0.848 | 2.074 | 1.00 | 57.96 N |
| ATOM | 2287 | CA | VAL | L | 150 | 27.376 | 0.114 | 1.337 | 1.00 | 58.18 C |
| ATOM | 2289 | CB | VAL | L | 150 | 26.215 | −0.328 | 2.264 | 1.00 | 58.19 C |
| ATOM | 2291 | CG1 | VAL | L | 150 | 24.997 | −0.773 | 1.465 | 1.00 | 58.61 C |
| ATOM | 2295 | CG2 | VAL | L | 150 | 26.671 | −1.450 | 3.162 | 1.00 | 57.44 C |
| ATOM | 2299 | C | VAL | L | 150 | 26.872 | 1.031 | 0.221 | 1.00 | 58.47 C |
| ATOM | 2300 | O | VAL | L | 150 | 26.562 | 2.197 | 0.462 | 1.00 | 59.48 O |
| ATOM | 2302 | N | GLN | L | 151 | 26.813 | 0.507 | −1.000 | 1.00 | 58.94 N |
| ATOM | 2303 | CA | GLN | L | 151 | 26.348 | 1.278 | −2.148 | 1.00 | 57.56 C |
| ATOM | 2305 | CB | GLN | L | 151 | 27.503 | 1.532 | −3.125 | 1.00 | 59.31 C |
| ATOM | 2308 | CG | GLN | L | 151 | 27.396 | 2.851 | −3.907 | 1.00 | 61.39 C |
| ATOM | 2311 | CD | GLN | L | 151 | 27.697 | 4.095 | −3.057 | 1.00 | 66.79 C |
| ATOM | 2312 | OE1 | GLN | L | 151 | 27.803 | 5.202 | −3.585 | 1.00 | 66.18 O |
| ATOM | 2313 | NE2 | GLN | L | 151 | 27.835 | 3.913 | −1.740 | 1.00 | 68.31 N |
| ATOM | 2316 | C | GLN | L | 151 | 25.224 | 0.532 | −2.849 | 1.00 | 56.33 C |
| ATOM | 2317 | O | GLN | L | 151 | 25.377 | −0.639 | −3.201 | 1.00 | 55.81 O |
| ATOM | 2319 | N | TRP | L | 152 | 24.098 | 1.213 | −3.045 | 1.00 | 54.22 N |
| ATOM | 2320 | CA | TRP | L | 152 | 22.950 | 0.625 | −3.727 | 1.00 | 53.68 C |
| ATOM | 2322 | CB | TRP | L | 152 | 21.648 | 1.180 | −3.155 | 1.00 | 53.40 C |
| ATOM | 2325 | CG | TRP | L | 152 | 21.233 | 0.523 | −1.879 | 1.00 | 52.23 C |
| ATOM | 2326 | CD1 | TRP | L | 152 | 21.240 | 1.076 | −0.634 | 1.00 | 51.07 C |
| ATOM | 2328 | NE1 | TRP | L | 152 | 20.794 | 0.165 | 0.288 | 1.00 | 52.84 N |
| ATOM | 2330 | CE2 | TRP | L | 152 | 20.489 | −1.008 | −0.355 | 1.00 | 54.44 C |
| ATOM | 2331 | CD2 | TRP | L | 152 | 20.753 | −0.817 | −1.725 | 1.00 | 50.08 C |
| ATOM | 2332 | CE3 | TRP | L | 152 | 20.525 | −1.877 | −2.612 | 1.00 | 50.38 C |
| ATOM | 2334 | CZ3 | TRP | L | 152 | 20.037 | −3.079 | −2.110 | 1.00 | 51.18 C |
| ATOM | 2336 | CH2 | TRP | L | 152 | 19.778 | −3.240 | −0.742 | 1.00 | 52.04 C |
| ATOM | 2338 | CZ2 | TRP | L | 152 | 19.995 | −2.220 | 0.153 | 1.00 | 54.12 C |
| ATOM | 2340 | C | TRP | L | 152 | 22.991 | 0.875 | −5.228 | 1.00 | 53.15 C |
| ATOM | 2341 | O | TRP | L | 152 | 23.531 | 1.882 | −5.690 | 1.00 | 52.79 O |
| ATOM | 2343 | N | LYS | L | 153 | 22.404 | −0.053 | −5.978 | 1.00 | 53.15 N |
| ATOM | 2344 | CA | LYS | L | 153 | 22.346 | 0.031 | −7.432 | 1.00 | 53.18 C |
| ATOM | 2346 | CB | LYS | L | 153 | 23.557 | −0.673 | −8.051 | 1.00 | 53.70 C |
| ATOM | 2349 | CG | LYS | L | 153 | 24.873 | 0.100 | −7.936 | 1.00 | 55.50 C |
| ATOM | 2352 | CD | LYS | L | 153 | 26.052 | −0.682 | −8.519 | 1.00 | 55.28 C |
| ATOM | 2355 | CE | LYS | L | 153 | 27.224 | 0.234 | −8.863 | 1.00 | 56.21 C |
| ATOM | 2358 | NZ | LYS | L | 153 | 28.422 | −0.504 | −9.376 | 1.00 | 56.19 N |
| ATOM | 2362 | C | LYS | L | 153 | 21.063 | −0.615 | −7.950 | 1.00 | 52.54 C |
| ATOM | 2363 | O | LYS | L | 153 | 20.824 | −1.806 | −7.731 | 1.00 | 50.96 O |
| ATOM | 2365 | N | VAL | L | 154 | 20.232 | 0.184 | −8.614 | 1.00 | 52.66 N |
| ATOM | 2366 | CA | VAL | L | 154 | 19.081 | −0.328 | −9.355 | 1.00 | 52.24 C |
| ATOM | 2368 | CB | VAL | L | 154 | 17.738 | 0.298 | −8.896 | 1.00 | 52.32 C |
| ATOM | 2370 | CG1 | VAL | L | 154 | 16.572 | −0.510 | −9.434 | 1.00 | 53.43 C |
| ATOM | 2374 | CG2 | VAL | L | 154 | 17.653 | 0.382 | −7.384 | 1.00 | 53.10 C |
| ATOM | 2378 | C | VAL | L | 154 | 19.328 | 0.032 | −10.807 | 1.00 | 51.53 C |
| ATOM | 2379 | O | VAL | L | 154 | 19.328 | 1.211 | −11.154 | 1.00 | 51.98 O |
| ATOM | 2381 | N | ASP | L | 155 | 19.555 | −0.978 | −11.646 | 1.00 | 51.01 N |
| ATOM | 2382 | CA | ASP | L | 155 | 19.963 | −0.759 | −13.035 | 1.00 | 51.37 C |
| ATOM | 2384 | CB | ASP | L | 155 | 18.781 | −0.282 | −13.892 | 1.00 | 50.97 C |
| ATOM | 2387 | CG | ASP | L | 155 | 17.664 | −1.309 | −13.992 | 1.00 | 50.99 C |
| ATOM | 2388 | OD1 | ASP | L | 155 | 17.870 | −2.481 | −13.619 | 1.00 | 53.87 O |
| ATOM | 2389 | OD2 | ASP | L | 155 | 16.568 | −0.937 | −14.459 | 1.00 | 50.60 O |
| ATOM | 2390 | C | ASP | L | 155 | 21.113 | 0.257 | −13.111 | 1.00 | 51.64 C |
| ATOM | 2391 | O | ASP | L | 155 | 20.938 | 1.362 | −13.631 | 1.00 | 52.33 O |
| ATOM | 2393 | N | ASN | L | 156 | 22.268 | −0.114 | −12.551 | 1.00 | 51.53 N |
| ATOM | 2394 | CA | ASN | L | 156 | 23.492 | 0.712 | −12.576 | 1.00 | 50.82 C |
| ATOM | 2396 | CB | ASN | L | 156 | 24.104 | 0.732 | −13.990 | 1.00 | 51.40 C |
| ATOM | 2399 | CG | ASN | L | 156 | 24.537 | −0.645 | −14.472 | 1.00 | 52.43 C |
| ATOM | 2400 | OD1 | ASN | L | 156 | 24.242 | −1.661 | −13.844 | 1.00 | 55.43 O |
| ATOM | 2401 | ND2 | ASN | L | 156 | 25.240 | −0.680 | −15.602 | 1.00 | 51.24 N |
| ATOM | 2404 | C | ASN | L | 156 | 23.320 | 2.160 | −12.092 | 1.00 | 50.40 C |
| ATOM | 2405 | O | ASN | L | 156 | 24.190 | 2.999 | −12.340 | 1.00 | 51.06 O |
| ATOM | 2407 | N | ALA | L | 157 | 22.214 | 2.451 | −11.408 | 1.00 | 49.53 N |
| ATOM | 2408 | CA | ALA | L | 157 | 21.925 | 3.804 | −10.944 | 1.00 | 48.75 C |
| ATOM | 2410 | CB | ALA | L | 157 | 20.508 | 4.206 | −11.317 | 1.00 | 48.22 C |
| ATOM | 2414 | C | ALA | L | 157 | 22.139 | 3.888 | −9.430 | 1.00 | 48.32 C |
| ATOM | 2415 | O | ALA | L | 157 | 21.503 | 3.166 | −8.657 | 1.00 | 47.52 O |
| ATOM | 2417 | N | LEU | L | 158 | 23.058 | 4.759 | −9.021 | 1.00 | 47.40 N |
| ATOM | 2418 | CA | LEU | L | 158 | 23.330 | 4.994 | −7.610 | 1.00 | 47.17 C |
| ATOM | 2420 | CB | LEU | L | 158 | 24.492 | 5.986 | −7.434 | 1.00 | 46.49 C |
| ATOM | 2423 | CG | LEU | L | 158 | 24.748 | 6.565 | −6.037 | 1.00 | 45.89 C |
| ATOM | 2425 | CD1 | LEU | L | 158 | 24.997 | 5.451 | −5.035 | 1.00 | 46.28 C |

-continued

| ATOM | 2429 | CD2 | LEU | L | 158 | 25.913 | 7.549 | −6.052 | 1.00 | 44.85 | C |
| ATOM | 2433 | C | LEU | L | 158 | 22.077 | 5.528 | −6.935 | 1.00 | 47.55 | C |
| ATOM | 2434 | O | LEU | L | 158 | 21.603 | 6.618 | −7.254 | 1.00 | 46.05 | O |
| ATOM | 2436 | N | GLN | L | 159 | 21.533 | 4.741 | −6.013 | 1.00 | 49.28 | N |
| ATOM | 2437 | CA | GLN | L | 159 | 20.472 | 5.216 | −5.133 | 1.00 | 48.82 | C |
| ATOM | 2439 | CB | GLN | L | 159 | 19.651 | 4.048 | −4.581 | 1.00 | 49.37 | C |
| ATOM | 2442 | CG | GLN | L | 159 | 19.097 | 3.118 | −5.657 | 1.00 | 52.12 | C |
| ATOM | 2445 | CD | GLN | L | 159 | 18.509 | 3.864 | −6.848 | 1.00 | 54.32 | C |
| ATOM | 2446 | OE1 | GLN | L | 159 | 18.903 | 3.636 | −7.986 | 1.00 | 60.88 | O |
| ATOM | 2447 | NE2 | GLN | L | 159 | 17.572 | 4.767 | −6.585 | 1.00 | 57.08 | N |
| ATOM | 2450 | C | GLN | L | 159 | 21.130 | 5.993 | −4.009 | 1.00 | 47.54 | C |
| ATOM | 2451 | O | GLN | L | 159 | 22.099 | 5.528 | −3.418 | 1.00 | 46.19 | O |
| ATOM | 2453 | N | SER | L | 160 | 20.629 | 7.192 | −3.741 | 1.00 | 47.41 | N |
| ATOM | 2454 | CA | SER | L | 160 | 21.212 | 8.031 | −2.710 | 1.00 | 48.52 | C |
| ATOM | 2456 | CB | SER | L | 160 | 22.254 | 8.969 | −3.322 | 1.00 | 48.45 | C |
| ATOM | 2459 | OG | SER | L | 160 | 23.003 | 9.634 | −2.318 | 1.00 | 46.22 | O |
| ATOM | 2461 | C | SER | L | 160 | 20.130 | 8.823 | −1.983 | 1.00 | 49.43 | C |
| ATOM | 2462 | O | SER | L | 160 | 19.366 | 9.578 | −2.606 | 1.00 | 50.03 | O |
| ATOM | 2464 | N | GLY | L | 161 | 20.076 | 8.636 | −0.663 | 1.00 | 49.49 | N |
| ATOM | 2465 | CA | GLY | L | 161 | 19.109 | 9.308 | 0.198 | 1.00 | 49.44 | C |
| ATOM | 2468 | C | GLY | L | 161 | 18.032 | 8.357 | 0.668 | 1.00 | 49.96 | C |
| ATOM | 2469 | O | GLY | L | 161 | 17.681 | 8.346 | 1.846 | 1.00 | 51.28 | O |
| ATOM | 2471 | N | ASN | L | 162 | 17.525 | 7.542 | −0.255 | 1.00 | 50.03 | N |
| ATOM | 2472 | CA | ASN | L | 162 | 16.399 | 6.632 | 0.013 | 1.00 | 49.79 | C |
| ATOM | 2474 | CB | ASN | L | 162 | 15.590 | 6.382 | −1.277 | 1.00 | 49.15 | C |
| ATOM | 2477 | CG | ASN | L | 162 | 16.409 | 5.740 | −2.391 | 1.00 | 47.76 | C |
| ATOM | 2478 | OD1 | ASN | L | 162 | 15.871 | 5.419 | −3.452 | 1.00 | 48.43 | O |
| ATOM | 2479 | ND2 | ASN | L | 162 | 17.706 | 5.559 | −2.163 | 1.00 | 45.16 | N |
| ATOM | 2482 | C | ASN | L | 162 | 16.752 | 5.294 | 0.673 | 1.00 | 50.25 | C |
| ATOM | 2483 | O | ASN | L | 162 | 16.049 | 4.302 | 0.466 | 1.00 | 51.32 | O |
| ATOM | 2485 | N | SER | L | 163 | 17.823 | 5.260 | 1.465 | 1.00 | 49.85 | N |
| ATOM | 2486 | CA | SER | L | 163 | 18.153 | 4.063 | 2.234 | 1.00 | 50.83 | C |
| ATOM | 2488 | CB | SER | L | 163 | 19.187 | 3.198 | 1.504 | 1.00 | 51.81 | C |
| ATOM | 2491 | OG | SER | L | 163 | 20.504 | 3.455 | 1.971 | 1.00 | 52.20 | O |
| ATOM | 2493 | C | SER | L | 163 | 18.703 | 4.450 | 3.587 | 1.00 | 51.11 | C |
| ATOM | 2494 | O | SER | L | 163 | 19.406 | 5.450 | 3.697 | 1.00 | 52.65 | O |
| ATOM | 2496 | N | GLN | L | 164 | 18.400 | 3.650 | 4.605 | 1.00 | 50.62 | N |
| ATOM | 2497 | CA | GLN | L | 164 | 18.932 | 3.884 | 5.944 | 1.00 | 51.13 | C |
| ATOM | 2499 | CB | GLN | L | 164 | 17.890 | 4.551 | 6.852 | 1.00 | 50.47 | C |
| ATOM | 2502 | CG | GLN | L | 164 | 16.469 | 4.025 | 6.735 | 1.00 | 50.21 | C |
| ATOM | 2505 | CD | GLN | L | 164 | 15.444 | 4.939 | 7.416 | 1.00 | 50.71 | C |
| ATOM | 2506 | OE1 | GLN | L | 164 | 15.783 | 5.749 | 8.291 | 1.00 | 45.21 | O |
| ATOM | 2507 | NE2 | GLN | L | 164 | 14.181 | 4.810 | 7.010 | 1.00 | 48.25 | N |
| ATOM | 2510 | C | GLN | L | 164 | 19.496 | 2.608 | 6.565 | 1.00 | 52.13 | C |
| ATOM | 2511 | O | GLN | L | 164 | 19.087 | 1.496 | 6.229 | 1.00 | 53.65 | O |
| ATOM | 2513 | N | GLU | L | 165 | 20.461 | 2.778 | 7.459 | 1.00 | 52.75 | N |
| ATOM | 2514 | CA | GLU | L | 165 | 21.192 | 1.650 | 7.995 | 1.00 | 53.30 | C |
| ATOM | 2516 | CB | GLU | L | 165 | 22.575 | 1.550 | 7.351 | 1.00 | 54.18 | C |
| ATOM | 2519 | CG | GLU | L | 165 | 23.491 | 2.736 | 7.593 | 1.00 | 55.28 | C |
| ATOM | 2522 | CD | GLU | L | 165 | 24.625 | 2.819 | 6.573 | 1.00 | 56.57 | C |
| ATOM | 2523 | OE1 | GLU | L | 165 | 24.447 | 2.363 | 5.415 | 1.00 | 55.10 | O |
| ATOM | 2524 | OE2 | GLU | L | 165 | 25.694 | 3.362 | 6.929 | 1.00 | 59.92 | O |
| ATOM | 2525 | C | GLU | L | 165 | 21.326 | 1.678 | 9.501 | 1.00 | 52.77 | C |
| ATOM | 2526 | O | GLU | L | 165 | 21.321 | 2.730 | 10.133 | 1.00 | 51.98 | O |
| ATOM | 2528 | N | SER | L | 166 | 21.449 | 0.483 | 10.056 | 1.00 | 53.19 | N |
| ATOM | 2529 | CA | SER | L | 166 | 21.531 | 0.279 | 11.483 | 1.00 | 54.36 | C |
| ATOM | 2531 | CB | SER | L | 166 | 20.221 | −0.321 | 12.005 | 1.00 | 54.68 | C |
| ATOM | 2534 | OG | SER | L | 166 | 20.280 | −0.576 | 13.397 | 1.00 | 55.03 | O |
| ATOM | 2536 | C | SER | L | 166 | 22.696 | −0.666 | 11.719 | 1.00 | 54.89 | C |
| ATOM | 2537 | O | SER | L | 166 | 23.051 | −1.459 | 10.836 | 1.00 | 54.89 | O |
| ATOM | 2539 | N | VAL | L | 167 | 23.293 | −0.573 | 12.903 | 1.00 | 54.47 | N |
| ATOM | 2540 | CA | VAL | L | 167 | 24.500 | −1.330 | 13.203 | 1.00 | 54.81 | C |
| ATOM | 2542 | CB | VAL | L | 167 | 25.770 | −0.492 | 12.891 | 1.00 | 55.11 | C |
| ATOM | 2544 | CG1 | VAL | L | 167 | 25.720 | 0.876 | 13.583 | 1.00 | 56.53 | C |
| ATOM | 2548 | CG2 | VAL | L | 167 | 27.037 | −1.250 | 13.266 | 1.00 | 56.23 | C |
| ATOM | 2552 | C | VAL | L | 167 | 24.488 | −1.790 | 14.650 | 1.00 | 54.84 | C |
| ATOM | 2553 | O | VAL | L | 167 | 24.076 | −1.044 | 15.538 | 1.00 | 56.13 | O |
| ATOM | 2555 | N | THR | L | 168 | 24.916 | −3.028 | 14.882 | 1.00 | 55.33 | N |
| ATOM | 2556 | CA | THR | L | 168 | 24.980 | −3.565 | 16.241 | 1.00 | 55.31 | C |
| ATOM | 2558 | CB | THR | L | 168 | 24.971 | −5.111 | 16.273 | 1.00 | 55.44 | C |
| ATOM | 2560 | OG1 | THR | L | 168 | 26.006 | −5.625 | 15.424 | 1.00 | 55.55 | O |
| ATOM | 2562 | CG2 | THR | L | 168 | 23.618 | −5.655 | 15.831 | 1.00 | 55.37 | C |
| ATOM | 2566 | C | THR | L | 168 | 26.236 | −3.078 | 16.945 | 1.00 | 55.40 | C |
| ATOM | 2567 | O | THR | L | 168 | 27.163 | −2.533 | 16.328 | 1.00 | 54.29 | O |
| ATOM | 2569 | N | GLU | L | 169 | 26.252 | −3.266 | 18.255 | 1.00 | 55.10 | N |
| ATOM | 2570 | CA | GLU | L | 169 | 27.441 | −2.977 | 19.021 | 1.00 | 55.62 | C |
| ATOM | 2572 | CB | GLU | L | 169 | 27.093 | −2.753 | 20.496 | 1.00 | 56.82 | C |
| ATOM | 2575 | CG | GLU | L | 169 | 26.233 | −1.508 | 20.728 | 1.00 | 59.20 | C |
| ATOM | 2578 | CD | GLU | L | 169 | 26.990 | −0.208 | 20.486 | 1.00 | 61.22 | C |

-continued

| ATOM | 2579 | OE1 | GLU | L | 169 | 27.626 | −0.065 | 19.418 | 1.00 | 62.62 | O |
|---|---|---|---|---|---|---|---|---|---|---|---|
| ATOM | 2580 | OE2 | GLU | L | 169 | 26.944 | 0.674 | 21.370 | 1.00 | 63.58 | O |
| ATOM | 2581 | C | GLU | L | 169 | 28.433 | −4.112 | 18.853 | 1.00 | 54.99 | C |
| ATOM | 2582 | O | GLU | L | 169 | 28.114 | −5.178 | 18.308 | 1.00 | 54.03 | O |
| ATOM | 2584 | N | GLN | L | 170 | 29.652 | −3.865 | 19.303 | 1.00 | 54.11 | N |
| ATOM | 2585 | CA | GLN | L | 170 | 30.684 | −4.874 | 19.224 | 1.00 | 53.03 | C |
| ATOM | 2587 | CB | GLN | L | 170 | 31.979 | −4.392 | 19.883 | 1.00 | 51.58 | C |
| ATOM | 2590 | CG | GLN | L | 170 | 33.223 | −4.813 | 19.137 | 1.00 | 51.46 | C |
| ATOM | 2593 | CD | GLN | L | 170 | 34.485 | −4.253 | 19.745 | 1.00 | 52.07 | C |
| ATOM | 2594 | OE1 | GLN | L | 170 | 34.439 | −3.524 | 20.742 | 1.00 | 49.88 | O |
| ATOM | 2595 | NE2 | GLN | L | 170 | 35.630 | −4.590 | 19.152 | 1.00 | 46.95 | N |
| ATOM | 2598 | C | GLN | L | 170 | 30.144 | −6.114 | 19.919 | 1.00 | 52.15 | C |
| ATOM | 2599 | O | GLN | L | 170 | 29.643 | −6.026 | 21.042 | 1.00 | 50.29 | O |
| ATOM | 2601 | N | ASP | L | 171 | 30.211 | −7.255 | 19.237 | 1.00 | 52.42 | N |
| ATOM | 2602 | CA | ASP | L | 171 | 29.774 | −8.507 | 19.834 | 1.00 | 52.53 | C |
| ATOM | 2604 | CB | ASP | L | 171 | 29.965 | −9.676 | 18.871 | 1.00 | 51.89 | C |
| ATOM | 2607 | CG | ASP | L | 171 | 29.331 | −10.959 | 19.380 | 1.00 | 52.53 | C |
| ATOM | 2608 | OD1 | ASP | L | 171 | 30.060 | −11.948 | 19.596 | 1.00 | 50.33 | O |
| ATOM | 2609 | OD2 | ASP | L | 171 | 28.102 | −10.981 | 19.581 | 1.00 | 55.53 | O |
| ATOM | 2610 | C | ASP | L | 171 | 30.576 | −8.737 | 21.109 | 1.00 | 53.44 | C |
| ATOM | 2611 | O | ASP | L | 171 | 31.779 | −8.472 | 21.149 | 1.00 | 54.47 | O |
| ATOM | 2613 | N | SER | L | 172 | 29.899 | −9.204 | 22.153 | 1.00 | 53.54 | N |
| ATOM | 2614 | CA | SER | L | 172 | 30.549 | −9.528 | 23.417 | 1.00 | 52.97 | C |
| ATOM | 2616 | CB | SER | L | 172 | 29.492 | −9.784 | 24.489 | 1.00 | 52.34 | C |
| ATOM | 2619 | OG | SER | L | 172 | 28.735 | −10.939 | 24.176 | 1.00 | 50.12 | O |
| ATOM | 2621 | C | SER | L | 172 | 31.463 | −10.752 | 23.307 | 1.00 | 53.20 | C |
| ATOM | 2622 | O | SER | L | 172 | 32.451 | −10.846 | 24.029 | 1.00 | 53.94 | O |
| ATOM | 2624 | N | LYS | L | 173 | 31.130 | −11.682 | 22.410 | 1.00 | 54.24 | N |
| ATOM | 2625 | CA | LYS | L | 173 | 31.874 | −12.948 | 22.269 | 1.00 | 54.74 | C |
| ATOM | 2627 | CB | LYS | L | 173 | 30.917 | −14.117 | 21.952 | 1.00 | 54.91 | C |
| ATOM | 2630 | CG | LYS | L | 173 | 30.235 | −14.727 | 23.197 | 1.00 | 56.21 | C |
| ATOM | 2633 | CD | LYS | L | 173 | 29.281 | −15.895 | 22.862 | 1.00 | 56.16 | C |
| ATOM | 2636 | CE | LYS | L | 173 | 27.807 | −15.456 | 22.793 | 1.00 | 56.39 | C |
| ATOM | 2639 | NZ | LYS | L | 173 | 26.865 | −16.573 | 22.464 | 1.00 | 55.49 | N |
| ATOM | 2643 | C | LYS | L | 173 | 33.019 | −12.899 | 21.240 | 1.00 | 55.61 | C |
| ATOM | 2644 | O | LYS | L | 173 | 34.143 | −13.294 | 21.562 | 1.00 | 56.17 | O |
| ATOM | 2646 | N | ASP | L | 174 | 32.742 | −12.427 | 20.019 | 1.00 | 55.43 | N |
| ATOM | 2647 | CA | ASP | L | 174 | 33.746 | −12.427 | 18.937 | 1.00 | 54.22 | C |
| ATOM | 2649 | CB | ASP | L | 174 | 33.286 | −13.348 | 17.794 | 1.00 | 54.45 | C |
| ATOM | 2652 | CG | ASP | L | 174 | 32.373 | −12.651 | 16.793 | 1.00 | 57.15 | C |
| ATOM | 2653 | OD1 | ASP | L | 174 | 31.531 | −11.820 | 17.198 | 1.00 | 59.32 | O |
| ATOM | 2654 | OD2 | ASP | L | 174 | 32.505 | −12.944 | 15.583 | 1.00 | 60.82 | O |
| ATOM | 2655 | C | ASP | L | 174 | 34.146 | −11.022 | 18.416 | 1.00 | 53.53 | C |
| ATOM | 2656 | O | ASP | L | 174 | 34.848 | −10.903 | 17.405 | 1.00 | 53.00 | O |
| ATOM | 2658 | N | SER | L | 175 | 33.695 | −9.973 | 19.108 | 1.00 | 53.42 | N |
| ATOM | 2659 | CA | SER | L | 175 | 34.211 | −8.596 | 18.929 | 1.00 | 52.83 | C |
| ATOM | 2661 | CB | SER | L | 175 | 35.713 | −8.567 | 19.235 | 1.00 | 52.50 | C |
| ATOM | 2664 | OG | SER | L | 175 | 36.013 | −9.360 | 20.373 | 1.00 | 51.82 | O |
| ATOM | 2666 | C | SER | L | 175 | 33.949 | −7.948 | 17.557 | 1.00 | 51.62 | C |
| ATOM | 2667 | O | SER | L | 175 | 34.665 | −7.033 | 17.151 | 1.00 | 49.10 | O |
| ATOM | 2669 | N | THR | L | 176 | 32.901 | −8.401 | 16.880 | 1.00 | 51.67 | N |
| ATOM | 2670 | CA | THR | L | 176 | 32.591 | −7.963 | 15.529 | 1.00 | 52.24 | C |
| ATOM | 2672 | CB | THR | L | 176 | 32.355 | −9.170 | 14.617 | 1.00 | 52.18 | C |
| ATOM | 2674 | OG1 | THR | L | 176 | 31.345 | −10.007 | 15.192 | 1.00 | 52.78 | O |
| ATOM | 2676 | CG2 | THR | L | 176 | 33.639 | −9.974 | 14.444 | 1.00 | 53.91 | C |
| ATOM | 2680 | C | THR | L | 176 | 31.330 | −7.116 | 15.498 | 1.00 | 52.64 | C |
| ATOM | 2681 | O | THR | L | 176 | 30.546 | −7.110 | 16.451 | 1.00 | 52.97 | O |
| ATOM | 2683 | N | TYR | L | 177 | 31.146 | −6.404 | 14.390 | 1.00 | 52.05 | N |
| ATOM | 2684 | CA | TYR | L | 177 | 29.936 | −5.636 | 14.155 | 1.00 | 52.18 | C |
| ATOM | 2686 | CB | TYR | L | 177 | 30.280 | −4.207 | 13.731 | 1.00 | 52.28 | C |
| ATOM | 2689 | CG | TYR | L | 177 | 31.123 | −3.476 | 14.741 | 1.00 | 50.99 | C |
| ATOM | 2690 | CD1 | TYR | L | 177 | 30.535 | −2.826 | 15.813 | 1.00 | 53.06 | C |
| ATOM | 2692 | CE1 | TYR | L | 177 | 31.296 | −2.161 | 16.762 | 1.00 | 52.96 | C |
| ATOM | 2694 | CZ | TYR | L | 177 | 32.666 | −2.140 | 16.639 | 1.00 | 53.33 | C |
| ATOM | 2695 | OH | TYR | L | 177 | 33.414 | −1.478 | 17.591 | 1.00 | 52.32 | O |
| ATOM | 2697 | CE2 | TYR | L | 177 | 33.282 | −2.787 | 15.575 | 1.00 | 52.90 | C |
| ATOM | 2699 | CD2 | TYR | L | 177 | 32.507 | −3.452 | 14.638 | 1.00 | 51.48 | C |
| ATOM | 2701 | C | TYR | L | 177 | 29.129 | −6.316 | 13.069 | 1.00 | 52.44 | C |
| ATOM | 2702 | O | TYR | L | 177 | 29.671 | −7.081 | 12.271 | 1.00 | 52.38 | O |
| ATOM | 2704 | N | SER | L | 178 | 27.832 | −6.041 | 13.050 | 1.00 | 52.19 | N |
| ATOM | 2705 | CA | SER | L | 178 | 26.975 | −6.447 | 11.947 | 1.00 | 52.95 | C |
| ATOM | 2707 | CB | SER | L | 178 | 26.069 | −7.599 | 12.362 | 1.00 | 53.30 | C |
| ATOM | 2710 | OG | SER | L | 178 | 26.832 | −8.717 | 12.776 | 1.00 | 52.50 | O |
| ATOM | 2712 | C | SER | L | 178 | 26.158 | −5.242 | 11.523 | 1.00 | 53.54 | C |
| ATOM | 2713 | O | SER | L | 178 | 25.941 | −4.335 | 12.323 | 1.00 | 54.29 | O |
| ATOM | 2715 | N | LEU | L | 179 | 25.706 | −5.234 | 10.269 | 1.00 | 54.64 | N |
| ATOM | 2716 | CA | LEU | L | 179 | 25.068 | −4.045 | 9.676 | 1.00 | 55.24 | C |
| ATOM | 2718 | CB | LEU | L | 179 | 26.134 | −3.110 | 9.076 | 1.00 | 55.63 | C |
| ATOM | 2721 | CG | LEU | L | 179 | 25.724 | −1.776 | 8.435 | 1.00 | 53.31 | C |

-continued

| | | | | | | | | | | |
|---|---|---|---|---|---|---|---|---|---|---|
| ATOM | 2723 | CD1 | LEU | L | 179 | 26.905 | −0.836 | 8.428 | 1.00 | 52.32 C |
| ATOM | 2727 | CD2 | LEU | L | 179 | 25.209 | −1.941 | 7.020 | 1.00 | 52.03 C |
| ATOM | 2731 | C | LEU | L | 179 | 24.033 | −4.401 | 8.609 | 1.00 | 55.66 C |
| ATOM | 2732 | O | LEU | L | 179 | 24.249 | −5.293 | 7.779 | 1.00 | 55.17 O |
| ATOM | 2734 | N | SER | L | 180 | 22.915 | −3.680 | 8.649 | 1.00 | 55.32 N |
| ATOM | 2735 | CA | SER | L | 180 | 21.857 | −3.796 | 7.663 | 1.00 | 53.86 C |
| ATOM | 2737 | CB | SER | L | 180 | 20.564 | −4.282 | 8.317 | 1.00 | 53.72 C |
| ATOM | 2740 | OG | SER | L | 180 | 20.049 | −3.313 | 9.219 | 1.00 | 52.78 O |
| ATOM | 2742 | C | SER | L | 180 | 21.623 | −2.430 | 7.038 | 1.00 | 53.33 C |
| ATOM | 2743 | O | SER | L | 180 | 21.507 | −1.435 | 7.742 | 1.00 | 52.83 O |
| ATOM | 2745 | N | SER | L | 181 | 21.576 | −2.402 | 5.711 | 1.00 | 53.68 N |
| ATOM | 2746 | CA | SER | L | 181 | 21.180 | −1.231 | 4.942 | 1.00 | 52.42 C |
| ATOM | 2748 | CB | SER | L | 181 | 22.240 | −0.925 | 3.877 | 1.00 | 52.92 C |
| ATOM | 2751 | OG | SER | L | 181 | 21.837 | 0.122 | 3.010 | 1.00 | 53.65 O |
| ATOM | 2753 | C | SER | L | 181 | 19.850 | −1.582 | 4.290 | 1.00 | 51.14 C |
| ATOM | 2754 | O | SER | L | 181 | 19.709 | −2.670 | 3.726 | 1.00 | 49.09 O |
| ATOM | 2756 | N | THR | L | 182 | 18.872 | −0.680 | 4.380 | 1.00 | 50.15 N |
| ATOM | 2757 | CA | THR | L | 182 | 17.566 | −0.920 | 3.762 | 1.00 | 50.23 C |
| ATOM | 2759 | CB | THR | L | 182 | 16.461 | −1.088 | 4.807 | 1.00 | 49.71 C |
| ATOM | 2761 | OG1 | THR | L | 182 | 16.864 | −2.069 | 5.767 | 1.00 | 48.24 O |
| ATOM | 2763 | CG2 | THR | L | 182 | 15.150 | −1.527 | 4.142 | 1.00 | 49.34 C |
| ATOM | 2767 | C | THR | L | 182 | 17.160 | 0.193 | 2.811 | 1.00 | 48.67 C |
| ATOM | 2768 | O | THR | L | 182 | 17.108 | 1.352 | 3.197 | 1.00 | 44.88 O |
| ATOM | 2770 | N | LEU | L | 183 | 16.866 | −0.201 | 1.571 | 1.00 | 50.93 N |
| ATOM | 2771 | CA | LEU | L | 183 | 16.392 | 0.696 | 0.512 | 1.00 | 51.96 C |
| ATOM | 2773 | CB | LEU | L | 183 | 17.008 | 0.278 | −0.822 | 1.00 | 51.13 C |
| ATOM | 2776 | CG | LEU | L | 183 | 16.652 | 1.052 | −2.091 | 1.00 | 51.40 C |
| ATOM | 2778 | CD1 | LEU | L | 183 | 17.427 | 2.356 | −2.178 | 1.00 | 51.77 C |
| ATOM | 2782 | CD2 | LEU | L | 183 | 16.941 | 0.193 | −3.303 | 1.00 | 51.95 C |
| ATOM | 2786 | C | LEU | L | 183 | 14.871 | 0.624 | 0.415 | 1.00 | 51.99 C |
| ATOM | 2787 | O | LEU | L | 183 | 14.291 | −0.452 | 0.518 | 1.00 | 50.98 O |
| ATOM | 2789 | N | THR | L | 184 | 14.236 | 1.769 | 0.192 | 1.00 | 54.25 N |
| ATOM | 2790 | CA | THR | L | 184 | 12.777 | 1.873 | 0.233 | 1.00 | 55.46 C |
| ATOM | 2792 | CB | THR | L | 184 | 12.338 | 2.678 | 1.477 | 1.00 | 56.62 C |
| ATOM | 2794 | OG1 | THR | L | 184 | 13.184 | 2.343 | 2.586 | 1.00 | 57.44 O |
| ATOM | 2796 | CG2 | THR | L | 184 | 10.883 | 2.378 | 1.843 | 1.00 | 56.53 C |
| ATOM | 2800 | C | THR | L | 184 | 12.243 | 2.549 | −1.032 | 1.00 | 56.07 C |
| ATOM | 2801 | O | THR | L | 184 | 12.634 | 3.675 | −1.346 | 1.00 | 56.07 O |
| ATOM | 2803 | N | LEU | L | 185 | 11.366 | 1.849 | −1.757 | 1.00 | 56.92 N |
| ATOM | 2804 | CA | LEU | L | 185 | 10.762 | 2.369 | −2.997 | 1.00 | 57.75 C |
| ATOM | 2806 | CB | LEU | L | 185 | 11.253 | 1.588 | −4.215 | 1.00 | 58.07 C |
| ATOM | 2809 | CG | LEU | L | 185 | 12.739 | 1.270 | −4.323 | 1.00 | 61.99 C |
| ATOM | 2811 | CD1 | LEU | L | 185 | 12.994 | 0.556 | −5.651 | 1.00 | 61.55 C |
| ATOM | 2815 | CD2 | LEU | L | 185 | 13.605 | 2.537 | −4.182 | 1.00 | 65.29 C |
| ATOM | 2819 | C | LEU | L | 185 | 9.251 | 2.245 | −2.978 | 1.00 | 57.44 C |
| ATOM | 2820 | O | LEU | L | 185 | 8.691 | 1.457 | −2.215 | 1.00 | 57.24 O |
| ATOM | 2822 | N | SER | L | 186 | 8.594 | 3.005 | −3.845 | 1.00 | 57.30 N |
| ATOM | 2823 | CA | SER | L | 186 | 7.167 | 2.816 | −4.076 | 1.00 | 58.49 C |
| ATOM | 2825 | CB | SER | L | 186 | 6.544 | 4.052 | −4.740 | 1.00 | 58.90 C |
| ATOM | 2828 | OG | SER | L | 186 | 7.098 | 4.296 | −6.022 | 1.00 | 58.65 O |
| ATOM | 2830 | C | SER | L | 186 | 6.958 | 1.579 | −4.951 | 1.00 | 58.87 C |
| ATOM | 2831 | O | SER | L | 186 | 7.773 | 1.289 | −5.835 | 1.00 | 58.94 O |
| ATOM | 2833 | N | LYS | L | 187 | 5.871 | 0.853 | −4.690 | 1.00 | 58.84 N |
| ATOM | 2834 | CA | LYS | L | 187 | 5.470 | −0.293 | −5.514 | 1.00 | 58.71 C |
| ATOM | 2836 | CB | LYS | L | 187 | 3.960 | −0.565 | −5.364 | 1.00 | 59.52 C |
| ATOM | 2839 | CG | LYS | L | 187 | 3.036 | 0.684 | −5.440 | 1.00 | 58.94 C |
| ATOM | 2842 | CD | LYS | L | 187 | 1.740 | 0.409 | −6.220 | 1.00 | 58.51 C |
| ATOM | 2845 | CE | LYS | L | 187 | 1.980 | 0.425 | −7.730 | 1.00 | 56.51 C |
| ATOM | 2848 | NZ | LYS | L | 187 | 0.818 | −0.065 | −8.500 | 1.00 | 55.30 N |
| ATOM | 2852 | C | LYS | L | 187 | 5.813 | −0.114 | −7.001 | 1.00 | 58.68 C |
| ATOM | 2853 | O | LYS | L | 187 | 6.413 | −0.997 | −7.614 | 1.00 | 58.00 O |
| ATOM | 2855 | N | ALA | L | 188 | 5.445 | 1.042 | −7.557 | 1.00 | 58.37 N |
| ATOM | 2856 | CA | ALA | L | 188 | 5.601 | 1.322 | −8.983 | 1.00 | 57.88 C |
| ATOM | 2858 | CB | ALA | L | 188 | 4.815 | 2.576 | −9.366 | 1.00 | 57.08 C |
| ATOM | 2862 | C | ALA | L | 188 | 7.069 | 1.486 | −9.357 | 1.00 | 57.89 C |
| ATOM | 2863 | O | ALA | L | 188 | 7.530 | 0.906 | −10.343 | 1.00 | 56.89 O |
| ATOM | 2865 | N | ASP | L | 189 | 7.797 | 2.269 | −8.560 | 1.00 | 58.23 N |
| ATOM | 2866 | CA | ASP | L | 189 | 9.216 | 2.533 | −8.816 | 1.00 | 57.62 C |
| ATOM | 2868 | CB | ASP | L | 189 | 9.774 | 3.565 | −7.822 | 1.00 | 57.08 C |
| ATOM | 2871 | CG | ASP | L | 189 | 9.154 | 4.956 | −8.001 | 1.00 | 59.38 C |
| ATOM | 2872 | OD1 | ASP | L | 189 | 7.976 | 5.040 | −8.407 | 1.00 | 62.30 O |
| ATOM | 2873 | OD2 | ASP | L | 189 | 9.835 | 5.970 | −7.728 | 1.00 | 60.32 O |
| ATOM | 2874 | C | ASP | L | 189 | 10.028 | 1.235 | −8.788 | 1.00 | 57.16 C |
| ATOM | 2875 | O | ASP | L | 189 | 11.018 | 1.101 | −9.516 | 1.00 | 56.54 O |
| ATOM | 2877 | N | TYR | L | 190 | 9.587 | 0.278 | −7.970 | 1.00 | 56.48 N |
| ATOM | 2878 | CA | TYR | L | 190 | 10.200 | −1.050 | −7.921 | 1.00 | 56.08 C |
| ATOM | 2880 | CB | TYR | L | 190 | 9.757 | −1.801 | −6.659 | 1.00 | 55.94 C |
| ATOM | 2883 | CG | TYR | L | 190 | 10.393 | −3.170 | −6.508 | 1.00 | 56.42 C |
| ATOM | 2884 | CD1 | TYR | L | 190 | 11.645 | −3.318 | −5.916 | 1.00 | 54.49 C |

-continued

| | | | | | | | | | | |
|---|---|---|---|---|---|---|---|---|---|---|
| ATOM | 2886 | CE1 | TYR | L | 190 | 12.234 | −4.576 | −5.780 | 1.00 | 54.37 C |
| ATOM | 2888 | CZ | TYR | L | 190 | 11.569 | −5.703 | −6.241 | 1.00 | 54.25 C |
| ATOM | 2889 | OH | TYR | L | 190 | 12.148 | −6.947 | −6.113 | 1.00 | 53.12 O |
| ATOM | 2891 | CE2 | TYR | L | 190 | 10.325 | −5.581 | −6.833 | 1.00 | 54.89 C |
| ATOM | 2893 | CD2 | TYR | L | 190 | 9.743 | −4.319 | −6.965 | 1.00 | 56.09 C |
| ATOM | 2895 | C | TYR | L | 190 | 9.869 | −1.879 | −9.168 | 1.00 | 55.03 C |
| ATOM | 2896 | O | TYR | L | 190 | 10.770 | −2.327 | −9.879 | 1.00 | 54.57 O |
| ATOM | 2898 | N | GLU | L | 191 | 8.577 | −2.074 | −9.425 | 1.00 | 54.94 N |
| ATOM | 2899 | CA | GLU | L | 191 | 8.106 | −2.881 | −10.562 | 1.00 | 54.92 C |
| ATOM | 2901 | CB | GLU | L | 191 | 6.616 | −2.629 | −10.815 | 1.00 | 54.51 C |
| ATOM | 2904 | CG | GLU | L | 191 | 5.679 | −3.328 | −9.839 | 1.00 | 54.43 C |
| ATOM | 2907 | CD | GLU | L | 191 | 4.256 | −2.776 | −9.894 | 1.00 | 55.51 C |
| ATOM | 2908 | OE1 | GLU | L | 191 | 3.731 | −2.563 | −11.008 | 1.00 | 52.00 O |
| ATOM | 2909 | OE2 | GLU | L | 191 | 3.659 | −2.553 | −8.819 | 1.00 | 59.15 O |
| ATOM | 2910 | C | GLU | L | 191 | 8.882 | −2.617 | −11.855 | 1.00 | 55.01 C |
| ATOM | 2911 | O | GLU | L | 191 | 9.134 | −3.545 | −12.626 | 1.00 | 54.87 O |
| ATOM | 2913 | N | LYS | L | 192 | 9.250 | −1.353 | −12.076 | 1.00 | 54.95 N |
| ATOM | 2914 | CA | LYS | L | 192 | 9.967 | −0.920 | −13.283 | 1.00 | 54.67 C |
| ATOM | 2916 | CB | LYS | L | 192 | 10.267 | 0.584 | −13.214 | 1.00 | 54.20 C |
| ATOM | 2919 | CG | LYS | L | 192 | 9.045 | 1.485 | −13.303 | 1.00 | 54.04 C |
| ATOM | 2922 | CD | LYS | L | 192 | 9.440 | 2.936 | −13.570 | 1.00 | 54.63 C |
| ATOM | 2925 | CE | LYS | L | 192 | 8.286 | 3.894 | −13.307 | 1.00 | 55.33 C |
| ATOM | 2928 | NZ | LYS | L | 192 | 7.975 | 3.990 | −11.849 | 1.00 | 57.07 N |
| ATOM | 2932 | C | LYS | L | 192 | 11.284 | −1.658 | −13.550 | 1.00 | 54.85 C |
| ATOM | 2933 | O | LYS | L | 192 | 11.530 | −2.125 | −14.669 | 1.00 | 54.13 O |
| ATOM | 2935 | N | HIS | L | 193 | 12.122 | −1.761 | −12.524 | 1.00 | 54.78 N |
| ATOM | 2936 | CA | HIS | L | 193 | 13.516 | −2.156 | −12.715 | 1.00 | 55.43 C |
| ATOM | 2938 | CB | HIS | L | 193 | 14.414 | −1.237 | −11.897 | 1.00 | 55.85 C |
| ATOM | 2941 | CG | HIS | L | 193 | 14.109 | 0.216 | −12.099 | 1.00 | 56.95 C |
| ATOM | 2942 | ND1 | HIS | L | 193 | 14.181 | 0.824 | −13.335 | 1.00 | 55.07 N |
| ATOM | 2944 | CE1 | HIS | L | 193 | 13.847 | 2.097 | −13.216 | 1.00 | 56.78 C |
| ATOM | 2946 | NE2 | HIS | L | 193 | 13.555 | 2.335 | −11.949 | 1.00 | 56.59 N |
| ATOM | 2948 | CD2 | HIS | L | 193 | 13.705 | 1.174 | −11.230 | 1.00 | 55.90 C |
| ATOM | 2950 | C | HIS | L | 193 | 13.773 | −3.621 | −12.386 | 1.00 | 55.24 C |
| ATOM | 2951 | O | HIS | L | 193 | 12.971 | −4.261 | −11.711 | 1.00 | 55.40 O |
| ATOM | 2953 | N | LYS | L | 194 | 14.893 | −4.142 | −12.883 | 1.00 | 55.20 N |
| ATOM | 2954 | CA | LYS | L | 194 | 15.186 | −5.571 | −12.815 | 1.00 | 55.83 C |
| ATOM | 2956 | CB | LYS | L | 194 | 15.388 | −6.135 | −14.222 | 1.00 | 55.21 C |
| ATOM | 2959 | CG | LYS | L | 194 | 15.712 | −7.623 | −14.244 | 1.00 | 54.79 C |
| ATOM | 2962 | CD | LYS | L | 194 | 15.212 | −8.306 | −15.509 | 1.00 | 55.94 C |
| ATOM | 2965 | CE | LYS | L | 194 | 13.725 | −8.643 | −15.422 | 1.00 | 55.81 C |
| ATOM | 2968 | NZ | LYS | L | 194 | 13.258 | −9.413 | −16.613 | 1.00 | 52.91 N |
| ATOM | 2972 | C | LYS | L | 194 | 16.403 | −5.882 | −11.950 | 1.00 | 56.71 C |
| ATOM | 2973 | O | LYS | L | 194 | 16.323 | −6.726 | −11.052 | 1.00 | 56.77 O |
| ATOM | 2975 | N | VAL | L | 195 | 17.527 | −5.221 | −12.232 | 1.00 | 57.29 N |
| ATOM | 2976 | CA | VAL | L | 195 | 18.760 | −5.426 | −11.462 | 1.00 | 57.20 C |
| ATOM | 2978 | CB | VAL | L | 195 | 20.017 | −4.910 | −12.214 | 1.00 | 56.95 C |
| ATOM | 2980 | CG1 | VAL | L | 195 | 21.264 | −4.968 | −11.317 | 1.00 | 55.76 C |
| ATOM | 2984 | CG2 | VAL | L | 195 | 20.242 | −5.710 | −13.487 | 1.00 | 57.16 C |
| ATOM | 2988 | C | VAL | L | 195 | 18.666 | −4.720 | −10.112 | 1.00 | 57.79 C |
| ATOM | 2989 | O | VAL | L | 195 | 18.367 | −3.527 | −10.047 | 1.00 | 58.39 O |
| ATOM | 2991 | N | TYR | L | 196 | 18.912 | −5.474 | −9.043 | 1.00 | 57.72 N |
| ATOM | 2992 | CA | TYR | L | 196 | 19.020 | −4.922 | −7.699 | 1.00 | 57.74 C |
| ATOM | 2994 | CB | TYR | L | 196 | 17.791 | −5.289 | −6.865 | 1.00 | 57.31 C |
| ATOM | 2997 | CG | TYR | L | 196 | 16.614 | −4.418 | −7.220 | 1.00 | 57.57 C |
| ATOM | 2998 | CD1 | TYR | L | 196 | 15.773 | −4.750 | −8.277 | 1.00 | 58.23 C |
| ATOM | 3000 | CE1 | TYR | L | 196 | 14.703 | −3.934 | −8.628 | 1.00 | 57.87 C |
| ATOM | 3002 | CZ | TYR | L | 196 | 14.478 | −2.764 | −7.927 | 1.00 | 57.41 C |
| ATOM | 3003 | OH | TYR | L | 196 | 13.425 | −1.951 | −8.269 | 1.00 | 57.51 O |
| ATOM | 3005 | CE2 | TYR | L | 196 | 15.310 | −2.408 | −6.880 | 1.00 | 57.56 C |
| ATOM | 3007 | CD2 | TYR | L | 196 | 16.374 | −3.232 | −6.537 | 1.00 | 56.51 C |
| ATOM | 3009 | C | TYR | L | 196 | 20.297 | −5.449 | −7.075 | 1.00 | 58.27 C |
| ATOM | 3010 | O | TYR | L | 196 | 20.447 | −6.657 | −6.909 | 1.00 | 58.76 O |
| ATOM | 3012 | N | ALA | L | 197 | 21.211 | −4.531 | −6.748 | 1.00 | 58.60 N |
| ATOM | 3013 | CA | ALA | L | 197 | 22.565 | −4.872 | −6.305 | 1.00 | 58.40 C |
| ATOM | 3015 | CB | ALA | L | 197 | 23.549 | −4.628 | −7.437 | 1.00 | 59.04 C |
| ATOM | 3019 | C | ALA | L | 197 | 23.000 | −4.082 | −5.069 | 1.00 | 58.97 C |
| ATOM | 3020 | O | ALA | L | 197 | 22.730 | −2.881 | −4.951 | 1.00 | 58.74 O |
| ATOM | 3022 | N | CYS | L | 198 | 23.686 | −4.770 | −4.159 | 1.00 | 58.92 N |
| ATOM | 3023 | CA | CYS | L | 198 | 24.255 | −4.149 | −2.970 | 1.00 | 58.33 C |
| ATOM | 3025 | CB | CYS | L | 198 | 23.729 | −4.828 | −1.699 | 1.00 | 58.04 C |
| ATOM | 3028 | SG | CYS | L | 198 | 24.536 | −4.228 | −0.198 | 1.00 | 60.24 S |
| ATOM | 3030 | C | CYS | L | 198 | 25.777 | −4.258 | −3.035 | 1.00 | 58.31 C |
| ATOM | 3031 | O | CYS | L | 198 | 26.338 | −5.317 | −2.755 | 1.00 | 59.22 O |
| ATOM | 3033 | N | GLU | L | 199 | 26.438 | −3.161 | −3.401 | 1.00 | 57.62 N |
| ATOM | 3034 | CA | GLU | L | 199 | 27.897 | −3.131 | −3.520 | 1.00 | 56.85 C |
| ATOM | 3036 | CB | GLU | L | 199 | 28.321 | −2.162 | −4.627 | 1.00 | 58.52 C |
| ATOM | 3039 | CG | GLU | L | 199 | 29.835 | −1.997 | −4.819 | 1.00 | 58.08 C |
| ATOM | 3042 | CD | GLU | L | 199 | 30.172 | −1.011 | −5.924 | 1.00 | 58.08 C |

-continued

| ATOM | 3043 | OE1 | GLU | L | 199 | 29.237 | −0.417 | −6.507 | 1.00 | 57.49 | O |
| --- | --- | --- | --- | --- | --- | --- | --- | --- | --- | --- | --- |
| ATOM | 3044 | OE2 | GLU | L | 199 | 31.372 | −0.830 | −6.214 | 1.00 | 62.44 | O |
| ATOM | 3045 | C | GLU | L | 199 | 28.533 | −2.731 | −2.192 | 1.00 | 54.23 | C |
| ATOM | 3046 | O | GLU | L | 199 | 28.288 | −1.643 | −1.679 | 1.00 | 51.14 | O |
| ATOM | 3048 | N | VAL | L | 200 | 29.365 | −3.619 | −1.660 | 1.00 | 53.99 | N |
| ATOM | 3049 | CA | VAL | L | 200 | 29.944 | −3.454 | −0.334 | 1.00 | 54.70 | C |
| ATOM | 3051 | CB | VAL | L | 200 | 29.566 | −4.623 | 0.588 | 1.00 | 54.98 | C |
| ATOM | 3053 | CG1 | VAL | L | 200 | 30.293 | −4.515 | 1.931 | 1.00 | 53.68 | C |
| ATOM | 3057 | CG2 | VAL | L | 200 | 28.056 | −4.668 | 0.780 | 1.00 | 55.59 | C |
| ATOM | 3061 | C | VAL | L | 200 | 31.451 | −3.394 | −0.424 | 1.00 | 54.23 | C |
| ATOM | 3062 | O | VAL | L | 200 | 32.065 | −4.194 | −1.120 | 1.00 | 54.92 | O |
| ATOM | 3064 | N | THR | L | 201 | 32.035 | −2.462 | 0.320 | 1.00 | 53.64 | N |
| ATOM | 3065 | CA | THR | L | 201 | 33.462 | −2.191 | 0.263 | 1.00 | 53.08 | C |
| ATOM | 3067 | CB | THR | L | 201 | 33.784 | −0.993 | −0.669 | 1.00 | 52.20 | C |
| ATOM | 3069 | OG1 | THR | L | 201 | 34.574 | −0.028 | 0.034 | 1.00 | 49.12 | O |
| ATOM | 3071 | CG2 | THR | L | 201 | 32.506 | −0.314 | −1.187 | 1.00 | 51.65 | C |
| ATOM | 3075 | C | THR | L | 201 | 33.993 | −1.946 | 1.673 | 1.00 | 53.49 | C |
| ATOM | 3076 | O | THR | L | 201 | 33.421 | −1.162 | 2.433 | 1.00 | 51.44 | O |
| ATOM | 3078 | N | HIS | L | 202 | 35.097 | −2.620 | 1.998 | 1.00 | 55.44 | N |
| ATOM | 3079 | CA | HIS | L | 202 | 35.626 | −2.679 | 3.358 | 1.00 | 55.07 | C |
| ATOM | 3081 | CB | HIS | L | 202 | 34.893 | −3.782 | 4.121 | 1.00 | 56.07 | C |
| ATOM | 3084 | CG | HIS | L | 202 | 35.118 | −3.758 | 5.599 | 1.00 | 56.86 | C |
| ATOM | 3085 | ND1 | HIS | L | 202 | 35.185 | −4.906 | 6.358 | 1.00 | 58.23 | N |
| ATOM | 3087 | CE1 | HIS | L | 202 | 35.384 | −4.585 | 7.623 | 1.00 | 63.59 | C |
| ATOM | 3089 | NE2 | HIS | L | 202 | 35.454 | −3.269 | 7.711 | 1.00 | 66.38 | N |
| ATOM | 3091 | CD2 | HIS | L | 202 | 35.290 | −2.727 | 6.459 | 1.00 | 59.85 | C |
| ATOM | 3093 | C | HIS | L | 202 | 37.131 | −2.958 | 3.375 | 1.00 | 54.78 | C |
| ATOM | 3094 | O | HIS | L | 202 | 37.687 | −3.510 | 2.427 | 1.00 | 54.71 | O |
| ATOM | 3096 | N | GLN | L | 203 | 37.776 | −2.566 | 4.470 | 1.00 | 55.38 | N |
| ATOM | 3097 | CA | GLN | L | 203 | 39.191 | −2.850 | 4.721 | 1.00 | 54.85 | C |
| ATOM | 3099 | CB | GLN | L | 203 | 39.525 | −2.454 | 6.163 | 1.00 | 55.05 | C |
| ATOM | 3102 | CG | GLN | L | 203 | 41.007 | −2.434 | 6.502 | 1.00 | 54.46 | C |
| ATOM | 3105 | CD | GLN | L | 203 | 41.269 | −1.875 | 7.885 | 1.00 | 53.29 | C |
| ATOM | 3106 | OE1 | GLN | L | 203 | 40.338 | −1.593 | 8.637 | 1.00 | 57.10 | O |
| ATOM | 3107 | NE2 | GLN | L | 203 | 42.538 | −1.711 | 8.229 | 1.00 | 49.23 | N |
| ATOM | 3110 | C | GLN | L | 203 | 39.564 | −4.320 | 4.493 | 1.00 | 54.95 | C |
| ATOM | 3111 | O | GLN | L | 203 | 40.635 | −4.615 | 3.962 | 1.00 | 54.35 | O |
| ATOM | 3113 | N | GLY | L | 204 | 38.675 | −5.230 | 4.894 | 1.00 | 55.44 | N |
| ATOM | 3114 | CA | GLY | L | 204 | 38.931 | −6.673 | 4.828 | 1.00 | 54.77 | C |
| ATOM | 3117 | C | GLY | L | 204 | 38.742 | −7.345 | 3.477 | 1.00 | 54.51 | C |
| ATOM | 3118 | O | GLY | L | 204 | 39.022 | −8.536 | 3.341 | 1.00 | 54.11 | O |
| ATOM | 3120 | N | LEU | L | 205 | 38.258 | −6.595 | 2.486 | 1.00 | 54.73 | N |
| ATOM | 3121 | CA | LEU | L | 205 | 38.124 | −7.087 | 1.109 | 1.00 | 54.23 | C |
| ATOM | 3123 | CB | LEU | L | 205 | 36.699 | −6.850 | 0.582 | 1.00 | 54.64 | C |
| ATOM | 3126 | CG | LEU | L | 205 | 35.499 | −7.332 | 1.416 | 1.00 | 56.74 | C |
| ATOM | 3128 | CD1 | LEU | L | 205 | 34.249 | −6.519 | 1.087 | 1.00 | 58.06 | C |
| ATOM | 3132 | CD2 | LEU | L | 205 | 35.234 | −8.821 | 1.220 | 1.00 | 55.58 | C |
| ATOM | 3136 | C | LEU | L | 205 | 39.127 | −6.356 | 0.214 | 1.00 | 53.26 | C |
| ATOM | 3137 | O | LEU | L | 205 | 39.269 | −5.137 | 0.304 | 1.00 | 53.34 | O |
| ATOM | 3139 | N | SER | L | 206 | 39.821 | −7.100 | −0.641 | 1.00 | 52.19 | N |
| ATOM | 3140 | CA | SER | L | 206 | 40.758 | −6.501 | −1.598 | 1.00 | 51.87 | C |
| ATOM | 3142 | CB | SER | L | 206 | 41.622 | −7.582 | −2.254 | 1.00 | 51.36 | C |
| ATOM | 3145 | OG | SER | L | 206 | 40.855 | −8.730 | −2.575 | 1.00 | 49.90 | O |
| ATOM | 3147 | C | SER | L | 206 | 40.027 | −5.684 | −2.666 | 1.00 | 51.02 | C |
| ATOM | 3148 | O | SER | L | 206 | 40.561 | −4.696 | −3.167 | 1.00 | 49.33 | O |
| ATOM | 3150 | N | SER | L | 207 | 38.811 | −6.113 | −3.005 | 1.00 | 51.49 | N |
| ATOM | 3151 | CA | SER | L | 207 | 37.929 | −5.394 | −3.930 | 1.00 | 52.61 | C |
| ATOM | 3153 | CB | SER | L | 207 | 37.900 | −6.089 | −5.288 | 1.00 | 51.42 | C |
| ATOM | 3156 | OG | SER | L | 207 | 38.982 | −6.983 | −5.412 | 1.00 | 50.93 | O |
| ATOM | 3158 | C | SER | L | 207 | 36.516 | −5.380 | −3.354 | 1.00 | 54.16 | C |
| ATOM | 3159 | O | SER | L | 207 | 36.223 | −6.133 | −2.427 | 1.00 | 56.06 | O |
| ATOM | 3161 | N | PRO | L | 208 | 35.626 | −4.538 | −3.906 | 1.00 | 54.93 | N |
| ATOM | 3162 | CA | PRO | L | 208 | 34.249 | −4.559 | −3.416 | 1.00 | 54.53 | C |
| ATOM | 3164 | CB | PRO | L | 208 | 33.649 | −3.278 | −3.997 | 1.00 | 54.14 | C |
| ATOM | 3167 | CG | PRO | L | 208 | 34.428 | −3.025 | −5.226 | 1.00 | 55.93 | C |
| ATOM | 3170 | CD | PRO | L | 208 | 35.819 | −3.541 | −4.973 | 1.00 | 55.59 | C |
| ATOM | 3173 | C | PRO | L | 208 | 33.461 | −5.792 | −3.876 | 1.00 | 55.09 | C |
| ATOM | 3174 | O | PRO | L | 208 | 33.719 | −6.342 | −4.951 | 1.00 | 54.84 | O |
| ATOM | 3175 | N | VAL | L | 209 | 32.518 | −6.213 | −3.037 | 1.00 | 56.28 | N |
| ATOM | 3176 | CA | VAL | L | 209 | 31.626 | −7.329 | −3.320 | 1.00 | 56.34 | C |
| ATOM | 3178 | CB | VAL | L | 209 | 31.488 | −8.255 | −2.089 | 1.00 | 56.85 | C |
| ATOM | 3180 | CG1 | VAL | L | 209 | 30.517 | −9.395 | −2.371 | 1.00 | 57.34 | C |
| ATOM | 3184 | CG2 | VAL | L | 209 | 32.852 | −8.799 | −1.670 | 1.00 | 57.07 | C |
| ATOM | 3188 | C | VAL | L | 209 | 30.262 | −6.747 | −3.662 | 1.00 | 56.83 | C |
| ATOM | 3189 | O | VAL | L | 209 | 29.897 | −5.688 | −3.151 | 1.00 | 56.98 | O |
| ATOM | 3191 | N | THR | L | 210 | 29.516 | −7.438 | −4.523 | 1.00 | 57.27 | N |
| ATOM | 3192 | CA | THR | L | 210 | 28.193 | −6.979 | −4.959 | 1.00 | 57.11 | C |
| ATOM | 3194 | CB | THR | L | 210 | 28.281 | −6.236 | −6.327 | 1.00 | 57.73 | C |
| ATOM | 3196 | OG1 | THR | L | 210 | 29.064 | −5.046 | −6.175 | 1.00 | 59.95 | O |

-continued

| | | | | | | | | | | |
|---|---|---|---|---|---|---|---|---|---|---|
| ATOM | 3198 | CG2 | THR | L | 210 | 26.896 | −5.848 | −6.855 | 1.00 | 57.29 C |
| ATOM | 3202 | C | THR | L | 210 | 27.198 | −8.143 | −5.051 | 1.00 | 56.72 C |
| ATOM | 3203 | O | THR | L | 210 | 27.092 | −8.797 | −6.090 | 1.00 | 56.88 O |
| ATOM | 3205 | N | LYS | L | 211 | 26.479 | −8.398 | −3.958 | 1.00 | 55.82 N |
| ATOM | 3206 | CA | LYS | L | 211 | 25.370 | −9.358 | −3.978 | 1.00 | 55.38 C |
| ATOM | 3208 | CB | LYS | L | 211 | 25.107 | −9.956 | −2.587 | 1.00 | 55.13 C |
| ATOM | 3211 | CG | LYS | L | 211 | 25.494 | −11.445 | −2.441 | 1.00 | 56.34 C |
| ATOM | 3214 | CD | LYS | L | 211 | 27.009 | −11.694 | −2.368 | 1.00 | 57.34 C |
| ATOM | 3217 | CE | LYS | L | 211 | 27.667 | −11.925 | −3.737 | 1.00 | 58.85 C |
| ATOM | 3220 | NZ | LYS | L | 211 | 27.153 | −13.124 | −4.467 | 1.00 | 59.52 N |
| ATOM | 3224 | C | LYS | L | 211 | 24.113 | −8.702 | −4.563 | 1.00 | 54.52 C |
| ATOM | 3225 | O | LYS | L | 211 | 23.800 | −7.549 | −4.264 | 1.00 | 52.98 O |
| ATOM | 3227 | N | SER | L | 212 | 23.406 | −9.451 | −5.406 | 1.00 | 54.59 N |
| ATOM | 3228 | CA | SER | L | 212 | 22.364 | −8.887 | −6.257 | 1.00 | 54.55 C |
| ATOM | 3230 | CB | SER | L | 212 | 23.016 | −8.276 | −7.490 | 1.00 | 54.31 C |
| ATOM | 3233 | OG | SER | L | 212 | 23.769 | −9.253 | −8.179 | 1.00 | 53.91 O |
| ATOM | 3235 | C | SER | L | 212 | 21.351 | −9.928 | −6.715 | 1.00 | 54.64 C |
| ATOM | 3236 | O | SER | L | 212 | 21.641 | −11.127 | −6.717 | 1.00 | 54.46 O |
| ATOM | 3238 | N | PHE | L | 213 | 20.170 | −9.466 | −7.122 | 1.00 | 54.88 N |
| ATOM | 3239 | CA | PHE | L | 213 | 19.120 | −10.369 | −7.606 | 1.00 | 54.74 C |
| ATOM | 3241 | CB | PHE | L | 213 | 18.186 | −10.776 | −6.461 | 1.00 | 55.51 C |
| ATOM | 3244 | CG | PHE | L | 213 | 17.297 | −9.663 | −5.958 | 1.00 | 56.79 C |
| ATOM | 3245 | CD1 | PHE | L | 213 | 16.051 | −9.438 | −6.528 | 1.00 | 56.38 C |
| ATOM | 3247 | CE1 | PHE | L | 213 | 15.221 | −8.421 | −6.063 | 1.00 | 55.82 C |
| ATOM | 3249 | CZ | PHE | L | 213 | 15.628 | −7.628 | −5.008 | 1.00 | 55.42 C |
| ATOM | 3251 | CE2 | PHE | L | 213 | 16.867 | −7.849 | −4.422 | 1.00 | 57.19 C |
| ATOM | 3253 | CD2 | PHE | L | 213 | 17.693 | −8.863 | −4.897 | 1.00 | 57.95 C |
| ATOM | 3255 | C | PHE | L | 213 | 18.303 | −9.786 | −8.753 | 1.00 | 54.51 C |
| ATOM | 3256 | O | PHE | L | 213 | 18.350 | −8.582 | −9.013 | 1.00 | 55.25 O |
| ATOM | 3258 | N | ASN | L | 214 | 17.562 | −10.669 | −9.426 | 1.00 | 53.54 N |
| ATOM | 3259 | CA | ASN | L | 214 | 16.636 | −10.307 | −10.499 | 1.00 | 52.36 C |
| ATOM | 3261 | CB | ASN | L | 214 | 17.158 | −10.830 | −11.848 | 1.00 | 53.00 C |
| ATOM | 3264 | CG | ASN | L | 214 | 18.501 | −10.238 | −12.242 | 1.00 | 51.37 C |
| ATOM | 3265 | OD1 | ASN | L | 214 | 18.974 | −9.257 | −11.659 | 1.00 | 45.19 O |
| ATOM | 3266 | ND2 | ASN | L | 214 | 19.118 | −10.833 | −13.261 | 1.00 | 48.36 N |
| ATOM | 3269 | C | ASN | L | 214 | 15.221 | −10.853 | −10.196 | 1.00 | 51.48 C |
| ATOM | 3270 | O | ASN | L | 214 | 14.630 | −10.487 | −9.184 | 1.00 | 51.07 O |
| ATOM | 3272 | N | ARG | L | 215 | 14.683 | −11.721 | −11.058 | 1.00 | 51.10 N |
| ATOM | 3273 | CA | ARG | L | 215 | 13.342 | −12.286 | −10.879 | 1.00 | 50.13 C |
| ATOM | 3275 | CB | ARG | L | 215 | 12.269 | −11.313 | −11.388 | 1.00 | 50.15 C |
| ATOM | 3278 | CG | ARG | L | 215 | 11.837 | −10.215 | −10.400 | 1.00 | 48.63 C |
| ATOM | 3281 | CD | ARG | L | 215 | 12.491 | −8.850 | −10.667 | 1.00 | 50.31 C |
| ATOM | 3284 | NE | ARG | L | 215 | 11.646 | −7.745 | −10.197 | 1.00 | 51.54 N |
| ATOM | 3286 | CZ | ARG | L | 215 | 10.960 | −6.898 | −10.974 | 1.00 | 52.47 C |
| ATOM | 3287 | NH1 | ARG | L | 215 | 11.003 | −6.976 | −12.306 | 1.00 | 48.09 N |
| ATOM | 3290 | NH2 | ARG | L | 215 | 10.224 | −5.946 | −10.407 | 1.00 | 51.46 N |
| ATOM | 3293 | C | ARG | L | 215 | 13.221 | −13.618 | −11.623 | 1.00 | 47.98 C |
| ATOM | 3294 | O | ARG | L | 215 | 13.342 | −14.686 | −11.027 | 1.00 | 45.06 O |
| ATOM | 3296 | N | GLU | H | 2 | 18.755 | −9.742 | 45.341 | 1.00 | 56.61 N |
| ATOM | 3297 | CA | GLU | H | 2 | 18.462 | −8.275 | 45.177 | 1.00 | 58.49 C |
| ATOM | 3299 | CB | GLU | H | 2 | 19.732 | −7.423 | 45.229 | 1.00 | 58.68 C |
| ATOM | 3302 | CG | GLU | H | 2 | 20.202 | −7.083 | 46.631 | 1.00 | 62.61 C |
| ATOM | 3305 | CD | GLU | H | 2 | 21.482 | −7.799 | 47.043 | 1.00 | 67.23 C |
| ATOM | 3306 | OE1 | GLU | H | 2 | 21.816 | −8.863 | 46.460 | 1.00 | 64.18 O |
| ATOM | 3307 | OE2 | GLU | H | 2 | 22.153 | −7.282 | 47.967 | 1.00 | 70.83 O |
| ATOM | 3308 | C | GLU | H | 2 | 17.780 | −7.990 | 43.863 | 1.00 | 58.26 C |
| ATOM | 3309 | O | GLU | H | 2 | 18.380 | −8.172 | 42.806 | 1.00 | 60.92 O |
| ATOM | 3313 | N | GLN | H | 3 | 16.547 | −7.507 | 43.933 | 1.00 | 56.73 N |
| ATOM | 3314 | CA | GLN | H | 3 | 15.727 | −7.340 | 42.747 | 1.00 | 56.52 C |
| ATOM | 3316 | CB | GLN | H | 3 | 14.787 | −8.532 | 42.573 | 1.00 | 57.42 C |
| ATOM | 3319 | CG | GLN | H | 3 | 15.473 | −9.832 | 42.190 | 1.00 | 61.67 C |
| ATOM | 3322 | CD | GLN | H | 3 | 14.760 | −10.546 | 41.052 | 1.00 | 67.16 C |
| ATOM | 3323 | OE1 | GLN | H | 3 | 14.535 | −9.964 | 39.985 | 1.00 | 66.35 O |
| ATOM | 3324 | NE2 | GLN | H | 3 | 14.407 | −11.814 | 41.270 | 1.00 | 68.91 N |
| ATOM | 3327 | C | GLN | H | 3 | 14.899 | −6.081 | 42.836 | 1.00 | 56.35 C |
| ATOM | 3328 | O | GLN | H | 3 | 14.308 | −5.789 | 43.881 | 1.00 | 58.04 O |
| ATOM | 3330 | N | LEU | H | 4 | 14.879 | −5.332 | 41.739 | 1.00 | 54.56 N |
| ATOM | 3331 | CA | LEU | H | 4 | 13.946 | −4.246 | 41.558 | 1.00 | 53.97 C |
| ATOM | 3333 | CB | LEU | H | 4 | 14.676 | −2.909 | 41.550 | 1.00 | 53.64 C |
| ATOM | 3336 | CG | LEU | H | 4 | 15.263 | −2.479 | 42.897 | 1.00 | 54.63 C |
| ATOM | 3338 | CD1 | LEU | H | 4 | 16.194 | −1.298 | 42.717 | 1.00 | 56.96 C |
| ATOM | 3342 | CD2 | LEU | H | 4 | 14.182 | −2.121 | 43.876 | 1.00 | 55.34 C |
| ATOM | 3346 | C | LEU | H | 4 | 13.241 | −4.493 | 40.237 | 1.00 | 53.83 C |
| ATOM | 3347 | O | LEU | H | 4 | 13.875 | −4.524 | 39.190 | 1.00 | 52.85 O |
| ATOM | 3349 | N | VAL | H | 5 | 11.933 | −4.713 | 40.294 | 1.00 | 54.49 N |
| ATOM | 3350 | CA | VAL | H | 5 | 11.143 | −4.951 | 39.101 | 1.00 | 54.69 C |
| ATOM | 3352 | CB | VAL | H | 5 | 10.267 | −6.208 | 39.252 | 1.00 | 54.27 C |
| ATOM | 3354 | CG1 | VAL | H | 5 | 9.321 | −6.347 | 38.059 | 1.00 | 51.60 C |
| ATOM | 3358 | CG2 | VAL | H | 5 | 11.137 | −7.447 | 39.403 | 1.00 | 52.80 C |

-continued

| | | | | | | | | | | |
|---|---|---|---|---|---|---|---|---|---|---|
| ATOM | 3362 | C | VAL | H | 5 | 10.252 | −3.752 | 38.861 | 1.00 | 55.02 C |
| ATOM | 3363 | O | VAL | H | 5 | 9.437 | −3.422 | 39.717 | 1.00 | 57.50 O |
| ATOM | 3365 | N | GLU | H | 6 | 10.398 | −3.127 | 37.695 | 1.00 | 54.85 N |
| ATOM | 3366 | CA | GLU | H | 6 | 9.617 | −1.945 | 37.318 | 1.00 | 55.62 C |
| ATOM | 3368 | CB | GLU | H | 6 | 10.446 | −1.017 | 36.429 | 1.00 | 56.41 C |
| ATOM | 3371 | CG | GLU | H | 6 | 11.417 | −0.136 | 37.185 | 1.00 | 58.95 C |
| ATOM | 3374 | CD | GLU | H | 6 | 12.278 | 0.686 | 36.253 | 1.00 | 61.09 C |
| ATOM | 3375 | OE1 | GLU | H | 6 | 11.732 | 1.630 | 35.639 | 1.00 | 66.14 O |
| ATOM | 3376 | OE2 | GLU | H | 6 | 13.488 | 0.385 | 36.135 | 1.00 | 64.83 O |
| ATOM | 3377 | C | GLU | H | 6 | 8.326 | −2.289 | 36.580 | 1.00 | 55.06 C |
| ATOM | 3378 | O | GLU | H | 6 | 8.244 | −3.302 | 35.875 | 1.00 | 53.72 O |
| ATOM | 3380 | N | SER | H | 7 | 7.329 | −1.420 | 36.752 | 1.00 | 55.54 N |
| ATOM | 3381 | CA | SER | H | 7 | 6.017 | −1.562 | 36.125 | 1.00 | 55.81 C |
| ATOM | 3383 | CB | SER | H | 7 | 5.046 | −2.276 | 37.068 | 1.00 | 54.71 C |
| ATOM | 3386 | OG | SER | H | 7 | 5.521 | −3.561 | 37.436 | 1.00 | 51.44 O |
| ATOM | 3388 | C | SER | H | 7 | 5.462 | −0.179 | 35.774 | 1.00 | 57.33 C |
| ATOM | 3389 | O | SER | H | 7 | 5.658 | 0.783 | 36.521 | 1.00 | 57.12 O |
| ATOM | 3391 | N | GLY | H | 8 | 4.750 | −0.105 | 34.649 | 1.00 | 58.14 N |
| ATOM | 3392 | CA | GLY | H | 8 | 4.306 | 1.159 | 34.062 | 1.00 | 57.37 C |
| ATOM | 3395 | C | GLY | H | 8 | 5.145 | 1.481 | 32.836 | 1.00 | 58.01 C |
| ATOM | 3396 | O | GLY | H | 8 | 6.054 | 0.731 | 32.475 | 1.00 | 58.79 O |
| ATOM | 3398 | N | GLY | H | 9 | 4.844 | 2.604 | 32.192 | 1.00 | 57.77 N |
| ATOM | 3399 | CA | GLY | H | 9 | 5.608 | 3.053 | 31.028 | 1.00 | 56.11 C |
| ATOM | 3402 | C | GLY | H | 9 | 4.769 | 2.983 | 29.773 | 1.00 | 55.34 C |
| ATOM | 3403 | O | GLY | H | 9 | 3.687 | 2.407 | 29.787 | 1.00 | 56.26 O |
| ATOM | 3405 | N | GLY | H | 10 | 5.267 | 3.574 | 28.690 | 1.00 | 54.03 N |
| ATOM | 3406 | CA | GLY | H | 10 | 4.579 | 3.548 | 27.405 | 1.00 | 52.92 C |
| ATOM | 3409 | C | GLY | H | 10 | 4.240 | 4.935 | 26.908 | 1.00 | 52.43 C |
| ATOM | 3410 | O | GLY | H | 10 | 4.818 | 5.928 | 27.360 | 1.00 | 52.36 O |
| ATOM | 3412 | N | LEU | H | 11 | 3.289 | 4.994 | 25.977 | 1.00 | 51.79 N |
| ATOM | 3413 | CA | LEU | H | 11 | 2.924 | 6.236 | 25.295 | 1.00 | 50.93 C |
| ATOM | 3415 | CB | LEU | H | 11 | 2.307 | 5.910 | 23.925 | 1.00 | 51.75 C |
| ATOM | 3418 | CG | LEU | H | 11 | 1.987 | 7.022 | 22.911 | 1.00 | 51.71 C |
| ATOM | 3420 | CD1 | LEU | H | 11 | 3.132 | 8.017 | 22.730 | 1.00 | 50.18 C |
| ATOM | 3424 | CD2 | LEU | H | 11 | 1.605 | 6.397 | 21.575 | 1.00 | 49.22 C |
| ATOM | 3428 | C | LEU | H | 11 | 1.958 | 7.076 | 26.126 | 1.00 | 49.59 C |
| ATOM | 3429 | O | LEU | H | 11 | 1.003 | 6.558 | 26.708 | 1.00 | 47.51 O |
| ATOM | 3431 | N | VAL | H | 12 | 2.231 | 8.376 | 26.181 | 1.00 | 50.70 N |
| ATOM | 3432 | CA | VAL | H | 12 | 1.328 | 9.354 | 26.796 | 1.00 | 51.32 C |
| ATOM | 3434 | CB | VAL | H | 12 | 1.680 | 9.660 | 28.253 | 1.00 | 51.22 C |
| ATOM | 3436 | CG1 | VAL | H | 12 | 1.292 | 8.503 | 29.149 | 1.00 | 56.15 C |
| ATOM | 3440 | CG2 | VAL | H | 12 | 3.164 | 9.983 | 28.401 | 1.00 | 54.78 C |
| ATOM | 3444 | C | VAL | H | 12 | 1.381 | 10.660 | 26.033 | 1.00 | 50.66 C |
| ATOM | 3445 | O | VAL | H | 12 | 2.434 | 11.057 | 25.530 | 1.00 | 51.00 O |
| ATOM | 3447 | N | LYS | H | 13 | 0.232 | 11.317 | 25.945 | 1.00 | 50.88 N |
| ATOM | 3448 | CA | LYS | H | 13 | 0.142 | 12.621 | 25.305 | 1.00 | 51.70 C |
| ATOM | 3450 | CB | LYS | H | 13 | −1.325 | 12.980 | 25.040 | 1.00 | 52.29 C |
| ATOM | 3453 | CG | LYS | H | 13 | −1.902 | 12.304 | 23.802 | 1.00 | 51.28 C |
| ATOM | 3456 | CD | LYS | H | 13 | −3.423 | 12.333 | 23.790 | 1.00 | 52.82 C |
| ATOM | 3459 | CE | LYS | H | 13 | −3.984 | 12.401 | 22.377 | 1.00 | 55.83 C |
| ATOM | 3462 | NZ | LYS | H | 13 | −3.195 | 11.584 | 21.423 | 1.00 | 57.61 N |
| ATOM | 3466 | C | LYS | H | 13 | 0.834 | 13.687 | 26.175 | 1.00 | 51.36 C |
| ATOM | 3467 | O | LYS | H | 13 | 0.913 | 13.537 | 27.393 | 1.00 | 49.24 O |
| ATOM | 3469 | N | PRO | H | 14 | 1.390 | 14.740 | 25.545 | 1.00 | 51.89 N |
| ATOM | 3470 | CA | PRO | H | 14 | 1.950 | 15.847 | 26.328 | 1.00 | 51.17 C |
| ATOM | 3472 | CB | PRO | H | 14 | 2.458 | 16.817 | 25.251 | 1.00 | 50.70 C |
| ATOM | 3475 | CG | PRO | H | 14 | 2.688 | 15.960 | 24.054 | 1.00 | 50.32 C |
| ATOM | 3478 | CD | PRO | H | 14 | 1.586 | 14.949 | 24.098 | 1.00 | 51.84 C |
| ATOM | 3481 | C | PRO | H | 14 | 0.908 | 16.519 | 27.219 | 1.00 | 49.57 C |
| ATOM | 3482 | O | PRO | H | 14 | −0.220 | 16.746 | 26.786 | 1.00 | 50.07 O |
| ATOM | 3483 | N | GLY | H | 15 | 1.292 | 16.811 | 28.457 | 1.00 | 49.10 N |
| ATOM | 3484 | CA | GLY | H | 15 | 0.380 | 17.376 | 29.457 | 1.00 | 50.81 C |
| ATOM | 3487 | C | GLY | H | 15 | −0.372 | 16.329 | 30.257 | 1.00 | 51.04 C |
| ATOM | 3488 | O | GLY | H | 15 | −1.115 | 16.659 | 31.190 | 1.00 | 50.77 O |
| ATOM | 3490 | N | GLY | H | 16 | −0.173 | 15.065 | 29.886 | 1.00 | 52.18 N |
| ATOM | 3491 | CA | GLY | H | 16 | −0.841 | 13.939 | 30.517 | 1.00 | 52.36 C |
| ATOM | 3494 | C | GLY | H | 16 | −0.041 | 13.363 | 31.665 | 1.00 | 53.40 C |
| ATOM | 3495 | O | GLY | H | 16 | 0.891 | 13.996 | 32.177 | 1.00 | 52.35 O |
| ATOM | 3497 | N | SER | H | 17 | −0.413 | 12.143 | 32.049 | 1.00 | 55.01 N |
| ATOM | 3498 | CA | SER | H | 17 | 0.021 | 11.542 | 33.305 | 1.00 | 54.42 C |
| ATOM | 3500 | CB | SER | H | 17 | −1.057 | 11.724 | 34.379 | 1.00 | 54.25 C |
| ATOM | 3503 | OG | SER | H | 17 | −0.966 | 13.005 | 34.960 | 1.00 | 56.38 O |
| ATOM | 3505 | C | SER | H | 17 | 0.291 | 10.071 | 33.153 | 1.00 | 54.71 C |
| ATOM | 3506 | O | SER | H | 17 | −0.162 | 9.432 | 32.206 | 1.00 | 55.94 O |
| ATOM | 3508 | N | LEU | H | 18 | 1.001 | 9.535 | 34.133 | 1.00 | 56.53 N |
| ATOM | 3509 | CA | LEU | H | 18 | 1.470 | 8.163 | 34.108 | 1.00 | 55.73 C |
| ATOM | 3511 | CB | LEU | H | 18 | 2.472 | 8.001 | 32.975 | 1.00 | 55.68 C |
| ATOM | 3514 | CG | LEU | H | 18 | 3.170 | 6.673 | 32.760 | 1.00 | 59.03 C |
| ATOM | 3516 | CD1 | LEU | H | 18 | 2.195 | 5.476 | 32.790 | 1.00 | 64.04 C |

-continued

| ATOM | 3520 | CD2 | LEU | H | 18 | 3.907 | 6.751 | 31.424 | 1.00 | 59.16 | C |
|------|------|-----|-----|---|----|-------|-------|--------|------|-------|---|
| ATOM | 3524 | C | LEU | H | 18 | 2.148 | 7.911 | 35.438 | 1.00 | 56.06 | C |
| ATOM | 3525 | O | LEU | H | 18 | 2.808 | 8.807 | 35.988 | 1.00 | 55.85 | O |
| ATOM | 3527 | N | ARG | H | 19 | 1.965 | 6.715 | 35.979 | 1.00 | 56.64 | N |
| ATOM | 3528 | CA | ARG | H | 19 | 2.626 | 6.344 | 37.221 | 1.00 | 56.43 | C |
| ATOM | 3530 | CB | ARG | H | 19 | 1.612 | 6.041 | 38.319 | 1.00 | 56.80 | C |
| ATOM | 3533 | CG | ARG | H | 19 | 2.217 | 6.081 | 39.716 | 1.00 | 58.31 | C |
| ATOM | 3536 | CD | ARG | H | 19 | 1.362 | 5.365 | 40.734 | 1.00 | 61.31 | C |
| ATOM | 3539 | NE | ARG | H | 19 | 1.337 | 3.920 | 40.503 | 1.00 | 67.58 | N |
| ATOM | 3541 | CZ | ARG | H | 19 | 0.699 | 3.041 | 41.276 | 1.00 | 70.39 | C |
| ATOM | 3542 | NH1 | ARG | H | 19 | 0.033 | 3.450 | 42.356 | 1.00 | 69.73 | N |
| ATOM | 3545 | NH2 | ARG | H | 19 | 0.730 | 1.743 | 40.971 | 1.00 | 69.82 | N |
| ATOM | 3548 | C | ARG | H | 19 | 3.505 | 5.130 | 37.006 | 1.00 | 55.52 | C |
| ATOM | 3549 | O | ARG | H | 19 | 3.079 | 4.128 | 36.416 | 1.00 | 56.01 | O |
| ATOM | 3551 | N | LEU | H | 20 | 4.739 | 5.236 | 37.481 | 1.00 | 54.58 | N |
| ATOM | 3552 | CA | LEU | H | 20 | 5.632 | 4.098 | 37.531 | 1.00 | 55.42 | C |
| ATOM | 3554 | CB | LEU | H | 20 | 7.043 | 4.463 | 37.043 | 1.00 | 55.00 | C |
| ATOM | 3557 | CG | LEU | H | 20 | 7.138 | 5.242 | 35.725 | 1.00 | 55.68 | C |
| ATOM | 3559 | CD1 | LEU | H | 20 | 8.580 | 5.646 | 35.434 | 1.00 | 58.29 | C |
| ATOM | 3563 | CD2 | LEU | H | 20 | 6.554 | 4.446 | 34.561 | 1.00 | 55.92 | C |
| ATOM | 3567 | C | LEU | H | 20 | 5.673 | 3.616 | 38.963 | 1.00 | 54.49 | C |
| ATOM | 3568 | O | LEU | H | 20 | 5.455 | 4.382 | 39.891 | 1.00 | 55.30 | O |
| ATOM | 3570 | N | SER | H | 21 | 5.936 | 2.332 | 39.126 | 1.00 | 56.12 | N |
| ATOM | 3571 | CA | SER | H | 21 | 6.166 | 1.746 | 40.428 | 1.00 | 56.93 | C |
| ATOM | 3573 | CB | SER | H | 21 | 4.907 | 1.045 | 40.921 | 1.00 | 57.53 | C |
| ATOM | 3576 | OG | SER | H | 21 | 4.584 | −0.051 | 40.081 | 1.00 | 60.54 | O |
| ATOM | 3578 | C | SER | H | 21 | 7.309 | 0.750 | 40.288 | 1.00 | 58.71 | C |
| ATOM | 3579 | O | SER | H | 21 | 7.715 | 0.398 | 39.169 | 1.00 | 59.16 | O |
| ATOM | 3581 | N | CYS | H | 22 | 7.811 | 0.285 | 41.425 | 1.00 | 59.31 | N |
| ATOM | 3582 | CA | CYS | H | 22 | 8.981 | −0.567 | 41.442 | 1.00 | 56.83 | C |
| ATOM | 3584 | CB | CYS | H | 22 | 10.227 | 0.308 | 41.431 | 1.00 | 59.46 | C |
| ATOM | 3587 | SG | CYS | H | 22 | 11.797 | −0.553 | 41.533 | 1.00 | 65.61 | S |
| ATOM | 3589 | C | CYS | H | 22 | 8.927 | −1.433 | 42.683 | 1.00 | 55.37 | C |
| ATOM | 3590 | O | CYS | H | 22 | 8.959 | −0.926 | 43.802 | 1.00 | 53.14 | O |
| ATOM | 3592 | N | ALA | H | 23 | 8.798 | −2.742 | 42.473 | 1.00 | 55.34 | N |
| ATOM | 3593 | CA | ALA | H | 23 | 8.735 | −3.712 | 43.563 | 1.00 | 53.47 | C |
| ATOM | 3595 | CB | ALA | H | 23 | 7.811 | −4.829 | 43.212 | 1.00 | 53.08 | C |
| ATOM | 3599 | C | ALA | H | 23 | 10.129 | −4.258 | 43.833 | 1.00 | 52.42 | C |
| ATOM | 3600 | O | ALA | H | 23 | 10.822 | −4.679 | 42.908 | 1.00 | 50.73 | O |
| ATOM | 3602 | N | ALA | H | 24 | 10.518 | −4.246 | 45.108 | 1.00 | 52.07 | N |
| ATOM | 3603 | CA | ALA | H | 24 | 11.829 | −4.693 | 45.552 | 1.00 | 51.43 | C |
| ATOM | 3605 | CB | ALA | H | 24 | 12.466 | −3.626 | 46.466 | 1.00 | 51.29 | C |
| ATOM | 3609 | C | ALA | H | 24 | 11.704 | −5.998 | 46.309 | 1.00 | 50.38 | C |
| ATOM | 3610 | O | ALA | H | 24 | 10.778 | −6.162 | 47.107 | 1.00 | 49.98 | O |
| ATOM | 3612 | N | SER | H | 25 | 12.638 | −6.915 | 46.069 | 1.00 | 50.32 | N |
| ATOM | 3613 | CA | SER | H | 25 | 12.796 | −8.098 | 46.925 | 1.00 | 50.66 | C |
| ATOM | 3615 | CB | SER | H | 25 | 12.191 | −9.335 | 46.269 | 1.00 | 50.25 | C |
| ATOM | 3618 | OG | SER | H | 25 | 13.117 | −9.930 | 45.384 | 1.00 | 50.11 | O |
| ATOM | 3620 | C | SER | H | 25 | 14.274 | −8.338 | 47.167 | 1.00 | 50.55 | C |
| ATOM | 3621 | O | SER | H | 25 | 15.113 | −7.773 | 46.466 | 1.00 | 49.47 | O |
| ATOM | 3623 | N | GLY | H | 26 | 14.588 | −9.170 | 48.160 | 1.00 | 50.83 | N |
| ATOM | 3624 | CA | GLY | H | 26 | 15.965 | −9.604 | 48.400 | 1.00 | 50.46 | C |
| ATOM | 3627 | C | GLY | H | 26 | 16.773 | −8.832 | 49.428 | 1.00 | 50.67 | C |
| ATOM | 3628 | O | GLY | H | 26 | 17.641 | −9.409 | 50.055 | 1.00 | 51.46 | O |
| ATOM | 3630 | N | PHE | H | 27 | 16.509 | −7.534 | 49.598 | 1.00 | 52.07 | N |
| ATOM | 3631 | CA | PHE | H | 27 | 17.244 | −6.692 | 50.565 | 1.00 | 50.72 | C |
| ATOM | 3633 | CB | PHE | H | 27 | 18.154 | −5.700 | 49.825 | 1.00 | 50.11 | C |
| ATOM | 3636 | CG | PHE | H | 27 | 17.418 | −4.738 | 48.957 | 1.00 | 50.40 | C |
| ATOM | 3637 | CD1 | PHE | H | 27 | 17.043 | −5.092 | 47.668 | 1.00 | 51.35 | C |
| ATOM | 3639 | CE1 | PHE | H | 27 | 16.363 | −4.197 | 46.848 | 1.00 | 48.63 | C |
| ATOM | 3641 | CZ | PHE | H | 27 | 16.050 | −2.941 | 47.321 | 1.00 | 50.70 | C |
| ATOM | 3643 | CE2 | PHE | H | 27 | 16.426 | −2.568 | 48.601 | 1.00 | 50.42 | C |
| ATOM | 3645 | CD2 | PHE | H | 27 | 17.104 | −3.469 | 49.416 | 1.00 | 52.69 | C |
| ATOM | 3647 | C | PHE | H | 27 | 16.301 | −5.966 | 51.539 | 1.00 | 49.97 | C |
| ATOM | 3648 | O | PHE | H | 27 | 15.099 | −6.212 | 51.537 | 1.00 | 48.25 | O |
| ATOM | 3650 | N | SER | H | 28 | 16.857 | −5.095 | 52.385 | 1.00 | 51.01 | N |
| ATOM | 3651 | CA | SER | H | 28 | 16.082 | −4.395 | 53.417 | 1.00 | 50.58 | C |
| ATOM | 3653 | CB | SER | H | 28 | 16.892 | −4.261 | 54.708 | 1.00 | 51.28 | C |
| ATOM | 3656 | OG | SER | H | 28 | 16.076 | −3.756 | 55.757 | 1.00 | 52.89 | O |
| ATOM | 3658 | C | SER | H | 28 | 15.612 | −3.024 | 52.943 | 1.00 | 49.79 | C |
| ATOM | 3659 | O | SER | H | 28 | 16.250 | −1.986 | 53.193 | 1.00 | 48.90 | O |
| ATOM | 3661 | N | PHE | H | 29 | 14.472 | −3.047 | 52.266 | 1.00 | 49.18 | N |
| ATOM | 3662 | CA | PHE | H | 29 | 13.891 | −1.875 | 51.626 | 1.00 | 50.01 | C |
| ATOM | 3664 | CB | PHE | H | 29 | 12.496 | −2.230 | 51.131 | 1.00 | 48.32 | C |
| ATOM | 3667 | CG | PHE | H | 29 | 11.828 | −1.151 | 50.327 | 1.00 | 48.58 | C |
| ATOM | 3668 | CD1 | PHE | H | 29 | 12.051 | −1.046 | 48.972 | 1.00 | 47.02 | C |
| ATOM | 3670 | CE1 | PHE | H | 29 | 11.428 | −0.069 | 48.227 | 1.00 | 45.47 | C |
| ATOM | 3672 | CZ | PHE | H | 29 | 10.555 | 0.794 | 48.824 | 1.00 | 48.47 | C |
| ATOM | 3674 | CE2 | PHE | H | 29 | 10.304 | 0.696 | 50.183 | 1.00 | 47.66 | C |

-continued

| | | | | | | | | | | |
|---|---|---|---|---|---|---|---|---|---|---|
| ATOM | 3676 | CD2 | PHE | H | 29 | 10.938 | −0.269 | 50.924 | 1.00 | 47.81 C |
| ATOM | 3678 | C | PHE | H | 29 | 13.836 | −0.677 | 52.563 | 1.00 | 50.10 C |
| ATOM | 3679 | O | PHE | H | 29 | 14.166 | 0.423 | 52.168 | 1.00 | 49.59 O |
| ATOM | 3681 | N | SER | H | 30 | 13.451 | −0.905 | 53.811 | 1.00 | 52.28 N |
| ATOM | 3682 | CA | SER | H | 30 | 13.308 | 0.187 | 54.768 | 1.00 | 54.39 C |
| ATOM | 3684 | CB | SER | H | 30 | 12.611 | −0.285 | 56.038 | 1.00 | 54.51 C |
| ATOM | 3687 | OG | SER | H | 30 | 11.244 | 0.062 | 55.986 | 1.00 | 60.29 O |
| ATOM | 3689 | C | SER | H | 30 | 14.622 | 0.839 | 55.142 | 1.00 | 55.97 C |
| ATOM | 3690 | O | SER | H | 30 | 14.633 | 1.979 | 55.575 | 1.00 | 58.83 O |
| ATOM | 3692 | N | ASP | H | 31 | 15.725 | 0.120 | 54.986 | 1.00 | 57.11 N |
| ATOM | 3693 | CA | ASP | H | 31 | 17.050 | 0.679 | 55.274 | 1.00 | 57.16 C |
| ATOM | 3695 | CB | ASP | H | 31 | 17.986 | −0.438 | 55.773 | 1.00 | 57.00 C |
| ATOM | 3698 | CG | ASP | H | 31 | 17.502 | −1.068 | 57.085 | 1.00 | 58.67 C |
| ATOM | 3699 | OD1 | ASP | H | 31 | 17.234 | −0.317 | 58.043 | 1.00 | 63.08 O |
| ATOM | 3700 | OD2 | ASP | H | 31 | 17.384 | −2.310 | 57.167 | 1.00 | 58.40 O |
| ATOM | 3701 | C | ASP | H | 31 | 17.672 | 1.401 | 54.057 | 1.00 | 57.43 C |
| ATOM | 3702 | O | ASP | H | 31 | 18.842 | 1.792 | 54.101 | 1.00 | 55.59 O |
| ATOM | 3704 | N | CYS | H | 32 | 16.896 | 1.594 | 52.989 | 1.00 | 56.14 N |
| ATOM | 3705 | CA | CYS | H | 32 | 17.442 | 2.115 | 51.750 | 1.00 | 57.19 C |
| ATOM | 3707 | CB | CYS | H | 32 | 17.338 | 1.047 | 50.664 | 1.00 | 57.68 C |
| ATOM | 3710 | SG | CYS | H | 32 | 18.330 | −0.413 | 51.027 | 1.00 | 60.48 S |
| ATOM | 3712 | C | CYS | H | 32 | 16.779 | 3.403 | 51.269 | 1.00 | 57.32 C |
| ATOM | 3713 | O | CYS | H | 32 | 15.572 | 3.595 | 51.407 | 1.00 | 56.26 O |
| ATOM | 3715 | N | ARG | H | 33 | 17.592 | 4.295 | 50.716 | 1.00 | 58.05 N |
| ATOM | 3716 | CA | ARG | H | 33 | 17.075 | 5.390 | 49.915 | 1.00 | 59.05 C |
| ATOM | 3718 | CB | ARG | H | 33 | 18.127 | 6.483 | 49.699 | 1.00 | 60.10 C |
| ATOM | 3721 | CG | ARG | H | 33 | 18.419 | 7.317 | 50.911 | 1.00 | 61.65 C |
| ATOM | 3724 | CD | ARG | H | 33 | 19.060 | 8.657 | 50.536 | 1.00 | 63.60 C |
| ATOM | 3727 | NE | ARG | H | 33 | 19.339 | 9.429 | 51.748 | 1.00 | 66.43 N |
| ATOM | 3729 | CZ | ARG | H | 33 | 20.535 | 9.583 | 52.312 | 1.00 | 66.37 C |
| ATOM | 3730 | NH1 | ARG | H | 33 | 21.632 | 9.065 | 51.772 | 1.00 | 71.77 N |
| ATOM | 3733 | NH2 | ARG | H | 33 | 20.639 | 10.291 | 53.426 | 1.00 | 68.04 N |
| ATOM | 3736 | C | ARG | H | 33 | 16.685 | 4.807 | 48.567 | 1.00 | 58.44 C |
| ATOM | 3737 | O | ARG | H | 33 | 17.428 | 4.004 | 48.000 | 1.00 | 58.55 O |
| ATOM | 3739 | N | MET | H | 34 | 15.521 | 5.202 | 48.065 | 1.00 | 56.95 N |
| ATOM | 3740 | CA | MET | H | 34 | 15.090 | 4.804 | 46.745 | 1.00 | 56.14 C |
| ATOM | 3742 | CB | MET | H | 34 | 13.629 | 4.351 | 46.770 | 1.00 | 56.70 C |
| ATOM | 3745 | CG | MET | H | 34 | 13.337 | 3.183 | 47.740 | 1.00 | 58.76 C |
| ATOM | 3748 | SD | MET | H | 34 | 14.315 | 1.675 | 47.451 | 1.00 | 58.81 S |
| ATOM | 3749 | CE | MET | H | 34 | 13.826 | 1.233 | 45.797 | 1.00 | 60.09 C |
| ATOM | 3753 | C | MET | H | 34 | 15.291 | 6.000 | 45.834 | 1.00 | 54.94 C |
| ATOM | 3754 | O | MET | H | 34 | 15.118 | 7.140 | 46.250 | 1.00 | 55.91 O |
| ATOM | 3756 | N | TYR | H | 35 | 15.700 | 5.737 | 44.600 | 1.00 | 54.70 N |
| ATOM | 3757 | CA | TYR | H | 35 | 15.919 | 6.792 | 43.624 | 1.00 | 55.83 C |
| ATOM | 3759 | CB | TYR | H | 35 | 17.406 | 6.942 | 43.276 | 1.00 | 56.48 C |
| ATOM | 3762 | CG | TYR | H | 35 | 18.380 | 6.794 | 44.427 | 1.00 | 57.63 C |
| ATOM | 3763 | CD1 | TYR | H | 35 | 18.827 | 7.899 | 45.132 | 1.00 | 54.66 C |
| ATOM | 3765 | CE1 | TYR | H | 35 | 19.727 | 7.767 | 46.157 | 1.00 | 54.12 C |
| ATOM | 3767 | CZ | TYR | H | 35 | 20.198 | 6.522 | 46.491 | 1.00 | 55.23 C |
| ATOM | 3768 | OH | TYR | H | 35 | 21.087 | 6.378 | 47.517 | 1.00 | 55.85 O |
| ATOM | 3770 | CE2 | TYR | H | 35 | 19.775 | 5.413 | 45.813 | 1.00 | 58.29 C |
| ATOM | 3772 | CD2 | TYR | H | 35 | 18.881 | 5.550 | 44.779 | 1.00 | 57.08 C |
| ATOM | 3774 | C | TYR | H | 35 | 15.182 | 6.475 | 42.338 | 1.00 | 55.62 C |
| ATOM | 3775 | O | TYR | H | 35 | 14.958 | 5.304 | 42.015 | 1.00 | 53.71 O |
| ATOM | 3777 | N | TRP | H | 36 | 14.811 | 7.533 | 41.613 | 1.00 | 55.28 N |
| ATOM | 3778 | CA | TRP | H | 36 | 14.484 | 7.414 | 40.206 | 1.00 | 55.09 C |
| ATOM | 3780 | CB | TRP | H | 36 | 13.076 | 7.920 | 39.909 | 1.00 | 55.00 C |
| ATOM | 3783 | CG | TRP | H | 36 | 12.005 | 7.017 | 40.432 | 1.00 | 55.14 C |
| ATOM | 3784 | CD1 | TRP | H | 36 | 11.352 | 7.141 | 41.611 | 1.00 | 54.77 C |
| ATOM | 3786 | NE1 | TRP | H | 36 | 10.437 | 6.132 | 41.760 | 1.00 | 55.42 N |
| ATOM | 3788 | CE2 | TRP | H | 36 | 10.487 | 5.323 | 40.656 | 1.00 | 56.93 C |
| ATOM | 3789 | CD2 | TRP | H | 36 | 11.469 | 5.850 | 39.795 | 1.00 | 55.90 C |
| ATOM | 3790 | CE3 | TRP | H | 36 | 11.718 | 5.204 | 38.577 | 1.00 | 54.80 C |
| ATOM | 3792 | CZ3 | TRP | H | 36 | 10.987 | 4.076 | 38.263 | 1.00 | 53.18 C |
| ATOM | 3794 | CH2 | TRP | H | 36 | 10.014 | 3.573 | 39.141 | 1.00 | 55.17 C |
| ATOM | 3796 | CZ2 | TRP | H | 36 | 9.748 | 4.181 | 40.339 | 1.00 | 55.56 C |
| ATOM | 3798 | C | TRP | H | 36 | 15.518 | 8.170 | 39.380 | 1.00 | 55.00 C |
| ATOM | 3799 | O | TRP | H | 36 | 15.969 | 9.259 | 39.753 | 1.00 | 56.65 O |
| ATOM | 3801 | N | LEU | H | 37 | 15.906 | 7.559 | 38.270 | 1.00 | 54.61 N |
| ATOM | 3802 | CA | LEU | H | 37 | 16.780 | 8.178 | 37.280 | 1.00 | 54.88 C |
| ATOM | 3804 | CB | LEU | H | 37 | 18.220 | 7.663 | 37.386 | 1.00 | 54.64 C |
| ATOM | 3807 | CG | LEU | H | 37 | 18.783 | 7.212 | 38.736 | 1.00 | 54.68 C |
| ATOM | 3809 | CD1 | LEU | H | 37 | 20.234 | 7.604 | 38.853 | 1.00 | 53.68 C |
| ATOM | 3813 | CD2 | LEU | H | 37 | 18.635 | 5.705 | 38.917 | 1.00 | 55.23 C |
| ATOM | 3817 | C | LEU | H | 37 | 16.219 | 7.864 | 35.886 | 1.00 | 54.80 C |
| ATOM | 3818 | O | LEU | H | 37 | 15.391 | 6.948 | 35.728 | 1.00 | 53.49 O |
| ATOM | 3820 | N | ARG | H | 38 | 16.667 | 8.631 | 34.889 | 1.00 | 53.19 N |
| ATOM | 3821 | CA | ARG | H | 38 | 16.189 | 8.473 | 33.524 | 1.00 | 53.67 C |
| ATOM | 3823 | CB | ARG | H | 38 | 15.041 | 9.436 | 33.227 | 1.00 | 54.81 C |

| | | | | | -continued | | | | | |
|---|---|---|---|---|---|---|---|---|---|---|
| ATOM | 3826 | CG | ARG | H | 38 | 15.461 | 10.895 | 33.059 | 1.00 | 55.37 | C |
| ATOM | 3829 | CD | ARG | H | 38 | 14.294 | 11.769 | 32.632 | 1.00 | 52.74 | C |
| ATOM | 3832 | NE | ARG | H | 38 | 14.603 | 13.177 | 32.842 | 1.00 | 53.44 | N |
| ATOM | 3834 | CZ | ARG | H | 38 | 13.768 | 14.174 | 32.571 | 1.00 | 51.46 | C |
| ATOM | 3835 | NH1 | ARG | H | 38 | 12.556 | 13.927 | 32.099 | 1.00 | 54.21 | N |
| ATOM | 3838 | NH2 | ARG | H | 38 | 14.146 | 15.428 | 32.794 | 1.00 | 47.99 | N |
| ATOM | 3841 | C | ARG | H | 38 | 17.297 | 8.679 | 32.510 | 1.00 | 53.96 | C |
| ATOM | 3842 | O | ARG | H | 38 | 18.345 | 9.266 | 32.812 | 1.00 | 53.44 | O |
| ATOM | 3844 | N | GLN | H | 39 | 17.026 | 8.203 | 31.299 | 1.00 | 53.60 | N |
| ATOM | 3845 | CA | GLN | H | 39 | 17.998 | 8.180 | 30.212 | 1.00 | 53.28 | C |
| ATOM | 3847 | CB | GLN | H | 39 | 18.878 | 6.932 | 30.337 | 1.00 | 52.42 | C |
| ATOM | 3850 | CG | GLN | H | 39 | 19.753 | 6.609 | 29.129 | 1.00 | 51.84 | C |
| ATOM | 3853 | CD | GLN | H | 39 | 20.733 | 5.489 | 29.426 | 1.00 | 50.24 | C |
| ATOM | 3854 | OE1 | GLN | H | 39 | 20.371 | 4.476 | 30.024 | 1.00 | 48.74 | O |
| ATOM | 3855 | NE2 | GLN | H | 39 | 21.983 | 5.677 | 29.033 | 1.00 | 36.18 | N |
| ATOM | 3858 | C | GLN | H | 39 | 17.249 | 8.207 | 28.877 | 1.00 | 53.61 | C |
| ATOM | 3859 | O | GLN | H | 39 | 16.462 | 7.304 | 28.571 | 1.00 | 53.97 | O |
| ATOM | 3861 | N | ALA | H | 40 | 17.488 | 9.259 | 28.100 | 1.00 | 53.97 | N |
| ATOM | 3862 | CA | ALA | H | 40 | 16.848 | 9.433 | 26.796 | 1.00 | 54.45 | C |
| ATOM | 3864 | CB | ALA | H | 40 | 16.897 | 10.908 | 26.385 | 1.00 | 54.42 | C |
| ATOM | 3868 | C | ALA | H | 40 | 17.510 | 8.543 | 25.726 | 1.00 | 54.55 | C |
| ATOM | 3869 | O | ALA | H | 40 | 18.671 | 8.140 | 25.882 | 1.00 | 54.41 | O |
| ATOM | 3871 | N | PRO | H | 41 | 16.774 | 8.225 | 24.639 | 1.00 | 53.53 | N |
| ATOM | 3872 | CA | PRO | H | 41 | 17.395 | 7.361 | 23.643 | 1.00 | 53.62 | C |
| ATOM | 3874 | CB | PRO | H | 41 | 16.354 | 7.291 | 22.515 | 1.00 | 52.51 | C |
| ATOM | 3877 | CG | PRO | H | 41 | 15.076 | 7.676 | 23.139 | 1.00 | 54.06 | C |
| ATOM | 3880 | CD | PRO | H | 41 | 15.412 | 8.627 | 24.249 | 1.00 | 53.29 | C |
| ATOM | 3883 | C | PRO | H | 41 | 18.684 | 8.015 | 23.168 | 1.00 | 53.95 | C |
| ATOM | 3884 | O | PRO | H | 41 | 18.679 | 9.210 | 22.857 | 1.00 | 54.39 | O |
| ATOM | 3885 | N | GLY | H | 42 | 19.781 | 7.260 | 23.180 | 1.00 | 52.90 | N |
| ATOM | 3886 | CA | GLY | H | 42 | 21.064 | 7.759 | 22.713 | 1.00 | 52.60 | C |
| ATOM | 3889 | C | GLY | H | 42 | 21.788 | 8.724 | 23.638 | 1.00 | 53.38 | C |
| ATOM | 3890 | O | GLY | H | 42 | 22.838 | 9.236 | 23.270 | 1.00 | 56.12 | O |
| ATOM | 3892 | N | LYS | H | 43 | 21.267 | 8.960 | 24.839 | 1.00 | 53.22 | N |
| ATOM | 3893 | CA | LYS | H | 43 | 21.878 | 9.921 | 25.771 | 1.00 | 53.86 | C |
| ATOM | 3895 | CB | LYS | H | 43 | 20.853 | 11.003 | 26.128 | 1.00 | 55.45 | C |
| ATOM | 3898 | CG | LYS | H | 43 | 21.004 | 12.300 | 25.356 | 1.00 | 57.82 | C |
| ATOM | 3901 | CD | LYS | H | 43 | 21.144 | 12.083 | 23.846 | 1.00 | 61.25 | C |
| ATOM | 3904 | CE | LYS | H | 43 | 21.021 | 13.402 | 23.092 | 1.00 | 62.25 | C |
| ATOM | 3907 | NZ | LYS | H | 43 | 19.853 | 14.216 | 23.574 | 1.00 | 64.79 | N |
| ATOM | 3911 | C | LYS | H | 43 | 22.460 | 9.274 | 27.047 | 1.00 | 53.34 | C |
| ATOM | 3912 | O | LYS | H | 43 | 22.428 | 8.052 | 27.201 | 1.00 | 54.25 | O |
| ATOM | 3914 | N | GLY | H | 44 | 23.008 | 10.102 | 27.938 | 1.00 | 50.96 | N |
| ATOM | 3915 | CA | GLY | H | 44 | 23.567 | 9.640 | 29.201 | 1.00 | 52.62 | C |
| ATOM | 3918 | C | GLY | H | 44 | 22.519 | 9.464 | 30.286 | 1.00 | 53.64 | C |
| ATOM | 3919 | O | GLY | H | 44 | 21.330 | 9.362 | 30.003 | 1.00 | 55.33 | O |
| ATOM | 3921 | N | LEU | H | 45 | 22.966 | 9.440 | 31.539 | 1.00 | 55.02 | N |
| ATOM | 3922 | CA | LEU | H | 45 | 22.087 | 9.189 | 32.691 | 1.00 | 55.09 | C |
| ATOM | 3924 | CB | LEU | H | 45 | 22.784 | 8.240 | 33.690 | 1.00 | 55.16 | C |
| ATOM | 3927 | CG | LEU | H | 45 | 22.784 | 6.710 | 33.461 | 1.00 | 54.66 | C |
| ATOM | 3929 | CD1 | LEU | H | 45 | 22.710 | 6.332 | 32.014 | 1.00 | 58.85 | C |
| ATOM | 3933 | CD2 | LEU | H | 45 | 24.002 | 6.033 | 34.107 | 1.00 | 55.72 | C |
| ATOM | 3937 | C | LEU | H | 45 | 21.720 | 10.511 | 33.381 | 1.00 | 55.25 | C |
| ATOM | 3938 | O | LEU | H | 45 | 22.527 | 11.438 | 33.428 | 1.00 | 54.95 | O |
| ATOM | 3940 | N | GLU | H | 46 | 20.504 | 10.592 | 33.914 | 1.00 | 55.05 | N |
| ATOM | 3941 | CA | GLU | H | 46 | 20.095 | 11.745 | 34.717 | 1.00 | 55.03 | C |
| ATOM | 3943 | CB | GLU | H | 46 | 19.177 | 12.655 | 33.903 | 1.00 | 54.16 | C |
| ATOM | 3946 | CG | GLU | H | 46 | 18.809 | 13.958 | 34.619 | 1.00 | 56.93 | C |
| ATOM | 3949 | CD | GLU | H | 46 | 17.682 | 14.733 | 33.958 | 1.00 | 57.58 | C |
| ATOM | 3950 | OE1 | GLU | H | 46 | 17.159 | 14.286 | 32.914 | 1.00 | 60.12 | O |
| ATOM | 3951 | OE2 | GLU | H | 46 | 17.322 | 15.798 | 34.499 | 1.00 | 58.36 | O |
| ATOM | 3952 | C | GLU | H | 46 | 19.382 | 11.317 | 36.008 | 1.00 | 55.43 | C |
| ATOM | 3953 | O | GLU | H | 46 | 18.308 | 10.716 | 35.958 | 1.00 | 57.18 | O |
| ATOM | 3955 | N | TRP | H | 47 | 19.963 | 11.630 | 37.161 | 1.00 | 53.89 | N |
| ATOM | 3956 | CA | TRP | H | 47 | 19.242 | 11.444 | 38.424 | 1.00 | 53.72 | C |
| ATOM | 3958 | CB | TRP | H | 47 | 20.182 | 11.565 | 39.635 | 1.00 | 52.58 | C |
| ATOM | 3961 | CG | TRP | H | 47 | 19.435 | 11.666 | 40.879 | 1.00 | 50.71 | C |
| ATOM | 3962 | CD1 | TRP | H | 47 | 18.956 | 10.642 | 41.637 | 1.00 | 50.80 | C |
| ATOM | 3964 | NE1 | TRP | H | 47 | 18.274 | 11.135 | 42.718 | 1.00 | 48.04 | N |
| ATOM | 3966 | CE2 | TRP | H | 47 | 18.285 | 12.503 | 42.656 | 1.00 | 51.75 | C |
| ATOM | 3967 | CD2 | TRP | H | 47 | 19.009 | 12.867 | 41.507 | 1.00 | 53.78 | C |
| ATOM | 3968 | CE3 | TRP | H | 47 | 19.177 | 14.224 | 41.216 | 1.00 | 52.61 | C |
| ATOM | 3970 | CZ3 | TRP | H | 47 | 18.617 | 15.154 | 42.062 | 1.00 | 51.30 | C |
| ATOM | 3972 | CH2 | TRP | H | 47 | 17.886 | 14.762 | 43.184 | 1.00 | 50.32 | C |
| ATOM | 3974 | CZ2 | TRP | H | 47 | 17.714 | 13.445 | 43.500 | 1.00 | 53.66 | C |
| ATOM | 3976 | C | TRP | H | 47 | 18.119 | 12.486 | 38.512 | 1.00 | 53.45 | C |
| ATOM | 3977 | O | TRP | H | 47 | 18.337 | 13.670 | 38.220 | 1.00 | 54.17 | O |
| ATOM | 3979 | N | ILE | H | 48 | 16.924 | 12.056 | 38.906 | 1.00 | 53.21 | N |
| ATOM | 3980 | CA | ILE | H | 48 | 15.785 | 12.981 | 38.988 | 1.00 | 53.31 | C |

-continued

| | | | | | | | | | | |
|---|---|---|---|---|---|---|---|---|---|---|
| ATOM | 3982 | CB | ILE | H | 48 | 14.741 | 12.734 | 37.881 | 1.00 | 51.93 C |
| ATOM | 3984 | CG1 | ILE | H | 48 | 14.315 | 11.266 | 37.851 | 1.00 | 51.93 C |
| ATOM | 3987 | CD1 | ILE | H | 48 | 13.205 | 10.986 | 36.853 | 1.00 | 54.53 C |
| ATOM | 3991 | CG2 | ILE | H | 48 | 15.290 | 13.171 | 36.542 | 1.00 | 53.73 C |
| ATOM | 3995 | C | ILE | H | 48 | 15.028 | 12.975 | 40.297 | 1.00 | 53.62 C |
| ATOM | 3996 | O | ILE | H | 48 | 14.338 | 13.948 | 40.607 | 1.00 | 53.55 O |
| ATOM | 3998 | N | GLY | H | 49 | 15.116 | 11.883 | 41.049 | 1.00 | 54.16 N |
| ATOM | 3999 | CA | GLY | H | 49 | 14.315 | 11.749 | 42.262 | 1.00 | 53.84 C |
| ATOM | 4002 | C | GLY | H | 49 | 14.977 | 10.899 | 43.324 | 1.00 | 54.20 C |
| ATOM | 4003 | O | GLY | H | 49 | 15.670 | 9.919 | 43.022 | 1.00 | 55.43 O |
| ATOM | 4005 | N | VAL | H | 50 | 14.750 | 11.289 | 44.572 | 1.00 | 53.42 N |
| ATOM | 4006 | CA | VAL | H | 50 | 15.205 | 10.542 | 45.721 | 1.00 | 54.34 C |
| ATOM | 4008 | CB | VAL | H | 50 | 16.579 | 11.083 | 46.218 | 1.00 | 54.61 C |
| ATOM | 4010 | CG1 | VAL | H | 50 | 16.465 | 12.522 | 46.717 | 1.00 | 53.17 C |
| ATOM | 4014 | CG2 | VAL | H | 50 | 17.151 | 10.175 | 47.300 | 1.00 | 54.06 C |
| ATOM | 4018 | C | VAL | H | 50 | 14.150 | 10.628 | 46.840 | 1.00 | 55.50 C |
| ATOM | 4019 | O | VAL | H | 50 | 13.432 | 11.635 | 46.945 | 1.00 | 54.71 O |
| ATOM | 4021 | N | ILE | H | 51 | 14.067 | 9.567 | 47.653 | 1.00 | 54.88 N |
| ATOM | 4022 | CA | ILE | H | 51 | 13.206 | 9.525 | 48.850 | 1.00 | 53.35 C |
| ATOM | 4024 | CB | ILE | H | 51 | 11.815 | 8.922 | 48.542 | 1.00 | 52.77 C |
| ATOM | 4026 | CG1 | ILE | H | 51 | 10.865 | 9.075 | 49.736 | 1.00 | 53.45 C |
| ATOM | 4029 | CD1 | ILE | H | 51 | 9.419 | 8.785 | 49.378 | 1.00 | 51.87 C |
| ATOM | 4033 | CG2 | ILE | H | 51 | 11.925 | 7.456 | 48.142 | 1.00 | 54.42 C |
| ATOM | 4037 | C | ILE | H | 51 | 13.919 | 8.724 | 49.943 | 1.00 | 53.48 C |
| ATOM | 4038 | O | ILE | H | 51 | 14.509 | 7.685 | 49.667 | 1.00 | 53.93 O |
| ATOM | 4040 | N | SER | H | 52 | 13.868 | 9.222 | 51.177 | 1.00 | 53.39 N |
| ATOM | 4041 | CA | SER | H | 52 | 14.720 | 8.725 | 52.261 | 1.00 | 52.60 C |
| ATOM | 4043 | CB | SER | H | 52 | 15.337 | 9.910 | 53.029 | 1.00 | 52.57 C |
| ATOM | 4046 | OG | SER | H | 52 | 16.207 | 9.490 | 54.078 | 1.00 | 50.59 O |
| ATOM | 4048 | C | SER | H | 52 | 13.969 | 7.823 | 53.227 | 1.00 | 52.36 C |
| ATOM | 4049 | O | SER | H | 52 | 12.773 | 7.610 | 53.102 | 1.00 | 54.55 O |
| ATOM | 4051 | N | VAL | H | 53 | 14.695 | 7.310 | 54.207 | 1.00 | 52.51 N |
| ATOM | 4052 | CA | VAL | H | 53 | 14.135 | 6.431 | 55.223 | 1.00 | 52.84 C |
| ATOM | 4054 | CB | VAL | H | 53 | 15.272 | 5.667 | 55.964 | 1.00 | 53.27 C |
| ATOM | 4056 | CG1 | VAL | H | 53 | 16.249 | 6.620 | 56.672 | 1.00 | 54.13 C |
| ATOM | 4060 | CG2 | VAL | H | 53 | 16.036 | 4.814 | 54.990 | 1.00 | 52.80 C |
| ATOM | 4064 | C | VAL | H | 53 | 13.217 | 7.158 | 56.230 | 1.00 | 53.50 C |
| ATOM | 4065 | O | VAL | H | 53 | 13.110 | 8.397 | 56.241 | 1.00 | 52.19 O |
| ATOM | 4067 | N | LYS | H | 54 | 12.545 | 6.361 | 57.060 | 1.00 | 54.84 N |
| ATOM | 4068 | CA | LYS | H | 54 | 11.631 | 6.861 | 58.088 | 1.00 | 54.42 C |
| ATOM | 4070 | CB | LYS | H | 54 | 11.018 | 5.685 | 58.846 | 1.00 | 54.08 C |
| ATOM | 4073 | CG | LYS | H | 54 | 9.967 | 6.062 | 59.887 | 1.00 | 56.89 C |
| ATOM | 4076 | CD | LYS | H | 54 | 10.081 | 5.197 | 61.154 | 1.00 | 57.07 C |
| ATOM | 4079 | CE | LYS | H | 54 | 8.962 | 5.500 | 62.151 | 1.00 | 57.48 C |
| ATOM | 4082 | NZ | LYS | H | 54 | 8.849 | 4.444 | 63.192 | 1.00 | 58.62 N |
| ATOM | 4086 | C | LYS | H | 54 | 12.335 | 7.797 | 59.076 | 1.00 | 53.83 C |
| ATOM | 4087 | O | LYS | H | 54 | 11.767 | 8.800 | 59.494 | 1.00 | 52.64 O |
| ATOM | 4089 | N | SER | H | 55 | 13.573 | 7.485 | 59.444 | 1.00 | 55.82 N |
| ATOM | 4090 | CA | SER | H | 55 | 14.296 | 8.314 | 60.414 | 1.00 | 56.55 C |
| ATOM | 4092 | CB | SER | H | 55 | 15.515 | 7.574 | 61.001 | 1.00 | 56.38 C |
| ATOM | 4095 | OG | SER | H | 55 | 16.585 | 7.446 | 60.077 | 1.00 | 60.01 O |
| ATOM | 4097 | C | SER | H | 55 | 14.674 | 9.690 | 59.839 | 1.00 | 56.53 C |
| ATOM | 4098 | O | SER | H | 55 | 15.064 | 10.577 | 60.584 | 1.00 | 58.47 O |
| ATOM | 4100 | N | GLU | H | 56 | 14.546 | 9.870 | 58.527 | 1.00 | 57.07 N |
| ATOM | 4101 | CA | GLU | H | 56 | 14.610 | 11.209 | 57.913 | 1.00 | 58.15 C |
| ATOM | 4103 | CB | GLU | H | 56 | 15.557 | 11.211 | 56.708 | 1.00 | 57.35 C |
| ATOM | 4106 | CG | GLU | H | 56 | 17.022 | 11.218 | 57.083 | 1.00 | 58.37 C |
| ATOM | 4109 | CD | GLU | H | 56 | 17.899 | 11.848 | 56.006 | 1.00 | 62.26 C |
| ATOM | 4110 | OE1 | GLU | H | 56 | 17.802 | 11.443 | 54.820 | 1.00 | 58.50 O |
| ATOM | 4111 | OE2 | GLU | H | 56 | 18.690 | 12.754 | 56.358 | 1.00 | 71.61 O |
| ATOM | 4112 | C | GLU | H | 56 | 13.210 | 11.716 | 57.502 | 1.00 | 57.12 C |
| ATOM | 4113 | O | GLU | H | 56 | 13.074 | 12.711 | 56.781 | 1.00 | 53.66 O |
| ATOM | 4115 | N | ASN | H | 57 | 12.188 | 11.026 | 58.001 | 1.00 | 57.56 N |
| ATOM | 4116 | CA | ASN | H | 57 | 10.781 | 11.347 | 57.756 | 1.00 | 57.52 C |
| ATOM | 4118 | CB | ASN | H | 57 | 10.403 | 12.689 | 58.390 | 1.00 | 56.72 C |
| ATOM | 4121 | CG | ASN | H | 57 | 10.492 | 12.653 | 59.895 | 1.00 | 55.01 C |
| ATOM | 4122 | OD1 | ASN | H | 57 | 9.794 | 11.894 | 60.551 | 1.00 | 56.76 O |
| ATOM | 4123 | ND2 | ASN | H | 57 | 11.366 | 13.457 | 60.444 | 1.00 | 51.60 N |
| ATOM | 4126 | C | ASN | H | 57 | 10.425 | 11.308 | 56.284 | 1.00 | 58.12 C |
| ATOM | 4127 | O | ASN | H | 57 | 9.737 | 12.204 | 55.773 | 1.00 | 59.67 O |
| ATOM | 4129 | N | TYR | H | 58 | 10.906 | 10.273 | 55.600 | 1.00 | 56.23 N |
| ATOM | 4130 | CA | TYR | H | 58 | 10.567 | 10.075 | 54.199 | 1.00 | 55.76 C |
| ATOM | 4132 | CB | TYR | H | 58 | 9.114 | 9.597 | 54.095 | 1.00 | 56.09 C |
| ATOM | 4135 | CG | TYR | H | 58 | 8.885 | 8.332 | 54.868 | 1.00 | 55.13 C |
| ATOM | 4136 | CD1 | TYR | H | 58 | 9.609 | 7.189 | 54.566 | 1.00 | 57.73 C |
| ATOM | 4138 | CE1 | TYR | H | 58 | 9.433 | 6.020 | 55.271 | 1.00 | 61.32 C |
| ATOM | 4140 | CZ | TYR | H | 58 | 8.519 | 5.977 | 56.302 | 1.00 | 60.40 C |
| ATOM | 4141 | OH | TYR | H | 58 | 8.358 | 4.795 | 56.987 | 1.00 | 57.92 O |
| ATOM | 4143 | CE2 | TYR | H | 58 | 7.784 | 7.103 | 56.627 | 1.00 | 56.82 C |

-continued

| ATOM | 4145 | CD2 | TYR | H | 58 | 7.975 | 8.274 | 55.908 | 1.00 | 55.38 | C |
|------|------|-----|-----|---|----|-------|-------|--------|------|-------|---|
| ATOM | 4147 | C | TYR | H | 58 | 10.791 | 11.338 | 53.371 | 1.00 | 54.33 | C |
| ATOM | 4148 | O | TYR | H | 58 | 10.063 | 11.604 | 52.420 | 1.00 | 55.27 | O |
| ATOM | 4150 | N | GLY | H | 59 | 11.814 | 12.103 | 53.739 | 1.00 | 53.44 | N |
| ATOM | 4151 | CA | GLY | H | 59 | 12.173 | 13.319 | 53.032 | 1.00 | 53.86 | C |
| ATOM | 4154 | C | GLY | H | 59 | 12.521 | 13.029 | 51.583 | 1.00 | 53.68 | C |
| ATOM | 4155 | O | GLY | H | 59 | 13.165 | 12.020 | 51.282 | 1.00 | 52.58 | O |
| ATOM | 4157 | N | ALA | H | 60 | 12.080 | 13.913 | 50.689 | 1.00 | 52.83 | N |
| ATOM | 4158 | CA | ALA | H | 60 | 12.232 | 13.701 | 49.262 | 1.00 | 52.99 | C |
| ATOM | 4160 | CB | ALA | H | 60 | 10.890 | 13.456 | 48.633 | 1.00 | 53.67 | C |
| ATOM | 4164 | C | ALA | H | 60 | 12.882 | 14.898 | 48.633 | 1.00 | 51.87 | C |
| ATOM | 4165 | O | ALA | H | 60 | 12.797 | 15.989 | 49.191 | 1.00 | 52.10 | O |
| ATOM | 4167 | N | ASN | H | 61 | 13.540 | 14.678 | 47.486 | 1.00 | 52.93 | N |
| ATOM | 4168 | CA | ASN | H | 61 | 14.198 | 15.752 | 46.711 | 1.00 | 53.25 | C |
| ATOM | 4170 | CB | ASN | H | 61 | 15.607 | 16.027 | 47.251 | 1.00 | 51.65 | C |
| ATOM | 4173 | CG | ASN | H | 61 | 15.936 | 17.513 | 47.317 | 1.00 | 55.58 | C |
| ATOM | 4174 | OD1 | ASN | H | 61 | 16.572 | 17.976 | 48.270 | 1.00 | 58.39 | O |
| ATOM | 4175 | ND2 | ASN | H | 61 | 15.503 | 18.268 | 46.311 | 1.00 | 50.08 | N |
| ATOM | 4178 | C | ASN | H | 61 | 14.250 | 15.418 | 45.208 | 1.00 | 54.37 | C |
| ATOM | 4179 | O | ASN | H | 61 | 14.214 | 14.254 | 44.822 | 1.00 | 56.21 | O |
| ATOM | 4181 | N | TYR | H | 62 | 14.321 | 16.448 | 44.366 | 1.00 | 54.90 | N |
| ATOM | 4182 | CA | TYR | H | 62 | 14.248 | 16.282 | 42.912 | 1.00 | 53.39 | C |
| ATOM | 4184 | CB | TYR | H | 62 | 12.856 | 16.731 | 42.457 | 1.00 | 51.38 | C |
| ATOM | 4187 | CG | TYR | H | 62 | 11.762 | 15.994 | 43.186 | 1.00 | 51.30 | C |
| ATOM | 4188 | CD1 | TYR | H | 62 | 11.241 | 16.483 | 44.385 | 1.00 | 45.49 | C |
| ATOM | 4190 | CE1 | TYR | H | 62 | 10.251 | 15.788 | 45.064 | 1.00 | 47.65 | C |
| ATOM | 4192 | CZ | TYR | H | 62 | 9.781 | 14.581 | 44.548 | 1.00 | 49.19 | C |
| ATOM | 4193 | OH | TYR | H | 62 | 8.807 | 13.882 | 45.202 | 1.00 | 48.16 | O |
| ATOM | 4195 | CE2 | TYR | H | 62 | 10.285 | 14.078 | 43.371 | 1.00 | 49.98 | C |
| ATOM | 4197 | CD2 | TYR | H | 62 | 11.278 | 14.777 | 42.701 | 1.00 | 51.03 | C |
| ATOM | 4199 | C | TYR | H | 62 | 15.316 | 17.054 | 42.118 | 1.00 | 53.24 | C |
| ATOM | 4200 | O | TYR | H | 62 | 15.916 | 18.008 | 42.612 | 1.00 | 52.50 | O |
| ATOM | 4202 | N | ALA | H | 63 | 15.541 | 16.627 | 40.879 | 1.00 | 53.98 | N |
| ATOM | 4203 | CA | ALA | H | 63 | 16.221 | 17.462 | 39.884 | 1.00 | 55.25 | C |
| ATOM | 4205 | CB | ALA | H | 63 | 16.659 | 16.617 | 38.708 | 1.00 | 54.70 | C |
| ATOM | 4209 | C | ALA | H | 63 | 15.286 | 18.602 | 39.407 | 1.00 | 56.77 | C |
| ATOM | 4210 | O | ALA | H | 63 | 14.079 | 18.406 | 39.239 | 1.00 | 56.91 | O |
| ATOM | 4212 | N | GLU | H | 64 | 15.836 | 19.789 | 39.168 | 1.00 | 56.51 | N |
| ATOM | 4213 | CA | GLU | H | 64 | 14.994 | 20.932 | 38.802 | 1.00 | 56.86 | C |
| ATOM | 4215 | CB | GLU | H | 64 | 15.802 | 22.237 | 38.752 | 1.00 | 57.10 | C |
| ATOM | 4218 | CG | GLU | H | 64 | 16.589 | 22.572 | 40.018 | 1.00 | 56.07 | C |
| ATOM | 4221 | CD | GLU | H | 64 | 15.771 | 22.446 | 41.281 | 1.00 | 54.00 | C |
| ATOM | 4222 | OE1 | GLU | H | 64 | 16.361 | 22.118 | 42.329 | 1.00 | 53.38 | O |
| ATOM | 4223 | OE2 | GLU | H | 64 | 14.546 | 22.667 | 41.223 | 1.00 | 52.25 | O |
| ATOM | 4224 | C | GLU | H | 64 | 14.249 | 20.764 | 37.477 | 1.00 | 56.81 | C |
| ATOM | 4225 | O | GLU | H | 64 | 13.353 | 21.540 | 37.183 | 1.00 | 59.92 | O |
| ATOM | 4227 | N | SER | H | 65 | 14.623 | 19.780 | 36.672 | 1.00 | 55.43 | N |
| ATOM | 4228 | CA | SER | H | 65 | 13.892 | 19.501 | 35.445 | 1.00 | 55.11 | C |
| ATOM | 4230 | CB | SER | H | 65 | 14.669 | 18.527 | 34.574 | 1.00 | 54.51 | C |
| ATOM | 4233 | OG | SER | H | 65 | 14.942 | 17.329 | 35.277 | 1.00 | 56.31 | O |
| ATOM | 4235 | C | SER | H | 65 | 12.517 | 18.913 | 35.713 | 1.00 | 56.54 | C |
| ATOM | 4236 | O | SER | H | 65 | 11.627 | 19.048 | 34.878 | 1.00 | 60.25 | O |
| ATOM | 4238 | N | VAL | H | 66 | 12.352 | 18.268 | 36.870 | 1.00 | 55.56 | N |
| ATOM | 4239 | CA | VAL | H | 66 | 11.148 | 17.498 | 37.186 | 1.00 | 53.62 | C |
| ATOM | 4241 | CB | VAL | H | 66 | 11.497 | 16.020 | 37.346 | 1.00 | 53.48 | C |
| ATOM | 4243 | CG1 | VAL | H | 66 | 12.080 | 15.482 | 36.067 | 1.00 | 56.93 | C |
| ATOM | 4247 | CG2 | VAL | H | 66 | 12.467 | 15.813 | 38.485 | 1.00 | 54.82 | C |
| ATOM | 4251 | C | VAL | H | 66 | 10.353 | 17.949 | 38.433 | 1.00 | 53.53 | C |
| ATOM | 4252 | O | VAL | H | 66 | 9.247 | 17.447 | 38.676 | 1.00 | 52.87 | O |
| ATOM | 4254 | N | ARG | H | 67 | 10.888 | 18.893 | 39.207 | 1.00 | 52.02 | N |
| ATOM | 4255 | CA | ARG | H | 67 | 10.225 | 19.323 | 40.428 | 1.00 | 51.19 | C |
| ATOM | 4257 | CB | ARG | H | 67 | 11.082 | 20.301 | 41.212 | 1.00 | 49.41 | C |
| ATOM | 4260 | CG | ARG | H | 67 | 10.703 | 20.369 | 42.673 | 1.00 | 49.96 | C |
| ATOM | 4263 | CD | ARG | H | 67 | 11.358 | 21.550 | 43.380 | 1.00 | 54.84 | C |
| ATOM | 4266 | NE | ARG | H | 67 | 12.801 | 21.393 | 43.493 | 1.00 | 56.17 | N |
| ATOM | 4268 | CZ | ARG | H | 67 | 13.408 | 20.610 | 44.377 | 1.00 | 59.32 | C |
| ATOM | 4269 | NH1 | ARG | H | 67 | 14.730 | 20.534 | 44.359 | 1.00 | 64.31 | N |
| ATOM | 4272 | NH2 | ARG | H | 67 | 12.716 | 19.912 | 45.274 | 1.00 | 55.70 | N |
| ATOM | 4275 | C | ARG | H | 67 | 8.891 | 19.969 | 40.122 | 1.00 | 51.27 | C |
| ATOM | 4276 | O | ARG | H | 67 | 8.801 | 20.857 | 39.268 | 1.00 | 52.23 | O |
| ATOM | 4278 | N | GLY | H | 68 | 7.862 | 19.510 | 40.832 | 1.00 | 52.42 | N |
| ATOM | 4279 | CA | GLY | H | 68 | 6.503 | 20.039 | 40.711 | 1.00 | 52.66 | C |
| ATOM | 4282 | C | GLY | H | 68 | 5.699 | 19.349 | 39.622 | 1.00 | 53.68 | C |
| ATOM | 4283 | O | GLY | H | 68 | 4.521 | 19.673 | 39.409 | 1.00 | 55.43 | O |
| ATOM | 4285 | N | ARG | H | 69 | 6.346 | 18.419 | 38.919 | 1.00 | 52.71 | N |
| ATOM | 4286 | CA | ARG | H | 69 | 5.698 | 17.625 | 37.881 | 1.00 | 53.37 | C |
| ATOM | 4288 | CB | ARG | H | 69 | 6.392 | 17.866 | 36.547 | 1.00 | 53.70 | C |
| ATOM | 4291 | CG | ARG | H | 69 | 6.292 | 19.303 | 36.063 | 1.00 | 51.13 | C |
| ATOM | 4294 | CD | ARG | H | 69 | 7.483 | 19.685 | 35.184 | 1.00 | 53.14 | C |

-continued

| | | | | | | | | | | |
|---|---|---|---|---|---|---|---|---|---|---|
| ATOM | 4297 | NE | ARG | H | 69 | 7.428 | 19.013 | 33.886 | 1.00 | 56.05 N |
| ATOM | 4299 | CZ | ARG | H | 69 | 8.304 | 18.120 | 33.425 | 1.00 | 53.79 C |
| ATOM | 4300 | NH1 | ARG | H | 69 | 9.377 | 17.763 | 34.117 | 1.00 | 50.39 N |
| ATOM | 4303 | NH2 | ARG | H | 69 | 8.110 | 17.588 | 32.232 | 1.00 | 51.24 N |
| ATOM | 4306 | C | ARG | H | 69 | 5.752 | 16.146 | 38.221 | 1.00 | 53.87 C |
| ATOM | 4307 | O | ARG | H | 69 | 4.798 | 15.407 | 37.991 | 1.00 | 55.13 O |
| ATOM | 4309 | N | PHE | H | 70 | 6.893 | 15.720 | 38.748 | 1.00 | 54.83 N |
| ATOM | 4310 | CA | PHE | H | 70 | 7.119 | 14.337 | 39.137 | 1.00 | 54.86 C |
| ATOM | 4312 | CB | PHE | H | 70 | 8.495 | 13.875 | 38.625 | 1.00 | 53.83 C |
| ATOM | 4315 | CG | PHE | H | 70 | 8.574 | 13.666 | 37.117 | 1.00 | 53.73 C |
| ATOM | 4316 | CD1 | PHE | H | 70 | 7.621 | 14.190 | 36.245 | 1.00 | 55.06 C |
| ATOM | 4318 | CE1 | PHE | H | 70 | 7.708 | 13.992 | 34.883 | 1.00 | 52.84 C |
| ATOM | 4320 | CZ | PHE | H | 70 | 8.751 | 13.282 | 34.358 | 1.00 | 49.93 C |
| ATOM | 4322 | CE2 | PHE | H | 70 | 9.711 | 12.761 | 35.199 | 1.00 | 55.26 C |
| ATOM | 4324 | CD2 | PHE | H | 70 | 9.624 | 12.957 | 36.573 | 1.00 | 54.83 C |
| ATOM | 4326 | C | PHE | H | 70 | 7.085 | 14.284 | 40.657 | 1.00 | 56.58 C |
| ATOM | 4327 | O | PHE | H | 70 | 7.650 | 15.152 | 41.325 | 1.00 | 60.03 O |
| ATOM | 4329 | N | THR | H | 71 | 6.424 | 13.281 | 41.215 | 1.00 | 56.18 N |
| ATOM | 4330 | CA | THR | H | 71 | 6.453 | 13.076 | 42.657 | 1.00 | 56.15 C |
| ATOM | 4332 | CB | THR | H | 71 | 5.082 | 13.333 | 43.264 | 1.00 | 57.19 C |
| ATOM | 4334 | OG1 | THR | H | 71 | 4.725 | 14.704 | 43.054 | 1.00 | 59.72 O |
| ATOM | 4336 | CG2 | THR | H | 71 | 5.068 | 13.010 | 44.759 | 1.00 | 55.03 C |
| ATOM | 4340 | C | THR | H | 71 | 6.865 | 11.649 | 42.972 | 1.00 | 57.89 C |
| ATOM | 4341 | O | THR | H | 71 | 6.399 | 10.705 | 42.330 | 1.00 | 58.11 O |
| ATOM | 4343 | N | ILE | H | 72 | 7.727 | 11.504 | 43.977 | 1.00 | 58.52 N |
| ATOM | 4344 | CA | ILE | H | 72 | 8.215 | 10.198 | 44.434 | 1.00 | 56.69 C |
| ATOM | 4346 | CB | ILE | H | 72 | 9.763 | 10.185 | 44.490 | 1.00 | 57.00 C |
| ATOM | 4348 | CG1 | ILE | H | 72 | 10.293 | 8.757 | 44.597 | 1.00 | 60.26 C |
| ATOM | 4351 | CD1 | ILE | H | 72 | 11.817 | 8.686 | 44.564 | 1.00 | 60.94 C |
| ATOM | 4355 | CG2 | ILE | H | 72 | 10.289 | 11.024 | 45.643 | 1.00 | 58.10 C |
| ATOM | 4359 | C | ILE | H | 72 | 7.612 | 9.864 | 45.799 | 1.00 | 53.96 C |
| ATOM | 4360 | O | ILE | H | 72 | 7.488 | 10.734 | 46.647 | 1.00 | 55.60 O |
| ATOM | 4362 | N | SER | H | 73 | 7.207 | 8.613 | 45.994 | 1.00 | 53.36 N |
| ATOM | 4363 | CA | SER | H | 73 | 6.670 | 8.160 | 47.284 | 1.00 | 53.31 C |
| ATOM | 4365 | CB | SER | H | 73 | 5.154 | 8.279 | 47.301 | 1.00 | 51.35 C |
| ATOM | 4368 | OG | SER | H | 73 | 4.614 | 7.733 | 46.124 | 1.00 | 55.02 O |
| ATOM | 4370 | C | SER | H | 73 | 7.094 | 6.725 | 47.552 | 1.00 | 52.52 C |
| ATOM | 4371 | O | SER | H | 73 | 7.775 | 6.106 | 46.728 | 1.00 | 53.63 O |
| ATOM | 4373 | N | ARG | H | 74 | 6.725 | 6.195 | 48.710 | 1.00 | 51.43 N |
| ATOM | 4374 | CA | ARG | H | 74 | 7.070 | 4.812 | 49.010 | 1.00 | 52.90 C |
| ATOM | 4376 | CB | ARG | H | 74 | 8.498 | 4.728 | 49.566 | 1.00 | 53.14 C |
| ATOM | 4379 | CG | ARG | H | 74 | 8.693 | 5.350 | 50.950 | 1.00 | 52.48 C |
| ATOM | 4382 | CD | ARG | H | 74 | 10.188 | 5.505 | 51.302 | 1.00 | 53.69 C |
| ATOM | 4385 | NE | ARG | H | 74 | 10.863 | 4.218 | 51.487 | 1.00 | 54.77 N |
| ATOM | 4387 | CZ | ARG | H | 74 | 12.183 | 4.060 | 51.565 | 1.00 | 57.39 C |
| ATOM | 4388 | NH1 | ARG | H | 74 | 13.000 | 5.105 | 51.483 | 1.00 | 60.70 N |
| ATOM | 4391 | NH2 | ARG | H | 74 | 12.692 | 2.848 | 51.714 | 1.00 | 59.30 N |
| ATOM | 4394 | C | ARG | H | 74 | 6.111 | 4.152 | 49.977 | 1.00 | 52.64 C |
| ATOM | 4395 | O | ARG | H | 74 | 5.481 | 4.820 | 50.791 | 1.00 | 53.87 O |
| ATOM | 4397 | N | ASP | H | 75 | 6.020 | 2.830 | 49.883 | 1.00 | 52.49 N |
| ATOM | 4398 | CA | ASP | H | 75 | 5.254 | 2.028 | 50.829 | 1.00 | 52.32 C |
| ATOM | 4400 | CB | ASP | H | 75 | 4.044 | 1.429 | 50.125 | 1.00 | 51.92 C |
| ATOM | 4403 | CG | ASP | H | 75 | 3.049 | 0.833 | 51.089 | 1.00 | 53.70 C |
| ATOM | 4404 | OD1 | ASP | H | 75 | 3.464 | 0.322 | 52.152 | 1.00 | 51.27 O |
| ATOM | 4405 | OD2 | ASP | H | 75 | 1.844 | 0.873 | 50.774 | 1.00 | 56.20 O |
| ATOM | 4406 | C | ASP | H | 75 | 6.139 | 0.924 | 51.418 | 1.00 | 52.67 C |
| ATOM | 4407 | O | ASP | H | 75 | 6.259 | −0.160 | 50.838 | 1.00 | 52.67 O |
| ATOM | 4409 | N | ASP | H | 76 | 6.758 | 1.202 | 52.568 | 1.00 | 52.46 N |
| ATOM | 4410 | CA | ASP | H | 76 | 7.703 | 0.264 | 53.184 | 1.00 | 52.19 C |
| ATOM | 4412 | CB | ASP | H | 76 | 8.272 | 0.836 | 54.489 | 1.00 | 52.72 C |
| ATOM | 4415 | CG | ASP | H | 76 | 9.379 | 1.863 | 54.264 | 1.00 | 53.94 C |
| ATOM | 4416 | OD1 | ASP | H | 76 | 9.929 | 1.939 | 53.146 | 1.00 | 53.65 O |
| ATOM | 4417 | OD2 | ASP | H | 76 | 9.723 | 2.582 | 55.224 | 1.00 | 54.29 O |
| ATOM | 4418 | C | ASP | H | 76 | 7.052 | −1.100 | 53.442 | 1.00 | 53.19 C |
| ATOM | 4419 | O | ASP | H | 76 | 7.680 | −2.142 | 53.256 | 1.00 | 53.58 O |
| ATOM | 4421 | N | SER | H | 77 | 5.782 | −1.091 | 53.842 | 1.00 | 54.06 N |
| ATOM | 4422 | CA | SER | H | 77 | 5.055 | −2.330 | 54.139 | 1.00 | 52.40 C |
| ATOM | 4424 | CB | SER | H | 77 | 3.737 | −2.015 | 54.843 | 1.00 | 49.84 C |
| ATOM | 4427 | OG | SER | H | 77 | 2.786 | −1.555 | 53.906 | 1.00 | 49.87 O |
| ATOM | 4429 | C | SER | H | 77 | 4.795 | −3.203 | 52.896 | 1.00 | 51.23 C |
| ATOM | 4430 | O | SER | H | 77 | 4.546 | −4.406 | 53.028 | 1.00 | 50.69 O |
| ATOM | 4432 | N | LYS | H | 78 | 4.837 | −2.598 | 51.710 | 1.00 | 50.63 N |
| ATOM | 4433 | CA | LYS | H | 78 | 4.704 | −3.336 | 50.444 | 1.00 | 52.65 C |
| ATOM | 4435 | CB | LYS | H | 78 | 3.556 | −2.753 | 49.598 | 1.00 | 52.68 C |
| ATOM | 4438 | CG | LYS | H | 78 | 2.167 | −3.315 | 49.926 | 1.00 | 58.32 C |
| ATOM | 4441 | CD | LYS | H | 78 | 1.083 | −2.835 | 48.937 | 1.00 | 58.24 C |
| ATOM | 4444 | CE | LYS | H | 78 | 0.847 | −1.321 | 49.052 | 1.00 | 65.58 C |
| ATOM | 4447 | NZ | LYS | H | 78 | −0.474 | −0.849 | 48.507 | 1.00 | 65.69 N |
| ATOM | 4451 | C | LYS | H | 78 | 6.006 | −3.293 | 49.641 | 1.00 | 51.77 C |

-continued

| ATOM | 4452 | O | LYS | H | 78 | 5.987 | −3.500 | 48.436 | 1.00 | 49.77 | O |
|---|---|---|---|---|---|---|---|---|---|---|---|
| ATOM | 4454 | N | ASN | H | 79 | 7.126 | −3.020 | 50.317 | 1.00 | 52.69 | N |
| ATOM | 4455 | CA | ASN | H | 79 | 8.454 | −2.872 | 49.687 | 1.00 | 52.41 | C |
| ATOM | 4457 | CB | ASN | H | 79 | 9.226 | −4.205 | 49.718 | 1.00 | 51.45 | C |
| ATOM | 4460 | CG | ASN | H | 79 | 9.598 | −4.638 | 51.134 | 1.00 | 52.85 | C |
| ATOM | 4461 | OD1 | ASN | H | 79 | 10.001 | −3.824 | 51.958 | 1.00 | 55.11 | O |
| ATOM | 4462 | ND2 | ASN | H | 79 | 9.456 | −5.926 | 51.419 | 1.00 | 55.23 | N |
| ATOM | 4465 | C | ASN | H | 79 | 8.438 | −2.292 | 48.261 | 1.00 | 53.98 | C |
| ATOM | 4466 | O | ASN | H | 79 | 9.052 | −2.860 | 47.349 | 1.00 | 55.36 | O |
| ATOM | 4468 | N | THR | H | 80 | 7.767 | −1.146 | 48.090 | 1.00 | 53.60 | N |
| ATOM | 4469 | CA | THR | H | 80 | 7.587 | −0.522 | 46.771 | 1.00 | 52.30 | C |
| ATOM | 4471 | CB | THR | H | 80 | 6.134 | −0.719 | 46.280 | 1.00 | 53.91 | C |
| ATOM | 4473 | OG1 | THR | H | 80 | 5.827 | −2.120 | 46.225 | 1.00 | 52.33 | O |
| ATOM | 4475 | CG2 | THR | H | 80 | 5.914 | −0.074 | 44.893 | 1.00 | 54.14 | C |
| ATOM | 4479 | C | THR | H | 80 | 7.868 | 0.980 | 46.765 | 1.00 | 51.52 | C |
| ATOM | 4480 | O | THR | H | 80 | 7.515 | 1.690 | 47.700 | 1.00 | 52.39 | O |
| ATOM | 4482 | N | VAL | H | 81 | 8.475 | 1.465 | 45.687 | 1.00 | 52.20 | N |
| ATOM | 4483 | CA | VAL | H | 81 | 8.656 | 2.903 | 45.475 | 1.00 | 51.81 | C |
| ATOM | 4485 | CB | VAL | H | 81 | 10.150 | 3.283 | 45.354 | 1.00 | 52.16 | C |
| ATOM | 4487 | CG1 | VAL | H | 81 | 10.811 | 2.602 | 44.172 | 1.00 | 51.14 | C |
| ATOM | 4491 | CG2 | VAL | H | 81 | 10.323 | 4.805 | 45.275 | 1.00 | 53.07 | C |
| ATOM | 4495 | C | VAL | H | 81 | 7.903 | 3.308 | 44.218 | 1.00 | 51.61 | C |
| ATOM | 4496 | O | VAL | H | 81 | 7.889 | 2.561 | 43.248 | 1.00 | 53.26 | O |
| ATOM | 4498 | N | TYR | H | 82 | 7.279 | 4.487 | 44.245 | 1.00 | 52.19 | N |
| ATOM | 4499 | CA | TYR | H | 82 | 6.498 | 4.991 | 43.114 | 1.00 | 52.06 | C |
| ATOM | 4501 | CB | TYR | H | 82 | 5.083 | 5.299 | 43.552 | 1.00 | 50.72 | C |
| ATOM | 4504 | CG | TYR | H | 82 | 4.404 | 4.144 | 44.218 | 1.00 | 50.09 | C |
| ATOM | 4505 | CD1 | TYR | H | 82 | 3.833 | 3.127 | 43.469 | 1.00 | 48.59 | C |
| ATOM | 4507 | CE1 | TYR | H | 82 | 3.203 | 2.069 | 44.084 | 1.00 | 49.96 | C |
| ATOM | 4509 | CZ | TYR | H | 82 | 3.145 | 2.025 | 45.465 | 1.00 | 48.45 | C |
| ATOM | 4510 | OH | TYR | H | 82 | 2.524 | 0.983 | 46.107 | 1.00 | 51.38 | O |
| ATOM | 4512 | CE2 | TYR | H | 82 | 3.706 | 3.024 | 46.217 | 1.00 | 47.82 | C |
| ATOM | 4514 | CD2 | TYR | H | 82 | 4.323 | 4.074 | 45.598 | 1.00 | 46.84 | C |
| ATOM | 4516 | C | TYR | H | 82 | 7.082 | 6.259 | 42.529 | 1.00 | 52.74 | C |
| ATOM | 4517 | O | TYR | H | 82 | 7.774 | 6.997 | 43.226 | 1.00 | 53.39 | O |
| ATOM | 4519 | N | LEU | H | 83 | 6.806 | 6.493 | 41.245 | 1.00 | 52.93 | N |
| ATOM | 4520 | CA | LEU | H | 83 | 7.028 | 7.793 | 40.627 | 1.00 | 54.16 | C |
| ATOM | 4522 | CB | LEU | H | 83 | 8.197 | 7.775 | 39.650 | 1.00 | 54.70 | C |
| ATOM | 4525 | CG | LEU | H | 83 | 8.521 | 9.122 | 38.990 | 1.00 | 54.80 | C |
| ATOM | 4527 | CD1 | LEU | H | 83 | 9.090 | 10.097 | 40.007 | 1.00 | 57.34 | C |
| ATOM | 4531 | CD2 | LEU | H | 83 | 9.497 | 8.937 | 37.821 | 1.00 | 58.27 | C |
| ATOM | 4535 | C | LEU | H | 83 | 5.775 | 8.205 | 39.891 | 1.00 | 54.10 | C |
| ATOM | 4536 | O | LEU | H | 83 | 5.322 | 7.509 | 38.991 | 1.00 | 53.76 | O |
| ATOM | 4538 | N | GLN | H | 84 | 5.233 | 9.351 | 40.285 | 1.00 | 55.40 | N |
| ATOM | 4539 | CA | GLN | H | 84 | 4.024 | 9.905 | 39.705 | 1.00 | 55.25 | C |
| ATOM | 4541 | CB | GLN | H | 84 | 3.123 | 10.470 | 40.808 | 1.00 | 54.66 | C |
| ATOM | 4544 | CG | GLN | H | 84 | 1.861 | 11.151 | 40.325 | 1.00 | 55.13 | C |
| ATOM | 4547 | CD | GLN | H | 84 | 0.886 | 10.190 | 39.690 | 1.00 | 57.62 | C |
| ATOM | 4548 | OE1 | GLN | H | 84 | 0.420 | 9.238 | 40.325 | 1.00 | 60.12 | O |
| ATOM | 4549 | NE2 | GLN | H | 84 | 0.572 | 10.428 | 38.423 | 1.00 | 58.65 | N |
| ATOM | 4552 | C | GLN | H | 84 | 4.458 | 11.001 | 38.748 | 1.00 | 55.58 | C |
| ATOM | 4553 | O | GLN | H | 84 | 5.028 | 12.007 | 39.160 | 1.00 | 56.38 | O |
| ATOM | 4555 | N | MET | H | 85 | 4.196 | 10.793 | 37.467 | 1.00 | 56.10 | N |
| ATOM | 4556 | CA | MET | H | 85 | 4.655 | 11.708 | 36.446 | 1.00 | 56.22 | C |
| ATOM | 4558 | CB | MET | H | 85 | 5.404 | 10.931 | 35.374 | 1.00 | 56.39 | C |
| ATOM | 4561 | CG | MET | H | 85 | 6.554 | 10.126 | 35.912 | 1.00 | 55.02 | C |
| ATOM | 4564 | SD | MET | H | 85 | 7.564 | 9.425 | 34.599 | 1.00 | 55.69 | S |
| ATOM | 4565 | CE | MET | H | 85 | 6.437 | 8.181 | 34.006 | 1.00 | 65.06 | C |
| ATOM | 4569 | C | MET | H | 85 | 3.476 | 12.461 | 35.840 | 1.00 | 57.09 | C |
| ATOM | 4570 | O | MET | H | 85 | 2.667 | 11.877 | 35.100 | 1.00 | 56.63 | O |
| ATOM | 4572 | N | ASN | H | 86 | 3.392 | 13.752 | 36.172 | 1.00 | 55.80 | N |
| ATOM | 4573 | CA | ASN | H | 86 | 2.342 | 14.645 | 35.688 | 1.00 | 54.96 | C |
| ATOM | 4575 | CB | ASN | H | 86 | 1.591 | 15.252 | 36.872 | 1.00 | 54.56 | C |
| ATOM | 4578 | CG | ASN | H | 86 | 0.807 | 14.223 | 37.657 | 1.00 | 54.97 | C |
| ATOM | 4579 | OD1 | ASN | H | 86 | 0.563 | 13.118 | 37.180 | 1.00 | 58.89 | O |
| ATOM | 4580 | ND2 | ASN | H | 86 | 0.403 | 14.584 | 38.867 | 1.00 | 48.38 | N |
| ATOM | 4583 | C | ASN | H | 86 | 2.912 | 15.769 | 34.824 | 1.00 | 55.55 | C |
| ATOM | 4584 | O | ASN | H | 86 | 4.109 | 16.065 | 34.885 | 1.00 | 57.17 | O |
| ATOM | 4586 | N | SER | H | 87 | 2.048 | 16.390 | 34.023 | 1.00 | 54.90 | N |
| ATOM | 4587 | CA | SER | H | 87 | 2.438 | 17.509 | 33.169 | 1.00 | 54.23 | C |
| ATOM | 4589 | CB | SER | H | 87 | 2.870 | 18.711 | 34.011 | 1.00 | 53.82 | C |
| ATOM | 4592 | OG | SER | H | 87 | 1.885 | 19.061 | 34.958 | 1.00 | 52.89 | O |
| ATOM | 4594 | C | SER | H | 87 | 3.569 | 17.106 | 32.246 | 1.00 | 53.30 | C |
| ATOM | 4595 | O | SER | H | 87 | 4.558 | 17.818 | 32.098 | 1.00 | 53.56 | O |
| ATOM | 4597 | N | LEU | H | 88 | 3.419 | 15.954 | 31.620 | 1.00 | 53.53 | N |
| ATOM | 4598 | CA | LEU | H | 88 | 4.496 | 15.411 | 30.811 | 1.00 | 55.13 | C |
| ATOM | 4600 | CB | LEU | H | 88 | 4.195 | 13.969 | 30.411 | 1.00 | 55.58 | C |
| ATOM | 4603 | CG | LEU | H | 88 | 4.303 | 13.013 | 31.602 | 1.00 | 56.69 | C |
| ATOM | 4605 | CD1 | LEU | H | 88 | 3.719 | 11.652 | 31.255 | 1.00 | 59.85 | C |

-continued

| ATOM | 4609 | CD2 | LEU | H | 88 | 5.742 | 12.880 | 32.063 | 1.00 | 53.31 | C |
|---|---|---|---|---|---|---|---|---|---|---|---|
| ATOM | 4613 | C | LEU | H | 88 | 4.797 | 16.264 | 29.582 | 1.00 | 55.36 | C |
| ATOM | 4614 | O | LEU | H | 88 | 3.910 | 16.647 | 28.826 | 1.00 | 55.54 | O |
| ATOM | 4616 | N | LYS | H | 89 | 6.075 | 16.571 | 29.430 | 1.00 | 56.89 | N |
| ATOM | 4617 | CA | LYS | H | 89 | 6.593 | 17.291 | 28.289 | 1.00 | 56.73 | C |
| ATOM | 4619 | CB | LYS | H | 89 | 7.677 | 18.282 | 28.745 | 1.00 | 56.42 | C |
| ATOM | 4622 | CG | LYS | H | 89 | 7.183 | 19.408 | 29.666 | 1.00 | 56.90 | C |
| ATOM | 4625 | CD | LYS | H | 89 | 8.360 | 20.143 | 30.348 | 1.00 | 59.61 | C |
| ATOM | 4628 | CE | LYS | H | 89 | 8.042 | 21.628 | 30.672 | 1.00 | 62.83 | C |
| ATOM | 4631 | NZ | LYS | H | 89 | 7.226 | 21.848 | 31.909 | 1.00 | 64.95 | N |
| ATOM | 4635 | C | LYS | H | 89 | 7.181 | 16.257 | 27.333 | 1.00 | 56.57 | C |
| ATOM | 4636 | O | LYS | H | 89 | 7.568 | 15.159 | 27.751 | 1.00 | 55.89 | O |
| ATOM | 4638 | N | THR | H | 90 | 7.243 | 16.609 | 26.052 | 1.00 | 56.34 | N |
| ATOM | 4639 | CA | THR | H | 90 | 7.896 | 15.761 | 25.050 | 1.00 | 55.88 | C |
| ATOM | 4641 | CB | THR | H | 90 | 7.869 | 16.378 | 23.610 | 1.00 | 55.65 | C |
| ATOM | 4643 | OG1 | THR | H | 90 | 9.055 | 15.993 | 22.913 | 1.00 | 59.72 | O |
| ATOM | 4645 | CG2 | THR | H | 90 | 7.788 | 17.903 | 23.608 | 1.00 | 56.91 | C |
| ATOM | 4649 | C | THR | H | 90 | 9.332 | 15.374 | 25.438 | 1.00 | 54.81 | C |
| ATOM | 4650 | O | THR | H | 90 | 9.747 | 14.239 | 25.218 | 1.00 | 53.84 | O |
| ATOM | 4652 | N | GLU | H | 91 | 10.068 | 16.300 | 26.047 | 1.00 | 55.64 | N |
| ATOM | 4653 | CA | GLU | H | 91 | 11.484 | 16.056 | 26.429 | 1.00 | 56.87 | C |
| ATOM | 4655 | CB | GLU | H | 91 | 12.257 | 17.364 | 26.706 | 1.00 | 57.54 | C |
| ATOM | 4658 | CG | GLU | H | 91 | 11.434 | 18.554 | 27.241 | 1.00 | 64.21 | C |
| ATOM | 4661 | CD | GLU | H | 91 | 10.746 | 19.361 | 26.125 | 1.00 | 69.95 | C |
| ATOM | 4662 | OE1 | GLU | H | 91 | 11.348 | 19.508 | 25.042 | 1.00 | 70.88 | O |
| ATOM | 4663 | OE2 | GLU | H | 91 | 9.608 | 19.850 | 26.327 | 1.00 | 71.83 | O |
| ATOM | 4664 | C | GLU | H | 91 | 11.683 | 15.078 | 27.594 | 1.00 | 57.19 | C |
| ATOM | 4665 | O | GLU | H | 91 | 12.819 | 14.729 | 27.924 | 1.00 | 58.19 | O |
| ATOM | 4667 | N | ASP | H | 92 | 10.592 | 14.629 | 28.209 | 1.00 | 57.31 | N |
| ATOM | 4668 | CA | ASP | H | 92 | 10.663 | 13.575 | 29.213 | 1.00 | 55.45 | C |
| ATOM | 4670 | CB | ASP | H | 92 | 9.405 | 13.567 | 30.070 | 1.00 | 56.63 | C |
| ATOM | 4673 | CG | ASP | H | 92 | 9.185 | 14.859 | 30.815 | 1.00 | 56.78 | C |
| ATOM | 4674 | OD1 | ASP | H | 92 | 10.104 | 15.341 | 31.507 | 1.00 | 53.91 | O |
| ATOM | 4675 | OD2 | ASP | H | 92 | 8.053 | 15.371 | 30.736 | 1.00 | 57.74 | O |
| ATOM | 4676 | C | ASP | H | 92 | 10.796 | 12.188 | 28.584 | 1.00 | 54.42 | C |
| ATOM | 4677 | O | ASP | H | 92 | 10.985 | 11.207 | 29.306 | 1.00 | 53.82 | O |
| ATOM | 4679 | N | THR | H | 93 | 10.660 | 12.077 | 27.263 | 1.00 | 52.40 | N |
| ATOM | 4680 | CA | THR | H | 93 | 10.750 | 10.762 | 26.650 | 1.00 | 53.62 | C |
| ATOM | 4682 | CB | THR | H | 93 | 10.605 | 10.793 | 25.129 | 1.00 | 51.83 | C |
| ATOM | 4684 | OG1 | THR | H | 93 | 9.224 | 10.943 | 24.787 | 1.00 | 55.50 | O |
| ATOM | 4686 | CG2 | THR | H | 93 | 11.088 | 9.509 | 24.524 | 1.00 | 51.40 | C |
| ATOM | 4690 | C | THR | H | 93 | 12.086 | 10.158 | 27.040 | 1.00 | 54.49 | C |
| ATOM | 4691 | O | THR | H | 93 | 13.130 | 10.748 | 26.788 | 1.00 | 56.62 | O |
| ATOM | 4693 | N | ALA | H | 94 | 12.041 | 8.995 | 27.681 | 1.00 | 55.02 | N |
| ATOM | 4694 | CA | ALA | H | 94 | 13.245 | 8.322 | 28.147 | 1.00 | 54.50 | C |
| ATOM | 4696 | CB | ALA | H | 94 | 13.992 | 9.207 | 29.138 | 1.00 | 55.34 | C |
| ATOM | 4700 | C | ALA | H | 94 | 12.905 | 6.993 | 28.799 | 1.00 | 54.91 | C |
| ATOM | 4701 | O | ALA | H | 94 | 11.755 | 6.733 | 29.151 | 1.00 | 56.76 | O |
| ATOM | 4703 | N | VAL | H | 95 | 13.923 | 6.154 | 28.954 | 1.00 | 54.19 | N |
| ATOM | 4704 | CA | VAL | H | 95 | 13.817 | 4.972 | 29.787 | 1.00 | 53.16 | C |
| ATOM | 4706 | CB | VAL | H | 95 | 14.904 | 3.945 | 29.443 | 1.00 | 51.92 | C |
| ATOM | 4708 | CG1 | VAL | H | 95 | 14.937 | 2.804 | 30.472 | 1.00 | 52.53 | C |
| ATOM | 4712 | CG2 | VAL | H | 95 | 14.657 | 3.397 | 28.063 | 1.00 | 50.97 | C |
| ATOM | 4716 | C | VAL | H | 95 | 13.958 | 5.430 | 31.227 | 1.00 | 53.10 | C |
| ATOM | 4717 | O | VAL | H | 95 | 14.866 | 6.198 | 31.536 | 1.00 | 53.44 | O |
| ATOM | 4719 | N | TYR | H | 96 | 13.059 | 4.963 | 32.094 | 1.00 | 52.44 | N |
| ATOM | 4720 | CA | TYR | H | 96 | 13.074 | 5.335 | 33.510 | 1.00 | 52.33 | C |
| ATOM | 4722 | CB | TYR | H | 96 | 11.703 | 5.872 | 33.940 | 1.00 | 51.22 | C |
| ATOM | 4725 | CG | TYR | H | 96 | 11.478 | 7.299 | 33.484 | 1.00 | 49.91 | C |
| ATOM | 4726 | CD1 | TYR | H | 96 | 11.312 | 7.602 | 32.137 | 1.00 | 50.04 | C |
| ATOM | 4728 | CE1 | TYR | H | 96 | 11.124 | 8.904 | 31.715 | 1.00 | 50.07 | C |
| ATOM | 4730 | CZ | TYR | H | 96 | 11.104 | 9.924 | 32.648 | 1.00 | 49.82 | C |
| ATOM | 4731 | OH | TYR | H | 96 | 10.933 | 11.231 | 32.255 | 1.00 | 48.27 | O |
| ATOM | 4733 | CE2 | TYR | H | 96 | 11.264 | 9.642 | 33.988 | 1.00 | 49.93 | C |
| ATOM | 4735 | CD2 | TYR | H | 96 | 11.450 | 8.343 | 34.395 | 1.00 | 50.15 | C |
| ATOM | 4737 | C | TYR | H | 96 | 13.492 | 4.151 | 34.369 | 1.00 | 52.95 | C |
| ATOM | 4738 | O | TYR | H | 96 | 13.086 | 3.024 | 34.111 | 1.00 | 51.55 | O |
| ATOM | 4740 | N | TYR | H | 97 | 14.302 | 4.440 | 35.391 | 1.00 | 54.42 | N |
| ATOM | 4741 | CA | TYR | H | 97 | 14.959 | 3.445 | 36.240 | 1.00 | 53.98 | C |
| ATOM | 4743 | CB | TYR | H | 97 | 16.467 | 3.553 | 36.036 | 1.00 | 53.03 | C |
| ATOM | 4746 | CG | TYR | H | 97 | 16.998 | 2.998 | 34.744 | 1.00 | 50.86 | C |
| ATOM | 4747 | CD1 | TYR | H | 97 | 17.041 | 1.639 | 34.527 | 1.00 | 50.22 | C |
| ATOM | 4749 | CE1 | TYR | H | 97 | 17.529 | 1.126 | 33.352 | 1.00 | 53.55 | C |
| ATOM | 4751 | CZ | TYR | H | 97 | 18.017 | 1.977 | 32.380 | 1.00 | 54.65 | C |
| ATOM | 4752 | OH | TYR | H | 97 | 18.512 | 1.448 | 31.218 | 1.00 | 54.65 | O |
| ATOM | 4754 | CE2 | TYR | H | 97 | 18.010 | 3.335 | 32.576 | 1.00 | 52.02 | C |
| ATOM | 4756 | CD2 | TYR | H | 97 | 17.505 | 3.837 | 33.760 | 1.00 | 53.12 | C |
| ATOM | 4758 | C | TYR | H | 97 | 14.683 | 3.725 | 37.733 | 1.00 | 55.90 | C |
| ATOM | 4759 | O | TYR | H | 97 | 14.844 | 4.855 | 38.177 | 1.00 | 57.82 | O |

| | | | | | -continued | | | | | |
|---|---|---|---|---|---|---|---|---|---|---|
| ATOM | 4761 | N | CYS | H | 98 | 14.278 | 2.717 | 38.508 | 1.00 | 55.79 N |
| ATOM | 4762 | CA | CYS | H | 98 | 14.275 | 2.856 | 39.968 | 1.00 | 55.82 C |
| ATOM | 4764 | CB | CYS | H | 98 | 13.126 | 2.101 | 40.654 | 1.00 | 54.75 C |
| ATOM | 4767 | SG | CYS | H | 98 | 12.996 | 0.403 | 40.142 | 1.00 | 68.78 S |
| ATOM | 4769 | C | CYS | H | 98 | 15.603 | 2.306 | 40.412 | 1.00 | 55.31 C |
| ATOM | 4770 | O | CYS | H | 98 | 16.133 | 1.390 | 39.783 | 1.00 | 56.26 O |
| ATOM | 4772 | N | SER | H | 99 | 16.165 | 2.884 | 41.464 | 1.00 | 54.18 N |
| ATOM | 4773 | CA | SER | H | 99 | 17.404 | 2.367 | 42.023 | 1.00 | 53.10 C |
| ATOM | 4775 | CB | SER | H | 99 | 18.616 | 3.118 | 41.509 | 1.00 | 53.02 C |
| ATOM | 4778 | OG | SER | H | 99 | 19.783 | 2.461 | 41.947 | 1.00 | 49.61 O |
| ATOM | 4780 | C | SER | H | 99 | 17.358 | 2.490 | 43.505 | 1.00 | 52.12 C |
| ATOM | 4781 | O | SER | H | 99 | 16.516 | 3.193 | 44.031 | 1.00 | 53.03 O |
| ATOM | 4783 | N | ALA | H | 100 | 18.282 | 1.816 | 44.174 | 1.00 | 52.50 N |
| ATOM | 4784 | CA | ALA | H | 100 | 18.261 | 1.732 | 45.628 | 1.00 | 52.90 C |
| ATOM | 4786 | CB | ALA | H | 100 | 17.339 | 0.585 | 46.067 | 1.00 | 52.69 C |
| ATOM | 4790 | C | ALA | H | 100 | 19.660 | 1.526 | 46.205 | 1.00 | 54.07 C |
| ATOM | 4791 | O | ALA | H | 100 | 20.464 | 0.762 | 45.642 | 1.00 | 55.42 O |
| ATOM | 4793 | N | SER | H | 101 | 19.939 | 2.212 | 47.319 | 1.00 | 54.31 N |
| ATOM | 4794 | CA | SER | H | 101 | 21.122 | 1.943 | 48.152 | 1.00 | 52.63 C |
| ATOM | 4796 | CB | SER | H | 101 | 22.304 | 2.818 | 47.736 | 1.00 | 53.45 C |
| ATOM | 4799 | OG | SER | H | 101 | 22.061 | 4.188 | 48.003 | 1.00 | 47.14 O |
| ATOM | 4801 | C | SER | H | 101 | 20.820 | 2.153 | 49.638 | 1.00 | 53.12 C |
| ATOM | 4802 | O | SER | H | 101 | 19.904 | 2.895 | 50.007 | 1.00 | 51.79 O |
| ATOM | 4804 | N | TYR | H | 102 | 21.611 | 1.493 | 50.482 | 1.00 | 54.90 N |
| ATOM | 4805 | CA | TYR | H | 102 | 21.468 | 1.578 | 51.947 | 1.00 | 52.96 C |
| ATOM | 4807 | CB | TYR | H | 102 | 22.464 | 0.633 | 52.627 | 1.00 | 52.10 C |
| ATOM | 4810 | CG | TYR | H | 102 | 22.006 | −0.797 | 52.615 | 1.00 | 55.07 C |
| ATOM | 4811 | CD1 | TYR | H | 102 | 20.940 | −1.193 | 53.410 | 1.00 | 54.91 C |
| ATOM | 4813 | CE1 | TYR | H | 102 | 20.491 | −2.507 | 53.419 | 1.00 | 54.68 C |
| ATOM | 4815 | CZ | TYR | H | 102 | 21.102 | −3.454 | 52.627 | 1.00 | 54.77 C |
| ATOM | 4816 | OH | TYR | H | 102 | 20.611 | −4.741 | 52.691 | 1.00 | 56.57 O |
| ATOM | 4818 | CE2 | TYR | H | 102 | 22.172 | −3.102 | 51.811 | 1.00 | 52.66 C |
| ATOM | 4820 | CD2 | TYR | H | 102 | 22.625 | −1.765 | 51.815 | 1.00 | 57.72 C |
| ATOM | 4822 | C | TYR | H | 102 | 21.662 | 3.007 | 52.469 | 1.00 | 51.08 C |
| ATOM | 4823 | O | TYR | H | 102 | 22.641 | 3.653 | 52.147 | 1.00 | 48.10 O |
| ATOM | 4825 | N | TYR | H | 103 | 20.714 | 3.488 | 53.267 | 1.00 | 52.21 N |
| ATOM | 4826 | CA | TYR | H | 103 | 20.837 | 4.781 | 53.924 | 1.00 | 52.09 C |
| ATOM | 4828 | CB | TYR | H | 103 | 19.742 | 4.958 | 54.983 | 1.00 | 50.42 C |
| ATOM | 4831 | CG | TYR | H | 103 | 19.961 | 6.180 | 55.868 | 1.00 | 51.64 C |
| ATOM | 4832 | CD1 | TYR | H | 103 | 19.505 | 7.442 | 55.471 | 1.00 | 55.51 C |
| ATOM | 4834 | CE1 | TYR | H | 103 | 19.708 | 8.564 | 56.249 | 1.00 | 47.49 C |
| ATOM | 4836 | CZ | TYR | H | 103 | 20.389 | 8.450 | 57.422 | 1.00 | 47.70 C |
| ATOM | 4837 | OH | TYR | H | 103 | 20.590 | 9.574 | 58.175 | 1.00 | 52.37 O |
| ATOM | 4839 | CE2 | TYR | H | 103 | 20.869 | 7.216 | 57.846 | 1.00 | 50.51 C |
| ATOM | 4841 | CD2 | TYR | H | 103 | 20.650 | 6.087 | 57.068 | 1.00 | 45.38 C |
| ATOM | 4843 | C | TYR | H | 103 | 22.207 | 4.933 | 54.594 | 1.00 | 54.36 C |
| ATOM | 4844 | O | TYR | H | 103 | 22.695 | 4.023 | 55.260 | 1.00 | 56.44 O |
| ATOM | 4846 | N | ARG | H | 104 | 22.810 | 6.103 | 54.413 | 1.00 | 55.01 N |
| ATOM | 4847 | CA | ARG | H | 104 | 24.032 | 6.471 | 55.113 | 1.00 | 52.47 C |
| ATOM | 4849 | CB | ARG | H | 104 | 25.154 | 6.712 | 54.105 | 1.00 | 51.34 C |
| ATOM | 4852 | CG | ARG | H | 104 | 25.431 | 5.571 | 53.177 | 1.00 | 48.98 C |
| ATOM | 4855 | CD | ARG | H | 104 | 26.500 | 5.962 | 52.181 | 1.00 | 53.59 C |
| ATOM | 4858 | NE | ARG | H | 104 | 27.759 | 6.218 | 52.870 | 1.00 | 59.16 N |
| ATOM | 4860 | CZ | ARG | H | 104 | 28.588 | 5.266 | 53.288 | 1.00 | 56.60 C |
| ATOM | 4861 | NH1 | ARG | H | 104 | 28.310 | 3.989 | 53.064 | 1.00 | 60.42 N |
| ATOM | 4864 | NH2 | ARG | H | 104 | 29.699 | 5.592 | 53.932 | 1.00 | 58.88 N |
| ATOM | 4867 | C | ARG | H | 104 | 23.805 | 7.761 | 55.896 | 1.00 | 51.92 C |
| ATOM | 4868 | O | ARG | H | 104 | 22.878 | 8.523 | 55.604 | 1.00 | 49.09 O |
| ATOM | 4870 | N | TYR | H | 105 | 24.672 | 8.006 | 56.876 | 1.00 | 53.28 N |
| ATOM | 4871 | CA | TYR | H | 105 | 24.710 | 9.292 | 57.579 | 1.00 | 53.37 C |
| ATOM | 4873 | CB | TYR | H | 105 | 25.341 | 9.130 | 58.969 | 1.00 | 54.72 C |
| ATOM | 4876 | CG | TYR | H | 105 | 24.659 | 8.197 | 59.964 | 1.00 | 51.95 C |
| ATOM | 4877 | CD1 | TYR | H | 105 | 23.344 | 8.398 | 60.366 | 1.00 | 55.79 C |
| ATOM | 4879 | CE1 | TYR | H | 105 | 22.734 | 7.557 | 61.330 | 1.00 | 54.92 C |
| ATOM | 4881 | CZ | TYR | H | 105 | 23.454 | 6.527 | 61.888 | 1.00 | 53.31 C |
| ATOM | 4882 | OH | TYR | H | 105 | 22.870 | 5.700 | 62.804 | 1.00 | 56.11 O |
| ATOM | 4884 | CE2 | TYR | H | 105 | 24.764 | 6.310 | 61.512 | 1.00 | 54.94 C |
| ATOM | 4886 | CD2 | TYR | H | 105 | 25.365 | 7.151 | 60.562 | 1.00 | 55.89 C |
| ATOM | 4888 | C | TYR | H | 105 | 25.517 | 10.346 | 56.787 | 1.00 | 53.19 C |
| ATOM | 4889 | O | TYR | H | 105 | 25.500 | 11.519 | 57.126 | 1.00 | 55.29 O |
| ATOM | 4891 | N | ASP | H | 106 | 26.245 | 9.891 | 55.765 | 1.00 | 54.09 N |
| ATOM | 4892 | CA | ASP | H | 106 | 27.063 | 10.709 | 54.846 | 1.00 | 53.00 C |
| ATOM | 4894 | CB | ASP | H | 106 | 27.798 | 9.766 | 53.872 | 1.00 | 53.09 C |
| ATOM | 4897 | CG | ASP | H | 106 | 29.014 | 9.177 | 54.422 | 1.00 | 54.22 C |
| ATOM | 4898 | OD1 | ASP | H | 106 | 29.776 | 8.637 | 53.613 | 1.00 | 54.29 O |
| ATOM | 4899 | OD2 | ASP | H | 106 | 29.233 | 9.265 | 55.639 | 1.00 | 64.11 O |
| ATOM | 4900 | C | ASP | H | 106 | 26.277 | 11.592 | 53.899 | 1.00 | 54.00 C |
| ATOM | 4901 | O | ASP | H | 106 | 25.058 | 11.556 | 53.861 | 1.00 | 59.96 O |
| ATOM | 4903 | N | VAL | H | 107 | 27.020 | 12.328 | 53.075 | 1.00 | 53.17 N |

-continued

| | | | | | | | | | | |
|---|---|---|---|---|---|---|---|---|---|---|
| ATOM | 4904 | CA | VAL | H | 107 | 26.528 | 12.882 | 51.822 | 1.00 | 51.23 C |
| ATOM | 4906 | CB | VAL | H | 107 | 27.299 | 14.164 | 51.419 | 1.00 | 51.31 C |
| ATOM | 4908 | CG1 | VAL | H | 107 | 27.340 | 15.164 | 52.583 | 1.00 | 50.27 C |
| ATOM | 4912 | CG2 | VAL | H | 107 | 28.710 | 13.843 | 50.917 | 1.00 | 53.04 C |
| ATOM | 4916 | C | VAL | H | 107 | 26.647 | 11.829 | 50.709 | 1.00 | 51.93 C |
| ATOM | 4917 | O | VAL | H | 107 | 26.268 | 12.070 | 49.557 | 1.00 | 50.89 O |
| ATOM | 4919 | N | GLY | H | 108 | 27.211 | 10.677 | 51.060 | 1.00 | 52.61 N |
| ATOM | 4920 | CA | GLY | H | 108 | 27.216 | 9.480 | 50.226 | 1.00 | 52.18 C |
| ATOM | 4923 | C | GLY | H | 108 | 25.843 | 8.997 | 49.798 | 1.00 | 52.13 C |
| ATOM | 4924 | O | GLY | H | 108 | 25.001 | 8.680 | 50.639 | 1.00 | 54.07 O |
| ATOM | 4926 | N | ALA | H | 109 | 25.631 | 8.972 | 48.482 | 1.00 | 50.43 N |
| ATOM | 4927 | CA | ALA | H | 109 | 24.467 | 8.357 | 47.862 | 1.00 | 49.42 C |
| ATOM | 4929 | CB | ALA | H | 109 | 23.346 | 9.340 | 47.756 | 1.00 | 48.70 C |
| ATOM | 4933 | C | ALA | H | 109 | 24.852 | 7.856 | 46.474 | 1.00 | 49.64 C |
| ATOM | 4934 | O | ALA | H | 109 | 25.498 | 8.573 | 45.708 | 1.00 | 49.95 O |
| ATOM | 4936 | N | TRP | H | 110 | 24.460 | 6.621 | 46.158 | 1.00 | 51.19 N |
| ATOM | 4937 | CA | TRP | H | 110 | 24.741 | 6.028 | 44.850 | 1.00 | 51.18 C |
| ATOM | 4939 | CB | TRP | H | 110 | 26.165 | 5.497 | 44.814 | 1.00 | 51.84 C |
| ATOM | 4942 | CG | TRP | H | 110 | 26.467 | 4.314 | 45.676 | 1.00 | 52.98 C |
| ATOM | 4943 | CD1 | TRP | H | 110 | 26.327 | 2.998 | 45.340 | 1.00 | 54.46 C |
| ATOM | 4945 | NE1 | TRP | H | 110 | 26.759 | 2.202 | 46.371 | 1.00 | 54.88 N |
| ATOM | 4947 | CE2 | TRP | H | 110 | 27.207 | 2.998 | 47.389 | 1.00 | 48.87 C |
| ATOM | 4948 | CD2 | TRP | H | 110 | 27.041 | 4.334 | 46.985 | 1.00 | 52.18 C |
| ATOM | 4949 | CE3 | TRP | H | 110 | 27.415 | 5.351 | 47.859 | 1.00 | 52.85 C |
| ATOM | 4951 | CZ3 | TRP | H | 110 | 27.942 | 5.010 | 49.078 | 1.00 | 53.94 C |
| ATOM | 4953 | CH2 | TRP | H | 110 | 28.104 | 3.672 | 49.447 | 1.00 | 51.64 C |
| ATOM | 4955 | CZ2 | TRP | H | 110 | 27.739 | 2.655 | 48.616 | 1.00 | 48.54 C |
| ATOM | 4957 | C | TRP | H | 110 | 23.737 | 4.950 | 44.457 | 1.00 | 52.28 C |
| ATOM | 4958 | O | TRP | H | 110 | 22.784 | 4.695 | 45.197 | 1.00 | 53.53 O |
| ATOM | 4960 | N | PHE | H | 111 | 23.944 | 4.331 | 43.291 | 1.00 | 51.09 N |
| ATOM | 4961 | CA | PHE | H | 111 | 22.916 | 3.485 | 42.675 | 1.00 | 50.65 C |
| ATOM | 4963 | CB | PHE | H | 111 | 22.488 | 4.117 | 41.340 | 1.00 | 50.25 C |
| ATOM | 4966 | CG | PHE | H | 111 | 22.282 | 5.612 | 41.448 | 1.00 | 49.04 C |
| ATOM | 4967 | CD1 | PHE | H | 111 | 21.319 | 6.129 | 42.291 | 1.00 | 51.73 C |
| ATOM | 4969 | CE1 | PHE | H | 111 | 21.149 | 7.495 | 42.429 | 1.00 | 51.55 C |
| ATOM | 4971 | CZ | PHE | H | 111 | 21.944 | 8.357 | 41.737 | 1.00 | 50.40 C |
| ATOM | 4973 | CE2 | PHE | H | 111 | 22.919 | 7.861 | 40.912 | 1.00 | 51.14 C |
| ATOM | 4975 | CD2 | PHE | H | 111 | 23.092 | 6.493 | 40.777 | 1.00 | 49.18 C |
| ATOM | 4977 | C | PHE | H | 111 | 23.408 | 2.041 | 42.566 | 1.00 | 50.05 C |
| ATOM | 4978 | O | PHE | H | 111 | 24.051 | 1.647 | 41.607 | 1.00 | 47.70 O |
| ATOM | 4980 | N | ALA | H | 112 | 23.101 | 1.264 | 43.597 | 1.00 | 50.93 N |
| ATOM | 4981 | CA | ALA | H | 112 | 23.694 | −0.047 | 43.781 | 1.00 | 52.55 C |
| ATOM | 4983 | CB | ALA | H | 112 | 23.730 | −0.390 | 45.248 | 1.00 | 52.52 C |
| ATOM | 4987 | C | ALA | H | 112 | 22.926 | −1.109 | 43.022 | 1.00 | 54.37 C |
| ATOM | 4988 | O | ALA | H | 112 | 23.525 | −1.917 | 42.311 | 1.00 | 55.53 O |
| ATOM | 4990 | N | TYR | H | 113 | 21.605 | −1.109 | 43.205 | 1.00 | 55.46 N |
| ATOM | 4991 | CA | TYR | H | 113 | 20.693 | −2.020 | 42.515 | 1.00 | 54.22 C |
| ATOM | 4993 | CB | TYR | H | 113 | 19.841 | −2.817 | 43.511 | 1.00 | 57.01 C |
| ATOM | 4996 | CG | TYR | H | 113 | 20.528 | −3.137 | 44.809 | 1.00 | 59.26 C |
| ATOM | 4997 | CD1 | TYR | H | 113 | 21.598 | −4.025 | 44.852 | 1.00 | 61.30 C |
| ATOM | 4999 | CE1 | TYR | H | 113 | 22.234 | −4.333 | 46.053 | 1.00 | 60.62 C |
| ATOM | 5001 | CZ | TYR | H | 113 | 21.798 | −3.738 | 47.223 | 1.00 | 63.36 C |
| ATOM | 5002 | OH | TYR | H | 113 | 22.433 | −4.021 | 48.409 | 1.00 | 67.49 O |
| ATOM | 5004 | CE2 | TYR | H | 113 | 20.734 | −2.854 | 47.205 | 1.00 | 60.66 C |
| ATOM | 5006 | CD2 | TYR | H | 113 | 20.106 | −2.558 | 46.001 | 1.00 | 61.94 C |
| ATOM | 5008 | C | TYR | H | 113 | 19.768 | −1.207 | 41.624 | 1.00 | 52.67 C |
| ATOM | 5009 | O | TYR | H | 113 | 19.360 | −0.097 | 41.973 | 1.00 | 51.12 O |
| ATOM | 5011 | N | TRP | H | 114 | 19.413 | −1.789 | 40.491 | 1.00 | 51.26 N |
| ATOM | 5012 | CA | TRP | H | 114 | 18.654 | −1.098 | 39.470 | 1.00 | 52.96 C |
| ATOM | 5014 | CB | TRP | H | 114 | 19.516 | −0.908 | 38.228 | 1.00 | 53.95 C |
| ATOM | 5017 | CG | TRP | H | 114 | 20.589 | 0.070 | 38.419 | 1.00 | 53.77 C |
| ATOM | 5018 | CD1 | TRP | H | 114 | 21.685 | −0.081 | 39.182 | 1.00 | 52.61 C |
| ATOM | 5020 | NE1 | TRP | H | 114 | 22.457 | 1.048 | 39.123 | 1.00 | 57.47 N |
| ATOM | 5022 | CE2 | TRP | H | 114 | 21.855 | 1.960 | 38.301 | 1.00 | 57.60 C |
| ATOM | 5023 | CD2 | TRP | H | 114 | 20.667 | 1.378 | 37.841 | 1.00 | 57.75 C |
| ATOM | 5024 | CE3 | TRP | H | 114 | 19.852 | 2.106 | 36.967 | 1.00 | 55.44 C |
| ATOM | 5026 | CZ3 | TRP | H | 114 | 20.251 | 3.369 | 36.591 | 1.00 | 55.64 C |
| ATOM | 5028 | CH2 | TRP | H | 114 | 21.445 | 3.924 | 37.067 | 1.00 | 55.42 C |
| ATOM | 5030 | CZ2 | TRP | H | 114 | 22.259 | 3.236 | 37.920 | 1.00 | 56.16 C |
| ATOM | 5032 | C | TRP | H | 114 | 17.443 | −1.888 | 39.051 | 1.00 | 53.33 C |
| ATOM | 5033 | O | TRP | H | 114 | 17.467 | −3.114 | 39.040 | 1.00 | 54.38 O |
| ATOM | 5035 | N | GLY | H | 115 | 16.390 | −1.165 | 38.679 | 1.00 | 53.62 N |
| ATOM | 5036 | CA | GLY | H | 115 | 15.269 | −1.742 | 37.967 | 1.00 | 50.08 C |
| ATOM | 5039 | C | GLY | H | 115 | 15.730 | −2.006 | 36.552 | 1.00 | 50.47 C |
| ATOM | 5040 | O | GLY | H | 115 | 16.763 | −1.481 | 36.115 | 1.00 | 49.63 O |
| ATOM | 5042 | N | GLN | H | 116 | 14.958 | −2.818 | 35.834 | 1.00 | 50.79 N |
| ATOM | 5043 | CA | GLN | H | 116 | 15.284 | −3.206 | 34.462 | 1.00 | 48.84 C |
| ATOM | 5045 | CB | GLN | H | 116 | 14.426 | −4.401 | 34.035 | 1.00 | 48.23 C |
| ATOM | 5048 | CG | GLN | H | 116 | 12.972 | −4.094 | 33.619 | 1.00 | 50.59 C |

| | | | | | | | | | | | |
|---|---|---|---|---|---|---|---|---|---|---|---|
| ATOM | 5051 | CD | GLN | H | 116 | 11.966 | −4.161 | 34.765 | 1.00 | 55.01 | C |
| ATOM | 5052 | OE1 | GLN | H | 116 | 12.343 | −4.196 | 35.942 | 1.00 | 56.76 | O |
| ATOM | 5053 | NE2 | GLN | H | 116 | 10.674 | −4.176 | 34.424 | 1.00 | 46.00 | N |
| ATOM | 5056 | C | GLN | H | 116 | 15.106 | −2.069 | 33.454 | 1.00 | 48.66 | C |
| ATOM | 5057 | O | GLN | H | 116 | 15.481 | −2.215 | 32.284 | 1.00 | 48.67 | O |
| ATOM | 5059 | N | GLY | H | 117 | 14.512 | −0.960 | 33.901 | 1.00 | 47.82 | N |
| ATOM | 5060 | CA | GLY | H | 117 | 14.163 | 0.149 | 33.025 | 1.00 | 47.97 | C |
| ATOM | 5063 | C | GLY | H | 117 | 12.816 | −0.040 | 32.340 | 1.00 | 47.94 | C |
| ATOM | 5064 | O | GLY | H | 117 | 12.427 | −1.177 | 32.024 | 1.00 | 47.46 | O |
| ATOM | 5066 | N | THR | H | 118 | 12.111 | 1.075 | 32.111 | 1.00 | 47.47 | N |
| ATOM | 5067 | CA | THR | H | 118 | 10.911 | 1.093 | 31.261 | 1.00 | 48.10 | C |
| ATOM | 5069 | CB | THR | H | 118 | 9.619 | 0.852 | 32.078 | 1.00 | 49.92 | C |
| ATOM | 5071 | OG1 | THR | H | 118 | 8.500 | 0.736 | 31.188 | 1.00 | 53.21 | O |
| ATOM | 5073 | CG2 | THR | H | 118 | 9.366 | 1.980 | 33.097 | 1.00 | 48.82 | C |
| ATOM | 5077 | C | THR | H | 118 | 10.785 | 2.397 | 30.472 | 1.00 | 48.24 | C |
| ATOM | 5078 | O | THR | H | 118 | 10.965 | 3.489 | 31.020 | 1.00 | 51.02 | O |
| ATOM | 5080 | N | LEU | H | 119 | 10.461 | 2.276 | 29.187 | 1.00 | 49.10 | N |
| ATOM | 5081 | CA | LEU | H | 119 | 10.445 | 3.423 | 28.261 | 1.00 | 48.79 | C |
| ATOM | 5083 | CB | LEU | H | 119 | 10.652 | 2.953 | 26.815 | 1.00 | 47.98 | C |
| ATOM | 5086 | CG | LEU | H | 119 | 10.711 | 4.035 | 25.728 | 1.00 | 48.73 | C |
| ATOM | 5088 | CD1 | LEU | H | 119 | 11.952 | 4.892 | 25.873 | 1.00 | 50.29 | C |
| ATOM | 5092 | CD2 | LEU | H | 119 | 10.674 | 3.408 | 24.360 | 1.00 | 47.50 | C |
| ATOM | 5096 | C | LEU | H | 119 | 9.157 | 4.241 | 28.352 | 1.00 | 49.28 | C |
| ATOM | 5097 | O | LEU | H | 119 | 8.055 | 3.704 | 28.236 | 1.00 | 48.59 | O |
| ATOM | 5099 | N | VAL | H | 120 | 9.318 | 5.548 | 28.553 | 1.00 | 49.87 | N |
| ATOM | 5100 | CA | VAL | H | 120 | 8.206 | 6.488 | 28.527 | 1.00 | 49.43 | C |
| ATOM | 5102 | CB | VAL | H | 120 | 8.222 | 7.432 | 29.740 | 1.00 | 48.77 | C |
| ATOM | 5104 | CG1 | VAL | H | 120 | 6.952 | 8.280 | 29.774 | 1.00 | 47.34 | C |
| ATOM | 5108 | CG2 | VAL | H | 120 | 8.344 | 6.634 | 31.017 | 1.00 | 51.75 | C |
| ATOM | 5112 | C | VAL | H | 120 | 8.327 | 7.305 | 27.257 | 1.00 | 48.47 | C |
| ATOM | 5113 | O | VAL | H | 120 | 9.391 | 7.837 | 26.960 | 1.00 | 46.71 | O |
| ATOM | 5115 | N | THR | H | 121 | 7.235 | 7.391 | 26.508 | 1.00 | 49.08 | N |
| ATOM | 5116 | CA | THR | H | 121 | 7.230 | 8.126 | 25.253 | 1.00 | 50.28 | C |
| ATOM | 5118 | CB | THR | H | 121 | 7.036 | 7.190 | 24.057 | 1.00 | 49.88 | C |
| ATOM | 5120 | OG1 | THR | H | 121 | 8.009 | 6.141 | 24.111 | 1.00 | 52.48 | O |
| ATOM | 5122 | CG2 | THR | H | 121 | 7.202 | 7.949 | 22.772 | 1.00 | 50.04 | C |
| ATOM | 5126 | C | THR | H | 121 | 6.138 | 9.183 | 25.274 | 1.00 | 50.24 | C |
| ATOM | 5127 | O | THR | H | 121 | 4.951 | 8.868 | 25.238 | 1.00 | 49.85 | O |
| ATOM | 5129 | N | VAL | H | 122 | 6.557 | 10.442 | 25.356 | 1.00 | 51.36 | N |
| ATOM | 5130 | CA | VAL | H | 122 | 5.629 | 11.563 | 25.361 | 1.00 | 50.98 | C |
| ATOM | 5132 | CB | VAL | H | 122 | 6.113 | 12.694 | 26.276 | 1.00 | 50.97 | C |
| ATOM | 5134 | CG1 | VAL | H | 122 | 5.019 | 13.776 | 26.393 | 1.00 | 54.22 | C |
| ATOM | 5138 | CG2 | VAL | H | 122 | 6.500 | 12.140 | 27.637 | 1.00 | 48.86 | C |
| ATOM | 5142 | C | VAL | H | 122 | 5.495 | 12.073 | 23.926 | 1.00 | 50.50 | C |
| ATOM | 5143 | O | VAL | H | 122 | 6.457 | 12.578 | 23.348 | 1.00 | 50.93 | O |
| ATOM | 5145 | N | SER | H | 123 | 4.311 | 11.919 | 23.351 | 1.00 | 49.36 | N |
| ATOM | 5146 | CA | SER | H | 123 | 4.106 | 12.238 | 21.948 | 1.00 | 50.02 | C |
| ATOM | 5148 | CB | SER | H | 123 | 4.747 | 11.172 | 21.074 | 1.00 | 50.11 | C |
| ATOM | 5151 | OG | SER | H | 123 | 4.358 | 11.332 | 19.727 | 1.00 | 50.26 | O |
| ATOM | 5153 | C | SER | H | 123 | 2.630 | 12.332 | 21.615 | 1.00 | 50.86 | C |
| ATOM | 5154 | O | SER | H | 123 | 1.784 | 11.868 | 22.380 | 1.00 | 51.80 | O |
| ATOM | 5156 | N | SER | H | 124 | 2.327 | 12.953 | 20.479 | 1.00 | 51.04 | N |
| ATOM | 5157 | CA | SER | H | 124 | 0.946 | 13.049 | 20.001 | 1.00 | 51.63 | C |
| ATOM | 5159 | CB | SER | H | 124 | 0.691 | 14.405 | 19.340 | 1.00 | 51.59 | C |
| ATOM | 5162 | OG | SER | H | 124 | 0.880 | 15.454 | 20.278 | 1.00 | 53.09 | O |
| ATOM | 5164 | C | SER | H | 124 | 0.620 | 11.935 | 19.027 | 1.00 | 51.16 | C |
| ATOM | 5165 | O | SER | H | 124 | −0.554 | 11.669 | 18.770 | 1.00 | 52.25 | O |
| ATOM | 5167 | N | ALA | H | 125 | 1.661 | 11.290 | 18.497 | 1.00 | 51.66 | N |
| ATOM | 5168 | CA | ALA | H | 125 | 1.514 | 10.276 | 17.454 | 1.00 | 52.03 | C |
| ATOM | 5170 | CB | ALA | H | 125 | 2.876 | 9.893 | 16.879 | 1.00 | 50.83 | C |
| ATOM | 5174 | C | ALA | H | 125 | 0.797 | 9.049 | 18.002 | 1.00 | 52.57 | C |
| ATOM | 5175 | O | ALA | H | 125 | 0.989 | 8.672 | 19.157 | 1.00 | 53.54 | O |
| ATOM | 5177 | N | SER | H | 126 | −0.040 | 8.443 | 17.166 | 1.00 | 53.66 | N |
| ATOM | 5178 | CA | SER | H | 126 | −0.878 | 7.333 | 17.590 | 1.00 | 53.99 | C |
| ATOM | 5180 | CB | SER | H | 126 | −2.092 | 7.182 | 16.662 | 1.00 | 54.29 | C |
| ATOM | 5183 | OG | SER | H | 126 | −2.543 | 8.446 | 16.187 | 1.00 | 56.55 | O |
| ATOM | 5185 | C | SER | H | 126 | −0.063 | 6.048 | 17.610 | 1.00 | 54.14 | C |
| ATOM | 5186 | O | SER | H | 126 | 0.919 | 5.908 | 16.872 | 1.00 | 53.05 | O |
| ATOM | 5188 | N | THR | H | 127 | −0.475 | 5.122 | 18.471 | 1.00 | 54.72 | N |
| ATOM | 5189 | CA | THR | H | 127 | 0.147 | 3.807 | 18.552 | 1.00 | 54.76 | C |
| ATOM | 5191 | CB | THR | H | 127 | −0.336 | 3.026 | 19.821 | 1.00 | 54.51 | C |
| ATOM | 5193 | OG1 | THR | H | 127 | 0.498 | 3.377 | 20.933 | 1.00 | 57.82 | O |
| ATOM | 5195 | CG2 | THR | H | 127 | −0.275 | 1.504 | 19.638 | 1.00 | 55.20 | C |
| ATOM | 5199 | C | THR | H | 127 | −0.130 | 3.043 | 17.247 | 1.00 | 54.70 | C |
| ATOM | 5200 | O | THR | H | 127 | −1.238 | 3.093 | 16.713 | 1.00 | 54.82 | O |
| ATOM | 5202 | N | LYS | H | 128 | 0.894 | 2.358 | 16.743 | 1.00 | 54.60 | N |
| ATOM | 5203 | CA | LYS | H | 128 | 0.817 | 1.628 | 15.482 | 1.00 | 54.47 | C |
| ATOM | 5205 | CB | LYS | H | 128 | 1.498 | 2.452 | 14.385 | 1.00 | 54.89 | C |
| ATOM | 5208 | CG | LYS | H | 128 | 0.750 | 2.547 | 13.060 | 1.00 | 56.98 | C |

-continued

| ATOM | 5211 | CD | LYS | H | 128 | 1.116 | 1.443 | 12.065 | 1.00 | 59.81 | C |
| ATOM | 5214 | CE | LYS | H | 128 | 0.059 | 0.341 | 12.025 | 1.00 | 62.15 | C |
| ATOM | 5217 | NZ | LYS | H | 128 | 0.349 | −0.698 | 10.986 | 1.00 | 61.29 | N |
| ATOM | 5221 | C | LYS | H | 128 | 1.513 | 0.274 | 15.667 | 1.00 | 54.39 | C |
| ATOM | 5222 | O | LYS | H | 128 | 2.680 | 0.220 | 16.073 | 1.00 | 55.32 | O |
| ATOM | 5224 | N | GLY | H | 129 | 0.788 | −0.813 | 15.405 | 1.00 | 53.07 | N |
| ATOM | 5225 | CA | GLY | H | 129 | 1.356 | −2.153 | 15.482 | 1.00 | 52.52 | C |
| ATOM | 5228 | C | GLY | H | 129 | 2.272 | −2.381 | 14.295 | 1.00 | 53.52 | C |
| ATOM | 5229 | O | GLY | H | 129 | 2.113 | −1.738 | 13.259 | 1.00 | 54.78 | O |
| ATOM | 5231 | N | PRO | H | 130 | 3.249 | −3.288 | 14.432 | 1.00 | 53.18 | N |
| ATOM | 5232 | CA | PRO | H | 130 | 4.123 | −3.569 | 13.303 | 1.00 | 51.86 | C |
| ATOM | 5234 | CB | PRO | H | 130 | 5.320 | −4.254 | 13.955 | 1.00 | 52.61 | C |
| ATOM | 5237 | CG | PRO | H | 130 | 4.738 | −4.961 | 15.128 | 1.00 | 53.44 | C |
| ATOM | 5240 | CD | PRO | H | 130 | 3.602 | −4.094 | 15.615 | 1.00 | 53.56 | C |
| ATOM | 5243 | C | PRO | H | 130 | 3.464 | −4.506 | 12.310 | 1.00 | 51.39 | C |
| ATOM | 5244 | O | PRO | H | 130 | 2.349 | −4.970 | 12.540 | 1.00 | 50.84 | O |
| ATOM | 5245 | N | SER | H | 131 | 4.166 | −4.764 | 11.212 | 1.00 | 51.24 | N |
| ATOM | 5246 | CA | SER | H | 131 | 3.730 | −5.690 | 10.184 | 1.00 | 51.19 | C |
| ATOM | 5248 | CB | SER | H | 131 | 3.213 | −4.915 | 8.975 | 1.00 | 51.90 | C |
| ATOM | 5251 | OG | SER | H | 131 | 2.876 | −3.586 | 9.343 | 1.00 | 54.06 | O |
| ATOM | 5253 | C | SER | H | 131 | 4.963 | −6.486 | 9.810 | 1.00 | 51.56 | C |
| ATOM | 5254 | O | SER | H | 131 | 5.942 | −5.916 | 9.327 | 1.00 | 53.23 | O |
| ATOM | 5256 | N | VAL | H | 132 | 4.930 | −7.793 | 10.041 | 1.00 | 50.73 | N |
| ATOM | 5257 | CA | VAL | H | 132 | 6.133 | −8.604 | 9.925 | 1.00 | 51.25 | C |
| ATOM | 5259 | CB | VAL | H | 132 | 6.152 | −9.686 | 11.011 | 1.00 | 51.00 | C |
| ATOM | 5261 | CG1 | VAL | H | 132 | 7.345 | −10.632 | 10.830 | 1.00 | 52.31 | C |
| ATOM | 5265 | CG2 | VAL | H | 132 | 6.188 | −9.028 | 12.390 | 1.00 | 50.95 | C |
| ATOM | 5269 | C | VAL | H | 132 | 6.250 | −9.230 | 8.536 | 1.00 | 52.46 | C |
| ATOM | 5270 | O | VAL | H | 132 | 5.284 | −9.813 | 8.041 | 1.00 | 53.84 | O |
| ATOM | 5272 | N | PHE | H | 133 | 7.428 | −9.096 | 7.914 | 1.00 | 52.65 | N |
| ATOM | 5273 | CA | PHE | H | 133 | 7.707 | −9.687 | 6.594 | 1.00 | 52.17 | C |
| ATOM | 5275 | CB | PHE | H | 133 | 7.969 | −8.609 | 5.538 | 1.00 | 52.59 | C |
| ATOM | 5278 | CG | PHE | H | 133 | 6.910 | −7.544 | 5.473 | 1.00 | 53.24 | C |
| ATOM | 5279 | CD1 | PHE | H | 133 | 5.643 | −7.835 | 4.994 | 1.00 | 54.08 | C |
| ATOM | 5281 | CE1 | PHE | H | 133 | 4.662 | −6.844 | 4.931 | 1.00 | 55.48 | C |
| ATOM | 5283 | CZ | PHE | H | 133 | 4.949 | −5.543 | 5.355 | 1.00 | 54.52 | C |
| ATOM | 5285 | CE2 | PHE | H | 133 | 6.209 | −5.241 | 5.825 | 1.00 | 54.83 | C |
| ATOM | 5287 | CD2 | PHE | H | 133 | 7.186 | −6.239 | 5.882 | 1.00 | 56.63 | C |
| ATOM | 5289 | C | PHE | H | 133 | 8.918 | −10.617 | 6.661 | 1.00 | 51.93 | C |
| ATOM | 5290 | O | PHE | H | 133 | 9.834 | −10.390 | 7.455 | 1.00 | 51.06 | O |
| ATOM | 5292 | N | PRO | H | 134 | 8.919 | −11.681 | 5.835 | 1.00 | 52.34 | N |
| ATOM | 5293 | CA | PRO | H | 134 | 10.043 | −12.604 | 5.795 | 1.00 | 52.10 | C |
| ATOM | 5295 | CB | PRO | H | 134 | 9.427 | −13.869 | 5.206 | 1.00 | 51.71 | C |
| ATOM | 5298 | CG | PRO | H | 134 | 8.381 | −13.369 | 4.299 | 1.00 | 51.88 | C |
| ATOM | 5301 | CD | PRO | H | 134 | 7.846 | −12.102 | 4.915 | 1.00 | 52.55 | C |
| ATOM | 5304 | C | PRO | H | 134 | 11.174 | −12.121 | 4.902 | 1.00 | 52.32 | C |
| ATOM | 5305 | O | PRO | H | 134 | 10.939 | −11.720 | 3.759 | 1.00 | 51.87 | O |
| ATOM | 5306 | N | LEU | H | 135 | 12.388 | −12.158 | 5.443 | 1.00 | 52.14 | N |
| ATOM | 5307 | CA | LEU | H | 135 | 13.596 | −12.021 | 4.654 | 1.00 | 52.42 | C |
| ATOM | 5309 | CB | LEU | H | 135 | 14.631 | −11.190 | 5.416 | 1.00 | 52.10 | C |
| ATOM | 5312 | CG | LEU | H | 135 | 14.162 | −9.791 | 5.852 | 1.00 | 52.50 | C |
| ATOM | 5314 | CD1 | LEU | H | 135 | 15.200 | −9.132 | 6.751 | 1.00 | 50.35 | C |
| ATOM | 5318 | CD2 | LEU | H | 135 | 13.847 | −8.891 | 4.653 | 1.00 | 51.15 | C |
| ATOM | 5322 | C | LEU | H | 135 | 14.113 | −13.436 | 4.354 | 1.00 | 53.24 | C |
| ATOM | 5323 | O | LEU | H | 135 | 15.104 | −13.885 | 4.928 | 1.00 | 53.43 | O |
| ATOM | 5325 | N | ALA | H | 136 | 13.420 | −14.141 | 3.460 | 1.00 | 53.42 | N |
| ATOM | 5326 | CA | ALA | H | 136 | 13.774 | −15.519 | 3.110 | 1.00 | 53.65 | C |
| ATOM | 5328 | CB | ALA | H | 136 | 12.647 | −16.165 | 2.289 | 1.00 | 53.57 | C |
| ATOM | 5332 | C | ALA | H | 136 | 15.103 | −15.584 | 2.344 | 1.00 | 54.09 | C |
| ATOM | 5333 | O | ALA | H | 136 | 15.536 | −14.579 | 1.778 | 1.00 | 53.45 | O |
| ATOM | 5335 | N | PRO | H | 137 | 15.758 | −16.768 | 2.329 | 1.00 | 54.99 | N |
| ATOM | 5336 | CA | PRO | H | 137 | 16.987 | −16.954 | 1.540 | 1.00 | 54.30 | C |
| ATOM | 5338 | CB | PRO | H | 137 | 17.382 | −18.412 | 1.832 | 1.00 | 54.19 | C |
| ATOM | 5341 | CG | PRO | H | 137 | 16.133 | −19.065 | 2.312 | 1.00 | 55.25 | C |
| ATOM | 5344 | CD | PRO | H | 137 | 15.397 | −17.999 | 3.062 | 1.00 | 54.79 | C |
| ATOM | 5347 | C | PRO | H | 137 | 16.768 | −16.751 | 0.044 | 1.00 | 53.70 | C |
| ATOM | 5348 | O | PRO | H | 137 | 17.609 | −17.150 | −0.759 | 1.00 | 54.54 | O |
| ATOM | 5349 | N | LEU | H | 149 | 19.007 | −15.644 | 6.377 | 1.00 | 46.99 | N |
| ATOM | 5350 | CA | LEU | H | 149 | 17.577 | −15.368 | 6.508 | 1.00 | 48.77 | C |
| ATOM | 5352 | CB | LEU | H | 149 | 16.769 | −16.672 | 6.471 | 1.00 | 49.04 | C |
| ATOM | 5355 | CG | LEU | H | 149 | 16.823 | −17.619 | 7.684 | 1.00 | 47.39 | C |
| ATOM | 5357 | CD1 | LEU | H | 149 | 15.953 | −17.140 | 8.854 | 1.00 | 47.18 | C |
| ATOM | 5361 | CD2 | LEU | H | 149 | 16.415 | −19.030 | 7.269 | 1.00 | 47.12 | C |
| ATOM | 5365 | C | LEU | H | 149 | 17.233 | −14.576 | 7.779 | 1.00 | 50.43 | C |
| ATOM | 5366 | O | LEU | H | 149 | 18.015 | −14.548 | 8.740 | 1.00 | 50.30 | O |
| ATOM | 5368 | N | GLY | H | 150 | 16.045 | −13.959 | 7.777 | 1.00 | 51.43 | N |
| ATOM | 5369 | CA | GLY | H | 150 | 15.605 | −13.104 | 8.880 | 1.00 | 51.42 | C |
| ATOM | 5372 | C | GLY | H | 150 | 14.151 | −12.655 | 8.827 | 1.00 | 51.75 | C |
| ATOM | 5373 | O | GLY | H | 150 | 13.316 | −13.295 | 8.197 | 1.00 | 50.93 | O |

-continued

| | | | | | | | | | | |
|---|---|---|---|---|---|---|---|---|---|---|
| ATOM | 5375 | N | CYS | H | 151 | 13.878 | −11.532 | 9.496 | 1.00 | 53.64 N |
| ATOM | 5376 | CA | CYS | H | 151 | 12.529 | −10.982 | 9.702 | 1.00 | 54.19 C |
| ATOM | 5378 | CB | CYS | H | 151 | 12.042 | −11.333 | 11.110 | 1.00 | 54.88 C |
| ATOM | 5381 | SG | CYS | H | 151 | 10.798 | −12.603 | 11.183 | 1.00 | 60.09 S |
| ATOM | 5383 | C | CYS | H | 151 | 12.527 | −9.454 | 9.593 | 1.00 | 54.57 C |
| ATOM | 5384 | O | CYS | H | 151 | 13.247 | −8.784 | 10.333 | 1.00 | 54.96 O |
| ATOM | 5386 | N | LEU | H | 152 | 11.698 | −8.898 | 8.716 | 1.00 | 54.14 N |
| ATOM | 5387 | CA | LEU | H | 152 | 11.592 | −7.444 | 8.593 | 1.00 | 53.95 C |
| ATOM | 5389 | CB | LEU | H | 152 | 11.585 | −7.039 | 7.118 | 1.00 | 54.15 C |
| ATOM | 5392 | CG | LEU | H | 152 | 11.440 | −5.543 | 6.833 | 1.00 | 53.66 C |
| ATOM | 5394 | CD1 | LEU | H | 152 | 12.388 | −4.729 | 7.709 | 1.00 | 51.76 C |
| ATOM | 5398 | CD2 | LEU | H | 152 | 11.674 | −5.254 | 5.360 | 1.00 | 52.94 C |
| ATOM | 5402 | C | LEU | H | 152 | 10.348 | −6.895 | 9.292 | 1.00 | 53.79 C |
| ATOM | 5403 | O | LEU | H | 152 | 9.239 | −7.018 | 8.779 | 1.00 | 53.53 O |
| ATOM | 5405 | N | VAL | H | 153 | 10.547 | −6.270 | 10.450 | 1.00 | 54.57 N |
| ATOM | 5406 | CA | VAL | H | 153 | 9.450 | −5.703 | 11.249 | 1.00 | 54.88 C |
| ATOM | 5408 | CB | VAL | H | 153 | 9.752 | −5.781 | 12.777 | 1.00 | 55.19 C |
| ATOM | 5410 | CG1 | VAL | H | 153 | 8.507 | −5.449 | 13.583 | 1.00 | 57.25 C |
| ATOM | 5414 | CG2 | VAL | H | 153 | 10.276 | −7.157 | 13.167 | 1.00 | 55.23 C |
| ATOM | 5418 | C | VAL | H | 153 | 9.266 | −4.237 | 10.871 | 1.00 | 54.80 C |
| ATOM | 5419 | O | VAL | H | 153 | 10.080 | −3.403 | 11.257 | 1.00 | 55.94 O |
| ATOM | 5421 | N | LYS | H | 154 | 8.204 | −3.909 | 10.138 | 1.00 | 54.35 N |
| ATOM | 5422 | CA | LYS | H | 154 | 8.077 | −2.561 | 9.574 | 1.00 | 54.32 C |
| ATOM | 5424 | CB | LYS | H | 154 | 7.939 | −2.639 | 8.046 | 1.00 | 53.57 C |
| ATOM | 5427 | CG | LYS | H | 154 | 8.284 | −1.329 | 7.332 | 1.00 | 54.14 C |
| ATOM | 5430 | CD | LYS | H | 154 | 8.017 | −1.395 | 5.832 | 1.00 | 54.01 C |
| ATOM | 5433 | CE | LYS | H | 154 | 7.848 | −0.003 | 5.215 | 1.00 | 52.46 C |
| ATOM | 5436 | NZ | LYS | H | 154 | 9.110 | 0.785 | 5.227 | 1.00 | 53.22 N |
| ATOM | 5440 | C | LYS | H | 154 | 6.929 | −1.729 | 10.169 | 1.00 | 54.37 C |
| ATOM | 5441 | O | LYS | H | 154 | 5.906 | −2.271 | 10.591 | 1.00 | 53.67 O |
| ATOM | 5443 | N | ASP | H | 155 | 7.141 | −0.407 | 10.201 | 1.00 | 54.97 N |
| ATOM | 5444 | CA | ASP | H | 155 | 6.102 | 0.610 | 10.466 | 1.00 | 54.72 C |
| ATOM | 5446 | CB | ASP | H | 155 | 5.071 | 0.640 | 9.319 | 1.00 | 55.06 C |
| ATOM | 5449 | CG | ASP | H | 155 | 5.623 | 1.239 | 8.026 | 1.00 | 57.44 C |
| ATOM | 5450 | OD1 | ASP | H | 155 | 6.609 | 2.012 | 8.083 | 1.00 | 59.72 O |
| ATOM | 5451 | OD2 | ASP | H | 155 | 5.054 | 0.939 | 6.945 | 1.00 | 57.21 O |
| ATOM | 5452 | C | ASP | H | 155 | 5.372 | 0.480 | 11.812 | 1.00 | 54.47 C |
| ATOM | 5453 | O | ASP | H | 155 | 4.239 | 0.007 | 11.862 | 1.00 | 55.92 O |
| ATOM | 5455 | N | TYR | H | 156 | 5.999 | 0.932 | 12.891 | 1.00 | 53.14 N |
| ATOM | 5456 | CA | TYR | H | 156 | 5.372 | 0.832 | 14.202 | 1.00 | 53.82 C |
| ATOM | 5458 | CB | TYR | H | 156 | 5.726 | −0.512 | 14.833 | 1.00 | 53.59 C |
| ATOM | 5461 | CG | TYR | H | 156 | 7.155 | −0.623 | 15.313 | 1.00 | 54.20 C |
| ATOM | 5462 | CD1 | TYR | H | 156 | 8.131 | −1.255 | 14.545 | 1.00 | 53.44 C |
| ATOM | 5464 | CE1 | TYR | H | 156 | 9.444 | −1.365 | 15.002 | 1.00 | 53.05 C |
| ATOM | 5466 | CZ | TYR | H | 156 | 9.780 | −0.833 | 16.243 | 1.00 | 55.08 C |
| ATOM | 5467 | OH | TYR | H | 156 | 11.062 | −0.918 | 16.741 | 1.00 | 57.00 O |
| ATOM | 5469 | CE2 | TYR | H | 156 | 8.825 | −0.205 | 17.012 | 1.00 | 53.99 C |
| ATOM | 5471 | CD2 | TYR | H | 156 | 7.527 | −0.107 | 16.549 | 1.00 | 55.19 C |
| ATOM | 5473 | C | TYR | H | 156 | 5.716 | 1.986 | 15.157 | 1.00 | 54.11 C |
| ATOM | 5474 | O | TYR | H | 156 | 6.721 | 2.691 | 14.984 | 1.00 | 53.40 O |
| ATOM | 5476 | N | PHE | H | 157 | 4.861 | 2.164 | 16.165 | 1.00 | 54.32 N |
| ATOM | 5477 | CA | PHE | H | 157 | 5.008 | 3.237 | 17.154 | 1.00 | 54.59 C |
| ATOM | 5479 | CB | PHE | H | 157 | 4.508 | 4.556 | 16.573 | 1.00 | 54.71 C |
| ATOM | 5482 | CG | PHE | H | 157 | 4.879 | 5.745 | 17.387 | 1.00 | 52.98 C |
| ATOM | 5483 | CD1 | PHE | H | 157 | 6.082 | 6.397 | 17.169 | 1.00 | 53.25 C |
| ATOM | 5485 | CE1 | PHE | H | 157 | 6.437 | 7.503 | 17.922 | 1.00 | 55.80 C |
| ATOM | 5487 | CZ | PHE | H | 157 | 5.582 | 7.970 | 18.925 | 1.00 | 55.72 C |
| ATOM | 5489 | CE2 | PHE | H | 157 | 4.376 | 7.325 | 19.147 | 1.00 | 56.54 C |
| ATOM | 5491 | CD2 | PHE | H | 157 | 4.032 | 6.213 | 18.374 | 1.00 | 55.21 C |
| ATOM | 5493 | C | PHE | H | 157 | 4.225 | 2.926 | 18.432 | 1.00 | 54.76 C |
| ATOM | 5494 | O | PHE | H | 157 | 3.140 | 2.351 | 18.375 | 1.00 | 55.93 O |
| ATOM | 5496 | N | PRO | H | 158 | 4.784 | 3.266 | 19.598 | 1.00 | 55.16 N |
| ATOM | 5497 | CA | PRO | H | 158 | 6.124 | 3.745 | 19.872 | 1.00 | 55.88 C |
| ATOM | 5499 | CB | PRO | H | 158 | 5.985 | 4.360 | 21.268 | 1.00 | 55.39 C |
| ATOM | 5502 | CG | PRO | H | 158 | 4.988 | 3.528 | 21.915 | 1.00 | 54.26 C |
| ATOM | 5505 | CD | PRO | H | 158 | 4.000 | 3.155 | 20.841 | 1.00 | 56.33 C |
| ATOM | 5508 | C | PRO | H | 158 | 7.076 | 2.564 | 19.916 | 1.00 | 56.55 C |
| ATOM | 5509 | O | PRO | H | 158 | 6.733 | 1.480 | 19.454 | 1.00 | 56.07 O |
| ATOM | 5510 | N | GLU | H | 159 | 8.268 | 2.782 | 20.457 | 1.00 | 56.52 N |
| ATOM | 5511 | CA | GLU | H | 159 | 9.156 | 1.689 | 20.798 | 1.00 | 55.94 C |
| ATOM | 5513 | CB | GLU | H | 159 | 10.574 | 2.224 | 21.030 | 1.00 | 56.82 C |
| ATOM | 5516 | CG | GLU | H | 159 | 11.320 | 2.633 | 19.770 | 1.00 | 56.39 C |
| ATOM | 5519 | CD | GLU | H | 159 | 12.266 | 1.559 | 19.284 | 1.00 | 60.65 C |
| ATOM | 5520 | OE1 | GLU | H | 159 | 13.453 | 1.884 | 19.064 | 1.00 | 62.67 O |
| ATOM | 5521 | OE2 | GLU | H | 159 | 11.832 | 0.391 | 19.139 | 1.00 | 63.04 O |
| ATOM | 5522 | C | GLU | H | 159 | 8.593 | 1.061 | 22.073 | 1.00 | 55.33 C |
| ATOM | 5523 | O | GLU | H | 159 | 7.690 | 1.635 | 22.686 | 1.00 | 55.74 O |
| ATOM | 5525 | N | PRO | H | 160 | 9.098 | −0.125 | 22.467 | 1.00 | 53.85 N |
| ATOM | 5526 | CA | PRO | H | 160 | 10.004 | −1.007 | 21.746 | 1.00 | 52.78 C |

-continued

| ATOM | 5528 | CB | PRO | H | 160 | 10.924 | −1.496 | 22.858 | 1.00 | 52.15 | C |
| ATOM | 5531 | CG | PRO | H | 160 | 10.013 | −1.591 | 24.054 | 1.00 | 52.29 | C |
| ATOM | 5534 | CD | PRO | H | 160 | 8.825 | −0.668 | 23.810 | 1.00 | 53.50 | C |
| ATOM | 5537 | C | PRO | H | 160 | 9.298 | −2.204 | 21.123 | 1.00 | 52.45 | C |
| ATOM | 5538 | O | PRO | H | 160 | 8.115 | −2.454 | 21.391 | 1.00 | 51.11 | O |
| ATOM | 5539 | N | VAL | H | 161 | 10.041 | −2.930 | 20.294 | 1.00 | 52.65 | N |
| ATOM | 5540 | CA | VAL | H | 161 | 9.637 | −4.244 | 19.803 | 1.00 | 52.85 | C |
| ATOM | 5542 | CB | VAL | H | 161 | 9.481 | −4.254 | 18.265 | 1.00 | 53.15 | C |
| ATOM | 5544 | CG1 | VAL | H | 161 | 9.358 | −5.673 | 17.732 | 1.00 | 54.39 | C |
| ATOM | 5548 | CG2 | VAL | H | 161 | 8.278 | −3.433 | 17.846 | 1.00 | 54.62 | C |
| ATOM | 5552 | C | VAL | H | 161 | 10.744 | −5.208 | 20.191 | 1.00 | 53.06 | C |
| ATOM | 5553 | O | VAL | H | 161 | 11.919 | −4.851 | 20.132 | 1.00 | 54.73 | O |
| ATOM | 5555 | N | THR | H | 162 | 10.378 | −6.421 | 20.589 | 1.00 | 52.31 | N |
| ATOM | 5556 | CA | THR | H | 162 | 11.365 | −7.453 | 20.858 | 1.00 | 52.49 | C |
| ATOM | 5558 | CB | THR | H | 162 | 11.239 | −7.974 | 22.277 | 1.00 | 52.92 | C |
| ATOM | 5560 | OG1 | THR | H | 162 | 9.893 | −8.409 | 22.503 | 1.00 | 56.03 | O |
| ATOM | 5562 | CG2 | THR | H | 162 | 11.589 | −6.881 | 23.266 | 1.00 | 52.72 | C |
| ATOM | 5566 | C | THR | H | 162 | 11.172 | −8.598 | 19.884 | 1.00 | 52.24 | C |
| ATOM | 5567 | O | THR | H | 162 | 10.049 | −8.861 | 19.448 | 1.00 | 51.87 | O |
| ATOM | 5569 | N | VAL | H | 163 | 12.276 | −9.262 | 19.544 | 1.00 | 52.59 | N |
| ATOM | 5570 | CA | VAL | H | 163 | 12.278 | −10.397 | 18.611 | 1.00 | 52.64 | C |
| ATOM | 5572 | CB | VAL | H | 163 | 12.914 | −10.023 | 17.259 | 1.00 | 51.61 | C |
| ATOM | 5574 | CG1 | VAL | H | 163 | 12.349 | −10.910 | 16.156 | 1.00 | 52.12 | C |
| ATOM | 5578 | CG2 | VAL | H | 163 | 12.684 | −8.561 | 16.934 | 1.00 | 51.50 | C |
| ATOM | 5582 | C | VAL | H | 163 | 13.077 | −11.570 | 19.180 | 1.00 | 52.73 | C |
| ATOM | 5583 | O | VAL | H | 163 | 14.023 | −11.370 | 19.935 | 1.00 | 52.59 | O |
| ATOM | 5585 | N | SER | H | 164 | 12.706 | −12.789 | 18.809 | 1.00 | 53.15 | N |
| ATOM | 5586 | CA | SER | H | 164 | 13.407 | −13.981 | 19.292 | 1.00 | 53.63 | C |
| ATOM | 5588 | CB | SER | H | 164 | 12.991 | −14.308 | 20.726 | 1.00 | 54.08 | C |
| ATOM | 5591 | OG | SER | H | 164 | 11.600 | −14.575 | 20.804 | 1.00 | 54.40 | O |
| ATOM | 5593 | C | SER | H | 164 | 13.068 | −15.151 | 18.399 | 1.00 | 53.97 | C |
| ATOM | 5594 | O | SER | H | 164 | 11.940 | −15.246 | 17.925 | 1.00 | 55.13 | O |
| ATOM | 5596 | N | TRP | H | 165 | 14.028 | −16.048 | 18.187 | 1.00 | 54.13 | N |
| ATOM | 5597 | CA | TRP | H | 165 | 13.863 | −17.128 | 17.209 | 1.00 | 54.37 | C |
| ATOM | 5599 | CB | TRP | H | 165 | 15.104 | −17.243 | 16.319 | 1.00 | 53.74 | C |
| ATOM | 5602 | CG | TRP | H | 165 | 15.227 | −16.085 | 15.383 | 1.00 | 52.17 | C |
| ATOM | 5603 | CD1 | TRP | H | 165 | 15.778 | −14.864 | 15.653 | 1.00 | 50.28 | C |
| ATOM | 5605 | NE1 | TRP | H | 165 | 15.692 | −14.053 | 14.549 | 1.00 | 51.40 | N |
| ATOM | 5607 | CE2 | TRP | H | 165 | 15.070 | −14.740 | 13.538 | 1.00 | 52.68 | C |
| ATOM | 5608 | CD2 | TRP | H | 165 | 14.758 | −16.025 | 14.031 | 1.00 | 53.23 | C |
| ATOM | 5609 | CE3 | TRP | H | 165 | 14.113 | −16.937 | 13.183 | 1.00 | 52.56 | C |
| ATOM | 5611 | CZ3 | TRP | H | 165 | 13.805 | −16.537 | 11.880 | 1.00 | 51.23 | C |
| ATOM | 5613 | CH2 | TRP | H | 165 | 14.124 | −15.251 | 11.424 | 1.00 | 51.34 | C |
| ATOM | 5615 | CZ2 | TRP | H | 165 | 14.756 | −14.342 | 12.232 | 1.00 | 51.54 | C |
| ATOM | 5617 | C | TRP | H | 165 | 13.559 | −18.450 | 17.886 | 1.00 | 54.67 | C |
| ATOM | 5618 | O | TRP | H | 165 | 14.261 | −18.855 | 18.814 | 1.00 | 55.34 | O |
| ATOM | 5620 | N | ASN | H | 166 | 12.503 | −19.108 | 17.414 | 1.00 | 54.61 | N |
| ATOM | 5621 | CA | ASN | H | 166 | 12.048 | −20.369 | 17.985 | 1.00 | 55.19 | C |
| ATOM | 5623 | CB | ASN | H | 166 | 13.069 | −21.484 | 17.723 | 1.00 | 55.05 | C |
| ATOM | 5626 | CG | ASN | H | 166 | 13.551 | −21.508 | 16.286 | 1.00 | 55.74 | C |
| ATOM | 5627 | OD1 | ASN | H | 166 | 13.259 | −20.600 | 15.503 | 1.00 | 57.20 | O |
| ATOM | 5628 | ND2 | ASN | H | 166 | 14.304 | −22.545 | 15.933 | 1.00 | 54.79 | N |
| ATOM | 5631 | C | ASN | H | 166 | 11.774 | −20.231 | 19.479 | 1.00 | 55.45 | C |
| ATOM | 5632 | O | ASN | H | 166 | 12.207 | −21.058 | 20.276 | 1.00 | 56.31 | O |
| ATOM | 5634 | N | SER | H | 167 | 11.070 | −19.162 | 19.843 | 1.00 | 56.10 | N |
| ATOM | 5635 | CA | SER | H | 167 | 10.640 | −18.914 | 21.225 | 1.00 | 56.38 | C |
| ATOM | 5637 | CB | SER | H | 167 | 9.587 | −19.947 | 21.633 | 1.00 | 56.14 | C |
| ATOM | 5640 | OG | SER | H | 167 | 8.594 | −20.058 | 20.628 | 1.00 | 58.09 | O |
| ATOM | 5642 | C | SER | H | 167 | 11.787 | −18.884 | 22.242 | 1.00 | 56.39 | C |
| ATOM | 5643 | O | SER | H | 167 | 11.624 | −19.324 | 23.379 | 1.00 | 56.24 | O |
| ATOM | 5645 | N | GLY | H | 168 | 12.935 | −18.349 | 21.827 | 1.00 | 56.67 | N |
| ATOM | 5646 | CA | GLY | H | 168 | 14.110 | −18.236 | 22.696 | 1.00 | 56.47 | C |
| ATOM | 5649 | C | GLY | H | 168 | 15.189 | −19.290 | 22.472 | 1.00 | 56.51 | C |
| ATOM | 5650 | O | GLY | H | 168 | 16.337 | −19.085 | 22.879 | 1.00 | 56.55 | O |
| ATOM | 5652 | N | ALA | H | 169 | 14.836 | −20.399 | 21.811 | 1.00 | 56.03 | N |
| ATOM | 5653 | CA | ALA | H | 169 | 15.723 | −21.579 | 21.688 | 1.00 | 55.57 | C |
| ATOM | 5655 | CB | ALA | H | 169 | 14.903 | −22.822 | 21.329 | 1.00 | 54.96 | C |
| ATOM | 5659 | C | ALA | H | 169 | 16.880 | −21.424 | 20.697 | 1.00 | 55.09 | C |
| ATOM | 5660 | O | ALA | H | 169 | 17.771 | −22.269 | 20.654 | 1.00 | 54.27 | O |
| ATOM | 5662 | N | LEU | H | 170 | 16.850 | −20.359 | 19.900 | 1.00 | 54.95 | N |
| ATOM | 5663 | CA | LEU | H | 170 | 17.897 | −20.063 | 18.927 | 1.00 | 54.71 | C |
| ATOM | 5665 | CB | LEU | H | 170 | 17.330 | −20.216 | 17.510 | 1.00 | 54.56 | C |
| ATOM | 5668 | CG | LEU | H | 170 | 18.010 | −19.512 | 16.328 | 1.00 | 55.49 | C |
| ATOM | 5670 | CD1 | LEU | H | 170 | 19.522 | −19.754 | 16.291 | 1.00 | 56.23 | C |
| ATOM | 5674 | CD2 | LEU | H | 170 | 17.354 | −19.965 | 15.031 | 1.00 | 55.06 | C |
| ATOM | 5678 | C | LEU | H | 170 | 18.408 | −18.640 | 19.166 | 1.00 | 54.84 | C |
| ATOM | 5679 | O | LEU | H | 170 | 17.719 | −17.669 | 18.836 | 1.00 | 55.29 | O |
| ATOM | 5681 | N | THR | H | 171 | 19.606 | −18.519 | 19.740 | 1.00 | 54.01 | N |
| ATOM | 5682 | CA | THR | H | 171 | 20.159 | −17.211 | 20.120 | 1.00 | 53.50 | C |

-continued

| | | | | | | | | | | |
|---|---|---|---|---|---|---|---|---|---|---|
| ATOM | 5684 | CB | THR | H | 171 | 20.488 | −17.149 | 21.617 | 1.00 | 53.39 C |
| ATOM | 5686 | OG1 | THR | H | 171 | 21.473 | −18.142 | 21.930 | 1.00 | 53.51 O |
| ATOM | 5688 | CG2 | THR | H | 171 | 19.228 | −17.355 | 22.465 | 1.00 | 52.71 C |
| ATOM | 5692 | C | THR | H | 171 | 21.433 | −16.842 | 19.377 | 1.00 | 52.81 C |
| ATOM | 5693 | O | THR | H | 171 | 21.532 | −15.747 | 18.843 | 1.00 | 51.22 O |
| ATOM | 5695 | N | SER | H | 172 | 22.410 | −17.745 | 19.367 | 1.00 | 53.12 N |
| ATOM | 5696 | CA | SER | H | 172 | 23.724 | −17.446 | 18.787 | 1.00 | 53.23 C |
| ATOM | 5698 | CB | SER | H | 172 | 24.791 | −18.436 | 19.288 | 1.00 | 53.49 C |
| ATOM | 5701 | OG | SER | H | 172 | 24.888 | −19.583 | 18.459 | 1.00 | 53.14 O |
| ATOM | 5703 | C | SER | H | 172 | 23.662 | −17.425 | 17.251 | 1.00 | 53.04 C |
| ATOM | 5704 | O | SER | H | 172 | 23.128 | −18.347 | 16.622 | 1.00 | 52.57 O |
| ATOM | 5706 | N | GLY | H | 173 | 24.219 | −16.369 | 16.662 | 1.00 | 52.83 N |
| ATOM | 5707 | CA | GLY | H | 173 | 24.089 | −16.111 | 15.231 | 1.00 | 53.02 C |
| ATOM | 5710 | C | GLY | H | 173 | 23.077 | −15.012 | 14.956 | 1.00 | 53.10 C |
| ATOM | 5711 | O | GLY | H | 173 | 23.185 | −14.303 | 13.961 | 1.00 | 52.33 O |
| ATOM | 5713 | N | VAL | H | 174 | 22.090 | −14.872 | 15.839 | 1.00 | 53.83 N |
| ATOM | 5714 | CA | VAL | H | 174 | 21.074 | −13.829 | 15.703 | 1.00 | 54.56 C |
| ATOM | 5716 | CB | VAL | H | 174 | 19.909 | −14.004 | 16.720 | 1.00 | 54.65 C |
| ATOM | 5718 | CG1 | VAL | H | 174 | 18.953 | −12.816 | 16.674 | 1.00 | 53.10 C |
| ATOM | 5722 | CG2 | VAL | H | 174 | 19.154 | −15.302 | 16.457 | 1.00 | 56.10 C |
| ATOM | 5726 | C | VAL | H | 174 | 21.691 | −12.454 | 15.922 | 1.00 | 55.19 C |
| ATOM | 5727 | O | VAL | H | 174 | 22.483 | −12.263 | 16.848 | 1.00 | 54.90 O |
| ATOM | 5729 | N | HIS | H | 175 | 21.318 | −11.517 | 15.049 | 1.00 | 55.07 N |
| ATOM | 5730 | CA | HIS | H | 175 | 21.626 | −10.101 | 15.204 | 1.00 | 53.78 C |
| ATOM | 5732 | CB | HIS | H | 175 | 22.630 | −9.647 | 14.146 | 1.00 | 55.18 C |
| ATOM | 5735 | CG | HIS | H | 175 | 24.013 | −10.175 | 14.355 | 1.00 | 56.38 C |
| ATOM | 5736 | ND1 | HIS | H | 175 | 24.871 | −9.660 | 15.303 | 1.00 | 56.74 N |
| ATOM | 5738 | CE1 | HIS | H | 175 | 26.018 | −10.312 | 15.253 | 1.00 | 58.40 C |
| ATOM | 5740 | NE2 | HIS | H | 175 | 25.936 | −11.228 | 14.304 | 1.00 | 58.07 N |
| ATOM | 5742 | CD2 | HIS | H | 175 | 24.693 | −11.162 | 13.725 | 1.00 | 55.44 C |
| ATOM | 5744 | C | HIS | H | 175 | 20.344 | −9.310 | 15.025 | 1.00 | 52.26 C |
| ATOM | 5745 | O | HIS | H | 175 | 19.908 | −9.074 | 13.896 | 1.00 | 52.01 O |
| ATOM | 5747 | N | THR | H | 176 | 19.726 | −8.919 | 16.131 | 1.00 | 50.96 N |
| ATOM | 5748 | CA | THR | H | 176 | 18.593 | −8.005 | 16.071 | 1.00 | 50.96 C |
| ATOM | 5750 | CB | THR | H | 176 | 17.641 | −8.207 | 17.247 | 1.00 | 50.09 C |
| ATOM | 5752 | OG1 | THR | H | 176 | 17.200 | −9.569 | 17.260 | 1.00 | 49.15 O |
| ATOM | 5754 | CG2 | THR | H | 176 | 16.435 | −7.272 | 17.144 | 1.00 | 48.81 C |
| ATOM | 5758 | C | THR | H | 176 | 19.140 | −6.584 | 16.058 | 1.00 | 50.24 C |
| ATOM | 5759 | O | THR | H | 176 | 19.942 | −6.218 | 16.923 | 1.00 | 49.54 O |
| ATOM | 5761 | N | PHE | H | 177 | 18.721 | −5.798 | 15.066 | 1.00 | 50.40 N |
| ATOM | 5762 | CA | PHE | H | 177 | 19.301 | −4.472 | 14.839 | 1.00 | 50.56 C |
| ATOM | 5764 | CB | PHE | H | 177 | 19.302 | −4.126 | 13.352 | 1.00 | 49.81 C |
| ATOM | 5767 | CG | PHE | H | 177 | 20.236 | −4.974 | 12.534 | 1.00 | 48.87 C |
| ATOM | 5768 | CD1 | PHE | H | 177 | 19.775 | −6.109 | 11.876 | 1.00 | 47.29 C |
| ATOM | 5770 | CE1 | PHE | H | 177 | 20.640 | −6.896 | 11.125 | 1.00 | 49.15 C |
| ATOM | 5772 | CZ | PHE | H | 177 | 21.986 | −6.545 | 11.015 | 1.00 | 48.85 C |
| ATOM | 5774 | CE2 | PHE | H | 177 | 22.456 | −5.409 | 11.661 | 1.00 | 49.17 C |
| ATOM | 5776 | CD2 | PHE | H | 177 | 21.583 | −4.632 | 12.418 | 1.00 | 49.41 C |
| ATOM | 5778 | C | PHE | H | 177 | 18.556 | −3.395 | 15.602 | 1.00 | 50.98 C |
| ATOM | 5779 | O | PHE | H | 177 | 17.347 | −3.500 | 15.792 | 1.00 | 51.24 O |
| ATOM | 5781 | N | PRO | H | 178 | 19.281 | −2.353 | 16.050 | 1.00 | 52.21 N |
| ATOM | 5782 | CA | PRO | H | 178 | 18.612 | −1.172 | 16.589 | 1.00 | 51.10 C |
| ATOM | 5784 | CB | PRO | H | 178 | 19.745 | −0.146 | 16.741 | 1.00 | 50.08 C |
| ATOM | 5787 | CG | PRO | H | 178 | 20.984 | −0.911 | 16.801 | 1.00 | 50.78 C |
| ATOM | 5790 | CD | PRO | H | 178 | 20.752 | −2.225 | 16.087 | 1.00 | 52.81 C |
| ATOM | 5793 | C | PRO | H | 178 | 17.586 | −0.657 | 15.596 | 1.00 | 51.37 C |
| ATOM | 5794 | O | PRO | H | 178 | 17.849 | −0.631 | 14.392 | 1.00 | 53.28 O |
| ATOM | 5795 | N | ALA | H | 179 | 16.425 | −0.260 | 16.092 | 1.00 | 51.75 N |
| ATOM | 5796 | CA | ALA | H | 179 | 15.386 | 0.271 | 15.230 | 1.00 | 52.20 C |
| ATOM | 5798 | CB | ALA | H | 179 | 14.126 | 0.544 | 16.021 | 1.00 | 53.05 C |
| ATOM | 5802 | C | ALA | H | 179 | 15.853 | 1.541 | 14.541 | 1.00 | 52.48 C |
| ATOM | 5803 | O | ALA | H | 179 | 16.837 | 2.172 | 14.949 | 1.00 | 50.37 O |
| ATOM | 5805 | N | VAL | H | 180 | 15.137 | 1.893 | 13.481 | 1.00 | 52.84 N |
| ATOM | 5806 | CA | VAL | H | 180 | 15.411 | 3.103 | 12.739 | 1.00 | 53.15 C |
| ATOM | 5808 | CB | VAL | H | 180 | 16.018 | 2.787 | 11.373 | 1.00 | 52.57 C |
| ATOM | 5810 | CG1 | VAL | H | 180 | 16.049 | 4.022 | 10.507 | 1.00 | 53.76 C |
| ATOM | 5814 | CG2 | VAL | H | 180 | 17.418 | 2.223 | 11.543 | 1.00 | 54.03 C |
| ATOM | 5818 | C | VAL | H | 180 | 14.125 | 3.893 | 12.578 | 1.00 | 52.96 C |
| ATOM | 5819 | O | VAL | H | 180 | 13.071 | 3.338 | 12.301 | 1.00 | 53.63 O |
| ATOM | 5821 | N | LEU | H | 181 | 14.234 | 5.200 | 12.752 | 1.00 | 53.47 N |
| ATOM | 5822 | CA | LEU | H | 181 | 13.091 | 6.078 | 12.664 | 1.00 | 54.62 C |
| ATOM | 5824 | CB | LEU | H | 181 | 13.286 | 7.260 | 13.606 | 1.00 | 53.92 C |
| ATOM | 5827 | CG | LEU | H | 181 | 12.173 | 8.295 | 13.667 | 1.00 | 53.57 C |
| ATOM | 5829 | CD1 | LEU | H | 181 | 10.804 | 7.646 | 13.619 | 1.00 | 56.77 C |
| ATOM | 5833 | CD2 | LEU | H | 181 | 12.330 | 9.105 | 14.930 | 1.00 | 54.91 C |
| ATOM | 5837 | C | LEU | H | 181 | 12.908 | 6.546 | 11.228 | 1.00 | 55.19 C |
| ATOM | 5838 | O | LEU | H | 181 | 13.681 | 7.361 | 10.721 | 1.00 | 55.15 O |
| ATOM | 5840 | N | GLN | H | 182 | 11.892 | 6.006 | 10.567 | 1.00 | 56.48 N |
| ATOM | 5841 | CA | GLN | H | 182 | 11.571 | 6.408 | 9.198 | 1.00 | 57.31 C |

-continued

| | | | | | | | | | | |
|---|---|---|---|---|---|---|---|---|---|---|
| ATOM | 5843 | CB | GLN | H | 182 | 10.562 | 5.436 | 8.568 | 1.00 | 56.69 C |
| ATOM | 5846 | CG | GLN | H | 182 | 11.143 | 4.041 | 8.305 | 1.00 | 56.48 C |
| ATOM | 5849 | CD | GLN | H | 182 | 10.089 | 2.935 | 8.250 | 1.00 | 59.11 C |
| ATOM | 5850 | OE1 | GLN | H | 182 | 9.146 | 2.918 | 9.044 | 1.00 | 64.81 O |
| ATOM | 5851 | NE2 | GLN | H | 182 | 10.265 | 1.990 | 7.329 | 1.00 | 55.62 N |
| ATOM | 5854 | C | GLN | H | 182 | 11.032 | 7.842 | 9.200 | 1.00 | 58.24 C |
| ATOM | 5855 | O | GLN | H | 182 | 10.706 | 8.391 | 10.263 | 1.00 | 57.97 O |
| ATOM | 5857 | N | SER | H | 183 | 10.957 | 8.454 | 8.020 | 1.00 | 57.77 N |
| ATOM | 5858 | CA | SER | H | 183 | 10.542 | 9.852 | 7.924 | 1.00 | 57.23 C |
| ATOM | 5860 | CB | SER | H | 183 | 10.719 | 10.378 | 6.511 | 1.00 | 55.75 C |
| ATOM | 5863 | OG | SER | H | 183 | 9.603 | 10.023 | 5.738 | 1.00 | 57.78 O |
| ATOM | 5865 | C | SER | H | 183 | 9.090 | 9.993 | 8.347 | 1.00 | 57.27 C |
| ATOM | 5866 | O | SER | H | 183 | 8.704 | 10.997 | 8.938 | 1.00 | 59.06 O |
| ATOM | 5868 | N | SER | H | 184 | 8.303 | 8.962 | 8.059 | 1.00 | 57.26 N |
| ATOM | 5869 | CA | SER | H | 184 | 6.907 | 8.872 | 8.487 | 1.00 | 57.21 C |
| ATOM | 5871 | CB | SER | H | 184 | 6.339 | 7.542 | 8.015 | 1.00 | 57.40 C |
| ATOM | 5874 | OG | SER | H | 184 | 7.181 | 6.483 | 8.434 | 1.00 | 57.06 O |
| ATOM | 5876 | C | SER | H | 184 | 6.684 | 8.964 | 10.001 | 1.00 | 57.94 C |
| ATOM | 5877 | O | SER | H | 184 | 5.545 | 9.107 | 10.446 | 1.00 | 58.79 O |
| ATOM | 5879 | N | GLY | H | 185 | 7.750 | 8.854 | 10.793 | 1.00 | 57.97 N |
| ATOM | 5880 | CA | GLY | H | 185 | 7.628 | 8.854 | 12.252 | 1.00 | 57.40 C |
| ATOM | 5883 | C | GLY | H | 185 | 7.417 | 7.461 | 12.829 | 1.00 | 57.11 C |
| ATOM | 5884 | O | GLY | H | 185 | 7.483 | 7.265 | 14.039 | 1.00 | 58.00 O |
| ATOM | 5886 | N | LEU | H | 186 | 7.154 | 6.490 | 11.964 | 1.00 | 57.04 N |
| ATOM | 5887 | CA | LEU | H | 186 | 7.085 | 5.105 | 12.372 | 1.00 | 56.45 C |
| ATOM | 5889 | CB | LEU | H | 186 | 6.257 | 4.300 | 11.376 | 1.00 | 55.19 C |
| ATOM | 5892 | CG | LEU | H | 186 | 4.829 | 4.795 | 11.146 | 1.00 | 53.58 C |
| ATOM | 5894 | CD1 | LEU | H | 186 | 4.129 | 3.972 | 10.075 | 1.00 | 53.03 C |
| ATOM | 5898 | CD2 | LEU | H | 186 | 4.039 | 4.755 | 12.446 | 1.00 | 54.82 C |
| ATOM | 5902 | C | LEU | H | 186 | 8.499 | 4.554 | 12.438 | 1.00 | 56.74 C |
| ATOM | 5903 | O | LEU | H | 186 | 9.391 | 5.013 | 11.723 | 1.00 | 55.76 O |
| ATOM | 5905 | N | TYR | H | 187 | 8.697 | 3.580 | 13.318 | 1.00 | 57.41 N |
| ATOM | 5906 | CA | TYR | H | 187 | 9.970 | 2.886 | 13.424 | 1.00 | 57.88 C |
| ATOM | 5908 | CB | TYR | H | 187 | 10.238 | 2.471 | 14.868 | 1.00 | 59.35 C |
| ATOM | 5911 | CG | TYR | H | 187 | 10.617 | 3.620 | 15.767 | 1.00 | 62.62 C |
| ATOM | 5912 | CD1 | TYR | H | 187 | 11.901 | 4.153 | 15.731 | 1.00 | 63.67 C |
| ATOM | 5914 | CE1 | TYR | H | 187 | 12.260 | 5.210 | 16.559 | 1.00 | 62.88 C |
| ATOM | 5916 | CZ | TYR | H | 187 | 11.333 | 5.743 | 17.431 | 1.00 | 60.29 C |
| ATOM | 5917 | OH | TYR | H | 187 | 11.712 | 6.786 | 18.234 | 1.00 | 62.21 O |
| ATOM | 5919 | CE2 | TYR | H | 187 | 10.048 | 5.236 | 17.490 | 1.00 | 60.31 C |
| ATOM | 5921 | CD2 | TYR | H | 187 | 9.695 | 4.178 | 16.662 | 1.00 | 63.69 C |
| ATOM | 5923 | C | TYR | H | 187 | 9.958 | 1.648 | 12.548 | 1.00 | 58.14 C |
| ATOM | 5924 | O | TYR | H | 187 | 8.899 | 1.185 | 12.130 | 1.00 | 59.34 O |
| ATOM | 5926 | N | SER | H | 188 | 11.145 | 1.115 | 12.285 | 1.00 | 57.39 N |
| ATOM | 5927 | CA | SER | H | 188 | 11.293 | −0.161 | 11.611 | 1.00 | 56.96 C |
| ATOM | 5929 | CB | SER | H | 188 | 11.241 | 0.037 | 10.108 | 1.00 | 57.73 C |
| ATOM | 5932 | OG | SER | H | 188 | 11.937 | −1.002 | 9.451 | 1.00 | 60.59 O |
| ATOM | 5934 | C | SER | H | 188 | 12.618 | −0.788 | 12.003 | 1.00 | 56.89 C |
| ATOM | 5935 | O | SER | H | 188 | 13.582 | −0.075 | 12.283 | 1.00 | 58.30 O |
| ATOM | 5937 | N | LEU | H | 189 | 12.659 | −2.118 | 12.033 | 1.00 | 55.93 N |
| ATOM | 5938 | CA | LEU | H | 189 | 13.890 | −2.850 | 12.336 | 1.00 | 56.36 C |
| ATOM | 5940 | CB | LEU | H | 189 | 14.096 | −2.967 | 13.855 | 1.00 | 56.13 C |
| ATOM | 5943 | CG | LEU | H | 189 | 13.239 | −3.899 | 14.722 | 1.00 | 55.37 C |
| ATOM | 5945 | CD1 | LEU | H | 189 | 13.532 | −5.378 | 14.521 | 1.00 | 55.17 C |
| ATOM | 5949 | CD2 | LEU | H | 189 | 13.455 | −3.554 | 16.182 | 1.00 | 56.81 C |
| ATOM | 5953 | C | LEU | H | 189 | 13.931 | −4.236 | 11.680 | 1.00 | 57.58 C |
| ATOM | 5954 | O | LEU | H | 189 | 12.971 | −4.670 | 11.035 | 1.00 | 59.39 O |
| ATOM | 5956 | N | SER | H | 190 | 15.060 | −4.920 | 11.843 | 1.00 | 57.17 N |
| ATOM | 5957 | CA | SER | H | 190 | 15.222 | −6.278 | 11.341 | 1.00 | 55.83 C |
| ATOM | 5959 | CB | SER | H | 190 | 16.051 | −6.275 | 10.057 | 1.00 | 55.58 C |
| ATOM | 5962 | OG | SER | H | 190 | 15.542 | −5.322 | 9.144 | 1.00 | 55.88 O |
| ATOM | 5964 | C | SER | H | 190 | 15.904 | −7.144 | 12.381 | 1.00 | 55.29 C |
| ATOM | 5965 | O | SER | H | 190 | 16.632 | −6.650 | 13.245 | 1.00 | 55.43 O |
| ATOM | 5967 | N | SER | H | 191 | 15.647 | −8.440 | 12.299 | 1.00 | 55.26 N |
| ATOM | 5968 | CA | SER | H | 191 | 16.392 | −9.420 | 13.062 | 1.00 | 55.03 C |
| ATOM | 5970 | CB | SER | H | 191 | 15.520 | −10.066 | 14.127 | 1.00 | 54.46 C |
| ATOM | 5973 | OG | SER | H | 191 | 16.321 | −10.813 | 15.017 | 1.00 | 51.63 O |
| ATOM | 5975 | C | SER | H | 191 | 16.914 | −10.470 | 12.098 | 1.00 | 55.74 C |
| ATOM | 5976 | O | SER | H | 191 | 16.236 | −10.831 | 11.132 | 1.00 | 55.17 O |
| ATOM | 5978 | N | VAL | H | 192 | 18.112 | −10.969 | 12.380 | 1.00 | 56.08 N |
| ATOM | 5979 | CA | VAL | H | 192 | 18.844 | −11.790 | 11.430 | 1.00 | 54.96 C |
| ATOM | 5981 | CB | VAL | H | 192 | 19.663 | −10.854 | 10.508 | 1.00 | 53.98 C |
| ATOM | 5983 | CG1 | VAL | H | 192 | 21.127 | −11.276 | 10.402 | 1.00 | 53.64 C |
| ATOM | 5987 | CG2 | VAL | H | 192 | 18.999 | −10.750 | 9.140 | 1.00 | 53.30 C |
| ATOM | 5991 | C | VAL | H | 192 | 19.711 | −12.838 | 12.138 | 1.00 | 55.11 C |
| ATOM | 5992 | O | VAL | H | 192 | 19.478 | −14.047 | 12.017 | 1.00 | 55.73 O |
| ATOM | 5994 | N | CYS | H | 207 | 10.632 | −17.018 | 14.378 | 1.00 | 55.43 N |
| ATOM | 5995 | CA | CYS | H | 207 | 10.729 | −15.566 | 14.521 | 1.00 | 56.24 C |
| ATOM | 5997 | CB | CYS | H | 207 | 10.796 | −14.899 | 13.152 | 1.00 | 56.42 C |

-continued

| ATOM | 6000 | SG | CYS | H | 207 | 10.656 | −13.085 | 13.167 | 1.00 | 57.75 | S |
|---|---|---|---|---|---|---|---|---|---|---|---|
| ATOM | 6002 | C | CYS | H | 207 | 9.539 | −15.008 | 15.285 | 1.00 | 56.52 | C |
| ATOM | 6003 | O | CYS | H | 207 | 8.453 | −14.868 | 14.723 | 1.00 | 56.56 | O |
| ATOM | 6005 | N | ASN | H | 208 | 9.761 | −14.676 | 16.557 | 1.00 | 57.08 | N |
| ATOM | 6006 | CA | ASN | H | 208 | 8.695 | −14.254 | 17.472 | 1.00 | 56.60 | C |
| ATOM | 6008 | CB | ASN | H | 208 | 8.783 | −15.025 | 18.791 | 1.00 | 55.66 | C |
| ATOM | 6011 | CG | ASN | H | 208 | 8.787 | −16.517 | 18.592 | 1.00 | 53.76 | C |
| ATOM | 6012 | OD1 | ASN | H | 208 | 9.796 | −17.178 | 18.823 | 1.00 | 51.70 | O |
| ATOM | 6013 | ND2 | ASN | H | 208 | 7.663 | −17.058 | 18.149 | 1.00 | 49.89 | N |
| ATOM | 6016 | C | ASN | H | 208 | 8.767 | −12.765 | 17.762 | 1.00 | 56.85 | C |
| ATOM | 6017 | O | ASN | H | 208 | 9.413 | −12.339 | 18.721 | 1.00 | 57.67 | O |
| ATOM | 6019 | N | VAL | H | 209 | 8.105 | −11.976 | 16.924 | 1.00 | 56.05 | N |
| ATOM | 6020 | CA | VAL | H | 209 | 8.006 | −10.541 | 17.149 | 1.00 | 56.06 | C |
| ATOM | 6022 | CB | VAL | H | 209 | 7.655 | −9.797 | 15.837 | 1.00 | 55.08 | C |
| ATOM | 6024 | CG1 | VAL | H | 209 | 7.410 | −8.313 | 16.086 | 1.00 | 54.24 | C |
| ATOM | 6028 | CG2 | VAL | H | 209 | 8.772 | −9.984 | 14.815 | 1.00 | 54.17 | C |
| ATOM | 6032 | C | VAL | H | 209 | 6.969 | −10.285 | 18.251 | 1.00 | 56.23 | C |
| ATOM | 6033 | O | VAL | H | 209 | 6.042 | −11.074 | 18.438 | 1.00 | 56.87 | O |
| ATOM | 6035 | N | ASN | H | 210 | 7.151 | −9.198 | 18.994 | 1.00 | 56.35 | N |
| ATOM | 6036 | CA | ASN | H | 210 | 6.243 | −8.837 | 20.071 | 1.00 | 56.02 | C |
| ATOM | 6038 | CB | ASN | H | 210 | 6.656 | −9.595 | 21.332 | 1.00 | 56.52 | C |
| ATOM | 6041 | CG | ASN | H | 210 | 5.617 | −9.532 | 22.429 | 1.00 | 57.82 | C |
| ATOM | 6042 | OD1 | ASN | H | 210 | 4.434 | −9.302 | 22.179 | 1.00 | 62.49 | O |
| ATOM | 6043 | ND2 | ASN | H | 210 | 6.058 | −9.751 | 23.661 | 1.00 | 60.77 | N |
| ATOM | 6046 | C | ASN | H | 210 | 6.277 | −7.322 | 20.302 | 1.00 | 55.82 | C |
| ATOM | 6047 | O | ASN | H | 210 | 7.320 | −6.780 | 20.665 | 1.00 | 56.48 | O |
| ATOM | 6049 | N | HIS | H | 211 | 5.155 | −6.644 | 20.049 | 1.00 | 55.43 | N |
| ATOM | 6050 | CA | HIS | H | 211 | 5.041 | −5.189 | 20.237 | 1.00 | 55.23 | C |
| ATOM | 6052 | CB | HIS | H | 211 | 4.803 | −4.472 | 18.910 | 1.00 | 55.50 | C |
| ATOM | 6055 | CG | HIS | H | 211 | 4.696 | −2.978 | 19.031 | 1.00 | 56.91 | C |
| ATOM | 6056 | ND1 | HIS | H | 211 | 5.665 | −2.209 | 19.639 | 1.00 | 58.04 | N |
| ATOM | 6058 | CE1 | HIS | H | 211 | 5.311 | −0.937 | 19.588 | 1.00 | 55.70 | C |
| ATOM | 6060 | NE2 | HIS | H | 211 | 4.151 | −0.848 | 18.962 | 1.00 | 55.60 | N |
| ATOM | 6062 | CD2 | HIS | H | 211 | 3.747 | −2.110 | 18.601 | 1.00 | 57.37 | C |
| ATOM | 6064 | C | HIS | H | 211 | 3.892 | −4.899 | 21.180 | 1.00 | 55.66 | C |
| ATOM | 6065 | O | HIS | H | 211 | 2.745 | −4.762 | 20.760 | 1.00 | 56.02 | O |
| ATOM | 6067 | N | LYS | H | 212 | 4.214 | −4.792 | 22.462 | 1.00 | 56.17 | N |
| ATOM | 6068 | CA | LYS | H | 212 | 3.198 | −4.730 | 23.507 | 1.00 | 55.44 | C |
| ATOM | 6070 | CB | LYS | H | 212 | 3.837 | −4.961 | 24.880 | 1.00 | 55.30 | C |
| ATOM | 6073 | CG | LYS | H | 212 | 4.241 | −6.417 | 25.068 | 1.00 | 56.91 | C |
| ATOM | 6076 | CD | LYS | H | 212 | 5.050 | −6.679 | 26.329 | 1.00 | 57.02 | C |
| ATOM | 6079 | CE | LYS | H | 212 | 5.528 | −8.128 | 26.343 | 1.00 | 57.36 | C |
| ATOM | 6082 | NZ | LYS | H | 212 | 5.745 | −8.644 | 27.711 | 1.00 | 58.76 | N |
| ATOM | 6086 | C | LYS | H | 212 | 2.332 | −3.470 | 23.496 | 1.00 | 54.93 | C |
| ATOM | 6087 | O | LYS | H | 212 | 1.142 | −3.559 | 23.786 | 1.00 | 56.04 | O |
| ATOM | 6089 | N | PRO | H | 213 | 2.902 | −2.300 | 23.148 | 1.00 | 54.30 | N |
| ATOM | 6090 | CA | PRO | H | 213 | 2.045 | −1.103 | 23.109 | 1.00 | 53.96 | C |
| ATOM | 6092 | CB | PRO | H | 213 | 2.941 | −0.045 | 22.453 | 1.00 | 52.86 | C |
| ATOM | 6095 | CG | PRO | H | 213 | 4.322 | −0.486 | 22.782 | 1.00 | 53.71 | C |
| ATOM | 6098 | CD | PRO | H | 213 | 4.298 | −1.985 | 22.793 | 1.00 | 53.61 | C |
| ATOM | 6101 | C | PRO | H | 213 | 0.756 | −1.308 | 22.305 | 1.00 | 53.55 | C |
| ATOM | 6102 | O | PRO | H | 213 | −0.318 | −0.951 | 22.784 | 1.00 | 53.75 | O |
| ATOM | 6103 | N | SER | H | 214 | 0.877 | −1.894 | 21.111 | 1.00 | 52.97 | N |
| ATOM | 6104 | CA | SER | H | 214 | −0.274 | −2.218 | 20.260 | 1.00 | 52.11 | C |
| ATOM | 6106 | CB | SER | H | 214 | 0.141 | −2.171 | 18.787 | 1.00 | 51.61 | C |
| ATOM | 6109 | OG | SER | H | 214 | 0.941 | −3.290 | 18.451 | 1.00 | 48.22 | O |
| ATOM | 6111 | C | SER | H | 214 | −0.871 | −3.602 | 20.576 | 1.00 | 51.53 | C |
| ATOM | 6112 | O | SER | H | 214 | −1.894 | −3.988 | 20.003 | 1.00 | 49.67 | O |
| ATOM | 6114 | N | ASN | H | 215 | −0.219 | −4.333 | 21.482 | 1.00 | 50.52 | N |
| ATOM | 6115 | CA | ASN | H | 215 | −0.587 | −5.697 | 21.824 | 1.00 | 50.79 | C |
| ATOM | 6117 | CB | ASN | H | 215 | −1.947 | −5.724 | 22.530 | 1.00 | 50.96 | C |
| ATOM | 6120 | CG | ASN | H | 215 | −2.207 | −7.030 | 23.260 | 1.00 | 49.61 | C |
| ATOM | 6121 | OD1 | ASN | H | 215 | −1.329 | −7.563 | 23.943 | 1.00 | 43.81 | O |
| ATOM | 6122 | ND2 | ASN | H | 215 | −3.418 | −7.549 | 23.118 | 1.00 | 44.87 | N |
| ATOM | 6125 | C | ASN | H | 215 | −0.566 | −6.596 | 20.584 | 1.00 | 50.66 | C |
| ATOM | 6126 | O | ASN | H | 215 | −1.523 | −7.311 | 20.291 | 1.00 | 49.48 | O |
| ATOM | 6128 | N | THR | H | 216 | 0.546 | −6.534 | 19.858 | 1.00 | 51.75 | N |
| ATOM | 6129 | CA | THR | H | 216 | 0.783 | −7.383 | 18.695 | 1.00 | 52.28 | C |
| ATOM | 6131 | CB | THR | H | 216 | 1.427 | −6.596 | 17.533 | 1.00 | 52.32 | C |
| ATOM | 6133 | OG1 | THR | H | 216 | 0.564 | −5.525 | 17.130 | 1.00 | 54.18 | O |
| ATOM | 6135 | CG2 | THR | H | 216 | 1.688 | −7.504 | 16.338 | 1.00 | 50.91 | C |
| ATOM | 6139 | C | THR | H | 216 | 1.734 | −8.503 | 19.088 | 1.00 | 53.09 | C |
| ATOM | 6140 | O | THR | H | 216 | 2.838 | −8.253 | 19.579 | 1.00 | 54.22 | O |
| ATOM | 6142 | N | LYS | H | 217 | 1.291 | −9.736 | 18.882 | 1.00 | 53.84 | N |
| ATOM | 6143 | CA | LYS | H | 217 | 2.140 | −10.900 | 19.049 | 1.00 | 53.18 | C |
| ATOM | 6145 | CB | LYS | H | 217 | 1.735 | −11.689 | 20.301 | 1.00 | 54.58 | C |
| ATOM | 6148 | CG | LYS | H | 217 | 2.588 | −12.925 | 20.601 | 1.00 | 56.14 | C |
| ATOM | 6151 | CD | LYS | H | 217 | 4.077 | −12.657 | 20.389 | 1.00 | 59.75 | C |
| ATOM | 6154 | CE | LYS | H | 217 | 4.965 | −13.729 | 21.000 | 1.00 | 59.59 | C |

-continued

| | | | | | | | | | | |
|---|---|---|---|---|---|---|---|---|---|---|
| ATOM | 6157 | NZ | LYS | H | 217 | 6.397 | −13.496 | 20.640 | 1.00 | 57.35 N |
| ATOM | 6161 | C | LYS | H | 217 | 1.989 | −11.748 | 17.798 | 1.00 | 52.45 C |
| ATOM | 6162 | O | LYS | H | 217 | 0.918 | −12.300 | 17.550 | 1.00 | 52.10 O |
| ATOM | 6164 | N | VAL | H | 218 | 3.059 | −11.833 | 17.012 | 1.00 | 50.92 N |
| ATOM | 6165 | CA | VAL | H | 218 | 3.043 | −12.569 | 15.753 | 1.00 | 51.32 C |
| ATOM | 6167 | CB | VAL | H | 218 | 2.928 | −11.605 | 14.542 | 1.00 | 51.04 C |
| ATOM | 6169 | CG1 | VAL | H | 218 | 3.798 | −10.388 | 14.743 | 1.00 | 53.14 C |
| ATOM | 6173 | CG2 | VAL | H | 218 | 3.278 | −12.301 | 13.223 | 1.00 | 50.80 C |
| ATOM | 6177 | C | VAL | H | 218 | 4.287 | −13.452 | 15.637 | 1.00 | 51.09 C |
| ATOM | 6178 | O | VAL | H | 218 | 5.373 | −13.061 | 16.067 | 1.00 | 50.45 O |
| ATOM | 6180 | N | ASP | H | 219 | 4.101 | −14.645 | 15.062 | 1.00 | 51.30 N |
| ATOM | 6181 | CA | ASP | H | 219 | 5.170 | −15.634 | 14.887 | 1.00 | 51.12 C |
| ATOM | 6183 | CB | ASP | H | 219 | 4.891 | −16.894 | 15.734 | 1.00 | 51.20 C |
| ATOM | 6186 | CG | ASP | H | 219 | 4.837 | −16.610 | 17.252 | 1.00 | 51.57 C |
| ATOM | 6187 | OD1 | ASP | H | 219 | 5.390 | −15.582 | 17.706 | 1.00 | 51.74 O |
| ATOM | 6188 | OD2 | ASP | H | 219 | 4.251 | −17.434 | 17.998 | 1.00 | 47.82 O |
| ATOM | 6189 | C | ASP | H | 219 | 5.293 | −16.020 | 13.409 | 1.00 | 50.40 C |
| ATOM | 6190 | O | ASP | H | 219 | 6.351 | −15.865 | 12.791 | 1.00 | 48.83 O |
| ATOM | 6192 | N | ASP | A | 1 | −34.411 | −5.350 | 50.267 | 1.00 | 62.89 N |
| ATOM | 6193 | CA | ASP | A | 1 | −33.058 | −5.496 | 49.658 | 1.00 | 62.67 C |
| ATOM | 6195 | CB | ASP | A | 1 | −33.165 | −5.591 | 48.131 | 1.00 | 63.84 C |
| ATOM | 6198 | CG | ASP | A | 1 | −34.000 | −6.776 | 47.659 | 1.00 | 67.09 C |
| ATOM | 6199 | OD1 | ASP | A | 1 | −34.688 | −7.402 | 48.504 | 1.00 | 66.69 O |
| ATOM | 6200 | OD2 | ASP | A | 1 | −33.971 | −7.068 | 46.432 | 1.00 | 65.56 O |
| ATOM | 6201 | C | ASP | A | 1 | −32.150 | −4.313 | 49.999 | 1.00 | 61.98 C |
| ATOM | 6202 | O | ASP | A | 1 | −32.607 | −3.283 | 50.484 | 1.00 | 61.81 O |
| ATOM | 6206 | N | ILE | A | 2 | −30.855 | −4.493 | 49.766 | 1.00 | 60.61 N |
| ATOM | 6207 | CA | ILE | A | 2 | −29.931 | −3.385 | 49.582 | 1.00 | 59.42 C |
| ATOM | 6209 | CB | ILE | A | 2 | −28.597 | −3.603 | 50.327 | 1.00 | 58.74 C |
| ATOM | 6211 | CG1 | ILE | A | 2 | −28.849 | −3.911 | 51.803 | 1.00 | 60.40 C |
| ATOM | 6214 | CD1 | ILE | A | 2 | −27.599 | −3.849 | 52.685 | 1.00 | 61.03 C |
| ATOM | 6218 | CG2 | ILE | A | 2 | −27.723 | −2.376 | 50.230 | 1.00 | 59.49 C |
| ATOM | 6222 | C | ILE | A | 2 | −29.693 | −3.318 | 48.077 | 1.00 | 58.25 C |
| ATOM | 6223 | O | ILE | A | 2 | −29.661 | −4.351 | 47.403 | 1.00 | 57.52 O |
| ATOM | 6225 | N | VAL | A | 3 | −29.548 | −2.107 | 47.549 | 1.00 | 57.16 N |
| ATOM | 6226 | CA | VAL | A | 3 | −29.382 | −1.901 | 46.112 | 1.00 | 56.68 C |
| ATOM | 6228 | CB | VAL | A | 3 | −30.429 | −0.887 | 45.575 | 1.00 | 55.38 C |
| ATOM | 6230 | CG1 | VAL | A | 3 | −29.871 | 0.533 | 45.508 | 1.00 | 58.42 C |
| ATOM | 6234 | CG2 | VAL | A | 3 | −30.923 | −1.313 | 44.218 | 1.00 | 54.30 C |
| ATOM | 6238 | C | VAL | A | 3 | −27.939 | −1.469 | 45.805 | 1.00 | 56.42 C |
| ATOM | 6239 | O | VAL | A | 3 | −27.361 | −0.677 | 46.544 | 1.00 | 56.80 O |
| ATOM | 6241 | N | MET | A | 4 | −27.366 | −2.015 | 44.730 | 1.00 | 55.69 N |
| ATOM | 6242 | CA | MET | A | 4 | −25.977 | −1.755 | 44.352 | 1.00 | 54.40 C |
| ATOM | 6244 | CB | MET | A | 4 | −25.188 | −3.062 | 44.257 | 1.00 | 55.52 C |
| ATOM | 6247 | CG | MET | A | 4 | −25.150 | −3.850 | 45.542 | 1.00 | 57.44 C |
| ATOM | 6250 | SD | MET | A | 4 | −24.211 | −3.014 | 46.833 | 1.00 | 59.92 S |
| ATOM | 6251 | CE | MET | A | 4 | −25.341 | −3.183 | 48.192 | 1.00 | 63.07 C |
| ATOM | 6255 | C | MET | A | 4 | −25.930 | −1.058 | 43.008 | 1.00 | 53.29 C |
| ATOM | 6256 | O | MET | A | 4 | −26.354 | −1.611 | 41.996 | 1.00 | 52.73 O |
| ATOM | 6258 | N | THR | A | 5 | −25.396 | 0.155 | 42.999 | 1.00 | 52.96 N |
| ATOM | 6259 | CA | THR | A | 5 | −25.404 | 0.983 | 41.805 | 1.00 | 54.17 C |
| ATOM | 6261 | CB | THR | A | 5 | −26.084 | 2.344 | 42.084 | 1.00 | 53.75 C |
| ATOM | 6263 | OG1 | THR | A | 5 | −27.384 | 2.129 | 42.650 | 1.00 | 54.50 O |
| ATOM | 6265 | CG2 | THR | A | 5 | −26.206 | 3.151 | 40.808 | 1.00 | 51.76 C |
| ATOM | 6269 | C | THR | A | 5 | −23.984 | 1.230 | 41.327 | 1.00 | 54.59 C |
| ATOM | 6270 | O | THR | A | 5 | −23.268 | 2.047 | 41.900 | 1.00 | 56.57 O |
| ATOM | 6272 | N | GLN | A | 6 | −23.567 | 0.515 | 40.288 | 1.00 | 54.82 N |
| ATOM | 6273 | CA | GLN | A | 6 | −22.250 | 0.747 | 39.716 | 1.00 | 53.99 C |
| ATOM | 6275 | CB | GLN | A | 6 | −21.759 | −0.456 | 38.916 | 1.00 | 54.48 C |
| ATOM | 6278 | CG | GLN | A | 6 | −21.411 | −1.646 | 39.772 | 1.00 | 54.04 C |
| ATOM | 6281 | CD | GLN | A | 6 | −20.882 | −2.784 | 38.949 | 1.00 | 53.42 C |
| ATOM | 6282 | OE1 | GLN | A | 6 | −21.480 | −3.855 | 38.903 | 1.00 | 53.23 O |
| ATOM | 6283 | NE2 | GLN | A | 6 | −19.763 | −2.556 | 38.273 | 1.00 | 53.75 N |
| ATOM | 6286 | C | GLN | A | 6 | −22.328 | 1.968 | 38.833 | 1.00 | 54.63 C |
| ATOM | 6287 | O | GLN | A | 6 | −23.404 | 2.320 | 38.338 | 1.00 | 55.98 O |
| ATOM | 6289 | N | SER | A | 7 | −21.176 | 2.605 | 38.640 | 1.00 | 54.86 N |
| ATOM | 6290 | CA | SER | A | 7 | −21.079 | 3.872 | 37.925 | 1.00 | 52.70 C |
| ATOM | 6292 | CB | SER | A | 7 | −21.507 | 5.002 | 38.864 | 1.00 | 51.79 C |
| ATOM | 6295 | OG | SER | A | 7 | −20.677 | 6.136 | 38.726 | 1.00 | 55.10 O |
| ATOM | 6297 | C | SER | A | 7 | −19.634 | 4.073 | 37.471 | 1.00 | 51.64 C |
| ATOM | 6298 | O | SER | A | 7 | −18.734 | 3.985 | 38.292 | 1.00 | 51.21 O |
| ATOM | 6300 | N | PRO | A | 8 | −19.396 | 4.318 | 36.169 | 1.00 | 51.31 N |
| ATOM | 6301 | CA | PRO | A | 8 | −20.311 | 4.405 | 35.038 | 1.00 | 51.31 C |
| ATOM | 6303 | CB | PRO | A | 8 | −19.504 | 5.193 | 34.013 | 1.00 | 51.28 C |
| ATOM | 6306 | CG | PRO | A | 8 | −18.107 | 4.767 | 34.259 | 1.00 | 51.39 C |
| ATOM | 6309 | CD | PRO | A | 8 | −18.002 | 4.546 | 35.745 | 1.00 | 51.55 C |
| ATOM | 6312 | C | PRO | A | 8 | −20.652 | 3.029 | 34.480 | 1.00 | 51.44 C |
| ATOM | 6313 | O | PRO | A | 8 | −20.041 | 2.038 | 34.881 | 1.00 | 52.24 O |
| ATOM | 6314 | N | ASP | A | 9 | −21.616 | 2.982 | 33.561 | 1.00 | 51.77 N |

|      |      |     |     |   |    |         |        |        |      |       |   |
|------|------|-----|-----|---|----|---------|--------|--------|------|-------|---|
| ATOM | 6315 | CA  | ASP | A | 9  | −22.070 | 1.726  | 32.961 | 1.00 | 52.74 | C |
| ATOM | 6317 | CB  | ASP | A | 9  | −23.361 | 1.935  | 32.150 | 1.00 | 52.67 | C |
| ATOM | 6320 | CG  | ASP | A | 9  | −24.619 | 1.938  | 33.022 | 1.00 | 55.81 | C |
| ATOM | 6321 | OD1 | ASP | A | 9  | −24.841 | 0.965  | 33.793 | 1.00 | 56.53 | O |
| ATOM | 6322 | OD2 | ASP | A | 9  | −25.396 | 2.913  | 32.914 | 1.00 | 57.39 | O |
| ATOM | 6323 | C   | ASP | A | 9  | −20.998 | 1.124  | 32.065 | 1.00 | 53.19 | C |
| ATOM | 6324 | O   | ASP | A | 9  | −20.723 | −0.073 | 32.140 | 1.00 | 54.60 | O |
| ATOM | 6326 | N   | SER | A | 10 | −20.411 | 1.964  | 31.219 | 1.00 | 53.70 | N |
| ATOM | 6327 | CA  | SER | A | 10 | −19.372 | 1.558  | 30.281 | 1.00 | 55.01 | C |
| ATOM | 6329 | CB  | SER | A | 10 | −19.858 | 1.711  | 28.842 | 1.00 | 55.57 | C |
| ATOM | 6332 | OG  | SER | A | 10 | −21.249 | 1.977  | 28.793 | 1.00 | 60.63 | O |
| ATOM | 6334 | C   | SER | A | 10 | −18.159 | 2.455  | 30.473 | 1.00 | 56.39 | C |
| ATOM | 6335 | O   | SER | A | 10 | −18.296 | 3.657  | 30.737 | 1.00 | 56.62 | O |
| ATOM | 6337 | N   | LEU | A | 11 | −16.974 | 1.876  | 30.321 | 1.00 | 56.64 | N |
| ATOM | 6338 | CA  | LEU | A | 11 | −15.742 | 2.626  | 30.481 | 1.00 | 56.45 | C |
| ATOM | 6340 | CB  | LEU | A | 11 | −15.107 | 2.333  | 31.846 | 1.00 | 57.19 | C |
| ATOM | 6343 | CG  | LEU | A | 11 | −13.760 | 3.026  | 32.092 | 1.00 | 57.84 | C |
| ATOM | 6345 | CD1 | LEU | A | 11 | −13.862 | 4.552  | 31.927 | 1.00 | 59.14 | C |
| ATOM | 6349 | CD2 | LEU | A | 11 | −13.227 | 2.665  | 33.459 | 1.00 | 57.21 | C |
| ATOM | 6353 | C   | LEU | A | 11 | −14.782 | 2.266  | 29.365 | 1.00 | 56.22 | C |
| ATOM | 6354 | O   | LEU | A | 11 | −14.583 | 1.095  | 29.062 | 1.00 | 56.51 | O |
| ATOM | 6356 | N   | ALA | A | 12 | −14.197 | 3.285  | 28.751 | 1.00 | 56.13 | N |
| ATOM | 6357 | CA  | ALA | A | 12 | −13.225 | 3.081  | 27.703 | 1.00 | 56.48 | C |
| ATOM | 6359 | CB  | ALA | A | 12 | −13.791 | 3.520  | 26.383 | 1.00 | 56.72 | C |
| ATOM | 6363 | C   | ALA | A | 12 | −11.979 | 3.876  | 28.059 | 1.00 | 57.47 | C |
| ATOM | 6364 | O   | ALA | A | 12 | −12.067 | 5.022  | 28.510 | 1.00 | 58.00 | O |
| ATOM | 6366 | N   | VAL | A | 13 | −10.820 | 3.250  | 27.882 | 1.00 | 57.30 | N |
| ATOM | 6367 | CA  | VAL | A | 13 | −9.556  | 3.864  | 28.247 | 1.00 | 56.51 | C |
| ATOM | 6369 | CB  | VAL | A | 13 | −9.416  | 3.927  | 29.802 | 1.00 | 56.78 | C |
| ATOM | 6371 | CG1 | VAL | A | 13 | −8.584  | 2.759  | 30.351 | 1.00 | 57.74 | C |
| ATOM | 6375 | CG2 | VAL | A | 13 | −8.838  | 5.263  | 30.259 | 1.00 | 58.51 | C |
| ATOM | 6379 | C   | VAL | A | 13 | −8.407  | 3.087  | 27.594 | 1.00 | 56.26 | C |
| ATOM | 6380 | O   | VAL | A | 13 | −8.499  | 1.869  | 27.413 | 1.00 | 56.31 | O |
| ATOM | 6382 | N   | SER | A | 14 | −7.337  | 3.796  | 27.239 | 1.00 | 54.96 | N |
| ATOM | 6383 | CA  | SER | A | 14 | −6.213  | 3.202  | 26.504 | 1.00 | 54.21 | C |
| ATOM | 6385 | CB  | SER | A | 14 | −5.243  | 4.293  | 26.033 | 1.00 | 54.54 | C |
| ATOM | 6388 | OG  | SER | A | 14 | −5.831  | 5.115  | 25.042 | 1.00 | 55.88 | O |
| ATOM | 6390 | C   | SER | A | 14 | −5.433  | 2.177  | 27.323 | 1.00 | 52.87 | C |
| ATOM | 6391 | O   | SER | A | 14 | −5.550  | 2.126  | 28.543 | 1.00 | 51.72 | O |
| ATOM | 6393 | N   | LEU | A | 15 | −4.629  | 1.371  | 26.630 | 1.00 | 52.43 | N |
| ATOM | 6394 | CA  | LEU | A | 15 | −3.735  | 0.405  | 27.280 | 1.00 | 52.14 | C |
| ATOM | 6396 | CB  | LEU | A | 15 | −2.943  | −0.414 | 26.242 | 1.00 | 51.79 | C |
| ATOM | 6399 | CG  | LEU | A | 15 | −3.565  | −1.665 | 25.605 | 1.00 | 49.60 | C |
| ATOM | 6401 | CD1 | LEU | A | 15 | −2.507  | −2.445 | 24.837 | 1.00 | 45.32 | C |
| ATOM | 6405 | CD2 | LEU | A | 15 | −4.215  | −2.565 | 26.644 | 1.00 | 52.34 | C |
| ATOM | 6409 | C   | LEU | A | 15 | −2.756  | 1.101  | 28.222 | 1.00 | 51.43 | C |
| ATOM | 6410 | O   | LEU | A | 15 | −2.328  | 2.226  | 27.975 | 1.00 | 51.94 | O |
| ATOM | 6412 | N   | GLY | A | 16 | −2.414  | 0.423  | 29.310 | 1.00 | 51.71 | N |
| ATOM | 6413 | CA  | GLY | A | 16 | −1.516  | 0.978  | 30.315 | 1.00 | 52.44 | C |
| ATOM | 6416 | C   | GLY | A | 16 | −2.109  | 2.106  | 31.147 | 1.00 | 52.76 | C |
| ATOM | 6417 | O   | GLY | A | 16 | −1.501  | 2.534  | 32.136 | 1.00 | 53.41 | O |
| ATOM | 6419 | N   | GLU | A | 17 | −3.298  | 2.574  | 30.766 | 1.00 | 52.43 | N |
| ATOM | 6420 | CA  | GLU | A | 17 | −3.942  | 3.714  | 31.413 | 1.00 | 52.43 | C |
| ATOM | 6422 | CB  | GLU | A | 17 | −4.888  | 4.401  | 30.419 | 1.00 | 52.30 | C |
| ATOM | 6425 | CG  | GLU | A | 17 | −5.165  | 5.874  | 30.679 | 1.00 | 53.08 | C |
| ATOM | 6428 | CD  | GLU | A | 17 | −5.608  | 6.614  | 29.418 | 1.00 | 54.16 | C |
| ATOM | 6429 | OE1 | GLU | A | 17 | −6.464  | 6.083  | 28.671 | 1.00 | 52.55 | O |
| ATOM | 6430 | OE2 | GLU | A | 17 | −5.087  | 7.726  | 29.173 | 1.00 | 55.19 | O |
| ATOM | 6431 | C   | GLU | A | 17 | −4.699  | 3.256  | 32.661 | 1.00 | 52.05 | C |
| ATOM | 6432 | O   | GLU | A | 17 | −5.048  | 2.081  | 32.803 | 1.00 | 51.50 | O |
| ATOM | 6434 | N   | ARG | A | 18 | −4.944  | 4.192  | 33.568 | 1.00 | 52.76 | N |
| ATOM | 6435 | CA  | ARG | A | 18 | −5.617  | 3.885  | 34.824 | 1.00 | 52.69 | C |
| ATOM | 6437 | CB  | ARG | A | 18 | −5.244  | 4.921  | 35.890 | 1.00 | 52.82 | C |
| ATOM | 6440 | CG  | ARG | A | 18 | −6.057  | 4.835  | 37.167 | 1.00 | 54.81 | C |
| ATOM | 6443 | CD  | ARG | A | 18 | −5.311  | 5.391  | 38.364 | 1.00 | 57.22 | C |
| ATOM | 6446 | NE  | ARG | A | 18 | −6.232  | 5.823  | 39.418 | 1.00 | 61.94 | N |
| ATOM | 6448 | CZ  | ARG | A | 18 | −6.736  | 7.054  | 39.534 | 1.00 | 64.92 | C |
| ATOM | 6449 | NH1 | ARG | A | 18 | −7.568  | 7.332  | 40.535 | 1.00 | 63.87 | N |
| ATOM | 6452 | NH2 | ARG | A | 18 | −6.418  | 8.016  | 38.663 | 1.00 | 63.06 | N |
| ATOM | 6455 | C   | ARG | A | 18 | −7.126  | 3.846  | 34.607 | 1.00 | 51.84 | C |
| ATOM | 6456 | O   | ARG | A | 18 | −7.671  | 4.634  | 33.825 | 1.00 | 50.14 | O |
| ATOM | 6458 | N   | ALA | A | 19 | −7.794  | 2.930  | 35.303 | 1.00 | 50.97 | N |
| ATOM | 6459 | CA  | ALA | A | 19 | −9.232  | 2.775  | 35.168 | 1.00 | 52.04 | C |
| ATOM | 6461 | CB  | ALA | A | 19 | −9.542  | 1.633  | 34.229 | 1.00 | 52.55 | C |
| ATOM | 6465 | C   | ALA | A | 19 | −9.895  | 2.545  | 36.518 | 1.00 | 52.46 | C |
| ATOM | 6466 | O   | ALA | A | 19 | −9.438  | 1.725  | 37.314 | 1.00 | 54.85 | O |
| ATOM | 6468 | N   | THR | A | 20 | −10.988 | 3.262  | 36.755 | 1.00 | 52.38 | N |
| ATOM | 6469 | CA  | THR | A | 20 | −11.682 | 3.234  | 38.030 | 1.00 | 52.68 | C |
| ATOM | 6471 | CB  | THR | A | 20 | −11.642 | 4.618  | 38.677 | 1.00 | 52.17 | C |

-continued

| | | | | | | | | | | | |
|---|---|---|---|---|---|---|---|---|---|---|---|
| ATOM | 6473 | OG1 | THR | A | 20 | −10.299 | 4.882 | 39.094 | 1.00 | 53.12 | O |
| ATOM | 6475 | CG2 | THR | A | 20 | −12.587 | 4.709 | 39.886 | 1.00 | 51.87 | C |
| ATOM | 6479 | C | THR | A | 20 | −13.121 | 2.807 | 37.819 | 1.00 | 53.77 | C |
| ATOM | 6480 | O | THR | A | 20 | −13.714 | 3.140 | 36.796 | 1.00 | 54.57 | O |
| ATOM | 6482 | N | ILE | A | 21 | −13.666 | 2.055 | 38.776 | 1.00 | 53.63 | N |
| ATOM | 6483 | CA | ILE | A | 21 | −15.078 | 1.694 | 38.771 | 1.00 | 54.12 | C |
| ATOM | 6485 | CB | ILE | A | 21 | −15.312 | 0.215 | 38.397 | 1.00 | 54.52 | C |
| ATOM | 6487 | CG1 | ILE | A | 21 | −14.723 | −0.085 | 37.011 | 1.00 | 53.22 | C |
| ATOM | 6490 | CD1 | ILE | A | 21 | −14.581 | −1.556 | 36.724 | 1.00 | 53.52 | C |
| ATOM | 6494 | CG2 | ILE | A | 21 | −16.825 | −0.123 | 38.428 | 1.00 | 52.99 | C |
| ATOM | 6498 | C | ILE | A | 21 | −15.642 | 1.952 | 40.150 | 1.00 | 54.97 | C |
| ATOM | 6499 | O | ILE | A | 21 | −15.121 | 1.447 | 41.143 | 1.00 | 57.00 | O |
| ATOM | 6501 | N | ASN | A | 22 | −16.722 | 2.725 | 40.189 | 1.00 | 55.69 | N |
| ATOM | 6502 | CA | ASN | A | 22 | −17.374 | 3.130 | 41.425 | 1.00 | 56.19 | C |
| ATOM | 6504 | CB | ASN | A | 22 | −17.885 | 4.574 | 41.297 | 1.00 | 56.94 | C |
| ATOM | 6507 | CG | ASN | A | 22 | −17.326 | 5.483 | 42.355 | 1.00 | 58.56 | C |
| ATOM | 6508 | OD1 | ASN | A | 22 | −17.781 | 5.482 | 43.502 | 1.00 | 60.89 | O |
| ATOM | 6509 | ND2 | ASN | A | 22 | −16.327 | 6.273 | 41.977 | 1.00 | 59.32 | N |
| ATOM | 6512 | C | ASN | A | 22 | −18.544 | 2.199 | 41.699 | 1.00 | 56.65 | C |
| ATOM | 6513 | O | ASN | A | 22 | −19.209 | 1.750 | 40.768 | 1.00 | 58.28 | O |
| ATOM | 6515 | N | CYS | A | 23 | −18.803 | 1.925 | 42.972 | 1.00 | 57.08 | N |
| ATOM | 6516 | CA | CYS | A | 23 | −19.936 | 1.101 | 43.362 | 1.00 | 56.36 | C |
| ATOM | 6518 | CB | CYS | A | 23 | −19.491 | −0.362 | 43.491 | 1.00 | 56.50 | C |
| ATOM | 6521 | SG | CYS | A | 23 | −20.630 | −1.402 | 44.393 | 1.00 | 62.63 | S |
| ATOM | 6523 | C | CYS | A | 23 | −20.547 | 1.643 | 44.658 | 1.00 | 55.22 | C |
| ATOM | 6524 | O | CYS | A | 23 | −19.828 | 1.883 | 45.626 | 1.00 | 54.61 | O |
| ATOM | 6526 | N | ARG | A | 24 | −21.865 | 1.860 | 44.660 | 1.00 | 55.40 | N |
| ATOM | 6527 | CA | ARG | A | 24 | −22.569 | 2.419 | 45.822 | 1.00 | 55.68 | C |
| ATOM | 6529 | CB | ARG | A | 24 | −23.126 | 3.801 | 45.499 | 1.00 | 56.07 | C |
| ATOM | 6532 | CG | ARG | A | 24 | −23.595 | 4.537 | 46.745 | 1.00 | 57.94 | C |
| ATOM | 6535 | CD | ARG | A | 24 | −24.590 | 5.617 | 46.447 | 1.00 | 61.37 | C |
| ATOM | 6538 | NE | ARG | A | 24 | −24.492 | 6.684 | 47.437 | 1.00 | 68.16 | N |
| ATOM | 6540 | CZ | ARG | A | 24 | −23.520 | 7.595 | 47.469 | 1.00 | 71.66 | C |
| ATOM | 6541 | NH1 | ARG | A | 24 | −22.534 | 7.580 | 46.574 | 1.00 | 73.60 | N |
| ATOM | 6544 | NH2 | ARG | A | 24 | −23.523 | 8.528 | 48.409 | 1.00 | 73.88 | N |
| ATOM | 6547 | C | ARG | A | 24 | −23.727 | 1.542 | 46.314 | 1.00 | 54.23 | C |
| ATOM | 6548 | O | ARG | A | 24 | −24.450 | 0.970 | 45.508 | 1.00 | 55.74 | O |
| ATOM | 6550 | N | ALA | A | 25 | −23.912 | 1.494 | 47.638 | 1.00 | 52.44 | N |
| ATOM | 6551 | CA | ALA | A | 25 | −24.962 | 0.703 | 48.297 | 1.00 | 51.11 | C |
| ATOM | 6553 | CB | ALA | A | 25 | −24.324 | −0.161 | 49.370 | 1.00 | 50.89 | C |
| ATOM | 6557 | C | ALA | A | 25 | −26.056 | 1.600 | 48.918 | 1.00 | 49.83 | C |
| ATOM | 6558 | O | ALA | A | 25 | −25.788 | 2.755 | 49.242 | 1.00 | 49.35 | O |
| ATOM | 6560 | N | SER | A | 26 | −27.274 | 1.071 | 49.087 | 1.00 | 49.01 | N |
| ATOM | 6561 | CA | SER | A | 26 | −28.400 | 1.832 | 49.681 | 1.00 | 48.88 | C |
| ATOM | 6563 | CB | SER | A | 26 | −29.728 | 1.065 | 49.615 | 1.00 | 46.84 | C |
| ATOM | 6566 | OG | SER | A | 26 | −29.680 | −0.006 | 48.714 | 1.00 | 49.73 | O |
| ATOM | 6568 | C | SER | A | 26 | −28.161 | 2.111 | 51.143 | 1.00 | 48.80 | C |
| ATOM | 6569 | O | SER | A | 26 | −28.505 | 3.176 | 51.651 | 1.00 | 48.99 | O |
| ATOM | 6571 | N | LYS | A | 27 | −27.626 | 1.099 | 51.816 | 1.00 | 49.72 | N |
| ATOM | 6572 | CA | LYS | A | 27 | −27.365 | 1.113 | 53.243 | 1.00 | 50.92 | C |
| ATOM | 6574 | CB | LYS | A | 27 | −28.191 | 0.021 | 53.952 | 1.00 | 52.36 | C |
| ATOM | 6577 | CG | LYS | A | 27 | −29.471 | 0.520 | 54.631 | 1.00 | 54.84 | C |
| ATOM | 6580 | CD | LYS | A | 27 | −30.459 | −0.614 | 54.982 | 1.00 | 55.28 | C |
| ATOM | 6583 | CE | LYS | A | 27 | −29.811 | −1.810 | 55.703 | 1.00 | 58.27 | C |
| ATOM | 6586 | NZ | LYS | A | 27 | −30.839 | −2.772 | 56.233 | 1.00 | 58.20 | N |
| ATOM | 6590 | C | LYS | A | 27 | −25.896 | 0.818 | 53.416 | 1.00 | 49.94 | C |
| ATOM | 6591 | O | LYS | A | 27 | −25.240 | 0.347 | 52.485 | 1.00 | 48.23 | O |
| ATOM | 6593 | N | SER | A | 28 | −25.388 | 1.080 | 54.616 | 1.00 | 52.04 | N |
| ATOM | 6594 | CA | SER | A | 28 | −24.003 | 0.771 | 54.941 | 1.00 | 52.27 | C |
| ATOM | 6596 | CB | SER | A | 28 | −23.594 | 1.359 | 56.287 | 1.00 | 52.57 | C |
| ATOM | 6599 | OG | SER | A | 28 | −22.310 | 0.879 | 56.662 | 1.00 | 55.08 | O |
| ATOM | 6601 | C | SER | A | 28 | −23.849 | −0.724 | 54.997 | 1.00 | 52.92 | C |
| ATOM | 6602 | O | SER | A | 28 | −24.727 | −1.409 | 55.523 | 1.00 | 54.03 | O |
| ATOM | 6604 | N | VAL | A | 29 | −22.733 | −1.206 | 54.448 | 1.00 | 53.35 | N |
| ATOM | 6605 | CA | VAL | A | 29 | −22.382 | −2.627 | 54.442 | 1.00 | 53.35 | C |
| ATOM | 6607 | CB | VAL | A | 29 | −22.083 | −3.120 | 52.992 | 1.00 | 53.96 | C |
| ATOM | 6609 | CG1 | VAL | A | 29 | −20.827 | −2.481 | 52.424 | 1.00 | 55.20 | C |
| ATOM | 6613 | CG2 | VAL | A | 29 | −23.248 | −2.838 | 52.078 | 1.00 | 55.72 | C |
| ATOM | 6617 | C | VAL | A | 29 | −21.179 | −2.888 | 55.369 | 1.00 | 53.13 | C |
| ATOM | 6618 | O | VAL | A | 29 | −20.337 | −3.725 | 55.097 | 1.00 | 53.14 | O |
| ATOM | 6620 | N | SER | A | 30 | −21.110 | −2.173 | 56.485 | 1.00 | 55.25 | N |
| ATOM | 6621 | CA | SER | A | 30 | −19.919 | −2.210 | 57.329 | 1.00 | 54.74 | C |
| ATOM | 6623 | CB | SER | A | 30 | −19.150 | −0.888 | 57.190 | 1.00 | 54.89 | C |
| ATOM | 6626 | OG | SER | A | 30 | −18.834 | −0.622 | 55.828 | 1.00 | 55.23 | O |
| ATOM | 6628 | C | SER | A | 30 | −20.249 | −2.486 | 58.801 | 1.00 | 54.12 | C |
| ATOM | 6629 | O | SER | A | 30 | −20.890 | −1.670 | 59.445 | 1.00 | 54.38 | O |
| ATOM | 6631 | N | THR | A | 31 | −19.838 | −3.657 | 59.295 | 1.00 | 53.64 | N |
| ATOM | 6632 | CA | THR | A | 31 | −19.766 | −3.965 | 60.733 | 1.00 | 53.55 | C |
| ATOM | 6634 | CB | THR | A | 31 | −21.041 | −4.675 | 61.274 | 1.00 | 53.52 | C |

-continued

| | | | | | | | | | | |
|---|---|---|---|---|---|---|---|---|---|---|
| ATOM | 6636 | OG1 | THR | A | 31 | −21.744 | −5.300 | 60.193 | 1.00 | 53.91 O |
| ATOM | 6638 | CG2 | THR | A | 31 | −21.977 | −3.690 | 61.993 | 1.00 | 53.02 C |
| ATOM | 6642 | C | THR | A | 31 | −18.555 | −4.869 | 61.010 | 1.00 | 53.72 C |
| ATOM | 6643 | O | THR | A | 31 | −18.047 | −5.548 | 60.112 | 1.00 | 53.44 O |
| ATOM | 6645 | N | SER | A | 32 | −18.106 | −4.868 | 62.259 | 1.00 | 53.57 N |
| ATOM | 6646 | CA | SER | A | 32 | −16.932 | −5.638 | 62.692 | 1.00 | 53.74 C |
| ATOM | 6648 | CB | SER | A | 32 | −17.252 | −7.130 | 62.755 | 1.00 | 52.83 C |
| ATOM | 6651 | OG | SER | A | 32 | −18.435 | −7.346 | 63.496 | 1.00 | 56.13 O |
| ATOM | 6653 | C | SER | A | 32 | −15.694 | −5.373 | 61.823 | 1.00 | 53.92 C |
| ATOM | 6654 | O | SER | A | 32 | −15.058 | −6.295 | 61.308 | 1.00 | 54.25 O |
| ATOM | 6656 | N | GLY | A | 33 | −15.362 | −4.092 | 61.673 | 1.00 | 54.78 N |
| ATOM | 6657 | CA | GLY | A | 33 | −14.157 | −3.675 | 60.958 | 1.00 | 54.44 C |
| ATOM | 6660 | C | GLY | A | 33 | −14.032 | −4.386 | 59.635 | 1.00 | 54.01 C |
| ATOM | 6661 | O | GLY | A | 33 | −12.944 | −4.815 | 59.253 | 1.00 | 55.52 O |
| ATOM | 6663 | N | TYR | A | 34 | −15.170 | −4.530 | 58.961 | 1.00 | 53.14 N |
| ATOM | 6664 | CA | TYR | A | 34 | −15.244 | −5.167 | 57.661 | 1.00 | 52.80 C |
| ATOM | 6666 | CB | TYR | A | 34 | −15.715 | −6.611 | 57.793 | 1.00 | 53.20 C |
| ATOM | 6669 | CG | TYR | A | 34 | −14.664 | −7.634 | 58.102 | 1.00 | 52.44 C |
| ATOM | 6670 | CD1 | TYR | A | 34 | −13.507 | −7.724 | 57.346 | 1.00 | 51.21 C |
| ATOM | 6672 | CE1 | TYR | A | 34 | −12.557 | −8.700 | 57.616 | 1.00 | 54.76 C |
| ATOM | 6674 | CZ | TYR | A | 34 | −12.774 | −9.610 | 58.637 | 1.00 | 53.21 C |
| ATOM | 6675 | OH | TYR | A | 34 | −11.839 | −10.571 | 58.906 | 1.00 | 53.19 O |
| ATOM | 6677 | CE2 | TYR | A | 34 | −13.919 | −9.549 | 59.393 | 1.00 | 54.25 C |
| ATOM | 6679 | CD2 | TYR | A | 34 | −14.862 | −8.570 | 59.118 | 1.00 | 57.68 C |
| ATOM | 6681 | C | TYR | A | 34 | −16.261 | −4.432 | 56.813 | 1.00 | 51.48 C |
| ATOM | 6682 | O | TYR | A | 34 | −17.321 | −4.049 | 57.304 | 1.00 | 49.85 O |
| ATOM | 6684 | N | SER | A | 35 | −15.938 | −4.235 | 55.544 | 1.00 | 50.36 N |
| ATOM | 6685 | CA | SER | A | 35 | −16.916 | −3.762 | 54.606 | 1.00 | 51.65 C |
| ATOM | 6687 | CB | SER | A | 35 | −16.390 | −2.575 | 53.821 | 1.00 | 50.96 C |
| ATOM | 6690 | OG | SER | A | 35 | −16.136 | −1.489 | 54.702 | 1.00 | 50.03 O |
| ATOM | 6692 | C | SER | A | 35 | −17.232 | −4.944 | 53.723 | 1.00 | 52.86 C |
| ATOM | 6693 | O | SER | A | 35 | −16.390 | −5.399 | 52.959 | 1.00 | 53.24 O |
| ATOM | 6695 | N | TYR | A | 36 | −18.450 | −5.457 | 53.869 | 1.00 | 54.35 N |
| ATOM | 6696 | CA | TYR | A | 36 | −18.875 | −6.664 | 53.189 | 1.00 | 55.09 C |
| ATOM | 6698 | CB | TYR | A | 36 | −20.046 | −7.277 | 53.946 | 1.00 | 55.65 C |
| ATOM | 6701 | CG | TYR | A | 36 | −19.615 | −7.768 | 55.323 | 1.00 | 58.22 C |
| ATOM | 6702 | CD1 | TYR | A | 36 | −18.954 | −8.995 | 55.480 | 1.00 | 56.18 C |
| ATOM | 6704 | CE1 | TYR | A | 36 | −18.555 | −9.446 | 56.736 | 1.00 | 56.58 C |
| ATOM | 6706 | CZ | TYR | A | 36 | −18.795 | −8.665 | 57.854 | 1.00 | 56.60 C |
| ATOM | 6707 | OH | TYR | A | 36 | −18.397 | −9.096 | 59.101 | 1.00 | 54.95 O |
| ATOM | 6709 | CE2 | TYR | A | 36 | −19.437 | −7.441 | 57.723 | 1.00 | 56.91 C |
| ATOM | 6711 | CD2 | TYR | A | 36 | −19.838 | −6.998 | 56.462 | 1.00 | 56.88 C |
| ATOM | 6713 | C | TYR | A | 36 | −19.189 | −6.399 | 51.717 | 1.00 | 56.74 C |
| ATOM | 6714 | O | TYR | A | 36 | −20.360 | −6.314 | 51.315 | 1.00 | 58.41 O |
| ATOM | 6716 | N | ILE | A | 37 | −18.110 | −6.270 | 50.933 | 1.00 | 56.11 N |
| ATOM | 6717 | CA | ILE | A | 37 | −18.155 | −5.894 | 49.511 | 1.00 | 55.20 C |
| ATOM | 6719 | CB | ILE | A | 37 | −17.755 | −4.408 | 49.294 | 1.00 | 54.78 C |
| ATOM | 6721 | CG1 | ILE | A | 37 | −18.826 | −3.479 | 49.851 | 1.00 | 58.08 C |
| ATOM | 6724 | CD1 | ILE | A | 37 | −20.089 | −3.396 | 48.995 | 1.00 | 61.32 C |
| ATOM | 6728 | CG2 | ILE | A | 37 | −17.547 | −4.081 | 47.806 | 1.00 | 54.99 C |
| ATOM | 6732 | C | ILE | A | 37 | −17.181 | −6.759 | 48.733 | 1.00 | 54.28 C |
| ATOM | 6733 | O | ILE | A | 37 | −16.086 | −7.045 | 49.197 | 1.00 | 51.48 O |
| ATOM | 6735 | N | TYR | A | 38 | −17.577 | −7.160 | 47.534 | 1.00 | 54.21 N |
| ATOM | 6736 | CA | TYR | A | 38 | −16.772 | −8.069 | 46.737 | 1.00 | 55.52 C |
| ATOM | 6738 | CB | TYR | A | 38 | −17.335 | −9.484 | 46.899 | 1.00 | 56.13 C |
| ATOM | 6741 | CG | TYR | A | 38 | −17.734 | −9.751 | 48.331 | 1.00 | 53.82 C |
| ATOM | 6742 | CD1 | TYR | A | 38 | −16.800 | −10.179 | 49.249 | 1.00 | 56.52 C |
| ATOM | 6744 | CE1 | TYR | A | 38 | −17.136 | −10.402 | 50.559 | 1.00 | 54.97 C |
| ATOM | 6746 | CZ | TYR | A | 38 | −18.421 | −10.179 | 50.968 | 1.00 | 55.92 C |
| ATOM | 6747 | OH | TYR | A | 38 | −18.746 | −10.407 | 52.278 | 1.00 | 57.07 O |
| ATOM | 6749 | CE2 | TYR | A | 38 | −19.372 | −9.739 | 50.077 | 1.00 | 53.57 C |
| ATOM | 6751 | CD2 | TYR | A | 38 | −19.021 | −9.517 | 48.772 | 1.00 | 51.57 C |
| ATOM | 6753 | C | TYR | A | 38 | −16.798 | −7.601 | 45.290 | 1.00 | 55.89 C |
| ATOM | 6754 | O | TYR | A | 38 | −17.738 | −6.915 | 44.896 | 1.00 | 57.00 O |
| ATOM | 6756 | N | TRP | A | 39 | −15.764 | −7.943 | 44.515 | 1.00 | 55.58 N |
| ATOM | 6757 | CA | TRP | A | 39 | −15.670 | −7.535 | 43.101 | 1.00 | 55.14 C |
| ATOM | 6759 | CB | TRP | A | 39 | −14.585 | −6.481 | 42.881 | 1.00 | 53.93 C |
| ATOM | 6762 | CG | TRP | A | 39 | −14.865 | −5.137 | 43.472 | 1.00 | 54.45 C |
| ATOM | 6763 | CD1 | TRP | A | 39 | −14.481 | −4.691 | 44.699 | 1.00 | 55.89 C |
| ATOM | 6765 | NE1 | TRP | A | 39 | −14.903 | −3.397 | 44.887 | 1.00 | 54.96 N |
| ATOM | 6767 | CE2 | TRP | A | 39 | −15.561 | −2.977 | 43.765 | 1.00 | 49.30 C |
| ATOM | 6768 | CD2 | TRP | A | 39 | −15.559 | −4.049 | 42.850 | 1.00 | 51.41 C |
| ATOM | 6769 | CE3 | TRP | A | 39 | −16.177 | −3.876 | 41.610 | 1.00 | 53.35 C |
| ATOM | 6771 | CZ3 | TRP | A | 39 | −16.766 | −2.659 | 41.327 | 1.00 | 54.21 C |
| ATOM | 6773 | CH2 | TRP | A | 39 | −16.752 | −1.613 | 42.261 | 1.00 | 54.27 C |
| ATOM | 6775 | CZ2 | TRP | A | 39 | −16.154 | −1.755 | 43.482 | 1.00 | 52.84 C |
| ATOM | 6777 | C | TRP | A | 39 | −15.372 | −8.720 | 42.192 | 1.00 | 55.86 C |
| ATOM | 6778 | O | TRP | A | 39 | −14.481 | −9.524 | 42.466 | 1.00 | 56.12 O |
| ATOM | 6780 | N | TYR | A | 40 | −16.099 | −8.794 | 41.083 | 1.00 | 55.71 N |

-continued

| | | | | | | | | | | |
|---|---|---|---|---|---|---|---|---|---|---|
| ATOM | 6781 | CA | TYR | A | 40 | −15.950 | −9.885 | 40.151 | 1.00 | 54.20 C |
| ATOM | 6783 | CB | TYR | A | 40 | −17.236 | −10.677 | 40.105 | 1.00 | 53.85 C |
| ATOM | 6786 | CG | TYR | A | 40 | −17.621 | −11.220 | 41.452 | 1.00 | 53.84 C |
| ATOM | 6787 | CD1 | TYR | A | 40 | −17.003 | −12.350 | 41.960 | 1.00 | 52.48 C |
| ATOM | 6789 | CE1 | TYR | A | 40 | −17.341 | −12.857 | 43.177 | 1.00 | 51.31 C |
| ATOM | 6791 | CZ | TYR | A | 40 | −18.309 | −12.240 | 43.922 | 1.00 | 52.90 C |
| ATOM | 6792 | OH | TYR | A | 40 | −18.644 | −12.744 | 45.154 | 1.00 | 53.71 O |
| ATOM | 6794 | CE2 | TYR | A | 40 | −18.938 | −11.109 | 43.448 | 1.00 | 54.72 C |
| ATOM | 6796 | CD2 | TYR | A | 40 | −18.591 | −10.606 | 42.218 | 1.00 | 53.75 C |
| ATOM | 6798 | C | TYR | A | 40 | −15.604 | −9.392 | 38.765 | 1.00 | 54.49 C |
| ATOM | 6799 | O | TYR | A | 40 | −15.945 | −8.274 | 38.387 | 1.00 | 54.57 O |
| ATOM | 6801 | N | GLN | A | 41 | −14.908 | −10.245 | 38.021 | 1.00 | 55.19 N |
| ATOM | 6802 | CA | GLN | A | 41 | −14.630 | −10.023 | 36.610 | 1.00 | 54.66 C |
| ATOM | 6804 | CB | GLN | A | 41 | −13.134 | −10.155 | 36.356 | 1.00 | 54.91 C |
| ATOM | 6807 | CG | GLN | A | 41 | −12.718 | −10.065 | 34.891 | 1.00 | 54.62 C |
| ATOM | 6810 | CD | GLN | A | 41 | −11.217 | −10.069 | 34.731 | 1.00 | 53.29 C |
| ATOM | 6811 | OE1 | GLN | A | 41 | −10.549 | −11.071 | 34.995 | 1.00 | 50.58 O |
| ATOM | 6812 | NE2 | GLN | A | 41 | −10.674 | −8.942 | 34.310 | 1.00 | 52.61 N |
| ATOM | 6815 | C | GLN | A | 41 | −15.368 | −11.101 | 35.832 | 1.00 | 54.45 C |
| ATOM | 6816 | O | GLN | A | 41 | −15.259 | −12.277 | 36.181 | 1.00 | 53.70 O |
| ATOM | 6818 | N | GLN | A | 42 | −16.123 | −10.704 | 34.803 | 1.00 | 53.94 N |
| ATOM | 6819 | CA | GLN | A | 42 | −16.718 | −11.669 | 33.868 | 1.00 | 54.62 C |
| ATOM | 6821 | CB | GLN | A | 42 | −18.245 | −11.740 | 34.003 | 1.00 | 54.68 C |
| ATOM | 6824 | CG | GLN | A | 42 | −18.860 | −12.891 | 33.170 | 1.00 | 53.39 C |
| ATOM | 6827 | CD | GLN | A | 42 | −20.365 | −13.000 | 33.293 | 1.00 | 51.05 C |
| ATOM | 6828 | OE1 | GLN | A | 42 | −21.074 | −12.000 | 33.336 | 1.00 | 48.41 O |
| ATOM | 6829 | NE2 | GLN | A | 42 | −20.859 | −14.225 | 33.336 | 1.00 | 49.52 N |
| ATOM | 6832 | C | GLN | A | 42 | −16.346 | −11.360 | 32.416 | 1.00 | 55.58 C |
| ATOM | 6833 | O | GLN | A | 42 | −16.720 | −10.306 | 31.882 | 1.00 | 55.08 O |
| ATOM | 6835 | N | LYS | A | 43 | −15.626 | −12.294 | 31.789 | 1.00 | 55.46 N |
| ATOM | 6836 | CA | LYS | A | 43 | −15.292 | −12.209 | 30.366 | 1.00 | 55.65 C |
| ATOM | 6838 | CB | LYS | A | 43 | −13.932 | −12.839 | 30.086 | 1.00 | 54.68 C |
| ATOM | 6841 | CG | LYS | A | 43 | −12.775 | −12.062 | 30.668 | 1.00 | 54.75 C |
| ATOM | 6844 | CD | LYS | A | 43 | −11.503 | −12.885 | 30.686 | 1.00 | 55.94 C |
| ATOM | 6847 | CE | LYS | A | 43 | −10.375 | −12.126 | 31.358 | 1.00 | 58.33 C |
| ATOM | 6850 | NZ | LYS | A | 43 | −9.035 | −12.660 | 31.001 | 1.00 | 57.56 N |
| ATOM | 6854 | C | LYS | A | 43 | −16.347 | −12.935 | 29.549 | 1.00 | 56.58 C |
| ATOM | 6855 | O | LYS | A | 43 | −16.790 | −14.023 | 29.929 | 1.00 | 57.00 O |
| ATOM | 6857 | N | PRO | A | 44 | −16.740 | −12.357 | 28.406 | 1.00 | 57.55 N |
| ATOM | 6858 | CA | PRO | A | 44 | −17.830 | −12.946 | 27.623 | 1.00 | 57.67 C |
| ATOM | 6860 | CB | PRO | A | 44 | −17.746 | −12.218 | 26.277 | 1.00 | 58.27 C |
| ATOM | 6863 | CG | PRO | A | 44 | −16.494 | −11.352 | 26.338 | 1.00 | 59.33 C |
| ATOM | 6866 | CD | PRO | A | 44 | −16.175 | −11.155 | 27.771 | 1.00 | 57.79 C |
| ATOM | 6869 | C | PRO | A | 44 | −17.649 | −14.450 | 27.435 | 1.00 | 58.24 C |
| ATOM | 6870 | O | PRO | A | 44 | −16.535 | −14.906 | 27.170 | 1.00 | 59.17 O |
| ATOM | 6871 | N | GLY | A | 45 | −18.730 | −15.206 | 27.607 | 1.00 | 58.29 N |
| ATOM | 6872 | CA | GLY | A | 45 | −18.689 | −16.661 | 27.482 | 1.00 | 58.14 C |
| ATOM | 6875 | C | GLY | A | 45 | −18.251 | −17.423 | 28.727 | 1.00 | 58.93 C |
| ATOM | 6876 | O | GLY | A | 45 | −18.321 | −18.655 | 28.745 | 1.00 | 58.45 O |
| ATOM | 6878 | N | GLN | A | 46 | −17.829 | −16.715 | 29.780 | 1.00 | 58.95 N |
| ATOM | 6879 | CA | GLN | A | 46 | −17.197 | −17.370 | 30.944 | 1.00 | 58.13 C |
| ATOM | 6881 | CB | GLN | A | 46 | −15.761 | −16.887 | 31.082 | 1.00 | 57.66 C |
| ATOM | 6884 | CG | GLN | A | 46 | −14.876 | −17.334 | 29.967 | 1.00 | 57.84 C |
| ATOM | 6887 | CD | GLN | A | 46 | −13.556 | −16.649 | 30.013 | 1.00 | 58.02 C |
| ATOM | 6888 | OE1 | GLN | A | 46 | −13.096 | −16.241 | 31.074 | 1.00 | 59.99 O |
| ATOM | 6889 | NE2 | GLN | A | 46 | −12.933 | −16.500 | 28.858 | 1.00 | 62.54 N |
| ATOM | 6892 | C | GLN | A | 46 | −17.893 | −17.159 | 32.288 | 1.00 | 57.25 C |
| ATOM | 6893 | O | GLN | A | 46 | −18.670 | −16.216 | 32.456 | 1.00 | 56.93 O |
| ATOM | 6895 | N | PRO | A | 47 | −17.597 | −18.035 | 33.263 | 1.00 | 56.40 N |
| ATOM | 6896 | CA | PRO | A | 47 | −18.057 | −17.725 | 34.613 | 1.00 | 56.63 C |
| ATOM | 6898 | CB | PRO | A | 47 | −17.583 | −18.928 | 35.452 | 1.00 | 56.08 C |
| ATOM | 6901 | CG | PRO | A | 47 | −16.489 | −19.565 | 34.647 | 1.00 | 56.71 C |
| ATOM | 6904 | CD | PRO | A | 47 | −16.862 | −19.312 | 33.208 | 1.00 | 56.14 C |
| ATOM | 6907 | C | PRO | A | 47 | −17.395 | −16.451 | 35.108 | 1.00 | 55.38 C |
| ATOM | 6908 | O | PRO | A | 47 | −16.299 | −16.119 | 34.660 | 1.00 | 55.28 O |
| ATOM | 6909 | N | PRO | A | 48 | −18.068 | −15.720 | 35.999 | 1.00 | 54.95 N |
| ATOM | 6910 | CA | PRO | A | 48 | −17.354 | −14.666 | 36.712 | 1.00 | 54.76 C |
| ATOM | 6912 | CB | PRO | A | 48 | −18.432 | −14.047 | 37.617 | 1.00 | 55.39 C |
| ATOM | 6915 | CG | PRO | A | 48 | −19.744 | −14.474 | 37.009 | 1.00 | 55.42 C |
| ATOM | 6918 | CD | PRO | A | 48 | −19.495 | −15.784 | 36.356 | 1.00 | 53.86 C |
| ATOM | 6921 | C | PRO | A | 48 | −16.195 | −15.218 | 37.547 | 1.00 | 54.08 C |
| ATOM | 6922 | O | PRO | A | 48 | −16.126 | −16.416 | 37.839 | 1.00 | 53.70 O |
| ATOM | 6923 | N | LYS | A | 49 | −15.308 | −14.319 | 37.940 | 1.00 | 54.11 N |
| ATOM | 6924 | CA | LYS | A | 49 | −14.078 | −14.662 | 38.626 | 1.00 | 53.40 C |
| ATOM | 6926 | CB | LYS | A | 49 | −12.924 | −14.574 | 37.616 | 1.00 | 53.57 C |
| ATOM | 6929 | CG | LYS | A | 49 | −11.519 | −14.593 | 38.178 | 1.00 | 54.85 C |
| ATOM | 6932 | CD | LYS | A | 49 | −10.495 | −14.468 | 37.056 | 1.00 | 54.92 C |
| ATOM | 6935 | CE | LYS | A | 49 | −9.116 | −14.072 | 37.583 | 1.00 | 58.10 C |
| ATOM | 6938 | NZ | LYS | A | 49 | −8.308 | −13.354 | 36.545 | 1.00 | 59.59 N |

-continued

| | | | | | | | | | | | |
|---|---|---|---|---|---|---|---|---|---|---|---|
| ATOM | 6942 | C | LYS | A | 49 | −13.917 | −13.654 | 39.743 | 1.00 | 51.86 | C |
| ATOM | 6943 | O | LYS | A | 49 | −14.029 | −12.458 | 39.508 | 1.00 | 51.35 | O |
| ATOM | 6945 | N | LEU | A | 50 | −13.682 | −14.133 | 40.959 | 1.00 | 53.13 | N |
| ATOM | 6946 | CA | LEU | A | 50 | −13.545 | −13.245 | 42.122 | 1.00 | 53.31 | C |
| ATOM | 6948 | CB | LEU | A | 50 | −13.620 | −14.020 | 43.441 | 1.00 | 51.20 | C |
| ATOM | 6951 | CG | LEU | A | 50 | −13.397 | −13.212 | 44.724 | 1.00 | 51.81 | C |
| ATOM | 6953 | CD1 | LEU | A | 50 | −14.486 | −12.193 | 44.949 | 1.00 | 53.08 | C |
| ATOM | 6957 | CD2 | LEU | A | 50 | −13.322 | −14.132 | 45.921 | 1.00 | 53.48 | C |
| ATOM | 6961 | C | LEU | A | 50 | −12.225 | −12.528 | 42.057 | 1.00 | 54.02 | C |
| ATOM | 6962 | O | LEU | A | 50 | −11.183 | −13.162 | 41.943 | 1.00 | 56.64 | O |
| ATOM | 6964 | N | LEU | A | 51 | −12.276 | −11.207 | 42.155 | 1.00 | 54.52 | N |
| ATOM | 6965 | CA | LEU | A | 51 | −11.071 | −10.397 | 42.184 | 1.00 | 55.06 | C |
| ATOM | 6967 | CB | LEU | A | 51 | −11.276 | −9.123 | 41.358 | 1.00 | 56.57 | C |
| ATOM | 6970 | CG | LEU | A | 51 | −11.540 | −9.333 | 39.867 | 1.00 | 55.21 | C |
| ATOM | 6972 | CD1 | LEU | A | 51 | −11.735 | −7.987 | 39.175 | 1.00 | 54.74 | C |
| ATOM | 6976 | CD2 | LEU | A | 51 | −10.409 | −10.130 | 39.247 | 1.00 | 54.47 | C |
| ATOM | 6980 | C | LEU | A | 51 | −10.712 | −10.014 | 43.603 | 1.00 | 53.83 | C |
| ATOM | 6981 | O | LEU | A | 51 | −9.638 | −10.356 | 44.104 | 1.00 | 52.66 | O |
| ATOM | 6983 | N | ILE | A | 52 | −11.628 | −9.292 | 44.234 | 1.00 | 53.69 | N |
| ATOM | 6984 | CA | ILE | A | 52 | −11.381 | −8.680 | 45.521 | 1.00 | 54.72 | C |
| ATOM | 6986 | CB | ILE | A | 52 | −11.218 | −7.150 | 45.370 | 1.00 | 55.20 | C |
| ATOM | 6988 | CG1 | ILE | A | 52 | −10.026 | −6.877 | 44.444 | 1.00 | 57.47 | C |
| ATOM | 6991 | CD1 | ILE | A | 52 | −9.359 | −5.528 | 44.627 | 1.00 | 58.35 | C |
| ATOM | 6995 | CG2 | ILE | A | 52 | −11.043 | −6.456 | 46.750 | 1.00 | 55.97 | C |
| ATOM | 6999 | C | ILE | A | 52 | −12.518 | −9.029 | 46.459 | 1.00 | 53.90 | C |
| ATOM | 7000 | O | ILE | A | 52 | −13.674 | −9.081 | 46.048 | 1.00 | 55.25 | O |
| ATOM | 7002 | N | TYR | A | 53 | −12.183 | −9.283 | 47.719 | 1.00 | 52.27 | N |
| ATOM | 7003 | CA | TYR | A | 53 | −13.179 | −9.683 | 48.691 | 1.00 | 51.84 | C |
| ATOM | 7005 | CB | TYR | A | 53 | −13.201 | −11.209 | 48.844 | 1.00 | 50.98 | C |
| ATOM | 7008 | CG | TYR | A | 53 | −11.973 | −11.804 | 49.485 | 1.00 | 50.18 | C |
| ATOM | 7009 | CD1 | TYR | A | 53 | −10.886 | −12.204 | 48.721 | 1.00 | 52.88 | C |
| ATOM | 7011 | CE1 | TYR | A | 53 | −9.771 | −12.740 | 49.311 | 1.00 | 50.55 | C |
| ATOM | 7013 | CZ | TYR | A | 53 | −9.738 | −12.895 | 50.678 | 1.00 | 51.51 | C |
| ATOM | 7014 | OH | TYR | A | 53 | −8.636 | −13.418 | 51.302 | 1.00 | 53.71 | O |
| ATOM | 7016 | CE2 | TYR | A | 53 | −10.797 | −12.498 | 51.452 | 1.00 | 53.37 | C |
| ATOM | 7018 | CD2 | TYR | A | 53 | −11.899 | −11.958 | 50.857 | 1.00 | 53.24 | C |
| ATOM | 7020 | C | TYR | A | 53 | −12.952 | −8.978 | 50.023 | 1.00 | 52.24 | C |
| ATOM | 7021 | O | TYR | A | 53 | −11.810 | −8.709 | 50.417 | 1.00 | 50.39 | O |
| ATOM | 7023 | N | LEU | A | 54 | −14.070 | −8.693 | 50.693 | 1.00 | 51.91 | N |
| ATOM | 7024 | CA | LEU | A | 54 | −14.142 | −7.791 | 51.839 | 1.00 | 51.34 | C |
| ATOM | 7026 | CB | LEU | A | 54 | −13.530 | −8.446 | 53.072 | 1.00 | 53.03 | C |
| ATOM | 7029 | CG | LEU | A | 54 | −14.257 | −9.740 | 53.462 | 1.00 | 55.48 | C |
| ATOM | 7031 | CD1 | LEU | A | 54 | −13.459 | −10.524 | 54.486 | 1.00 | 56.22 | C |
| ATOM | 7035 | CD2 | LEU | A | 54 | −15.664 | −9.444 | 53.983 | 1.00 | 58.34 | C |
| ATOM | 7039 | C | LEU | A | 54 | −13.532 | −6.425 | 51.529 | 1.00 | 51.04 | C |
| ATOM | 7040 | O | LEU | A | 54 | −12.740 | −5.887 | 52.296 | 1.00 | 53.31 | O |
| ATOM | 7042 | N | ALA | A | 55 | −13.920 | −5.888 | 50.373 | 1.00 | 51.41 | N |
| ATOM | 7043 | CA | ALA | A | 55 | −13.646 | −4.503 | 49.947 | 1.00 | 51.08 | C |
| ATOM | 7045 | CB | ALA | A | 55 | −13.919 | −3.508 | 51.088 | 1.00 | 49.76 | C |
| ATOM | 7049 | C | ALA | A | 55 | −12.258 | −4.270 | 49.347 | 1.00 | 51.09 | C |
| ATOM | 7050 | O | ALA | A | 55 | −12.118 | −3.509 | 48.369 | 1.00 | 49.89 | O |
| ATOM | 7052 | N | SER | A | 56 | −11.246 | −4.915 | 49.932 | 1.00 | 49.94 | N |
| ATOM | 7053 | CA | SER | A | 56 | −9.855 | −4.603 | 49.608 | 1.00 | 48.78 | C |
| ATOM | 7055 | CB | SER | A | 56 | −9.346 | −3.566 | 50.594 | 1.00 | 46.21 | C |
| ATOM | 7058 | OG | SER | A | 56 | −9.611 | −4.007 | 51.902 | 1.00 | 52.26 | O |
| ATOM | 7060 | C | SER | A | 56 | −8.874 | −5.777 | 49.567 | 1.00 | 46.29 | C |
| ATOM | 7061 | O | SER | A | 56 | −7.741 | −5.593 | 49.124 | 1.00 | 44.20 | O |
| ATOM | 7063 | N | ILE | A | 57 | −9.277 | −6.972 | 49.986 | 1.00 | 46.78 | N |
| ATOM | 7064 | CA | ILE | A | 57 | −8.342 | −8.101 | 49.975 | 1.00 | 48.96 | C |
| ATOM | 7066 | CB | ILE | A | 57 | −8.703 | −9.197 | 50.987 | 1.00 | 48.05 | C |
| ATOM | 7068 | CG1 | ILE | A | 57 | −8.893 | −8.610 | 52.390 | 1.00 | 48.51 | C |
| ATOM | 7071 | CD1 | ILE | A | 57 | −9.619 | −9.541 | 53.371 | 1.00 | 49.13 | C |
| ATOM | 7075 | CG2 | ILE | A | 57 | −7.615 | −10.239 | 51.019 | 1.00 | 46.24 | C |
| ATOM | 7079 | C | ILE | A | 57 | −8.281 | −8.733 | 48.588 | 1.00 | 50.59 | C |
| ATOM | 7080 | O | ILE | A | 57 | −9.301 | −9.163 | 48.049 | 1.00 | 52.03 | O |
| ATOM | 7082 | N | LEU | A | 58 | −7.074 | −8.800 | 48.034 | 1.00 | 50.85 | N |
| ATOM | 7083 | CA | LEU | A | 58 | −6.845 | −9.365 | 46.707 | 1.00 | 51.56 | C |
| ATOM | 7085 | CB | LEU | A | 58 | −5.473 | −8.913 | 46.196 | 1.00 | 50.88 | C |
| ATOM | 7088 | CG | LEU | A | 58 | −5.054 | −9.229 | 44.764 | 1.00 | 50.99 | C |
| ATOM | 7090 | CD1 | LEU | A | 58 | −6.046 | −8.664 | 43.744 | 1.00 | 52.86 | C |
| ATOM | 7094 | CD2 | LEU | A | 58 | −3.665 | −8.674 | 44.530 | 1.00 | 51.73 | C |
| ATOM | 7098 | C | LEU | A | 58 | −6.904 | −10.897 | 46.745 | 1.00 | 53.01 | C |
| ATOM | 7099 | O | LEU | A | 58 | −6.243 | −11.534 | 47.571 | 1.00 | 52.97 | O |
| ATOM | 7101 | N | GLU | A | 59 | −7.699 | −11.490 | 45.861 | 1.00 | 53.69 | N |
| ATOM | 7102 | CA | GLU | A | 59 | −7.753 | −12.941 | 45.770 | 1.00 | 54.08 | C |
| ATOM | 7104 | CB | GLU | A | 59 | −8.912 | −13.381 | 44.868 | 1.00 | 54.86 | C |
| ATOM | 7107 | CG | GLU | A | 59 | −9.010 | −14.896 | 44.584 | 1.00 | 57.29 | C |
| ATOM | 7110 | CD | GLU | A | 59 | −9.437 | −15.736 | 45.791 | 1.00 | 60.28 | C |
| ATOM | 7111 | OE1 | GLU | A | 59 | −9.639 | −15.172 | 46.882 | 1.00 | 62.11 | O |

-continued

| | | | | | | | | | | |
|---|---|---|---|---|---|---|---|---|---|---|
| ATOM | 7112 | OE2 | GLU | A | 59 | −9.585 | −16.973 | 45.635 | 1.00 | 59.47 O |
| ATOM | 7113 | C | GLU | A | 59 | −6.410 | −13.436 | 45.237 | 1.00 | 54.90 C |
| ATOM | 7114 | O | GLU | A | 59 | −5.736 | −12.742 | 44.469 | 1.00 | 53.94 O |
| ATOM | 7116 | N | SER | A | 60 | −6.013 | −14.632 | 45.658 | 1.00 | 56.06 N |
| ATOM | 7117 | CA | SER | A | 60 | −4.727 | −15.176 | 45.237 | 1.00 | 56.26 C |
| ATOM | 7119 | CB | SER | A | 60 | −4.332 | −16.402 | 46.075 | 1.00 | 55.50 C |
| ATOM | 7122 | OG | SER | A | 60 | −4.715 | −17.609 | 45.446 | 1.00 | 58.42 O |
| ATOM | 7124 | C | SER | A | 60 | −4.814 | −15.511 | 43.749 | 1.00 | 56.72 C |
| ATOM | 7125 | O | SER | A | 60 | −5.868 | −15.936 | 43.271 | 1.00 | 57.74 O |
| ATOM | 7127 | N | GLY | A | 61 | −3.722 | −15.287 | 43.022 | 1.00 | 56.44 N |
| ATOM | 7128 | CA | GLY | A | 61 | −3.703 | −15.481 | 41.571 | 1.00 | 56.26 C |
| ATOM | 7131 | C | GLY | A | 61 | −4.197 | −14.284 | 40.767 | 1.00 | 56.56 C |
| ATOM | 7132 | O | GLY | A | 61 | −4.145 | −14.292 | 39.544 | 1.00 | 57.60 O |
| ATOM | 7134 | N | VAL | A | 62 | −4.679 | −13.247 | 41.441 | 1.00 | 56.92 N |
| ATOM | 7135 | CA | VAL | A | 62 | −5.113 | −12.039 | 40.753 | 1.00 | 55.52 C |
| ATOM | 7137 | CB | VAL | A | 62 | −6.345 | −11.413 | 41.432 | 1.00 | 56.32 C |
| ATOM | 7139 | CG1 | VAL | A | 62 | −6.833 | −10.187 | 40.647 | 1.00 | 56.97 C |
| ATOM | 7143 | CG2 | VAL | A | 62 | −7.456 | −12.453 | 41.555 | 1.00 | 54.97 C |
| ATOM | 7147 | C | VAL | A | 62 | −3.959 | −11.047 | 40.758 | 1.00 | 53.94 C |
| ATOM | 7148 | O | VAL | A | 62 | −3.345 | −10.829 | 41.797 | 1.00 | 51.87 O |
| ATOM | 7150 | N | PRO | A | 63 | −3.637 | −10.477 | 39.587 | 1.00 | 54.41 N |
| ATOM | 7151 | CA | PRO | A | 63 | −2.656 | −9.408 | 39.462 | 1.00 | 54.10 C |
| ATOM | 7153 | CB | PRO | A | 63 | −2.759 | −9.015 | 37.986 | 1.00 | 54.17 C |
| ATOM | 7156 | CG | PRO | A | 63 | −3.230 | −10.228 | 37.301 | 1.00 | 53.64 C |
| ATOM | 7159 | CD | PRO | A | 63 | −4.166 | −10.881 | 38.269 | 1.00 | 56.16 C |
| ATOM | 7162 | C | PRO | A | 63 | −2.944 | −8.195 | 40.352 | 1.00 | 54.03 C |
| ATOM | 7163 | O | PRO | A | 63 | −4.086 | −7.750 | 40.449 | 1.00 | 50.84 O |
| ATOM | 7164 | N | ASP | A | 64 | −1.883 | −7.657 | 40.955 | 1.00 | 55.52 N |
| ATOM | 7165 | CA | ASP | A | 64 | −1.972 | −6.565 | 41.941 | 1.00 | 56.14 C |
| ATOM | 7167 | CB | ASP | A | 64 | −0.768 | −6.594 | 42.906 | 1.00 | 57.41 C |
| ATOM | 7170 | CG | ASP | A | 64 | 0.494 | −7.131 | 42.257 | 1.00 | 59.16 C |
| ATOM | 7171 | OD1 | ASP | A | 64 | 0.572 | −8.359 | 42.044 | 1.00 | 63.24 O |
| ATOM | 7172 | OD2 | ASP | A | 64 | 1.403 | −6.336 | 41.964 | 1.00 | 61.08 O |
| ATOM | 7173 | C | ASP | A | 64 | −2.134 | −5.164 | 41.330 | 1.00 | 56.14 C |
| ATOM | 7174 | O | ASP | A | 64 | −2.122 | −4.159 | 42.046 | 1.00 | 55.96 O |
| ATOM | 7176 | N | ARG | A | 65 | −2.293 | −5.084 | 40.013 | 1.00 | 55.75 N |
| ATOM | 7177 | CA | ARG | A | 65 | −2.857 | −3.871 | 39.422 | 1.00 | 54.91 C |
| ATOM | 7179 | CB | ARG | A | 65 | −2.768 | −3.869 | 37.890 | 1.00 | 52.92 C |
| ATOM | 7182 | CG | ARG | A | 65 | −3.238 | −5.140 | 37.206 | 1.00 | 53.78 C |
| ATOM | 7185 | CD | ARG | A | 65 | −3.464 | −4.930 | 35.707 | 1.00 | 54.01 C |
| ATOM | 7188 | NE | ARG | A | 65 | −2.866 | −6.013 | 34.918 | 1.00 | 55.33 N |
| ATOM | 7190 | CZ | ARG | A | 65 | −3.466 | −7.149 | 34.569 | 1.00 | 53.08 C |
| ATOM | 7191 | NH1 | ARG | A | 65 | −4.712 | −7.385 | 34.918 | 1.00 | 58.22 N |
| ATOM | 7194 | NH2 | ARG | A | 65 | −2.817 | −8.057 | 33.859 | 1.00 | 50.59 N |
| ATOM | 7197 | C | ARG | A | 65 | −4.310 | −3.707 | 39.900 | 1.00 | 55.59 C |
| ATOM | 7198 | O | ARG | A | 65 | −4.839 | −2.593 | 39.895 | 1.00 | 57.22 O |
| ATOM | 7200 | N | PHE | A | 66 | −4.937 | −4.809 | 40.329 | 1.00 | 54.50 N |
| ATOM | 7201 | CA | PHE | A | 66 | −6.304 | −4.775 | 40.860 | 1.00 | 53.47 C |
| ATOM | 7203 | CB | PHE | A | 66 | −7.025 | −6.106 | 40.638 | 1.00 | 53.02 C |
| ATOM | 7206 | CG | PHE | A | 66 | −7.353 | −6.388 | 39.207 | 1.00 | 52.34 C |
| ATOM | 7207 | CD1 | PHE | A | 66 | −8.426 | −5.763 | 38.597 | 1.00 | 54.62 C |
| ATOM | 7209 | CE1 | PHE | A | 66 | −8.736 | −6.027 | 37.261 | 1.00 | 55.04 C |
| ATOM | 7211 | CZ | PHE | A | 66 | −7.971 | −6.926 | 36.541 | 1.00 | 53.88 C |
| ATOM | 7213 | CE2 | PHE | A | 66 | −6.898 | −7.555 | 37.148 | 1.00 | 52.38 C |
| ATOM | 7215 | CD2 | PHE | A | 66 | −6.594 | −7.286 | 38.467 | 1.00 | 55.32 C |
| ATOM | 7217 | C | PHE | A | 66 | −6.330 | −4.457 | 42.345 | 1.00 | 52.53 C |
| ATOM | 7218 | O | PHE | A | 66 | −5.888 | −5.262 | 43.167 | 1.00 | 53.67 O |
| ATOM | 7220 | N | SER | A | 67 | −6.879 | −3.292 | 42.673 | 1.00 | 51.14 N |
| ATOM | 7221 | CA | SER | A | 67 | −7.042 | −2.869 | 44.050 | 1.00 | 51.37 C |
| ATOM | 7223 | CB | SER | A | 67 | −6.077 | −1.735 | 44.363 | 1.00 | 50.33 C |
| ATOM | 7226 | OG | SER | A | 67 | −6.054 | −0.799 | 43.298 | 1.00 | 55.07 O |
| ATOM | 7228 | C | SER | A | 67 | −8.470 | −2.406 | 44.281 | 1.00 | 51.76 C |
| ATOM | 7229 | O | SER | A | 67 | −9.132 | −1.929 | 43.360 | 1.00 | 52.61 O |
| ATOM | 7231 | N | GLY | A | 68 | −8.931 | −2.561 | 45.519 | 1.00 | 51.87 N |
| ATOM | 7232 | CA | GLY | A | 68 | −10.273 | −2.167 | 45.929 | 1.00 | 51.41 C |
| ATOM | 7235 | C | GLY | A | 68 | −10.196 | −1.332 | 47.192 | 1.00 | 51.27 C |
| ATOM | 7236 | O | GLY | A | 68 | −9.432 | −1.650 | 48.092 | 1.00 | 50.99 O |
| ATOM | 7238 | N | SER | A | 69 | −10.981 | −0.260 | 47.256 | 1.00 | 51.77 N |
| ATOM | 7239 | CA | SER | A | 69 | −10.959 | 0.650 | 48.391 | 1.00 | 52.17 C |
| ATOM | 7241 | CB | SER | A | 69 | −10.138 | 1.864 | 48.024 | 1.00 | 50.86 C |
| ATOM | 7244 | OG | SER | A | 69 | −10.575 | 2.340 | 46.777 | 1.00 | 59.28 O |
| ATOM | 7246 | C | SER | A | 69 | −12.382 | 1.049 | 48.788 | 1.00 | 53.47 C |
| ATOM | 7247 | O | SER | A | 69 | −13.348 | 0.465 | 48.298 | 1.00 | 55.90 O |
| ATOM | 7249 | N | GLY | A | 70 | −12.509 | 2.006 | 49.709 | 1.00 | 54.20 N |
| ATOM | 7250 | CA | GLY | A | 70 | −13.807 | 2.514 | 50.139 | 1.00 | 53.73 C |
| ATOM | 7253 | C | GLY | A | 70 | −14.384 | 1.787 | 51.341 | 1.00 | 54.85 C |
| ATOM | 7254 | O | GLY | A | 70 | −13.969 | 0.677 | 51.669 | 1.00 | 56.68 O |
| ATOM | 7256 | N | SER | A | 71 | −15.356 | 2.427 | 51.989 | 1.00 | 54.91 N |
| ATOM | 7257 | CA | SER | A | 71 | −16.000 | 1.913 | 53.191 | 1.00 | 54.12 C |

-continued

| | | | | | | | | | | | |
|---|---|---|---|---|---|---|---|---|---|---|---|
| ATOM | 7259 | CB | SER | A | 71 | −15.161 | 2.242 | 54.422 | 1.00 | 53.07 | C |
| ATOM | 7262 | OG | SER | A | 71 | −15.441 | 3.559 | 54.890 | 1.00 | 57.24 | O |
| ATOM | 7264 | C | SER | A | 71 | −17.379 | 2.545 | 53.367 | 1.00 | 55.67 | C |
| ATOM | 7265 | O | SER | A | 71 | −17.686 | 3.581 | 52.771 | 1.00 | 55.30 | O |
| ATOM | 7267 | N | GLY | A | 72 | −18.189 | 1.941 | 54.232 | 1.00 | 57.09 | N |
| ATOM | 7268 | CA | GLY | A | 72 | −19.520 | 2.452 | 54.532 | 1.00 | 55.83 | C |
| ATOM | 7271 | C | GLY | A | 72 | −20.460 | 2.161 | 53.381 | 1.00 | 57.35 | C |
| ATOM | 7272 | O | GLY | A | 72 | −21.050 | 1.073 | 53.303 | 1.00 | 59.43 | O |
| ATOM | 7274 | N | THR | A | 73 | −20.574 | 3.120 | 52.469 | 1.00 | 55.93 | N |
| ATOM | 7275 | CA | THR | A | 73 | −21.540 | 3.030 | 51.390 | 1.00 | 54.91 | C |
| ATOM | 7277 | CB | THR | A | 73 | −22.703 | 4.005 | 51.659 | 1.00 | 53.72 | C |
| ATOM | 7279 | OG1 | THR | A | 73 | −23.872 | 3.536 | 50.984 | 1.00 | 58.09 | O |
| ATOM | 7281 | CG2 | THR | A | 73 | −22.369 | 5.433 | 51.220 | 1.00 | 52.98 | C |
| ATOM | 7285 | C | THR | A | 73 | −20.958 | 3.236 | 49.985 | 1.00 | 55.23 | C |
| ATOM | 7286 | O | THR | A | 73 | −21.652 | 3.020 | 48.991 | 1.00 | 56.02 | O |
| ATOM | 7288 | N | ASP | A | 74 | −19.692 | 3.642 | 49.908 | 1.00 | 56.51 | N |
| ATOM | 7289 | CA | ASP | A | 74 | −19.025 | 3.942 | 48.639 | 1.00 | 56.04 | C |
| ATOM | 7291 | CB | ASP | A | 74 | −18.639 | 5.423 | 48.556 | 1.00 | 55.46 | C |
| ATOM | 7294 | CG | ASP | A | 74 | −19.844 | 6.352 | 48.540 | 1.00 | 61.93 | C |
| ATOM | 7295 | OD1 | ASP | A | 74 | −19.639 | 7.577 | 48.680 | 1.00 | 68.46 | O |
| ATOM | 7296 | OD2 | ASP | A | 74 | −20.993 | 5.880 | 48.381 | 1.00 | 67.34 | O |
| ATOM | 7297 | C | ASP | A | 74 | −17.767 | 3.107 | 48.533 | 1.00 | 54.94 | C |
| ATOM | 7298 | O | ASP | A | 74 | −16.970 | 3.067 | 49.468 | 1.00 | 52.69 | O |
| ATOM | 7300 | N | PHE | A | 75 | −17.595 | 2.443 | 47.390 | 1.00 | 54.87 | N |
| ATOM | 7301 | CA | PHE | A | 75 | −16.428 | 1.604 | 47.141 | 1.00 | 55.21 | C |
| ATOM | 7303 | CB | PHE | A | 75 | −16.782 | 0.146 | 47.387 | 1.00 | 55.21 | C |
| ATOM | 7306 | CG | PHE | A | 75 | −17.312 | −0.082 | 48.744 | 1.00 | 52.92 | C |
| ATOM | 7307 | CD1 | PHE | A | 75 | −16.460 | −0.417 | 49.765 | 1.00 | 52.09 | C |
| ATOM | 7309 | CE1 | PHE | A | 75 | −16.937 | −0.591 | 51.044 | 1.00 | 56.53 | C |
| ATOM | 7311 | CZ | PHE | A | 75 | −18.289 | −0.390 | 51.321 | 1.00 | 58.39 | C |
| ATOM | 7313 | CE2 | PHE | A | 75 | −19.154 | −0.030 | 50.298 | 1.00 | 56.60 | C |
| ATOM | 7315 | CD2 | PHE | A | 75 | −18.657 | 0.131 | 49.019 | 1.00 | 54.00 | C |
| ATOM | 7317 | C | PHE | A | 75 | −15.904 | 1.784 | 45.745 | 1.00 | 55.28 | C |
| ATOM | 7318 | O | PHE | A | 75 | −16.603 | 2.291 | 44.872 | 1.00 | 56.32 | O |
| ATOM | 7320 | N | THR | A | 76 | −14.661 | 1.367 | 45.546 | 1.00 | 56.75 | N |
| ATOM | 7321 | CA | THR | A | 76 | −13.986 | 1.540 | 44.266 | 1.00 | 56.78 | C |
| ATOM | 7323 | CB | THR | A | 76 | −13.141 | 2.821 | 44.276 | 1.00 | 55.69 | C |
| ATOM | 7325 | OG1 | THR | A | 76 | −13.948 | 3.914 | 44.720 | 1.00 | 57.58 | O |
| ATOM | 7327 | CG2 | THR | A | 76 | −12.597 | 3.122 | 42.892 | 1.00 | 55.81 | C |
| ATOM | 7331 | C | THR | A | 76 | −13.072 | 0.363 | 43.931 | 1.00 | 56.89 | C |
| ATOM | 7332 | O | THR | A | 76 | −12.251 | −0.053 | 44.756 | 1.00 | 55.38 | O |
| ATOM | 7334 | N | LEU | A | 77 | −13.235 | −0.169 | 42.722 | 1.00 | 56.38 | N |
| ATOM | 7335 | CA | LEU | A | 77 | −12.234 | −1.043 | 42.127 | 1.00 | 56.83 | C |
| ATOM | 7337 | CB | LEU | A | 77 | −12.893 | −2.085 | 41.230 | 1.00 | 57.48 | C |
| ATOM | 7340 | CG | LEU | A | 77 | −11.940 | −3.084 | 40.571 | 1.00 | 56.79 | C |
| ATOM | 7342 | CD1 | LEU | A | 77 | −11.533 | −4.145 | 41.568 | 1.00 | 56.56 | C |
| ATOM | 7346 | CD2 | LEU | A | 77 | −12.587 | −3.712 | 39.346 | 1.00 | 57.61 | C |
| ATOM | 7350 | C | LEU | A | 77 | −11.308 | −0.175 | 41.288 | 1.00 | 56.72 | C |
| ATOM | 7351 | O | LEU | A | 77 | −11.775 | 0.701 | 40.565 | 1.00 | 57.99 | O |
| ATOM | 7353 | N | THR | A | 78 | −10.004 | −0.414 | 41.374 | 1.00 | 56.10 | N |
| ATOM | 7354 | CA | THR | A | 78 | −9.041 | 0.313 | 40.552 | 1.00 | 55.74 | C |
| ATOM | 7356 | CB | THR | A | 78 | −8.213 | 1.289 | 41.404 | 1.00 | 54.03 | C |
| ATOM | 7358 | OG1 | THR | A | 78 | −9.085 | 2.273 | 41.958 | 1.00 | 53.94 | O |
| ATOM | 7360 | CG2 | THR | A | 78 | −7.172 | 1.996 | 40.570 | 1.00 | 54.92 | C |
| ATOM | 7364 | C | THR | A | 78 | −8.121 | −0.657 | 39.806 | 1.00 | 55.53 | C |
| ATOM | 7365 | O | THR | A | 78 | −7.576 | −1.595 | 40.404 | 1.00 | 52.71 | O |
| ATOM | 7367 | N | ILE | A | 79 | −7.977 | −0.423 | 38.497 | 1.00 | 55.87 | N |
| ATOM | 7368 | CA | ILE | A | 79 | −6.981 | −1.110 | 37.668 | 1.00 | 57.16 | C |
| ATOM | 7370 | CB | ILE | A | 79 | −7.603 | −1.777 | 36.408 | 1.00 | 57.32 | C |
| ATOM | 7372 | CG1 | ILE | A | 79 | −8.932 | −2.461 | 36.740 | 1.00 | 57.61 | C |
| ATOM | 7375 | CD1 | ILE | A | 79 | −9.640 | −3.041 | 35.524 | 1.00 | 58.33 | C |
| ATOM | 7379 | CG2 | ILE | A | 79 | −6.610 | −2.779 | 35.789 | 1.00 | 56.93 | C |
| ATOM | 7383 | C | ILE | A | 79 | −5.921 | −0.106 | 37.213 | 1.00 | 56.44 | C |
| ATOM | 7384 | O | ILE | A | 79 | −6.125 | 0.637 | 36.249 | 1.00 | 57.25 | O |
| ATOM | 7386 | N | SER | A | 80 | −4.793 | −0.083 | 37.911 | 1.00 | 57.15 | N |
| ATOM | 7387 | CA | SER | A | 80 | −3.686 | 0.812 | 37.559 | 1.00 | 58.14 | C |
| ATOM | 7389 | CB | SER | A | 80 | −2.757 | 1.013 | 38.755 | 1.00 | 59.15 | C |
| ATOM | 7392 | OG | SER | A | 80 | −2.139 | −0.213 | 39.116 | 1.00 | 59.69 | O |
| ATOM | 7394 | C | SER | A | 80 | −2.901 | 0.190 | 36.426 | 1.00 | 57.23 | C |
| ATOM | 7395 | O | SER | A | 80 | −2.210 | −0.800 | 36.631 | 1.00 | 59.05 | O |
| ATOM | 7397 | N | SER | A | 81 | −2.999 | 0.761 | 35.238 | 1.00 | 55.34 | N |
| ATOM | 7398 | CA | SER | A | 81 | −2.395 | 0.150 | 34.060 | 1.00 | 56.22 | C |
| ATOM | 7400 | CB | SER | A | 81 | −0.949 | −0.300 | 34.348 | 1.00 | 55.71 | C |
| ATOM | 7403 | OG | SER | A | 81 | −0.171 | −0.335 | 33.169 | 1.00 | 56.15 | O |
| ATOM | 7405 | C | SER | A | 81 | −3.274 | −1.012 | 33.557 | 1.00 | 55.92 | C |
| ATOM | 7406 | O | SER | A | 81 | −3.194 | −2.132 | 34.052 | 1.00 | 55.71 | O |
| ATOM | 7408 | N | LEU | A | 82 | −4.116 | −0.720 | 32.569 | 1.00 | 54.92 | N |
| ATOM | 7409 | CA | LEU | A | 82 | −5.085 | −1.677 | 32.040 | 1.00 | 54.27 | C |
| ATOM | 7411 | CB | LEU | A | 82 | −6.288 | −0.921 | 31.487 | 1.00 | 53.66 | C |

-continued

| | | | | | | | | | | |
|---|---|---|---|---|---|---|---|---|---|---|
| ATOM | 7414 | CG | LEU | A | 82 | −7.345 | −1.788 | 30.812 | 1.00 | 54.67 C |
| ATOM | 7416 | CD1 | LEU | A | 82 | −8.290 | −2.386 | 31.864 | 1.00 | 56.13 C |
| ATOM | 7420 | CD2 | LEU | A | 82 | −8.110 | −0.980 | 29.774 | 1.00 | 54.60 C |
| ATOM | 7424 | C | LEU | A | 82 | −4.495 | −2.506 | 30.912 | 1.00 | 53.85 C |
| ATOM | 7425 | O | LEU | A | 82 | −4.050 | −1.950 | 29.914 | 1.00 | 53.85 O |
| ATOM | 7427 | N | GLN | A | 83 | −4.530 | −3.829 | 31.044 | 1.00 | 53.85 N |
| ATOM | 7428 | CA | GLN | A | 83 | −4.055 | −4.716 | 29.975 | 1.00 | 54.02 C |
| ATOM | 7430 | CB | GLN | A | 83 | −3.403 | −5.979 | 30.540 | 1.00 | 53.64 C |
| ATOM | 7433 | CG | GLN | A | 83 | −2.419 | −5.723 | 31.659 | 1.00 | 53.69 C |
| ATOM | 7436 | CD | GLN | A | 83 | −1.535 | −4.528 | 31.408 | 1.00 | 52.02 C |
| ATOM | 7437 | OE1 | GLN | A | 83 | −0.933 | −4.395 | 30.339 | 1.00 | 50.05 O |
| ATOM | 7438 | NE2 | GLN | A | 83 | −1.462 | −3.636 | 32.392 | 1.00 | 49.57 N |
| ATOM | 7441 | C | GLN | A | 83 | −5.186 | −5.113 | 29.043 | 1.00 | 54.44 C |
| ATOM | 7442 | O | GLN | A | 83 | −6.362 | −4.903 | 29.350 | 1.00 | 55.00 O |
| ATOM | 7444 | N | ALA | A | 84 | −4.808 | −5.699 | 27.908 | 1.00 | 53.86 N |
| ATOM | 7445 | CA | ALA | A | 84 | −5.759 | −6.107 | 26.885 | 1.00 | 54.10 C |
| ATOM | 7447 | CB | ALA | A | 84 | −5.022 | −6.624 | 25.656 | 1.00 | 53.64 C |
| ATOM | 7451 | C | ALA | A | 84 | −6.728 | −7.164 | 27.408 | 1.00 | 54.54 C |
| ATOM | 7452 | O | ALA | A | 84 | −7.925 | −7.109 | 27.108 | 1.00 | 53.93 O |
| ATOM | 7454 | N | GLU | A | 85 | −6.215 | −8.102 | 28.208 | 1.00 | 55.06 N |
| ATOM | 7455 | CA | GLU | A | 85 | −7.039 | −9.191 | 28.750 | 1.00 | 55.56 C |
| ATOM | 7457 | CB | GLU | A | 85 | −6.190 | −10.452 | 28.996 | 1.00 | 56.05 C |
| ATOM | 7460 | CG | GLU | A | 85 | −5.453 | −10.532 | 30.340 | 1.00 | 57.21 C |
| ATOM | 7463 | CD | GLU | A | 85 | −4.196 | −9.679 | 30.405 | 1.00 | 63.04 C |
| ATOM | 7464 | OE1 | GLU | A | 85 | −3.691 | −9.227 | 29.344 | 1.00 | 68.17 O |
| ATOM | 7465 | OE2 | GLU | A | 85 | −3.708 | −9.473 | 31.537 | 1.00 | 59.53 O |
| ATOM | 7466 | C | GLU | A | 85 | −7.843 | −8.804 | 30.008 | 1.00 | 55.93 C |
| ATOM | 7467 | O | GLU | A | 85 | −8.433 | −9.674 | 30.669 | 1.00 | 55.78 O |
| ATOM | 7469 | N | ASP | A | 86 | −7.866 | −7.508 | 30.331 | 1.00 | 55.50 N |
| ATOM | 7470 | CA | ASP | A | 86 | −8.756 | −6.975 | 31.373 | 1.00 | 55.34 C |
| ATOM | 7472 | CB | ASP | A | 86 | −8.094 | −5.793 | 32.097 | 1.00 | 55.33 C |
| ATOM | 7475 | CG | ASP | A | 86 | −6.767 | −6.168 | 32.737 | 1.00 | 56.50 C |
| ATOM | 7476 | OD1 | ASP | A | 86 | −6.478 | −7.378 | 32.813 | 1.00 | 62.79 O |
| ATOM | 7477 | OD2 | ASP | A | 86 | −6.010 | −5.263 | 33.163 | 1.00 | 57.49 O |
| ATOM | 7478 | C | ASP | A | 86 | −10.104 | −6.547 | 30.779 | 1.00 | 54.55 C |
| ATOM | 7479 | O | ASP | A | 86 | −11.024 | −6.167 | 31.507 | 1.00 | 54.08 O |
| ATOM | 7481 | N | VAL | A | 87 | −10.220 | −6.611 | 29.458 | 1.00 | 53.82 N |
| ATOM | 7482 | CA | VAL | A | 87 | −11.446 | −6.211 | 28.789 | 1.00 | 53.67 C |
| ATOM | 7484 | CB | VAL | A | 87 | −11.226 | −6.076 | 27.246 | 1.00 | 53.52 C |
| ATOM | 7486 | CG1 | VAL | A | 87 | −11.322 | −7.423 | 26.532 | 1.00 | 54.55 C |
| ATOM | 7490 | CG2 | VAL | A | 87 | −12.189 | −5.081 | 26.652 | 1.00 | 53.97 C |
| ATOM | 7494 | C | VAL | A | 87 | −12.524 | −7.221 | 29.194 | 1.00 | 52.94 C |
| ATOM | 7495 | O | VAL | A | 87 | −12.381 | −8.421 | 28.960 | 1.00 | 51.45 O |
| ATOM | 7497 | N | ALA | A | 88 | −13.567 | −6.722 | 29.861 | 1.00 | 53.57 N |
| ATOM | 7498 | CA | ALA | A | 88 | −14.594 | −7.563 | 30.505 | 1.00 | 52.41 C |
| ATOM | 7500 | CB | ALA | A | 88 | −13.940 | −8.539 | 31.490 | 1.00 | 51.52 C |
| ATOM | 7504 | C | ALA | A | 88 | −15.632 | −6.696 | 31.234 | 1.00 | 52.14 C |
| ATOM | 7505 | O | ALA | A | 88 | −15.485 | −5.475 | 31.329 | 1.00 | 51.35 O |
| ATOM | 7507 | N | VAL | A | 89 | −16.685 | −7.334 | 31.741 | 1.00 | 53.01 N |
| ATOM | 7508 | CA | VAL | A | 89 | −17.688 | −6.654 | 32.573 | 1.00 | 52.63 C |
| ATOM | 7510 | CB | VAL | A | 89 | −19.114 | −7.097 | 32.208 | 1.00 | 51.69 C |
| ATOM | 7512 | CG1 | VAL | A | 89 | −20.134 | −6.425 | 33.113 | 1.00 | 52.60 C |
| ATOM | 7516 | CG2 | VAL | A | 89 | −19.407 | −6.766 | 30.742 | 1.00 | 49.94 C |
| ATOM | 7520 | C | VAL | A | 89 | −17.411 | −6.918 | 34.059 | 1.00 | 52.90 C |
| ATOM | 7521 | O | VAL | A | 89 | −17.124 | −8.049 | 34.444 | 1.00 | 55.74 O |
| ATOM | 7523 | N | TYR | A | 90 | −17.498 | −5.870 | 34.881 | 1.00 | 52.72 N |
| ATOM | 7524 | CA | TYR | A | 90 | −17.139 | −5.941 | 36.303 | 1.00 | 52.61 C |
| ATOM | 7526 | CB | TYR | A | 90 | −16.036 | −4.927 | 36.603 | 1.00 | 51.58 C |
| ATOM | 7529 | CG | TYR | A | 90 | −14.706 | −5.298 | 35.992 | 1.00 | 52.00 C |
| ATOM | 7530 | CD1 | TYR | A | 90 | −14.322 | −4.801 | 34.746 | 1.00 | 50.13 C |
| ATOM | 7532 | CE1 | TYR | A | 90 | −13.102 | −5.150 | 34.182 | 1.00 | 48.99 C |
| ATOM | 7534 | CZ | TYR | A | 90 | −12.256 | −6.008 | 34.865 | 1.00 | 50.14 C |
| ATOM | 7535 | OH | TYR | A | 90 | −11.043 | −6.366 | 34.335 | 1.00 | 51.47 O |
| ATOM | 7537 | CE2 | TYR | A | 90 | −12.615 | −6.512 | 36.092 | 1.00 | 51.56 C |
| ATOM | 7539 | CD2 | TYR | A | 90 | −13.834 | −6.159 | 36.652 | 1.00 | 51.85 C |
| ATOM | 7541 | C | TYR | A | 90 | −18.328 | −5.684 | 37.230 | 1.00 | 52.79 C |
| ATOM | 7542 | O | TYR | A | 90 | −19.021 | −4.675 | 37.101 | 1.00 | 53.04 O |
| ATOM | 7544 | N | TYR | A | 91 | −18.537 | −6.593 | 38.178 | 1.00 | 54.01 N |
| ATOM | 7545 | CA | TYR | A | 91 | −19.675 | −6.534 | 39.103 | 1.00 | 54.80 C |
| ATOM | 7547 | CB | TYR | A | 91 | −20.503 | −7.823 | 38.999 | 1.00 | 53.92 C |
| ATOM | 7550 | CG | TYR | A | 91 | −21.130 | −8.084 | 37.645 | 1.00 | 54.43 C |
| ATOM | 7551 | CD1 | TYR | A | 91 | −22.388 | −7.586 | 37.333 | 1.00 | 50.63 C |
| ATOM | 7553 | CE1 | TYR | A | 91 | −22.978 | −7.832 | 36.096 | 1.00 | 50.12 C |
| ATOM | 7555 | CZ | TYR | A | 91 | −22.309 | −8.588 | 35.155 | 1.00 | 52.43 C |
| ATOM | 7556 | OH | TYR | A | 91 | −22.892 | −8.831 | 33.934 | 1.00 | 53.15 O |
| ATOM | 7558 | CE2 | TYR | A | 91 | −21.054 | −9.100 | 35.435 | 1.00 | 54.13 C |
| ATOM | 7560 | CD2 | TYR | A | 91 | −20.471 | −8.848 | 36.681 | 1.00 | 54.93 C |
| ATOM | 7562 | C | TYR | A | 91 | −19.210 | −6.376 | 40.554 | 1.00 | 55.26 C |
| ATOM | 7563 | O | TYR | A | 91 | −18.219 | −6.979 | 40.950 | 1.00 | 55.07 O |

-continued

| | | | | | | | | | | |
|---|---|---|---|---|---|---|---|---|---|---|
| ATOM | 7565 | N | CYS | A | 92 | −19.925 | −5.568 | 41.340 | 1.00 | 56.72 N |
| ATOM | 7566 | CA | CYS | A | 92 | −19.740 | −5.557 | 42.799 | 1.00 | 56.96 C |
| ATOM | 7568 | CB | CYS | A | 92 | −19.608 | −4.140 | 43.392 | 1.00 | 55.92 C |
| ATOM | 7571 | SG | CYS | A | 92 | −21.050 | −3.071 | 43.241 | 1.00 | 63.17 S |
| ATOM | 7573 | C | CYS | A | 92 | −20.898 | −6.307 | 43.433 | 1.00 | 57.25 C |
| ATOM | 7574 | O | CYS | A | 92 | −21.929 | −6.541 | 42.797 | 1.00 | 56.74 O |
| ATOM | 7576 | N | GLN | A | 93 | −20.715 | −6.679 | 44.693 | 1.00 | 56.62 N |
| ATOM | 7577 | CA | GLN | A | 93 | −21.663 | −7.523 | 45.393 | 1.00 | 56.15 C |
| ATOM | 7579 | CB | GLN | A | 93 | −21.379 | −8.986 | 45.037 | 1.00 | 57.98 C |
| ATOM | 7582 | CG | GLN | A | 93 | −22.295 | −10.036 | 45.683 | 1.00 | 58.17 C |
| ATOM | 7585 | CD | GLN | A | 93 | −21.580 | −10.882 | 46.714 | 1.00 | 56.58 C |
| ATOM | 7586 | OE1 | GLN | A | 93 | −20.509 | −11.433 | 46.447 | 1.00 | 55.72 O |
| ATOM | 7587 | NE2 | GLN | A | 93 | −22.174 | −11.003 | 47.894 | 1.00 | 53.83 N |
| ATOM | 7590 | C | GLN | A | 93 | −21.493 | −7.275 | 46.879 | 1.00 | 56.63 C |
| ATOM | 7591 | O | GLN | A | 93 | −20.373 | −7.026 | 47.336 | 1.00 | 59.58 O |
| ATOM | 7593 | N | HIS | A | 94 | −22.598 | −7.313 | 47.621 | 1.00 | 55.54 N |
| ATOM | 7594 | CA | HIS | A | 94 | −22.579 | −7.114 | 49.072 | 1.00 | 54.51 C |
| ATOM | 7596 | CB | HIS | A | 94 | −23.499 | −5.950 | 49.449 | 1.00 | 54.63 C |
| ATOM | 7599 | CG | HIS | A | 94 | −24.944 | −6.329 | 49.558 | 1.00 | 53.37 C |
| ATOM | 7600 | ND1 | HIS | A | 94 | −25.520 | −6.729 | 50.743 | 1.00 | 54.18 N |
| ATOM | 7602 | CE1 | HIS | A | 94 | −26.795 | −7.008 | 50.542 | 1.00 | 57.87 C |
| ATOM | 7604 | NE2 | HIS | A | 94 | −27.068 | −6.801 | 49.267 | 1.00 | 56.34 N |
| ATOM | 7606 | CD2 | HIS | A | 94 | −25.925 | −6.381 | 48.629 | 1.00 | 56.76 C |
| ATOM | 7608 | C | HIS | A | 94 | −23.044 | −8.396 | 49.770 | 1.00 | 53.97 C |
| ATOM | 7609 | O | HIS | A | 94 | −23.712 | −9.220 | 49.148 | 1.00 | 54.58 O |
| ATOM | 7611 | N | SER | A | 95 | −22.698 | −8.567 | 51.048 | 1.00 | 53.62 N |
| ATOM | 7612 | CA | SER | A | 95 | −23.309 | −9.635 | 51.857 | 1.00 | 53.91 C |
| ATOM | 7614 | CB | SER | A | 95 | −22.408 | −10.880 | 51.916 | 1.00 | 52.95 C |
| ATOM | 7617 | OG | SER | A | 95 | −21.462 | −10.790 | 52.959 | 1.00 | 52.57 O |
| ATOM | 7619 | C | SER | A | 95 | −23.744 | −9.218 | 53.275 | 1.00 | 53.46 C |
| ATOM | 7620 | O | SER | A | 95 | −23.901 | −10.066 | 54.145 | 1.00 | 55.35 O |
| ATOM | 7622 | N | ARG | A | 96 | −24.000 | −7.927 | 53.466 | 1.00 | 52.66 N |
| ATOM | 7623 | CA | ARG | A | 96 | −24.400 | −7.369 | 54.752 | 1.00 | 52.63 C |
| ATOM | 7625 | CB | ARG | A | 96 | −24.627 | −5.861 | 54.610 | 1.00 | 53.08 C |
| ATOM | 7628 | CG | ARG | A | 96 | −24.999 | −5.168 | 55.909 | 1.00 | 52.58 C |
| ATOM | 7631 | CD | ARG | A | 96 | −23.848 | −5.201 | 56.891 | 1.00 | 52.12 C |
| ATOM | 7634 | NE | ARG | A | 96 | −24.241 | −4.734 | 58.219 | 1.00 | 53.82 N |
| ATOM | 7636 | CZ | ARG | A | 96 | −24.848 | −5.478 | 59.142 | 1.00 | 51.83 C |
| ATOM | 7637 | NH1 | ARG | A | 96 | −25.172 | −6.742 | 58.896 | 1.00 | 57.15 N |
| ATOM | 7640 | NH2 | ARG | A | 96 | −25.135 | −4.952 | 60.321 | 1.00 | 49.85 N |
| ATOM | 7643 | C | ARG | A | 96 | −25.661 | −7.996 | 55.326 | 1.00 | 52.29 C |
| ATOM | 7644 | O | ARG | A | 96 | −25.788 | −8.152 | 56.536 | 1.00 | 51.71 O |
| ATOM | 7646 | N | GLU | A | 97 | −26.609 | −8.315 | 54.454 | 1.00 | 52.96 N |
| ATOM | 7647 | CA | GLU | A | 97 | −27.821 | −9.034 | 54.846 | 1.00 | 53.56 C |
| ATOM | 7649 | CB | GLU | A | 97 | −28.880 | −8.047 | 55.339 | 1.00 | 53.02 C |
| ATOM | 7652 | CG | GLU | A | 97 | −29.345 | −7.073 | 54.253 | 1.00 | 58.84 C |
| ATOM | 7655 | CD | GLU | A | 97 | −30.179 | −5.913 | 54.775 | 1.00 | 59.30 C |
| ATOM | 7656 | OE1 | GLU | A | 97 | −29.786 | −5.305 | 55.796 | 1.00 | 65.24 O |
| ATOM | 7657 | OE2 | GLU | A | 97 | −31.216 | −5.600 | 54.139 | 1.00 | 64.70 O |
| ATOM | 7658 | C | GLU | A | 97 | −28.325 | −9.822 | 53.632 | 1.00 | 52.14 C |
| ATOM | 7659 | O | GLU | A | 97 | −27.807 | −9.672 | 52.530 | 1.00 | 53.56 O |
| ATOM | 7661 | N | LEU | A | 98 | −29.315 | −10.672 | 53.832 | 1.00 | 50.29 N |
| ATOM | 7662 | CA | LEU | A | 98 | −30.009 | −11.282 | 52.706 | 1.00 | 51.31 C |
| ATOM | 7664 | CB | LEU | A | 98 | −30.608 | −12.631 | 53.113 | 1.00 | 50.51 C |
| ATOM | 7667 | CG | LEU | A | 98 | −29.833 | −13.898 | 52.731 | 1.00 | 51.04 C |
| ATOM | 7669 | CD1 | LEU | A | 98 | −28.413 | −13.809 | 53.106 | 1.00 | 56.07 C |
| ATOM | 7673 | CD2 | LEU | A | 98 | −30.444 | −15.092 | 53.411 | 1.00 | 53.98 C |
| ATOM | 7677 | C | LEU | A | 98 | −31.101 | −10.320 | 52.226 | 1.00 | 50.17 C |
| ATOM | 7678 | O | LEU | A | 98 | −31.675 | −9.604 | 53.038 | 1.00 | 55.19 O |
| ATOM | 7680 | N | PRO | A | 99 | −31.386 | −10.278 | 50.917 | 1.00 | 47.74 N |
| ATOM | 7681 | CA | PRO | A | 99 | −30.712 | −10.973 | 49.831 | 1.00 | 49.71 C |
| ATOM | 7683 | CB | PRO | A | 99 | −31.673 | −10.808 | 48.655 | 1.00 | 48.71 C |
| ATOM | 7686 | CG | PRO | A | 99 | −32.405 | −9.597 | 48.940 | 1.00 | 46.65 C |
| ATOM | 7689 | CD | PRO | A | 99 | −32.524 | −9.489 | 50.425 | 1.00 | 45.81 C |
| ATOM | 7692 | C | PRO | A | 99 | −29.355 | −10.366 | 49.478 | 1.00 | 51.03 C |
| ATOM | 7693 | O | PRO | A | 99 | −29.139 | −9.155 | 49.638 | 1.00 | 51.72 O |
| ATOM | 7694 | N | TRP | A | 100 | −28.459 | −11.229 | 49.007 | 1.00 | 50.96 N |
| ATOM | 7695 | CA | TRP | A | 100 | −27.146 | −10.831 | 48.527 | 1.00 | 50.00 C |
| ATOM | 7697 | CB | TRP | A | 100 | −26.174 | −12.012 | 48.639 | 1.00 | 50.47 C |
| ATOM | 7700 | CG | TRP | A | 100 | −25.953 | −12.494 | 50.040 | 1.00 | 50.98 C |
| ATOM | 7701 | CD1 | TRP | A | 100 | −25.847 | −11.729 | 51.151 | 1.00 | 54.01 C |
| ATOM | 7703 | NE1 | TRP | A | 100 | −25.616 | −12.512 | 52.253 | 1.00 | 54.49 N |
| ATOM | 7705 | CE2 | TRP | A | 100 | −25.562 | −13.822 | 51.861 | 1.00 | 49.41 C |
| ATOM | 7706 | CD2 | TRP | A | 100 | −25.770 | −13.850 | 50.469 | 1.00 | 52.99 C |
| ATOM | 7707 | CE3 | TRP | A | 100 | −25.763 | −15.087 | 49.809 | 1.00 | 55.37 C |
| ATOM | 7709 | CZ3 | TRP | A | 100 | −25.561 | −16.243 | 50.562 | 1.00 | 56.13 C |
| ATOM | 7711 | CH2 | TRP | A | 100 | −25.364 | −16.175 | 51.957 | 1.00 | 54.04 C |
| ATOM | 7713 | CZ2 | TRP | A | 100 | −25.369 | −14.977 | 52.616 | 1.00 | 48.69 C |
| ATOM | 7715 | C | TRP | A | 100 | −27.257 | −10.352 | 47.071 | 1.00 | 48.92 C |

| | | | | | | | | | | | |
|---|---|---|---|---|---|---|---|---|---|---|---|
| ATOM | 7716 | O | TRP | A | 100 | −27.376 | −11.155 | 46.147 | 1.00 | 48.02 | O |
| ATOM | 7718 | N | THR | A | 101 | −27.224 | −9.040 | 46.868 | 1.00 | 48.80 | N |
| ATOM | 7719 | CA | THR | A | 101 | −27.430 | −8.471 | 45.533 | 1.00 | 48.58 | C |
| ATOM | 7721 | CB | THR | A | 101 | −28.487 | −7.372 | 45.566 | 1.00 | 47.16 | C |
| ATOM | 7723 | OG1 | THR | A | 101 | −28.111 | −6.378 | 46.531 | 1.00 | 49.81 | O |
| ATOM | 7725 | CG2 | THR | A | 101 | −29.840 | −7.962 | 45.940 | 1.00 | 44.07 | C |
| ATOM | 7729 | C | THR | A | 101 | −26.138 | −7.948 | 44.869 | 1.00 | 48.42 | C |
| ATOM | 7730 | O | THR | A | 101 | −25.174 | −7.547 | 45.540 | 1.00 | 46.67 | O |
| ATOM | 7732 | N | PHE | A | 102 | −26.141 | −7.990 | 43.539 | 1.00 | 47.33 | N |
| ATOM | 7733 | CA | PHE | A | 102 | −25.065 | −7.461 | 42.728 | 1.00 | 48.71 | C |
| ATOM | 7735 | CB | PHE | A | 102 | −24.836 | −8.375 | 41.530 | 1.00 | 49.22 | C |
| ATOM | 7738 | CG | PHE | A | 102 | −24.308 | −9.735 | 41.871 | 1.00 | 48.06 | C |
| ATOM | 7739 | CD1 | PHE | A | 102 | −22.948 | −9.990 | 41.839 | 1.00 | 47.28 | C |
| ATOM | 7741 | CE1 | PHE | A | 102 | −22.459 | −11.242 | 42.114 | 1.00 | 47.72 | C |
| ATOM | 7743 | CZ | PHE | A | 102 | −23.320 | −12.274 | 42.410 | 1.00 | 49.08 | C |
| ATOM | 7745 | CE2 | PHE | A | 102 | −24.672 | −12.045 | 42.429 | 1.00 | 52.29 | C |
| ATOM | 7747 | CD2 | PHE | A | 102 | −25.165 | −10.776 | 42.151 | 1.00 | 50.38 | C |
| ATOM | 7749 | C | PHE | A | 102 | −25.392 | −6.054 | 42.183 | 1.00 | 48.86 | C |
| ATOM | 7750 | O | PHE | A | 102 | −26.530 | −5.583 | 42.243 | 1.00 | 46.85 | O |
| ATOM | 7752 | N | GLY | A | 103 | −24.373 | −5.393 | 41.651 | 1.00 | 50.32 | N |
| ATOM | 7753 | CA | GLY | A | 103 | −24.561 | −4.175 | 40.865 | 1.00 | 51.64 | C |
| ATOM | 7756 | C | GLY | A | 103 | −24.857 | −4.527 | 39.417 | 1.00 | 52.58 | C |
| ATOM | 7757 | O | GLY | A | 103 | −24.665 | −5.672 | 39.009 | 1.00 | 53.77 | O |
| ATOM | 7759 | N | GLN | A | 104 | −25.307 | −3.547 | 38.634 | 1.00 | 51.82 | N |
| ATOM | 7760 | CA | GLN | A | 104 | −25.784 | −3.819 | 37.275 | 1.00 | 51.41 | C |
| ATOM | 7762 | CB | GLN | A | 104 | −26.653 | −2.660 | 36.755 | 1.00 | 51.48 | C |
| ATOM | 7765 | CG | GLN | A | 104 | −25.918 | −1.472 | 36.086 | 1.00 | 54.19 | C |
| ATOM | 7768 | CD | GLN | A | 104 | −25.046 | −0.637 | 37.035 | 1.00 | 54.97 | C |
| ATOM | 7769 | OE1 | GLN | A | 104 | −25.432 | −0.328 | 38.165 | 1.00 | 52.40 | O |
| ATOM | 7770 | NE2 | GLN | A | 104 | −23.870 | −0.249 | 36.552 | 1.00 | 53.59 | N |
| ATOM | 7773 | C | GLN | A | 104 | −24.658 | −4.168 | 36.288 | 1.00 | 51.25 | C |
| ATOM | 7774 | O | GLN | A | 104 | −24.925 | −4.495 | 35.128 | 1.00 | 51.06 | O |
| ATOM | 7776 | N | GLY | A | 105 | −23.410 | −4.097 | 36.746 | 1.00 | 52.04 | N |
| ATOM | 7777 | CA | GLY | A | 105 | −22.253 | −4.457 | 35.920 | 1.00 | 53.02 | C |
| ATOM | 7780 | C | GLY | A | 105 | −21.667 | −3.266 | 35.187 | 1.00 | 52.44 | C |
| ATOM | 7781 | O | GLY | A | 105 | −22.410 | −2.394 | 34.746 | 1.00 | 54.03 | O |
| ATOM | 7783 | N | THR | A | 106 | −20.338 | −3.222 | 35.069 | 1.00 | 52.03 | N |
| ATOM | 7784 | CA | THR | A | 106 | −19.651 | −2.143 | 34.341 | 1.00 | 52.72 | C |
| ATOM | 7786 | CB | THR | A | 106 | −18.836 | −1.204 | 35.291 | 1.00 | 52.36 | C |
| ATOM | 7788 | OG1 | THR | A | 106 | −19.726 | −0.394 | 36.070 | 1.00 | 49.16 | O |
| ATOM | 7790 | CG2 | THR | A | 106 | −17.921 | −0.278 | 34.499 | 1.00 | 51.63 | C |
| ATOM | 7794 | C | THR | A | 106 | −18.729 | −2.726 | 33.265 | 1.00 | 52.67 | C |
| ATOM | 7795 | O | THR | A | 106 | −17.800 | −3.476 | 33.563 | 1.00 | 52.64 | O |
| ATOM | 7797 | N | LYS | A | 107 | −18.997 | −2.356 | 32.019 | 1.00 | 53.56 | N |
| ATOM | 7798 | CA | LYS | A | 107 | −18.216 | −2.797 | 30.865 | 1.00 | 54.50 | C |
| ATOM | 7800 | CB | LYS | A | 107 | −19.056 | −2.633 | 29.584 | 1.00 | 55.33 | C |
| ATOM | 7803 | CG | LYS | A | 107 | −18.694 | −3.555 | 28.426 | 1.00 | 55.32 | C |
| ATOM | 7806 | CD | LYS | A | 107 | −19.661 | −3.351 | 27.255 | 1.00 | 57.23 | C |
| ATOM | 7809 | CE | LYS | A | 107 | −19.892 | −4.643 | 26.463 | 1.00 | 59.97 | C |
| ATOM | 7812 | NZ | LYS | A | 107 | −20.999 | −4.524 | 25.456 | 1.00 | 58.78 | N |
| ATOM | 7816 | C | LYS | A | 107 | −16.937 | −1.960 | 30.763 | 1.00 | 54.40 | C |
| ATOM | 7817 | O | LYS | A | 107 | −16.979 | −0.728 | 30.828 | 1.00 | 53.19 | O |
| ATOM | 7819 | N | VAL | A | 108 | −15.804 | −2.637 | 30.606 | 1.00 | 54.82 | N |
| ATOM | 7820 | CA | VAL | A | 108 | −14.511 | −1.969 | 30.472 | 1.00 | 55.05 | C |
| ATOM | 7822 | CB | VAL | A | 108 | −13.567 | −2.356 | 31.613 | 1.00 | 54.32 | C |
| ATOM | 7824 | CG1 | VAL | A | 108 | −12.180 | −1.740 | 31.403 | 1.00 | 54.65 | C |
| ATOM | 7828 | CG2 | VAL | A | 108 | −14.159 | −1.908 | 32.934 | 1.00 | 54.76 | C |
| ATOM | 7832 | C | VAL | A | 108 | −13.879 | −2.342 | 29.139 | 1.00 | 55.39 | C |
| ATOM | 7833 | O | VAL | A | 108 | −13.765 | −3.524 | 28.815 | 1.00 | 56.54 | O |
| ATOM | 7835 | N | GLU | A | 109 | −13.461 | −1.330 | 28.380 | 1.00 | 55.65 | N |
| ATOM | 7836 | CA | GLU | A | 109 | −13.000 | −1.520 | 27.010 | 1.00 | 55.70 | C |
| ATOM | 7838 | CB | GLU | A | 109 | −14.096 | −1.111 | 26.023 | 1.00 | 55.49 | C |
| ATOM | 7841 | CG | GLU | A | 109 | −15.315 | −2.019 | 26.060 | 1.00 | 57.22 | C |
| ATOM | 7844 | CD | GLU | A | 109 | −16.368 | −1.649 | 25.026 | 1.00 | 59.67 | C |
| ATOM | 7845 | OE1 | GLU | A | 109 | −17.384 | −2.374 | 24.913 | 1.00 | 65.87 | O |
| ATOM | 7846 | OE2 | GLU | A | 109 | −16.187 | −0.641 | 24.314 | 1.00 | 65.28 | O |
| ATOM | 7847 | C | GLU | A | 109 | −11.735 | −0.738 | 26.727 | 1.00 | 54.66 | C |
| ATOM | 7848 | O | GLU | A | 109 | −11.360 | 0.158 | 27.483 | 1.00 | 54.68 | O |
| ATOM | 7850 | N | ILE | A | 110 | −11.092 | −1.095 | 25.619 | 1.00 | 54.72 | N |
| ATOM | 7851 | CA | ILE | A | 110 | −9.846 | −0.474 | 25.179 | 1.00 | 54.28 | C |
| ATOM | 7853 | CB | ILE | A | 110 | −8.905 | −1.525 | 24.520 | 1.00 | 53.48 | C |
| ATOM | 7855 | CG1 | ILE | A | 110 | −8.066 | −2.224 | 25.588 | 1.00 | 53.77 | C |
| ATOM | 7858 | CD1 | ILE | A | 110 | −8.881 | −3.021 | 26.591 | 1.00 | 58.37 | C |
| ATOM | 7862 | CG2 | ILE | A | 110 | −7.955 | −0.889 | 23.512 | 1.00 | 55.60 | C |
| ATOM | 7866 | C | ILE | A | 110 | −10.124 | 0.675 | 24.210 | 1.00 | 53.88 | C |
| ATOM | 7867 | O | ILE | A | 110 | −10.812 | 0.493 | 23.211 | 1.00 | 53.96 | O |
| ATOM | 7869 | N | LYS | A | 111 | −9.601 | 1.859 | 24.529 | 1.00 | 53.81 | N |
| ATOM | 7870 | CA | LYS | A | 111 | −9.520 | 2.957 | 23.566 | 1.00 | 53.70 | C |
| ATOM | 7872 | CB | LYS | A | 111 | −9.334 | 4.321 | 24.247 | 1.00 | 54.81 | C |

-continued

| | | | | | | | | | | |
|---|---|---|---|---|---|---|---|---|---|---|
| ATOM | 7875 | CG | LYS | A | 111 | −10.597 | 5.186 | 24.332 | 1.00 | 55.76 C |
| ATOM | 7878 | CD | LYS | A | 111 | −10.225 | 6.673 | 24.356 | 1.00 | 54.86 C |
| ATOM | 7881 | CE | LYS | A | 111 | −11.443 | 7.572 | 24.436 | 1.00 | 56.09 C |
| ATOM | 7884 | NZ | LYS | A | 111 | −11.130 | 8.946 | 23.941 | 1.00 | 56.07 N |
| ATOM | 7888 | C | LYS | A | 111 | −8.353 | 2.674 | 22.622 | 1.00 | 52.73 C |
| ATOM | 7889 | O | LYS | A | 111 | −7.286 | 2.224 | 23.040 | 1.00 | 52.75 O |
| ATOM | 7891 | N | ARG | A | 112 | −8.564 | 2.970 | 21.349 | 1.00 | 52.16 N |
| ATOM | 7892 | CA | ARG | A | 112 | −7.737 | 2.438 | 20.279 | 1.00 | 51.34 C |
| ATOM | 7894 | CB | ARG | A | 112 | −8.366 | 1.124 | 19.796 | 1.00 | 51.68 C |
| ATOM | 7897 | CG | ARG | A | 112 | −7.402 | 0.056 | 19.307 | 1.00 | 50.70 C |
| ATOM | 7900 | CD | ARG | A | 112 | −8.101 | −0.871 | 18.306 | 1.00 | 49.45 C |
| ATOM | 7903 | NE | ARG | A | 112 | −8.000 | −0.347 | 16.947 | 1.00 | 43.37 N |
| ATOM | 7905 | CZ | ARG | A | 112 | −7.017 | −0.634 | 16.096 | 1.00 | 42.48 C |
| ATOM | 7906 | NH1 | ARG | A | 112 | −6.042 | −1.475 | 16.420 | 1.00 | 43.80 N |
| ATOM | 7909 | NH2 | ARG | A | 112 | −7.016 | −0.084 | 14.896 | 1.00 | 45.43 N |
| ATOM | 7912 | C | ARG | A | 112 | −7.694 | 3.438 | 19.130 | 1.00 | 50.60 C |
| ATOM | 7913 | O | ARG | A | 112 | −8.498 | 4.370 | 19.071 | 1.00 | 49.78 O |
| ATOM | 7915 | N | THR | A | 113 | −6.761 | 3.245 | 18.210 | 1.00 | 50.40 N |
| ATOM | 7916 | CA | THR | A | 113 | −6.773 | 4.017 | 16.978 | 1.00 | 50.07 C |
| ATOM | 7918 | CB | THR | A | 113 | −5.461 | 3.877 | 16.187 | 1.00 | 49.90 C |
| ATOM | 7920 | OG1 | THR | A | 113 | −5.318 | 2.529 | 15.726 | 1.00 | 51.67 O |
| ATOM | 7922 | CG2 | THR | A | 113 | −4.261 | 4.250 | 17.053 | 1.00 | 50.19 C |
| ATOM | 7926 | C | THR | A | 113 | −7.939 | 3.511 | 16.138 | 1.00 | 49.54 C |
| ATOM | 7927 | O | THR | A | 113 | −8.385 | 2.377 | 16.300 | 1.00 | 48.69 O |
| ATOM | 7929 | N | VAL | A | 114 | −8.434 | 4.366 | 15.254 | 1.00 | 49.70 N |
| ATOM | 7930 | CA | VAL | A | 114 | −9.531 | 4.005 | 14.377 | 1.00 | 49.23 C |
| ATOM | 7932 | CB | VAL | A | 114 | −10.137 | 5.246 | 13.694 | 1.00 | 48.83 C |
| ATOM | 7934 | CG1 | VAL | A | 114 | −11.138 | 4.839 | 12.602 | 1.00 | 48.71 C |
| ATOM | 7938 | CG2 | VAL | A | 114 | −10.793 | 6.150 | 14.726 | 1.00 | 47.21 C |
| ATOM | 7942 | C | VAL | A | 114 | −9.026 | 3.029 | 13.318 | 1.00 | 49.85 C |
| ATOM | 7943 | O | VAL | A | 114 | −7.996 | 3.270 | 12.679 | 1.00 | 49.97 O |
| ATOM | 7945 | N | ALA | A | 115 | −9.758 | 1.927 | 13.161 | 1.00 | 50.08 N |
| ATOM | 7946 | CA | ALA | A | 115 | −9.490 | 0.922 | 12.138 | 1.00 | 49.55 C |
| ATOM | 7948 | CB | ALA | A | 115 | −9.220 | −0.438 | 12.781 | 1.00 | 48.81 C |
| ATOM | 7952 | C | ALA | A | 115 | −10.706 | 0.833 | 11.230 | 1.00 | 49.65 C |
| ATOM | 7953 | O | ALA | A | 115 | −11.824 | 0.691 | 11.723 | 1.00 | 49.77 O |
| ATOM | 7955 | N | ALA | A | 116 | −10.488 | 0.920 | 9.917 | 1.00 | 49.56 N |
| ATOM | 7956 | CA | ALA | A | 116 | −11.565 | 0.786 | 8.935 | 1.00 | 49.41 C |
| ATOM | 7958 | CB | ALA | A | 116 | −11.090 | 1.241 | 7.563 | 1.00 | 48.58 C |
| ATOM | 7962 | C | ALA | A | 116 | −12.057 | −0.663 | 8.864 | 1.00 | 50.01 C |
| ATOM | 7963 | O | ALA | A | 116 | −11.254 | −1.595 | 8.956 | 1.00 | 49.43 O |
| ATOM | 7965 | N | PRO | A | 117 | −13.382 | −0.860 | 8.710 | 1.00 | 50.75 N |
| ATOM | 7966 | CA | PRO | A | 117 | −13.883 | −2.212 | 8.464 | 1.00 | 50.58 C |
| ATOM | 7968 | CB | PRO | A | 117 | −15.382 | −2.104 | 8.759 | 1.00 | 50.21 C |
| ATOM | 7971 | CG | PRO | A | 117 | −15.719 | −0.667 | 8.592 | 1.00 | 49.70 C |
| ATOM | 7974 | CD | PRO | A | 117 | −14.465 | 0.141 | 8.756 | 1.00 | 50.74 C |
| ATOM | 7977 | C | PRO | A | 117 | −13.672 | −2.625 | 7.012 | 1.00 | 51.44 C |
| ATOM | 7978 | O | PRO | A | 117 | −14.023 | −1.872 | 6.102 | 1.00 | 50.88 O |
| ATOM | 7979 | N | SER | A | 118 | −13.084 | −3.797 | 6.799 | 1.00 | 51.74 N |
| ATOM | 7980 | CA | SER | A | 118 | −13.089 | −4.407 | 5.479 | 1.00 | 50.75 C |
| ATOM | 7982 | CB | SER | A | 118 | −12.096 | −5.571 | 5.408 | 1.00 | 50.93 C |
| ATOM | 7985 | OG | SER | A | 118 | −10.764 | −5.122 | 5.578 | 1.00 | 50.05 O |
| ATOM | 7987 | C | SER | A | 118 | −14.511 | −4.906 | 5.266 | 1.00 | 51.06 C |
| ATOM | 7988 | O | SER | A | 118 | −15.121 | −5.420 | 6.204 | 1.00 | 51.50 O |
| ATOM | 7990 | N | VAL | A | 119 | −15.041 | −4.730 | 4.053 | 1.00 | 50.99 N |
| ATOM | 7991 | CA | VAL | A | 119 | −16.410 | −5.150 | 3.722 | 1.00 | 49.93 C |
| ATOM | 7993 | CB | VAL | A | 119 | −17.306 | −3.929 | 3.399 | 1.00 | 49.47 C |
| ATOM | 7995 | CG1 | VAL | A | 119 | −18.764 | −4.355 | 3.228 | 1.00 | 47.94 C |
| ATOM | 7999 | CG2 | VAL | A | 119 | −17.177 | −2.859 | 4.497 | 1.00 | 48.88 C |
| ATOM | 8003 | C | VAL | A | 119 | −16.418 | −6.133 | 2.548 | 1.00 | 49.26 C |
| ATOM | 8004 | O | VAL | A | 119 | −16.619 | −7.338 | 2.728 | 1.00 | 48.94 O |
| ATOM | 8006 | N | VAL | A | 137 | −26.350 | −11.364 | 3.345 | 1.00 | 52.92 N |
| ATOM | 8007 | CA | VAL | A | 137 | −25.473 | −11.254 | 4.508 | 1.00 | 53.45 C |
| ATOM | 8009 | CB | VAL | A | 137 | −24.879 | −12.620 | 4.906 | 1.00 | 52.41 C |
| ATOM | 8011 | CG1 | VAL | A | 137 | −23.918 | −12.468 | 6.093 | 1.00 | 50.85 C |
| ATOM | 8015 | CG2 | VAL | A | 137 | −25.990 | −13.602 | 5.241 | 1.00 | 52.25 C |
| ATOM | 8019 | C | VAL | A | 137 | −24.315 | −10.284 | 4.276 | 1.00 | 53.76 C |
| ATOM | 8020 | O | VAL | A | 137 | −23.485 | −10.509 | 3.401 | 1.00 | 54.18 O |
| ATOM | 8022 | N | CYS | A | 138 | −24.252 | −9.233 | 5.091 | 1.00 | 54.63 N |
| ATOM | 8023 | CA | CYS | A | 138 | −23.176 | −8.246 | 5.022 | 1.00 | 54.74 C |
| ATOM | 8025 | CB | CYS | A | 138 | −23.751 | −6.836 | 5.120 | 1.00 | 55.44 C |
| ATOM | 8028 | SG | CYS | A | 138 | −22.624 | −5.571 | 4.524 | 1.00 | 56.29 S |
| ATOM | 8030 | C | CYS | A | 138 | −22.171 | −8.457 | 6.147 | 1.00 | 55.03 C |
| ATOM | 8031 | O | CYS | A | 138 | −22.554 | −8.786 | 7.268 | 1.00 | 56.14 O |
| ATOM | 8033 | N | LEU | A | 139 | −20.890 | −8.256 | 5.848 | 1.00 | 54.31 N |
| ATOM | 8034 | CA | LEU | A | 139 | −19.826 | −8.442 | 6.830 | 1.00 | 53.98 C |
| ATOM | 8036 | CB | LEU | A | 139 | −18.983 | −9.663 | 6.469 | 1.00 | 53.28 C |
| ATOM | 8039 | CG | LEU | A | 139 | −17.700 | −9.830 | 7.293 | 1.00 | 53.23 C |
| ATOM | 8041 | CD1 | LEU | A | 139 | −18.030 | −9.996 | 8.772 | 1.00 | 51.68 C |

-continued

| ATOM | 8045 | CD2 | LEU | A | 139 | −16.892 | −11.000 | 6.782 | 1.00 | 52.53 | C |
| ATOM | 8049 | C | LEU | A | 139 | −18.914 | −7.226 | 6.903 | 1.00 | 54.68 | C |
| ATOM | 8050 | O | LEU | A | 139 | −18.308 | −6.845 | 5.904 | 1.00 | 56.02 | O |
| ATOM | 8052 | N | LEU | A | 140 | −18.804 | −6.637 | 8.090 | 1.00 | 54.60 | N |
| ATOM | 8053 | CA | LEU | A | 140 | −17.828 | −5.576 | 8.349 | 1.00 | 54.27 | C |
| ATOM | 8055 | CB | LEU | A | 140 | −18.487 | −4.378 | 9.045 | 1.00 | 54.07 | C |
| ATOM | 8058 | CG | LEU | A | 140 | −19.584 | −3.624 | 8.280 | 1.00 | 52.55 | C |
| ATOM | 8060 | CD1 | LEU | A | 140 | −20.827 | −4.478 | 8.019 | 1.00 | 51.87 | C |
| ATOM | 8064 | CD2 | LEU | A | 140 | −19.961 | −2.385 | 9.053 | 1.00 | 52.40 | C |
| ATOM | 8068 | C | LEU | A | 140 | −16.749 | −6.175 | 9.237 | 1.00 | 54.38 | C |
| ATOM | 8069 | O | LEU | A | 140 | −17.044 | −6.627 | 10.343 | 1.00 | 55.50 | O |
| ATOM | 8071 | N | ASN | A | 141 | −15.506 | −6.189 | 8.762 | 1.00 | 54.13 | N |
| ATOM | 8072 | CA | ASN | A | 141 | −14.439 | −6.912 | 9.455 | 1.00 | 54.40 | C |
| ATOM | 8074 | CB | ASN | A | 141 | −13.759 | −7.887 | 8.484 | 1.00 | 54.36 | C |
| ATOM | 8077 | CG | ASN | A | 141 | −13.104 | −9.081 | 9.185 | 1.00 | 53.38 | C |
| ATOM | 8078 | OD1 | ASN | A | 141 | −12.731 | −10.048 | 8.530 | 1.00 | 51.81 | O |
| ATOM | 8079 | ND2 | ASN | A | 141 | −12.964 | −9.019 | 10.504 | 1.00 | 55.85 | N |
| ATOM | 8082 | C | ASN | A | 141 | −13.395 | −5.990 | 10.102 | 1.00 | 55.01 | C |
| ATOM | 8083 | O | ASN | A | 141 | −12.799 | −5.139 | 9.433 | 1.00 | 55.64 | O |
| ATOM | 8085 | N | ASN | A | 142 | −13.206 | −6.180 | 11.411 | 1.00 | 54.47 | N |
| ATOM | 8086 | CA | ASN | A | 142 | −12.149 | −5.547 | 12.213 | 1.00 | 53.54 | C |
| ATOM | 8088 | CB | ASN | A | 142 | −10.787 | −6.176 | 11.889 | 1.00 | 52.77 | C |
| ATOM | 8091 | CG | ASN | A | 142 | −10.739 | −7.670 | 12.205 | 1.00 | 52.05 | C |
| ATOM | 8092 | OD1 | ASN | A | 142 | −11.202 | −8.112 | 13.256 | 1.00 | 51.93 | O |
| ATOM | 8093 | ND2 | ASN | A | 142 | −10.185 | −8.451 | 11.288 | 1.00 | 51.89 | N |
| ATOM | 8096 | C | ASN | A | 142 | −12.095 | −4.024 | 12.130 | 1.00 | 53.21 | C |
| ATOM | 8097 | O | ASN | A | 142 | −11.225 | −3.457 | 11.475 | 1.00 | 54.01 | O |
| ATOM | 8099 | N | PHE | A | 143 | −13.030 | −3.374 | 12.823 | 1.00 | 54.16 | N |
| ATOM | 8100 | CA | PHE | A | 143 | −13.115 | −1.909 | 12.864 | 1.00 | 54.45 | C |
| ATOM | 8102 | CB | PHE | A | 143 | −14.330 | −1.421 | 12.072 | 1.00 | 55.13 | C |
| ATOM | 8105 | CG | PHE | A | 143 | −15.656 | −1.852 | 12.649 | 1.00 | 54.31 | C |
| ATOM | 8106 | CD1 | PHE | A | 143 | −16.322 | −1.050 | 13.563 | 1.00 | 55.41 | C |
| ATOM | 8108 | CE1 | PHE | A | 143 | −17.550 | −1.440 | 14.095 | 1.00 | 55.65 | C |
| ATOM | 8110 | CZ | PHE | A | 143 | −18.123 | −2.642 | 13.708 | 1.00 | 55.84 | C |
| ATOM | 8112 | CE2 | PHE | A | 143 | −17.469 | −3.451 | 12.792 | 1.00 | 55.98 | C |
| ATOM | 8114 | CD2 | PHE | A | 143 | −16.243 | −3.051 | 12.264 | 1.00 | 55.54 | C |
| ATOM | 8116 | C | PHE | A | 143 | −13.192 | −1.366 | 14.288 | 1.00 | 54.61 | C |
| ATOM | 8117 | O | PHE | A | 143 | −13.381 | −2.124 | 15.243 | 1.00 | 54.71 | O |
| ATOM | 8119 | N | TYR | A | 144 | −13.047 | −0.048 | 14.417 | 1.00 | 54.02 | N |
| ATOM | 8120 | CA | TYR | A | 144 | −13.157 | 0.619 | 15.716 | 1.00 | 54.45 | C |
| ATOM | 8122 | CB | TYR | A | 144 | −11.862 | 0.444 | 16.533 | 1.00 | 53.86 | C |
| ATOM | 8125 | CG | TYR | A | 144 | −11.971 | 0.974 | 17.951 | 1.00 | 54.68 | C |
| ATOM | 8126 | CD1 | TYR | A | 144 | −11.704 | 2.313 | 18.237 | 1.00 | 55.07 | C |
| ATOM | 8128 | CE1 | TYR | A | 144 | −11.823 | 2.811 | 19.528 | 1.00 | 52.91 | C |
| ATOM | 8130 | CZ | TYR | A | 144 | −12.214 | 1.970 | 20.547 | 1.00 | 53.28 | C |
| ATOM | 8131 | OH | TYR | A | 144 | −12.329 | 2.469 | 21.822 | 1.00 | 55.54 | O |
| ATOM | 8133 | CE2 | TYR | A | 144 | −12.489 | 0.637 | 20.293 | 1.00 | 53.44 | C |
| ATOM | 8135 | CD2 | TYR | A | 144 | −12.367 | 0.145 | 19.002 | 1.00 | 54.46 | C |
| ATOM | 8137 | C | TYR | A | 144 | −13.458 | 2.108 | 15.518 | 1.00 | 55.01 | C |
| ATOM | 8138 | O | TYR | A | 144 | −12.868 | 2.735 | 14.637 | 1.00 | 55.16 | O |
| ATOM | 8140 | N | PRO | A | 145 | −14.368 | 2.685 | 16.332 | 1.00 | 55.73 | N |
| ATOM | 8141 | CA | PRO | A | 145 | −15.161 | 2.107 | 17.412 | 1.00 | 56.70 | C |
| ATOM | 8143 | CB | PRO | A | 145 | −15.390 | 3.309 | 18.333 | 1.00 | 56.28 | C |
| ATOM | 8146 | CG | PRO | A | 145 | −15.447 | 4.472 | 17.417 | 1.00 | 55.85 | C |
| ATOM | 8149 | CD | PRO | A | 145 | −14.665 | 4.121 | 16.174 | 1.00 | 55.75 | C |
| ATOM | 8152 | C | PRO | A | 145 | −16.492 | 1.517 | 16.917 | 1.00 | 57.75 | C |
| ATOM | 8153 | O | PRO | A | 145 | −16.688 | 1.363 | 15.709 | 1.00 | 58.63 | O |
| ATOM | 8154 | N | ARG | A | 146 | −17.388 | 1.192 | 17.848 | 1.00 | 58.22 | N |
| ATOM | 8155 | CA | ARG | A | 146 | −18.698 | 0.625 | 17.525 | 1.00 | 58.14 | C |
| ATOM | 8157 | CB | ARG | A | 146 | −19.180 | −0.236 | 18.699 | 1.00 | 58.94 | C |
| ATOM | 8160 | CG | ARG | A | 146 | −20.125 | −1.365 | 18.309 | 1.00 | 60.14 | C |
| ATOM | 8163 | CD | ARG | A | 146 | −20.915 | −1.924 | 19.508 | 1.00 | 61.01 | C |
| ATOM | 8166 | NE | ARG | A | 146 | −20.064 | −2.473 | 20.570 | 1.00 | 64.92 | N |
| ATOM | 8168 | CZ | ARG | A | 146 | −20.469 | −3.339 | 21.502 | 1.00 | 64.17 | C |
| ATOM | 8169 | NH1 | ARG | A | 146 | −21.721 | −3.785 | 21.519 | 1.00 | 65.11 | N |
| ATOM | 8172 | NH2 | ARG | A | 146 | −19.611 | −3.774 | 22.420 | 1.00 | 62.06 | N |
| ATOM | 8175 | C | ARG | A | 146 | −19.726 | 1.722 | 17.227 | 1.00 | 56.33 | C |
| ATOM | 8176 | O | ARG | A | 146 | −19.790 | 2.254 | 16.122 | 1.00 | 54.77 | O |
| ATOM | 8178 | N | SER | A | 160 | −36.742 | −0.105 | 5.921 | 1.00 | 47.65 | N |
| ATOM | 8179 | CA | SER | A | 160 | −36.853 | −1.554 | 5.872 | 1.00 | 48.11 | C |
| ATOM | 8181 | CB | SER | A | 160 | −35.716 | −2.138 | 5.035 | 1.00 | 47.68 | C |
| ATOM | 8184 | OG | SER | A | 160 | −35.706 | −1.600 | 3.728 | 1.00 | 46.12 | O |
| ATOM | 8186 | C | SER | A | 160 | −36.801 | −2.152 | 7.273 | 1.00 | 48.80 | C |
| ATOM | 8187 | O | SER | A | 160 | −36.028 | −1.701 | 8.114 | 1.00 | 49.61 | O |
| ATOM | 8189 | N | GLY | A | 161 | −37.626 | −3.166 | 7.516 | 1.00 | 49.18 | N |
| ATOM | 8190 | CA | GLY | A | 161 | −37.570 | −3.947 | 8.754 | 1.00 | 49.41 | C |
| ATOM | 8193 | C | GLY | A | 161 | −37.327 | −5.418 | 8.458 | 1.00 | 49.98 | C |
| ATOM | 8194 | O | GLY | A | 161 | −37.954 | −6.290 | 9.060 | 1.00 | 50.56 | O |
| ATOM | 8196 | N | ASN | A | 162 | −36.405 | −5.686 | 7.532 | 1.00 | 50.18 | N |

-continued

| | | | | | | | | | | |
|---|---|---|---|---|---|---|---|---|---|---|
| ATOM | 8197 | CA | ASN | A | 162 | −36.124 | −7.045 | 7.036 | 1.00 | 49.88 C |
| ATOM | 8199 | CB | ASN | A | 162 | −36.604 | −7.178 | 5.583 | 1.00 | 48.98 C |
| ATOM | 8202 | CG | ASN | A | 162 | −36.151 | −6.017 | 4.705 | 1.00 | 47.85 C |
| ATOM | 8203 | OD1 | ASN | A | 162 | −34.971 | −5.662 | 4.674 | 1.00 | 48.45 O |
| ATOM | 8204 | ND2 | ASN | A | 162 | −37.093 | −5.414 | 3.997 | 1.00 | 46.18 N |
| ATOM | 8207 | C | ASN | A | 162 | −34.637 | −7.415 | 7.150 | 1.00 | 50.21 C |
| ATOM | 8208 | O | ASN | A | 162 | −34.149 | −8.318 | 6.461 | 1.00 | 50.61 O |
| ATOM | 8210 | N | SER | A | 163 | −33.930 | −6.710 | 8.028 | 1.00 | 50.15 N |
| ATOM | 8211 | CA | SER | A | 163 | −32.514 | −6.947 | 8.262 | 1.00 | 50.83 C |
| ATOM | 8213 | CB | SER | A | 163 | −31.660 | −5.957 | 7.466 | 1.00 | 51.23 C |
| ATOM | 8216 | OG | SER | A | 163 | −31.782 | −4.635 | 7.975 | 1.00 | 50.65 O |
| ATOM | 8218 | C | SER | A | 163 | −32.217 | −6.788 | 9.743 | 1.00 | 51.26 C |
| ATOM | 8219 | O | SER | A | 163 | −32.763 | −5.896 | 10.392 | 1.00 | 52.28 O |
| ATOM | 8221 | N | GLN | A | 164 | −31.349 | −7.649 | 10.264 | 1.00 | 50.89 N |
| ATOM | 8222 | CA | GLN | A | 164 | −30.905 | −7.576 | 11.659 | 1.00 | 51.71 C |
| ATOM | 8224 | CB | GLN | A | 164 | −31.667 | −8.593 | 12.522 | 1.00 | 51.48 C |
| ATOM | 8227 | CG | GLN | A | 164 | −31.821 | −9.978 | 11.880 | 1.00 | 51.08 C |
| ATOM | 8230 | CD | GLN | A | 164 | −32.641 | −10.939 | 12.710 | 1.00 | 49.96 C |
| ATOM | 8231 | OE1 | GLN | A | 164 | −33.117 | −10.596 | 13.790 | 1.00 | 46.20 O |
| ATOM | 8232 | NE2 | GLN | A | 164 | −32.812 | −12.156 | 12.206 | 1.00 | 47.01 N |
| ATOM | 8235 | C | GLN | A | 164 | −29.392 | −7.816 | 11.712 | 1.00 | 53.01 C |
| ATOM | 8236 | O | GLN | A | 164 | −28.825 | −8.434 | 10.807 | 1.00 | 54.44 O |
| ATOM | 8238 | N | GLU | A | 165 | −28.730 | −7.323 | 12.752 | 1.00 | 53.17 N |
| ATOM | 8239 | CA | GLU | A | 165 | −27.273 | −7.427 | 12.807 | 1.00 | 53.68 C |
| ATOM | 8241 | CB | GLU | A | 165 | −26.621 | −6.082 | 12.460 | 1.00 | 54.11 C |
| ATOM | 8244 | CG | GLU | A | 165 | −27.462 | −4.861 | 12.792 | 1.00 | 55.35 C |
| ATOM | 8247 | CD | GLU | A | 165 | −26.721 | −3.563 | 12.526 | 1.00 | 55.26 C |
| ATOM | 8248 | OE1 | GLU | A | 165 | −25.626 | −3.379 | 13.095 | 1.00 | 54.38 O |
| ATOM | 8249 | OE2 | GLU | A | 165 | −27.236 | −2.724 | 11.759 | 1.00 | 57.24 O |
| ATOM | 8250 | C | GLU | A | 165 | −26.745 | −7.959 | 14.134 | 1.00 | 52.96 C |
| ATOM | 8251 | O | GLU | A | 165 | −27.397 | −7.832 | 15.165 | 1.00 | 52.13 O |
| ATOM | 8253 | N | SER | A | 166 | −25.564 | −8.572 | 14.083 | 1.00 | 53.53 N |
| ATOM | 8254 | CA | SER | A | 166 | −24.878 | −9.080 | 15.280 | 1.00 | 54.46 C |
| ATOM | 8256 | CB | SER | A | 166 | −24.863 | −10.612 | 15.298 | 1.00 | 54.98 C |
| ATOM | 8259 | OG | SER | A | 166 | −24.240 | −11.106 | 16.475 | 1.00 | 53.82 O |
| ATOM | 8261 | C | SER | A | 166 | −23.448 | −8.552 | 15.333 | 1.00 | 54.86 C |
| ATOM | 8262 | O | SER | A | 166 | −22.759 | −8.503 | 14.309 | 1.00 | 55.52 O |
| ATOM | 8264 | N | VAL | A | 167 | −23.010 | −8.181 | 16.535 | 1.00 | 54.69 N |
| ATOM | 8265 | CA | VAL | A | 167 | −21.699 | −7.567 | 16.753 | 1.00 | 54.47 C |
| ATOM | 8267 | CB | VAL | A | 167 | −21.848 | −6.073 | 17.172 | 1.00 | 54.48 C |
| ATOM | 8269 | CG1 | VAL | A | 167 | −22.861 | −5.898 | 18.303 | 1.00 | 54.93 C |
| ATOM | 8273 | CG2 | VAL | A | 167 | −20.500 | −5.469 | 17.555 | 1.00 | 55.79 C |
| ATOM | 8277 | C | VAL | A | 167 | −20.898 | −8.361 | 17.798 | 1.00 | 54.48 C |
| ATOM | 8278 | O | VAL | A | 167 | −21.455 | −8.820 | 18.795 | 1.00 | 54.42 O |
| ATOM | 8280 | N | THR | A | 168 | −19.598 | −8.534 | 17.556 | 1.00 | 55.27 N |
| ATOM | 8281 | CA | THR | A | 168 | −18.714 | −9.250 | 18.492 | 1.00 | 55.17 C |
| ATOM | 8283 | CB | THR | A | 168 | −17.457 | −9.839 | 17.785 | 1.00 | 55.15 C |
| ATOM | 8285 | OG1 | THR | A | 168 | −16.790 | −8.812 | 17.036 | 1.00 | 55.27 O |
| ATOM | 8287 | CG2 | THR | A | 168 | −17.832 | −10.990 | 16.860 | 1.00 | 54.96 C |
| ATOM | 8291 | C | THR | A | 168 | −18.221 | −8.341 | 19.618 | 1.00 | 55.08 C |
| ATOM | 8292 | O | THR | A | 168 | −18.278 | −7.111 | 19.517 | 1.00 | 54.83 O |
| ATOM | 8294 | N | GLU | A | 169 | −17.733 | −8.967 | 20.686 | 1.00 | 55.14 N |
| ATOM | 8295 | CA | GLU | A | 169 | −16.988 | −8.264 | 21.733 | 1.00 | 55.30 C |
| ATOM | 8297 | CB | GLU | A | 169 | −16.850 | −9.140 | 22.981 | 1.00 | 55.53 C |
| ATOM | 8300 | CG | GLU | A | 169 | −18.177 | −9.504 | 23.636 | 1.00 | 57.81 C |
| ATOM | 8303 | CD | GLU | A | 169 | −18.696 | −8.433 | 24.581 | 1.00 | 60.48 C |
| ATOM | 8304 | OE1 | GLU | A | 169 | −18.468 | −7.232 | 24.330 | 1.00 | 62.19 O |
| ATOM | 8305 | OE2 | GLU | A | 169 | −19.348 | −8.798 | 25.582 | 1.00 | 63.26 O |
| ATOM | 8306 | C | GLU | A | 169 | −15.600 | −7.886 | 21.207 | 1.00 | 55.10 C |
| ATOM | 8307 | O | GLU | A | 169 | −15.083 | −8.525 | 20.290 | 1.00 | 56.12 O |
| ATOM | 8309 | N | GLN | A | 170 | −15.006 | −6.847 | 21.787 | 1.00 | 53.52 N |
| ATOM | 8310 | CA | GLN | A | 170 | −13.671 | −6.387 | 21.394 | 1.00 | 52.45 C |
| ATOM | 8312 | CB | GLN | A | 170 | −13.160 | −5.354 | 22.405 | 1.00 | 52.40 C |
| ATOM | 8315 | CG | GLN | A | 170 | −12.549 | −4.110 | 21.796 | 1.00 | 51.45 C |
| ATOM | 8318 | CD | GLN | A | 170 | −12.176 | −3.075 | 22.841 | 1.00 | 51.48 C |
| ATOM | 8319 | OE1 | GLN | A | 170 | −12.497 | −3.218 | 24.024 | 1.00 | 49.48 O |
| ATOM | 8320 | NE2 | GLN | A | 170 | −11.490 | −2.024 | 22.409 | 1.00 | 48.24 N |
| ATOM | 8323 | C | GLN | A | 170 | −12.700 | −7.572 | 21.308 | 1.00 | 51.71 C |
| ATOM | 8324 | O | GLN | A | 170 | −12.640 | −8.401 | 22.220 | 1.00 | 50.99 O |
| ATOM | 8326 | N | ASP | A | 171 | −11.954 | −7.651 | 20.209 | 1.00 | 51.94 N |
| ATOM | 8327 | CA | ASP | A | 171 | −11.039 | −8.770 | 19.956 | 1.00 | 52.82 C |
| ATOM | 8329 | CB | ASP | A | 171 | −10.508 | −8.685 | 18.517 | 1.00 | 52.66 C |
| ATOM | 8332 | CG | ASP | A | 171 | −9.890 | −9.991 | 18.027 | 1.00 | 52.81 C |
| ATOM | 8333 | OD1 | ASP | A | 171 | −9.208 | −10.685 | 18.811 | 1.00 | 50.99 O |
| ATOM | 8334 | OD2 | ASP | A | 171 | −10.073 | −10.309 | 16.832 | 1.00 | 55.51 O |
| ATOM | 8335 | C | ASP | A | 171 | −9.866 | −8.779 | 20.948 | 1.00 | 53.35 C |
| ATOM | 8336 | O | ASP | A | 171 | −9.300 | −7.727 | 21.252 | 1.00 | 53.94 O |
| ATOM | 8338 | N | SER | A | 172 | −9.491 | −9.969 | 21.424 | 1.00 | 53.69 N |
| ATOM | 8339 | CA | SER | A | 172 | −8.437 | −10.121 | 22.450 | 1.00 | 53.40 C |

-continued

| | | | | | | | | | | |
|---|---|---|---|---|---|---|---|---|---|---|
| ATOM | 8341 | CB | SER | A | 172 | −8.504 | −11.513 | 23.092 | 1.00 | 52.64 C |
| ATOM | 8344 | OG | SER | A | 172 | −8.211 | −12.525 | 22.143 | 1.00 | 50.98 O |
| ATOM | 8346 | C | SER | A | 172 | −7.010 | −9.873 | 21.943 | 1.00 | 53.76 C |
| ATOM | 8347 | O | SER | A | 172 | −6.064 | −9.888 | 22.735 | 1.00 | 53.69 O |
| ATOM | 8349 | N | LYS | A | 173 | −6.853 | −9.666 | 20.635 | 1.00 | 54.72 N |
| ATOM | 8350 | CA | LYS | A | 173 | −5.566 | −9.281 | 20.054 | 1.00 | 54.91 C |
| ATOM | 8352 | CB | LYS | A | 173 | −5.212 | −10.179 | 18.861 | 1.00 | 55.00 C |
| ATOM | 8355 | CG | LYS | A | 173 | −4.851 | −11.607 | 19.240 | 1.00 | 55.63 C |
| ATOM | 8358 | CD | LYS | A | 173 | −4.326 | −12.380 | 18.041 | 1.00 | 54.81 C |
| ATOM | 8361 | CE | LYS | A | 173 | −4.517 | −13.870 | 18.212 | 1.00 | 54.73 C |
| ATOM | 8364 | NZ | LYS | A | 173 | −4.018 | −14.612 | 17.028 | 1.00 | 54.59 N |
| ATOM | 8368 | C | LYS | A | 173 | −5.584 | −7.815 | 19.620 | 1.00 | 55.44 C |
| ATOM | 8369 | O | LYS | A | 173 | −4.912 | −6.975 | 20.224 | 1.00 | 56.78 O |
| ATOM | 8371 | N | ASP | A | 174 | −6.371 | −7.508 | 18.592 | 1.00 | 54.48 N |
| ATOM | 8372 | CA | ASP | A | 174 | −6.323 | −6.189 | 17.953 | 1.00 | 53.90 C |
| ATOM | 8374 | CB | ASP | A | 174 | −6.367 | −6.333 | 16.419 | 1.00 | 54.32 C |
| ATOM | 8377 | CG | ASP | A | 174 | −7.598 | −7.076 | 15.920 | 1.00 | 55.74 C |
| ATOM | 8378 | OD1 | ASP | A | 174 | −8.095 | −7.970 | 16.627 | 1.00 | 58.47 O |
| ATOM | 8379 | OD2 | ASP | A | 174 | −8.060 | −6.781 | 14.802 | 1.00 | 59.46 O |
| ATOM | 8380 | C | ASP | A | 174 | −7.392 | −5.203 | 18.440 | 1.00 | 53.26 C |
| ATOM | 8381 | O | ASP | A | 174 | −7.563 | −4.141 | 17.841 | 1.00 | 53.00 O |
| ATOM | 8383 | N | SER | A | 175 | −8.094 | −5.544 | 19.522 | 1.00 | 52.51 N |
| ATOM | 8384 | CA | SER | A | 175 | −9.109 | −4.664 | 20.123 | 1.00 | 52.19 C |
| ATOM | 8386 | CB | SER | A | 175 | −8.430 | −3.523 | 20.881 | 1.00 | 51.48 C |
| ATOM | 8389 | OG | SER | A | 175 | −7.405 | −4.015 | 21.710 | 1.00 | 50.96 O |
| ATOM | 8391 | C | SER | A | 175 | −10.098 | −4.078 | 19.107 | 1.00 | 51.93 C |
| ATOM | 8392 | O | SER | A | 175 | −10.425 | −2.886 | 19.168 | 1.00 | 50.08 O |
| ATOM | 8394 | N | THR | A | 176 | −10.568 | −4.920 | 18.185 | 1.00 | 52.18 N |
| ATOM | 8395 | CA | THR | A | 176 | −11.485 | −4.490 | 17.120 | 1.00 | 52.77 C |
| ATOM | 8397 | CB | THR | A | 176 | −10.864 | −4.662 | 15.714 | 1.00 | 52.54 C |
| ATOM | 8399 | OG1 | THR | A | 176 | −10.547 | −6.042 | 15.491 | 1.00 | 54.57 O |
| ATOM | 8401 | CG2 | THR | A | 176 | −9.608 | −3.816 | 15.559 | 1.00 | 53.68 C |
| ATOM | 8405 | C | THR | A | 176 | −12.802 | −5.258 | 17.144 | 1.00 | 52.28 C |
| ATOM | 8406 | O | THR | A | 176 | −12.895 | −6.338 | 17.718 | 1.00 | 52.14 O |
| ATOM | 8408 | N | TYR | A | 177 | −13.809 | −4.679 | 16.497 | 1.00 | 52.77 N |
| ATOM | 8409 | CA | TYR | A | 177 | −15.143 | −5.267 | 16.413 | 1.00 | 53.30 C |
| ATOM | 8411 | CB | TYR | A | 177 | −16.212 | −4.228 | 16.792 | 1.00 | 53.44 C |
| ATOM | 8414 | CG | TYR | A | 177 | −16.077 | −3.644 | 18.190 | 1.00 | 52.52 C |
| ATOM | 8415 | CD1 | TYR | A | 177 | −16.263 | −4.434 | 19.317 | 1.00 | 51.79 C |
| ATOM | 8417 | CE1 | TYR | A | 177 | −16.146 | −3.901 | 20.592 | 1.00 | 52.84 C |
| ATOM | 8419 | CZ | TYR | A | 177 | −15.855 | −2.561 | 20.751 | 1.00 | 52.74 C |
| ATOM | 8420 | OH | TYR | A | 177 | −15.740 | −2.029 | 22.010 | 1.00 | 51.71 O |
| ATOM | 8422 | CE2 | TYR | A | 177 | −15.680 | −1.752 | 19.651 | 1.00 | 53.28 C |
| ATOM | 8424 | CD2 | TYR | A | 177 | −15.795 | −2.293 | 18.378 | 1.00 | 53.10 C |
| ATOM | 8426 | C | TYR | A | 177 | −15.425 | −5.785 | 14.998 | 1.00 | 53.07 C |
| ATOM | 8427 | O | TYR | A | 177 | −14.957 | −5.211 | 14.018 | 1.00 | 52.16 O |
| ATOM | 8429 | N | SER | A | 178 | −16.180 | −6.880 | 14.912 | 1.00 | 53.72 N |
| ATOM | 8430 | CA | SER | A | 178 | −16.719 | −7.389 | 13.648 | 1.00 | 53.81 C |
| ATOM | 8432 | CB | SER | A | 178 | −16.131 | −8.761 | 13.302 | 1.00 | 53.62 C |
| ATOM | 8435 | OG | SER | A | 178 | −14.794 | −8.646 | 12.846 | 1.00 | 52.54 O |
| ATOM | 8437 | C | SER | A | 178 | −18.234 | −7.487 | 13.778 | 1.00 | 54.33 C |
| ATOM | 8438 | O | SER | A | 178 | −18.761 | −7.673 | 14.876 | 1.00 | 54.29 O |
| ATOM | 8440 | N | LEU | A | 179 | −18.928 | −7.372 | 12.652 | 1.00 | 54.92 N |
| ATOM | 8441 | CA | LEU | A | 179 | −20.377 | −7.195 | 12.657 | 1.00 | 55.07 C |
| ATOM | 8443 | CB | LEU | A | 179 | −20.692 | −5.692 | 12.767 | 1.00 | 55.89 C |
| ATOM | 8446 | CG | LEU | A | 179 | −22.136 | −5.172 | 12.675 | 1.00 | 54.50 C |
| ATOM | 8448 | CD1 | LEU | A | 179 | −22.265 | −3.878 | 13.485 | 1.00 | 53.09 C |
| ATOM | 8452 | CD2 | LEU | A | 179 | −22.590 | −4.957 | 11.224 | 1.00 | 52.26 C |
| ATOM | 8456 | C | LEU | A | 179 | −21.017 | −7.792 | 11.400 | 1.00 | 55.70 C |
| ATOM | 8457 | O | LEU | A | 179 | −20.570 | −7.521 | 10.277 | 1.00 | 56.43 O |
| ATOM | 8459 | N | SER | A | 180 | −22.062 | −8.596 | 11.596 | 1.00 | 55.16 N |
| ATOM | 8460 | CA | SER | A | 180 | −22.848 | −9.144 | 10.485 | 1.00 | 54.15 C |
| ATOM | 8462 | CB | SER | A | 180 | −22.985 | −10.668 | 10.614 | 1.00 | 54.76 C |
| ATOM | 8465 | OG | SER | A | 180 | −23.683 | −11.046 | 11.797 | 1.00 | 53.36 O |
| ATOM | 8467 | C | SER | A | 180 | −24.234 | −8.504 | 10.442 | 1.00 | 53.39 C |
| ATOM | 8468 | O | SER | A | 180 | −24.947 | −8.505 | 11.439 | 1.00 | 53.06 O |
| ATOM | 8470 | N | SER | A | 181 | −24.592 | −7.938 | 9.293 | 1.00 | 53.50 N |
| ATOM | 8471 | CA | SER | A | 181 | −25.956 | −7.467 | 9.040 | 1.00 | 52.75 C |
| ATOM | 8473 | CB | SER | A | 181 | −25.960 | −6.000 | 8.621 | 1.00 | 52.81 C |
| ATOM | 8476 | OG | SER | A | 181 | −27.293 | −5.552 | 8.453 | 1.00 | 52.98 O |
| ATOM | 8478 | C | SER | A | 181 | −26.581 | −8.325 | 7.943 | 1.00 | 51.46 C |
| ATOM | 8479 | O | SER | A | 181 | −26.160 | −8.258 | 6.788 | 1.00 | 50.02 O |
| ATOM | 8481 | N | THR | A | 182 | −27.585 | −9.118 | 8.317 | 1.00 | 50.26 N |
| ATOM | 8482 | CA | THR | A | 182 | −28.130 | −10.183 | 7.471 | 1.00 | 49.62 C |
| ATOM | 8484 | CB | THR | A | 182 | −28.230 | −11.499 | 8.285 | 1.00 | 49.53 C |
| ATOM | 8486 | OG1 | THR | A | 182 | −26.922 | −11.879 | 8.732 | 1.00 | 48.74 O |
| ATOM | 8488 | CG2 | THR | A | 182 | −28.835 | −12.636 | 7.463 | 1.00 | 49.54 C |
| ATOM | 8492 | C | THR | A | 182 | −29.496 | −9.818 | 6.895 | 1.00 | 47.65 C |
| ATOM | 8493 | O | THR | A | 182 | −30.334 | −9.249 | 7.584 | 1.00 | 45.40 O |

-continued

| | | | | | | | | | | |
|---|---|---|---|---|---|---|---|---|---|---|
| ATOM | 8495 | N | GLU | B | 2 | −10.619 | −25.043 | 44.227 | 1.00 | 57.08 N |
| ATOM | 8496 | CA | GLU | B | 2 | −10.247 | −25.315 | 42.812 | 1.00 | 58.19 C |
| ATOM | 8498 | CB | GLU | B | 2 | −9.263 | −26.489 | 42.721 | 1.00 | 58.76 C |
| ATOM | 8501 | CG | GLU | B | 2 | −7.890 | −26.169 | 43.263 | 1.00 | 61.44 C |
| ATOM | 8504 | CD | GLU | B | 2 | −6.782 | −26.549 | 42.304 | 1.00 | 65.00 C |
| ATOM | 8505 | OE1 | GLU | B | 2 | −6.864 | −26.192 | 41.106 | 1.00 | 62.53 O |
| ATOM | 8506 | OE2 | GLU | B | 2 | −5.816 | −27.197 | 42.749 | 1.00 | 69.73 O |
| ATOM | 8507 | C | GLU | B | 2 | −11.445 | −25.567 | 41.894 | 1.00 | 58.94 C |
| ATOM | 8508 | O | GLU | B | 2 | −11.996 | −24.629 | 41.316 | 1.00 | 62.34 O |
| ATOM | 8512 | N | GLN | B | 3 | −11.857 | −26.829 | 41.792 | 1.00 | 57.51 N |
| ATOM | 8513 | CA | GLN | B | 3 | −12.697 | −27.301 | 40.695 | 1.00 | 56.95 C |
| ATOM | 8515 | CB | GLN | B | 3 | −12.164 | −28.657 | 40.217 | 1.00 | 59.45 C |
| ATOM | 8518 | CG | GLN | B | 3 | −11.163 | −28.600 | 39.065 | 1.00 | 62.13 C |
| ATOM | 8521 | CD | GLN | B | 3 | −11.856 | −28.624 | 37.717 | 1.00 | 65.49 C |
| ATOM | 8522 | OE1 | GLN | B | 3 | −11.426 | −29.315 | 36.799 | 1.00 | 65.20 O |
| ATOM | 8523 | NE2 | GLN | B | 3 | −12.956 | −27.884 | 37.603 | 1.00 | 68.30 N |
| ATOM | 8526 | C | GLN | B | 3 | −14.169 | −27.462 | 41.073 | 1.00 | 56.52 C |
| ATOM | 8527 | O | GLN | B | 3 | −14.493 | −28.179 | 42.024 | 1.00 | 57.38 O |
| ATOM | 8529 | N | LEU | B | 4 | −15.049 | −26.787 | 40.332 | 1.00 | 55.34 N |
| ATOM | 8530 | CA | LEU | B | 4 | −16.489 | −27.070 | 40.366 | 1.00 | 54.52 C |
| ATOM | 8532 | CB | LEU | B | 4 | −17.298 | −25.874 | 40.847 | 1.00 | 53.96 C |
| ATOM | 8535 | CG | LEU | B | 4 | −17.243 | −25.570 | 42.343 | 1.00 | 55.82 C |
| ATOM | 8537 | CD1 | LEU | B | 4 | −17.456 | −24.082 | 42.582 | 1.00 | 57.87 C |
| ATOM | 8541 | CD2 | LEU | B | 4 | −18.255 | −26.389 | 43.121 | 1.00 | 55.41 C |
| ATOM | 8545 | C | LEU | B | 4 | −16.932 | −27.430 | 38.965 | 1.00 | 54.14 C |
| ATOM | 8546 | O | LEU | B | 4 | −17.100 | −26.561 | 38.109 | 1.00 | 51.87 O |
| ATOM | 8548 | N | VAL | B | 5 | −17.082 | −28.725 | 38.721 | 1.00 | 54.92 N |
| ATOM | 8549 | CA | VAL | B | 5 | −17.660 | −29.186 | 37.475 | 1.00 | 55.15 C |
| ATOM | 8551 | CB | VAL | B | 5 | −16.917 | −30.432 | 36.881 | 1.00 | 54.37 C |
| ATOM | 8553 | CG1 | VAL | B | 5 | −17.087 | −31.674 | 37.735 | 1.00 | 54.00 C |
| ATOM | 8557 | CG2 | VAL | B | 5 | −17.388 | −30.706 | 35.461 | 1.00 | 54.09 C |
| ATOM | 8561 | C | VAL | B | 5 | −19.146 | −29.400 | 37.756 | 1.00 | 55.56 C |
| ATOM | 8562 | O | VAL | B | 5 | −19.533 | −29.729 | 38.877 | 1.00 | 56.25 O |
| ATOM | 8564 | N | GLU | B | 6 | −19.960 | −29.210 | 36.725 | 1.00 | 56.11 N |
| ATOM | 8565 | CA | GLU | B | 6 | −21.390 | −28.975 | 36.863 | 1.00 | 56.43 C |
| ATOM | 8567 | CB | GLU | B | 6 | −21.649 | −27.482 | 36.654 | 1.00 | 57.11 C |
| ATOM | 8570 | CG | GLU | B | 6 | −22.951 | −26.943 | 37.183 | 1.00 | 57.87 C |
| ATOM | 8573 | CD | GLU | B | 6 | −23.194 | −25.525 | 36.691 | 1.00 | 61.03 C |
| ATOM | 8574 | OE1 | GLU | B | 6 | −22.325 | −24.652 | 36.915 | 1.00 | 64.83 O |
| ATOM | 8575 | OE2 | GLU | B | 6 | −24.244 | −25.291 | 36.059 | 1.00 | 67.42 O |
| ATOM | 8576 | C | GLU | B | 6 | −22.107 | −29.799 | 35.798 | 1.00 | 55.21 C |
| ATOM | 8577 | O | GLU | B | 6 | −21.562 | −30.010 | 34.716 | 1.00 | 54.09 O |
| ATOM | 8579 | N | SER | B | 7 | −23.318 | −30.259 | 36.098 | 1.00 | 55.29 N |
| ATOM | 8580 | CA | SER | B | 7 | −24.021 | −31.203 | 35.218 | 1.00 | 55.46 C |
| ATOM | 8582 | CB | SER | B | 7 | −23.842 | −32.643 | 35.722 | 1.00 | 54.36 C |
| ATOM | 8585 | OG | SER | B | 7 | −22.474 | −32.978 | 35.905 | 1.00 | 51.02 O |
| ATOM | 8587 | C | SER | B | 7 | −25.507 | −30.891 | 35.125 | 1.00 | 56.51 C |
| ATOM | 8588 | O | SER | B | 7 | −26.108 | −30.385 | 36.083 | 1.00 | 57.60 O |
| ATOM | 8590 | N | GLY | B | 8 | −26.092 | −31.196 | 33.970 | 1.00 | 56.40 N |
| ATOM | 8591 | CA | GLY | B | 8 | −27.522 | −30.986 | 33.728 | 1.00 | 56.69 C |
| ATOM | 8594 | C | GLY | B | 8 | −27.799 | −29.744 | 32.903 | 1.00 | 57.21 C |
| ATOM | 8595 | O | GLY | B | 8 | −26.883 | −28.991 | 32.568 | 1.00 | 58.60 O |
| ATOM | 8597 | N | GLY | B | 9 | −29.067 | −29.539 | 32.560 | 1.00 | 57.00 N |
| ATOM | 8598 | CA | GLY | B | 9 | −29.489 | −28.322 | 31.870 | 1.00 | 56.00 C |
| ATOM | 8601 | C | GLY | B | 9 | −30.020 | −28.553 | 30.474 | 1.00 | 54.36 C |
| ATOM | 8602 | O | GLY | B | 9 | −29.999 | −29.669 | 29.965 | 1.00 | 53.60 O |
| ATOM | 8604 | N | GLY | B | 10 | −30.494 | −27.473 | 29.863 | 1.00 | 53.60 N |
| ATOM | 8605 | CA | GLY | B | 10 | −31.076 | −27.513 | 28.532 | 1.00 | 52.66 C |
| ATOM | 8608 | C | GLY | B | 10 | −32.545 | −27.157 | 28.551 | 1.00 | 52.35 C |
| ATOM | 8609 | O | GLY | B | 10 | −33.019 | −26.454 | 29.451 | 1.00 | 52.72 O |
| ATOM | 8611 | N | LEU | B | 11 | −33.268 | −27.676 | 27.561 | 1.00 | 52.28 N |
| ATOM | 8612 | CA | LEU | B | 11 | −34.657 | −27.285 | 27.281 | 1.00 | 51.37 C |
| ATOM | 8614 | CB | LEU | B | 11 | −34.945 | −27.495 | 25.788 | 1.00 | 50.49 C |
| ATOM | 8617 | CG | LEU | B | 11 | −36.305 | −27.092 | 25.221 | 1.00 | 50.40 C |
| ATOM | 8619 | CD1 | LEU | B | 11 | −36.770 | −25.732 | 25.714 | 1.00 | 50.55 C |
| ATOM | 8623 | CD2 | LEU | B | 11 | −36.229 | −27.104 | 23.713 | 1.00 | 49.33 C |
| ATOM | 8627 | C | LEU | B | 11 | −35.689 | −28.041 | 28.129 | 1.00 | 50.09 C |
| ATOM | 8628 | O | LEU | B | 11 | −35.608 | −29.258 | 28.279 | 1.00 | 48.56 O |
| ATOM | 8630 | N | VAL | B | 12 | −36.643 | −27.304 | 28.696 | 1.00 | 51.19 N |
| ATOM | 8631 | CA | VAL | B | 12 | −37.828 | −27.895 | 29.354 | 1.00 | 52.09 C |
| ATOM | 8633 | CB | VAL | B | 12 | −37.734 | −27.909 | 30.890 | 1.00 | 51.33 C |
| ATOM | 8635 | CG1 | VAL | B | 12 | −36.587 | −28.792 | 31.361 | 1.00 | 55.61 C |
| ATOM | 8639 | CG2 | VAL | B | 12 | −37.589 | −26.499 | 31.417 | 1.00 | 54.73 C |
| ATOM | 8643 | C | VAL | B | 12 | −39.084 | −27.106 | 29.028 | 1.00 | 51.94 C |
| ATOM | 8644 | O | VAL | B | 12 | −39.020 | −25.921 | 28.711 | 1.00 | 54.02 O |
| ATOM | 8646 | N | LYS | B | 13 | −40.228 | −27.764 | 29.135 | 1.00 | 51.40 N |
| ATOM | 8647 | CA | LYS | B | 13 | −41.496 | −27.076 | 29.018 | 1.00 | 51.60 C |
| ATOM | 8649 | CB | LYS | B | 13 | −42.591 | −28.079 | 28.666 | 1.00 | 52.55 C |
| ATOM | 8652 | CG | LYS | B | 13 | −42.497 | −28.541 | 27.218 | 1.00 | 51.71 C |

-continued

| | | | | | | | | | | |
|---|---|---|---|---|---|---|---|---|---|---|
| ATOM | 8655 | CD | LYS | B | 13 | −43.403 | −29.713 | 26.932 | 1.00 | 53.42 C |
| ATOM | 8658 | CE | LYS | B | 13 | −44.022 | −29.609 | 25.535 | 1.00 | 57.86 C |
| ATOM | 8661 | NZ | LYS | B | 13 | −43.026 | −29.251 | 24.488 | 1.00 | 60.17 N |
| ATOM | 8665 | C | LYS | B | 13 | −41.819 | −26.296 | 30.310 | 1.00 | 51.77 C |
| ATOM | 8666 | O | LYS | B | 13 | −41.368 | −26.677 | 31.404 | 1.00 | 50.24 O |
| ATOM | 8668 | N | PRO | B | 14 | −42.560 | −25.174 | 30.180 | 1.00 | 51.25 N |
| ATOM | 8669 | CA | PRO | B | 14 | −43.053 | −24.450 | 31.345 | 1.00 | 50.84 C |
| ATOM | 8671 | CB | PRO | B | 14 | −43.947 | −23.368 | 30.739 | 1.00 | 50.58 C |
| ATOM | 8674 | CG | PRO | B | 14 | −43.419 | −23.163 | 29.392 | 1.00 | 51.33 C |
| ATOM | 8677 | CD | PRO | B | 14 | −42.959 | −24.509 | 28.930 | 1.00 | 51.92 C |
| ATOM | 8680 | C | PRO | B | 14 | −43.876 | −25.361 | 32.230 | 1.00 | 50.15 C |
| ATOM | 8681 | O | PRO | B | 14 | −44.657 | −26.166 | 31.722 | 1.00 | 48.51 O |
| ATOM | 8682 | N | GLY | B | 15 | −43.680 | −25.245 | 33.539 | 1.00 | 49.84 N |
| ATOM | 8683 | CA | GLY | B | 15 | −44.306 | −26.149 | 34.496 | 1.00 | 50.35 C |
| ATOM | 8686 | C | GLY | B | 15 | −43.468 | −27.389 | 34.719 | 1.00 | 50.13 C |
| ATOM | 8687 | O | GLY | B | 15 | −43.669 | −28.109 | 35.693 | 1.00 | 49.66 O |
| ATOM | 8689 | N | GLY | B | 16 | −42.513 | −27.628 | 33.824 | 1.00 | 51.34 N |
| ATOM | 8690 | CA | GLY | B | 16 | −41.660 | −28.798 | 33.892 | 1.00 | 51.56 C |
| ATOM | 8693 | C | GLY | B | 16 | −40.668 | −28.748 | 35.033 | 1.00 | 51.79 C |
| ATOM | 8694 | O | GLY | B | 16 | −40.675 | −27.832 | 35.860 | 1.00 | 50.14 O |
| ATOM | 8696 | N | SER | B | 17 | −39.800 | −29.749 | 35.056 | 1.00 | 53.70 N |
| ATOM | 8697 | CA | SER | B | 17 | −38.873 | −29.950 | 36.152 | 1.00 | 54.04 C |
| ATOM | 8699 | CB | SER | B | 17 | −39.341 | −31.118 | 37.016 | 1.00 | 53.95 C |
| ATOM | 8702 | OG | SER | B | 17 | −39.022 | −30.879 | 38.371 | 1.00 | 57.07 O |
| ATOM | 8704 | C | SER | B | 17 | −37.479 | −30.228 | 35.628 | 1.00 | 54.29 C |
| ATOM | 8705 | O | SER | B | 17 | −37.301 | −30.568 | 34.457 | 1.00 | 54.05 O |
| ATOM | 8707 | N | LEU | B | 18 | −36.497 | −30.088 | 36.514 | 1.00 | 56.13 N |
| ATOM | 8708 | CA | LEU | B | 18 | −35.094 | −30.239 | 36.147 | 1.00 | 55.96 C |
| ATOM | 8710 | CB | LEU | B | 18 | −34.684 | −29.083 | 35.248 | 1.00 | 55.43 C |
| ATOM | 8713 | CG | LEU | B | 18 | −33.469 | −29.297 | 34.377 | 1.00 | 57.88 C |
| ATOM | 8715 | CD1 | LEU | B | 18 | −33.559 | −30.610 | 33.593 | 1.00 | 62.27 C |
| ATOM | 8719 | CD2 | LEU | B | 18 | −33.357 | −28.112 | 33.446 | 1.00 | 59.37 C |
| ATOM | 8723 | C | LEU | B | 18 | −34.186 | −30.257 | 37.372 | 1.00 | 56.02 C |
| ATOM | 8724 | O | LEU | B | 18 | −34.433 | −29.546 | 38.358 | 1.00 | 56.21 O |
| ATOM | 8726 | N | ARG | B | 19 | −33.131 | −31.061 | 37.310 | 1.00 | 55.91 N |
| ATOM | 8727 | CA | ARG | B | 19 | −32.171 | −31.131 | 38.404 | 1.00 | 56.28 C |
| ATOM | 8729 | CB | ARG | B | 19 | −32.180 | −32.513 | 39.056 | 1.00 | 56.33 C |
| ATOM | 8732 | CG | ARG | B | 19 | −31.287 | −32.611 | 40.286 | 1.00 | 57.91 C |
| ATOM | 8735 | CD | ARG | B | 19 | −31.716 | −33.730 | 41.210 | 1.00 | 60.36 C |
| ATOM | 8738 | NE | ARG | B | 19 | −30.588 | −34.523 | 41.690 | 1.00 | 66.71 N |
| ATOM | 8740 | CZ | ARG | B | 19 | −29.875 | −35.367 | 40.938 | 1.00 | 68.93 C |
| ATOM | 8741 | NH1 | ARG | B | 19 | −30.131 | −35.517 | 39.646 | 1.00 | 71.03 N |
| ATOM | 8744 | NH2 | ARG | B | 19 | −28.880 | −36.060 | 41.474 | 1.00 | 67.69 N |
| ATOM | 8747 | C | ARG | B | 19 | −30.772 | −30.776 | 37.921 | 1.00 | 55.07 C |
| ATOM | 8748 | O | ARG | B | 19 | −30.311 | −31.277 | 36.898 | 1.00 | 55.74 O |
| ATOM | 8750 | N | LEU | B | 20 | −30.124 | −29.880 | 38.659 | 1.00 | 54.38 N |
| ATOM | 8751 | CA | LEU | B | 20 | −28.742 | −29.520 | 38.430 | 1.00 | 55.17 C |
| ATOM | 8753 | CB | LEU | B | 20 | −28.600 | −28.003 | 38.338 | 1.00 | 55.06 C |
| ATOM | 8756 | CG | LEU | B | 20 | −29.485 | −27.251 | 37.349 | 1.00 | 53.99 C |
| ATOM | 8758 | CD1 | LEU | B | 20 | −29.205 | −25.762 | 37.431 | 1.00 | 59.86 C |
| ATOM | 8762 | CD2 | LEU | B | 20 | −29.234 | −27.724 | 35.955 | 1.00 | 57.03 C |
| ATOM | 8766 | C | LEU | B | 20 | −27.898 | −30.045 | 39.589 | 1.00 | 55.45 C |
| ATOM | 8767 | O | LEU | B | 20 | −28.297 | −29.971 | 40.750 | 1.00 | 56.96 O |
| ATOM | 8769 | N | SER | B | 21 | −26.736 | −30.589 | 39.268 | 1.00 | 56.77 N |
| ATOM | 8770 | CA | SER | B | 21 | −25.786 | −31.031 | 40.280 | 1.00 | 57.56 C |
| ATOM | 8772 | CB | SER | B | 21 | −25.630 | −32.559 | 40.261 | 1.00 | 58.44 C |
| ATOM | 8775 | OG | SER | B | 21 | −25.331 | −33.044 | 38.964 | 1.00 | 61.05 O |
| ATOM | 8777 | C | SER | B | 21 | −24.470 | −30.330 | 40.000 | 1.00 | 58.45 C |
| ATOM | 8778 | O | SER | B | 21 | −24.350 | −29.591 | 39.022 | 1.00 | 59.84 O |
| ATOM | 8780 | N | CYS | B | 22 | −23.486 | −30.556 | 40.860 | 1.00 | 59.72 N |
| ATOM | 8781 | CA | CYS | B | 22 | −22.234 | −29.823 | 40.790 | 1.00 | 57.37 C |
| ATOM | 8783 | CB | CYS | B | 22 | −22.471 | −28.404 | 41.314 | 1.00 | 59.22 C |
| ATOM | 8786 | SG | CYS | B | 22 | −21.015 | −27.363 | 41.431 | 1.00 | 66.17 S |
| ATOM | 8788 | C | CYS | B | 22 | −21.172 | −30.549 | 41.606 | 1.00 | 55.34 C |
| ATOM | 8789 | O | CYS | B | 22 | −21.183 | −30.503 | 42.826 | 1.00 | 54.96 O |
| ATOM | 8791 | N | ALA | B | 23 | −20.269 | −31.245 | 40.927 | 1.00 | 54.59 N |
| ATOM | 8792 | CA | ALA | B | 23 | −19.203 | −31.985 | 41.605 | 1.00 | 53.62 C |
| ATOM | 8794 | CB | ALA | B | 23 | −18.717 | −33.133 | 40.725 | 1.00 | 53.08 C |
| ATOM | 8798 | C | ALA | B | 23 | −18.040 | −31.062 | 41.979 | 1.00 | 51.29 C |
| ATOM | 8799 | O | ALA | B | 23 | −17.522 | −30.341 | 41.127 | 1.00 | 49.95 O |
| ATOM | 8801 | N | ALA | B | 24 | −17.637 | −31.099 | 43.249 | 1.00 | 50.12 N |
| ATOM | 8802 | CA | ALA | B | 24 | −16.557 | −30.248 | 43.769 | 1.00 | 51.29 C |
| ATOM | 8804 | CB | ALA | B | 24 | −17.019 | −29.529 | 45.015 | 1.00 | 50.63 C |
| ATOM | 8808 | C | ALA | B | 24 | −15.278 | −31.031 | 44.076 | 1.00 | 51.65 C |
| ATOM | 8809 | O | ALA | B | 24 | −15.298 | −32.250 | 44.275 | 1.00 | 52.72 O |
| ATOM | 8811 | N | SER | B | 25 | −14.161 | −30.322 | 44.125 | 1.00 | 51.28 N |
| ATOM | 8812 | CA | SER | B | 25 | −12.893 | −30.948 | 44.491 | 1.00 | 51.56 C |
| ATOM | 8814 | CB | SER | B | 25 | −12.464 | −31.936 | 43.426 | 1.00 | 51.06 C |
| ATOM | 8817 | OG | SER | B | 25 | −12.485 | −31.294 | 42.169 | 1.00 | 54.28 O |

-continued

| | | | | | | | | | | |
|---|---|---|---|---|---|---|---|---|---|---|
| ATOM | 8819 | C | SER | B | 25 | −11.800 | −29.910 | 44.650 | 1.00 | 51.41 C |
| ATOM | 8820 | O | SER | B | 25 | −11.938 | −28.767 | 44.197 | 1.00 | 50.73 O |
| ATOM | 8822 | N | GLY | B | 26 | −10.710 | −30.327 | 45.284 | 1.00 | 50.89 N |
| ATOM | 8823 | CA | GLY | B | 26 | −9.582 | −29.446 | 45.538 | 1.00 | 51.21 C |
| ATOM | 8826 | C | GLY | B | 26 | −9.792 | −28.487 | 46.696 | 1.00 | 51.63 C |
| ATOM | 8827 | O | GLY | B | 26 | −9.025 | −27.543 | 46.850 | 1.00 | 54.29 O |
| ATOM | 8829 | N | PHE | B | 27 | −10.822 | −28.712 | 47.510 | 1.00 | 51.25 N |
| ATOM | 8830 | CA | PHE | B | 27 | −11.032 | −27.918 | 48.732 | 1.00 | 50.85 C |
| ATOM | 8832 | CB | PHE | B | 27 | −11.564 | −26.505 | 48.420 | 1.00 | 50.94 C |
| ATOM | 8835 | CG | PHE | B | 27 | −12.918 | −26.490 | 47.771 | 1.00 | 49.96 C |
| ATOM | 8836 | CD1 | PHE | B | 27 | −13.042 | −26.584 | 46.395 | 1.00 | 50.30 C |
| ATOM | 8838 | CE1 | PHE | B | 27 | −14.275 | −26.584 | 45.791 | 1.00 | 49.66 C |
| ATOM | 8840 | CZ | PHE | B | 27 | −15.421 | −26.480 | 46.562 | 1.00 | 52.41 C |
| ATOM | 8842 | CE2 | PHE | B | 27 | −15.313 | −26.384 | 47.937 | 1.00 | 52.69 C |
| ATOM | 8844 | CD2 | PHE | B | 27 | −14.062 | −26.386 | 48.534 | 1.00 | 52.95 C |
| ATOM | 8846 | C | PHE | B | 27 | −11.964 | −28.625 | 49.711 | 1.00 | 50.71 C |
| ATOM | 8847 | O | PHE | B | 27 | −12.604 | −29.626 | 49.383 | 1.00 | 49.79 O |
| ATOM | 8849 | N | SER | B | 28 | −12.037 | −28.093 | 50.921 | 1.00 | 51.23 N |
| ATOM | 8850 | CA | SER | B | 28 | −12.810 | −28.732 | 51.963 | 1.00 | 51.26 C |
| ATOM | 8852 | CB | SER | B | 28 | −12.317 | −28.294 | 53.343 | 1.00 | 51.82 C |
| ATOM | 8855 | OG | SER | B | 28 | −12.676 | −29.267 | 54.315 | 1.00 | 56.76 O |
| ATOM | 8857 | C | SER | B | 28 | −14.295 | −28.421 | 51.766 | 1.00 | 51.01 C |
| ATOM | 8858 | O | SER | B | 28 | −14.767 | −27.321 | 52.085 | 1.00 | 50.89 O |
| ATOM | 8860 | N | PHE | B | 29 | −15.020 | −29.401 | 51.232 | 1.00 | 49.80 N |
| ATOM | 8861 | CA | PHE | B | 29 | −16.424 | −29.226 | 50.894 | 1.00 | 50.56 C |
| ATOM | 8863 | CB | PHE | B | 29 | −16.922 | −30.445 | 50.129 | 1.00 | 48.59 C |
| ATOM | 8866 | CG | PHE | B | 29 | −18.296 | −30.281 | 49.564 | 1.00 | 48.64 C |
| ATOM | 8867 | CD1 | PHE | B | 29 | −18.499 | −29.536 | 48.408 | 1.00 | 48.66 C |
| ATOM | 8869 | CE1 | PHE | B | 29 | −19.767 | −29.381 | 47.881 | 1.00 | 45.83 C |
| ATOM | 8871 | CZ | PHE | B | 29 | −20.841 | −29.976 | 48.510 | 1.00 | 48.48 C |
| ATOM | 8873 | CE2 | PHE | B | 29 | −20.644 | −30.732 | 49.657 | 1.00 | 46.72 C |
| ATOM | 8875 | CD2 | PHE | B | 29 | −19.384 | −30.876 | 50.178 | 1.00 | 45.58 C |
| ATOM | 8877 | C | PHE | B | 29 | −17.270 | −29.001 | 52.145 | 1.00 | 50.93 C |
| ATOM | 8878 | O | PHE | B | 29 | −18.035 | −28.036 | 52.227 | 1.00 | 51.03 O |
| ATOM | 8880 | N | SER | B | 30 | −17.111 | −29.896 | 53.113 | 1.00 | 52.75 N |
| ATOM | 8881 | CA | SER | B | 30 | −17.761 | −29.786 | 54.420 | 1.00 | 54.67 C |
| ATOM | 8883 | CB | SER | B | 30 | −17.106 | −30.743 | 55.416 | 1.00 | 54.82 C |
| ATOM | 8886 | OG | SER | B | 30 | −16.120 | −31.537 | 54.777 | 1.00 | 62.14 O |
| ATOM | 8888 | C | SER | B | 30 | −17.679 | −28.375 | 55.009 | 1.00 | 56.32 C |
| ATOM | 8889 | O | SER | B | 30 | −18.636 | −27.918 | 55.635 | 1.00 | 58.67 O |
| ATOM | 8891 | N | ASP | B | 31 | −16.537 | −27.705 | 54.815 | 1.00 | 55.95 N |
| ATOM | 8892 | CA | ASP | B | 31 | −16.261 | −26.399 | 55.437 | 1.00 | 56.09 C |
| ATOM | 8894 | CB | ASP | B | 31 | −14.766 | −26.260 | 55.691 | 1.00 | 55.87 C |
| ATOM | 8897 | CG | ASP | B | 31 | −14.270 | −27.238 | 56.715 | 1.00 | 56.33 C |
| ATOM | 8898 | OD1 | ASP | B | 31 | −14.667 | −27.110 | 57.883 | 1.00 | 60.60 O |
| ATOM | 8899 | OD2 | ASP | B | 31 | −13.483 | −28.136 | 56.368 | 1.00 | 57.54 O |
| ATOM | 8900 | C | ASP | B | 31 | −16.752 | −25.194 | 54.629 | 1.00 | 56.83 C |
| ATOM | 8901 | O | ASP | B | 31 | −16.520 | −24.037 | 55.019 | 1.00 | 54.50 O |
| ATOM | 8903 | N | CYS | B | 32 | −17.449 | −25.471 | 53.527 | 1.00 | 56.79 N |
| ATOM | 8904 | CA | CYS | B | 32 | −17.879 | −24.441 | 52.606 | 1.00 | 57.15 C |
| ATOM | 8906 | CB | CYS | B | 32 | −17.375 | −24.770 | 51.212 | 1.00 | 56.78 C |
| ATOM | 8909 | SG | CYS | B | 32 | −15.670 | −24.337 | 51.018 | 1.00 | 62.87 S |
| ATOM | 8911 | C | CYS | B | 32 | −19.379 | −24.302 | 52.558 | 1.00 | 57.47 C |
| ATOM | 8912 | O | CYS | B | 32 | −20.100 | −25.295 | 52.661 | 1.00 | 57.32 O |
| ATOM | 8914 | N | ARG | B | 33 | −19.837 | −23.059 | 52.419 | 1.00 | 58.33 N |
| ATOM | 8915 | CA | ARG | B | 33 | −21.210 | −22.776 | 52.020 | 1.00 | 59.05 C |
| ATOM | 8917 | CB | ARG | B | 33 | −21.611 | −21.320 | 52.318 | 1.00 | 59.99 C |
| ATOM | 8920 | CG | ARG | B | 33 | −21.955 | −21.018 | 53.781 | 1.00 | 61.46 C |
| ATOM | 8923 | CD | ARG | B | 33 | −22.959 | −19.840 | 53.914 | 1.00 | 63.66 C |
| ATOM | 8926 | NE | ARG | B | 33 | −23.243 | −19.502 | 55.316 | 1.00 | 65.64 N |
| ATOM | 8928 | CZ | ARG | B | 33 | −22.510 | −18.677 | 56.073 | 1.00 | 66.84 C |
| ATOM | 8929 | NH1 | ARG | B | 33 | −21.434 | −18.058 | 55.592 | 1.00 | 70.69 N |
| ATOM | 8932 | NH2 | ARG | B | 33 | −22.854 | −18.466 | 57.332 | 1.00 | 66.86 N |
| ATOM | 8935 | C | ARG | B | 33 | −21.235 | −23.015 | 50.529 | 1.00 | 58.50 C |
| ATOM | 8936 | O | ARG | B | 33 | −20.234 | −22.734 | 49.853 | 1.00 | 59.17 O |
| ATOM | 8938 | N | MET | B | 34 | −22.349 | −23.554 | 50.023 | 1.00 | 57.59 N |
| ATOM | 8939 | CA | MET | B | 34 | −22.551 | −23.730 | 48.575 | 1.00 | 57.08 C |
| ATOM | 8941 | CB | MET | B | 34 | −22.892 | −25.185 | 48.246 | 1.00 | 56.43 C |
| ATOM | 8944 | CG | MET | B | 34 | −21.795 | −26.188 | 48.589 | 1.00 | 59.03 C |
| ATOM | 8947 | SD | MET | B | 34 | −20.187 | −25.877 | 47.796 | 1.00 | 55.54 S |
| ATOM | 8948 | CE | MET | B | 34 | −20.597 | −26.020 | 46.063 | 1.00 | 58.54 C |
| ATOM | 8952 | C | MET | B | 34 | −23.667 | −22.804 | 48.108 | 1.00 | 56.49 C |
| ATOM | 8953 | O | MET | B | 34 | −24.628 | −22.581 | 48.850 | 1.00 | 57.23 O |
| ATOM | 8955 | N | TYR | B | 35 | −23.535 | −22.266 | 46.892 | 1.00 | 55.09 N |
| ATOM | 8956 | CA | TYR | B | 35 | −24.489 | −21.283 | 46.355 | 1.00 | 55.50 C |
| ATOM | 8958 | CB | TYR | B | 35 | −23.839 | −19.904 | 46.252 | 1.00 | 56.01 C |
| ATOM | 8961 | CG | TYR | B | 35 | −23.056 | −19.483 | 47.468 | 1.00 | 56.77 C |
| ATOM | 8962 | CD1 | TYR | B | 35 | −23.701 | −18.927 | 48.564 | 1.00 | 55.10 C |
| ATOM | 8964 | CE1 | TYR | B | 35 | −23.006 | −18.536 | 49.686 | 1.00 | 52.25 C |

-continued

| ATOM | 8966 | CZ | TYR | B | 35 | −21.652 | −18.685 | 49.719 | 1.00 | 54.90 | C |
| ATOM | 8967 | OH | TYR | B | 35 | −20.987 | −18.280 | 50.842 | 1.00 | 57.35 | O |
| ATOM | 8969 | CE2 | TYR | B | 35 | −20.972 | −19.232 | 48.642 | 1.00 | 57.56 | C |
| ATOM | 8971 | CD2 | TYR | B | 35 | −21.678 | −19.629 | 47.522 | 1.00 | 55.05 | C |
| ATOM | 8973 | C | TYR | B | 35 | −24.941 | −21.656 | 44.964 | 1.00 | 54.79 | C |
| ATOM | 8974 | O | TYR | B | 35 | −24.202 | −22.305 | 44.248 | 1.00 | 56.20 | O |
| ATOM | 8976 | N | TRP | B | 36 | −26.141 | −21.232 | 44.574 | 1.00 | 54.86 | N |
| ATOM | 8977 | CA | TRP | B | 36 | −26.541 | −21.236 | 43.160 | 1.00 | 54.98 | C |
| ATOM | 8979 | CB | TRP | B | 36 | −27.751 | −22.131 | 42.898 | 1.00 | 54.48 | C |
| ATOM | 8982 | CG | TRP | B | 36 | −27.408 | −23.582 | 42.976 | 1.00 | 55.86 | C |
| ATOM | 8983 | CD1 | TRP | B | 36 | −27.541 | −24.395 | 44.064 | 1.00 | 54.37 | C |
| ATOM | 8985 | NE1 | TRP | B | 36 | −27.105 | −25.662 | 43.761 | 1.00 | 56.03 | N |
| ATOM | 8987 | CE2 | TRP | B | 36 | −26.673 | −25.689 | 42.460 | 1.00 | 57.33 | C |
| ATOM | 8988 | CD2 | TRP | B | 36 | −26.846 | −24.396 | 41.932 | 1.00 | 56.78 | C |
| ATOM | 8989 | CE3 | TRP | B | 36 | −26.486 | −24.158 | 40.599 | 1.00 | 56.68 | C |
| ATOM | 8991 | CZ3 | TRP | B | 36 | −25.970 | −25.208 | 39.843 | 1.00 | 54.32 | C |
| ATOM | 8993 | CH2 | TRP | B | 36 | −25.807 | −26.481 | 40.398 | 1.00 | 55.83 | C |
| ATOM | 8995 | CZ2 | TRP | B | 36 | −26.155 | −26.744 | 41.700 | 1.00 | 57.22 | C |
| ATOM | 8997 | C | TRP | B | 36 | −26.827 | −19.806 | 42.714 | 1.00 | 55.54 | C |
| ATOM | 8998 | O | TRP | B | 36 | −27.441 | −19.026 | 43.441 | 1.00 | 55.81 | O |
| ATOM | 9000 | N | LEU | B | 37 | −26.344 | −19.464 | 41.523 | 1.00 | 55.47 | N |
| ATOM | 9001 | CA | LEU | B | 37 | −26.583 | −18.159 | 40.935 | 1.00 | 54.90 | C |
| ATOM | 9003 | CB | LEU | B | 37 | −25.330 | −17.290 | 41.024 | 1.00 | 55.21 | C |
| ATOM | 9006 | CG | LEU | B | 37 | −24.711 | −17.145 | 42.408 | 1.00 | 54.85 | C |
| ATOM | 9008 | CD1 | LEU | B | 37 | −23.591 | −18.143 | 42.567 | 1.00 | 54.81 | C |
| ATOM | 9012 | CD2 | LEU | B | 37 | −24.186 | −15.745 | 42.607 | 1.00 | 55.66 | C |
| ATOM | 9016 | C | LEU | B | 37 | −26.967 | −18.341 | 39.484 | 1.00 | 53.45 | C |
| ATOM | 9017 | O | LEU | B | 37 | −26.745 | −19.405 | 38.912 | 1.00 | 53.70 | O |
| ATOM | 9019 | N | ARG | B | 38 | −27.539 | −17.308 | 38.884 | 1.00 | 51.89 | N |
| ATOM | 9020 | CA | ARG | B | 38 | −27.839 | −17.386 | 37.474 | 1.00 | 53.70 | C |
| ATOM | 9022 | CB | ARG | B | 38 | −29.251 | −17.929 | 37.253 | 1.00 | 54.93 | C |
| ATOM | 9025 | CG | ARG | B | 38 | −30.344 | −16.976 | 37.662 | 1.00 | 54.15 | C |
| ATOM | 9028 | CD | ARG | B | 38 | −31.695 | −17.639 | 37.583 | 1.00 | 52.86 | C |
| ATOM | 9031 | NE | ARG | B | 38 | −32.709 | −16.776 | 38.171 | 1.00 | 55.65 | N |
| ATOM | 9033 | CZ | ARG | B | 38 | −34.008 | −17.040 | 38.179 | 1.00 | 52.73 | C |
| ATOM | 9034 | NH1 | ARG | B | 38 | −34.467 | −18.163 | 37.654 | 1.00 | 56.57 | N |
| ATOM | 9037 | NH2 | ARG | B | 38 | −34.845 | −16.184 | 38.737 | 1.00 | 50.56 | N |
| ATOM | 9040 | C | ARG | B | 38 | −27.664 | −16.056 | 36.769 | 1.00 | 53.95 | C |
| ATOM | 9041 | O | ARG | B | 38 | −27.407 | −15.024 | 37.404 | 1.00 | 52.49 | O |
| ATOM | 9043 | N | GLN | B | 39 | −27.805 | −16.115 | 35.444 | 1.00 | 53.23 | N |
| ATOM | 9044 | CA | GLN | B | 39 | −27.607 | −14.973 | 34.570 | 1.00 | 53.43 | C |
| ATOM | 9046 | CB | GLN | B | 39 | −26.111 | −14.763 | 34.335 | 1.00 | 52.16 | C |
| ATOM | 9049 | CG | GLN | B | 39 | −25.794 | −13.536 | 33.524 | 1.00 | 51.85 | C |
| ATOM | 9052 | CD | GLN | B | 39 | −24.324 | −13.418 | 33.196 | 1.00 | 52.08 | C |
| ATOM | 9053 | OE1 | GLN | B | 39 | −23.727 | −14.341 | 32.626 | 1.00 | 50.41 | O |
| ATOM | 9054 | NE2 | GLN | B | 39 | −23.729 | −12.271 | 33.539 | 1.00 | 40.20 | N |
| ATOM | 9057 | C | GLN | B | 39 | −28.349 | −15.181 | 33.237 | 1.00 | 52.91 | C |
| ATOM | 9058 | O | GLN | B | 39 | −27.919 | −15.955 | 32.384 | 1.00 | 50.90 | O |
| ATOM | 9060 | N | ALA | B | 40 | −29.467 | −14.479 | 33.081 | 1.00 | 53.76 | N |
| ATOM | 9061 | CA | ALA | B | 40 | −30.296 | −14.578 | 31.886 | 1.00 | 53.31 | C |
| ATOM | 9063 | CB | ALA | B | 40 | −31.648 | −13.975 | 32.141 | 1.00 | 54.55 | C |
| ATOM | 9067 | C | ALA | B | 40 | −29.624 | −13.845 | 30.748 | 1.00 | 53.53 | C |
| ATOM | 9068 | O | ALA | B | 40 | −28.959 | −12.840 | 30.987 | 1.00 | 54.11 | O |
| ATOM | 9070 | N | PRO | B | 41 | −29.840 | −14.308 | 29.501 | 1.00 | 53.44 | N |
| ATOM | 9071 | CA | PRO | B | 41 | −29.039 | −13.847 | 28.366 | 1.00 | 53.05 | C |
| ATOM | 9073 | CB | PRO | B | 41 | −29.725 | −14.505 | 27.163 | 1.00 | 52.72 | C |
| ATOM | 9076 | CG | PRO | B | 41 | −30.438 | −15.665 | 27.719 | 1.00 | 52.85 | C |
| ATOM | 9079 | CD | PRO | B | 41 | −30.885 | −15.257 | 29.074 | 1.00 | 52.51 | C |
| ATOM | 9082 | C | PRO | B | 41 | −29.014 | −12.324 | 28.215 | 1.00 | 52.17 | C |
| ATOM | 9083 | O | PRO | B | 41 | −30.066 | −11.689 | 28.111 | 1.00 | 50.43 | O |
| ATOM | 9084 | N | GLY | B | 42 | −27.810 | −11.758 | 28.234 | 1.00 | 52.35 | N |
| ATOM | 9085 | CA | GLY | B | 42 | −27.619 | −10.316 | 28.112 | 1.00 | 53.15 | C |
| ATOM | 9088 | C | GLY | B | 42 | −27.682 | −9.540 | 29.420 | 1.00 | 54.04 | C |
| ATOM | 9089 | O | GLY | B | 42 | −27.270 | −8.384 | 29.467 | 1.00 | 55.99 | O |
| ATOM | 9091 | N | LYS | B | 43 | −28.191 | −10.159 | 30.482 | 1.00 | 53.44 | N |
| ATOM | 9092 | CA | LYS | B | 43 | −28.391 | −9.473 | 31.752 | 1.00 | 53.87 | C |
| ATOM | 9094 | CB | LYS | B | 43 | −29.770 | −9.812 | 32.310 | 1.00 | 55.93 | C |
| ATOM | 9097 | CG | LYS | B | 43 | −30.905 | −9.683 | 31.306 | 1.00 | 57.94 | C |
| ATOM | 9100 | CD | LYS | B | 43 | −30.919 | −8.333 | 30.608 | 1.00 | 60.93 | C |
| ATOM | 9103 | CE | LYS | B | 43 | −32.143 | −8.187 | 29.724 | 1.00 | 61.33 | C |
| ATOM | 9106 | NZ | LYS | B | 43 | −32.168 | −9.225 | 28.660 | 1.00 | 63.96 | N |
| ATOM | 9110 | C | LYS | B | 43 | −27.309 | −9.851 | 32.762 | 1.00 | 53.65 | C |
| ATOM | 9111 | O | LYS | B | 43 | −26.430 | −10.645 | 32.462 | 1.00 | 54.42 | O |
| ATOM | 9113 | N | GLY | B | 44 | −27.380 | −9.276 | 33.958 | 1.00 | 52.36 | N |
| ATOM | 9114 | CA | GLY | B | 44 | −26.357 | −9.474 | 34.968 | 1.00 | 53.12 | C |
| ATOM | 9117 | C | GLY | B | 44 | −26.629 | −10.664 | 35.861 | 1.00 | 54.61 | C |
| ATOM | 9118 | O | GLY | B | 44 | −27.464 | −11.508 | 35.551 | 1.00 | 57.61 | O |
| ATOM | 9120 | N | LEU | B | 45 | −25.932 | −10.701 | 36.992 | 1.00 | 55.46 | N |
| ATOM | 9121 | CA | LEU | B | 45 | −25.900 | −11.853 | 37.885 | 1.00 | 54.85 | C |

-continued

| ATOM | 9123 | CB | LEU | B | 45 | −24.515 | −11.947 | 38.530 | 1.00 | 54.97 | C |
|---|---|---|---|---|---|---|---|---|---|---|---|
| ATOM | 9126 | CG | LEU | B | 45 | −23.403 | −12.727 | 37.833 | 1.00 | 54.76 | C |
| ATOM | 9128 | CD1 | LEU | B | 45 | −23.460 | −12.538 | 36.350 | 1.00 | 60.04 | C |
| ATOM | 9132 | CD2 | LEU | B | 45 | −22.040 | −12.316 | 38.390 | 1.00 | 55.62 | C |
| ATOM | 9136 | C | LEU | B | 45 | −26.940 | −11.742 | 39.002 | 1.00 | 56.15 | C |
| ATOM | 9137 | O | LEU | B | 45 | −27.078 | −10.691 | 39.634 | 1.00 | 56.57 | O |
| ATOM | 9139 | N | GLU | B | 46 | −27.639 | −12.843 | 39.265 | 1.00 | 55.98 | N |
| ATOM | 9140 | CA | GLU | B | 46 | −28.593 | −12.919 | 40.362 | 1.00 | 55.75 | C |
| ATOM | 9142 | CB | GLU | B | 46 | −30.002 | −13.171 | 39.810 | 1.00 | 55.04 | C |
| ATOM | 9145 | CG | GLU | B | 46 | −31.140 | −13.062 | 40.842 | 1.00 | 56.99 | C |
| ATOM | 9148 | CD | GLU | B | 46 | −32.483 | −13.590 | 40.324 | 1.00 | 59.02 | C |
| ATOM | 9149 | OE1 | GLU | B | 46 | −32.580 | −13.917 | 39.121 | 1.00 | 62.34 | O |
| ATOM | 9150 | OE2 | GLU | B | 46 | −33.442 | −13.671 | 41.119 | 1.00 | 60.17 | O |
| ATOM | 9151 | C | GLU | B | 46 | −28.184 | −14.059 | 41.300 | 1.00 | 56.63 | C |
| ATOM | 9152 | O | GLU | B | 46 | −27.946 | −15.190 | 40.848 | 1.00 | 58.14 | O |
| ATOM | 9154 | N | TRP | B | 47 | −28.087 | −13.759 | 42.597 | 1.00 | 54.97 | N |
| ATOM | 9155 | CA | TRP | B | 47 | −27.993 | −14.812 | 43.608 | 1.00 | 54.73 | C |
| ATOM | 9157 | CB | TRP | B | 47 | −27.452 | −14.298 | 44.947 | 1.00 | 53.01 | C |
| ATOM | 9160 | CG | TRP | B | 47 | −27.611 | −15.321 | 45.990 | 1.00 | 51.23 | C |
| ATOM | 9161 | CD1 | TRP | B | 47 | −26.851 | −16.446 | 46.163 | 1.00 | 51.35 | C |
| ATOM | 9163 | NE1 | TRP | B | 47 | −27.335 | −17.187 | 47.215 | 1.00 | 49.44 | N |
| ATOM | 9165 | CE2 | TRP | B | 47 | −28.437 | −16.552 | 47.725 | 1.00 | 51.97 | C |
| ATOM | 9166 | CD2 | TRP | B | 47 | −28.643 | −15.378 | 46.966 | 1.00 | 51.78 | C |
| ATOM | 9167 | CE3 | TRP | B | 47 | −29.723 | −14.550 | 47.281 | 1.00 | 51.58 | C |
| ATOM | 9169 | CZ3 | TRP | B | 47 | −30.555 | −14.915 | 48.320 | 1.00 | 51.38 | C |
| ATOM | 9171 | CH2 | TRP | B | 47 | −30.325 | −16.083 | 49.059 | 1.00 | 49.92 | C |
| ATOM | 9173 | CZ2 | TRP | B | 47 | −29.276 | −16.914 | 48.775 | 1.00 | 52.11 | C |
| ATOM | 9175 | C | TRP | B | 47 | −29.385 | −15.390 | 43.827 | 1.00 | 54.17 | C |
| ATOM | 9176 | O | TRP | B | 47 | −30.326 | −14.628 | 44.030 | 1.00 | 55.25 | O |
| ATOM | 9178 | N | ILE | B | 48 | −29.504 | −16.722 | 43.811 | 1.00 | 54.39 | N |
| ATOM | 9179 | CA | ILE | B | 48 | −30.800 | −17.393 | 43.988 | 1.00 | 53.47 | C |
| ATOM | 9181 | CB | ILE | B | 48 | −31.279 | −18.055 | 42.681 | 1.00 | 52.77 | C |
| ATOM | 9183 | CG1 | ILE | B | 48 | −30.381 | −19.235 | 42.295 | 1.00 | 53.12 | C |
| ATOM | 9186 | CD1 | ILE | B | 48 | −30.981 | −20.127 | 41.226 | 1.00 | 54.34 | C |
| ATOM | 9190 | CG2 | ILE | B | 48 | −31.332 | −17.013 | 41.570 | 1.00 | 53.53 | C |
| ATOM | 9194 | C | ILE | B | 48 | −30.891 | −18.423 | 45.111 | 1.00 | 52.30 | C |
| ATOM | 9195 | O | ILE | B | 48 | −31.997 | −18.798 | 45.507 | 1.00 | 53.16 | O |
| ATOM | 9197 | N | GLY | B | 49 | −29.768 | −18.895 | 45.633 | 1.00 | 52.45 | N |
| ATOM | 9198 | CA | GLY | B | 49 | −29.852 | −19.812 | 46.763 | 1.00 | 53.11 | C |
| ATOM | 9201 | C | GLY | B | 49 | −28.557 | −20.165 | 47.446 | 1.00 | 52.97 | C |
| ATOM | 9202 | O | GLY | B | 49 | −27.521 | −20.253 | 46.802 | 1.00 | 54.06 | O |
| ATOM | 9204 | N | VAL | B | 50 | −28.632 | −20.403 | 48.754 | 1.00 | 53.18 | N |
| ATOM | 9205 | CA | VAL | B | 50 | −27.471 | −20.855 | 49.523 | 1.00 | 53.84 | C |
| ATOM | 9207 | CB | VAL | B | 50 | −26.856 | −19.717 | 50.363 | 1.00 | 53.71 | C |
| ATOM | 9209 | CG1 | VAL | B | 50 | −27.902 | −19.066 | 51.260 | 1.00 | 55.07 | C |
| ATOM | 9213 | CG2 | VAL | B | 50 | −25.682 | −20.236 | 51.203 | 1.00 | 52.34 | C |
| ATOM | 9217 | C | VAL | B | 50 | −27.850 | −21.991 | 50.459 | 1.00 | 55.14 | C |
| ATOM | 9218 | O | VAL | B | 50 | −28.969 | −22.016 | 50.971 | 1.00 | 56.13 | O |
| ATOM | 9220 | N | ILE | B | 51 | −26.908 | −22.919 | 50.666 | 1.00 | 55.41 | N |
| ATOM | 9221 | CA | ILE | B | 51 | −27.008 | −23.967 | 51.695 | 1.00 | 53.53 | C |
| ATOM | 9223 | CB | ILE | B | 51 | −27.197 | −25.352 | 51.072 | 1.00 | 52.94 | C |
| ATOM | 9225 | CG1 | ILE | B | 51 | −27.559 | −26.383 | 52.146 | 1.00 | 53.13 | C |
| ATOM | 9228 | CD1 | ILE | B | 51 | −28.330 | −27.584 | 51.604 | 1.00 | 52.90 | C |
| ATOM | 9232 | CG2 | ILE | B | 51 | −25.949 | −25.784 | 50.309 | 1.00 | 54.26 | C |
| ATOM | 9236 | C | ILE | B | 51 | −25.740 | −23.971 | 52.552 | 1.00 | 54.39 | C |
| ATOM | 9237 | O | ILE | B | 51 | −24.636 | −23.956 | 52.015 | 1.00 | 57.35 | O |
| ATOM | 9239 | N | SER | B | 52 | −25.899 | −24.003 | 53.874 | 1.00 | 53.14 | N |
| ATOM | 9240 | CA | SER | B | 52 | −24.781 | −23.839 | 54.801 | 1.00 | 52.08 | C |
| ATOM | 9242 | CB | SER | B | 52 | −25.221 | −22.962 | 55.975 | 1.00 | 51.15 | C |
| ATOM | 9245 | OG | SER | B | 52 | −24.131 | −22.645 | 56.820 | 1.00 | 50.26 | O |
| ATOM | 9247 | C | SER | B | 52 | −24.247 | −25.192 | 55.305 | 1.00 | 53.46 | C |
| ATOM | 9248 | O | SER | B | 52 | −24.642 | −26.256 | 54.819 | 1.00 | 54.16 | O |
| ATOM | 9250 | N | VAL | B | 53 | −23.357 | −25.135 | 56.293 | 1.00 | 52.86 | N |
| ATOM | 9251 | CA | VAL | B | 53 | −22.594 | −26.295 | 56.742 | 1.00 | 52.66 | C |
| ATOM | 9253 | CB | VAL | B | 53 | −21.214 | −25.846 | 57.268 | 1.00 | 53.38 | C |
| ATOM | 9255 | CG1 | VAL | B | 53 | −21.344 | −24.855 | 58.444 | 1.00 | 54.96 | C |
| ATOM | 9259 | CG2 | VAL | B | 53 | −20.422 | −25.216 | 56.139 | 1.00 | 51.78 | C |
| ATOM | 9263 | C | VAL | B | 53 | −23.343 | −27.137 | 57.783 | 1.00 | 54.05 | C |
| ATOM | 9264 | O | VAL | B | 53 | −24.492 | −26.853 | 58.105 | 1.00 | 54.07 | O |
| ATOM | 9266 | N | LYS | B | 54 | −22.698 | −28.186 | 58.288 | 1.00 | 54.87 | N |
| ATOM | 9267 | CA | LYS | B | 54 | −23.329 | −29.084 | 59.262 | 1.00 | 54.71 | C |
| ATOM | 9269 | CB | LYS | B | 54 | −22.444 | −30.307 | 59.510 | 1.00 | 54.04 | C |
| ATOM | 9272 | CG | LYS | B | 54 | −23.055 | −31.376 | 60.395 | 1.00 | 55.17 | C |
| ATOM | 9275 | CD | LYS | B | 54 | −21.987 | −32.332 | 60.885 | 1.00 | 56.41 | C |
| ATOM | 9278 | CE | LYS | B | 54 | −22.578 | −33.563 | 61.554 | 1.00 | 57.98 | C |
| ATOM | 9281 | NZ | LYS | B | 54 | −21.517 | −34.593 | 61.796 | 1.00 | 59.34 | N |
| ATOM | 9285 | C | LYS | B | 54 | −23.595 | −28.385 | 60.587 | 1.00 | 53.88 | C |
| ATOM | 9286 | O | LYS | B | 54 | −24.588 | −28.659 | 61.245 | 1.00 | 53.59 | O |
| ATOM | 9288 | N | SER | B | 55 | −22.699 | −27.490 | 60.978 | 1.00 | 55.35 | N |

-continued

| | | | | | | | | | | |
|---|---|---|---|---|---|---|---|---|---|---|
| ATOM | 9289 | CA | SER | B | 55 | −22.815 | −26.779 | 62.255 | 1.00 | 56.38 C |
| ATOM | 9291 | CB | SER | B | 55 | −21.518 | −26.019 | 62.561 | 1.00 | 57.30 C |
| ATOM | 9294 | OG | SER | B | 55 | −20.700 | −25.901 | 61.402 | 1.00 | 61.19 O |
| ATOM | 9296 | C | SER | B | 55 | −24.022 | −25.839 | 62.296 | 1.00 | 56.69 C |
| ATOM | 9297 | O | SER | B | 55 | −24.580 | −25.602 | 63.358 | 1.00 | 56.87 O |
| ATOM | 9299 | N | GLU | B | 56 | −24.418 | −25.313 | 61.138 | 1.00 | 57.23 N |
| ATOM | 9300 | CA | GLU | B | 56 | −25.676 | −24.582 | 61.009 | 1.00 | 57.48 C |
| ATOM | 9302 | CB | GLU | B | 56 | −25.498 | −23.388 | 60.055 | 1.00 | 57.50 C |
| ATOM | 9305 | CG | GLU | B | 56 | −24.838 | −22.151 | 60.682 | 1.00 | 58.69 C |
| ATOM | 9308 | CD | GLU | B | 56 | −25.187 | −20.859 | 59.924 | 1.00 | 61.99 C |
| ATOM | 9309 | OE1 | GLU | B | 56 | −25.070 | −20.837 | 58.682 | 1.00 | 60.54 O |
| ATOM | 9310 | OE2 | GLU | B | 56 | −25.583 | −19.863 | 60.566 | 1.00 | 70.96 O |
| ATOM | 9311 | C | GLU | B | 56 | −26.847 | −25.484 | 60.539 | 1.00 | 56.68 C |
| ATOM | 9312 | O | GLU | B | 56 | −27.827 | −24.984 | 59.991 | 1.00 | 56.23 O |
| ATOM | 9314 | N | ASN | B | 57 | −26.754 | −26.797 | 60.769 | 1.00 | 56.37 N |
| ATOM | 9315 | CA | ASN | B | 57 | −27.807 | −27.757 | 60.386 | 1.00 | 56.82 C |
| ATOM | 9317 | CB | ASN | B | 57 | −29.083 | −27.556 | 61.237 | 1.00 | 57.35 C |
| ATOM | 9320 | CG | ASN | B | 57 | −28.819 | −27.574 | 62.739 | 1.00 | 55.98 C |
| ATOM | 9321 | OD1 | ASN | B | 57 | −28.299 | −28.552 | 63.285 | 1.00 | 58.87 O |
| ATOM | 9322 | ND2 | ASN | B | 57 | −29.217 | −26.505 | 63.419 | 1.00 | 49.56 N |
| ATOM | 9325 | C | ASN | B | 57 | −28.190 | −27.711 | 58.891 | 1.00 | 57.60 C |
| ATOM | 9326 | O | ASN | B | 57 | −29.367 | −27.807 | 58.532 | 1.00 | 57.42 O |
| ATOM | 9328 | N | TYR | B | 58 | −27.198 | −27.552 | 58.023 | 1.00 | 57.86 N |
| ATOM | 9329 | CA | TYR | B | 58 | −27.428 | −27.504 | 56.570 | 1.00 | 56.14 C |
| ATOM | 9331 | CB | TYR | B | 58 | −27.682 | −28.910 | 56.038 | 1.00 | 55.95 C |
| ATOM | 9334 | CG | TYR | B | 58 | −26.587 | −29.893 | 56.375 | 1.00 | 55.36 C |
| ATOM | 9335 | CD1 | TYR | B | 58 | −25.282 | −29.670 | 55.960 | 1.00 | 55.28 C |
| ATOM | 9337 | CE1 | TYR | B | 58 | −24.276 | −30.570 | 56.257 | 1.00 | 59.89 C |
| ATOM | 9339 | CZ | TYR | B | 58 | −24.570 | −31.719 | 56.982 | 1.00 | 60.17 C |
| ATOM | 9340 | OH | TYR | B | 58 | −23.574 | −32.620 | 57.288 | 1.00 | 56.52 O |
| ATOM | 9342 | CE2 | TYR | B | 58 | −25.863 | −31.959 | 57.408 | 1.00 | 56.62 C |
| ATOM | 9344 | CD2 | TYR | B | 58 | −26.862 | −31.050 | 57.101 | 1.00 | 55.43 C |
| ATOM | 9346 | C | TYR | B | 58 | −28.573 | −26.568 | 56.175 | 1.00 | 54.78 C |
| ATOM | 9347 | O | TYR | B | 58 | −29.306 | −26.817 | 55.209 | 1.00 | 54.62 O |
| ATOM | 9349 | N | GLY | B | 59 | −28.710 | −25.481 | 56.926 | 1.00 | 54.25 N |
| ATOM | 9350 | CA | GLY | B | 59 | −29.779 | −24.509 | 56.700 | 1.00 | 54.82 C |
| ATOM | 9353 | C | GLY | B | 59 | −29.661 | −23.869 | 55.334 | 1.00 | 53.54 C |
| ATOM | 9354 | O | GLY | B | 59 | −28.552 | −23.694 | 54.836 | 1.00 | 53.40 O |
| ATOM | 9356 | N | ALA | B | 60 | −30.805 | −23.529 | 54.738 | 1.00 | 53.00 N |
| ATOM | 9357 | CA | ALA | B | 60 | −30.864 | −22.996 | 53.373 | 1.00 | 52.32 C |
| ATOM | 9359 | CB | ALA | B | 60 | −31.502 | −24.016 | 52.448 | 1.00 | 51.71 C |
| ATOM | 9363 | C | ALA | B | 60 | −31.644 | −21.693 | 53.320 | 1.00 | 51.58 C |
| ATOM | 9364 | O | ALA | B | 60 | −32.417 | −21.382 | 54.220 | 1.00 | 53.08 O |
| ATOM | 9366 | N | ASN | B | 61 | −31.441 | −20.931 | 52.256 | 1.00 | 51.85 N |
| ATOM | 9367 | CA | ASN | B | 61 | −32.195 | −19.704 | 52.030 | 1.00 | 52.22 C |
| ATOM | 9369 | CB | ASN | B | 61 | −31.624 | −18.552 | 52.873 | 1.00 | 52.98 C |
| ATOM | 9372 | CG | ASN | B | 61 | −32.717 | −17.666 | 53.500 | 1.00 | 55.92 C |
| ATOM | 9373 | OD1 | ASN | B | 61 | −32.621 | −17.260 | 54.658 | 1.00 | 59.75 O |
| ATOM | 9374 | ND2 | ASN | B | 61 | −33.747 | −17.378 | 52.742 | 1.00 | 49.51 N |
| ATOM | 9377 | C | ASN | B | 61 | −32.155 | −19.372 | 50.541 | 1.00 | 53.18 C |
| ATOM | 9378 | O | ASN | B | 61 | −31.187 | −19.708 | 49.846 | 1.00 | 55.85 O |
| ATOM | 9380 | N | TYR | B | 62 | −33.207 | −18.716 | 50.061 | 1.00 | 52.93 N |
| ATOM | 9381 | CA | TYR | B | 62 | −33.451 | −18.542 | 48.634 | 1.00 | 52.14 C |
| ATOM | 9383 | CB | TYR | B | 62 | −34.603 | −19.448 | 48.199 | 1.00 | 50.84 C |
| ATOM | 9386 | CG | TYR | B | 62 | −34.363 | −20.911 | 48.494 | 1.00 | 49.79 C |
| ATOM | 9387 | CD1 | TYR | B | 62 | −34.676 | −21.454 | 49.733 | 1.00 | 42.10 C |
| ATOM | 9389 | CE1 | TYR | B | 62 | −34.444 | −22.775 | 50.009 | 1.00 | 44.59 C |
| ATOM | 9391 | CZ | TYR | B | 62 | −33.892 | −23.591 | 49.034 | 1.00 | 49.21 C |
| ATOM | 9392 | OH | TYR | B | 62 | −33.662 | −24.923 | 49.286 | 1.00 | 49.24 O |
| ATOM | 9394 | CE2 | TYR | B | 62 | −33.571 | −23.078 | 47.798 | 1.00 | 49.63 C |
| ATOM | 9396 | CD2 | TYR | B | 62 | −33.807 | −21.746 | 47.532 | 1.00 | 50.35 C |
| ATOM | 9398 | C | TYR | B | 62 | −33.822 | −17.109 | 48.322 | 1.00 | 52.40 C |
| ATOM | 9399 | O | TYR | B | 62 | −34.206 | −16.347 | 49.199 | 1.00 | 49.96 O |
| ATOM | 9401 | N | ALA | B | 63 | −33.686 | −16.748 | 47.057 | 1.00 | 54.42 N |
| ATOM | 9402 | CA | ALA | B | 63 | −34.194 | −15.482 | 46.568 | 1.00 | 54.68 C |
| ATOM | 9404 | CB | ALA | B | 63 | −33.541 | −15.119 | 45.257 | 1.00 | 54.68 C |
| ATOM | 9408 | C | ALA | B | 63 | −35.682 | −15.669 | 46.382 | 1.00 | 55.78 C |
| ATOM | 9409 | O | ALA | B | 63 | −36.134 | −16.765 | 46.070 | 1.00 | 55.96 O |
| ATOM | 9411 | N | GLU | B | 64 | −36.438 | −14.592 | 46.558 | 1.00 | 57.66 N |
| ATOM | 9412 | CA | GLU | B | 64 | −37.899 | −14.659 | 46.523 | 1.00 | 56.77 C |
| ATOM | 9414 | CB | GLU | B | 64 | −38.514 | −13.367 | 47.084 | 1.00 | 56.49 C |
| ATOM | 9417 | CG | GLU | B | 64 | −38.081 | −12.997 | 48.511 | 1.00 | 54.77 C |
| ATOM | 9420 | CD | GLU | B | 64 | −38.364 | −14.086 | 49.544 | 1.00 | 55.72 C |
| ATOM | 9421 | OE1 | GLU | B | 64 | −39.184 | −15.000 | 49.284 | 1.00 | 55.18 O |
| ATOM | 9422 | OE2 | GLU | B | 64 | −37.742 | −14.046 | 50.627 | 1.00 | 55.25 O |
| ATOM | 9423 | C | GLU | B | 64 | −38.475 | −14.949 | 45.134 | 1.00 | 56.79 C |
| ATOM | 9424 | O | GLU | B | 64 | −39.633 | −15.339 | 45.016 | 1.00 | 59.39 O |
| ATOM | 9426 | N | SER | B | 65 | −37.683 | −14.775 | 44.083 | 1.00 | 56.67 N |
| ATOM | 9427 | CA | SER | B | 65 | −38.166 | −15.095 | 42.740 | 1.00 | 56.33 C |

-continued

| ATOM | 9429 | CB | SER | B | 65 | −37.318 | −14.388 | 41.674 | 1.00 | 55.40 | C |
| ATOM | 9432 | OG | SER | B | 65 | −36.086 | −15.050 | 41.467 | 1.00 | 52.67 | O |
| ATOM | 9434 | C | SER | B | 65 | −38.163 | −16.609 | 42.495 | 1.00 | 56.91 | C |
| ATOM | 9435 | O | SER | B | 65 | −38.684 | −17.078 | 41.489 | 1.00 | 59.57 | O |
| ATOM | 9437 | N | VAL | B | 66 | −37.589 | −17.365 | 43.422 | 1.00 | 55.11 | N |
| ATOM | 9438 | CA | VAL | B | 66 | −37.310 | −18.779 | 43.207 | 1.00 | 53.81 | C |
| ATOM | 9440 | CB | VAL | B | 66 | −35.810 | −18.913 | 42.895 | 1.00 | 54.11 | C |
| ATOM | 9442 | CG1 | VAL | B | 66 | −35.076 | −19.720 | 43.946 | 1.00 | 58.69 | C |
| ATOM | 9446 | CG2 | VAL | B | 66 | −35.591 | −19.450 | 41.503 | 1.00 | 53.52 | C |
| ATOM | 9450 | C | VAL | B | 66 | −37.748 | −19.701 | 44.372 | 1.00 | 52.72 | C |
| ATOM | 9451 | O | VAL | B | 66 | −37.892 | −20.910 | 44.190 | 1.00 | 50.48 | O |
| ATOM | 9453 | N | ARG | B | 67 | −37.973 | −19.117 | 45.549 | 1.00 | 52.58 | N |
| ATOM | 9454 | CA | ARG | B | 67 | −38.397 | −19.840 | 46.755 | 1.00 | 51.78 | C |
| ATOM | 9456 | CB | ARG | B | 67 | −38.478 | −18.861 | 47.935 | 1.00 | 50.98 | C |
| ATOM | 9459 | CG | ARG | B | 67 | −38.942 | −19.441 | 49.267 | 1.00 | 52.10 | C |
| ATOM | 9462 | CD | ARG | B | 67 | −39.295 | −18.353 | 50.288 | 1.00 | 53.07 | C |
| ATOM | 9465 | NE | ARG | B | 67 | −38.205 | −18.050 | 51.211 | 1.00 | 56.20 | N |
| ATOM | 9467 | CZ | ARG | B | 67 | −37.204 | −17.209 | 50.958 | 1.00 | 60.91 | C |
| ATOM | 9468 | NH1 | ARG | B | 67 | −37.121 | −16.579 | 49.798 | 1.00 | 69.43 | N |
| ATOM | 9471 | NH2 | ARG | B | 67 | −36.264 | −16.989 | 51.858 | 1.00 | 54.63 | N |
| ATOM | 9474 | C | ARG | B | 67 | −39.740 | −20.514 | 46.548 | 1.00 | 51.61 | C |
| ATOM | 9475 | O | ARG | B | 67 | −40.662 | −19.918 | 45.994 | 1.00 | 52.70 | O |
| ATOM | 9477 | N | GLY | B | 68 | −39.838 | −21.760 | 46.999 | 1.00 | 52.22 | N |
| ATOM | 9478 | CA | GLY | B | 68 | −41.040 | −22.571 | 46.817 | 1.00 | 51.72 | C |
| ATOM | 9481 | C | GLY | B | 68 | −41.021 | −23.390 | 45.541 | 1.00 | 52.26 | C |
| ATOM | 9482 | O | GLY | B | 68 | −41.893 | −24.240 | 45.340 | 1.00 | 55.36 | O |
| ATOM | 9484 | N | ARG | B | 69 | −40.044 | −23.142 | 44.671 | 1.00 | 51.46 | N |
| ATOM | 9485 | CA | ARG | B | 69 | −39.971 | −23.827 | 43.379 | 1.00 | 52.71 | C |
| ATOM | 9487 | CB | ARG | B | 69 | −40.192 | −22.832 | 42.241 | 1.00 | 53.50 | C |
| ATOM | 9490 | CG | ARG | B | 69 | −41.606 | −22.293 | 42.200 | 1.00 | 51.31 | C |
| ATOM | 9493 | CD | ARG | B | 69 | −41.877 | −21.449 | 40.975 | 1.00 | 52.31 | C |
| ATOM | 9496 | NE | ARG | B | 69 | −40.846 | −20.441 | 40.752 | 1.00 | 55.92 | N |
| ATOM | 9498 | CZ | ARG | B | 69 | −40.002 | −20.412 | 39.721 | 1.00 | 51.70 | C |
| ATOM | 9499 | NH1 | ARG | B | 69 | −40.047 | −21.326 | 38.767 | 1.00 | 49.27 | N |
| ATOM | 9502 | NH2 | ARG | B | 69 | −39.119 | −19.435 | 39.635 | 1.00 | 46.31 | N |
| ATOM | 9505 | C | ARG | B | 69 | −38.648 | −24.533 | 43.186 | 1.00 | 53.27 | C |
| ATOM | 9506 | O | ARG | B | 69 | −38.609 | −25.664 | 42.709 | 1.00 | 55.74 | O |
| ATOM | 9508 | N | PHE | B | 70 | −37.565 | −23.844 | 43.523 | 1.00 | 54.04 | N |
| ATOM | 9509 | CA | PHE | B | 70 | −36.230 | −24.410 | 43.467 | 1.00 | 54.35 | C |
| ATOM | 9511 | CB | PHE | B | 70 | −35.240 | −23.406 | 42.886 | 1.00 | 53.43 | C |
| ATOM | 9514 | CG | PHE | B | 70 | −35.491 | −23.036 | 41.441 | 1.00 | 55.01 | C |
| ATOM | 9515 | CD1 | PHE | B | 70 | −36.716 | −23.262 | 40.817 | 1.00 | 52.51 | C |
| ATOM | 9517 | CE1 | PHE | B | 70 | −36.912 | −22.898 | 39.497 | 1.00 | 52.41 | C |
| ATOM | 9519 | CZ | PHE | B | 70 | −35.905 | −22.289 | 38.788 | 1.00 | 49.52 | C |
| ATOM | 9521 | CE2 | PHE | B | 70 | −34.689 | −22.046 | 39.391 | 1.00 | 53.29 | C |
| ATOM | 9523 | CD2 | PHE | B | 70 | −34.483 | −22.417 | 40.706 | 1.00 | 55.29 | C |
| ATOM | 9525 | C | PHE | B | 70 | −35.798 | −24.759 | 44.883 | 1.00 | 55.98 | C |
| ATOM | 9526 | O | PHE | B | 70 | −36.134 | −24.040 | 45.843 | 1.00 | 57.10 | O |
| ATOM | 9528 | N | THR | B | 71 | −35.046 | −25.856 | 45.004 | 1.00 | 56.70 | N |
| ATOM | 9529 | CA | THR | B | 71 | −34.500 | −26.311 | 46.284 | 1.00 | 56.44 | C |
| ATOM | 9531 | CB | THR | B | 71 | −35.271 | −27.527 | 46.796 | 1.00 | 56.36 | C |
| ATOM | 9533 | OG1 | THR | B | 71 | −36.640 | −27.166 | 47.016 | 1.00 | 57.34 | O |
| ATOM | 9535 | CG2 | THR | B | 71 | −34.660 | −28.047 | 48.098 | 1.00 | 55.70 | C |
| ATOM | 9539 | C | THR | B | 71 | −33.017 | −26.688 | 46.165 | 1.00 | 57.57 | C |
| ATOM | 9540 | O | THR | B | 71 | −32.606 | −27.292 | 45.169 | 1.00 | 56.61 | O |
| ATOM | 9542 | N | ILE | B | 72 | −32.229 | −26.334 | 47.190 | 1.00 | 58.19 | N |
| ATOM | 9543 | CA | ILE | B | 72 | −30.821 | −26.747 | 47.287 | 1.00 | 57.13 | C |
| ATOM | 9545 | CB | ILE | B | 72 | −29.888 | −25.635 | 47.795 | 1.00 | 57.16 | C |
| ATOM | 9547 | CG1 | ILE | B | 72 | −30.201 | −24.315 | 47.142 | 1.00 | 60.50 | C |
| ATOM | 9550 | CD1 | ILE | B | 72 | −29.264 | −23.249 | 47.597 | 1.00 | 62.72 | C |
| ATOM | 9554 | CG2 | ILE | B | 72 | −28.412 | −25.953 | 47.491 | 1.00 | 57.36 | C |
| ATOM | 9558 | C | ILE | B | 72 | −30.679 | −27.864 | 48.289 | 1.00 | 54.97 | C |
| ATOM | 9559 | O | ILE | B | 72 | −31.323 | −27.846 | 49.331 | 1.00 | 55.85 | O |
| ATOM | 9561 | N | SER | B | 73 | −29.812 | −28.820 | 47.973 | 1.00 | 53.85 | N |
| ATOM | 9562 | CA | SER | B | 73 | −29.405 | −29.849 | 48.920 | 1.00 | 53.27 | C |
| ATOM | 9564 | CB | SER | B | 73 | −30.334 | −31.055 | 48.839 | 1.00 | 51.63 | C |
| ATOM | 9567 | OG | SER | B | 73 | −30.422 | −31.532 | 47.506 | 1.00 | 55.19 | O |
| ATOM | 9569 | C | SER | B | 73 | −27.976 | −30.252 | 48.593 | 1.00 | 52.79 | C |
| ATOM | 9570 | O | SER | B | 73 | −27.455 | −29.921 | 47.519 | 1.00 | 52.93 | O |
| ATOM | 9572 | N | ARG | B | 74 | −27.348 | −30.969 | 49.518 | 1.00 | 51.93 | N |
| ATOM | 9573 | CA | ARG | B | 74 | −25.943 | −31.305 | 49.393 | 1.00 | 51.59 | C |
| ATOM | 9575 | CB | ARG | B | 74 | −25.108 | −30.273 | 50.136 | 1.00 | 50.64 | C |
| ATOM | 9578 | CG | ARG | B | 74 | −25.368 | −30.224 | 51.630 | 1.00 | 49.70 | C |
| ATOM | 9581 | CD | ARG | B | 74 | −24.673 | −29.044 | 52.284 | 1.00 | 53.08 | C |
| ATOM | 9584 | NE | ARG | B | 74 | −23.217 | −29.088 | 52.125 | 1.00 | 54.58 | N |
| ATOM | 9586 | CZ | ARG | B | 74 | −22.418 | −28.029 | 52.210 | 1.00 | 57.86 | C |
| ATOM | 9587 | NH1 | ARG | B | 74 | −22.916 | −26.820 | 52.450 | 1.00 | 60.01 | N |
| ATOM | 9590 | NH2 | ARG | B | 74 | −21.109 | −28.176 | 52.039 | 1.00 | 61.08 | N |
| ATOM | 9593 | C | ARG | B | 74 | −25.631 | −32.683 | 49.939 | 1.00 | 52.07 | C |

-continued

| | | | | | | | | | | |
|---|---|---|---|---|---|---|---|---|---|---|
| ATOM | 9594 | O | ARG | B | 74 | −26.329 | −33.202 | 50.810 | 1.00 | 52.51 O |
| ATOM | 9596 | N | ASP | B | 75 | −24.569 | −33.272 | 49.413 | 1.00 | 52.35 N |
| ATOM | 9597 | CA | ASP | B | 75 | −24.046 | −34.514 | 49.934 | 1.00 | 51.94 C |
| ATOM | 9599 | CB | ASP | B | 75 | −24.294 | −35.638 | 48.937 | 1.00 | 50.84 C |
| ATOM | 9602 | CG | ASP | B | 75 | −24.053 | −37.002 | 49.533 | 1.00 | 52.31 C |
| ATOM | 9603 | OD1 | ASP | B | 75 | −23.303 | −37.086 | 50.530 | 1.00 | 50.83 O |
| ATOM | 9604 | OD2 | ASP | B | 75 | −24.621 | −37.987 | 49.008 | 1.00 | 53.27 O |
| ATOM | 9605 | C | ASP | B | 75 | −22.550 | −34.329 | 50.217 | 1.00 | 52.87 C |
| ATOM | 9606 | O | ASP | B | 75 | −21.706 | −34.446 | 49.317 | 1.00 | 52.64 O |
| ATOM | 9608 | N | ASP | B | 76 | −22.226 | −34.028 | 51.472 | 1.00 | 52.56 N |
| ATOM | 9609 | CA | ASP | B | 76 | −20.828 | −33.858 | 51.871 | 1.00 | 52.98 C |
| ATOM | 9611 | CB | ASP | B | 76 | −20.722 | −33.459 | 53.350 | 1.00 | 52.94 C |
| ATOM | 9614 | CG | ASP | B | 76 | −21.218 | −32.046 | 53.622 | 1.00 | 54.99 C |
| ATOM | 9615 | OD1 | ASP | B | 76 | −21.386 | −31.259 | 52.662 | 1.00 | 52.49 O |
| ATOM | 9616 | OD2 | ASP | B | 76 | −21.441 | −31.724 | 54.813 | 1.00 | 56.04 O |
| ATOM | 9617 | C | ASP | B | 76 | −19.979 | −35.114 | 51.600 | 1.00 | 53.20 C |
| ATOM | 9618 | O | ASP | B | 76 | −18.778 | −35.011 | 51.300 | 1.00 | 52.44 O |
| ATOM | 9620 | N | SER | B | 77 | −20.599 | −36.289 | 51.698 | 1.00 | 52.38 N |
| ATOM | 9621 | CA | SER | B | 77 | −19.895 | −37.539 | 51.416 | 1.00 | 52.35 C |
| ATOM | 9623 | CB | SER | B | 77 | −20.690 | −38.740 | 51.919 | 1.00 | 51.38 C |
| ATOM | 9626 | OG | SER | B | 77 | −21.713 | −39.071 | 51.000 | 1.00 | 50.69 O |
| ATOM | 9628 | C | SER | B | 77 | −19.607 | −37.726 | 49.925 | 1.00 | 51.61 C |
| ATOM | 9629 | O | SER | B | 77 | −18.793 | −38.558 | 49.570 | 1.00 | 51.60 O |
| ATOM | 9631 | N | LYS | B | 78 | −20.289 | −36.981 | 49.058 | 1.00 | 52.03 N |
| ATOM | 9632 | CA | LYS | B | 78 | −20.003 | −37.013 | 47.619 | 1.00 | 53.43 C |
| ATOM | 9634 | CB | LYS | B | 78 | −21.240 | −37.511 | 46.848 | 1.00 | 53.95 C |
| ATOM | 9637 | CG | LYS | B | 78 | −21.445 | −39.026 | 46.955 | 1.00 | 57.91 C |
| ATOM | 9640 | CD | LYS | B | 78 | −22.436 | −39.586 | 45.932 | 1.00 | 57.80 C |
| ATOM | 9643 | CE | LYS | B | 78 | −23.887 | −39.403 | 46.376 | 1.00 | 65.44 C |
| ATOM | 9646 | NZ | LYS | B | 78 | −24.870 | −40.098 | 45.483 | 1.00 | 64.81 N |
| ATOM | 9650 | C | LYS | B | 78 | −19.507 | −35.658 | 47.073 | 1.00 | 52.27 C |
| ATOM | 9651 | O | LYS | B | 78 | −19.393 | −35.480 | 45.866 | 1.00 | 49.95 O |
| ATOM | 9653 | N | ASN | B | 79 | −19.187 | −34.724 | 47.971 | 1.00 | 52.77 N |
| ATOM | 9654 | CA | ASN | B | 79 | −18.720 | −33.383 | 47.604 | 1.00 | 52.21 C |
| ATOM | 9656 | CB | ASN | B | 79 | −17.231 | −33.416 | 47.241 | 1.00 | 49.93 C |
| ATOM | 9659 | CG | ASN | B | 79 | −16.335 | −33.377 | 48.464 | 1.00 | 51.60 C |
| ATOM | 9660 | OD1 | ASN | B | 79 | −16.767 | −33.666 | 49.578 | 1.00 | 53.74 O |
| ATOM | 9661 | ND2 | ASN | B | 79 | −15.080 | −33.004 | 48.262 | 1.00 | 54.23 N |
| ATOM | 9664 | C | ASN | B | 79 | −19.550 | −32.739 | 46.494 | 1.00 | 52.81 C |
| ATOM | 9665 | O | ASN | B | 79 | −19.016 | −32.212 | 45.524 | 1.00 | 55.10 O |
| ATOM | 9667 | N | THR | B | 80 | −20.864 | −32.775 | 46.653 | 1.00 | 52.23 N |
| ATOM | 9668 | CA | THR | B | 80 | −21.765 | −32.401 | 45.577 | 1.00 | 51.61 C |
| ATOM | 9670 | CB | THR | B | 80 | −22.325 | −33.657 | 44.898 | 1.00 | 52.29 C |
| ATOM | 9672 | OG1 | THR | B | 80 | −21.240 | −34.462 | 44.422 | 1.00 | 49.01 O |
| ATOM | 9674 | CG2 | THR | B | 80 | −23.238 | −33.292 | 43.736 | 1.00 | 52.69 C |
| ATOM | 9678 | C | THR | B | 80 | −22.926 | −31.575 | 46.101 | 1.00 | 50.80 C |
| ATOM | 9679 | O | THR | B | 80 | −23.485 | −31.884 | 47.151 | 1.00 | 50.17 O |
| ATOM | 9681 | N | VAL | B | 81 | −23.285 | −30.526 | 45.367 | 1.00 | 50.84 N |
| ATOM | 9682 | CA | VAL | B | 81 | −24.454 | −29.720 | 45.712 | 1.00 | 52.11 C |
| ATOM | 9684 | CB | VAL | B | 81 | −24.060 | −28.280 | 46.065 | 1.00 | 51.35 C |
| ATOM | 9686 | CG1 | VAL | B | 81 | −23.434 | −27.559 | 44.864 | 1.00 | 53.00 C |
| ATOM | 9690 | CG2 | VAL | B | 81 | −25.268 | −27.525 | 46.603 | 1.00 | 51.31 C |
| ATOM | 9694 | C | VAL | B | 81 | −25.482 | −29.762 | 44.575 | 1.00 | 52.11 C |
| ATOM | 9695 | O | VAL | B | 81 | −25.107 | −29.781 | 43.406 | 1.00 | 53.31 O |
| ATOM | 9697 | N | TYR | B | 82 | −26.767 | −29.798 | 44.925 | 1.00 | 51.73 N |
| ATOM | 9698 | CA | TYR | B | 82 | −27.840 | −29.960 | 43.930 | 1.00 | 53.05 C |
| ATOM | 9700 | CB | TYR | B | 82 | −28.661 | −31.238 | 44.187 | 1.00 | 51.60 C |
| ATOM | 9703 | CG | TYR | B | 82 | −27.877 | −32.528 | 44.256 | 1.00 | 50.27 C |
| ATOM | 9704 | CD1 | TYR | B | 82 | −27.556 | −33.229 | 43.105 | 1.00 | 49.45 C |
| ATOM | 9706 | CE1 | TYR | B | 82 | −26.841 | −34.430 | 43.164 | 1.00 | 48.96 C |
| ATOM | 9708 | CZ | TYR | B | 82 | −26.456 | −34.942 | 44.390 | 1.00 | 49.17 C |
| ATOM | 9709 | OH | TYR | B | 82 | −25.747 | −36.122 | 44.449 | 1.00 | 51.97 O |
| ATOM | 9711 | CE2 | TYR | B | 82 | −26.773 | −34.266 | 45.552 | 1.00 | 48.85 C |
| ATOM | 9713 | CD2 | TYR | B | 82 | −27.488 | −33.067 | 45.480 | 1.00 | 48.53 C |
| ATOM | 9715 | C | TYR | B | 82 | −28.817 | −28.790 | 43.957 | 1.00 | 53.68 C |
| ATOM | 9716 | O | TYR | B | 82 | −29.086 | −28.230 | 45.025 | 1.00 | 53.44 O |
| ATOM | 9718 | N | LEU | B | 83 | −29.359 | −28.447 | 42.786 | 1.00 | 53.66 N |
| ATOM | 9719 | CA | LEU | B | 83 | −30.510 | −27.540 | 42.687 | 1.00 | 54.91 C |
| ATOM | 9721 | CB | LEU | B | 83 | −30.124 | −26.220 | 42.031 | 1.00 | 55.04 C |
| ATOM | 9724 | CG | LEU | B | 83 | −31.220 | −25.153 | 41.963 | 1.00 | 54.30 C |
| ATOM | 9726 | CD1 | LEU | B | 83 | −31.369 | −24.472 | 43.283 | 1.00 | 56.42 C |
| ATOM | 9730 | CD2 | LEU | B | 83 | −30.880 | −24.129 | 40.903 | 1.00 | 58.69 C |
| ATOM | 9734 | C | LEU | B | 83 | −31.645 | −28.194 | 41.892 | 1.00 | 55.59 C |
| ATOM | 9735 | O | LEU | B | 83 | −31.608 | −28.229 | 40.660 | 1.00 | 54.62 O |
| ATOM | 9737 | N | GLN | B | 84 | −32.639 | −28.713 | 42.617 | 1.00 | 56.31 N |
| ATOM | 9738 | CA | GLN | B | 84 | −33.860 | −29.249 | 42.033 | 1.00 | 55.50 C |
| ATOM | 9740 | CB | GLN | B | 84 | −34.578 | −30.146 | 43.050 | 1.00 | 55.99 C |
| ATOM | 9743 | CG | GLN | B | 84 | −35.857 | −30.834 | 42.548 | 1.00 | 55.42 C |
| ATOM | 9746 | CD | GLN | B | 84 | −35.587 | −31.896 | 41.500 | 1.00 | 56.92 C |

-continued

| | | | | | | | | | | |
|---|---|---|---|---|---|---|---|---|---|---|
| ATOM | 9747 | OE1 | GLN | B | 84 | −34.722 | −32.760 | 41.667 | 1.00 | 55.45 O |
| ATOM | 9748 | NE2 | GLN | B | 84 | −36.332 | −31.834 | 40.409 | 1.00 | 59.02 N |
| ATOM | 9751 | C | GLN | B | 84 | −34.737 | −28.063 | 41.667 | 1.00 | 56.02 C |
| ATOM | 9752 | O | GLN | B | 84 | −35.104 | −27.273 | 42.527 | 1.00 | 55.65 O |
| ATOM | 9754 | N | MET | B | 85 | −35.048 | −27.928 | 40.383 | 1.00 | 57.32 N |
| ATOM | 9755 | CA | MET | B | 85 | −35.857 | −26.819 | 39.892 | 1.00 | 56.07 C |
| ATOM | 9757 | CB | MET | B | 85 | −35.164 | −26.145 | 38.705 | 1.00 | 55.29 C |
| ATOM | 9760 | CG | MET | B | 85 | −33.773 | −25.651 | 39.030 | 1.00 | 54.69 C |
| ATOM | 9763 | SD | MET | B | 85 | −32.923 | −24.798 | 37.686 | 1.00 | 55.74 S |
| ATOM | 9764 | CE | MET | B | 85 | −32.627 | −26.160 | 36.572 | 1.00 | 64.07 C |
| ATOM | 9768 | C | MET | B | 85 | −37.211 | −27.371 | 39.473 | 1.00 | 56.77 C |
| ATOM | 9769 | O | MET | B | 85 | −37.298 | −28.211 | 38.563 | 1.00 | 55.53 O |
| ATOM | 9771 | N | ASN | B | 86 | −38.259 | −26.917 | 40.157 | 1.00 | 55.85 N |
| ATOM | 9772 | CA | ASN | B | 86 | −39.625 | −27.314 | 39.832 | 1.00 | 54.92 C |
| ATOM | 9774 | CB | ASN | B | 86 | −40.265 | −28.020 | 41.020 | 1.00 | 53.97 C |
| ATOM | 9777 | CG | ASN | B | 86 | −39.564 | −29.313 | 41.376 | 1.00 | 55.14 C |
| ATOM | 9778 | OD1 | ASN | B | 86 | −38.758 | −29.837 | 40.602 | 1.00 | 62.05 O |
| ATOM | 9779 | ND2 | ASN | B | 86 | −39.861 | −29.836 | 42.555 | 1.00 | 48.25 N |
| ATOM | 9782 | C | ASN | B | 86 | −40.461 | −26.113 | 39.441 | 1.00 | 55.08 C |
| ATOM | 9783 | O | ASN | B | 86 | −40.068 | −24.977 | 39.703 | 1.00 | 56.57 O |
| ATOM | 9785 | N | SER | B | 87 | −41.603 | −26.378 | 38.804 | 1.00 | 54.35 N |
| ATOM | 9786 | CA | SER | B | 87 | −42.563 | −25.345 | 38.413 | 1.00 | 53.73 C |
| ATOM | 9788 | CB | SER | B | 87 | −43.197 | −24.694 | 39.659 | 1.00 | 53.16 C |
| ATOM | 9791 | OG | SER | B | 87 | −43.769 | −25.650 | 40.542 | 1.00 | 50.56 O |
| ATOM | 9793 | C | SER | B | 87 | −41.890 | −24.287 | 37.537 | 1.00 | 54.03 C |
| ATOM | 9794 | O | SER | B | 87 | −42.020 | −23.087 | 37.776 | 1.00 | 55.01 O |
| ATOM | 9796 | N | LEU | B | 88 | −41.168 | −24.734 | 36.520 | 1.00 | 53.64 N |
| ATOM | 9797 | CA | LEU | B | 88 | −40.330 | −23.823 | 35.749 | 1.00 | 54.98 C |
| ATOM | 9799 | CB | LEU | B | 88 | −39.379 | −24.603 | 34.834 | 1.00 | 55.57 C |
| ATOM | 9802 | CG | LEU | B | 88 | −38.251 | −25.274 | 35.613 | 1.00 | 56.38 C |
| ATOM | 9804 | CD1 | LEU | B | 88 | −37.610 | −26.381 | 34.813 | 1.00 | 57.26 C |
| ATOM | 9808 | CD2 | LEU | B | 88 | −37.213 | −24.236 | 36.068 | 1.00 | 54.65 C |
| ATOM | 9812 | C | LEU | B | 88 | −41.127 | −22.817 | 34.931 | 1.00 | 55.40 C |
| ATOM | 9813 | O | LEU | B | 88 | −41.974 | −23.192 | 34.126 | 1.00 | 57.09 O |
| ATOM | 9815 | N | LYS | B | 89 | −40.844 | −21.538 | 35.161 | 1.00 | 57.08 N |
| ATOM | 9816 | CA | LYS | B | 89 | −41.357 | −20.438 | 34.340 | 1.00 | 56.55 C |
| ATOM | 9818 | CB | LYS | B | 89 | −41.600 | −19.193 | 35.203 | 1.00 | 55.69 C |
| ATOM | 9821 | CG | LYS | B | 89 | −42.761 | −19.321 | 36.163 | 1.00 | 55.59 C |
| ATOM | 9824 | CD | LYS | B | 89 | −42.532 | −18.509 | 37.434 | 1.00 | 58.84 C |
| ATOM | 9827 | CE | LYS | B | 89 | −43.827 | −18.307 | 38.216 | 1.00 | 61.73 C |
| ATOM | 9830 | NZ | LYS | B | 89 | −44.545 | −19.585 | 38.493 | 1.00 | 63.76 N |
| ATOM | 9834 | C | LYS | B | 89 | −40.371 | −20.095 | 33.213 | 1.00 | 56.57 C |
| ATOM | 9835 | O | LYS | B | 89 | −39.182 | −20.443 | 33.266 | 1.00 | 54.37 O |
| ATOM | 9837 | N | THR | B | 90 | −40.891 | −19.402 | 32.203 | 1.00 | 56.99 N |
| ATOM | 9838 | CA | THR | B | 90 | −40.110 | −18.979 | 31.036 | 1.00 | 56.12 C |
| ATOM | 9840 | CB | THR | B | 90 | −41.011 | −18.347 | 29.916 | 1.00 | 55.05 C |
| ATOM | 9842 | OG1 | THR | B | 90 | −40.211 | −17.544 | 29.051 | 1.00 | 59.38 O |
| ATOM | 9844 | CG2 | THR | B | 90 | −42.119 | −17.466 | 30.484 | 1.00 | 56.71 C |
| ATOM | 9848 | C | THR | B | 90 | −38.943 | −18.051 | 31.421 | 1.00 | 55.29 C |
| ATOM | 9849 | O | THR | B | 90 | −37.840 | −18.188 | 30.892 | 1.00 | 54.64 O |
| ATOM | 9851 | N | GLU | B | 91 | −39.167 | −17.140 | 32.364 | 1.00 | 56.38 N |
| ATOM | 9852 | CA | GLU | B | 91 | −38.101 | −16.212 | 32.795 | 1.00 | 57.43 C |
| ATOM | 9854 | CB | GLU | B | 91 | −38.669 | −14.971 | 33.512 | 1.00 | 58.33 C |
| ATOM | 9857 | CG | GLU | B | 91 | −39.371 | −15.239 | 34.842 | 1.00 | 64.12 C |
| ATOM | 9860 | CD | GLU | B | 91 | −40.824 | −15.645 | 34.683 | 1.00 | 70.42 C |
| ATOM | 9861 | OE1 | GLU | B | 91 | −41.286 | −15.821 | 33.523 | 1.00 | 70.14 O |
| ATOM | 9862 | OE2 | GLU | B | 91 | −41.499 | −15.784 | 35.731 | 1.00 | 70.97 O |
| ATOM | 9863 | C | GLU | B | 91 | −36.978 | −16.851 | 33.639 | 1.00 | 56.22 C |
| ATOM | 9864 | O | GLU | B | 91 | −35.985 | −16.202 | 33.926 | 1.00 | 56.66 O |
| ATOM | 9866 | N | ASP | B | 92 | −37.126 | −18.115 | 34.025 | 1.00 | 56.07 N |
| ATOM | 9867 | CA | ASP | B | 92 | −36.012 | −18.861 | 34.611 | 1.00 | 55.37 C |
| ATOM | 9869 | CB | ASP | B | 92 | −36.458 | −20.245 | 35.103 | 1.00 | 56.00 C |
| ATOM | 9872 | CG | ASP | B | 92 | −37.489 | −20.180 | 36.228 | 1.00 | 56.68 C |
| ATOM | 9873 | OD1 | ASP | B | 92 | −37.443 | −19.252 | 37.057 | 1.00 | 54.69 O |
| ATOM | 9874 | OD2 | ASP | B | 92 | −38.343 | −21.080 | 36.291 | 1.00 | 55.56 O |
| ATOM | 9875 | C | ASP | B | 92 | −34.893 | −19.045 | 33.592 | 1.00 | 55.02 C |
| ATOM | 9876 | O | ASP | B | 92 | −33.745 | −19.273 | 33.975 | 1.00 | 56.48 O |
| ATOM | 9878 | N | THR | B | 93 | −35.229 | −18.969 | 32.301 | 1.00 | 53.61 N |
| ATOM | 9879 | CA | THR | B | 93 | −34.240 | −19.095 | 31.230 | 1.00 | 54.02 C |
| ATOM | 9881 | CB | THR | B | 93 | −34.794 | −18.615 | 29.864 | 1.00 | 53.54 C |
| ATOM | 9883 | OG1 | THR | B | 93 | −35.888 | −19.450 | 29.460 | 1.00 | 54.04 O |
| ATOM | 9885 | CG2 | THR | B | 93 | −33.721 | −18.663 | 28.791 | 1.00 | 51.70 C |
| ATOM | 9889 | C | THR | B | 93 | −32.993 | −18.298 | 31.588 | 1.00 | 54.58 C |
| ATOM | 9890 | O | THR | B | 93 | −33.043 | −17.074 | 31.704 | 1.00 | 56.03 O |
| ATOM | 9892 | N | ALA | B | 94 | −31.890 | −19.009 | 31.795 | 1.00 | 54.48 N |
| ATOM | 9893 | CA | ALA | B | 94 | −30.639 | −18.398 | 32.213 | 1.00 | 53.89 C |
| ATOM | 9895 | CB | ALA | B | 94 | −30.812 | −17.734 | 33.549 | 1.00 | 54.78 C |
| ATOM | 9899 | C | ALA | B | 94 | −29.551 | −19.453 | 32.305 | 1.00 | 54.97 C |
| ATOM | 9900 | O | ALA | B | 94 | −29.835 | −20.654 | 32.289 | 1.00 | 57.34 O |

-continued

| | | | | | | | | | | |
|---|---|---|---|---|---|---|---|---|---|---|
| ATOM | 9902 | N | VAL | B | 95 | −28.303 | −19.000 | 32.395 | 1.00 | 54.16 N |
| ATOM | 9903 | CA | VAL | B | 95 | −27.167 | −19.888 | 32.656 | 1.00 | 52.86 C |
| ATOM | 9905 | CB | VAL | B | 95 | −25.848 | −19.336 | 32.055 | 1.00 | 51.41 C |
| ATOM | 9907 | CG1 | VAL | B | 95 | −24.635 | −20.044 | 32.630 | 1.00 | 51.86 C |
| ATOM | 9911 | CG2 | VAL | B | 95 | −25.858 | −19.474 | 30.549 | 1.00 | 49.75 C |
| ATOM | 9915 | C | VAL | B | 95 | −27.054 | −19.984 | 34.163 | 1.00 | 53.07 C |
| ATOM | 9916 | O | VAL | B | 95 | −26.937 | −18.958 | 34.828 | 1.00 | 54.33 O |
| ATOM | 9918 | N | TYR | B | 96 | −27.105 | −21.201 | 34.704 | 1.00 | 53.08 N |
| ATOM | 9919 | CA | TYR | B | 96 | −27.027 | −21.399 | 36.160 | 1.00 | 53.07 C |
| ATOM | 9921 | CB | TYR | B | 96 | −28.024 | −22.463 | 36.605 | 1.00 | 51.09 C |
| ATOM | 9924 | CG | TYR | B | 96 | −29.449 | −21.980 | 36.555 | 1.00 | 49.90 C |
| ATOM | 9925 | CD1 | TYR | B | 96 | −30.114 | −21.836 | 35.344 | 1.00 | 48.90 C |
| ATOM | 9927 | CE1 | TYR | B | 96 | −31.406 | −21.386 | 35.298 | 1.00 | 48.16 C |
| ATOM | 9929 | CZ | TYR | B | 96 | −32.063 | −21.082 | 36.478 | 1.00 | 49.56 C |
| ATOM | 9930 | OH | TYR | B | 96 | −33.364 | −20.634 | 36.452 | 1.00 | 49.14 O |
| ATOM | 9932 | CE2 | TYR | B | 96 | −31.422 | −21.218 | 37.688 | 1.00 | 48.55 C |
| ATOM | 9934 | CD2 | TYR | B | 96 | −30.129 | −21.660 | 37.719 | 1.00 | 49.45 C |
| ATOM | 9936 | C | TYR | B | 96 | −25.605 | −21.786 | 36.573 | 1.00 | 54.19 C |
| ATOM | 9937 | O | TYR | B | 96 | −24.992 | −22.657 | 35.945 | 1.00 | 54.08 O |
| ATOM | 9939 | N | TYR | B | 97 | −25.089 | −21.128 | 37.614 | 1.00 | 53.45 N |
| ATOM | 9940 | CA | TYR | B | 97 | −23.738 | −21.374 | 38.126 | 1.00 | 53.72 C |
| ATOM | 9942 | CB | TYR | B | 97 | −22.932 | −20.071 | 38.162 | 1.00 | 53.06 C |
| ATOM | 9945 | CG | TYR | B | 97 | −22.673 | −19.409 | 36.815 | 1.00 | 52.93 C |
| ATOM | 9946 | CD1 | TYR | B | 97 | −21.601 | −19.805 | 36.006 | 1.00 | 50.63 C |
| ATOM | 9948 | CE1 | TYR | B | 97 | −21.355 | −19.193 | 34.790 | 1.00 | 50.03 C |
| ATOM | 9950 | CZ | TYR | B | 97 | −22.176 | −18.172 | 34.374 | 1.00 | 52.12 C |
| ATOM | 9951 | OH | TYR | B | 97 | −21.957 | −17.551 | 33.176 | 1.00 | 53.65 O |
| ATOM | 9953 | CE2 | TYR | B | 97 | −23.232 | −17.755 | 35.155 | 1.00 | 52.35 C |
| ATOM | 9955 | CD2 | TYR | B | 97 | −23.472 | −18.367 | 36.371 | 1.00 | 51.39 C |
| ATOM | 9957 | C | TYR | B | 97 | −23.824 | −21.899 | 39.549 | 1.00 | 55.05 C |
| ATOM | 9958 | O | TYR | B | 97 | −24.636 | −21.391 | 40.324 | 1.00 | 57.89 O |
| ATOM | 9960 | N | CYS | B | 98 | −23.019 | −22.909 | 39.898 | 1.00 | 54.63 N |
| ATOM | 9961 | CA | CYS | B | 98 | −22.827 | −23.276 | 41.309 | 1.00 | 55.19 C |
| ATOM | 9963 | CB | CYS | B | 98 | −22.713 | −24.790 | 41.528 | 1.00 | 54.48 C |
| ATOM | 9966 | SG | CYS | B | 98 | −21.534 | −25.613 | 40.472 | 1.00 | 68.35 S |
| ATOM | 9968 | C | CYS | B | 98 | −21.579 | −22.571 | 41.798 | 1.00 | 54.49 C |
| ATOM | 9969 | O | CYS | B | 98 | −20.642 | −22.367 | 41.026 | 1.00 | 55.68 O |
| ATOM | 9971 | N | SER | B | 99 | −21.564 | −22.175 | 43.066 | 1.00 | 53.13 N |
| ATOM | 9972 | CA | SER | B | 99 | −20.394 | −21.490 | 43.627 | 1.00 | 53.77 C |
| ATOM | 9974 | CB | SER | B | 99 | −20.594 | −19.965 | 43.597 | 1.00 | 53.95 C |
| ATOM | 9977 | OG | SER | B | 99 | −19.434 | −19.277 | 44.022 | 1.00 | 49.57 O |
| ATOM | 9979 | C | SER | B | 99 | −20.113 | −21.972 | 45.042 | 1.00 | 52.56 C |
| ATOM | 9980 | O | SER | B | 99 | −20.932 | −22.659 | 45.637 | 1.00 | 53.56 O |
| ATOM | 9982 | N | ALA | B | 100 | −18.950 | −21.617 | 45.576 | 1.00 | 52.16 N |
| ATOM | 9983 | CA | ALA | B | 100 | −18.620 | −21.956 | 46.955 | 1.00 | 52.43 C |
| ATOM | 9985 | CB | ALA | B | 100 | −18.032 | −23.345 | 47.004 | 1.00 | 52.84 C |
| ATOM | 9989 | C | ALA | B | 100 | −17.668 | −20.949 | 47.619 | 1.00 | 53.04 C |
| ATOM | 9990 | O | ALA | B | 100 | −16.899 | −20.255 | 46.945 | 1.00 | 52.36 O |
| ATOM | 9992 | N | SER | B | 101 | −17.756 | −20.870 | 48.947 | 1.00 | 53.97 N |
| ATOM | 9993 | CA | SER | B | 101 | −16.791 | −20.137 | 49.786 | 1.00 | 52.83 C |
| ATOM | 9995 | CB | SER | B | 101 | −17.125 | −18.648 | 49.854 | 1.00 | 54.11 C |
| ATOM | 9998 | OG | SER | B | 101 | −18.316 | −18.425 | 50.589 | 1.00 | 46.21 O |
| ATOM | 10000 | C | SER | B | 101 | −16.822 | −20.701 | 51.193 | 1.00 | 52.47 C |
| ATOM | 10001 | O | SER | B | 101 | −17.836 | −21.237 | 51.612 | 1.00 | 53.65 O |
| ATOM | 10003 | N | TYR | B | 102 | −15.730 | −20.544 | 51.932 | 1.00 | 52.80 N |
| ATOM | 10004 | CA | TYR | B | 102 | −15.628 | −21.122 | 53.265 | 1.00 | 51.97 C |
| ATOM | 10006 | CB | TYR | B | 102 | −14.222 | −20.916 | 53.833 | 1.00 | 52.49 C |
| ATOM | 10009 | CG | TYR | B | 102 | −13.183 | −21.826 | 53.220 | 1.00 | 54.73 C |
| ATOM | 10010 | CD1 | TYR | B | 102 | −12.084 | −21.318 | 52.538 | 1.00 | 50.64 C |
| ATOM | 10012 | CE1 | TYR | B | 102 | −11.143 | −22.161 | 51.985 | 1.00 | 52.41 C |
| ATOM | 10014 | CZ | TYR | B | 102 | −11.303 | −23.533 | 52.102 | 1.00 | 53.41 C |
| ATOM | 10015 | OH | TYR | B | 102 | −10.394 | −24.418 | 51.559 | 1.00 | 53.51 O |
| ATOM | 10017 | CE2 | TYR | B | 102 | −12.387 | −24.048 | 52.770 | 1.00 | 53.95 C |
| ATOM | 10019 | CD2 | TYR | B | 102 | −13.313 | −23.205 | 53.320 | 1.00 | 56.68 C |
| ATOM | 10021 | C | TYR | B | 102 | −16.666 | −20.543 | 54.227 | 1.00 | 51.78 C |
| ATOM | 10022 | O | TYR | B | 102 | −16.870 | −19.331 | 54.287 | 1.00 | 50.00 O |
| ATOM | 10024 | N | TYR | B | 103 | −17.332 | −21.415 | 54.978 | 1.00 | 51.38 N |
| ATOM | 10025 | CA | TYR | B | 103 | −18.215 | −20.959 | 56.037 | 1.00 | 52.05 C |
| ATOM | 10027 | CB | TYR | B | 103 | −18.696 | −22.141 | 56.886 | 1.00 | 51.00 C |
| ATOM | 10030 | CG | TYR | B | 103 | −19.436 | −21.711 | 58.120 | 1.00 | 49.10 C |
| ATOM | 10031 | CD1 | TYR | B | 103 | −20.698 | −21.163 | 58.034 | 1.00 | 53.66 C |
| ATOM | 10033 | CE1 | TYR | B | 103 | −21.377 | −20.747 | 59.166 | 1.00 | 49.68 C |
| ATOM | 10035 | CZ | TYR | B | 103 | −20.777 | −20.859 | 60.388 | 1.00 | 46.64 C |
| ATOM | 10036 | OH | TYR | B | 103 | −21.439 | −20.449 | 61.520 | 1.00 | 51.79 O |
| ATOM | 10038 | CE2 | TYR | B | 103 | −19.526 | −21.394 | 60.487 | 1.00 | 50.57 C |
| ATOM | 10040 | CD2 | TYR | B | 103 | −18.863 | −21.815 | 59.358 | 1.00 | 46.30 C |
| ATOM | 10042 | C | TYR | B | 103 | −17.476 | −19.958 | 56.922 | 1.00 | 54.26 C |
| ATOM | 10043 | O | TYR | B | 103 | −16.319 | −20.191 | 57.294 | 1.00 | 58.94 O |
| ATOM | 10045 | N | ARG | B | 104 | −18.133 | −18.846 | 57.244 | 1.00 | 53.89 N |

-continued

| ATOM | 10046 | CA | ARG | B | 104 | −17.620 | −17.890 | 58.233 | 1.00 | 52.36 | C |
| ATOM | 10048 | CB | ARG | B | 104 | −17.416 | −16.517 | 57.591 | 1.00 | 51.34 | C |
| ATOM | 10051 | CG | ARG | B | 104 | −16.383 | −16.520 | 56.488 | 1.00 | 51.26 | C |
| ATOM | 10054 | CD | ARG | B | 104 | −16.401 | −15.220 | 55.742 | 1.00 | 53.11 | C |
| ATOM | 10057 | NE | ARG | B | 104 | −16.093 | −14.115 | 56.633 | 1.00 | 55.60 | N |
| ATOM | 10059 | CZ | ARG | B | 104 | −14.873 | −13.650 | 56.861 | 1.00 | 54.62 | C |
| ATOM | 10060 | NH1 | ARG | B | 104 | −13.831 | −14.178 | 56.247 | 1.00 | 57.54 | N |
| ATOM | 10063 | NH2 | ARG | B | 104 | −14.701 | −12.636 | 57.699 | 1.00 | 57.92 | N |
| ATOM | 10066 | C | ARG | B | 104 | −18.588 | −17.770 | 59.402 | 1.00 | 51.58 | C |
| ATOM | 10067 | O | ARG | B | 104 | −19.765 | −18.069 | 59.270 | 1.00 | 49.33 | O |
| ATOM | 10069 | N | TYR | B | 105 | −18.096 | −17.319 | 60.548 | 1.00 | 53.11 | N |
| ATOM | 10070 | CA | TYR | B | 105 | −18.973 | −17.062 | 61.691 | 1.00 | 53.34 | C |
| ATOM | 10072 | CB | TYR | B | 105 | −18.178 | −16.993 | 62.986 | 1.00 | 54.09 | C |
| ATOM | 10075 | CG | TYR | B | 105 | −17.639 | −18.301 | 63.486 | 1.00 | 53.00 | C |
| ATOM | 10076 | CD1 | TYR | B | 105 | −18.422 | −19.447 | 63.478 | 1.00 | 54.00 | C |
| ATOM | 10078 | CE1 | TYR | B | 105 | −17.937 | −20.631 | 63.962 | 1.00 | 54.01 | C |
| ATOM | 10080 | CZ | TYR | B | 105 | −16.662 | −20.682 | 64.478 | 1.00 | 53.68 | C |
| ATOM | 10081 | OH | TYR | B | 105 | −16.192 | −21.872 | 64.948 | 1.00 | 57.62 | O |
| ATOM | 10083 | CE2 | TYR | B | 105 | −15.863 | −19.560 | 64.514 | 1.00 | 53.46 | C |
| ATOM | 10085 | CD2 | TYR | B | 105 | −16.355 | −18.378 | 64.025 | 1.00 | 55.08 | C |
| ATOM | 10087 | C | TYR | B | 105 | −19.740 | −15.754 | 61.565 | 1.00 | 54.37 | C |
| ATOM | 10088 | O | TYR | B | 105 | −20.695 | −15.543 | 62.306 | 1.00 | 58.57 | O |
| ATOM | 10090 | N | ASP | B | 106 | −19.314 | −14.870 | 60.667 | 1.00 | 52.73 | N |
| ATOM | 10091 | CA | ASP | B | 106 | −19.924 | −13.560 | 60.547 | 1.00 | 52.30 | C |
| ATOM | 10093 | CB | ASP | B | 106 | −18.844 | −12.463 | 60.565 | 1.00 | 53.61 | C |
| ATOM | 10096 | CG | ASP | B | 106 | −18.021 | −12.388 | 59.269 | 1.00 | 54.59 | C |
| ATOM | 10097 | OD1 | ASP | B | 106 | −18.312 | −13.140 | 58.311 | 1.00 | 53.22 | O |
| ATOM | 10098 | OD2 | ASP | B | 106 | −17.074 | −11.568 | 59.222 | 1.00 | 54.25 | O |
| ATOM | 10099 | C | ASP | B | 106 | −20.805 | −13.445 | 59.309 | 1.00 | 54.57 | C |
| ATOM | 10100 | O | ASP | B | 106 | −21.054 | −14.415 | 58.583 | 1.00 | 58.76 | O |
| ATOM | 10102 | N | VAL | B | 107 | −21.248 | −12.225 | 59.061 | 1.00 | 54.02 | N |
| ATOM | 10103 | CA | VAL | B | 107 | −22.125 | −11.899 | 57.947 | 1.00 | 52.17 | C |
| ATOM | 10105 | CB | VAL | B | 107 | −22.685 | −10.488 | 58.246 | 1.00 | 51.49 | C |
| ATOM | 10107 | CG1 | VAL | B | 107 | −23.697 | −10.585 | 59.361 | 1.00 | 52.19 | C |
| ATOM | 10111 | CG2 | VAL | B | 107 | −23.302 | −9.837 | 57.068 | 1.00 | 56.32 | C |
| ATOM | 10115 | C | VAL | B | 107 | −21.441 | −12.024 | 56.547 | 1.00 | 52.08 | C |
| ATOM | 10116 | O | VAL | B | 107 | −22.039 | −11.719 | 55.520 | 1.00 | 50.75 | O |
| ATOM | 10118 | N | GLY | B | 108 | −20.202 | −12.506 | 56.497 | 1.00 | 52.12 | N |
| ATOM | 10119 | CA | GLY | B | 108 | −19.478 | −12.612 | 55.233 | 1.00 | 52.33 | C |
| ATOM | 10122 | C | GLY | B | 108 | −19.911 | −13.769 | 54.345 | 1.00 | 52.52 | C |
| ATOM | 10123 | O | GLY | B | 108 | −19.943 | −14.926 | 54.782 | 1.00 | 54.48 | O |
| ATOM | 10125 | N | ALA | B | 109 | −20.251 | −13.463 | 53.097 | 1.00 | 50.38 | N |
| ATOM | 10126 | CA | ALA | B | 109 | −20.533 | −14.504 | 52.105 | 1.00 | 50.55 | C |
| ATOM | 10128 | CB | ALA | B | 109 | −21.955 | −14.975 | 52.225 | 1.00 | 50.23 | C |
| ATOM | 10132 | C | ALA | B | 109 | −20.251 | −13.999 | 50.686 | 1.00 | 51.08 | C |
| ATOM | 10133 | O | ALA | B | 109 | −20.675 | −12.897 | 50.290 | 1.00 | 51.57 | O |
| ATOM | 10135 | N | TRP | B | 110 | −19.510 | −14.787 | 49.922 | 1.00 | 51.10 | N |
| ATOM | 10136 | CA | TRP | B | 110 | −19.153 | −14.376 | 48.568 | 1.00 | 51.34 | C |
| ATOM | 10138 | CB | TRP | B | 110 | −17.991 | −13.378 | 48.584 | 1.00 | 50.07 | C |
| ATOM | 10141 | CG | TRP | B | 110 | −16.712 | −13.934 | 49.046 | 1.00 | 52.07 | C |
| ATOM | 10142 | CD1 | TRP | B | 110 | −15.805 | −14.622 | 48.297 | 1.00 | 54.76 | C |
| ATOM | 10144 | NE1 | TRP | B | 110 | −14.719 | −14.971 | 49.065 | 1.00 | 54.63 | N |
| ATOM | 10146 | CE2 | TRP | B | 110 | −14.908 | −14.502 | 50.339 | 1.00 | 50.63 | C |
| ATOM | 10147 | CD2 | TRP | B | 110 | −16.156 | −13.839 | 50.364 | 1.00 | 54.61 | C |
| ATOM | 10148 | CE3 | TRP | B | 110 | −16.594 | −13.267 | 51.568 | 1.00 | 55.01 | C |
| ATOM | 10150 | CZ3 | TRP | B | 110 | −15.776 | −13.373 | 52.692 | 1.00 | 55.26 | C |
| ATOM | 10152 | CH2 | TRP | B | 110 | −14.540 | −14.041 | 52.629 | 1.00 | 51.97 | C |
| ATOM | 10154 | CZ2 | TRP | B | 110 | −14.093 | −14.611 | 51.467 | 1.00 | 48.32 | C |
| ATOM | 10156 | C | TRP | B | 110 | −18.875 | −15.608 | 47.720 | 1.00 | 51.67 | C |
| ATOM | 10157 | O | TRP | B | 110 | −19.025 | −16.739 | 48.191 | 1.00 | 54.15 | O |
| ATOM | 10159 | N | PHE | B | 111 | −18.505 | −15.392 | 46.468 | 1.00 | 49.72 | N |
| ATOM | 10160 | CA | PHE | B | 111 | −18.537 | −16.454 | 45.488 | 1.00 | 50.72 | C |
| ATOM | 10162 | CB | PHE | B | 111 | −19.567 | −16.075 | 44.418 | 1.00 | 51.31 | C |
| ATOM | 10165 | CG | PHE | B | 111 | −20.890 | −15.600 | 45.011 | 1.00 | 51.22 | C |
| ATOM | 10166 | CD1 | PHE | B | 111 | −21.367 | −14.316 | 44.770 | 1.00 | 51.31 | C |
| ATOM | 10168 | CE1 | PHE | B | 111 | −22.568 | −13.887 | 45.332 | 1.00 | 53.15 | C |
| ATOM | 10170 | CZ | PHE | B | 111 | −23.300 | −14.742 | 46.165 | 1.00 | 52.64 | C |
| ATOM | 10172 | CE2 | PHE | B | 111 | −22.827 | −16.017 | 46.418 | 1.00 | 51.14 | C |
| ATOM | 10174 | CD2 | PHE | B | 111 | −21.628 | −16.435 | 45.847 | 1.00 | 51.50 | C |
| ATOM | 10176 | C | PHE | B | 111 | −17.127 | −16.718 | 44.953 | 1.00 | 51.07 | C |
| ATOM | 10177 | O | PHE | B | 111 | −16.697 | −16.131 | 43.960 | 1.00 | 49.39 | O |
| ATOM | 10179 | N | ALA | B | 112 | −16.423 | −17.627 | 45.636 | 1.00 | 51.90 | N |
| ATOM | 10180 | CA | ALA | B | 112 | −14.972 | −17.785 | 45.494 | 1.00 | 52.28 | C |
| ATOM | 10182 | CB | ALA | B | 112 | −14.369 | −18.279 | 46.807 | 1.00 | 52.43 | C |
| ATOM | 10186 | C | ALA | B | 112 | −14.562 | −18.706 | 44.349 | 1.00 | 54.01 | C |
| ATOM | 10187 | O | ALA | B | 112 | −13.589 | −18.423 | 43.642 | 1.00 | 54.86 | O |
| ATOM | 10189 | N | TYR | B | 113 | −15.277 | −19.816 | 44.187 | 1.00 | 54.23 | N |
| ATOM | 10190 | CA | TYR | B | 113 | −15.046 | −20.741 | 43.071 | 1.00 | 54.55 | C |
| ATOM | 10192 | CB | TYR | B | 113 | −14.529 | −22.095 | 43.591 | 1.00 | 57.92 | C |

-continued

| | | | | | | | | | | |
|---|---|---|---|---|---|---|---|---|---|---|
| ATOM | 10195 | CG | TYR | B | 113 | −13.599 | −21.915 | 44.769 | 1.00 | 59.49 C |
| ATOM | 10196 | CD1 | TYR | B | 113 | −12.394 | −21.228 | 44.629 | 1.00 | 59.51 C |
| ATOM | 10198 | CE1 | TYR | B | 113 | −11.555 | −21.029 | 45.712 | 1.00 | 59.73 C |
| ATOM | 10200 | CZ | TYR | B | 113 | −11.924 | −21.508 | 46.961 | 1.00 | 62.35 C |
| ATOM | 10201 | OH | TYR | B | 113 | −11.107 | −21.307 | 48.051 | 1.00 | 65.57 O |
| ATOM | 10203 | CE2 | TYR | B | 113 | −13.112 | −22.190 | 47.125 | 1.00 | 61.64 C |
| ATOM | 10205 | CD2 | TYR | B | 113 | −13.947 | −22.383 | 46.033 | 1.00 | 63.21 C |
| ATOM | 10207 | C | TYR | B | 113 | −16.357 | −20.874 | 42.306 | 1.00 | 54.00 C |
| ATOM | 10208 | O | TYR | B | 113 | −17.426 | −20.586 | 42.869 | 1.00 | 54.33 O |
| ATOM | 10210 | N | TRP | B | 114 | −16.283 | −21.260 | 41.029 | 1.00 | 50.42 N |
| ATOM | 10211 | CA | TRP | B | 114 | −17.471 | −21.300 | 40.176 | 1.00 | 51.94 C |
| ATOM | 10213 | CB | TRP | B | 114 | −17.543 | −20.046 | 39.296 | 1.00 | 53.17 C |
| ATOM | 10216 | CG | TRP | B | 114 | −17.786 | −18.763 | 40.023 | 1.00 | 53.22 C |
| ATOM | 10217 | CD1 | TRP | B | 114 | −16.930 | −18.132 | 40.868 | 1.00 | 53.88 C |
| ATOM | 10219 | NE1 | TRP | B | 114 | −17.499 | −16.975 | 41.346 | 1.00 | 57.40 N |
| ATOM | 10221 | CE2 | TRP | B | 114 | −18.742 | −16.826 | 40.791 | 1.00 | 58.34 C |
| ATOM | 10222 | CD2 | TRP | B | 114 | −18.959 | −17.938 | 39.948 | 1.00 | 57.89 C |
| ATOM | 10223 | CE3 | TRP | B | 114 | −20.178 | −18.038 | 39.262 | 1.00 | 56.51 C |
| ATOM | 10225 | CZ3 | TRP | B | 114 | −21.126 | −17.026 | 39.429 | 1.00 | 55.40 C |
| ATOM | 10227 | CH2 | TRP | B | 114 | −20.877 | −15.929 | 40.278 | 1.00 | 54.29 C |
| ATOM | 10229 | CZ2 | TRP | B | 114 | −19.697 | −15.814 | 40.967 | 1.00 | 55.22 C |
| ATOM | 10231 | C | TRP | B | 114 | −17.482 | −22.501 | 39.261 | 1.00 | 51.60 C |
| ATOM | 10232 | O | TRP | B | 114 | −16.434 | −22.951 | 38.831 | 1.00 | 54.50 O |
| ATOM | 10234 | N | GLY | B | 115 | −18.671 | −23.002 | 38.939 | 1.00 | 51.17 N |
| ATOM | 10235 | CA | GLY | B | 115 | −18.827 | −23.991 | 37.874 | 1.00 | 50.06 C |
| ATOM | 10238 | C | GLY | B | 115 | −18.732 | −23.314 | 36.522 | 1.00 | 49.72 C |
| ATOM | 10239 | O | GLY | B | 115 | −18.733 | −22.088 | 36.451 | 1.00 | 50.08 O |
| ATOM | 10241 | N | GLN | B | 116 | −18.657 | −24.103 | 35.450 | 1.00 | 48.81 N |
| ATOM | 10242 | CA | GLN | B | 116 | −18.618 | −23.544 | 34.085 | 1.00 | 48.45 C |
| ATOM | 10244 | CB | GLN | B | 116 | −18.281 | −24.582 | 32.986 | 1.00 | 49.52 C |
| ATOM | 10247 | CG | GLN | B | 116 | −17.847 | −25.990 | 33.413 | 1.00 | 52.27 C |
| ATOM | 10250 | CD | GLN | B | 116 | −19.019 | −26.866 | 33.840 | 1.00 | 53.91 C |
| ATOM | 10251 | OE1 | GLN | B | 116 | −19.926 | −27.143 | 33.054 | 1.00 | 53.87 O |
| ATOM | 10252 | NE2 | GLN | B | 116 | −19.002 | −27.301 | 35.093 | 1.00 | 48.40 N |
| ATOM | 10255 | C | GLN | B | 116 | −19.952 | −22.909 | 33.723 | 1.00 | 46.90 C |
| ATOM | 10256 | O | GLN | B | 116 | −20.043 | −22.171 | 32.740 | 1.00 | 44.48 O |
| ATOM | 10258 | N | GLY | B | 117 | −20.985 | −23.233 | 34.504 | 1.00 | 47.53 N |
| ATOM | 10259 | CA | GLY | B | 117 | −22.349 | −22.806 | 34.230 | 1.00 | 47.80 C |
| ATOM | 10262 | C | GLY | B | 117 | −22.985 | −23.749 | 33.237 | 1.00 | 47.66 C |
| ATOM | 10263 | O | GLY | B | 117 | −22.282 | −24.502 | 32.570 | 1.00 | 49.32 O |
| ATOM | 10265 | N | THR | B | 118 | −24.313 | −23.727 | 33.138 | 1.00 | 48.93 N |
| ATOM | 10266 | CA | THR | B | 118 | −25.018 | −24.482 | 32.085 | 1.00 | 48.76 C |
| ATOM | 10268 | CB | THR | B | 118 | −25.210 | −25.981 | 32.464 | 1.00 | 48.89 C |
| ATOM | 10270 | OG1 | THR | B | 118 | −25.548 | −26.734 | 31.291 | 1.00 | 53.32 O |
| ATOM | 10272 | CG2 | THR | B | 118 | −26.274 | −26.165 | 33.519 | 1.00 | 46.00 C |
| ATOM | 10276 | C | THR | B | 118 | −26.351 | −23.835 | 31.727 | 1.00 | 48.20 C |
| ATOM | 10277 | O | THR | B | 118 | −27.108 | −23.424 | 32.604 | 1.00 | 51.12 O |
| ATOM | 10279 | N | LEU | B | 119 | −26.629 | −23.742 | 30.433 | 1.00 | 48.41 N |
| ATOM | 10280 | CA | LEU | B | 119 | −27.837 | −23.082 | 29.954 | 1.00 | 48.50 C |
| ATOM | 10282 | CB | LEU | B | 119 | −27.752 | −22.797 | 28.450 | 1.00 | 47.16 C |
| ATOM | 10285 | CG | LEU | B | 119 | −28.871 | −21.914 | 27.879 | 1.00 | 48.41 C |
| ATOM | 10287 | CD1 | LEU | B | 119 | −28.763 | −20.489 | 28.376 | 1.00 | 50.05 C |
| ATOM | 10291 | CD2 | LEU | B | 119 | −28.854 | −21.927 | 26.373 | 1.00 | 48.50 C |
| ATOM | 10295 | C | LEU | B | 119 | −29.071 | −23.931 | 30.250 | 1.00 | 49.81 C |
| ATOM | 10296 | O | LEU | B | 119 | −29.124 | −25.120 | 29.897 | 1.00 | 48.20 O |
| ATOM | 10298 | N | VAL | B | 120 | −30.044 | −23.300 | 30.916 | 1.00 | 50.44 N |
| ATOM | 10299 | CA | VAL | B | 120 | −31.374 | −23.871 | 31.149 | 1.00 | 49.07 C |
| ATOM | 10301 | CB | VAL | B | 120 | −31.696 | −23.910 | 32.634 | 1.00 | 48.16 C |
| ATOM | 10303 | CG1 | VAL | B | 120 | −33.125 | −24.369 | 32.865 | 1.00 | 47.73 C |
| ATOM | 10307 | CG2 | VAL | B | 120 | −30.711 | −24.804 | 33.347 | 1.00 | 50.96 C |
| ATOM | 10311 | C | VAL | B | 120 | −32.394 | −22.990 | 30.446 | 1.00 | 48.51 C |
| ATOM | 10312 | O | VAL | B | 120 | −32.524 | −21.814 | 30.774 | 1.00 | 47.70 O |
| ATOM | 10314 | N | THR | B | 121 | −33.109 | −23.568 | 29.485 | 1.00 | 49.00 N |
| ATOM | 10315 | CA | THR | B | 121 | −34.019 | −22.825 | 28.627 | 1.00 | 49.43 C |
| ATOM | 10317 | CB | THR | B | 121 | −33.644 | −22.974 | 27.128 | 1.00 | 50.87 C |
| ATOM | 10319 | OG1 | THR | B | 121 | −32.226 | −22.823 | 26.946 | 1.00 | 54.94 O |
| ATOM | 10321 | CG2 | THR | B | 121 | −34.391 | −21.944 | 26.283 | 1.00 | 50.14 C |
| ATOM | 10325 | C | THR | B | 121 | −35.409 | −23.381 | 28.802 | 1.00 | 49.73 C |
| ATOM | 10326 | O | THR | B | 121 | −35.670 | −24.532 | 28.455 | 1.00 | 49.51 O |
| ATOM | 10328 | N | VAL | B | 122 | −36.306 | −22.560 | 29.335 | 1.00 | 50.80 N |
| ATOM | 10329 | CA | VAL | B | 122 | −37.697 | −22.951 | 29.521 | 1.00 | 49.91 C |
| ATOM | 10331 | CB | VAL | B | 122 | −38.254 | −22.403 | 30.852 | 1.00 | 51.14 C |
| ATOM | 10333 | CG1 | VAL | B | 122 | −39.628 | −23.022 | 31.162 | 1.00 | 53.69 C |
| ATOM | 10337 | CG2 | VAL | B | 122 | −37.264 | −22.651 | 32.004 | 1.00 | 49.84 C |
| ATOM | 10341 | C | VAL | B | 122 | −38.514 | −22.410 | 28.352 | 1.00 | 48.98 C |
| ATOM | 10342 | O | VAL | B | 122 | −38.596 | −21.198 | 28.168 | 1.00 | 48.36 O |
| ATOM | 10344 | N | SER | B | 123 | −39.097 | −23.311 | 27.562 | 1.00 | 49.19 N |
| ATOM | 10345 | CA | SER | B | 123 | −39.938 | −22.948 | 26.404 | 1.00 | 49.47 C |
| ATOM | 10347 | CB | SER | B | 123 | −39.063 | −22.518 | 25.225 | 1.00 | 50.02 C |

-continued

| | | | | | | | | | | |
|---|---|---|---|---|---|---|---|---|---|---|
| ATOM | 10350 | OG | SER | B | 123 | −39.798 | −22.400 | 24.021 | 1.00 | 47.49 O |
| ATOM | 10352 | C | SER | B | 123 | −40.804 | −24.120 | 25.974 | 1.00 | 49.56 C |
| ATOM | 10353 | O | SER | B | 123 | −40.503 | −25.268 | 26.290 | 1.00 | 49.63 O |
| ATOM | 10355 | N | SER | B | 124 | −41.881 | −23.832 | 25.252 | 1.00 | 50.64 N |
| ATOM | 10356 | CA | SER | B | 124 | −42.711 | −24.892 | 24.666 | 1.00 | 51.03 C |
| ATOM | 10358 | CB | SER | B | 124 | −44.201 | −24.604 | 24.887 | 1.00 | 50.91 C |
| ATOM | 10361 | OG | SER | B | 124 | −44.578 | −23.356 | 24.346 | 1.00 | 51.52 O |
| ATOM | 10363 | C | SER | B | 124 | −42.401 | −25.118 | 23.174 | 1.00 | 51.23 C |
| ATOM | 10364 | O | SER | B | 124 | −42.993 | −25.990 | 22.531 | 1.00 | 51.97 O |
| ATOM | 10366 | N | ALA | B | 125 | −41.465 | −24.339 | 22.635 | 1.00 | 51.66 N |
| ATOM | 10367 | CA | ALA | B | 125 | −40.969 | −24.535 | 21.272 | 1.00 | 51.70 C |
| ATOM | 10369 | CB | ALA | B | 125 | −40.193 | −23.310 | 20.824 | 1.00 | 51.31 C |
| ATOM | 10373 | C | ALA | B | 125 | −40.072 | −25.771 | 21.211 | 1.00 | 52.38 C |
| ATOM | 10374 | O | ALA | B | 125 | −39.141 | −25.901 | 22.004 | 1.00 | 53.23 O |
| ATOM | 10376 | N | SER | B | 126 | −40.338 | −26.674 | 20.269 | 1.00 | 53.10 N |
| ATOM | 10377 | CA | SER | B | 126 | −39.575 | −27.926 | 20.184 | 1.00 | 53.58 C |
| ATOM | 10379 | CB | SER | B | 126 | −40.368 | −29.007 | 19.440 | 1.00 | 53.05 C |
| ATOM | 10382 | OG | SER | B | 126 | −41.300 | −28.435 | 18.542 | 1.00 | 56.47 O |
| ATOM | 10384 | C | SER | B | 126 | −38.166 | −27.747 | 19.586 | 1.00 | 54.18 C |
| ATOM | 10385 | O | SER | B | 126 | −37.827 | −26.702 | 19.016 | 1.00 | 52.27 O |
| ATOM | 10387 | N | THR | B | 127 | −37.359 | −28.793 | 19.739 | 1.00 | 54.57 N |
| ATOM | 10388 | CA | THR | B | 127 | −35.938 | −28.748 | 19.441 | 1.00 | 54.14 C |
| ATOM | 10390 | CB | THR | B | 127 | −35.205 | −29.901 | 20.166 | 1.00 | 54.37 C |
| ATOM | 10392 | OG1 | THR | B | 127 | −35.526 | −29.864 | 21.563 | 1.00 | 58.43 O |
| ATOM | 10394 | CG2 | THR | B | 127 | −33.697 | −29.796 | 20.009 | 1.00 | 55.13 C |
| ATOM | 10398 | C | THR | B | 127 | −35.703 | −28.831 | 17.941 | 1.00 | 53.64 C |
| ATOM | 10399 | O | THR | B | 127 | −36.071 | −29.816 | 17.313 | 1.00 | 55.32 O |
| ATOM | 10401 | N | LYS | B | 128 | −35.087 | −27.793 | 17.378 | 1.00 | 53.39 N |
| ATOM | 10402 | CA | LYS | B | 128 | −34.868 | −27.684 | 15.938 | 1.00 | 54.12 C |
| ATOM | 10404 | CB | LYS | B | 128 | −35.488 | −26.374 | 15.421 | 1.00 | 55.29 C |
| ATOM | 10407 | CG | LYS | B | 128 | −36.405 | −26.501 | 14.176 | 1.00 | 57.14 C |
| ATOM | 10410 | CD | LYS | B | 128 | −35.818 | −25.867 | 12.899 | 1.00 | 60.15 C |
| ATOM | 10413 | CE | LYS | B | 128 | −35.289 | −26.900 | 11.908 | 1.00 | 60.15 C |
| ATOM | 10416 | NZ | LYS | B | 128 | −34.401 | −26.272 | 10.887 | 1.00 | 58.48 N |
| ATOM | 10420 | C | LYS | B | 128 | −33.373 | −27.708 | 15.644 | 1.00 | 53.97 C |
| ATOM | 10421 | O | LYS | B | 128 | −32.579 | −27.153 | 16.402 | 1.00 | 56.83 O |
| ATOM | 10423 | N | GLY | B | 129 | −32.999 | −28.365 | 14.550 | 1.00 | 52.74 N |
| ATOM | 10424 | CA | GLY | B | 129 | −31.609 | −28.460 | 14.123 | 1.00 | 52.53 C |
| ATOM | 10427 | C | GLY | B | 129 | −31.348 | −27.524 | 12.957 | 1.00 | 53.65 C |
| ATOM | 10428 | O | GLY | B | 129 | −32.216 | −27.344 | 12.096 | 1.00 | 55.42 O |
| ATOM | 10430 | N | PRO | B | 130 | −30.134 | −26.955 | 12.887 | 1.00 | 52.88 N |
| ATOM | 10431 | CA | PRO | B | 130 | −29.880 | −25.847 | 11.978 | 1.00 | 51.85 C |
| ATOM | 10433 | CB | PRO | B | 130 | −28.570 | −25.274 | 12.503 | 1.00 | 52.02 C |
| ATOM | 10436 | CG | PRO | B | 130 | −27.857 | −26.454 | 13.040 | 1.00 | 52.63 C |
| ATOM | 10439 | CD | PRO | B | 130 | −28.915 | −27.348 | 13.616 | 1.00 | 53.25 C |
| ATOM | 10442 | C | PRO | B | 130 | −29.694 | −26.297 | 10.543 | 1.00 | 50.96 C |
| ATOM | 10443 | O | PRO | B | 130 | −29.504 | −27.483 | 10.293 | 1.00 | 49.72 O |
| ATOM | 10444 | N | SER | B | 131 | −29.770 | −25.341 | 9.620 | 1.00 | 50.80 N |
| ATOM | 10445 | CA | SER | B | 131 | −29.361 | −25.546 | 8.238 | 1.00 | 51.40 C |
| ATOM | 10447 | CB | SER | B | 131 | −30.365 | −24.945 | 7.254 | 1.00 | 51.80 C |
| ATOM | 10450 | OG | SER | B | 131 | −31.597 | −25.637 | 7.266 | 1.00 | 53.81 O |
| ATOM | 10452 | C | SER | B | 131 | −28.041 | −24.829 | 8.079 | 1.00 | 51.38 C |
| ATOM | 10453 | O | SER | B | 131 | −27.904 | −23.685 | 8.514 | 1.00 | 52.12 O |
| ATOM | 10455 | N | VAL | B | 132 | −27.075 | −25.498 | 7.459 | 1.00 | 50.81 N |
| ATOM | 10456 | CA | VAL | B | 132 | −25.760 | −24.914 | 7.260 | 1.00 | 51.30 C |
| ATOM | 10458 | CB | VAL | B | 132 | −24.634 | −25.875 | 7.699 | 1.00 | 50.80 C |
| ATOM | 10460 | CG1 | VAL | B | 132 | −23.266 | −25.228 | 7.489 | 1.00 | 51.91 C |
| ATOM | 10464 | CG2 | VAL | B | 132 | −24.818 | −26.263 | 9.154 | 1.00 | 51.85 C |
| ATOM | 10468 | C | VAL | B | 132 | −25.581 | −24.529 | 5.800 | 1.00 | 51.62 C |
| ATOM | 10469 | O | VAL | B | 132 | −25.290 | −25.378 | 4.961 | 1.00 | 52.48 O |
| ATOM | 10471 | N | PHE | B | 133 | −25.764 | −23.245 | 5.505 | 1.00 | 52.30 N |
| ATOM | 10472 | CA | PHE | B | 133 | −25.522 | −22.713 | 4.163 | 1.00 | 52.24 C |
| ATOM | 10474 | CB | PHE | B | 133 | −26.550 | −21.636 | 3.821 | 1.00 | 52.74 C |
| ATOM | 10477 | CG | PHE | B | 133 | −27.970 | −22.097 | 3.952 | 1.00 | 53.46 C |
| ATOM | 10478 | CD1 | PHE | B | 133 | −28.580 | −22.807 | 2.929 | 1.00 | 54.14 C |
| ATOM | 10480 | CE1 | PHE | B | 133 | −29.889 | −23.236 | 3.048 | 1.00 | 53.90 C |
| ATOM | 10482 | CZ | PHE | B | 133 | −30.605 | −22.962 | 4.198 | 1.00 | 53.29 C |
| ATOM | 10484 | CE2 | PHE | B | 133 | −30.012 | −22.259 | 5.226 | 1.00 | 54.94 C |
| ATOM | 10486 | CD2 | PHE | B | 133 | −28.697 | −21.829 | 5.102 | 1.00 | 56.08 C |
| ATOM | 10488 | C | PHE | B | 133 | −24.113 | −22.124 | 4.077 | 1.00 | 52.45 C |
| ATOM | 10489 | O | PHE | B | 133 | −23.610 | −21.578 | 5.062 | 1.00 | 53.33 O |
| ATOM | 10491 | N | PRO | B | 134 | −23.472 | −22.227 | 2.899 | 1.00 | 51.97 N |
| ATOM | 10492 | CA | PRO | B | 134 | −22.132 | −21.683 | 2.723 | 1.00 | 51.57 C |
| ATOM | 10494 | CB | PRO | B | 134 | −21.638 | −22.420 | 1.480 | 1.00 | 52.22 C |
| ATOM | 10497 | CG | PRO | B | 134 | −22.869 | −22.623 | 0.665 | 1.00 | 50.46 C |
| ATOM | 10500 | CD | PRO | B | 134 | −23.975 | −22.851 | 1.658 | 1.00 | 52.33 C |
| ATOM | 10503 | C | PRO | B | 134 | −22.165 | −20.175 | 2.464 | 1.00 | 51.61 C |
| ATOM | 10504 | O | PRO | B | 134 | −23.246 | −19.605 | 2.290 | 1.00 | 51.20 O |
| ATOM | 10505 | N | LEU | B | 135 | −20.989 | −19.545 | 2.442 | 1.00 | 51.72 N |

-continued

| ATOM | 10506 | CA  | LEU | B | 135 | −20.849 | −18.131 | 2.060  | 1.00 | 51.73 | C |
| ATOM | 10508 | CB  | LEU | B | 135 | −20.709 | −17.249 | 3.302  | 1.00 | 51.84 | C |
| ATOM | 10511 | CG  | LEU | B | 135 | −21.907 | −17.206 | 4.258  | 1.00 | 50.97 | C |
| ATOM | 10513 | CD1 | LEU | B | 135 | −21.518 | −16.558 | 5.576  | 1.00 | 49.13 | C |
| ATOM | 10517 | CD2 | LEU | B | 135 | −23.079 | −16.472 | 3.628  | 1.00 | 49.92 | C |
| ATOM | 10521 | C   | LEU | B | 135 | −19.642 | −17.923 | 1.144  | 1.00 | 51.94 | C |
| ATOM | 10522 | O   | LEU | B | 135 | −19.785 | −17.582 | −0.036 | 1.00 | 51.14 | O |
| ATOM | 10524 | N   | GLY | B | 150 | −17.257 | −18.194 | 4.805  | 1.00 | 50.98 | N |
| ATOM | 10525 | CA  | GLY | B | 150 | −17.955 | −18.404 | 6.068  | 1.00 | 51.58 | C |
| ATOM | 10528 | C   | GLY | B | 150 | −19.010 | −19.500 | 6.050  | 1.00 | 51.76 | C |
| ATOM | 10529 | O   | GLY | B | 150 | −19.250 | −20.138 | 5.029  | 1.00 | 51.44 | O |
| ATOM | 10531 | N   | CYS | B | 151 | −19.636 | −19.715 | 7.203  | 1.00 | 53.60 | N |
| ATOM | 10532 | CA  | CYS | B | 151 | −20.713 | −20.692 | 7.351  | 1.00 | 54.06 | C |
| ATOM | 10534 | CB  | CYS | B | 151 | −20.242 | −21.878 | 8.193  | 1.00 | 55.07 | C |
| ATOM | 10537 | SG  | CYS | B | 151 | −19.457 | −23.203 | 7.250  | 1.00 | 58.07 | S |
| ATOM | 10539 | C   | CYS | B | 151 | −21.934 | −20.045 | 8.007  | 1.00 | 54.00 | C |
| ATOM | 10540 | O   | CYS | B | 151 | −21.836 | −19.455 | 9.082  | 1.00 | 52.58 | O |
| ATOM | 10542 | N   | LEU | B | 152 | −23.080 | −20.155 | 7.345  | 1.00 | 54.08 | N |
| ATOM | 10543 | CA  | LEU | B | 152 | −24.332 | −19.644 | 7.884  | 1.00 | 54.21 | C |
| ATOM | 10545 | CB  | LEU | B | 152 | −25.193 | −19.028 | 6.775  | 1.00 | 54.31 | C |
| ATOM | 10548 | CG  | LEU | B | 152 | −26.653 | −18.648 | 7.066  | 1.00 | 53.56 | C |
| ATOM | 10550 | CD1 | LEU | B | 152 | −26.873 | −18.037 | 8.452  | 1.00 | 50.58 | C |
| ATOM | 10554 | CD2 | LEU | B | 152 | −27.135 | −17.700 | 5.974  | 1.00 | 53.72 | C |
| ATOM | 10558 | C   | LEU | B | 152 | −25.060 | −20.794 | 8.551  | 1.00 | 54.49 | C |
| ATOM | 10559 | O   | LEU | B | 152 | −25.333 | −21.814 | 7.919  | 1.00 | 53.81 | O |
| ATOM | 10561 | N   | VAL | B | 153 | −25.348 | −20.620 | 9.837  | 1.00 | 54.89 | N |
| ATOM | 10562 | CA  | VAL | B | 153 | −26.092 | −21.592 | 10.615 | 1.00 | 55.00 | C |
| ATOM | 10564 | CB  | VAL | B | 153 | −25.368 | −21.915 | 11.934 | 1.00 | 55.96 | C |
| ATOM | 10566 | CG1 | VAL | B | 153 | −25.982 | −23.146 | 12.593 | 1.00 | 57.04 | C |
| ATOM | 10570 | CG2 | VAL | B | 153 | −23.865 | −22.118 | 11.683 | 1.00 | 55.95 | C |
| ATOM | 10574 | C   | VAL | B | 153 | −27.465 | −20.984 | 10.888 | 1.00 | 55.09 | C |
| ATOM | 10575 | O   | VAL | B | 153 | −27.587 | −20.031 | 11.665 | 1.00 | 55.00 | O |
| ATOM | 10577 | N   | LYS | B | 154 | −28.489 | −21.539 | 10.238 | 1.00 | 54.89 | N |
| ATOM | 10578 | CA  | LYS | B | 154 | −29.812 | −20.923 | 10.195 | 1.00 | 54.47 | C |
| ATOM | 10580 | CB  | LYS | B | 154 | −30.191 | −20.627 | 8.743  | 1.00 | 53.92 | C |
| ATOM | 10583 | CG  | LYS | B | 154 | −31.503 | −19.884 | 8.617  | 1.00 | 54.64 | C |
| ATOM | 10586 | CD  | LYS | B | 154 | −31.628 | −19.138 | 7.310  | 1.00 | 53.53 | C |
| ATOM | 10589 | CE  | LYS | B | 154 | −32.944 | −18.382 | 7.259  | 1.00 | 52.78 | C |
| ATOM | 10592 | NZ  | LYS | B | 154 | −33.058 | −17.372 | 8.345  | 1.00 | 53.36 | N |
| ATOM | 10596 | C   | LYS | B | 154 | −30.906 | −21.777 | 10.850 | 1.00 | 54.58 | C |
| ATOM | 10597 | O   | LYS | B | 154 | −30.892 | −23.003 | 10.743 | 1.00 | 53.65 | O |
| ATOM | 10599 | N   | ASP | B | 155 | −31.838 | −21.099 | 11.526 | 1.00 | 54.82 | N |
| ATOM | 10600 | CA  | ASP | B | 155 | −33.038 | −21.706 | 12.110 | 1.00 | 54.65 | C |
| ATOM | 10602 | CB  | ASP | B | 155 | −34.035 | −22.075 | 11.008 | 1.00 | 55.54 | C |
| ATOM | 10605 | CG  | ASP | B | 155 | −34.593 | −20.859 | 10.287 | 1.00 | 57.21 | C |
| ATOM | 10606 | OD1 | ASP | B | 155 | −34.802 | −19.812 | 10.934 | 1.00 | 59.60 | O |
| ATOM | 10607 | OD2 | ASP | B | 155 | −34.832 | −20.958 | 9.065  | 1.00 | 58.84 | O |
| ATOM | 10608 | C   | ASP | B | 155 | −32.765 | −22.929 | 12.977 | 1.00 | 54.95 | C |
| ATOM | 10609 | O   | ASP | B | 155 | −32.877 | −24.067 | 12.504 | 1.00 | 54.96 | O |
| ATOM | 10611 | N   | TYR | B | 156 | −32.417 | −22.682 | 14.241 | 1.00 | 54.53 | N |
| ATOM | 10612 | CA  | TYR | B | 156 | −32.275 | −23.744 | 15.244 | 1.00 | 54.05 | C |
| ATOM | 10614 | CB  | TYR | B | 156 | −30.817 | −24.189 | 15.391 | 1.00 | 54.00 | C |
| ATOM | 10617 | CG  | TYR | B | 156 | −29.877 | −23.147 | 15.979 | 1.00 | 55.08 | C |
| ATOM | 10618 | CD1 | TYR | B | 156 | −29.226 | −22.230 | 15.159 | 1.00 | 54.02 | C |
| ATOM | 10620 | CE1 | TYR | B | 156 | −28.362 | −21.279 | 15.685 | 1.00 | 52.80 | C |
| ATOM | 10622 | CZ  | TYR | B | 156 | −28.135 | −21.236 | 17.042 | 1.00 | 53.30 | C |
| ATOM | 10623 | OH  | TYR | B | 156 | −27.276 | −20.288 | 17.538 | 1.00 | 55.28 | O |
| ATOM | 10625 | CE2 | TYR | B | 156 | −28.761 | −22.137 | 17.888 | 1.00 | 53.76 | C |
| ATOM | 10627 | CD2 | TYR | B | 156 | −29.624 | −23.093 | 17.353 | 1.00 | 55.51 | C |
| ATOM | 10629 | C   | TYR | B | 156 | −32.798 | −23.297 | 16.595 | 1.00 | 54.11 | C |
| ATOM | 10630 | O   | TYR | B | 156 | −32.922 | −22.106 | 16.862 | 1.00 | 54.77 | O |
| ATOM | 10632 | N   | PHE | B | 157 | −33.092 | −24.270 | 17.445 | 1.00 | 54.54 | N |
| ATOM | 10633 | CA  | PHE | B | 157 | −33.561 | −24.013 | 18.802 | 1.00 | 54.76 | C |
| ATOM | 10635 | CB  | PHE | B | 157 | −35.047 | −23.645 | 18.789 | 1.00 | 54.48 | C |
| ATOM | 10638 | CG  | PHE | B | 157 | −35.577 | −23.162 | 20.117 | 1.00 | 54.78 | C |
| ATOM | 10639 | CD1 | PHE | B | 157 | −35.537 | −21.814 | 20.451 | 1.00 | 55.46 | C |
| ATOM | 10641 | CE1 | PHE | B | 157 | −36.044 | −21.358 | 21.680 | 1.00 | 55.34 | C |
| ATOM | 10643 | CZ  | PHE | B | 157 | −36.593 | −22.252 | 22.580 | 1.00 | 54.44 | C |
| ATOM | 10645 | CE2 | PHE | B | 157 | −36.646 | −23.597 | 22.261 | 1.00 | 56.51 | C |
| ATOM | 10647 | CD2 | PHE | B | 157 | −36.144 | −24.050 | 21.026 | 1.00 | 56.92 | C |
| ATOM | 10649 | C   | PHE | B | 157 | −33.324 | −25.300 | 19.588 | 1.00 | 55.42 | C |
| ATOM | 10650 | O   | PHE | B | 157 | −33.478 | −26.383 | 19.039 | 1.00 | 57.32 | O |
| ATOM | 10652 | N   | PRO | B | 158 | −32.883 | −25.199 | 20.848 | 1.00 | 55.16 | N |
| ATOM | 10653 | CA  | PRO | B | 158 | −32.460 | −24.025 | 21.604 | 1.00 | 55.61 | C |
| ATOM | 10655 | CB  | PRO | B | 158 | −32.567 | −24.512 | 23.049 | 1.00 | 56.14 | C |
| ATOM | 10658 | CG  | PRO | B | 158 | −32.202 | −25.956 | 22.955 | 1.00 | 55.07 | C |
| ATOM | 10661 | CD  | PRO | B | 158 | −32.786 | −26.429 | 21.653 | 1.00 | 54.87 | C |
| ATOM | 10664 | C   | PRO | B | 158 | −31.012 | −23.633 | 21.298 | 1.00 | 55.52 | C |
| ATOM | 10665 | O   | PRO | B | 158 | −30.384 | −24.213 | 20.422 | 1.00 | 55.39 | O |

-continued

| | | | | | | | | | | |
|---|---|---|---|---|---|---|---|---|---|---|
| ATOM | 10666 | N | GLU | B | 159 | −30.494 | −22.644 | 22.017 | 1.00 | 56.01 N |
| ATOM | 10667 | CA | GLU | B | 159 | −29.056 | −22.412 | 22.066 | 1.00 | 55.50 C |
| ATOM | 10669 | CB | GLU | B | 159 | −28.759 | −21.113 | 22.811 | 1.00 | 55.51 C |
| ATOM | 10672 | CG | GLU | B | 159 | −29.104 | −19.859 | 22.047 | 1.00 | 57.18 C |
| ATOM | 10675 | CD | GLU | B | 159 | −27.952 | −19.375 | 21.194 | 1.00 | 61.22 C |
| ATOM | 10676 | OE1 | GLU | B | 159 | −27.540 | −18.209 | 21.369 | 1.00 | 63.05 O |
| ATOM | 10677 | OE2 | GLU | B | 159 | −27.447 | −20.165 | 20.363 | 1.00 | 62.01 O |
| ATOM | 10678 | C | GLU | B | 159 | −28.407 | −23.575 | 22.815 | 1.00 | 55.02 C |
| ATOM | 10679 | O | GLU | B | 159 | −29.092 | −24.305 | 23.538 | 1.00 | 56.36 O |
| ATOM | 10681 | N | PRO | B | 160 | −27.084 | −23.744 | 22.679 | 1.00 | 53.60 N |
| ATOM | 10682 | CA | PRO | B | 160 | −26.167 | −23.063 | 21.803 | 1.00 | 52.61 C |
| ATOM | 10684 | CB | PRO | B | 160 | −24.990 | −22.789 | 22.733 | 1.00 | 51.90 C |
| ATOM | 10687 | CG | PRO | B | 160 | −24.969 | −23.998 | 23.654 | 1.00 | 52.09 C |
| ATOM | 10690 | CD | PRO | B | 160 | −26.343 | −24.645 | 23.578 | 1.00 | 54.16 C |
| ATOM | 10693 | C | PRO | B | 160 | −25.693 | −23.925 | 20.641 | 1.00 | 52.11 C |
| ATOM | 10694 | O | PRO | B | 160 | −25.957 | −25.128 | 20.587 | 1.00 | 50.42 O |
| ATOM | 10695 | N | VAL | B | 161 | −24.989 | −23.278 | 19.721 | 1.00 | 53.03 N |
| ATOM | 10696 | CA | VAL | B | 161 | −24.278 | −23.947 | 18.647 | 1.00 | 52.97 C |
| ATOM | 10698 | CB | VAL | B | 161 | −24.822 | −23.531 | 17.260 | 1.00 | 52.23 C |
| ATOM | 10700 | CG1 | VAL | B | 161 | −23.858 | −23.891 | 16.149 | 1.00 | 53.59 C |
| ATOM | 10704 | CG2 | VAL | B | 161 | −26.153 | −24.195 | 17.006 | 1.00 | 54.81 C |
| ATOM | 10708 | C | VAL | B | 161 | −22.818 | −23.559 | 18.771 | 1.00 | 53.12 C |
| ATOM | 10709 | O | VAL | B | 161 | −22.501 | −22.440 | 19.179 | 1.00 | 53.70 O |
| ATOM | 10711 | N | THR | B | 162 | −21.938 | −24.495 | 18.434 | 1.00 | 52.95 N |
| ATOM | 10712 | CA | THR | B | 162 | −20.509 | −24.234 | 18.386 | 1.00 | 52.79 C |
| ATOM | 10714 | CB | THR | B | 162 | −19.732 | −25.158 | 19.341 | 1.00 | 52.78 C |
| ATOM | 10716 | OG1 | THR | B | 162 | −19.589 | −26.459 | 18.754 | 1.00 | 56.12 O |
| ATOM | 10718 | CG2 | THR | B | 162 | −20.461 | −25.277 | 20.676 | 1.00 | 52.34 C |
| ATOM | 10722 | C | THR | B | 162 | −20.029 | −24.448 | 16.959 | 1.00 | 52.48 C |
| ATOM | 10723 | O | THR | B | 162 | −20.527 | −25.322 | 16.249 | 1.00 | 52.28 O |
| ATOM | 10725 | N | VAL | B | 163 | −19.066 | −23.635 | 16.546 | 1.00 | 52.43 N |
| ATOM | 10726 | CA | VAL | B | 163 | −18.519 | −23.701 | 15.207 | 1.00 | 51.71 C |
| ATOM | 10728 | CB | VAL | B | 163 | −18.977 | −22.506 | 14.343 | 1.00 | 50.84 C |
| ATOM | 10730 | CG1 | VAL | B | 163 | −18.816 | −22.837 | 12.873 | 1.00 | 50.88 C |
| ATOM | 10734 | CG2 | VAL | B | 163 | −20.421 | −22.129 | 14.641 | 1.00 | 50.99 C |
| ATOM | 10738 | C | VAL | B | 163 | −16.998 | −23.685 | 15.293 | 1.00 | 51.91 C |
| ATOM | 10739 | O | VAL | B | 163 | −16.417 | −22.849 | 15.983 | 1.00 | 50.40 O |
| ATOM | 10741 | N | SER | B | 164 | −16.366 | −24.623 | 14.594 | 1.00 | 53.30 N |
| ATOM | 10742 | CA | SER | B | 164 | −14.915 | −24.645 | 14.434 | 1.00 | 53.24 C |
| ATOM | 10744 | CB | SER | B | 164 | −14.309 | −25.834 | 15.184 | 1.00 | 53.81 C |
| ATOM | 10747 | OG | SER | B | 164 | −14.376 | −27.024 | 14.415 | 1.00 | 54.22 O |
| ATOM | 10749 | C | SER | B | 164 | −14.576 | −24.726 | 12.951 | 1.00 | 53.06 C |
| ATOM | 10750 | O | SER | B | 164 | −15.450 | −24.994 | 12.124 | 1.00 | 53.23 O |
| ATOM | 10752 | N | TRP | B | 165 | −13.310 | −24.485 | 12.620 | 1.00 | 53.53 N |
| ATOM | 10753 | CA | TRP | B | 165 | −12.838 | −24.590 | 11.240 | 1.00 | 54.03 C |
| ATOM | 10755 | CB | TRP | B | 165 | −12.416 | −23.215 | 10.701 | 1.00 | 53.15 C |
| ATOM | 10758 | CG | TRP | B | 165 | −13.602 | −22.329 | 10.439 | 1.00 | 52.43 C |
| ATOM | 10759 | CD1 | TRP | B | 165 | −14.224 | −21.497 | 11.334 | 1.00 | 51.83 C |
| ATOM | 10761 | NE1 | TRP | B | 165 | −15.292 | −20.868 | 10.734 | 1.00 | 51.54 N |
| ATOM | 10763 | CE2 | TRP | B | 165 | −15.386 | −21.294 | 9.435 | 1.00 | 52.27 C |
| ATOM | 10764 | CD2 | TRP | B | 165 | −14.336 | −22.218 | 9.212 | 1.00 | 52.52 C |
| ATOM | 10765 | CE3 | TRP | B | 165 | −14.208 | −22.807 | 7.944 | 1.00 | 52.13 C |
| ATOM | 10767 | CZ3 | TRP | B | 165 | −15.114 | −22.455 | 6.946 | 1.00 | 51.05 C |
| ATOM | 10769 | CH2 | TRP | B | 165 | −16.145 | −21.527 | 7.196 | 1.00 | 51.97 C |
| ATOM | 10771 | CZ2 | TRP | B | 165 | −16.299 | −20.941 | 8.433 | 1.00 | 52.34 C |
| ATOM | 10773 | C | TRP | B | 165 | −11.707 | −25.611 | 11.150 | 1.00 | 54.86 C |
| ATOM | 10774 | O | TRP | B | 165 | −10.758 | −25.571 | 11.941 | 1.00 | 55.61 O |
| ATOM | 10776 | N | ASN | B | 166 | −11.839 | −26.535 | 10.196 | 1.00 | 54.82 N |
| ATOM | 10777 | CA | ASN | B | 166 | −10.924 | −27.665 | 10.043 | 1.00 | 54.89 C |
| ATOM | 10779 | CB | ASN | B | 166 | −9.587 | −27.186 | 9.465 | 1.00 | 54.64 C |
| ATOM | 10782 | CG | ASN | B | 166 | −9.735 | −26.565 | 8.084 | 1.00 | 55.47 C |
| ATOM | 10783 | OD1 | ASN | B | 166 | −10.793 | −26.653 | 7.462 | 1.00 | 57.53 O |
| ATOM | 10784 | ND2 | ASN | B | 166 | −8.670 | −25.938 | 7.597 | 1.00 | 54.29 N |
| ATOM | 10787 | C | ASN | B | 166 | −10.714 | −28.440 | 11.350 | 1.00 | 55.57 C |
| ATOM | 10788 | O | ASN | B | 166 | −9.596 | −28.836 | 11.674 | 1.00 | 56.25 O |
| ATOM | 10790 | N | SER | B | 167 | −11.803 | −28.649 | 12.090 | 1.00 | 56.35 N |
| ATOM | 10791 | CA | SER | B | 167 | −11.769 | −29.335 | 13.386 | 1.00 | 56.44 C |
| ATOM | 10793 | CB | SER | B | 167 | −11.582 | −30.843 | 13.192 | 1.00 | 56.83 C |
| ATOM | 10796 | OG | SER | B | 167 | −12.694 | −31.411 | 12.524 | 1.00 | 59.25 O |
| ATOM | 10798 | C | SER | B | 167 | −10.681 | −28.787 | 14.309 | 1.00 | 56.60 C |
| ATOM | 10799 | O | SER | B | 167 | −9.582 | −29.337 | 14.386 | 1.00 | 56.11 O |
| ATOM | 10801 | N | GLY | B | 168 | −10.987 | −27.685 | 14.989 | 1.00 | 56.94 N |
| ATOM | 10802 | CA | GLY | B | 168 | −10.068 | −27.079 | 15.946 | 1.00 | 56.24 C |
| ATOM | 10805 | C | GLY | B | 168 | −8.907 | −26.322 | 15.319 | 1.00 | 56.00 C |
| ATOM | 10806 | O | GLY | B | 168 | −8.587 | −25.219 | 15.752 | 1.00 | 56.18 O |
| ATOM | 10808 | N | ALA | B | 169 | −8.276 | −26.907 | 14.304 | 1.00 | 55.35 N |
| ATOM | 10809 | CA | ALA | B | 169 | −7.036 | −26.363 | 13.746 | 1.00 | 55.70 C |
| ATOM | 10811 | CB | ALA | B | 169 | −6.641 | −27.128 | 12.471 | 1.00 | 54.85 C |
| ATOM | 10815 | C | ALA | B | 169 | −7.107 | −24.857 | 13.468 | 1.00 | 55.84 C |

-continued

| | | | | | | | | | | |
|---|---|---|---|---|---|---|---|---|---|---|
| ATOM | 10816 | O | ALA | B | 169 | −6.441 | −24.064 | 14.141 | 1.00 | 55.07 O |
| ATOM | 10818 | N | LEU | B | 170 | −7.930 | −24.477 | 12.493 | 1.00 | 55.93 N |
| ATOM | 10819 | CA | LEU | B | 170 | −7.988 | −23.098 | 12.003 | 1.00 | 55.07 C |
| ATOM | 10821 | CB | LEU | B | 170 | −8.675 | −23.077 | 10.633 | 1.00 | 54.39 C |
| ATOM | 10824 | CG | LEU | B | 170 | −8.881 | −21.726 | 9.955 | 1.00 | 55.49 C |
| ATOM | 10826 | CD1 | LEU | B | 170 | −7.600 | −20.904 | 9.982 | 1.00 | 56.43 C |
| ATOM | 10830 | CD2 | LEU | B | 170 | −9.366 | −21.930 | 8.527 | 1.00 | 54.96 C |
| ATOM | 10834 | C | LEU | B | 170 | −8.700 | −22.159 | 12.990 | 1.00 | 54.79 C |
| ATOM | 10835 | O | LEU | B | 170 | −9.921 | −21.993 | 12.934 | 1.00 | 54.70 O |
| ATOM | 10837 | N | THR | B | 171 | −7.919 | −21.552 | 13.886 | 1.00 | 54.41 N |
| ATOM | 10838 | CA | THR | B | 171 | −8.439 | −20.655 | 14.931 | 1.00 | 53.99 C |
| ATOM | 10840 | CB | THR | B | 171 | −7.620 | −20.756 | 16.262 | 1.00 | 54.29 C |
| ATOM | 10842 | OG1 | THR | B | 171 | −6.212 | −20.826 | 15.973 | 1.00 | 54.71 O |
| ATOM | 10844 | CG2 | THR | B | 171 | −8.039 | −21.971 | 17.085 | 1.00 | 53.13 C |
| ATOM | 10848 | C | THR | B | 171 | −8.420 | −19.188 | 14.508 | 1.00 | 53.64 C |
| ATOM | 10849 | O | THR | B | 171 | −9.437 | −18.497 | 14.609 | 1.00 | 52.66 O |
| ATOM | 10851 | N | SER | B | 172 | −7.255 | −18.717 | 14.058 | 1.00 | 53.25 N |
| ATOM | 10852 | CA | SER | B | 172 | −7.043 | −17.292 | 13.799 | 1.00 | 53.18 C |
| ATOM | 10854 | CB | SER | B | 172 | −5.549 | −16.974 | 13.670 | 1.00 | 53.75 C |
| ATOM | 10857 | OG | SER | B | 172 | −5.068 | −17.268 | 12.366 | 1.00 | 53.04 O |
| ATOM | 10859 | C | SER | B | 172 | −7.782 | −16.833 | 12.543 | 1.00 | 52.72 C |
| ATOM | 10860 | O | SER | B | 172 | −7.923 | −17.594 | 11.585 | 1.00 | 51.57 O |
| ATOM | 10862 | N | GLY | B | 173 | −8.245 | −15.583 | 12.571 | 1.00 | 52.76 N |
| ATOM | 10863 | CA | GLY | B | 173 | −9.048 | −15.001 | 11.496 | 1.00 | 53.18 C |
| ATOM | 10866 | C | GLY | B | 173 | −10.546 | −15.149 | 11.726 | 1.00 | 54.24 C |
| ATOM | 10867 | O | GLY | B | 173 | −11.343 | −14.422 | 11.124 | 1.00 | 54.13 O |
| ATOM | 10869 | N | VAL | B | 174 | −10.925 | −16.077 | 12.607 | 1.00 | 54.26 N |
| ATOM | 10870 | CA | VAL | B | 174 | −12.318 | −16.467 | 12.786 | 1.00 | 54.61 C |
| ATOM | 10872 | CB | VAL | B | 174 | −12.425 | −17.841 | 13.519 | 1.00 | 55.14 C |
| ATOM | 10874 | CG1 | VAL | B | 174 | −13.874 | −18.157 | 13.936 | 1.00 | 53.49 C |
| ATOM | 10878 | CG2 | VAL | B | 174 | −11.861 | −18.954 | 12.639 | 1.00 | 56.13 C |
| ATOM | 10882 | C | VAL | B | 174 | −13.089 | −15.404 | 13.567 | 1.00 | 55.82 C |
| ATOM | 10883 | O | VAL | B | 174 | −12.572 | −14.845 | 14.541 | 1.00 | 55.91 O |
| ATOM | 10885 | N | HIS | B | 175 | −14.319 | −15.131 | 13.123 | 1.00 | 55.64 N |
| ATOM | 10886 | CA | HIS | B | 175 | −15.271 | −14.306 | 13.879 | 1.00 | 53.98 C |
| ATOM | 10888 | CB | HIS | B | 175 | −15.350 | −12.882 | 13.313 | 1.00 | 54.89 C |
| ATOM | 10891 | CG | HIS | B | 175 | −14.168 | −12.028 | 13.654 | 1.00 | 55.41 C |
| ATOM | 10892 | ND1 | HIS | B | 175 | −13.902 | −11.606 | 14.939 | 1.00 | 56.66 N |
| ATOM | 10894 | CE1 | HIS | B | 175 | −12.803 | −10.871 | 14.941 | 1.00 | 58.66 C |
| ATOM | 10896 | NE2 | HIS | B | 175 | −12.349 | −10.797 | 13.702 | 1.00 | 58.90 N |
| ATOM | 10898 | CD2 | HIS | B | 175 | −13.185 | −11.512 | 12.877 | 1.00 | 56.60 C |
| ATOM | 10900 | C | HIS | B | 175 | −16.651 | −14.960 | 13.872 | 1.00 | 52.07 C |
| ATOM | 10901 | O | HIS | B | 175 | −17.406 | −14.827 | 12.913 | 1.00 | 52.28 O |
| ATOM | 10903 | N | THR | B | 176 | −16.959 | −15.679 | 14.945 | 1.00 | 50.90 N |
| ATOM | 10904 | CA | THR | B | 176 | −18.259 | −16.310 | 15.116 | 1.00 | 50.65 C |
| ATOM | 10906 | CB | THR | B | 176 | −18.135 | −17.652 | 15.848 | 1.00 | 49.92 C |
| ATOM | 10908 | OG1 | THR | B | 176 | −17.176 | −18.475 | 15.165 | 1.00 | 50.40 O |
| ATOM | 10910 | CG2 | THR | B | 176 | −19.475 | −18.371 | 15.896 | 1.00 | 49.15 C |
| ATOM | 10914 | C | THR | B | 176 | −19.168 | −15.358 | 15.885 | 1.00 | 49.46 C |
| ATOM | 10915 | O | THR | B | 176 | −18.838 | −14.912 | 16.975 | 1.00 | 48.82 O |
| ATOM | 10917 | N | PHE | B | 177 | −20.312 | −15.044 | 15.293 | 1.00 | 49.87 N |
| ATOM | 10918 | CA | PHE | B | 177 | −21.176 | −13.992 | 15.800 | 1.00 | 50.35 C |
| ATOM | 10920 | CB | PHE | B | 177 | −21.945 | −13.342 | 14.642 | 1.00 | 49.43 C |
| ATOM | 10923 | CG | PHE | B | 177 | −21.070 | −12.582 | 13.700 | 1.00 | 48.44 C |
| ATOM | 10924 | CD1 | PHE | B | 177 | −20.562 | −13.183 | 12.559 | 1.00 | 48.42 C |
| ATOM | 10926 | CE1 | PHE | B | 177 | −19.739 | −12.480 | 11.697 | 1.00 | 48.71 C |
| ATOM | 10928 | CZ | PHE | B | 177 | −19.414 | −11.165 | 11.977 | 1.00 | 48.09 C |
| ATOM | 10930 | CE2 | PHE | B | 177 | −19.909 | −10.563 | 13.113 | 1.00 | 47.31 C |
| ATOM | 10932 | CD2 | PHE | B | 177 | −20.730 | −11.267 | 13.967 | 1.00 | 48.42 C |
| ATOM | 10934 | C | PHE | B | 177 | −22.160 | −14.508 | 16.845 | 1.00 | 50.87 C |
| ATOM | 10935 | O | PHE | B | 177 | −22.620 | −15.653 | 16.763 | 1.00 | 49.53 O |
| ATOM | 10937 | N | PRO | B | 178 | −22.485 | −13.658 | 17.838 | 1.00 | 51.19 N |
| ATOM | 10938 | CA | PRO | B | 178 | −23.611 | −13.934 | 18.713 | 1.00 | 50.97 C |
| ATOM | 10940 | CB | PRO | B | 178 | −23.845 | −12.600 | 19.421 | 1.00 | 49.54 C |
| ATOM | 10943 | CG | PRO | B | 178 | −22.546 | −11.938 | 19.420 | 1.00 | 50.84 C |
| ATOM | 10946 | CD | PRO | B | 178 | −21.801 | −12.405 | 18.202 | 1.00 | 51.45 C |
| ATOM | 10949 | C | PRO | B | 178 | −24.832 | −14.308 | 17.892 | 1.00 | 51.79 C |
| ATOM | 10950 | O | PRO | B | 178 | −25.114 | −13.670 | 16.870 | 1.00 | 51.45 O |
| ATOM | 10951 | N | ALA | B | 179 | −25.543 | −15.343 | 18.325 | 1.00 | 52.55 N |
| ATOM | 10952 | CA | ALA | B | 179 | −26.758 | −15.743 | 17.638 | 1.00 | 52.43 C |
| ATOM | 10954 | CB | ALA | B | 179 | −27.279 | −17.070 | 18.169 | 1.00 | 53.11 C |
| ATOM | 10958 | C | ALA | B | 179 | −27.789 | −14.645 | 17.815 | 1.00 | 52.27 C |
| ATOM | 10959 | O | ALA | B | 179 | −27.708 | −13.856 | 18.754 | 1.00 | 51.59 O |
| ATOM | 10961 | N | VAL | B | 180 | −28.735 | −14.598 | 16.885 | 1.00 | 52.97 N |
| ATOM | 10962 | CA | VAL | B | 180 | −29.787 | −13.596 | 16.871 | 1.00 | 53.18 C |
| ATOM | 10964 | CB | VAL | B | 180 | −29.653 | −12.712 | 15.617 | 1.00 | 52.02 C |
| ATOM | 10966 | CG1 | VAL | B | 180 | −30.919 | −11.934 | 15.343 | 1.00 | 53.61 C |
| ATOM | 10970 | CG2 | VAL | B | 180 | −28.484 | −11.765 | 15.788 | 1.00 | 53.87 C |
| ATOM | 10974 | C | VAL | B | 180 | −31.122 | −14.330 | 16.895 | 1.00 | 54.16 C |

-continued

| | | | | | | | | | | |
|---|---|---|---|---|---|---|---|---|---|---|
| ATOM | 10975 | O | VAL | B | 180 | −31.280 | −15.363 | 16.242 | 1.00 | 55.58 O |
| ATOM | 10977 | N | LEU | B | 181 | −32.078 | −13.820 | 17.662 | 1.00 | 53.82 N |
| ATOM | 10978 | CA | LEU | B | 181 | −33.393 | −14.423 | 17.674 | 1.00 | 54.37 C |
| ATOM | 10980 | CB | LEU | B | 181 | −34.050 | −14.301 | 19.044 | 1.00 | 54.04 C |
| ATOM | 10983 | CG | LEU | B | 181 | −35.393 | −15.025 | 19.231 | 1.00 | 53.59 C |
| ATOM | 10985 | CD1 | LEU | B | 181 | −35.511 | −16.323 | 18.446 | 1.00 | 53.80 C |
| ATOM | 10989 | CD2 | LEU | B | 181 | −35.626 | −15.296 | 20.708 | 1.00 | 54.14 C |
| ATOM | 10993 | C | LEU | B | 181 | −34.237 | −13.755 | 16.606 | 1.00 | 55.94 C |
| ATOM | 10994 | O | LEU | B | 181 | −34.463 | −12.546 | 16.644 | 1.00 | 56.27 O |
| ATOM | 10996 | N | GLN | B | 182 | −34.681 | −14.553 | 15.639 | 1.00 | 56.99 N |
| ATOM | 10997 | CA | GLN | B | 182 | −35.534 | −14.076 | 14.563 | 1.00 | 56.96 C |
| ATOM | 10999 | CB | GLN | B | 182 | −35.501 | −15.068 | 13.394 | 1.00 | 56.74 C |
| ATOM | 11002 | CG | GLN | B | 182 | −34.139 | −15.166 | 12.715 | 1.00 | 56.72 C |
| ATOM | 11005 | CD | GLN | B | 182 | −33.890 | −16.517 | 12.071 | 1.00 | 57.96 C |
| ATOM | 11006 | OE1 | GLN | B | 182 | −33.863 | −16.640 | 10.845 | 1.00 | 62.10 O |
| ATOM | 11007 | NE2 | GLN | B | 182 | −33.702 | −17.537 | 12.895 | 1.00 | 55.29 N |
| ATOM | 11010 | C | GLN | B | 182 | −36.959 | −13.898 | 15.090 | 1.00 | 58.09 C |
| ATOM | 11011 | O | GLN | B | 182 | −37.246 | −14.218 | 16.255 | 1.00 | 57.07 O |
| ATOM | 11013 | N | SER | B | 183 | −37.841 | −13.374 | 14.234 | 1.00 | 57.94 N |
| ATOM | 11014 | CA | SER | B | 183 | −39.255 | −13.215 | 14.577 | 1.00 | 57.43 C |
| ATOM | 11016 | CB | SER | B | 183 | −39.954 | −12.272 | 13.593 | 1.00 | 57.09 C |
| ATOM | 11019 | OG | SER | B | 183 | −40.108 | −12.869 | 12.318 | 1.00 | 57.50 O |
| ATOM | 11021 | C | SER | B | 183 | −39.965 | −14.569 | 14.603 | 1.00 | 57.57 C |
| ATOM | 11022 | O | SER | B | 183 | −40.976 | −14.727 | 15.290 | 1.00 | 57.40 O |
| ATOM | 11024 | N | SER | B | 184 | −39.425 | −15.537 | 13.857 | 1.00 | 58.06 N |
| ATOM | 11025 | CA | SER | B | 184 | −39.964 | −16.905 | 13.809 | 1.00 | 57.73 C |
| ATOM | 11027 | CB | SER | B | 184 | −39.379 | −17.666 | 12.605 | 1.00 | 57.67 C |
| ATOM | 11030 | OG | SER | B | 184 | −37.958 | −17.609 | 12.579 | 1.00 | 56.30 O |
| ATOM | 11032 | C | SER | B | 184 | −39.720 | −17.698 | 15.104 | 1.00 | 57.79 C |
| ATOM | 11033 | O | SER | B | 184 | −40.263 | −18.790 | 15.279 | 1.00 | 57.78 O |
| ATOM | 11035 | N | GLY | B | 185 | −38.908 | −17.153 | 16.007 | 1.00 | 57.52 N |
| ATOM | 11036 | CA | GLY | B | 185 | −38.628 | −17.802 | 17.280 | 1.00 | 57.44 C |
| ATOM | 11039 | C | GLY | B | 185 | −37.419 | −18.718 | 17.222 | 1.00 | 57.41 C |
| ATOM | 11040 | O | GLY | B | 185 | −37.057 | −19.320 | 18.228 | 1.00 | 58.57 O |
| ATOM | 11042 | N | LEU | B | 186 | −36.785 | −18.812 | 16.054 | 1.00 | 57.04 N |
| ATOM | 11043 | CA | LEU | B | 186 | −35.582 | −19.628 | 15.870 | 1.00 | 56.95 C |
| ATOM | 11045 | CB | LEU | B | 186 | −35.674 | −20.413 | 14.553 | 1.00 | 56.42 C |
| ATOM | 11048 | CG | LEU | B | 186 | −37.010 | −21.124 | 14.292 | 1.00 | 54.96 C |
| ATOM | 11050 | CD1 | LEU | B | 186 | −36.956 | −21.958 | 13.014 | 1.00 | 52.21 C |
| ATOM | 11054 | CD2 | LEU | B | 186 | −37.401 | −21.989 | 15.489 | 1.00 | 54.82 C |
| ATOM | 11058 | C | LEU | B | 186 | −34.314 | −18.755 | 15.883 | 1.00 | 57.67 C |
| ATOM | 11059 | O | LEU | B | 186 | −34.372 | −17.549 | 15.613 | 1.00 | 57.57 O |
| ATOM | 11061 | N | TYR | B | 187 | −33.175 | −19.371 | 16.202 | 1.00 | 58.06 N |
| ATOM | 11062 | CA | TYR | B | 187 | −31.894 | −18.670 | 16.243 | 1.00 | 57.81 C |
| ATOM | 11064 | CB | TYR | B | 187 | −31.019 | −19.189 | 17.382 | 1.00 | 59.04 C |
| ATOM | 11067 | CG | TYR | B | 187 | −31.534 | −18.780 | 18.730 | 1.00 | 61.73 C |
| ATOM | 11068 | CD1 | TYR | B | 187 | −31.416 | −17.467 | 19.160 | 1.00 | 63.16 C |
| ATOM | 11070 | CE1 | TYR | B | 187 | −31.902 | −17.073 | 20.393 | 1.00 | 62.08 C |
| ATOM | 11072 | CZ | TYR | B | 187 | −32.519 | −17.996 | 21.206 | 1.00 | 60.34 C |
| ATOM | 11073 | OH | TYR | B | 187 | −32.993 | −17.596 | 22.429 | 1.00 | 62.56 O |
| ATOM | 11075 | CE2 | TYR | B | 187 | −32.655 | −19.310 | 20.801 | 1.00 | 60.08 C |
| ATOM | 11077 | CD2 | TYR | B | 187 | −32.168 | −19.694 | 19.568 | 1.00 | 63.07 C |
| ATOM | 11079 | C | TYR | B | 187 | −31.159 | −18.823 | 14.930 | 1.00 | 58.28 C |
| ATOM | 11080 | O | TYR | B | 187 | −31.404 | −19.766 | 14.171 | 1.00 | 58.80 O |
| ATOM | 11082 | N | SER | B | 188 | −30.254 | −17.882 | 14.677 | 1.00 | 58.08 N |
| ATOM | 11083 | CA | SER | B | 188 | −29.443 | −17.870 | 13.465 | 1.00 | 57.89 C |
| ATOM | 11085 | CB | SER | B | 188 | −30.237 | −17.265 | 12.299 | 1.00 | 58.09 C |
| ATOM | 11088 | OG | SER | B | 188 | −29.429 | −17.130 | 11.146 | 1.00 | 58.62 O |
| ATOM | 11090 | C | SER | B | 188 | −28.161 | −17.073 | 13.712 | 1.00 | 58.02 C |
| ATOM | 11091 | O | SER | B | 188 | −28.202 | −15.983 | 14.297 | 1.00 | 58.64 O |
| ATOM | 11093 | N | LEU | B | 189 | −27.030 | −17.630 | 13.282 | 1.00 | 56.99 N |
| ATOM | 11094 | CA | LEU | B | 189 | −25.739 | −16.958 | 13.402 | 1.00 | 56.45 C |
| ATOM | 11096 | CB | LEU | B | 189 | −25.023 | −17.360 | 14.705 | 1.00 | 56.10 C |
| ATOM | 11099 | CG | LEU | B | 189 | −24.424 | −18.773 | 14.886 | 1.00 | 55.79 C |
| ATOM | 11101 | CD1 | LEU | B | 189 | −23.070 | −18.949 | 14.183 | 1.00 | 55.76 C |
| ATOM | 11105 | CD2 | LEU | B | 189 | −24.276 | −19.121 | 16.374 | 1.00 | 55.78 C |
| ATOM | 11109 | C | LEU | B | 189 | −24.875 | −17.277 | 12.190 | 1.00 | 57.46 C |
| ATOM | 11110 | O | LEU | B | 189 | −25.180 | −18.190 | 11.415 | 1.00 | 58.38 O |
| ATOM | 11112 | N | SER | B | 190 | −23.805 | −16.503 | 12.032 | 1.00 | 56.80 N |
| ATOM | 11113 | CA | SER | B | 190 | −22.800 | −16.763 | 11.021 | 1.00 | 55.83 C |
| ATOM | 11115 | CB | SER | B | 190 | −22.747 | −15.619 | 10.013 | 1.00 | 55.86 C |
| ATOM | 11118 | OG | SER | B | 190 | −23.635 | −15.867 | 8.938 | 1.00 | 55.59 O |
| ATOM | 11120 | C | SER | B | 190 | −21.438 | −16.944 | 11.666 | 1.00 | 55.69 C |
| ATOM | 11121 | O | SER | B | 190 | −21.196 | −16.468 | 12.770 | 1.00 | 55.67 O |
| ATOM | 11123 | N | SER | B | 191 | −20.566 | −17.663 | 10.964 | 1.00 | 56.15 N |
| ATOM | 11124 | CA | SER | B | 191 | −19.149 | −17.770 | 11.305 | 1.00 | 55.29 C |
| ATOM | 11126 | CB | SER | B | 191 | −18.817 | −19.177 | 11.814 | 1.00 | 55.19 C |
| ATOM | 11129 | OG | SER | B | 191 | −17.557 | −19.211 | 12.463 | 1.00 | 52.68 O |
| ATOM | 11131 | C | SER | B | 191 | −18.360 | −17.444 | 10.036 | 1.00 | 55.60 C |

-continued

| ATOM | 11132 | O | SER | B | 191 | −18.728 | −17.875 | 8.943 | 1.00 | 55.41 | O |
|---|---|---|---|---|---|---|---|---|---|---|---|
| ATOM | 11134 | N | VAL | B | 192 | −17.288 | −16.676 | 10.181 | 1.00 | 55.17 | N |
| ATOM | 11135 | CA | VAL | B | 192 | −16.591 | −16.131 | 9.029 | 1.00 | 54.48 | C |
| ATOM | 11137 | CB | VAL | B | 192 | −17.286 | −14.828 | 8.565 | 1.00 | 53.82 | C |
| ATOM | 11139 | CG1 | VAL | B | 192 | −16.980 | −13.665 | 9.518 | 1.00 | 52.71 | C |
| ATOM | 11143 | CG2 | VAL | B | 192 | −16.897 | −14.491 | 7.137 | 1.00 | 53.89 | C |
| ATOM | 11147 | C | VAL | B | 192 | −15.117 | −15.875 | 9.342 | 1.00 | 54.97 | C |
| ATOM | 11148 | O | VAL | B | 192 | −14.650 | −16.163 | 10.448 | 1.00 | 55.22 | O |
| ATOM | 11150 | N | CYS | B | 207 | −16.049 | −25.963 | 7.676 | 1.00 | 54.86 | N |
| ATOM | 11151 | CA | CYS | B | 207 | −16.419 | −25.637 | 9.056 | 1.00 | 56.53 | C |
| ATOM | 11153 | CB | CYS | B | 207 | −17.285 | −24.369 | 9.099 | 1.00 | 56.31 | C |
| ATOM | 11156 | SG | CYS | B | 207 | −19.022 | −24.617 | 8.655 | 1.00 | 58.00 | S |
| ATOM | 11158 | C | CYS | B | 207 | −17.154 | −26.805 | 9.724 | 1.00 | 56.35 | C |
| ATOM | 11159 | O | CYS | B | 207 | −17.791 | −27.615 | 9.048 | 1.00 | 56.18 | O |
| ATOM | 11161 | N | ASN | B | 208 | −17.044 | −26.889 | 11.048 | 1.00 | 56.47 | N |
| ATOM | 11162 | CA | ASN | B | 208 | −17.747 | −27.902 | 11.840 | 1.00 | 56.52 | C |
| ATOM | 11164 | CB | ASN | B | 208 | −16.786 | −28.635 | 12.797 | 1.00 | 56.78 | C |
| ATOM | 11167 | CG | ASN | B | 208 | −15.723 | −29.443 | 12.078 | 1.00 | 54.16 | C |
| ATOM | 11168 | OD1 | ASN | B | 208 | −15.494 | −29.263 | 10.887 | 1.00 | 51.91 | O |
| ATOM | 11169 | ND2 | ASN | B | 208 | −15.068 | −30.345 | 12.808 | 1.00 | 48.76 | N |
| ATOM | 11172 | C | ASN | B | 208 | −18.821 | −27.242 | 12.685 | 1.00 | 56.17 | C |
| ATOM | 11173 | O | ASN | B | 208 | −18.540 | −26.794 | 13.797 | 1.00 | 56.49 | O |
| ATOM | 11175 | N | VAL | B | 209 | −20.045 | −27.178 | 12.175 | 1.00 | 55.42 | N |
| ATOM | 11176 | CA | VAL | B | 209 | −21.166 | −26.722 | 12.998 | 1.00 | 55.89 | C |
| ATOM | 11178 | CB | VAL | B | 209 | −22.338 | −26.194 | 12.141 | 1.00 | 55.09 | C |
| ATOM | 11180 | CG1 | VAL | B | 209 | −23.559 | −25.895 | 13.007 | 1.00 | 53.33 | C |
| ATOM | 11184 | CG2 | VAL | B | 209 | −21.909 | −24.955 | 11.367 | 1.00 | 53.58 | C |
| ATOM | 11188 | C | VAL | B | 209 | −21.607 | −27.885 | 13.895 | 1.00 | 56.01 | C |
| ATOM | 11189 | O | VAL | B | 209 | −21.630 | −29.037 | 13.459 | 1.00 | 56.65 | O |
| ATOM | 11191 | N | ASN | B | 210 | −21.925 | −27.581 | 15.150 | 1.00 | 56.29 | N |
| ATOM | 11192 | CA | ASN | B | 210 | −22.360 | −28.596 | 16.112 | 1.00 | 56.44 | C |
| ATOM | 11194 | CB | ASN | B | 210 | −21.183 | −29.037 | 16.993 | 1.00 | 56.72 | C |
| ATOM | 11197 | CG | ASN | B | 210 | −21.601 | −30.009 | 18.092 | 1.00 | 57.71 | C |
| ATOM | 11198 | OD1 | ASN | B | 210 | −21.491 | −31.226 | 17.943 | 1.00 | 61.62 | O |
| ATOM | 11199 | ND2 | ASN | B | 210 | −22.091 | −29.470 | 19.198 | 1.00 | 61.75 | N |
| ATOM | 11202 | C | ASN | B | 210 | −23.501 | −28.066 | 16.976 | 1.00 | 56.60 | C |
| ATOM | 11203 | O | ASN | B | 210 | −23.357 | −27.019 | 17.613 | 1.00 | 57.84 | O |
| ATOM | 11205 | N | HIS | B | 211 | −24.620 | −28.796 | 17.000 | 1.00 | 55.66 | N |
| ATOM | 11206 | CA | HIS | B | 211 | −25.807 | −28.392 | 17.756 | 1.00 | 56.04 | C |
| ATOM | 11208 | CB | HIS | B | 211 | −26.929 | −27.966 | 16.796 | 1.00 | 55.63 | C |
| ATOM | 11211 | CG | HIS | B | 211 | −28.188 | −27.528 | 17.482 | 1.00 | 56.30 | C |
| ATOM | 11212 | ND1 | HIS | B | 211 | −28.188 | −26.697 | 18.582 | 1.00 | 57.16 | N |
| ATOM | 11214 | CE1 | HIS | B | 211 | −29.433 | −26.482 | 18.966 | 1.00 | 55.91 | C |
| ATOM | 11216 | NE2 | HIS | B | 211 | −30.241 | −27.133 | 18.149 | 1.00 | 55.11 | N |
| ATOM | 11218 | CD2 | HIS | B | 211 | −29.487 | −27.797 | 17.215 | 1.00 | 54.92 | C |
| ATOM | 11220 | C | HIS | B | 211 | −26.257 | −29.529 | 18.680 | 1.00 | 56.66 | C |
| ATOM | 11221 | O | HIS | B | 211 | −27.142 | −30.323 | 18.341 | 1.00 | 57.63 | O |
| ATOM | 11223 | N | LYS | B | 212 | −25.646 | −29.587 | 19.861 | 1.00 | 56.14 | N |
| ATOM | 11224 | CA | LYS | B | 212 | −25.885 | −30.680 | 20.807 | 1.00 | 55.28 | C |
| ATOM | 11226 | CB | LYS | B | 212 | −25.077 | −30.473 | 22.090 | 1.00 | 54.88 | C |
| ATOM | 11229 | CG | LYS | B | 212 | −23.642 | −30.927 | 21.951 | 1.00 | 56.58 | C |
| ATOM | 11232 | CD | LYS | B | 212 | −22.683 | −30.153 | 22.846 | 1.00 | 56.60 | C |
| ATOM | 11235 | CE | LYS | B | 212 | −21.232 | −30.476 | 22.470 | 1.00 | 57.54 | C |
| ATOM | 11238 | NZ | LYS | B | 212 | −20.252 | −29.606 | 23.168 | 1.00 | 59.75 | N |
| ATOM | 11242 | C | LYS | B | 212 | −27.353 | −30.926 | 21.143 | 1.00 | 54.35 | C |
| ATOM | 11243 | O | LYS | B | 212 | −27.778 | −32.075 | 21.153 | 1.00 | 54.94 | O |
| ATOM | 11245 | N | PRO | B | 213 | −28.127 | −29.859 | 21.424 | 1.00 | 54.43 | N |
| ATOM | 11246 | CA | PRO | B | 213 | −29.548 | −30.017 | 21.764 | 1.00 | 53.34 | C |
| ATOM | 11248 | CB | PRO | B | 213 | −30.072 | −28.580 | 21.733 | 1.00 | 52.85 | C |
| ATOM | 11251 | CG | PRO | B | 213 | −28.905 | −27.756 | 22.105 | 1.00 | 54.65 | C |
| ATOM | 11254 | CD | PRO | B | 213 | −27.716 | −28.441 | 21.487 | 1.00 | 54.93 | C |
| ATOM | 11257 | C | PRO | B | 213 | −30.357 | −30.876 | 20.798 | 1.00 | 53.66 | C |
| ATOM | 11258 | O | PRO | B | 213 | −31.285 | −31.559 | 21.228 | 1.00 | 54.84 | O |
| ATOM | 11259 | N | SER | B | 214 | −30.023 | −30.829 | 19.509 | 1.00 | 53.19 | N |
| ATOM | 11260 | CA | SER | B | 214 | −30.718 | −31.623 | 18.505 | 1.00 | 51.84 | C |
| ATOM | 11262 | CB | SER | B | 214 | −31.213 | −30.723 | 17.372 | 1.00 | 52.17 | C |
| ATOM | 11265 | OG | SER | B | 214 | −30.219 | −30.578 | 16.372 | 1.00 | 49.60 | O |
| ATOM | 11267 | C | SER | B | 214 | −29.824 | −32.709 | 17.921 | 1.00 | 51.68 | C |
| ATOM | 11268 | O | SER | B | 214 | −30.157 | −33.280 | 16.881 | 1.00 | 50.86 | O |
| ATOM | 11270 | N | ASN | B | 215 | −28.693 | −32.990 | 18.571 | 1.00 | 51.08 | N |
| ATOM | 11271 | CA | ASN | B | 215 | −27.734 | −33.986 | 18.065 | 1.00 | 51.21 | C |
| ATOM | 11273 | CB | ASN | B | 215 | −28.305 | −35.398 | 18.265 | 1.00 | 51.21 | C |
| ATOM | 11276 | CG | ASN | B | 215 | −27.589 | −36.160 | 19.348 | 1.00 | 51.03 | C |
| ATOM | 11277 | OD1 | ASN | B | 215 | −27.975 | −36.125 | 20.526 | 1.00 | 42.90 | O |
| ATOM | 11278 | ND2 | ASN | B | 215 | −26.519 | −36.846 | 18.959 | 1.00 | 48.48 | N |
| ATOM | 11281 | C | ASN | B | 215 | −27.314 | −33.784 | 16.598 | 1.00 | 50.17 | C |
| ATOM | 11282 | O | ASN | B | 215 | −27.053 | −34.746 | 15.887 | 1.00 | 47.72 | O |
| ATOM | 11284 | N | THR | B | 216 | −27.226 | −32.529 | 16.170 | 1.00 | 50.54 | N |
| ATOM | 11285 | CA | THR | B | 216 | −26.949 | −32.199 | 14.782 | 1.00 | 51.78 | C |

| | | | | | -continued | | | | | |
|---|---|---|---|---|---|---|---|---|---|---|
| ATOM | 11287 | CB | THR | B | 216 | −27.861 | −31.051 | 14.300 | 1.00 | 51.31 | C |
| ATOM | 11289 | OG1 | THR | B | 216 | −29.231 | −31.446 | 14.428 | 1.00 | 51.33 | O |
| ATOM | 11291 | CG2 | THR | B | 216 | −27.567 | −30.676 | 12.849 | 1.00 | 49.41 | C |
| ATOM | 11295 | C | THR | B | 216 | −25.497 | −31.793 | 14.576 | 1.00 | 53.65 | C |
| ATOM | 11296 | O | THR | B | 216 | −25.179 | −30.605 | 14.568 | 1.00 | 55.97 | O |
| ATOM | 11298 | N | LYS | B | 217 | −24.614 | −32.779 | 14.416 | 1.00 | 54.64 | N |
| ATOM | 11299 | CA | LYS | B | 217 | −23.261 | −32.518 | 13.904 | 1.00 | 53.77 | C |
| ATOM | 11301 | CB | LYS | B | 217 | −22.290 | −33.680 | 14.186 | 1.00 | 55.54 | C |
| ATOM | 11304 | CG | LYS | B | 217 | −21.547 | −33.608 | 15.529 | 1.00 | 56.86 | C |
| ATOM | 11307 | CD | LYS | B | 217 | −20.019 | −33.579 | 15.321 | 1.00 | 59.77 | C |
| ATOM | 11310 | CE | LYS | B | 217 | −19.232 | −33.967 | 16.583 | 1.00 | 59.68 | C |
| ATOM | 11313 | NZ | LYS | B | 217 | −19.541 | −33.154 | 17.804 | 1.00 | 57.76 | N |
| ATOM | 11317 | C | LYS | B | 217 | −23.371 | −32.314 | 12.403 | 1.00 | 52.56 | C |
| ATOM | 11318 | O | LYS | B | 217 | −24.271 | −32.868 | 11.771 | 1.00 | 52.15 | O |
| ATOM | 11320 | N | VAL | B | 218 | −22.460 | −31.521 | 11.843 | 1.00 | 51.64 | N |
| ATOM | 11321 | CA | VAL | B | 218 | −22.422 | −31.266 | 10.395 | 1.00 | 51.59 | C |
| ATOM | 11323 | CB | VAL | B | 218 | −23.644 | −30.411 | 9.924 | 1.00 | 51.11 | C |
| ATOM | 11325 | CG1 | VAL | B | 218 | −23.941 | −29.302 | 10.916 | 1.00 | 52.27 | C |
| ATOM | 11329 | CG2 | VAL | B | 218 | −23.440 | −29.849 | 8.514 | 1.00 | 51.13 | C |
| ATOM | 11333 | C | VAL | B | 218 | −21.102 | −30.600 | 9.986 | 1.00 | 51.07 | C |
| ATOM | 11334 | O | VAL | B | 218 | −20.607 | −29.703 | 10.678 | 1.00 | 50.95 | O |
| ATOM | 11336 | N | ASP | B | 219 | −20.545 | −31.063 | 8.865 | 1.00 | 51.19 | N |
| ATOM | 11337 | CA | ASP | B | 219 | −19.296 | −30.543 | 8.311 | 1.00 | 51.13 | C |
| ATOM | 11339 | CB | ASP | B | 219 | −18.227 | −31.643 | 8.275 | 1.00 | 50.74 | C |
| ATOM | 11342 | CG | ASP | B | 219 | −17.914 | −32.205 | 9.649 | 1.00 | 50.73 | C |
| ATOM | 11343 | OD1 | ASP | B | 219 | −18.449 | −33.279 | 9.992 | 1.00 | 50.08 | O |
| ATOM | 11344 | OD2 | ASP | B | 219 | −17.138 | −31.572 | 10.390 | 1.00 | 48.77 | O |
| ATOM | 11345 | C | ASP | B | 219 | −19.534 | −30.014 | 6.899 | 1.00 | 51.08 | C |
| ATOM | 11346 | O | ASP | B | 219 | −19.593 | −30.788 | 5.942 | 1.00 | 50.93 | O |
| ATOM | 11348 | N | LYS | B | 220 | −19.689 | −28.697 | 6.775 | 1.00 | 51.69 | N |
| ATOM | 11349 | CA | LYS | B | 220 | −19.817 | −28.042 | 5.464 | 1.00 | 51.82 | C |
| ATOM | 11351 | CB | LYS | B | 220 | −20.766 | −26.833 | 5.555 | 1.00 | 51.81 | C |
| ATOM | 11354 | CG | LYS | B | 220 | −20.751 | −25.871 | 4.357 | 1.00 | 51.08 | C |
| ATOM | 11357 | CD | LYS | B | 220 | −21.316 | −26.491 | 3.090 | 1.00 | 51.47 | C |
| ATOM | 11360 | CE | LYS | B | 220 | −22.839 | −26.556 | 3.120 | 1.00 | 50.51 | C |
| ATOM | 11363 | NZ | LYS | B | 220 | −23.408 | −26.913 | 1.786 | 1.00 | 47.07 | N |
| ATOM | 11367 | C | LYS | B | 220 | −18.436 | −27.613 | 4.980 | 1.00 | 52.28 | C |
| ATOM | 11368 | O | LYS | B | 220 | −17.534 | −27.376 | 5.790 | 1.00 | 52.85 | O |
| ATOM | 11370 | N | LYS | C | 26 | 28.164 | −13.137 | 51.471 | 1.00 | 60.01 | N |
| ATOM | 11371 | CA | LYS | C | 26 | 29.169 | −13.369 | 52.563 | 1.00 | 59.98 | C |
| ATOM | 11373 | CB | LYS | C | 26 | 30.565 | −12.872 | 52.150 | 1.00 | 60.63 | C |
| ATOM | 11376 | CG | LYS | C | 26 | 31.654 | −13.161 | 53.179 | 1.00 | 58.50 | C |
| ATOM | 11379 | CD | LYS | C | 26 | 32.994 | −13.488 | 52.532 | 1.00 | 60.70 | C |
| ATOM | 11382 | CE | LYS | C | 26 | 33.823 | −12.249 | 52.201 | 1.00 | 63.05 | C |
| ATOM | 11385 | NZ | LYS | C | 26 | 35.179 | −12.625 | 51.670 | 1.00 | 61.96 | N |
| ATOM | 11389 | C | LYS | C | 26 | 28.736 | −12.699 | 53.867 | 1.00 | 59.05 | C |
| ATOM | 11390 | O | LYS | C | 26 | 28.399 | −11.512 | 53.886 | 1.00 | 58.89 | O |
| ATOM | 11394 | N | LYS | C | 27 | 28.748 | −13.467 | 54.953 | 1.00 | 57.05 | N |
| ATOM | 11395 | CA | LYS | C | 27 | 28.266 | −12.976 | 56.224 | 1.00 | 55.84 | C |
| ATOM | 11397 | CB | LYS | C | 27 | 28.153 | −14.119 | 57.221 | 1.00 | 55.53 | C |
| ATOM | 11400 | CG | LYS | C | 27 | 27.478 | −13.719 | 58.526 | 1.00 | 58.17 | C |
| ATOM | 11403 | CD | LYS | C | 27 | 27.092 | −14.934 | 59.391 | 1.00 | 58.02 | C |
| ATOM | 11406 | CE | LYS | C | 27 | 25.952 | −14.596 | 60.370 | 1.00 | 62.26 | C |
| ATOM | 11409 | NZ | LYS | C | 27 | 24.573 | −14.553 | 59.739 | 1.00 | 67.83 | N |
| ATOM | 11413 | C | LYS | C | 27 | 29.219 | −11.907 | 56.733 | 1.00 | 56.17 | C |
| ATOM | 11414 | O | LYS | C | 27 | 30.427 | −12.127 | 56.786 | 1.00 | 60.04 | O |
| ATOM | 11416 | N | VAL | C | 28 | 28.675 | −10.746 | 57.083 | 1.00 | 54.84 | N |
| ATOM | 11417 | CA | VAL | C | 28 | 29.463 | −9.623 | 57.596 | 1.00 | 51.88 | C |
| ATOM | 11419 | CB | VAL | C | 28 | 29.184 | −8.356 | 56.767 | 1.00 | 50.96 | C |
| ATOM | 11421 | CG1 | VAL | C | 28 | 29.497 | −7.086 | 57.541 | 1.00 | 54.32 | C |
| ATOM | 11425 | CG2 | VAL | C | 28 | 29.992 | −8.395 | 55.481 | 1.00 | 53.31 | C |
| ATOM | 11429 | C | VAL | C | 28 | 29.162 | −9.397 | 59.086 | 1.00 | 50.48 | C |
| ATOM | 11430 | O | VAL | C | 28 | 28.006 | −9.408 | 59.496 | 1.00 | 49.04 | O |
| ATOM | 11432 | N | VAL | C | 29 | 30.204 | −9.191 | 59.889 | 1.00 | 48.62 | N |
| ATOM | 11433 | CA | VAL | C | 29 | 30.038 | −8.995 | 61.325 | 1.00 | 48.51 | C |
| ATOM | 11435 | CB | VAL | C | 29 | 30.320 | −10.315 | 62.063 | 1.00 | 47.93 | C |
| ATOM | 11437 | CG1 | VAL | C | 29 | 30.342 | −10.127 | 63.598 | 1.00 | 47.74 | C |
| ATOM | 11441 | CG2 | VAL | C | 29 | 29.290 | −11.342 | 61.645 | 1.00 | 45.01 | C |
| ATOM | 11445 | C | VAL | C | 29 | 30.923 | −7.854 | 61.849 | 1.00 | 48.33 | C |
| ATOM | 11446 | O | VAL | C | 29 | 32.099 | −7.792 | 61.525 | 1.00 | 51.32 | O |
| ATOM | 11448 | N | LEU | C | 30 | 30.349 | −6.968 | 62.664 | 1.00 | 47.56 | N |
| ATOM | 11449 | CA | LEU | C | 30 | 31.028 | −5.753 | 63.103 | 1.00 | 48.48 | C |
| ATOM | 11451 | CB | LEU | C | 30 | 30.105 | −4.559 | 62.958 | 1.00 | 46.33 | C |
| ATOM | 11454 | CG | LEU | C | 30 | 29.439 | −4.407 | 61.599 | 1.00 | 48.81 | C |
| ATOM | 11456 | CD1 | LEU | C | 30 | 28.714 | −3.095 | 61.584 | 1.00 | 50.91 | C |
| ATOM | 11460 | CD2 | LEU | C | 30 | 30.445 | −4.468 | 60.459 | 1.00 | 53.26 | C |
| ATOM | 11464 | C | LEU | C | 30 | 31.465 | −5.825 | 64.544 | 1.00 | 50.16 | C |
| ATOM | 11465 | O | LEU | C | 30 | 30.711 | −6.301 | 65.381 | 1.00 | 53.16 | O |
| ATOM | 11467 | N | GLY | C | 31 | 32.671 | −5.337 | 64.839 | 1.00 | 50.43 | N |

| | | | | | | | | | | |
|---|---|---|---|---|---|---|---|---|---|---|
| ATOM | 11468 | CA | GLY | C | 31 | 33.162 | −5.274 | 66.215 | 1.00 | 51.69 C |
| ATOM | 11471 | C | GLY | C | 31 | 33.683 | −3.894 | 66.561 | 1.00 | 52.83 C |
| ATOM | 11472 | O | GLY | C | 31 | 34.135 | −3.173 | 65.682 | 1.00 | 54.58 O |
| ATOM | 11474 | N | LYS | C | 32 | 33.606 | −3.517 | 67.836 | 1.00 | 53.59 N |
| ATOM | 11475 | CA | LYS | C | 32 | 34.333 | −2.340 | 68.334 | 1.00 | 55.03 C |
| ATOM | 11477 | CB | LYS | C | 32 | 33.679 | −1.722 | 69.582 | 1.00 | 57.09 C |
| ATOM | 11480 | CG | LYS | C | 32 | 32.264 | −1.227 | 69.410 | 1.00 | 57.40 C |
| ATOM | 11483 | CD | LYS | C | 32 | 31.542 | −1.099 | 70.753 | 1.00 | 58.52 C |
| ATOM | 11486 | CE | LYS | C | 32 | 32.280 | −0.194 | 71.735 | 1.00 | 60.64 C |
| ATOM | 11489 | NZ | LYS | C | 32 | 31.338 | 0.582 | 72.579 | 1.00 | 62.18 N |
| ATOM | 11493 | C | LYS | C | 32 | 35.752 | −2.729 | 68.732 | 1.00 | 54.41 C |
| ATOM | 11494 | O | LYS | C | 32 | 35.966 | −3.763 | 69.391 | 1.00 | 51.25 O |
| ATOM | 11496 | N | LYS | C | 33 | 36.704 | −1.879 | 68.342 | 1.00 | 53.74 N |
| ATOM | 11497 | CA | LYS | C | 33 | 38.079 | −1.907 | 68.851 | 1.00 | 53.62 C |
| ATOM | 11499 | CB | LYS | C | 33 | 38.753 | −0.584 | 68.493 | 1.00 | 52.86 C |
| ATOM | 11502 | CG | LYS | C | 33 | 40.175 | −0.401 | 68.966 | 1.00 | 53.21 C |
| ATOM | 11505 | CD | LYS | C | 33 | 40.697 | 0.950 | 68.448 | 1.00 | 54.88 C |
| ATOM | 11508 | CE | LYS | C | 33 | 42.126 | 1.230 | 68.873 | 1.00 | 56.32 C |
| ATOM | 11511 | NZ | LYS | C | 33 | 42.898 | 1.847 | 67.763 | 1.00 | 59.96 N |
| ATOM | 11515 | C | LYS | C | 33 | 38.095 | −2.113 | 70.364 | 1.00 | 52.83 C |
| ATOM | 11516 | O | LYS | C | 33 | 37.467 | −1.352 | 71.102 | 1.00 | 52.70 O |
| ATOM | 11518 | N | GLY | C | 34 | 38.769 | −3.167 | 70.819 | 1.00 | 52.99 N |
| ATOM | 11519 | CA | GLY | C | 34 | 38.898 | −3.452 | 72.257 | 1.00 | 53.22 C |
| ATOM | 11522 | C | GLY | C | 34 | 37.936 | −4.485 | 72.827 | 1.00 | 52.44 C |
| ATOM | 11523 | O | GLY | C | 34 | 38.268 | −5.188 | 73.781 | 1.00 | 50.64 O |
| ATOM | 11525 | N | ASP | C | 35 | 36.742 | −4.586 | 72.257 | 1.00 | 53.38 N |
| ATOM | 11526 | CA | ASP | C | 35 | 35.770 | −5.574 | 72.719 | 1.00 | 54.95 C |
| ATOM | 11528 | CB | ASP | C | 35 | 34.368 | −5.274 | 72.165 | 1.00 | 56.98 C |
| ATOM | 11531 | CG | ASP | C | 35 | 33.727 | −4.056 | 72.806 | 1.00 | 63.61 C |
| ATOM | 11532 | OD1 | ASP | C | 35 | 34.421 | −3.325 | 73.557 | 1.00 | 70.58 O |
| ATOM | 11533 | OD2 | ASP | C | 35 | 32.523 | −3.830 | 72.547 | 1.00 | 72.74 O |
| ATOM | 11534 | C | ASP | C | 35 | 36.188 | −6.968 | 72.301 | 1.00 | 52.79 C |
| ATOM | 11535 | O | ASP | C | 35 | 37.206 | −7.153 | 71.653 | 1.00 | 52.66 O |
| ATOM | 11537 | N | THR | C | 36 | 35.404 | −7.953 | 72.700 | 1.00 | 52.25 N |
| ATOM | 11538 | CA | THR | C | 36 | 35.542 | −9.270 | 72.130 | 1.00 | 53.63 C |
| ATOM | 11540 | CB | THR | C | 36 | 35.588 | −10.390 | 73.201 | 1.00 | 53.74 C |
| ATOM | 11542 | OG1 | THR | C | 36 | 34.273 | −10.880 | 73.433 | 1.00 | 55.27 O |
| ATOM | 11544 | CG2 | THR | C | 36 | 36.191 | −9.900 | 74.515 | 1.00 | 54.22 C |
| ATOM | 11548 | C | THR | C | 36 | 34.373 | −9.493 | 71.173 | 1.00 | 54.02 C |
| ATOM | 11549 | O | THR | C | 36 | 33.337 | −8.825 | 71.266 | 1.00 | 53.73 O |
| ATOM | 11551 | N | VAL | C | 37 | 34.557 | −10.415 | 70.238 | 1.00 | 54.25 N |
| ATOM | 11552 | CA | VAL | C | 37 | 33.502 | −10.784 | 69.310 | 1.00 | 54.17 C |
| ATOM | 11554 | CB | VAL | C | 37 | 33.690 | −10.133 | 67.929 | 1.00 | 53.80 C |
| ATOM | 11556 | CG1 | VAL | C | 37 | 35.001 | −10.564 | 67.299 | 1.00 | 56.09 C |
| ATOM | 11560 | CG2 | VAL | C | 37 | 32.510 | −10.467 | 67.004 | 1.00 | 54.53 C |
| ATOM | 11564 | C | VAL | C | 37 | 33.499 | −12.290 | 69.177 | 1.00 | 54.74 C |
| ATOM | 11565 | O | VAL | C | 37 | 34.540 | −12.929 | 69.362 | 1.00 | 54.93 O |
| ATOM | 11567 | N | GLU | C | 38 | 32.326 | −12.846 | 68.878 | 1.00 | 55.08 N |
| ATOM | 11568 | CA | GLU | C | 38 | 32.159 | −14.281 | 68.700 | 1.00 | 54.83 C |
| ATOM | 11570 | CB | GLU | C | 38 | 31.117 | −14.816 | 69.684 | 1.00 | 55.08 C |
| ATOM | 11573 | CG | GLU | C | 38 | 30.929 | −16.326 | 69.617 | 1.00 | 57.61 C |
| ATOM | 11576 | CD | GLU | C | 38 | 30.170 | −16.914 | 70.808 | 1.00 | 60.50 C |
| ATOM | 11577 | OE1 | GLU | C | 38 | 30.197 | −16.329 | 71.920 | 1.00 | 67.06 O |
| ATOM | 11578 | OE2 | GLU | C | 38 | 29.550 | −17.986 | 70.623 | 1.00 | 70.26 O |
| ATOM | 11579 | C | GLU | C | 38 | 31.734 | −14.567 | 67.267 | 1.00 | 53.48 C |
| ATOM | 11580 | O | GLU | C | 38 | 30.671 | −14.137 | 66.835 | 1.00 | 54.35 O |
| ATOM | 11582 | N | LEU | C | 39 | 32.578 | −15.273 | 66.524 | 1.00 | 51.18 N |
| ATOM | 11583 | CA | LEU | C | 39 | 32.232 | −15.688 | 65.183 | 1.00 | 50.96 C |
| ATOM | 11585 | CB | LEU | C | 39 | 33.442 | −15.564 | 64.262 | 1.00 | 51.16 C |
| ATOM | 11588 | CG | LEU | C | 39 | 34.228 | −14.243 | 64.260 | 1.00 | 56.33 C |
| ATOM | 11590 | CD1 | LEU | C | 39 | 35.338 | −14.271 | 63.195 | 1.00 | 55.53 C |
| ATOM | 11594 | CD2 | LEU | C | 39 | 33.316 | −13.030 | 64.047 | 1.00 | 58.88 C |
| ATOM | 11598 | C | LEU | C | 39 | 31.728 | −17.141 | 65.255 | 1.00 | 51.32 C |
| ATOM | 11599 | O | LEU | C | 39 | 32.482 | −18.054 | 65.607 | 1.00 | 50.22 O |
| ATOM | 11601 | N | THR | C | 40 | 30.452 | −17.351 | 64.934 | 1.00 | 49.60 N |
| ATOM | 11602 | CA | THR | C | 40 | 29.842 | −18.664 | 65.100 | 1.00 | 48.53 C |
| ATOM | 11604 | CB | THR | C | 40 | 28.295 | −18.599 | 65.232 | 1.00 | 47.90 C |
| ATOM | 11606 | OG1 | THR | C | 40 | 27.721 | −18.140 | 64.013 | 1.00 | 49.16 O |
| ATOM | 11608 | CG2 | THR | C | 40 | 27.879 | −17.660 | 66.343 | 1.00 | 49.93 C |
| ATOM | 11612 | C | THR | C | 40 | 30.193 | −19.581 | 63.952 | 1.00 | 45.05 C |
| ATOM | 11613 | O | THR | C | 40 | 30.483 | −19.144 | 62.859 | 1.00 | 42.59 O |
| ATOM | 11615 | N | CYS | C | 41 | 30.185 | −20.868 | 64.233 | 1.00 | 46.96 N |
| ATOM | 11616 | CA | CYS | C | 41 | 30.311 | −21.876 | 63.206 | 1.00 | 46.67 C |
| ATOM | 11618 | CB | CYS | C | 41 | 31.772 | −22.189 | 62.931 | 1.00 | 47.21 C |
| ATOM | 11621 | SG | CYS | C | 41 | 32.041 | −23.392 | 61.602 | 1.00 | 51.63 S |
| ATOM | 11623 | C | CYS | C | 41 | 29.590 | −23.098 | 63.736 | 1.00 | 46.73 C |
| ATOM | 11624 | O | CYS | C | 41 | 30.068 | −23.759 | 64.656 | 1.00 | 48.14 O |
| ATOM | 11626 | N | THR | C | 42 | 28.412 | −23.360 | 63.192 | 1.00 | 44.51 N |
| ATOM | 11627 | CA | THR | C | 42 | 27.601 | −24.442 | 63.668 | 1.00 | 45.24 C |

-continued

| | | | | | | | | | |
|---|---|---|---|---|---|---|---|---|---|
| ATOM | 11629 | CB | THR | C | 42 | 26.185 | −23.975 | 63.991 | 1.00 | 45.83 | C |
| ATOM | 11631 | OG1 | THR | C | 42 | 26.251 | −22.803 | 64.806 | 1.00 | 47.28 | O |
| ATOM | 11633 | CG2 | THR | C | 42 | 25.410 | −25.059 | 64.732 | 1.00 | 44.75 | C |
| ATOM | 11637 | C | THR | C | 42 | 27.557 | −25.476 | 62.577 | 1.00 | 46.40 | C |
| ATOM | 11638 | O | THR | C | 42 | 27.142 | −25.184 | 61.455 | 1.00 | 47.68 | O |
| ATOM | 11640 | N | ALA | C | 43 | 27.992 | −26.683 | 62.910 | 1.00 | 46.08 | N |
| ATOM | 11641 | CA | ALA | C | 43 | 27.946 | −27.780 | 61.981 | 1.00 | 47.28 | C |
| ATOM | 11643 | CB | ALA | C | 43 | 28.871 | −28.877 | 62.440 | 1.00 | 47.90 | C |
| ATOM | 11647 | C | ALA | C | 43 | 26.520 | −28.299 | 61.854 | 1.00 | 47.86 | C |
| ATOM | 11648 | O | ALA | C | 43 | 25.673 | −28.014 | 62.699 | 1.00 | 46.45 | O |
| ATOM | 11650 | N | SER | C | 44 | 26.272 | −29.060 | 60.788 | 1.00 | 49.88 | N |
| ATOM | 11651 | CA | SER | C | 44 | 24.988 | −29.714 | 60.563 | 1.00 | 51.53 | C |
| ATOM | 11653 | CB | SER | C | 44 | 24.991 | −30.481 | 59.241 | 1.00 | 52.86 | C |
| ATOM | 11656 | OG | SER | C | 44 | 24.590 | −29.632 | 58.181 | 1.00 | 59.29 | O |
| ATOM | 11658 | C | SER | C | 44 | 24.640 | −30.664 | 61.685 | 1.00 | 51.75 | C |
| ATOM | 11659 | O | SER | C | 44 | 23.523 | −30.652 | 62.176 | 1.00 | 53.82 | O |
| ATOM | 11661 | N | GLN | C | 45 | 25.599 | −31.485 | 62.088 | 1.00 | 52.81 | N |
| ATOM | 11662 | CA | GLN | C | 45 | 25.367 | −32.476 | 63.134 | 1.00 | 54.12 | C |
| ATOM | 11664 | CB | GLN | C | 45 | 26.247 | −33.695 | 62.887 | 1.00 | 55.04 | C |
| ATOM | 11667 | CG | GLN | C | 45 | 25.933 | −34.407 | 61.572 | 1.00 | 55.90 | C |
| ATOM | 11670 | CD | GLN | C | 45 | 27.048 | −35.325 | 61.108 | 1.00 | 55.97 | C |
| ATOM | 11671 | OE1 | GLN | C | 45 | 28.232 | −35.050 | 61.325 | 1.00 | 64.59 | O |
| ATOM | 11672 | NE2 | GLN | C | 45 | 26.676 | −36.419 | 60.452 | 1.00 | 59.45 | N |
| ATOM | 11675 | C | GLN | C | 45 | 25.664 | −31.889 | 64.506 | 1.00 | 54.60 | C |
| ATOM | 11676 | O | GLN | C | 45 | 26.526 | −31.023 | 64.626 | 1.00 | 56.59 | O |
| ATOM | 11678 | N | LYS | C | 46 | 24.953 | −32.362 | 65.533 | 1.00 | 54.27 | N |
| ATOM | 11679 | CA | LYS | C | 46 | 25.227 | −31.980 | 66.924 | 1.00 | 54.48 | C |
| ATOM | 11681 | CB | LYS | C | 46 | 23.968 | −32.086 | 67.794 | 1.00 | 54.52 | C |
| ATOM | 11684 | CG | LYS | C | 46 | 22.783 | −31.267 | 67.365 | 1.00 | 52.41 | C |
| ATOM | 11687 | CD | LYS | C | 46 | 21.924 | −30.866 | 68.572 | 1.00 | 54.77 | C |
| ATOM | 11690 | CE | LYS | C | 46 | 21.458 | −32.064 | 69.406 | 1.00 | 57.20 | C |
| ATOM | 11693 | NZ | LYS | C | 46 | 20.435 | −31.672 | 70.427 | 1.00 | 56.68 | N |
| ATOM | 11697 | C | LYS | C | 46 | 26.303 | −32.886 | 67.536 | 1.00 | 54.76 | C |
| ATOM | 11698 | O | LYS | C | 46 | 26.115 | −33.467 | 68.603 | 1.00 | 53.95 | O |
| ATOM | 11700 | N | LYS | C | 47 | 27.431 | −32.999 | 66.858 | 1.00 | 56.37 | N |
| ATOM | 11701 | CA | LYS | C | 47 | 28.505 | −33.874 | 67.280 | 1.00 | 56.39 | C |
| ATOM | 11703 | CB | LYS | C | 47 | 28.653 | −35.010 | 66.261 | 1.00 | 56.71 | C |
| ATOM | 11706 | CG | LYS | C | 47 | 29.576 | −36.134 | 66.686 | 1.00 | 57.86 | C |
| ATOM | 11709 | CD | LYS | C | 47 | 29.487 | −37.345 | 65.752 | 1.00 | 58.87 | C |
| ATOM | 11712 | CE | LYS | C | 47 | 30.158 | −38.579 | 66.391 | 1.00 | 62.40 | C |
| ATOM | 11715 | NZ | LYS | C | 47 | 29.723 | −39.892 | 65.808 | 1.00 | 62.09 | N |
| ATOM | 11719 | C | LYS | C | 47 | 29.761 | −33.015 | 67.360 | 1.00 | 56.23 | C |
| ATOM | 11720 | O | LYS | C | 47 | 29.801 | −31.925 | 66.786 | 1.00 | 55.56 | O |
| ATOM | 11722 | N | SER | C | 48 | 30.766 | −33.480 | 68.096 | 1.00 | 56.31 | N |
| ATOM | 11723 | CA | SER | C | 48 | 32.079 | −32.832 | 68.102 | 1.00 | 56.56 | C |
| ATOM | 11725 | CB | SER | C | 48 | 32.761 | −33.040 | 69.452 | 1.00 | 57.19 | C |
| ATOM | 11728 | OG | SER | C | 48 | 33.877 | −32.182 | 69.593 | 1.00 | 61.69 | O |
| ATOM | 11730 | C | SER | C | 48 | 32.947 | −33.401 | 66.967 | 1.00 | 55.96 | C |
| ATOM | 11731 | O | SER | C | 48 | 33.245 | −34.588 | 66.950 | 1.00 | 55.51 | O |
| ATOM | 11733 | N | ILE | C | 49 | 33.326 | −32.559 | 66.009 | 1.00 | 55.40 | N |
| ATOM | 11734 | CA | ILE | C | 49 | 34.099 | −33.003 | 64.849 | 1.00 | 54.42 | C |
| ATOM | 11736 | CB | ILE | C | 49 | 33.361 | −32.770 | 63.506 | 1.00 | 55.01 | C |
| ATOM | 11738 | CG1 | ILE | C | 49 | 31.858 | −33.008 | 63.637 | 1.00 | 55.05 | C |
| ATOM | 11741 | CD1 | ILE | C | 49 | 31.500 | −34.398 | 64.102 | 1.00 | 61.71 | C |
| ATOM | 11745 | CG2 | ILE | C | 49 | 33.979 | −33.638 | 62.392 | 1.00 | 56.17 | C |
| ATOM | 11749 | C | ILE | C | 49 | 35.362 | −32.182 | 64.778 | 1.00 | 53.51 | C |
| ATOM | 11750 | O | ILE | C | 49 | 35.442 | −31.136 | 65.418 | 1.00 | 52.65 | O |
| ATOM | 11752 | N | GLN | C | 50 | 36.331 | −32.660 | 63.991 | 1.00 | 53.17 | N |
| ATOM | 11753 | CA | GLN | C | 50 | 37.566 | −31.925 | 63.699 | 1.00 | 52.52 | C |
| ATOM | 11755 | CB | GLN | C | 50 | 38.513 | −32.783 | 62.851 | 1.00 | 52.60 | C |
| ATOM | 11758 | CG | GLN | C | 50 | 39.904 | −32.186 | 62.617 | 1.00 | 54.35 | C |
| ATOM | 11761 | CD | GLN | C | 50 | 40.876 | −32.469 | 63.759 | 1.00 | 59.17 | C |
| ATOM | 11762 | OE1 | GLN | C | 50 | 41.207 | −33.626 | 64.041 | 1.00 | 62.37 | O |
| ATOM | 11763 | NE2 | GLN | C | 50 | 41.346 | −31.411 | 64.411 | 1.00 | 57.50 | N |
| ATOM | 11766 | C | GLN | C | 50 | 37.252 | −30.628 | 62.957 | 1.00 | 50.99 | C |
| ATOM | 11767 | O | GLN | C | 50 | 36.667 | −30.653 | 61.875 | 1.00 | 50.10 | O |
| ATOM | 11769 | N | PHE | C | 51 | 37.631 | −29.500 | 63.547 | 1.00 | 49.43 | N |
| ATOM | 11770 | CA | PHE | C | 51 | 37.421 | −28.218 | 62.906 | 1.00 | 51.04 | C |
| ATOM | 11772 | CB | PHE | C | 51 | 36.202 | −27.512 | 63.508 | 1.00 | 51.97 | C |
| ATOM | 11775 | CG | PHE | C | 51 | 36.476 | −26.821 | 64.814 | 1.00 | 52.93 | C |
| ATOM | 11776 | CD1 | PHE | C | 51 | 36.221 | −27.461 | 66.016 | 1.00 | 55.61 | C |
| ATOM | 11778 | CE1 | PHE | C | 51 | 36.471 | −26.819 | 67.231 | 1.00 | 55.44 | C |
| ATOM | 11780 | CZ | PHE | C | 51 | 36.985 | −25.524 | 67.238 | 1.00 | 53.11 | C |
| ATOM | 11782 | CE2 | PHE | C | 51 | 37.240 | −24.878 | 66.041 | 1.00 | 50.74 | C |
| ATOM | 11784 | CD2 | PHE | C | 51 | 36.977 | −25.520 | 64.840 | 1.00 | 50.87 | C |
| ATOM | 11786 | C | PHE | C | 51 | 38.662 | −27.349 | 63.033 | 1.00 | 50.80 | C |
| ATOM | 11787 | O | PHE | C | 51 | 39.440 | −27.512 | 63.976 | 1.00 | 50.32 | O |
| ATOM | 11789 | N | HIS | C | 52 | 38.846 | −26.449 | 62.064 | 1.00 | 50.35 | N |
| ATOM | 11790 | CA | HIS | C | 52 | 39.877 | −25.414 | 62.131 | 1.00 | 51.58 | C |

-continued

| | | | | | | | | | | |
|---|---|---|---|---|---|---|---|---|---|---|
| ATOM | 11792 | CB | HIS | C | 52 | 41.092 | −25.721 | 61.239 | 1.00 | 54.29 C |
| ATOM | 11795 | CG | HIS | C | 52 | 41.352 | −27.177 | 61.032 | 1.00 | 61.03 C |
| ATOM | 11796 | ND1 | HIS | C | 52 | 42.530 | −27.782 | 61.420 | 1.00 | 64.68 N |
| ATOM | 11798 | CE1 | HIS | C | 52 | 42.485 | −29.065 | 61.103 | 1.00 | 69.28 C |
| ATOM | 11800 | NE2 | HIS | C | 52 | 41.319 | −29.313 | 60.529 | 1.00 | 71.55 N |
| ATOM | 11802 | CD2 | HIS | C | 52 | 40.595 | −28.147 | 60.466 | 1.00 | 64.78 C |
| ATOM | 11804 | C | HIS | C | 52 | 39.303 | −24.101 | 61.648 | 1.00 | 49.52 C |
| ATOM | 11805 | O | HIS | C | 52 | 38.661 | −24.047 | 60.606 | 1.00 | 45.19 O |
| ATOM | 11807 | N | TRP | C | 53 | 39.564 | −23.041 | 62.398 | 1.00 | 50.33 N |
| ATOM | 11808 | CA | TRP | C | 53 | 39.377 | −21.692 | 61.901 | 1.00 | 50.90 C |
| ATOM | 11810 | CB | TRP | C | 53 | 39.007 | −20.760 | 63.037 | 1.00 | 50.92 C |
| ATOM | 11813 | CG | TRP | C | 53 | 37.574 | −20.747 | 63.361 | 1.00 | 52.00 C |
| ATOM | 11814 | CD1 | TRP | C | 53 | 36.930 | −21.525 | 64.281 | 1.00 | 50.78 C |
| ATOM | 11816 | NE1 | TRP | C | 53 | 35.598 | −21.206 | 64.309 | 1.00 | 50.62 N |
| ATOM | 11818 | CE2 | TRP | C | 53 | 35.357 | −20.200 | 63.409 | 1.00 | 52.10 C |
| ATOM | 11819 | CD2 | TRP | C | 53 | 36.585 | −19.884 | 62.794 | 1.00 | 51.07 C |
| ATOM | 11820 | CE3 | TRP | C | 53 | 36.619 | −18.874 | 61.828 | 1.00 | 51.36 C |
| ATOM | 11822 | CZ3 | TRP | C | 53 | 35.429 | −18.217 | 61.505 | 1.00 | 52.54 C |
| ATOM | 11824 | CH2 | TRP | C | 53 | 34.218 | −18.557 | 62.138 | 1.00 | 50.79 C |
| ATOM | 11826 | CZ2 | TRP | C | 53 | 34.164 | −19.537 | 63.090 | 1.00 | 51.23 C |
| ATOM | 11828 | C | TRP | C | 53 | 40.684 | −21.215 | 61.288 | 1.00 | 50.71 C |
| ATOM | 11829 | O | TRP | C | 53 | 41.751 | −21.492 | 61.837 | 1.00 | 49.29 O |
| ATOM | 11831 | N | LYS | C | 54 | 40.606 | −20.502 | 60.164 | 1.00 | 51.43 N |
| ATOM | 11832 | CA | LYS | C | 54 | 41.786 | −19.846 | 59.592 | 1.00 | 54.01 C |
| ATOM | 11834 | CB | LYS | C | 54 | 42.523 | −20.771 | 58.615 | 1.00 | 54.33 C |
| ATOM | 11837 | CG | LYS | C | 54 | 41.668 | −21.433 | 57.559 | 1.00 | 57.34 C |
| ATOM | 11840 | CD | LYS | C | 54 | 42.530 | −22.177 | 56.525 | 1.00 | 59.68 C |
| ATOM | 11843 | CE | LYS | C | 54 | 43.137 | −23.468 | 57.082 | 1.00 | 65.29 C |
| ATOM | 11846 | NZ | LYS | C | 54 | 44.174 | −23.216 | 58.126 | 1.00 | 64.51 N |
| ATOM | 11850 | C | LYS | C | 54 | 41.465 | −18.499 | 58.944 | 1.00 | 53.86 C |
| ATOM | 11851 | O | LYS | C | 54 | 40.311 | −18.213 | 58.620 | 1.00 | 54.20 O |
| ATOM | 11853 | N | ASN | C | 55 | 42.492 | −17.661 | 58.793 | 1.00 | 53.28 N |
| ATOM | 11854 | CA | ASN | C | 55 | 42.309 | −16.338 | 58.195 | 1.00 | 52.70 C |
| ATOM | 11856 | CB | ASN | C | 55 | 43.340 | −15.327 | 58.710 | 1.00 | 52.32 C |
| ATOM | 11859 | CG | ASN | C | 55 | 44.748 | −15.578 | 58.175 | 1.00 | 56.98 C |
| ATOM | 11860 | OD1 | ASN | C | 55 | 44.954 | −16.362 | 57.243 | 1.00 | 62.48 O |
| ATOM | 11861 | ND2 | ASN | C | 55 | 45.726 | −14.908 | 58.770 | 1.00 | 52.08 N |
| ATOM | 11864 | C | ASN | C | 55 | 42.361 | −16.476 | 56.685 | 1.00 | 52.05 C |
| ATOM | 11865 | O | ASN | C | 55 | 42.626 | −17.565 | 56.178 | 1.00 | 53.34 O |
| ATOM | 11867 | N | SER | C | 56 | 42.107 | −15.378 | 55.977 | 1.00 | 51.78 N |
| ATOM | 11868 | CA | SER | C | 56 | 41.969 | −15.402 | 54.520 | 1.00 | 50.44 C |
| ATOM | 11870 | CB | SER | C | 56 | 41.379 | −14.088 | 54.002 | 1.00 | 52.03 C |
| ATOM | 11873 | OG | SER | C | 56 | 42.232 | −12.986 | 54.269 | 1.00 | 47.78 O |
| ATOM | 11875 | C | SER | C | 56 | 43.280 | −15.681 | 53.808 | 1.00 | 49.37 C |
| ATOM | 11876 | O | SER | C | 56 | 43.266 | −16.096 | 52.660 | 1.00 | 49.39 O |
| ATOM | 11878 | N | ASN | C | 57 | 44.407 | −15.451 | 54.480 | 1.00 | 48.93 N |
| ATOM | 11879 | CA | ASN | C | 57 | 45.716 | −15.845 | 53.942 | 1.00 | 48.85 C |
| ATOM | 11881 | CB | ASN | C | 57 | 46.818 | −14.913 | 54.464 | 1.00 | 46.84 C |
| ATOM | 11884 | CG | ASN | C | 57 | 48.106 | −15.016 | 53.666 | 1.00 | 47.55 C |
| ATOM | 11885 | OD1 | ASN | C | 57 | 48.100 | −15.441 | 52.507 | 1.00 | 41.91 O |
| ATOM | 11886 | ND2 | ASN | C | 57 | 49.226 | −14.631 | 54.290 | 1.00 | 40.76 N |
| ATOM | 11889 | C | ASN | C | 57 | 46.057 | −17.310 | 54.255 | 1.00 | 49.15 C |
| ATOM | 11890 | O | ASN | C | 57 | 47.199 | −17.725 | 54.094 | 1.00 | 49.21 O |
| ATOM | 11892 | N | GLN | C | 58 | 45.061 | −18.085 | 54.698 | 1.00 | 49.87 N |
| ATOM | 11893 | CA | GLN | C | 58 | 45.193 | −19.533 | 54.929 | 1.00 | 49.83 C |
| ATOM | 11895 | CB | GLN | C | 58 | 45.604 | −20.260 | 53.637 | 1.00 | 51.88 C |
| ATOM | 11898 | CG | GLN | C | 58 | 44.591 | −20.107 | 52.509 | 1.00 | 57.51 C |
| ATOM | 11901 | CD | GLN | C | 58 | 43.262 | −20.740 | 52.868 | 1.00 | 63.74 C |
| ATOM | 11902 | OE1 | GLN | C | 58 | 43.185 | −21.955 | 53.077 | 1.00 | 70.68 O |
| ATOM | 11903 | NE2 | GLN | C | 58 | 42.215 | −19.919 | 52.976 | 1.00 | 60.17 N |
| ATOM | 11906 | C | GLN | C | 58 | 46.136 | −19.887 | 56.074 | 1.00 | 48.57 C |
| ATOM | 11907 | O | GLN | C | 58 | 46.795 | −20.919 | 56.049 | 1.00 | 48.86 O |
| ATOM | 11909 | N | ILE | C | 59 | 46.171 | −19.028 | 57.083 | 1.00 | 47.49 N |
| ATOM | 11910 | CA | ILE | C | 59 | 46.969 | −19.247 | 58.275 | 1.00 | 47.89 C |
| ATOM | 11912 | CB | ILE | C | 59 | 47.631 | −17.929 | 58.699 | 1.00 | 46.22 C |
| ATOM | 11914 | CG1 | ILE | C | 59 | 48.799 | −17.640 | 57.752 | 1.00 | 48.38 C |
| ATOM | 11917 | CD1 | ILE | C | 59 | 49.292 | −16.207 | 57.795 | 1.00 | 51.54 C |
| ATOM | 11921 | CG2 | ILE | C | 59 | 48.118 | −17.981 | 60.146 | 1.00 | 46.49 C |
| ATOM | 11925 | C | ILE | C | 59 | 46.080 | −19.816 | 59.382 | 1.00 | 47.68 C |
| ATOM | 11926 | O | ILE | C | 59 | 45.030 | −19.252 | 59.694 | 1.00 | 47.67 O |
| ATOM | 11928 | N | LYS | C | 60 | 46.496 | −20.934 | 59.969 | 1.00 | 48.47 N |
| ATOM | 11929 | CA | LYS | C | 60 | 45.711 | −21.585 | 61.023 | 1.00 | 50.47 C |
| ATOM | 11931 | CB | LYS | C | 60 | 46.325 | −22.940 | 61.414 | 1.00 | 52.15 C |
| ATOM | 11934 | CG | LYS | C | 60 | 46.128 | −24.058 | 60.372 | 1.00 | 55.65 C |
| ATOM | 11937 | CD | LYS | C | 60 | 47.158 | −25.182 | 60.533 | 1.00 | 56.86 C |
| ATOM | 11940 | CE | LYS | C | 60 | 46.864 | −26.390 | 59.628 | 1.00 | 60.51 C |
| ATOM | 11943 | NZ | LYS | C | 60 | 45.893 | −27.364 | 60.218 | 1.00 | 59.92 N |
| ATOM | 11947 | C | LYS | C | 60 | 45.616 | −20.693 | 62.255 | 1.00 | 49.45 C |
| ATOM | 11948 | O | LYS | C | 60 | 46.640 | −20.319 | 62.834 | 1.00 | 49.71 O |

-continued

| | | | | | | | | | | |
|---|---|---|---|---|---|---|---|---|---|---|
| ATOM | 11950 | N | ILE | C | 61 | 44.391 | −20.342 | 62.643 | 1.00 | 48.86 N |
| ATOM | 11951 | CA | ILE | C | 61 | 44.159 | −19.597 | 63.884 | 1.00 | 49.70 C |
| ATOM | 11953 | CB | ILE | C | 61 | 42.869 | −18.756 | 63.846 | 1.00 | 49.40 C |
| ATOM | 11955 | CG1 | ILE | C | 61 | 42.859 | −17.792 | 62.645 | 1.00 | 55.67 C |
| ATOM | 11958 | CD1 | ILE | C | 61 | 43.969 | −16.746 | 62.640 | 1.00 | 60.68 C |
| ATOM | 11962 | CG2 | ILE | C | 61 | 42.694 | −18.019 | 65.173 | 1.00 | 47.13 C |
| ATOM | 11966 | C | ILE | C | 61 | 44.044 | −20.575 | 65.053 | 1.00 | 49.52 C |
| ATOM | 11967 | O | ILE | C | 61 | 44.846 | −20.539 | 65.995 | 1.00 | 49.21 O |
| ATOM | 11969 | N | LEU | C | 62 | 43.031 | −21.433 | 64.992 | 1.00 | 49.01 N |
| ATOM | 11970 | CA | LEU | C | 62 | 42.840 | −22.452 | 66.001 | 1.00 | 48.54 C |
| ATOM | 11972 | CB | LEU | C | 62 | 42.273 | −21.854 | 67.304 | 1.00 | 49.35 C |
| ATOM | 11975 | CG | LEU | C | 62 | 40.911 | −21.151 | 67.410 | 1.00 | 49.77 C |
| ATOM | 11977 | CD1 | LEU | C | 62 | 39.740 | −22.087 | 67.148 | 1.00 | 55.73 C |
| ATOM | 11981 | CD2 | LEU | C | 62 | 40.772 | −20.551 | 68.803 | 1.00 | 49.08 C |
| ATOM | 11985 | C | LEU | C | 62 | 41.978 | −23.611 | 65.521 | 1.00 | 47.29 C |
| ATOM | 11986 | O | LEU | C | 62 | 41.242 | −23.524 | 64.530 | 1.00 | 43.42 O |
| ATOM | 11988 | N | GLY | C | 63 | 42.105 | −24.712 | 66.242 | 1.00 | 47.91 N |
| ATOM | 11989 | CA | GLY | C | 63 | 41.293 | −25.883 | 66.000 | 1.00 | 49.38 C |
| ATOM | 11992 | C | GLY | C | 63 | 41.284 | −26.752 | 67.230 | 1.00 | 49.12 C |
| ATOM | 11993 | O | GLY | C | 63 | 41.922 | −26.428 | 68.227 | 1.00 | 48.47 O |
| ATOM | 11995 | N | ASN | C | 64 | 40.547 | −27.852 | 67.158 | 1.00 | 49.67 N |
| ATOM | 11996 | CA | ASN | C | 64 | 40.516 | −28.815 | 68.243 | 1.00 | 50.30 C |
| ATOM | 11998 | CB | ASN | C | 64 | 39.090 | −29.278 | 68.522 | 1.00 | 51.03 C |
| ATOM | 12001 | CG | ASN | C | 64 | 38.447 | −29.982 | 67.332 | 1.00 | 53.00 C |
| ATOM | 12002 | OD1 | ASN | C | 64 | 37.229 | −30.141 | 67.292 | 1.00 | 52.75 O |
| ATOM | 12003 | ND2 | ASN | C | 64 | 39.257 | −30.399 | 66.363 | 1.00 | 51.45 N |
| ATOM | 12006 | C | ASN | C | 64 | 41.389 | −30.014 | 67.936 | 1.00 | 51.71 C |
| ATOM | 12007 | O | ASN | C | 64 | 41.810 | −30.222 | 66.795 | 1.00 | 54.54 O |
| ATOM | 12009 | N | GLN | C | 65 | 41.673 | −30.779 | 68.981 | 1.00 | 51.60 N |
| ATOM | 12010 | CA | GLN | C | 65 | 42.219 | −32.120 | 68.858 | 1.00 | 50.36 C |
| ATOM | 12012 | CB | GLN | C | 65 | 43.735 | −32.119 | 68.999 | 1.00 | 51.11 C |
| ATOM | 12015 | CG | GLN | C | 65 | 44.467 | −32.563 | 67.748 | 1.00 | 53.84 C |
| ATOM | 12018 | CD | GLN | C | 65 | 45.705 | −33.364 | 68.068 | 1.00 | 52.74 C |
| ATOM | 12019 | OE1 | GLN | C | 65 | 45.986 | −33.649 | 69.231 | 1.00 | 53.47 O |
| ATOM | 12020 | NE2 | GLN | C | 65 | 46.447 | −33.748 | 67.035 | 1.00 | 60.86 N |
| ATOM | 12023 | C | GLN | C | 65 | 41.589 | −32.919 | 69.968 | 1.00 | 48.91 C |
| ATOM | 12024 | O | GLN | C | 65 | 42.148 | −33.020 | 71.054 | 1.00 | 50.08 O |
| ATOM | 12026 | N | GLY | C | 66 | 40.400 | −33.447 | 69.704 | 1.00 | 47.30 N |
| ATOM | 12027 | CA | GLY | C | 66 | 39.597 | −34.060 | 70.746 | 1.00 | 47.50 C |
| ATOM | 12030 | C | GLY | C | 66 | 38.984 | −32.964 | 71.589 | 1.00 | 47.01 C |
| ATOM | 12031 | O | GLY | C | 66 | 38.156 | −32.197 | 71.091 | 1.00 | 49.82 O |
| ATOM | 12033 | N | SER | C | 67 | 39.395 | −32.881 | 72.855 | 1.00 | 46.08 N |
| ATOM | 12034 | CA | SER | C | 67 | 38.905 | −31.842 | 73.769 | 1.00 | 46.10 C |
| ATOM | 12036 | CB | SER | C | 67 | 38.529 | −32.450 | 75.114 | 1.00 | 44.60 C |
| ATOM | 12039 | OG | SER | C | 67 | 39.682 | −32.937 | 75.756 | 1.00 | 45.61 O |
| ATOM | 12041 | C | SER | C | 67 | 39.924 | −30.725 | 73.996 | 1.00 | 46.42 C |
| ATOM | 12042 | O | SER | C | 67 | 39.612 | −29.734 | 74.653 | 1.00 | 44.76 O |
| ATOM | 12044 | N | PHE | C | 68 | 41.135 | −30.890 | 73.465 | 1.00 | 47.67 N |
| ATOM | 12045 | CA | PHE | C | 68 | 42.190 | −29.894 | 73.630 | 1.00 | 46.14 C |
| ATOM | 12047 | CB | PHE | C | 68 | 43.585 | −30.532 | 73.555 | 1.00 | 46.58 C |
| ATOM | 12050 | CG | PHE | C | 68 | 43.782 | −31.729 | 74.459 | 1.00 | 45.25 C |
| ATOM | 12051 | CD1 | PHE | C | 68 | 43.144 | −31.822 | 75.690 | 1.00 | 42.29 C |
| ATOM | 12053 | CE1 | PHE | C | 68 | 43.345 | −32.925 | 76.509 | 1.00 | 45.51 C |
| ATOM | 12055 | CZ | PHE | C | 68 | 44.203 | −33.948 | 76.105 | 1.00 | 48.47 C |
| ATOM | 12057 | CE2 | PHE | C | 68 | 44.854 | −33.861 | 74.883 | 1.00 | 46.46 C |
| ATOM | 12059 | CD2 | PHE | C | 68 | 44.646 | −32.755 | 74.074 | 1.00 | 46.23 C |
| ATOM | 12061 | C | PHE | C | 68 | 42.060 | −28.866 | 72.521 | 1.00 | 45.92 C |
| ATOM | 12062 | O | PHE | C | 68 | 41.804 | −29.227 | 71.376 | 1.00 | 46.72 O |
| ATOM | 12064 | N | LEU | C | 69 | 42.238 | −27.592 | 72.868 | 1.00 | 44.98 N |
| ATOM | 12065 | CA | LEU | C | 69 | 42.315 | −26.508 | 71.887 | 1.00 | 43.95 C |
| ATOM | 12067 | CB | LEU | C | 69 | 41.911 | −25.192 | 72.543 | 1.00 | 43.59 C |
| ATOM | 12070 | CG | LEU | C | 69 | 41.955 | −23.900 | 71.725 | 1.00 | 42.68 C |
| ATOM | 12072 | CD1 | LEU | C | 69 | 40.875 | −23.875 | 70.643 | 1.00 | 43.98 C |
| ATOM | 12076 | CD2 | LEU | C | 69 | 41.794 | −22.710 | 72.655 | 1.00 | 43.54 C |
| ATOM | 12080 | C | LEU | C | 69 | 43.740 | −26.374 | 71.363 | 1.00 | 44.13 C |
| ATOM | 12081 | O | LEU | C | 69 | 44.700 | −26.472 | 72.129 | 1.00 | 44.01 O |
| ATOM | 12083 | N | THR | C | 70 | 43.872 | −26.145 | 70.061 | 1.00 | 44.55 N |
| ATOM | 12084 | CA | THR | C | 70 | 45.177 | −25.928 | 69.432 | 1.00 | 45.70 C |
| ATOM | 12086 | CB | THR | C | 70 | 45.547 | −27.096 | 68.492 | 1.00 | 45.37 C |
| ATOM | 12088 | OG1 | THR | C | 70 | 44.538 | −27.258 | 67.484 | 1.00 | 50.25 O |
| ATOM | 12090 | CG2 | THR | C | 70 | 45.659 | −28.392 | 69.281 | 1.00 | 46.74 C |
| ATOM | 12094 | C | THR | C | 70 | 45.194 | −24.580 | 68.689 | 1.00 | 45.58 C |
| ATOM | 12095 | O | THR | C | 70 | 44.170 | −24.093 | 68.225 | 1.00 | 41.96 O |
| ATOM | 12097 | N | LYS | C | 71 | 46.366 | −23.968 | 68.612 | 1.00 | 47.29 N |
| ATOM | 12098 | CA | LYS | C | 71 | 46.482 | −22.610 | 68.115 | 1.00 | 49.01 C |
| ATOM | 12100 | CB | LYS | C | 71 | 46.656 | −21.637 | 69.290 | 1.00 | 48.87 C |
| ATOM | 12103 | CG | LYS | C | 71 | 45.527 | −21.721 | 70.320 | 1.00 | 51.79 C |
| ATOM | 12106 | CD | LYS | C | 71 | 45.729 | −20.796 | 71.513 | 1.00 | 51.26 C |
| ATOM | 12109 | CE | LYS | C | 71 | 44.727 | −19.663 | 71.535 | 1.00 | 54.67 C |

-continued

| ATOM | 12112 | NZ | LYS | C | 71 | 44.920 | −18.739 | 72.704 | 1.00 | 53.55 | N |
| --- | --- | --- | --- | --- | --- | --- | --- | --- | --- | --- | --- |
| ATOM | 12116 | C | LYS | C | 71 | 47.664 | −22.517 | 67.170 | 1.00 | 49.45 | C |
| ATOM | 12117 | O | LYS | C | 71 | 48.778 | −22.844 | 67.546 | 1.00 | 52.94 | O |
| ATOM | 12119 | N | GLY | C | 72 | 47.417 | −22.082 | 65.942 | 1.00 | 50.42 | N |
| ATOM | 12120 | CA | GLY | C | 72 | 48.480 | −21.863 | 64.970 | 1.00 | 52.01 | C |
| ATOM | 12123 | C | GLY | C | 72 | 49.279 | −20.592 | 65.234 | 1.00 | 53.24 | C |
| ATOM | 12124 | O | GLY | C | 72 | 49.119 | −19.953 | 66.282 | 1.00 | 52.05 | O |
| ATOM | 12126 | N | PRO | C | 73 | 50.145 | −20.209 | 64.277 | 1.00 | 55.29 | N |
| ATOM | 12127 | CA | PRO | C | 73 | 51.111 | −19.144 | 64.492 | 1.00 | 56.96 | C |
| ATOM | 12129 | CB | PRO | C | 73 | 52.349 | −19.682 | 63.768 | 1.00 | 57.24 | C |
| ATOM | 12132 | CG | PRO | C | 73 | 51.760 | −20.496 | 62.593 | 1.00 | 57.57 | C |
| ATOM | 12135 | CD | PRO | C | 73 | 50.296 | −20.776 | 62.924 | 1.00 | 55.20 | C |
| ATOM | 12138 | C | PRO | C | 73 | 50.679 | −17.812 | 63.893 | 1.00 | 57.99 | C |
| ATOM | 12139 | O | PRO | C | 73 | 51.506 | −17.088 | 63.338 | 1.00 | 57.92 | O |
| ATOM | 12140 | N | SER | C | 74 | 49.397 | −17.485 | 63.999 | 1.00 | 59.72 | N |
| ATOM | 12141 | CA | SER | C | 74 | 48.945 | −16.159 | 63.608 | 1.00 | 62.22 | C |
| ATOM | 12143 | CB | SER | C | 74 | 47.426 | −16.122 | 63.404 | 1.00 | 62.70 | C |
| ATOM | 12146 | OG | SER | C | 74 | 46.735 | −16.009 | 64.635 | 1.00 | 64.56 | O |
| ATOM | 12148 | C | SER | C | 74 | 49.372 | −15.191 | 64.704 | 1.00 | 63.86 | C |
| ATOM | 12149 | O | SER | C | 74 | 49.746 | −15.619 | 65.799 | 1.00 | 65.56 | O |
| ATOM | 12151 | N | LYS | C | 75 | 49.333 | −13.894 | 64.405 | 1.00 | 65.11 | N |
| ATOM | 12152 | CA | LYS | C | 75 | 49.570 | −12.864 | 65.424 | 1.00 | 65.91 | C |
| ATOM | 12154 | CB | LYS | C | 75 | 49.800 | −11.484 | 64.787 | 1.00 | 67.46 | C |
| ATOM | 12157 | CG | LYS | C | 75 | 51.264 | −11.222 | 64.374 | 1.00 | 69.39 | C |
| ATOM | 12160 | CD | LYS | C | 75 | 51.624 | −9.727 | 64.412 | 1.00 | 69.10 | C |
| ATOM | 12163 | CE | LYS | C | 75 | 50.724 | −8.870 | 63.504 | 1.00 | 68.97 | C |
| ATOM | 12166 | NZ | LYS | C | 75 | 51.058 | −7.414 | 63.608 | 1.00 | 67.31 | N |
| ATOM | 12170 | C | LYS | C | 75 | 48.410 | −12.795 | 66.416 | 1.00 | 64.56 | C |
| ATOM | 12171 | O | LYS | C | 75 | 48.538 | −12.234 | 67.497 | 1.00 | 65.96 | O |
| ATOM | 12173 | N | LEU | C | 76 | 47.290 | −13.391 | 66.043 | 1.00 | 63.47 | N |
| ATOM | 12174 | CA | LEU | C | 76 | 46.102 | −13.423 | 66.873 | 1.00 | 64.07 | C |
| ATOM | 12176 | CB | LEU | C | 76 | 44.911 | −13.842 | 65.999 | 1.00 | 63.13 | C |
| ATOM | 12179 | CG | LEU | C | 76 | 43.567 | −13.140 | 66.168 | 1.00 | 64.68 | C |
| ATOM | 12181 | CD1 | LEU | C | 76 | 43.696 | −11.710 | 66.667 | 1.00 | 67.11 | C |
| ATOM | 12185 | CD2 | LEU | C | 76 | 42.834 | −13.158 | 64.846 | 1.00 | 64.16 | C |
| ATOM | 12189 | C | LEU | C | 76 | 46.244 | −14.388 | 68.064 | 1.00 | 65.87 | C |
| ATOM | 12190 | O | LEU | C | 76 | 45.465 | −14.306 | 69.020 | 1.00 | 67.90 | O |
| ATOM | 12192 | N | ASN | C | 77 | 47.252 | −15.269 | 68.011 | 1.00 | 64.59 | N |
| ATOM | 12193 | CA | ASN | C | 77 | 47.359 | −16.442 | 68.889 | 1.00 | 61.96 | C |
| ATOM | 12195 | CB | ASN | C | 77 | 48.829 | −16.865 | 69.053 | 1.00 | 62.45 | C |
| ATOM | 12198 | CG | ASN | C | 77 | 48.981 | −18.257 | 69.689 | 1.00 | 63.63 | C |
| ATOM | 12199 | OD1 | ASN | C | 77 | 48.095 | −18.736 | 70.402 | 1.00 | 61.38 | O |
| ATOM | 12200 | ND2 | ASN | C | 77 | 50.111 | −18.904 | 69.426 | 1.00 | 60.68 | N |
| ATOM | 12203 | C | ASN | C | 77 | 46.713 | −16.292 | 70.260 | 1.00 | 60.33 | C |
| ATOM | 12204 | O | ASN | C | 77 | 45.728 | −16.963 | 70.571 | 1.00 | 60.02 | O |
| ATOM | 12206 | N | ASP | C | 78 | 47.264 | −15.406 | 71.074 | 1.00 | 59.78 | N |
| ATOM | 12207 | CA | ASP | C | 78 | 46.886 | −15.344 | 72.484 | 1.00 | 59.37 | C |
| ATOM | 12209 | CB | ASP | C | 78 | 47.933 | −14.574 | 73.307 | 1.00 | 60.96 | C |
| ATOM | 12212 | CG | ASP | C | 78 | 48.142 | −13.139 | 72.817 | 1.00 | 68.22 | C |
| ATOM | 12213 | OD1 | ASP | C | 78 | 47.528 | −12.745 | 71.794 | 1.00 | 74.99 | O |
| ATOM | 12214 | OD2 | ASP | C | 78 | 48.931 | −12.407 | 73.451 | 1.00 | 70.19 | O |
| ATOM | 12215 | C | ASP | C | 78 | 45.496 | −14.760 | 72.696 | 1.00 | 56.69 | C |
| ATOM | 12216 | O | ASP | C | 78 | 44.914 | −14.967 | 73.749 | 1.00 | 57.54 | O |
| ATOM | 12218 | N | ARG | C | 79 | 44.959 | −14.049 | 71.706 | 1.00 | 55.44 | N |
| ATOM | 12219 | CA | ARG | C | 79 | 43.624 | −13.439 | 71.833 | 1.00 | 55.03 | C |
| ATOM | 12221 | CB | ARG | C | 79 | 43.627 | −12.036 | 71.230 | 1.00 | 54.51 | C |
| ATOM | 12224 | CG | ARG | C | 79 | 44.768 | −11.182 | 71.759 | 1.00 | 54.43 | C |
| ATOM | 12227 | CD | ARG | C | 79 | 44.593 | −9.700 | 71.522 | 1.00 | 52.55 | C |
| ATOM | 12230 | NE | ARG | C | 79 | 45.095 | −9.286 | 70.212 | 1.00 | 53.43 | N |
| ATOM | 12232 | CZ | ARG | C | 79 | 44.361 | −9.177 | 69.106 | 1.00 | 48.10 | C |
| ATOM | 12233 | NH1 | ARG | C | 79 | 43.072 | −9.453 | 69.118 | 1.00 | 46.25 | N |
| ATOM | 12236 | NH2 | ARG | C | 79 | 44.926 | −8.782 | 67.979 | 1.00 | 50.99 | N |
| ATOM | 12239 | C | ARG | C | 79 | 42.473 | −14.273 | 71.251 | 1.00 | 54.28 | C |
| ATOM | 12240 | O | ARG | C | 79 | 41.306 | −13.936 | 71.457 | 1.00 | 52.66 | O |
| ATOM | 12242 | N | ALA | C | 80 | 42.801 | −15.356 | 70.545 | 1.00 | 54.83 | N |
| ATOM | 12243 | CA | ALA | C | 80 | 41.790 | −16.283 | 70.020 | 1.00 | 55.71 | C |
| ATOM | 12245 | CB | ALA | C | 80 | 42.296 | −16.985 | 68.778 | 1.00 | 55.69 | C |
| ATOM | 12249 | C | ALA | C | 80 | 41.424 | −17.321 | 71.060 | 1.00 | 55.74 | C |
| ATOM | 12250 | O | ALA | C | 80 | 42.289 | −17.745 | 71.823 | 1.00 | 56.62 | O |
| ATOM | 12252 | N | ASP | C | 81 | 40.147 | −17.715 | 71.077 | 1.00 | 55.46 | N |
| ATOM | 12253 | CA | ASP | C | 81 | 39.658 | −18.824 | 71.902 | 1.00 | 55.03 | C |
| ATOM | 12255 | CB | ASP | C | 81 | 39.338 | −18.347 | 73.328 | 1.00 | 55.68 | C |
| ATOM | 12258 | CG | ASP | C | 81 | 39.621 | −19.416 | 74.395 | 1.00 | 59.76 | C |
| ATOM | 12259 | OD1 | ASP | C | 81 | 39.527 | −20.630 | 74.092 | 1.00 | 69.94 | O |
| ATOM | 12260 | OD2 | ASP | C | 81 | 39.943 | −19.041 | 75.545 | 1.00 | 65.85 | O |
| ATOM | 12261 | C | ASP | C | 81 | 38.405 | −19.446 | 71.268 | 1.00 | 54.83 | C |
| ATOM | 12262 | O | ASP | C | 81 | 37.948 | −19.001 | 70.212 | 1.00 | 52.87 | O |
| ATOM | 12264 | N | SER | C | 82 | 37.866 | −20.481 | 71.911 | 1.00 | 53.85 | N |
| ATOM | 12265 | CA | SER | C | 82 | 36.600 | −21.077 | 71.500 | 1.00 | 54.26 | C |

-continued

| | | | | | | | | | | |
|---|---|---|---|---|---|---|---|---|---|---|
| ATOM | 12267 | CB | SER | C | 82 | 36.856 | −22.356 | 70.703 | 1.00 | 53.01 C |
| ATOM | 12270 | OG | SER | C | 82 | 35.686 | −22.766 | 70.020 | 1.00 | 48.51 O |
| ATOM | 12272 | C | SER | C | 82 | 35.741 | −21.351 | 72.737 | 1.00 | 54.89 C |
| ATOM | 12273 | O | SER | C | 82 | 36.020 | −20.811 | 73.801 | 1.00 | 53.62 O |
| ATOM | 12275 | N | ARG | C | 83 | 34.686 | −22.155 | 72.590 | 1.00 | 57.39 N |
| ATOM | 12276 | CA | ARG | C | 83 | 33.909 | −22.651 | 73.738 | 1.00 | 58.61 C |
| ATOM | 12278 | CB | ARG | C | 83 | 32.495 | −22.086 | 73.729 | 1.00 | 59.21 C |
| ATOM | 12281 | CG | ARG | C | 83 | 32.444 | −20.636 | 74.096 | 1.00 | 62.88 C |
| ATOM | 12284 | CD | ARG | C | 83 | 31.035 | −20.086 | 73.991 | 1.00 | 65.60 C |
| ATOM | 12287 | NE | ARG | C | 83 | 30.976 | −18.734 | 74.525 | 1.00 | 68.85 N |
| ATOM | 12289 | CZ | ARG | C | 83 | 31.002 | −18.435 | 75.823 | 1.00 | 72.92 C |
| ATOM | 12290 | NH1 | ARG | C | 83 | 31.079 | −19.388 | 76.756 | 1.00 | 72.34 N |
| ATOM | 12293 | NH2 | ARG | C | 83 | 30.950 | −17.164 | 76.194 | 1.00 | 73.93 N |
| ATOM | 12296 | C | ARG | C | 83 | 33.839 | −24.165 | 73.722 | 1.00 | 57.52 C |
| ATOM | 12297 | O | ARG | C | 83 | 32.949 | −24.745 | 73.099 | 1.00 | 57.14 O |
| ATOM | 12299 | N | ARG | C | 84 | 34.771 | −24.796 | 74.427 | 1.00 | 57.71 N |
| ATOM | 12300 | CA | ARG | C | 84 | 34.871 | −26.264 | 74.461 | 1.00 | 58.06 C |
| ATOM | 12302 | CB | ARG | C | 84 | 36.059 | −26.707 | 75.336 | 1.00 | 56.96 C |
| ATOM | 12305 | CG | ARG | C | 84 | 37.400 | −26.156 | 74.852 | 1.00 | 57.30 C |
| ATOM | 12308 | CD | ARG | C | 84 | 38.611 | −26.749 | 75.562 | 1.00 | 56.98 C |
| ATOM | 12311 | NE | ARG | C | 84 | 38.487 | −26.721 | 77.021 | 1.00 | 57.55 N |
| ATOM | 12313 | CZ | ARG | C | 84 | 38.165 | −27.766 | 77.787 | 1.00 | 53.66 C |
| ATOM | 12314 | NH1 | ARG | C | 84 | 37.933 | −28.959 | 77.249 | 1.00 | 53.42 N |
| ATOM | 12317 | NH2 | ARG | C | 84 | 38.073 | −27.617 | 79.108 | 1.00 | 51.09 N |
| ATOM | 12320 | C | ARG | C | 84 | 33.567 | −26.929 | 74.929 | 1.00 | 57.61 C |
| ATOM | 12321 | O | ARG | C | 84 | 33.255 | −28.056 | 74.537 | 1.00 | 56.95 O |
| ATOM | 12323 | N | SER | C | 85 | 32.805 | −26.224 | 75.759 | 1.00 | 57.66 N |
| ATOM | 12324 | CA | SER | C | 85 | 31.504 | −26.707 | 76.187 | 1.00 | 58.22 C |
| ATOM | 12326 | CB | SER | C | 85 | 30.854 | −25.700 | 77.136 | 1.00 | 57.05 C |
| ATOM | 12329 | OG | SER | C | 85 | 31.486 | −24.440 | 77.018 | 1.00 | 56.63 O |
| ATOM | 12331 | C | SER | C | 85 | 30.628 | −26.970 | 74.966 | 1.00 | 59.49 C |
| ATOM | 12332 | O | SER | C | 85 | 30.105 | −28.067 | 74.795 | 1.00 | 62.80 O |
| ATOM | 12334 | N | LEU | C | 86 | 30.530 | −25.983 | 74.086 | 1.00 | 59.43 N |
| ATOM | 12335 | CA | LEU | C | 86 | 29.652 | −26.067 | 72.916 | 1.00 | 59.07 C |
| ATOM | 12337 | CB | LEU | C | 86 | 29.493 | −24.677 | 72.289 | 1.00 | 60.30 C |
| ATOM | 12340 | CG | LEU | C | 86 | 29.013 | −23.547 | 73.201 | 1.00 | 61.10 C |
| ATOM | 12342 | CD1 | LEU | C | 86 | 28.992 | −22.214 | 72.435 | 1.00 | 62.00 C |
| ATOM | 12346 | CD2 | LEU | C | 86 | 27.652 | −23.888 | 73.780 | 1.00 | 59.65 C |
| ATOM | 12350 | C | LEU | C | 86 | 30.090 | −27.052 | 71.815 | 1.00 | 57.92 C |
| ATOM | 12351 | O | LEU | C | 86 | 29.343 | −27.261 | 70.860 | 1.00 | 57.94 O |
| ATOM | 12353 | N | TRP | C | 87 | 31.276 | −27.647 | 71.941 | 1.00 | 56.42 N |
| ATOM | 12354 | CA | TRP | C | 87 | 31.819 | −28.542 | 70.902 | 1.00 | 56.36 C |
| ATOM | 12356 | CB | TRP | C | 87 | 33.262 | −28.955 | 71.242 | 1.00 | 53.05 C |
| ATOM | 12359 | CG | TRP | C | 87 | 34.266 | −27.856 | 71.027 | 1.00 | 49.88 C |
| ATOM | 12360 | CD1 | TRP | C | 87 | 34.011 | −26.574 | 70.624 | 1.00 | 49.46 C |
| ATOM | 12362 | NE1 | TRP | C | 87 | 35.173 | −25.860 | 70.554 | 1.00 | 50.06 N |
| ATOM | 12364 | CE2 | TRP | C | 87 | 36.214 | −26.670 | 70.923 | 1.00 | 51.72 C |
| ATOM | 12365 | CD2 | TRP | C | 87 | 35.677 | −27.934 | 71.232 | 1.00 | 49.41 C |
| ATOM | 12366 | CE3 | TRP | C | 87 | 36.545 | −28.953 | 71.637 | 1.00 | 48.38 C |
| ATOM | 12368 | CZ3 | TRP | C | 87 | 37.892 | −28.682 | 71.720 | 1.00 | 48.78 C |
| ATOM | 12370 | CH2 | TRP | C | 87 | 38.397 | −27.415 | 71.405 | 1.00 | 49.18 C |
| ATOM | 12372 | CZ2 | TRP | C | 87 | 37.578 | −26.398 | 71.008 | 1.00 | 49.49 C |
| ATOM | 12374 | C | TRP | C | 87 | 30.964 | −29.781 | 70.666 | 1.00 | 56.44 C |
| ATOM | 12375 | O | TRP | C | 87 | 30.622 | −30.106 | 69.521 | 1.00 | 56.65 O |
| ATOM | 12377 | N | ASP | C | 88 | 30.627 | −30.466 | 71.752 | 1.00 | 57.30 N |
| ATOM | 12378 | CA | ASP | C | 88 | 29.741 | −31.628 | 71.698 | 1.00 | 57.07 C |
| ATOM | 12380 | CB | ASP | C | 88 | 29.238 | −31.981 | 73.101 | 1.00 | 58.07 C |
| ATOM | 12383 | CG | ASP | C | 88 | 30.359 | −32.068 | 74.125 | 1.00 | 61.73 C |
| ATOM | 12384 | OD1 | ASP | C | 88 | 30.513 | −33.143 | 74.743 | 1.00 | 63.87 O |
| ATOM | 12385 | OD2 | ASP | C | 88 | 31.087 | −31.061 | 74.306 | 1.00 | 65.80 O |
| ATOM | 12386 | C | ASP | C | 88 | 28.548 | −31.338 | 70.786 | 1.00 | 57.36 C |
| ATOM | 12387 | O | ASP | C | 88 | 28.242 | −32.114 | 69.876 | 1.00 | 58.34 O |
| ATOM | 12389 | N | GLN | C | 89 | 27.914 | −30.188 | 71.011 | 1.00 | 55.42 N |
| ATOM | 12390 | CA | GLN | C | 89 | 26.702 | −29.809 | 70.292 | 1.00 | 54.39 C |
| ATOM | 12392 | CB | GLN | C | 89 | 25.920 | −28.778 | 71.117 | 1.00 | 54.91 C |
| ATOM | 12395 | CG | GLN | C | 89 | 25.355 | −29.367 | 72.410 | 1.00 | 58.10 C |
| ATOM | 12398 | CD | GLN | C | 89 | 24.678 | −30.737 | 72.191 | 1.00 | 66.71 C |
| ATOM | 12399 | OE1 | GLN | C | 89 | 23.583 | −30.817 | 71.625 | 1.00 | 72.60 O |
| ATOM | 12400 | NE2 | GLN | C | 89 | 25.341 | −31.815 | 72.625 | 1.00 | 62.85 N |
| ATOM | 12403 | C | GLN | C | 89 | 26.902 | −29.324 | 68.852 | 1.00 | 52.31 C |
| ATOM | 12404 | O | GLN | C | 89 | 25.933 | −28.969 | 68.195 | 1.00 | 49.09 O |
| ATOM | 12406 | N | GLY | C | 90 | 28.140 | −29.330 | 68.360 | 1.00 | 52.74 N |
| ATOM | 12407 | CA | GLY | C | 90 | 28.442 | −28.926 | 66.981 | 1.00 | 52.64 C |
| ATOM | 12410 | C | GLY | C | 90 | 28.722 | −27.442 | 66.755 | 1.00 | 52.34 C |
| ATOM | 12411 | O | GLY | C | 90 | 28.834 | −27.003 | 65.613 | 1.00 | 53.04 O |
| ATOM | 12413 | N | ASN | C | 91 | 28.839 | −26.669 | 67.831 | 1.00 | 51.54 N |
| ATOM | 12414 | CA | ASN | C | 91 | 29.204 | −25.257 | 67.741 | 1.00 | 50.86 C |
| ATOM | 12416 | CB | ASN | C | 91 | 28.387 | −24.426 | 68.738 | 1.00 | 51.53 C |
| ATOM | 12419 | CG | ASN | C | 91 | 27.044 | −24.010 | 68.180 | 1.00 | 52.68 C |

-continued

| | | | | | | | | | | |
|---|---|---|---|---|---|---|---|---|---|---|
| ATOM | 12420 | OD1 | ASN | C | 91 | 26.975 | −23.418 | 67.106 | 1.00 | 53.48 O |
| ATOM | 12421 | ND2 | ASN | C | 91 | 25.967 | −24.335 | 68.891 | 1.00 | 58.97 N |
| ATOM | 12424 | C | ASN | C | 91 | 30.690 | −25.062 | 67.997 | 1.00 | 50.03 C |
| ATOM | 12425 | O | ASN | C | 91 | 31.192 | −25.424 | 69.057 | 1.00 | 50.42 O |
| ATOM | 12427 | N | PHE | C | 92 | 31.383 | −24.475 | 67.023 | 1.00 | 50.70 N |
| ATOM | 12428 | CA | PHE | C | 92 | 32.838 | −24.291 | 67.079 | 1.00 | 50.26 C |
| ATOM | 12430 | CB | PHE | C | 92 | 33.505 | −25.135 | 65.992 | 1.00 | 51.29 C |
| ATOM | 12433 | CG | PHE | C | 92 | 32.976 | −26.540 | 65.909 | 1.00 | 53.12 C |
| ATOM | 12434 | CD1 | PHE | C | 92 | 33.031 | −27.384 | 67.015 | 1.00 | 52.44 C |
| ATOM | 12436 | CE1 | PHE | C | 92 | 32.532 | −28.680 | 66.951 | 1.00 | 54.20 C |
| ATOM | 12438 | CZ | PHE | C | 92 | 31.978 | −29.147 | 65.771 | 1.00 | 56.26 C |
| ATOM | 12440 | CE2 | PHE | C | 92 | 31.915 | −28.311 | 64.658 | 1.00 | 55.76 C |
| ATOM | 12442 | CD2 | PHE | C | 92 | 32.411 | −27.016 | 64.732 | 1.00 | 54.62 C |
| ATOM | 12444 | C | PHE | C | 92 | 33.212 | −22.821 | 66.899 | 1.00 | 49.64 C |
| ATOM | 12445 | O | PHE | C | 92 | 33.858 | −22.468 | 65.926 | 1.00 | 47.94 O |
| ATOM | 12447 | N | PRO | C | 93 | 32.790 | −21.952 | 67.836 | 1.00 | 49.91 N |
| ATOM | 12448 | CA | PRO | C | 93 | 33.041 | −20.515 | 67.700 | 1.00 | 48.95 C |
| ATOM | 12450 | CB | PRO | C | 93 | 32.271 | −19.916 | 68.880 | 1.00 | 48.64 C |
| ATOM | 12453 | CG | PRO | C | 93 | 32.208 | −21.002 | 69.874 | 1.00 | 50.23 C |
| ATOM | 12456 | CD | PRO | C | 93 | 32.045 | −22.255 | 69.071 | 1.00 | 49.54 C |
| ATOM | 12459 | C | PRO | C | 93 | 34.509 | −20.104 | 67.807 | 1.00 | 48.69 C |
| ATOM | 12460 | O | PRO | C | 93 | 35.252 | −20.647 | 68.625 | 1.00 | 47.80 O |
| ATOM | 12461 | N | LEU | C | 94 | 34.905 | −19.149 | 66.970 | 1.00 | 47.68 N |
| ATOM | 12462 | CA | LEU | C | 94 | 36.141 | −18.413 | 67.153 | 1.00 | 47.35 C |
| ATOM | 12464 | CB | LEU | C | 94 | 36.734 | −17.993 | 65.811 | 1.00 | 47.54 C |
| ATOM | 12467 | CG | LEU | C | 94 | 37.947 | −17.060 | 65.785 | 1.00 | 44.95 C |
| ATOM | 12469 | CD1 | LEU | C | 94 | 39.010 | −17.545 | 66.720 | 1.00 | 46.78 C |
| ATOM | 12473 | CD2 | LEU | C | 94 | 38.501 | −16.986 | 64.380 | 1.00 | 45.52 C |
| ATOM | 12477 | C | LEU | C | 94 | 35.758 | −17.193 | 67.943 | 1.00 | 47.76 C |
| ATOM | 12478 | O | LEU | C | 94 | 34.848 | −16.467 | 67.544 | 1.00 | 49.08 O |
| ATOM | 12480 | N | ILE | C | 95 | 36.424 | −16.990 | 69.076 | 1.00 | 48.89 N |
| ATOM | 12481 | CA | ILE | C | 95 | 36.196 | −15.830 | 69.931 | 1.00 | 49.35 C |
| ATOM | 12483 | CB | ILE | C | 95 | 35.779 | −16.251 | 71.352 | 1.00 | 49.40 C |
| ATOM | 12485 | CG1 | ILE | C | 95 | 34.377 | −16.871 | 71.334 | 1.00 | 49.70 C |
| ATOM | 12488 | CD1 | ILE | C | 95 | 34.099 | −17.771 | 72.528 | 1.00 | 50.42 C |
| ATOM | 12492 | CG2 | ILE | C | 95 | 35.830 | −15.051 | 72.301 | 1.00 | 48.17 C |
| ATOM | 12496 | C | ILE | C | 95 | 37.481 | −15.047 | 70.033 | 1.00 | 49.05 C |
| ATOM | 12497 | O | ILE | C | 95 | 38.464 | −15.539 | 70.575 | 1.00 | 52.28 O |
| ATOM | 12499 | N | ILE | C | 96 | 37.464 | −13.820 | 69.542 | 1.00 | 49.49 N |
| ATOM | 12500 | CA | ILE | C | 96 | 38.635 | −12.960 | 69.587 | 1.00 | 51.44 C |
| ATOM | 12502 | CB | ILE | C | 96 | 38.871 | −12.309 | 68.219 | 1.00 | 51.82 C |
| ATOM | 12504 | CG1 | ILE | C | 96 | 39.147 | −13.405 | 67.175 | 1.00 | 53.58 C |
| ATOM | 12507 | CD1 | ILE | C | 96 | 38.880 | −12.987 | 65.737 | 1.00 | 50.22 C |
| ATOM | 12511 | CG2 | ILE | C | 96 | 40.026 | −11.307 | 68.285 | 1.00 | 49.59 C |
| ATOM | 12515 | C | ILE | C | 96 | 38.453 | −11.888 | 70.662 | 1.00 | 52.26 C |
| ATOM | 12516 | O | ILE | C | 96 | 37.537 | −11.072 | 70.574 | 1.00 | 48.81 O |
| ATOM | 12518 | N | LYS | C | 97 | 39.346 | −11.899 | 71.655 | 1.00 | 55.67 N |
| ATOM | 12519 | CA | LYS | C | 97 | 39.336 | −10.941 | 72.777 | 1.00 | 58.16 C |
| ATOM | 12521 | CB | LYS | C | 97 | 40.023 | −11.537 | 74.022 | 1.00 | 59.75 C |
| ATOM | 12524 | CG | LYS | C | 97 | 39.806 | −13.056 | 74.261 | 1.00 | 66.39 C |
| ATOM | 12527 | CD | LYS | C | 97 | 41.097 | −13.770 | 74.749 | 1.00 | 66.00 C |
| ATOM | 12530 | CE | LYS | C | 97 | 41.082 | −15.278 | 74.423 | 1.00 | 66.98 C |
| ATOM | 12533 | NZ | LYS | C | 97 | 42.370 | −15.967 | 74.749 | 1.00 | 63.46 N |
| ATOM | 12537 | C | LYS | C | 97 | 40.120 | −9.694 | 72.371 | 1.00 | 57.90 C |
| ATOM | 12538 | O | LYS | C | 97 | 41.092 | −9.805 | 71.616 | 1.00 | 58.73 O |
| ATOM | 12540 | N | ASN | C | 98 | 39.725 | −8.524 | 72.868 | 1.00 | 55.01 N |
| ATOM | 12541 | CA | ASN | C | 98 | 40.537 | −7.309 | 72.695 | 1.00 | 56.09 C |
| ATOM | 12543 | CB | ASN | C | 98 | 41.855 | −7.411 | 73.477 | 1.00 | 56.23 C |
| ATOM | 12546 | CG | ASN | C | 98 | 41.650 | −7.488 | 74.980 | 1.00 | 64.42 C |
| ATOM | 12547 | OD1 | ASN | C | 98 | 42.620 | −7.553 | 75.737 | 1.00 | 73.67 O |
| ATOM | 12548 | ND2 | ASN | C | 98 | 40.391 | −7.478 | 75.425 | 1.00 | 76.01 N |
| ATOM | 12551 | C | ASN | C | 98 | 40.854 | −6.997 | 71.238 | 1.00 | 54.18 C |
| ATOM | 12552 | O | ASN | C | 98 | 41.997 | −7.118 | 70.798 | 1.00 | 53.05 O |
| ATOM | 12554 | N | LEU | C | 99 | 39.840 | −6.564 | 70.506 | 1.00 | 52.80 N |
| ATOM | 12555 | CA | LEU | C | 99 | 39.943 | −6.439 | 69.065 | 1.00 | 53.17 C |
| ATOM | 12557 | CB | LEU | C | 99 | 38.549 | −6.345 | 68.442 | 1.00 | 52.14 C |
| ATOM | 12560 | CG | LEU | C | 99 | 37.763 | −7.658 | 68.493 | 1.00 | 49.63 C |
| ATOM | 12562 | CD1 | LEU | C | 99 | 36.258 | −7.425 | 68.480 | 1.00 | 50.11 C |
| ATOM | 12566 | CD2 | LEU | C | 99 | 38.185 | −8.592 | 67.365 | 1.00 | 47.55 C |
| ATOM | 12570 | C | LEU | C | 99 | 40.788 | −5.255 | 68.623 | 1.00 | 53.85 C |
| ATOM | 12571 | O | LEU | C | 99 | 40.670 | −4.155 | 69.170 | 1.00 | 54.38 O |
| ATOM | 12573 | N | LYS | C | 100 | 41.641 | −5.511 | 67.630 | 1.00 | 54.72 N |
| ATOM | 12574 | CA | LYS | C | 100 | 42.381 | −4.478 | 66.906 | 1.00 | 55.03 C |
| ATOM | 12576 | CB | LYS | C | 100 | 43.879 | −4.809 | 66.862 | 1.00 | 53.16 C |
| ATOM | 12579 | CG | LYS | C | 100 | 44.446 | −5.120 | 68.235 | 1.00 | 57.21 C |
| ATOM | 12582 | CD | LYS | C | 100 | 45.951 | −5.258 | 68.269 | 1.00 | 56.55 C |
| ATOM | 12585 | CE | LYS | C | 100 | 46.397 | −5.802 | 69.623 | 1.00 | 54.62 C |
| ATOM | 12588 | NZ | LYS | C | 100 | 47.884 | −5.823 | 69.749 | 1.00 | 61.43 N |
| ATOM | 12592 | C | LYS | C | 100 | 41.815 | −4.372 | 65.491 | 1.00 | 56.37 C |

-continued

| ATOM | 12593 | O | LYS | C | 100 | 41.201 | −5.322 | 64.979 | 1.00 | 56.17 | O |
| --- | --- | --- | --- | --- | --- | --- | --- | --- | --- | --- | --- |
| ATOM | 12595 | N | ILE | C | 101 | 42.032 | −3.215 | 64.866 | 1.00 | 56.50 | N |
| ATOM | 12596 | CA | ILE | C | 101 | 41.509 | −2.943 | 63.531 | 1.00 | 55.45 | C |
| ATOM | 12598 | CB | ILE | C | 101 | 41.833 | −1.489 | 63.057 | 1.00 | 55.19 | C |
| ATOM | 12600 | CG1 | ILE | C | 101 | 40.871 | −0.465 | 63.668 | 1.00 | 54.74 | C |
| ATOM | 12603 | CD1 | ILE | C | 101 | 40.566 | −0.635 | 65.131 | 1.00 | 54.39 | C |
| ATOM | 12607 | CG2 | ILE | C | 101 | 41.694 | −1.359 | 61.538 | 1.00 | 56.87 | C |
| ATOM | 12611 | C | ILE | C | 101 | 42.058 | −3.980 | 62.553 | 1.00 | 54.95 | C |
| ATOM | 12612 | O | ILE | C | 101 | 41.334 | −4.454 | 61.683 | 1.00 | 54.33 | O |
| ATOM | 12614 | N | GLU | C | 102 | 43.324 | −4.356 | 62.725 | 1.00 | 55.84 | N |
| ATOM | 12615 | CA | GLU | C | 102 | 43.979 | −5.315 | 61.814 | 1.00 | 56.73 | C |
| ATOM | 12617 | CB | GLU | C | 102 | 45.506 | −5.336 | 61.987 | 1.00 | 58.00 | C |
| ATOM | 12620 | CG | GLU | C | 102 | 45.998 | −5.602 | 63.400 | 1.00 | 64.70 | C |
| ATOM | 12623 | CD | GLU | C | 102 | 46.065 | −4.338 | 64.258 | 1.00 | 73.67 | C |
| ATOM | 12624 | OE1 | GLU | C | 102 | 45.506 | −3.283 | 63.850 | 1.00 | 74.00 | O |
| ATOM | 12625 | OE2 | GLU | C | 102 | 46.674 | −4.410 | 65.351 | 1.00 | 78.25 | O |
| ATOM | 12626 | C | GLU | C | 102 | 43.439 | −6.738 | 61.897 | 1.00 | 55.16 | C |
| ATOM | 12627 | O | GLU | C | 102 | 43.764 | −7.553 | 61.048 | 1.00 | 56.66 | O |
| ATOM | 12629 | N | ASP | C | 103 | 42.625 | −7.039 | 62.902 | 1.00 | 53.48 | N |
| ATOM | 12630 | CA | ASP | C | 103 | 41.923 | −8.320 | 62.942 | 1.00 | 52.84 | C |
| ATOM | 12632 | CB | ASP | C | 103 | 41.302 | −8.555 | 64.316 | 1.00 | 52.09 | C |
| ATOM | 12635 | CG | ASP | C | 103 | 42.343 | −8.645 | 65.420 | 1.00 | 52.06 | C |
| ATOM | 12636 | OD1 | ASP | C | 103 | 43.532 | −8.926 | 65.128 | 1.00 | 45.27 | O |
| ATOM | 12637 | OD2 | ASP | C | 103 | 41.965 | −8.426 | 66.586 | 1.00 | 47.52 | O |
| ATOM | 12638 | C | ASP | C | 103 | 40.838 | −8.384 | 61.872 | 1.00 | 51.90 | C |
| ATOM | 12639 | O | ASP | C | 103 | 40.330 | −9.462 | 61.556 | 1.00 | 47.95 | O |
| ATOM | 12641 | N | SER | C | 104 | 40.472 | −7.229 | 61.323 | 1.00 | 52.59 | N |
| ATOM | 12642 | CA | SER | C | 104 | 39.541 | −7.201 | 60.211 | 1.00 | 53.58 | C |
| ATOM | 12644 | CB | SER | C | 104 | 39.267 | −5.774 | 59.765 | 1.00 | 52.91 | C |
| ATOM | 12647 | OG | SER | C | 104 | 38.857 | −4.998 | 60.868 | 1.00 | 55.45 | O |
| ATOM | 12649 | C | SER | C | 104 | 40.116 | −8.013 | 59.052 | 1.00 | 54.73 | C |
| ATOM | 12650 | O | SER | C | 104 | 41.226 | −7.739 | 58.576 | 1.00 | 54.05 | O |
| ATOM | 12652 | N | ASP | C | 105 | 39.334 | −9.006 | 58.626 | 1.00 | 54.20 | N |
| ATOM | 12653 | CA | ASP | C | 105 | 39.711 | −9.976 | 57.613 | 1.00 | 51.83 | C |
| ATOM | 12655 | CB | ASP | C | 105 | 40.834 | −10.857 | 58.168 | 1.00 | 52.72 | C |
| ATOM | 12658 | CG | ASP | C | 105 | 41.569 | −11.648 | 57.094 | 1.00 | 54.56 | C |
| ATOM | 12659 | OD1 | ASP | C | 105 | 41.063 | −11.799 | 55.963 | 1.00 | 51.16 | O |
| ATOM | 12660 | OD2 | ASP | C | 105 | 42.675 | −12.135 | 57.402 | 1.00 | 57.46 | O |
| ATOM | 12661 | C | ASP | C | 105 | 38.472 | −10.832 | 57.341 | 1.00 | 50.25 | C |
| ATOM | 12662 | O | ASP | C | 105 | 37.481 | −10.733 | 58.053 | 1.00 | 47.82 | O |
| ATOM | 12664 | N | THR | C | 106 | 38.508 | −11.663 | 56.311 | 1.00 | 51.72 | N |
| ATOM | 12665 | CA | THR | C | 106 | 37.584 | −12.791 | 56.258 | 1.00 | 50.98 | C |
| ATOM | 12667 | CB | THR | C | 106 | 37.240 | −13.207 | 54.842 | 1.00 | 50.93 | C |
| ATOM | 12669 | OG1 | THR | C | 106 | 36.247 | −12.319 | 54.329 | 1.00 | 54.88 | O |
| ATOM | 12671 | CG2 | THR | C | 106 | 36.672 | −14.618 | 54.820 | 1.00 | 54.12 | C |
| ATOM | 12675 | C | THR | C | 106 | 38.215 | −13.964 | 56.994 | 1.00 | 49.63 | C |
| ATOM | 12676 | O | THR | C | 106 | 39.396 | −14.260 | 56.810 | 1.00 | 48.56 | O |
| ATOM | 12678 | N | TYR | C | 107 | 37.403 | −14.614 | 57.821 | 1.00 | 47.37 | N |
| ATOM | 12679 | CA | TYR | C | 107 | 37.806 | −15.780 | 58.583 | 1.00 | 48.49 | C |
| ATOM | 12681 | CB | TYR | C | 107 | 37.531 | −15.521 | 60.061 | 1.00 | 46.75 | C |
| ATOM | 12684 | CG | TYR | C | 107 | 38.492 | −14.538 | 60.692 | 1.00 | 45.97 | C |
| ATOM | 12685 | CD1 | TYR | C | 107 | 38.156 | −13.201 | 60.838 | 1.00 | 46.31 | C |
| ATOM | 12687 | CE1 | TYR | C | 107 | 39.030 | −12.308 | 61.413 | 1.00 | 43.07 | C |
| ATOM | 12689 | CZ | TYR | C | 107 | 40.260 | −12.744 | 61.842 | 1.00 | 38.51 | C |
| ATOM | 12690 | OH | TYR | C | 107 | 41.138 | −11.866 | 62.410 | 1.00 | 39.85 | O |
| ATOM | 12692 | CE2 | TYR | C | 107 | 40.620 | −14.062 | 61.708 | 1.00 | 42.91 | C |
| ATOM | 12694 | CD2 | TYR | C | 107 | 39.739 | −14.950 | 61.141 | 1.00 | 44.33 | C |
| ATOM | 12696 | C | TYR | C | 107 | 37.040 | −17.023 | 58.098 | 1.00 | 49.31 | C |
| ATOM | 12697 | O | TYR | C | 107 | 35.852 | −16.943 | 57.757 | 1.00 | 50.98 | O |
| ATOM | 12699 | N | ILE | C | 108 | 37.719 | −18.165 | 58.069 | 1.00 | 48.86 | N |
| ATOM | 12700 | CA | ILE | C | 108 | 37.170 | −19.380 | 57.450 | 1.00 | 50.48 | C |
| ATOM | 12702 | CB | ILE | C | 108 | 37.996 | −19.833 | 56.211 | 1.00 | 49.66 | C |
| ATOM | 12704 | CG1 | ILE | C | 108 | 38.380 | −18.639 | 55.331 | 1.00 | 49.00 | C |
| ATOM | 12707 | CD1 | ILE | C | 108 | 39.364 | −18.987 | 54.240 | 1.00 | 49.70 | C |
| ATOM | 12711 | CG2 | ILE | C | 108 | 37.205 | −20.837 | 55.385 | 1.00 | 48.20 | C |
| ATOM | 12715 | C | ILE | C | 108 | 37.092 | −20.553 | 58.427 | 1.00 | 51.00 | C |
| ATOM | 12716 | O | ILE | C | 108 | 38.063 | −20.881 | 59.094 | 1.00 | 50.60 | O |
| ATOM | 12718 | N | CYS | C | 109 | 35.928 | −21.189 | 58.484 | 1.00 | 53.24 | N |
| ATOM | 12719 | CA | CYS | C | 109 | 35.703 | −22.307 | 59.364 | 1.00 | 54.78 | C |
| ATOM | 12721 | CB | CYS | C | 109 | 34.418 | −22.111 | 60.143 | 1.00 | 53.67 | C |
| ATOM | 12724 | SG | CYS | C | 109 | 34.102 | −23.412 | 61.332 | 1.00 | 56.28 | S |
| ATOM | 12726 | C | CYS | C | 109 | 35.624 | −23.553 | 58.507 | 1.00 | 57.51 | C |
| ATOM | 12727 | O | CYS | C | 109 | 34.681 | −23.734 | 57.736 | 1.00 | 57.78 | O |
| ATOM | 12729 | N | GLU | C | 110 | 36.645 | −24.392 | 58.649 | 1.00 | 61.09 | N |
| ATOM | 12730 | CA | GLU | C | 110 | 36.827 | −25.600 | 57.864 | 1.00 | 63.08 | C |
| ATOM | 12732 | CB | GLU | C | 110 | 38.312 | −25.678 | 57.432 | 1.00 | 64.52 | C |
| ATOM | 12735 | CG | GLU | C | 110 | 38.649 | −26.539 | 56.182 | 1.00 | 65.80 | C |
| ATOM | 12738 | CD | GLU | C | 110 | 40.165 | −26.558 | 55.829 | 1.00 | 68.32 | C |
| ATOM | 12739 | OE1 | GLU | C | 110 | 40.902 | −25.606 | 56.192 | 1.00 | 70.02 | O |

-continued

| | | | | | | | | | | |
|---|---|---|---|---|---|---|---|---|---|---|
| ATOM | 12740 | OE2 | GLU | C | 110 | 40.616 | −27.535 | 55.176 | 1.00 | 72.71 | O |
| ATOM | 12741 | C | GLU | C | 110 | 36.435 | −26.799 | 58.746 | 1.00 | 64.18 | C |
| ATOM | 12742 | O | GLU | C | 110 | 36.989 | −26.967 | 59.835 | 1.00 | 64.29 | O |
| ATOM | 12744 | N | VAL | C | 111 | 35.481 | −27.616 | 58.294 | 1.00 | 65.46 | N |
| ATOM | 12745 | CA | VAL | C | 111 | 35.103 | −28.842 | 59.029 | 1.00 | 67.28 | C |
| ATOM | 12747 | CB | VAL | C | 111 | 33.592 | −28.943 | 59.253 | 1.00 | 67.09 | C |
| ATOM | 12749 | CG1 | VAL | C | 111 | 32.827 | −28.804 | 57.929 | 1.00 | 71.87 | C |
| ATOM | 12753 | CG2 | VAL | C | 111 | 33.150 | −27.890 | 60.269 | 1.00 | 62.06 | C |
| ATOM | 12757 | C | VAL | C | 111 | 35.687 | −30.118 | 58.385 | 1.00 | 70.68 | C |
| ATOM | 12758 | O | VAL | C | 111 | 36.897 | −30.356 | 58.527 | 1.00 | 74.31 | O |
| ATOM | 12760 | N | GLU | C | 112 | 34.875 | −30.953 | 57.723 | 1.00 | 70.85 | N |
| ATOM | 12761 | CA | GLU | C | 112 | 35.412 | −32.098 | 56.967 | 1.00 | 70.44 | C |
| ATOM | 12763 | CB | GLU | C | 112 | 34.302 | −33.088 | 56.544 | 1.00 | 72.33 | C |
| ATOM | 12766 | CG | GLU | C | 112 | 33.117 | −32.488 | 55.740 | 1.00 | 76.96 | C |
| ATOM | 12769 | CD | GLU | C | 112 | 31.783 | −32.493 | 56.496 | 1.00 | 83.20 | C |
| ATOM | 12770 | OE1 | GLU | C | 112 | 31.267 | −33.595 | 56.799 | 1.00 | 82.70 | O |
| ATOM | 12771 | OE2 | GLU | C | 112 | 31.239 | −31.394 | 56.764 | 1.00 | 83.34 | O |
| ATOM | 12772 | C | GLU | C | 112 | 36.208 | −31.542 | 55.776 | 1.00 | 69.64 | C |
| ATOM | 12773 | O | GLU | C | 112 | 37.237 | −30.902 | 55.974 | 1.00 | 68.45 | O |
| ATOM | 12775 | N | ASP | C | 113 | 35.750 | −31.761 | 54.550 | 1.00 | 69.24 | N |
| ATOM | 12776 | CA | ASP | C | 113 | 36.288 | −31.019 | 53.421 | 1.00 | 68.90 | C |
| ATOM | 12778 | CB | ASP | C | 113 | 36.375 | −31.920 | 52.173 | 1.00 | 70.79 | C |
| ATOM | 12781 | CG | ASP | C | 113 | 35.010 | −32.440 | 51.699 | 1.00 | 75.31 | C |
| ATOM | 12782 | OD1 | ASP | C | 113 | 34.967 | −33.039 | 50.597 | 1.00 | 74.76 | O |
| ATOM | 12783 | OD2 | ASP | C | 113 | 33.993 | −32.263 | 52.416 | 1.00 | 77.85 | O |
| ATOM | 12784 | C | ASP | C | 113 | 35.488 | −29.731 | 53.144 | 1.00 | 67.66 | C |
| ATOM | 12785 | O | ASP | C | 113 | 35.714 | −29.080 | 52.130 | 1.00 | 68.60 | O |
| ATOM | 12787 | N | GLN | C | 114 | 34.581 | −29.351 | 54.050 | 1.00 | 66.10 | N |
| ATOM | 12788 | CA | GLN | C | 114 | 33.674 | −28.212 | 53.822 | 1.00 | 64.38 | C |
| ATOM | 12790 | CB | GLN | C | 114 | 32.254 | −28.566 | 54.275 | 1.00 | 64.59 | C |
| ATOM | 12793 | CG | GLN | C | 114 | 31.610 | −29.698 | 53.477 | 1.00 | 64.96 | C |
| ATOM | 12796 | CD | GLN | C | 114 | 31.648 | −29.456 | 51.981 | 1.00 | 64.44 | C |
| ATOM | 12797 | OE1 | GLN | C | 114 | 32.238 | −30.237 | 51.230 | 1.00 | 69.81 | O |
| ATOM | 12798 | NE2 | GLN | C | 114 | 31.041 | −28.357 | 51.542 | 1.00 | 58.73 | N |
| ATOM | 12801 | C | GLN | C | 114 | 34.140 | −26.926 | 54.508 | 1.00 | 62.41 | C |
| ATOM | 12802 | O | GLN | C | 114 | 34.875 | −26.978 | 55.491 | 1.00 | 62.74 | O |
| ATOM | 12804 | N | LYS | C | 115 | 33.707 | −25.781 | 53.976 | 1.00 | 59.25 | N |
| ATOM | 12805 | CA | LYS | C | 115 | 34.153 | −24.466 | 54.454 | 1.00 | 58.31 | C |
| ATOM | 12807 | CB | LYS | C | 115 | 35.215 | −23.882 | 53.522 | 1.00 | 58.36 | C |
| ATOM | 12810 | CG | LYS | C | 115 | 36.517 | −24.629 | 53.525 | 1.00 | 61.04 | C |
| ATOM | 12813 | CD | LYS | C | 115 | 37.409 | −24.182 | 52.387 | 1.00 | 61.58 | C |
| ATOM | 12816 | CE | LYS | C | 115 | 38.614 | −25.107 | 52.219 | 1.00 | 62.86 | C |
| ATOM | 12819 | NZ | LYS | C | 115 | 39.216 | −24.941 | 50.868 | 1.00 | 62.77 | N |
| ATOM | 12823 | C | LYS | C | 115 | 33.012 | −23.475 | 54.513 | 1.00 | 55.16 | C |
| ATOM | 12824 | O | LYS | C | 115 | 32.016 | −23.631 | 53.817 | 1.00 | 54.49 | O |
| ATOM | 12826 | N | GLU | C | 116 | 33.202 | −22.434 | 55.315 | 1.00 | 53.47 | N |
| ATOM | 12827 | CA | GLU | C | 116 | 32.199 | −21.395 | 55.545 | 1.00 | 53.55 | C |
| ATOM | 12829 | CB | GLU | C | 116 | 31.223 | −21.864 | 56.623 | 1.00 | 51.70 | C |
| ATOM | 12832 | CG | GLU | C | 116 | 30.510 | −20.767 | 57.366 | 1.00 | 53.11 | C |
| ATOM | 12835 | CD | GLU | C | 116 | 29.298 | −21.269 | 58.117 | 1.00 | 54.70 | C |
| ATOM | 12836 | OE1 | GLU | C | 116 | 29.472 | −21.756 | 59.251 | 1.00 | 50.98 | O |
| ATOM | 12837 | OE2 | GLU | C | 116 | 28.169 | −21.160 | 57.575 | 1.00 | 61.27 | O |
| ATOM | 12838 | C | GLU | C | 116 | 32.906 | −20.100 | 55.966 | 1.00 | 52.91 | C |
| ATOM | 12839 | O | GLU | C | 116 | 33.875 | −20.146 | 56.713 | 1.00 | 50.94 | O |
| ATOM | 12841 | N | GLU | C | 117 | 32.417 | −18.955 | 55.494 | 1.00 | 53.45 | N |
| ATOM | 12842 | CA | GLU | C | 117 | 33.135 | −17.684 | 55.652 | 1.00 | 54.09 | C |
| ATOM | 12844 | CB | GLU | C | 117 | 33.458 | −17.091 | 54.277 | 1.00 | 53.32 | C |
| ATOM | 12847 | CG | GLU | C | 117 | 34.366 | −17.962 | 53.438 | 1.00 | 54.45 | C |
| ATOM | 12850 | CD | GLU | C | 117 | 34.934 | −17.245 | 52.227 | 1.00 | 56.38 | C |
| ATOM | 12851 | OE1 | GLU | C | 117 | 34.742 | −16.012 | 52.092 | 1.00 | 60.16 | O |
| ATOM | 12852 | OE2 | GLU | C | 117 | 35.586 | −17.927 | 51.407 | 1.00 | 57.41 | O |
| ATOM | 12853 | C | GLU | C | 117 | 32.375 | −16.635 | 56.453 | 1.00 | 53.34 | C |
| ATOM | 12854 | O | GLU | C | 117 | 31.165 | −16.477 | 56.280 | 1.00 | 53.72 | O |
| ATOM | 12856 | N | VAL | C | 118 | 33.098 | −15.910 | 57.311 | 1.00 | 52.42 | N |
| ATOM | 12857 | CA | VAL | C | 118 | 32.570 | −14.709 | 57.956 | 1.00 | 53.21 | C |
| ATOM | 12859 | CB | VAL | C | 118 | 32.438 | −14.861 | 59.483 | 1.00 | 54.38 | C |
| ATOM | 12861 | CG1 | VAL | C | 118 | 31.290 | −13.987 | 59.994 | 1.00 | 55.42 | C |
| ATOM | 12865 | CG2 | VAL | C | 118 | 32.209 | −16.302 | 59.877 | 1.00 | 57.17 | C |
| ATOM | 12869 | C | VAL | C | 118 | 33.525 | −13.564 | 57.717 | 1.00 | 52.25 | C |
| ATOM | 12870 | O | VAL | C | 118 | 34.717 | −13.733 | 57.916 | 1.00 | 55.22 | O |
| ATOM | 12872 | N | GLN | C | 119 | 33.013 | −12.415 | 57.287 | 1.00 | 51.56 | N |
| ATOM | 12873 | CA | GLN | C | 119 | 33.826 | −11.208 | 57.171 | 1.00 | 52.32 | C |
| ATOM | 12875 | CB | GLN | C | 119 | 33.404 | −10.353 | 55.980 | 1.00 | 52.94 | C |
| ATOM | 12878 | CG | GLN | C | 119 | 34.306 | −9.138 | 55.680 | 1.00 | 54.41 | C |
| ATOM | 12881 | CD | GLN | C | 119 | 33.673 | −8.152 | 54.668 | 1.00 | 58.73 | C |
| ATOM | 12882 | OE1 | GLN | C | 119 | 33.008 | −8.557 | 53.706 | 1.00 | 67.09 | O |
| ATOM | 12883 | NE2 | GLN | C | 119 | 33.876 | −6.856 | 54.899 | 1.00 | 65.24 | N |
| ATOM | 12886 | C | GLN | C | 119 | 33.644 | −10.422 | 58.442 | 1.00 | 51.96 | C |
| ATOM | 12887 | O | GLN | C | 119 | 32.522 | −10.058 | 58.792 | 1.00 | 50.71 | O |

| | | | | | -continued | | | | | |
|---|---|---|---|---|---|---|---|---|---|---|
| ATOM | 12889 | N | LEU | C | 120 | 34.758 | −10.192 | 59.136 | 1.00 | 52.15 N |
| ATOM | 12890 | CA | LEU | C | 120 | 34.803 | −9.365 | 60.333 | 1.00 | 50.35 C |
| ATOM | 12892 | CB | LEU | C | 120 | 35.768 | −9.954 | 61.350 | 1.00 | 47.65 C |
| ATOM | 12895 | CG | LEU | C | 120 | 35.959 | −9.089 | 62.597 | 1.00 | 48.62 C |
| ATOM | 12897 | CD1 | LEU | C | 120 | 34.628 | −8.828 | 63.304 | 1.00 | 41.97 C |
| ATOM | 12901 | CD2 | LEU | C | 120 | 36.966 | −9.735 | 63.541 | 1.00 | 49.72 C |
| ATOM | 12905 | C | LEU | C | 120 | 35.282 | −7.967 | 59.973 | 1.00 | 51.47 C |
| ATOM | 12906 | O | LEU | C | 120 | 36.336 | −7.804 | 59.349 | 1.00 | 52.89 O |
| ATOM | 12908 | N | LEU | C | 121 | 34.517 | −6.960 | 60.369 | 1.00 | 50.82 N |
| ATOM | 12909 | CA | LEU | C | 121 | 34.991 | −5.593 | 60.292 | 1.00 | 52.00 C |
| ATOM | 12911 | CB | LEU | C | 121 | 34.101 | −4.758 | 59.361 | 1.00 | 53.51 C |
| ATOM | 12914 | CG | LEU | C | 121 | 33.904 | −5.313 | 57.943 | 1.00 | 51.77 C |
| ATOM | 12916 | CD1 | LEU | C | 121 | 33.007 | −4.396 | 57.146 | 1.00 | 50.39 C |
| ATOM | 12920 | CD2 | LEU | C | 121 | 35.229 | −5.512 | 57.232 | 1.00 | 49.89 C |
| ATOM | 12924 | C | LEU | C | 121 | 35.004 | −5.012 | 61.696 | 1.00 | 52.38 C |
| ATOM | 12925 | O | LEU | C | 121 | 33.953 | −4.858 | 62.310 | 1.00 | 53.44 O |
| ATOM | 12927 | N | VAL | C | 122 | 36.198 | −4.711 | 62.207 | 1.00 | 53.37 N |
| ATOM | 12928 | CA | VAL | C | 122 | 36.356 | −4.034 | 63.500 | 1.00 | 53.90 C |
| ATOM | 12930 | CB | VAL | C | 122 | 37.611 | −4.500 | 64.228 | 1.00 | 53.89 C |
| ATOM | 12932 | CG1 | VAL | C | 122 | 37.757 | −3.765 | 65.569 | 1.00 | 52.63 C |
| ATOM | 12936 | CG2 | VAL | C | 122 | 37.580 | −6.012 | 64.410 | 1.00 | 56.49 C |
| ATOM | 12940 | C | VAL | C | 122 | 36.493 | −2.532 | 63.293 | 1.00 | 54.43 C |
| ATOM | 12941 | O | VAL | C | 122 | 37.331 | −2.101 | 62.500 | 1.00 | 55.12 O |
| ATOM | 12943 | N | PHE | C | 123 | 35.686 | −1.751 | 64.013 | 1.00 | 54.82 N |
| ATOM | 12944 | CA | PHE | C | 123 | 35.684 | −0.292 | 63.889 | 1.00 | 56.06 C |
| ATOM | 12946 | CB | PHE | C | 123 | 34.286 | 0.234 | 63.544 | 1.00 | 56.94 C |
| ATOM | 12949 | CG | PHE | C | 123 | 33.877 | −0.018 | 62.126 | 1.00 | 53.01 C |
| ATOM | 12950 | CD1 | PHE | C | 123 | 34.573 | 0.568 | 61.078 | 1.00 | 55.73 C |
| ATOM | 12952 | CE1 | PHE | C | 123 | 34.209 | 0.331 | 59.758 | 1.00 | 58.17 C |
| ATOM | 12954 | CZ | PHE | C | 123 | 33.138 | −0.490 | 59.482 | 1.00 | 56.84 C |
| ATOM | 12956 | CE2 | PHE | C | 123 | 32.434 | −1.073 | 60.525 | 1.00 | 58.38 C |
| ATOM | 12958 | CD2 | PHE | C | 123 | 32.804 | −0.833 | 61.837 | 1.00 | 51.88 C |
| ATOM | 12960 | C | PHE | C | 123 | 36.135 | 0.355 | 65.171 | 1.00 | 57.02 C |
| ATOM | 12961 | O | PHE | C | 123 | 35.908 | −0.172 | 66.250 | 1.00 | 57.02 O |
| ATOM | 12963 | N | GLY | C | 124 | 36.778 | 1.507 | 65.040 | 1.00 | 59.18 N |
| ATOM | 12964 | CA | GLY | C | 124 | 37.255 | 2.262 | 66.188 | 1.00 | 60.08 C |
| ATOM | 12967 | C | GLY | C | 124 | 36.881 | 3.722 | 66.047 | 1.00 | 61.27 C |
| ATOM | 12968 | O | GLY | C | 124 | 36.670 | 4.219 | 64.934 | 1.00 | 57.87 O |
| ATOM | 12970 | N | LEU | C | 125 | 36.801 | 4.403 | 67.186 | 1.00 | 63.32 N |
| ATOM | 12971 | CA | LEU | C | 125 | 36.464 | 5.818 | 67.233 | 1.00 | 64.26 C |
| ATOM | 12973 | CB | LEU | C | 125 | 35.060 | 5.986 | 67.810 | 1.00 | 65.00 C |
| ATOM | 12976 | CG | LEU | C | 125 | 34.523 | 7.414 | 67.873 | 1.00 | 65.30 C |
| ATOM | 12978 | CD1 | LEU | C | 125 | 34.674 | 8.084 | 66.512 | 1.00 | 65.34 C |
| ATOM | 12982 | CD2 | LEU | C | 125 | 33.070 | 7.418 | 68.341 | 1.00 | 64.50 C |
| ATOM | 12986 | C | LEU | C | 125 | 37.485 | 6.545 | 68.103 | 1.00 | 64.66 C |
| ATOM | 12987 | O | LEU | C | 125 | 37.717 | 6.143 | 69.230 | 1.00 | 66.76 O |
| ATOM | 12989 | N | THR | C | 126 | 38.077 | 7.615 | 67.582 | 1.00 | 64.70 N |
| ATOM | 12990 | CA | THR | C | 126 | 39.171 | 8.308 | 68.261 | 1.00 | 66.19 C |
| ATOM | 12992 | CB | THR | C | 126 | 40.550 | 7.724 | 67.837 | 1.00 | 65.47 C |
| ATOM | 12994 | OG1 | THR | C | 126 | 41.511 | 8.780 | 67.721 | 1.00 | 67.12 O |
| ATOM | 12996 | CG2 | THR | C | 126 | 40.479 | 7.036 | 66.502 | 1.00 | 66.34 C |
| ATOM | 13000 | C | THR | C | 126 | 39.193 | 9.837 | 68.035 | 1.00 | 67.79 C |
| ATOM | 13001 | O | THR | C | 126 | 39.015 | 10.317 | 66.907 | 1.00 | 68.05 O |
| ATOM | 13003 | N | ALA | C | 127 | 39.432 | 10.584 | 69.117 | 1.00 | 68.20 N |
| ATOM | 13004 | CA | ALA | C | 127 | 39.708 | 12.021 | 69.040 | 1.00 | 68.54 C |
| ATOM | 13006 | CB | ALA | C | 127 | 39.517 | 12.678 | 70.404 | 1.00 | 66.69 C |
| ATOM | 13010 | C | ALA | C | 127 | 41.132 | 12.268 | 68.537 | 1.00 | 69.70 C |
| ATOM | 13011 | O | ALA | C | 127 | 42.056 | 11.533 | 68.882 | 1.00 | 69.66 O |
| ATOM | 13013 | N | ASN | C | 128 | 41.307 | 13.310 | 67.726 | 1.00 | 71.66 N |
| ATOM | 13014 | CA | ASN | C | 128 | 42.642 | 13.728 | 67.280 | 1.00 | 72.32 C |
| ATOM | 13016 | CB | ASN | C | 128 | 42.549 | 14.719 | 66.112 | 1.00 | 73.36 C |
| ATOM | 13019 | CG | ASN | C | 128 | 41.821 | 14.129 | 64.898 | 1.00 | 75.66 C |
| ATOM | 13020 | OD1 | ASN | C | 128 | 40.979 | 13.230 | 65.033 | 1.00 | 74.10 O |
| ATOM | 13021 | ND2 | ASN | C | 128 | 42.140 | 14.637 | 63.711 | 1.00 | 70.84 N |
| ATOM | 13024 | C | ASN | C | 128 | 43.422 | 14.337 | 68.441 | 1.00 | 72.77 C |
| ATOM | 13025 | O | ASN | C | 128 | 44.572 | 13.977 | 68.672 | 1.00 | 73.63 O |
| ATOM | 13027 | N | SER | C | 129 | 42.778 | 15.243 | 69.176 | 1.00 | 73.54 N |
| ATOM | 13028 | CA | SER | C | 129 | 43.343 | 15.808 | 70.408 | 1.00 | 72.84 C |
| ATOM | 13030 | CB | SER | C | 129 | 42.825 | 17.236 | 70.626 | 1.00 | 74.19 C |
| ATOM | 13033 | OG | SER | C | 129 | 42.779 | 17.967 | 69.413 | 1.00 | 76.55 O |
| ATOM | 13035 | C | SER | C | 129 | 42.975 | 14.936 | 71.614 | 1.00 | 71.58 C |
| ATOM | 13036 | O | SER | C | 129 | 42.510 | 13.810 | 71.463 | 1.00 | 72.40 O |
| ATOM | 13038 | N | ASP | C | 130 | 43.198 | 15.468 | 72.812 | 1.00 | 71.16 N |
| ATOM | 13039 | CA | ASP | C | 130 | 42.730 | 14.850 | 74.053 | 1.00 | 69.49 C |
| ATOM | 13041 | CB | ASP | C | 130 | 43.382 | 15.546 | 75.265 | 1.00 | 70.05 C |
| ATOM | 13044 | CG | ASP | C | 130 | 43.197 | 14.783 | 76.576 | 1.00 | 71.63 C |
| ATOM | 13045 | OD1 | ASP | C | 130 | 42.504 | 13.740 | 76.599 | 1.00 | 73.08 O |
| ATOM | 13046 | OD2 | ASP | C | 130 | 43.753 | 15.242 | 77.599 | 1.00 | 72.89 O |
| ATOM | 13047 | C | ASP | C | 130 | 41.198 | 14.954 | 74.116 | 1.00 | 68.54 C |

-continued

| | | | | | | | | | | |
|---|---|---|---|---|---|---|---|---|---|---|
| ATOM | 13048 | O | ASP | C | 130 | 40.596 | 15.819 | 73.470 | 1.00 | 69.62 O |
| ATOM | 13050 | N | THR | C | 131 | 40.582 | 14.052 | 74.876 | 1.00 | 65.67 N |
| ATOM | 13051 | CA | THR | C | 131 | 39.136 | 14.034 | 75.078 | 1.00 | 61.78 C |
| ATOM | 13053 | CB | THR | C | 131 | 38.667 | 12.615 | 75.546 | 1.00 | 60.74 C |
| ATOM | 13055 | OG1 | THR | C | 131 | 37.349 | 12.355 | 75.069 | 1.00 | 61.20 O |
| ATOM | 13057 | CG2 | THR | C | 131 | 38.714 | 12.438 | 77.073 | 1.00 | 58.94 C |
| ATOM | 13061 | C | THR | C | 131 | 38.749 | 15.147 | 76.068 | 1.00 | 59.98 C |
| ATOM | 13062 | O | THR | C | 131 | 37.696 | 15.770 | 75.928 | 1.00 | 58.13 O |
| ATOM | 13064 | N | HIS | C | 132 | 39.622 | 15.395 | 77.050 | 1.00 | 58.56 N |
| ATOM | 13065 | CA | HIS | C | 132 | 39.476 | 16.513 | 77.990 | 1.00 | 57.41 C |
| ATOM | 13067 | CB | HIS | C | 132 | 40.223 | 16.234 | 79.302 | 1.00 | 59.02 C |
| ATOM | 13070 | CG | HIS | C | 132 | 39.864 | 14.925 | 79.943 | 1.00 | 61.69 C |
| ATOM | 13071 | ND1 | HIS | C | 132 | 40.534 | 13.750 | 79.668 | 1.00 | 65.34 N |
| ATOM | 13073 | CE1 | HIS | C | 132 | 40.009 | 12.767 | 80.375 | 1.00 | 60.86 C |
| ATOM | 13075 | NE2 | HIS | C | 132 | 39.021 | 13.261 | 81.099 | 1.00 | 62.30 N |
| ATOM | 13077 | CD2 | HIS | C | 132 | 38.915 | 14.609 | 80.855 | 1.00 | 59.02 C |
| ATOM | 13079 | C | HIS | C | 132 | 40.025 | 17.779 | 77.333 | 1.00 | 55.34 C |
| ATOM | 13080 | O | HIS | C | 132 | 41.202 | 17.846 | 77.008 | 1.00 | 57.95 O |
| ATOM | 13082 | N | LEU | C | 133 | 39.179 | 18.787 | 77.162 | 1.00 | 53.02 N |
| ATOM | 13083 | CA | LEU | C | 133 | 39.434 | 19.851 | 76.197 | 1.00 | 50.98 C |
| ATOM | 13085 | CB | LEU | C | 133 | 38.708 | 19.471 | 74.921 | 1.00 | 50.94 C |
| ATOM | 13088 | CG | LEU | C | 133 | 39.339 | 19.853 | 73.596 | 1.00 | 55.43 C |
| ATOM | 13090 | CD1 | LEU | C | 133 | 40.569 | 18.968 | 73.285 | 1.00 | 57.77 C |
| ATOM | 13094 | CD2 | LEU | C | 133 | 38.279 | 19.745 | 72.495 | 1.00 | 53.54 C |
| ATOM | 13098 | C | LEU | C | 133 | 38.912 | 21.197 | 76.688 | 1.00 | 48.12 C |
| ATOM | 13099 | O | LEU | C | 133 | 37.886 | 21.241 | 77.346 | 1.00 | 49.92 O |
| ATOM | 13101 | N | LEU | C | 134 | 39.598 | 22.290 | 76.368 | 1.00 | 45.02 N |
| ATOM | 13102 | CA | LEU | C | 134 | 39.136 | 23.634 | 76.772 | 1.00 | 44.51 C |
| ATOM | 13104 | CB | LEU | C | 134 | 40.233 | 24.694 | 76.620 | 1.00 | 42.50 C |
| ATOM | 13107 | CG | LEU | C | 134 | 41.098 | 24.970 | 77.850 | 1.00 | 41.84 C |
| ATOM | 13109 | CD1 | LEU | C | 134 | 41.712 | 23.689 | 78.383 | 1.00 | 41.05 C |
| ATOM | 13113 | CD2 | LEU | C | 134 | 42.168 | 26.005 | 77.527 | 1.00 | 43.34 C |
| ATOM | 13117 | C | LEU | C | 134 | 37.927 | 24.090 | 75.972 | 1.00 | 44.51 C |
| ATOM | 13118 | O | LEU | C | 134 | 37.749 | 23.701 | 74.824 | 1.00 | 43.86 O |
| ATOM | 13120 | N | GLN | C | 135 | 37.113 | 24.947 | 76.578 | 1.00 | 46.00 N |
| ATOM | 13121 | CA | GLN | C | 135 | 35.953 | 25.515 | 75.898 | 1.00 | 45.14 C |
| ATOM | 13123 | CB | GLN | C | 135 | 35.086 | 26.294 | 76.880 | 1.00 | 44.72 C |
| ATOM | 13126 | CG | GLN | C | 135 | 33.868 | 26.907 | 76.226 | 1.00 | 46.28 C |
| ATOM | 13129 | CD | GLN | C | 135 | 32.920 | 27.494 | 77.227 | 1.00 | 45.70 C |
| ATOM | 13130 | OE1 | GLN | C | 135 | 31.768 | 27.060 | 77.324 | 1.00 | 53.66 O |
| ATOM | 13131 | NE2 | GLN | C | 135 | 33.392 | 28.481 | 77.988 | 1.00 | 28.37 N |
| ATOM | 13134 | C | GLN | C | 135 | 36.350 | 26.428 | 74.732 | 1.00 | 43.60 C |
| ATOM | 13135 | O | GLN | C | 135 | 37.233 | 27.287 | 74.863 | 1.00 | 42.29 O |
| ATOM | 13137 | N | GLY | C | 136 | 35.672 | 26.242 | 73.605 | 1.00 | 42.19 N |
| ATOM | 13138 | CA | GLY | C | 136 | 35.973 | 26.982 | 72.387 | 1.00 | 44.99 C |
| ATOM | 13141 | C | GLY | C | 136 | 36.978 | 26.289 | 71.478 | 1.00 | 45.49 C |
| ATOM | 13142 | O | GLY | C | 136 | 37.163 | 26.714 | 70.340 | 1.00 | 44.08 O |
| ATOM | 13144 | N | GLN | C | 137 | 37.639 | 25.241 | 71.979 | 1.00 | 46.91 N |
| ATOM | 13145 | CA | GLN | C | 137 | 38.539 | 24.421 | 71.160 | 1.00 | 47.59 C |
| ATOM | 13147 | CB | GLN | C | 137 | 39.455 | 23.527 | 72.014 | 1.00 | 46.17 C |
| ATOM | 13150 | CG | GLN | C | 137 | 40.366 | 24.241 | 72.991 | 1.00 | 42.61 C |
| ATOM | 13153 | CD | GLN | C | 137 | 41.387 | 25.092 | 72.305 | 1.00 | 47.64 C |
| ATOM | 13154 | OE1 | GLN | C | 137 | 41.485 | 26.294 | 72.556 | 1.00 | 57.64 O |
| ATOM | 13155 | NE2 | GLN | C | 137 | 42.150 | 24.486 | 71.416 | 1.00 | 51.71 N |
| ATOM | 13158 | C | GLN | C | 137 | 37.681 | 23.531 | 70.284 | 1.00 | 48.99 C |
| ATOM | 13159 | O | GLN | C | 137 | 36.523 | 23.276 | 70.588 | 1.00 | 50.44 O |
| ATOM | 13161 | N | SER | C | 138 | 38.254 | 23.054 | 69.193 | 1.00 | 52.18 N |
| ATOM | 13162 | CA | SER | C | 138 | 37.536 | 22.187 | 68.282 | 1.00 | 53.77 C |
| ATOM | 13164 | CB | SER | C | 138 | 37.931 | 22.500 | 66.848 | 1.00 | 54.12 C |
| ATOM | 13167 | OG | SER | C | 138 | 37.621 | 23.846 | 66.541 | 1.00 | 60.63 O |
| ATOM | 13169 | C | SER | C | 138 | 37.853 | 20.742 | 68.615 | 1.00 | 55.38 C |
| ATOM | 13170 | O | SER | C | 138 | 38.875 | 20.436 | 69.223 | 1.00 | 55.88 O |
| ATOM | 13172 | N | LEU | C | 139 | 36.960 | 19.858 | 68.207 | 1.00 | 57.14 N |
| ATOM | 13173 | CA | LEU | C | 139 | 37.120 | 18.437 | 68.415 | 1.00 | 57.11 C |
| ATOM | 13175 | CB | LEU | C | 139 | 36.086 | 17.970 | 69.427 | 1.00 | 58.66 C |
| ATOM | 13178 | CG | LEU | C | 139 | 35.830 | 16.472 | 69.507 | 1.00 | 60.28 C |
| ATOM | 13180 | CD1 | LEU | C | 139 | 37.148 | 15.751 | 69.779 | 1.00 | 65.64 C |
| ATOM | 13184 | CD2 | LEU | C | 139 | 34.777 | 16.173 | 70.583 | 1.00 | 59.13 C |
| ATOM | 13188 | C | LEU | C | 139 | 36.890 | 17.736 | 67.089 | 1.00 | 57.54 C |
| ATOM | 13189 | O | LEU | C | 139 | 35.884 | 17.990 | 66.423 | 1.00 | 57.65 O |
| ATOM | 13191 | N | THR | C | 140 | 37.819 | 16.873 | 66.701 | 1.00 | 55.84 N |
| ATOM | 13192 | CA | THR | C | 140 | 37.641 | 16.056 | 65.511 | 1.00 | 55.23 C |
| ATOM | 13194 | CB | THR | C | 140 | 38.803 | 16.234 | 64.522 | 1.00 | 54.09 C |
| ATOM | 13196 | OG1 | THR | C | 140 | 38.839 | 17.585 | 64.062 | 1.00 | 49.54 O |
| ATOM | 13198 | CG2 | THR | C | 140 | 38.643 | 15.300 | 63.320 | 1.00 | 55.04 C |
| ATOM | 13202 | C | THR | C | 140 | 37.575 | 14.596 | 65.925 | 1.00 | 55.52 C |
| ATOM | 13203 | O | THR | C | 140 | 38.542 | 14.067 | 66.467 | 1.00 | 55.17 O |
| ATOM | 13205 | N | LEU | C | 141 | 36.436 | 13.955 | 65.673 | 1.00 | 56.14 N |
| ATOM | 13206 | CA | LEU | C | 141 | 36.301 | 12.509 | 65.856 | 1.00 | 56.06 C |

-continued

| ATOM | 13208 | CB | LEU | C | 141 | 34.885 | 12.138 | 66.284 | 1.00 | 55.13 | C |
| ATOM | 13211 | CG | LEU | C | 141 | 34.393 | 12.856 | 67.543 | 1.00 | 54.55 | C |
| ATOM | 13213 | CD1 | LEU | C | 141 | 33.072 | 12.277 | 67.984 | 1.00 | 55.40 | C |
| ATOM | 13217 | CD2 | LEU | C | 141 | 35.414 | 12.769 | 68.678 | 1.00 | 55.73 | C |
| ATOM | 13221 | C | LEU | C | 141 | 36.656 | 11.826 | 64.555 | 1.00 | 56.15 | C |
| ATOM | 13222 | O | LEU | C | 141 | 36.362 | 12.341 | 63.479 | 1.00 | 57.21 | O |
| ATOM | 13224 | N | THR | C | 142 | 37.316 | 10.680 | 64.654 | 1.00 | 57.30 | N |
| ATOM | 13225 | CA | THR | C | 142 | 37.834 | 9.996 | 63.474 | 1.00 | 58.06 | C |
| ATOM | 13227 | CB | THR | C | 142 | 39.313 | 10.341 | 63.258 | 1.00 | 57.47 | C |
| ATOM | 13229 | OG1 | THR | C | 142 | 39.463 | 11.763 | 63.254 | 1.00 | 61.17 | O |
| ATOM | 13231 | CG2 | THR | C | 142 | 39.825 | 9.791 | 61.935 | 1.00 | 56.93 | C |
| ATOM | 13235 | C | THR | C | 142 | 37.650 | 8.481 | 63.599 | 1.00 | 58.80 | C |
| ATOM | 13236 | O | THR | C | 142 | 38.083 | 7.868 | 64.577 | 1.00 | 57.62 | O |
| ATOM | 13238 | N | LEU | C | 143 | 36.976 | 7.896 | 62.612 | 1.00 | 58.40 | N |
| ATOM | 13239 | CA | LEU | C | 143 | 36.783 | 6.457 | 62.565 | 1.00 | 58.37 | C |
| ATOM | 13241 | CB | LEU | C | 143 | 35.722 | 6.080 | 61.520 | 1.00 | 57.10 | C |
| ATOM | 13244 | CG | LEU | C | 143 | 34.273 | 5.905 | 61.977 | 1.00 | 55.46 | C |
| ATOM | 13246 | CD1 | LEU | C | 143 | 33.895 | 6.843 | 63.108 | 1.00 | 56.46 | C |
| ATOM | 13250 | CD2 | LEU | C | 143 | 33.340 | 6.100 | 60.799 | 1.00 | 57.96 | C |
| ATOM | 13254 | C | LEU | C | 143 | 38.102 | 5.790 | 62.214 | 1.00 | 58.83 | C |
| ATOM | 13255 | O | LEU | C | 143 | 38.830 | 6.280 | 61.355 | 1.00 | 60.93 | O |
| ATOM | 13257 | N | GLU | C | 144 | 38.412 | 4.693 | 62.893 | 1.00 | 57.52 | N |
| ATOM | 13258 | CA | GLU | C | 144 | 39.456 | 3.797 | 62.440 | 1.00 | 58.34 | C |
| ATOM | 13260 | CB | GLU | C | 144 | 40.271 | 3.263 | 63.603 | 1.00 | 58.84 | C |
| ATOM | 13263 | CG | GLU | C | 144 | 40.925 | 4.355 | 64.417 | 1.00 | 61.40 | C |
| ATOM | 13266 | CD | GLU | C | 144 | 41.677 | 3.805 | 65.593 | 1.00 | 60.71 | C |
| ATOM | 13267 | OE1 | GLU | C | 144 | 42.697 | 3.121 | 65.361 | 1.00 | 70.68 | O |
| ATOM | 13268 | OE2 | GLU | C | 144 | 41.237 | 4.031 | 66.742 | 1.00 | 60.94 | O |
| ATOM | 13269 | C | GLU | C | 144 | 38.767 | 2.666 | 61.719 | 1.00 | 58.59 | C |
| ATOM | 13270 | O | GLU | C | 144 | 37.847 | 2.049 | 62.259 | 1.00 | 60.83 | O |
| ATOM | 13272 | N | SER | C | 145 | 39.234 | 2.397 | 60.504 | 1.00 | 58.97 | N |
| ATOM | 13273 | CA | SER | C | 145 | 38.552 | 1.542 | 59.544 | 1.00 | 57.62 | C |
| ATOM | 13275 | CB | SER | C | 145 | 37.951 | 2.412 | 58.441 | 1.00 | 58.80 | C |
| ATOM | 13278 | OG | SER | C | 145 | 36.697 | 2.930 | 58.829 | 1.00 | 66.00 | O |
| ATOM | 13280 | C | SER | C | 145 | 39.522 | 0.592 | 58.878 | 1.00 | 56.23 | C |
| ATOM | 13281 | O | SER | C | 145 | 40.648 | 0.982 | 58.555 | 1.00 | 57.81 | O |
| ATOM | 13283 | N | PRO | C | 146 | 39.087 | −0.649 | 58.634 | 1.00 | 54.08 | N |
| ATOM | 13284 | CA | PRO | C | 146 | 39.866 | −1.520 | 57.764 | 1.00 | 53.84 | C |
| ATOM | 13286 | CB | PRO | C | 146 | 39.318 | −2.912 | 58.076 | 1.00 | 53.93 | C |
| ATOM | 13289 | CG | PRO | C | 146 | 37.921 | −2.677 | 58.529 | 1.00 | 54.99 | C |
| ATOM | 13292 | CD | PRO | C | 146 | 37.883 | −1.313 | 59.161 | 1.00 | 53.90 | C |
| ATOM | 13295 | C | PRO | C | 146 | 39.669 | −1.159 | 56.295 | 1.00 | 53.49 | C |
| ATOM | 13296 | O | PRO | C | 146 | 38.703 | −0.482 | 55.957 | 1.00 | 53.16 | O |
| ATOM | 13297 | N | PRO | C | 147 | 40.562 | −1.637 | 55.416 | 1.00 | 55.44 | N |
| ATOM | 13298 | CA | PRO | C | 147 | 40.616 | −1.167 | 54.030 | 1.00 | 55.00 | C |
| ATOM | 13300 | CB | PRO | C | 147 | 41.714 | −2.038 | 53.405 | 1.00 | 55.62 | C |
| ATOM | 13303 | CG | PRO | C | 147 | 42.539 | −2.479 | 54.534 | 1.00 | 57.05 | C |
| ATOM | 13306 | CD | PRO | C | 147 | 41.590 | −2.661 | 55.674 | 1.00 | 56.94 | C |
| ATOM | 13309 | C | PRO | C | 147 | 39.320 | −1.266 | 53.215 | 1.00 | 54.73 | C |
| ATOM | 13310 | O | PRO | C | 147 | 38.941 | −0.298 | 52.544 | 1.00 | 57.19 | O |
| ATOM | 13311 | N | GLY | C | 148 | 38.652 | −2.411 | 53.249 | 1.00 | 52.29 | N |
| ATOM | 13312 | CA | GLY | C | 148 | 37.464 | −2.595 | 52.408 | 1.00 | 52.17 | C |
| ATOM | 13315 | C | GLY | C | 148 | 36.237 | −1.789 | 52.824 | 1.00 | 50.22 | C |
| ATOM | 13316 | O | GLY | C | 148 | 35.320 | −1.594 | 52.040 | 1.00 | 46.84 | O |
| ATOM | 13318 | N | SER | C | 149 | 36.237 | −1.310 | 54.062 | 1.00 | 50.79 | N |
| ATOM | 13319 | CA | SER | C | 149 | 35.034 | −0.845 | 54.733 | 1.00 | 51.54 | C |
| ATOM | 13321 | CB | SER | C | 149 | 35.307 | −0.734 | 56.238 | 1.00 | 52.67 | C |
| ATOM | 13324 | OG | SER | C | 149 | 36.156 | 0.374 | 56.504 | 1.00 | 53.58 | O |
| ATOM | 13326 | C | SER | C | 149 | 34.540 | 0.504 | 54.230 | 1.00 | 51.45 | C |
| ATOM | 13327 | O | SER | C | 149 | 35.192 | 1.177 | 53.433 | 1.00 | 52.31 | O |
| ATOM | 13329 | N | SER | C | 150 | 33.400 | 0.918 | 54.757 | 1.00 | 50.20 | N |
| ATOM | 13330 | CA | SER | C | 150 | 32.718 | 2.076 | 54.246 | 1.00 | 50.72 | C |
| ATOM | 13332 | CB | SER | C | 150 | 31.914 | 1.653 | 53.026 | 1.00 | 51.30 | C |
| ATOM | 13335 | OG | SER | C | 150 | 31.170 | 2.752 | 52.557 | 1.00 | 57.24 | O |
| ATOM | 13337 | C | SER | C | 150 | 31.780 | 2.701 | 55.274 | 1.00 | 49.72 | C |
| ATOM | 13338 | O | SER | C | 150 | 30.622 | 2.963 | 54.966 | 1.00 | 49.54 | O |
| ATOM | 13340 | N | PRO | C | 151 | 32.279 | 2.961 | 56.492 | 1.00 | 47.89 | N |
| ATOM | 13341 | CA | PRO | C | 151 | 31.375 | 3.391 | 57.546 | 1.00 | 47.74 | C |
| ATOM | 13343 | CB | PRO | C | 151 | 32.236 | 3.256 | 58.801 | 1.00 | 47.05 | C |
| ATOM | 13346 | CG | PRO | C | 151 | 33.612 | 3.492 | 58.314 | 1.00 | 46.59 | C |
| ATOM | 13349 | CD | PRO | C | 151 | 33.674 | 2.879 | 56.966 | 1.00 | 47.73 | C |
| ATOM | 13352 | C | PRO | C | 151 | 30.860 | 4.827 | 57.380 | 1.00 | 46.51 | C |
| ATOM | 13353 | O | PRO | C | 151 | 31.380 | 5.591 | 56.570 | 1.00 | 44.35 | O |
| ATOM | 13354 | N | SER | C | 152 | 29.789 | 5.135 | 58.107 | 1.00 | 47.30 | N |
| ATOM | 13355 | CA | SER | C | 152 | 29.282 | 6.494 | 58.285 | 1.00 | 49.22 | C |
| ATOM | 13357 | CB | SER | C | 152 | 27.880 | 6.724 | 57.679 | 1.00 | 49.04 | C |
| ATOM | 13360 | OG | SER | C | 152 | 27.697 | 6.074 | 56.434 | 1.00 | 56.60 | O |
| ATOM | 13362 | C | SER | C | 152 | 29.148 | 6.603 | 59.771 | 1.00 | 50.48 | C |
| ATOM | 13363 | O | SER | C | 152 | 29.031 | 5.591 | 60.455 | 1.00 | 50.84 | O |

-continued

| | | | | | | | | | | |
|---|---|---|---|---|---|---|---|---|---|---|
| ATOM | 13365 | N | VAL | C | 153 | 29.116 | 7.828 | 60.272 | 1.00 | 52.23 N |
| ATOM | 13366 | CA | VAL | C | 153 | 29.083 | 8.051 | 61.700 | 1.00 | 51.85 C |
| ATOM | 13368 | CB | VAL | C | 153 | 30.483 | 8.458 | 62.225 | 1.00 | 50.48 C |
| ATOM | 13370 | CG1 | VAL | C | 153 | 31.040 | 9.642 | 61.457 | 1.00 | 52.69 C |
| ATOM | 13374 | CG2 | VAL | C | 153 | 30.433 | 8.752 | 63.698 | 1.00 | 52.75 C |
| ATOM | 13378 | C | VAL | C | 153 | 28.024 | 9.092 | 62.031 | 1.00 | 52.30 C |
| ATOM | 13379 | O | VAL | C | 153 | 27.772 | 10.003 | 61.247 | 1.00 | 48.78 O |
| ATOM | 13381 | N | GLN | C | 154 | 27.380 | 8.904 | 63.180 | 1.00 | 53.85 N |
| ATOM | 13382 | CA | GLN | C | 154 | 26.485 | 9.892 | 63.751 | 1.00 | 54.16 C |
| ATOM | 13384 | CB | GLN | C | 154 | 25.026 | 9.537 | 63.502 | 1.00 | 54.93 C |
| ATOM | 13387 | CG | GLN | C | 154 | 24.088 | 10.066 | 64.583 | 1.00 | 53.16 C |
| ATOM | 13390 | CD | GLN | C | 154 | 22.652 | 9.871 | 64.241 | 1.00 | 50.89 C |
| ATOM | 13391 | OE1 | GLN | C | 154 | 22.007 | 8.953 | 64.737 | 1.00 | 53.15 O |
| ATOM | 13392 | NE2 | GLN | C | 154 | 22.131 | 10.735 | 63.394 | 1.00 | 39.18 N |
| ATOM | 13395 | C | GLN | C | 154 | 26.724 | 9.934 | 65.242 | 1.00 | 56.50 C |
| ATOM | 13396 | O | GLN | C | 154 | 26.533 | 8.935 | 65.939 | 1.00 | 57.26 O |
| ATOM | 13398 | N | CYS | C | 155 | 27.121 | 11.100 | 65.726 | 1.00 | 57.78 N |
| ATOM | 13399 | CA | CYS | C | 155 | 27.325 | 11.307 | 67.143 | 1.00 | 56.92 C |
| ATOM | 13401 | CB | CYS | C | 155 | 28.694 | 11.905 | 67.380 | 1.00 | 57.67 C |
| ATOM | 13404 | SG | CYS | C | 155 | 29.955 | 10.746 | 66.917 | 1.00 | 61.13 S |
| ATOM | 13406 | C | CYS | C | 155 | 26.250 | 12.214 | 67.688 | 1.00 | 57.19 C |
| ATOM | 13407 | O | CYS | C | 155 | 25.771 | 13.133 | 67.018 | 1.00 | 55.37 O |
| ATOM | 13409 | N | ARG | C | 156 | 25.875 | 11.932 | 68.922 | 1.00 | 57.40 N |
| ATOM | 13410 | CA | ARG | C | 156 | 24.841 | 12.660 | 69.605 | 1.00 | 56.08 C |
| ATOM | 13412 | CB | ARG | C | 156 | 23.671 | 11.705 | 69.799 | 1.00 | 56.11 C |
| ATOM | 13415 | CG | ARG | C | 156 | 22.543 | 12.210 | 70.658 | 1.00 | 59.89 C |
| ATOM | 13418 | CD | ARG | C | 156 | 21.253 | 11.382 | 70.489 | 1.00 | 63.64 C |
| ATOM | 13421 | NE | ARG | C | 156 | 21.484 | 10.021 | 69.980 | 1.00 | 68.96 N |
| ATOM | 13423 | CZ | ARG | C | 156 | 20.962 | 9.505 | 68.862 | 1.00 | 69.73 C |
| ATOM | 13424 | NH1 | ARG | C | 156 | 20.138 | 10.201 | 68.078 | 1.00 | 64.69 N |
| ATOM | 13427 | NH2 | ARG | C | 156 | 21.264 | 8.258 | 68.527 | 1.00 | 75.77 N |
| ATOM | 13430 | C | ARG | C | 156 | 25.464 | 13.118 | 70.926 | 1.00 | 54.21 C |
| ATOM | 13431 | O | ARG | C | 156 | 25.943 | 12.282 | 71.697 | 1.00 | 52.54 O |
| ATOM | 13433 | N | SER | C | 157 | 25.514 | 14.437 | 71.157 | 1.00 | 52.79 N |
| ATOM | 13434 | CA | SER | C | 157 | 26.035 | 14.999 | 72.429 | 1.00 | 52.24 C |
| ATOM | 13436 | CB | SER | C | 157 | 26.209 | 16.528 | 72.325 | 1.00 | 53.85 C |
| ATOM | 13439 | OG | SER | C | 157 | 24.962 | 17.211 | 72.264 | 1.00 | 55.35 O |
| ATOM | 13441 | C | SER | C | 157 | 25.127 | 14.648 | 73.617 | 1.00 | 49.81 C |
| ATOM | 13442 | O | SER | C | 157 | 24.094 | 14.010 | 73.455 | 1.00 | 50.61 O |
| ATOM | 13444 | N | PRO | C | 158 | 25.510 | 15.049 | 74.828 | 1.00 | 47.61 N |
| ATOM | 13445 | CA | PRO | C | 158 | 24.577 | 14.786 | 75.926 | 1.00 | 46.50 C |
| ATOM | 13447 | CB | PRO | C | 158 | 25.363 | 15.206 | 77.177 | 1.00 | 44.45 C |
| ATOM | 13450 | CG | PRO | C | 158 | 26.807 | 15.244 | 76.732 | 1.00 | 47.62 C |
| ATOM | 13453 | CD | PRO | C | 158 | 26.762 | 15.661 | 75.296 | 1.00 | 49.56 C |
| ATOM | 13456 | C | PRO | C | 158 | 23.259 | 15.558 | 75.805 | 1.00 | 44.87 C |
| ATOM | 13457 | O | PRO | C | 158 | 22.320 | 15.281 | 76.553 | 1.00 | 44.21 O |
| ATOM | 13458 | N | ARG | C | 159 | 23.184 | 16.503 | 74.871 | 1.00 | 43.29 N |
| ATOM | 13459 | CA | ARG | C | 159 | 21.946 | 17.248 | 74.630 | 1.00 | 43.47 C |
| ATOM | 13461 | CB | ARG | C | 159 | 22.263 | 18.680 | 74.225 | 1.00 | 38.69 C |
| ATOM | 13464 | CG | ARG | C | 159 | 22.867 | 19.454 | 75.363 | 1.00 | 39.57 C |
| ATOM | 13467 | CD | ARG | C | 159 | 23.619 | 20.649 | 74.859 | 1.00 | 46.59 C |
| ATOM | 13470 | NE | ARG | C | 159 | 22.789 | 21.472 | 73.985 | 1.00 | 52.09 N |
| ATOM | 13472 | CZ | ARG | C | 159 | 23.241 | 22.245 | 72.998 | 1.00 | 53.47 C |
| ATOM | 13473 | NH1 | ARG | C | 159 | 22.373 | 22.943 | 72.276 | 1.00 | 55.12 N |
| ATOM | 13476 | NH2 | ARG | C | 159 | 24.543 | 22.328 | 72.722 | 1.00 | 50.97 N |
| ATOM | 13479 | C | ARG | C | 159 | 21.048 | 16.591 | 73.593 | 1.00 | 42.68 C |
| ATOM | 13480 | O | ARG | C | 159 | 19.992 | 17.112 | 73.276 | 1.00 | 41.59 O |
| ATOM | 13482 | N | GLY | C | 160 | 21.461 | 15.447 | 73.064 | 1.00 | 44.46 N |
| ATOM | 13483 | CA | GLY | C | 160 | 20.621 | 14.708 | 72.140 | 1.00 | 46.94 C |
| ATOM | 13486 | C | GLY | C | 160 | 20.629 | 15.230 | 70.713 | 1.00 | 48.82 C |
| ATOM | 13487 | O | GLY | C | 160 | 19.939 | 14.673 | 69.859 | 1.00 | 49.55 O |
| ATOM | 13489 | N | LYS | C | 161 | 21.405 | 16.285 | 70.445 | 1.00 | 50.66 N |
| ATOM | 13490 | CA | LYS | C | 161 | 21.554 | 16.821 | 69.087 | 1.00 | 51.33 C |
| ATOM | 13492 | CB | LYS | C | 161 | 21.989 | 18.286 | 69.118 | 1.00 | 52.12 C |
| ATOM | 13495 | CG | LYS | C | 161 | 20.814 | 19.259 | 69.051 | 1.00 | 54.16 C |
| ATOM | 13498 | CD | LYS | C | 161 | 21.059 | 20.552 | 69.833 | 1.00 | 54.75 C |
| ATOM | 13501 | CE | LYS | C | 161 | 20.208 | 21.712 | 69.279 | 1.00 | 60.67 C |
| ATOM | 13504 | NZ | LYS | C | 161 | 18.936 | 21.257 | 68.624 | 1.00 | 62.40 N |
| ATOM | 13508 | C | LYS | C | 161 | 22.517 | 15.977 | 68.246 | 1.00 | 52.08 C |
| ATOM | 13509 | O | LYS | C | 161 | 23.698 | 15.823 | 68.577 | 1.00 | 51.42 O |
| ATOM | 13511 | N | ASN | C | 162 | 21.973 | 15.418 | 67.165 | 1.00 | 53.76 N |
| ATOM | 13512 | CA | ASN | C | 162 | 22.719 | 14.558 | 66.248 | 1.00 | 53.27 C |
| ATOM | 13514 | CB | ASN | C | 162 | 21.762 | 13.682 | 65.414 | 1.00 | 52.35 C |
| ATOM | 13517 | CG | ASN | C | 162 | 21.140 | 12.541 | 66.232 | 1.00 | 54.54 C |
| ATOM | 13518 | OD1 | ASN | C | 162 | 19.929 | 12.431 | 66.352 | 1.00 | 56.59 O |
| ATOM | 13519 | ND2 | ASN | C | 162 | 21.980 | 11.697 | 66.801 | 1.00 | 64.74 N |
| ATOM | 13522 | C | ASN | C | 162 | 23.632 | 15.371 | 65.335 | 1.00 | 53.02 C |
| ATOM | 13523 | O | ASN | C | 162 | 23.293 | 16.464 | 64.904 | 1.00 | 52.72 O |
| ATOM | 13525 | N | ILE | C | 163 | 24.810 | 14.825 | 65.076 | 1.00 | 54.51 N |

-continued

| | | | | | | | | | | |
|---|---|---|---|---|---|---|---|---|---|---|
| ATOM | 13526 | CA | ILE | C | 163 | 25.796 | 15.426 | 64.182 | 1.00 | 54.29 C |
| ATOM | 13528 | CB | ILE | C | 163 | 26.833 | 16.317 | 64.956 | 1.00 | 55.78 C |
| ATOM | 13530 | CG1 | ILE | C | 163 | 28.259 | 16.124 | 64.434 | 1.00 | 56.60 C |
| ATOM | 13533 | CD1 | ILE | C | 163 | 29.290 | 16.963 | 65.166 | 1.00 | 58.16 C |
| ATOM | 13537 | CG2 | ILE | C | 163 | 26.826 | 16.026 | 66.463 | 1.00 | 59.34 C |
| ATOM | 13541 | C | ILE | C | 163 | 26.429 | 14.256 | 63.430 | 1.00 | 52.97 C |
| ATOM | 13542 | O | ILE | C | 163 | 26.642 | 13.185 | 64.011 | 1.00 | 52.84 O |
| ATOM | 13544 | N | GLN | C | 164 | 26.708 | 14.457 | 62.144 | 1.00 | 51.29 N |
| ATOM | 13545 | CA | GLN | C | 164 | 26.970 | 13.348 | 61.228 | 1.00 | 51.18 C |
| ATOM | 13547 | CB | GLN | C | 164 | 25.715 | 13.058 | 60.400 | 1.00 | 49.19 C |
| ATOM | 13550 | CG | GLN | C | 164 | 24.463 | 12.853 | 61.257 | 1.00 | 49.09 C |
| ATOM | 13553 | CD | GLN | C | 164 | 23.235 | 12.547 | 60.446 | 1.00 | 48.60 C |
| ATOM | 13554 | OE1 | GLN | C | 164 | 22.120 | 12.617 | 60.949 | 1.00 | 45.05 O |
| ATOM | 13555 | NE2 | GLN | C | 164 | 23.429 | 12.201 | 59.181 | 1.00 | 42.88 N |
| ATOM | 13558 | C | GLN | C | 164 | 28.143 | 13.602 | 60.292 | 1.00 | 52.81 C |
| ATOM | 13559 | O | GLN | C | 164 | 28.612 | 14.730 | 60.147 | 1.00 | 54.69 O |
| ATOM | 13561 | N | GLY | C | 165 | 28.605 | 12.536 | 59.645 | 1.00 | 53.15 N |
| ATOM | 13562 | CA | GLY | C | 165 | 29.761 | 12.618 | 58.765 | 1.00 | 51.77 C |
| ATOM | 13565 | C | GLY | C | 165 | 30.208 | 11.267 | 58.257 | 1.00 | 50.80 C |
| ATOM | 13566 | O | GLY | C | 165 | 29.573 | 10.249 | 58.541 | 1.00 | 50.17 O |
| ATOM | 13568 | N | GLY | C | 166 | 31.305 | 11.276 | 57.501 | 1.00 | 49.63 N |
| ATOM | 13569 | CA | GLY | C | 166 | 31.852 | 10.072 | 56.877 | 1.00 | 50.14 C |
| ATOM | 13572 | C | GLY | C | 166 | 32.712 | 9.269 | 57.821 | 1.00 | 49.13 C |
| ATOM | 13573 | O | GLY | C | 166 | 32.198 | 8.633 | 58.735 | 1.00 | 48.51 O |
| ATOM | 13575 | N | LYS | C | 167 | 34.022 | 9.287 | 57.579 | 1.00 | 50.12 N |
| ATOM | 13576 | CA | LYS | C | 167 | 35.004 | 8.694 | 58.493 | 1.00 | 51.62 C |
| ATOM | 13578 | CB | LYS | C | 167 | 36.231 | 8.219 | 57.716 | 1.00 | 51.14 C |
| ATOM | 13581 | CG | LYS | C | 167 | 35.879 | 7.157 | 56.684 | 1.00 | 50.23 C |
| ATOM | 13584 | CD | LYS | C | 167 | 37.022 | 6.193 | 56.362 | 1.00 | 50.34 C |
| ATOM | 13587 | CE | LYS | C | 167 | 37.566 | 6.339 | 54.943 | 1.00 | 53.65 C |
| ATOM | 13590 | NZ | LYS | C | 167 | 37.725 | 4.997 | 54.263 | 1.00 | 52.26 N |
| ATOM | 13594 | C | LYS | C | 167 | 35.414 | 9.699 | 59.560 | 1.00 | 51.64 C |
| ATOM | 13595 | O | LYS | C | 167 | 36.056 | 9.349 | 60.545 | 1.00 | 50.45 O |
| ATOM | 13597 | N | THR | C | 168 | 35.030 | 10.951 | 59.345 | 1.00 | 54.51 N |
| ATOM | 13598 | CA | THR | C | 168 | 35.330 | 12.037 | 60.260 | 1.00 | 55.70 C |
| ATOM | 13600 | CB | THR | C | 168 | 36.499 | 12.885 | 59.715 | 1.00 | 55.88 C |
| ATOM | 13602 | OG1 | THR | C | 168 | 37.732 | 12.253 | 60.079 | 1.00 | 58.05 O |
| ATOM | 13604 | CG2 | THR | C | 168 | 36.488 | 14.322 | 60.268 | 1.00 | 56.12 C |
| ATOM | 13608 | C | THR | C | 168 | 34.105 | 12.915 | 60.485 | 1.00 | 56.05 C |
| ATOM | 13609 | O | THR | C | 168 | 33.313 | 13.156 | 59.570 | 1.00 | 56.23 O |
| ATOM | 13611 | N | LEU | C | 169 | 33.954 | 13.360 | 61.726 | 1.00 | 57.16 N |
| ATOM | 13612 | CA | LEU | C | 169 | 33.083 | 14.481 | 62.051 | 1.00 | 59.11 C |
| ATOM | 13614 | CB | LEU | C | 169 | 31.708 | 14.011 | 62.551 | 1.00 | 60.26 C |
| ATOM | 13617 | CG | LEU | C | 169 | 31.620 | 13.203 | 63.845 | 1.00 | 59.74 C |
| ATOM | 13619 | CD1 | LEU | C | 169 | 31.716 | 14.080 | 65.070 | 1.00 | 63.90 C |
| ATOM | 13623 | CD2 | LEU | C | 169 | 30.319 | 12.452 | 63.870 | 1.00 | 62.44 C |
| ATOM | 13627 | C | LEU | C | 169 | 33.790 | 15.353 | 63.077 | 1.00 | 57.74 C |
| ATOM | 13628 | O | LEU | C | 169 | 34.628 | 14.868 | 63.842 | 1.00 | 54.79 O |
| ATOM | 13630 | N | SER | C | 170 | 33.449 | 16.638 | 63.069 | 1.00 | 58.40 N |
| ATOM | 13631 | CA | SER | C | 170 | 34.145 | 17.635 | 63.858 | 1.00 | 59.45 C |
| ATOM | 13633 | CB | SER | C | 170 | 35.186 | 18.324 | 62.990 | 1.00 | 58.68 C |
| ATOM | 13636 | OG | SER | C | 170 | 35.812 | 19.369 | 63.719 | 1.00 | 66.56 O |
| ATOM | 13638 | C | SER | C | 170 | 33.214 | 18.702 | 64.395 | 1.00 | 59.30 C |
| ATOM | 13639 | O | SER | C | 170 | 32.517 | 19.342 | 63.623 | 1.00 | 61.92 O |
| ATOM | 13641 | N | VAL | C | 171 | 33.213 | 18.902 | 65.709 | 1.00 | 60.36 N |
| ATOM | 13642 | CA | VAL | C | 171 | 32.604 | 20.093 | 66.304 | 1.00 | 61.92 C |
| ATOM | 13644 | CB | VAL | C | 171 | 31.946 | 19.800 | 67.667 | 1.00 | 62.56 C |
| ATOM | 13646 | CG1 | VAL | C | 171 | 31.675 | 21.111 | 68.441 | 1.00 | 64.73 C |
| ATOM | 13650 | CG2 | VAL | C | 171 | 30.664 | 19.013 | 67.471 | 1.00 | 63.91 C |
| ATOM | 13654 | C | VAL | C | 171 | 33.683 | 21.135 | 66.527 | 1.00 | 62.32 C |
| ATOM | 13655 | O | VAL | C | 171 | 34.661 | 20.861 | 67.223 | 1.00 | 64.51 O |
| ATOM | 13657 | N | SER | C | 172 | 33.514 | 22.320 | 65.940 | 1.00 | 61.27 N |
| ATOM | 13658 | CA | SER | C | 172 | 34.406 | 23.444 | 66.229 | 1.00 | 62.74 C |
| ATOM | 13660 | CB | SER | C | 172 | 34.711 | 24.258 | 64.971 | 1.00 | 62.68 C |
| ATOM | 13663 | OG | SER | C | 172 | 33.522 | 24.736 | 64.381 | 1.00 | 64.10 O |
| ATOM | 13665 | C | SER | C | 172 | 33.754 | 24.326 | 67.282 | 1.00 | 64.49 C |
| ATOM | 13666 | O | SER | C | 172 | 32.520 | 24.449 | 67.323 | 1.00 | 67.37 O |
| ATOM | 13668 | N | GLN | C | 173 | 34.572 | 24.931 | 68.137 | 1.00 | 61.64 N |
| ATOM | 13669 | CA | GLN | C | 173 | 34.050 | 25.722 | 69.244 | 1.00 | 59.97 C |
| ATOM | 13671 | CB | GLN | C | 173 | 33.278 | 26.931 | 68.723 | 1.00 | 61.20 C |
| ATOM | 13674 | CG | GLN | C | 173 | 34.083 | 27.852 | 67.871 | 1.00 | 60.16 C |
| ATOM | 13677 | CD | GLN | C | 173 | 33.290 | 29.058 | 67.500 | 1.00 | 60.41 C |
| ATOM | 13678 | OE1 | GLN | C | 173 | 32.284 | 28.956 | 66.793 | 1.00 | 57.88 O |
| ATOM | 13679 | NE2 | GLN | C | 173 | 33.719 | 30.219 | 67.985 | 1.00 | 61.41 N |
| ATOM | 13682 | C | GLN | C | 173 | 33.156 | 24.895 | 70.176 | 1.00 | 58.42 C |
| ATOM | 13683 | O | GLN | C | 173 | 31.954 | 25.138 | 70.301 | 1.00 | 57.60 O |
| ATOM | 13685 | N | LEU | C | 174 | 33.767 | 23.927 | 70.842 | 1.00 | 57.29 N |
| ATOM | 13686 | CA | LEU | C | 174 | 33.060 | 23.051 | 71.770 | 1.00 | 55.11 C |
| ATOM | 13688 | CB | LEU | C | 174 | 34.032 | 21.984 | 72.284 | 1.00 | 54.98 C |

-continued

| | | | | | | | | | | |
|---|---|---|---|---|---|---|---|---|---|---|
| ATOM | 13691 | CG | LEU | C | 174 | 33.514 | 20.660 | 72.857 | 1.00 | 57.86 C |
| ATOM | 13693 | CD1 | LEU | C | 174 | 32.168 | 20.248 | 72.279 | 1.00 | 57.73 C |
| ATOM | 13697 | CD2 | LEU | C | 174 | 34.558 | 19.548 | 72.648 | 1.00 | 56.96 C |
| ATOM | 13701 | C | LEU | C | 174 | 32.479 | 23.879 | 72.917 | 1.00 | 51.79 C |
| ATOM | 13702 | O | LEU | C | 174 | 33.158 | 24.752 | 73.442 | 1.00 | 53.25 O |
| ATOM | 13704 | N | GLU | C | 175 | 31.221 | 23.617 | 73.278 | 1.00 | 49.51 N |
| ATOM | 13705 | CA | GLU | C | 175 | 30.515 | 24.363 | 74.339 | 1.00 | 47.81 C |
| ATOM | 13707 | CB | GLU | C | 175 | 29.102 | 24.732 | 73.891 | 1.00 | 46.65 C |
| ATOM | 13710 | CG | GLU | C | 175 | 29.026 | 25.677 | 72.721 | 1.00 | 49.04 C |
| ATOM | 13713 | CD | GLU | C | 175 | 27.613 | 25.804 | 72.179 | 1.00 | 51.02 C |
| ATOM | 13714 | OE1 | GLU | C | 175 | 27.064 | 24.786 | 71.716 | 1.00 | 58.42 O |
| ATOM | 13715 | OE2 | GLU | C | 175 | 27.052 | 26.918 | 72.210 | 1.00 | 57.27 O |
| ATOM | 13716 | C | GLU | C | 175 | 30.390 | 23.562 | 75.631 | 1.00 | 44.63 C |
| ATOM | 13717 | O | GLU | C | 175 | 30.128 | 22.354 | 75.613 | 1.00 | 39.63 O |
| ATOM | 13719 | N | LEU | C | 176 | 30.524 | 24.259 | 76.756 | 1.00 | 44.39 N |
| ATOM | 13720 | CA | LEU | C | 176 | 30.380 | 23.638 | 78.074 | 1.00 | 43.53 C |
| ATOM | 13722 | CB | LEU | C | 176 | 30.285 | 24.706 | 79.164 | 1.00 | 41.00 C |
| ATOM | 13725 | CG | LEU | C | 176 | 30.257 | 24.229 | 80.617 | 1.00 | 41.24 C |
| ATOM | 13727 | CD1 | LEU | C | 176 | 31.241 | 23.066 | 80.863 | 1.00 | 39.80 C |
| ATOM | 13731 | CD2 | LEU | C | 176 | 30.551 | 25.397 | 81.560 | 1.00 | 38.79 C |
| ATOM | 13735 | C | LEU | C | 176 | 29.160 | 22.729 | 78.148 | 1.00 | 44.00 C |
| ATOM | 13736 | O | LEU | C | 176 | 29.223 | 21.630 | 78.708 | 1.00 | 42.30 O |
| ATOM | 13738 | N | GLN | C | 177 | 28.053 | 23.177 | 77.565 | 1.00 | 45.38 N |
| ATOM | 13739 | CA | GLN | C | 177 | 26.797 | 22.451 | 77.705 | 1.00 | 47.50 C |
| ATOM | 13741 | CB | GLN | C | 177 | 25.603 | 23.315 | 77.296 | 1.00 | 49.76 C |
| ATOM | 13744 | CG | GLN | C | 177 | 25.538 | 23.635 | 75.807 | 1.00 | 55.28 C |
| ATOM | 13747 | CD | GLN | C | 177 | 24.236 | 24.285 | 75.410 | 1.00 | 50.75 C |
| ATOM | 13748 | OE1 | GLN | C | 177 | 23.259 | 24.259 | 76.160 | 1.00 | 51.96 O |
| ATOM | 13749 | NE2 | GLN | C | 177 | 24.215 | 24.870 | 74.217 | 1.00 | 54.32 N |
| ATOM | 13752 | C | GLN | C | 177 | 26.759 | 21.130 | 76.960 | 1.00 | 47.08 C |
| ATOM | 13753 | O | GLN | C | 177 | 25.878 | 20.313 | 77.216 | 1.00 | 47.81 O |
| ATOM | 13755 | N | ASP | C | 178 | 27.698 | 20.935 | 76.035 | 1.00 | 48.66 N |
| ATOM | 13756 | CA | ASP | C | 178 | 27.913 | 19.638 | 75.387 | 1.00 | 47.73 C |
| ATOM | 13758 | CB | ASP | C | 178 | 28.383 | 19.837 | 73.947 | 1.00 | 49.15 C |
| ATOM | 13761 | CG | ASP | C | 178 | 27.313 | 20.434 | 73.063 | 1.00 | 53.90 C |
| ATOM | 13762 | OD1 | ASP | C | 178 | 26.238 | 19.801 | 72.937 | 1.00 | 57.06 O |
| ATOM | 13763 | OD2 | ASP | C | 178 | 27.558 | 21.522 | 72.483 | 1.00 | 54.50 O |
| ATOM | 13764 | C | ASP | C | 178 | 28.932 | 18.768 | 76.132 | 1.00 | 45.84 C |
| ATOM | 13765 | O | ASP | C | 178 | 29.294 | 17.700 | 75.647 | 1.00 | 44.87 O |
| ATOM | 13767 | N | SER | C | 179 | 29.402 | 19.210 | 77.298 | 1.00 | 44.40 N |
| ATOM | 13768 | CA | SER | C | 179 | 30.276 | 18.366 | 78.102 | 1.00 | 44.05 C |
| ATOM | 13770 | CB | SER | C | 179 | 30.708 | 19.046 | 79.381 | 1.00 | 39.93 C |
| ATOM | 13773 | OG | SER | C | 179 | 31.755 | 18.292 | 79.959 | 1.00 | 35.87 O |
| ATOM | 13775 | C | SER | C | 179 | 29.553 | 17.096 | 78.496 | 1.00 | 45.97 C |
| ATOM | 13776 | O | SER | C | 179 | 28.377 | 17.139 | 78.850 | 1.00 | 47.73 O |
| ATOM | 13778 | N | GLY | C | 180 | 30.258 | 15.973 | 78.450 | 1.00 | 46.96 N |
| ATOM | 13779 | CA | GLY | C | 180 | 29.717 | 14.726 | 78.962 | 1.00 | 47.05 C |
| ATOM | 13782 | C | GLY | C | 180 | 29.989 | 13.557 | 78.057 | 1.00 | 48.32 C |
| ATOM | 13783 | O | GLY | C | 180 | 30.950 | 13.556 | 77.290 | 1.00 | 50.20 O |
| ATOM | 13785 | N | THR | C | 181 | 29.126 | 12.556 | 78.166 | 1.00 | 51.42 N |
| ATOM | 13786 | CA | THR | C | 181 | 29.191 | 11.357 | 77.347 | 1.00 | 51.57 C |
| ATOM | 13788 | CB | THR | C | 181 | 28.468 | 10.176 | 78.019 | 1.00 | 50.15 C |
| ATOM | 13790 | OG1 | THR | C | 181 | 29.088 | 9.868 | 79.267 | 1.00 | 48.31 O |
| ATOM | 13792 | CG2 | THR | C | 181 | 28.520 | 8.951 | 77.136 | 1.00 | 52.72 C |
| ATOM | 13796 | C | THR | C | 181 | 28.484 | 11.599 | 76.036 | 1.00 | 52.53 C |
| ATOM | 13797 | O | THR | C | 181 | 27.288 | 11.889 | 76.024 | 1.00 | 54.75 O |
| ATOM | 13799 | N | TRP | C | 182 | 29.213 | 11.458 | 74.937 | 1.00 | 53.02 N |
| ATOM | 13800 | CA | TRP | C | 182 | 28.601 | 11.436 | 73.619 | 1.00 | 54.10 C |
| ATOM | 13802 | CB | TRP | C | 182 | 29.541 | 12.043 | 72.586 | 1.00 | 55.45 C |
| ATOM | 13805 | CG | TRP | C | 182 | 29.727 | 13.504 | 72.758 | 1.00 | 56.76 C |
| ATOM | 13806 | CD1 | TRP | C | 182 | 30.085 | 14.155 | 73.898 | 1.00 | 60.16 C |
| ATOM | 13808 | NE1 | TRP | C | 182 | 30.149 | 15.503 | 73.672 | 1.00 | 59.10 N |
| ATOM | 13810 | CE2 | TRP | C | 182 | 29.843 | 15.745 | 72.362 | 1.00 | 53.99 C |
| ATOM | 13811 | CD2 | TRP | C | 182 | 29.576 | 14.506 | 71.756 | 1.00 | 55.33 C |
| ATOM | 13812 | CE3 | TRP | C | 182 | 29.224 | 14.478 | 70.404 | 1.00 | 59.35 C |
| ATOM | 13814 | CZ3 | TRP | C | 182 | 29.164 | 15.671 | 69.711 | 1.00 | 59.52 C |
| ATOM | 13816 | CH2 | TRP | C | 182 | 29.449 | 16.890 | 70.344 | 1.00 | 58.91 C |
| ATOM | 13818 | CZ2 | TRP | C | 182 | 29.787 | 16.943 | 71.666 | 1.00 | 57.26 C |
| ATOM | 13820 | C | TRP | C | 182 | 28.282 | 9.986 | 73.273 | 1.00 | 55.33 C |
| ATOM | 13821 | O | TRP | C | 182 | 28.917 | 9.065 | 73.791 | 1.00 | 55.48 O |
| ATOM | 13823 | N | THR | C | 183 | 27.292 | 9.787 | 72.410 | 1.00 | 55.73 N |
| ATOM | 13824 | CA | THR | C | 183 | 26.933 | 8.456 | 71.952 | 1.00 | 55.94 C |
| ATOM | 13826 | CB | THR | C | 183 | 25.531 | 8.068 | 72.443 | 1.00 | 57.10 C |
| ATOM | 13828 | OG1 | THR | C | 183 | 25.506 | 8.113 | 73.877 | 1.00 | 56.95 O |
| ATOM | 13830 | CG2 | THR | C | 183 | 25.143 | 6.658 | 71.961 | 1.00 | 56.74 C |
| ATOM | 13834 | C | THR | C | 183 | 26.964 | 8.447 | 70.442 | 1.00 | 55.99 C |
| ATOM | 13835 | O | THR | C | 183 | 26.160 | 9.128 | 69.814 | 1.00 | 58.49 O |
| ATOM | 13837 | N | CYS | C | 184 | 27.897 | 7.692 | 69.862 | 1.00 | 55.92 N |
| ATOM | 13838 | CA | CYS | C | 184 | 28.028 | 7.604 | 68.404 | 1.00 | 56.60 C |

| | | | | | | | | | | |
|---|---|---|---|---|---|---|---|---|---|---|
| ATOM | 13840 | CB | CYS | C | 184 | 29.453 | 7.931 | 67.966 | 1.00 | 58.31 C |
| ATOM | 13843 | SG | CYS | C | 184 | 30.084 | 9.514 | 68.543 | 1.00 | 65.31 S |
| ATOM | 13845 | C | CYS | C | 184 | 27.652 | 6.230 | 67.846 | 1.00 | 55.76 C |
| ATOM | 13846 | O | CYS | C | 184 | 28.143 | 5.205 | 68.309 | 1.00 | 56.36 O |
| ATOM | 13848 | N | THR | C | 185 | 26.790 | 6.227 | 66.836 | 1.00 | 52.97 N |
| ATOM | 13849 | CA | THR | C | 185 | 26.487 | 5.032 | 66.082 | 1.00 | 52.39 C |
| ATOM | 13851 | CB | THR | C | 185 | 25.005 | 4.987 | 65.731 | 1.00 | 51.66 C |
| ATOM | 13853 | OG1 | THR | C | 185 | 24.236 | 5.242 | 66.904 | 1.00 | 55.04 O |
| ATOM | 13855 | CG2 | THR | C | 185 | 24.626 | 3.640 | 65.164 | 1.00 | 52.45 C |
| ATOM | 13859 | C | THR | C | 185 | 27.276 | 5.038 | 64.782 | 1.00 | 52.20 C |
| ATOM | 13860 | O | THR | C | 185 | 27.112 | 5.932 | 63.953 | 1.00 | 54.60 O |
| ATOM | 13862 | N | VAL | C | 186 | 28.145 | 4.053 | 64.602 | 1.00 | 52.40 N |
| ATOM | 13863 | CA | VAL | C | 186 | 28.777 | 3.833 | 63.299 | 1.00 | 51.70 C |
| ATOM | 13865 | CB | VAL | C | 186 | 30.227 | 3.320 | 63.427 | 1.00 | 51.97 C |
| ATOM | 13867 | CG1 | VAL | C | 186 | 30.646 | 2.516 | 62.219 | 1.00 | 52.91 C |
| ATOM | 13871 | CG2 | VAL | C | 186 | 31.174 | 4.491 | 63.617 | 1.00 | 53.74 C |
| ATOM | 13875 | C | VAL | C | 186 | 27.890 | 2.863 | 62.525 | 1.00 | 51.87 C |
| ATOM | 13876 | O | VAL | C | 186 | 27.232 | 2.017 | 63.119 | 1.00 | 54.33 O |
| ATOM | 13878 | N | LEU | C | 187 | 27.870 | 3.014 | 61.202 | 1.00 | 49.51 N |
| ATOM | 13879 | CA | LEU | C | 187 | 26.944 | 2.312 | 60.325 | 1.00 | 46.53 C |
| ATOM | 13881 | CB | LEU | C | 187 | 25.860 | 3.285 | 59.871 | 1.00 | 46.55 C |
| ATOM | 13884 | CG | LEU | C | 187 | 24.714 | 2.822 | 58.980 | 1.00 | 45.89 C |
| ATOM | 13886 | CD1 | LEU | C | 187 | 23.966 | 1.675 | 59.621 | 1.00 | 49.43 C |
| ATOM | 13890 | CD2 | LEU | C | 187 | 23.780 | 3.986 | 58.754 | 1.00 | 42.85 C |
| ATOM | 13894 | C | LEU | C | 187 | 27.709 | 1.783 | 59.122 | 1.00 | 45.36 C |
| ATOM | 13895 | O | LEU | C | 187 | 28.382 | 2.541 | 58.414 | 1.00 | 42.71 O |
| ATOM | 13897 | N | GLN | C | 188 | 27.606 | 0.474 | 58.917 | 1.00 | 44.20 N |
| ATOM | 13898 | CA | GLN | C | 188 | 28.295 | −0.230 | 57.846 | 1.00 | 45.92 C |
| ATOM | 13900 | CB | GLN | C | 188 | 29.492 | −0.999 | 58.428 | 1.00 | 44.75 C |
| ATOM | 13903 | CG | GLN | C | 188 | 30.114 | −2.072 | 57.560 | 1.00 | 40.45 C |
| ATOM | 13906 | CD | GLN | C | 188 | 30.611 | −1.544 | 56.240 | 1.00 | 34.48 C |
| ATOM | 13907 | OE1 | GLN | C | 188 | 30.129 | −1.937 | 55.183 | 1.00 | 42.07 O |
| ATOM | 13908 | NE2 | GLN | C | 188 | 31.582 | −0.657 | 56.290 | 1.00 | 26.66 N |
| ATOM | 13911 | C | GLN | C | 188 | 27.232 | −1.148 | 57.257 | 1.00 | 48.74 C |
| ATOM | 13912 | O | GLN | C | 188 | 26.934 | −2.211 | 57.827 | 1.00 | 49.49 O |
| ATOM | 13914 | N | ASN | C | 189 | 26.642 | −0.692 | 56.142 | 1.00 | 51.03 N |
| ATOM | 13915 | CA | ASN | C | 189 | 25.413 | −1.256 | 55.553 | 1.00 | 51.55 C |
| ATOM | 13917 | CB | ASN | C | 189 | 25.676 | −2.697 | 55.060 | 1.00 | 54.40 C |
| ATOM | 13920 | CG | ASN | C | 189 | 26.290 | −2.747 | 53.664 | 1.00 | 56.61 C |
| ATOM | 13921 | OD1 | ASN | C | 189 | 26.306 | −1.753 | 52.937 | 1.00 | 57.14 O |
| ATOM | 13922 | ND2 | ASN | C | 189 | 26.792 | −3.920 | 53.286 | 1.00 | 53.90 N |
| ATOM | 13925 | C | ASN | C | 189 | 24.175 | −1.169 | 56.489 | 1.00 | 52.25 C |
| ATOM | 13926 | O | ASN | C | 189 | 24.025 | −0.211 | 57.254 | 1.00 | 50.29 O |
| ATOM | 13928 | N | GLN | C | 190 | 23.264 | −2.133 | 56.363 | 1.00 | 53.26 N |
| ATOM | 13929 | CA | GLN | C | 190 | 22.233 | −2.430 | 57.364 | 1.00 | 53.65 C |
| ATOM | 13931 | CB | GLN | C | 190 | 21.779 | −3.893 | 57.182 | 1.00 | 53.30 C |
| ATOM | 13934 | CG | GLN | C | 190 | 20.279 | −4.140 | 57.320 | 1.00 | 57.71 C |
| ATOM | 13937 | CD | GLN | C | 190 | 19.801 | −5.469 | 56.659 | 1.00 | 60.12 C |
| ATOM | 13938 | OE1 | GLN | C | 190 | 20.177 | −5.785 | 55.519 | 1.00 | 68.35 O |
| ATOM | 13939 | NE2 | GLN | C | 190 | 18.948 | −6.224 | 57.371 | 1.00 | 54.81 N |
| ATOM | 13942 | C | GLN | C | 190 | 22.740 | −2.206 | 58.806 | 1.00 | 52.57 C |
| ATOM | 13943 | O | GLN | C | 190 | 22.121 | −1.475 | 59.574 | 1.00 | 53.06 O |
| ATOM | 13945 | N | LYS | C | 191 | 23.893 | −2.798 | 59.130 | 1.00 | 51.26 N |
| ATOM | 13946 | CA | LYS | C | 191 | 24.366 | −2.982 | 60.520 | 1.00 | 50.33 C |
| ATOM | 13948 | CB | LYS | C | 191 | 25.378 | −4.132 | 60.557 | 1.00 | 51.36 C |
| ATOM | 13951 | CG | LYS | C | 191 | 24.881 | −5.444 | 59.999 | 1.00 | 51.36 C |
| ATOM | 13954 | CD | LYS | C | 191 | 25.973 | −6.152 | 59.210 | 1.00 | 52.98 C |
| ATOM | 13957 | CE | LYS | C | 191 | 25.556 | −7.573 | 58.849 | 1.00 | 56.10 C |
| ATOM | 13960 | NZ | LYS | C | 191 | 25.402 | −8.412 | 60.083 | 1.00 | 56.31 N |
| ATOM | 13964 | C | LYS | C | 191 | 25.035 | −1.772 | 61.192 | 1.00 | 48.05 C |
| ATOM | 13965 | O | LYS | C | 191 | 25.643 | −0.936 | 60.525 | 1.00 | 47.80 O |
| ATOM | 13967 | N | LYS | C | 192 | 24.963 | −1.733 | 62.526 | 1.00 | 45.81 N |
| ATOM | 13968 | CA | LYS | C | 192 | 25.579 | −0.672 | 63.323 | 1.00 | 46.03 C |
| ATOM | 13970 | CB | LYS | C | 192 | 24.541 | 0.300 | 63.897 | 1.00 | 44.66 C |
| ATOM | 13973 | CG | LYS | C | 192 | 23.234 | 0.419 | 63.151 | 1.00 | 47.30 C |
| ATOM | 13976 | CD | LYS | C | 192 | 22.445 | 1.606 | 63.671 | 1.00 | 44.85 C |
| ATOM | 13979 | CE | LYS | C | 192 | 20.989 | 1.548 | 63.286 | 1.00 | 45.32 C |
| ATOM | 13982 | NZ | LYS | C | 192 | 20.428 | 2.916 | 63.195 | 1.00 | 43.18 N |
| ATOM | 13986 | C | LYS | C | 192 | 26.366 | −1.182 | 64.518 | 1.00 | 45.85 C |
| ATOM | 13987 | O | LYS | C | 192 | 26.203 | −2.301 | 64.979 | 1.00 | 45.34 O |
| ATOM | 13989 | N | VAL | C | 193 | 27.184 | −0.290 | 65.051 | 1.00 | 48.81 N |
| ATOM | 13990 | CA | VAL | C | 193 | 27.940 | −0.528 | 66.270 | 1.00 | 49.30 C |
| ATOM | 13992 | CB | VAL | C | 193 | 29.374 | −1.022 | 65.933 | 1.00 | 47.83 C |
| ATOM | 13994 | CG1 | VAL | C | 193 | 29.947 | −0.279 | 64.745 | 1.00 | 48.63 C |
| ATOM | 13998 | CG2 | VAL | C | 193 | 30.287 | −0.882 | 67.110 | 1.00 | 50.20 C |
| ATOM | 14002 | C | VAL | C | 193 | 27.907 | 0.790 | 67.077 | 1.00 | 49.53 C |
| ATOM | 14003 | O | VAL | C | 193 | 27.955 | 1.865 | 66.490 | 1.00 | 49.16 O |
| ATOM | 14005 | N | GLU | C | 194 | 27.784 | 0.708 | 68.404 | 1.00 | 51.78 N |
| ATOM | 14006 | CA | GLU | C | 194 | 27.653 | 1.912 | 69.239 | 1.00 | 53.26 C |

-continued

| | | | | | | | | | | |
|---|---|---|---|---|---|---|---|---|---|---|
| ATOM | 14008 | CB | GLU | C | 194 | 26.448 | 1.801 | 70.179 | 1.00 | 53.82 C |
| ATOM | 14011 | CG | GLU | C | 194 | 25.765 | 3.138 | 70.458 | 1.00 | 55.02 C |
| ATOM | 14014 | CD | GLU | C | 194 | 24.825 | 3.092 | 71.662 | 1.00 | 57.08 C |
| ATOM | 14015 | OE1 | GLU | C | 194 | 25.344 | 3.124 | 72.806 | 1.00 | 58.59 O |
| ATOM | 14016 | OE2 | GLU | C | 194 | 23.580 | 3.040 | 71.462 | 1.00 | 52.08 O |
| ATOM | 14017 | C | GLU | C | 194 | 28.915 | 2.181 | 70.055 | 1.00 | 53.30 C |
| ATOM | 14018 | O | GLU | C | 194 | 29.534 | 1.264 | 70.578 | 1.00 | 53.86 O |
| ATOM | 14020 | N | PHE | C | 195 | 29.286 | 3.452 | 70.146 | 1.00 | 54.73 N |
| ATOM | 14021 | CA | PHE | C | 195 | 30.432 | 3.900 | 70.929 | 1.00 | 55.20 C |
| ATOM | 14023 | CB | PHE | C | 195 | 31.439 | 4.581 | 70.020 | 1.00 | 53.63 C |
| ATOM | 14026 | CG | PHE | C | 195 | 32.159 | 3.651 | 69.097 | 1.00 | 53.31 C |
| ATOM | 14027 | CD1 | PHE | C | 195 | 33.329 | 3.026 | 69.497 | 1.00 | 50.92 C |
| ATOM | 14029 | CE1 | PHE | C | 195 | 34.011 | 2.185 | 68.648 | 1.00 | 49.87 C |
| ATOM | 14031 | CZ | PHE | C | 195 | 33.532 | 1.954 | 67.373 | 1.00 | 53.60 C |
| ATOM | 14033 | CE2 | PHE | C | 195 | 32.368 | 2.573 | 66.953 | 1.00 | 55.58 C |
| ATOM | 14035 | CD2 | PHE | C | 195 | 31.691 | 3.428 | 67.815 | 1.00 | 54.78 C |
| ATOM | 14037 | C | PHE | C | 195 | 29.973 | 4.920 | 71.967 | 1.00 | 56.05 C |
| ATOM | 14038 | O | PHE | C | 195 | 29.085 | 5.721 | 71.697 | 1.00 | 58.22 O |
| ATOM | 14040 | N | LYS | C | 196 | 30.567 | 4.896 | 73.153 | 1.00 | 56.59 N |
| ATOM | 14041 | CA | LYS | C | 196 | 30.411 | 6.006 | 74.088 | 1.00 | 57.72 C |
| ATOM | 14043 | CB | LYS | C | 196 | 29.777 | 5.567 | 75.404 | 1.00 | 56.84 C |
| ATOM | 14046 | CG | LYS | C | 196 | 28.278 | 5.340 | 75.268 | 1.00 | 61.21 C |
| ATOM | 14049 | CD | LYS | C | 196 | 27.572 | 5.335 | 76.609 | 1.00 | 62.04 C |
| ATOM | 14052 | CE | LYS | C | 196 | 26.103 | 5.760 | 76.490 | 1.00 | 63.05 C |
| ATOM | 14055 | NZ | LYS | C | 196 | 25.589 | 6.237 | 77.822 | 1.00 | 64.58 N |
| ATOM | 14059 | C | LYS | C | 196 | 31.761 | 6.630 | 74.314 | 1.00 | 57.71 C |
| ATOM | 14060 | O | LYS | C | 196 | 32.777 | 5.946 | 74.338 | 1.00 | 58.77 O |
| ATOM | 14062 | N | ILE | C | 197 | 31.774 | 7.941 | 74.456 | 1.00 | 59.12 N |
| ATOM | 14063 | CA | ILE | C | 197 | 33.023 | 8.652 | 74.595 | 1.00 | 61.05 C |
| ATOM | 14065 | CB | ILE | C | 197 | 33.650 | 8.914 | 73.217 | 1.00 | 60.77 C |
| ATOM | 14067 | CG1 | ILE | C | 197 | 35.032 | 9.538 | 73.361 | 1.00 | 62.63 C |
| ATOM | 14070 | CD1 | ILE | C | 197 | 35.667 | 9.879 | 72.034 | 1.00 | 63.56 C |
| ATOM | 14074 | CG2 | ILE | C | 197 | 32.756 | 9.795 | 72.362 | 1.00 | 63.71 C |
| ATOM | 14078 | C | ILE | C | 197 | 32.767 | 9.938 | 75.363 | 1.00 | 61.22 C |
| ATOM | 14079 | O | ILE | C | 197 | 31.947 | 10.761 | 74.954 | 1.00 | 63.17 O |
| ATOM | 14081 | N | ASP | C | 198 | 33.460 | 10.078 | 76.493 | 1.00 | 61.92 N |
| ATOM | 14082 | CA | ASP | C | 198 | 33.315 | 11.225 | 77.389 | 1.00 | 61.85 C |
| ATOM | 14084 | CB | ASP | C | 198 | 33.735 | 10.836 | 78.812 | 1.00 | 61.19 C |
| ATOM | 14087 | CG | ASP | C | 198 | 32.729 | 9.908 | 79.483 | 1.00 | 66.39 C |
| ATOM | 14088 | OD1 | ASP | C | 198 | 33.121 | 9.156 | 80.403 | 1.00 | 63.50 O |
| ATOM | 14089 | OD2 | ASP | C | 198 | 31.538 | 9.930 | 79.086 | 1.00 | 67.52 O |
| ATOM | 14090 | C | ASP | C | 198 | 34.150 | 12.395 | 76.917 | 1.00 | 61.02 C |
| ATOM | 14091 | O | ASP | C | 198 | 35.350 | 12.404 | 77.126 | 1.00 | 62.43 O |
| ATOM | 14093 | N | ILE | C | 199 | 33.514 | 13.363 | 76.260 | 1.00 | 61.99 N |
| ATOM | 14094 | CA | ILE | C | 199 | 34.177 | 14.610 | 75.885 | 1.00 | 62.43 C |
| ATOM | 14096 | CB | ILE | C | 199 | 33.641 | 15.220 | 74.576 | 1.00 | 64.37 C |
| ATOM | 14098 | CG1 | ILE | C | 199 | 34.198 | 14.489 | 73.354 | 1.00 | 69.62 C |
| ATOM | 14101 | CD1 | ILE | C | 199 | 34.269 | 12.983 | 73.482 | 1.00 | 74.01 C |
| ATOM | 14105 | CG2 | ILE | C | 199 | 34.065 | 16.681 | 74.450 | 1.00 | 62.51 C |
| ATOM | 14109 | C | ILE | C | 199 | 33.934 | 15.591 | 77.012 | 1.00 | 63.20 C |
| ATOM | 14110 | O | ILE | C | 199 | 32.833 | 16.110 | 77.154 | 1.00 | 63.65 O |
| ATOM | 14112 | N | VAL | C | 200 | 34.976 | 15.776 | 77.814 | 1.00 | 61.56 N |
| ATOM | 14113 | CA | VAL | C | 200 | 34.967 | 16.676 | 78.945 | 1.00 | 58.21 C |
| ATOM | 14115 | CB | VAL | C | 200 | 35.951 | 16.179 | 79.992 | 1.00 | 56.92 C |
| ATOM | 14117 | CG1 | VAL | C | 200 | 36.215 | 17.238 | 81.045 | 1.00 | 54.06 C |
| ATOM | 14121 | CG2 | VAL | C | 200 | 35.436 | 14.887 | 80.605 | 1.00 | 56.77 C |
| ATOM | 14125 | C | VAL | C | 200 | 35.415 | 18.041 | 78.469 | 1.00 | 58.15 C |
| ATOM | 14126 | O | VAL | C | 200 | 36.495 | 18.158 | 77.887 | 1.00 | 60.20 O |
| ATOM | 14128 | N | VAL | C | 201 | 34.603 | 19.072 | 78.695 | 1.00 | 56.11 N |
| ATOM | 14129 | CA | VAL | C | 201 | 35.046 | 20.430 | 78.375 | 1.00 | 55.47 C |
| ATOM | 14131 | CB | VAL | C | 201 | 34.115 | 21.190 | 77.381 | 1.00 | 54.61 C |
| ATOM | 14133 | CG1 | VAL | C | 201 | 32.718 | 20.835 | 77.589 | 1.00 | 58.30 C |
| ATOM | 14137 | CG2 | VAL | C | 201 | 34.295 | 22.711 | 77.477 | 1.00 | 55.72 C |
| ATOM | 14141 | C | VAL | C | 201 | 35.338 | 21.198 | 79.660 | 1.00 | 54.91 C |
| ATOM | 14142 | O | VAL | C | 201 | 34.556 | 21.184 | 80.617 | 1.00 | 55.55 O |
| ATOM | 14144 | N | LEU | C | 202 | 36.507 | 21.833 | 79.661 | 1.00 | 54.19 N |
| ATOM | 14145 | CA | LEU | C | 202 | 37.038 | 22.547 | 80.809 | 1.00 | 53.61 C |
| ATOM | 14147 | CB | LEU | C | 202 | 38.562 | 22.359 | 80.883 | 1.00 | 55.10 C |
| ATOM | 14150 | CG | LEU | C | 202 | 39.088 | 20.915 | 80.763 | 1.00 | 55.91 C |
| ATOM | 14152 | CD1 | LEU | C | 202 | 40.534 | 20.872 | 80.268 | 1.00 | 59.24 C |
| ATOM | 14156 | CD2 | LEU | C | 202 | 38.970 | 20.203 | 82.085 | 1.00 | 55.43 C |
| ATOM | 14160 | C | LEU | C | 202 | 36.690 | 24.014 | 80.603 | 1.00 | 50.53 C |
| ATOM | 14161 | O | LEU | C | 202 | 36.819 | 24.509 | 79.493 | 1.00 | 45.58 O |
| ATOM | 14163 | N | ALA | C | 203 | 36.248 | 24.690 | 81.666 | 1.00 | 49.45 N |
| ATOM | 14164 | CA | ALA | C | 203 | 35.725 | 26.049 | 81.558 | 1.00 | 48.94 C |
| ATOM | 14166 | CB | ALA | C | 203 | 34.464 | 26.044 | 80.695 | 1.00 | 49.85 C |
| ATOM | 14170 | C | ALA | C | 203 | 35.397 | 26.661 | 82.909 | 1.00 | 48.75 C |
| ATOM | 14171 | O | ALA | C | 203 | 35.269 | 25.953 | 83.904 | 1.00 | 51.06 O |
| ATOM | 14173 | N | PHE | C | 204 | 35.243 | 27.982 | 82.931 | 1.00 | 46.88 N |

-continued

| | | | | | | | | | | |
|---|---|---|---|---|---|---|---|---|---|---|
| ATOM | 14174 | CA | PHE | C | 204 | 34.678 | 28.665 | 84.089 | 1.00 | 44.42 | C |
| ATOM | 14176 | CB | PHE | C | 204 | 34.998 | 30.164 | 84.065 | 1.00 | 43.59 | C |
| ATOM | 14179 | CG | PHE | C | 204 | 36.445 | 30.474 | 84.271 | 1.00 | 41.29 | C |
| ATOM | 14180 | CD1 | PHE | C | 204 | 37.012 | 30.355 | 85.529 | 1.00 | 41.92 | C |
| ATOM | 14182 | CE1 | PHE | C | 204 | 38.355 | 30.627 | 85.735 | 1.00 | 41.92 | C |
| ATOM | 14184 | CZ | PHE | C | 204 | 39.147 | 31.031 | 84.671 | 1.00 | 40.62 | C |
| ATOM | 14186 | CE2 | PHE | C | 204 | 38.592 | 31.157 | 83.406 | 1.00 | 41.05 | C |
| ATOM | 14188 | CD2 | PHE | C | 204 | 37.247 | 30.878 | 83.209 | 1.00 | 40.69 | C |
| ATOM | 14190 | C | PHE | C | 204 | 33.180 | 28.472 | 84.017 | 1.00 | 43.70 | C |
| ATOM | 14191 | O | PHE | C | 204 | 32.628 | 28.441 | 82.929 | 1.00 | 44.89 | O |
| ATOM | 14193 | N | GLN | C | 205 | 32.514 | 28.375 | 85.161 | 1.00 | 41.85 | N |
| ATOM | 14194 | CA | GLN | C | 205 | 31.058 | 28.270 | 85.172 | 1.00 | 41.47 | C |
| ATOM | 14196 | CB | GLN | C | 205 | 30.555 | 28.033 | 86.580 | 1.00 | 40.99 | C |
| ATOM | 14199 | CG | GLN | C | 205 | 31.150 | 26.813 | 87.223 | 1.00 | 40.41 | C |
| ATOM | 14202 | CD | GLN | C | 205 | 30.457 | 26.449 | 88.495 | 1.00 | 38.27 | C |
| ATOM | 14203 | OE1 | GLN | C | 205 | 29.376 | 26.950 | 88.800 | 1.00 | 36.94 | O |
| ATOM | 14204 | NE2 | GLN | C | 205 | 31.076 | 25.571 | 89.255 | 1.00 | 41.62 | N |
| ATOM | 14207 | C | GLN | C | 205 | 30.354 | 29.500 | 84.606 | 1.00 | 42.28 | C |
| ATOM | 14208 | O | GLN | C | 205 | 29.230 | 29.407 | 84.085 | 1.00 | 42.60 | O |
| ATOM | 14210 | N | LYS | C | 206 | 30.999 | 30.653 | 84.721 | 1.00 | 44.49 | N |
| ATOM | 14211 | CA | LYS | C | 206 | 30.414 | 31.897 | 84.241 | 1.00 | 46.15 | C |
| ATOM | 14213 | CB | LYS | C | 206 | 30.145 | 32.842 | 85.421 | 1.00 | 48.93 | C |
| ATOM | 14216 | CG | LYS | C | 206 | 28.766 | 32.668 | 86.074 | 1.00 | 56.59 | C |
| ATOM | 14219 | CD | LYS | C | 206 | 27.563 | 32.894 | 85.102 | 1.00 | 65.83 | C |
| ATOM | 14222 | CE | LYS | C | 206 | 27.577 | 34.277 | 84.394 | 1.00 | 70.35 | C |
| ATOM | 14225 | NZ | LYS | C | 206 | 26.461 | 34.471 | 83.403 | 1.00 | 63.81 | N |
| ATOM | 14229 | C | LYS | C | 206 | 31.298 | 32.573 | 83.194 | 1.00 | 45.29 | C |
| ATOM | 14230 | O | LYS | C | 206 | 32.529 | 32.561 | 83.291 | 1.00 | 44.31 | O |
| ATOM | 14232 | N | ALA | C | 207 | 30.655 | 33.154 | 82.185 | 1.00 | 43.87 | N |
| ATOM | 14233 | CA | ALA | C | 207 | 31.370 | 33.903 | 81.155 | 1.00 | 44.67 | C |
| ATOM | 14235 | CB | ALA | C | 207 | 30.504 | 34.090 | 79.926 | 1.00 | 41.97 | C |
| ATOM | 14239 | C | ALA | C | 207 | 31.762 | 35.254 | 81.709 | 1.00 | 44.74 | C |
| ATOM | 14240 | O | ALA | C | 207 | 32.826 | 35.769 | 81.420 | 1.00 | 43.21 | O |
| ATOM | 14242 | N | SER | C | 208 | 30.872 | 35.819 | 82.511 | 1.00 | 47.30 | N |
| ATOM | 14243 | CA | SER | C | 208 | 31.007 | 37.180 | 82.957 | 1.00 | 47.65 | C |
| ATOM | 14245 | CB | SER | C | 208 | 30.285 | 38.115 | 81.994 | 1.00 | 47.36 | C |
| ATOM | 14248 | OG | SER | C | 208 | 30.415 | 39.462 | 82.420 | 1.00 | 53.29 | O |
| ATOM | 14250 | C | SER | C | 208 | 30.447 | 37.350 | 84.358 | 1.00 | 48.57 | C |
| ATOM | 14251 | O | SER | C | 208 | 29.727 | 36.494 | 84.891 | 1.00 | 50.08 | O |
| ATOM | 14253 | N | SER | C | 209 | 30.760 | 38.505 | 84.917 | 1.00 | 49.32 | N |
| ATOM | 14254 | CA | SER | C | 209 | 30.621 | 38.769 | 86.321 | 1.00 | 48.98 | C |
| ATOM | 14256 | CB | SER | C | 209 | 31.751 | 38.037 | 87.045 | 1.00 | 50.62 | C |
| ATOM | 14259 | OG | SER | C | 209 | 32.210 | 38.728 | 88.188 | 1.00 | 59.43 | O |
| ATOM | 14261 | C | SER | C | 209 | 30.713 | 40.286 | 86.491 | 1.00 | 47.64 | C |
| ATOM | 14262 | O | SER | C | 209 | 31.487 | 40.943 | 85.799 | 1.00 | 47.90 | O |
| ATOM | 14264 | N | ILE | C | 210 | 29.909 | 40.844 | 87.385 | 1.00 | 46.95 | N |
| ATOM | 14265 | CA | ILE | C | 210 | 29.902 | 42.287 | 87.597 | 1.00 | 47.27 | C |
| ATOM | 14267 | CB | ILE | C | 210 | 29.042 | 43.031 | 86.530 | 1.00 | 47.38 | C |
| ATOM | 14269 | CG1 | ILE | C | 210 | 29.102 | 44.548 | 86.763 | 1.00 | 49.06 | C |
| ATOM | 14272 | CD1 | ILE | C | 210 | 28.607 | 45.379 | 85.596 | 1.00 | 49.19 | C |
| ATOM | 14276 | CG2 | ILE | C | 210 | 27.597 | 42.528 | 86.520 | 1.00 | 46.24 | C |
| ATOM | 14280 | C | ILE | C | 210 | 29.446 | 42.661 | 89.009 | 1.00 | 46.41 | C |
| ATOM | 14281 | O | ILE | C | 210 | 28.397 | 42.225 | 89.479 | 1.00 | 45.11 | O |
| ATOM | 14283 | N | VAL | C | 211 | 30.246 | 43.489 | 89.672 | 1.00 | 46.59 | N |
| ATOM | 14284 | CA | VAL | C | 211 | 29.962 | 43.879 | 91.035 | 1.00 | 46.30 | C |
| ATOM | 14286 | CB | VAL | C | 211 | 30.907 | 43.149 | 92.044 | 1.00 | 46.18 | C |
| ATOM | 14288 | CG1 | VAL | C | 211 | 32.351 | 43.226 | 91.608 | 1.00 | 47.36 | C |
| ATOM | 14292 | CG2 | VAL | C | 211 | 30.733 | 43.682 | 93.460 | 1.00 | 48.64 | C |
| ATOM | 14296 | C | VAL | C | 211 | 29.999 | 45.403 | 91.130 | 1.00 | 44.55 | C |
| ATOM | 14297 | O | VAL | C | 211 | 30.917 | 46.046 | 90.634 | 1.00 | 40.49 | O |
| ATOM | 14299 | N | TYR | C | 212 | 28.942 | 45.946 | 91.730 | 1.00 | 45.51 | N |
| ATOM | 14300 | CA | TYR | C | 212 | 28.722 | 47.374 | 91.878 | 1.00 | 48.17 | C |
| ATOM | 14302 | CB | TYR | C | 212 | 27.258 | 47.732 | 91.553 | 1.00 | 47.46 | C |
| ATOM | 14305 | CG | TYR | C | 212 | 26.786 | 47.358 | 90.148 | 1.00 | 48.61 | C |
| ATOM | 14306 | CD1 | TYR | C | 212 | 26.505 | 48.339 | 89.196 | 1.00 | 47.15 | C |
| ATOM | 14308 | CE1 | TYR | C | 212 | 26.072 | 48.000 | 87.912 | 1.00 | 46.34 | C |
| ATOM | 14310 | CZ | TYR | C | 212 | 25.912 | 46.664 | 87.572 | 1.00 | 48.17 | C |
| ATOM | 14311 | OH | TYR | C | 212 | 25.487 | 46.307 | 86.314 | 1.00 | 47.91 | O |
| ATOM | 14313 | CE2 | TYR | C | 212 | 26.180 | 45.672 | 88.494 | 1.00 | 47.49 | C |
| ATOM | 14315 | CD2 | TYR | C | 212 | 26.612 | 46.019 | 89.775 | 1.00 | 50.98 | C |
| ATOM | 14317 | C | TYR | C | 212 | 29.032 | 47.672 | 93.340 | 1.00 | 49.98 | C |
| ATOM | 14318 | O | TYR | C | 212 | 28.768 | 46.819 | 94.187 | 1.00 | 50.87 | O |
| ATOM | 14320 | N | LYS | C | 213 | 29.570 | 48.860 | 93.644 | 1.00 | 51.40 | N |
| ATOM | 14321 | CA | LYS | C | 213 | 30.138 | 49.127 | 94.976 | 1.00 | 52.57 | C |
| ATOM | 14323 | CB | LYS | C | 213 | 31.559 | 48.533 | 95.041 | 1.00 | 53.08 | C |
| ATOM | 14326 | CG | LYS | C | 213 | 31.822 | 47.630 | 96.247 | 1.00 | 54.03 | C |
| ATOM | 14329 | CD | LYS | C | 213 | 30.942 | 46.381 | 96.218 | 1.00 | 53.27 | C |
| ATOM | 14332 | CE | LYS | C | 213 | 31.320 | 45.380 | 97.282 | 1.00 | 54.67 | C |
| ATOM | 14335 | NZ | LYS | C | 213 | 30.348 | 44.249 | 97.333 | 1.00 | 55.09 | N |

| | | | | | | | | | | |
|---|---|---|---|---|---|---|---|---|---|---|
| ATOM | 14339 | C | LYS | C | 213 | 30.196 | 50.612 | 95.379 | 1.00 | 53.57 C |
| ATOM | 14340 | O | LYS | C | 213 | 30.429 | 51.483 | 94.549 | 1.00 | 52.52 O |
| ATOM | 14342 | N | LYS | C | 214 | 29.981 | 50.883 | 96.666 | 1.00 | 55.25 N |
| ATOM | 14343 | CA | LYS | C | 214 | 30.251 | 52.205 | 97.243 | 1.00 | 55.95 C |
| ATOM | 14345 | CB | LYS | C | 214 | 29.592 | 52.366 | 98.621 | 1.00 | 56.83 C |
| ATOM | 14348 | CG | LYS | C | 214 | 28.067 | 52.405 | 98.612 | 1.00 | 58.82 C |
| ATOM | 14351 | CD | LYS | C | 214 | 27.471 | 52.174 | 100.009 | 1.00 | 57.13 C |
| ATOM | 14354 | CE | LYS | C | 214 | 25.950 | 52.033 | 99.949 | 1.00 | 57.89 C |
| ATOM | 14357 | NZ | LYS | C | 214 | 25.388 | 51.233 | 101.062 | 1.00 | 59.14 N |
| ATOM | 14361 | C | LYS | C | 214 | 31.756 | 52.357 | 97.402 | 1.00 | 56.14 C |
| ATOM | 14362 | O | LYS | C | 214 | 32.459 | 51.377 | 97.661 | 1.00 | 55.57 O |
| ATOM | 14364 | N | GLU | C | 215 | 32.248 | 53.584 | 97.264 | 1.00 | 56.42 N |
| ATOM | 14365 | CA | GLU | C | 215 | 33.672 | 53.853 | 97.440 | 1.00 | 56.75 C |
| ATOM | 14367 | CB | GLU | C | 215 | 33.974 | 55.340 | 97.242 | 1.00 | 56.84 C |
| ATOM | 14370 | CG | GLU | C | 215 | 35.464 | 55.690 | 97.250 | 1.00 | 57.52 C |
| ATOM | 14373 | CD | GLU | C | 215 | 35.724 | 57.190 | 97.290 | 1.00 | 59.53 C |
| ATOM | 14374 | OE1 | GLU | C | 215 | 34.754 | 57.977 | 97.260 | 1.00 | 65.50 O |
| ATOM | 14375 | OE2 | GLU | C | 215 | 36.905 | 57.587 | 97.355 | 1.00 | 65.80 O |
| ATOM | 14376 | C | GLU | C | 215 | 34.111 | 53.421 | 98.836 | 1.00 | 55.85 C |
| ATOM | 14377 | O | GLU | C | 215 | 33.486 | 53.793 | 99.825 | 1.00 | 54.87 O |
| ATOM | 14379 | N | GLY | C | 216 | 35.174 | 52.625 | 98.900 | 1.00 | 55.70 N |
| ATOM | 14380 | CA | GLY | C | 216 | 35.746 | 52.191 | 100.171 | 1.00 | 55.61 C |
| ATOM | 14383 | C | GLY | C | 216 | 35.405 | 50.757 | 100.525 | 1.00 | 55.64 C |
| ATOM | 14384 | O | GLY | C | 216 | 36.227 | 50.060 | 101.125 | 1.00 | 56.14 O |
| ATOM | 14386 | N | GLU | C | 217 | 34.197 | 50.319 | 100.163 | 1.00 | 54.60 N |
| ATOM | 14387 | CA | GLU | C | 217 | 33.743 | 48.962 | 100.464 | 1.00 | 54.10 C |
| ATOM | 14389 | CB | GLU | C | 217 | 32.343 | 48.705 | 99.891 | 1.00 | 54.35 C |
| ATOM | 14392 | CG | GLU | C | 217 | 31.191 | 49.326 | 100.692 | 1.00 | 56.49 C |
| ATOM | 14395 | CD | GLU | C | 217 | 29.816 | 48.763 | 100.301 | 1.00 | 58.03 C |
| ATOM | 14396 | OE1 | GLU | C | 217 | 29.488 | 48.746 | 99.092 | 1.00 | 60.23 O |
| ATOM | 14397 | OE2 | GLU | C | 217 | 29.060 | 48.337 | 101.206 | 1.00 | 63.81 O |
| ATOM | 14398 | C | GLU | C | 217 | 34.716 | 47.939 | 99.903 | 1.00 | 51.94 C |
| ATOM | 14399 | O | GLU | C | 217 | 35.206 | 48.094 | 98.791 | 1.00 | 49.07 O |
| ATOM | 14401 | N | GLN | C | 218 | 35.009 | 46.912 | 100.697 | 1.00 | 52.70 N |
| ATOM | 14402 | CA | GLN | C | 218 | 35.832 | 45.788 | 100.254 | 1.00 | 52.78 C |
| ATOM | 14404 | CB | GLN | C | 218 | 36.166 | 44.864 | 101.433 | 1.00 | 52.99 C |
| ATOM | 14407 | CG | GLN | C | 218 | 37.024 | 43.652 | 101.074 | 1.00 | 52.54 C |
| ATOM | 14410 | CD | GLN | C | 218 | 37.133 | 42.643 | 102.201 | 1.00 | 51.80 C |
| ATOM | 14411 | OE1 | GLN | C | 218 | 37.783 | 42.892 | 103.223 | 1.00 | 47.06 O |
| ATOM | 14412 | NE2 | GLN | C | 218 | 36.511 | 41.485 | 102.010 | 1.00 | 47.09 N |
| ATOM | 14415 | C | GLN | C | 218 | 35.075 | 45.019 | 99.177 | 1.00 | 52.58 C |
| ATOM | 14416 | O | GLN | C | 218 | 33.849 | 44.915 | 99.240 | 1.00 | 51.73 O |
| ATOM | 14418 | N | VAL | C | 219 | 35.814 | 44.487 | 98.202 | 1.00 | 53.06 N |
| ATOM | 14419 | CA | VAL | C | 219 | 35.235 | 43.821 | 97.038 | 1.00 | 53.35 C |
| ATOM | 14421 | CB | VAL | C | 219 | 35.668 | 44.525 | 95.756 | 1.00 | 52.52 C |
| ATOM | 14423 | CG1 | VAL | C | 219 | 34.956 | 43.905 | 94.545 | 1.00 | 55.27 C |
| ATOM | 14427 | CG2 | VAL | C | 219 | 35.413 | 46.025 | 95.867 | 1.00 | 50.71 C |
| ATOM | 14431 | C | VAL | C | 219 | 35.685 | 42.368 | 96.917 | 1.00 | 54.20 C |
| ATOM | 14432 | O | VAL | C | 219 | 36.879 | 42.095 | 96.923 | 1.00 | 53.66 O |
| ATOM | 14434 | N | GLU | C | 220 | 34.726 | 41.448 | 96.790 | 1.00 | 55.43 N |
| ATOM | 14435 | CA | GLU | C | 220 | 35.018 | 40.027 | 96.546 | 1.00 | 55.04 C |
| ATOM | 14437 | CB | GLU | C | 220 | 34.121 | 39.120 | 97.396 | 1.00 | 55.39 C |
| ATOM | 14440 | CG | GLU | C | 220 | 34.056 | 39.469 | 98.889 | 1.00 | 55.85 C |
| ATOM | 14443 | CD | GLU | C | 220 | 35.313 | 39.106 | 99.667 | 1.00 | 54.78 C |
| ATOM | 14444 | OE1 | GLU | C | 220 | 35.300 | 39.287 | 100.900 | 1.00 | 56.96 O |
| ATOM | 14445 | OE2 | GLU | C | 220 | 36.305 | 38.644 | 99.068 | 1.00 | 50.64 O |
| ATOM | 14446 | C | GLU | C | 220 | 34.808 | 39.697 | 95.072 | 1.00 | 55.11 C |
| ATOM | 14447 | O | GLU | C | 220 | 33.986 | 40.315 | 94.403 | 1.00 | 55.17 O |
| ATOM | 14449 | N | PHE | C | 221 | 35.557 | 38.713 | 94.587 | 1.00 | 55.52 N |
| ATOM | 14450 | CA | PHE | C | 221 | 35.558 | 38.316 | 93.180 | 1.00 | 54.61 C |
| ATOM | 14452 | CB | PHE | C | 221 | 36.736 | 38.954 | 92.446 | 1.00 | 56.74 C |
| ATOM | 14455 | CG | PHE | C | 221 | 36.448 | 40.290 | 91.824 | 1.00 | 57.01 C |
| ATOM | 14456 | CD1 | PHE | C | 221 | 35.319 | 40.488 | 91.039 | 1.00 | 59.62 C |
| ATOM | 14458 | CE1 | PHE | C | 221 | 35.079 | 41.707 | 90.442 | 1.00 | 60.01 C |
| ATOM | 14460 | CZ | PHE | C | 221 | 35.984 | 42.750 | 90.607 | 1.00 | 62.05 C |
| ATOM | 14462 | CE2 | PHE | C | 221 | 37.126 | 42.560 | 91.372 | 1.00 | 59.83 C |
| ATOM | 14464 | CD2 | PHE | C | 221 | 37.357 | 41.333 | 91.963 | 1.00 | 58.66 C |
| ATOM | 14466 | C | PHE | C | 221 | 35.755 | 36.814 | 93.099 | 1.00 | 53.59 C |
| ATOM | 14467 | O | PHE | C | 221 | 36.796 | 36.311 | 93.519 | 1.00 | 51.58 O |
| ATOM | 14469 | N | SER | C | 222 | 34.788 | 36.102 | 92.534 | 1.00 | 54.29 N |
| ATOM | 14470 | CA | SER | C | 222 | 34.844 | 34.643 | 92.515 | 1.00 | 54.22 C |
| ATOM | 14472 | CB | SER | C | 222 | 33.697 | 34.079 | 93.341 | 1.00 | 52.62 C |
| ATOM | 14475 | OG | SER | C | 222 | 34.172 | 33.030 | 94.157 | 1.00 | 54.46 O |
| ATOM | 14477 | C | SER | C | 222 | 34.803 | 34.082 | 91.093 | 1.00 | 54.63 C |
| ATOM | 14478 | O | SER | C | 222 | 34.035 | 34.562 | 90.263 | 1.00 | 56.26 O |
| ATOM | 14480 | N | PHE | C | 223 | 35.627 | 33.066 | 90.827 | 1.00 | 53.95 N |
| ATOM | 14481 | CA | PHE | C | 223 | 35.737 | 32.460 | 89.494 | 1.00 | 53.72 C |
| ATOM | 14483 | CB | PHE | C | 223 | 37.087 | 32.810 | 88.867 | 1.00 | 55.45 C |
| ATOM | 14486 | CG | PHE | C | 223 | 37.410 | 34.261 | 88.945 | 1.00 | 57.79 C |

-continued

| | | | | | | | | | |
|---|---|---|---|---|---|---|---|---|---|
| ATOM | 14487 | CD1 | PHE | C | 223 | 37.148 | 35.106 | 87.885 | 1.00 | 59.55 | C |
| ATOM | 14489 | CE1 | PHE | C | 223 | 37.439 | 36.457 | 87.972 | 1.00 | 59.44 | C |
| ATOM | 14491 | CZ | PHE | C | 223 | 37.974 | 36.972 | 89.136 | 1.00 | 56.41 | C |
| ATOM | 14493 | CE2 | PHE | C | 223 | 38.223 | 36.136 | 90.195 | 1.00 | 57.94 | C |
| ATOM | 14495 | CD2 | PHE | C | 223 | 37.940 | 34.794 | 90.101 | 1.00 | 59.58 | C |
| ATOM | 14497 | C | PHE | C | 223 | 35.567 | 30.949 | 89.574 | 1.00 | 52.46 | C |
| ATOM | 14498 | O | PHE | C | 223 | 36.512 | 30.192 | 89.351 | 1.00 | 51.78 | O |
| ATOM | 14500 | N | PRO | C | 224 | 34.351 | 30.498 | 89.905 | 1.00 | 51.98 | N |
| ATOM | 14501 | CA | PRO | C | 224 | 34.119 | 29.061 | 89.983 | 1.00 | 51.20 | C |
| ATOM | 14503 | CB | PRO | C | 224 | 32.643 | 28.960 | 90.367 | 1.00 | 49.21 | C |
| ATOM | 14506 | CG | PRO | C | 224 | 32.063 | 30.267 | 89.992 | 1.00 | 50.96 | C |
| ATOM | 14509 | CD | PRO | C | 224 | 33.136 | 31.264 | 90.215 | 1.00 | 51.52 | C |
| ATOM | 14512 | C | PRO | C | 224 | 34.382 | 28.363 | 88.651 | 1.00 | 49.85 | C |
| ATOM | 14513 | O | PRO | C | 224 | 34.005 | 28.871 | 87.588 | 1.00 | 48.29 | O |
| ATOM | 14514 | N | LEU | C | 225 | 35.044 | 27.214 | 88.735 | 1.00 | 49.32 | N |
| ATOM | 14515 | CA | LEU | C | 225 | 35.375 | 26.409 | 87.576 | 1.00 | 50.30 | C |
| ATOM | 14517 | CB | LEU | C | 225 | 36.752 | 25.793 | 87.761 | 1.00 | 49.70 | C |
| ATOM | 14520 | CG | LEU | C | 225 | 37.909 | 26.787 | 87.649 | 1.00 | 50.42 | C |
| ATOM | 14522 | CD1 | LEU | C | 225 | 39.138 | 26.257 | 88.374 | 1.00 | 51.05 | C |
| ATOM | 14526 | CD2 | LEU | C | 225 | 38.212 | 27.098 | 86.194 | 1.00 | 48.90 | C |
| ATOM | 14530 | C | LEU | C | 225 | 34.353 | 25.303 | 87.364 | 1.00 | 50.79 | C |
| ATOM | 14531 | O | LEU | C | 225 | 33.601 | 24.950 | 88.269 | 1.00 | 51.80 | O |
| ATOM | 14533 | N | ALA | C | 226 | 34.318 | 24.774 | 86.150 | 1.00 | 51.03 | N |
| ATOM | 14534 | CA | ALA | C | 226 | 33.535 | 23.585 | 85.868 | 1.00 | 51.57 | C |
| ATOM | 14536 | CB | ALA | C | 226 | 33.521 | 23.301 | 84.381 | 1.00 | 51.65 | C |
| ATOM | 14540 | C | ALA | C | 226 | 34.162 | 22.429 | 86.627 | 1.00 | 50.65 | C |
| ATOM | 14541 | O | ALA | C | 226 | 35.369 | 22.275 | 86.631 | 1.00 | 51.36 | O |
| ATOM | 14543 | N | PHE | C | 227 | 33.345 | 21.623 | 87.283 | 1.00 | 50.74 | N |
| ATOM | 14544 | CA | PHE | C | 227 | 33.859 | 20.562 | 88.134 | 1.00 | 53.88 | C |
| ATOM | 14546 | CB | PHE | C | 227 | 32.796 | 19.489 | 88.341 | 1.00 | 50.95 | C |
| ATOM | 14549 | CG | PHE | C | 227 | 33.324 | 18.242 | 88.973 | 1.00 | 47.51 | C |
| ATOM | 14550 | CD1 | PHE | C | 227 | 33.177 | 17.019 | 88.347 | 1.00 | 39.76 | C |
| ATOM | 14552 | CE1 | PHE | C | 227 | 33.668 | 15.869 | 88.926 | 1.00 | 47.50 | C |
| ATOM | 14554 | CZ | PHE | C | 227 | 34.329 | 15.936 | 90.156 | 1.00 | 49.06 | C |
| ATOM | 14556 | CE2 | PHE | C | 227 | 34.489 | 17.157 | 90.786 | 1.00 | 46.39 | C |
| ATOM | 14558 | CD2 | PHE | C | 227 | 33.993 | 18.303 | 90.189 | 1.00 | 43.47 | C |
| ATOM | 14560 | C | PHE | C | 227 | 35.134 | 19.905 | 87.595 | 1.00 | 57.01 | C |
| ATOM | 14561 | O | PHE | C | 227 | 36.095 | 19.703 | 88.341 | 1.00 | 58.36 | O |
| ATOM | 14563 | N | THR | C | 228 | 35.131 | 19.562 | 86.311 | 1.00 | 59.43 | N |
| ATOM | 14564 | CA | THR | C | 228 | 36.256 | 18.844 | 85.706 | 1.00 | 62.28 | C |
| ATOM | 14566 | CB | THR | C | 228 | 36.067 | 18.638 | 84.201 | 1.00 | 63.18 | C |
| ATOM | 14568 | OG1 | THR | C | 228 | 37.332 | 18.260 | 83.644 | 1.00 | 67.90 | O |
| ATOM | 14570 | CG2 | THR | C | 228 | 35.570 | 19.918 | 83.504 | 1.00 | 64.97 | C |
| ATOM | 14574 | C | THR | C | 228 | 37.661 | 19.457 | 85.869 | 1.00 | 64.19 | C |
| ATOM | 14575 | O | THR | C | 228 | 38.642 | 18.712 | 85.976 | 1.00 | 63.72 | O |
| ATOM | 14577 | N | VAL | C | 229 | 37.756 | 20.791 | 85.875 | 1.00 | 65.75 | N |
| ATOM | 14578 | CA | VAL | C | 229 | 39.066 | 21.494 | 85.906 | 1.00 | 66.45 | C |
| ATOM | 14580 | CB | VAL | C | 229 | 39.058 | 22.863 | 85.068 | 1.00 | 68.23 | C |
| ATOM | 14582 | CG1 | VAL | C | 229 | 37.655 | 23.450 | 84.889 | 1.00 | 67.49 | C |
| ATOM | 14586 | CG2 | VAL | C | 229 | 40.026 | 23.921 | 85.637 | 1.00 | 67.21 | C |
| ATOM | 14590 | C | VAL | C | 229 | 39.662 | 21.680 | 87.318 | 1.00 | 66.08 | C |
| ATOM | 14591 | O | VAL | C | 229 | 40.829 | 22.049 | 87.453 | 1.00 | 64.25 | O |
| ATOM | 14593 | N | GLU | C | 230 | 38.884 | 21.358 | 88.350 | 1.00 | 67.35 | N |
| ATOM | 14594 | CA | GLU | C | 230 | 39.255 | 21.631 | 89.744 | 1.00 | 68.15 | C |
| ATOM | 14596 | CB | GLU | C | 230 | 38.043 | 21.422 | 90.651 | 1.00 | 68.56 | C |
| ATOM | 14599 | CG | GLU | C | 230 | 36.860 | 22.324 | 90.385 | 1.00 | 70.87 | C |
| ATOM | 14602 | CD | GLU | C | 230 | 35.747 | 22.097 | 91.405 | 1.00 | 73.82 | C |
| ATOM | 14603 | OE1 | GLU | C | 230 | 35.631 | 20.959 | 91.924 | 1.00 | 79.59 | O |
| ATOM | 14604 | OE2 | GLU | C | 230 | 34.993 | 23.051 | 91.695 | 1.00 | 80.44 | O |
| ATOM | 14605 | C | GLU | C | 230 | 40.419 | 20.808 | 90.324 | 1.00 | 67.98 | C |
| ATOM | 14606 | O | GLU | C | 230 | 40.823 | 21.055 | 91.466 | 1.00 | 69.49 | O |
| ATOM | 14608 | N | LYS | C | 231 | 40.941 | 19.829 | 89.582 | 1.00 | 67.30 | N |
| ATOM | 14609 | CA | LYS | C | 231 | 42.073 | 19.017 | 90.063 | 1.00 | 66.42 | C |
| ATOM | 14611 | CB | LYS | C | 231 | 41.608 | 17.576 | 90.295 | 1.00 | 67.27 | C |
| ATOM | 14614 | CG | LYS | C | 231 | 41.010 | 17.387 | 91.680 | 1.00 | 69.67 | C |
| ATOM | 14617 | CD | LYS | C | 231 | 40.456 | 15.988 | 91.915 | 1.00 | 70.79 | C |
| ATOM | 14620 | CE | LYS | C | 231 | 39.836 | 15.889 | 93.324 | 1.00 | 74.18 | C |
| ATOM | 14623 | NZ | LYS | C | 231 | 39.333 | 14.521 | 93.669 | 1.00 | 74.04 | N |
| ATOM | 14627 | C | LYS | C | 231 | 43.307 | 19.074 | 89.151 | 1.00 | 63.49 | C |
| ATOM | 14628 | O | LYS | C | 231 | 44.230 | 18.276 | 89.283 | 1.00 | 62.46 | O |
| ATOM | 14630 | N | LEU | C | 232 | 43.330 | 20.067 | 88.270 | 1.00 | 61.95 | N |
| ATOM | 14631 | CA | LEU | C | 232 | 44.328 | 20.178 | 87.216 | 1.00 | 61.41 | C |
| ATOM | 14633 | CB | LEU | C | 232 | 43.640 | 20.603 | 85.918 | 1.00 | 62.35 | C |
| ATOM | 14636 | CG | LEU | C | 232 | 42.863 | 19.549 | 85.129 | 1.00 | 61.71 | C |
| ATOM | 14638 | CD1 | LEU | C | 232 | 41.838 | 18.851 | 85.987 | 1.00 | 68.58 | C |
| ATOM | 14642 | CD2 | LEU | C | 232 | 42.208 | 20.203 | 83.930 | 1.00 | 62.39 | C |
| ATOM | 14646 | C | LEU | C | 232 | 45.410 | 21.207 | 87.562 | 1.00 | 60.34 | C |
| ATOM | 14647 | O | LEU | C | 232 | 45.138 | 22.207 | 88.234 | 1.00 | 60.57 | O |
| ATOM | 14649 | N | THR | C | 233 | 46.632 | 20.963 | 87.091 | 1.00 | 58.14 | N |

-continued

| | | | | | | | | | | |
|---|---|---|---|---|---|---|---|---|---|---|
| ATOM | 14650 | CA | THR | C | 233 | 47.716 | 21.947 | 87.215 | 1.00 | 57.26 C |
| ATOM | 14652 | CB | THR | C | 233 | 49.106 | 21.312 | 87.039 | 1.00 | 56.18 C |
| ATOM | 14654 | OG1 | THR | C | 233 | 49.327 | 20.343 | 88.075 | 1.00 | 56.61 O |
| ATOM | 14656 | CG2 | THR | C | 233 | 50.187 | 22.377 | 87.099 | 1.00 | 56.96 C |
| ATOM | 14660 | C | THR | C | 233 | 47.542 | 23.080 | 86.190 | 1.00 | 55.74 C |
| ATOM | 14661 | O | THR | C | 233 | 47.146 | 22.854 | 85.043 | 1.00 | 54.68 O |
| ATOM | 14663 | N | GLY | C | 234 | 47.832 | 24.305 | 86.606 | 1.00 | 53.66 N |
| ATOM | 14664 | CA | GLY | C | 234 | 47.617 | 25.433 | 85.730 | 1.00 | 53.19 C |
| ATOM | 14667 | C | GLY | C | 234 | 48.256 | 26.705 | 86.212 | 1.00 | 51.79 C |
| ATOM | 14668 | O | GLY | C | 234 | 48.789 | 26.773 | 87.317 | 1.00 | 51.14 O |
| ATOM | 14670 | N | SER | C | 235 | 48.190 | 27.711 | 85.351 | 1.00 | 51.72 N |
| ATOM | 14671 | CA | SER | C | 235 | 48.648 | 29.054 | 85.664 | 1.00 | 52.13 C |
| ATOM | 14673 | CB | SER | C | 235 | 50.064 | 29.272 | 85.132 | 1.00 | 52.74 C |
| ATOM | 14676 | OG | SER | C | 235 | 50.230 | 28.636 | 83.876 | 1.00 | 59.91 O |
| ATOM | 14678 | C | SER | C | 235 | 47.677 | 30.048 | 85.048 | 1.00 | 49.69 C |
| ATOM | 14679 | O | SER | C | 235 | 47.068 | 29.767 | 84.021 | 1.00 | 47.18 O |
| ATOM | 14681 | N | GLY | C | 236 | 47.527 | 31.201 | 85.690 | 1.00 | 48.98 N |
| ATOM | 14682 | CA | GLY | C | 236 | 46.566 | 32.191 | 85.244 | 1.00 | 48.93 C |
| ATOM | 14685 | C | GLY | C | 236 | 46.867 | 33.601 | 85.700 | 1.00 | 48.65 C |
| ATOM | 14686 | O | GLY | C | 236 | 47.683 | 33.826 | 86.586 | 1.00 | 48.83 O |
| ATOM | 14688 | N | GLU | C | 237 | 46.167 | 34.550 | 85.096 | 1.00 | 49.66 N |
| ATOM | 14689 | CA | GLU | C | 237 | 46.495 | 35.950 | 85.231 | 1.00 | 50.05 C |
| ATOM | 14691 | CB | GLU | C | 237 | 47.498 | 36.314 | 84.146 | 1.00 | 49.39 C |
| ATOM | 14694 | CG | GLU | C | 237 | 48.141 | 37.671 | 84.328 | 1.00 | 50.62 C |
| ATOM | 14697 | CD | GLU | C | 237 | 49.331 | 37.892 | 83.410 | 1.00 | 49.34 C |
| ATOM | 14698 | OE1 | GLU | C | 237 | 50.023 | 38.915 | 83.596 | 1.00 | 43.92 O |
| ATOM | 14699 | OE2 | GLU | C | 237 | 49.572 | 37.047 | 82.515 | 1.00 | 46.20 O |
| ATOM | 14700 | C | GLU | C | 237 | 45.251 | 36.820 | 85.092 | 1.00 | 51.27 C |
| ATOM | 14701 | O | GLU | C | 237 | 44.408 | 36.578 | 84.229 | 1.00 | 51.12 O |
| ATOM | 14703 | N | LEU | C | 238 | 45.145 | 37.829 | 85.952 | 1.00 | 52.08 N |
| ATOM | 14704 | CA | LEU | C | 238 | 44.088 | 38.829 | 85.865 | 1.00 | 51.50 C |
| ATOM | 14706 | CB | LEU | C | 238 | 43.587 | 39.180 | 87.263 | 1.00 | 51.30 C |
| ATOM | 14709 | CG | LEU | C | 238 | 42.230 | 39.867 | 87.446 | 1.00 | 52.07 C |
| ATOM | 14711 | CD1 | LEU | C | 238 | 42.282 | 40.692 | 88.707 | 1.00 | 48.98 C |
| ATOM | 14715 | CD2 | LEU | C | 238 | 41.808 | 40.752 | 86.297 | 1.00 | 57.12 C |
| ATOM | 14719 | C | LEU | C | 238 | 44.652 | 40.078 | 85.208 | 1.00 | 52.61 C |
| ATOM | 14720 | O | LEU | C | 238 | 45.466 | 40.779 | 85.809 | 1.00 | 56.47 O |
| ATOM | 14722 | N | TRP | C | 239 | 44.240 | 40.350 | 83.975 | 1.00 | 52.26 N |
| ATOM | 14723 | CA | TRP | C | 239 | 44.584 | 41.604 | 83.313 | 1.00 | 52.01 C |
| ATOM | 14725 | CB | TRP | C | 239 | 44.808 | 41.387 | 81.822 | 1.00 | 52.69 C |
| ATOM | 14728 | CG | TRP | C | 239 | 46.004 | 40.578 | 81.512 | 1.00 | 52.47 C |
| ATOM | 14729 | CD1 | TRP | C | 239 | 46.090 | 39.211 | 81.472 | 1.00 | 51.83 C |
| ATOM | 14731 | NE1 | TRP | C | 239 | 47.369 | 38.832 | 81.136 | 1.00 | 51.73 N |
| ATOM | 14733 | CE2 | TRP | C | 239 | 48.132 | 39.958 | 80.952 | 1.00 | 52.18 C |
| ATOM | 14734 | CD2 | TRP | C | 239 | 47.300 | 41.077 | 81.182 | 1.00 | 51.43 C |
| ATOM | 14735 | CE3 | TRP | C | 239 | 47.841 | 42.363 | 81.058 | 1.00 | 49.98 C |
| ATOM | 14737 | CZ3 | TRP | C | 239 | 49.185 | 42.492 | 80.715 | 1.00 | 51.19 C |
| ATOM | 14739 | CH2 | TRP | C | 239 | 49.989 | 41.362 | 80.492 | 1.00 | 51.43 C |
| ATOM | 14741 | CZ2 | TRP | C | 239 | 49.482 | 40.089 | 80.605 | 1.00 | 51.88 C |
| ATOM | 14743 | C | TRP | C | 239 | 43.425 | 42.552 | 83.499 | 1.00 | 51.25 C |
| ATOM | 14744 | O | TRP | C | 239 | 42.278 | 42.146 | 83.351 | 1.00 | 48.99 O |
| ATOM | 14746 | N | TRP | C | 240 | 43.727 | 43.815 | 83.794 | 1.00 | 52.34 N |
| ATOM | 14747 | CA | TRP | C | 240 | 42.699 | 44.814 | 84.076 | 1.00 | 53.06 C |
| ATOM | 14749 | CB | TRP | C | 240 | 42.779 | 45.206 | 85.545 | 1.00 | 53.29 C |
| ATOM | 14752 | CG | TRP | C | 240 | 41.596 | 45.948 | 85.999 | 1.00 | 53.25 C |
| ATOM | 14753 | CD1 | TRP | C | 240 | 41.419 | 47.292 | 85.980 | 1.00 | 53.47 C |
| ATOM | 14755 | NE1 | TRP | C | 240 | 40.186 | 47.613 | 86.478 | 1.00 | 52.91 N |
| ATOM | 14757 | CE2 | TRP | C | 240 | 39.536 | 46.459 | 86.823 | 1.00 | 54.15 C |
| ATOM | 14758 | CD2 | TRP | C | 240 | 40.399 | 45.389 | 86.529 | 1.00 | 55.70 C |
| ATOM | 14759 | CE3 | TRP | C | 240 | 39.972 | 44.081 | 86.789 | 1.00 | 57.67 C |
| ATOM | 14761 | CZ3 | TRP | C | 240 | 38.714 | 43.889 | 87.331 | 1.00 | 55.91 C |
| ATOM | 14763 | CH2 | TRP | C | 240 | 37.875 | 44.981 | 87.614 | 1.00 | 56.10 C |
| ATOM | 14765 | CZ2 | TRP | C | 240 | 38.267 | 46.268 | 87.365 | 1.00 | 55.23 C |
| ATOM | 14767 | C | TRP | C | 240 | 42.844 | 46.069 | 83.203 | 1.00 | 53.20 C |
| ATOM | 14768 | O | TRP | C | 240 | 43.957 | 46.490 | 82.914 | 1.00 | 52.68 O |
| ATOM | 14770 | N | GLN | C | 241 | 41.717 | 46.659 | 82.799 | 1.00 | 53.23 N |
| ATOM | 14771 | CA | GLN | C | 241 | 41.699 | 47.940 | 82.072 | 1.00 | 54.32 C |
| ATOM | 14773 | CB | GLN | C | 241 | 41.372 | 47.717 | 80.596 | 1.00 | 53.81 C |
| ATOM | 14776 | CG | GLN | C | 241 | 41.333 | 48.994 | 79.760 | 1.00 | 53.12 C |
| ATOM | 14779 | CD | GLN | C | 241 | 41.006 | 48.736 | 78.296 | 1.00 | 53.30 C |
| ATOM | 14780 | OE1 | GLN | C | 241 | 40.582 | 47.641 | 77.923 | 1.00 | 46.07 O |
| ATOM | 14781 | NE2 | GLN | C | 241 | 41.198 | 49.755 | 77.458 | 1.00 | 51.31 N |
| ATOM | 14784 | C | GLN | C | 241 | 40.663 | 48.872 | 82.702 | 1.00 | 55.22 C |
| ATOM | 14785 | O | GLN | C | 241 | 39.470 | 48.577 | 82.681 | 1.00 | 54.52 O |
| ATOM | 14787 | N | ALA | C | 242 | 41.117 | 50.014 | 83.213 | 1.00 | 56.80 N |
| ATOM | 14788 | CA | ALA | C | 242 | 40.366 | 50.742 | 84.236 | 1.00 | 57.99 C |
| ATOM | 14790 | CB | ALA | C | 242 | 41.268 | 50.929 | 85.462 | 1.00 | 58.03 C |
| ATOM | 14794 | C | ALA | C | 242 | 39.716 | 52.089 | 83.846 | 1.00 | 59.52 C |
| ATOM | 14795 | O | ALA | C | 242 | 39.595 | 52.974 | 84.699 | 1.00 | 61.31 O |

-continued

| | | | | | | | | | | |
|---|---|---|---|---|---|---|---|---|---|---|
| ATOM | 14797 | N | GLU | C | 243 | 39.266 | 52.242 | 82.600 | 1.00 | 60.54 N |
| ATOM | 14798 | CA | GLU | C | 243 | 38.531 | 53.464 | 82.173 | 1.00 | 61.09 C |
| ATOM | 14800 | CB | GLU | C | 243 | 37.263 | 53.702 | 83.032 | 1.00 | 61.18 C |
| ATOM | 14803 | CG | GLU | C | 243 | 36.330 | 54.792 | 82.474 | 1.00 | 60.52 C |
| ATOM | 14806 | CD | GLU | C | 243 | 35.196 | 55.186 | 83.421 | 1.00 | 61.11 C |
| ATOM | 14807 | OE1 | GLU | C | 243 | 35.351 | 56.183 | 84.171 | 1.00 | 57.89 O |
| ATOM | 14808 | OE2 | GLU | C | 243 | 34.145 | 54.512 | 83.401 | 1.00 | 59.35 O |
| ATOM | 14809 | C | GLU | C | 243 | 39.412 | 54.727 | 82.163 | 1.00 | 61.71 C |
| ATOM | 14810 | O | GLU | C | 243 | 39.424 | 55.502 | 83.119 | 1.00 | 61.42 O |
| ATOM | 14812 | N | ARG | C | 244 | 40.104 | 54.927 | 81.044 | 1.00 | 62.33 N |
| ATOM | 14813 | CA | ARG | C | 244 | 41.129 | 55.959 | 80.844 | 1.00 | 62.50 C |
| ATOM | 14815 | CB | ARG | C | 244 | 41.330 | 56.908 | 82.046 | 1.00 | 63.30 C |
| ATOM | 14818 | CG | ARG | C | 244 | 42.099 | 56.339 | 83.272 | 1.00 | 64.05 C |
| ATOM | 14821 | CD | ARG | C | 244 | 43.612 | 56.658 | 83.262 | 1.00 | 64.05 C |
| ATOM | 14824 | NE | ARG | C | 244 | 43.888 | 58.096 | 83.155 | 1.00 | 63.61 N |
| ATOM | 14826 | CZ | ARG | C | 244 | 44.500 | 58.705 | 82.133 | 1.00 | 64.13 C |
| ATOM | 14827 | NH1 | ARG | C | 244 | 44.671 | 60.022 | 82.173 | 1.00 | 63.73 N |
| ATOM | 14830 | NH2 | ARG | C | 244 | 44.952 | 58.030 | 81.077 | 1.00 | 62.98 N |
| ATOM | 14833 | C | ARG | C | 244 | 42.424 | 55.241 | 80.485 | 1.00 | 63.61 C |
| ATOM | 14834 | O | ARG | C | 244 | 43.214 | 55.742 | 79.682 | 1.00 | 66.59 O |
| ATOM | 14836 | N | ALA | C | 245 | 42.616 | 54.059 | 81.071 | 1.00 | 63.14 N |
| ATOM | 14837 | CA | ALA | C | 245 | 43.802 | 53.230 | 80.846 | 1.00 | 62.60 C |
| ATOM | 14839 | CB | ALA | C | 245 | 43.623 | 51.874 | 81.526 | 1.00 | 63.00 C |
| ATOM | 14843 | C | ALA | C | 245 | 44.117 | 53.022 | 79.370 | 1.00 | 61.76 C |
| ATOM | 14844 | O | ALA | C | 245 | 45.282 | 53.082 | 78.968 | 1.00 | 59.83 O |
| ATOM | 14846 | N | SER | C | 246 | 43.080 | 52.748 | 78.577 | 1.00 | 62.06 N |
| ATOM | 14847 | CA | SER | C | 246 | 43.225 | 52.490 | 77.132 | 1.00 | 63.25 C |
| ATOM | 14849 | CB | SER | C | 246 | 43.945 | 53.661 | 76.438 | 1.00 | 63.50 C |
| ATOM | 14852 | OG | SER | C | 246 | 45.059 | 53.215 | 75.681 | 1.00 | 63.10 O |
| ATOM | 14854 | C | SER | C | 246 | 43.910 | 51.152 | 76.776 | 1.00 | 63.94 C |
| ATOM | 14855 | O | SER | C | 246 | 43.932 | 50.763 | 75.606 | 1.00 | 62.97 O |
| ATOM | 14857 | N | SER | C | 247 | 44.437 | 50.456 | 77.787 | 1.00 | 64.20 N |
| ATOM | 14858 | CA | SER | C | 247 | 45.252 | 49.252 | 77.606 | 1.00 | 63.13 C |
| ATOM | 14860 | CB | SER | C | 247 | 46.611 | 49.607 | 76.978 | 1.00 | 62.58 C |
| ATOM | 14863 | OG | SER | C | 247 | 47.167 | 50.782 | 77.554 | 1.00 | 61.80 O |
| ATOM | 14865 | C | SER | C | 247 | 45.434 | 48.549 | 78.965 | 1.00 | 63.42 C |
| ATOM | 14866 | O | SER | C | 247 | 45.598 | 49.215 | 79.999 | 1.00 | 63.66 O |
| ATOM | 14868 | N | SER | C | 248 | 45.413 | 47.214 | 78.959 | 1.00 | 61.92 N |
| ATOM | 14869 | CA | SER | C | 248 | 45.346 | 46.439 | 80.203 | 1.00 | 61.13 C |
| ATOM | 14871 | CB | SER | C | 248 | 44.736 | 45.058 | 79.948 | 1.00 | 61.93 C |
| ATOM | 14874 | OG | SER | C | 248 | 45.534 | 44.305 | 79.054 | 1.00 | 63.11 O |
| ATOM | 14876 | C | SER | C | 248 | 46.692 | 46.264 | 80.895 | 1.00 | 59.90 C |
| ATOM | 14877 | O | SER | C | 248 | 47.670 | 45.897 | 80.255 | 1.00 | 59.40 O |
| ATOM | 14879 | N | LYS | C | 249 | 46.727 | 46.528 | 82.203 | 1.00 | 59.67 N |
| ATOM | 14880 | CA | LYS | C | 249 | 47.884 | 46.206 | 83.048 | 1.00 | 58.19 C |
| ATOM | 14882 | CB | LYS | C | 249 | 48.237 | 47.371 | 83.990 | 1.00 | 57.21 C |
| ATOM | 14885 | CG | LYS | C | 249 | 47.360 | 47.533 | 85.225 | 1.00 | 58.66 C |
| ATOM | 14888 | CD | LYS | C | 249 | 47.904 | 48.649 | 86.142 | 1.00 | 59.90 C |
| ATOM | 14891 | CE | LYS | C | 249 | 46.980 | 48.945 | 87.333 | 1.00 | 59.35 C |
| ATOM | 14894 | NZ | LYS | C | 249 | 45.554 | 49.194 | 86.912 | 1.00 | 58.33 N |
| ATOM | 14898 | C | LYS | C | 249 | 47.618 | 44.922 | 83.834 | 1.00 | 56.62 C |
| ATOM | 14899 | O | LYS | C | 249 | 46.466 | 44.603 | 84.147 | 1.00 | 56.93 O |
| ATOM | 14901 | N | SER | C | 250 | 48.683 | 44.183 | 84.138 | 1.00 | 55.39 N |
| ATOM | 14902 | CA | SER | C | 250 | 48.556 | 42.921 | 84.879 | 1.00 | 54.20 C |
| ATOM | 14904 | CB | SER | C | 250 | 49.763 | 42.000 | 84.642 | 1.00 | 53.70 C |
| ATOM | 14907 | OG | SER | C | 250 | 49.641 | 40.785 | 85.366 | 1.00 | 47.84 O |
| ATOM | 14909 | C | SER | C | 250 | 48.410 | 43.230 | 86.360 | 1.00 | 52.24 C |
| ATOM | 14910 | O | SER | C | 250 | 49.211 | 43.974 | 86.915 | 1.00 | 52.45 O |
| ATOM | 14912 | N | TRP | C | 251 | 47.379 | 42.661 | 86.982 | 1.00 | 50.50 N |
| ATOM | 14913 | CA | TRP | C | 251 | 47.109 | 42.861 | 88.406 | 1.00 | 49.58 C |
| ATOM | 14915 | CB | TRP | C | 251 | 45.596 | 42.900 | 88.662 | 1.00 | 48.98 C |
| ATOM | 14918 | CG | TRP | C | 251 | 44.996 | 44.280 | 88.617 | 1.00 | 49.55 C |
| ATOM | 14919 | CD1 | TRP | C | 251 | 45.534 | 45.402 | 88.037 | 1.00 | 49.34 C |
| ATOM | 14921 | NE1 | TRP | C | 251 | 44.688 | 46.466 | 88.200 | 1.00 | 47.82 N |
| ATOM | 14923 | CE2 | TRP | C | 251 | 43.574 | 46.051 | 88.882 | 1.00 | 49.06 C |
| ATOM | 14924 | CD2 | TRP | C | 251 | 43.731 | 44.678 | 89.157 | 1.00 | 47.03 C |
| ATOM | 14925 | CE3 | TRP | C | 251 | 42.720 | 44.008 | 89.856 | 1.00 | 48.73 C |
| ATOM | 14927 | CZ3 | TRP | C | 251 | 41.590 | 44.719 | 90.248 | 1.00 | 49.10 C |
| ATOM | 14929 | CH2 | TRP | C | 251 | 41.463 | 46.087 | 89.960 | 1.00 | 50.83 C |
| ATOM | 14931 | CZ2 | TRP | C | 251 | 42.442 | 46.770 | 89.283 | 1.00 | 49.80 C |
| ATOM | 14933 | C | TRP | C | 251 | 47.757 | 41.762 | 89.244 | 1.00 | 48.60 C |
| ATOM | 14934 | O | TRP | C | 251 | 48.449 | 42.043 | 90.224 | 1.00 | 47.76 O |
| ATOM | 14936 | N | ILE | C | 252 | 47.540 | 40.512 | 88.847 | 1.00 | 47.01 N |
| ATOM | 14937 | CA | ILE | C | 252 | 48.033 | 39.384 | 89.615 | 1.00 | 45.92 C |
| ATOM | 14939 | CB | ILE | C | 252 | 47.026 | 39.030 | 90.731 | 1.00 | 44.48 C |
| ATOM | 14941 | CG1 | ILE | C | 252 | 47.670 | 38.165 | 91.809 | 1.00 | 44.56 C |
| ATOM | 14944 | CD1 | ILE | C | 252 | 46.904 | 38.174 | 93.094 | 1.00 | 46.91 C |
| ATOM | 14948 | CG2 | ILE | C | 252 | 45.804 | 38.358 | 90.157 | 1.00 | 43.65 C |
| ATOM | 14952 | C | ILE | C | 252 | 48.315 | 38.177 | 88.715 | 1.00 | 46.47 C |

-continued

| ATOM | 14953 | O   | ILE | C | 252 | 47.797 | 38.076 | 87.595  | 1.00 | 47.24 | O |
|------|-------|-----|-----|---|-----|--------|--------|---------|------|-------|---|
| ATOM | 14955 | N   | THR | C | 253 | 49.148 | 37.277 | 89.230  | 1.00 | 45.39 | N |
| ATOM | 14956 | CA  | THR | C | 253 | 49.623 | 36.103 | 88.519  | 1.00 | 44.64 | C |
| ATOM | 14958 | CB  | THR | C | 253 | 50.991 | 36.430 | 87.863  | 1.00 | 44.18 | C |
| ATOM | 14960 | OG1 | THR | C | 253 | 50.779 | 36.916 | 86.536  | 1.00 | 44.41 | O |
| ATOM | 14962 | CG2 | THR | C | 253 | 51.914 | 35.250 | 87.796  | 1.00 | 44.21 | C |
| ATOM | 14966 | C   | THR | C | 253 | 49.718 | 34.988 | 89.555  | 1.00 | 44.74 | C |
| ATOM | 14967 | O   | THR | C | 253 | 50.139 | 35.236 | 90.689  | 1.00 | 43.55 | O |
| ATOM | 14969 | N   | PHE | C | 254 | 49.316 | 33.771 | 89.181  | 1.00 | 45.62 | N |
| ATOM | 14970 | CA  | PHE | C | 254 | 49.211 | 32.672 | 90.155  | 1.00 | 46.51 | C |
| ATOM | 14972 | CB  | PHE | C | 254 | 47.912 | 32.819 | 90.944  | 1.00 | 46.44 | C |
| ATOM | 14975 | CG  | PHE | C | 254 | 46.706 | 32.632 | 90.106  | 1.00 | 44.57 | C |
| ATOM | 14976 | CD1 | PHE | C | 254 | 46.226 | 33.672 | 89.336  | 1.00 | 46.93 | C |
| ATOM | 14978 | CE1 | PHE | C | 254 | 45.109 | 33.492 | 88.523  | 1.00 | 51.75 | C |
| ATOM | 14980 | CZ  | PHE | C | 254 | 44.470 | 32.253 | 88.478  | 1.00 | 47.49 | C |
| ATOM | 14982 | CE2 | PHE | C | 254 | 44.959 | 31.203 | 89.239  | 1.00 | 45.96 | C |
| ATOM | 14984 | CD2 | PHE | C | 254 | 46.076 | 31.396 | 90.041  | 1.00 | 46.05 | C |
| ATOM | 14986 | C   | PHE | C | 254 | 49.233 | 31.268 | 89.541  | 1.00 | 47.34 | C |
| ATOM | 14987 | O   | PHE | C | 254 | 48.806 | 31.071 | 88.400  | 1.00 | 47.65 | O |
| ATOM | 14989 | N   | ASP | C | 255 | 49.689 | 30.293 | 90.328  | 1.00 | 47.51 | N |
| ATOM | 14990 | CA  | ASP | C | 255 | 49.701 | 28.891 | 89.910  | 1.00 | 47.48 | C |
| ATOM | 14992 | CB  | ASP | C | 255 | 51.072 | 28.289 | 90.158  | 1.00 | 48.12 | C |
| ATOM | 14995 | CG  | ASP | C | 255 | 52.072 | 28.695 | 89.113  | 1.00 | 52.79 | C |
| ATOM | 14996 | OD1 | ASP | C | 255 | 51.671 | 29.342 | 88.121  | 1.00 | 55.48 | O |
| ATOM | 14997 | OD2 | ASP | C | 255 | 53.262 | 28.359 | 89.278  | 1.00 | 61.66 | O |
| ATOM | 14998 | C   | ASP | C | 255 | 48.653 | 28.054 | 90.622  | 1.00 | 47.00 | C |
| ATOM | 14999 | O   | ASP | C | 255 | 48.396 | 28.239 | 91.805  | 1.00 | 46.38 | O |
| ATOM | 15001 | N   | LEU | C | 256 | 48.058 | 27.127 | 89.880  | 1.00 | 47.65 | N |
| ATOM | 15002 | CA  | LEU | C | 256 | 47.085 | 26.186 | 90.418  | 1.00 | 47.62 | C |
| ATOM | 15004 | CB  | LEU | C | 256 | 45.805 | 26.227 | 89.588  | 1.00 | 47.25 | C |
| ATOM | 15007 | CG  | LEU | C | 256 | 44.667 | 25.297 | 90.000  | 1.00 | 48.43 | C |
| ATOM | 15009 | CD1 | LEU | C | 256 | 44.353 | 25.465 | 91.470  | 1.00 | 49.72 | C |
| ATOM | 15013 | CD2 | LEU | C | 256 | 43.428 | 25.564 | 89.159  | 1.00 | 46.55 | C |
| ATOM | 15017 | C   | LEU | C | 256 | 47.688 | 24.785 | 90.385  | 1.00 | 47.74 | C |
| ATOM | 15018 | O   | LEU | C | 256 | 48.224 | 24.361 | 89.365  | 1.00 | 47.04 | O |
| ATOM | 15020 | N   | LYS | C | 257 | 47.625 | 24.089 | 91.515  | 1.00 | 49.23 | N |
| ATOM | 15021 | CA  | LYS | C | 257 | 48.102 | 22.714 | 91.610  | 1.00 | 49.52 | C |
| ATOM | 15023 | CB  | LYS | C | 257 | 49.616 | 22.682 | 91.786  | 1.00 | 49.85 | C |
| ATOM | 15026 | CG  | LYS | C | 257 | 50.180 | 21.273 | 91.835  | 1.00 | 51.35 | C |
| ATOM | 15029 | CD  | LYS | C | 257 | 51.472 | 21.146 | 91.043  | 1.00 | 56.71 | C |
| ATOM | 15032 | CE  | LYS | C | 257 | 51.781 | 19.682 | 90.720  | 1.00 | 59.11 | C |
| ATOM | 15035 | NZ  | LYS | C | 257 | 53.033 | 19.521 | 89.910  | 1.00 | 62.57 | N |
| ATOM | 15039 | C   | LYS | C | 257 | 47.439 | 22.003 | 92.778  | 1.00 | 49.14 | C |
| ATOM | 15040 | O   | LYS | C | 257 | 47.587 | 22.435 | 93.922  | 1.00 | 49.80 | O |
| ATOM | 15042 | N   | ASN | C | 258 | 46.715 | 20.925 | 92.482  | 1.00 | 47.65 | N |
| ATOM | 15043 | CA  | ASN | C | 258 | 46.021 | 20.140 | 93.503  | 1.00 | 51.51 | C |
| ATOM | 15045 | CB  | ASN | C | 258 | 47.027 | 19.327 | 94.353  | 1.00 | 52.58 | C |
| ATOM | 15048 | CG  | ASN | C | 258 | 47.408 | 17.987 | 93.711  | 1.00 | 56.47 | C |
| ATOM | 15049 | OD1 | ASN | C | 258 | 47.016 | 17.680 | 92.582  | 1.00 | 57.19 | O |
| ATOM | 15050 | ND2 | ASN | C | 258 | 48.174 | 17.184 | 94.442  | 1.00 | 55.28 | N |
| ATOM | 15053 | C   | ASN | C | 258 | 45.123 | 20.990 | 94.401  | 1.00 | 50.58 | C |
| ATOM | 15054 | O   | ASN | C | 258 | 45.204 | 20.917 | 95.619  | 1.00 | 49.41 | O |
| ATOM | 15056 | N   | LYS | C | 259 | 44.274 | 21.802 | 93.778  | 1.00 | 53.21 | N |
| ATOM | 15057 | CA  | LYS | C | 259 | 43.327 | 22.690 | 94.485  | 1.00 | 53.98 | C |
| ATOM | 15059 | CB  | LYS | C | 259 | 42.461 | 21.907 | 95.498  | 1.00 | 54.69 | C |
| ATOM | 15062 | CG  | LYS | C | 259 | 41.936 | 20.542 | 95.001  | 1.00 | 59.35 | C |
| ATOM | 15065 | CD  | LYS | C | 259 | 40.428 | 20.517 | 94.664  | 1.00 | 66.23 | C |
| ATOM | 15068 | CE  | LYS | C | 259 | 39.543 | 20.004 | 95.824  | 1.00 | 67.76 | C |
| ATOM | 15071 | NZ  | LYS | C | 259 | 39.204 | 21.046 | 96.851  | 1.00 | 64.81 | N |
| ATOM | 15075 | C   | LYS | C | 259 | 43.987 | 23.902 | 95.181  | 1.00 | 53.79 | C |
| ATOM | 15076 | O   | LYS | C | 259 | 43.284 | 24.840 | 95.564  | 1.00 | 54.56 | O |
| ATOM | 15078 | N   | GLU | C | 260 | 45.316 | 23.892 | 95.325  | 1.00 | 52.48 | N |
| ATOM | 15079 | CA  | GLU | C | 260 | 46.051 | 24.958 | 96.023  | 1.00 | 52.41 | C |
| ATOM | 15081 | CB  | GLU | C | 260 | 47.304 | 24.394 | 96.716  | 1.00 | 52.76 | C |
| ATOM | 15084 | CG  | GLU | C | 260 | 47.064 | 23.808 | 98.100  | 1.00 | 55.53 | C |
| ATOM | 15087 | CD  | GLU | C | 260 | 48.361 | 23.501 | 98.847  | 1.00 | 58.26 | C |
| ATOM | 15088 | OE1 | GLU | C | 260 | 48.306 | 23.278 | 100.076 | 1.00 | 64.23 | O |
| ATOM | 15089 | OE2 | GLU | C | 260 | 49.438 | 23.482 | 98.210  | 1.00 | 68.33 | O |
| ATOM | 15090 | C   | GLU | C | 260 | 46.465 | 26.084 | 95.067  | 1.00 | 50.41 | C |
| ATOM | 15091 | O   | GLU | C | 260 | 46.881 | 25.818 | 93.943  | 1.00 | 51.33 | O |
| ATOM | 15093 | N   | VAL | C | 261 | 46.380 | 27.331 | 95.534  | 1.00 | 48.09 | N |
| ATOM | 15094 | CA  | VAL | C | 261 | 46.668 | 28.509 | 94.713  | 1.00 | 46.83 | C |
| ATOM | 15096 | CB  | VAL | C | 261 | 45.421 | 29.423 | 94.586  | 1.00 | 45.44 | C |
| ATOM | 15098 | CG1 | VAL | C | 261 | 45.711 | 30.604 | 93.687  | 1.00 | 46.97 | C |
| ATOM | 15102 | CG2 | VAL | C | 261 | 44.240 | 28.650 | 94.044  | 1.00 | 45.02 | C |
| ATOM | 15106 | C   | VAL | C | 261 | 47.836 | 29.324 | 95.289  | 1.00 | 45.24 | C |
| ATOM | 15107 | O   | VAL | C | 261 | 47.718 | 29.920 | 96.358  | 1.00 | 41.26 | O |
| ATOM | 15109 | N   | SER | C | 262 | 48.952 | 29.335 | 94.559  | 1.00 | 46.20 | N |
| ATOM | 15110 | CA  | SER | C | 262 | 50.138 | 30.128 | 94.894  | 1.00 | 47.83 | C |

-continued

| ATOM | 15112 | CB  | SER | C | 262 | 51.396 | 29.311 | 94.621 | 1.00 | 47.10 | C |
| ATOM | 15115 | OG  | SER | C | 262 | 51.506 | 28.252 | 95.542 | 1.00 | 51.61 | O |
| ATOM | 15117 | C   | SER | C | 262 | 50.204 | 31.391 | 94.045 | 1.00 | 49.15 | C |
| ATOM | 15118 | O   | SER | C | 262 | 50.085 | 31.304 | 92.823 | 1.00 | 51.69 | O |
| ATOM | 15120 | N   | VAL | C | 263 | 50.436 | 32.550 | 94.665 | 1.00 | 48.68 | N |
| ATOM | 15121 | CA  | VAL | C | 263 | 50.494 | 33.810 | 93.907 | 1.00 | 48.91 | C |
| ATOM | 15123 | CB  | VAL | C | 263 | 49.712 | 34.981 | 94.607 | 1.00 | 48.17 | C |
| ATOM | 15125 | CG1 | VAL | C | 263 | 48.663 | 34.440 | 95.578 | 1.00 | 46.85 | C |
| ATOM | 15129 | CG2 | VAL | C | 263 | 50.627 | 35.953 | 95.327 | 1.00 | 51.31 | C |
| ATOM | 15133 | C   | VAL | C | 263 | 51.958 | 34.168 | 93.579 | 1.00 | 49.79 | C |
| ATOM | 15134 | O   | VAL | C | 263 | 52.799 | 34.316 | 94.472 | 1.00 | 48.47 | O |
| ATOM | 15136 | N   | LYS | C | 264 | 52.262 | 34.289 | 92.291 | 1.00 | 50.90 | N |
| ATOM | 15137 | CA  | LYS | C | 264 | 53.635 | 34.529 | 91.850 | 1.00 | 51.12 | C |
| ATOM | 15139 | CB  | LYS | C | 264 | 53.896 | 33.805 | 90.540 | 1.00 | 51.57 | C |
| ATOM | 15142 | CG  | LYS | C | 264 | 53.756 | 32.305 | 90.607 | 1.00 | 55.55 | C |
| ATOM | 15145 | CD  | LYS | C | 264 | 54.067 | 31.680 | 89.244 | 1.00 | 56.56 | C |
| ATOM | 15148 | CE  | LYS | C | 264 | 53.023 | 32.050 | 88.179 | 1.00 | 58.78 | C |
| ATOM | 15151 | NZ  | LYS | C | 264 | 53.138 | 31.219 | 86.946 | 1.00 | 58.89 | N |
| ATOM | 15155 | C   | LYS | C | 264 | 53.967 | 36.001 | 91.653 | 1.00 | 49.17 | C |
| ATOM | 15156 | O   | LYS | C | 264 | 55.116 | 36.387 | 91.786 | 1.00 | 48.14 | O |
| ATOM | 15158 | N   | ARG | C | 265 | 52.973 | 36.810 | 91.307 | 1.00 | 49.03 | N |
| ATOM | 15159 | CA  | ARG | C | 265 | 53.209 | 38.210 | 90.960 | 1.00 | 50.08 | C |
| ATOM | 15161 | CB  | ARG | C | 265 | 53.455 | 38.332 | 89.458 | 1.00 | 50.30 | C |
| ATOM | 15164 | CG  | ARG | C | 265 | 54.691 | 39.104 | 89.043 | 1.00 | 49.45 | C |
| ATOM | 15167 | CD  | ARG | C | 265 | 55.041 | 38.759 | 87.605 | 1.00 | 49.01 | C |
| ATOM | 15170 | NE  | ARG | C | 265 | 56.273 | 39.395 | 87.136 | 1.00 | 52.33 | N |
| ATOM | 15172 | CZ  | ARG | C | 265 | 56.916 | 39.068 | 86.011 | 1.00 | 50.45 | C |
| ATOM | 15173 | NH1 | ARG | C | 265 | 58.028 | 39.706 | 85.664 | 1.00 | 49.84 | N |
| ATOM | 15176 | NH2 | ARG | C | 265 | 56.455 | 38.107 | 85.222 | 1.00 | 53.21 | N |
| ATOM | 15179 | C   | ARG | C | 265 | 51.974 | 38.995 | 91.339 | 1.00 | 50.17 | C |
| ATOM | 15180 | O   | ARG | C | 265 | 50.869 | 38.489 | 91.224 | 1.00 | 51.12 | O |
| ATOM | 15182 | N   | VAL | C | 266 | 52.156 | 40.224 | 91.804 | 1.00 | 51.61 | N |
| ATOM | 15183 | CA  | VAL | C | 266 | 51.040 | 41.033 | 92.284 | 1.00 | 53.46 | C |
| ATOM | 15185 | CB  | VAL | C | 266 | 50.835 | 40.893 | 93.811 | 1.00 | 54.83 | C |
| ATOM | 15187 | CG1 | VAL | C | 266 | 49.637 | 41.726 | 94.278 | 1.00 | 56.37 | C |
| ATOM | 15191 | CG2 | VAL | C | 266 | 50.653 | 39.430 | 94.207 | 1.00 | 58.89 | C |
| ATOM | 15195 | C   | VAL | C | 266 | 51.319 | 42.484 | 92.002 | 1.00 | 53.73 | C |
| ATOM | 15196 | O   | VAL | C | 266 | 52.465 | 42.910 | 92.032 | 1.00 | 54.06 | O |
| ATOM | 15198 | N   | THR | C | 267 | 50.268 | 43.247 | 91.733 | 1.00 | 55.45 | N |
| ATOM | 15199 | CA  | THR | C | 267 | 50.418 | 44.685 | 91.566 | 1.00 | 55.96 | C |
| ATOM | 15201 | CB  | THR | C | 267 | 49.238 | 45.339 | 90.782 | 1.00 | 56.37 | C |
| ATOM | 15203 | OG1 | THR | C | 267 | 49.562 | 46.699 | 90.459 | 1.00 | 54.71 | O |
| ATOM | 15205 | CG2 | THR | C | 267 | 47.946 | 45.320 | 91.593 | 1.00 | 57.41 | C |
| ATOM | 15209 | C   | THR | C | 267 | 50.539 | 45.347 | 92.928 | 1.00 | 56.70 | C |
| ATOM | 15210 | O   | THR | C | 267 | 49.844 | 44.978 | 93.885 | 1.00 | 55.32 | O |
| ATOM | 15212 | N   | GLN | C | 268 | 51.465 | 46.298 | 93.001 | 1.00 | 57.43 | N |
| ATOM | 15213 | CA  | GLN | C | 268 | 51.418 | 47.354 | 94.000 | 1.00 | 56.91 | C |
| ATOM | 15215 | CB  | GLN | C | 268 | 52.780 | 48.060 | 94.120 | 1.00 | 56.93 | C |
| ATOM | 15218 | CG  | GLN | C | 268 | 53.514 | 48.362 | 92.784 | 1.00 | 56.06 | C |
| ATOM | 15221 | CD  | GLN | C | 268 | 54.714 | 49.288 | 92.955 | 1.00 | 54.89 | C |
| ATOM | 15222 | OE1 | GLN | C | 268 | 54.943 | 50.186 | 92.146 | 1.00 | 51.57 | O |
| ATOM | 15223 | NE2 | GLN | C | 268 | 55.481 | 49.073 | 94.013 | 1.00 | 52.66 | N |
| ATOM | 15226 | C   | GLN | C | 268 | 50.336 | 48.319 | 93.518 | 1.00 | 57.79 | C |
| ATOM | 15227 | O   | GLN | C | 268 | 50.519 | 48.967 | 92.493 | 1.00 | 59.74 | O |
| ATOM | 15229 | N   | ASP | C | 269 | 49.200 | 48.374 | 94.219 | 1.00 | 57.82 | N |
| ATOM | 15230 | CA  | ASP | C | 269 | 48.039 | 49.205 | 93.813 | 1.00 | 57.20 | C |
| ATOM | 15232 | CB  | ASP | C | 269 | 48.487 | 50.617 | 93.397 | 1.00 | 56.58 | C |
| ATOM | 15235 | CG  | ASP | C | 269 | 47.428 | 51.663 | 93.652 | 1.00 | 57.36 | C |
| ATOM | 15236 | OD1 | ASP | C | 269 | 46.776 | 52.122 | 92.695 | 1.00 | 59.34 | O |
| ATOM | 15237 | OD2 | ASP | C | 269 | 47.242 | 52.032 | 94.821 | 1.00 | 60.71 | O |
| ATOM | 15238 | C   | ASP | C | 269 | 47.184 | 48.568 | 92.683 | 1.00 | 55.97 | C |
| ATOM | 15239 | O   | ASP | C | 269 | 47.613 | 48.507 | 91.529 | 1.00 | 52.98 | O |
| ATOM | 15241 | N   | PRO | C | 270 | 45.984 | 48.058 | 93.016 | 1.00 | 56.48 | N |
| ATOM | 15242 | CA  | PRO | C | 270 | 45.418 | 47.872 | 94.354 | 1.00 | 58.21 | C |
| ATOM | 15244 | CB  | PRO | C | 270 | 43.958 | 47.479 | 94.078 | 1.00 | 57.77 | C |
| ATOM | 15247 | CG  | PRO | C | 270 | 43.956 | 46.913 | 92.715 | 1.00 | 55.92 | C |
| ATOM | 15250 | CD  | PRO | C | 270 | 45.066 | 47.595 | 91.961 | 1.00 | 57.28 | C |
| ATOM | 15253 | C   | PRO | C | 270 | 46.142 | 46.750 | 95.087 | 1.00 | 58.74 | C |
| ATOM | 15254 | O   | PRO | C | 270 | 46.739 | 45.884 | 94.444 | 1.00 | 58.59 | O |
| ATOM | 15255 | N   | LYS | C | 271 | 46.098 | 46.767 | 96.416 | 1.00 | 60.62 | N |
| ATOM | 15256 | CA  | LYS | C | 271 | 46.734 | 45.714 | 97.208 | 1.00 | 61.47 | C |
| ATOM | 15258 | CB  | LYS | C | 271 | 47.033 | 46.190 | 98.629 | 1.00 | 61.51 | C |
| ATOM | 15261 | CG  | LYS | C | 271 | 48.022 | 47.357 | 98.669 | 1.00 | 60.55 | C |
| ATOM | 15264 | CD  | LYS | C | 271 | 49.267 | 47.031 | 99.497 | 1.00 | 61.33 | C |
| ATOM | 15267 | CE  | LYS | C | 271 | 50.385 | 48.047 | 99.261 | 1.00 | 63.15 | C |
| ATOM | 15270 | NZ  | LYS | C | 271 | 51.744 | 47.472 | 99.468 | 1.00 | 62.50 | N |
| ATOM | 15274 | C   | LYS | C | 271 | 45.836 | 44.483 | 97.195 | 1.00 | 62.96 | C |
| ATOM | 15275 | O   | LYS | C | 271 | 44.858 | 44.395 | 97.942 | 1.00 | 64.70 | O |
| ATOM | 15277 | N   | LEU | C | 272 | 46.196 | 43.539 | 96.329 | 1.00 | 62.64 | N |

-continued

| | | | | | | | | | | |
|---|---|---|---|---|---|---|---|---|---|---|
| ATOM | 15278 | CA | LEU | C | 272 | 45.325 | 42.439 | 95.933 | 1.00 | 62.58 C |
| ATOM | 15280 | CB | LEU | C | 272 | 45.549 | 42.156 | 94.438 | 1.00 | 63.18 C |
| ATOM | 15283 | CG | LEU | C | 272 | 44.366 | 42.188 | 93.468 | 1.00 | 61.62 C |
| ATOM | 15285 | CD1 | LEU | C | 272 | 43.627 | 40.889 | 93.484 | 1.00 | 62.32 C |
| ATOM | 15289 | CD2 | LEU | C | 272 | 43.421 | 43.347 | 93.770 | 1.00 | 62.98 C |
| ATOM | 15293 | C | LEU | C | 272 | 45.657 | 41.196 | 96.752 | 1.00 | 62.94 C |
| ATOM | 15294 | O | LEU | C | 272 | 46.822 | 40.800 | 96.816 | 1.00 | 63.09 O |
| ATOM | 15296 | N | GLN | C | 273 | 44.647 | 40.576 | 97.363 | 1.00 | 63.24 N |
| ATOM | 15297 | CA | GLN | C | 273 | 44.861 | 39.377 | 98.201 | 1.00 | 64.03 C |
| ATOM | 15299 | CB | GLN | C | 273 | 44.604 | 39.670 | 99.694 | 1.00 | 63.96 C |
| ATOM | 15302 | CG | GLN | C | 273 | 43.360 | 40.522 | 100.034 | 1.00 | 66.07 C |
| ATOM | 15305 | CD | GLN | C | 273 | 43.506 | 41.289 | 101.360 | 1.00 | 66.75 C |
| ATOM | 15306 | OE1 | GLN | C | 273 | 44.102 | 40.789 | 102.316 | 1.00 | 69.08 O |
| ATOM | 15307 | NE2 | GLN | C | 273 | 42.963 | 42.509 | 101.411 | 1.00 | 66.69 N |
| ATOM | 15310 | C | GLN | C | 273 | 44.029 | 38.186 | 97.719 | 1.00 | 64.15 C |
| ATOM | 15311 | O | GLN | C | 273 | 42.802 | 38.198 | 97.804 | 1.00 | 66.11 O |
| ATOM | 15313 | N | MET | C | 274 | 44.711 | 37.157 | 97.218 | 1.00 | 63.20 N |
| ATOM | 15314 | CA | MET | C | 274 | 44.049 | 36.003 | 96.617 | 1.00 | 62.63 C |
| ATOM | 15316 | CB | MET | C | 274 | 44.845 | 35.499 | 95.412 | 1.00 | 62.63 C |
| ATOM | 15319 | CG | MET | C | 274 | 44.157 | 34.381 | 94.641 | 1.00 | 63.68 C |
| ATOM | 15322 | SD | MET | C | 274 | 44.652 | 34.271 | 92.906 | 1.00 | 66.50 S |
| ATOM | 15323 | CE | MET | C | 274 | 43.761 | 35.674 | 92.237 | 1.00 | 67.97 C |
| ATOM | 15327 | C | MET | C | 274 | 43.880 | 34.872 | 97.612 | 1.00 | 61.22 C |
| ATOM | 15328 | O | MET | C | 274 | 44.754 | 34.620 | 98.430 | 1.00 | 61.87 O |
| ATOM | 15330 | N | GLY | C | 275 | 42.748 | 34.186 | 97.521 | 1.00 | 60.68 N |
| ATOM | 15331 | CA | GLY | C | 275 | 42.475 | 33.023 | 98.345 | 1.00 | 60.59 C |
| ATOM | 15334 | C | GLY | C | 275 | 43.493 | 31.915 | 98.151 | 1.00 | 60.84 C |
| ATOM | 15335 | O | GLY | C | 275 | 44.138 | 31.798 | 97.106 | 1.00 | 60.35 O |
| ATOM | 15337 | N | LYS | C | 276 | 43.603 | 31.077 | 99.169 | 1.00 | 61.47 N |
| ATOM | 15338 | CA | LYS | C | 276 | 44.681 | 30.095 | 99.270 | 1.00 | 61.21 C |
| ATOM | 15340 | CB | LYS | C | 276 | 44.967 | 29.785 | 100.748 | 1.00 | 62.19 C |
| ATOM | 15343 | CG | LYS | C | 276 | 43.720 | 29.409 | 101.590 | 1.00 | 65.47 C |
| ATOM | 15346 | CD | LYS | C | 276 | 43.103 | 30.615 | 102.333 | 1.00 | 67.04 C |
| ATOM | 15349 | CE | LYS | C | 276 | 41.612 | 30.417 | 102.632 | 1.00 | 66.23 C |
| ATOM | 15352 | NZ | LYS | C | 276 | 41.367 | 29.395 | 103.692 | 1.00 | 59.95 N |
| ATOM | 15356 | C | LYS | C | 276 | 44.351 | 28.807 | 98.518 | 1.00 | 60.48 C |
| ATOM | 15357 | O | LYS | C | 276 | 45.243 | 28.020 | 98.207 | 1.00 | 59.19 O |
| ATOM | 15359 | N | LYS | C | 277 | 43.064 | 28.609 | 98.234 | 1.00 | 59.98 N |
| ATOM | 15360 | CA | LYS | C | 277 | 42.549 | 27.351 | 97.701 | 1.00 | 59.13 C |
| ATOM | 15362 | CB | LYS | C | 277 | 42.187 | 26.416 | 98.863 | 1.00 | 59.67 C |
| ATOM | 15365 | CG | LYS | C | 277 | 43.362 | 25.594 | 99.395 | 1.00 | 62.99 C |
| ATOM | 15368 | CD | LYS | C | 277 | 43.094 | 25.014 | 100.790 | 1.00 | 63.32 C |
| ATOM | 15371 | CE | LYS | C | 277 | 43.454 | 26.007 | 101.910 | 1.00 | 67.77 C |
| ATOM | 15374 | NZ | LYS | C | 277 | 43.650 | 25.350 | 103.249 | 1.00 | 66.56 N |
| ATOM | 15378 | C | LYS | C | 277 | 41.329 | 27.599 | 96.806 | 1.00 | 56.72 C |
| ATOM | 15379 | O | LYS | C | 277 | 40.806 | 28.710 | 96.753 | 1.00 | 57.13 O |
| ATOM | 15381 | N | LEU | C | 278 | 40.881 | 26.571 | 96.096 | 1.00 | 54.32 N |
| ATOM | 15382 | CA | LEU | C | 278 | 39.716 | 26.713 | 95.227 | 1.00 | 52.98 C |
| ATOM | 15384 | CB | LEU | C | 278 | 39.525 | 25.478 | 94.362 | 1.00 | 51.77 C |
| ATOM | 15387 | CG | LEU | C | 278 | 40.576 | 25.328 | 93.271 | 1.00 | 54.79 C |
| ATOM | 15389 | CD1 | LEU | C | 278 | 40.435 | 23.980 | 92.607 | 1.00 | 57.28 C |
| ATOM | 15393 | CD2 | LEU | C | 278 | 40.467 | 26.454 | 92.242 | 1.00 | 56.60 C |
| ATOM | 15397 | C | LEU | C | 278 | 38.469 | 26.932 | 96.054 | 1.00 | 50.20 C |
| ATOM | 15398 | O | LEU | C | 278 | 38.413 | 26.492 | 97.202 | 1.00 | 48.54 O |
| ATOM | 15400 | N | PRO | C | 279 | 37.465 | 27.624 | 95.484 | 1.00 | 48.92 N |
| ATOM | 15401 | CA | PRO | C | 279 | 37.466 | 28.241 | 94.163 | 1.00 | 48.87 C |
| ATOM | 15403 | CB | PRO | C | 279 | 35.991 | 28.569 | 93.940 | 1.00 | 48.66 C |
| ATOM | 15406 | CG | PRO | C | 279 | 35.480 | 28.845 | 95.289 | 1.00 | 47.76 C |
| ATOM | 15409 | CD | PRO | C | 279 | 36.183 | 27.855 | 96.174 | 1.00 | 48.41 C |
| ATOM | 15412 | C | PRO | C | 279 | 38.294 | 29.529 | 94.104 | 1.00 | 49.11 C |
| ATOM | 15413 | O | PRO | C | 279 | 38.301 | 30.310 | 95.059 | 1.00 | 48.14 O |
| ATOM | 15414 | N | LEU | C | 280 | 38.974 | 29.736 | 92.976 | 1.00 | 48.91 N |
| ATOM | 15415 | CA | LEU | C | 280 | 39.736 | 30.954 | 92.735 | 1.00 | 48.31 C |
| ATOM | 15417 | CB | LEU | C | 280 | 40.032 | 31.141 | 91.245 | 1.00 | 45.56 C |
| ATOM | 15420 | CG | LEU | C | 280 | 40.723 | 30.005 | 90.488 | 1.00 | 45.81 C |
| ATOM | 15422 | CD1 | LEU | C | 280 | 40.958 | 30.396 | 89.043 | 1.00 | 46.69 C |
| ATOM | 15426 | CD2 | LEU | C | 280 | 42.033 | 29.620 | 91.134 | 1.00 | 44.94 C |
| ATOM | 15430 | C | LEU | C | 280 | 38.916 | 32.122 | 93.248 | 1.00 | 48.75 C |
| ATOM | 15431 | O | LEU | C | 280 | 37.744 | 32.272 | 92.909 | 1.00 | 48.16 O |
| ATOM | 15433 | N | HIS | C | 281 | 39.522 | 32.937 | 94.094 | 1.00 | 51.52 N |
| ATOM | 15434 | CA | HIS | C | 281 | 38.776 | 33.987 | 94.749 | 1.00 | 52.97 C |
| ATOM | 15436 | CB | HIS | C | 281 | 37.944 | 33.388 | 95.882 | 1.00 | 55.29 C |
| ATOM | 15439 | CG | HIS | C | 281 | 37.171 | 34.401 | 96.666 | 1.00 | 55.78 C |
| ATOM | 15440 | ND1 | HIS | C | 281 | 37.540 | 34.798 | 97.932 | 1.00 | 57.68 N |
| ATOM | 15442 | CE1 | HIS | C | 281 | 36.676 | 35.691 | 98.379 | 1.00 | 60.74 C |
| ATOM | 15444 | NE2 | HIS | C | 281 | 35.760 | 35.890 | 97.447 | 1.00 | 60.85 N |
| ATOM | 15446 | CD2 | HIS | C | 281 | 36.045 | 35.093 | 96.365 | 1.00 | 59.12 C |
| ATOM | 15448 | C | HIS | C | 281 | 39.718 | 35.029 | 95.295 | 1.00 | 53.59 C |
| ATOM | 15449 | O | HIS | C | 281 | 40.495 | 34.745 | 96.199 | 1.00 | 54.41 O |

-continued

| | | | | | | | | | | |
|---|---|---|---|---|---|---|---|---|---|---|
| ATOM | 15451 | N | LEU | C | 282 | 39.662 | 36.231 | 94.740 | 1.00 | 54.10 N |
| ATOM | 15452 | CA | LEU | C | 282 | 40.476 | 37.311 | 95.256 | 1.00 | 55.59 C |
| ATOM | 15454 | CB | LEU | C | 282 | 41.479 | 37.827 | 94.216 | 1.00 | 57.69 C |
| ATOM | 15457 | CG | LEU | C | 282 | 41.109 | 38.746 | 93.043 | 1.00 | 61.91 C |
| ATOM | 15459 | CD1 | LEU | C | 282 | 40.456 | 40.052 | 93.499 | 1.00 | 64.07 C |
| ATOM | 15463 | CD2 | LEU | C | 282 | 40.245 | 38.068 | 92.016 | 1.00 | 65.90 C |
| ATOM | 15467 | C | LEU | C | 282 | 39.587 | 38.411 | 95.763 | 1.00 | 55.77 C |
| ATOM | 15468 | O | LEU | C | 282 | 38.398 | 38.461 | 95.427 | 1.00 | 53.36 O |
| ATOM | 15470 | N | THR | C | 283 | 40.179 | 39.281 | 96.586 | 1.00 | 56.22 N |
| ATOM | 15471 | CA | THR | C | 283 | 39.478 | 40.441 | 97.127 | 1.00 | 56.13 C |
| ATOM | 15473 | CB | THR | C | 283 | 38.901 | 40.176 | 98.553 | 1.00 | 56.10 C |
| ATOM | 15475 | OG1 | THR | C | 283 | 38.975 | 41.369 | 99.347 | 1.00 | 51.35 O |
| ATOM | 15477 | CG2 | THR | C | 283 | 39.633 | 39.028 | 99.265 | 1.00 | 56.68 C |
| ATOM | 15481 | C | THR | C | 283 | 40.317 | 41.721 | 97.119 | 1.00 | 56.00 C |
| ATOM | 15482 | O | THR | C | 283 | 41.525 | 41.702 | 97.367 | 1.00 | 55.55 O |
| ATOM | 15484 | N | LEU | C | 284 | 39.647 | 42.825 | 96.797 | 1.00 | 56.47 N |
| ATOM | 15485 | CA | LEU | C | 284 | 40.190 | 44.152 | 96.991 | 1.00 | 57.17 C |
| ATOM | 15487 | CB | LEU | C | 284 | 39.660 | 45.129 | 95.952 | 1.00 | 56.86 C |
| ATOM | 15490 | CG | LEU | C | 284 | 40.173 | 45.008 | 94.524 | 1.00 | 58.84 C |
| ATOM | 15492 | CD1 | LEU | C | 284 | 39.788 | 43.674 | 93.911 | 1.00 | 61.44 C |
| ATOM | 15496 | CD2 | LEU | C | 284 | 39.624 | 46.161 | 93.700 | 1.00 | 58.80 C |
| ATOM | 15500 | C | LEU | C | 284 | 39.715 | 44.618 | 98.344 | 1.00 | 57.25 C |
| ATOM | 15501 | O | LEU | C | 284 | 38.510 | 44.690 | 98.572 | 1.00 | 56.00 O |
| ATOM | 15503 | N | PRO | C | 285 | 40.647 | 44.941 | 99.251 | 1.00 | 59.41 N |
| ATOM | 15504 | CA | PRO | C | 285 | 40.234 | 45.538 | 100.531 | 1.00 | 60.45 C |
| ATOM | 15506 | CB | PRO | C | 285 | 41.563 | 45.785 | 101.268 | 1.00 | 60.29 C |
| ATOM | 15509 | CG | PRO | C | 285 | 42.650 | 45.570 | 100.265 | 1.00 | 60.05 C |
| ATOM | 15512 | CD | PRO | C | 285 | 42.104 | 44.738 | 99.160 | 1.00 | 59.55 C |
| ATOM | 15515 | C | PRO | C | 285 | 39.435 | 46.847 | 100.401 | 1.00 | 60.94 C |
| ATOM | 15516 | O | PRO | C | 285 | 38.739 | 47.228 | 101.343 | 1.00 | 61.14 O |
| ATOM | 15517 | N | GLN | C | 286 | 39.500 | 47.490 | 99.233 | 1.00 | 62.02 N |
| ATOM | 15518 | CA | GLN | C | 286 | 39.100 | 48.892 | 99.067 | 1.00 | 63.02 C |
| ATOM | 15520 | CB | GLN | C | 286 | 40.281 | 49.809 | 99.434 | 1.00 | 64.74 C |
| ATOM | 15523 | CG | GLN | C | 286 | 41.704 | 49.172 | 99.295 | 1.00 | 70.58 C |
| ATOM | 15526 | CD | GLN | C | 286 | 42.080 | 48.713 | 97.865 | 1.00 | 75.12 C |
| ATOM | 15527 | OE1 | GLN | C | 286 | 42.483 | 49.522 | 97.027 | 1.00 | 77.23 O |
| ATOM | 15528 | NE2 | GLN | C | 286 | 41.985 | 47.408 | 97.609 | 1.00 | 71.67 N |
| ATOM | 15531 | C | GLN | C | 286 | 38.612 | 49.227 | 97.643 | 1.00 | 62.97 C |
| ATOM | 15532 | O | GLN | C | 286 | 39.400 | 49.249 | 96.690 | 1.00 | 62.71 O |
| ATOM | 15534 | N | ALA | C | 287 | 37.318 | 49.499 | 97.498 | 1.00 | 62.09 N |
| ATOM | 15535 | CA | ALA | C | 287 | 36.791 | 49.964 | 96.216 | 1.00 | 61.81 C |
| ATOM | 15537 | CB | ALA | C | 287 | 35.293 | 49.800 | 96.159 | 1.00 | 62.58 C |
| ATOM | 15541 | C | ALA | C | 287 | 37.167 | 51.427 | 96.013 | 1.00 | 61.81 C |
| ATOM | 15542 | O | ALA | C | 287 | 37.006 | 52.247 | 96.919 | 1.00 | 60.71 O |
| ATOM | 15544 | N | LEU | C | 288 | 37.677 | 51.741 | 94.825 | 1.00 | 61.62 N |
| ATOM | 15545 | CA | LEU | C | 288 | 38.071 | 53.107 | 94.485 | 1.00 | 60.16 C |
| ATOM | 15547 | CB | LEU | C | 288 | 39.554 | 53.325 | 94.791 | 1.00 | 61.22 C |
| ATOM | 15550 | CG | LEU | C | 288 | 39.958 | 53.460 | 96.260 | 1.00 | 64.94 C |
| ATOM | 15552 | CD1 | LEU | C | 288 | 41.489 | 53.510 | 96.400 | 1.00 | 65.46 C |
| ATOM | 15556 | CD2 | LEU | C | 288 | 39.302 | 54.701 | 96.880 | 1.00 | 65.41 C |
| ATOM | 15560 | C | LEU | C | 288 | 37.814 | 53.415 | 93.012 | 1.00 | 58.56 C |
| ATOM | 15561 | O | LEU | C | 288 | 37.878 | 52.514 | 92.168 | 1.00 | 58.21 O |
| ATOM | 15563 | N | PRO | C | 289 | 37.527 | 54.692 | 92.695 | 1.00 | 56.06 N |
| ATOM | 15564 | CA | PRO | C | 289 | 37.300 | 55.065 | 91.305 | 1.00 | 55.45 C |
| ATOM | 15566 | CB | PRO | C | 289 | 37.254 | 56.605 | 91.344 | 1.00 | 56.33 C |
| ATOM | 15569 | CG | PRO | C | 289 | 37.631 | 57.008 | 92.731 | 1.00 | 55.40 C |
| ATOM | 15572 | CD | PRO | C | 289 | 37.373 | 55.842 | 93.603 | 1.00 | 56.31 C |
| ATOM | 15575 | C | PRO | C | 289 | 38.396 | 54.575 | 90.354 | 1.00 | 53.92 C |
| ATOM | 15576 | O | PRO | C | 289 | 38.083 | 54.128 | 89.250 | 1.00 | 54.03 O |
| ATOM | 15577 | N | GLN | C | 290 | 39.656 | 54.644 | 90.781 | 1.00 | 52.07 N |
| ATOM | 15578 | CA | GLN | C | 290 | 40.785 | 54.321 | 89.896 | 1.00 | 51.62 C |
| ATOM | 15580 | CB | GLN | C | 290 | 42.111 | 54.860 | 90.453 | 1.00 | 51.09 C |
| ATOM | 15583 | CG | GLN | C | 290 | 42.518 | 54.334 | 91.836 | 1.00 | 50.62 C |
| ATOM | 15586 | CD | GLN | C | 290 | 42.359 | 55.372 | 92.944 | 1.00 | 48.92 C |
| ATOM | 15587 | OE1 | GLN | C | 290 | 41.281 | 55.935 | 93.141 | 1.00 | 50.38 O |
| ATOM | 15588 | NE2 | GLN | C | 290 | 43.436 | 55.619 | 93.677 | 1.00 | 38.93 N |
| ATOM | 15591 | C | GLN | C | 290 | 40.916 | 52.826 | 89.565 | 1.00 | 51.22 C |
| ATOM | 15592 | O | GLN | C | 290 | 41.587 | 52.462 | 88.595 | 1.00 | 51.06 O |
| ATOM | 15594 | N | TYR | C | 291 | 40.276 | 51.967 | 90.355 | 1.00 | 50.25 N |
| ATOM | 15595 | CA | TYR | C | 291 | 40.289 | 50.529 | 90.089 | 1.00 | 49.57 C |
| ATOM | 15597 | CB | TYR | C | 291 | 40.384 | 49.746 | 91.397 | 1.00 | 51.28 C |
| ATOM | 15600 | CG | TYR | C | 291 | 41.530 | 50.188 | 92.263 | 1.00 | 50.55 C |
| ATOM | 15601 | CD1 | TYR | C | 291 | 42.804 | 50.358 | 91.719 | 1.00 | 53.72 C |
| ATOM | 15603 | CE1 | TYR | C | 291 | 43.866 | 50.770 | 92.498 | 1.00 | 55.53 C |
| ATOM | 15605 | CZ | TYR | C | 291 | 43.664 | 51.024 | 93.843 | 1.00 | 55.96 C |
| ATOM | 15606 | OH | TYR | C | 291 | 44.724 | 51.428 | 94.608 | 1.00 | 54.10 O |
| ATOM | 15608 | CE2 | TYR | C | 291 | 42.407 | 50.866 | 94.409 | 1.00 | 53.50 C |
| ATOM | 15610 | CD2 | TYR | C | 291 | 41.350 | 50.445 | 93.617 | 1.00 | 51.86 C |
| ATOM | 15612 | C | TYR | C | 291 | 39.067 | 50.068 | 89.313 | 1.00 | 48.31 C |

-continued

| | | | | | | | | | | |
|---|---|---|---|---|---|---|---|---|---|---|
| ATOM | 15613 | O | TYR | C | 291 | 38.974 | 48.891 | 88.970 | 1.00 | 46.37 O |
| ATOM | 15615 | N | ALA | C | 292 | 38.142 | 50.991 | 89.039 | 1.00 | 47.83 N |
| ATOM | 15616 | CA | ALA | C | 292 | 36.881 | 50.663 | 88.368 | 1.00 | 47.22 C |
| ATOM | 15618 | CB | ALA | C | 292 | 35.852 | 51.766 | 88.573 | 1.00 | 47.73 C |
| ATOM | 15622 | C | ALA | C | 292 | 37.133 | 50.459 | 86.897 | 1.00 | 45.67 C |
| ATOM | 15623 | O | ALA | C | 292 | 37.833 | 51.244 | 86.280 | 1.00 | 48.25 O |
| ATOM | 15625 | N | GLY | C | 293 | 36.550 | 49.408 | 86.337 | 1.00 | 45.01 N |
| ATOM | 15626 | CA | GLY | C | 293 | 36.777 | 49.063 | 84.943 | 1.00 | 45.06 C |
| ATOM | 15629 | C | GLY | C | 293 | 36.457 | 47.617 | 84.628 | 1.00 | 43.41 C |
| ATOM | 15630 | O | GLY | C | 293 | 35.526 | 47.044 | 85.188 | 1.00 | 44.31 O |
| ATOM | 15632 | N | SER | C | 294 | 37.231 | 47.031 | 83.724 | 1.00 | 43.46 N |
| ATOM | 15633 | CA | SER | C | 294 | 36.982 | 45.670 | 83.282 | 1.00 | 45.43 C |
| ATOM | 15635 | CB | SER | C | 294 | 36.201 | 45.666 | 81.982 | 1.00 | 44.75 C |
| ATOM | 15638 | OG | SER | C | 294 | 35.833 | 44.339 | 81.659 | 1.00 | 45.27 O |
| ATOM | 15640 | C | SER | C | 294 | 38.262 | 44.887 | 83.067 | 1.00 | 45.48 C |
| ATOM | 15641 | O | SER | C | 294 | 39.237 | 45.404 | 82.518 | 1.00 | 43.96 O |
| ATOM | 15643 | N | GLY | C | 295 | 38.235 | 43.626 | 83.479 | 1.00 | 47.01 N |
| ATOM | 15644 | CA | GLY | C | 295 | 39.391 | 42.760 | 83.350 | 1.00 | 49.10 C |
| ATOM | 15647 | C | GLY | C | 295 | 39.055 | 41.414 | 82.769 | 1.00 | 49.83 C |
| ATOM | 15648 | O | GLY | C | 295 | 37.922 | 41.158 | 82.367 | 1.00 | 50.35 O |
| ATOM | 15650 | N | ASN | C | 296 | 40.066 | 40.558 | 82.716 | 1.00 | 52.72 N |
| ATOM | 15651 | CA | ASN | C | 296 | 39.915 | 39.184 | 82.250 | 1.00 | 54.40 C |
| ATOM | 15653 | CB | ASN | C | 296 | 40.311 | 39.046 | 80.761 | 1.00 | 55.45 C |
| ATOM | 15656 | CG | ASN | C | 296 | 39.126 | 39.164 | 79.808 | 1.00 | 60.32 C |
| ATOM | 15657 | OD1 | ASN | C | 296 | 37.970 | 39.045 | 80.220 | 1.00 | 69.70 O |
| ATOM | 15658 | ND2 | ASN | C | 296 | 39.413 | 39.388 | 78.519 | 1.00 | 56.58 N |
| ATOM | 15661 | C | ASN | C | 296 | 40.820 | 38.299 | 83.077 | 1.00 | 54.20 C |
| ATOM | 15662 | O | ASN | C | 296 | 42.043 | 38.426 | 83.003 | 1.00 | 54.47 O |
| ATOM | 15664 | N | LEU | C | 297 | 40.226 | 37.419 | 83.873 | 1.00 | 54.66 N |
| ATOM | 15665 | CA | LEU | C | 297 | 40.972 | 36.321 | 84.474 | 1.00 | 54.56 C |
| ATOM | 15667 | CB | LEU | C | 297 | 40.152 | 35.637 | 85.564 | 1.00 | 53.85 C |
| ATOM | 15670 | CG | LEU | C | 297 | 41.010 | 34.824 | 86.531 | 1.00 | 54.84 C |
| ATOM | 15672 | CD1 | LEU | C | 297 | 41.612 | 35.742 | 87.598 | 1.00 | 55.62 C |
| ATOM | 15676 | CD2 | LEU | C | 297 | 40.222 | 33.704 | 87.181 | 1.00 | 56.64 C |
| ATOM | 15680 | C | LEU | C | 297 | 41.253 | 35.334 | 83.353 | 1.00 | 54.66 C |
| ATOM | 15681 | O | LEU | C | 297 | 40.333 | 34.948 | 82.648 | 1.00 | 56.15 O |
| ATOM | 15683 | N | THR | C | 298 | 42.509 | 34.944 | 83.166 | 1.00 | 53.50 N |
| ATOM | 15684 | CA | THR | C | 298 | 42.867 | 34.024 | 82.086 | 1.00 | 52.46 C |
| ATOM | 15686 | CB | THR | C | 298 | 43.818 | 34.682 | 81.056 | 1.00 | 52.13 C |
| ATOM | 15688 | OG1 | THR | C | 298 | 44.623 | 35.673 | 81.703 | 1.00 | 58.09 O |
| ATOM | 15690 | CG2 | THR | C | 298 | 43.037 | 35.353 | 79.958 | 1.00 | 51.47 C |
| ATOM | 15694 | C | THR | C | 298 | 43.555 | 32.834 | 82.689 | 1.00 | 50.44 C |
| ATOM | 15695 | O | THR | C | 298 | 44.479 | 33.016 | 83.453 | 1.00 | 49.47 O |
| ATOM | 15697 | N | LEU | C | 299 | 43.112 | 31.624 | 82.345 | 1.00 | 51.46 N |
| ATOM | 15698 | CA | LEU | C | 299 | 43.686 | 30.385 | 82.911 | 1.00 | 52.21 C |
| ATOM | 15700 | CB | LEU | C | 299 | 42.630 | 29.640 | 83.740 | 1.00 | 51.12 C |
| ATOM | 15703 | CG | LEU | C | 299 | 43.014 | 28.884 | 85.016 | 1.00 | 51.18 C |
| ATOM | 15705 | CD1 | LEU | C | 299 | 42.167 | 27.628 | 85.149 | 1.00 | 52.26 C |
| ATOM | 15709 | CD2 | LEU | C | 299 | 44.471 | 28.518 | 85.085 | 1.00 | 54.18 C |
| ATOM | 15713 | C | LEU | C | 299 | 44.183 | 29.443 | 81.820 | 1.00 | 52.74 C |
| ATOM | 15714 | O | LEU | C | 299 | 43.394 | 28.986 | 80.987 | 1.00 | 56.41 O |
| ATOM | 15716 | N | ALA | C | 300 | 45.477 | 29.138 | 81.821 | 1.00 | 50.94 N |
| ATOM | 15717 | CA | ALA | C | 300 | 46.000 | 28.075 | 80.959 | 1.00 | 50.98 C |
| ATOM | 15719 | CB | ALA | C | 300 | 47.303 | 28.479 | 80.326 | 1.00 | 49.38 C |
| ATOM | 15723 | C | ALA | C | 300 | 46.171 | 26.792 | 81.761 | 1.00 | 49.99 C |
| ATOM | 15724 | O | ALA | C | 300 | 46.526 | 26.826 | 82.931 | 1.00 | 48.15 O |
| ATOM | 15726 | N | LEU | C | 301 | 45.915 | 25.661 | 81.119 | 1.00 | 52.33 N |
| ATOM | 15727 | CA | LEU | C | 301 | 46.000 | 24.363 | 81.777 | 1.00 | 52.08 C |
| ATOM | 15729 | CB | LEU | C | 301 | 44.660 | 23.672 | 81.642 | 1.00 | 51.48 C |
| ATOM | 15732 | CG | LEU | C | 301 | 43.514 | 24.413 | 82.338 | 1.00 | 53.12 C |
| ATOM | 15734 | CD1 | LEU | C | 301 | 42.183 | 23.764 | 81.989 | 1.00 | 55.00 C |
| ATOM | 15738 | CD2 | LEU | C | 301 | 43.704 | 24.452 | 83.855 | 1.00 | 54.54 C |
| ATOM | 15742 | C | LEU | C | 301 | 47.130 | 23.489 | 81.214 | 1.00 | 52.91 C |
| ATOM | 15743 | O | LEU | C | 301 | 47.392 | 23.499 | 80.006 | 1.00 | 53.94 O |
| ATOM | 15745 | N | GLU | C | 302 | 47.813 | 22.756 | 82.100 | 1.00 | 52.53 N |
| ATOM | 15746 | CA | GLU | C | 302 | 48.928 | 21.876 | 81.701 | 1.00 | 51.61 C |
| ATOM | 15748 | CB | GLU | C | 302 | 49.450 | 21.067 | 82.895 | 1.00 | 49.30 C |
| ATOM | 15751 | CG | GLU | C | 302 | 50.804 | 20.385 | 82.667 | 1.00 | 53.13 C |
| ATOM | 15754 | CD | GLU | C | 302 | 51.221 | 19.463 | 83.823 | 1.00 | 53.07 C |
| ATOM | 15755 | OE1 | GLU | C | 302 | 52.254 | 19.727 | 84.471 | 1.00 | 48.58 O |
| ATOM | 15756 | OE2 | GLU | C | 302 | 50.509 | 18.473 | 84.086 | 1.00 | 57.14 O |
| ATOM | 15757 | C | GLU | C | 302 | 48.503 | 20.930 | 80.566 | 1.00 | 51.69 C |
| ATOM | 15758 | O | GLU | C | 302 | 47.457 | 20.281 | 80.635 | 1.00 | 51.41 O |
| ATOM | 15760 | N | ALA | C | 303 | 49.301 | 20.899 | 79.504 | 1.00 | 51.40 N |
| ATOM | 15761 | CA | ALA | C | 303 | 49.089 | 19.992 | 78.386 | 1.00 | 51.60 C |
| ATOM | 15763 | CB | ALA | C | 303 | 49.238 | 18.545 | 78.849 | 1.00 | 49.45 C |
| ATOM | 15767 | C | ALA | C | 303 | 47.749 | 20.197 | 77.677 | 1.00 | 53.60 C |
| ATOM | 15768 | O | ALA | C | 303 | 47.310 | 19.324 | 76.935 | 1.00 | 55.31 O |
| ATOM | 15770 | N | LYS | C | 304 | 47.094 | 21.334 | 77.898 | 1.00 | 54.59 N |

-continued

| | | | | | | | | | | |
|---|---|---|---|---|---|---|---|---|---|---|
| ATOM | 15771 | CA | LYS | C | 304 | 45.888 | 21.676 | 77.150 | 1.00 | 54.23 C |
| ATOM | 15773 | CB | LYS | C | 304 | 44.696 | 21.969 | 78.062 | 1.00 | 55.42 C |
| ATOM | 15776 | CG | LYS | C | 304 | 44.341 | 20.880 | 79.069 | 1.00 | 58.77 C |
| ATOM | 15779 | CD | LYS | C | 304 | 44.177 | 19.500 | 78.445 | 1.00 | 65.40 C |
| ATOM | 15782 | CE | LYS | C | 304 | 43.549 | 18.512 | 79.432 | 1.00 | 68.77 C |
| ATOM | 15785 | NZ | LYS | C | 304 | 44.119 | 18.611 | 80.811 | 1.00 | 75.82 N |
| ATOM | 15789 | C | LYS | C | 304 | 46.203 | 22.909 | 76.341 | 1.00 | 54.72 C |
| ATOM | 15790 | O | LYS | C | 304 | 46.881 | 23.817 | 76.808 | 1.00 | 55.64 O |
| ATOM | 15792 | N | THR | C | 305 | 45.699 | 22.932 | 75.122 | 1.00 | 56.26 N |
| ATOM | 15793 | CA | THR | C | 305 | 45.961 | 24.010 | 74.197 | 1.00 | 56.85 C |
| ATOM | 15795 | CB | THR | C | 305 | 46.020 | 23.434 | 72.747 | 1.00 | 57.67 C |
| ATOM | 15797 | OG1 | THR | C | 305 | 46.833 | 24.270 | 71.905 | 1.00 | 62.10 O |
| ATOM | 15799 | CG2 | THR | C | 305 | 44.623 | 23.253 | 72.144 | 1.00 | 56.44 C |
| ATOM | 15803 | C | THR | C | 305 | 44.868 | 25.072 | 74.415 | 1.00 | 58.13 C |
| ATOM | 15804 | O | THR | C | 305 | 43.740 | 24.733 | 74.788 | 1.00 | 61.03 O |
| ATOM | 15806 | N | GLY | C | 306 | 45.210 | 26.346 | 74.225 | 1.00 | 57.84 N |
| ATOM | 15807 | CA | GLY | C | 306 | 44.277 | 27.454 | 74.484 | 1.00 | 56.97 C |
| ATOM | 15810 | C | GLY | C | 306 | 44.309 | 27.975 | 75.919 | 1.00 | 57.05 C |
| ATOM | 15811 | O | GLY | C | 306 | 45.099 | 27.515 | 76.750 | 1.00 | 58.91 O |
| ATOM | 15813 | N | LYS | C | 307 | 43.449 | 28.950 | 76.204 | 1.00 | 55.87 N |
| ATOM | 15814 | CA | LYS | C | 307 | 43.263 | 29.479 | 77.559 | 1.00 | 55.32 C |
| ATOM | 15816 | CB | LYS | C | 307 | 43.977 | 30.833 | 77.712 | 1.00 | 54.88 C |
| ATOM | 15819 | CG | LYS | C | 307 | 45.503 | 30.764 | 77.759 | 1.00 | 55.79 C |
| ATOM | 15822 | CD | LYS | C | 307 | 46.178 | 31.828 | 76.862 | 1.00 | 55.83 C |
| ATOM | 15825 | CE | LYS | C | 307 | 46.583 | 33.078 | 77.612 | 1.00 | 53.46 C |
| ATOM | 15828 | NZ | LYS | C | 307 | 47.798 | 32.841 | 78.423 | 1.00 | 46.54 N |
| ATOM | 15832 | C | LYS | C | 307 | 41.772 | 29.664 | 77.863 | 1.00 | 54.09 C |
| ATOM | 15833 | O | LYS | C | 307 | 41.002 | 30.086 | 77.007 | 1.00 | 52.18 O |
| ATOM | 15835 | N | LEU | C | 308 | 41.374 | 29.360 | 79.092 | 1.00 | 55.57 N |
| ATOM | 15836 | CA | LEU | C | 308 | 40.048 | 29.748 | 79.594 | 1.00 | 54.38 C |
| ATOM | 15838 | CB | LEU | C | 308 | 39.630 | 28.873 | 80.766 | 1.00 | 51.97 C |
| ATOM | 15841 | CG | LEU | C | 308 | 39.722 | 27.373 | 80.526 | 1.00 | 52.51 C |
| ATOM | 15843 | CD1 | LEU | C | 308 | 39.420 | 26.638 | 81.805 | 1.00 | 51.52 C |
| ATOM | 15847 | CD2 | LEU | C | 308 | 38.771 | 26.979 | 79.413 | 1.00 | 53.45 C |
| ATOM | 15851 | C | LEU | C | 308 | 40.112 | 31.194 | 80.070 | 1.00 | 54.94 C |
| ATOM | 15852 | O | LEU | C | 308 | 41.188 | 31.696 | 80.411 | 1.00 | 53.89 O |
| ATOM | 15854 | N | HIS | C | 309 | 38.963 | 31.857 | 80.104 | 1.00 | 54.30 N |
| ATOM | 15855 | CA | HIS | C | 309 | 38.892 | 33.193 | 80.667 | 1.00 | 54.34 C |
| ATOM | 15857 | CB | HIS | C | 309 | 39.417 | 34.219 | 79.675 | 1.00 | 54.86 C |
| ATOM | 15860 | CG | HIS | C | 309 | 38.779 | 34.123 | 78.337 | 1.00 | 56.38 C |
| ATOM | 15861 | ND1 | HIS | C | 309 | 37.620 | 34.795 | 78.021 | 1.00 | 61.79 N |
| ATOM | 15863 | CE1 | HIS | C | 309 | 37.276 | 34.512 | 76.777 | 1.00 | 62.46 C |
| ATOM | 15865 | NE2 | HIS | C | 309 | 38.170 | 33.676 | 76.278 | 1.00 | 65.05 N |
| ATOM | 15867 | CD2 | HIS | C | 309 | 39.120 | 33.414 | 77.237 | 1.00 | 61.15 C |
| ATOM | 15869 | C | HIS | C | 309 | 37.488 | 33.566 | 81.112 | 1.00 | 54.11 C |
| ATOM | 15870 | O | HIS | C | 309 | 36.505 | 32.971 | 80.680 | 1.00 | 55.91 O |
| ATOM | 15872 | N | GLN | C | 310 | 37.422 | 34.550 | 82.002 | 1.00 | 53.63 N |
| ATOM | 15873 | CA | GLN | C | 310 | 36.171 | 35.055 | 82.549 | 1.00 | 53.49 C |
| ATOM | 15875 | CB | GLN | C | 310 | 35.883 | 34.435 | 83.921 | 1.00 | 51.89 C |
| ATOM | 15878 | CG | GLN | C | 310 | 34.777 | 35.146 | 84.698 | 1.00 | 53.15 C |
| ATOM | 15881 | CD | GLN | C | 310 | 34.332 | 34.402 | 85.939 | 1.00 | 54.86 C |
| ATOM | 15882 | OE1 | GLN | C | 310 | 34.822 | 33.311 | 86.248 | 1.00 | 62.77 O |
| ATOM | 15883 | NE2 | GLN | C | 310 | 33.391 | 34.992 | 86.662 | 1.00 | 51.39 N |
| ATOM | 15886 | C | GLN | C | 310 | 36.329 | 36.546 | 82.688 | 1.00 | 53.43 C |
| ATOM | 15887 | O | GLN | C | 310 | 37.351 | 36.994 | 83.202 | 1.00 | 57.46 O |
| ATOM | 15889 | N | GLU | C | 311 | 35.340 | 37.317 | 82.243 | 1.00 | 52.22 N |
| ATOM | 15890 | CA | GLU | C | 311 | 35.429 | 38.761 | 82.361 | 1.00 | 53.58 C |
| ATOM | 15892 | CB | GLU | C | 311 | 34.816 | 39.467 | 81.147 | 1.00 | 54.22 C |
| ATOM | 15895 | CG | GLU | C | 311 | 33.398 | 40.014 | 81.329 | 1.00 | 59.50 C |
| ATOM | 15898 | CD | GLU | C | 311 | 33.042 | 41.104 | 80.318 | 1.00 | 58.01 C |
| ATOM | 15899 | OE1 | GLU | C | 311 | 33.860 | 41.389 | 79.413 | 1.00 | 57.32 O |
| ATOM | 15900 | OE2 | GLU | C | 311 | 31.933 | 41.675 | 80.434 | 1.00 | 62.91 O |
| ATOM | 15901 | C | GLU | C | 311 | 34.846 | 39.250 | 83.699 | 1.00 | 53.73 C |
| ATOM | 15902 | O | GLU | C | 311 | 33.908 | 38.661 | 84.252 | 1.00 | 53.70 O |
| ATOM | 15904 | N | VAL | C | 312 | 35.444 | 40.323 | 84.215 | 1.00 | 53.28 N |
| ATOM | 15905 | CA | VAL | C | 312 | 35.098 | 40.873 | 85.517 | 1.00 | 52.30 C |
| ATOM | 15907 | CB | VAL | C | 312 | 36.175 | 40.622 | 86.598 | 1.00 | 53.43 C |
| ATOM | 15909 | CG1 | VAL | C | 312 | 35.628 | 39.717 | 87.701 | 1.00 | 57.05 C |
| ATOM | 15913 | CG2 | VAL | C | 312 | 37.450 | 40.058 | 85.992 | 1.00 | 56.18 C |
| ATOM | 15917 | C | VAL | C | 312 | 34.939 | 42.357 | 85.395 | 1.00 | 51.99 C |
| ATOM | 15918 | O | VAL | C | 312 | 35.651 | 43.001 | 84.624 | 1.00 | 51.64 O |
| ATOM | 15920 | N | ASN | C | 313 | 34.017 | 42.892 | 86.191 | 1.00 | 51.65 N |
| ATOM | 15921 | CA | ASN | C | 313 | 33.638 | 44.286 | 86.119 | 1.00 | 49.32 C |
| ATOM | 15923 | CB | ASN | C | 313 | 32.438 | 44.426 | 85.196 | 1.00 | 48.44 C |
| ATOM | 15926 | CG | ASN | C | 313 | 32.815 | 44.221 | 83.759 | 1.00 | 45.89 C |
| ATOM | 15927 | OD1 | ASN | C | 313 | 32.339 | 43.308 | 83.095 | 1.00 | 38.92 O |
| ATOM | 15928 | ND2 | ASN | C | 313 | 33.724 | 45.049 | 83.281 | 1.00 | 51.95 N |
| ATOM | 15931 | C | ASN | C | 313 | 33.344 | 44.875 | 87.483 | 1.00 | 48.98 C |
| ATOM | 15932 | O | ASN | C | 313 | 32.650 | 44.265 | 88.303 | 1.00 | 46.07 O |

-continued

| ATOM | 15934 | N | LEU | C | 314 | 33.889 | 46.070 | 87.709 | 1.00 | 48.99 | N |
|------|-------|------|-----|---|-----|--------|--------|--------|------|-------|---|
| ATOM | 15935 | CA | LEU | C | 314 | 33.756 | 46.762 | 88.980 | 1.00 | 47.98 | C |
| ATOM | 15937 | CB | LEU | C | 314 | 35.114 | 46.840 | 89.677 | 1.00 | 48.55 | C |
| ATOM | 15940 | CG | LEU | C | 314 | 35.188 | 46.913 | 91.208 | 1.00 | 48.14 | C |
| ATOM | 15942 | CD1 | LEU | C | 314 | 33.922 | 47.434 | 91.875 | 1.00 | 49.00 | C |
| ATOM | 15946 | CD2 | LEU | C | 314 | 36.402 | 47.749 | 91.612 | 1.00 | 46.00 | C |
| ATOM | 15950 | C | LEU | C | 314 | 33.246 | 48.156 | 88.705 | 1.00 | 46.12 | C |
| ATOM | 15951 | O | LEU | C | 314 | 33.892 | 48.914 | 87.986 | 1.00 | 44.60 | O |
| ATOM | 15953 | N | VAL | C | 315 | 32.084 | 48.476 | 89.268 | 1.00 | 46.55 | N |
| ATOM | 15954 | CA | VAL | C | 315 | 31.492 | 49.810 | 89.165 | 1.00 | 48.31 | C |
| ATOM | 15956 | CB | VAL | C | 315 | 30.033 | 49.743 | 88.660 | 1.00 | 48.87 | C |
| ATOM | 15958 | CG1 | VAL | C | 315 | 29.352 | 51.142 | 88.711 | 1.00 | 48.61 | C |
| ATOM | 15962 | CG2 | VAL | C | 315 | 29.979 | 49.150 | 87.257 | 1.00 | 46.96 | C |
| ATOM | 15966 | C | VAL | C | 315 | 31.492 | 50.423 | 90.550 | 1.00 | 48.60 | C |
| ATOM | 15967 | O | VAL | C | 315 | 31.057 | 49.773 | 91.494 | 1.00 | 48.35 | O |
| ATOM | 15969 | N | VAL | C | 316 | 31.978 | 51.658 | 90.684 | 1.00 | 50.12 | N |
| ATOM | 15970 | CA | VAL | C | 316 | 31.987 | 52.322 | 91.996 | 1.00 | 51.50 | C |
| ATOM | 15972 | CB | VAL | C | 316 | 33.420 | 52.384 | 92.641 | 1.00 | 50.80 | C |
| ATOM | 15974 | CG1 | VAL | C | 316 | 34.016 | 53.791 | 92.611 | 1.00 | 51.53 | C |
| ATOM | 15978 | CG2 | VAL | C | 316 | 34.362 | 51.365 | 91.993 | 1.00 | 48.64 | C |
| ATOM | 15982 | C | VAL | C | 316 | 31.301 | 53.696 | 91.965 | 1.00 | 53.36 | C |
| ATOM | 15983 | O | VAL | C | 316 | 31.335 | 54.408 | 90.955 | 1.00 | 52.62 | O |
| ATOM | 15985 | N | MET | C | 317 | 30.678 | 54.043 | 93.092 | 1.00 | 55.34 | N |
| ATOM | 15986 | CA | MET | C | 317 | 29.909 | 55.271 | 93.242 | 1.00 | 55.75 | C |
| ATOM | 15988 | CB | MET | C | 317 | 28.457 | 54.914 | 93.573 | 1.00 | 55.48 | C |
| ATOM | 15991 | CG | MET | C | 317 | 27.571 | 56.095 | 93.955 | 1.00 | 56.94 | C |
| ATOM | 15994 | SD | MET | C | 317 | 25.975 | 55.578 | 94.619 | 1.00 | 59.40 | S |
| ATOM | 15995 | CE | MET | C | 317 | 25.119 | 55.060 | 93.131 | 1.00 | 58.37 | C |
| ATOM | 15999 | C | MET | C | 317 | 30.514 | 56.104 | 94.365 | 1.00 | 56.25 | C |
| ATOM | 16000 | O | MET | C | 317 | 30.941 | 55.552 | 95.378 | 1.00 | 56.82 | O |
| ATOM | 16002 | N | ARG | C | 318 | 30.555 | 57.425 | 94.171 | 1.00 | 57.90 | N |
| ATOM | 16003 | CA | ARG | C | 318 | 30.971 | 58.400 | 95.207 | 1.00 | 57.97 | C |
| ATOM | 16005 | CB | ARG | C | 318 | 32.270 | 59.107 | 94.775 | 1.00 | 57.36 | C |
| ATOM | 16008 | CG | ARG | C | 318 | 32.761 | 60.231 | 95.695 | 1.00 | 58.75 | C |
| ATOM | 16011 | CD | ARG | C | 318 | 33.948 | 60.981 | 95.107 | 1.00 | 60.71 | C |
| ATOM | 16014 | NE | ARG | C | 318 | 35.186 | 60.207 | 95.163 | 1.00 | 63.93 | N |
| ATOM | 16016 | CZ | ARG | C | 318 | 36.370 | 60.640 | 94.729 | 1.00 | 65.87 | C |
| ATOM | 16017 | NH1 | ARG | C | 318 | 36.503 | 61.846 | 94.182 | 1.00 | 67.21 | N |
| ATOM | 16020 | NH2 | ARG | C | 318 | 37.433 | 59.850 | 94.833 | 1.00 | 66.87 | N |
| ATOM | 16023 | C | ARG | C | 318 | 29.824 | 59.409 | 95.401 | 1.00 | 57.93 | C |
| ATOM | 16024 | O | ARG | C | 318 | 28.942 | 59.500 | 94.542 | 1.00 | 59.39 | O |
| ATOM | 16026 | N | ALA | C | 319 | 29.811 | 60.148 | 96.513 | 1.00 | 56.94 | N |
| ATOM | 16027 | CA | ALA | C | 319 | 28.779 | 61.175 | 96.717 | 1.00 | 56.32 | C |
| ATOM | 16029 | CB | ALA | C | 319 | 27.472 | 60.512 | 97.139 | 1.00 | 55.67 | C |
| ATOM | 16033 | C | ALA | C | 319 | 29.149 | 62.293 | 97.712 | 1.00 | 56.15 | C |
| ATOM | 16034 | O | ALA | C | 319 | 29.554 | 62.022 | 98.843 | 1.00 | 54.59 | O |
| ATOM | 16036 | N | THR | C | 320 | 29.015 | 63.543 | 97.256 | 1.00 | 56.55 | N |
| ATOM | 16037 | CA | THR | C | 320 | 28.993 | 64.741 | 98.111 | 1.00 | 56.45 | C |
| ATOM | 16039 | CB | THR | C | 320 | 30.386 | 65.083 | 98.735 | 1.00 | 57.04 | C |
| ATOM | 16041 | OG1 | THR | C | 320 | 30.835 | 64.004 | 99.564 | 1.00 | 55.35 | O |
| ATOM | 16043 | CG2 | THR | C | 320 | 30.328 | 66.378 | 99.589 | 1.00 | 56.22 | C |
| ATOM | 16047 | C | THR | C | 320 | 28.498 | 65.922 | 97.261 | 1.00 | 57.29 | C |
| ATOM | 16048 | O | THR | C | 320 | 27.834 | 66.842 | 97.751 | 1.00 | 58.33 | O |
| ATOM | 16050 | N | VAL | C | 330 | 29.705 | 58.049 | 89.659 | 1.00 | 55.06 | N |
| ATOM | 16051 | CA | VAL | C | 330 | 29.701 | 56.652 | 89.240 | 1.00 | 56.85 | C |
| ATOM | 16053 | CB | VAL | C | 330 | 28.305 | 56.237 | 88.691 | 1.00 | 56.62 | C |
| ATOM | 16055 | CG1 | VAL | C | 330 | 28.388 | 55.089 | 87.689 | 1.00 | 55.47 | C |
| ATOM | 16059 | CG2 | VAL | C | 330 | 27.390 | 55.852 | 89.841 | 1.00 | 56.71 | C |
| ATOM | 16063 | C | VAL | C | 330 | 30.804 | 56.391 | 88.208 | 1.00 | 57.90 | C |
| ATOM | 16064 | O | VAL | C | 330 | 30.755 | 56.915 | 87.091 | 1.00 | 59.13 | O |
| ATOM | 16066 | N | TRP | C | 331 | 31.788 | 55.578 | 88.598 | 1.00 | 57.92 | N |
| ATOM | 16067 | CA | TRP | C | 331 | 32.913 | 55.208 | 87.731 | 1.00 | 57.68 | C |
| ATOM | 16069 | CB | TRP | C | 331 | 34.254 | 55.418 | 88.452 | 1.00 | 58.00 | C |
| ATOM | 16072 | CG | TRP | C | 331 | 34.369 | 56.735 | 89.167 | 1.00 | 58.37 | C |
| ATOM | 16073 | CD1 | TRP | C | 331 | 33.790 | 57.076 | 90.359 | 1.00 | 59.27 | C |
| ATOM | 16075 | NE1 | TRP | C | 331 | 34.120 | 58.364 | 90.698 | 1.00 | 58.13 | N |
| ATOM | 16077 | CE2 | TRP | C | 331 | 34.930 | 58.883 | 89.725 | 1.00 | 58.30 | C |
| ATOM | 16078 | CD2 | TRP | C | 331 | 35.112 | 57.879 | 88.744 | 1.00 | 57.76 | C |
| ATOM | 16079 | CE3 | TRP | C | 331 | 35.910 | 58.159 | 87.631 | 1.00 | 59.16 | C |
| ATOM | 16081 | CZ3 | TRP | C | 331 | 36.496 | 59.423 | 87.531 | 1.00 | 59.85 | C |
| ATOM | 16083 | CH2 | TRP | C | 331 | 36.295 | 60.398 | 88.526 | 1.00 | 59.38 | C |
| ATOM | 16085 | CZ2 | TRP | C | 331 | 35.518 | 60.147 | 89.625 | 1.00 | 59.26 | C |
| ATOM | 16087 | C | TRP | C | 331 | 32.768 | 53.742 | 87.329 | 1.00 | 57.31 | C |
| ATOM | 16088 | O | TRP | C | 331 | 32.085 | 52.978 | 88.005 | 1.00 | 56.27 | O |
| ATOM | 16090 | N | GLY | C | 332 | 33.416 | 53.357 | 86.233 | 1.00 | 57.45 | N |
| ATOM | 16091 | CA | GLY | C | 332 | 33.375 | 51.975 | 85.751 | 1.00 | 57.64 | C |
| ATOM | 16094 | C | GLY | C | 332 | 32.506 | 51.791 | 84.518 | 1.00 | 57.59 | C |
| ATOM | 16095 | O | GLY | C | 332 | 31.910 | 52.752 | 84.025 | 1.00 | 57.31 | O |
| ATOM | 16097 | N | PRO | C | 333 | 32.414 | 50.545 | 84.018 | 1.00 | 58.46 | N |

-continued

| ATOM | 16098 | CA | PRO | C | 333 | 31.732 | 50.235 | 82.768 | 1.00 | 59.07 | C |
| ATOM | 16100 | CB | PRO | C | 333 | 32.371 | 48.904 | 82.358 | 1.00 | 59.60 | C |
| ATOM | 16103 | CG | PRO | C | 333 | 32.650 | 48.223 | 83.648 | 1.00 | 59.05 | C |
| ATOM | 16106 | CD | PRO | C | 333 | 32.967 | 49.328 | 84.645 | 1.00 | 59.59 | C |
| ATOM | 16109 | C | PRO | C | 333 | 30.225 | 50.084 | 82.942 | 1.00 | 59.62 | C |
| ATOM | 16110 | O | PRO | C | 333 | 29.701 | 48.973 | 82.883 | 1.00 | 60.90 | O |
| ATOM | 16111 | N | THR | C | 334 | 29.541 | 51.201 | 83.166 | 1.00 | 60.47 | N |
| ATOM | 16112 | CA | THR | C | 334 | 28.085 | 51.216 | 83.248 | 1.00 | 60.23 | C |
| ATOM | 16114 | CB | THR | C | 334 | 27.570 | 52.473 | 83.979 | 1.00 | 59.50 | C |
| ATOM | 16116 | OG1 | THR | C | 334 | 28.134 | 53.648 | 83.377 | 1.00 | 59.67 | O |
| ATOM | 16118 | CG2 | THR | C | 334 | 27.935 | 52.432 | 85.446 | 1.00 | 59.63 | C |
| ATOM | 16122 | C | THR | C | 334 | 27.488 | 51.245 | 81.856 | 1.00 | 60.60 | C |
| ATOM | 16123 | O | THR | C | 334 | 28.079 | 51.811 | 80.939 | 1.00 | 59.82 | O |
| ATOM | 16125 | N | SER | C | 335 | 26.317 | 50.634 | 81.707 | 1.00 | 62.05 | N |
| ATOM | 16126 | CA | SER | C | 335 | 25.449 | 50.904 | 80.565 | 1.00 | 63.29 | C |
| ATOM | 16128 | CB | SER | C | 335 | 24.318 | 49.883 | 80.516 | 1.00 | 63.64 | C |
| ATOM | 16131 | OG | SER | C | 335 | 23.435 | 50.161 | 79.450 | 1.00 | 65.85 | O |
| ATOM | 16133 | C | SER | C | 335 | 24.893 | 52.339 | 80.711 | 1.00 | 64.34 | C |
| ATOM | 16134 | O | SER | C | 335 | 24.634 | 52.793 | 81.831 | 1.00 | 63.83 | O |
| ATOM | 16136 | N | PRO | C | 336 | 24.720 | 53.063 | 79.590 | 1.00 | 64.64 | N |
| ATOM | 16137 | CA | PRO | C | 336 | 24.385 | 54.496 | 79.689 | 1.00 | 64.48 | C |
| ATOM | 16139 | CB | PRO | C | 336 | 24.532 | 54.987 | 78.239 | 1.00 | 64.30 | C |
| ATOM | 16142 | CG | PRO | C | 336 | 24.291 | 53.782 | 77.409 | 1.00 | 65.37 | C |
| ATOM | 16145 | CD | PRO | C | 336 | 24.838 | 52.621 | 78.187 | 1.00 | 64.06 | C |
| ATOM | 16148 | C | PRO | C | 336 | 22.981 | 54.821 | 80.249 | 1.00 | 65.44 | C |
| ATOM | 16149 | O | PRO | C | 336 | 22.066 | 55.133 | 79.479 | 1.00 | 66.87 | O |
| ATOM | 16150 | N | LYS | C | 337 | 22.831 | 54.758 | 81.579 | 1.00 | 64.56 | N |
| ATOM | 16151 | CA | LYS | C | 337 | 21.564 | 55.093 | 82.266 | 1.00 | 62.95 | C |
| ATOM | 16153 | CB | LYS | C | 337 | 20.710 | 53.834 | 82.472 | 1.00 | 62.05 | C |
| ATOM | 16156 | CG | LYS | C | 337 | 20.170 | 53.233 | 81.178 | 1.00 | 62.02 | C |
| ATOM | 16159 | CD | LYS | C | 337 | 21.107 | 52.176 | 80.566 | 1.00 | 61.81 | C |
| ATOM | 16162 | CE | LYS | C | 337 | 21.019 | 52.134 | 79.034 | 1.00 | 60.44 | C |
| ATOM | 16165 | NZ | LYS | C | 337 | 19.635 | 52.350 | 78.526 | 1.00 | 59.46 | N |
| ATOM | 16169 | C | LYS | C | 337 | 21.810 | 55.788 | 83.615 | 1.00 | 61.03 | C |
| ATOM | 16170 | O | LYS | C | 337 | 20.879 | 56.051 | 84.383 | 1.00 | 58.00 | O |
| ATOM | 16172 | N | ARG | C | 354 | 20.546 | 61.328 | 83.040 | 1.00 | 55.99 | N |
| ATOM | 16173 | CA | ARG | C | 354 | 20.589 | 59.985 | 82.461 | 1.00 | 56.57 | C |
| ATOM | 16175 | CB | ARG | C | 354 | 19.567 | 59.876 | 81.322 | 1.00 | 57.24 | C |
| ATOM | 16178 | CG | ARG | C | 354 | 19.072 | 58.458 | 81.004 | 1.00 | 56.58 | C |
| ATOM | 16181 | CD | ARG | C | 354 | 18.319 | 58.462 | 79.677 | 1.00 | 57.64 | C |
| ATOM | 16184 | NE | ARG | C | 354 | 17.457 | 57.294 | 79.483 | 1.00 | 59.21 | N |
| ATOM | 16186 | CZ | ARG | C | 354 | 17.869 | 56.084 | 79.098 | 1.00 | 62.12 | C |
| ATOM | 16187 | NH1 | ARG | C | 354 | 19.160 | 55.835 | 78.874 | 1.00 | 63.09 | N |
| ATOM | 16190 | NH2 | ARG | C | 354 | 16.980 | 55.105 | 78.944 | 1.00 | 60.23 | N |
| ATOM | 16193 | C | ARG | C | 354 | 21.989 | 59.617 | 81.947 | 1.00 | 56.42 | C |
| ATOM | 16194 | O | ARG | C | 354 | 22.176 | 58.550 | 81.353 | 1.00 | 56.98 | O |
| ATOM | 16196 | N | GLU | C | 355 | 22.963 | 60.496 | 82.181 | 1.00 | 55.97 | N |
| ATOM | 16197 | CA | GLU | C | 355 | 24.348 | 60.265 | 81.743 | 1.00 | 56.10 | C |
| ATOM | 16199 | CB | GLU | C | 355 | 25.094 | 61.595 | 81.495 | 1.00 | 56.26 | C |
| ATOM | 16202 | CG | GLU | C | 355 | 24.971 | 62.665 | 82.594 | 1.00 | 58.07 | C |
| ATOM | 16205 | CD | GLU | C | 355 | 25.775 | 63.924 | 82.291 | 1.00 | 59.24 | C |
| ATOM | 16206 | OE1 | GLU | C | 355 | 26.180 | 64.108 | 81.121 | 1.00 | 63.00 | O |
| ATOM | 16207 | OE2 | GLU | C | 355 | 25.991 | 64.736 | 83.223 | 1.00 | 59.75 | O |
| ATOM | 16208 | C | GLU | C | 355 | 25.066 | 59.333 | 82.739 | 1.00 | 55.60 | C |
| ATOM | 16209 | O | GLU | C | 355 | 24.707 | 58.153 | 82.826 | 1.00 | 56.66 | O |
| ATOM | 16211 | N | LYS | C | 356 | 26.080 | 59.821 | 83.458 | 1.00 | 53.49 | N |
| ATOM | 16212 | CA | LYS | C | 356 | 26.651 | 59.066 | 84.580 | 1.00 | 51.84 | C |
| ATOM | 16214 | CB | LYS | C | 356 | 27.597 | 57.966 | 84.071 | 1.00 | 53.18 | C |
| ATOM | 16217 | CG | LYS | C | 356 | 28.828 | 58.448 | 83.315 | 1.00 | 54.06 | C |
| ATOM | 16220 | CD | LYS | C | 356 | 29.508 | 57.283 | 82.569 | 1.00 | 53.29 | C |
| ATOM | 16223 | CE | LYS | C | 356 | 30.107 | 56.250 | 83.520 | 1.00 | 54.75 | C |
| ATOM | 16226 | NZ | LYS | C | 356 | 30.751 | 55.123 | 82.792 | 1.00 | 55.37 | N |
| ATOM | 16230 | C | LYS | C | 356 | 27.350 | 59.955 | 85.605 | 1.00 | 49.04 | C |
| ATOM | 16231 | O | LYS | C | 356 | 28.331 | 59.548 | 86.225 | 1.00 | 45.89 | O |
| ATOM | 16233 | N | ALA | C | 357 | 26.806 | 61.159 | 85.790 | 1.00 | 48.50 | N |
| ATOM | 16234 | CA | ALA | C | 357 | 27.351 | 62.157 | 86.714 | 1.00 | 46.63 | C |
| ATOM | 16236 | CB | ALA | C | 357 | 28.579 | 62.816 | 86.112 | 1.00 | 45.61 | C |
| ATOM | 16240 | C | ALA | C | 357 | 26.298 | 63.215 | 87.034 | 1.00 | 45.31 | C |
| ATOM | 16241 | O | ALA | C | 357 | 25.644 | 63.728 | 86.128 | 1.00 | 45.63 | O |
| ATOM | 16243 | N | VAL | C | 358 | 26.125 | 63.520 | 88.320 | 1.00 | 44.05 | N |
| ATOM | 16244 | CA | VAL | C | 358 | 25.309 | 64.657 | 88.759 | 1.00 | 42.95 | C |
| ATOM | 16246 | CB | VAL | C | 358 | 23.887 | 64.238 | 89.194 | 1.00 | 41.93 | C |
| ATOM | 16248 | CG1 | VAL | C | 358 | 23.062 | 65.487 | 89.580 | 1.00 | 44.44 | C |
| ATOM | 16252 | CG2 | VAL | C | 358 | 23.187 | 63.431 | 88.093 | 1.00 | 39.41 | C |
| ATOM | 16256 | C | VAL | C | 358 | 25.986 | 65.344 | 89.938 | 1.00 | 41.70 | C |
| ATOM | 16257 | O | VAL | C | 358 | 26.273 | 64.705 | 90.950 | 1.00 | 40.16 | O |
| ATOM | 16259 | N | GLN | C | 369 | 20.802 | 59.693 | 99.692 | 1.00 | 58.70 | N |
| ATOM | 16260 | CA | GLN | C | 369 | 20.248 | 58.830 | 98.652 | 1.00 | 58.80 | C |
| ATOM | 16262 | CB | GLN | C | 369 | 18.712 | 58.912 | 98.650 | 1.00 | 58.56 | C |

-continued

| ATOM | 16265 | CG | GLN | C | 369 | 18.019 | 57.828 | 99.472 | 1.00 | 58.03 | C |
| --- | --- | --- | --- | --- | --- | --- | --- | --- | --- | --- | --- |
| ATOM | 16268 | CD | GLN | C | 369 | 17.886 | 56.511 | 98.719 | 1.00 | 58.02 | C |
| ATOM | 16269 | OE1 | GLN | C | 369 | 16.807 | 55.919 | 98.665 | 1.00 | 56.87 | O |
| ATOM | 16270 | NE2 | GLN | C | 369 | 18.981 | 56.051 | 98.129 | 1.00 | 57.80 | N |
| ATOM | 16273 | C | GLN | C | 369 | 20.805 | 59.160 | 97.260 | 1.00 | 58.81 | C |
| ATOM | 16274 | O | GLN | C | 369 | 20.224 | 59.951 | 96.517 | 1.00 | 58.46 | O |
| ATOM | 16276 | N | CYS | C | 370 | 21.934 | 58.546 | 96.920 | 1.00 | 58.82 | N |
| ATOM | 16277 | CA | CYS | C | 370 | 22.497 | 58.633 | 95.577 | 1.00 | 58.96 | C |
| ATOM | 16279 | CB | CYS | C | 370 | 23.986 | 58.982 | 95.644 | 1.00 | 58.34 | C |
| ATOM | 16282 | SG | CYS | C | 370 | 24.823 | 59.093 | 94.034 | 1.00 | 58.56 | S |
| ATOM | 16284 | C | CYS | C | 370 | 22.299 | 57.266 | 94.940 | 1.00 | 58.95 | C |
| ATOM | 16285 | O | CYS | C | 370 | 22.869 | 56.297 | 95.414 | 1.00 | 59.29 | O |
| ATOM | 16287 | N | LEU | C | 371 | 21.487 | 57.185 | 93.886 | 1.00 | 59.28 | N |
| ATOM | 16288 | CA | LEU | C | 371 | 21.130 | 55.892 | 93.290 | 1.00 | 60.81 | C |
| ATOM | 16290 | CB | LEU | C | 371 | 19.635 | 55.612 | 93.451 | 1.00 | 61.08 | C |
| ATOM | 16293 | CG | LEU | C | 371 | 19.071 | 55.621 | 94.878 | 1.00 | 62.29 | C |
| ATOM | 16295 | CD1 | LEU | C | 371 | 18.817 | 57.048 | 95.375 | 1.00 | 61.30 | C |
| ATOM | 16299 | CD2 | LEU | C | 371 | 17.792 | 54.792 | 94.941 | 1.00 | 61.35 | C |
| ATOM | 16303 | C | LEU | C | 371 | 21.491 | 55.780 | 91.810 | 1.00 | 61.35 | C |
| ATOM | 16304 | O | LEU | C | 371 | 21.272 | 56.713 | 91.035 | 1.00 | 60.21 | O |
| ATOM | 16306 | N | LEU | C | 372 | 22.030 | 54.616 | 91.434 | 1.00 | 62.36 | N |
| ATOM | 16307 | CA | LEU | C | 372 | 22.347 | 54.292 | 90.043 | 1.00 | 62.61 | C |
| ATOM | 16309 | CB | LEU | C | 372 | 23.659 | 53.503 | 89.972 | 1.00 | 62.88 | C |
| ATOM | 16312 | CG | LEU | C | 372 | 24.294 | 53.140 | 88.618 | 1.00 | 62.86 | C |
| ATOM | 16314 | CD1 | LEU | C | 372 | 23.871 | 51.756 | 88.154 | 1.00 | 63.96 | C |
| ATOM | 16318 | CD2 | LEU | C | 372 | 24.010 | 54.179 | 87.545 | 1.00 | 61.39 | C |
| ATOM | 16322 | C | LEU | C | 372 | 21.177 | 53.500 | 89.461 | 1.00 | 62.81 | C |
| ATOM | 16323 | O | LEU | C | 372 | 20.928 | 52.364 | 89.859 | 1.00 | 62.23 | O |
| ATOM | 16325 | N | SER | C | 373 | 20.470 | 54.117 | 88.515 | 1.00 | 64.42 | N |
| ATOM | 16326 | CA | SER | C | 373 | 19.113 | 53.705 | 88.144 | 1.00 | 64.55 | C |
| ATOM | 16328 | CB | SER | C | 373 | 18.329 | 54.911 | 87.605 | 1.00 | 64.64 | C |
| ATOM | 16331 | OG | SER | C | 373 | 17.017 | 54.536 | 87.230 | 1.00 | 63.48 | O |
| ATOM | 16333 | C | SER | C | 373 | 19.049 | 52.511 | 87.180 | 1.00 | 65.11 | C |
| ATOM | 16334 | O | SER | C | 373 | 19.255 | 51.380 | 87.610 | 1.00 | 65.77 | O |
| ATOM | 16336 | N | ASP | C | 374 | 18.795 | 52.765 | 85.892 | 1.00 | 66.20 | N |
| ATOM | 16337 | CA | ASP | C | 374 | 18.306 | 51.744 | 84.933 | 1.00 | 66.59 | C |
| ATOM | 16339 | CB | ASP | C | 374 | 19.238 | 50.520 | 84.834 | 1.00 | 66.84 | C |
| ATOM | 16342 | CG | ASP | C | 374 | 18.656 | 49.396 | 83.962 | 1.00 | 67.39 | C |
| ATOM | 16343 | OD1 | ASP | C | 374 | 17.629 | 49.613 | 83.271 | 1.00 | 67.44 | O |
| ATOM | 16344 | OD2 | ASP | C | 374 | 19.230 | 48.284 | 83.976 | 1.00 | 67.12 | O |
| ATOM | 16345 | C | ASP | C | 374 | 16.863 | 51.304 | 85.253 | 1.00 | 67.09 | C |
| ATOM | 16346 | O | ASP | C | 374 | 16.644 | 50.266 | 85.898 | 1.00 | 66.14 | O |
| ATOM | 16348 | N | SER | C | 375 | 15.897 | 52.094 | 84.769 | 1.00 | 66.87 | N |
| ATOM | 16349 | CA | SER | C | 375 | 14.466 | 51.872 | 85.017 | 1.00 | 66.49 | C |
| ATOM | 16351 | CB | SER | C | 375 | 14.014 | 50.519 | 84.447 | 1.00 | 65.83 | C |
| ATOM | 16354 | OG | SER | C | 375 | 14.576 | 50.279 | 83.166 | 1.00 | 64.07 | O |
| ATOM | 16356 | C | SER | C | 375 | 14.162 | 51.980 | 86.521 | 1.00 | 66.91 | C |
| ATOM | 16357 | O | SER | C | 375 | 14.897 | 52.645 | 87.258 | 1.00 | 66.74 | O |
| ATOM | 16359 | N | GLY | C | 376 | 13.079 | 51.347 | 86.973 | 1.00 | 67.56 | N |
| ATOM | 16360 | CA | GLY | C | 376 | 12.790 | 51.242 | 88.405 | 1.00 | 67.85 | C |
| ATOM | 16363 | C | GLY | C | 376 | 13.810 | 50.390 | 89.148 | 1.00 | 68.64 | C |
| ATOM | 16364 | O | GLY | C | 376 | 13.990 | 50.545 | 90.360 | 1.00 | 68.85 | O |
| ATOM | 16366 | N | GLN | C | 377 | 14.475 | 49.493 | 88.413 | 1.00 | 68.94 | N |
| ATOM | 16367 | CA | GLN | C | 377 | 15.485 | 48.581 | 88.964 | 1.00 | 68.70 | C |
| ATOM | 16369 | CB | GLN | C | 377 | 15.870 | 47.539 | 87.901 | 1.00 | 67.76 | C |
| ATOM | 16372 | CG | GLN | C | 377 | 16.831 | 46.447 | 88.365 | 1.00 | 66.43 | C |
| ATOM | 16375 | CD | GLN | C | 377 | 16.306 | 45.645 | 89.539 | 1.00 | 60.07 | C |
| ATOM | 16376 | OE1 | GLN | C | 377 | 15.103 | 45.434 | 89.680 | 1.00 | 52.17 | O |
| ATOM | 16377 | NE2 | GLN | C | 377 | 17.215 | 45.187 | 90.389 | 1.00 | 59.82 | N |
| ATOM | 16380 | C | GLN | C | 377 | 16.726 | 49.340 | 89.446 | 1.00 | 69.09 | C |
| ATOM | 16381 | O | GLN | C | 377 | 17.379 | 50.020 | 88.659 | 1.00 | 69.17 | O |
| ATOM | 16383 | N | VAL | C | 378 | 17.040 | 49.211 | 90.736 | 1.00 | 69.57 | N |
| ATOM | 16384 | CA | VAL | C | 378 | 18.168 | 49.919 | 91.356 | 1.00 | 69.61 | C |
| ATOM | 16386 | CB | VAL | C | 378 | 17.785 | 50.471 | 92.747 | 1.00 | 68.96 | C |
| ATOM | 16388 | CG1 | VAL | C | 378 | 18.987 | 51.135 | 93.419 | 1.00 | 67.72 | C |
| ATOM | 16392 | CG2 | VAL | C | 378 | 16.615 | 51.447 | 92.628 | 1.00 | 67.99 | C |
| ATOM | 16396 | C | VAL | C | 378 | 19.377 | 49.001 | 91.510 | 1.00 | 69.56 | C |
| ATOM | 16397 | O | VAL | C | 378 | 19.230 | 47.810 | 91.768 | 1.00 | 67.72 | O |
| ATOM | 16399 | N | LEU | C | 379 | 20.569 | 49.573 | 91.353 | 1.00 | 70.96 | N |
| ATOM | 16400 | CA | LEU | C | 379 | 21.818 | 48.824 | 91.472 | 1.00 | 72.24 | C |
| ATOM | 16402 | CB | LEU | C | 379 | 22.551 | 48.821 | 90.129 | 1.00 | 71.75 | C |
| ATOM | 16405 | CG | LEU | C | 379 | 21.825 | 48.183 | 88.943 | 1.00 | 70.13 | C |
| ATOM | 16407 | CD1 | LEU | C | 379 | 22.418 | 48.670 | 87.631 | 1.00 | 68.84 | C |
| ATOM | 16411 | CD2 | LEU | C | 379 | 21.875 | 46.669 | 89.023 | 1.00 | 69.36 | C |
| ATOM | 16415 | C | LEU | C | 379 | 22.766 | 49.354 | 92.556 | 1.00 | 73.37 | C |
| ATOM | 16416 | O | LEU | C | 379 | 23.766 | 48.701 | 92.840 | 1.00 | 72.68 | O |
| ATOM | 16418 | N | LEU | C | 380 | 22.465 | 50.513 | 93.153 | 1.00 | 75.64 | N |
| ATOM | 16419 | CA | LEU | C | 380 | 23.341 | 51.118 | 94.179 | 1.00 | 77.70 | C |
| ATOM | 16421 | CB | LEU | C | 380 | 24.597 | 51.731 | 93.519 | 1.00 | 77.62 | C |

-continued

| | | | | | | | | | | |
|---|---|---|---|---|---|---|---|---|---|---|
| ATOM | 16424 | CG | LEU | C | 380 | 25.868 | 50.880 | 93.318 | 1.00 | 74.95 C |
| ATOM | 16426 | CD1 | LEU | C | 380 | 26.868 | 51.568 | 92.394 | 1.00 | 71.94 C |
| ATOM | 16430 | CD2 | LEU | C | 380 | 26.525 | 50.562 | 94.651 | 1.00 | 74.30 C |
| ATOM | 16434 | C | LEU | C | 380 | 22.640 | 52.186 | 95.051 | 1.00 | 79.41 C |
| ATOM | 16435 | O | LEU | C | 380 | 21.567 | 52.685 | 94.704 | 1.00 | 78.89 O |
| ATOM | 16437 | N | GLU | C | 381 | 23.263 | 52.509 | 96.187 | 1.00 | 82.32 N |
| ATOM | 16438 | CA | GLU | C | 381 | 22.857 | 53.631 | 97.051 | 1.00 | 83.82 C |
| ATOM | 16440 | CB | GLU | C | 381 | 21.840 | 53.174 | 98.118 | 1.00 | 84.66 C |
| ATOM | 16443 | CG | GLU | C | 381 | 21.539 | 54.238 | 99.213 | 1.00 | 86.27 C |
| ATOM | 16446 | CD | GLU | C | 381 | 20.385 | 53.893 | 100.145 | 1.00 | 88.12 C |
| ATOM | 16447 | OE1 | GLU | C | 381 | 19.818 | 52.779 | 100.049 | 1.00 | 94.19 O |
| ATOM | 16448 | OE2 | GLU | C | 381 | 20.056 | 54.758 | 100.989 | 1.00 | 90.42 O |
| ATOM | 16449 | C | GLU | C | 381 | 24.098 | 54.259 | 97.716 | 1.00 | 84.49 C |
| ATOM | 16450 | O | GLU | C | 381 | 25.192 | 53.713 | 97.605 | 1.00 | 83.91 O |
| ATOM | 16452 | N | SER | C | 382 | 23.932 | 55.426 | 98.352 | 1.00 | 86.31 N |
| ATOM | 16453 | CA | SER | C | 382 | 24.911 | 55.965 | 99.324 | 1.00 | 85.92 C |
| ATOM | 16455 | CB | SER | C | 382 | 25.856 | 56.980 | 98.665 | 1.00 | 86.71 C |
| ATOM | 16458 | OG | SER | C | 382 | 26.433 | 56.470 | 97.471 | 1.00 | 86.98 O |
| ATOM | 16460 | C | SER | C | 382 | 24.207 | 56.625 | 100.518 | 1.00 | 84.88 C |
| ATOM | 16461 | O | SER | C | 382 | 23.001 | 56.886 | 100.487 | 1.00 | 83.67 O |
| ATOM | 16463 | N | LYS | D | 26 | −0.972 | −25.299 | 48.770 | 1.00 | 70.07 N |
| ATOM | 16464 | CA | LYS | D | 26 | 0.051 | −24.786 | 49.737 | 1.00 | 68.39 C |
| ATOM | 16466 | CB | LYS | D | 26 | 0.832 | −23.618 | 49.123 | 1.00 | 69.11 C |
| ATOM | 16469 | CG | LYS | D | 26 | 1.769 | −24.038 | 47.974 | 1.00 | 72.87 C |
| ATOM | 16472 | CD | LYS | D | 26 | 2.589 | −25.283 | 48.338 | 1.00 | 73.86 C |
| ATOM | 16475 | CE | LYS | D | 26 | 3.816 | −25.450 | 47.480 | 1.00 | 71.75 C |
| ATOM | 16478 | NZ | LYS | D | 26 | 4.579 | −26.640 | 47.939 | 1.00 | 72.71 N |
| ATOM | 16482 | C | LYS | D | 26 | −0.557 | −24.407 | 51.094 | 1.00 | 66.49 C |
| ATOM | 16483 | O | LYS | D | 26 | −1.600 | −23.758 | 51.173 | 1.00 | 66.25 O |
| ATOM | 16487 | N | LYS | D | 27 | 0.123 | −24.833 | 52.151 | 1.00 | 64.50 N |
| ATOM | 16488 | CA | LYS | D | 27 | −0.417 | −24.823 | 53.502 | 1.00 | 64.07 C |
| ATOM | 16490 | CB | LYS | D | 27 | 0.569 | −25.506 | 54.470 | 1.00 | 64.67 C |
| ATOM | 16493 | CG | LYS | D | 27 | 0.480 | −27.028 | 54.535 | 1.00 | 67.71 C |
| ATOM | 16496 | CD | LYS | D | 27 | 0.688 | −27.542 | 55.988 | 1.00 | 70.79 C |
| ATOM | 16499 | CE | LYS | D | 27 | −0.572 | −27.377 | 56.894 | 1.00 | 73.69 C |
| ATOM | 16502 | NZ | LYS | D | 27 | −1.594 | −28.479 | 56.725 | 1.00 | 73.86 N |
| ATOM | 16506 | C | LYS | D | 27 | −0.739 | −23.435 | 54.058 | 1.00 | 61.47 C |
| ATOM | 16507 | O | LYS | D | 27 | −0.069 | −22.453 | 53.754 | 1.00 | 60.62 O |
| ATOM | 16509 | N | VAL | D | 28 | −1.783 | −23.393 | 54.880 | 1.00 | 59.37 N |
| ATOM | 16510 | CA | VAL | D | 28 | −2.031 | −22.309 | 55.807 | 1.00 | 58.01 C |
| ATOM | 16512 | CB | VAL | D | 28 | −3.452 | −21.751 | 55.652 | 1.00 | 58.42 C |
| ATOM | 16514 | CG1 | VAL | D | 28 | −3.819 | −20.811 | 56.804 | 1.00 | 61.21 C |
| ATOM | 16518 | CG2 | VAL | D | 28 | −3.579 | −21.025 | 54.331 | 1.00 | 61.55 C |
| ATOM | 16522 | C | VAL | D | 28 | −1.844 | −22.880 | 57.207 | 1.00 | 56.58 C |
| ATOM | 16523 | O | VAL | D | 28 | −2.271 | −23.997 | 57.497 | 1.00 | 59.08 O |
| ATOM | 16525 | N | VAL | D | 29 | −1.177 | −22.111 | 58.058 | 1.00 | 54.64 N |
| ATOM | 16526 | CA | VAL | D | 29 | −0.961 | −22.467 | 59.449 | 1.00 | 53.80 C |
| ATOM | 16528 | CB | VAL | D | 29 | 0.498 | −22.932 | 59.693 | 1.00 | 53.90 C |
| ATOM | 16530 | CG1 | VAL | D | 29 | 0.776 | −23.135 | 61.189 | 1.00 | 51.83 C |
| ATOM | 16534 | CG2 | VAL | D | 29 | 0.795 | −24.202 | 58.904 | 1.00 | 51.54 C |
| ATOM | 16538 | C | VAL | D | 29 | −1.257 | −21.223 | 60.279 | 1.00 | 53.97 C |
| ATOM | 16539 | O | VAL | D | 29 | −0.766 | −20.133 | 59.963 | 1.00 | 52.71 O |
| ATOM | 16541 | N | LEU | D | 30 | −2.071 | −21.391 | 61.324 | 1.00 | 53.89 N |
| ATOM | 16542 | CA | LEU | D | 30 | −2.430 | −20.289 | 62.212 | 1.00 | 53.55 C |
| ATOM | 16544 | CB | LEU | D | 30 | −3.918 | −20.339 | 62.549 | 1.00 | 53.06 C |
| ATOM | 16547 | CG | LEU | D | 30 | −4.900 | −20.448 | 61.381 | 1.00 | 54.18 C |
| ATOM | 16549 | CD1 | LEU | D | 30 | −6.303 | −20.192 | 61.905 | 1.00 | 59.32 C |
| ATOM | 16553 | CD2 | LEU | D | 30 | −4.590 | −19.502 | 60.227 | 1.00 | 54.65 C |
| ATOM | 16557 | C | LEU | D | 30 | −1.627 | −20.376 | 63.493 | 1.00 | 53.27 C |
| ATOM | 16558 | O | LEU | D | 30 | −1.193 | −21.451 | 63.880 | 1.00 | 52.96 O |
| ATOM | 16560 | N | GLY | D | 31 | −1.429 | −19.249 | 64.159 | 1.00 | 53.29 N |
| ATOM | 16561 | CA | GLY | D | 31 | −0.822 | −19.271 | 65.489 | 1.00 | 53.17 C |
| ATOM | 16564 | C | GLY | D | 31 | −1.371 | −18.159 | 66.360 | 1.00 | 54.11 C |
| ATOM | 16565 | O | GLY | D | 31 | −1.911 | −17.167 | 65.849 | 1.00 | 55.12 O |
| ATOM | 16567 | N | LYS | D | 32 | −1.232 | −18.323 | 67.673 | 1.00 | 52.40 N |
| ATOM | 16568 | CA | LYS | D | 32 | −1.629 | −17.289 | 68.625 | 1.00 | 51.94 C |
| ATOM | 16570 | CB | LYS | D | 32 | −2.201 | −17.907 | 69.908 | 1.00 | 51.79 C |
| ATOM | 16573 | CG | LYS | D | 32 | −3.591 | −18.450 | 69.728 | 1.00 | 52.03 C |
| ATOM | 16576 | CD | LYS | D | 32 | −3.938 | −19.514 | 70.756 | 1.00 | 52.98 C |
| ATOM | 16579 | CE | LYS | D | 32 | −4.253 | −18.888 | 72.094 | 1.00 | 56.55 C |
| ATOM | 16582 | NZ | LYS | D | 32 | −4.665 | −19.917 | 73.078 | 1.00 | 57.22 N |
| ATOM | 16586 | C | LYS | D | 32 | −0.458 | −16.404 | 68.990 | 1.00 | 50.45 C |
| ATOM | 16587 | O | LYS | D | 32 | 0.622 | −16.907 | 69.321 | 1.00 | 52.17 O |
| ATOM | 16589 | N | LYS | D | 33 | −0.684 | −15.094 | 68.937 | 1.00 | 48.86 N |
| ATOM | 16590 | CA | LYS | D | 33 | 0.235 | −14.097 | 69.502 | 1.00 | 50.09 C |
| ATOM | 16592 | CB | LYS | D | 33 | −0.508 | −12.773 | 69.730 | 1.00 | 50.39 C |
| ATOM | 16595 | CG | LYS | D | 33 | 0.355 | −11.659 | 70.268 | 1.00 | 49.11 C |
| ATOM | 16598 | CD | LYS | D | 33 | −0.438 | −10.367 | 70.469 | 1.00 | 50.58 C |
| ATOM | 16601 | CE | LYS | D | 33 | 0.404 | −9.121 | 70.104 | 1.00 | 53.39 C |

-continued

| ATOM | 16604 | NZ | LYS | D | 33 | 0.406 | −8.081 | 71.177 | 1.00 | 51.91 | N |
| ATOM | 16608 | C | LYS | D | 33 | 0.786 | −14.585 | 70.834 | 1.00 | 49.48 | C |
| ATOM | 16609 | O | LYS | D | 33 | 0.027 | −14.969 | 71.710 | 1.00 | 49.63 | O |
| ATOM | 16611 | N | GLY | D | 34 | 2.102 | −14.586 | 70.981 | 1.00 | 49.59 | N |
| ATOM | 16612 | CA | GLY | D | 34 | 2.726 | −15.016 | 72.227 | 1.00 | 50.05 | C |
| ATOM | 16615 | C | GLY | D | 34 | 3.196 | −16.456 | 72.219 | 1.00 | 50.34 | C |
| ATOM | 16616 | O | GLY | D | 34 | 4.199 | −16.774 | 72.861 | 1.00 | 49.43 | O |
| ATOM | 16618 | N | ASP | D | 35 | 2.487 | −17.331 | 71.504 | 1.00 | 50.76 | N |
| ATOM | 16619 | CA | ASP | D | 35 | 2.855 | −18.748 | 71.462 | 1.00 | 52.67 | C |
| ATOM | 16621 | CB | ASP | D | 35 | 1.652 | −19.614 | 71.058 | 1.00 | 55.52 | C |
| ATOM | 16624 | CG | ASP | D | 35 | 0.666 | −19.839 | 72.204 | 1.00 | 59.08 | C |
| ATOM | 16625 | OD1 | ASP | D | 35 | 0.924 | −19.367 | 73.335 | 1.00 | 60.68 | O |
| ATOM | 16626 | OD2 | ASP | D | 35 | −0.372 | −20.496 | 71.959 | 1.00 | 57.54 | O |
| ATOM | 16627 | C | ASP | D | 35 | 4.015 | −19.007 | 70.506 | 1.00 | 52.90 | C |
| ATOM | 16628 | O | ASP | D | 35 | 4.542 | −18.075 | 69.882 | 1.00 | 52.10 | O |
| ATOM | 16630 | N | THR | D | 36 | 4.412 | −20.278 | 70.404 | 1.00 | 52.81 | N |
| ATOM | 16631 | CA | THR | D | 36 | 5.355 | −20.706 | 69.370 | 1.00 | 54.31 | C |
| ATOM | 16633 | CB | THR | D | 36 | 6.680 | −21.345 | 69.946 | 1.00 | 53.67 | C |
| ATOM | 16635 | OG1 | THR | D | 36 | 6.758 | −22.730 | 69.619 | 1.00 | 53.00 | O |
| ATOM | 16637 | CG2 | THR | D | 36 | 6.809 | −21.155 | 71.451 | 1.00 | 50.20 | C |
| ATOM | 16641 | C | THR | D | 36 | 4.641 | −21.637 | 68.374 | 1.00 | 55.43 | C |
| ATOM | 16642 | O | THR | D | 36 | 3.597 | −22.211 | 68.684 | 1.00 | 56.70 | O |
| ATOM | 16644 | N | VAL | D | 37 | 5.192 | −21.758 | 67.173 | 1.00 | 55.62 | N |
| ATOM | 16645 | CA | VAL | D | 37 | 4.557 | −22.533 | 66.113 | 1.00 | 56.79 | C |
| ATOM | 16647 | CB | VAL | D | 37 | 3.693 | −21.636 | 65.179 | 1.00 | 57.33 | C |
| ATOM | 16649 | CG1 | VAL | D | 37 | 4.497 | −20.478 | 64.613 | 1.00 | 55.95 | C |
| ATOM | 16653 | CG2 | VAL | D | 37 | 3.092 | −22.452 | 64.036 | 1.00 | 56.59 | C |
| ATOM | 16657 | C | VAL | D | 37 | 5.630 | −23.197 | 65.284 | 1.00 | 58.92 | C |
| ATOM | 16658 | O | VAL | D | 37 | 6.700 | −22.626 | 65.087 | 1.00 | 61.79 | O |
| ATOM | 16660 | N | GLU | D | 38 | 5.343 | −24.395 | 64.791 | 1.00 | 59.07 | N |
| ATOM | 16661 | CA | GLU | D | 38 | 6.296 | −25.128 | 63.974 | 1.00 | 58.43 | C |
| ATOM | 16663 | CB | GLU | D | 38 | 6.443 | −26.554 | 64.489 | 1.00 | 58.79 | C |
| ATOM | 16666 | CG | GLU | D | 38 | 7.785 | −27.159 | 64.161 | 1.00 | 62.23 | C |
| ATOM | 16669 | CD | GLU | D | 38 | 7.847 | −28.632 | 64.465 | 1.00 | 61.22 | C |
| ATOM | 16670 | OE1 | GLU | D | 38 | 8.439 | −28.990 | 65.505 | 1.00 | 62.32 | O |
| ATOM | 16671 | OE2 | GLU | D | 38 | 7.298 | −29.426 | 63.665 | 1.00 | 66.72 | O |
| ATOM | 16672 | C | GLU | D | 38 | 5.828 | −25.161 | 62.536 | 1.00 | 57.06 | C |
| ATOM | 16673 | O | GLU | D | 38 | 4.700 | −25.561 | 62.269 | 1.00 | 57.08 | O |
| ATOM | 16675 | N | LEU | D | 39 | 6.690 | −24.726 | 61.619 | 1.00 | 56.71 | N |
| ATOM | 16676 | CA | LEU | D | 39 | 6.435 | −24.857 | 60.177 | 1.00 | 56.29 | C |
| ATOM | 16678 | CB | LEU | D | 39 | 6.842 | −23.580 | 59.439 | 1.00 | 55.01 | C |
| ATOM | 16681 | CG | LEU | D | 39 | 5.910 | −22.357 | 59.491 | 1.00 | 55.10 | C |
| ATOM | 16683 | CD1 | LEU | D | 39 | 5.167 | −22.201 | 60.815 | 1.00 | 57.18 | C |
| ATOM | 16687 | CD2 | LEU | D | 39 | 6.686 | −21.084 | 59.187 | 1.00 | 54.50 | C |
| ATOM | 16691 | C | LEU | D | 39 | 7.219 | −26.066 | 59.654 | 1.00 | 56.51 | C |
| ATOM | 16692 | O | LEU | D | 39 | 8.417 | −26.177 | 59.893 | 1.00 | 57.54 | O |
| ATOM | 16694 | N | THR | D | 40 | 6.546 | −26.986 | 58.964 | 1.00 | 56.72 | N |
| ATOM | 16695 | CA | THR | D | 40 | 7.193 | −28.235 | 58.538 | 1.00 | 56.15 | C |
| ATOM | 16697 | CB | THR | D | 40 | 6.242 | −29.451 | 58.618 | 1.00 | 52.85 | C |
| ATOM | 16699 | OG1 | THR | D | 40 | 4.954 | −29.055 | 58.178 | 1.00 | 56.31 | O |
| ATOM | 16701 | CG2 | THR | D | 40 | 6.124 | −29.982 | 60.044 | 1.00 | 52.49 | C |
| ATOM | 16705 | C | THR | D | 40 | 7.763 | −28.145 | 57.124 | 1.00 | 56.08 | C |
| ATOM | 16706 | O | THR | D | 40 | 7.207 | −27.487 | 56.247 | 1.00 | 55.50 | O |
| ATOM | 16708 | N | CYS | D | 41 | 8.895 | −28.812 | 56.934 | 1.00 | 58.22 | N |
| ATOM | 16709 | CA | CYS | D | 41 | 9.509 | −28.976 | 55.631 | 1.00 | 57.45 | C |
| ATOM | 16711 | CB | CYS | D | 41 | 10.559 | −27.905 | 55.416 | 1.00 | 58.21 | C |
| ATOM | 16714 | SG | CYS | D | 41 | 11.141 | −27.805 | 53.737 | 1.00 | 63.90 | S |
| ATOM | 16716 | C | CYS | D | 41 | 10.151 | −30.353 | 55.616 | 1.00 | 56.20 | C |
| ATOM | 16717 | O | CYS | D | 41 | 10.810 | −30.730 | 56.588 | 1.00 | 52.79 | O |
| ATOM | 16719 | N | THR | D | 42 | 9.942 | −31.105 | 54.535 | 1.00 | 56.12 | N |
| ATOM | 16720 | CA | THR | D | 42 | 10.312 | −32.528 | 54.514 | 1.00 | 56.46 | C |
| ATOM | 16722 | CB | THR | D | 42 | 9.088 | −33.445 | 54.715 | 1.00 | 54.82 | C |
| ATOM | 16724 | OG1 | THR | D | 42 | 8.125 | −32.783 | 55.532 | 1.00 | 53.40 | O |
| ATOM | 16726 | CG2 | THR | D | 42 | 9.490 | −34.747 | 55.375 | 1.00 | 54.76 | C |
| ATOM | 16730 | C | THR | D | 42 | 10.958 | −32.957 | 53.216 | 1.00 | 56.00 | C |
| ATOM | 16731 | O | THR | D | 42 | 10.642 | −32.435 | 52.154 | 1.00 | 56.61 | O |
| ATOM | 16733 | N | ALA | D | 43 | 11.854 | −33.931 | 53.326 | 1.00 | 56.98 | N |
| ATOM | 16734 | CA | ALA | D | 43 | 12.476 | −34.573 | 52.175 | 1.00 | 56.62 | C |
| ATOM | 16736 | CB | ALA | D | 43 | 13.949 | −34.867 | 52.466 | 1.00 | 56.05 | C |
| ATOM | 16740 | C | ALA | D | 43 | 11.727 | −35.866 | 51.847 | 1.00 | 55.96 | C |
| ATOM | 16741 | O | ALA | D | 43 | 11.087 | −36.465 | 52.713 | 1.00 | 55.99 | O |
| ATOM | 16743 | N | SER | D | 44 | 11.797 | −36.271 | 50.585 | 1.00 | 55.94 | N |
| ATOM | 16744 | CA | SER | D | 44 | 11.268 | −37.558 | 50.144 | 1.00 | 56.44 | C |
| ATOM | 16746 | CB | SER | D | 44 | 11.459 | −37.701 | 48.635 | 1.00 | 56.20 | C |
| ATOM | 16749 | OG | SER | D | 44 | 12.711 | −37.154 | 48.241 | 1.00 | 53.10 | O |
| ATOM | 16751 | C | SER | D | 44 | 12.007 | −38.671 | 50.873 | 1.00 | 56.04 | C |
| ATOM | 16752 | O | SER | D | 44 | 11.390 | −39.561 | 51.451 | 1.00 | 53.30 | O |
| ATOM | 16754 | N | GLN | D | 45 | 13.336 | −38.590 | 50.831 | 1.00 | 58.20 | N |
| ATOM | 16755 | CA | GLN | D | 45 | 14.216 | −39.446 | 51.625 | 1.00 | 59.66 | C |

| | | | | | -continued | | | | |
|---|---|---|---|---|---|---|---|---|---|
| ATOM | 16757 | CB | GLN | D | 45 | 15.662 | −39.399 | 51.088 | 1.00 | 59.52 | C |
| ATOM | 16760 | CG | GLN | D | 45 | 16.113 | −40.648 | 50.336 | 1.00 | 59.58 | C |
| ATOM | 16763 | CD | GLN | D | 45 | 15.594 | −40.720 | 48.908 | 1.00 | 61.12 | C |
| ATOM | 16764 | OE1 | GLN | D | 45 | 16.353 | −41.015 | 47.987 | 1.00 | 63.26 | O |
| ATOM | 16765 | NE2 | GLN | D | 45 | 14.301 | −40.457 | 48.716 | 1.00 | 57.52 | N |
| ATOM | 16768 | C | GLN | D | 45 | 14.211 | −39.040 | 53.106 | 1.00 | 61.15 | C |
| ATOM | 16769 | O | GLN | D | 45 | 14.201 | −37.853 | 53.439 | 1.00 | 61.13 | O |
| ATOM | 16771 | N | LYS | D | 46 | 14.213 | −40.041 | 53.984 | 1.00 | 62.76 | N |
| ATOM | 16772 | CA | LYS | D | 46 | 14.443 | −39.841 | 55.415 | 1.00 | 61.86 | C |
| ATOM | 16774 | CB | LYS | D | 46 | 13.874 | −41.028 | 56.208 | 1.00 | 63.45 | C |
| ATOM | 16777 | CG | LYS | D | 46 | 14.158 | −41.056 | 57.718 | 1.00 | 64.10 | C |
| ATOM | 16780 | CD | LYS | D | 46 | 14.047 | −42.495 | 58.285 | 1.00 | 65.12 | C |
| ATOM | 16783 | CE | LYS | D | 46 | 15.307 | −43.340 | 58.010 | 1.00 | 66.80 | C |
| ATOM | 16786 | NZ | LYS | D | 46 | 16.189 | −43.537 | 59.201 | 1.00 | 67.16 | N |
| ATOM | 16790 | C | LYS | D | 46 | 15.955 | −39.713 | 55.604 | 1.00 | 61.37 | C |
| ATOM | 16791 | O | LYS | D | 46 | 16.646 | −40.699 | 55.895 | 1.00 | 59.89 | O |
| ATOM | 16793 | N | LYS | D | 47 | 16.465 | −38.502 | 55.379 | 1.00 | 60.22 | N |
| ATOM | 16794 | CA | LYS | D | 47 | 17.882 | −38.196 | 55.597 | 1.00 | 58.96 | C |
| ATOM | 16796 | CB | LYS | D | 47 | 18.768 | −38.913 | 54.566 | 1.00 | 58.43 | C |
| ATOM | 16799 | CG | LYS | D | 47 | 18.892 | −38.229 | 53.206 | 1.00 | 58.50 | C |
| ATOM | 16802 | CD | LYS | D | 47 | 20.154 | −38.708 | 52.466 | 1.00 | 59.64 | C |
| ATOM | 16805 | CE | LYS | D | 47 | 21.012 | −37.545 | 51.966 | 1.00 | 58.15 | C |
| ATOM | 16808 | NZ | LYS | D | 47 | 22.463 | −37.872 | 51.976 | 1.00 | 56.58 | N |
| ATOM | 16812 | C | LYS | D | 47 | 18.133 | −36.676 | 55.597 | 1.00 | 57.82 | C |
| ATOM | 16813 | O | LYS | D | 47 | 17.205 | −35.893 | 55.386 | 1.00 | 55.11 | O |
| ATOM | 16815 | N | SER | D | 48 | 19.386 | −36.277 | 55.841 | 1.00 | 57.37 | N |
| ATOM | 16816 | CA | SER | D | 48 | 19.769 | −34.858 | 55.924 | 1.00 | 56.74 | C |
| ATOM | 16818 | CB | SER | D | 48 | 20.745 | −34.623 | 57.082 | 1.00 | 56.60 | C |
| ATOM | 16821 | OG | SER | D | 48 | 21.324 | −33.327 | 57.023 | 1.00 | 54.06 | O |
| ATOM | 16823 | C | SER | D | 48 | 20.396 | −34.351 | 54.625 | 1.00 | 56.51 | C |
| ATOM | 16824 | O | SER | D | 48 | 21.374 | −34.904 | 54.132 | 1.00 | 57.70 | O |
| ATOM | 16826 | N | ILE | D | 49 | 19.824 | −33.279 | 54.095 | 1.00 | 56.29 | N |
| ATOM | 16827 | CA | ILE | D | 49 | 20.289 | −32.646 | 52.868 | 1.00 | 55.70 | C |
| ATOM | 16829 | CB | ILE | D | 49 | 19.423 | −33.051 | 51.652 | 1.00 | 55.14 | C |
| ATOM | 16831 | CG1 | ILE | D | 49 | 17.946 | −32.685 | 51.896 | 1.00 | 54.71 | C |
| ATOM | 16834 | CD1 | ILE | D | 49 | 16.973 | −33.274 | 50.903 | 1.00 | 54.63 | C |
| ATOM | 16838 | CG2 | ILE | D | 49 | 19.584 | −34.531 | 51.369 | 1.00 | 53.70 | C |
| ATOM | 16842 | C | ILE | D | 49 | 20.187 | −31.146 | 53.078 | 1.00 | 55.75 | C |
| ATOM | 16843 | O | ILE | D | 49 | 19.677 | −30.696 | 54.105 | 1.00 | 55.41 | O |
| ATOM | 16845 | N | GLN | D | 50 | 20.663 | −30.375 | 52.110 | 1.00 | 55.80 | N |
| ATOM | 16846 | CA | GLN | D | 50 | 20.532 | −28.928 | 52.185 | 1.00 | 56.67 | C |
| ATOM | 16848 | CB | GLN | D | 50 | 21.509 | −28.205 | 51.257 | 1.00 | 56.80 | C |
| ATOM | 16851 | CG | GLN | D | 50 | 21.608 | −28.688 | 49.830 | 1.00 | 59.40 | C |
| ATOM | 16854 | CD | GLN | D | 50 | 23.041 | −28.605 | 49.319 | 1.00 | 61.14 | C |
| ATOM | 16855 | OE1 | GLN | D | 50 | 23.985 | −29.005 | 50.011 | 1.00 | 62.03 | O |
| ATOM | 16856 | NE2 | GLN | D | 50 | 23.211 | −28.073 | 48.110 | 1.00 | 66.64 | N |
| ATOM | 16859 | C | GLN | D | 50 | 19.110 | −28.457 | 51.934 | 1.00 | 56.30 | C |
| ATOM | 16860 | O | GLN | D | 50 | 18.373 | −29.058 | 51.153 | 1.00 | 56.88 | O |
| ATOM | 16862 | N | PHE | D | 51 | 18.749 | −27.385 | 52.639 | 1.00 | 56.44 | N |
| ATOM | 16863 | CA | PHE | D | 51 | 17.451 | −26.730 | 52.530 | 1.00 | 55.94 | C |
| ATOM | 16865 | CB | PHE | D | 51 | 16.441 | −27.440 | 53.415 | 1.00 | 56.79 | C |
| ATOM | 16868 | CG | PHE | D | 51 | 16.728 | −27.292 | 54.879 | 1.00 | 58.03 | C |
| ATOM | 16869 | CD1 | PHE | D | 51 | 17.545 | −28.199 | 55.532 | 1.00 | 53.74 | C |
| ATOM | 16871 | CE1 | PHE | D | 51 | 17.826 | −28.056 | 56.880 | 1.00 | 55.86 | C |
| ATOM | 16873 | CZ | PHE | D | 51 | 17.296 | −26.991 | 57.592 | 1.00 | 57.32 | C |
| ATOM | 16875 | CE2 | PHE | D | 51 | 16.482 | −26.067 | 56.945 | 1.00 | 59.39 | C |
| ATOM | 16877 | CD2 | PHE | D | 51 | 16.203 | −26.220 | 55.596 | 1.00 | 59.32 | C |
| ATOM | 16879 | C | PHE | D | 51 | 17.604 | −25.293 | 53.013 | 1.00 | 55.25 | C |
| ATOM | 16880 | O | PHE | D | 51 | 18.505 | −24.996 | 53.790 | 1.00 | 55.07 | O |
| ATOM | 16882 | N | HIS | D | 52 | 16.722 | −24.408 | 52.572 | 1.00 | 56.19 | N |
| ATOM | 16883 | CA | HIS | D | 52 | 16.763 | −23.011 | 53.000 | 1.00 | 57.41 | C |
| ATOM | 16885 | CB | HIS | D | 52 | 17.381 | −22.122 | 51.906 | 1.00 | 60.64 | C |
| ATOM | 16888 | CG | HIS | D | 52 | 18.869 | −22.264 | 51.761 | 1.00 | 65.48 | C |
| ATOM | 16889 | ND1 | HIS | D | 52 | 19.500 | −22.228 | 50.536 | 1.00 | 65.43 | N |
| ATOM | 16891 | CE1 | HIS | D | 52 | 20.805 | −22.370 | 50.711 | 1.00 | 74.78 | C |
| ATOM | 16893 | NE2 | HIS | D | 52 | 21.042 | −22.502 | 52.005 | 1.00 | 72.58 | N |
| ATOM | 16895 | CD2 | HIS | D | 52 | 19.849 | −22.433 | 52.684 | 1.00 | 71.76 | C |
| ATOM | 16897 | C | HIS | D | 52 | 15.365 | −22.512 | 53.290 | 1.00 | 54.41 | C |
| ATOM | 16898 | O | HIS | D | 52 | 14.497 | −22.648 | 52.448 | 1.00 | 56.90 | O |
| ATOM | 16900 | N | TRP | D | 53 | 15.150 | −21.947 | 54.474 | 1.00 | 52.48 | N |
| ATOM | 16901 | CA | TRP | D | 53 | 13.927 | −21.194 | 54.761 | 1.00 | 52.75 | C |
| ATOM | 16903 | CB | TRP | D | 53 | 13.524 | −21.317 | 56.227 | 1.00 | 53.44 | C |
| ATOM | 16906 | CG | TRP | D | 53 | 12.823 | −22.553 | 56.599 | 1.00 | 52.10 | C |
| ATOM | 16907 | CD1 | TRP | D | 53 | 13.330 | −23.582 | 57.314 | 1.00 | 54.09 | C |
| ATOM | 16909 | NE1 | TRP | D | 53 | 12.376 | −24.549 | 57.498 | 1.00 | 55.56 | N |
| ATOM | 16911 | CE2 | TRP | D | 53 | 11.216 | −24.145 | 56.896 | 1.00 | 56.54 | C |
| ATOM | 16912 | CD2 | TRP | D | 53 | 11.460 | −22.882 | 56.328 | 1.00 | 54.78 | C |
| ATOM | 16913 | CE3 | TRP | D | 53 | 10.422 | −22.237 | 55.650 | 1.00 | 57.50 | C |
| ATOM | 16915 | CZ3 | TRP | D | 53 | 9.185 | −22.874 | 55.565 | 1.00 | 55.10 | C |

-continued

| ATOM | 16917 | CH2 | TRP | D | 53 | 8.976 | −24.132 | 56.142 | 1.00 | 52.76 | C |
|------|-------|-----|-----|---|----|-------|---------|--------|------|-------|---|
| ATOM | 16919 | CZ2 | TRP | D | 53 | 9.973 | −24.780 | 56.812 | 1.00 | 56.22 | C |
| ATOM | 16921 | C | TRP | D | 53 | 14.133 | −19.710 | 54.488 | 1.00 | 50.73 | C |
| ATOM | 16922 | O | TRP | D | 53 | 14.954 | −19.074 | 55.142 | 1.00 | 49.83 | O |
| ATOM | 16924 | N | LYS | D | 54 | 13.372 | −19.151 | 53.554 | 1.00 | 49.78 | N |
| ATOM | 16925 | CA | LYS | D | 54 | 13.342 | −17.702 | 53.368 | 1.00 | 51.35 | C |
| ATOM | 16927 | CB | LYS | D | 54 | 13.936 | −17.299 | 52.015 | 1.00 | 52.23 | C |
| ATOM | 16930 | CG | LYS | D | 54 | 13.494 | −18.136 | 50.823 | 1.00 | 59.55 | C |
| ATOM | 16933 | CD | LYS | D | 54 | 14.165 | −17.674 | 49.518 | 1.00 | 57.29 | C |
| ATOM | 16936 | CE | LYS | D | 54 | 15.659 | −18.026 | 49.465 | 1.00 | 60.10 | C |
| ATOM | 16939 | NZ | LYS | D | 54 | 16.260 | −17.667 | 48.137 | 1.00 | 60.94 | N |
| ATOM | 16943 | C | LYS | D | 54 | 11.929 | −17.171 | 53.543 | 1.00 | 49.66 | C |
| ATOM | 16944 | O | LYS | D | 54 | 10.992 | −17.955 | 53.701 | 1.00 | 52.00 | O |
| ATOM | 16946 | N | ASN | D | 55 | 11.777 | −15.847 | 53.566 | 1.00 | 48.11 | N |
| ATOM | 16947 | CA | ASN | D | 55 | 10.438 | −15.226 | 53.629 | 1.00 | 47.08 | C |
| ATOM | 16949 | CB | ASN | D | 55 | 10.382 | −14.060 | 54.636 | 1.00 | 45.61 | C |
| ATOM | 16952 | CG | ASN | D | 55 | 11.364 | −12.934 | 54.328 | 1.00 | 45.87 | C |
| ATOM | 16953 | OD1 | ASN | D | 55 | 11.766 | −12.707 | 53.185 | 1.00 | 51.14 | O |
| ATOM | 16954 | ND2 | ASN | D | 55 | 11.749 | −12.216 | 55.367 | 1.00 | 42.58 | N |
| ATOM | 16957 | C | ASN | D | 55 | 9.949 | −14.803 | 52.250 | 1.00 | 45.23 | C |
| ATOM | 16958 | O | ASN | D | 55 | 10.677 | −14.916 | 51.255 | 1.00 | 43.06 | O |
| ATOM | 16960 | N | SER | D | 56 | 8.712 | −14.332 | 52.184 | 1.00 | 45.71 | N |
| ATOM | 16961 | CA | SER | D | 56 | 8.129 | −13.887 | 50.918 | 1.00 | 47.48 | C |
| ATOM | 16963 | CB | SER | D | 56 | 6.729 | −13.336 | 51.137 | 1.00 | 47.80 | C |
| ATOM | 16966 | OG | SER | D | 56 | 6.760 | −12.163 | 51.935 | 1.00 | 56.48 | O |
| ATOM | 16968 | C | SER | D | 56 | 8.975 | −12.822 | 50.239 | 1.00 | 47.97 | C |
| ATOM | 16969 | O | SER | D | 56 | 8.996 | −12.723 | 49.010 | 1.00 | 49.96 | O |
| ATOM | 16971 | N | ASN | D | 57 | 9.681 | −12.030 | 51.039 | 1.00 | 48.45 | N |
| ATOM | 16972 | CA | ASN | D | 57 | 10.582 | −11.026 | 50.503 | 1.00 | 48.84 | C |
| ATOM | 16974 | CB | ASN | D | 57 | 10.779 | −9.912 | 51.519 | 1.00 | 49.41 | C |
| ATOM | 16977 | CG | ASN | D | 57 | 11.347 | −8.669 | 50.893 | 1.00 | 55.44 | C |
| ATOM | 16978 | OD1 | ASN | D | 57 | 10.792 | −8.147 | 49.915 | 1.00 | 61.49 | O |
| ATOM | 16979 | ND2 | ASN | D | 57 | 12.477 | −8.195 | 51.426 | 1.00 | 53.54 | N |
| ATOM | 16982 | C | ASN | D | 57 | 11.947 | −11.566 | 50.054 | 1.00 | 49.04 | C |
| ATOM | 16983 | O | ASN | D | 57 | 12.839 | −10.792 | 49.716 | 1.00 | 52.24 | O |
| ATOM | 16985 | N | GLN | D | 58 | 12.103 | −12.887 | 50.025 | 1.00 | 49.96 | N |
| ATOM | 16986 | CA | GLN | D | 58 | 13.347 | −13.534 | 49.594 | 1.00 | 48.57 | C |
| ATOM | 16988 | CB | GLN | D | 58 | 13.730 | −13.128 | 48.164 | 1.00 | 45.71 | C |
| ATOM | 16991 | CG | GLN | D | 58 | 12.647 | −13.412 | 47.154 | 1.00 | 50.64 | C |
| ATOM | 16994 | CD | GLN | D | 58 | 12.163 | −14.845 | 47.250 | 1.00 | 52.50 | C |
| ATOM | 16995 | OE1 | GLN | D | 58 | 12.964 | −15.777 | 47.241 | 1.00 | 56.11 | O |
| ATOM | 16996 | NE2 | GLN | D | 58 | 10.854 | −15.027 | 47.379 | 1.00 | 52.19 | N |
| ATOM | 16999 | C | GLN | D | 58 | 14.469 | −13.205 | 50.550 | 1.00 | 49.00 | C |
| ATOM | 17000 | O | GLN | D | 58 | 15.547 | −12.836 | 50.126 | 1.00 | 51.30 | O |
| ATOM | 17002 | N | ILE | D | 59 | 14.216 | −13.313 | 51.846 | 1.00 | 48.94 | N |
| ATOM | 17003 | CA | ILE | D | 59 | 15.280 | −13.109 | 52.808 | 1.00 | 50.70 | C |
| ATOM | 17005 | CB | ILE | D | 59 | 15.011 | −11.958 | 53.781 | 1.00 | 51.81 | C |
| ATOM | 17007 | CG1 | ILE | D | 59 | 14.727 | −10.656 | 53.024 | 1.00 | 55.07 | C |
| ATOM | 17010 | CD1 | ILE | D | 59 | 13.930 | −9.640 | 53.860 | 1.00 | 56.17 | C |
| ATOM | 17014 | CG2 | ILE | D | 59 | 16.220 | −11.772 | 54.702 | 1.00 | 49.77 | C |
| ATOM | 17018 | C | ILE | D | 59 | 15.468 | −14.371 | 53.600 | 1.00 | 48.73 | C |
| ATOM | 17019 | O | ILE | D | 59 | 14.518 | −14.910 | 54.147 | 1.00 | 48.05 | O |
| ATOM | 17021 | N | LYS | D | 60 | 16.714 | −14.816 | 53.667 | 1.00 | 48.78 | N |
| ATOM | 17022 | CA | LYS | D | 60 | 17.053 | −16.074 | 54.300 | 1.00 | 48.95 | C |
| ATOM | 17024 | CB | LYS | D | 60 | 18.524 | −16.429 | 54.029 | 1.00 | 49.85 | C |
| ATOM | 17027 | CG | LYS | D | 60 | 18.798 | −17.096 | 52.692 | 0.30 | 46.20 | C |
| ATOM | 17030 | CD | LYS | D | 60 | 20.124 | −17.851 | 52.722 | 0.30 | 46.66 | C |
| ATOM | 17033 | CE | LYS | D | 60 | 20.077 | −19.091 | 53.641 | 0.30 | 44.65 | C |
| ATOM | 17036 | NZ | LYS | D | 60 | 20.254 | −18.797 | 55.102 | 0.30 | 36.58 | N |
| ATOM | 17040 | C | LYS | D | 60 | 16.799 | −15.980 | 55.798 | 1.00 | 48.12 | C |
| ATOM | 17041 | O | LYS | D | 60 | 17.073 | −14.952 | 56.408 | 1.00 | 49.83 | O |
| ATOM | 17043 | N | ILE | D | 61 | 16.263 | −17.048 | 56.377 | 1.00 | 46.84 | N |
| ATOM | 17044 | CA | ILE | D | 61 | 16.004 | −17.101 | 57.807 | 1.00 | 48.02 | C |
| ATOM | 17046 | CB | ILE | D | 61 | 14.568 | −17.543 | 58.091 | 1.00 | 47.34 | C |
| ATOM | 17048 | CG1 | ILE | D | 61 | 13.605 | −16.480 | 57.567 | 1.00 | 47.70 | C |
| ATOM | 17051 | CD1 | ILE | D | 61 | 12.185 | −16.946 | 57.481 | 1.00 | 51.20 | C |
| ATOM | 17055 | CG2 | ILE | D | 61 | 14.364 | −17.778 | 59.590 | 1.00 | 45.19 | C |
| ATOM | 17059 | C | ILE | D | 61 | 16.983 | −18.060 | 58.442 | 1.00 | 47.57 | C |
| ATOM | 17060 | O | ILE | D | 61 | 17.777 | −17.670 | 59.302 | 1.00 | 49.36 | O |
| ATOM | 17062 | N | LEU | D | 62 | 16.922 | −19.312 | 58.006 | 1.00 | 47.97 | N |
| ATOM | 17063 | CA | LEU | D | 62 | 17.907 | −20.315 | 58.387 | 1.00 | 49.02 | C |
| ATOM | 17065 | CB | LEU | D | 62 | 17.633 | −20.815 | 59.808 | 1.00 | 49.88 | C |
| ATOM | 17068 | CG | LEU | D | 62 | 16.373 | −21.658 | 60.038 | 1.00 | 51.80 | C |
| ATOM | 17070 | CD1 | LEU | D | 62 | 16.556 | −23.107 | 59.576 | 1.00 | 51.48 | C |
| ATOM | 17074 | CD2 | LEU | D | 62 | 15.986 | −21.620 | 61.522 | 1.00 | 54.14 | C |
| ATOM | 17078 | C | LEU | D | 62 | 17.914 | −21.478 | 57.387 | 1.00 | 46.99 | C |
| ATOM | 17079 | O | LEU | D | 62 | 16.960 | −21.645 | 56.629 | 1.00 | 44.87 | O |
| ATOM | 17081 | N | GLY | D | 63 | 18.977 | −22.281 | 57.398 | 1.00 | 45.20 | N |
| ATOM | 17082 | CA | GLY | D | 63 | 19.095 | −23.384 | 56.454 | 1.00 | 45.81 | C |

| | | | | | | | | | | |
|---|---|---|---|---|---|---|---|---|---|---|
| ATOM | 17085 | C | GLY | D | 63 | 20.321 | −24.244 | 56.646 | 1.00 | 45.70 C |
| ATOM | 17086 | O | GLY | D | 63 | 21.120 | −24.004 | 57.537 | 1.00 | 47.29 O |
| ATOM | 17088 | N | ASN | D | 64 | 20.461 | −25.262 | 55.808 | 1.00 | 46.43 N |
| ATOM | 17089 | CA | ASN | D | 64 | 21.592 | −26.177 | 55.877 | 1.00 | 47.37 C |
| ATOM | 17091 | CB | ASN | D | 64 | 21.072 | −27.607 | 56.017 | 1.00 | 46.87 C |
| ATOM | 17094 | CG | ASN | D | 64 | 22.184 | −28.647 | 56.095 | 1.00 | 47.06 C |
| ATOM | 17095 | OD1 | ASN | D | 64 | 23.368 | −28.346 | 55.903 | 1.00 | 48.32 O |
| ATOM | 17096 | ND2 | ASN | D | 64 | 21.796 | −29.891 | 56.374 | 1.00 | 41.91 N |
| ATOM | 17099 | C | ASN | D | 64 | 22.456 | −26.023 | 54.625 | 1.00 | 47.39 C |
| ATOM | 17100 | O | ASN | D | 64 | 22.122 | −26.560 | 53.587 | 1.00 | 43.38 O |
| ATOM | 17102 | N | GLN | D | 65 | 23.562 | −25.285 | 54.737 | 1.00 | 51.03 N |
| ATOM | 17103 | CA | GLN | D | 65 | 24.438 | −24.981 | 53.586 | 1.00 | 53.34 C |
| ATOM | 17105 | CB | GLN | D | 65 | 25.055 | −23.579 | 53.704 | 1.00 | 55.42 C |
| ATOM | 17108 | CG | GLN | D | 65 | 24.310 | −22.502 | 52.924 | 1.00 | 63.21 C |
| ATOM | 17111 | CD | GLN | D | 65 | 24.798 | −22.366 | 51.483 | 1.00 | 68.32 C |
| ATOM | 17112 | OE1 | GLN | D | 65 | 24.951 | −23.356 | 50.765 | 1.00 | 70.29 O |
| ATOM | 17113 | NE2 | GLN | D | 65 | 25.041 | −21.128 | 51.058 | 1.00 | 73.15 N |
| ATOM | 17116 | C | GLN | D | 65 | 25.541 | −26.008 | 53.425 | 1.00 | 53.91 C |
| ATOM | 17117 | O | GLN | D | 65 | 26.731 | −25.674 | 53.472 | 1.00 | 51.75 O |
| ATOM | 17119 | N | GLY | D | 66 | 25.139 | −27.257 | 53.212 | 1.00 | 54.62 N |
| ATOM | 17120 | CA | GLY | D | 66 | 26.101 | −28.329 | 53.080 | 1.00 | 54.56 C |
| ATOM | 17123 | C | GLY | D | 66 | 26.970 | −28.383 | 54.319 | 1.00 | 54.68 C |
| ATOM | 17124 | O | GLY | D | 66 | 28.044 | −27.760 | 54.374 | 1.00 | 51.82 O |
| ATOM | 17126 | N | SER | D | 67 | 26.464 | −29.095 | 55.324 | 1.00 | 54.02 N |
| ATOM | 17127 | CA | SER | D | 67 | 27.208 | −29.417 | 56.544 | 1.00 | 52.50 C |
| ATOM | 17129 | CB | SER | D | 67 | 28.623 | −29.922 | 56.218 | 1.00 | 54.69 C |
| ATOM | 17132 | OG | SER | D | 67 | 29.527 | −28.864 | 55.946 | 1.00 | 57.84 O |
| ATOM | 17134 | C | SER | D | 67 | 27.278 | −28.304 | 57.588 | 1.00 | 50.53 C |
| ATOM | 17135 | O | SER | D | 67 | 27.774 | −28.556 | 58.679 | 1.00 | 50.40 O |
| ATOM | 17137 | N | PHE | D | 68 | 26.790 | −27.097 | 57.270 | 1.00 | 48.69 N |
| ATOM | 17138 | CA | PHE | D | 68 | 26.647 | −26.012 | 58.266 | 1.00 | 46.25 C |
| ATOM | 17140 | CB | PHE | D | 68 | 27.448 | −24.781 | 57.861 | 1.00 | 40.88 C |
| ATOM | 17143 | CG | PHE | D | 68 | 28.900 | −25.032 | 57.735 | 1.00 | 32.87 C |
| ATOM | 17144 | CD1 | PHE | D | 68 | 29.686 | −25.157 | 58.861 | 1.00 | 31.54 C |
| ATOM | 17146 | CE1 | PHE | D | 68 | 31.042 | −25.409 | 58.749 | 1.00 | 35.24 C |
| ATOM | 17148 | CZ | PHE | D | 68 | 31.617 | −25.535 | 57.490 | 1.00 | 33.93 C |
| ATOM | 17150 | CE2 | PHE | D | 68 | 30.828 | −25.414 | 56.361 | 1.00 | 29.46 C |
| ATOM | 17152 | CD2 | PHE | D | 68 | 29.483 | −25.161 | 56.490 | 1.00 | 27.19 C |
| ATOM | 17154 | C | PHE | D | 68 | 25.214 | −25.559 | 58.415 | 1.00 | 46.69 C |
| ATOM | 17155 | O | PHE | D | 68 | 24.543 | −25.334 | 57.413 | 1.00 | 48.40 O |
| ATOM | 17157 | N | LEU | D | 69 | 24.753 | −25.394 | 59.655 | 1.00 | 46.80 N |
| ATOM | 17158 | CA | LEU | D | 69 | 23.548 | −24.591 | 59.901 | 1.00 | 46.79 C |
| ATOM | 17160 | CB | LEU | D | 69 | 23.087 | −24.663 | 61.360 | 1.00 | 46.74 C |
| ATOM | 17163 | CG | LEU | D | 69 | 21.998 | −23.668 | 61.820 | 1.00 | 45.52 C |
| ATOM | 17165 | CD1 | LEU | D | 69 | 20.760 | −23.686 | 60.959 | 1.00 | 41.15 C |
| ATOM | 17169 | CD2 | LEU | D | 69 | 21.589 | −23.957 | 63.245 | 1.00 | 47.27 C |
| ATOM | 17173 | C | LEU | D | 69 | 23.900 | −23.161 | 59.557 | 1.00 | 45.81 C |
| ATOM | 17174 | O | LEU | D | 69 | 24.979 | −22.703 | 59.891 | 1.00 | 47.19 O |
| ATOM | 17176 | N | THR | D | 70 | 23.005 | −22.469 | 58.866 | 1.00 | 46.57 N |
| ATOM | 17177 | CA | THR | D | 70 | 23.187 | −21.054 | 58.576 | 1.00 | 47.35 C |
| ATOM | 17179 | CB | THR | D | 70 | 23.338 | −20.791 | 57.070 | 1.00 | 47.00 C |
| ATOM | 17181 | OG1 | THR | D | 70 | 22.235 | −21.360 | 56.357 | 1.00 | 46.70 O |
| ATOM | 17183 | CG2 | THR | D | 70 | 24.638 | −21.392 | 56.562 | 1.00 | 50.03 C |
| ATOM | 17187 | C | THR | D | 70 | 22.034 | −20.223 | 59.087 | 1.00 | 47.73 C |
| ATOM | 17188 | O | THR | D | 70 | 20.910 | −20.692 | 59.220 | 1.00 | 46.85 O |
| ATOM | 17190 | N | LYS | D | 71 | 22.342 | −18.971 | 59.375 | 1.00 | 50.00 N |
| ATOM | 17191 | CA | LYS | D | 71 | 21.350 | −17.998 | 59.771 | 1.00 | 50.04 C |
| ATOM | 17193 | CB | LYS | D | 71 | 21.643 | −17.485 | 61.181 | 1.00 | 51.04 C |
| ATOM | 17196 | CG | LYS | D | 71 | 20.584 | −17.852 | 62.195 | 1.00 | 52.33 C |
| ATOM | 17199 | CD | LYS | D | 71 | 20.433 | −19.353 | 62.415 | 1.00 | 50.52 C |
| ATOM | 17202 | CE | LYS | D | 71 | 19.581 | −19.606 | 63.664 | 1.00 | 50.66 C |
| ATOM | 17205 | NZ | LYS | D | 71 | 18.387 | −18.706 | 63.713 | 1.00 | 48.48 N |
| ATOM | 17209 | C | LYS | D | 71 | 21.375 | −16.850 | 58.786 | 1.00 | 49.81 C |
| ATOM | 17210 | O | LYS | D | 71 | 22.444 | −16.374 | 58.390 | 1.00 | 48.80 O |
| ATOM | 17212 | N | GLY | D | 72 | 20.186 | −16.411 | 58.397 | 1.00 | 50.56 N |
| ATOM | 17213 | CA | GLY | D | 72 | 20.036 | −15.260 | 57.523 | 1.00 | 50.17 C |
| ATOM | 17216 | C | GLY | D | 72 | 19.851 | −14.012 | 58.345 | 1.00 | 49.84 C |
| ATOM | 17217 | O | GLY | D | 72 | 19.948 | −14.053 | 59.555 | 1.00 | 48.81 O |
| ATOM | 17219 | N | PRO | D | 73 | 19.590 | −12.883 | 57.689 | 1.00 | 54.03 N |
| ATOM | 17220 | CA | PRO | D | 73 | 19.564 | −11.653 | 58.450 | 1.00 | 56.41 C |
| ATOM | 17222 | CB | PRO | D | 73 | 20.030 | −10.613 | 57.426 | 1.00 | 54.90 C |
| ATOM | 17225 | CG | PRO | D | 73 | 19.691 | −11.191 | 56.084 | 1.00 | 52.53 C |
| ATOM | 17228 | CD | PRO | D | 73 | 19.353 | −12.643 | 56.255 | 1.00 | 54.44 C |
| ATOM | 17231 | C | PRO | D | 73 | 18.206 | −11.271 | 59.009 | 1.00 | 57.46 C |
| ATOM | 17232 | O | PRO | D | 73 | 18.136 | −10.300 | 59.746 | 1.00 | 58.04 O |
| ATOM | 17233 | N | SER | D | 74 | 17.145 | −12.013 | 58.702 | 1.00 | 60.01 N |
| ATOM | 17234 | CA | SER | D | 74 | 15.787 | −11.515 | 58.996 | 1.00 | 62.77 C |
| ATOM | 17236 | CB | SER | D | 74 | 14.712 | −12.548 | 58.621 | 1.00 | 62.96 C |
| ATOM | 17239 | OG | SER | D | 74 | 14.458 | −13.464 | 59.663 | 1.00 | 63.94 O |

-continued

| ATOM | 17241 | C | SER | D | 74 | 15.597 | −11.030 | 60.449 | 1.00 | 64.15 | C |
| ATOM | 17242 | O | SER | D | 74 | 16.318 | −11.443 | 61.361 | 1.00 | 62.42 | O |
| ATOM | 17244 | N | LYS | D | 75 | 14.625 | −10.138 | 60.636 | 1.00 | 66.84 | N |
| ATOM | 17245 | CA | LYS | D | 75 | 14.279 | −9.587 | 61.962 | 1.00 | 68.12 | C |
| ATOM | 17247 | CB | LYS | D | 75 | 13.081 | −8.642 | 61.836 | 1.00 | 69.75 | C |
| ATOM | 17250 | CG | LYS | D | 75 | 13.321 | −7.416 | 60.932 | 1.00 | 74.63 | C |
| ATOM | 17253 | CD | LYS | D | 75 | 12.030 | −6.950 | 60.233 | 1.00 | 73.74 | C |
| ATOM | 17256 | CE | LYS | D | 75 | 11.693 | −7.826 | 59.033 | 1.00 | 77.18 | C |
| ATOM | 17259 | NZ | LYS | D | 75 | 10.457 | −7.378 | 58.346 | 1.00 | 77.76 | N |
| ATOM | 17263 | C | LYS | D | 75 | 13.919 | −10.716 | 62.924 | 1.00 | 66.42 | C |
| ATOM | 17264 | O | LYS | D | 75 | 14.211 | −10.671 | 64.112 | 1.00 | 66.11 | O |
| ATOM | 17266 | N | LEU | D | 76 | 13.271 | −11.720 | 62.355 | 1.00 | 65.63 | N |
| ATOM | 17267 | CA | LEU | D | 76 | 12.923 | −12.973 | 63.002 | 1.00 | 66.08 | C |
| ATOM | 17269 | CB | LEU | D | 76 | 12.475 | −13.947 | 61.902 | 1.00 | 64.61 | C |
| ATOM | 17272 | CG | LEU | D | 76 | 11.362 | −14.952 | 62.158 | 1.00 | 64.39 | C |
| ATOM | 17274 | CD1 | LEU | D | 76 | 10.236 | −14.368 | 62.993 | 1.00 | 65.34 | C |
| ATOM | 17278 | CD2 | LEU | D | 76 | 10.848 | −15.416 | 60.821 | 1.00 | 64.63 | C |
| ATOM | 17282 | C | LEU | D | 76 | 14.055 | −13.632 | 63.788 | 1.00 | 67.24 | C |
| ATOM | 17283 | O | LEU | D | 76 | 13.810 | −14.283 | 64.803 | 1.00 | 68.33 | O |
| ATOM | 17285 | N | ASN | D | 77 | 15.284 | −13.438 | 63.317 | 1.00 | 68.57 | N |
| ATOM | 17286 | CA | ASN | D | 77 | 16.424 | −14.319 | 63.616 | 1.00 | 68.10 | C |
| ATOM | 17288 | CB | ASN | D | 77 | 17.739 | −13.624 | 63.226 | 1.00 | 70.44 | C |
| ATOM | 17291 | CG | ASN | D | 77 | 18.948 | −14.524 | 63.405 | 1.00 | 72.93 | C |
| ATOM | 17292 | OD1 | ASN | D | 77 | 18.880 | −15.725 | 63.137 | 1.00 | 86.20 | O |
| ATOM | 17293 | ND2 | ASN | D | 77 | 20.057 | −13.952 | 63.865 | 1.00 | 79.02 | N |
| ATOM | 17296 | C | ASN | D | 77 | 16.557 | −14.864 | 65.036 | 1.00 | 66.80 | C |
| ATOM | 17297 | O | ASN | D | 77 | 16.778 | −16.057 | 65.228 | 1.00 | 66.29 | O |
| ATOM | 17299 | N | ASP | D | 78 | 16.453 | −13.986 | 66.020 | 1.00 | 65.64 | N |
| ATOM | 17300 | CA | ASP | D | 78 | 16.637 | −14.388 | 67.414 | 1.00 | 65.69 | C |
| ATOM | 17302 | CB | ASP | D | 78 | 16.609 | −13.171 | 68.367 | 1.00 | 68.23 | C |
| ATOM | 17305 | CG | ASP | D | 78 | 15.950 | −11.923 | 67.742 | 1.00 | 75.84 | C |
| ATOM | 17306 | OD1 | ASP | D | 78 | 16.384 | −11.495 | 66.641 | 1.00 | 77.97 | O |
| ATOM | 17307 | OD2 | ASP | D | 78 | 15.006 | −11.366 | 68.356 | 1.00 | 82.19 | O |
| ATOM | 17308 | C | ASP | D | 78 | 15.620 | −15.453 | 67.835 | 1.00 | 63.86 | C |
| ATOM | 17309 | O | ASP | D | 78 | 15.970 | −16.422 | 68.498 | 1.00 | 66.28 | O |
| ATOM | 17311 | N | ARG | D | 79 | 14.376 | −15.298 | 67.409 | 1.00 | 61.25 | N |
| ATOM | 17312 | CA | ARG | D | 79 | 13.315 | −16.224 | 67.789 | 1.00 | 59.74 | C |
| ATOM | 17314 | CB | ARG | D | 79 | 11.995 | −15.460 | 67.921 | 1.00 | 60.80 | C |
| ATOM | 17317 | CG | ARG | D | 79 | 12.082 | −14.278 | 68.866 | 1.00 | 57.42 | C |
| ATOM | 17320 | CD | ARG | D | 79 | 10.792 | −13.535 | 68.954 | 1.00 | 51.87 | C |
| ATOM | 17323 | NE | ARG | D | 79 | 10.540 | −12.706 | 67.782 | 1.00 | 45.36 | N |
| ATOM | 17325 | CZ | ARG | D | 79 | 9.474 | −12.786 | 66.984 | 1.00 | 45.37 | C |
| ATOM | 17326 | NH1 | ARG | D | 79 | 8.518 | −13.673 | 67.182 | 1.00 | 50.15 | N |
| ATOM | 17329 | NH2 | ARG | D | 79 | 9.358 | −11.956 | 65.971 | 1.00 | 44.62 | N |
| ATOM | 17332 | C | ARG | D | 79 | 13.126 | −17.375 | 66.801 | 1.00 | 60.30 | C |
| ATOM | 17333 | O | ARG | D | 79 | 12.179 | −18.156 | 66.948 | 1.00 | 60.79 | O |
| ATOM | 17335 | N | ALA | D | 80 | 14.009 | −17.492 | 65.807 | 1.00 | 58.46 | N |
| ATOM | 17336 | CA | ALA | D | 80 | 13.840 | −18.492 | 64.754 | 1.00 | 59.12 | C |
| ATOM | 17338 | CB | ALA | D | 80 | 14.048 | −17.862 | 63.398 | 1.00 | 59.56 | C |
| ATOM | 17342 | C | ALA | D | 80 | 14.798 | −19.651 | 64.945 | 1.00 | 59.62 | C |
| ATOM | 17343 | O | ALA | D | 80 | 15.998 | −19.453 | 65.106 | 1.00 | 60.02 | O |
| ATOM | 17345 | N | ASP | D | 81 | 14.266 | −20.865 | 64.904 | 1.00 | 60.29 | N |
| ATOM | 17346 | CA | ASP | D | 81 | 15.062 | −22.060 | 65.175 | 1.00 | 60.41 | C |
| ATOM | 17348 | CB | ASP | D | 81 | 14.874 | −22.462 | 66.641 | 1.00 | 62.39 | C |
| ATOM | 17351 | CG | ASP | D | 81 | 15.973 | −21.941 | 67.541 | 1.00 | 68.41 | C |
| ATOM | 17352 | OD1 | ASP | D | 81 | 17.160 | −22.209 | 67.247 | 1.00 | 73.38 | O |
| ATOM | 17353 | OD2 | ASP | D | 81 | 15.647 | −21.285 | 68.557 | 1.00 | 78.40 | O |
| ATOM | 17354 | C | ASP | D | 81 | 14.693 | −23.248 | 64.289 | 1.00 | 59.67 | C |
| ATOM | 17355 | O | ASP | D | 81 | 13.712 | −23.211 | 63.549 | 1.00 | 61.22 | O |
| ATOM | 17357 | N | SER | D | 82 | 15.499 | −24.301 | 64.376 | 1.00 | 58.72 | N |
| ATOM | 17358 | CA | SER | D | 82 | 15.156 | −25.602 | 63.817 | 1.00 | 57.80 | C |
| ATOM | 17360 | CB | SER | D | 82 | 15.860 | −25.821 | 62.481 | 1.00 | 56.33 | C |
| ATOM | 17363 | OG | SER | D | 82 | 15.184 | −26.817 | 61.740 | 1.00 | 50.78 | O |
| ATOM | 17365 | C | SER | D | 82 | 15.551 | −26.682 | 64.813 | 1.00 | 57.70 | C |
| ATOM | 17366 | O | SER | D | 82 | 15.729 | −26.396 | 65.997 | 1.00 | 56.12 | O |
| ATOM | 17368 | N | ARG | D | 83 | 15.680 | −27.918 | 64.336 | 1.00 | 58.91 | N |
| ATOM | 17369 | CA | ARG | D | 83 | 16.119 | −29.032 | 65.172 | 1.00 | 59.68 | C |
| ATOM | 17371 | CB | ARG | D | 83 | 14.924 | −29.834 | 65.673 | 1.00 | 60.12 | C |
| ATOM | 17374 | CG | ARG | D | 83 | 14.142 | −29.177 | 66.783 | 1.00 | 64.04 | C |
| ATOM | 17377 | CD | ARG | D | 83 | 13.154 | −30.175 | 67.390 | 1.00 | 68.81 | C |
| ATOM | 17380 | NE | ARG | D | 83 | 11.880 | −29.545 | 67.744 | 1.00 | 78.30 | N |
| ATOM | 17382 | CZ | ARG | D | 83 | 10.823 | −30.198 | 68.219 | 1.00 | 77.56 | C |
| ATOM | 17383 | NH1 | ARG | D | 83 | 10.876 | −31.512 | 68.430 | 1.00 | 80.28 | N |
| ATOM | 17386 | NH2 | ARG | D | 83 | 9.713 | −29.527 | 68.504 | 1.00 | 77.52 | N |
| ATOM | 17389 | C | ARG | D | 83 | 17.017 | −29.948 | 64.370 | 1.00 | 58.80 | C |
| ATOM | 17390 | O | ARG | D | 83 | 16.529 | −30.726 | 63.552 | 1.00 | 61.64 | O |
| ATOM | 17392 | N | ARG | D | 84 | 18.322 | −29.865 | 64.614 | 1.00 | 56.78 | N |
| ATOM | 17393 | CA | ARG | D | 84 | 19.302 | −30.633 | 63.844 | 1.00 | 54.30 | C |
| ATOM | 17395 | CB | ARG | D | 84 | 20.715 | −30.087 | 64.072 | 1.00 | 52.76 | C |

-continued

| | | | | | | | | | | |
|---|---|---|---|---|---|---|---|---|---|---|
| ATOM | 17398 | CG | ARG | D | 84 | 20.904 | −28.678 | 63.526 | 1.00 | 51.98 C |
| ATOM | 17401 | CD | ARG | D | 84 | 22.248 | −28.092 | 63.895 | 1.00 | 48.11 C |
| ATOM | 17404 | NE | ARG | D | 84 | 22.330 | −27.885 | 65.335 | 1.00 | 42.65 N |
| ATOM | 17406 | CZ | ARG | D | 84 | 23.441 | −27.955 | 66.058 | 1.00 | 31.61 C |
| ATOM | 17407 | NH1 | ARG | D | 84 | 24.608 | −28.236 | 65.498 | 1.00 | 35.68 N |
| ATOM | 17410 | NH2 | ARG | D | 84 | 23.373 | −27.764 | 67.364 | 1.00 | 29.89 N |
| ATOM | 17413 | C | ARG | D | 84 | 19.234 | −32.120 | 64.184 | 1.00 | 54.47 C |
| ATOM | 17414 | O | ARG | D | 84 | 19.664 | −32.968 | 63.393 | 1.00 | 55.00 O |
| ATOM | 17416 | N | SER | D | 85 | 18.704 | −32.423 | 65.368 | 1.00 | 53.86 N |
| ATOM | 17417 | CA | SER | D | 85 | 18.418 | −33.796 | 65.762 | 1.00 | 52.88 C |
| ATOM | 17419 | CB | SER | D | 85 | 17.788 | −33.820 | 67.159 | 1.00 | 52.10 C |
| ATOM | 17422 | OG | SER | D | 85 | 16.624 | −33.014 | 67.211 | 1.00 | 44.20 O |
| ATOM | 17424 | C | SER | D | 85 | 17.488 | −34.461 | 64.737 | 1.00 | 53.46 C |
| ATOM | 17425 | O | SER | D | 85 | 17.667 | −35.628 | 64.396 | 1.00 | 53.22 O |
| ATOM | 17427 | N | LEU | D | 86 | 16.523 | −33.693 | 64.228 | 1.00 | 53.24 N |
| ATOM | 17428 | CA | LEU | D | 86 | 15.552 | −34.189 | 63.247 | 1.00 | 52.03 C |
| ATOM | 17430 | CB | LEU | D | 86 | 14.224 | −33.431 | 63.386 | 1.00 | 51.29 C |
| ATOM | 17433 | CG | LEU | D | 86 | 13.619 | −33.340 | 64.787 | 1.00 | 49.20 C |
| ATOM | 17435 | CD1 | LEU | D | 86 | 12.214 | −32.800 | 64.702 | 1.00 | 47.44 C |
| ATOM | 17439 | CD2 | LEU | D | 86 | 13.630 | −34.689 | 65.486 | 1.00 | 50.30 C |
| ATOM | 17443 | C | LEU | D | 86 | 16.014 | −34.104 | 61.790 | 1.00 | 51.46 C |
| ATOM | 17444 | O | LEU | D | 86 | 15.376 | −34.680 | 60.912 | 1.00 | 53.05 O |
| ATOM | 17446 | N | TRP | D | 87 | 17.098 | −33.388 | 61.511 | 1.00 | 49.89 N |
| ATOM | 17447 | CA | TRP | D | 87 | 17.565 | −33.286 | 60.130 | 1.00 | 50.40 C |
| ATOM | 17449 | CB | TRP | D | 87 | 18.816 | −32.411 | 60.021 | 1.00 | 48.30 C |
| ATOM | 17452 | CG | TRP | D | 87 | 18.540 | −30.943 | 60.244 | 1.00 | 48.36 C |
| ATOM | 17453 | CD1 | TRP | D | 87 | 17.376 | −30.383 | 60.693 | 1.00 | 48.54 C |
| ATOM | 17455 | NE1 | TRP | D | 87 | 17.513 | −29.022 | 60.793 | 1.00 | 49.53 N |
| ATOM | 17457 | CE2 | TRP | D | 87 | 18.780 | −28.672 | 60.411 | 1.00 | 43.98 C |
| ATOM | 17458 | CD2 | TRP | D | 87 | 19.458 | −29.856 | 60.060 | 1.00 | 43.71 C |
| ATOM | 17459 | CE3 | TRP | D | 87 | 20.780 | −29.770 | 59.624 | 1.00 | 44.96 C |
| ATOM | 17461 | CZ3 | TRP | D | 87 | 21.376 | −28.528 | 59.561 | 1.00 | 48.05 C |
| ATOM | 17463 | CH2 | TRP | D | 87 | 20.673 | −27.365 | 59.918 | 1.00 | 46.51 C |
| ATOM | 17465 | CZ2 | TRP | D | 87 | 19.377 | −27.419 | 60.340 | 1.00 | 44.34 C |
| ATOM | 17467 | C | TRP | D | 87 | 17.830 | −34.669 | 59.571 | 1.00 | 50.61 C |
| ATOM | 17468 | O | TRP | D | 87 | 17.669 | −34.890 | 58.379 | 1.00 | 50.87 O |
| ATOM | 17470 | N | ASP | D | 88 | 18.212 | −35.595 | 60.451 | 1.00 | 53.34 N |
| ATOM | 17471 | CA | ASP | D | 88 | 18.494 | −36.991 | 60.081 | 1.00 | 53.92 C |
| ATOM | 17473 | CB | ASP | D | 88 | 19.123 | −37.738 | 61.260 | 1.00 | 54.55 C |
| ATOM | 17476 | CG | ASP | D | 88 | 20.589 | −37.455 | 61.401 | 1.00 | 59.30 C |
| ATOM | 17477 | OD1 | ASP | D | 88 | 21.101 | −36.570 | 60.673 | 1.00 | 59.28 O |
| ATOM | 17478 | OD2 | ASP | D | 88 | 21.232 | −38.133 | 62.234 | 1.00 | 69.41 O |
| ATOM | 17479 | C | ASP | D | 88 | 17.287 | −37.786 | 59.610 | 1.00 | 53.60 C |
| ATOM | 17480 | O | ASP | D | 88 | 17.455 | −38.845 | 59.018 | 1.00 | 55.99 O |
| ATOM | 17482 | N | GLN | D | 89 | 16.088 | −37.302 | 59.893 | 1.00 | 51.21 N |
| ATOM | 17483 | CA | GLN | D | 89 | 14.887 | −37.953 | 59.425 | 1.00 | 52.09 C |
| ATOM | 17485 | CB | GLN | D | 89 | 13.964 | −38.252 | 60.611 | 1.00 | 52.89 C |
| ATOM | 17488 | CG | GLN | D | 89 | 14.633 | −38.947 | 61.791 | 1.00 | 55.87 C |
| ATOM | 17491 | CD | GLN | D | 89 | 15.023 | −40.398 | 61.500 | 1.00 | 65.01 C |
| ATOM | 17492 | OE1 | GLN | D | 89 | 15.962 | −40.664 | 60.747 | 1.00 | 71.22 O |
| ATOM | 17493 | NE2 | GLN | D | 89 | 14.318 | −41.340 | 62.122 | 1.00 | 64.03 N |
| ATOM | 17496 | C | GLN | D | 89 | 14.180 | −37.071 | 58.382 | 1.00 | 52.21 C |
| ATOM | 17497 | O | GLN | D | 89 | 12.944 | −37.020 | 58.343 | 1.00 | 51.02 O |
| ATOM | 17499 | N | GLY | D | 90 | 14.964 | −36.383 | 57.543 | 1.00 | 50.99 N |
| ATOM | 17500 | CA | GLY | D | 90 | 14.426 | −35.471 | 56.518 | 1.00 | 50.85 C |
| ATOM | 17503 | C | GLY | D | 90 | 13.410 | −34.456 | 57.031 | 1.00 | 51.11 C |
| ATOM | 17504 | O | GLY | D | 90 | 12.399 | −34.172 | 56.377 | 1.00 | 49.62 O |
| ATOM | 17506 | N | ASN | D | 91 | 13.680 | −33.906 | 58.209 | 1.00 | 50.10 N |
| ATOM | 17507 | CA | ASN | D | 91 | 12.744 | −33.010 | 58.862 | 1.00 | 49.16 C |
| ATOM | 17509 | CB | ASN | D | 91 | 12.176 | −33.674 | 60.105 | 1.00 | 48.68 C |
| ATOM | 17512 | CG | ASN | D | 91 | 10.987 | −32.939 | 60.664 | 1.00 | 47.44 C |
| ATOM | 17513 | OD1 | ASN | D | 91 | 10.008 | −33.549 | 61.065 | 1.00 | 41.58 O |
| ATOM | 17514 | ND2 | ASN | D | 91 | 11.060 | −31.620 | 60.685 | 1.00 | 53.16 N |
| ATOM | 17517 | C | ASN | D | 91 | 13.456 | −31.715 | 59.210 | 1.00 | 49.71 C |
| ATOM | 17518 | O | ASN | D | 91 | 14.389 | −31.710 | 60.019 | 1.00 | 50.12 O |
| ATOM | 17520 | N | PHE | D | 92 | 13.004 | −30.626 | 58.586 | 1.00 | 48.98 N |
| ATOM | 17521 | CA | PHE | D | 92 | 13.711 | −29.357 | 58.588 | 1.00 | 47.76 C |
| ATOM | 17523 | CB | PHE | D | 92 | 14.259 | −29.065 | 57.193 | 1.00 | 49.53 C |
| ATOM | 17526 | CG | PHE | D | 92 | 14.925 | −30.240 | 56.558 | 1.00 | 51.11 C |
| ATOM | 17527 | CD1 | PHE | D | 92 | 15.832 | −31.009 | 57.274 | 1.00 | 53.50 C |
| ATOM | 17529 | CE1 | PHE | D | 92 | 16.440 | −32.099 | 56.697 | 1.00 | 54.86 C |
| ATOM | 17531 | CZ | PHE | D | 92 | 16.150 | −32.440 | 55.385 | 1.00 | 57.58 C |
| ATOM | 17533 | CE2 | PHE | D | 92 | 15.244 | −31.690 | 54.662 | 1.00 | 55.72 C |
| ATOM | 17535 | CD2 | PHE | D | 92 | 14.639 | −30.592 | 55.250 | 1.00 | 55.78 C |
| ATOM | 17537 | C | PHE | D | 92 | 12.761 | −28.270 | 59.001 | 1.00 | 46.74 C |
| ATOM | 17538 | O | PHE | D | 92 | 12.443 | −27.391 | 58.204 | 1.00 | 46.60 O |
| ATOM | 17540 | N | PRO | D | 93 | 12.319 | −28.307 | 60.262 | 1.00 | 46.04 N |
| ATOM | 17541 | CA | PRO | D | 93 | 11.266 | −27.408 | 60.661 | 1.00 | 46.87 C |
| ATOM | 17543 | CB | PRO | D | 93 | 10.712 | −28.060 | 61.925 | 1.00 | 48.35 C |

| | | | | | | | | | | |
|---|---|---|---|---|---|---|---|---|---|---|
| ATOM | 17546 | CG | PRO | D | 93 | 11.861 | −28.786 | 62.509 | 1.00 | 46.63 C |
| ATOM | 17549 | CD | PRO | D | 93 | 12.796 | −29.127 | 61.388 | 1.00 | 46.27 C |
| ATOM | 17552 | C | PRO | D | 93 | 11.815 | −26.043 | 60.987 | 1.00 | 48.35 C |
| ATOM | 17553 | O | PRO | D | 93 | 12.992 | −25.913 | 61.351 | 1.00 | 48.65 O |
| ATOM | 17554 | N | LEU | D | 94 | 10.959 | −25.041 | 60.826 | 1.00 | 48.56 N |
| ATOM | 17555 | CA | LEU | D | 94 | 11.221 | −23.685 | 61.269 | 1.00 | 47.67 C |
| ATOM | 17557 | CB | LEU | D | 94 | 10.887 | −22.698 | 60.160 | 1.00 | 46.80 C |
| ATOM | 17560 | CG | LEU | D | 94 | 10.929 | −21.208 | 60.495 | 1.00 | 47.25 C |
| ATOM | 17562 | CD1 | LEU | D | 94 | 12.293 | −20.835 | 61.068 | 1.00 | 48.22 C |
| ATOM | 17566 | CD2 | LEU | D | 94 | 10.604 | −20.384 | 59.242 | 1.00 | 45.98 C |
| ATOM | 17570 | C | LEU | D | 94 | 10.313 | −23.454 | 62.457 | 1.00 | 49.54 C |
| ATOM | 17571 | O | LEU | D | 94 | 9.080 | −23.465 | 62.310 | 1.00 | 48.55 O |
| ATOM | 17573 | N | ILE | D | 95 | 10.917 | −23.268 | 63.632 | 1.00 | 50.54 N |
| ATOM | 17574 | CA | ILE | D | 95 | 10.169 | −23.016 | 64.864 | 1.00 | 50.79 C |
| ATOM | 17576 | CB | ILE | D | 95 | 10.653 | −23.912 | 66.021 | 1.00 | 49.82 C |
| ATOM | 17578 | CG1 | ILE | D | 95 | 10.956 | −25.322 | 65.511 | 1.00 | 50.38 C |
| ATOM | 17581 | CD1 | ILE | D | 95 | 11.032 | −26.388 | 66.588 | 1.00 | 49.96 C |
| ATOM | 17585 | CG2 | ILE | D | 95 | 9.604 | −23.951 | 67.120 | 1.00 | 51.11 C |
| ATOM | 17589 | C | ILE | D | 95 | 10.307 | −21.546 | 65.270 | 1.00 | 53.06 C |
| ATOM | 17590 | O | ILE | D | 95 | 11.423 | −20.995 | 65.279 | 1.00 | 56.14 O |
| ATOM | 17592 | N | ILE | D | 96 | 9.181 | −20.919 | 65.615 | 1.00 | 52.52 N |
| ATOM | 17593 | CA | ILE | D | 96 | 9.170 | −19.500 | 65.963 | 1.00 | 52.98 C |
| ATOM | 17595 | CB | ILE | D | 96 | 8.468 | −18.688 | 64.868 | 1.00 | 51.34 C |
| ATOM | 17597 | CG1 | ILE | D | 96 | 9.101 | −19.011 | 63.512 | 1.00 | 50.27 C |
| ATOM | 17600 | CD1 | ILE | D | 96 | 8.559 | −18.211 | 62.354 | 1.00 | 54.15 C |
| ATOM | 17604 | CG2 | ILE | D | 96 | 8.557 | −17.193 | 65.164 | 1.00 | 51.83 C |
| ATOM | 17608 | C | ILE | D | 96 | 8.522 | −19.241 | 67.336 | 1.00 | 54.32 C |
| ATOM | 17609 | O | ILE | D | 96 | 7.325 | −19.424 | 67.491 | 1.00 | 55.46 O |
| ATOM | 17611 | N | LYS | D | 97 | 9.341 | −18.793 | 68.296 | 1.00 | 55.29 N |
| ATOM | 17612 | CA | LYS | D | 97 | 8.935 | −18.449 | 69.670 | 1.00 | 56.12 C |
| ATOM | 17614 | CB | LYS | D | 97 | 10.170 | −18.334 | 70.578 | 1.00 | 57.63 C |
| ATOM | 17617 | CG | LYS | D | 97 | 11.124 | −19.532 | 70.601 | 1.00 | 62.44 C |
| ATOM | 17620 | CD | LYS | D | 97 | 12.533 | −19.131 | 71.085 | 1.00 | 62.68 C |
| ATOM | 17623 | CE | LYS | D | 97 | 13.637 | −19.851 | 70.277 | 1.00 | 68.50 C |
| ATOM | 17626 | NZ | LYS | D | 97 | 15.035 | −19.394 | 70.616 | 1.00 | 67.47 N |
| ATOM | 17630 | C | LYS | D | 97 | 8.240 | −17.091 | 69.740 | 1.00 | 56.64 C |
| ATOM | 17631 | O | LYS | D | 97 | 8.506 | −16.204 | 68.924 | 1.00 | 54.64 O |
| ATOM | 17633 | N | ASN | D | 98 | 7.383 | −16.916 | 70.744 | 1.00 | 56.52 N |
| ATOM | 17634 | CA | ASN | D | 98 | 6.769 | −15.619 | 71.011 | 1.00 | 55.97 C |
| ATOM | 17636 | CB | ASN | D | 98 | 7.737 | −14.729 | 71.770 | 1.00 | 56.98 C |
| ATOM | 17639 | CG | ASN | D | 98 | 8.271 | −15.388 | 72.998 | 1.00 | 61.78 C |
| ATOM | 17640 | OD1 | ASN | D | 98 | 9.489 | −15.509 | 73.171 | 1.00 | 69.09 O |
| ATOM | 17641 | ND2 | ASN | D | 98 | 7.368 | −15.844 | 73.864 | 1.00 | 67.30 N |
| ATOM | 17644 | C | ASN | D | 98 | 6.323 | −14.908 | 69.745 | 1.00 | 55.57 C |
| ATOM | 17645 | O | ASN | D | 98 | 6.728 | −13.770 | 69.467 | 1.00 | 57.09 O |
| ATOM | 17647 | N | LEU | D | 99 | 5.483 | −15.591 | 68.980 | 1.00 | 53.56 N |
| ATOM | 17648 | CA | LEU | D | 99 | 4.948 | −15.035 | 67.756 | 1.00 | 52.64 C |
| ATOM | 17650 | CB | LEU | D | 99 | 3.770 | −15.873 | 67.280 | 1.00 | 53.96 C |
| ATOM | 17653 | CG | LEU | D | 99 | 4.075 | −17.191 | 66.583 | 1.00 | 51.73 C |
| ATOM | 17655 | CD1 | LEU | D | 99 | 2.873 | −18.088 | 66.695 | 1.00 | 52.25 C |
| ATOM | 17659 | CD2 | LEU | D | 99 | 4.445 | −16.943 | 65.131 | 1.00 | 49.58 C |
| ATOM | 17663 | C | LEU | D | 99 | 4.453 | −13.629 | 67.988 | 1.00 | 50.70 C |
| ATOM | 17664 | O | LEU | D | 99 | 3.723 | −13.381 | 68.943 | 1.00 | 50.72 O |
| ATOM | 17666 | N | LYS | D | 100 | 4.866 | −12.717 | 67.121 | 1.00 | 49.61 N |
| ATOM | 17667 | CA | LYS | D | 100 | 4.215 | −11.424 | 66.997 | 1.00 | 50.36 C |
| ATOM | 17669 | CB | LYS | D | 100 | 5.235 | −10.338 | 66.669 | 1.00 | 51.27 C |
| ATOM | 17672 | CG | LYS | D | 100 | 6.370 | −10.242 | 67.678 | 1.00 | 54.97 C |
| ATOM | 17675 | CD | LYS | D | 100 | 7.345 | −9.134 | 67.337 | 1.00 | 51.88 C |
| ATOM | 17678 | CE | LYS | D | 100 | 8.586 | −9.224 | 68.205 | 1.00 | 55.94 C |
| ATOM | 17681 | NZ | LYS | D | 100 | 9.628 | −8.233 | 67.777 | 1.00 | 65.64 N |
| ATOM | 17685 | C | LYS | D | 100 | 3.167 | −11.519 | 65.884 | 1.00 | 50.00 C |
| ATOM | 17686 | O | LYS | D | 100 | 3.186 | −12.460 | 65.081 | 1.00 | 47.49 O |
| ATOM | 17688 | N | ILE | D | 101 | 2.246 | −10.557 | 65.842 | 1.00 | 50.48 N |
| ATOM | 17689 | CA | ILE | D | 101 | 1.294 | −10.491 | 64.745 | 1.00 | 49.48 C |
| ATOM | 17691 | CB | ILE | D | 101 | 0.272 | −9.331 | 64.879 | 1.00 | 51.04 C |
| ATOM | 17693 | CG1 | ILE | D | 101 | −1.038 | −9.808 | 65.517 | 1.00 | 52.16 C |
| ATOM | 17696 | CD1 | ILE | D | 101 | −0.890 | −10.467 | 66.844 | 1.00 | 58.31 C |
| ATOM | 17700 | CG2 | ILE | D | 101 | −0.102 | −8.761 | 63.501 | 1.00 | 52.45 C |
| ATOM | 17704 | C | ILE | D | 101 | 2.065 | −10.336 | 63.453 | 1.00 | 49.70 C |
| ATOM | 17705 | O | ILE | D | 101 | 1.709 | −10.968 | 62.460 | 1.00 | 51.08 O |
| ATOM | 17707 | N | GLU | D | 102 | 3.124 | −9.517 | 63.467 | 1.00 | 48.47 N |
| ATOM | 17708 | CA | GLU | D | 102 | 3.848 | −9.191 | 62.233 | 1.00 | 47.42 C |
| ATOM | 17710 | CB | GLU | D | 102 | 4.536 | −7.815 | 62.318 | 1.00 | 48.71 C |
| ATOM | 17713 | CG | GLU | D | 102 | 5.879 | −7.740 | 63.067 | 1.00 | 56.38 C |
| ATOM | 17716 | CD | GLU | D | 102 | 5.794 | −6.997 | 64.401 | 1.00 | 61.88 C |
| ATOM | 17717 | OE1 | GLU | D | 102 | 4.836 | −7.259 | 65.184 | 1.00 | 62.54 O |
| ATOM | 17718 | OE2 | GLU | D | 102 | 6.700 | −6.163 | 64.655 | 1.00 | 56.63 O |
| ATOM | 17719 | C | GLU | D | 102 | 4.819 | −10.268 | 61.729 | 1.00 | 46.05 C |
| ATOM | 17720 | O | GLU | D | 102 | 5.528 | −10.030 | 60.758 | 1.00 | 45.71 O |

-continued

| | | | | | | | | | | |
|---|---|---|---|---|---|---|---|---|---|---|
| ATOM | 17722 | N | ASP | D | 103 | 4.853 | −11.436 | 62.375 | 1.00 | 47.39 N |
| ATOM | 17723 | CA | ASP | D | 103 | 5.526 | −12.626 | 61.814 | 1.00 | 47.66 C |
| ATOM | 17725 | CB | ASP | D | 103 | 5.779 | −13.697 | 62.887 | 1.00 | 47.98 C |
| ATOM | 17728 | CG | ASP | D | 103 | 6.707 | −13.237 | 63.990 | 1.00 | 49.22 C |
| ATOM | 17729 | OD1 | ASP | D | 103 | 7.691 | −12.543 | 63.703 | 1.00 | 55.42 O |
| ATOM | 17730 | OD2 | ASP | D | 103 | 6.464 | −13.592 | 65.158 | 1.00 | 56.95 O |
| ATOM | 17731 | C | ASP | D | 103 | 4.683 | −13.276 | 60.715 | 1.00 | 48.59 C |
| ATOM | 17732 | O | ASP | D | 103 | 5.165 | −14.165 | 60.001 | 1.00 | 48.20 O |
| ATOM | 17734 | N | SER | D | 104 | 3.410 | −12.877 | 60.618 | 1.00 | 49.63 N |
| ATOM | 17735 | CA | SER | D | 104 | 2.503 | −13.423 | 59.607 | 1.00 | 47.43 C |
| ATOM | 17737 | CB | SER | D | 104 | 1.097 | −12.835 | 59.724 | 1.00 | 46.44 C |
| ATOM | 17740 | OG | SER | D | 104 | 0.576 | −12.950 | 61.035 | 1.00 | 47.73 O |
| ATOM | 17742 | C | SER | D | 104 | 3.076 | −13.096 | 58.244 | 1.00 | 47.63 C |
| ATOM | 17743 | O | SER | D | 104 | 3.334 | −11.927 | 57.925 | 1.00 | 49.32 O |
| ATOM | 17745 | N | ASP | D | 105 | 3.292 | −14.150 | 57.471 | 1.00 | 46.35 N |
| ATOM | 17746 | CA | ASP | D | 105 | 3.961 | −14.081 | 56.187 | 1.00 | 45.68 C |
| ATOM | 17748 | CB | ASP | D | 105 | 5.454 | −13.751 | 56.379 | 1.00 | 44.54 C |
| ATOM | 17751 | CG | ASP | D | 105 | 6.113 | −13.157 | 55.126 | 1.00 | 45.86 C |
| ATOM | 17752 | OD1 | ASP | D | 105 | 5.564 | −13.269 | 54.003 | 1.00 | 40.32 O |
| ATOM | 17753 | OD2 | ASP | D | 105 | 7.202 | −12.567 | 55.274 | 1.00 | 46.39 O |
| ATOM | 17754 | C | ASP | D | 105 | 3.802 | −15.454 | 55.504 | 1.00 | 45.18 C |
| ATOM | 17755 | O | ASP | D | 105 | 3.259 | −16.411 | 56.081 | 1.00 | 39.80 O |
| ATOM | 17757 | N | THR | D | 106 | 4.250 | −15.517 | 54.261 | 1.00 | 45.62 N |
| ATOM | 17758 | CA | THR | D | 106 | 4.394 | −16.758 | 53.564 | 1.00 | 46.95 C |
| ATOM | 17760 | CB | THR | D | 106 | 3.878 | −16.656 | 52.124 | 1.00 | 45.75 C |
| ATOM | 17762 | OG1 | THR | D | 106 | 2.455 | −16.789 | 52.146 | 1.00 | 43.96 O |
| ATOM | 17764 | CG2 | THR | D | 106 | 4.454 | −17.747 | 51.236 | 1.00 | 46.64 C |
| ATOM | 17768 | C | THR | D | 106 | 5.865 | −17.100 | 53.628 | 1.00 | 49.23 C |
| ATOM | 17769 | O | THR | D | 106 | 6.714 | −16.306 | 53.231 | 1.00 | 53.20 O |
| ATOM | 17771 | N | TYR | D | 107 | 6.149 | −18.280 | 54.166 | 1.00 | 50.82 N |
| ATOM | 17772 | CA | TYR | D | 107 | 7.497 | −18.771 | 54.304 | 1.00 | 50.99 C |
| ATOM | 17774 | CB | TYR | D | 107 | 7.712 | −19.296 | 55.710 | 1.00 | 49.84 C |
| ATOM | 17777 | CG | TYR | D | 107 | 7.688 | −18.190 | 56.719 | 1.00 | 47.46 C |
| ATOM | 17778 | CD1 | TYR | D | 107 | 6.502 | −17.814 | 57.335 | 1.00 | 48.00 C |
| ATOM | 17780 | CE1 | TYR | D | 107 | 6.465 | −16.776 | 58.261 | 1.00 | 49.53 C |
| ATOM | 17782 | CZ | TYR | D | 107 | 7.623 | −16.097 | 58.571 | 1.00 | 51.13 C |
| ATOM | 17783 | OH | TYR | D | 107 | 7.589 | −15.069 | 59.492 | 1.00 | 49.82 O |
| ATOM | 17785 | CE2 | TYR | D | 107 | 8.822 | −16.447 | 57.953 | 1.00 | 51.42 C |
| ATOM | 17787 | CD2 | TYR | D | 107 | 8.845 | −17.487 | 57.030 | 1.00 | 46.99 C |
| ATOM | 17789 | C | TYR | D | 107 | 7.709 | −19.846 | 53.271 | 1.00 | 53.47 C |
| ATOM | 17790 | O | TYR | D | 107 | 6.800 | −20.614 | 52.983 | 1.00 | 55.68 O |
| ATOM | 17792 | N | ILE | D | 108 | 8.912 | −19.873 | 52.705 | 1.00 | 54.50 N |
| ATOM | 17793 | CA | ILE | D | 108 | 9.221 | −20.712 | 51.571 | 1.00 | 54.69 C |
| ATOM | 17795 | CB | ILE | D | 108 | 9.639 | −19.874 | 50.370 | 1.00 | 55.47 C |
| ATOM | 17797 | CG1 | ILE | D | 108 | 8.763 | −18.620 | 50.247 | 1.00 | 58.98 C |
| ATOM | 17800 | CD1 | ILE | D | 108 | 9.438 | −17.485 | 49.470 | 1.00 | 59.41 C |
| ATOM | 17804 | CG2 | ILE | D | 108 | 9.564 | −20.713 | 49.106 | 1.00 | 54.90 C |
| ATOM | 17808 | C | ILE | D | 108 | 10.393 | −21.572 | 51.946 | 1.00 | 54.85 C |
| ATOM | 17809 | O | ILE | D | 108 | 11.366 | −21.072 | 52.483 | 1.00 | 55.07 O |
| ATOM | 17811 | N | CYS | D | 109 | 10.302 | −22.861 | 51.649 | 1.00 | 57.10 N |
| ATOM | 17812 | CA | CYS | D | 109 | 11.345 | −23.814 | 51.988 | 1.00 | 55.92 C |
| ATOM | 17814 | CB | CYS | D | 109 | 10.786 | −24.891 | 52.921 | 1.00 | 58.35 C |
| ATOM | 17817 | SG | CYS | D | 109 | 12.043 | −25.973 | 53.691 | 1.00 | 63.70 S |
| ATOM | 17819 | C | CYS | D | 109 | 11.873 | −24.437 | 50.708 | 1.00 | 54.59 C |
| ATOM | 17820 | O | CYS | D | 109 | 11.207 | −25.266 | 50.094 | 1.00 | 53.53 O |
| ATOM | 17822 | N | GLU | D | 110 | 13.067 | −24.026 | 50.301 | 1.00 | 53.89 N |
| ATOM | 17823 | CA | GLU | D | 110 | 13.667 | −24.522 | 49.078 | 1.00 | 54.43 C |
| ATOM | 17825 | CB | GLU | D | 110 | 14.624 | −23.488 | 48.502 | 1.00 | 53.55 C |
| ATOM | 17828 | CG | GLU | D | 110 | 14.007 | −22.109 | 48.290 | 1.00 | 57.55 C |
| ATOM | 17831 | CD | GLU | D | 110 | 15.000 | −21.092 | 47.744 | 1.00 | 59.72 C |
| ATOM | 17832 | OE1 | GLU | D | 110 | 16.207 | −21.178 | 48.083 | 1.00 | 69.01 O |
| ATOM | 17833 | OE2 | GLU | D | 110 | 14.571 | −20.203 | 46.976 | 1.00 | 62.17 O |
| ATOM | 17834 | C | GLU | D | 110 | 14.407 | −25.808 | 49.414 | 1.00 | 54.19 C |
| ATOM | 17835 | O | GLU | D | 110 | 15.289 | −25.802 | 50.271 | 1.00 | 53.94 O |
| ATOM | 17837 | N | VAL | D | 111 | 14.035 | −26.906 | 48.756 | 1.00 | 54.36 N |
| ATOM | 17838 | CA | VAL | D | 111 | 14.659 | −28.211 | 48.988 | 1.00 | 55.10 C |
| ATOM | 17840 | CB | VAL | D | 111 | 14.183 | −28.822 | 50.327 | 1.00 | 53.51 C |
| ATOM | 17842 | CG1 | VAL | D | 111 | 12.685 | −29.136 | 50.305 | 1.00 | 51.44 C |
| ATOM | 17846 | CG2 | VAL | D | 111 | 14.997 | −30.056 | 50.669 | 1.00 | 54.35 C |
| ATOM | 17850 | C | VAL | D | 111 | 14.394 | −29.194 | 47.832 | 1.00 | 57.12 C |
| ATOM | 17851 | O | VAL | D | 111 | 13.244 | −29.495 | 47.522 | 1.00 | 58.09 O |
| ATOM | 17853 | N | GLU | D | 112 | 15.462 | −29.684 | 47.201 | 1.00 | 59.76 N |
| ATOM | 17854 | CA | GLU | D | 112 | 15.366 | −30.585 | 46.039 | 1.00 | 61.43 C |
| ATOM | 17856 | CB | GLU | D | 112 | 14.718 | −31.931 | 46.424 | 1.00 | 62.31 C |
| ATOM | 17859 | CG | GLU | D | 112 | 15.297 | −32.668 | 47.631 | 1.00 | 61.85 C |
| ATOM | 17862 | CD | GLU | D | 112 | 14.346 | −33.755 | 48.145 | 1.00 | 62.28 C |
| ATOM | 17863 | OE1 | GLU | D | 112 | 13.305 | −33.413 | 48.754 | 1.00 | 60.57 O |
| ATOM | 17864 | OE2 | GLU | D | 112 | 14.632 | −34.952 | 47.939 | 1.00 | 62.56 O |
| ATOM | 17865 | C | GLU | D | 112 | 14.573 | −29.964 | 44.870 | 1.00 | 63.64 C |

| | | | | | | | | | | |
|---|---|---|---|---|---|---|---|---|---|---|
| ATOM | 17866 | O | GLU | D | 112 | 13.701 | −30.619 | 44.279 | 1.00 | 64.99 O |
| ATOM | 17868 | N | ASP | D | 113 | 14.867 | −28.709 | 44.535 | 1.00 | 64.25 N |
| ATOM | 17869 | CA | ASP | D | 113 | 14.118 | −27.990 | 43.487 | 1.00 | 64.40 C |
| ATOM | 17871 | CB | ASP | D | 113 | 14.372 | −28.605 | 42.108 | 1.00 | 64.94 C |
| ATOM | 17874 | CG | ASP | D | 113 | 15.826 | −28.914 | 41.881 | 1.00 | 67.23 C |
| ATOM | 17875 | OD1 | ASP | D | 113 | 16.661 | −28.062 | 42.245 | 1.00 | 69.33 O |
| ATOM | 17876 | OD2 | ASP | D | 113 | 16.134 | −30.007 | 41.357 | 1.00 | 72.39 O |
| ATOM | 17877 | C | ASP | D | 113 | 12.626 | −27.993 | 43.771 | 1.00 | 63.70 C |
| ATOM | 17878 | O | ASP | D | 113 | 11.822 | −28.188 | 42.870 | 1.00 | 62.08 O |
| ATOM | 17880 | N | GLN | D | 114 | 12.280 | −27.808 | 45.042 | 1.00 | 65.47 N |
| ATOM | 17881 | CA | GLN | D | 114 | 10.899 | −27.615 | 45.475 | 1.00 | 66.02 C |
| ATOM | 17883 | CB | GLN | D | 114 | 10.473 | −28.703 | 46.462 | 1.00 | 65.08 C |
| ATOM | 17886 | CG | GLN | D | 114 | 10.479 | −30.093 | 45.884 | 1.00 | 64.18 C |
| ATOM | 17889 | CD | GLN | D | 114 | 9.546 | −30.225 | 44.701 | 1.00 | 63.51 C |
| ATOM | 17890 | OE1 | GLN | D | 114 | 9.862 | −30.898 | 43.724 | 1.00 | 63.23 O |
| ATOM | 17891 | NE2 | GLN | D | 114 | 8.392 | −29.570 | 44.777 | 1.00 | 61.91 N |
| ATOM | 17894 | C | GLN | D | 114 | 10.801 | −26.276 | 46.169 | 1.00 | 66.99 C |
| ATOM | 17895 | O | GLN | D | 114 | 11.816 | −25.649 | 46.472 | 1.00 | 67.91 O |
| ATOM | 17897 | N | LYS | D | 115 | 9.572 | −25.845 | 46.417 | 1.00 | 67.54 N |
| ATOM | 17898 | CA | LYS | D | 115 | 9.323 | −24.680 | 47.237 | 1.00 | 68.05 C |
| ATOM | 17900 | CB | LYS | D | 115 | 9.155 | −23.438 | 46.354 | 1.00 | 67.67 C |
| ATOM | 17903 | CG | LYS | D | 115 | 10.415 | −23.040 | 45.562 | 1.00 | 71.79 C |
| ATOM | 17906 | CD | LYS | D | 115 | 10.427 | −21.540 | 45.151 | 1.00 | 73.30 C |
| ATOM | 17909 | CE | LYS | D | 115 | 11.334 | −20.674 | 46.061 | 1.00 | 78.19 C |
| ATOM | 17912 | NZ | LYS | D | 115 | 10.941 | −19.217 | 46.127 | 1.00 | 75.63 N |
| ATOM | 17916 | C | LYS | D | 115 | 8.087 | −24.929 | 48.110 | 1.00 | 67.97 C |
| ATOM | 17917 | O | LYS | D | 115 | 6.983 | −24.519 | 47.753 | 1.00 | 70.14 O |
| ATOM | 17919 | N | GLU | D | 116 | 8.277 | −25.613 | 49.243 | 1.00 | 66.62 N |
| ATOM | 17920 | CA | GLU | D | 116 | 7.189 | −25.823 | 50.214 | 1.00 | 65.87 C |
| ATOM | 17922 | CB | GLU | D | 116 | 7.588 | −26.693 | 51.424 | 1.00 | 67.20 C |
| ATOM | 17925 | CG | GLU | D | 116 | 8.674 | −27.768 | 51.232 | 1.00 | 72.35 C |
| ATOM | 17928 | CD | GLU | D | 116 | 8.164 | −29.092 | 50.704 | 1.00 | 74.69 C |
| ATOM | 17929 | OE1 | GLU | D | 116 | 8.984 | −29.834 | 50.107 | 1.00 | 70.69 O |
| ATOM | 17930 | OE2 | GLU | D | 116 | 6.964 | −29.399 | 50.903 | 1.00 | 81.52 O |
| ATOM | 17931 | C | GLU | D | 116 | 6.791 | −24.452 | 50.745 | 1.00 | 64.53 C |
| ATOM | 17932 | O | GLU | D | 116 | 7.580 | −23.816 | 51.433 | 1.00 | 64.43 O |
| ATOM | 17934 | N | GLU | D | 117 | 5.582 | −24.001 | 50.418 | 1.00 | 63.26 N |
| ATOM | 17935 | CA | GLU | D | 117 | 5.091 | −22.683 | 50.834 | 1.00 | 61.06 C |
| ATOM | 17937 | CB | GLU | D | 117 | 4.436 | −21.948 | 49.665 | 1.00 | 60.98 C |
| ATOM | 17940 | CG | GLU | D | 117 | 5.315 | −20.920 | 48.984 | 1.00 | 63.22 C |
| ATOM | 17943 | CD | GLU | D | 117 | 4.647 | −20.310 | 47.757 | 1.00 | 65.19 C |
| ATOM | 17944 | OE1 | GLU | D | 117 | 3.434 | −20.558 | 47.533 | 1.00 | 64.15 O |
| ATOM | 17945 | OE2 | GLU | D | 117 | 5.341 | −19.587 | 47.009 | 1.00 | 73.03 O |
| ATOM | 17946 | C | GLU | D | 117 | 4.070 | −22.824 | 51.936 | 1.00 | 58.20 C |
| ATOM | 17947 | O | GLU | D | 117 | 2.997 | −23.374 | 51.724 | 1.00 | 58.52 O |
| ATOM | 17949 | N | VAL | D | 118 | 4.405 | −22.317 | 53.110 | 1.00 | 56.15 N |
| ATOM | 17950 | CA | VAL | D | 118 | 3.475 | −22.273 | 54.213 | 1.00 | 55.15 C |
| ATOM | 17952 | CB | VAL | D | 118 | 4.103 | −22.845 | 55.483 | 1.00 | 55.28 C |
| ATOM | 17954 | CG1 | VAL | D | 118 | 3.188 | −22.623 | 56.672 | 1.00 | 59.84 C |
| ATOM | 17958 | CG2 | VAL | D | 118 | 4.383 | −24.328 | 55.309 | 1.00 | 61.55 C |
| ATOM | 17962 | C | VAL | D | 118 | 3.115 | −20.818 | 54.453 | 1.00 | 52.51 C |
| ATOM | 17963 | O | VAL | D | 118 | 3.993 | −19.973 | 54.545 | 1.00 | 46.39 O |
| ATOM | 17965 | N | GLN | D | 119 | 1.818 | −20.540 | 54.554 | 1.00 | 52.44 N |
| ATOM | 17966 | CA | GLN | D | 119 | 1.344 | −19.240 | 54.986 | 1.00 | 52.03 C |
| ATOM | 17968 | CB | GLN | D | 119 | 0.089 | −18.818 | 54.236 | 1.00 | 50.69 C |
| ATOM | 17971 | CG | GLN | D | 119 | −0.631 | −17.671 | 54.922 | 1.00 | 53.87 C |
| ATOM | 17974 | CD | GLN | D | 119 | −1.306 | −16.724 | 53.962 | 1.00 | 55.76 C |
| ATOM | 17975 | OE1 | GLN | D | 119 | −2.405 | −16.997 | 53.458 | 1.00 | 57.45 O |
| ATOM | 17976 | NE2 | GLN | D | 119 | −0.665 | −15.578 | 53.723 | 1.00 | 56.47 N |
| ATOM | 17979 | C | GLN | D | 119 | 1.059 | −19.272 | 56.478 | 1.00 | 50.84 C |
| ATOM | 17980 | O | GLN | D | 119 | 0.174 | −19.975 | 56.936 | 1.00 | 48.06 O |
| ATOM | 17982 | N | LEU | D | 120 | 1.818 | −18.491 | 57.232 | 1.00 | 52.34 N |
| ATOM | 17983 | CA | LEU | D | 120 | 1.591 | −18.369 | 58.655 | 1.00 | 52.02 C |
| ATOM | 17985 | CB | LEU | D | 120 | 2.914 | −18.234 | 59.416 | 1.00 | 52.51 C |
| ATOM | 17988 | CG | LEU | D | 120 | 2.787 | −17.939 | 60.914 | 1.00 | 50.64 C |
| ATOM | 17990 | CD1 | LEU | D | 120 | 1.981 | −19.026 | 61.621 | 1.00 | 47.00 C |
| ATOM | 17994 | CD2 | LEU | D | 120 | 4.156 | −17.778 | 61.533 | 1.00 | 52.44 C |
| ATOM | 17998 | C | LEU | D | 120 | 0.759 | −17.132 | 58.867 | 1.00 | 50.99 C |
| ATOM | 17999 | O | LEU | D | 120 | 1.141 | −16.065 | 58.410 | 1.00 | 50.93 O |
| ATOM | 18001 | N | LEU | D | 121 | −0.374 | −17.300 | 59.552 | 1.00 | 51.58 N |
| ATOM | 18002 | CA | LEU | D | 121 | −1.225 | −16.205 | 60.006 | 1.00 | 50.99 C |
| ATOM | 18004 | CB | LEU | D | 121 | −2.630 | −16.346 | 59.413 | 1.00 | 50.35 C |
| ATOM | 18007 | CG | LEU | D | 121 | −2.689 | −15.954 | 57.929 | 1.00 | 52.37 C |
| ATOM | 18009 | CD1 | LEU | D | 121 | −3.940 | −16.455 | 57.222 | 1.00 | 53.89 C |
| ATOM | 18013 | CD2 | LEU | D | 121 | −2.587 | −14.461 | 57.789 | 1.00 | 56.04 C |
| ATOM | 18017 | C | LEU | D | 121 | −1.293 | −16.221 | 61.528 | 1.00 | 52.40 C |
| ATOM | 18018 | O | LEU | D | 121 | −1.696 | −17.243 | 62.133 | 1.00 | 55.35 O |
| ATOM | 18020 | N | VAL | D | 122 | −0.901 | −15.099 | 62.139 | 1.00 | 50.06 N |
| ATOM | 18021 | CA | VAL | D | 122 | −0.848 | −14.970 | 63.596 | 1.00 | 51.75 C |

-continued

| | | | | | | | | | | |
|---|---|---|---|---|---|---|---|---|---|---|
| ATOM | 18023 | CB | VAL | D | 122 | 0.512 | −14.425 | 64.017 | 1.00 | 50.92 C |
| ATOM | 18025 | CG1 | VAL | D | 122 | 0.522 | −14.084 | 65.503 | 1.00 | 53.45 C |
| ATOM | 18029 | CG2 | VAL | D | 122 | 1.584 | −15.436 | 63.683 | 1.00 | 51.19 C |
| ATOM | 18033 | C | VAL | D | 122 | −1.948 | −14.055 | 64.153 | 1.00 | 53.51 C |
| ATOM | 18034 | O | VAL | D | 122 | −2.012 | −12.882 | 63.782 | 1.00 | 57.15 O |
| ATOM | 18036 | N | PHE | D | 123 | −2.787 | −14.582 | 65.054 | 1.00 | 53.51 N |
| ATOM | 18037 | CA | PHE | D | 123 | −3.913 | −13.821 | 65.627 | 1.00 | 53.99 C |
| ATOM | 18039 | CB | PHE | D | 123 | −5.248 | −14.512 | 65.363 | 1.00 | 54.15 C |
| ATOM | 18042 | CG | PHE | D | 123 | −5.569 | −14.697 | 63.915 | 1.00 | 54.30 C |
| ATOM | 18043 | CD1 | PHE | D | 123 | −5.834 | −13.610 | 63.111 | 1.00 | 49.61 C |
| ATOM | 18045 | CE1 | PHE | D | 123 | −6.140 | −13.780 | 61.786 | 1.00 | 49.05 C |
| ATOM | 18047 | CZ | PHE | D | 123 | −6.180 | −15.040 | 61.243 | 1.00 | 53.38 C |
| ATOM | 18049 | CE2 | PHE | D | 123 | −5.919 | −16.140 | 62.033 | 1.00 | 54.85 C |
| ATOM | 18051 | CD2 | PHE | D | 123 | −5.624 | −15.967 | 63.363 | 1.00 | 55.54 C |
| ATOM | 18053 | C | PHE | D | 123 | −3.813 | −13.680 | 67.131 | 1.00 | 55.49 C |
| ATOM | 18054 | O | PHE | D | 123 | −3.332 | −14.579 | 67.804 | 1.00 | 54.10 O |
| ATOM | 18056 | N | GLY | D | 124 | −4.309 | −12.557 | 67.647 | 1.00 | 57.23 N |
| ATOM | 18057 | CA | GLY | D | 124 | −4.513 | −12.364 | 69.084 | 1.00 | 56.46 C |
| ATOM | 18060 | C | GLY | D | 124 | −5.910 | −11.830 | 69.380 | 1.00 | 56.28 C |
| ATOM | 18061 | O | GLY | D | 124 | −6.446 | −11.046 | 68.608 | 1.00 | 57.45 O |
| ATOM | 18063 | N | LEU | D | 125 | −6.484 | −12.254 | 70.505 | 1.00 | 55.86 N |
| ATOM | 18064 | CA | LEU | D | 125 | −7.801 | −11.808 | 70.973 | 1.00 | 55.02 C |
| ATOM | 18066 | CB | LEU | D | 125 | −8.688 | −13.024 | 71.239 | 1.00 | 55.80 C |
| ATOM | 18069 | CG | LEU | D | 125 | −10.175 | −12.762 | 71.473 | 1.00 | 56.79 C |
| ATOM | 18071 | CD1 | LEU | D | 125 | −10.796 | −12.208 | 70.205 | 1.00 | 61.17 C |
| ATOM | 18075 | CD2 | LEU | D | 125 | −10.888 | −14.021 | 71.887 | 1.00 | 55.80 C |
| ATOM | 18079 | C | LEU | D | 125 | −7.663 | −11.006 | 72.270 | 1.00 | 55.05 C |
| ATOM | 18080 | O | LEU | D | 125 | −6.934 | −11.397 | 73.173 | 1.00 | 57.75 O |
| ATOM | 18082 | N | THR | D | 126 | −8.397 | −9.909 | 72.384 | 1.00 | 55.30 N |
| ATOM | 18083 | CA | THR | D | 126 | −8.227 | −8.988 | 73.505 | 1.00 | 54.22 C |
| ATOM | 18085 | CB | THR | D | 126 | −7.120 | −7.994 | 73.183 | 1.00 | 53.58 C |
| ATOM | 18087 | OG1 | THR | D | 126 | −7.204 | −6.891 | 74.083 | 1.00 | 61.96 O |
| ATOM | 18089 | CG2 | THR | D | 126 | −7.258 | −7.467 | 71.759 | 1.00 | 53.99 C |
| ATOM | 18093 | C | THR | D | 126 | −9.504 | −8.204 | 73.839 | 1.00 | 53.09 C |
| ATOM | 18094 | O | THR | D | 126 | −10.285 | −7.879 | 72.952 | 1.00 | 55.22 O |
| ATOM | 18096 | N | ALA | D | 127 | −9.701 | −7.888 | 75.116 | 1.00 | 52.00 N |
| ATOM | 18097 | CA | ALA | D | 127 | −10.840 | −7.073 | 75.553 | 1.00 | 53.40 C |
| ATOM | 18099 | CB | ALA | D | 127 | −11.373 | −7.588 | 76.872 | 1.00 | 51.75 C |
| ATOM | 18103 | C | ALA | D | 127 | −10.469 | −5.584 | 75.683 | 1.00 | 54.20 C |
| ATOM | 18104 | O | ALA | D | 127 | −9.404 | −5.239 | 76.188 | 1.00 | 51.57 O |
| ATOM | 18106 | N | ASN | D | 128 | −11.374 | −4.712 | 75.246 | 1.00 | 56.15 N |
| ATOM | 18107 | CA | ASN | D | 128 | −11.171 | −3.262 | 75.325 | 1.00 | 58.00 C |
| ATOM | 18109 | CB | ASN | D | 128 | −12.225 | −2.518 | 74.497 | 1.00 | 59.23 C |
| ATOM | 18112 | CG | ASN | D | 128 | −12.291 | −2.998 | 73.061 | 1.00 | 64.71 C |
| ATOM | 18113 | OD1 | ASN | D | 128 | −11.567 | −3.919 | 72.665 | 1.00 | 73.27 O |
| ATOM | 18114 | ND2 | ASN | D | 128 | −13.168 | −2.383 | 72.272 | 1.00 | 63.61 N |
| ATOM | 18117 | C | ASN | D | 128 | −11.237 | −2.718 | 76.741 | 1.00 | 58.78 C |
| ATOM | 18118 | O | ASN | D | 128 | −10.745 | −1.622 | 77.001 | 1.00 | 60.88 O |
| ATOM | 18120 | N | SER | D | 129 | −11.874 | −3.466 | 77.640 | 1.00 | 60.02 N |
| ATOM | 18121 | CA | SER | D | 129 | −12.130 | −3.007 | 79.009 | 1.00 | 60.62 C |
| ATOM | 18123 | CB | SER | D | 129 | −13.618 | −2.661 | 79.199 | 1.00 | 61.16 C |
| ATOM | 18126 | OG | SER | D | 129 | −14.214 | −2.210 | 77.991 | 1.00 | 60.11 O |
| ATOM | 18128 | C | SER | D | 129 | −11.753 | −4.095 | 79.999 | 1.00 | 60.55 C |
| ATOM | 18129 | O | SER | D | 129 | −11.497 | −5.231 | 79.623 | 1.00 | 60.80 O |
| ATOM | 18131 | N | ASP | D | 130 | −11.736 | −3.742 | 81.274 | 1.00 | 60.66 N |
| ATOM | 18132 | CA | ASP | D | 130 | −11.507 | −4.729 | 82.311 | 1.00 | 59.83 C |
| ATOM | 18134 | CB | ASP | D | 130 | −11.679 | −4.100 | 83.703 | 1.00 | 61.23 C |
| ATOM | 18137 | CG | ASP | D | 130 | −11.121 | −4.966 | 84.826 | 1.00 | 62.22 C |
| ATOM | 18138 | OD1 | ASP | D | 130 | −10.602 | −6.079 | 84.564 | 1.00 | 64.41 O |
| ATOM | 18139 | OD2 | ASP | D | 130 | −11.205 | −4.515 | 85.989 | 1.00 | 67.18 O |
| ATOM | 18140 | C | ASP | D | 130 | −12.529 | −5.828 | 82.088 | 1.00 | 58.25 C |
| ATOM | 18141 | O | ASP | D | 130 | −13.691 | −5.531 | 81.808 | 1.00 | 58.54 O |
| ATOM | 18143 | N | THR | D | 131 | −12.078 | −7.080 | 82.182 | 1.00 | 57.24 N |
| ATOM | 18144 | CA | THR | D | 131 | −12.936 | −8.263 | 82.022 | 1.00 | 55.57 C |
| ATOM | 18146 | CB | THR | D | 131 | −12.107 | −9.487 | 81.621 | 1.00 | 53.38 C |
| ATOM | 18148 | OG1 | THR | D | 131 | −11.023 | −9.652 | 82.539 | 1.00 | 51.04 O |
| ATOM | 18150 | CG2 | THR | D | 131 | −11.555 | −9.312 | 80.238 | 1.00 | 53.52 C |
| ATOM | 18154 | C | THR | D | 131 | −13.727 | −8.614 | 83.293 | 1.00 | 56.21 C |
| ATOM | 18155 | O | THR | D | 131 | −14.560 | −9.530 | 83.278 | 1.00 | 56.72 O |
| ATOM | 18157 | N | HIS | D | 132 | −13.441 | −7.904 | 84.386 | 1.00 | 55.72 N |
| ATOM | 18158 | CA | HIS | D | 132 | −14.231 | −7.967 | 85.612 | 1.00 | 55.30 C |
| ATOM | 18160 | CB | HIS | D | 132 | −13.324 | −7.885 | 86.839 | 1.00 | 54.37 C |
| ATOM | 18163 | CG | HIS | D | 132 | −12.323 | −8.997 | 86.932 | 1.00 | 53.87 C |
| ATOM | 18164 | ND1 | HIS | D | 132 | −11.677 | −9.518 | 85.830 | 1.00 | 53.67 N |
| ATOM | 18166 | CE1 | HIS | D | 132 | −10.855 | −10.477 | 86.217 | 1.00 | 53.49 C |
| ATOM | 18168 | NE2 | HIS | D | 132 | −10.935 | −10.589 | 87.531 | 1.00 | 47.90 N |
| ATOM | 18170 | CD2 | HIS | D | 132 | −11.845 | −9.675 | 88.003 | 1.00 | 48.56 C |
| ATOM | 18172 | C | HIS | D | 132 | −15.165 | −6.772 | 85.581 | 1.00 | 55.24 C |
| ATOM | 18173 | O | HIS | D | 132 | −14.716 | −5.644 | 85.422 | 1.00 | 55.81 O |

-continued

| | | | | | | | | | | |
|---|---|---|---|---|---|---|---|---|---|---|
| ATOM | 18175 | N | LEU | D | 133 | −16.463 | −7.002 | 85.715 | 1.00 | 56.37 N |
| ATOM | 18176 | CA | LEU | D | 133 | −17.423 | −5.916 | 85.520 | 1.00 | 57.71 C |
| ATOM | 18178 | CB | LEU | D | 133 | −17.647 | −5.664 | 84.021 | 1.00 | 58.30 C |
| ATOM | 18181 | CG | LEU | D | 133 | −17.733 | −6.894 | 83.101 | 1.00 | 61.86 C |
| ATOM | 18183 | CD1 | LEU | D | 133 | −18.682 | −7.954 | 83.631 | 1.00 | 63.60 C |
| ATOM | 18187 | CD2 | LEU | D | 133 | −18.151 | −6.484 | 81.692 | 1.00 | 59.41 C |
| ATOM | 18191 | C | LEU | D | 133 | −18.752 | −6.176 | 86.211 | 1.00 | 58.35 C |
| ATOM | 18192 | O | LEU | D | 133 | −19.010 | −7.278 | 86.690 | 1.00 | 59.32 O |
| ATOM | 18194 | N | LEU | D | 134 | −19.592 | −5.145 | 86.239 | 1.00 | 57.45 N |
| ATOM | 18195 | CA | LEU | D | 134 | −20.888 | −5.206 | 86.905 | 1.00 | 56.42 C |
| ATOM | 18197 | CB | LEU | D | 134 | −21.272 | −3.816 | 87.422 | 1.00 | 56.74 C |
| ATOM | 18200 | CG | LEU | D | 134 | −20.602 | −3.324 | 88.715 | 1.00 | 57.94 C |
| ATOM | 18202 | CD1 | LEU | D | 134 | −20.972 | −1.869 | 88.950 | 1.00 | 58.59 C |
| ATOM | 18206 | CD2 | LEU | D | 134 | −19.087 | −3.487 | 88.705 | 1.00 | 57.62 C |
| ATOM | 18210 | C | LEU | D | 134 | −21.985 | −5.767 | 85.983 | 1.00 | 55.19 C |
| ATOM | 18211 | O | LEU | D | 134 | −21.936 | −5.619 | 84.759 | 1.00 | 52.52 O |
| ATOM | 18213 | N | GLN | D | 135 | −22.973 | −6.411 | 86.593 | 1.00 | 55.25 N |
| ATOM | 18214 | CA | GLN | D | 135 | −24.077 | −7.019 | 85.862 | 1.00 | 55.61 C |
| ATOM | 18216 | CB | GLN | D | 135 | −25.138 | −7.535 | 86.830 | 1.00 | 54.63 C |
| ATOM | 18219 | CG | GLN | D | 135 | −26.085 | −8.545 | 86.219 | 1.00 | 55.78 C |
| ATOM | 18222 | CD | GLN | D | 135 | −26.989 | −9.173 | 87.254 | 1.00 | 59.32 C |
| ATOM | 18223 | OE1 | GLN | D | 135 | −27.752 | −8.478 | 87.925 | 1.00 | 67.47 O |
| ATOM | 18224 | NE2 | GLN | D | 135 | −26.902 | −10.492 | 87.403 | 1.00 | 65.64 N |
| ATOM | 18227 | C | GLN | D | 135 | −24.720 | −6.014 | 84.932 | 1.00 | 55.52 C |
| ATOM | 18228 | O | GLN | D | 135 | −24.922 | −4.865 | 85.302 | 1.00 | 55.92 O |
| ATOM | 18230 | N | GLY | D | 136 | −25.042 | −6.448 | 83.721 | 1.00 | 56.26 N |
| ATOM | 18231 | CA | GLY | D | 136 | −25.713 | −5.583 | 82.757 | 1.00 | 55.42 C |
| ATOM | 18234 | C | GLY | D | 136 | −24.780 | −4.745 | 81.899 | 1.00 | 54.75 C |
| ATOM | 18235 | O | GLY | D | 136 | −25.234 | −4.094 | 80.962 | 1.00 | 57.84 O |
| ATOM | 18237 | N | GLN | D | 137 | −23.485 | −4.746 | 82.208 | 1.00 | 51.86 N |
| ATOM | 18238 | CA | GLN | D | 137 | −22.515 | −4.062 | 81.370 | 1.00 | 51.09 C |
| ATOM | 18240 | CB | GLN | D | 137 | −21.275 | −3.681 | 82.177 | 1.00 | 49.94 C |
| ATOM | 18243 | CG | GLN | D | 137 | −21.522 | −2.546 | 83.144 | 1.00 | 47.82 C |
| ATOM | 18246 | CD | GLN | D | 137 | −20.256 | −2.046 | 83.813 | 1.00 | 49.66 C |
| ATOM | 18247 | OE1 | GLN | D | 137 | −19.324 | −2.808 | 84.049 | 1.00 | 50.76 O |
| ATOM | 18248 | NE2 | GLN | D | 137 | −20.227 | −0.762 | 84.141 | 1.00 | 52.11 N |
| ATOM | 18251 | C | GLN | D | 137 | −22.135 | −4.930 | 80.163 | 1.00 | 51.27 C |
| ATOM | 18252 | O | GLN | D | 137 | −22.430 | −6.129 | 80.126 | 1.00 | 50.43 O |
| ATOM | 18254 | N | SER | D | 138 | −21.499 | −4.302 | 79.175 | 1.00 | 51.61 N |
| ATOM | 18255 | CA | SER | D | 138 | −21.092 | −4.967 | 77.937 | 1.00 | 50.74 C |
| ATOM | 18257 | CB | SER | D | 138 | −21.717 | −4.279 | 76.725 | 1.00 | 50.04 C |
| ATOM | 18260 | OG | SER | D | 138 | −23.126 | −4.236 | 76.843 | 1.00 | 53.94 O |
| ATOM | 18262 | C | SER | D | 138 | −19.589 | −4.941 | 77.774 | 1.00 | 49.32 C |
| ATOM | 18263 | O | SER | D | 138 | −18.960 | −3.919 | 77.967 | 1.00 | 49.49 O |
| ATOM | 18265 | N | LEU | D | 139 | −19.026 | −6.082 | 77.413 | 1.00 | 51.10 N |
| ATOM | 18266 | CA | LEU | D | 139 | −17.615 | −6.199 | 77.090 | 1.00 | 51.33 C |
| ATOM | 18268 | CB | LEU | D | 139 | −17.012 | −7.375 | 77.846 | 1.00 | 51.35 C |
| ATOM | 18271 | CG | LEU | D | 139 | −15.514 | −7.557 | 77.618 | 1.00 | 52.96 C |
| ATOM | 18273 | CD1 | LEU | D | 139 | −14.712 | −6.447 | 78.345 | 1.00 | 55.77 C |
| ATOM | 18277 | CD2 | LEU | D | 139 | −15.090 | −8.948 | 78.054 | 1.00 | 53.61 C |
| ATOM | 18281 | C | LEU | D | 139 | −17.462 | −6.449 | 75.593 | 1.00 | 51.20 C |
| ATOM | 18282 | O | LEU | D | 139 | −18.159 | −7.301 | 75.026 | 1.00 | 49.61 O |
| ATOM | 18284 | N | THR | D | 140 | −16.541 | −5.727 | 74.960 | 1.00 | 50.52 N |
| ATOM | 18285 | CA | THR | D | 140 | −16.297 | −5.906 | 73.533 | 1.00 | 50.83 C |
| ATOM | 18287 | CB | THR | D | 140 | −16.548 | −4.610 | 72.684 | 1.00 | 51.00 C |
| ATOM | 18289 | OG1 | THR | D | 140 | −15.605 | −4.555 | 71.606 | 1.00 | 53.65 O |
| ATOM | 18291 | CG2 | THR | D | 140 | −16.445 | −3.333 | 73.514 | 1.00 | 49.90 C |
| ATOM | 18295 | C | THR | D | 140 | −14.901 | −6.462 | 73.299 | 1.00 | 50.83 C |
| ATOM | 18296 | O | THR | D | 140 | −13.904 | −5.865 | 73.714 | 1.00 | 51.00 O |
| ATOM | 18298 | N | LEU | D | 141 | −14.850 | −7.615 | 72.633 | 1.00 | 51.97 N |
| ATOM | 18299 | CA | LEU | D | 141 | −13.595 | −8.269 | 72.271 | 1.00 | 52.74 C |
| ATOM | 18301 | CB | LEU | D | 141 | −13.757 | −9.784 | 72.305 | 1.00 | 51.17 C |
| ATOM | 18304 | CG | LEU | D | 141 | −14.179 | −10.370 | 73.646 | 1.00 | 48.01 C |
| ATOM | 18306 | CD1 | LEU | D | 141 | −14.347 | −11.865 | 73.499 | 1.00 | 44.17 C |
| ATOM | 18310 | CD2 | LEU | D | 141 | −13.176 | −10.026 | 74.750 | 1.00 | 47.63 C |
| ATOM | 18314 | C | LEU | D | 141 | −13.149 | −7.855 | 70.883 | 1.00 | 53.26 C |
| ATOM | 18315 | O | LEU | D | 141 | −13.986 | −7.583 | 70.020 | 1.00 | 54.40 O |
| ATOM | 18317 | N | THR | D | 142 | −11.832 | −7.840 | 70.670 | 1.00 | 53.92 N |
| ATOM | 18318 | CA | THR | D | 142 | −11.238 | −7.422 | 69.386 | 1.00 | 55.49 C |
| ATOM | 18320 | CB | THR | D | 142 | −10.629 | −6.013 | 69.492 | 1.00 | 54.17 C |
| ATOM | 18322 | OG1 | THR | D | 142 | −11.548 | −5.162 | 70.182 | 1.00 | 57.68 O |
| ATOM | 18324 | CG2 | THR | D | 142 | −10.347 | −5.435 | 68.130 | 1.00 | 52.38 C |
| ATOM | 18328 | C | THR | D | 142 | −10.141 | −8.376 | 68.938 | 1.00 | 56.34 C |
| ATOM | 18329 | O | THR | D | 142 | −9.446 | −8.959 | 69.762 | 1.00 | 58.22 O |
| ATOM | 18331 | N | LEU | D | 143 | −9.995 | −8.527 | 67.626 | 1.00 | 56.33 N |
| ATOM | 18332 | CA | LEU | D | 143 | −8.968 | −9.388 | 67.053 | 1.00 | 56.03 C |
| ATOM | 18334 | CB | LEU | D | 143 | −9.534 | −10.202 | 65.900 | 1.00 | 56.84 C |
| ATOM | 18337 | CG | LEU | D | 143 | −10.257 | −11.498 | 66.244 | 1.00 | 60.58 C |
| ATOM | 18339 | CD1 | LEU | D | 143 | −11.411 | −11.224 | 67.182 | 1.00 | 60.22 C |

-continued

| | | | | | | | | | | |
|---|---|---|---|---|---|---|---|---|---|---|
| ATOM | 18343 | CD2 | LEU | D | 143 | −10.718 | −12.189 | 64.950 | 1.00 | 58.03 C |
| ATOM | 18347 | C | LEU | D | 143 | −7.825 | −8.560 | 66.510 | 1.00 | 56.02 C |
| ATOM | 18348 | O | LEU | D | 143 | −8.048 | −7.626 | 65.729 | 1.00 | 57.30 O |
| ATOM | 18350 | N | GLU | D | 144 | −6.605 | −8.899 | 66.913 | 1.00 | 54.80 N |
| ATOM | 18351 | CA | GLU | D | 144 | −5.420 | −8.371 | 66.251 | 1.00 | 55.99 C |
| ATOM | 18353 | CB | GLU | D | 144 | −4.266 | −8.183 | 67.241 | 1.00 | 55.63 C |
| ATOM | 18356 | CG | GLU | D | 144 | −3.362 | −7.002 | 66.890 | 1.00 | 60.69 C |
| ATOM | 18359 | CD | GLU | D | 144 | −2.114 | −6.926 | 67.752 | 1.00 | 63.94 C |
| ATOM | 18360 | OE1 | GLU | D | 144 | −2.146 | −7.458 | 68.887 | 1.00 | 72.09 O |
| ATOM | 18361 | OE2 | GLU | D | 144 | −1.106 | −6.333 | 67.292 | 1.00 | 69.98 O |
| ATOM | 18362 | C | GLU | D | 144 | −5.069 | −9.365 | 65.144 | 1.00 | 54.60 C |
| ATOM | 18363 | O | GLU | D | 144 | −4.844 | −10.552 | 65.412 | 1.00 | 56.41 O |
| ATOM | 18365 | N | SER | D | 145 | −5.056 | −8.890 | 63.903 | 1.00 | 52.86 N |
| ATOM | 18366 | CA | SER | D | 145 | −4.920 | −9.768 | 62.736 | 1.00 | 53.37 C |
| ATOM | 18368 | CB | SER | D | 145 | −6.304 | −10.028 | 62.117 | 1.00 | 52.48 C |
| ATOM | 18371 | OG | SER | D | 145 | −6.858 | −8.858 | 61.516 | 1.00 | 53.25 O |
| ATOM | 18373 | C | SER | D | 145 | −3.978 | −9.148 | 61.701 | 1.00 | 52.37 C |
| ATOM | 18374 | O | SER | D | 145 | −3.958 | −7.933 | 61.554 | 1.00 | 54.29 O |
| ATOM | 18376 | N | PRO | D | 146 | −3.210 | −9.978 | 60.968 | 1.00 | 51.88 N |
| ATOM | 18377 | CA | PRO | D | 146 | −2.262 | −9.416 | 59.997 | 1.00 | 51.04 C |
| ATOM | 18379 | CB | PRO | D | 146 | −1.402 | −10.611 | 59.627 | 1.00 | 51.10 C |
| ATOM | 18382 | CG | PRO | D | 146 | −2.321 | −11.785 | 59.786 | 1.00 | 50.23 C |
| ATOM | 18385 | CD | PRO | D | 146 | −3.185 | −11.453 | 60.966 | 1.00 | 50.99 C |
| ATOM | 18388 | C | PRO | D | 146 | −2.969 | −8.894 | 58.761 | 1.00 | 50.82 C |
| ATOM | 18389 | O | PRO | D | 146 | −4.080 | −9.315 | 58.478 | 1.00 | 50.19 O |
| ATOM | 18390 | N | PRO | D | 147 | −2.333 | −7.976 | 58.025 | 1.00 | 53.17 N |
| ATOM | 18391 | CA | PRO | D | 147 | −2.921 | −7.335 | 56.845 | 1.00 | 53.12 C |
| ATOM | 18393 | CB | PRO | D | 147 | −1.728 | −6.624 | 56.223 | 1.00 | 53.31 C |
| ATOM | 18396 | CG | PRO | D | 147 | −0.891 | −6.266 | 57.385 | 1.00 | 55.28 C |
| ATOM | 18399 | CD | PRO | D | 147 | −0.986 | −7.447 | 58.301 | 1.00 | 54.19 C |
| ATOM | 18402 | C | PRO | D | 147 | −3.591 | −8.251 | 55.810 | 1.00 | 53.13 C |
| ATOM | 18403 | O | PRO | D | 147 | −4.637 | −7.897 | 55.263 | 1.00 | 54.73 O |
| ATOM | 18404 | N | GLY | D | 148 | −3.021 | −9.408 | 55.523 | 1.00 | 53.41 N |
| ATOM | 18405 | CA | GLY | D | 148 | −3.678 | −10.313 | 54.567 | 1.00 | 55.58 C |
| ATOM | 18408 | C | GLY | D | 148 | −5.009 | −10.913 | 55.038 | 1.00 | 55.14 C |
| ATOM | 18409 | O | GLY | D | 148 | −5.930 | −11.116 | 54.251 | 1.00 | 50.96 O |
| ATOM | 18411 | N | SER | D | 149 | −5.094 | −11.147 | 56.343 | 1.00 | 54.71 N |
| ATOM | 18412 | CA | SER | D | 149 | −6.037 | −12.068 | 56.941 | 1.00 | 53.77 C |
| ATOM | 18414 | CB | SER | D | 149 | −5.726 | −12.207 | 58.427 | 1.00 | 54.85 C |
| ATOM | 18417 | OG | SER | D | 149 | −6.017 | −10.996 | 59.084 | 1.00 | 56.72 O |
| ATOM | 18419 | C | SER | D | 149 | −7.484 | −11.671 | 56.790 | 1.00 | 52.08 C |
| ATOM | 18420 | O | SER | D | 149 | −7.798 | −10.581 | 56.317 | 1.00 | 50.36 O |
| ATOM | 18422 | N | SER | D | 150 | −8.353 | −12.583 | 57.231 | 1.00 | 50.75 N |
| ATOM | 18423 | CA | SER | D | 150 | −9.764 | −12.537 | 56.923 | 1.00 | 48.63 C |
| ATOM | 18425 | CB | SER | D | 150 | −9.936 | −13.290 | 55.605 | 1.00 | 48.04 C |
| ATOM | 18428 | OG | SER | D | 150 | −11.094 | −12.867 | 54.941 | 1.00 | 50.58 O |
| ATOM | 18430 | C | SER | D | 150 | −10.674 | −13.168 | 58.002 | 1.00 | 47.91 C |
| ATOM | 18431 | O | SER | D | 150 | −11.739 | −13.675 | 57.675 | 1.00 | 47.31 O |
| ATOM | 18433 | N | PRO | D | 151 | −10.292 | −13.096 | 59.294 | 1.00 | 46.40 N |
| ATOM | 18434 | CA | PRO | D | 151 | −10.920 | −13.946 | 60.312 | 1.00 | 46.91 C |
| ATOM | 18436 | CB | PRO | D | 151 | −10.002 | −13.750 | 61.507 | 1.00 | 45.83 C |
| ATOM | 18439 | CG | PRO | D | 151 | −9.565 | −12.344 | 61.370 | 1.00 | 46.53 C |
| ATOM | 18442 | CD | PRO | D | 151 | −9.286 | −12.207 | 59.905 | 1.00 | 47.48 C |
| ATOM | 18445 | C | PRO | D | 151 | −12.345 | −13.588 | 60.748 | 1.00 | 47.44 C |
| ATOM | 18446 | O | PRO | D | 151 | −12.781 | −12.453 | 60.554 | 1.00 | 46.11 O |
| ATOM | 18447 | N | SER | D | 152 | −13.038 | −14.567 | 61.343 | 1.00 | 47.38 N |
| ATOM | 18448 | CA | SER | D | 152 | −14.302 | −14.340 | 62.069 | 1.00 | 49.80 C |
| ATOM | 18450 | CB | SER | D | 152 | −15.513 | −14.738 | 61.218 | 1.00 | 49.91 C |
| ATOM | 18453 | OG | SER | D | 152 | −15.484 | −16.117 | 60.872 | 1.00 | 57.34 O |
| ATOM | 18455 | C | SER | D | 152 | −14.287 | −15.102 | 63.416 | 1.00 | 49.58 C |
| ATOM | 18456 | O | SER | D | 152 | −13.391 | −15.889 | 63.667 | 1.00 | 49.21 O |
| ATOM | 18458 | N | VAL | D | 153 | −15.263 | −14.859 | 64.286 | 1.00 | 50.80 N |
| ATOM | 18459 | CA | VAL | D | 153 | −15.117 | −15.231 | 65.700 | 1.00 | 52.57 C |
| ATOM | 18461 | CB | VAL | D | 153 | −14.724 | −14.022 | 66.570 | 1.00 | 51.92 C |
| ATOM | 18463 | CG1 | VAL | D | 153 | −14.374 | −14.475 | 67.987 | 1.00 | 50.90 C |
| ATOM | 18467 | CG2 | VAL | D | 153 | −13.580 | −13.278 | 65.971 | 1.00 | 58.01 C |
| ATOM | 18471 | C | VAL | D | 153 | −16.394 | −15.718 | 66.337 | 1.00 | 54.01 C |
| ATOM | 18472 | O | VAL | D | 153 | −17.450 | −15.115 | 66.142 | 1.00 | 54.00 O |
| ATOM | 18474 | N | GLN | D | 154 | −16.276 | −16.761 | 67.154 | 1.00 | 54.05 N |
| ATOM | 18475 | CA | GLN | D | 154 | −17.400 | −17.252 | 67.935 | 1.00 | 56.08 C |
| ATOM | 18477 | CB | GLN | D | 154 | −17.918 | −18.552 | 67.327 | 1.00 | 55.99 C |
| ATOM | 18480 | CG | GLN | D | 154 | −19.218 | −19.058 | 67.913 | 1.00 | 54.19 C |
| ATOM | 18483 | CD | GLN | D | 154 | −19.696 | −20.309 | 67.194 | 1.00 | 53.64 C |
| ATOM | 18484 | OE1 | GLN | D | 154 | −18.987 | −21.308 | 67.153 | 1.00 | 57.94 O |
| ATOM | 18485 | NE2 | GLN | D | 154 | −20.884 | −20.253 | 66.611 | 1.00 | 37.30 N |
| ATOM | 18488 | C | GLN | D | 154 | −16.949 | −17.482 | 69.369 | 1.00 | 57.47 C |
| ATOM | 18489 | O | GLN | D | 154 | −15.963 | −18.170 | 69.589 | 1.00 | 59.08 O |
| ATOM | 18491 | N | CYS | D | 155 | −17.646 | −16.887 | 70.334 | 1.00 | 58.37 N |
| ATOM | 18492 | CA | CYS | D | 155 | −17.365 | −17.138 | 71.743 | 1.00 | 57.77 C |

|      |       |     |     |   |     |         |         |        |      |       |   |
|------|-------|-----|-----|---|-----|---------|---------|--------|------|-------|---|
| ATOM | 18494 | CB  | CYS | D | 155 | −17.093 | −15.846 | 72.494 | 1.00 | 57.38 | C |
| ATOM | 18497 | SG  | CYS | D | 155 | −15.687 | −14.948 | 71.865 | 1.00 | 62.04 | S |
| ATOM | 18499 | C   | CYS | D | 155 | −18.541 | −17.855 | 72.359 | 1.00 | 58.98 | C |
| ATOM | 18500 | O   | CYS | D | 155 | −19.691 | −17.628 | 71.973 | 1.00 | 60.03 | O |
| ATOM | 18502 | N   | ARG | D | 156 | −18.235 | −18.724 | 73.316 | 1.00 | 59.42 | N |
| ATOM | 18503 | CA  | ARG | D | 156 | −19.221 | −19.569 | 73.972 | 1.00 | 58.07 | C |
| ATOM | 18505 | CB  | ARG | D | 156 | −18.858 | −21.040 | 73.762 | 1.00 | 57.21 | C |
| ATOM | 18508 | CG  | ARG | D | 156 | −19.934 | −22.026 | 74.198 | 1.00 | 60.46 | C |
| ATOM | 18511 | CD  | ARG | D | 156 | −19.441 | −23.477 | 74.171 | 1.00 | 61.19 | C |
| ATOM | 18514 | NE  | ARG | D | 156 | −18.865 | −23.822 | 72.873 | 1.00 | 64.19 | N |
| ATOM | 18516 | CZ  | ARG | D | 156 | −19.563 | −24.033 | 71.761 | 1.00 | 62.39 | C |
| ATOM | 18517 | NH1 | ARG | D | 156 | −20.881 | −23.951 | 71.755 | 1.00 | 66.24 | N |
| ATOM | 18520 | NH2 | ARG | D | 156 | −18.936 | −24.323 | 70.635 | 1.00 | 65.74 | N |
| ATOM | 18523 | C   | ARG | D | 156 | −19.231 | −19.230 | 75.463 | 1.00 | 57.80 | C |
| ATOM | 18524 | O   | ARG | D | 156 | −18.180 | −19.208 | 76.103 | 1.00 | 56.95 | O |
| ATOM | 18526 | N   | SER | D | 157 | −20.418 | −18.962 | 76.007 | 1.00 | 57.05 | N |
| ATOM | 18527 | CA  | SER | D | 157 | −20.577 | −18.702 | 77.437 | 1.00 | 55.35 | C |
| ATOM | 18529 | CB  | SER | D | 157 | −21.948 | −18.081 | 77.718 | 1.00 | 56.54 | C |
| ATOM | 18532 | OG  | SER | D | 157 | −22.981 | −19.056 | 77.651 | 1.00 | 59.97 | O |
| ATOM | 18534 | C   | SER | D | 157 | −20.454 | −19.990 | 78.237 | 1.00 | 52.36 | C |
| ATOM | 18535 | O   | SER | D | 157 | −20.618 | −21.076 | 77.699 | 1.00 | 49.84 | O |
| ATOM | 18537 | N   | PRO | D | 158 | −20.173 | −19.876 | 79.536 | 1.00 | 52.22 | N |
| ATOM | 18538 | CA  | PRO | D | 158 | −20.259 | −21.030 | 80.431 | 1.00 | 52.39 | C |
| ATOM | 18540 | CB  | PRO | D | 158 | −20.090 | −20.396 | 81.821 | 1.00 | 51.88 | C |
| ATOM | 18543 | CG  | PRO | D | 158 | −19.241 | −19.220 | 81.584 | 1.00 | 50.43 | C |
| ATOM | 18546 | CD  | PRO | D | 158 | −19.688 | −18.678 | 80.243 | 1.00 | 53.67 | C |
| ATOM | 18549 | C   | PRO | D | 158 | −21.575 | −21.836 | 80.353 | 1.00 | 50.69 | C |
| ATOM | 18550 | O   | PRO | D | 158 | −21.617 | −22.982 | 80.799 | 1.00 | 48.48 | O |
| ATOM | 18551 | N   | ARG | D | 159 | −22.635 | −21.247 | 79.804 | 1.00 | 50.89 | N |
| ATOM | 18552 | CA  | ARG | D | 159 | −23.885 | −21.981 | 79.594 | 1.00 | 51.66 | C |
| ATOM | 18554 | CB  | ARG | D | 159 | −25.085 | −21.063 | 79.813 | 1.00 | 51.61 | C |
| ATOM | 18557 | CG  | ARG | D | 159 | −25.122 | −20.441 | 81.202 | 1.00 | 52.14 | C |
| ATOM | 18560 | CD  | ARG | D | 159 | −26.509 | −20.012 | 81.617 | 1.00 | 54.01 | C |
| ATOM | 18563 | NE  | ARG | D | 159 | −27.332 | −19.661 | 80.465 | 1.00 | 58.30 | N |
| ATOM | 18565 | CZ  | ARG | D | 159 | −27.324 | −18.491 | 79.842 | 1.00 | 55.15 | C |
| ATOM | 18566 | NH1 | ARG | D | 159 | −26.559 | −17.490 | 80.264 | 1.00 | 55.94 | N |
| ATOM | 18569 | NH2 | ARG | D | 159 | −28.112 | −18.326 | 78.795 | 1.00 | 57.35 | N |
| ATOM | 18572 | C   | ARG | D | 159 | −23.964 | −22.633 | 78.212 | 1.00 | 50.78 | C |
| ATOM | 18573 | O   | ARG | D | 159 | −24.993 | −23.187 | 77.847 | 1.00 | 50.37 | O |
| ATOM | 18575 | N   | GLY | D | 160 | −22.871 | −22.573 | 77.458 | 1.00 | 51.66 | N |
| ATOM | 18576 | CA  | GLY | D | 160 | −22.768 | −23.246 | 76.177 | 1.00 | 51.11 | C |
| ATOM | 18579 | C   | GLY | D | 160 | −23.488 | −22.524 | 75.061 | 1.00 | 51.24 | C |
| ATOM | 18580 | O   | GLY | D | 160 | −23.803 | −23.139 | 74.045 | 1.00 | 52.19 | O |
| ATOM | 18582 | N   | LYS | D | 161 | −23.752 | −21.230 | 75.239 | 1.00 | 51.67 | N |
| ATOM | 18583 | CA  | LYS | D | 161 | −24.423 | −20.425 | 74.214 | 1.00 | 53.02 | C |
| ATOM | 18585 | CB  | LYS | D | 161 | −25.511 | −19.546 | 74.839 | 1.00 | 54.50 | C |
| ATOM | 18588 | CG  | LYS | D | 161 | −26.675 | −20.326 | 75.482 | 1.00 | 57.95 | C |
| ATOM | 18591 | CD  | LYS | D | 161 | −27.856 | −20.517 | 74.518 | 1.00 | 60.42 | C |
| ATOM | 18594 | CE  | LYS | D | 161 | −29.018 | −21.274 | 75.167 | 1.00 | 57.48 | C |
| ATOM | 18597 | NZ  | LYS | D | 161 | −28.624 | −22.645 | 75.620 | 1.00 | 57.99 | N |
| ATOM | 18601 | C   | LYS | D | 161 | −23.398 | −19.562 | 73.472 | 1.00 | 54.00 | C |
| ATOM | 18602 | O   | LYS | D | 161 | −22.539 | −18.925 | 74.096 | 1.00 | 54.45 | O |
| ATOM | 18604 | N   | ASN | D | 162 | −23.498 | −19.543 | 72.142 | 1.00 | 53.68 | N |
| ATOM | 18605 | CA  | ASN | D | 162 | −22.518 | −18.869 | 71.288 | 1.00 | 52.60 | C |
| ATOM | 18607 | CB  | ASN | D | 162 | −22.308 | −19.636 | 69.985 | 1.00 | 51.64 | C |
| ATOM | 18610 | CG  | ASN | D | 162 | −21.893 | −21.064 | 70.207 | 1.00 | 47.38 | C |
| ATOM | 18611 | OD1 | ASN | D | 162 | −22.541 | −21.978 | 69.722 | 1.00 | 39.51 | O |
| ATOM | 18612 | ND2 | ASN | D | 162 | −20.808 | −21.266 | 70.947 | 1.00 | 53.72 | N |
| ATOM | 18615 | C   | ASN | D | 162 | −22.954 | −17.479 | 70.910 | 1.00 | 51.70 | C |
| ATOM | 18616 | O   | ASN | D | 162 | −24.099 | −17.280 | 70.564 | 1.00 | 46.95 | O |
| ATOM | 18618 | N   | ILE | D | 163 | −22.021 | −16.534 | 70.985 | 1.00 | 55.12 | N |
| ATOM | 18619 | CA  | ILE | D | 163 | −22.137 | −15.217 | 70.362 | 1.00 | 54.68 | C |
| ATOM | 18621 | CB  | ILE | D | 163 | −21.825 | −14.094 | 71.388 | 1.00 | 54.18 | C |
| ATOM | 18623 | CG1 | ILE | D | 163 | −22.932 | −13.983 | 72.426 | 1.00 | 56.53 | C |
| ATOM | 18626 | CD1 | ILE | D | 163 | −22.601 | −13.031 | 73.582 | 1.00 | 57.98 | C |
| ATOM | 18630 | CG2 | ILE | D | 163 | −21.678 | −12.736 | 70.714 | 1.00 | 57.91 | C |
| ATOM | 18634 | C   | ILE | D | 163 | −21.090 | −15.193 | 69.246 | 1.00 | 54.27 | C |
| ATOM | 18635 | O   | ILE | D | 163 | −19.995 | −15.728 | 69.422 | 1.00 | 55.73 | O |
| ATOM | 18637 | N   | GLN | D | 164 | −21.386 | −14.571 | 68.113 | 1.00 | 53.58 | N |
| ATOM | 18638 | CA  | GLN | D | 164 | −20.374 | −14.477 | 67.060 | 1.00 | 55.90 | C |
| ATOM | 18640 | CB  | GLN | D | 164 | −20.562 | −15.598 | 66.020 | 1.00 | 56.53 | C |
| ATOM | 18643 | CG  | GLN | D | 164 | −21.976 | −15.837 | 65.517 | 1.00 | 57.92 | C |
| ATOM | 18646 | CD  | GLN | D | 164 | −22.156 | −17.247 | 64.967 | 1.00 | 58.23 | C |
| ATOM | 18647 | OE1 | GLN | D | 164 | −22.159 | −18.227 | 65.721 | 1.00 | 55.68 | O |
| ATOM | 18648 | NE2 | GLN | D | 164 | −22.309 | −17.355 | 63.649 | 1.00 | 58.55 | N |
| ATOM | 18651 | C   | GLN | D | 164 | −20.224 | −13.087 | 66.401 | 1.00 | 55.64 | C |
| ATOM | 18652 | O   | GLN | D | 164 | −21.046 | −12.207 | 66.591 | 1.00 | 55.44 | O |
| ATOM | 18654 | N   | GLY | D | 165 | −19.127 | −12.910 | 65.664 | 1.00 | 56.69 | N |
| ATOM | 18655 | CA  | GLY | D | 165 | −18.803 | −11.644 | 64.996 | 1.00 | 55.85 | C |

-continued

| ATOM | 18658 | C | GLY | D | 165 | −17.638 | −11.740 | 64.008 | 1.00 | 55.76 | C |
| ATOM | 18659 | O | GLY | D | 165 | −17.093 | −12.828 | 63.751 | 1.00 | 55.67 | O |
| ATOM | 18661 | N | GLY | D | 166 | −17.262 | −10.594 | 63.451 | 1.00 | 53.91 | N |
| ATOM | 18662 | CA | GLY | D | 166 | −16.180 | −10.524 | 62.475 | 1.00 | 54.74 | C |
| ATOM | 18665 | C | GLY | D | 166 | −14.819 | −10.374 | 63.137 | 1.00 | 54.81 | C |
| ATOM | 18666 | O | GLY | D | 166 | −14.302 | −11.332 | 63.708 | 1.00 | 52.62 | O |
| ATOM | 18668 | N | LYS | D | 167 | −14.241 | −9.173 | 63.034 | 1.00 | 54.46 | N |
| ATOM | 18669 | CA | LYS | D | 167 | −13.034 | −8.778 | 63.785 | 1.00 | 53.64 | C |
| ATOM | 18671 | CB | LYS | D | 167 | −12.273 | −7.697 | 63.027 | 1.00 | 52.66 | C |
| ATOM | 18674 | CG | LYS | D | 167 | −11.428 | −8.210 | 61.912 | 1.00 | 52.86 | C |
| ATOM | 18677 | CD | LYS | D | 167 | −10.998 | −7.067 | 61.034 | 1.00 | 53.75 | C |
| ATOM | 18680 | CE | LYS | D | 167 | −9.838 | −7.468 | 60.147 | 1.00 | 57.67 | C |
| ATOM | 18683 | NZ | LYS | D | 167 | −9.606 | −6.442 | 59.094 | 1.00 | 59.20 | N |
| ATOM | 18687 | C | LYS | D | 167 | −13.386 | −8.218 | 65.162 | 1.00 | 54.15 | C |
| ATOM | 18688 | O | LYS | D | 167 | −12.541 | −7.660 | 65.858 | 1.00 | 55.19 | O |
| ATOM | 18690 | N | THR | D | 168 | −14.636 | −8.383 | 65.561 | 1.00 | 54.22 | N |
| ATOM | 18691 | CA | THR | D | 168 | −15.181 | −7.681 | 66.704 | 1.00 | 52.82 | C |
| ATOM | 18693 | CB | THR | D | 168 | −15.570 | −6.232 | 66.283 | 1.00 | 51.78 | C |
| ATOM | 18695 | OG1 | THR | D | 168 | −14.506 | −5.346 | 66.634 | 1.00 | 46.88 | O |
| ATOM | 18697 | CG2 | THR | D | 168 | −16.886 | −5.737 | 66.921 | 1.00 | 50.02 | C |
| ATOM | 18701 | C | THR | D | 168 | −16.386 | −8.484 | 67.123 | 1.00 | 53.97 | C |
| ATOM | 18702 | O | THR | D | 168 | −17.118 | −8.984 | 66.265 | 1.00 | 55.63 | O |
| ATOM | 18704 | N | LEU | D | 169 | −16.581 | −8.643 | 68.426 | 1.00 | 54.93 | N |
| ATOM | 18705 | CA | LEU | D | 169 | −17.872 | −9.099 | 68.932 | 1.00 | 55.16 | C |
| ATOM | 18707 | CB | LEU | D | 169 | −17.999 | −10.636 | 68.888 | 1.00 | 56.29 | C |
| ATOM | 18710 | CG | LEU | D | 169 | −17.258 | −11.596 | 69.818 | 1.00 | 52.07 | C |
| ATOM | 18712 | CD1 | LEU | D | 169 | −17.574 | −11.393 | 71.281 | 1.00 | 57.77 | C |
| ATOM | 18716 | CD2 | LEU | D | 169 | −17.651 | −12.996 | 69.441 | 1.00 | 55.73 | C |
| ATOM | 18720 | C | LEU | D | 169 | −18.126 | −8.549 | 70.321 | 1.00 | 54.29 | C |
| ATOM | 18721 | O | LEU | D | 169 | −17.196 | −8.376 | 71.096 | 1.00 | 53.23 | O |
| ATOM | 18723 | N | SER | D | 170 | −19.391 | −8.269 | 70.618 | 1.00 | 55.77 | N |
| ATOM | 18724 | CA | SER | D | 170 | −19.785 | −7.758 | 71.931 | 1.00 | 57.83 | C |
| ATOM | 18726 | CB | SER | D | 170 | −20.657 | −6.500 | 71.783 | 1.00 | 58.00 | C |
| ATOM | 18729 | OG | SER | D | 170 | −21.101 | −6.046 | 73.058 | 1.00 | 59.15 | O |
| ATOM | 18731 | C | SER | D | 170 | −20.526 | −8.802 | 72.782 | 1.00 | 57.44 | C |
| ATOM | 18732 | O | SER | D | 170 | −21.492 | −9.430 | 72.339 | 1.00 | 56.56 | O |
| ATOM | 18734 | N | VAL | D | 171 | −20.060 | −8.975 | 74.012 | 1.00 | 57.99 | N |
| ATOM | 18735 | CA | VAL | D | 171 | −20.802 | −9.722 | 75.016 | 1.00 | 57.84 | C |
| ATOM | 18737 | CB | VAL | D | 171 | −19.858 | −10.498 | 75.993 | 1.00 | 58.86 | C |
| ATOM | 18739 | CG1 | VAL | D | 171 | −20.653 | −11.499 | 76.791 | 1.00 | 60.80 | C |
| ATOM | 18743 | CG2 | VAL | D | 171 | −18.706 | −11.199 | 75.247 | 1.00 | 57.33 | C |
| ATOM | 18747 | C | VAL | D | 171 | −21.577 | −8.645 | 75.767 | 1.00 | 56.77 | C |
| ATOM | 18748 | O | VAL | D | 171 | −20.987 | −7.864 | 76.507 | 1.00 | 55.92 | O |
| ATOM | 18750 | N | SER | D | 172 | −22.890 | −8.595 | 75.572 | 1.00 | 56.82 | N |
| ATOM | 18751 | CA | SER | D | 172 | −23.690 | −7.482 | 76.072 | 1.00 | 56.26 | C |
| ATOM | 18753 | CB | SER | D | 172 | −24.436 | −6.838 | 74.912 | 1.00 | 57.11 | C |
| ATOM | 18756 | OG | SER | D | 172 | −25.679 | −7.482 | 74.702 | 1.00 | 56.59 | O |
| ATOM | 18758 | C | SER | D | 172 | −24.695 | −7.874 | 77.148 | 1.00 | 55.50 | C |
| ATOM | 18759 | O | SER | D | 172 | −25.156 | −9.005 | 77.188 | 1.00 | 55.73 | O |
| ATOM | 18761 | N | GLN | D | 173 | −25.060 | −6.901 | 77.984 | 1.00 | 56.13 | N |
| ATOM | 18762 | CA | GLN | D | 173 | −25.981 | −7.108 | 79.106 | 1.00 | 55.53 | C |
| ATOM | 18764 | CB | GLN | D | 173 | −27.444 | −7.202 | 78.630 | 1.00 | 57.06 | C |
| ATOM | 18767 | CG | GLN | D | 173 | −28.321 | −5.996 | 79.001 | 1.00 | 60.28 | C |
| ATOM | 18770 | CD | GLN | D | 173 | −28.110 | −4.790 | 78.103 | 1.00 | 64.40 | C |
| ATOM | 18771 | OE1 | GLN | D | 173 | −28.261 | −3.644 | 78.536 | 1.00 | 65.46 | O |
| ATOM | 18772 | NE2 | GLN | D | 173 | −27.767 | −5.040 | 76.846 | 1.00 | 64.55 | N |
| ATOM | 18775 | C | GLN | D | 173 | −25.581 | −8.346 | 79.891 | 1.00 | 54.22 | C |
| ATOM | 18776 | O | GLN | D | 173 | −26.398 | −9.218 | 80.162 | 1.00 | 55.87 | O |
| ATOM | 18778 | N | LEU | D | 174 | −24.310 | −8.410 | 80.259 | 1.00 | 52.91 | N |
| ATOM | 18779 | CA | LEU | D | 174 | −23.783 | −9.560 | 80.979 | 1.00 | 51.93 | C |
| ATOM | 18781 | CB | LEU | D | 174 | −22.326 | −9.320 | 81.362 | 1.00 | 50.97 | C |
| ATOM | 18784 | CG | LEU | D | 174 | −21.354 | −9.712 | 80.254 | 1.00 | 46.31 | C |
| ATOM | 18786 | CD1 | LEU | D | 174 | −20.065 | −8.945 | 80.373 | 1.00 | 49.23 | C |
| ATOM | 18790 | CD2 | LEU | D | 174 | −21.096 | −11.210 | 80.299 | 1.00 | 43.88 | C |
| ATOM | 18794 | C | LEU | D | 174 | −24.592 | −9.907 | 82.224 | 1.00 | 51.33 | C |
| ATOM | 18795 | O | LEU | D | 174 | −24.772 | −9.068 | 83.105 | 1.00 | 51.12 | O |
| ATOM | 18797 | N | GLU | D | 175 | −25.070 | −11.153 | 82.269 | 1.00 | 51.60 | N |
| ATOM | 18798 | CA | GLU | D | 175 | −25.774 | −11.722 | 83.425 | 1.00 | 50.66 | C |
| ATOM | 18800 | CB | GLU | D | 175 | −26.857 | −12.668 | 82.939 | 1.00 | 50.66 | C |
| ATOM | 18803 | CG | GLU | D | 175 | −27.846 | −12.049 | 81.972 | 1.00 | 51.22 | C |
| ATOM | 18806 | CD | GLU | D | 175 | −28.754 | −13.087 | 81.336 | 1.00 | 51.50 | C |
| ATOM | 18807 | OE1 | GLU | D | 175 | −29.535 | −12.724 | 80.442 | 1.00 | 62.90 | O |
| ATOM | 18808 | OE2 | GLU | D | 175 | −28.679 | −14.272 | 81.710 | 1.00 | 53.40 | O |
| ATOM | 18809 | C | GLU | D | 175 | −24.824 | −12.509 | 84.332 | 1.00 | 49.28 | C |
| ATOM | 18810 | O | GLU | D | 175 | −23.757 | −12.939 | 83.901 | 1.00 | 49.68 | O |
| ATOM | 18812 | N | LEU | D | 176 | −25.231 | −12.718 | 85.580 | 1.00 | 49.05 | N |
| ATOM | 18813 | CA | LEU | D | 176 | −24.399 | −13.426 | 86.570 | 1.00 | 49.29 | C |
| ATOM | 18815 | CB | LEU | D | 176 | −24.979 | −13.255 | 87.977 | 1.00 | 47.46 | C |
| ATOM | 18818 | CG | LEU | D | 176 | −24.242 | −13.947 | 89.124 | 1.00 | 48.17 | C |

-continued

| | | | | | | | | | | |
|---|---|---|---|---|---|---|---|---|---|---|
| ATOM | 18820 | CD1 | LEU | D | 176 | −22.794 | −13.504 | 89.185 | 1.00 | 50.38 C |
| ATOM | 18824 | CD2 | LEU | D | 176 | −24.944 | −13.680 | 90.454 | 1.00 | 49.98 C |
| ATOM | 18828 | C | LEU | D | 176 | −24.252 | −14.918 | 86.243 | 1.00 | 49.36 C |
| ATOM | 18829 | O | LEU | D | 176 | −23.218 | −15.530 | 86.531 | 1.00 | 48.38 O |
| ATOM | 18831 | N | GLN | D | 177 | −25.286 | −15.495 | 85.637 | 1.00 | 49.89 N |
| ATOM | 18832 | CA | GLN | D | 177 | −25.223 | −16.873 | 85.168 | 1.00 | 50.51 C |
| ATOM | 18834 | CB | GLN | D | 177 | −26.621 | −17.376 | 84.774 | 1.00 | 50.29 C |
| ATOM | 18837 | CG | GLN | D | 177 | −27.297 | −16.643 | 83.600 | 1.00 | 52.73 C |
| ATOM | 18840 | CD | GLN | D | 177 | −28.427 | −17.463 | 82.946 | 1.00 | 53.51 C |
| ATOM | 18841 | OE1 | GLN | D | 177 | −28.711 | −17.296 | 81.754 | 1.00 | 44.77 O |
| ATOM | 18842 | NE2 | GLN | D | 177 | −29.056 | −18.368 | 83.720 | 1.00 | 53.31 N |
| ATOM | 18845 | C | GLN | D | 177 | −24.226 | −17.095 | 84.011 | 1.00 | 51.74 C |
| ATOM | 18846 | O | GLN | D | 177 | −24.220 | −18.162 | 83.411 | 1.00 | 54.21 O |
| ATOM | 18848 | N | ASP | D | 178 | −23.398 | −16.098 | 83.699 | 1.00 | 51.17 N |
| ATOM | 18849 | CA | ASP | D | 178 | −22.345 | −16.230 | 82.691 | 1.00 | 49.75 C |
| ATOM | 18851 | CB | ASP | D | 178 | −22.690 | −15.383 | 81.470 | 1.00 | 49.64 C |
| ATOM | 18854 | CG | ASP | D | 178 | −23.642 | −16.069 | 80.549 | 1.00 | 48.02 C |
| ATOM | 18855 | OD1 | ASP | D | 178 | −23.647 | −17.320 | 80.521 | 1.00 | 42.77 O |
| ATOM | 18856 | OD2 | ASP | D | 178 | −24.372 | −15.344 | 79.846 | 1.00 | 48.01 O |
| ATOM | 18857 | C | ASP | D | 178 | −20.966 | −15.804 | 83.182 | 1.00 | 50.41 C |
| ATOM | 18858 | O | ASP | D | 178 | −20.039 | −15.671 | 82.371 | 1.00 | 50.02 O |
| ATOM | 18860 | N | SER | D | 179 | −20.824 | −15.573 | 84.486 | 1.00 | 48.29 N |
| ATOM | 18861 | CA | SER | D | 179 | −19.514 | −15.338 | 85.058 | 1.00 | 46.97 C |
| ATOM | 18863 | CB | SER | D | 179 | −19.610 | −15.039 | 86.562 | 1.00 | 48.08 C |
| ATOM | 18866 | OG | SER | D | 179 | −18.618 | −14.113 | 86.975 | 1.00 | 46.52 O |
| ATOM | 18868 | C | SER | D | 179 | −18.773 | −16.636 | 84.805 | 1.00 | 45.33 C |
| ATOM | 18869 | O | SER | D | 179 | −19.289 | −17.696 | 85.103 | 1.00 | 44.47 O |
| ATOM | 18871 | N | GLY | D | 180 | −17.601 | −16.563 | 84.197 | 1.00 | 45.37 N |
| ATOM | 18872 | CA | GLY | D | 180 | −16.788 | −17.751 | 84.000 | 1.00 | 46.81 C |
| ATOM | 18875 | C | GLY | D | 180 | −15.836 | −17.664 | 82.831 | 1.00 | 47.08 C |
| ATOM | 18876 | O | GLY | D | 180 | −15.576 | −16.591 | 82.298 | 1.00 | 43.84 O |
| ATOM | 18878 | N | THR | D | 181 | −15.318 | −18.823 | 82.440 | 1.00 | 49.78 N |
| ATOM | 18879 | CA | THR | D | 181 | −14.489 | −18.922 | 81.258 | 1.00 | 50.28 C |
| ATOM | 18881 | CB | THR | D | 181 | −13.657 | −20.206 | 81.265 | 1.00 | 50.54 C |
| ATOM | 18883 | OG1 | THR | D | 181 | −12.930 | −20.290 | 82.494 | 1.00 | 53.85 O |
| ATOM | 18885 | CG2 | THR | D | 181 | −12.676 | −20.217 | 80.089 | 1.00 | 50.79 C |
| ATOM | 18889 | C | THR | D | 181 | −15.359 | −18.927 | 80.013 | 1.00 | 50.94 C |
| ATOM | 18890 | O | THR | D | 181 | −16.294 | −19.720 | 79.904 | 1.00 | 51.44 O |
| ATOM | 18892 | N | TRP | D | 182 | −15.047 | −18.025 | 79.088 | 1.00 | 51.77 N |
| ATOM | 18893 | CA | TRP | D | 182 | −15.644 | −18.023 | 77.762 | 1.00 | 50.98 C |
| ATOM | 18895 | CB | TRP | D | 182 | −16.042 | −16.615 | 77.338 | 1.00 | 50.58 C |
| ATOM | 18898 | CG | TRP | D | 182 | −17.226 | −16.064 | 78.063 | 1.00 | 50.41 C |
| ATOM | 18899 | CD1 | TRP | D | 182 | −17.333 | −15.856 | 79.396 | 1.00 | 51.75 C |
| ATOM | 18901 | NE1 | TRP | D | 182 | −18.562 | −15.327 | 79.694 | 1.00 | 53.78 N |
| ATOM | 18903 | CE2 | TRP | D | 182 | −19.272 | −15.170 | 78.537 | 1.00 | 47.89 C |
| ATOM | 18904 | CD2 | TRP | D | 182 | −18.458 | −15.619 | 77.484 | 1.00 | 48.06 C |
| ATOM | 18905 | CE3 | TRP | D | 182 | −18.959 | −15.579 | 76.176 | 1.00 | 50.74 C |
| ATOM | 18907 | CZ3 | TRP | D | 182 | −20.234 | −15.085 | 75.968 | 1.00 | 50.92 C |
| ATOM | 18909 | CH2 | TRP | D | 182 | −21.020 | −14.638 | 77.046 | 1.00 | 51.67 C |
| ATOM | 18911 | CZ2 | TRP | D | 182 | −20.555 | −14.669 | 78.333 | 1.00 | 49.51 C |
| ATOM | 18913 | C | TRP | D | 182 | −14.614 | −18.563 | 76.798 | 1.00 | 50.96 C |
| ATOM | 18914 | O | TRP | D | 182 | −13.423 | −18.292 | 76.952 | 1.00 | 51.34 O |
| ATOM | 18916 | N | THR | D | 183 | −15.084 | −19.326 | 75.811 | 1.00 | 51.16 N |
| ATOM | 18917 | CA | THR | D | 183 | −14.224 | −19.966 | 74.828 | 1.00 | 51.23 C |
| ATOM | 18919 | CB | THR | D | 183 | −14.473 | −21.474 | 74.759 | 1.00 | 49.60 C |
| ATOM | 18921 | OG1 | THR | D | 183 | −14.146 | −22.052 | 76.022 | 1.00 | 51.62 O |
| ATOM | 18923 | CG2 | THR | D | 183 | −13.616 | −22.127 | 73.681 | 1.00 | 49.58 C |
| ATOM | 18927 | C | THR | D | 183 | −14.467 | −19.367 | 73.463 | 1.00 | 51.31 C |
| ATOM | 18928 | O | THR | D | 183 | −15.477 | −19.642 | 72.821 | 1.00 | 51.31 O |
| ATOM | 18930 | N | CYS | D | 184 | −13.520 | −18.554 | 73.022 | 1.00 | 52.73 N |
| ATOM | 18931 | CA | CYS | D | 184 | −13.556 | −18.012 | 71.683 | 1.00 | 54.51 C |
| ATOM | 18933 | CB | CYS | D | 184 | −13.089 | −16.568 | 71.701 | 1.00 | 54.89 C |
| ATOM | 18936 | SG | CYS | D | 184 | −14.059 | −15.677 | 72.890 | 1.00 | 61.88 S |
| ATOM | 18938 | C | CYS | D | 184 | −12.747 | −18.851 | 70.696 | 1.00 | 54.85 C |
| ATOM | 18939 | O | CYS | D | 184 | −11.627 | −19.284 | 70.973 | 1.00 | 54.27 O |
| ATOM | 18941 | N | THR | D | 185 | −13.361 | −19.080 | 69.541 | 1.00 | 55.56 N |
| ATOM | 18942 | CA | THR | D | 185 | −12.731 | −19.745 | 68.418 | 1.00 | 55.00 C |
| ATOM | 18944 | CB | THR | D | 185 | −13.581 | −20.936 | 67.996 | 1.00 | 54.27 C |
| ATOM | 18946 | OG1 | THR | D | 185 | −13.714 | −21.824 | 69.111 | 1.00 | 52.72 O |
| ATOM | 18948 | CG2 | THR | D | 185 | −12.957 | −21.661 | 66.827 | 1.00 | 54.50 C |
| ATOM | 18952 | C | THR | D | 185 | −12.624 | −18.737 | 67.274 | 1.00 | 54.26 C |
| ATOM | 18953 | O | THR | D | 185 | −13.630 | −18.164 | 66.863 | 1.00 | 54.65 O |
| ATOM | 18955 | N | VAL | D | 186 | −11.403 | −18.511 | 66.790 | 1.00 | 54.25 N |
| ATOM | 18956 | CA | VAL | D | 186 | −11.143 | −17.616 | 65.656 | 1.00 | 54.15 C |
| ATOM | 18958 | CB | VAL | D | 186 | −9.885 | −16.759 | 65.880 | 1.00 | 53.88 C |
| ATOM | 18960 | CG1 | VAL | D | 186 | −9.613 | −15.890 | 64.659 | 1.00 | 54.27 C |
| ATOM | 18964 | CG2 | VAL | D | 186 | −10.032 | −15.904 | 67.135 | 1.00 | 54.96 C |
| ATOM | 18968 | C | VAL | D | 186 | −10.934 | −18.435 | 64.388 | 1.00 | 53.99 C |
| ATOM | 18969 | O | VAL | D | 186 | −10.098 | −19.339 | 64.357 | 1.00 | 58.08 O |

-continued

| | | | | | | | | | | |
|---|---|---|---|---|---|---|---|---|---|---|
| ATOM | 18971 | N | LEU | D | 187 | −11.668 | −18.090 | 63.340 | 1.00 | 52.20 N |
| ATOM | 18972 | CA | LEU | D | 187 | −11.724 | −18.886 | 62.121 | 1.00 | 52.50 C |
| ATOM | 18974 | CB | LEU | D | 187 | −13.188 | −19.191 | 61.782 | 1.00 | 53.49 C |
| ATOM | 18977 | CG | LEU | D | 187 | −13.543 | −20.514 | 61.106 | 1.00 | 50.97 C |
| ATOM | 18979 | CD1 | LEU | D | 187 | −15.009 | −20.458 | 60.738 | 1.00 | 52.54 C |
| ATOM | 18983 | CD2 | LEU | D | 187 | −12.701 | −20.774 | 59.889 | 1.00 | 50.31 C |
| ATOM | 18987 | C | LEU | D | 187 | −11.095 | −18.114 | 60.972 | 1.00 | 51.90 C |
| ATOM | 18988 | O | LEU | D | 187 | −11.479 | −16.970 | 60.713 | 1.00 | 51.92 O |
| ATOM | 18990 | N | GLN | D | 188 | −10.135 | −18.753 | 60.301 | 1.00 | 51.71 N |
| ATOM | 18991 | CA | GLN | D | 188 | −9.542 | −18.260 | 59.056 | 1.00 | 51.97 C |
| ATOM | 18993 | CB | GLN | D | 188 | −8.104 | −17.776 | 59.290 | 1.00 | 51.88 C |
| ATOM | 18996 | CG | GLN | D | 188 | −7.305 | −17.428 | 58.032 | 1.00 | 51.87 C |
| ATOM | 18999 | CD | GLN | D | 188 | −7.774 | −16.159 | 57.340 | 1.00 | 52.45 C |
| ATOM | 19000 | OE1 | GLN | D | 188 | −7.811 | −15.086 | 57.939 | 1.00 | 49.99 O |
| ATOM | 19001 | NE2 | GLN | D | 188 | −8.109 | −16.274 | 56.060 | 1.00 | 51.18 N |
| ATOM | 19004 | C | GLN | D | 188 | −9.580 | −19.408 | 58.049 | 1.00 | 51.58 C |
| ATOM | 19005 | O | GLN | D | 188 | −8.986 | −20.464 | 58.271 | 1.00 | 51.04 O |
| ATOM | 19007 | N | ASN | D | 189 | −10.275 | −19.173 | 56.942 | 1.00 | 52.77 N |
| ATOM | 19008 | CA | ASN | D | 189 | −10.585 | −20.195 | 55.943 | 1.00 | 52.62 C |
| ATOM | 19010 | CB | ASN | D | 189 | −9.323 | −20.728 | 55.258 | 1.00 | 53.17 C |
| ATOM | 19013 | CG | ASN | D | 189 | −8.532 | −19.638 | 54.566 | 1.00 | 52.86 C |
| ATOM | 19014 | OD1 | ASN | D | 189 | −9.057 | −18.569 | 54.258 | 1.00 | 43.61 O |
| ATOM | 19015 | ND2 | ASN | D | 189 | −7.249 | −19.903 | 54.326 | 1.00 | 61.59 N |
| ATOM | 19018 | C | ASN | D | 189 | −11.413 | −21.280 | 56.598 | 1.00 | 52.19 C |
| ATOM | 19019 | O | ASN | D | 189 | −12.591 | −21.048 | 56.875 | 1.00 | 55.59 O |
| ATOM | 19021 | N | GLN | D | 190 | −10.822 | −22.446 | 56.836 | 1.00 | 50.92 N |
| ATOM | 19022 | CA | GLN | D | 190 | −11.444 | −23.471 | 57.669 | 1.00 | 52.44 C |
| ATOM | 19024 | CB | GLN | D | 190 | −11.651 | −24.767 | 56.883 | 1.00 | 53.07 C |
| ATOM | 19027 | CG | GLN | D | 190 | −10.454 | −25.730 | 56.849 | 1.00 | 53.28 C |
| ATOM | 19030 | CD | GLN | D | 190 | −9.400 | −25.349 | 55.829 | 1.00 | 56.43 C |
| ATOM | 19031 | OE1 | GLN | D | 190 | −9.136 | −24.168 | 55.595 | 1.00 | 61.17 O |
| ATOM | 19032 | NE2 | GLN | D | 190 | −8.786 | −26.353 | 55.217 | 1.00 | 59.00 N |
| ATOM | 19035 | C | GLN | D | 190 | −10.619 | −23.768 | 58.907 | 1.00 | 52.71 C |
| ATOM | 19036 | O | GLN | D | 190 | −11.057 | −24.509 | 59.769 | 1.00 | 53.18 O |
| ATOM | 19038 | N | LYS | D | 191 | −9.416 | −23.215 | 58.975 | 1.00 | 53.72 N |
| ATOM | 19039 | CA | LYS | D | 191 | −8.512 | −23.477 | 60.083 | 1.00 | 54.18 C |
| ATOM | 19041 | CB | LYS | D | 191 | −7.066 | −23.170 | 59.657 | 1.00 | 55.20 C |
| ATOM | 19044 | CG | LYS | D | 191 | −6.186 | −24.396 | 59.362 | 1.00 | 57.49 C |
| ATOM | 19047 | CD | LYS | D | 191 | −6.532 | −25.122 | 58.058 | 1.00 | 56.87 C |
| ATOM | 19050 | CE | LYS | D | 191 | −5.260 | −25.485 | 57.235 | 1.00 | 57.44 C |
| ATOM | 19053 | NZ | LYS | D | 191 | −4.248 | −26.381 | 57.913 | 1.00 | 55.07 N |
| ATOM | 19057 | C | LYS | D | 191 | −8.926 | −22.639 | 61.306 | 1.00 | 53.32 C |
| ATOM | 19058 | O | LYS | D | 191 | −9.389 | −21.514 | 61.151 | 1.00 | 53.16 O |
| ATOM | 19060 | N | LYS | D | 192 | −8.751 | −23.186 | 62.511 | 1.00 | 52.86 N |
| ATOM | 19061 | CA | LYS | D | 192 | −9.222 | −22.530 | 63.739 | 1.00 | 53.91 C |
| ATOM | 19063 | CB | LYS | D | 192 | −10.485 | −23.231 | 64.289 | 1.00 | 54.14 C |
| ATOM | 19066 | CG | LYS | D | 192 | −11.578 | −23.484 | 63.243 | 1.00 | 56.41 C |
| ATOM | 19069 | CD | LYS | D | 192 | −12.966 | −23.785 | 63.836 | 1.00 | 55.44 C |
| ATOM | 19072 | CE | LYS | D | 192 | −13.208 | −25.259 | 64.121 | 1.00 | 57.49 C |
| ATOM | 19075 | NZ | LYS | D | 192 | −14.683 | −25.573 | 64.184 | 1.00 | 54.24 N |
| ATOM | 19079 | C | LYS | D | 192 | −8.155 | −22.468 | 64.836 | 1.00 | 53.61 C |
| ATOM | 19080 | O | LYS | D | 192 | −7.221 | −23.275 | 64.865 | 1.00 | 53.61 O |
| ATOM | 19082 | N | VAL | D | 193 | −8.314 | −21.500 | 65.739 | 1.00 | 53.25 N |
| ATOM | 19083 | CA | VAL | D | 193 | −7.480 | −21.391 | 66.932 | 1.00 | 52.90 C |
| ATOM | 19085 | CB | VAL | D | 193 | −6.271 | −20.508 | 66.646 | 1.00 | 51.67 C |
| ATOM | 19087 | CG1 | VAL | D | 193 | −6.695 | −19.172 | 66.048 | 1.00 | 56.14 C |
| ATOM | 19091 | CG2 | VAL | D | 193 | −5.466 | −20.312 | 67.888 | 1.00 | 52.21 C |
| ATOM | 19095 | C | VAL | D | 193 | −8.295 | −20.876 | 68.145 | 1.00 | 53.74 C |
| ATOM | 19096 | O | VAL | D | 193 | −9.103 | −19.961 | 68.009 | 1.00 | 53.84 O |
| ATOM | 19098 | N | GLU | D | 194 | −8.089 | −21.481 | 69.318 | 1.00 | 54.42 N |
| ATOM | 19099 | CA | GLU | D | 194 | −8.884 | −21.165 | 70.516 | 1.00 | 54.34 C |
| ATOM | 19101 | CB | GLU | D | 194 | −9.088 | −22.400 | 71.392 | 1.00 | 54.97 C |
| ATOM | 19104 | CG | GLU | D | 194 | −10.533 | −22.866 | 71.489 | 1.00 | 58.46 C |
| ATOM | 19107 | CD | GLU | D | 194 | −10.708 | −24.031 | 72.459 | 1.00 | 59.84 C |
| ATOM | 19108 | OE1 | GLU | D | 194 | −9.897 | −24.159 | 73.408 | 1.00 | 64.41 O |
| ATOM | 19109 | OE2 | GLU | D | 194 | −11.664 | −24.818 | 72.273 | 1.00 | 65.48 O |
| ATOM | 19110 | C | GLU | D | 194 | −8.285 | −20.090 | 71.401 | 1.00 | 53.11 C |
| ATOM | 19111 | O | GLU | D | 194 | −7.075 | −19.979 | 71.545 | 1.00 | 49.11 O |
| ATOM | 19113 | N | PHE | D | 195 | −9.178 | −19.318 | 72.009 | 1.00 | 55.14 N |
| ATOM | 19114 | CA | PHE | D | 195 | −8.841 | −18.333 | 73.024 | 1.00 | 54.95 C |
| ATOM | 19116 | CB | PHE | D | 195 | −9.022 | −16.912 | 72.479 | 1.00 | 53.77 C |
| ATOM | 19119 | CG | PHE | D | 195 | −7.913 | −16.471 | 71.567 | 1.00 | 52.09 C |
| ATOM | 19120 | CD1 | PHE | D | 195 | −6.778 | −15.867 | 72.077 | 1.00 | 49.99 C |
| ATOM | 19122 | CE1 | PHE | D | 195 | −5.742 | −15.474 | 71.241 | 1.00 | 53.83 C |
| ATOM | 19124 | CZ | PHE | D | 195 | −5.842 | −15.673 | 69.880 | 1.00 | 54.06 C |
| ATOM | 19126 | CE2 | PHE | D | 195 | −6.972 | −16.277 | 69.359 | 1.00 | 56.31 C |
| ATOM | 19128 | CD2 | PHE | D | 195 | −7.998 | −16.675 | 70.202 | 1.00 | 52.62 C |
| ATOM | 19130 | C | PHE | D | 195 | −9.775 | −18.567 | 74.195 | 1.00 | 56.67 C |
| ATOM | 19131 | O | PHE | D | 195 | −10.992 | −18.571 | 74.013 | 1.00 | 60.11 O |

| | | | | | | | | | | |
|---|---|---|---|---|---|---|---|---|---|---|
| ATOM | 19133 | N | LYS | D | 196 | −9.222 | −18.790 | 75.386 | 1.00 | 56.89 N |
| ATOM | 19134 | CA | LYS | D | 196 | −10.038 | −18.836 | 76.594 | 1.00 | 55.67 C |
| ATOM | 19136 | CB | LYS | D | 196 | −9.568 | −19.948 | 77.514 | 1.00 | 56.02 C |
| ATOM | 19139 | CG | LYS | D | 196 | −9.764 | −21.320 | 76.892 | 1.00 | 57.44 C |
| ATOM | 19142 | CD | LYS | D | 196 | −10.317 | −22.332 | 77.867 | 1.00 | 55.86 C |
| ATOM | 19145 | CE | LYS | D | 196 | −10.967 | −23.483 | 77.118 | 1.00 | 60.28 C |
| ATOM | 19148 | NZ | LYS | D | 196 | −11.462 | −24.566 | 78.016 | 1.00 | 64.78 N |
| ATOM | 19152 | C | LYS | D | 196 | −9.954 | −17.493 | 77.278 | 1.00 | 54.92 C |
| ATOM | 19153 | O | LYS | D | 196 | −8.906 | −16.861 | 77.251 | 1.00 | 55.80 O |
| ATOM | 19155 | N | ILE | D | 197 | −11.066 | −17.036 | 77.847 | 1.00 | 55.38 N |
| ATOM | 19156 | CA | ILE | D | 197 | −11.101 | −15.771 | 78.593 | 1.00 | 56.16 C |
| ATOM | 19158 | CB | ILE | D | 197 | −11.613 | −14.609 | 77.738 | 1.00 | 55.35 C |
| ATOM | 19160 | CG1 | ILE | D | 197 | −10.706 | −14.353 | 76.543 | 1.00 | 56.60 C |
| ATOM | 19163 | CD1 | ILE | D | 197 | −11.281 | −13.324 | 75.585 | 1.00 | 59.10 C |
| ATOM | 19167 | CG2 | ILE | D | 197 | −11.698 | −13.339 | 78.578 | 1.00 | 57.87 C |
| ATOM | 19171 | C | ILE | D | 197 | −12.043 | −15.837 | 79.790 | 1.00 | 56.32 C |
| ATOM | 19172 | O | ILE | D | 197 | −13.218 | −16.151 | 79.634 | 1.00 | 58.26 O |
| ATOM | 19174 | N | ASP | D | 198 | −11.541 | −15.487 | 80.969 | 1.00 | 56.33 N |
| ATOM | 19175 | CA | ASP | D | 198 | −12.382 | −15.371 | 82.158 | 1.00 | 56.33 C |
| ATOM | 19177 | CB | ASP | D | 198 | −11.550 | −15.677 | 83.400 | 1.00 | 55.36 C |
| ATOM | 19180 | CG | ASP | D | 198 | −11.030 | −17.106 | 83.402 | 1.00 | 60.37 C |
| ATOM | 19181 | OD1 | ASP | D | 198 | −11.799 | −18.020 | 83.025 | 1.00 | 58.17 O |
| ATOM | 19182 | OD2 | ASP | D | 198 | −9.852 | −17.322 | 83.769 | 1.00 | 69.19 O |
| ATOM | 19183 | C | ASP | D | 198 | −13.075 | −13.995 | 82.254 | 1.00 | 55.23 C |
| ATOM | 19184 | O | ASP | D | 198 | −12.421 | −12.956 | 82.331 | 1.00 | 54.15 O |
| ATOM | 19186 | N | ILE | D | 199 | −14.405 | −14.003 | 82.206 | 1.00 | 56.57 N |
| ATOM | 19187 | CA | ILE | D | 199 | −15.201 | −12.797 | 82.397 | 1.00 | 57.69 C |
| ATOM | 19189 | CB | ILE | D | 199 | −16.273 | −12.590 | 81.301 | 1.00 | 60.29 C |
| ATOM | 19191 | CG1 | ILE | D | 199 | −15.626 | −12.451 | 79.917 | 1.00 | 61.74 C |
| ATOM | 19194 | CD1 | ILE | D | 199 | −16.630 | −12.390 | 78.780 | 1.00 | 60.16 C |
| ATOM | 19198 | CG2 | ILE | D | 199 | −17.113 | −11.329 | 81.614 | 1.00 | 59.93 C |
| ATOM | 19202 | C | ILE | D | 199 | −15.915 | −12.897 | 83.727 | 1.00 | 57.55 C |
| ATOM | 19203 | O | ILE | D | 199 | −16.868 | −13.663 | 83.879 | 1.00 | 56.29 O |
| ATOM | 19205 | N | VAL | D | 200 | −15.451 | −12.101 | 84.681 | 1.00 | 57.25 N |
| ATOM | 19206 | CA | VAL | D | 200 | −16.000 | −12.078 | 86.019 | 1.00 | 55.36 C |
| ATOM | 19208 | CB | VAL | D | 200 | −14.883 | −11.799 | 87.032 | 1.00 | 55.51 C |
| ATOM | 19210 | CG1 | VAL | D | 200 | −15.409 | −11.884 | 88.468 | 1.00 | 54.19 C |
| ATOM | 19214 | CG2 | VAL | D | 200 | −13.722 | −12.773 | 86.798 | 1.00 | 55.91 C |
| ATOM | 19218 | C | VAL | D | 200 | −17.064 | −10.982 | 86.083 | 1.00 | 54.74 C |
| ATOM | 19219 | O | VAL | D | 200 | −16.771 | −9.811 | 85.834 | 1.00 | 55.37 O |
| ATOM | 19221 | N | VAL | D | 201 | −18.300 | −11.369 | 86.390 | 1.00 | 53.29 N |
| ATOM | 19222 | CA | VAL | D | 201 | −19.396 | −10.417 | 86.495 | 1.00 | 53.18 C |
| ATOM | 19224 | CB | VAL | D | 201 | −20.620 | −10.767 | 85.569 | 1.00 | 52.12 C |
| ATOM | 19226 | CG1 | VAL | D | 201 | −20.939 | −12.205 | 85.598 | 1.00 | 55.63 C |
| ATOM | 19230 | CG2 | VAL | D | 201 | −21.852 | −9.967 | 85.951 | 1.00 | 53.67 C |
| ATOM | 19234 | C | VAL | D | 201 | −19.783 | −10.281 | 87.960 | 1.00 | 53.05 C |
| ATOM | 19235 | O | VAL | D | 201 | −20.197 | −11.246 | 88.606 | 1.00 | 54.54 O |
| ATOM | 19237 | N | LEU | D | 202 | −19.622 | −9.064 | 88.472 | 1.00 | 53.67 N |
| ATOM | 19238 | CA | LEU | D | 202 | −19.914 | −8.743 | 89.863 | 1.00 | 53.57 C |
| ATOM | 19240 | CB | LEU | D | 202 | −19.071 | −7.558 | 90.329 | 1.00 | 54.33 C |
| ATOM | 19243 | CG | LEU | D | 202 | −17.573 | −7.621 | 90.015 | 1.00 | 55.39 C |
| ATOM | 19245 | CD1 | LEU | D | 202 | −16.893 | −6.356 | 90.508 | 1.00 | 57.32 C |
| ATOM | 19249 | CD2 | LEU | D | 202 | −16.942 | −8.854 | 90.640 | 1.00 | 55.32 C |
| ATOM | 19253 | C | LEU | D | 202 | −21.378 | −8.393 | 89.973 | 1.00 | 53.25 C |
| ATOM | 19254 | O | LEU | D | 202 | −21.896 | −7.634 | 89.154 | 1.00 | 53.35 O |
| ATOM | 19256 | N | ALA | D | 203 | −22.044 | −8.941 | 90.983 | 1.00 | 53.14 N |
| ATOM | 19257 | CA | ALA | D | 203 | −23.487 | −8.803 | 91.100 | 1.00 | 51.68 C |
| ATOM | 19259 | CB | ALA | D | 203 | −24.159 | −9.716 | 90.112 | 1.00 | 51.77 C |
| ATOM | 19263 | C | ALA | D | 203 | −23.964 | −9.145 | 92.482 | 1.00 | 50.63 C |
| ATOM | 19264 | O | ALA | D | 203 | −23.250 | −9.776 | 93.252 | 1.00 | 50.94 O |
| ATOM | 19266 | N | PHE | D | 204 | −25.180 | −8.715 | 92.790 | 1.00 | 51.21 N |
| ATOM | 19267 | CA | PHE | D | 204 | −25.920 | −9.279 | 93.907 | 1.00 | 52.04 C |
| ATOM | 19269 | CB | PHE | D | 204 | −27.061 | −8.350 | 94.333 | 1.00 | 51.17 C |
| ATOM | 19272 | CG | PHE | D | 204 | −26.613 | −7.128 | 95.115 | 1.00 | 53.91 C |
| ATOM | 19273 | CD1 | PHE | D | 204 | −26.036 | −7.260 | 96.380 | 1.00 | 54.70 C |
| ATOM | 19275 | CE1 | PHE | D | 204 | −25.637 | −6.135 | 97.110 | 1.00 | 50.70 C |
| ATOM | 19277 | CZ | PHE | D | 204 | −25.833 | −4.867 | 96.585 | 1.00 | 52.31 C |
| ATOM | 19279 | CE2 | PHE | D | 204 | −26.422 | −4.718 | 95.329 | 1.00 | 50.85 C |
| ATOM | 19281 | CD2 | PHE | D | 204 | −26.812 | −5.841 | 94.608 | 1.00 | 53.80 C |
| ATOM | 19283 | C | PHE | D | 204 | −26.470 | −10.659 | 93.479 | 1.00 | 52.33 C |
| ATOM | 19284 | O | PHE | D | 204 | −26.861 | −10.855 | 92.319 | 1.00 | 50.22 O |
| ATOM | 19286 | N | GLN | D | 205 | −26.499 | −11.617 | 94.407 | 1.00 | 53.43 N |
| ATOM | 19287 | CA | GLN | D | 205 | −27.111 | −12.924 | 94.120 | 1.00 | 54.28 C |
| ATOM | 19289 | CB | GLN | D | 205 | −27.053 | −13.857 | 95.335 | 1.00 | 53.60 C |
| ATOM | 19292 | CG | GLN | D | 205 | −25.652 | −14.326 | 95.670 | 1.00 | 53.48 C |
| ATOM | 19295 | CD | GLN | D | 205 | −25.592 | −15.311 | 96.816 | 1.00 | 49.76 C |
| ATOM | 19296 | OE1 | GLN | D | 205 | −26.521 | −16.081 | 97.059 | 1.00 | 40.19 O |
| ATOM | 19297 | NE2 | GLN | D | 205 | −24.479 | −15.297 | 97.520 | 1.00 | 42.54 N |
| ATOM | 19300 | C | GLN | D | 205 | −28.561 | −12.740 | 93.707 | 1.00 | 56.68 C |

-continued

| | | | | | | | | | | |
|---|---|---|---|---|---|---|---|---|---|---|
| ATOM | 19301 | O | GLN | D | 205 | −29.081 | −13.513 | 92.898 | 1.00 | 57.95 O |
| ATOM | 19303 | N | LYS | D | 206 | −29.186 | −11.700 | 94.266 | 1.00 | 58.26 N |
| ATOM | 19304 | CA | LYS | D | 206 | −30.613 | −11.461 | 94.154 | 1.00 | 58.72 C |
| ATOM | 19306 | CB | LYS | D | 206 | −31.237 | −11.589 | 95.545 | 1.00 | 59.92 C |
| ATOM | 19309 | CG | LYS | D | 206 | −32.640 | −12.164 | 95.539 | 1.00 | 64.22 C |
| ATOM | 19312 | CD | LYS | D | 206 | −32.661 | −13.680 | 95.295 | 1.00 | 62.70 C |
| ATOM | 19315 | CE | LYS | D | 206 | −34.081 | −14.153 | 95.008 | 1.00 | 62.49 C |
| ATOM | 19318 | NZ | LYS | D | 206 | −34.322 | −15.524 | 95.512 | 1.00 | 64.99 N |
| ATOM | 19322 | C | LYS | D | 206 | −30.927 | −10.081 | 93.556 | 1.00 | 59.53 C |
| ATOM | 19323 | O | LYS | D | 206 | −30.213 | −9.105 | 93.797 | 1.00 | 60.41 O |
| ATOM | 19325 | N | ALA | D | 207 | −32.010 | −10.014 | 92.787 | 1.00 | 58.87 N |
| ATOM | 19326 | CA | ALA | D | 207 | −32.402 | −8.796 | 92.081 | 1.00 | 58.07 C |
| ATOM | 19328 | CB | ALA | D | 207 | −33.087 | −9.165 | 90.786 | 1.00 | 58.28 C |
| ATOM | 19332 | C | ALA | D | 207 | −33.324 | −7.911 | 92.919 | 1.00 | 57.62 C |
| ATOM | 19333 | O | ALA | D | 207 | −33.273 | −6.683 | 92.831 | 1.00 | 56.63 O |
| ATOM | 19335 | N | SER | D | 208 | −34.176 | −8.544 | 93.719 | 1.00 | 57.90 N |
| ATOM | 19336 | CA | SER | D | 208 | −35.167 | −7.834 | 94.517 | 1.00 | 57.38 C |
| ATOM | 19338 | CB | SER | D | 208 | −36.352 | −7.428 | 93.639 | 1.00 | 58.01 C |
| ATOM | 19341 | OG | SER | D | 208 | −37.377 | −6.819 | 94.408 | 1.00 | 61.64 O |
| ATOM | 19343 | C | SER | D | 208 | −35.666 | −8.721 | 95.647 | 1.00 | 57.23 C |
| ATOM | 19344 | O | SER | D | 208 | −35.524 | −9.945 | 95.597 | 1.00 | 56.70 O |
| ATOM | 19346 | N | SER | D | 209 | −36.260 | −8.094 | 96.661 | 1.00 | 56.62 N |
| ATOM | 19347 | CA | SER | D | 209 | −36.893 | −8.826 | 97.751 | 1.00 | 55.04 C |
| ATOM | 19349 | CB | SER | D | 209 | −35.844 | −9.312 | 98.746 | 1.00 | 54.48 C |
| ATOM | 19352 | OG | SER | D | 209 | −35.068 | −8.233 | 99.226 | 1.00 | 52.23 O |
| ATOM | 19354 | C | SER | D | 209 | −37.939 | −7.976 | 98.460 | 1.00 | 55.00 C |
| ATOM | 19355 | O | SER | D | 209 | −37.902 | −6.745 | 98.404 | 1.00 | 56.00 O |
| ATOM | 19357 | N | ILE | D | 210 | −38.862 | −8.660 | 99.134 | 1.00 | 54.81 N |
| ATOM | 19358 | CA | ILE | D | 210 | −40.025 | −8.042 | 99.785 | 1.00 | 52.89 C |
| ATOM | 19360 | CB | ILE | D | 210 | −41.270 | −8.012 | 98.829 | 1.00 | 52.32 C |
| ATOM | 19362 | CG1 | ILE | D | 210 | −42.583 | −7.896 | 99.618 | 1.00 | 47.17 C |
| ATOM | 19365 | CD1 | ILE | D | 210 | −43.756 | −7.465 | 98.781 | 1.00 | 48.25 C |
| ATOM | 19369 | CG2 | ILE | D | 210 | −41.289 | −9.245 | 97.913 | 1.00 | 53.11 C |
| ATOM | 19373 | C | ILE | D | 210 | −40.335 | −8.805 | 101.074 | 1.00 | 53.18 C |
| ATOM | 19374 | O | ILE | D | 210 | −40.351 | −10.039 | 101.085 | 1.00 | 52.55 O |
| ATOM | 19376 | N | VAL | D | 211 | −40.586 | −8.063 | 102.152 | 1.00 | 53.22 N |
| ATOM | 19377 | CA | VAL | D | 211 | −40.730 | −8.646 | 103.489 | 1.00 | 52.62 C |
| ATOM | 19379 | CB | VAL | D | 211 | −39.474 | −8.323 | 104.352 | 1.00 | 53.09 C |
| ATOM | 19381 | CG1 | VAL | D | 211 | −39.696 | −8.653 | 105.830 | 1.00 | 53.12 C |
| ATOM | 19385 | CG2 | VAL | D | 211 | −38.247 | −9.067 | 103.814 | 1.00 | 50.71 C |
| ATOM | 19389 | C | VAL | D | 211 | −42.005 | −8.155 | 104.184 | 1.00 | 52.33 C |
| ATOM | 19390 | O | VAL | D | 211 | −42.456 | −7.028 | 103.960 | 1.00 | 51.82 O |
| ATOM | 19392 | N | TYR | D | 212 | −42.571 | −9.025 | 105.023 | 1.00 | 52.90 N |
| ATOM | 19393 | CA | TYR | D | 212 | −43.779 | −8.738 | 105.815 | 1.00 | 51.43 C |
| ATOM | 19395 | CB | TYR | D | 212 | −44.965 | −9.565 | 105.297 | 1.00 | 49.88 C |
| ATOM | 19398 | CG | TYR | D | 212 | −45.073 | −9.663 | 103.774 | 1.00 | 48.56 C |
| ATOM | 19399 | CD1 | TYR | D | 212 | −45.818 | −8.735 | 103.051 | 1.00 | 46.68 C |
| ATOM | 19401 | CE1 | TYR | D | 212 | −45.934 | −8.819 | 101.663 | 1.00 | 47.38 C |
| ATOM | 19403 | CZ | TYR | D | 212 | −45.302 | −9.838 | 100.979 | 1.00 | 47.61 C |
| ATOM | 19404 | OH | TYR | D | 212 | −45.426 | −9.896 | 99.611 | 1.00 | 42.73 O |
| ATOM | 19406 | CE2 | TYR | D | 212 | −44.554 | −10.782 | 101.673 | 1.00 | 49.03 C |
| ATOM | 19408 | CD2 | TYR | D | 212 | −44.445 | −10.692 | 103.068 | 1.00 | 46.32 C |
| ATOM | 19410 | C | TYR | D | 212 | −43.535 | −9.077 | 107.287 | 1.00 | 50.42 C |
| ATOM | 19411 | O | TYR | D | 212 | −43.717 | −8.238 | 108.175 | 1.00 | 52.05 O |
| ATOM | 19413 | N | GLU | D | 220 | −35.213 | −7.841 | 109.543 | 1.00 | 59.95 N |
| ATOM | 19414 | CA | GLU | D | 220 | −33.879 | −8.124 | 109.015 | 1.00 | 59.74 C |
| ATOM | 19416 | CB | GLU | D | 220 | −33.315 | −9.397 | 109.647 | 1.00 | 59.82 C |
| ATOM | 19419 | CG | GLU | D | 220 | −32.987 | −9.251 | 111.125 | 1.00 | 61.25 C |
| ATOM | 19422 | CD | GLU | D | 220 | −32.245 | −10.450 | 111.680 | 1.00 | 60.21 C |
| ATOM | 19423 | OE1 | GLU | D | 220 | −31.459 | −10.264 | 112.631 | 1.00 | 60.22 O |
| ATOM | 19424 | OE2 | GLU | D | 220 | −32.443 | −11.572 | 111.164 | 1.00 | 60.18 O |
| ATOM | 19425 | C | GLU | D | 220 | −33.889 | −8.289 | 107.503 | 1.00 | 58.67 C |
| ATOM | 19426 | O | GLU | D | 220 | −34.517 | −9.211 | 106.990 | 1.00 | 57.22 O |
| ATOM | 19428 | N | PHE | D | 221 | −33.204 | −7.387 | 106.799 | 1.00 | 58.96 N |
| ATOM | 19429 | CA | PHE | D | 221 | −32.934 | −7.561 | 105.367 | 1.00 | 58.57 C |
| ATOM | 19431 | CB | PHE | D | 221 | −32.969 | −6.227 | 104.609 | 1.00 | 58.00 C |
| ATOM | 19434 | CG | PHE | D | 221 | −34.318 | −5.561 | 104.601 | 1.00 | 58.68 C |
| ATOM | 19435 | CD1 | PHE | D | 221 | −35.425 | −6.215 | 104.078 | 1.00 | 59.95 C |
| ATOM | 19437 | CE1 | PHE | D | 221 | −36.672 | −5.599 | 104.068 | 1.00 | 60.49 C |
| ATOM | 19439 | CZ | PHE | D | 221 | −36.816 | −4.311 | 104.578 | 1.00 | 58.43 C |
| ATOM | 19441 | CE2 | PHE | D | 221 | −35.720 | −3.651 | 105.090 | 1.00 | 54.01 C |
| ATOM | 19443 | CD2 | PHE | D | 221 | −34.481 | −4.271 | 105.099 | 1.00 | 55.40 C |
| ATOM | 19445 | C | PHE | D | 221 | −31.572 | −8.221 | 105.177 | 1.00 | 57.72 C |
| ATOM | 19446 | O | PHE | D | 221 | −30.665 | −8.055 | 105.992 | 1.00 | 56.05 O |
| ATOM | 19448 | N | SER | D | 222 | −31.450 | −8.978 | 104.092 | 1.00 | 58.51 N |
| ATOM | 19449 | CA | SER | D | 222 | −30.214 | −9.666 | 103.745 | 1.00 | 58.79 C |
| ATOM | 19451 | CB | SER | D | 222 | −30.399 | −11.172 | 103.949 | 1.00 | 59.48 C |
| ATOM | 19454 | OG | SER | D | 222 | −29.224 | −11.894 | 103.631 | 1.00 | 62.22 O |
| ATOM | 19456 | C | SER | D | 222 | −29.879 | −9.350 | 102.284 | 1.00 | 59.36 C |

-continued

| | | | | | | | | | | |
|---|---|---|---|---|---|---|---|---|---|---|
| ATOM | 19457 | O | SER | D | 222 | −30.756 | −9.425 | 101.426 | 1.00 | 61.66 O |
| ATOM | 19459 | N | PHE | D | 223 | −28.623 | −8.984 | 102.008 | 1.00 | 58.05 N |
| ATOM | 19460 | CA | PHE | D | 223 | −28.178 | −8.624 | 100.650 | 1.00 | 54.78 C |
| ATOM | 19462 | CB | PHE | D | 223 | −27.819 | −7.141 | 100.586 | 1.00 | 53.03 C |
| ATOM | 19465 | CG | PHE | D | 223 | −28.917 | −6.233 | 101.035 | 1.00 | 54.85 C |
| ATOM | 19466 | CD1 | PHE | D | 223 | −29.821 | −5.712 | 100.119 | 1.00 | 56.51 C |
| ATOM | 19468 | CE1 | PHE | D | 223 | −30.838 | −4.861 | 100.524 | 1.00 | 51.18 C |
| ATOM | 19470 | CZ | PHE | D | 223 | −30.959 | −4.527 | 101.853 | 1.00 | 50.43 C |
| ATOM | 19472 | CE2 | PHE | D | 223 | −30.060 | −5.039 | 102.783 | 1.00 | 52.05 C |
| ATOM | 19474 | CD2 | PHE | D | 223 | −29.047 | −5.888 | 102.371 | 1.00 | 53.39 C |
| ATOM | 19476 | C | PHE | D | 223 | −26.967 | −9.448 | 100.216 | 1.00 | 52.76 C |
| ATOM | 19477 | O | PHE | D | 223 | −25.878 | −8.909 | 100.037 | 1.00 | 51.25 O |
| ATOM | 19479 | N | PRO | D | 224 | −27.151 | −10.764 | 100.030 | 1.00 | 51.69 N |
| ATOM | 19480 | CA | PRO | D | 224 | −26.022 | −11.597 | 99.628 | 1.00 | 51.38 C |
| ATOM | 19482 | CB | PRO | D | 224 | −26.621 | −13.004 | 99.599 | 1.00 | 51.22 C |
| ATOM | 19485 | CG | PRO | D | 224 | −28.071 | −12.789 | 99.378 | 1.00 | 51.52 C |
| ATOM | 19488 | CD | PRO | D | 224 | −28.392 | −11.546 | 100.144 | 1.00 | 51.23 C |
| ATOM | 19491 | C | PRO | D | 224 | −25.527 | −11.214 | 98.244 | 1.00 | 50.88 C |
| ATOM | 19492 | O | PRO | D | 224 | −26.333 | −10.894 | 97.370 | 1.00 | 52.45 O |
| ATOM | 19493 | N | LEU | D | 225 | −24.217 | −11.239 | 98.045 | 1.00 | 49.76 N |
| ATOM | 19494 | CA | LEU | D | 225 | −23.653 | −10.877 | 96.750 | 1.00 | 49.29 C |
| ATOM | 19496 | CB | LEU | D | 225 | −22.898 | −9.538 | 96.815 | 1.00 | 49.61 C |
| ATOM | 19499 | CG | LEU | D | 225 | −22.060 | −9.198 | 98.040 | 1.00 | 50.65 C |
| ATOM | 19501 | CD1 | LEU | D | 225 | −20.981 | −10.259 | 98.286 | 1.00 | 52.33 C |
| ATOM | 19505 | CD2 | LEU | D | 225 | −21.462 | −7.796 | 97.869 | 1.00 | 49.70 C |
| ATOM | 19509 | C | LEU | D | 225 | −22.788 | −11.994 | 96.201 | 1.00 | 46.53 C |
| ATOM | 19510 | O | LEU | D | 225 | −22.506 | −12.958 | 96.902 | 1.00 | 43.14 O |
| ATOM | 19512 | N | ALA | D | 226 | −22.401 | −11.858 | 94.936 | 1.00 | 45.37 N |
| ATOM | 19513 | CA | ALA | D | 226 | −21.691 | −12.909 | 94.229 | 1.00 | 48.01 C |
| ATOM | 19515 | CB | ALA | D | 226 | −21.555 | −12.563 | 92.771 | 1.00 | 49.85 C |
| ATOM | 19519 | C | ALA | D | 226 | −20.327 | −13.140 | 94.845 | 1.00 | 48.44 C |
| ATOM | 19520 | O | ALA | D | 226 | −19.714 | −12.217 | 95.368 | 1.00 | 50.48 O |
| ATOM | 19522 | N | PHE | D | 227 | −19.856 | −14.380 | 94.780 | 1.00 | 48.73 N |
| ATOM | 19523 | CA | PHE | D | 227 | −18.635 | −14.778 | 95.481 | 1.00 | 49.94 C |
| ATOM | 19525 | CB | PHE | D | 227 | −18.272 | −16.219 | 95.144 | 1.00 | 45.83 C |
| ATOM | 19528 | CG | PHE | D | 227 | −16.941 | −16.639 | 95.681 | 1.00 | 45.36 C |
| ATOM | 19529 | CD1 | PHE | D | 227 | −16.726 | −16.702 | 97.054 | 1.00 | 38.84 C |
| ATOM | 19531 | CE1 | PHE | D | 227 | −15.507 | −17.093 | 97.561 | 1.00 | 38.85 C |
| ATOM | 19533 | CZ | PHE | D | 227 | −14.476 | −17.423 | 96.694 | 1.00 | 40.38 C |
| ATOM | 19535 | CE2 | PHE | D | 227 | −14.672 | −17.365 | 95.324 | 1.00 | 40.67 C |
| ATOM | 19537 | CD2 | PHE | D | 227 | −15.901 | −16.972 | 94.820 | 1.00 | 41.54 C |
| ATOM | 19539 | C | PHE | D | 227 | −17.450 | −13.881 | 95.146 | 1.00 | 52.47 C |
| ATOM | 19540 | O | PHE | D | 227 | −16.638 | −13.553 | 96.016 | 1.00 | 53.85 O |
| ATOM | 19542 | N | THR | D | 228 | −17.371 | −13.478 | 93.883 | 1.00 | 54.11 N |
| ATOM | 19543 | CA | THR | D | 228 | −16.200 | −12.780 | 93.362 | 1.00 | 55.71 C |
| ATOM | 19545 | CB | THR | D | 228 | −16.258 | −12.767 | 91.826 | 1.00 | 56.84 C |
| ATOM | 19547 | OG1 | THR | D | 228 | −17.429 | −12.061 | 91.386 | 1.00 | 60.35 O |
| ATOM | 19549 | CG2 | THR | D | 228 | −16.313 | −14.218 | 91.288 | 1.00 | 58.07 C |
| ATOM | 19553 | C | THR | D | 228 | −16.017 | −11.354 | 93.929 | 1.00 | 56.66 C |
| ATOM | 19554 | O | THR | D | 228 | −14.903 | −10.813 | 93.931 | 1.00 | 55.94 O |
| ATOM | 19556 | N | VAL | D | 229 | −17.103 | −10.770 | 94.432 | 1.00 | 57.65 N |
| ATOM | 19557 | CA | VAL | D | 229 | −17.066 | −9.433 | 95.028 | 1.00 | 58.31 C |
| ATOM | 19559 | CB | VAL | D | 229 | −18.338 | −8.581 | 94.632 | 1.00 | 59.53 C |
| ATOM | 19561 | CG1 | VAL | D | 229 | −19.633 | −9.274 | 95.010 | 1.00 | 59.43 C |
| ATOM | 19565 | CG2 | VAL | D | 229 | −18.294 | −7.171 | 95.237 | 1.00 | 58.88 C |
| ATOM | 19569 | C | VAL | D | 229 | −16.863 | −9.463 | 96.553 | 1.00 | 58.58 C |
| ATOM | 19570 | O | VAL | D | 229 | −16.675 | −8.411 | 97.159 | 1.00 | 57.87 O |
| ATOM | 19572 | N | GLU | D | 230 | −16.872 | −10.652 | 97.164 | 1.00 | 58.66 N |
| ATOM | 19573 | CA | GLU | D | 230 | −16.688 | −10.780 | 98.623 | 1.00 | 58.69 C |
| ATOM | 19575 | CB | GLU | D | 230 | −16.587 | −12.249 | 99.041 | 1.00 | 59.30 C |
| ATOM | 19578 | CG | GLU | D | 230 | −17.917 | −12.993 | 99.104 | 1.00 | 59.66 C |
| ATOM | 19581 | CD | GLU | D | 230 | −17.836 | −14.286 | 99.913 | 1.00 | 59.55 C |
| ATOM | 19582 | OE1 | GLU | D | 230 | −16.879 | −14.455 | 100.706 | 1.00 | 56.54 O |
| ATOM | 19583 | OE2 | GLU | D | 230 | −18.741 | −15.134 | 99.754 | 1.00 | 62.58 O |
| ATOM | 19584 | C | GLU | D | 230 | −15.448 | −10.047 | 99.137 | 1.00 | 58.44 C |
| ATOM | 19585 | O | GLU | D | 230 | −15.510 | −9.310 | 100.127 | 1.00 | 58.12 O |
| ATOM | 19587 | N | LYS | D | 231 | −14.327 | −10.267 | 98.458 | 1.00 | 58.50 N |
| ATOM | 19588 | CA | LYS | D | 231 | −13.040 | −9.660 | 98.832 | 1.00 | 58.91 C |
| ATOM | 19590 | CB | LYS | D | 231 | −11.896 | −10.390 | 98.108 | 1.00 | 59.75 C |
| ATOM | 19593 | CG | LYS | D | 231 | −11.933 | −10.283 | 96.568 | 1.00 | 63.26 C |
| ATOM | 19596 | CD | LYS | D | 231 | −11.281 | −11.484 | 95.868 | 1.00 | 61.99 C |
| ATOM | 19599 | CE | LYS | D | 231 | −9.782 | −11.571 | 96.160 | 1.00 | 63.05 C |
| ATOM | 19602 | NZ | LYS | D | 231 | −9.486 | −12.136 | 97.506 | 1.00 | 59.26 N |
| ATOM | 19606 | C | LYS | D | 231 | −12.967 | −8.147 | 98.552 | 1.00 | 57.11 C |
| ATOM | 19607 | O | LYS | D | 231 | −12.388 | −7.388 | 99.330 | 1.00 | 56.09 O |
| ATOM | 19609 | N | LEU | D | 232 | −13.585 | −7.734 | 97.447 | 1.00 | 56.22 N |
| ATOM | 19610 | CA | LEU | D | 232 | −13.487 | −6.370 | 96.906 | 1.00 | 55.70 C |
| ATOM | 19612 | CB | LEU | D | 232 | −14.411 | −6.222 | 95.688 | 1.00 | 54.72 C |
| ATOM | 19615 | CG | LEU | D | 232 | −13.782 | −6.484 | 94.317 | 1.00 | 53.00 C |

-continued

| | | | | | | | | | | |
|---|---|---|---|---|---|---|---|---|---|---|
| ATOM | 19617 | CD1 | LEU | D | 232 | −12.892 | −7.721 | 94.302 | 1.00 | 53.46 C |
| ATOM | 19621 | CD2 | LEU | D | 232 | −14.865 | −6.587 | 93.261 | 1.00 | 53.75 C |
| ATOM | 19625 | C | LEU | D | 232 | −13.784 | −5.228 | 97.872 | 1.00 | 55.81 C |
| ATOM | 19626 | O | LEU | D | 232 | −14.479 | −5.399 | 98.874 | 1.00 | 55.92 O |
| ATOM | 19628 | N | THR | D | 233 | −13.241 | −4.059 | 97.531 | 1.00 | 55.71 N |
| ATOM | 19629 | CA | THR | D | 233 | −13.449 | −2.830 | 98.283 | 1.00 | 55.68 C |
| ATOM | 19631 | CB | THR | D | 233 | −12.124 | −2.059 | 98.484 | 1.00 | 55.16 C |
| ATOM | 19633 | OG1 | THR | D | 233 | −11.240 | −2.832 | 99.304 | 1.00 | 55.37 O |
| ATOM | 19635 | CG2 | THR | D | 233 | −12.355 | −0.708 | 99.150 | 1.00 | 55.13 C |
| ATOM | 19639 | C | THR | D | 233 | −14.461 | −1.956 | 97.548 | 1.00 | 56.35 C |
| ATOM | 19640 | O | THR | D | 233 | −14.484 | −1.922 | 96.315 | 1.00 | 58.15 O |
| ATOM | 19642 | N | GLY | D | 234 | −15.299 | −1.259 | 98.312 | 1.00 | 55.46 N |
| ATOM | 19643 | CA | GLY | D | 234 | −16.335 | −0.403 | 97.742 | 1.00 | 53.89 C |
| ATOM | 19646 | C | GLY | D | 234 | −17.175 | 0.280 | 98.805 | 1.00 | 52.41 C |
| ATOM | 19647 | O | GLY | D | 234 | −16.973 | 0.056 | 100.000 | 1.00 | 51.52 O |
| ATOM | 19649 | N | SER | D | 235 | −18.117 | 1.112 | 98.368 | 1.00 | 50.70 N |
| ATOM | 19650 | CA | SER | D | 235 | −19.027 | 1.795 | 99.286 | 1.00 | 51.48 C |
| ATOM | 19652 | CB | SER | D | 235 | −18.413 | 3.125 | 99.755 | 1.00 | 51.85 C |
| ATOM | 19655 | OG | SER | D | 235 | −17.958 | 3.920 | 98.671 | 1.00 | 51.16 O |
| ATOM | 19657 | C | SER | D | 235 | −20.418 | 2.002 | 98.667 | 1.00 | 50.36 C |
| ATOM | 19658 | O | SER | D | 235 | −20.557 | 2.020 | 97.446 | 1.00 | 48.75 O |
| ATOM | 19660 | N | GLY | D | 236 | −21.438 | 2.150 | 99.517 | 1.00 | 50.07 N |
| ATOM | 19661 | CA | GLY | D | 236 | −22.830 | 2.221 | 99.055 | 1.00 | 50.59 C |
| ATOM | 19664 | C | GLY | D | 236 | −23.830 | 2.842 | 100.024 | 1.00 | 50.40 C |
| ATOM | 19665 | O | GLY | D | 236 | −23.447 | 3.375 | 101.071 | 1.00 | 48.99 O |
| ATOM | 19667 | N | GLU | D | 237 | −25.117 | 2.778 | 99.661 | 1.00 | 49.95 N |
| ATOM | 19668 | CA | GLU | D | 237 | −26.188 | 3.358 | 100.483 | 1.00 | 50.06 C |
| ATOM | 19670 | CB | GLU | D | 237 | −26.135 | 4.891 | 100.413 | 1.00 | 51.02 C |
| ATOM | 19673 | CG | GLU | D | 237 | −26.434 | 5.461 | 99.041 | 1.00 | 51.07 C |
| ATOM | 19676 | CD | GLU | D | 237 | −26.503 | 6.962 | 99.049 | 1.00 | 49.31 C |
| ATOM | 19677 | OE1 | GLU | D | 237 | −26.995 | 7.520 | 98.052 | 1.00 | 51.35 O |
| ATOM | 19678 | OE2 | GLU | D | 237 | −26.072 | 7.582 | 100.046 | 1.00 | 47.04 O |
| ATOM | 19679 | C | GLU | D | 237 | −27.609 | 2.885 | 100.121 | 1.00 | 49.51 C |
| ATOM | 19680 | O | GLU | D | 237 | −27.807 | 2.203 | 99.115 | 1.00 | 48.94 O |
| ATOM | 19682 | N | LEU | D | 238 | −28.582 | 3.285 | 100.951 | 1.00 | 48.63 N |
| ATOM | 19683 | CA | LEU | D | 238 | −29.997 | 2.922 | 100.800 | 1.00 | 47.11 C |
| ATOM | 19685 | CB | LEU | D | 238 | −30.387 | 1.929 | 101.900 | 1.00 | 46.77 C |
| ATOM | 19688 | CG | LEU | D | 238 | −31.740 | 1.214 | 101.808 | 1.00 | 46.51 C |
| ATOM | 19690 | CD1 | LEU | D | 238 | −31.775 | 0.217 | 100.665 | 1.00 | 48.67 C |
| ATOM | 19694 | CD2 | LEU | D | 238 | −32.046 | 0.506 | 103.111 | 1.00 | 44.88 C |
| ATOM | 19698 | C | LEU | D | 238 | −30.875 | 4.171 | 100.895 | 1.00 | 46.43 C |
| ATOM | 19699 | O | LEU | D | 238 | −31.580 | 4.530 | 99.949 | 1.00 | 45.31 O |
| ATOM | 19701 | N | TRP | D | 251 | −32.641 | 5.527 | 104.561 | 1.00 | 50.37 N |
| ATOM | 19702 | CA | TRP | D | 251 | −31.384 | 6.174 | 104.211 | 1.00 | 51.69 C |
| ATOM | 19704 | CB | TRP | D | 251 | −31.554 | 7.699 | 104.243 | 1.00 | 51.63 C |
| ATOM | 19707 | CG | TRP | D | 251 | −32.285 | 8.266 | 103.072 | 1.00 | 52.07 C |
| ATOM | 19708 | CD1 | TRP | D | 251 | −31.855 | 8.288 | 101.783 | 1.00 | 54.18 C |
| ATOM | 19710 | NE1 | TRP | D | 251 | −32.786 | 8.902 | 100.977 | 1.00 | 54.39 N |
| ATOM | 19712 | CE2 | TRP | D | 251 | −33.845 | 9.305 | 101.746 | 1.00 | 54.58 C |
| ATOM | 19713 | CD2 | TRP | D | 251 | −33.563 | 8.925 | 103.080 | 1.00 | 54.77 C |
| ATOM | 19714 | CE3 | TRP | D | 251 | −34.497 | 9.234 | 104.083 | 1.00 | 56.49 C |
| ATOM | 19716 | CZ3 | TRP | D | 251 | −35.676 | 9.900 | 103.723 | 1.00 | 53.81 C |
| ATOM | 19718 | CH2 | TRP | D | 251 | −35.925 | 10.260 | 102.381 | 1.00 | 54.06 C |
| ATOM | 19720 | CZ2 | TRP | D | 251 | −35.025 | 9.973 | 101.383 | 1.00 | 53.59 C |
| ATOM | 19722 | C | TRP | D | 251 | −30.250 | 5.773 | 105.167 | 1.00 | 52.25 C |
| ATOM | 19723 | O | TRP | D | 251 | −30.239 | 6.208 | 106.312 | 1.00 | 53.10 O |
| ATOM | 19725 | N | ILE | D | 252 | −29.314 | 4.936 | 104.710 | 1.00 | 53.39 N |
| ATOM | 19726 | CA | ILE | D | 252 | −28.028 | 4.730 | 105.424 | 1.00 | 52.95 C |
| ATOM | 19728 | CB | ILE | D | 252 | −28.052 | 3.542 | 106.480 | 1.00 | 52.07 C |
| ATOM | 19730 | CG1 | ILE | D | 252 | −27.723 | 2.183 | 105.847 | 1.00 | 51.34 C |
| ATOM | 19733 | CD1 | ILE | D | 252 | −26.320 | 1.684 | 106.165 | 1.00 | 51.08 C |
| ATOM | 19737 | CG2 | ILE | D | 252 | −29.382 | 3.488 | 107.262 | 1.00 | 51.29 C |
| ATOM | 19741 | C | ILE | D | 252 | −26.858 | 4.583 | 104.427 | 1.00 | 52.71 C |
| ATOM | 19742 | O | ILE | D | 252 | −27.076 | 4.408 | 103.230 | 1.00 | 49.06 O |
| ATOM | 19744 | N | THR | D | 253 | −25.631 | 4.681 | 104.944 | 1.00 | 54.71 N |
| ATOM | 19745 | CA | THR | D | 253 | −24.398 | 4.687 | 104.137 | 1.00 | 56.15 C |
| ATOM | 19747 | CB | THR | D | 253 | −23.882 | 6.144 | 103.904 | 1.00 | 56.24 C |
| ATOM | 19749 | OG1 | THR | D | 253 | −24.964 | 7.000 | 103.515 | 1.00 | 55.03 O |
| ATOM | 19751 | CG2 | THR | D | 253 | −22.817 | 6.189 | 102.820 | 1.00 | 56.29 C |
| ATOM | 19755 | C | THR | D | 253 | −23.295 | 3.874 | 104.845 | 1.00 | 57.36 C |
| ATOM | 19756 | O | THR | D | 253 | −23.275 | 3.790 | 106.070 | 1.00 | 57.59 O |
| ATOM | 19758 | N | PHE | D | 254 | −22.381 | 3.284 | 104.073 | 1.00 | 58.47 N |
| ATOM | 19759 | CA | PHE | D | 254 | −21.344 | 2.399 | 104.622 | 1.00 | 58.61 C |
| ATOM | 19761 | CB | PHE | D | 254 | −21.974 | 1.061 | 105.015 | 1.00 | 59.53 C |
| ATOM | 19764 | CG | PHE | D | 254 | −22.626 | 0.348 | 103.864 | 1.00 | 59.96 C |
| ATOM | 19765 | CD1 | PHE | D | 254 | −21.960 | −0.672 | 103.191 | 1.00 | 62.00 C |
| ATOM | 19767 | CE1 | PHE | D | 254 | −22.553 | −1.329 | 102.110 | 1.00 | 60.92 C |
| ATOM | 19769 | CZ | PHE | D | 254 | −23.824 | −0.958 | 101.688 | 1.00 | 60.76 C |
| ATOM | 19771 | CE2 | PHE | D | 254 | −24.496 | 0.068 | 102.347 | 1.00 | 62.46 C |

-continued

| | | | | | | | | | | |
|---|---|---|---|---|---|---|---|---|---|---|
| ATOM | 19773 | CD2 | PHE | D | 254 | −23.894 | 0.717 | 103.429 | 1.00 | 61.56 C |
| ATOM | 19775 | C | PHE | D | 254 | −20.228 | 2.138 | 103.603 | 1.00 | 59.14 C |
| ATOM | 19776 | O | PHE | D | 254 | −20.462 | 2.195 | 102.392 | 1.00 | 58.60 O |
| ATOM | 19778 | N | ASP | D | 255 | −19.025 | 1.840 | 104.097 | 1.00 | 59.15 N |
| ATOM | 19779 | CA | ASP | D | 255 | −17.902 | 1.427 | 103.238 | 1.00 | 59.33 C |
| ATOM | 19781 | CB | ASP | D | 255 | −16.601 | 2.121 | 103.680 | 1.00 | 59.88 C |
| ATOM | 19784 | CG | ASP | D | 255 | −16.630 | 3.630 | 103.457 | 1.00 | 61.43 C |
| ATOM | 19785 | OD1 | ASP | D | 255 | −15.959 | 4.360 | 104.219 | 1.00 | 64.65 O |
| ATOM | 19786 | OD2 | ASP | D | 255 | −17.319 | 4.093 | 102.524 | 1.00 | 61.56 O |
| ATOM | 19787 | C | ASP | D | 255 | −17.754 | −0.105 | 103.267 | 1.00 | 58.94 C |
| ATOM | 19788 | O | ASP | D | 255 | −18.566 | −0.794 | 103.883 | 1.00 | 59.47 O |
| ATOM | 19790 | N | LEU | D | 256 | −16.738 | −0.636 | 102.589 | 1.00 | 58.57 N |
| ATOM | 19791 | CA | LEU | D | 256 | −16.494 | −2.080 | 102.572 | 1.00 | 58.36 C |
| ATOM | 19793 | CB | LEU | D | 256 | −17.392 | −2.742 | 101.514 | 1.00 | 59.64 C |
| ATOM | 19796 | CG | LEU | D | 256 | −17.652 | −4.255 | 101.579 | 1.00 | 59.62 C |
| ATOM | 19798 | CD1 | LEU | D | 256 | −18.794 | −4.625 | 100.639 | 1.00 | 57.95 C |
| ATOM | 19802 | CD2 | LEU | D | 256 | −16.403 | −5.070 | 101.253 | 1.00 | 61.83 C |
| ATOM | 19806 | C | LEU | D | 256 | −15.025 | −2.391 | 102.290 | 1.00 | 57.63 C |
| ATOM | 19807 | O | LEU | D | 256 | −14.608 | −2.389 | 101.142 | 1.00 | 58.03 O |
| ATOM | 19809 | N | LYS | D | 257 | −14.245 | −2.635 | 103.340 | 1.00 | 57.23 N |
| ATOM | 19810 | CA | LYS | D | 257 | −12.860 | −3.101 | 103.199 | 1.00 | 58.22 C |
| ATOM | 19812 | CB | LYS | D | 257 | −11.878 | −2.333 | 104.110 | 1.00 | 58.63 C |
| ATOM | 19815 | CG | LYS | D | 257 | −12.244 | −2.284 | 105.619 | 1.00 | 59.20 C |
| ATOM | 19818 | CD | LYS | D | 257 | −11.267 | −1.432 | 106.449 | 1.00 | 57.85 C |
| ATOM | 19821 | CE | LYS | D | 257 | −10.304 | −2.277 | 107.281 | 1.00 | 56.77 C |
| ATOM | 19824 | NZ | LYS | D | 257 | −9.670 | −3.373 | 106.496 | 1.00 | 57.61 N |
| ATOM | 19828 | C | LYS | D | 257 | −12.874 | −4.573 | 103.550 | 1.00 | 59.25 C |
| ATOM | 19829 | O | LYS | D | 257 | −13.511 | −4.962 | 104.533 | 1.00 | 59.96 O |
| ATOM | 19831 | N | ASN | D | 258 | −12.186 | −5.382 | 102.742 | 1.00 | 59.93 N |
| ATOM | 19832 | CA | ASN | D | 258 | −12.192 | −6.855 | 102.859 | 1.00 | 60.28 C |
| ATOM | 19834 | CB | ASN | D | 258 | −10.762 | −7.392 | 103.032 | 1.00 | 60.48 C |
| ATOM | 19837 | CG | ASN | D | 258 | −9.912 | −6.534 | 103.955 | 1.00 | 62.15 C |
| ATOM | 19838 | OD1 | ASN | D | 258 | −10.395 | −5.975 | 104.950 | 1.00 | 62.50 O |
| ATOM | 19839 | ND2 | ASN | D | 258 | −8.630 | −6.431 | 103.628 | 1.00 | 61.36 N |
| ATOM | 19842 | C | ASN | D | 258 | −13.121 | −7.449 | 103.936 | 1.00 | 61.13 C |
| ATOM | 19843 | O | ASN | D | 258 | −12.721 | −7.646 | 105.094 | 1.00 | 61.04 O |
| ATOM | 19845 | N | LYS | D | 259 | −14.370 | −7.701 | 103.535 | 1.00 | 60.67 N |
| ATOM | 19846 | CA | LYS | D | 259 | −15.369 | −8.388 | 104.364 | 1.00 | 59.67 C |
| ATOM | 19848 | CB | LYS | D | 259 | −14.845 | −9.762 | 104.817 | 1.00 | 60.46 C |
| ATOM | 19851 | CG | LYS | D | 259 | −14.222 | −10.634 | 103.717 | 1.00 | 60.39 C |
| ATOM | 19854 | CD | LYS | D | 259 | −15.054 | −11.876 | 103.418 | 1.00 | 63.03 C |
| ATOM | 19857 | CE | LYS | D | 259 | −14.284 | −12.876 | 102.557 | 1.00 | 63.79 C |
| ATOM | 19860 | NZ | LYS | D | 259 | −13.810 | −12.267 | 101.282 | 1.00 | 65.00 N |
| ATOM | 19864 | C | LYS | D | 259 | −15.858 | −7.599 | 105.594 | 1.00 | 58.60 C |
| ATOM | 19865 | O | LYS | D | 259 | −16.675 | −8.110 | 106.365 | 1.00 | 58.04 O |
| ATOM | 19867 | N | GLU | D | 260 | −15.388 | −6.367 | 105.769 | 1.00 | 57.41 N |
| ATOM | 19868 | CA | GLU | D | 260 | −15.715 | −5.584 | 106.958 | 1.00 | 58.11 C |
| ATOM | 19870 | CB | GLU | D | 260 | −14.436 | −5.189 | 107.699 | 1.00 | 58.58 C |
| ATOM | 19873 | CG | GLU | D | 260 | −13.694 | −6.372 | 108.326 | 1.00 | 57.98 C |
| ATOM | 19876 | CD | GLU | D | 260 | −12.214 | −6.098 | 108.524 | 1.00 | 57.61 C |
| ATOM | 19877 | OE1 | GLU | D | 260 | −11.422 | −6.519 | 107.652 | 1.00 | 58.27 O |
| ATOM | 19878 | OE2 | GLU | D | 260 | −11.846 | −5.452 | 109.532 | 1.00 | 50.23 O |
| ATOM | 19879 | C | GLU | D | 260 | −16.510 | −4.352 | 106.561 | 1.00 | 57.37 C |
| ATOM | 19880 | O | GLU | D | 260 | −16.196 | −3.716 | 105.561 | 1.00 | 57.22 O |
| ATOM | 19882 | N | VAL | D | 261 | −17.532 | −4.024 | 107.354 | 1.00 | 57.46 N |
| ATOM | 19883 | CA | VAL | D | 261 | −18.516 | −2.998 | 106.992 | 1.00 | 58.84 C |
| ATOM | 19885 | CB | VAL | D | 261 | −19.905 | −3.628 | 106.734 | 1.00 | 59.86 C |
| ATOM | 19887 | CG1 | VAL | D | 261 | −20.892 | −2.575 | 106.212 | 1.00 | 59.81 C |
| ATOM | 19891 | CG2 | VAL | D | 261 | −19.795 | −4.811 | 105.764 | 1.00 | 60.30 C |
| ATOM | 19895 | C | VAL | D | 261 | −18.671 | −1.968 | 108.102 | 1.00 | 59.18 C |
| ATOM | 19896 | O | VAL | D | 261 | −18.868 | −2.338 | 109.258 | 1.00 | 59.42 O |
| ATOM | 19898 | N | SER | D | 262 | −18.629 | −0.683 | 107.740 | 1.00 | 60.00 N |
| ATOM | 19899 | CA | SER | D | 262 | −18.540 | 0.413 | 108.720 | 1.00 | 60.19 C |
| ATOM | 19901 | CB | SER | D | 262 | −17.399 | 1.363 | 108.324 | 1.00 | 60.71 C |
| ATOM | 19904 | OG | SER | D | 262 | −16.147 | 0.701 | 108.372 | 1.00 | 62.28 O |
| ATOM | 19906 | C | SER | D | 262 | −19.858 | 1.188 | 108.957 | 1.00 | 60.12 C |
| ATOM | 19907 | O | SER | D | 262 | −20.755 | 0.682 | 109.635 | 1.00 | 59.04 O |
| ATOM | 19909 | N | VAL | D | 263 | −19.954 | 2.409 | 108.418 | 1.00 | 60.68 N |
| ATOM | 19910 | CA | VAL | D | 263 | −21.081 | 3.340 | 108.644 | 1.00 | 60.35 C |
| ATOM | 19912 | CB | VAL | D | 263 | −21.686 | 3.248 | 110.079 | 1.00 | 61.17 C |
| ATOM | 19914 | CG1 | VAL | D | 263 | −20.632 | 3.592 | 111.146 | 1.00 | 62.38 C |
| ATOM | 19918 | CG2 | VAL | D | 263 | −22.924 | 4.153 | 110.212 | 1.00 | 61.75 C |
| ATOM | 19922 | C | VAL | D | 263 | −20.611 | 4.783 | 108.403 | 1.00 | 59.28 C |
| ATOM | 19923 | O | VAL | D | 263 | −19.452 | 5.103 | 108.658 | 1.00 | 58.59 O |
| ATOM | 19925 | N | LYS | D | 264 | −21.509 | 5.643 | 107.920 | 1.00 | 58.75 N |
| ATOM | 19926 | CA | LYS | D | 264 | −21.179 | 7.048 | 107.660 | 1.00 | 59.03 C |
| ATOM | 19928 | CB | LYS | D | 264 | −20.917 | 7.266 | 106.163 | 1.00 | 59.18 C |
| ATOM | 19931 | CG | LYS | D | 264 | −20.205 | 6.100 | 105.469 | 1.00 | 59.90 C |
| ATOM | 19934 | CD | LYS | D | 264 | −19.627 | 6.481 | 104.105 | 1.00 | 59.76 C |

-continued

| | | | | | | | | | | |
|---|---|---|---|---|---|---|---|---|---|---|
| ATOM | 19937 | CE | LYS | D | 264 | −18.284 | 7.192 | 104.226 | 1.00 | 60.91 C |
| ATOM | 19940 | NZ | LYS | D | 264 | −17.578 | 7.263 | 102.920 | 1.00 | 60.55 N |
| ATOM | 19944 | C | LYS | D | 264 | −22.278 | 7.997 | 108.154 | 1.00 | 57.70 C |
| ATOM | 19945 | O | LYS | D | 264 | −23.445 | 7.617 | 108.277 | 1.00 | 56.11 O |
| ATOM | 19947 | N | PRO | D | 270 | −35.407 | 6.986 | 112.279 | 1.00 | 52.14 N |
| ATOM | 19948 | CA | PRO | D | 270 | −35.719 | 5.757 | 111.528 | 1.00 | 51.34 C |
| ATOM | 19950 | CB | PRO | D | 270 | −35.743 | 6.253 | 110.079 | 1.00 | 50.54 C |
| ATOM | 19953 | CG | PRO | D | 270 | −34.703 | 7.356 | 110.054 | 1.00 | 51.18 C |
| ATOM | 19956 | CD | PRO | D | 270 | −34.683 | 7.971 | 111.452 | 1.00 | 51.93 C |
| ATOM | 19959 | C | PRO | D | 270 | −34.663 | 4.659 | 111.685 | 1.00 | 50.66 C |
| ATOM | 19960 | O | PRO | D | 270 | −34.636 | 3.737 | 110.887 | 1.00 | 51.03 O |
| ATOM | 19961 | N | LYS | D | 271 | −33.860 | 4.733 | 112.747 | 1.00 | 51.49 N |
| ATOM | 19962 | CA | LYS | D | 271 | −32.496 | 4.174 | 112.765 | 1.00 | 51.51 C |
| ATOM | 19964 | CB | LYS | D | 271 | −31.701 | 4.719 | 113.964 | 1.00 | 51.04 C |
| ATOM | 19967 | CG | LYS | D | 271 | −31.364 | 6.212 | 113.893 | 1.00 | 49.35 C |
| ATOM | 19970 | CD | LYS | D | 271 | −32.364 | 7.076 | 114.659 | 1.00 | 45.19 C |
| ATOM | 19973 | CE | LYS | D | 271 | −32.011 | 8.551 | 114.566 | 1.00 | 45.44 C |
| ATOM | 19976 | NZ | LYS | D | 271 | −30.663 | 8.858 | 115.121 | 1.00 | 39.79 N |
| ATOM | 19980 | C | LYS | D | 271 | −32.373 | 2.648 | 112.742 | 1.00 | 51.79 C |
| ATOM | 19981 | O | LYS | D | 271 | −32.695 | 1.970 | 113.721 | 1.00 | 50.08 O |
| ATOM | 19983 | N | LEU | D | 272 | −31.875 | 2.144 | 111.607 | 1.00 | 53.53 N |
| ATOM | 19984 | CA | LEU | D | 272 | −31.443 | 0.751 | 111.437 | 1.00 | 54.28 C |
| ATOM | 19986 | CB | LEU | D | 272 | −31.143 | 0.445 | 109.949 | 1.00 | 55.19 C |
| ATOM | 19989 | CG | LEU | D | 272 | −32.233 | 0.095 | 108.919 | 1.00 | 57.39 C |
| ATOM | 19991 | CD1 | LEU | D | 272 | −32.691 | 1.328 | 108.125 | 1.00 | 57.44 C |
| ATOM | 19995 | CD2 | LEU | D | 272 | −33.420 | −0.646 | 109.553 | 1.00 | 60.69 C |
| ATOM | 19999 | C | LEU | D | 272 | −30.172 | 0.467 | 112.241 | 1.00 | 54.31 C |
| ATOM | 20000 | O | LEU | D | 272 | −29.619 | 1.352 | 112.889 | 1.00 | 53.68 O |
| ATOM | 20002 | N | GLN | D | 273 | −29.730 | −0.787 | 112.193 | 1.00 | 55.02 N |
| ATOM | 20003 | CA | GLN | D | 273 | −28.418 | −1.192 | 112.694 | 1.00 | 55.43 C |
| ATOM | 20005 | CB | GLN | D | 273 | −28.537 | −1.885 | 114.065 | 1.00 | 55.59 C |
| ATOM | 20008 | CG | GLN | D | 273 | −27.211 | −2.393 | 114.682 | 1.00 | 55.17 C |
| ATOM | 20011 | CD | GLN | D | 273 | −26.427 | −1.319 | 115.438 | 1.00 | 52.93 C |
| ATOM | 20012 | OE1 | GLN | D | 273 | −26.852 | −0.847 | 116.493 | 1.00 | 46.57 O |
| ATOM | 20013 | NE2 | GLN | D | 273 | −25.264 | −0.952 | 114.907 | 1.00 | 52.07 N |
| ATOM | 20016 | C | GLN | D | 273 | −27.824 | −2.130 | 111.645 | 1.00 | 55.53 C |
| ATOM | 20017 | O | GLN | D | 273 | −28.423 | −3.156 | 111.311 | 1.00 | 53.97 O |
| ATOM | 20019 | N | MET | D | 274 | −26.649 | −1.759 | 111.135 | 1.00 | 56.56 N |
| ATOM | 20020 | CA | MET | D | 274 | −25.996 | −2.452 | 110.018 | 1.00 | 56.36 C |
| ATOM | 20022 | CB | MET | D | 274 | −25.139 | −1.457 | 109.232 | 1.00 | 56.51 C |
| ATOM | 20025 | CG | MET | D | 274 | −24.377 | −2.029 | 108.049 | 1.00 | 57.12 C |
| ATOM | 20028 | SD | MET | D | 274 | −25.394 | −2.146 | 106.575 | 1.00 | 62.31 S |
| ATOM | 20029 | CE | MET | D | 274 | −26.064 | −3.793 | 106.744 | 1.00 | 61.34 C |
| ATOM | 20033 | C | MET | D | 274 | −25.111 | −3.590 | 110.505 | 1.00 | 56.37 C |
| ATOM | 20034 | O | MET | D | 274 | −24.346 | −3.433 | 111.458 | 1.00 | 56.65 O |
| ATOM | 20036 | N | GLY | D | 275 | −25.213 | −4.736 | 109.842 | 1.00 | 56.02 N |
| ATOM | 20037 | CA | GLY | D | 275 | −24.317 | −5.845 | 110.108 | 1.00 | 56.13 C |
| ATOM | 20040 | C | GLY | D | 275 | −22.872 | −5.409 | 109.977 | 1.00 | 55.95 C |
| ATOM | 20041 | O | GLY | D | 275 | −22.506 | −4.696 | 109.042 | 1.00 | 56.24 O |
| ATOM | 20043 | N | LYS | D | 276 | −22.063 | −5.833 | 110.939 | 1.00 | 55.59 N |
| ATOM | 20044 | CA | LYS | D | 276 | −20.625 | −5.551 | 110.972 | 1.00 | 56.11 C |
| ATOM | 20046 | CB | LYS | D | 276 | −20.015 | −6.060 | 112.294 | 1.00 | 57.11 C |
| ATOM | 20049 | CG | LYS | D | 276 | −20.541 | −7.441 | 112.778 | 1.00 | 59.85 C |
| ATOM | 20052 | CD | LYS | D | 276 | −21.743 | −7.331 | 113.755 | 1.00 | 59.41 C |
| ATOM | 20055 | CE | LYS | D | 276 | −22.885 | −8.312 | 113.417 | 1.00 | 56.36 C |
| ATOM | 20058 | NZ | LYS | D | 276 | −22.535 | −9.734 | 113.671 | 1.00 | 53.48 N |
| ATOM | 20062 | C | LYS | D | 276 | −19.857 | −6.148 | 109.785 | 1.00 | 55.14 C |
| ATOM | 20063 | O | LYS | D | 276 | −18.850 | −5.585 | 109.343 | 1.00 | 52.28 O |
| ATOM | 20065 | N | LYS | D | 277 | −20.339 | −7.283 | 109.277 | 1.00 | 56.31 N |
| ATOM | 20066 | CA | LYS | D | 277 | −19.621 | −8.057 | 108.259 | 1.00 | 57.40 C |
| ATOM | 20068 | CB | LYS | D | 277 | −18.921 | −9.249 | 108.927 | 1.00 | 57.72 C |
| ATOM | 20071 | CG | LYS | D | 277 | −17.927 | −8.868 | 110.022 | 1.00 | 57.34 C |
| ATOM | 20074 | CD | LYS | D | 277 | −17.523 | −10.071 | 110.859 | 1.00 | 57.47 C |
| ATOM | 20077 | CE | LYS | D | 277 | −18.669 | −10.561 | 111.737 | 1.00 | 58.38 C |
| ATOM | 20080 | NZ | LYS | D | 277 | −18.193 | −11.388 | 112.879 | 1.00 | 59.61 N |
| ATOM | 20084 | C | LYS | D | 277 | −20.542 | −8.558 | 107.133 | 1.00 | 56.99 C |
| ATOM | 20085 | O | LYS | D | 277 | −21.741 | −8.262 | 107.116 | 1.00 | 55.31 O |
| ATOM | 20087 | N | LEU | D | 278 | −19.955 | −9.299 | 106.191 | 1.00 | 57.67 N |
| ATOM | 20088 | CA | LEU | D | 278 | −20.701 | −9.944 | 105.104 | 1.00 | 58.46 C |
| ATOM | 20090 | CB | LEU | D | 278 | −19.786 | −10.222 | 103.909 | 1.00 | 57.52 C |
| ATOM | 20093 | CG | LEU | D | 278 | −19.118 | −9.015 | 103.258 | 1.00 | 56.25 C |
| ATOM | 20095 | CD1 | LEU | D | 278 | −18.172 | −9.487 | 102.182 | 1.00 | 56.25 C |
| ATOM | 20099 | CD2 | LEU | D | 278 | −20.146 | −8.045 | 102.688 | 1.00 | 55.60 C |
| ATOM | 20103 | C | LEU | D | 278 | −21.323 | −11.268 | 105.562 | 1.00 | 59.86 C |
| ATOM | 20104 | O | LEU | D | 278 | −20.766 | −11.941 | 106.432 | 1.00 | 61.13 O |
| ATOM | 20106 | N | PRO | D | 279 | −22.480 | −11.648 | 104.982 | 1.00 | 60.00 N |
| ATOM | 20107 | CA | PRO | D | 279 | −23.243 | −10.880 | 104.006 | 1.00 | 60.12 C |
| ATOM | 20109 | CB | PRO | D | 279 | −24.357 | −11.848 | 103.593 | 1.00 | 59.18 C |
| ATOM | 20112 | CG | PRO | D | 279 | −24.513 | −12.754 | 104.738 | 1.00 | 58.92 C |

-continued

| ATOM | 20115 | CD  | PRO | D | 279 | −23.133 | −12.934 | 105.284 | 1.00 | 60.28 | C |
| ATOM | 20118 | C   | PRO | D | 279 | −23.833 | −9.600  | 104.606 | 1.00 | 60.74 | C |
| ATOM | 20119 | O   | PRO | D | 279 | −24.045 | −9.517  | 105.826 | 1.00 | 59.77 | O |
| ATOM | 20120 | N   | LEU | D | 280 | −24.067 | −8.609  | 103.747 | 1.00 | 60.94 | N |
| ATOM | 20121 | CA  | LEU | D | 280 | −24.668 | −7.347  | 104.167 | 1.00 | 61.98 | C |
| ATOM | 20123 | CB  | LEU | D | 280 | −24.756 | −6.373  | 102.990 | 1.00 | 61.28 | C |
| ATOM | 20126 | CG  | LEU | D | 280 | −23.447 | −5.924  | 102.340 | 1.00 | 59.59 | C |
| ATOM | 20128 | CD1 | LEU | D | 280 | −23.741 | −5.124  | 101.080 | 1.00 | 57.60 | C |
| ATOM | 20132 | CD2 | LEU | D | 280 | −22.595 | −5.117  | 103.310 | 1.00 | 56.93 | C |
| ATOM | 20136 | C   | LEU | D | 280 | −26.064 | −7.627  | 104.707 | 1.00 | 63.30 | C |
| ATOM | 20137 | O   | LEU | D | 280 | −26.843 | −8.331  | 104.060 | 1.00 | 63.78 | O |
| ATOM | 20139 | N   | HIS | D | 281 | −26.375 | −7.089  | 105.885 | 1.00 | 63.81 | N |
| ATOM | 20140 | CA  | HIS | D | 281 | −27.627 | −7.413  | 106.569 | 1.00 | 64.50 | C |
| ATOM | 20142 | CB  | HIS | D | 281 | −27.597 | −8.897  | 106.978 | 1.00 | 65.93 | C |
| ATOM | 20145 | CG  | HIS | D | 281 | −28.273 | −9.200  | 108.278 | 1.00 | 68.64 | C |
| ATOM | 20146 | ND1 | HIS | D | 281 | −27.635 | −9.073  | 109.495 | 1.00 | 71.30 | N |
| ATOM | 20148 | CE1 | HIS | D | 281 | −28.466 | −9.416  | 110.463 | 1.00 | 72.61 | C |
| ATOM | 20150 | NE2 | HIS | D | 281 | −29.616 | −9.774  | 109.918 | 1.00 | 73.03 | N |
| ATOM | 20152 | CD2 | HIS | D | 281 | −29.519 | −9.653  | 108.552 | 1.00 | 71.01 | C |
| ATOM | 20154 | C   | HIS | D | 281 | −27.847 | −6.497  | 107.771 | 1.00 | 64.93 | C |
| ATOM | 20155 | O   | HIS | D | 281 | −26.887 | −6.139  | 108.448 | 1.00 | 66.37 | O |
| ATOM | 20157 | N   | LEU | D | 282 | −29.100 | −6.127  | 108.044 | 1.00 | 65.18 | N |
| ATOM | 20158 | CA  | LEU | D | 282 | −29.414 | −5.207  | 109.165 | 1.00 | 64.94 | C |
| ATOM | 20160 | CB  | LEU | D | 282 | −29.504 | −3.742  | 108.675 | 1.00 | 64.93 | C |
| ATOM | 20163 | CG  | LEU | D | 282 | −30.179 | −3.317  | 107.364 | 1.00 | 59.82 | C |
| ATOM | 20165 | CD1 | LEU | D | 282 | −31.439 | −4.116  | 107.110 | 1.00 | 58.97 | C |
| ATOM | 20169 | CD2 | LEU | D | 282 | −29.237 | −3.396  | 106.181 | 1.00 | 55.65 | C |
| ATOM | 20173 | C   | LEU | D | 282 | −30.663 | −5.571  | 109.995 | 1.00 | 64.05 | C |
| ATOM | 20174 | O   | LEU | D | 282 | −30.873 | −5.047  | 111.103 | 1.00 | 60.91 | O |
| ATOM | 20176 | N   | ASN | D | 296 | −34.359 | 0.575   | 97.016  | 1.00 | 50.09 | N |
| ATOM | 20177 | CA  | ASN | D | 296 | −33.094 | 0.452   | 96.299  | 1.00 | 52.29 | C |
| ATOM | 20179 | CB  | ASN | D | 296 | −32.986 | 1.533   | 95.214  | 1.00 | 52.45 | C |
| ATOM | 20182 | CG  | ASN | D | 296 | −33.804 | 1.211   | 93.976  | 1.00 | 54.86 | C |
| ATOM | 20183 | OD1 | ASN | D | 296 | −33.879 | 0.060   | 93.548  | 1.00 | 60.19 | O |
| ATOM | 20184 | ND2 | ASN | D | 296 | −34.407 | 2.236   | 93.383  | 1.00 | 54.83 | N |
| ATOM | 20187 | C   | ASN | D | 296 | −31.865 | 0.540   | 97.217  | 1.00 | 53.06 | C |
| ATOM | 20188 | O   | ASN | D | 296 | −31.675 | 1.540   | 97.909  | 1.00 | 53.59 | O |
| ATOM | 20190 | N   | LEU | D | 297 | −31.044 | −0.512  | 97.221  | 1.00 | 53.69 | N |
| ATOM | 20191 | CA  | LEU | D | 297 | −29.697 | −0.461  | 97.799  | 1.00 | 53.19 | C |
| ATOM | 20193 | CB  | LEU | D | 297 | −29.409 | −1.701  | 98.647  | 1.00 | 53.44 | C |
| ATOM | 20196 | CG  | LEU | D | 297 | −27.965 | −1.842  | 99.152  | 1.00 | 53.87 | C |
| ATOM | 20198 | CD1 | LEU | D | 297 | −27.598 | −0.706  | 100.107 | 1.00 | 56.29 | C |
| ATOM | 20202 | CD2 | LEU | D | 297 | −27.756 | −3.189  | 99.822  | 1.00 | 53.90 | C |
| ATOM | 20206 | C   | LEU | D | 297 | −28.678 | −0.379  | 96.668  | 1.00 | 53.65 | C |
| ATOM | 20207 | O   | LEU | D | 297 | −28.705 | −1.199  | 95.745  | 1.00 | 52.72 | O |
| ATOM | 20209 | N   | THR | D | 298 | −27.778 | 0.602   | 96.748  | 1.00 | 53.30 | N |
| ATOM | 20210 | CA  | THR | D | 298 | −26.740 | 0.802   | 95.731  | 1.00 | 52.65 | C |
| ATOM | 20212 | CB  | THR | D | 298 | −26.712 | 2.261   | 95.243  | 1.00 | 52.96 | C |
| ATOM | 20214 | OG1 | THR | D | 298 | −26.732 | 3.144   | 96.376  | 1.00 | 56.56 | O |
| ATOM | 20216 | CG2 | THR | D | 298 | −27.909 | 2.547   | 94.337  | 1.00 | 51.36 | C |
| ATOM | 20220 | C   | THR | D | 298 | −25.354 | 0.444   | 96.267  | 1.00 | 51.63 | C |
| ATOM | 20221 | O   | THR | D | 298 | −25.083 | 0.608   | 97.462  | 1.00 | 50.50 | O |
| ATOM | 20223 | N   | LEU | D | 299 | −24.489 | −0.051  | 95.378  | 1.00 | 50.62 | N |
| ATOM | 20224 | CA  | LEU | D | 299 | −23.102 | −0.371  | 95.728  | 1.00 | 50.11 | C |
| ATOM | 20226 | CB  | LEU | D | 299 | −22.945 | −1.867  | 96.060  | 1.00 | 49.91 | C |
| ATOM | 20229 | CG  | LEU | D | 299 | −21.560 | −2.321  | 96.554  | 1.00 | 50.78 | C |
| ATOM | 20231 | CD1 | LEU | D | 299 | −21.170 | −1.562  | 97.813  | 1.00 | 53.29 | C |
| ATOM | 20235 | CD2 | LEU | D | 299 | −21.500 | −3.822  | 96.807  | 1.00 | 49.65 | C |
| ATOM | 20239 | C   | LEU | D | 299 | −22.137 | 0.029   | 94.608  | 1.00 | 48.19 | C |
| ATOM | 20240 | O   | LEU | D | 299 | −22.326 | −0.337  | 93.447  | 1.00 | 46.34 | O |
| ATOM | 20242 | N   | ALA | D | 300 | −21.109 | 0.786   | 94.984  | 1.00 | 47.98 | N |
| ATOM | 20243 | CA  | ALA | D | 300 | −20.029 | 1.176   | 94.086  | 1.00 | 49.39 | C |
| ATOM | 20245 | CB  | ALA | D | 300 | −19.774 | 2.683   | 94.180  | 1.00 | 47.97 | C |
| ATOM | 20249 | C   | ALA | D | 300 | −18.775 | 0.398   | 94.469  | 1.00 | 50.12 | C |
| ATOM | 20250 | O   | ALA | D | 300 | −18.525 | 0.174   | 95.652  | 1.00 | 51.97 | O |
| ATOM | 20252 | N   | LEU | D | 301 | −18.000 | −0.018  | 93.469  | 1.00 | 50.08 | N |
| ATOM | 20253 | CA  | LEU | D | 301 | −16.776 | −0.784  | 93.688  | 1.00 | 51.34 | C |
| ATOM | 20255 | CB  | LEU | D | 301 | −16.918 | −2.185  | 93.089  | 1.00 | 51.28 | C |
| ATOM | 20258 | CG  | LEU | D | 301 | −18.125 | −2.982  | 93.590  | 1.00 | 52.15 | C |
| ATOM | 20260 | CD1 | LEU | D | 301 | −18.308 | −4.257  | 92.782  | 1.00 | 53.40 | C |
| ATOM | 20264 | CD2 | LEU | D | 301 | −17.987 | −3.295  | 95.072  | 1.00 | 52.51 | C |
| ATOM | 20268 | C   | LEU | D | 301 | −15.616 | −0.063  | 93.028  | 1.00 | 51.47 | C |
| ATOM | 20269 | O   | LEU | D | 301 | −15.746 | 0.413   | 91.904  | 1.00 | 51.57 | O |
| ATOM | 20271 | N   | GLU | D | 302 | −14.478 | 0.004   | 93.709  | 1.00 | 52.24 | N |
| ATOM | 20272 | CA  | GLU | D | 302 | −13.358 | 0.795   | 93.210  | 1.00 | 55.43 | C |
| ATOM | 20274 | CB  | GLU | D | 302 | −12.157 | 0.733   | 94.163  | 1.00 | 56.01 | C |
| ATOM | 20277 | CG  | GLU | D | 302 | −11.478 | −0.629  | 94.254  | 1.00 | 58.92 | C |
| ATOM | 20280 | CD  | GLU | D | 302 | −10.312 | −0.636  | 95.228  | 1.00 | 58.20 | C |
| ATOM | 20281 | OE1 | GLU | D | 302 | −9.570  | 0.365   | 95.278  | 1.00 | 58.05 | O |

-continued

| ATOM | 20282 | OE2 | GLU | D | 302 | −10.132 | −1.647 | 95.939 | 1.00 | 63.10 | O |
| ATOM | 20283 | C | GLU | D | 302 | −12.950 | 0.355 | 91.808 | 1.00 | 56.22 | C |
| ATOM | 20284 | O | GLU | D | 302 | −13.007 | −0.832 | 91.485 | 1.00 | 56.96 | O |
| ATOM | 20286 | N | ALA | D | 303 | −12.569 | 1.330 | 90.981 | 1.00 | 57.46 | N |
| ATOM | 20287 | CA | ALA | D | 303 | −12.082 | 1.089 | 89.619 | 1.00 | 57.59 | C |
| ATOM | 20289 | CB | ALA | D | 303 | −10.791 | 0.272 | 89.665 | 1.00 | 57.43 | C |
| ATOM | 20293 | C | ALA | D | 303 | −13.108 | 0.406 | 88.711 | 1.00 | 58.66 | C |
| ATOM | 20294 | O | ALA | D | 303 | −12.739 | −0.287 | 87.760 | 1.00 | 59.28 | O |
| ATOM | 20296 | N | LYS | D | 304 | −14.392 | 0.592 | 89.001 | 1.00 | 59.63 | N |
| ATOM | 20297 | CA | LYS | D | 304 | −15.438 | −0.130 | 88.281 | 1.00 | 60.18 | C |
| ATOM | 20299 | CB | LYS | D | 304 | −15.705 | −1.484 | 88.940 | 1.00 | 59.91 | C |
| ATOM | 20302 | CG | LYS | D | 304 | −14.534 | −2.431 | 88.804 | 1.00 | 59.97 | C |
| ATOM | 20305 | CD | LYS | D | 304 | −14.854 | −3.829 | 89.269 | 1.00 | 61.17 | C |
| ATOM | 20308 | CE | LYS | D | 304 | −13.582 | −4.652 | 89.400 | 1.00 | 61.13 | C |
| ATOM | 20311 | NZ | LYS | D | 304 | −12.779 | −4.644 | 88.141 | 1.00 | 61.23 | N |
| ATOM | 20315 | C | LYS | D | 304 | −16.717 | 0.688 | 88.167 | 1.00 | 60.58 | C |
| ATOM | 20316 | O | LYS | D | 304 | −17.590 | 0.634 | 89.037 | 1.00 | 60.60 | O |
| ATOM | 20318 | N | THR | D | 305 | −16.804 | 1.446 | 87.075 | 1.00 | 61.86 | N |
| ATOM | 20319 | CA | THR | D | 305 | −18.008 | 2.193 | 86.720 | 1.00 | 61.96 | C |
| ATOM | 20321 | CB | THR | D | 305 | −17.870 | 2.912 | 85.349 | 1.00 | 62.82 | C |
| ATOM | 20323 | OG1 | THR | D | 305 | −17.327 | 2.007 | 84.376 | 1.00 | 52.48 | O |
| ATOM | 20325 | CG2 | THR | D | 305 | −16.981 | 4.167 | 85.474 | 1.00 | 61.48 | C |
| ATOM | 20329 | C | THR | D | 305 | −19.231 | 1.282 | 86.671 | 1.00 | 63.59 | C |
| ATOM | 20330 | O | THR | D | 305 | −19.127 | 0.053 | 86.502 | 1.00 | 66.14 | O |
| ATOM | 20332 | N | GLY | D | 306 | −20.391 | 1.912 | 86.806 | 1.00 | 62.32 | N |
| ATOM | 20333 | CA | GLY | D | 306 | −21.633 | 1.204 | 87.038 | 1.00 | 61.13 | C |
| ATOM | 20336 | C | GLY | D | 306 | −21.986 | 1.308 | 88.505 | 1.00 | 59.96 | C |
| ATOM | 20337 | O | GLY | D | 306 | −21.334 | 2.010 | 89.277 | 1.00 | 57.92 | O |
| ATOM | 20339 | N | LYS | D | 307 | −23.027 | 0.592 | 88.890 | 1.00 | 60.51 | N |
| ATOM | 20340 | CA | LYS | D | 307 | −23.532 | 0.661 | 90.242 | 1.00 | 59.65 | C |
| ATOM | 20342 | CB | LYS | D | 307 | −24.377 | 1.935 | 90.399 | 1.00 | 59.54 | C |
| ATOM | 20345 | CG | LYS | D | 307 | −24.531 | 2.440 | 91.829 | 1.00 | 61.32 | C |
| ATOM | 20348 | CD | LYS | D | 307 | −23.604 | 3.621 | 92.159 | 1.00 | 62.72 | C |
| ATOM | 20351 | CE | LYS | D | 307 | −24.082 | 4.353 | 93.422 | 1.00 | 62.70 | C |
| ATOM | 20354 | NZ | LYS | D | 307 | −23.276 | 5.553 | 93.777 | 1.00 | 61.79 | N |
| ATOM | 20358 | C | LYS | D | 307 | −24.368 | −0.599 | 90.479 | 1.00 | 58.73 | C |
| ATOM | 20359 | O | LYS | D | 307 | −25.383 | −0.800 | 89.803 | 1.00 | 59.90 | O |
| ATOM | 20361 | N | LEU | D | 308 | −23.938 | −1.458 | 91.402 | 1.00 | 56.19 | N |
| ATOM | 20362 | CA | LEU | D | 308 | −24.768 | −2.601 | 91.793 | 1.00 | 55.13 | C |
| ATOM | 20364 | CB | LEU | D | 308 | −24.016 | −3.577 | 92.695 | 1.00 | 53.12 | C |
| ATOM | 20367 | CG | LEU | D | 308 | −22.843 | −4.301 | 92.045 | 1.00 | 51.17 | C |
| ATOM | 20369 | CD1 | LEU | D | 308 | −22.174 | −5.246 | 93.039 | 1.00 | 50.36 | C |
| ATOM | 20373 | CD2 | LEU | D | 308 | −23.292 | −5.048 | 90.796 | 1.00 | 50.21 | C |
| ATOM | 20377 | C | LEU | D | 308 | −26.023 | −2.086 | 92.486 | 1.00 | 53.53 | C |
| ATOM | 20378 | O | LEU | D | 308 | −26.006 | −1.055 | 93.145 | 1.00 | 51.81 | O |
| ATOM | 20380 | N | HIS | D | 309 | −27.108 | −2.824 | 92.330 | 1.00 | 53.59 | N |
| ATOM | 20381 | CA | HIS | D | 309 | −28.424 | −2.320 | 92.649 | 1.00 | 55.00 | C |
| ATOM | 20383 | CB | HIS | D | 309 | −28.987 | −1.629 | 91.395 | 1.00 | 56.99 | C |
| ATOM | 20386 | CG | HIS | D | 309 | −30.480 | −1.511 | 91.368 | 1.00 | 64.50 | C |
| ATOM | 20387 | ND1 | HIS | D | 309 | −31.286 | −2.422 | 90.719 | 1.00 | 69.23 | N |
| ATOM | 20389 | CE1 | HIS | D | 309 | −32.552 | −2.064 | 90.856 | 1.00 | 73.67 | C |
| ATOM | 20391 | NE2 | HIS | D | 309 | −32.596 | −0.949 | 91.565 | 1.00 | 74.96 | N |
| ATOM | 20393 | CD2 | HIS | D | 309 | −31.313 | −0.579 | 91.895 | 1.00 | 72.98 | C |
| ATOM | 20395 | C | HIS | D | 309 | −29.307 | −3.474 | 93.123 | 1.00 | 53.81 | C |
| ATOM | 20396 | O | HIS | D | 309 | −29.231 | −4.572 | 92.583 | 1.00 | 52.54 | O |
| ATOM | 20398 | N | GLN | D | 310 | −30.115 | −3.229 | 94.154 | 1.00 | 54.03 | N |
| ATOM | 20399 | CA | GLN | D | 310 | −31.121 | −4.201 | 94.603 | 1.00 | 54.20 | C |
| ATOM | 20401 | CB | GLN | D | 310 | −30.525 | −5.207 | 95.592 | 1.00 | 53.57 | C |
| ATOM | 20404 | CG | GLN | D | 310 | −31.569 | −6.159 | 96.165 | 1.00 | 51.93 | C |
| ATOM | 20407 | CD | GLN | D | 310 | −30.979 | −7.313 | 96.947 | 1.00 | 51.98 | C |
| ATOM | 20408 | OE1 | GLN | D | 310 | −29.793 | −7.622 | 96.840 | 1.00 | 51.04 | O |
| ATOM | 20409 | NE2 | GLN | D | 310 | −31.817 | −7.963 | 97.745 | 1.00 | 45.49 | N |
| ATOM | 20412 | C | GLN | D | 310 | −32.324 | −3.526 | 95.250 | 1.00 | 54.35 | C |
| ATOM | 20413 | O | GLN | D | 310 | −32.176 | −2.733 | 96.173 | 1.00 | 54.20 | O |
| ATOM | 20415 | N | GLU | D | 311 | −33.513 | −3.874 | 94.772 | 1.00 | 55.20 | N |
| ATOM | 20416 | CA | GLU | D | 311 | −34.751 | −3.402 | 95.378 | 1.00 | 56.10 | C |
| ATOM | 20418 | CB | GLU | D | 311 | −35.941 | −3.694 | 94.463 | 1.00 | 56.72 | C |
| ATOM | 20421 | CG | GLU | D | 311 | −36.211 | −2.636 | 93.410 | 1.00 | 57.24 | C |
| ATOM | 20424 | CD | GLU | D | 311 | −37.690 | −2.541 | 93.072 | 1.00 | 57.45 | C |
| ATOM | 20425 | OE1 | GLU | D | 311 | −38.048 | −2.680 | 91.883 | 1.00 | 60.36 | O |
| ATOM | 20426 | OE2 | GLU | D | 311 | −38.499 | −2.346 | 94.004 | 1.00 | 55.98 | O |
| ATOM | 20427 | C | GLU | D | 311 | −35.012 | −4.050 | 96.743 | 1.00 | 57.13 | C |
| ATOM | 20428 | O | GLU | D | 311 | −34.667 | −5.212 | 96.969 | 1.00 | 59.32 | O |
| ATOM | 20430 | N | VAL | D | 312 | −35.628 | −3.282 | 97.642 | 1.00 | 56.10 | N |
| ATOM | 20431 | CA | VAL | D | 312 | −36.108 | −3.791 | 98.925 | 1.00 | 54.35 | C |
| ATOM | 20433 | CB | VAL | D | 312 | −35.258 | −3.293 | 100.107 | 1.00 | 55.79 | C |
| ATOM | 20435 | CG1 | VAL | D | 312 | −35.394 | −4.253 | 101.295 | 1.00 | 55.16 | C |
| ATOM | 20439 | CG2 | VAL | D | 312 | −33.797 | −3.124 | 99.698 | 1.00 | 58.54 | C |
| ATOM | 20443 | C | VAL | D | 312 | −37.519 | −3.274 | 99.139 | 1.00 | 52.65 | C |

-continued

| ATOM | 20444 | O | VAL | D | 312 | -37.829 | -2.152 | 98.747 | 1.00 | 51.46 | O |
|---|---|---|---|---|---|---|---|---|---|---|---|
| ATOM | 20446 | N | ASN | D | 313 | -38.368 | -4.088 | 99.761 | 1.00 | 51.15 | N |
| ATOM | 20447 | CA | ASN | D | 313 | -39.753 | -3.699 | 100.019 | 1.00 | 49.70 | C |
| ATOM | 20449 | CB | ASN | D | 313 | -40.677 | -4.254 | 98.923 | 1.00 | 49.29 | C |
| ATOM | 20452 | CG | ASN | D | 313 | -40.109 | -4.077 | 97.511 | 1.00 | 47.00 | C |
| ATOM | 20453 | OD1 | ASN | D | 313 | -40.574 | -3.240 | 96.738 | 1.00 | 43.93 | O |
| ATOM | 20454 | ND2 | ASN | D | 313 | -39.104 | -4.872 | 97.175 | 1.00 | 47.81 | N |
| ATOM | 20457 | C | ASN | D | 313 | -40.223 | -4.171 | 101.403 | 1.00 | 48.99 | C |
| ATOM | 20458 | O | ASN | D | 313 | -39.804 | -5.227 | 101.879 | 1.00 | 50.76 | O |
| ATOM | 20460 | N | LEU | D | 314 | -41.089 | -3.384 | 102.040 | 1.00 | 46.64 | N |
| ATOM | 20461 | CA | LEU | D | 314 | -41.621 | -3.715 | 103.361 | 1.00 | 45.22 | C |
| ATOM | 20463 | CB | LEU | D | 314 | -40.802 | -3.006 | 104.438 | 1.00 | 45.62 | C |
| ATOM | 20466 | CG | LEU | D | 314 | -41.099 | -3.282 | 105.923 | 1.00 | 46.54 | C |
| ATOM | 20468 | CD1 | LEU | D | 314 | -40.589 | -4.654 | 106.338 | 1.00 | 47.51 | C |
| ATOM | 20472 | CD2 | LEU | D | 314 | -40.489 | -2.194 | 106.823 | 1.00 | 43.11 | C |
| ATOM | 20476 | C | LEU | D | 314 | -43.087 | -3.310 | 103.462 | 1.00 | 42.59 | C |
| ATOM | 20477 | O | LEU | D | 314 | -43.925 | -4.084 | 103.920 | 1.00 | 40.19 | O |
| ATOM | 20479 | O | HOH | S | 1 | 23.900 | 8.091 | 67.594 | 1.00 | 36.83 | O |
| ATOM | 20482 | O | HOH | S | 2 | 5.912 | 4.439 | 54.558 | 1.00 | 29.49 | O |
| ATOM | 20485 | O | HOH | S | 3 | -16.003 | -21.359 | 70.559 | 1.00 | 31.23 | O |
| ATOM | 20488 | O | HOH | S | 4 | 13.033 | -10.043 | 57.159 | 1.00 | 50.76 | O |
| ATOM | 20491 | O | HOH | S | 5 | -16.929 | -1.491 | 61.333 | 1.00 | 38.50 | O |
| ATOM | 20494 | O | HOH | S | 6 | -22.626 | -6.539 | 63.353 | 1.00 | 50.27 | O |
| ATOM | 20497 | O | HOH | S | 7 | 16.630 | -9.251 | 65.143 | 1.00 | 45.50 | O |
| ATOM | 20500 | O | HOH | S | 8 | 44.030 | 7.432 | 44.731 | 1.00 | 37.27 | O |
| ATOM | 20503 | O | HOH | S | 9 | 31.788 | -5.318 | 53.301 | 1.00 | 35.07 | O |
| ATOM | 20506 | O | HOH | S | 10 | -30.206 | -7.085 | 50.788 | 1.00 | 46.69 | O |
| ATOM | 20509 | O | HOH | S | 11 | 2.607 | -8.285 | 67.630 | 1.00 | 33.72 | O |
| ATOM | 20512 | O | HOH | S | 12 | 2.236 | 1.490 | 38.087 | 1.00 | 44.75 | O |
| ATOM | 20515 | O | HOH | S | 13 | 37.064 | -22.971 | 76.347 | 1.00 | 43.10 | O |
| ATOM | 20518 | O | HOH | S | 14 | 29.806 | -11.612 | 69.475 | 1.00 | 31.98 | O |
| ATOM | 20521 | O | HOH | S | 15 | -15.188 | 2.660 | 97.916 | 1.00 | 45.05 | O |
| ATOM | 20524 | O | HOH | S | 16 | -5.607 | -22.673 | 71.013 | 1.00 | 41.14 | O |
| ATOM | 20527 | O | HOH | S | 17 | -0.264 | 5.022 | 34.615 | 1.00 | 53.08 | O |
| ATOM | 20530 | O | HOH | S | 18 | 5.673 | 8.372 | 50.771 | 1.00 | 41.06 | O |
| ATOM | 20533 | O | HOH | S | 19 | 8.805 | 14.650 | 55.069 | 1.00 | 36.37 | O |
| ATOM | 20536 | O | HOH | S | 20 | -5.379 | -16.793 | 52.803 | 1.00 | 34.32 | O |
| ATOM | 20539 | O | HOH | S | 21 | -6.797 | -11.277 | 35.837 | 1.00 | 52.95 | O |
| ATOM | 20542 | O | HOH | S | 22 | 37.201 | 11.338 | 80.658 | 1.00 | 70.53 | O |
| ATOM | 20545 | O | HOH | S | 23 | 43.835 | 13.822 | 42.909 | 1.00 | 61.88 | O |
| ATOM | 20548 | O | HOH | S | 24 | 13.385 | -2.184 | 19.956 | 1.00 | 45.10 | O |
| ATOM | 20551 | O | HOH | S | 25 | 3.200 | -26.115 | 65.629 | 1.00 | 29.75 | O |
| ATOM | 20554 | O | HOH | S | 26 | -20.435 | -19.113 | 31.054 | 1.00 | 30.05 | O |
| ATOM | 20557 | O | HOH | S | 27 | 29.310 | -15.968 | 54.370 | 1.00 | 41.89 | O |
| ATOM | 20560 | O | HOH | S | 28 | -28.905 | -11.538 | 89.618 | 1.00 | 44.37 | O |
| ATOM | 20563 | O | HOH | S | 29 | -6.444 | -19.644 | 75.505 | 1.00 | 34.88 | O |
| ATOM | 20566 | O | HOH | S | 30 | -3.930 | -24.054 | 62.231 | 1.00 | 46.15 | O |
| ATOM | 20569 | O | HOH | S | 31 | -26.525 | -18.165 | 54.874 | 1.00 | 32.11 | O |
| ATOM | 20572 | O | HOH | S | 32 | -16.859 | -33.447 | 52.129 | 1.00 | 52.93 | O |
| ATOM | 20575 | O | HOH | S | 33 | 24.707 | -2.954 | 31.853 | 1.00 | 37.36 | O |
| ATOM | 20578 | O | HOH | S | 34 | -37.527 | -9.583 | 49.990 | 1.00 | 45.23 | O |
| ATOM | 20581 | O | HOH | S | 35 | -21.289 | -9.902 | 61.681 | 1.00 | 34.17 | O |
| ATOM | 20584 | O | HOH | S | 36 | 18.763 | 5.020 | 61.136 | 1.00 | 35.70 | O |
| ATOM | 20587 | O | HOH | S | 37 | 31.828 | -25.589 | 50.936 | 1.00 | 38.57 | O |
| ATOM | 20590 | O | HOH | S | 38 | 35.516 | -4.398 | 50.634 | 1.00 | 85.69 | O |
| ATOM | 20593 | O | HOH | S | 39 | 35.516 | -4.398 | 50.634 | 1.00 | 85.69 | O |
| ATOM | 20596 | O | HOH | S | 40 | -12.682 | 4.430 | 47.461 | 1.00 | 46.60 | O |

The invention claimed is:

1. A method for screening for a molecule capable of binding to CD4 comprising:
   (a) contacting a sample with one or more candidate molecules;
   (b) detecting whether the one or more candidate molecules binds to a region of human CD4 selected from the group consisting of:
      (i) amino acids 148 to 154,
      (ii) amino acids 164 to 168,
      (iii) amino acids 185 to 192; and
      (iv) combinations thereof,
   wherein the one or more candidate molecules are antibodies or antibody fragments comprising CDR1 and CDR2 of BT061 light chain, and CDR1 and CDR3 of BT061 heavy chain, optionally with amino acid substitutions in the sequences of the CDRs provided:

(i) the light chain CDR1 comprises: Ser32; Gly33; and Tyr 34;

(ii) the light chain CDR2 comprises: Leu54; and Ile57;

(iii) the heavy chain CDR1 comprises: Asp31, Glu31, Thr31, Cys31, Pro31,Met31 or Tyr31; and (iv) the heavy chain CDR3 comprises Tyr103, Phe103 or His103; Arg104; Tyr105; Asp106; and Trp110, Phe110, His 110 or Tyr110.

2. The method according to claim 1, wherein the step (b) further comprises detecting whether the one or more candidate molecules binds to an amino acid of human CD4 located at a position in human CD4 selected from the group consisting of:

(i) 26, (ii) 156, (iii) 159, (iv) 161, and (v) combinations thereof.

3. The method according to claim 1, wherein the amino acid substitutions in the sequence of CDR1 and CDR2 of BT061 light chain and CDR1 and CDR3 of BT061 heavy chain are selected from those set out in Table 4 and Table 5.

4. The method according to claim 1, wherein the antibody or antibody fragment comprises a light chain comprising Tyr 53 or Phe 53 and a heavy chain comprising Ser 28.

5. The method according to claim 1, wherein the antibody or antibody fragment comprises a light chain comprising Asp64 and/or a heavy chain comprising Glu 56.

6. The method according to claim 1, wherein the antibody or antibody fragment further comprises the CDR3 of BT061 light chain and/or the CDR2 of BT061 heavy chain optionally with amino acid substitutions in the sequences of these CDRs wherein the substitutions are selected from those set out in Table 4 and Table 5.

7. The method according to claim 6, further comprising a step (c) of contacting in vitro a molecule that binds to CD4+measured in step (b) with a CD4+cell or with a peptide or polypeptide comprising a region of human CD4 selected from the group consisting of:
(i) amino acids 148 to 154,
(ii) amino acids 164 to 168,
(iii) amino acids 185 to 192, and
(iv) combinations thereof.

8. A method according to claim 7, wherein step (c) comprises
(i) detecting the binding of the molecule measured in step (b) to a peptide or polypeptide comprising a region of human CD4 selected from the group consisting of: (A) amino acids 148 to 154, (B) amino acids 164 to 168, (C) amino acids 185 to 192, and (D) combinations thereof;
(ii) measuring the activation of CD4+CD25+ regulatory T cells; and/or
(iii) measuring the reduction of CD4 receptor expression on a CD4 expressing cell.

9. The method according to claim 8, wherein the step (i) comprises performing X ray crystallography or NMR and detecting the binding of a molecule to the peptide or polypeptide without a salt bridge.

10. The method according to claim 7, wherein the peptide or the polypeptide is fixed to a membrane or an equivalent suitable surface, or is coupled to a magnetic bead.

11. The method according to claim 7, wherein the peptide or polypeptide comprises the Ig-like C2-type 1 domain of human CD4, or comprises the Ig-like V-type domain and the Ig-like C2-type 1 domain of human CD4.

12. The method according to claim 7, wherein the peptide or polypeptide mimics the conformation of the wild-type CD4 epitope.

13. The method according to claim 8, wherein the CD4 expressing cells are PBMC.

14. The method according to claim 1, wherein steps (a) to (b) are conducted in vitro and said detecting comprises contacting the one or more candidate molecules with a peptide or polypeptide comprising a region of human CD4 selected from the group consisting of: (i) amino acids 148 to 154, (ii) amino acids 164 to 168, (iii) amino acids 185 to 192, and (iv) combinations thereof.

15. The method according to claim 14, wherein the one or more candidate molecules are a library of molecules.

16. The method according to claim 15, wherein the library is a phage display library.

17. The method according to claim 14, further comprising a step (c) of measuring the activation of CD4+CD25+ regulatory T cells by a molecule that binds to CD4+ measured in step (b), and/or a step (d) of measuring the reduction of CD4 receptor expression on a CD4 expressing cell by a molecule that binds to CD4+ measured in step (b).

18. The method according to claim 14, wherein the contacting step comprises further contacting the peptide or polypeptide and the one or more candidate molecules with a competitor antibody or antibody fragment having the heavy and light chain variable domains of BT061, and detecting if the one or more candidate molecules is able to block binding of the competitor antibody or antibody fragment to the peptide or polypeptide.

19. A method for screening for an antibody or antibody fragment capable of binding CD4 comprising:
(a) contacting a sample with an antibody or antibody fragment comprising CDR1 and CDR2 of BT061 light chain, and CDR1 and CDR3 of BT061 heavy chain, optionally with amino acid substitutions in the sequences of the CDRs provided:
(i) the light chain CDR1 comprises: Ser32; Gly33; and Tyr 34;
(ii) the light chain CDR2 comprises: Leu54; and Ile57;
(iii) the heavy chain CDR1 comprises Asp31, Glu31, Thr31, Cys31, Pro31, Met31 or Tyr31; and
(iv) the heavy chain CDR3 comprises Tyr103, Phe103 or His103; Arg104; Tyr105; Asp106; and Trp110, Phe110, His 110 or Tyr110,
(b) measuring the binding to CD4 by the antibody or antibody fragment, and
wherein the antibody or antibody fragment does not comprise CDR1, CDR2 and CDR3 of BT061 heavy chain and CDR1, CDR2 and CDR3 of BT061 light chain.

20. The method according to claim 19, wherein the amino acid substitutions in the sequences of CDR1 and CDR2 of BT061 light chain and CDR1 and CDR3 of BT061 heavy chain are selected from those set out in Table 4 and Table 5.

21. The method according to claim 19, wherein the antibody or antibody fragment comprises a light chain comprising Tyr53 or Phe53 and a heavy chain comprising Ser28.

22. The method according to claim 19, wherein the antibody or antibody fragment comprises a light chain comprising Asp64 and/or a heavy chain comprising Glu 56.

23. The method according to claim 19, wherein the antibody or antibody fragment further comprises the CDR3 of BT061 light chain, and/or the CDR2 of BT061 heavy chain, optionally with amino acid substitutions in the sequences of these CDRs wherein the substitutions are selected from those set out in Table 4 and Table 5.

24. The method according to claim 19, wherein steps (a) to (b) are conducted in vitro.

25. The method according to claim 24, wherein step (b) further comprises detecting whether the antibody or antibody fragment
(i) activates CD4+CD25+ regulatory T cells;
(ii) binds to a region of CD4 selected from the group consisting of: (a) amino acids 148 to 154; (b) amino acids 164 to 168, (c) amino acids 185 to 192, and (d) combinations thereof; and/or
(iii) down-regulates expression of CD4 on CD4 expressing cell.

26. A method of screening for the presence of CD4+CD25+ T regulatory cells in a sample comprising:
(a) contacting a labeled antibody or antibody fragment with the sample,
(b) washing the sample to remove unbound antibody, and
(c) measuring the labeled antibody or antibody fragment in the sample; wherein the antibody or antibody fragment comprises CDR1 and CDR2 of BT061 light chain, and CDR1 and CDR3 of BT061 heavy chain, optionally with amino acid substitutions in the sequences of the CDRs provided:
(i) the light chain CDR1 comprises: Ser32; Gly33; and Tyr 34;
(ii) the light chain CDR2 comprises: Leu54; and Ile57;
(iii) the heavy chain CDR1 comprises Asp31, Glu31, Thr31, Cys31, Pro31, Met31 or Tyr31; and
(iv) the heavy chain CDR3 comprises Tyr103, Phe103 or His103; Arg104; Tyr105; Asp106; and Trp110, Phe110, His 110 or Tyr110, wherein the antibody or antibody fragment does not comprise CDR1, CDR2 and CDR3 of BT061 heavy chain and CDR1, CDR2 and CDR3 of BT061 light chain.

27. A method of screening according to claim 26, wherein the CD4+CD25+ T regulatory cells are activated.

28. A method of screening according to claim 26, wherein the sample is a biological sample taken from a subject suffering from an autoimmune disease or from transplant rejection.

* * * * *